US011001861B2

(12) United States Patent
Martini et al.

(10) Patent No.: US 11,001,861 B2
(45) Date of Patent: May 11, 2021

(54) POLYNUCLEOTIDES ENCODING GALACTOSE-1-PHOSPHATE URIDYLYLTRANSFERASE FOR THE TREATMENT OF GALACTOSEMIA TYPE 1

(71) Applicant: ModernaTX, Inc., Cambridge, MA (US)

(72) Inventors: Paolo Martini, Boston, MA (US); Stephen Hoge, Cambridge, MA (US); Kerry Benenato, Cambridge, MA (US); Vladimir Presnyak, Manchester, NH (US); Iain McFadyen, Medford, MA (US); Ellalahewage Sathyajith Kumarasinghe, Cambridge, MA (US); Ding An, Waban, MA (US); Staci Sabnis, Cambridge, MA (US)

(73) Assignee: ModernaTX, Inc., Cambridge, MA (US)

( * ) Notice: Subject to any disclaimer, the term of this patent is extended or adjusted under 35 U.S.C. 154(b) by 22 days.

(21) Appl. No.: 16/302,341

(22) PCT Filed: May 18, 2017

(86) PCT No.: PCT/US2017/033420
§ 371 (c)(1),
(2) Date: Nov. 16, 2018

(87) PCT Pub. No.: WO2017/201348
PCT Pub. Date: Nov. 23, 2017

(65) Prior Publication Data

US 2019/0300906 A1 Oct. 3, 2019

Related U.S. Application Data

(60) Provisional application No. 62/338,437, filed on May 18, 2016.

(51) Int. Cl.

| | |
|---|---|
| ***C12N 15/88*** | (2006.01) |
| ***A61K 9/51*** | (2006.01) |
| ***B82Y 5/00*** | (2011.01) |
| ***C07K 14/14*** | (2006.01) |
| ***C12N 9/12*** | (2006.01) |
| ***G01N 33/68*** | (2006.01) |
| ***A61K 48/00*** | (2006.01) |

(52) U.S. Cl.
CPC ................ *C12N 15/88* (2013.01); *A61K 9/51* (2013.01); *A61K 48/005* (2013.01); *B82Y 5/00* (2013.01); *C07K 14/14* (2013.01); *C12N 9/1241* (2013.01); *G01N 33/6851* (2013.01); *C12Y 207/0701* (2013.01)

(58) Field of Classification Search
None
See application file for complete search history.

(56) References Cited

U.S. PATENT DOCUMENTS

| | | | |
|---|---|---|---|
| 9,095,552 | B2 | 8/2015 | Chakraborty et al. |
| 9,107,886 | B2 | 8/2015 | Chakraborty et al. |
| 9,114,113 | B2 | 8/2015 | Chakraborty et al. |
| 9,220,792 | B2 | 12/2015 | Chakraborty et al. |
| 9,233,141 | B2 | 1/2016 | Chakraborty et al. |
| 9,814,760 | B2 | 11/2017 | Bancel et al. |
| 2013/0259923 | A1 | 10/2013 | Bancel et al. |
| 2014/0148502 | A1 | 5/2014 | Bancel et al. |
| 2014/0155472 | A1 | 6/2014 | Bancel et al. |
| 2014/0155473 | A1 | 6/2014 | Bancel et al. |
| 2014/0155474 | A1 | 6/2014 | Bancel et al. |
| 2014/0155475 | A1 | 6/2014 | Bancel et al. |
| 2014/0193482 | A1 | 7/2014 | Bancel et al. |
| 2014/0194494 | A1 | 7/2014 | Bancel et al. |
| 2014/0200263 | A1 | 7/2014 | Bancel et al. |
| 2018/0311381 | A1 | 11/2018 | Bancel et al. |
| 2019/0175517 | A1 | 6/2019 | Martini et al. |
| 2019/0298657 | A1 | 10/2019 | Martini et al. |
| 2019/0298658 | A1 | 10/2019 | Benehato et al. |
| 2019/0390181 | A1 | 12/2019 | Benehato et al. |

(Continued)

FOREIGN PATENT DOCUMENTS

| | | |
|---|---|---|
| WO | WO2011068810 | 6/2011 |
| WO | WO2013086373 | 6/2013 |

(Continued)

OTHER PUBLICATIONS

Bosch AM. "Classical galactosaemia revisited," Journal Inherited Metabolic Disease , Aug. 2006, 29:516-525.

European Office Action in European Application No. 17728703.4, dated Feb. 28, 2020, 20 pages.

International Search Report and Written Opinion in International Application No. PCT/US2017/033420, dated May 18, 2017, 8 pages.

(Continued)

*Primary Examiner* — Brian J Davis
(74) *Attorney, Agent, or Firm* — Fish & Richardson P.C.

(57) ABSTRACT

The invention relates to mRNA therapy for the treatment of galactosemia type 1 (Gal-1). mRNAs for use in the invention, when administered in vivo, encode human galactose-1-phosphate uridylyltransferase (GALT), isoforms thereof, functional fragments thereof, and fusion proteins comprising GALT. mRNAs of the invention are preferably encapsulated in lipid nanoparticles (LNPs) to effect efficient delivery to cells and/or tissues in subjects, when administered thereto. mRNA therapies of the invention increase and/or restore deficient levels of GALT expression and/or activity in subjects. mRNA therapies of the invention further decrease levels of toxic metabolites associated with deficient GALT activity in subjects, namely galactose-1-phosphate (Gal-1-P).

50 Claims, 24 Drawing Sheets

Specification includes a Sequence Listing.

(56) References Cited

U.S. PATENT DOCUMENTS

| | | | |
|---|---|---|---|
| 2020/0078314 | A1 | 3/2020 | Martini et al. |
| 2020/0085916 | A1 | 3/2020 | Martini et al. |

FOREIGN PATENT DOCUMENTS

| | | | |
|---|---|---|---|
| WO | WO2013151666 | 10/2013 | |
| WO | WO 2014/144196 A1 * | 9/2014 | ........... G01N 33/543 |
| WO | WO2015074085 | 5/2015 | |
| WO | WO2015199952 | 12/2015 | |
| WO | WO2016176330 | 11/2016 | |
| WO | WO2017049245 | 3/2017 | |
| WO | WO2017191274 | 11/2017 | |

OTHER PUBLICATIONS

Karadag et al., "Literature review and outcome of classic galactosemia diagnosed in the neonatal period," Clinical Laboratory, Jan. 2013, 59:1139-1146.

Timson, "The molecular basis of galactosemia—Past, present and future," Gene, Sep. 2016, 589:133-141.

* cited by examiner

FIG. 1A SEQ ID NO: 1 (GALT; Galactose-1-phosphate uridylyltransferase, wt, isoform 1)

```
MSRSGTDPQQRQQASEADAAAATFRANDHQHIRYNPLQDEWVLVSAHRMKRPWQGQVEP
QLLKTVPRHDPLNPLCPGAIRANGEVNPQYDSTFLFDNDFPALQPDAPSPGPSDHPLFQ
AKSARGVCKVMCFHPWSDVTLPLMSVPEIRAVVDAWASVTEELGAQYPWVQIFENKGAM
MGCSNPHPHCQVWASSFLPDIAQREERSQQAYKSQHGEPLLMEYSRQELLRKERLVLTS
EHWLVLVPFWATWPYQTLLLPRRHVRRLPELTPAERDDLASIMKKLLTKYDNLFETSFP
YSMGWHGAPTGSEAGANWNHWQLHAHYYPPLLRSATVRKFMVGYEMLAQAQRDLTPEQA
AERLRALPEVHYHLGQKDRETATIA
```

See Galactose-1-phosphate uridylyltransferase, Uniprot Acc. No. P07902. This is the 'canonical' sequence. All positional information in related variants and isoforms refer to it.

FIG. 1B

| Feature | Position | Length | Description |
|---|---|---|---|
| Metal binding | 75 – 75 | 1 | Zinc binding site 1 |
| Metal binding | 184 – 184 | 1 | Zinc binding site 2 |
| Active site | 186 – 186 | 1 | Tele-UMP-histidine intermediate |
| Metal binding | 202 – 202 | 1 | Iron binding site 1 |
| Metal binding | 301 – 301 | 1 | Iron binding site 2 |
| Metal binding | 319 – 319 | 1 | Iron binding site 3 |
| Metal binding | 321 – 321 | 1 | Iron binding site 4 |

*All positional information refers to the 'canonical' sequence*

FIG. 1C

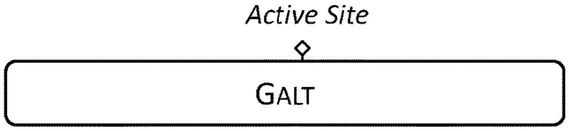

FIG. 1D

SEQ ID NO: 2

ATGTCGCGCAGTGGAACCGATCCTCAGCAACGCCAGCAGGCGTCAGAGGCGGACGCCGCAGCAGCAA
CCTTCCGGGCAAACGACCATCAGCATATCCGCTACAACCCGCTGCAGGATGAGTGGGTGCTGGTGTC
AGCTCACCGCATGAAGCGGCCCTGGCAGGGTCAAGTGGAGCCCCAGCTTCTGAAGACAGTGCCCCGC
CATGACCCTCTCAACCCTCTGTGTCCTGGGGCCATCCGAGCCAACGGAGAGGTGAATCCCCAGTACG
ATAGCACCTTCCTGTTTGACAACGACTTCCCAGCTCTGCAGCCTGATGCCCCCAGTCCAGGACCCAG
TGATCATCCCCTTTTCCAAGCAAAGTCTGCTCGAGGAGTCTGTAAGGTCATGTGCTTCCACCCCTGG
TCGGATGTAACGCTGCCACTCATGTCGGTCCCTGAGATCCGGGCTGTTGTTGATGCATGGGCCTCAG
TCACAGAGGAGCTGGGTGCCCAGTACCCTTGGGTGCAGATCTTTGAAAACAAAGGTGCCATGATGGG
CTGTTCTAACCCCCACCCCCACTGCCAGGTATGGGCCAGCAGTTTCCTGCCAGATATTGCCCAGCGT
GAGGAGCGATCTCAGCAGGCCTATAAGAGTCAGCATGGAGAGCCCCTGCTAATGGAGTACAGCCGCC
AGGAGCTACTCAGGAAGGAACGTCTGGTCCTAACCAGTGAGCACTGGTTAGTACTGGTCCCCTTCTG
GGCAACATGGCCCTACCAGACACTGCTGCTGCCCCGTCGGCATGTGCGGCGGCTACCTGAGCTGACC
CCTGCTGAGCGTGATGATCTAGCCTCCATCATGAAGAAGCTCTTGACCAAGTATGACAACCTCTTTG
AGACGTCCTTTCCCTACTCCATGGGCTGGCATGGGGCTCCCACAGGATCAGAGGCTGGGGCCAACTG
GAACCATTGGCAGCTGCACGCTCATTACTACCCTCCGCTCCTGCGCTCTGCCACTGTCCGGAAATTC
ATGGTTGGCTACGAAATGCTTGCTCAGGCTCAGAGGGACCTCACCCCTGAGCAGGCTGCAGAGAGAC
TAAGGGCACTTCCTGAGGTTCATTACCACCTGGGGCAGAAGGACAGGGAGACAGCAACCATCGCC

FIG. 2A SEQ ID NO: 3 (GALT; Galactose-1-phosphate uridylyltransferase, wt, isoform 2)

```
MTLSTLCVLGPSEPTESKVMCFHPWSDVTLPLMSVPEIRAVVDAWASVTEELGAQYPWV
QIFENKGAMMGCSNPHPHCQVWASSFLPDIAQREERSQQAYKSQHGEPLLMEYSRQELL
RKERLVLTSEHWLVLVPFWATWPYQTLLLPRRHVRRLPELTPAERDDLASIMKKLLTKY
DNLFETSFPYSMGWHGAPTGSEAGANWNHWQLHAHYYPPLLRSATVRKFMVGYEMLAQA
QRDLTPEQAAERLRALPEVHYHLGQKDRETATIA
```

See Galactose-1-phosphate uridylyltransferase Uniprot Acc. No. P07902-2.
Known as isoform 2. The sequence of this isoform differs from the canonical sequence as follows:
1-17: MSRSGTDPQQRQQASEA → MTLSTLCVLGPSEPTES
18-126: Missing

FIG. 2B

| Feature | Position | Length | Description |
|---|---|---|---|
| Metal binding | 75 – 75 | 1 | Zinc binding site 1 |
| Metal binding | 184 – 184 | 1 | Zinc binding site 2 |
| Active site | 186 – 186 | 1 | Tele-UMP-histidine intermediate |
| Metal binding | 202 – 202 | 1 | Iron binding site 1 |
| Metal binding | 301 – 301 | 1 | Iron binding site 2 |
| Metal binding | 319 – 319 | 1 | Iron binding site 3 |
| Metal binding | 321 – 321 | 1 | Iron binding site 4 |

*All positional information refers to the 'canonical' sequence*

FIG. 2C

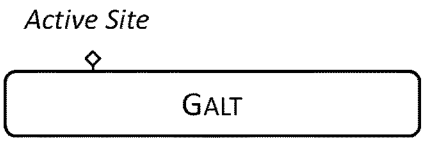

FIG. 2D

SEQ ID NO: 4

ATGACCCTCTCAACCCTCTGTGTCCTGGGGCCATCCGAGCCAACGGAGAGTAAGGTCATGTGCTTCC
ACCCCTGGTCGGATGTAACGCTGCCACTCATGTCGGTCCCTGAGATCCGGGCTGTTGTTGATGCATG
GGCCTCAGTCACAGAGGAGCTGGGTGCCCAGTACCCTTGGGTGCAGATCTTTGAAAACAAAGGTGCC
ATGATGGGCTGTTCTAACCCCCACCCCCACTGCCAGGTATGGGCCAGCAGTTTCCTGCCAGATATTG
CCCAGCGTGAGGAGCGATCTCAGCAGGCCTATAAGAGTCAGCATGGAGAGCCCCTGCTAATGGAGTA
CAGCCGCCAGGAGCTACTCAGGAAGGAACGTCTGGTCCTAACCAGTGAGCACTGGTTAGTACTGGTC
CCCTTCTGGGCAACATGGCCCTACCAGACACTGCTGCTGCCCCGTCGGCATGTGCGGCGGCTACCTG
AGCTGACCCCTGCTGAGCGTGATGATCTAGCCTCCATCATGAAGAAGCTCTTGACCAAGTATGACAA
CCTCTTTGAGACGTCCTTTCCCTACTCCATGGGCTGGCATGGGGCTCCCACAGGATCAGAGGCTGGG
GCCAACTGGAACCATTGGCAGCTGCACGCTCATTACTACCCTCCGCTCCTGCGCTCTGCCACTGTCC
GGAAATTCATGGTTGGCTACGAAATGCTTGCTCAGGCTCAGAGGGACCTCACCCCTGAGCAGGCTGC
AGAGAGACTAAGGGCACTTCCTGAGGTTCATTACCACCTGGGGCAGAAGGACAGGGAGACAGCAACC
ATCGCC

| Protein | Length | Theoretical Minimum U (%) | Theoretical Minimum U (abs) | | | | | | | |
|---|---|---|---|---|---|---|---|---|---|---|
| GALT Protein | 379 | 10.99% | 125 | | | | | | | |
| **Nucleic Acid** | **Length** | **U Content(abs)** | **U Content(%)** | **U Content v WT (%)** | **U Content v Theoretical Minimum (%)** | **UU pairs** | **UU pairs v WT (%)** | **UUU** | **UUUU** | **UUUUU** |
| GALT-WT | 1137 | 226 | 19.88% | 100.00% | 180.80% | 20 | 100.00% | 5 | 1 | 0 |
| GALT-CO01 | 1137 | 167 | 14.69% | 73.89% | 133.60% | 14 | 70.00% | 3 | 0 | 0 |
| GALT-CO02 | 1137 | 163 | 14.34% | 72.12% | 130.40% | 13 | 65.00% | 2 | 1 | 0 |
| GALT-CO03 | 1137 | 160 | 14.07% | 70.80% | 128.00% | 12 | 60.00% | 3 | 0 | 0 |
| GALT-CO04 | 1137 | 154 | 13.54% | 68.14% | 123.20% | 13 | 65.00% | 4 | 0 | 0 |
| GALT-CO05 | 1137 | 156 | 13.72% | 69.03% | 124.80% | 9 | 45.00% | 5 | 1 | 0 |
| GALT-CO06 | 1137 | 161 | 14.16% | 71.24% | 128.80% | 11 | 55.00% | 4 | 1 | 0 |
| GALT-CO07 | 1137 | 162 | 14.25% | 71.68% | 129.60% | 14 | 70.00% | 2 | 0 | 1 |
| GALT-CO08 | 1137 | 157 | 13.81% | 69.47% | 125.60% | 15 | 75.00% | 2 | 0 | 0 |
| GALT-CO09 | 1137 | 162 | 14.25% | 71.68% | 129.60% | 12 | 60.00% | 6 | 0 | 0 |
| GALT-CO10 | 1137 | 166 | 14.60% | 73.45% | 132.80% | 13 | 65.00% | 4 | 1 | 0 |
| GALT-CO11 | 1137 | 156 | 13.72% | 69.03% | 124.80% | 9 | 45.00% | 3 | 1 | 0 |
| GALT-CO12 | 1137 | 158 | 13.90% | 69.91% | 126.40% | 14 | 70.00% | 0 | 0 | 0 |
| GALT-CO13 | 1137 | 158 | 13.90% | 69.91% | 126.40% | 18 | 90.00% | 1 | 0 | 0 |
| GALT-CO14 | 1137 | 165 | 14.51% | 73.01% | 132.00% | 18 | 90.00% | 2 | 0 | 0 |
| GALT-CO15 | 1137 | 157 | 13.81% | 69.47% | 125.60% | 14 | 70.00% | 3 | 0 | 0 |
| GALT-CO16 | 1137 | 155 | 13.63% | 68.58% | 124.00% | 10 | 50.00% | 2 | 1 | 0 |
| GALT-CO17 | 1137 | 155 | 13.63% | 68.58% | 124.00% | 14 | 70.00% | 0 | 1 | 0 |
| GALT-CO18 | 1137 | 155 | 13.63% | 68.58% | 124.00% | 12 | 60.00% | 4 | 0 | 0 |
| GALT-CO19 | 1137 | 162 | 14.25% | 71.68% | 129.60% | 13 | 65.00% | 3 | 0 | 0 |
| GALT-CO20 | 1137 | 161 | 14.16% | 71.24% | 128.80% | 14 | 70.00% | 4 | 0 | 0 |
| GALT-CO21 | 1137 | 166 | 14.60% | 73.45% | 132.80% | 19 | 95.00% | 1 | 0 | 0 |
| GALT-CO22 | 1137 | 160 | 14.07% | 70.80% | 128.00% | 12 | 60.00% | 3 | 1 | 0 |
| GALT-CO23 | 1137 | 157 | 13.81% | 69.47% | 125.60% | 12 | 60.00% | 2 | 0 | 0 |
| GALT-CO24 | 1137 | 158 | 13.90% | 69.91% | 126.40% | 16 | 80.00% | 0 | 0 | 0 |
| GALT-CO25 | 1137 | 161 | 14.16% | 71.24% | 128.80% | 15 | 75.00% | 3 | 0 | 1 |
| | MAX | 167 | 14.69% | 73.89% | 133.60% | 19 | 95.00% | 6 | 1 | 1 |
| | MIN | 154 | 13.54% | 68.14% | 123.20% | 9 | 45.00% | 0 | 0 | 0 |
| | AVERAGE | 159.68 | 14.04% | 70.65% | 127.74% | 13.44 | 67.20% | 2.64 | 0.32 | 0.08 |
| | MEDIAN | 160 | 14.07% | 70.80% | 128.00% | 13 | 65.00% | 3 | 0 | 0 |
| | STD DEV | 3.82 | 0.34% | 1.69% | 3.05% | 2.53 | 12.67% | | | |

FIG. 3

| Protein | Length | Theoretical Maximum G (%) | Theoretical Maximum G (abs) | | |
|---|---|---|---|---|---|
| GALT Protein | 379 | 41.51% | 472 | | |
| **Nucleic Acid** | **Length** | **G Content(abs)** | **G Content(%)** | **G Content v WT (%)** | **G Content v Theoretical Maximum (%)** |
| GALT-WT | 1137 | 312 | 27.44% | 100.00% | 66.10% |
| GALT-CO01 | 1137 | 336 | 29.55% | 107.69% | 71.19% |
| GALT-CO02 | 1137 | 337 | 29.64% | 108.01% | 71.40% |
| GALT-CO03 | 1137 | 343 | 30.17% | 109.94% | 72.67% |
| GALT-CO04 | 1137 | 337 | 29.64% | 108.01% | 71.40% |
| GALT-CO05 | 1137 | 344 | 30.26% | 110.26% | 72.88% |
| GALT-CO06 | 1137 | 360 | 31.66% | 115.38% | 76.27% |
| GALT-CO07 | 1137 | 341 | 29.99% | 109.29% | 72.25% |
| GALT-CO08 | 1137 | 346 | 30.43% | 110.90% | 73.31% |
| GALT-CO09 | 1137 | 352 | 30.96% | 112.82% | 74.58% |
| GALT-CO10 | 1137 | 338 | 29.73% | 108.33% | 71.61% |
| GALT-CO11 | 1137 | 352 | 30.96% | 112.82% | 74.58% |
| GALT-CO12 | 1137 | 350 | 30.78% | 112.18% | 74.15% |
| GALT-CO13 | 1137 | 334 | 29.38% | 107.05% | 70.76% |
| GALT-CO14 | 1137 | 343 | 30.17% | 109.94% | 72.67% |
| GALT-CO15 | 1137 | 347 | 30.52% | 111.22% | 73.52% |
| GALT-CO16 | 1137 | 344 | 30.26% | 110.26% | 72.88% |
| GALT-CO17 | 1137 | 355 | 31.22% | 113.78% | 75.21% |
| GALT-CO18 | 1137 | 348 | 30.61% | 111.54% | 73.73% |
| GALT-CO19 | 1137 | 343 | 30.17% | 109.94% | 72.67% |
| GALT-CO20 | 1137 | 340 | 29.90% | 108.97% | 72.03% |
| GALT-CO21 | 1137 | 334 | 29.38% | 107.05% | 70.76% |
| GALT-CO22 | 1137 | 341 | 29.99% | 109.29% | 72.25% |
| GALT-CO23 | 1137 | 345 | 30.34% | 110.58% | 73.09% |
| GALT-CO24 | 1137 | 343 | 30.17% | 109.94% | 72.67% |
| GALT-CO25 | 1137 | 346 | 30.43% | 110.90% | 73.31% |
| | MAX | 360 | 31.66% | 115.38% | 76.27% |
| | MIN | 334 | 29.38% | 107.05% | 70.76% |
| | MEAN | 343.96 | 30.25% | 110.24% | 72.87% |
| | MEDIAN | 343 | 30.17% | 109.94% | 72.67% |
| | STD DEV | 6.49 | 0.57% | 2.08% | 1.38% |

FIG. 4

| Protein | Length | Theoretical Maximum C | Theoretical Maximum C (abs) | | |
|---|---|---|---|---|---|
| GALT Protein | 379 | 48.02% | 546 | | |
| **Nucleic Acid** | **Length** | **C Content(abs)** | **C Content(%)** | **C Content v WT (%)** | **C Content v Theoretical Maximum (%)** |
| GALT-WT | 1137 | 355 | 31.22% | 100.00% | 65.02% |
| GALT-CO01 | 1137 | 409 | 35.97% | 115.21% | 74.91% |
| GALT-CO02 | 1137 | 416 | 36.59% | 117.18% | 76.19% |
| GALT-CO03 | 1137 | 410 | 36.06% | 115.49% | 75.09% |
| GALT-CO04 | 1137 | 411 | 36.15% | 115.77% | 75.27% |
| GALT-CO05 | 1137 | 409 | 35.97% | 115.21% | 74.91% |
| GALT-CO06 | 1137 | 385 | 33.86% | 108.45% | 70.51% |
| GALT-CO07 | 1137 | 399 | 35.09% | 112.39% | 73.08% |
| GALT-CO08 | 1137 | 406 | 35.71% | 114.37% | 74.36% |
| GALT-CO09 | 1137 | 404 | 35.53% | 113.80% | 73.99% |
| GALT-CO10 | 1137 | 403 | 35.44% | 113.52% | 73.81% |
| GALT-CO11 | 1137 | 403 | 35.44% | 113.52% | 73.81% |
| GALT-CO12 | 1137 | 400 | 35.18% | 112.68% | 73.26% |
| GALT-CO13 | 1137 | 423 | 37.20% | 119.15% | 77.47% |
| GALT-CO14 | 1137 | 397 | 34.92% | 111.83% | 72.71% |
| GALT-CO15 | 1137 | 403 | 35.44% | 113.52% | 73.81% |
| GALT-CO16 | 1137 | 407 | 35.80% | 114.65% | 74.54% |
| GALT-CO17 | 1137 | 402 | 35.36% | 113.24% | 73.63% |
| GALT-CO18 | 1137 | 398 | 35.00% | 112.11% | 72.89% |
| GALT-CO19 | 1137 | 406 | 35.71% | 114.37% | 74.36% |
| GALT-CO20 | 1137 | 412 | 36.24% | 116.06% | 75.46% |
| GALT-CO21 | 1137 | 411 | 36.15% | 115.77% | 75.27% |
| GALT-CO22 | 1137 | 405 | 35.62% | 114.08% | 74.18% |
| GALT-CO23 | 1137 | 403 | 35.44% | 113.52% | 73.81% |
| GALT-CO24 | 1137 | 416 | 36.59% | 117.18% | 76.19% |
| GALT-CO25 | 1137 | 401 | 35.27% | 112.96% | 73.44% |
| | MAX | 423 | 37.20% | 119.15% | 77.47% |
| | MIN | 385 | 33.86% | 108.45% | 70.51% |
| | AVERAGE | 405.56 | 35.67% | 114.24% | 74.28% |
| | MEDIAN | 405 | 35.62% | 114.08% | 74.18% |
| | STD DEV | 7.52 | 0.66% | 2.12% | 1.38% |

FIG. 5

| Protein | Length | Theoretical Maximum GC | Theoretical Maximum GC (abs) | | |
|---|---|---|---|---|---|
| GALT Protein | 379 | 70.89% | 806 | | |
| **Nucleic Acid** | **Length** | **GC Content(abs)** | **GC Content(%)** | **GC Content v WT (%)** | **GC Content v Theoretical Maximum (%)** |
| GALT-WT | 1137 | 667 | 58.66% | 100.00% | 82.75% |
| GALT-CO01 | 1137 | 745 | 65.52% | 111.69% | 92.43% |
| GALT-CO02 | 1137 | 753 | 66.23% | 112.89% | 93.42% |
| GALT-CO03 | 1137 | 753 | 66.23% | 112.89% | 93.42% |
| GALT-CO04 | 1137 | 748 | 65.79% | 112.14% | 92.80% |
| GALT-CO05 | 1137 | 753 | 66.23% | 112.89% | 93.42% |
| GALT-CO06 | 1137 | 745 | 65.52% | 111.69% | 92.43% |
| GALT-CO07 | 1137 | 740 | 65.08% | 110.94% | 91.81% |
| GALT-CO08 | 1137 | 752 | 66.14% | 112.74% | 93.30% |
| GALT-CO09 | 1137 | 756 | 66.49% | 113.34% | 93.80% |
| GALT-CO10 | 1137 | 741 | 65.17% | 111.09% | 91.94% |
| GALT-CO11 | 1137 | 755 | 66.40% | 113.19% | 93.67% |
| GALT-CO12 | 1137 | 750 | 65.96% | 112.44% | 93.05% |
| GALT-CO13 | 1137 | 757 | 66.58% | 113.49% | 93.92% |
| GALT-CO14 | 1137 | 740 | 65.08% | 110.94% | 91.81% |
| GALT-CO15 | 1137 | 750 | 65.96% | 112.44% | 93.05% |
| GALT-CO16 | 1137 | 751 | 66.05% | 112.59% | 93.18% |
| GALT-CO17 | 1137 | 757 | 66.58% | 113.49% | 93.92% |
| GALT-CO18 | 1137 | 746 | 65.61% | 111.84% | 92.56% |
| GALT-CO19 | 1137 | 749 | 65.88% | 112.29% | 92.93% |
| GALT-CO20 | 1137 | 752 | 66.14% | 112.74% | 93.30% |
| GALT-CO21 | 1137 | 745 | 65.52% | 111.69% | 92.43% |
| GALT-CO22 | 1137 | 746 | 65.61% | 111.84% | 92.56% |
| GALT-CO23 | 1137 | 748 | 65.79% | 112.14% | 92.80% |
| GALT-CO24 | 1137 | 759 | 66.75% | 113.79% | 94.17% |
| GALT-CO25 | 1137 | 747 | 65.70% | 111.99% | 92.68% |
| | MAX | 759 | 66.75% | 113.79% | 94.17% |
| | MIN | 740 | 65.08% | 110.94% | 91.81% |
| | AVERAGE | 749.52 | 65.92% | 112.37% | 92.99% |
| | MEDIAN | 750 | 65.96% | 112.44% | 93.05% |
| | STD DEV | 5.31 | 0.47% | 0.80% | 0.66% |

FIG. 6

| Sequence | GC | GC 1st | GC 2nd | GC 3rd |
|---|---|---|---|---|
| GALT-WT | 58.66 | 65.96 | 44.85 | 65.17 |
| GALT-CO14 | 65.08 | 64.12 | 44.85 | 86.28 |
| GALT-CO07 | 65.08 | 63.06 | 44.85 | 87.34 |
| GALT-CO10 | 65.17 | 65.44 | 44.85 | 85.22 |
| GALT-CO06 | 65.52 | 63.06 | 44.85 | 88.65 |
| GALT-CO01 | 65.52 | 63.32 | 44.85 | 88.39 |
| GALT-CO21 | 65.52 | 63.85 | 44.85 | 87.86 |
| GALT-CO22 | 65.61 | 63.85 | 44.85 | 88.13 |
| GALT-CO18 | 65.61 | 62.27 | 44.85 | 89.71 |
| GALT-CO25 | 65.7 | 63.32 | 44.85 | 88.92 |
| GALT-CO04 | 65.79 | 64.12 | 44.85 | 88.39 |
| GALT-CO23 | 65.79 | 63.32 | 44.85 | 89.18 |
| GALT-CO19 | 65.88 | 64.91 | 44.85 | 87.86 |
| GALT-CO15 | 65.96 | 64.12 | 44.85 | 88.92 |
| GALT-CO12 | 65.96 | 64.12 | 44.85 | 88.92 |
| GALT-CO16 | 66.05 | 63.85 | 44.85 | 89.45 |
| GALT-CO20 | 66.14 | 65.44 | 44.85 | 88.13 |
| GALT-CO08 | 66.14 | 65.7 | 44.85 | 87.86 |
| GALT-CO05 | 66.23 | 63.59 | 44.85 | 90.24 |
| GALT-CO02 | 66.23 | 65.17 | 44.85 | 88.65 |
| GALT-CO03 | 66.23 | 64.12 | 44.85 | 89.71 |
| GALT-CO11 | 66.4 | 64.12 | 44.85 | 90.24 |
| GALT-CO09 | 66.49 | 64.64 | 44.85 | 89.97 |
| GALT-CO17 | 66.58 | 64.12 | 44.85 | 90.77 |
| GALT-CO13 | 66.58 | 64.38 | 44.85 | 90.5 |
| GALT-CO24 | 66.75 | 65.44 | 44.85 | 89.97 |
| Overall | 65.64 | 64.21 | 44.85 | 87.86 |

FIG. 7

Body Weight

POLYNUCLEOTIDES ENCODING GALACTOSE-1-PHOSPHATE URIDYLYLTRANSFERASE FOR THE TREATMENT OF GALACTOSEMIA TYPE 1

CROSS-REFERENCE TO RELATED APPLICATIONS

This application is the National Stage of International Application No. PCT/US2017/033420, filed on May 18, 2017, which claims the priority benefit of U.S. Provisional Application No. 62/338,437, filed on May 18, 2016. The disclosures of the prior applications are incorporated herein by reference in their entirety.

REFERENCE TO A SEQUENCE LISTING SUBMITTED ELECTRONICALLY VIA EFS-WEB

The content of the electronically submitted sequence listing (Name: 45817-0012US1_SL.txt, Size: 187,360 bytes; and Date of Creation: May 14, 2019) is herein incorporated by reference in its entirety.

BACKGROUND

Galactosemia type 1 ("Gal-1") is a rare, autosomal recessive metabolic disorder characterized by the inability to metabolize galactose. Bosch A M. *J Inherit Metab Dis.* 29: 516-525 (2006). Other aliases for Gal-1 are: galactose-1-phosphate uridylyltransferase deficiency, GALT deficiency, and classic galactosemia. Gal-1 usually presents in neonates after lactose ingestion and causes feeding difficulties, jaundice, hepatosplenomegaly, hepatocellular insufficiency, hypoglycemia, renal tubular dysfunction, muscle hypotonia, sepsis, cataracts, and possibly death in the short-term. Long-term symptoms include mental retardation, verbal dyspraxia, motor abnormalities, and hypergonadotropic hypogonadism. Bosch A M. J Inherit Metab Dis. 29: 516-525 (2006). It has an estimated incidence of 1 in 60,000 with a higher incidence in Europe and the United States. Current treatment for Gal-1 is primarily via dietary control to limit consumption of galactose and lactose, which is metabolized to galactose and glucose, to prevent accumulation of galactose. Karadag N. et al., *Clin Lab.* 59:1139-1146 (2013).

The principal gene associated with Gal-1 is Galactose-1-Phosphate Uridylyltransferase ("GALT"), which has two variants (NM_000155; NM_001258332; NP_000146; NP_001245261 also referred to as UDP-Glucose-Hexose-1-Phosphate Uridylyltransferase and Gal-1-P Uridylyltransferase). GALT is a metabolic enzyme (E.C. 2.7.7.12) that plays a critical role in the Leloir pathway of galactose metabolism. Specifically, GALT's biological function is to convert UDP-glucose and galactose-1-phosphate to glucose-1-phosphate and UDP-galactose. Timson D J, *Gene* (2015) doi: 10.1016/j.gene.2015.06.077. GALT is expressed in a variety of tissues, primarily the liver, localizes to the Golgi apparatus and cytoplasm of cells, and exists as a homodimer in its native form. The first isoform of human GALT is 379 amino acids, while its second isoform is 270 amino acids. Both isoforms have four iron binding sites and at least one zinc binding site.

A complete or partial loss of GALT function leads to abnormal buildup of galactose. For example, loss of GALT has been reported to lead to galactose levels greater than 100 mg/dL in an individual as compared to less than 10 mg/dL in normal individuals. Treatment for Gal-1 generally focuses on managing symptoms and preventing complications, e.g., through diet restrictions. There are no commercial therapeutics to treat Gal-1, thus, there is a need for improved therapy to treat Gal-1.

BRIEF SUMMARY

The present invention provides mRNA therapeutics for the treatment of galactosemia type 1 (Gal-1). The mRNA therapeutics of the invention are particularly well-suited for the treatment of Gal-1 as the technology provides for the intracellular delivery of mRNA encoding GALT followed by de novo synthesis of functional GALT protein within target cells. The instant invention features the incorporation of modified nucleotides within therapeutic mRNAs to (1) minimize unwanted immune activation (e.g., the innate immune response associated with the in vivo introduction of foreign nucleic acids) and (2) optimize the translation efficiency of mRNA to protein. Exemplary aspects of the invention feature a combination of nucleotide modification to reduce the innate immune response and sequence optimization, in particular, within the open reading frame (ORF) of therapeutic mRNAs encoding GALT to enhance protein expression.

In further embodiments, the mRNA therapeutic technology of the instant invention also features delivery of mRNA encoding GALT via a lipid nanoparticle (LNP) delivery system. The instant invention features novel ionizable lipid-based LNPs, which have improved properties when combined with mRNA encoding GALT and administered in vivo, for example, cellular uptake, intracellular transport and/or endosomal release or endosomal escape. The LNP formulations of the invention also demonstrate reduced immunogenicity associated with the in vivo administration of LNPs.

In certain aspects, the invention relates to compositions and delivery formulations comprising a polynucleotide, e.g., a ribonucleic acid (RNA), e.g., a messenger RNA (mRNA), encoding galactose-1-phosphate uridylyltransferase and methods for treating galactosemia type 1 (Gal-1) in a subject in need thereof by administering the same.

The present disclosure provides a pharmaceutical composition comprising a lipid nanoparticle encapsulated mRNA that comprises an open reading frame (ORF) encoding a galactose-1-phosphate uridylyltransferase (GALT) polypeptide, wherein the composition is suitable for administration to a human subject in need of treatment for galactosemia type 1 (Gal-1).

The present disclosure further provides a pharmaceutical composition comprising: (a) a mRNA that comprises (i) an open reading frame (ORF) encoding a galactose-1-phosphate uridylyltransferase (GALT) polypeptide, wherein the ORF comprises at least one chemically modified nucleobase, sugar, backbone, or any combination thereof and (ii) an untranslated region (UTR) comprising a microRNA (miRNA) binding site; and (b) a delivery agent, wherein the pharmaceutical composition is suitable for administration to a human subject in need of treatment for galactosemia type 1 (Gal-1).

The present disclosure further provides a pharmaceutical composition comprising an mRNA comprising an open reading frame (ORF) encoding a human galactose-1-phosphate uridylyltransferase (GALT) polypeptide, wherein the composition when administered to a subject in need thereof as a single intravenous dose is sufficient to reduce urinary, serum, and/or plasma levels of: (i) galactitol at least 2-fold, at least 5-fold, at least 10-fold, at least 20-fold or at least 50-fold as compared to the subject's baseline galactitol level or a reference galactitol level, for at least 24 hours, at least 48 hours, at least 72 hours, at least 96 hours, or at least 120 hours post-administration, (ii) galactonate at least 2-fold, at least 5-fold, at least 10-fold, at least 20-fold or at least 50-fold as compared to the subject's baseline galactonate level or a reference galactonate level, for at least 24 hours, at least 48 hours, at least 72 hours, at least 96 hours, or at least 120 hours post-administration, (iii) galactose at least 2-fold, at least 5-fold, at least 10-fold, at least 20-fold or at least 50-fold as compared to the subject's baseline galactose level or a reference galactose level, for at least 24 hours, at least 48 hours, at least 72 hours, at least 96 hours, or at least 120 hours post-administration, and/or (iv) 8-hydroxy-2-desoxyguanosine at least 2-fold, at least 5-fold, at least 10-fold, at least 20-fold or at least 50-fold as compared to the subject's baseline 8-hydroxy-2-desoxyguanosine level or a reference 8-hydroxy-2-desoxyguanosine level, for at least 24 hours, at least 48 hours, at least 72 hours, at least 96 hours, or at least 120 hours post-administration.

The present disclosure further provides a pharmaceutical composition comprising an mRNA comprising an open reading frame (ORF) encoding a human galactose-1-phosphate uridylyltransferase (GALT) polypeptide, wherein the composition when administered to a subject in need thereof as a single intravenous dose is sufficient to reduce urinary, serum, and/or plasma levels of: (i) galactitol by at least 20%, at least 30%, at least 40%, at least 50%, at least 60%, at least 70%, at least 80%, at least 90%, at least 95% or at least 98%, at least 99%, or 100% as compared to the subject's baseline galactitol level or a reference galactitol level, for at least 24 hours, at least 48 hours, at least 72 hours, at least 96 hours, or at least 120 hours post-administration, (ii) galactonate by at least 20%, at least 30%, at least 40%, at least 50%, at least 60%, at least 70%, at least 80%, at least 90%, at least 95% or at least 98%, at least 99%, or 100% as compared to the subject's baseline galactonate level or a reference galactonate level, for at least 24 hours, at least 48 hours, at least 72 hours, at least 96 hours, or at least 120 hours post-administration, (iii) galactose at least at least 20%, at least 30%, at least 40%, at least 50%, at least 60%, at least 70%, at least 80%, at least 90%, at least 95% or at least 98%, at least 99%, or 100% as compared to the subject's baseline galactose level or a reference galactose level, for at least 24 hours, at least 48 hours, at least 72 hours, at least 96 hours, or at least 120 hours post-administration, and/or (iii) 8-hydroxy-2-desoxyguanosine by at least 20%, at least 30%, at least 40%, at least 50%, at least 60%, at least 70%, at least 80%, at least 90%, at least 95% or at least 98%, at least 99%, or 100% as compared to the subject's baseline 8-hydroxy-2-desoxyguanosine level or a reference 8-hydroxy-2-desoxyguanosine level, for at least 24 hours, at least 48 hours, at least 72 hours, at least 96 hours, or at least 120 hours post-administration.

The present disclosure further provides a pharmaceutical composition comprising an mRNA comprising an open reading frame (ORF) encoding a human galactose-1-phosphate uridylyltransferase (GALT) polypeptide, wherein the composition when administered to a subject in need thereof as a single intravenous dose is sufficient to reduce levels of red blood cells (RBC) and/or liver galactose-1-phosphate (Gal-1-P) to at least within 50%, 60%, 70%, 80%, 90%, 95%, 98%, 99%, or 100% of normal physiological Gal-1-P level or a reference Gal-1-P level within at least 24 hours, at least 48 hours, at least 72 hours, at least 96 hours, or at least 120 hours post-administration.

The present disclosure further provides a pharmaceutical composition comprising an mRNA comprising an open reading frame (ORF) encoding a human galactose-1-phosphate uridylyltransferase (GALT) polypeptide, wherein the composition when administered to a subject in need thereof as a single intravenous dose is sufficient to: (i) maintain RBC and/or hepatic GALT activity levels at or above a reference physiological level for at least 24 hours, at least 48 hours, or at least 72 hours, at least 96 hours, or at least 120 hours post-administration, and/or (ii) maintain RBC and/or hepatic GALT activity levels at 50% or more of a reference RBC or hepatic GALT activity level for at least 24 hours, at least 48 hours, at least 72 hours, or at least 96 hours post-administration. In some embodiments, the pharmaceutical compositions disclosed herein further comprise a delivery agent.

The present disclosure provides a polynucleotide comprising an open reading frame (ORF) encoding a galactose-1-phosphate uridylyltransferase (GALT) polypeptide, wherein the uracil or thymine content of the ORF relative to the theoretical minimum uracil or thymine content of a nucleotide sequence encoding the GALT polypeptide (% $U_{TM}$ or % $T_{TM}$) is between 100% and about 150%. In some embodiments, the % $U_{TM}$ or % $T_{TM}$ is between about 105% and about 145%, about 105% and about 140%, about 110% and about 140%, about 110% and about 145%, about 115% and about 135%, about 105% and about 135%, about 110% and about 135%, about 115% and about 145%, or about 115% and about 140%. In some embodiments, the % $U_{TM}$ or % $T_{TM}$ is between (i) 110%, 111%, 112%, 113%, 114%, 115%, 116%, 117%, 118%, 119%, 120%, 121%, 122%, or 123% and (ii) 134%, 135%, 136%, 137%, 138%, 139%, or 140%.

In some embodiments, the uracil or thymine content in the ORF relative to the uracil or thymine content of the corresponding wild-type ORF (% $U_{WT}$ or % $T_{WT}$) is less than 100%. In some embodiments, the % $U_{WT}$ or % $T_{WT}$ is less than about 95%, less than about 90%, less than about 85%, less than 80%, less than 79%, less than 78%, less than 77%, less than 76%, less than 75%, or less than 74%. In some embodiments, the % $U_{WT}$ or % $T_{WT}$ is between 68% and 74%. In some embodiments, the uracil or thymine content in the ORF is less than about 50%, less than about 40%, less than about 30%, or less than about 20% of the total nucleotide content in the ORF. In some embodiments, the uracil or thymine content in the ORF relative to the total nucleotide content in the ORF (% $U_{TL}$ or % $T_{TL}$) is less than about 20%. In some embodiments, the % $U_{TL}$ or % $T_{TL}$ is between about 13% and about 15%.

In some embodiments, the guanine content of the ORF with respect to the theoretical maximum guanine content of a nucleotide sequence encoding the GALT polypeptide (% $G_{TMX}$) is less than 100%, less than about 90%, less than about 85%, or less than about 80%. In some embodiments, the % $G_{TMX}$ is between about 69% and about 80%, between about 70% and about 79%, between about 70% and about 78%, or between about 70% and about 77%. In some embodiments, the cytosine content of the ORF relative to the theoretical maximum cytosine content of a nucleotide sequence encoding the GALT polypeptide (% $C_{TMX}$) is less than 95%. In some embodiments, the % $C_{TMX}$ is between about 60% and about 80%, between about 65% and about 80%, between about 68% and about 79%, or between about 70% and about 78%.

In some embodiments, the guanine and cytosine content (G/C) of the ORF relative to the theoretical maximum G/C content in a nucleotide sequence encoding the GALT polypeptide (% $G/C_{TMX}$) is at least about 69%, at least about 70%, at least about 75%, at least about 80%, at least about 85%, at least about 90%, at least about 95%, or about 100%. In some embodiments, the % G/C$_{TMX}$ is between about 80% and about 100%, between about 85% and about 99%, between about 90% and about 97%, or between about 91% and about 95%. In some embodiments, the % G/C$_{TMX}$ is at least 2%, at least 3%, at least 4%, at least 5%, at least 6%, at least 7%, at least about 10%, or at least about 11% higher. In some embodiments, the average G/C content in the 3rd codon position in the ORF is at least 20%, at least 21%, at least 22%, at least 23%, at least 24%, at least 25%, at least 26%, at least 27%, at least 28%, at least 29%, or at least 30% higher than the average G/C content in the 3$^{rd}$ codon position in the corresponding wild-type ORF.

In some embodiments, the ORF further comprises at least one low-frequency codon.

In some embodiments of the polynucleotides disclosed herein, (i) the ORF has at least 88%, at least 89%, at least 90%, at least 91%, at least 92%, at least 93%, at least 94%, at least 95%, at least 96%, at least 97%, at least 98%, at least 99%, or 100% sequence identity to a sequence selected from the group consisting of SEQ ID NOs: 5 to 29 and 113 to 131; or (ii) the ORF has at least 89%, at least 90%, at least 91%, at least 92%, at least 93%, at least 94%, at least 95%, at least 96%, at least 97%, at least 98%, at least 99%, or 100% sequence identity to a nucleic acid sequence selected from the group consisting of SEQ ID NOs: 5 to 29 and 113 to 131; or (iii) the ORF has at least 85%, at least 90%, at least 91%, at least 92%, at least 93%, at least 94%, at least 95%, at least 96%, at least 97%, at least 98%, at least 99%, or 100% sequence identity to the nucleic acid sequence of SEQ ID NO: 124 or 126; or (iv) wherein the ORF has at least 95%, at least 96%, at least 97%, at least 98%, at least 99%, or 100% sequence identity to the nucleic acid sequence of SEQ ID NO: 124 or 126. In some embodiments, the ORF comprises the nucleic acid sequence of SEQ ID NO: 124 or 126.

In some embodiments, the GALT polypeptide comprises an amino acid sequence at least about 95%, at least about 96%, at least about 97%, at least about 98%, at least about 99%, or about 100% identical to (i) the polypeptide sequence of wild type GALT, isoform 1 (SEQ ID NO: 1) or (ii) the polypeptide sequence of wild type GALT, isoform 2 (SEQ ID NO: 3), and wherein the GALT polypeptide has galactose-1-phosphate uridylytransferase activity. In some embodiments, the GALT polypeptide is a variant, derivative, or mutant having a galactose-1-phosphate uridylyltransferase activity. In some embodiments, the GALT polypeptide is a GALT fusion protein. In some embodiments, the GALT fusion protein comprises heterologous protein moiety.

In some embodiments, the polynucleotide sequence further comprises a nucleotide sequence encoding a transit peptide.

In some embodiments, the polynucleotide is single stranded. In some embodiments, the polynucleotide is double stranded. In some embodiments, the polynucleotide is DNA. In some embodiments, the polynucleotide is RNA. In some embodiments, the polynucleotide is mRNA. In some embodiments, the polynucleotide comprises at least one chemically modified nucleobase, sugar, backbone, or any combination thereof. In some embodiments, the at least one chemically modified nucleobase is selected from the group consisting of pseudouracil (ψ), N1-methylpseudouracil (m1ψ), 2-thiouracil (s2U), 4'-thiouracil, 5-methylcytosine, 5-methyluracil, and any combinations thereof. In some embodiments, the at least one chemically modified nucleobase is selected from the group consisting of pseudouracil (ψ), N1-methylpseudouracil (m1ψ), 1-ethylpseudouracil, 2-thiouracil (s2U), 4'-thiouracil, 5-methylcytosine, 5-methyluracil, 5-methoxyuracil, and any combination thereof. In some embodiments, the at least one chemically modified nucleobase is 5-methoxyuracil. In some embodiments, at least about 25%, at least about 30%, at least about 40%, at least about 50%, at least about 60%, at least about 70%, at least about 80%, at least about 90%, at least about 95%, at least about 99%, or 100% of the uracils are 5-methoxyuracils. In some embodiments, at least about 25%, at least about 30%, at least about 40%, at least about 50%, at least about 60%, at least about 70%, at least about 80%, at least about 90%, at least about 95%, at least about 99%, or 100% of the uracils or thymines are chemically modified. In some embodiments, at least about 25%, at least about 30%, at least about 40%, at least about 50%, at least about 60%, at least about 70%, at least about 80%, at least about 90%, at least about 95%, at least about 99%, or 100% of the guanines are chemically modified. In some embodiments, at least about 25%, at least about 30%, at least about 40%, at least about 50%, at least about 60%, at least about 70%, at least about 80%, at least about 90%, at least about 95%, at least about 99%, or 100% of the cytosines are chemically modified. In some embodiments, at least about 25%, at least about 30%, at least about 40%, at least about 50%, at least about 60%, at least about 70%, at least about 80%, at least about 90%, at least about 95%, at least about 99%, or 100% of the adenines are chemically modified.

In some embodiments, the polynucleotide further comprises a micro RNA binding site.

In some embodiments, the polynucleotide comprises at least two different microRNA (miR) binding sites.

In some embodiments, the microRNA is expressed in an immune cell of hematopoietic lineage or a cell that expresses TLR7 and/or TLR8 and secretes pro-inflammatory cytokines and/or chemokines, and wherein the polynucleotide (e.g., mRNA) comprises one or more modified nucleobases.

In some embodiments, the mRNA comprises at least one first microRNA binding site of a microRNA abundant in an immune cell of hematopoietic lineage and at least one second microRNA binding site is of a microRNA abundant in endothelial cells.

In some embodiments, the mRNA comprises multiple copies of a first microRNA binding site and at least one copy of a second microRNA binding site.

In some embodiments, the mRNA comprises first and second microRNA binding sites of the same microRNA.

In some embodiments, the microRNA binding sites are of the 3p and 5p arms of the same microRNA.

In some embodiments, the microRNA binding site comprises one or more nucleotide sequences selected from Table 3 or Table 4.

In some embodiments, the microRNA binding site binds to miR-126, miR-142, miR-144, miR-146, miR-150, miR-155, miR-16, miR-21, miR-223, miR-24, miR-27, miR-26a, or any combination thereof.

In some embodiments, the microRNA binding site binds to miR126-3p, miR-142-3p, miR-142-5p, miR-155, or any combination thereof.

In some embodiments, the microRNA binding site is a miR-126 binding site. In some embodiments, at least one microRNA binding site is a miR-142 binding site. In some embodiments, one microRNA binding site is a miR-126 binding site and the second microRNA binding site is for a microRNA selected from the group consisting of miR-142-3p, miR-142-5p, miR-146-3p, miR-146-5p, miR-155, miR-16, miR-21, miR-223, miR-24 and miR-27.

In some embodiments, the mRNA comprises at least one miR-126-3p binding site and at least one miR-142-3p binding site. In some embodiments, the mRNA comprises at least one miR-142-3p binding site and at least one 142-5p binding site.

In some embodiments, the microRNA binding sites are located in the 5' UTR, 3' UTR, or both the 5' UTR and 3' UTR of the mRNA. In some embodiments, the microRNA binding sites are located in the 3' UTR of the mRNA. In some embodiments, the microRNA binding sites are located in the 5' UTR of the mRNA. In some embodiments, the microRNA binding sites are located in both the 5' UTR and 3' UTR of the mRNA. In some embodiments, at least one microRNA binding site is located in the 3' UTR immediately adjacent to the stop codon of the coding region of the mRNA. In some embodiments, at least one microRNA binding site is located in the 3' UTR 70-80 bases downstream of the stop codon of the coding region of the mRNA. In some embodiments, at least one microRNA binding site is located in the 5' UTR immediately preceding the start codon of the coding region of the mRNA. In some embodiments, at least one microRNA binding site is located in the 5' UTR 15-20 nucleotides preceding the start codon of the coding region of the mRNA. In some embodiments, at least one microRNA binding site is located in the 5' UTR 70-80 nucleotides preceding the start codon of the coding region of the mRNA.

In some embodiments, the mRNA comprises multiple copies of the same microRNA binding site positioned immediately adjacent to each other or with a spacer of less than 5, 5-10, 10-15, or 15-20 nucleotides.

In some embodiments, the mRNA comprises multiple copies of the same microRNA binding site located in the 3' UTR, wherein the first microRNA binding site is positioned immediately adjacent to the stop codon and the second and third microRNA binding sites are positioned 30-40 bases downstream of the 3' most residue of the first microRNA binding site.

In some embodiments, the microRNA binding site comprises one or more nucleotide sequences selected from SEQ ID NO: 32 and SEQ ID NO: 34. In some embodiments, the microRNA binding site binds to miR-142. In some embodiments, the microRNA binding site binds to miR-142-3p or miR-142-5p. In some embodiments, the miR142 comprises SEQ ID NO: 30.

In some some embodiments, the microRNA binding site comprises one or more nucleotide sequences selected from SEQ ID NO:96 and SEQ ID NO:156. In some embodiments, the miRNA binding site binds to miR-126. In some embodiments, the miRNA binding site binds to miR-126-3p or miR-126-5p. In some embodiments, the miR-126 comprises SEQ ID NO: 155.

In some embodiments, the mRNA comprises a 3' UTR comprising a microRNA binding site that binds to miR-142, miR-126, or a combination thereof.

In some embodiments, the polynucleotide, e.g., mRNA, further comprises a 3' UTR. In some embodiments, the 3' UTR comprises a nucleic acid sequence at least about 90%, at least about 95%, at least about 96%, at least about 97%, at least about 98%, at least about 99%, or 100% identical to a 3'UTR sequence selected from the group consisting of SEQ ID NOs: 53 to 77, 79, 97, 98, 101 to 108, 112, and 163 to 173 or any combination thereof. In some embodiments, the miRNA binding site is located within the 3' UTR. In some embodiments, the 3' UTR comprises a nucleic acid sequence selected from the group consisting of SEQ ID NOs: 53 to 77, 79, 97, 98, 101 to 108, 112, and 163 to 173, and any combination thereof.

In some embodiments, the polynucleotide, e.g., mRNA, further comprises a 5' UTR. In some embodiments, the 5' UTR comprises a nucleic acid sequence at least 90%, at least about 95%, at least about 96%, at least about 97%, at least about 98%, at least about 99%, or about 100% identical to a sequence selected from the group consisting of SEQ ID NO: 35-52 and 109-111, or any combination thereof. In some embodiments, the 5' UTR comprises a sequence selected from the group consisting of SEQ ID NO: 35-52, 109-111, and any combination thereof. In some embodiments, the mRNA comprises a 5' UTR comprising the nucleic acid sequence of SEQ ID NO: 35.

In some embodiments, the polynucleotide, e.g. mRNA, further comprises a 5' terminal cap. In some embodiments, the 5' terminal cap comprises a Cap0, Cap1, ARCA, inosine, N1-methyl-guanosine, 2'-fluoro-guanosine, 7-deaza-guanosine, 8-oxo-guanosine, 2-amino-guanosine, LNA-guanosine, 2-azidoguanosine, Cap2, Cap4, 5' methylG cap, or an analog thereof. In some embodiments, the 5' terminal cap comprises a Cap1.

In some embodiments, the polynucleotide, e.g., mRNA, further comprises a poly-A region. In some embodiments, the poly-A region is at least about 10, at least about 20, at least about 30, at least about 40, at least about 50, at least about 60, at least about 70, at least about 80, or at least about 90 nucleotides in length. In some embodiments, the poly-A region has about 10 to about 200, about 20 to about 180, about 50 to about 160, about 70 to about 140, or about 80 to about 120 nucleotides in length.

In some embodiments, the polynucleotide, e.g., mRNA, encodes a GALT polypeptide that is fused to one or more heterologous polypeptides. In some embodiments, the one or more heterologous polypeptides increase a pharmacokinetic property of the GALT polypeptide. In some embodiments, upon administration to a subject, the polynucleotide has (i) a longer plasma half-life; (ii) increased expression of a GALT polypeptide encoded by the ORF; (iii) a lower frequency of arrested translation resulting in an expression fragment; (iv) greater structural stability; or (v) any combination thereof, relative to a corresponding polynucleotide comprising SEQ ID NO: 2 or 4.

In some embodiments, the polynucleotide, e.g. mRNA, comprises (i) a 5'-terminal cap; (ii) a 5'-UTR; (iii) an ORF encoding a GALT polypeptide; (iv) a 3'-UTR; and (v) a poly-A region. In some embodiments, the 3'-UTR comprises a miRNA binding site. In some embodiments, the polynucleotide comprises a nucleic acid sequence selected from the group consisting of SEQ ID NO: 132-150 (e.g., SEQ ID NO: 143 or 145). In some embodiments the polynucleotide further comprises a 5'-terminal cap (e.g., Cap1) and a poly-A-tail region (e.g., about 100 nucleotides in length).

The present disclosure also provides a method of producing the polynucleotide, e.g., mRNA, of the invention, the method comprising modifying an ORF encoding a GALT polypeptide by substituting at least one uracil nucleobase with an adenine, guanine, or cytosine nucleobase, or by substituting at least one adenine, guanine, or cytosine nucleobase with a uracil nucleobase, wherein all the substitutions are synonymous substitutions. In some embodiments, the method further comprises replacing at least about 90%, at least about 95%, at least about 99%, or about 100% of uracils with 5-methoxyuracils.

The present disclosure also provides a composition comprising (a) the polynucleotide, e.g. mRNA, of the invention;

and (b) a delivery agent. In some embodiments, the delivery agent comprises a lipidoid, a liposome, a lipoplex, a lipid nanoparticle, a polymeric compound, a peptide, a protein, a cell, a nanoparticle mimic, a nanotube, or a conjugate. In some embodiments, the delivery agent comprises a lipid nanoparticle. In some embodiments, the lipid nanoparticle comprises a lipid selected from the group consisting of 3-(didodecylamino)-N1,N1,4-tridodecyl-1-piperazineethanamine (KL10), N1-[2-(didodecylamino)ethyl]-N1,N4,N4-tridodecyl-1,4-piperazinediethanamine (KL22), 14,25-ditridecyl-15,18,21,24-tetraaza-octatriacontane (KL25), 1,2-dilinoleyloxy-N,N-dimethylaminopropane (DLin-DMA), 2,2-dilinoleyl-4-dimethylaminomethyl-[1,3]-dioxolane (DLin-K-DMA), heptatriaconta-6,9,28,31-tetraen-19-yl 4-(dimethylamino)butanoate (DLin-MC3-DMA), 2,2-dilinoleyl-4-(2-dimethylaminoethyl)-[1,3]-dioxolane (DLin-KC2-DMA), 1,2-dioleyloxy-N,N-dimethylaminopropane (DODMA), (13Z,165Z)—N,N-dimethyl-3-nonydocosa-13-16-dien-1-amine (L608), 2-({8-[(3β)-cholest-5-en-3-yloxy]octyl}oxy)-N,N-dimethyl-3-[(9Z,12Z)-octadeca-9,12-dien-1-yloxy]propan-1-amine (Octyl-CLinDMA), (2R)-2-({8-[(3β)-cholest-5-en-3-yloxy]octyl}oxy)-N,N-dimethyl-3-[(9Z,12Z)-octadeca-9,12-dien-1-yloxy]propan-1-amine (Octyl-CLinDMA (2R)), (2S)-2-({8-[(3β)-cholest-5-en-3-yloxy]octyl}oxy)-N,N-dimethyl-3-[(9Z,12Z)-octadeca-9,12-dien-1-yloxy]propan-1-amine (Octyl-CLinDMA (2S)), and any combinations thereof. In some embodiments, the lipid nanoparticle comprises DLin-MC3-DMA.

In some embodiments, the delivery agent comprises a compound having the formula (I)

(I)

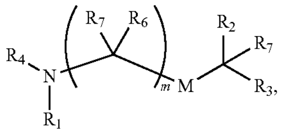

or a salt or stereoisomer thereof.

$R_1$ is selected from the group consisting of $C_{5-30}$ alkyl, $C_{5-20}$ alkenyl, —R*YR", —YR", and —R"M'R';

$R_2$ and $R_3$ are independently selected from the group consisting of H, $C_{1-14}$ alkyl, $C_{2-14}$ alkenyl, —R*YR", —YR", and —R*OR", or $R_2$ and $R_3$, together with the atom to which they are attached, form a heterocycle or carbocycle;

$R_4$ is selected from the group consisting of a $C_{3-6}$ carbocycle, —$(CH_2)_n$Q, —$(CH_2)_n$CHQR, —CHQR, —CQ$(R)_2$, and unsubstituted $C_{1-6}$ alkyl, where Q is selected from a carbocycle, heterocycle, —OR, —O$(CH_2)_n$N$(R)_2$, —C(O)OR, —OC(O)R, —$CX_3$, —$CX_2$H, —$CXH_2$, —CN, —N$(R)_2$, —C(O)N$(R)_2$, —N(R)C(O)R, —N(R)S$(O)_2$R, —N(R)C(O)N$(R)_2$, —N(R)C(S)N$(R)_2$, —N(R)$R_8$, —O$(CH_2)_n$OR, —N(R)C(═$NR_9$)N$(R)_2$, —N(R)C(═$CHR_9$)N$(R)_2$, —OC(O)N$(R)_2$, —N(R)C(O)OR, —N(OR)C(O)R, —N(OR)S$(O)_2$R, —N(OR)C(O)OR, —N(OR)C(O)N$(R)_2$, —N(OR)C(S)N$(R)_2$, —N(OR)C(═$NR_9$)N$(R)_2$, —N(OR)C(═$CHR_9$)N$(R)_2$, —C(═$NR_9$)N$(R)_2$, —C(═$NR_9$)R, —C(O)N(R)OR, and —C(R)N$(R)_2$C(O)OR, and each n is independently selected from 1, 2, 3, 4, and 5;

each $R_5$ is independently selected from the group consisting of $C_{1-3}$ alkyl, $C_{2-3}$ alkenyl, and H;

each $R_6$ is independently selected from the group consisting of $C_{1-3}$ alkyl, $C_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —S$(O)_2$—, —S—S—, an aryl group, and a heteroaryl group;

$R_7$ is selected from the group consisting of $C_{1-3}$ alkyl, $C_{2-3}$ alkenyl, and H;

$R_8$ is selected from the group consisting of $C_{3-6}$ carbocycle and heterocycle;

$R_9$ is selected from the group consisting of H, CN, $NO_2$, $C_{1-6}$ alkyl, —OR, —S$(O)_2$R, —S$(O)_2$N$(R)_2$, $C_{2-6}$ alkenyl, $C_{3-6}$ carbocycle and heterocycle;

each R is independently selected from the group consisting of $C_{1-3}$ alkyl, $C_{2-3}$ alkenyl, and H;

each R' is independently selected from the group consisting of $C_{1-18}$ alkyl, $C_{2-18}$ alkenyl, —R*YR", —YR", and H;

each R" is independently selected from the group consisting of $C_{3-14}$ alkyl and $C_{3-14}$ alkenyl;

each R* is independently selected from the group consisting of $C_{1-12}$ alkyl and $C_{2-12}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13; and provided when $R_4$ is —$(CH_2)_n$Q, —$(CH_2)_n$CHQR, —CHQR, or —CQ$(R)_2$, then (i) Q is not —N$(R)_2$ when n is 1, 2, 3, 4 or 5, or (ii) Q is not 5, 6, or 7-membered heterocycloalkyl when n is 1 or 2.

The present disclosure also provides a composition comprising a nucleotide sequence encoding a GALT polypeptide and a delivery agent, wherein the delivery agent comprises a compound having the Formula (I)

(I)

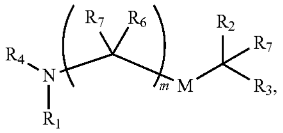

or a salt or stereoisomer thereof, wherein $R_1$ is selected from the group consisting of $C_{5-30}$ alkyl, $C_{5-20}$ alkenyl, —R*YR", —YR", and —R"M'R';

$R_2$ and $R_3$ are independently selected from the group consisting of H, $C_{1-14}$ alkyl, $C_{2-14}$ alkenyl, —R*YR", —YR", and —R*OR", or $R_2$ and $R_3$, together with the atom to which they are attached, form a heterocycle or carbocycle;

$R_4$ is selected from the group consisting of a $C_{3-6}$ carbocycle, —$(CH_2)_n$Q, —$(CH_2)_n$CHQR, —CHQR, —CQ$(R)_2$, and unsubstituted $C_{1-6}$ alkyl, where Q is selected from a carbocycle, heterocycle, —OR, —O$(CH_2)_n$N$(R)_2$, —C(O)OR, —OC(O)R, —$CX_3$, —$CX_2$H, —$CXH_2$, —CN, —N$(R)_2$, —C(O)N$(R)_2$, —N(R)C(O)R, —N(R)S$(O)_2$R, —N(R)C(O)N$(R)_2$, —N(R)C(S)N$(R)_2$, and —C(R)N$(R)_2$C(O)OR, —N(R)$R_8$, —O$(CH_2)_n$OR, —N(R)C(═$NR_9$)N$(R)_2$, —N(R)C(═$CHR_9$)N$(R)_2$, —OC(O)N$(R)_2$, —N(R)C(O)OR, —N(OR)C(O)R, —N(OR)S$(O)_2$R, —N(OR)C(O)OR, —N(OR)C(O)N$(R)_2$, —N(OR)C(S)N$(R)_2$, —N(OR)C(═$NR_9$)N$(R)_2$, —N(OR)C(═$CHR_9$)N$(R)_2$, —C(═$NR_9$)N$(R)_2$, —C(═$NR_9$)R, —C(O)N(R)OR, and each n is independently selected from 1, 2, 3, 4, and 5;

each $R_5$ is independently selected from the group consisting of $C_{1-3}$ alkyl, $C_{2-3}$ alkenyl, and H;

each $R_6$ is independently selected from the group consisting of $C_{1-3}$ alkyl, $C_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —$S(O)_2$—, —S—S—, an aryl group, and a heteroaryl group;

$R_7$ is selected from the group consisting of $C_{1-3}$ alkyl, $C_{2-3}$ alkenyl, and H;

$R_8$ is selected from the group consisting of $C_{3-6}$ carbocycle and heterocycle;

$R_9$ is selected from the group consisting of H, CN, $NO_2$, $C_{1-6}$ alkyl, —OR, —$S(O)_2R$, —$S(O)_2N(R)_2$, $C_{2-6}$ alkenyl, $C_{3-6}$ carbocycle and heterocycle;

each R is independently selected from the group consisting of $C_{1-3}$ alkyl, $C_{2-3}$ alkenyl, and H;

each R' is independently selected from the group consisting of $C_{1-18}$ alkyl, $C_{2-18}$ alkenyl, —R*YR", —YR", and H;

each R" is independently selected from the group consisting of $C_{3-14}$ alkyl and $C_{3-14}$ alkenyl;

each R* is independently selected from the group consisting of $C_{1-12}$ alkyl and $C_{2-12}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13; and provided when $R_4$ is —$(CH_2)_nQ$, —$(CH_2)_nCHQR$, —CHQR, or —$CQ(R)_2$, then (i) Q is not —$N(R)_2$ when n is 1, 2, 3, 4 or 5, or (ii) Q is not 5, 6, or 7-membered heterocycloalkyl when n is 1 or 2.

In some embodiments, the delivery agent comprises a compound having the Formula (I), or a salt or stereoisomer thereof, wherein $R_1$ is selected from the group consisting of $C_{5-30}$ alkyl, $C_{5-20}$ alkenyl, —R*YR", —YR", and —R"M'R';

$R_2$ and $R_3$ are independently selected from the group consisting of H, $C_{1-14}$ alkyl, $C_{2-14}$ alkenyl, —R*YR", —YR", and —R*OR", or $R_2$ and $R_3$, together with the atom to which they are attached, form a heterocycle or carbocycle;

$R_4$ is selected from the group consisting of a $C_{3-6}$ carbocycle, —$(CH_2)_nQ$, —$(CH_2)_nCHQR$, —CHQR, —$CQ(R)_2$, and unsubstituted $C_{1-6}$ alkyl, where Q is selected from a carbocycle, heterocycle, —OR, —$O(CH_2)_nN(R)_2$, —C(O)OR, —OC(O)R, —$CX_3$, —$CX_2H$, —$CXH_2$, —CN, —$N(R)_2$, —$C(O)N(R)_2$, —N(R)C(O)R, —$N(R)S(O)_2R$, —$N(R)C(O)N(R)_2$, —$N(R)C(S)N(R)_2$, and —$C(R)N(R)_2C(O)OR$, and each n is independently selected from 1, 2, 3, 4, and 5;

each $R_5$ is independently selected from the group consisting of $C_{1-3}$ alkyl, $C_{2-3}$ alkenyl, and H;

each $R_6$ is independently selected from the group consisting of $C_{1-3}$ alkyl, $C_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —$S(O)_2$—, —S—S—, an aryl group, and a heteroaryl group;

$R_7$ is selected from the group consisting of $C_{1-3}$ alkyl, $C_{2-3}$ alkenyl, and H;

each R is independently selected from the group consisting of $C_{1-3}$ alkyl, $C_{2-3}$ alkenyl, and H;

each R' is independently selected from the group consisting of $C_{1-18}$ alkyl, $C_{2-18}$ alkenyl, —R*YR", —YR", and H;

each R" is independently selected from the group consisting of $C_{3-14}$ alkyl and $C_{3-14}$ alkenyl;

each R* is independently selected from the group consisting of $C_{1-12}$ alkyl and $C_{2-12}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13; and provided when $R_4$ is —$(CH_2)_nQ$, —$(CH_2)_nCHQR$, —CHQR, or —$CQ(R)_2$, then (i) Q is not —$N(R)_2$ when n is 1, 2, 3, 4 or 5, or (ii) Q is not 5, 6, or 7-membered heterocycloalkyl when n is 1 or 2.

In some embodiments, the compound is of Formula (IA):

(IA)

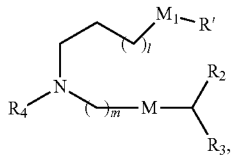

or a salt or stereoisomer thereof, wherein l is selected from 1, 2, 3, 4, and 5;

m is selected from 5, 6, 7, 8, and 9;

$M_1$ is a bond or M';

$R_4$ is unsubstituted $C_{1-3}$ alkyl, or —$(CH_2)_nQ$, in which n is 1, 2, 3, 4, or 5 and Q is OH, —$NHC(S)N(R)_2$, —$NHC(O)N(R)_2$, —N(R)C(O)R, —$N(R)S(O)_2R$, —$N(R)R_8$, —$NHC(=NR_9)N(R)_2$, —$NHC(=CHR_9)N(R)_2$, —$OC(O)N(R)_2$, —N(R)C(O)OR, heteroaryl, or heterocycloalkyl;

M and M' are independently selected from —C(O)O—, —OC(O)—, —C(O)N(R')—, —P(O)(OR')O—, —S—S—, an aryl group, and a heteroaryl group; and $R_2$ and $R_3$ are independently selected from the group consisting of H, $C_{1-14}$ alkyl, and $C_{2-14}$ alkenyl.

In some embodiments, m is 5, 7, or 9.

In some embodiments, the compound is of Formula (IA), or a salt or stereoisomer thereof, wherein l is selected from 1, 2, 3, 4, and 5;

m is selected from 5, 6, 7, 8, and 9;

$M_1$ is a bond or M';

$R_4$ is unsubstituted $C_{1-3}$ alkyl, or —$(CH_2)_nQ$, in which n is 1, 2, 3, 4, or 5 and Q is OH, —$NHC(S)N(R)_2$, or —$NHC(O)N(R)_2$;

M and M' are independently selected from —C(O)O—, —OC(O)—, —C(O)N(R')—, —P(O)(OR')O—, —S—S—, an aryl group, and a heteroaryl group; and $R_2$ and $R_3$ are independently selected from the group consisting of H, $C_{1-14}$ alkyl, and $C_{2-14}$ alkenyl.

In some embodiments, m is 5, 7, or 9.

In some embodiments, the compound is of Formula (II):

(II)

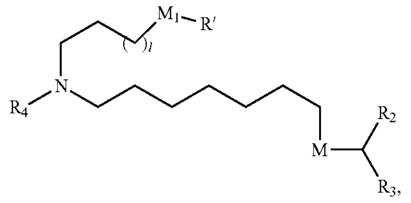

or a salt or stereoisomer thereof, wherein l is selected from 1, 2, 3, 4, and 5;

$M_1$ is a bond or M';

$R_4$ is unsubstituted $C_{1-3}$ alkyl, or —$(CH_2)_nQ$, in which n is 2, 3, or 4 and Q is OH, —$NHC(S)N(R)_2$, —$NHC(O)N(R)_2$—N(R)C(O)R, —$N(R)S(O)_2R$, —$N(R)R_8$, —$NHC(=NR_9)$ $N(R)_2$, —$NHC(=CHR_9)N(R)_2$, —$OC(O)N(R)_2$, —N(R)C(O)OR, heteroaryl or heterocycloalkyl;

M and M' are independently selected from —C(O)O—, —OC(O)—, —C(O)N(R')—, —P(O)(OR')O—, —S—S—, an aryl group, and a heteroaryl group; and $R_2$ and $R_3$ are independently selected from the group consisting of H, $C_{1-14}$ alkyl, and $C_{2-14}$ alkenyl.

In some embodiments, the compound is of Formula (II), or a salt or stereoisomer thereof, wherein l is selected from 1, 2, 3, 4, and 5;

$M_1$ is a bond or M';

$R_4$ is unsubstituted $C_{1-3}$ alkyl, or $—(CH_2)_nQ$, in which n is 2, 3, or 4 and Q is OH, $—NHC(S)N(R)_2$, or $—NHC(O)N(R)_2$;

M and M' are independently selected from —C(O)O—, —OC(O)—, —C(O)N(R')—, —P(O)(OR')O—, —S—S—, an aryl group, and a heteroaryl group; and $R_2$ and $R_3$ are independently selected from the group consisting of H, $C_{1-14}$ alkyl, and $C_{2-14}$ alkenyl.

In some embodiments, $M_1$ is M'.

In some embodiments, M and M' are independently —C(O)O— or —OC(O)—.

In some embodiments, l is 1, 3, or 5.

In some embodiments, the compound is selected from the group consisting of Compound 1 to Compound 232, salts and stereoisomers thereof, and any combination thereof.

In some embodiments, the compound is selected from the group consisting of Compound 1 to Compound 147, salts and stereoisomers thereof, and any combination thereof.

In some embodiments, the compound is of the Formula (IIa), (IIa)

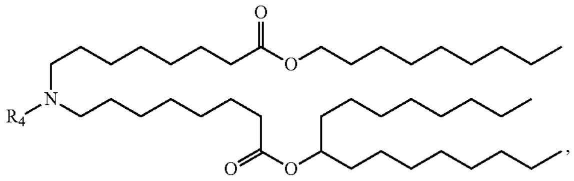

or a salt or stereoisomer thereof.

In some embodiments, the compound is of the Formula (IIb), (IIb)

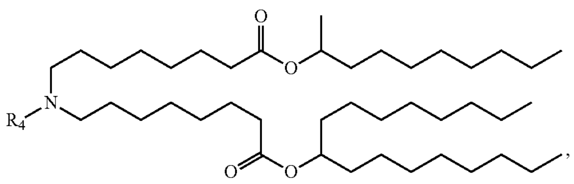

or a salt or stereoisomer thereof.

In some embodiments, the compound is of the Formula (IIc) or (IIe), (IIc)

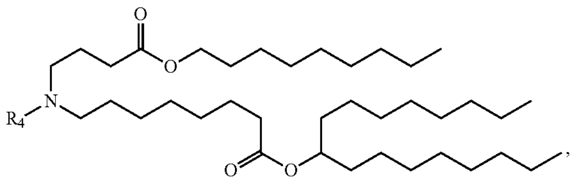

(IIe)

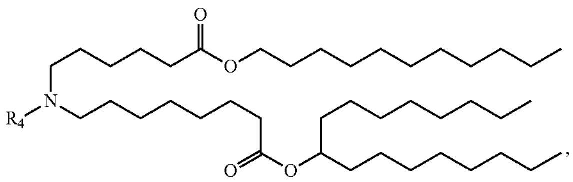

or a salt or stereoisomer thereof.

In some embodiments, $R_4$ is as described herein. In some embodiments, $R_4$ is selected from $—(CH_2)_nQ$ and $—(CH_2)_nCHQR$.

In some embodiments, the compound is of the Formula (IId), (IId)

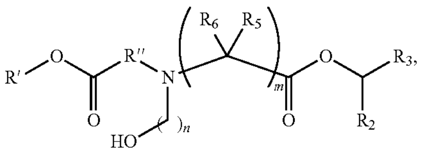

or a salt or stereoisomer thereof, wherein n is selected from 2, 3, and 4, m, R', R'', and $R_2$ through $R_6$ are as described herein. For example, each of $R_2$ and $R_3$ may be independently selected from the group consisting of $C_{5-14}$ alkyl and $C_{5-14}$ alkenyl.

In some embodiments, the compound is of the Formula (IId), or a salt or stereoisomer thereof, wherein $R_2$ and $R_3$ are independently selected from the group consisting of $C_{5-14}$ alkyl and $C_{5-14}$ alkenyl, n is selected from 2, 3, and 4, and R', R'', $R_5$, $R_6$ and m are as defined herein.

In some embodiments, $R_2$ is $C_8$ alkyl.

In some embodiments, $R_3$ is $C_5$ alkyl, $C_6$ alkyl, $C_7$ alkyl, $C_8$ alkyl, or $C_9$ alkyl.

In some embodiments, m is 5, 7, or 9.

In some embodiments, each $R_5$ is H.

In some embodiments, each $R_6$ is H.

In some embodiments, the delivery agent comprises a compound having the Formula (III)

(III)

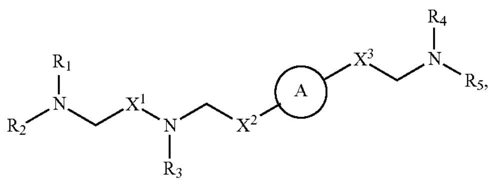

or salts or stereoisomers thereof, wherein ring A is

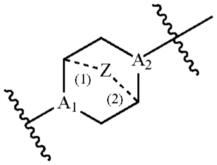
or
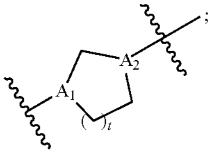
;

t is 1 or 2;

$A_1$ and $A_2$ are each independently selected from CH or N;

Z is $CH_2$ or absent wherein when Z is $CH_2$, the dashed lines (1) and (2) each represent a single bond; and when Z is absent, the dashed lines (1) and (2) are both absent;

$R_1$, $R_2$, $R_3$, $R_4$, and $R_5$ are independently selected from the group consisting of $C_{5-20}$ alkyl, $C_{5-20}$ alkenyl, —R"MR', —R*YR", —YR", and —R*OR";

each M is independently selected from the group consisting of —C(O)O—, —OC(O)—, —OC(O)O—, —C(O)N(R')—, —N(R')C(O)—, —C(O)—, —C(S)—, —C(S)S—, —SC(S)—, —CH(OH)—, —P(O)(OR')O—, —$S(O)_2$—, an aryl group, and a heteroaryl group;

$X^1$, $X^2$, and $X^3$ are independently selected from the group consisting of a bond, —$CH_2$—, —$(CH_2)_2$—, —CHR—, —CHY—, —C(O)—, —C(O)O—, —OC(O)—, —C(O)—$CH_2$—, —$CH_2$—C(O)—, —C(O)O—$CH_2$—, —OC(O)—$CH_2$—, —$CH_2$—C(O)O—, —$CH_2$—OC(O)—, —CH(OH)—, —C(S)—, and —CH(SH)—;

each Y is independently a $C_{3-6}$ carbocycle;

each R* is independently selected from the group consisting of $C_{1-12}$ alkyl and $C_{2-12}$ alkenyl;

each R is independently selected from the group consisting of $C_{1-3}$ alkyl and a $C_{3-6}$ carbocycle;

each R' is independently selected from the group consisting of $C_{1-12}$ alkyl, $C_{2-12}$ alkenyl, and H; and each R" is independently selected from the group consisting of $C_{3-12}$ alkyl and $C_{3-12}$ alkenyl, wherein when ring A is

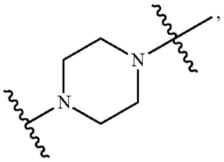 [SMILES: "," ; *N1CCN(*)CC1]
, then i) at least one of $X^1$, $X^2$, and $X^3$ is not —$CH_2$—; and/or ii) at least one of $R_1$, $R_2$, $R_3$, $R_4$, and $R_5$ is —R"MR'.

In some embodiments, the compound is of any of formulae (IIIa1)-(IIIa6):

(IIIa1)

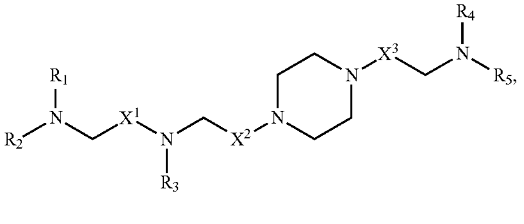

-continued (IIIa2)

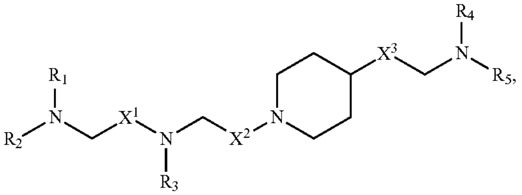

(IIIa3)

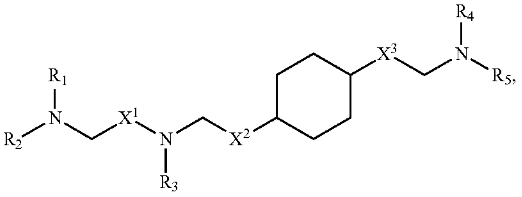

(IIIa4)

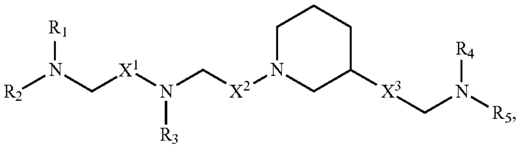

(IIIa5)

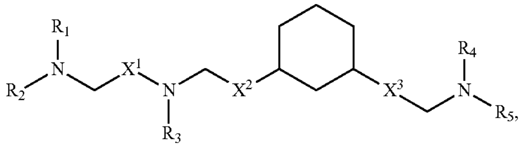
or (IIIa6)

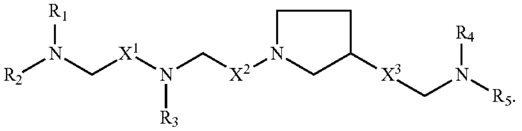

The compounds of Formula (III) or any of (IIIa1)-(IIIa6) include one or more of the following features when applicable.

In some embodiments, ring A is

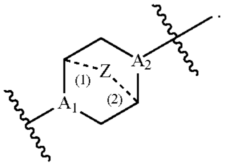

In some embodiments, ring A is

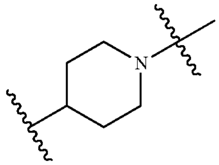
or
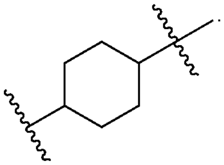
.

In some embodiments, ring A is

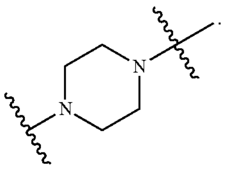 [SMILES: "." ; *N1CCN(*)CC1]

In some embodiments, ring A is

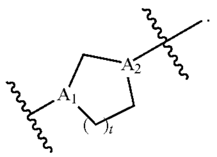

In some embodiments, ring A is

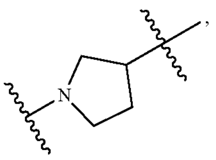

,

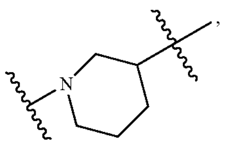

, or,

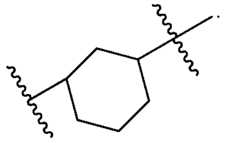

In some embodiments, ring A is

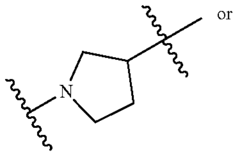

or

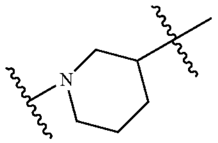

wherein ring, in which the N atom is connected with $X^2$.

In some embodiments, Z is $CH_2$.

In some embodiments, Z is absent.

In some embodiments, at least one of $A_1$ and $A_2$ is N.

In some embodiments, each of $A_1$ and $A_2$ is N.

In some embodiments, each of $A_1$ and $A_2$ is CH.

In some embodiments, $A_1$ is N and $A_2$ is CH.

In some embodiments, $A_1$ is CH and $A_2$ is N.

In some embodiments, at least one of $X^1$, $X^2$, and $X^3$ is not —$CH_2$—. For example, in certain embodiments, $X^1$ is not —$CH_2$—. In some embodiments, at least one of $X^1$, $X^2$, and $X^3$ is —C(O)—.

In some embodiments, $X^2$ is —C(O)—, —C(O)O—, —OC(O)—, —C(O)—$CH_2$—, —$CH_2$—C(O)—, —C(O)O—$CH_2$—, —OC(O)—$CH_2$—, —$CH_2$—C(O)O—, or —$CH_2$—OC(O)—.

In some embodiments, $X^3$ is —C(O)—, —C(O)O—, —OC(O)—, —C(O)—$CH_2$—, —$CH_2$—C(O)—, —C(O)O—$CH_2$—, —OC(O)—$CH_2$—, —$CH_2$—C(O)O—, or —$CH_2$—OC(O)—. In other embodiments, $X^3$ is —$CH_2$—.

In some embodiments, $X^3$ is a bond or —$(CH_2)_2$—.

In some embodiments, $R_1$ and $R_2$ are the same. In certain embodiments, $R_1$, and $R_3$ are the same. In some embodiments, $R_4$ and $R_5$ are the same. In certain embodiments, $R_1$, $R_2$, $R_3$, $R_4$, and $R_5$ are the same.

In some embodiments, at least one of $R_1$, $R_2$, $R_3$, $R_4$, and $R_5$ is —R"MR'. In some embodiments, at most one of $R_1$, $R_2$, $R_3$, $R_4$, and $R_5$ is —R"MR'. For example, at least one of $R_1$, $R_2$, and $R_3$ may be —R"MR', and/or at least one of $R_4$ and $R_5$ is —R"MR'. In certain embodiments, at least one M is —C(O)O—. In some embodiments, each M is —C(O)O—. In some embodiments, at least one M is —OC(O)—. In some embodiments, each M is —OC(O)—. In some embodiments, at least one M is —OC(O)O—. In some embodiments, each M is —OC(O)O—. In some embodiments, at least one R" is $C_3$ alkyl. In certain embodiments, each R" is $C_3$ alkyl. In some embodiments, at least one R" is $C_5$ alkyl. In certain embodiments, each R" is $C_5$ alkyl. In some embodiments, at least one R" is $C_6$ alkyl. In certain embodiments, each R" is $C_6$ alkyl. In some embodiments, at least one R" is $C_7$ alkyl. In certain embodiments, each R" is $C_7$ alkyl. In some embodiments, at least one R' is $C_5$ alkyl. In certain embodiments, each R' is $C_5$ alkyl. In other embodiments, at least one R' is $C_1$ alkyl. In certain embodiments, each R' is $C_1$ alkyl. In some embodiments, at least one R' is $C_2$ alkyl. In certain embodiments, each R' is $C_2$ alkyl.

In some embodiments, at least one of $R_1$, $R_2$, $R_3$, $R_4$, and $R_5$ is $C_{12}$ alkyl. In certain embodiments, each of $R_1$, $R_2$, $R_3$, $R_4$, and $R_5$ are $C_{12}$ alkyl.

In some embodiments, the delivery agent comprises a compound having the Formula (IV)

(IV)

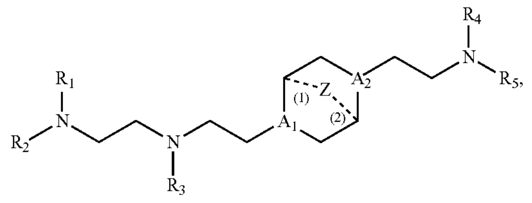

or salts or stereoisomer thereof, wherein $A_1$ and $A_2$ are each independently selected from CH or N and at least one of $A_1$ and $A_2$ is N;

Z is $CH_2$ or absent wherein when Z is $CH_2$, the dashed lines (1) and (2) each represent a single bond; and when Z is absent, the dashed lines (1) and (2) are both absent;

$R_1$, $R_2$, $R_3$, $R_4$, and $R_5$ are independently selected from the group consisting of $C_{6-20}$ alkyl and $C_{6-20}$ alkenyl;

wherein when ring A is

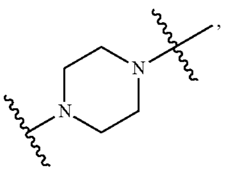

then i) $R_1$, $R_2$, $R_3$, $R_4$, and $R_5$ are the same, wherein Ri is not $C_{12}$ alkyl, $C_{18}$ alkyl, or $C_{18}$ alkenyl;

ii) only one of $R_1$, $R_2$, $R_3$, $R_4$, and $R_5$ is selected from $C_{6-20}$ alkenyl;

iii) at least one of $R_1$, $R_2$, $R_3$, $R_4$, and $R_5$ have a different number of carbon atoms than at least one other of $R_1$, $R_2$, $R_3$, $R_4$, and $R_5$;

iv) $R_1$, $R_2$, and $R_3$ are selected from $C_{6-20}$ alkenyl, and $R_4$ and $R_5$ are selected from $C_{6-20}$ alkyl; or v) $R_1$, $R_2$, and $R_3$ are selected from $C_{6-20}$ alkyl, and $R_4$ and $R_5$ are selected from $C_{6-20}$ alkenyl.

In some embodiments, the compound is of Formula (IVa):

(IVa)

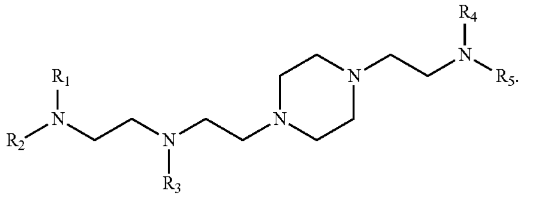

The compounds of Formula (IV) or (IVa) include one or more of the following features when applicable.

In some embodiments, Z is $CH_2$.

In some embodiments, Z is absent.

In some embodiments, at least one of $A_1$ and $A_2$ is N.

In some embodiments, each of $A_1$ and $A_2$ is N.

In some embodiments, each of $A_1$ and $A_2$ is CH.

In some embodiments, $A_1$ is N and $A_2$ is CH.

In some embodiments, $A_1$ is CH and $A_2$ is N.

In some embodiments, $R_1$, $R_2$, $R_3$, $R_4$, and $R_5$ are the same, and are not $C_{12}$ alkyl, $C_{18}$ alkyl, or $C_{18}$ alkenyl. In some embodiments, $R_1$, $R_2$, $R_3$, $R_4$, and $R_5$ are the same and are $C_9$ alkyl or $C_{14}$ alkyl.

In some embodiments, only one of $R_1$, $R_2$, $R_3$, $R_4$, and $R_5$ is selected from $C_{6-20}$ alkenyl. In certain such embodiments, $R_1$, $R_2$, $R_3$, $R_4$, and $R_5$ have the same number of carbon atoms. In some embodiments, $R_4$ is selected from $C_{5-20}$ alkenyl. For example, $R_4$ may be $C_{12}$ alkenyl or $C_{18}$ alkenyl.

In some embodiments, at least one of $R_1$, $R_2$, $R_3$, $R_4$, and $R_5$ have a different number of carbon atoms than at least one other of $R_1$, $R_2$, $R_3$, $R_4$, and $R_5$.

In certain embodiments, $R_1$, $R_2$, and $R_3$ are selected from $C_{6-20}$ alkenyl, and $R_4$ and $R_5$ are selected from $C_{6-20}$ alkyl. In other embodiments, $R_1$, $R_2$, and $R_3$ are selected from $C_{6-20}$ alkyl, and $R_4$ and $R_5$ are selected from $C_{6-20}$ alkenyl. In some embodiments, $R_1$, $R_2$, and $R_3$ have the same number of carbon atoms, and/or $R_4$ and $R_5$ have the same number of carbon atoms. For example, $R_1$, $R_2$, and $R_3$, or $R_4$ and $R_5$, may have 6, 8, 9, 12, 14, or 18 carbon atoms. In some embodiments, $R_1$, $R_2$, and $R_3$, or $R_4$ and $R_5$, are $C_{18}$ alkenyl (e.g., linoleyl). In some embodiments, $R_1$, $R_2$, and $R_3$, or $R_4$ and $R_5$, are alkyl groups including 6, 8, 9, 12, or 14 carbon atoms.

In some embodiments, $R_1$ has a different number of carbon atoms than $R_2$, $R_3$, $R_4$, and $R_5$. In other embodiments, $R_3$ has a different number of carbon atoms than $R_1$, $R_2$, $R_4$, and $R_5$. In further embodiments, $R_4$ has a different number of carbon atoms than $R_1$, $R_2$, $R_3$, and $R_5$.

In other embodiments, the delivery agent comprises a compound having the Formula (V)

(V)

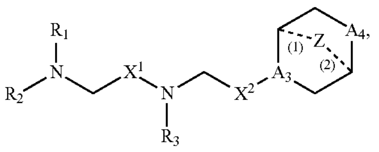

or salts or stereoisomers thereof, in which $A_3$ is CH or N;

$A_4$ is $CH_2$ or NH; and at least one of $A_3$ and $A_4$ is N or NH;

Z is $CH_2$ or absent wherein when Z is $CH_2$, the dashed lines (1) and (2) each represent a single bond; and when Z is absent, the dashed lines (1) and (2) are both absent;

$R_1$, $R_2$, and $R_3$ are independently selected from the group consisting of $C_{5-20}$ alkyl, $C_{5-20}$ alkenyl, —R"MR', —R*YR", —YR", and —R*OR";

each M is independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, $—S(O)_2—$, an aryl group, and a heteroaryl group;

$X^1$ and $X^2$ are independently selected from the group consisting of $—CH_2—$, $—(CH_2)_2—$, —CHR—, —CHY—, —C(O)—, —C(O)O—, —OC(O)—, $—C(O)—CH_2—$, $—CH_2—C(O)—$, $—C(O)O—CH_2—$, $—OC(O)—CH_2—$, $—CH_2—C(O)O—$, $—CH_2—OC(O)—$, —CH(OH)—, —C(S)—, and —CH(SH)—;

each Y is independently a $C_{3-6}$ carbocycle;

each R* is independently selected from the group consisting of $C_{1-12}$ alkyl and $C_{2-12}$ alkenyl;

each R is independently selected from the group consisting of $C_{1-3}$ alkyl and a $C_{3-6}$ carbocycle;

each R' is independently selected from the group consisting of $C_{1-12}$ alkyl, $C_{2-12}$ alkenyl, and H; and each R" is independently selected from the group consisting of $C_{3-12}$ alkyl and $C_{3-12}$ alkenyl.

In some embodiments, the compound is of Formula (Va):

(Va)

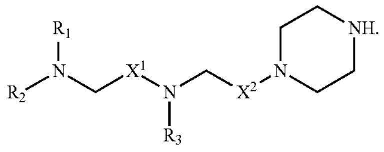

The compounds of Formula (V) or (Va) include one or more of the following features when applicable.

In some embodiments, Z is $CH_2$.

In some embodiments, Z is absent.

In some embodiments, at least one of $A_3$ and $A_4$ is N or NH.

In some embodiments, $A_3$ is N and $A_4$ is NH.

In some embodiments, $A_3$ is N and $A_4$ is $CH_2$.

In some embodiments, $A_3$ is CH and $A_4$ is NH.

In some embodiments, at least one of $X^1$ and $X^2$ is not $—CH_2—$. For example, in certain embodiments, $X^1$ is not $—CH_2—$. In some embodiments, at least one of $X^1$ and $X^2$ is —C(O)—.

In some embodiments, $X^2$ is —C(O)—, —C(O)O—, —OC(O)—, $—C(O)—CH_2—$, $—CH_2—C(O)—$, $—C(O)O—CH_2—$, $—OC(O)—CH_2—$, $—CH_2—C(O)O—$, or $—CH_2—OC(O)—$.

In some embodiments, $R_1$, $R_2$, and $R_3$ are independently selected from the group consisting of $C_{5-20}$ alkyl and $C_{5-20}$ alkenyl. In some embodiments, $R_1$, $R_2$, and $R_3$ are the same. In certain embodiments, $R_1$, $R_2$, and $R_3$ are $C_6$, $C_9$, $C_{12}$, or $C_{14}$ alkyl. In other embodiments, $R_1$, $R_2$, and $R_3$ are $C_{18}$ alkenyl. For example, $R_1$, $R_2$, and $R_3$ may be linoleyl.

In other embodiments, the delivery agent comprises a compound having the Formula (VI):

(VI)

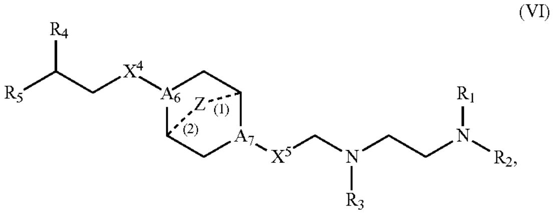

or salts or stereoisomers thereof, in which $A_6$ and $A_7$ are each independently selected from CH or N, wherein at least one of $A_6$ and $A_7$ is N;

Z is $CH_2$ or absent wherein when Z is $CH_2$, the dashed lines (1) and (2) each represent a single bond; and when Z is absent, the dashed lines (1) and (2) are both absent;

$X^4$ and $X^5$ are independently selected from the group consisting of $-CH_2-$, $-(CH_2)_2-$, $-CHR-$, $-CHY-$, $-C(O)-$, $-C(O)O-$, $-OC(O)-$, $-C(O)-CH_2-$, $-CH_2-C(O)-$, $-C(O)O-CH_2-$, $-OC(O)-CH_2-$, $-CH_2-C(O)O-$, $-CH_2-OC(O)-$, $-CH(OH)-$, $-C(S)-$, and $-CH(SH)-$;

$R_1$, $R_2$, $R_3$, $R_4$, and $R_5$ each are independently selected from the group consisting of $C_{5-20}$ alkyl, $C_{5-20}$ alkenyl, $-R''MR'$, $-R^*YR''$, $-YR''$, and $-R^*OR''$;

each M is independently selected from the group consisting of $-C(O)O-$, $-OC(O)-$, $-C(O)N(R')-$, $-N(R')C(O)-$, $-C(O)-$, $-C(S)-$, $-C(S)S-$, $-SC(S)-$, $-CH(OH)-$, $-P(O)(OR')O-$, $-S(O)_2-$, an aryl group, and a heteroaryl group;

each Y is independently a $C_{3-6}$ carbocycle;

each R* is independently selected from the group consisting of $C_{1-12}$ alkyl and $C_{2-12}$ alkenyl;

each R is independently selected from the group consisting of $C_{1-3}$ alkyl and a $C_{3-6}$ carbocycle;

each R' is independently selected from the group consisting of $C_{1-12}$ alkyl, $C_{2-12}$ alkenyl, and H; and each R" is independently selected from the group consisting of $C_{3-12}$ alkyl and $C_{3-12}$ alkenyl.

In some embodiments, $R_1$, $R_2$, $R_3$, $R_4$, and $R_5$ each are independently selected from the group consisting of $C_{6-20}$ alkyl and $C_{6-20}$ alkenyl.

In some embodiments, $R_1$ and $R_2$ are the same. In certain embodiments, $R_1$, $R_2$, and $R_3$ are the same. In some embodiments, $R_4$ and $R_5$ are the same. In certain embodiments, $R_1$, $R_2$, $R_3$, $R_4$, and $R_5$ are the same.

In some embodiments, at least one of $R_1$, $R_2$, $R_3$, $R_4$, and $R_5$ is $C_{9-12}$ alkyl. In certain embodiments, each of $R_1$, $R_2$, $R_3$, $R_4$, and $R_5$ independently is $C_9$, $C_{12}$ or $C_{14}$ alkyl. In certain embodiments, each of $R_1$, $R_2$, $R_3$, $R_4$, and $R_5$ is $C_9$ alkyl.

In some embodiments, $A_6$ is N and $A_7$ is N. In some embodiments, $A_6$ is CH and $A_7$ is N.

In some embodiments, $X^4$ is $-CH_2-$ and $X^5$ is $-C(O)-$. In some embodiments, $X^4$ and $X^5$ are $-C(O)-$.

In some embodiments, when $A_6$ is N and $A_7$ is N, at least one of $X^4$ and $X^5$ is not $-CH_2-$, e.g., at least one of $X^4$ and $X^5$ is $-C(O)-$. In some embodiments, when $A_6$ is N and $A_7$ is N, at least one of $R_1$, $R_2$, $R_3$, $R_4$, and $R_5$ is $-R''MR'$.

In some embodiments, at least one of $R_1$, $R_2$, $R_3$, $R_4$, and $R_5$ is not $-R''MR'$.

In some embodiments, the composition disclosed herein is a nanoparticle composition.

In some embodiments, the delivery agent further comprises a phospholipid. In some embodiments, the phospholipid is selected from the group consisting of 1,2-dilinoleoyl-sn-glycero-3-phosphocholine (DLPC), 1,2-dimyristoyl-sn-glycero-phosphocholine (DMPC), 1,2-dioleoyl-sn-glycero-3-phosphocholine (DOPC), 1,2-dipalmitoyl-sn-glycero-3-phosphocholine (DPPC), 1,2-distearoyl-sn-glycero-3-phosphocholine (DSPC), 1,2-diundecanoyl-sn-glycero-phosphocholine (DUPC), 1-palmitoyl-2-oleoyl-sn-glycero-3-phosphocholine (POPC), 1,2-di-O-octadecenyl-sn-glycero-3-phosphocholine (18:0 Diether PC), 1-oleoyl-2-cholesterylhemisuccinoyl-sn-glycero-3-phosphocholine (OChemsPC), 1-hexadecyl-sn-glycero-3-phosphocholine (C16 Lyso PC), 1,2-dilinolenoyl-sn-glycero-3-phosphocholine, 1,2-diarachidonoyl-sn-glycero-3-phosphocholine, 1,2-didocosahexaenoyl-sn-glycero-3-phosphocholine, 1,2-dioleoyl-sn-glycero-3-phosphoethanolamine (DOPE), 1,2-diphytanoyl-sn-glycero-3-phosphoethanolamine (ME 16:0 PE), 1,2-distearoyl-sn-glycero-3-phosphoethanolamine, 1,2-dilinoleoyl-sn-glycero-3-phosphoethanolamine, 1,2-dilinolenoyl-sn-glycero-3-phosphoethanolamine, 1,2-diarachidonoyl-sn-glycero-3-phosphoethanolamine, 1,2-didocosahexaenoyl-sn-glycero-3-phosphoethanolamine, 1,2-dioleoyl-sn-glycero-3-phospho-rac-(1-glycerol) sodium salt (DOPG), sphingomyelin, and any mixtures thereof.

In some embodiments, the delivery agent further comprises a structural lipid. In some embodiments, the structural lipid is selected from the group consisting of cholesterol, fecosterol, sitosterol, ergosterol, campesterol, stigmasterol, brassicasterol, tomatidine, ursolic acid, alpha-tocopherol, and any mixtures thereof.

In some embodiments, the delivery agent further comprises a PEG lipid. In some embodiments, the PEG lipid is selected from the group consisting of a PEG-modified phosphatidylethanolamine, a PEG-modified phosphatidic acid, a PEG-modified ceramide, a PEG-modified dialkylamine, a PEG-modified diacylglycerol, a PEG-modified dialkylglycerol, and any mixtures thereof. In some embodiments, the PEG lipid has the formula:

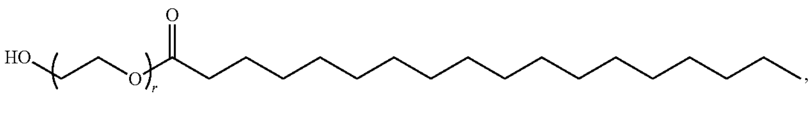

wherein r is an integer between 1 and 100. In some embodiments, the PEG lipid is Compound 428.

In some embodiments, the delivery agent further comprises an ionizable lipid selected from the group consisting of 3-(didodecylamino)-N1,N1,4-tridodecyl-1-piperazineethanamine (KL10), N1-[2-(didodecylamino)ethyl]-N1, N4,N4-tridodecyl-1,4-piperazinediethanamine (KL22), 14,25-ditridecyl-15,18,21,24-tetraaza-octatriacontane (KL25), 1,2-dilinoleyloxy-N,N-dimethylaminopropane (DLin-DMA), 2,2-dilinoleyl-4-dimethylaminomethyl-[1,3]-dioxolane (DLin-K-DMA), heptatriaconta-6,9,28,31-tetraen-19-yl 4-(dimethylamino)butanoate (DLin-MC3-DMA), 2,2-dilinoleyl-4-(2-dimethylaminoethyl)-[1,3]-dioxolane (DLin-KC2-DMA), 1,2-dioleyloxy-N,N-dimethylaminopropane (DODMA), 2-({8-[(3β)-cholest-5-en-3-yloxy]octyl}oxy)-N,N-dimethyl-3-[(9Z,12Z)-octadeca-9,12-di en-1-yloxy]propan-1-amine (Octyl-CLinDMA), (2R)-2-({8-[(3β)-cholest-5-en-3-yloxy]octyl}oxy)-N,N-dimethyl-3-[(9Z,12Z)-octadeca-9,12-dien-1-yloxy]propan-1-amine (Octyl-CLinDMA (2R)), and (2S)-2-({8-[(3β)-cholest-5-en-3-yloxy]octyl}oxy)-N,N-dimethyl-3-[(9Z,12Z)-octadeca-9,12-dien-1-yloxy]propan-1-amine (Octyl-CLinDMA (2S)).

In some embodiments, the delivery agent further comprises a phospholipid, a structural lipid, a PEG lipid, or any combination thereof. In some embodiments, the delivery agent comprises Compound 18, DSPC, Cholesterol, and Compound 428, e.g., with a mole ratio of about 50:10:38.5:1.5.

In some embodiments, the composition is formulated for in vivo delivery. In some embodiments, the composition is formulated for intramuscular, subcutaneous, or intradermal delivery.

The present disclosure further provides a polynucleotide comprising an mRNA comprising: (i) a 5' UTR, (ii) an open reading frame (ORF) encoding a human galactose-1-phosphate uridylyltransferase (GALT) polypeptide, wherein the ORF comprises a nucleic acid sequence selected from the group consisting of SEQ ID NOs: 5 to 29 and 113 to 131, and (iii) a 3' UTR comprising a microRNA binding site selected from miR-142, miR-126, or a combination thereof, wherein the mRNA comprises at least one chemically modified nucleobase.

The present disclosure further provides a polynucleotide comprising an mRNA comprising: (i) a 5'-terminal cap; (ii) a 5' UTR comprising a sequence selected from the group consisting of SEQ ID NO: 35-52, 109-111, and any combination thereof (iii) an open reading frame (ORF) encoding a human galactose-1-phosphate uridylyltransferase (GALT) polypeptide, wherein the ORF comprises a sequence selected from the group consisting of SEQ ID NOs: 5 to 29 and 113 to 131, wherein the mRNA comprises at least one chemically modified nucleobase selected from the group consisting of pseudouracil (ψ), N1-methylpseudouracil (m1ψ), 1-ethylpseudouracil, 2-thiouracil (s2U), 4'-thiouracil, 5-methylcytosine, 5-methyluracil, 5-methoxyuracil, and any combination thereof, and (iv) a 3' UTR comprising a nucleic acid sequence selected from the group consisting of SEQ ID NOs: 53 to 77, 79, 97, 98, 101 to 108, 112, and 163 to 173 and any combination thereof; and (v) a poly-A-region.

In some embodiments, the polynucleotide comprises an ORF comprising a nucleic acid sequence selected from SEQ ID NO: 124 or 126. In some embodiments, the polynucleotide comprises a nucleic acid sequence selected from SEQ ID NO: 143 or 145.

The present disclosure further provides a pharmaceutical composition comprising the polynucleotide and a delivery agent. In some embodiments, the delivery agent is a lipid nanoparticle comprising, e.g., a compound having the Formula (I), e.g., any of Compounds 1-232, e.g., Compound 18; a compound having the Formula (III), (IV), (V), or (VI), e.g., any of Compounds 233-342, e.g., Compound 236; or a compound having the Formula (VIII), e.g., any of Compounds 419-428, e.g., Compound 428, or any combination thereof. In some embodiments, the delivery agent is a lipid nanoparticle comprising Compound 18, Compound 236, a salt or a stereoisomer thereof, or any combination thereof. In some embodiments, the lipid nanoparticle or the delivery agent comprises Compound 18, DSPC, Cholesterol, and Compound 428, e.g., with a mole ratio of about 50:10:38.5:1.5.

In one aspect of the embodiments disclosed herein, the subject is a human subject in need of treatment or prophylaxis for galactosemia type 1 (Gal-1).

In one aspect of the embodiments disclosed herein, upon administration to the subject, the mRNA has: (i) a longer plasma half-life; (ii) increased expression of a GALT polypeptide encoded by the ORF; (iii) a lower frequency of arrested translation resulting in an expression fragment; (iv) greater structural stability; or (v) any combination thereof, relative to a corresponding mRNA having the nucleic acid sequence of SEQ ID NO: 2 or 4, and/or administered as naked mRNA.

In some embodiments, a pharmaceutical composition or polynucleotide disclosed herein is suitable for administration as a single unit dose or a plurality of single unit doses.

In some embodiments, a pharmaceutical composition or polynucleotide disclosed herein is suitable for reducing the level of one or more biomarkers of Gal-1 in the subject.

In some embodiments, a pharmaceutical composition or polynucleotide disclosed herein is for use in treating, preventing or delaying the onset of Gal-1 signs or symptoms in the subject. In some embodiments, the signs or symptoms include feeding difficulties, jaundice, hepatosplenomegaly, hepatocellular insufficiency, hypoglycemia, renal tubular dysfunction, muscle hypotonia, sepsis, cataracts, death, mental retardation, verbal dyspraxia, motor abnormalities, and hypergonadotropic hypogonadism, or a combination thereof.

The present disclosure also provides a host cell comprising the polynucleotide of the invention. In some embodiments, the host cell is a eukaryotic cell. The present disclosure also provides a vector comprising the polynucleotide of the invention. Also provided is a method of making a polynucleotide comprising enzymatically or chemically synthesizing the polynucleotide of the invention. The present disclosure also provides a polypeptide encoded by the polynucleotide of the invention, a composition comprising a polynucleotide of the invention, a host cell comprising a polynucleotide of the invention, or a vector comprising the polynucleotide of the invention or produced by the method disclosed herein.

The present disclosure also provides a method of expressing in vivo an active GALT polypeptide in a subject in need thereof comprising administering to the subject an effective amount of the polynucleotide of the invention, a composition comprising a polynucleotide of the invention, a host cell comprising a polynucleotide of the invention, or a vector comprising a polynucleotide of the invention. Also provided is a method of treating galactosemia type 1 (Gal-1) in a subject in need thereof comprising administering to the subject a therapeutically effective amount of the polynucleotide of the invention, a composition comprising a polynucleotide of the invention, a host cell comprising a polynucleotide of the invention, or a vector comprising the polynucleotide of the invention, wherein the administration alleviates the signs or symptoms of Gal-1 in the subject.

The present disclosure also provides a method to prevent or delay the onset of Gal-1 signs or symptoms in a subject in need thereof comprising administering to the subject a prophylactically effective amount of the polynucleotide of the invention, a composition comprising a polynucleotide of the invention, a host cell comprising a polynucleotide of the invention, or a vector comprising a polynucleotide of the invention before Gal-1 signs or symptoms manifest, wherein the administration prevents or delays the onset of Gal-1 signs or symptoms in the subject. Also provided is a method to ameliorate the signs or symptoms of Gal-1 in a subject in need thereof comprising administering to the subject a therapeutically effective amount of the polynucleotide of the invention, a composition comprising a polynucleotide of the invention, a host cell comprising a polynucleotide of the invention, or a vector comprising a polynucleotide of the invention before Gal-1 signs or symptoms manifest, wherein the administration ameliorates Gal-1 signs or symptoms in the subject.

The present disclosure further provides a method of expressing galactose-1-phosphate uridylytransferase (GALT) polypeptide in a human subject in need thereof comprising administering to the subject an effective amount of a pharmaceutical composition or a polynucleotide, e.g. an mRNA, described herein, wherein the pharmaceutical composition or polynucleotide is suitable for administrating as a single dose or as a plurality of single unit doses to the subject.

The present disclosure further provides a method of treating, preventing or delaying the onset of galactosemia type 1 (Gal-1) signs or symptoms in a human subject in need thereof comprising administering to the subject an effective amount of a pharmaceutical composition or a polynucleotide, e.g. an mRNA, described herein, wherein the administration treats, prevents or delays the onset of one or more of the signs or symptoms of Gal-1 in the subject.

The present disclosure further provides a method for the treatment of galactosemia type 1 (Gal-1), comprising administering to a human subject suffering from Gal-1 a single intravenous dose of a pharmaceutical composition or a polynucleotide described herein.

The present disclosure further provides a method of reducing a galactitol, galactonate, galactose, and/or 8-hydroxy-2-desoxyguanosine urinary, serum, and/or plasma level in a human subject comprising administering to the subject an effective amount of a pharmaceutical composition or a polynucleotide, e.g., an mRNA, described herein, wherein the administration reduces the galactitol, galactonate, galactose, and/or 8-hydroxy-2-desoxyguanosine urinary, serum, and/or plasma level in the subject. In some embodiments, (i) galactitol urinary, serum, and/or plasma level is reduced at least 20%, at least 30%, at least 40%, at least 50%, at least 60%, at least 70%, at least 80%, at least 90%, at least 95%, at least 100%, at least 2-fold, at least 5-fold, at least 10-fold, at least 20-fold, or at least 50-fold as compared to the subject's baseline galactitol urinary, serum, and/or plasma level or a reference galactitol urinary, serum, and/or plasma level, for at least 24 hours, at least 48 hours, at least 72 hours, at least 96 hours, or at least 120 hours post-administration, (ii) galactonate urinary, serum, and/or plasma level is reduced at least 20%, at least 30%, at least 40%, at least 50%, at least 60%, at least 70%, at least 80%, at least 90%, at least 95%, at least 100%, at least 2-fold, at least 5-fold, at least 10-fold, at least 20-fold, or at least 50-fold as compared to the subject's baseline galactonate urinary, serum, and/or plasma level or a reference galactonate urinary, serum, and/or plasma level, for at least 24 hours, at least 48 hours, at least 72 hours, at least 96 hours, or at least 120 hours post-administration, (iii) galactose urinary, serum, and/or plasma level is reduced at least 20%, at least 30%, at least 40%, at least 50%, at least 60%, at least 70%, at least 80%, at least 90%, at least 95%, at least 100%, at least 2-fold, at least 5-fold, at least 10-fold, at least 20-fold, or at least 50-fold as compared to the subject's baseline galactose urinary, serum, and/or plasma level or a reference galactose urinary, serum, and/or plasma level, for at least 24 hours, at least 48 hours, at least 72 hours, at least 96 hours, or at least 120 hours post-administration, and/or (iv) 8-hydroxy-2-desoxyguanosine urinary, serum, and/or plasma level is reduced at least 20%, at least 30%, at least 40%, at least 50%, at least 60%, at least 70%, at least 80%, at least 90%, at least 95%, at least 100%, at least 2-fold, at least 5-fold, at least 10-fold, at least 20-fold, or at least 50-fold as compared to the subject's baseline 8-hydroxy-2-desoxyguanosine urinary, serum, and/or plasma level or a reference 8-hydroxy-2-desoxyguanosine urinary, serum, and/or plasma level, for at least 24 hours, at least 48 hours, at least 72 hours, at least 96 hours, or at least 120 hours post-administration.

The present disclosure further provides a method of reducing a galactose-1-phosphate RBC and/or liver level in a human subject comprising administering to the subject an effective amount of a pharmaceutical composition or a polynucleotide described herein, wherein the administration reduces the galactose-1-phosphate RBC and/or liver level in the subject. In some embodiments, galactose-1-phosphate RBC and/or liver level is reduced to at least within at least within 20%, at least within 30%, at least within 40%, at least within 50%, at least within 60%, at least within 70%, at least within 80%, at least within 90%, at least within 95%, at least 100%, at least within 10-fold, at least within 5-fold, at least within 2-fold, or at least within 1.5-fold of normal physiological galactose-1-phosphate RBC and/or liver level or a reference galactose-1-phosphate RBC and/or liver level, e.g., within at least 24 hours, at least 48 hours, at least 72 hours, at least 96 hours, or at least 120 hours post-administration.

In some embodiments, 12 hours after the pharmaceutical composition or polynucleotide is administered to the subject, the GALT activity in the subject is increased at least 20%, at least 30%, at least 40%, at least 50%, at least 60%, at least 70%, at least 80%, at least 90%, at least 100%, at least 150%, at least 200%, at least 300%, at least 400%, at least 500%, or at least 600% compared to the subject's baseline GALT activity.

In some embodiments, the GALT activity is increased in the liver of the subject.

In some embodiments, the increased GALT activity persists for greater than 24, 36, 48, 60, 72, or 96 hours.

In some embodiments, the pharmaceutical composition or polynucleotide is administered to the subject the level of Gal-1-P in the subject is reduced by at least about 20%, at least about 30%, at least about 40%, at least about 50%, at least about 60%, at least about 70%, at least about 80%, at least about 90%, or 100% compared to the subject's baseline Gal-1-P.

In some embodiments, the level of Gal-1-P is reduced in the RBCs and/or liver of the subject.

In some embodiments, after the administration to the subject the level of Gal-1-P in the subject is reduced compared to the baseline level in the subject for at least one day, at least two days, at least three days, at least four days, at least five days, at least one week, at least two weeks, at least three weeks, or at least one month.

In some embodiments, after administration of the pharmaceutical composition or polynucleotide to the subject, e.g., within 24 hours, the level of galactitol in the subject is reduced by at least about 20%, at least about 30%, at least about 40%, at least about 50%, at least about 60%, at least about 70%, at least about 80%, at least about 90%, or 100% compared to the subject's baseline galactitol.

In some embodiments, the level of galactitol is reduced in one or more of the urine, serum, and/or plasma of the subject.

In some embodiments, after administration to the subject the level of galactitol in the subject is reduced compared to the baseline level in the subject for at least one day, at least two days, at least three days, at least four days, at least five days, at least one week, at least two weeks, at least three weeks, or at least one month.

In some embodiments, after administration of the pharmaceutical composition or polynucleotide to the subject, e.g., within 24 hours, the level of galactonate in the subject is reduced by at least about 20%, at least about 30%, at least about 40%, at least about 50%, at least about 60%, at least about 70%, at least about 80%, at least about 90%, or 100% compared to the subject's baseline galactonate.

In some embodiments, the level of galactonate is reduced in one or more of the urine, serum, and/or plasma of the subject.

In some embodiments, after administration to the subject the level of galactonate in the subject is reduced compared to the baseline level in the subject for at least one day, at least two days, at least three days, at least four days, at least five days, at least one week, at least two weeks, at least three weeks, or at least one month.

In some embodiments, after administration of the pharmaceutical composition or polynucleotide to the subject, e.g., within 24 hours, the level of 8-hydroxy-2-desoxyguanosine in the subject is reduced by at least about 20%, at least about 30%, at least about 40%, at least about 50%, at least about 60%, at least about 70%, at least about 80%, at least about 90%, or 100% compared to the subject's baseline 8-hydroxy-2-desoxyguanosine.

In some embodiments, the level of 8-hydroxy-2-desoxyguanosine is reduced in one or more of the urine, serum, and/or plasma of the subject.

In some embodiments, after administration to the subject the level of 8-hydroxy-2-desoxyguanosine in the subject is reduced compared to the baseline level in the subject for at least one day, at least two days, at least three days, at least four days, at least five days, at least one week, at least two weeks, at least three weeks, or at least one month.

In some embodiments, the pharmaceutical composition or polynucleotide is administered as a single dose of less than 1.5 mg/kg, less than 1.25 mg/kg, less than 1 mg/kg, or less than 0.75 mg/kg.

In some embodiments, the administration to the subject is about once a week, about once every two weeks, or about once a month.

In some embodiments, the pharmaceutical composition or polynucleotide is administered intravenously.

BRIEF DESCRIPTION OF THE DRAWINGS/FIGURES

FIGS. 1A, 1B, 1C, and 1D shows the protein sequence (FIG. 1A), table with domain features (FIG. 1B), graphic representation of domain structure (FIG. 1C), and nucleic acid sequence (FIG. 1D) of isoform 1 of GALT.

FIGS. 2A, 2B, 2C, and 2D shows the protein sequence (FIG. 2A), table with domain features (FIG. 2B), graphic representation of domain structure (FIG. 2C), and nucleic acid sequence (FIG. 2D) of isoform 2 of GALT. FIG. 2A also discloses SEQ ID NOS 178-179.

FIG. 3 shows uracil (U) metrics corresponding to wild type isoform 1 of GALT and 25 sequence optimized GALT polynucleotides. The column labeled "U content (%)" corresponds to the % $U_{TL}$ parameter. The column labeled "U Content v. WT (%)" corresponds to % $U_{WT}$. The column labeled "U Content v. Theoretical Minimum (%)" corresponds to % $U_{TM}$. The column labeled "UU pairs v. WT (%)" corresponds to % $UU_{WT}$.

FIG. 4 shows guanine (G) metrics corresponding to wild type isoform 1 of GALT and 25 sequence optimized GALT polynucleotides. The column labeled "G Content (%)" corresponds to % $G_{TL}$. The column labeled "G Content v. WT (%)" corresponds to % $G_{WT}$. The column labeled "G Content v. Theoretical Maximum (%)" corresponds to % $G_{TMX}$.

FIG. 5 shows cytosine (C) metrics corresponding to wild type isoform 1 of GALT and 25 sequence optimized GALT polynucleotides. The column labeled "C Content (%)" corresponds to % $C_{TL}$. The column labeled "C Content v. WT (%)" corresponds to % $C_{WT}$. The column labeled "C Content v. Theoretical Maximum (%)" corresponds to % $C_{TMX}$.

FIG. 6 shows guanine plus cytosine (G/C) metrics corresponding to wild type isoform 1 of GALT and 25 sequence optimized GALT polynucleotides. The column labeled "G/C Content (%)" corresponds to % $G/C_{TL}$. The column labeled "G/C Content v. WT (%)" corresponds to % $G/C_{WT}$. The column labeled "G/C Content v. Theoretical Maximum (%)" corresponds to % $G/C_{TMX}$.

FIG. 7 shows a comparison between the G/C compositional bias for codon positions 1, 2, 3 corresponding to the wild type isoform 1 of GALT and 25 sequence optimized GALT polynucleotides.

FIG. 8A is a Western blot showing GALT protein expression in normal fibroblasts (GM00637) and type 1 galactosemia patient fibroblasts (GM00638). The Western blot shows levels of GALT protein expression in normal and patient fibroblasts administered mRNA encoding either hGalt2, mGalt1, or mGalt2 ("overexpressed") and endogenous levels of GALT ("endogenous"). An mRNA encoding GFP was used as a control.

Figure 10A:
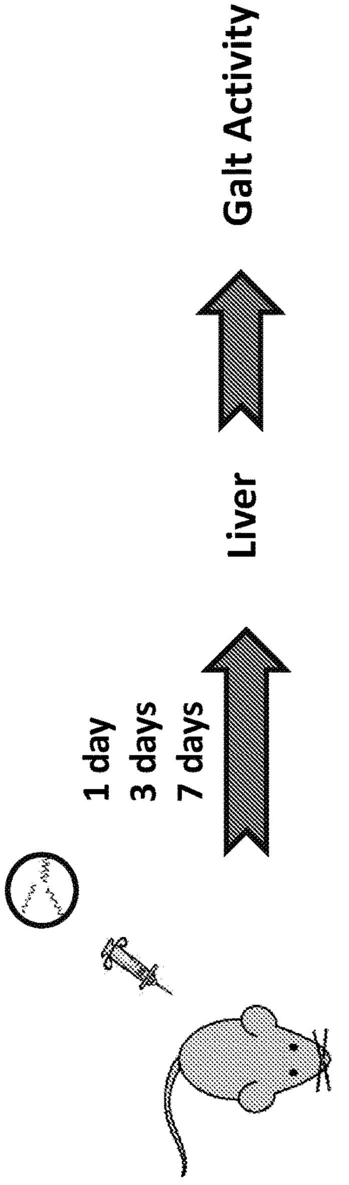

FIG. 10A is an experimental design diagram showing that wild-type mice were IV administered a single 0.3 mg/kg dose of mRNA encoding mouse Galt1 or a control mRNA encoding NTFIX (non-translated Factor IX), and GALT activity was measured in liver 1 day, 3 days, and 7 days post-administration.

Figure 10B:
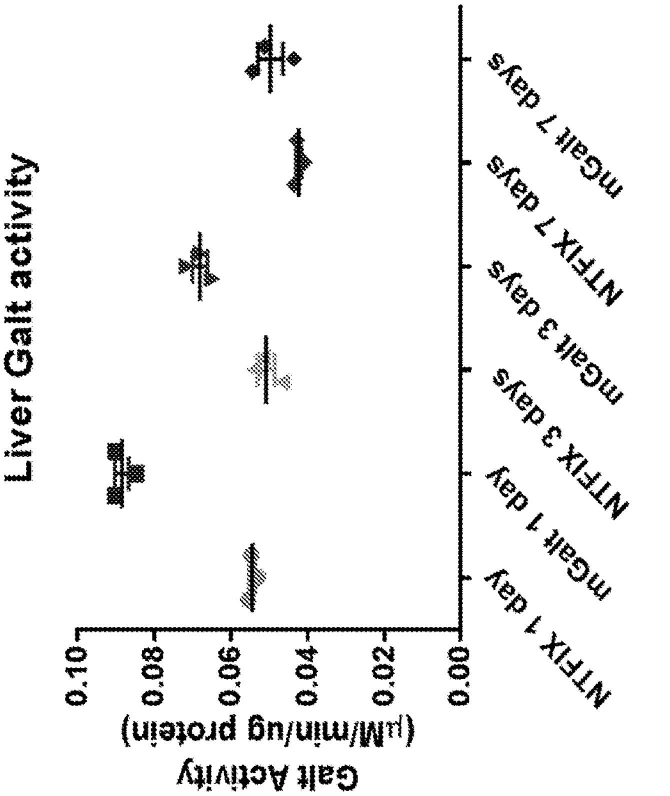

FIG. 10B shows GALT activity in liver 1 day, 3 days, and 7 days post-administration of a single 0.3 mg/kg dose of mRNA encoding mouse Galt1 to wild-type mice. mRNA encoding NTFIX was used as control.

Figure 11B:
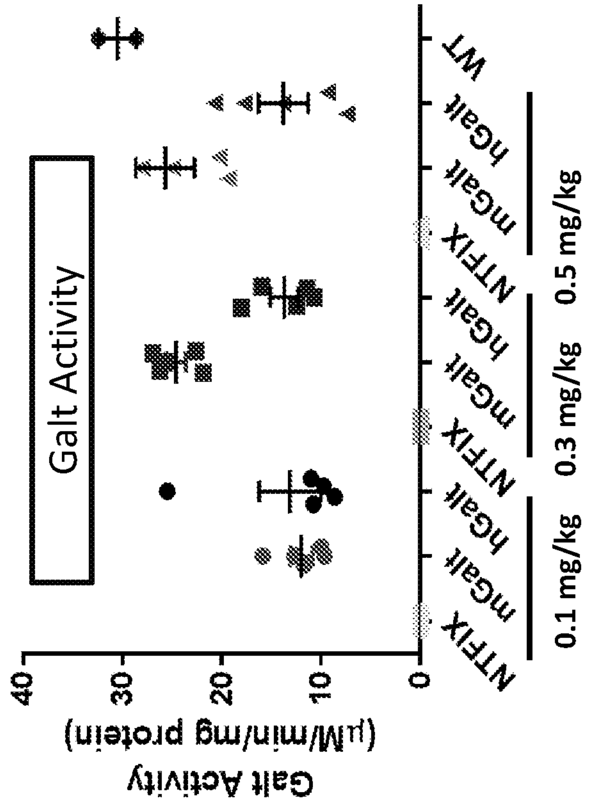
Figure 11A:
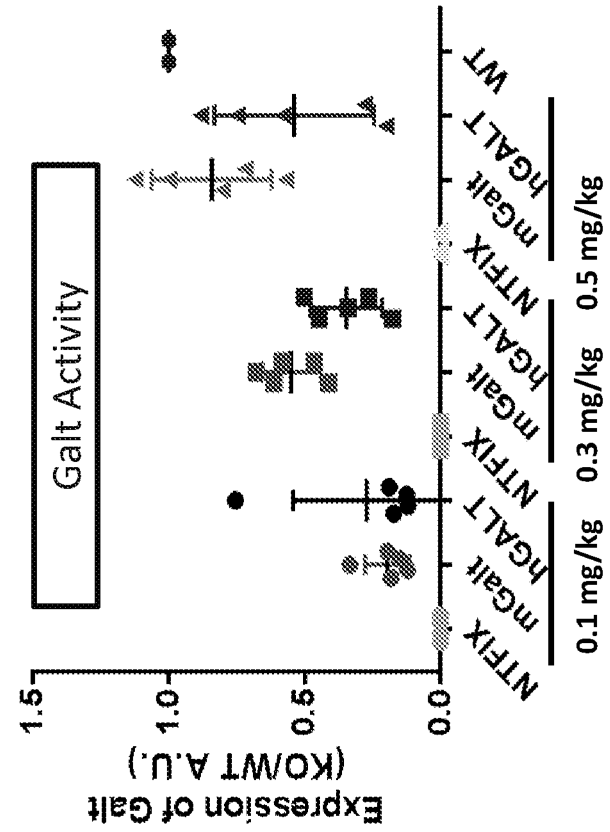

FIG. 11A shows protein expression levels of mouse GALT (mGalt1) and human GALT (hGalt1) in the liver 24 hours after administration of a single dose of 0.1 mg/kg, 0.3 mg/kg, or 0.5 mg/kg mRNA encoding mouse or human Galt1 to GALT knockout mice. mRNA encoding NTFIX was used as control. The expression levels were normalized to GALT protein expression in wild-type (WT) mice.

FIG. 11B shows GALT activity levels in the liver 24 hours after administration of a single dose of 0.1 mg/kg, 0.3 mg/kg, or 0.5 mg/kg mRNA encoding mouse or human Galt1 to GALT knockout mice. mRNA encoding NTFIX was used as control. Normal GALT activity level in wild-type (WT) mice in shown for comparison.

Figure 11D:
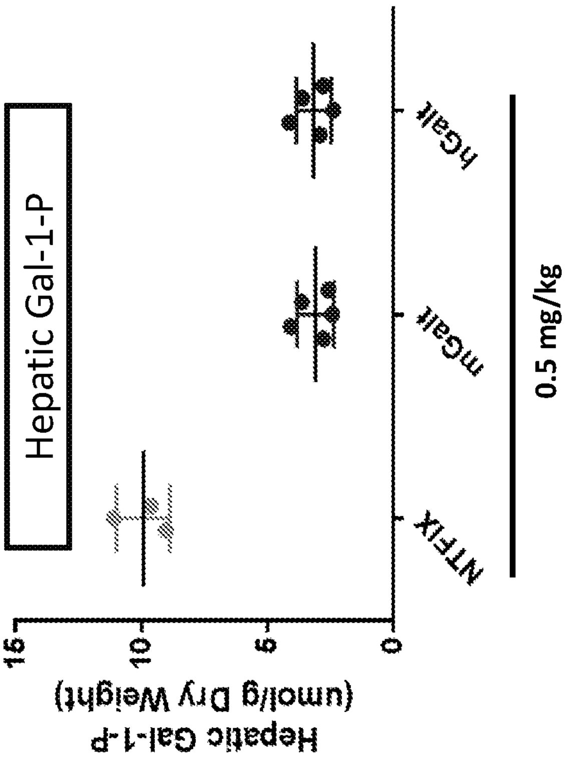
Figure 11C:
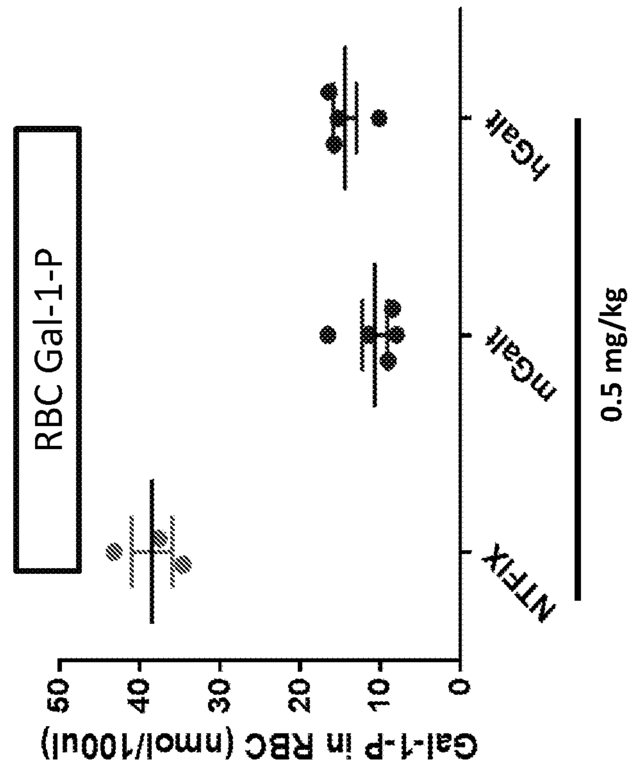

FIG. 11C shows galactose-1-phosphate (Gal-1-P) levels in red blood cells (RBC) from GALT knockout (KO) mice measured 24 hours after administration of a single dose of 0.5 mg/kg mRNA encoding mouse or human Galt1 to the KO mice. mRNA encoding NTFIX was used as control.

FIG. 11D shows galactose-1-phosphate (Gal-1-P) levels in liver from GALT knockout (KO) mice measured 24 hours after administration of a single dose of 0.5 mg/kg mRNA encoding mouse or human Galt1 to the KO mice. mRNA encoding NTFIX was used as control.

Figure 12A:
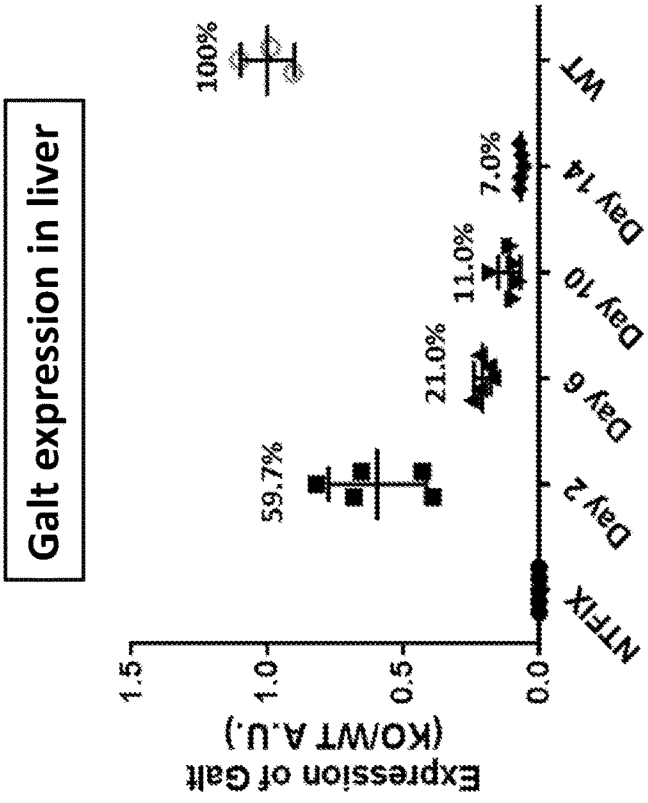

FIG. 12A shows expression levels of GALT protein in liver 2, 6, 10, and 14 days after a single administration of mRNA encoding mGalt1 to KO mice. The expression is normalized to endogenous GALT protein levels in WT mice. mRNA encoding NTFIX was used as control.

Figure 12B:
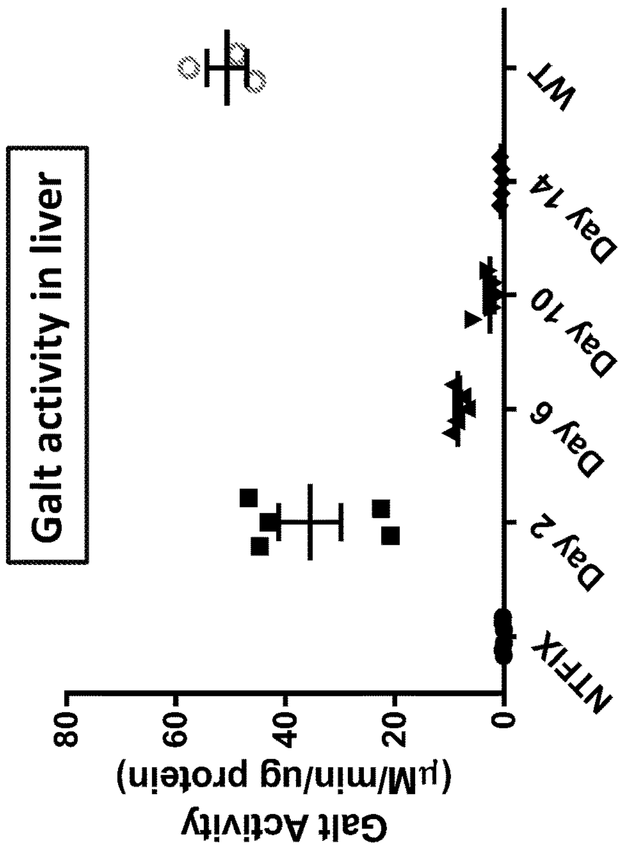

FIG. 12B shows activity levels of GALT in liver 2, 6, 10, and 14 days after a single administration of mRNA encoding mGalt1 to KO mice. KO mice injected with mRNA encoding NTFIX and wild-type (WT) mice were used as controls.

Figure 13C:
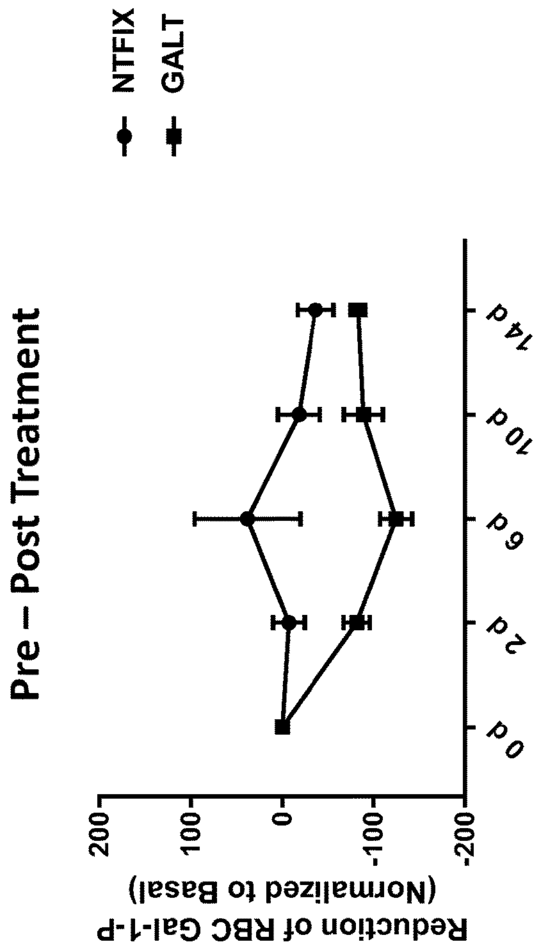
Figure 13A:
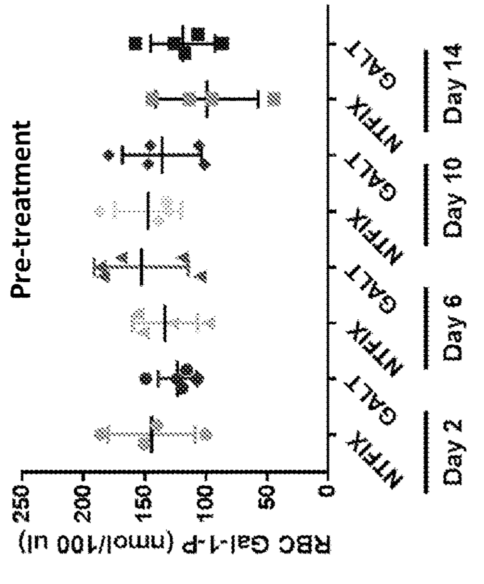

FIG. 13A shows galactose-1-phosphate (Gal-1-P) levels in red blood cells (RBC) prior to a single administration of mRNA encoding mGalt1 (pre-treatment) to KO mice. KO mice injected with mRNA encoding NTFIX and wild-type (WT) mice were used as controls.

Figure 13B:
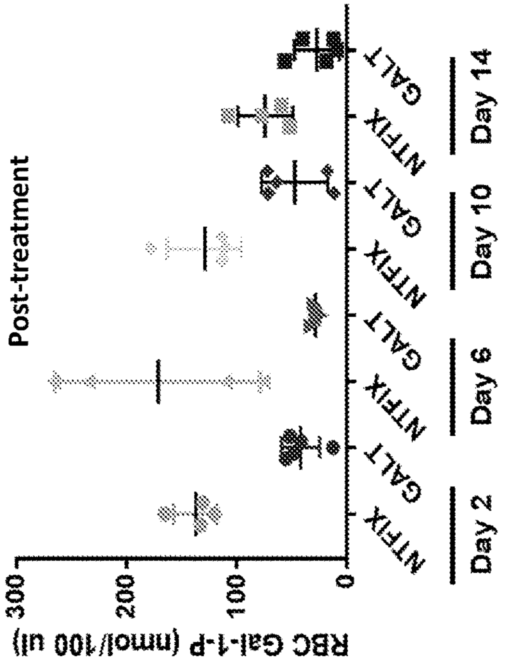

FIG. 13B shows galactose-1-phosphate (Gal-1-P) levels in red blood cells (RBC) 2, 6, 10, and 14 days after a single administration of mRNA encoding mGalt1 to KO mice. KO mice injected with mRNA encoding NTFIX and wild-type (WT) mice were used as controls.

FIG. 13C shows the difference between galactose-1-phosphate (Gal-1-P) levels prior to treatment (day 0) and post-treatment (2, 6, 10 and 14 days after administration) with a single intravenous injection of mRNA encoding mGalt1. KO mice injected with mRNA encoding NTFIX were used as controls.

Figure 14:
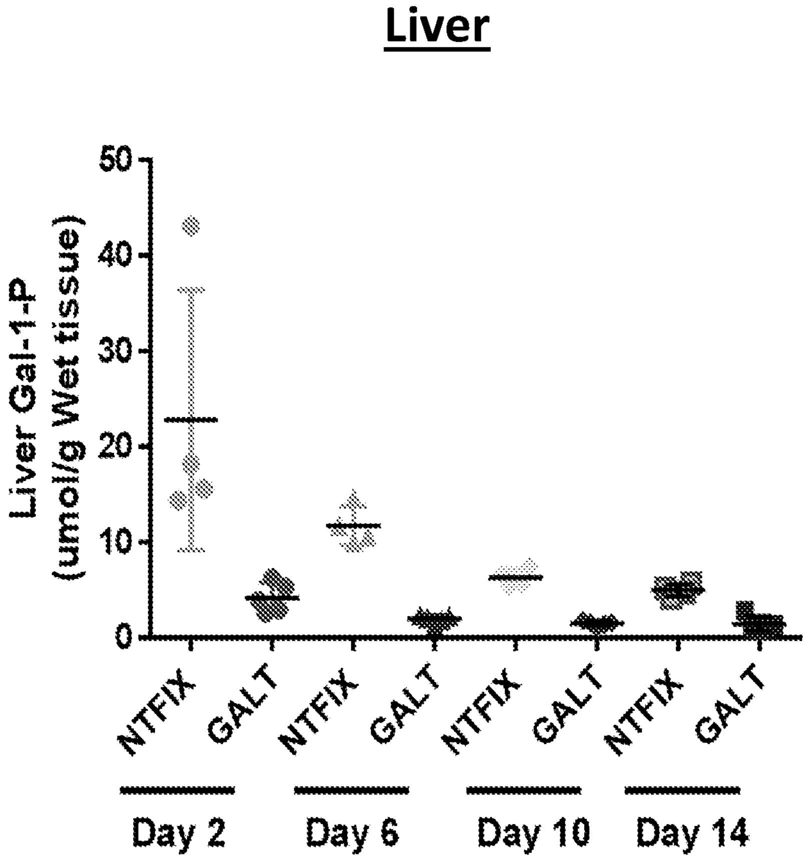

FIG. 14 shows galactose-1-phosphate (Gal-1-P) levels in liver 2, 6, 10, and 14 days after a single administration of mRNA encoding mGalt1 to KO mice. KO mice injected with mRNA encoding NTFIX was used as control.

Figure 15A:
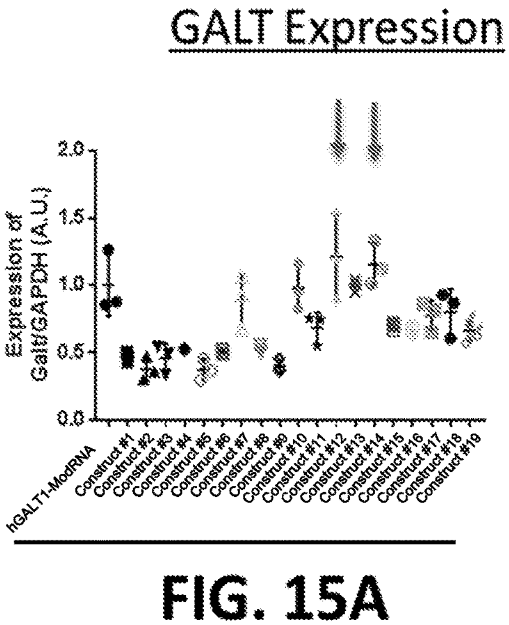

FIG. 15A shows relative GALT protein expression levels (Galt/GAPDH) in wild-type (CD1) mice 24 hours after IV administration of 0.5 mg/kg modified mRNA constructs encoding human Galt1 formulated in MC3 lipid nanoparticles (N=3/construct). Protein expression was determined by Western blot.

Figure 15B:
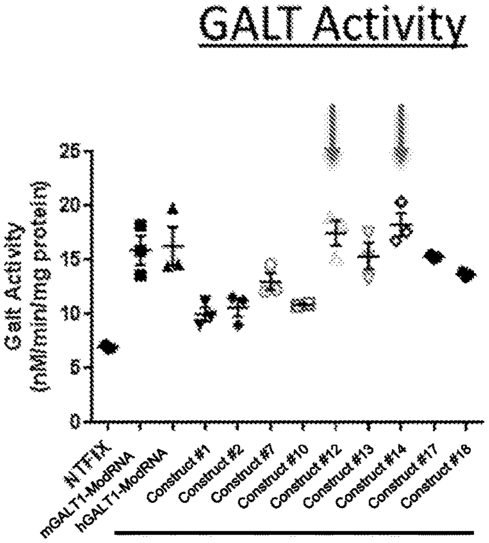

FIG. 15B shows GALT activity in wild-type (CD1) mice 24 hours after IV administration of 0.5 mg/kg modified mRNA constructs encoding human Galt1 formulated in MC3 lipid nanoparticles (N=3/construct). GALT activity was determined by HPLC.

Figure 15C:
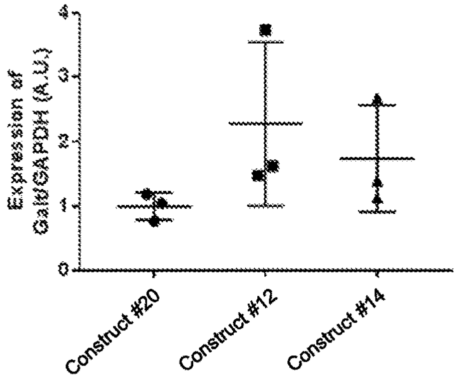

FIG. 15C shows relative GALT protein expression levels (Galt/GAPDH) in wild-type (CD1) mice 24 hours after IV administration of 0.5 mg/kg modified mRNA constructs encoding human Galt1 formulated in Compound 18 lipid nanoparticles (N=3/construct). Protein expression was determined by Western blot.

Figure 15D:
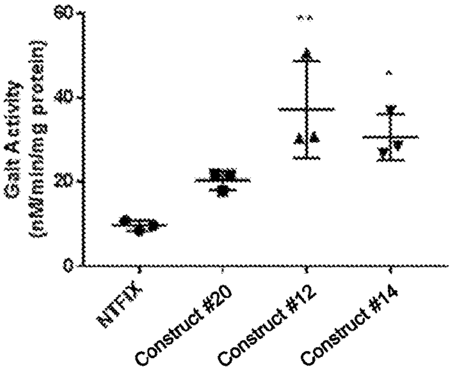

FIG. 15D shows GALT activity in wild-type (CD1) mice 24 hours after IV administration of 0.5 mg/kg modified mRNA constructs encoding human Galt1 formulated in Compound 18 lipid nanoparticles (N=3/construct). GALT activity was determined by HPLC.

Figure 16:
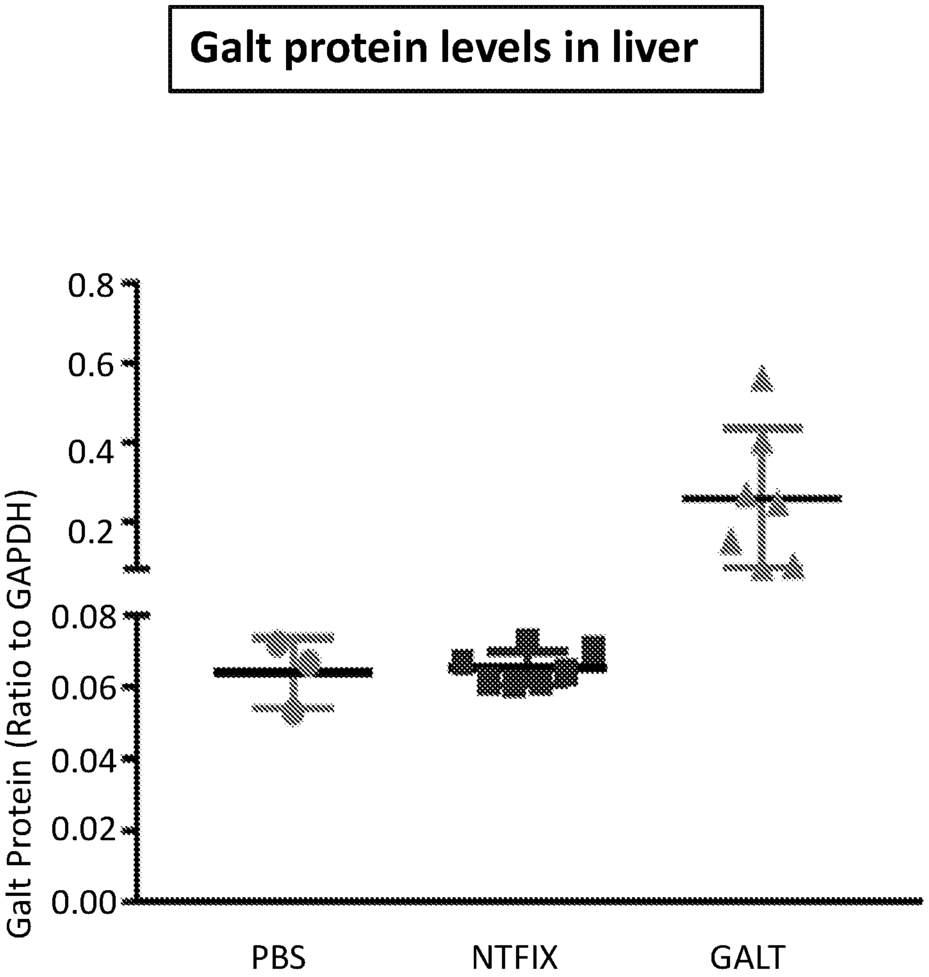

FIG. 16 shows GALT protein expression levels (ratio to GAPDH) in liver from GALT KO mice after administration of 4 tail vein intravenous doses of 0.2 mg/kg mRNA encoding human GALT (construct #12, n=8), mRNA encoding NTFIX (control, n=8), or PBS (n=3).

Figure 17A:
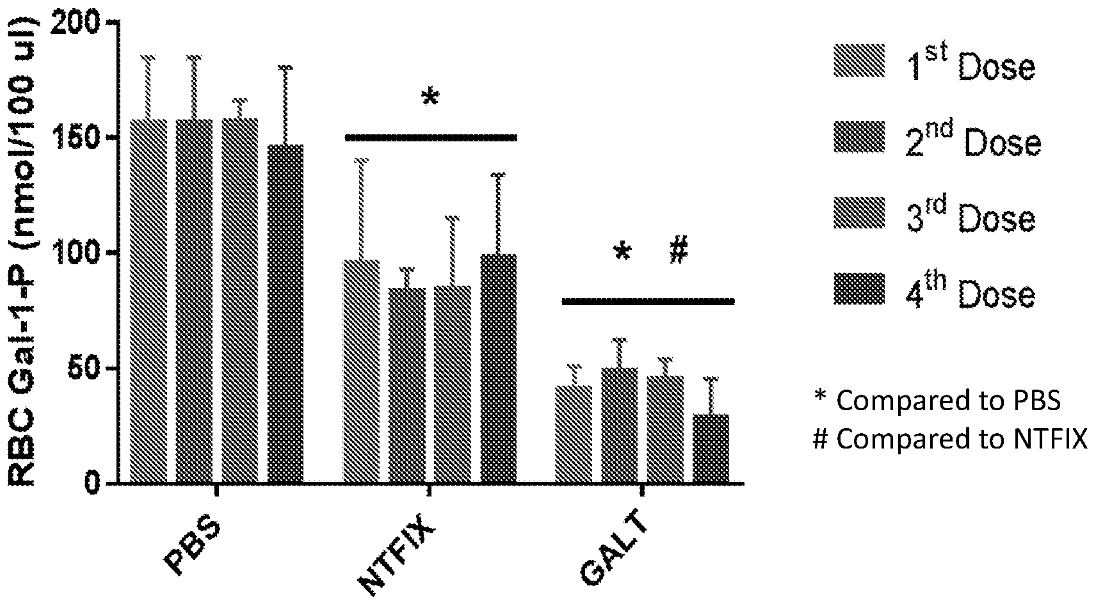
Figure 17B:
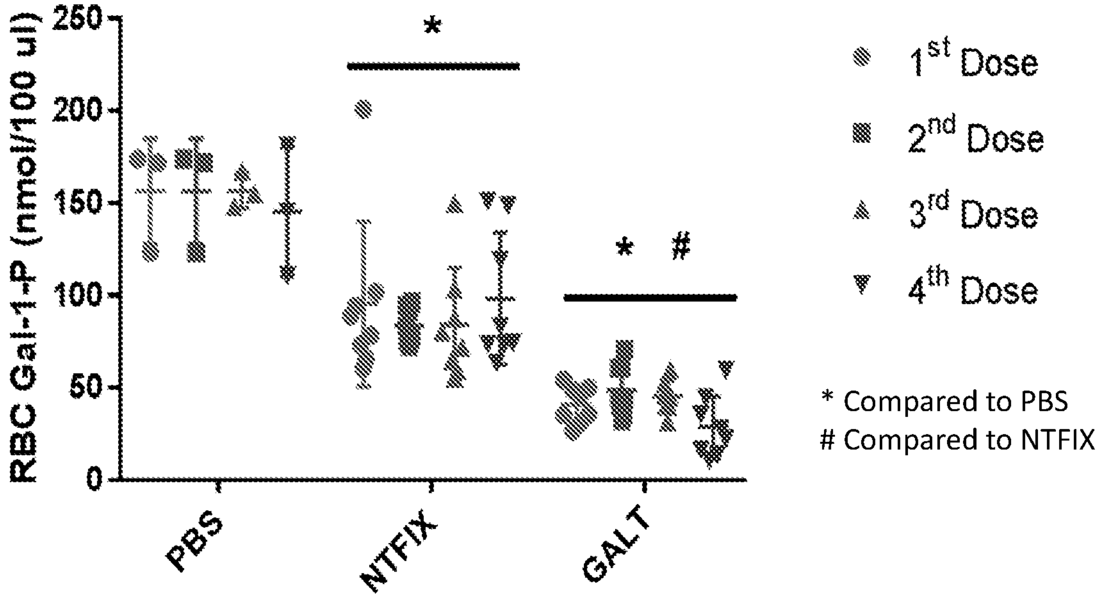
Figure 17C:
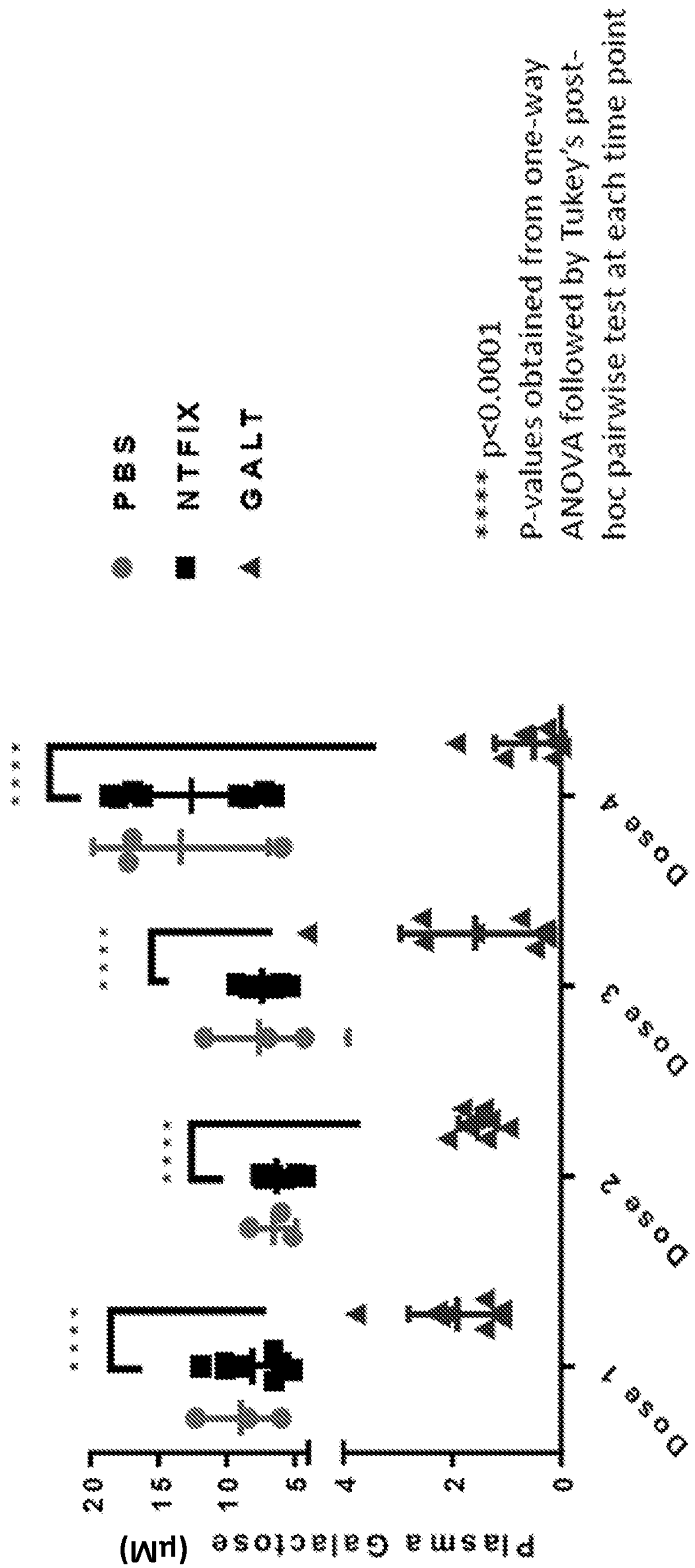

FIG. 17A, FIG. 17B, and FIG. 17C show galactose-1-phosphate (Gal-1-P) levels in red blood cells (RBC) as a group (FIG. 17A) and showing the data point for each mouse (FIG. 17B) and plasma galactose levels (FIG. 17C) from GALT KO mice after the $1^{st}$, $2^{nd}$, $3^{rd}$, and $4^{th}$ tail vein intravenous doses of 0.2 mg/kg mRNA encoding GALT (construct #12). mRNA encoding NTFIX was used as control.

Figure 18:
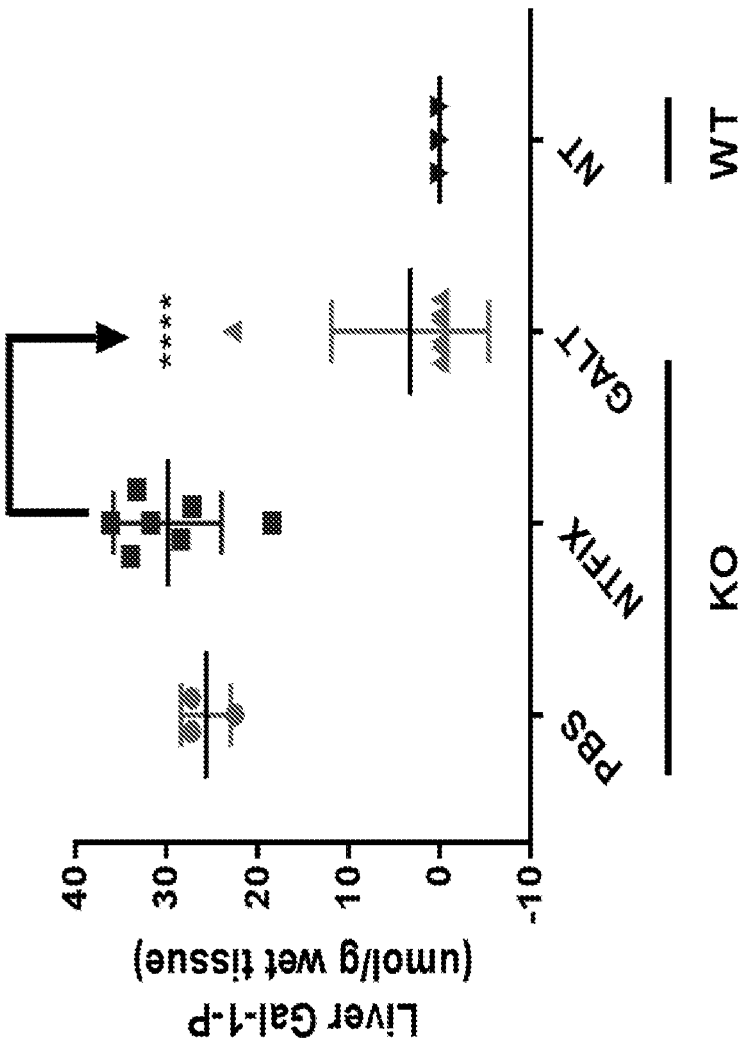

FIG. 18 show galactose-1-phosphate (Gal-1-P) levels in liver from GALT KO mice after administration of 4 tail vein intravenous doses of 0.2 mg/kg mRNA encoding human GALT (construct #12), mRNA encoding NTFIX (control), or PBS. Gal-1-P levels in the livers of non-treated animals (NT) are also shown.

Figure 19:
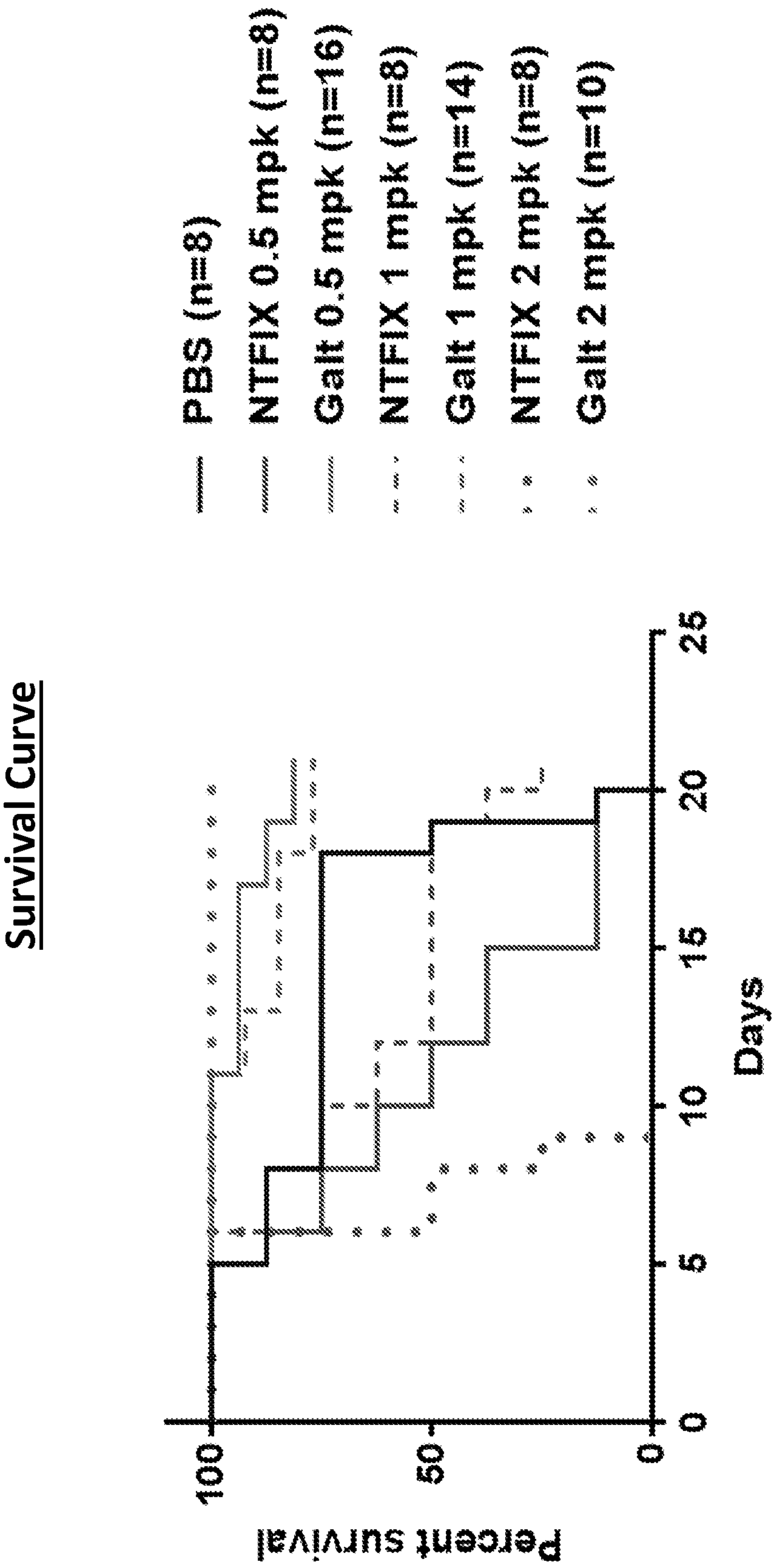

FIG. 19 shows a survival curve for neonatal GALT KO mice following administration of a single 0.5 mg/kg, 1 mg/kg, or 2 mg/kg intraperitoneal dose of mRNA encoding human Galt1 (construct #12) or control mRNA encoding NTFIX. The mRNA were formulated in Compound 18 lipid nanoparticle. PBS was used as a control.

Figure 20A:
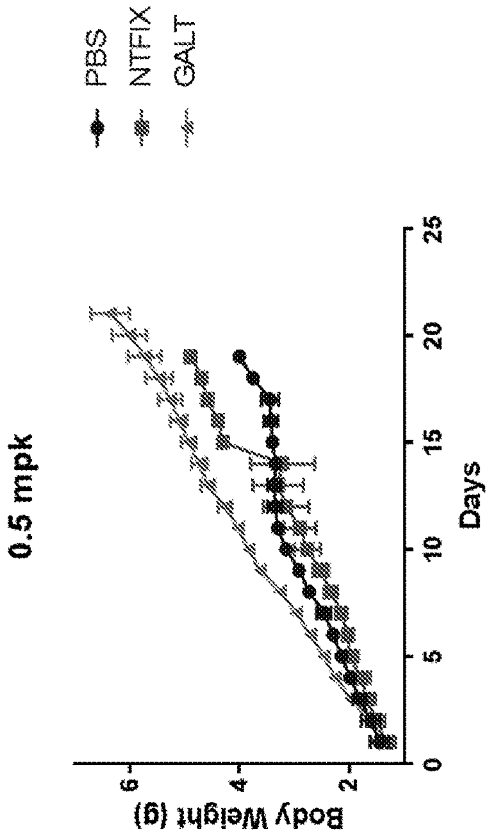
Figure 20B:
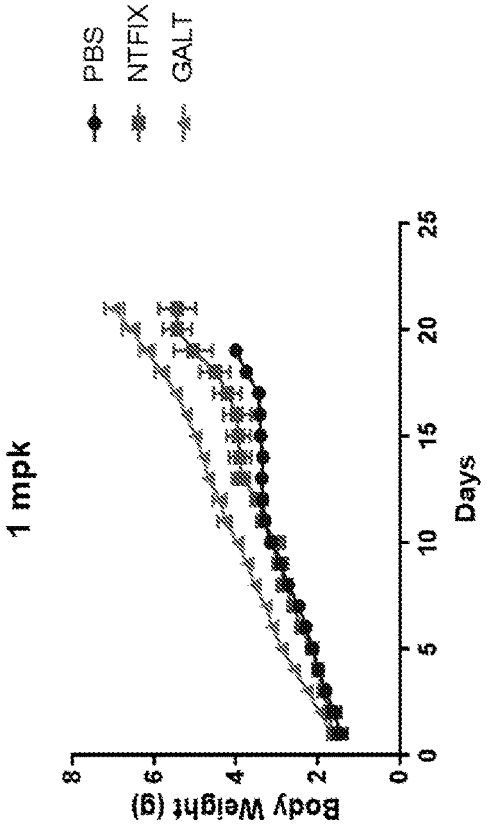
Figure 20C:
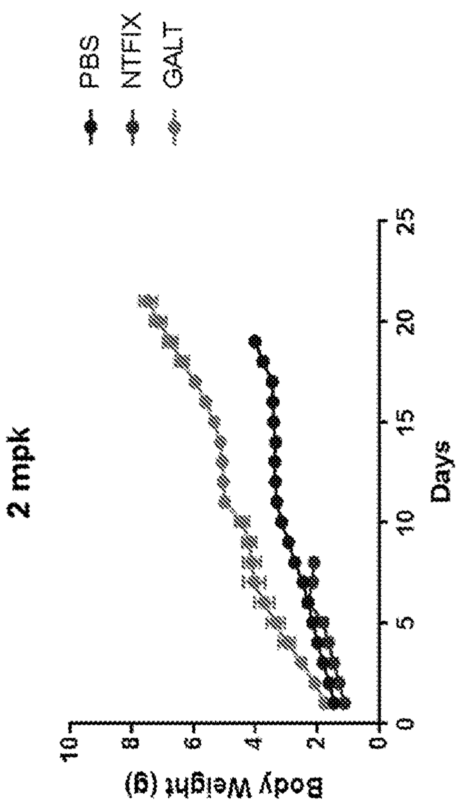

FIGS. 20A, 20B, and 20C show body weight in neonatal GALT KO mice administered a single 0.5 mg/kg (FIG. 20A), 1 mg/kg (FIG. 20B) or 2 mg/kg (FIG. 20C) intraperitoneal dose of mRNA encoding human Galt1 (construct #12) or control mRNA encoding NTFIX. The mRNA were formulated in Compound 18 lipid nanoparticle. PBS was used as a control.

DETAILED DESCRIPTION

The present invention provides mRNA therapeutics for the treatment of galactosemia type 1 (Gal-1). Gal-1 is a genetic metabolic disorder affecting the ability to metabolize galactose. Gal-1 is caused by mutations in the GALT gene, which codes for the enzyme galactose-1-phosphate uridylytransferase (GALT). Without galactose-1-phosphate uridylytransferase (GALT), the Leloir pathway of galactose metabolism is impaired, resulting in the abnormal accumulation of galactose. mRNA therapeutics are particularly well-suited for the treatment of Gal-1 as the technology provides for the intracellular delivery of mRNA encoding GALT followed by de novo synthesis of functional GALT protein within target cells. After delivery of mRNA to the target cells, the desired GALT protein is expressed by the cells' own translational machinery, and hence, fully functional GALT protein replaces the defective or missing protein.

One challenge associated with delivering nucleic acid-based therapeutics (e.g., mRNA therapeutics) in vivo stems from the innate immune response which can occur when the body's immune system encounters foreign nucleic acids. Foreign mRNAs can activate the immune system via recognition through toll-like receptors (TLRs), in particular TLR7/8, which is activated by single-stranded RNA (ssRNA). In nonimmune cells, the recognition of foreign mRNA can occur through the retinoic acid-inducible gene I (RIG-I). Immune recognition of foreign mRNAs can result in unwanted cytokine effects including interleukin-1β (IL-1β) production, tumor necrosis factor-α (TNF-α) distribution and a strong type I interferon (type I IFN) response. The instant invention features the incorporation of different modified nucleotides within therapeutic mRNAs to minimize the immune activation and optimize the translation efficiency of mRNA to protein. Particular aspects of the invention feature a combination of nucleotide modification to reduce the innate immune response and sequence optimization, in particular, within the open reading frame (ORF) of therapeutic mRNAs encoding GALT to enhance protein expression.

Certain embodiments of the mRNA therapeutic technology of the instant invention also features delivery of mRNA encoding GALT via a lipid nanoparticle (LNP) delivery system. Lipid nanoparticles (LNPs) are an ideal platform for the safe and effective delivery of mRNAs to target cells. LNPs have the unique ability to deliver nucleic acids by a mechanism involving cellular uptake, intracellular transport and endosomal release or endosomal escape. The instant invention features novel ionizable lipid-based LNPs combined with mRNA encoding GALT which have improved properties when administered in vivo. Without being bound in theory, it is believed that the novel ionizable lipid-based LNP formulations of the invention have improved properties, for example, cellular uptake, intracellular transport and/or endosomal release or endosomal escape. LNPs administered by systemic route (e.g., intravenous (IV) administration), for example, in a first administration, can accelerate the clearance of subsequently injected LNPs, for example, in further administrations. This phenomenon is known as accelerated blood clearance (ABC) and is a key challenge, in particular, when replacing deficient enzymes (e.g., GALT) in a therapeutic context. This is because repeat administration of mRNA therapeutics is in most instances essential to maintain necessary levels of enzyme in target tissues in subjects (e.g., subjects suffering from Gal-1.) Repeat dosing challenges can be addressed on multiple levels. mRNA engineering and/or efficient delivery by LNPs can result in increased levels and or enhanced duration of protein (e.g., GALT) being expressed following a first dose of administration, which in turn, can lengthen the time between first dose and subsequent dosing. It is known that the ABC phenomenon is, at least in part, transient in nature, with the immune responses underlying ABC resolving after sufficient time following systemic administration. As such, increasing the duration of protein expression and/or activity following systemic delivery of an mRNA therapeutic of the invention in one aspect, combats the ABC phenomenon. Moreover, LNPs can be engineered to avoid immune sensing and/or recognition and can thus further avoid ABC upon subsequent or repeat dosing. Exemplary aspect of the invention feature novel LNPs which have been engineered to have reduced ABC.

1. GALACTOSE-1-PHOSPHATE URIDYLYLTRANSFERASE (GALT)

Galactose-1-phosphate uridylyltransferase (GALT; EC 2.7.7.12) is the second enzyme of the Leloir pathway of galactose metabolism. GALT catalyzes the conversion of UDP-glucose and galactose 1-phosphate into glucose 1-phosphate and UDP-galactose. GALT exists as a dimer within the cell.

The most well-known health issue involving GALT is galactosemia type 1 (Gal-1), an autosomal recessive genetic disorder where insufficient galactose is metabolized, leading to a build-up of galactose in the cytoplasm. A variety of variant proteins have different levels of activity, with the severity of Gal-1 being correlated with the severity of the enzymes' mutations. Expression levels of GALT are also linked to Gal-1. For example, Duarte galactosemia is a milder form of Gal-1 in which patients express a functional GALT, though at lower levels because of mutations that lead to impaired GALT expression.

The coding sequence (CDS) for wild type GALT canonical mRNA sequence, corresponding to isoform 1, is described at the NCBI Reference Sequence database (RefSeq) under accession number NM_000155 ("*Homo sapiens* galactose-1-phosphate uridylyltransferase (GALT), transcript variant 1, mRNA"). The wild type GALT canonical protein sequence, corresponding to isoform 1, is described at the RefSeq database under accession number NP_000146 ("galactose-1-phosphate uridylyltransferase isoform 1 [*Homo sapiens*]"). The GALT isoform 1 protein is 379 amino acids long. It is noted that the specific nucleic acid sequences encoding the reference protein sequence in the Ref Seq sequences are the coding sequence (CDS) as indicated in the respective RefSeq database entry.

Isoform 2 is produced by alternative splicing. The RefSeq protein and mRNA sequences for isoform 2 of GALT are NP_001245261 and NM_001258332, respectively. Isoform 2 GALT is encoded by the CDS disclosed in each one of the above mentioned mRNA RefSeq entries. The isoform 2 polynucleotide contains an alternate N terminal sequence that encodes a shorter GALT than isoform 1. The GALT isoform 2 protein is 270 amino acids long, has alternative amino acids corresponding to positions 1-17 in isoform 1, and lacks the amino acids 18-126 in isoform 1.

In certain aspects, the invention provides a polynucleotide (e.g., a ribonucleic acid (RNA), e.g., a messenger RNA (mRNA)) comprising a nucleotide sequence (e.g., an open reading frame (ORF)) encoding a GALT polypeptide. In some embodiments, the GALT polypeptide of the invention is a wild type GALT isoform 1 or 2 protein. In some embodiments, the GALT polypeptide of the invention is a variant, a peptide or a polypeptide containing a substitution, and insertion and/or an addition, a deletion and/or a covalent modification with respect to a wild-type GALT isoform 1 or 2 sequence. In some embodiments, sequence tags or amino acids, can be added to the sequences encoded by the polynucleotides of the invention (e.g., at the N-terminal or C-terminal ends), e.g., for localization. In some embodiments, amino acid residues located at the carboxy, amino terminal, or internal regions of a polypeptide of the invention can optionally be deleted providing for fragments.

In some embodiments, the polynucleotide (e.g., a RNA, e.g., an mRNA) comprising a nucleotide sequence (e.g., an ORF) of the invention encodes a substitutional variant of a GALT isoform 1 or 2 sequence, which can comprise one, two, three or more than three substitutions. In some embodiments, the substitutional variant can comprise one or more conservative amino acids substitutions. In other embodiments, the variant is an insertional variant. In other embodiments, the variant is a deletional variant.

As recognized by those skilled in the art, GALT isoform 1 or 2 protein fragments, functional protein domains, variants, and homologous proteins (orthologs) are also considered to be within the scope of the GALT polypeptides of the invention. Nonlimiting examples of polypeptides encoded by the polynucleotides of the invention are shown in FIGS. 1 and 2. For example, FIG. 1 shows the amino acid sequence of human GALT wild type isoform 1.

Certain compositions and methods presented in this disclosure refer to the protein or polynucleotide sequences of GALT isoform 1. A person skilled in the art will understand that such disclosures are equally applicable to any other isoforms of GALT known in the art.

2. POLYNUCLEOTIDES AND OPEN READING FRAMES (ORFS)

The instant invention features mRNAs for use in treating (i.e., prophylactically and/or therapeutically treating) Gal-1. The mRNAs featured for use in the invention are administered to subjects and encode human galactose-1-phosphate uridylyltransferase (GALT) protein in vivo. Accordingly, the invention relates to polynucleotides, e.g., mRNA, comprising an open reading frame of linked nucleosides encoding human galactose-1-phosphate uridylyltransferase (GALT), isoforms thereof, functional fragments thereof, and fusion proteins comprising GALT. In some embodiments, the open reading frame is sequence-optimized. In particular embodiments, the invention provides sequence-optimized polynucleotides comprising nucleotides encoding the polypeptide sequence of isoforms 1 or 2 of human GALT, or sequence having high sequence identity with those sequence optimized polynucleotides.

In certain aspects, the invention provides polynucleotides (e.g., a RNA, e.g., an mRNA) that comprise a nucleotide sequence (e.g., an ORF) encoding one or more GALT polypeptides. In some embodiments, the encoded GALT polypeptide of the invention can be selected from:

(i) a full length GALT polypeptide (e.g., having the same or essentially the same length as wild-type GALT isoform 1 or 2);

(ii) a functional fragment of any of the GALT isoforms described herein (e.g., a truncated (e.g., deletion of carboxy, amino terminal, or internal regions) sequence shorter than one of wild-type isoforms 1 or 2; but still retaining GALT enzymatic activity);

(iii) a variant thereof (e.g., full length or truncated isoform 1 or 2 proteins in which one or more amino acids have been replaced, e.g., variants that retain all or most of the GALT activity of the polypeptide with respect to a reference isoform (such as any natural or artificial variants known in the art); or (iv) a fusion protein comprising (i) a full length GALT isoform 1 or 2 protein, a functional fragment or a variant thereof, and (ii) a heterologous protein.

In certain embodiments, the encoded GALT polypeptide is a mammalian GALT polypeptide, such as a human GALT polypeptide, a functional fragment or a variant thereof.

In some embodiments, the polynucleotide (e.g., a RNA, e.g., an mRNA) of the invention increases GALT protein expression levels and/or detectable GALT enzymatic activity levels in cells when introduced in those cells, e.g., by at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100%, compared to GALT protein expression levels and/or detectable GALT enzymatic activity levels in the cells prior to the administration of the polynucleotide of the invention. GALT protein expression levels and/or GALT enzymatic activity can be measured according to methods know in the art. In some embodiments, the polynucleotide is introduced to the cells in vitro. In some embodiments, the polynucleotide is introduced to the cells in vivo.

In some embodiments, the polynucleotides (e.g., a RNA, e.g., an mRNA) of the invention comprise a nucleotide sequence (e.g., an ORF) that encodes a wild-type human GALT, e.g., wild-type isoform 1 of human GALT (SEQ ID NO: 1, see FIG. 1) or wild-type isoform 2 of human GALT (SEQ ID NO: 3, see FIG. 2).

In some embodiments, the polynucleotide (e.g., a RNA, e.g., an mRNA) of the invention comprises a codon optimized nucleic acid sequence, wherein the open reading frame (ORF) of the codon optimized nucleic acid sequence is derived from a wild-type GALT sequence (e.g., wild-type isoforms 1 or 2). For example, for polynucleotides of invention comprising a sequence optimized ORF encoding GALT isoform 2, the corresponding wild type sequence is the native GALT isoform 2. Similarly, for an sequence optimized mRNA encoding a functional fragment of isoform 1, the corresponding wild type sequence is the corresponding fragment from GALT isoform 1.

In some embodiments, the polynucleotides (e.g., a RNA, e.g., an mRNA) of the invention comprise a nucleotide sequence encoding GALT isoform 1 having the full length sequence of human GALT isoform 1 (i.e., including the initiator methionine). In mature human GALT isoform 1, the initiator methionine can be removed to yield a "mature GALT" comprising amino acid residues of 2-379 of the translated product. The teachings of the present disclosure directed to the full sequence of human GALT (amino acids 1-379) are also applicable to the mature form of human GALT lacking the initiator methionine (amino acids 2-379). Thus, in some embodiments, the polynucleotides (e.g., a RNA, e.g., an mRNA) of the invention comprise a nucleotide sequence encoding GALT isoform 1 having the mature sequence of human GALT isoform 1 (i.e., lacking the initiator methionine). In some embodiments, the polynucleotide (e.g., a RNA, e.g., an mRNA) of the invention comprising a nucleotide sequence encoding GALT isoform 1 having the full length or mature sequence of human GALT isoform 1 is sequence optimized.

In some embodiments, the polynucleotides (e.g., a RNA, e.g., an mRNA) of the invention comprise a nucleotide sequence (e.g., an ORF) encoding a mutant GALT polypeptide. In some embodiments, the polynucleotides of the invention comprise an ORF encoding a GALT polypeptide that comprises at least one point mutation in the GALT sequence and retains GALT enzymatic activity. In some embodiments, the mutant GALT polypeptide has a GALT activity which is at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100% of the GALT activity of the corresponding wild-type GALT (i.e., the same GALT isoform but without the mutation(s)). In some embodiments, the polynucleotide (e.g., a RNA, e.g., an mRNA) of the invention comprising an ORF encoding a mutant GALT polypeptide is sequence optimized.

In some embodiments, the polynucleotide (e.g., a RNA, e.g., an mRNA) of the invention comprises a nucleotide sequence (e.g., an ORF) that encodes a GALT polypeptide with mutations that do not alter GALT enzymatic activity. Such mutant GALT polypeptides can be referred to as function-neutral. In some embodiments, the polynucleotide comprises an ORF that encodes a mutant GALT polypeptide comprising one or more function-neutral point mutations.

In some embodiments, the mutant GALT polypeptide has higher GALT enzymatic activity than the corresponding wild-type GALT. In some embodiments, the mutant GALT polypeptide has a GALT activity that is at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100% higher than the activity of the corresponding wild-type GALT (i.e., the same GALT isoform but without the mutation(s)).

In some embodiments, the polynucleotides (e.g., a RNA, e.g., an mRNA) of the invention comprise a nucleotide sequence (e.g., an ORF) encoding a functional GALT fragment, e.g., where one or more fragments correspond to a polypeptide subsequence of a wild type GALT polypeptide and retain GALT enzymatic activity. In some embodiments, the GALT fragment has a GALT activity which is at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100% of the GALT activity of the corresponding full length GALT. In some embodiments, the polynucleotides (e.g., a RNA, e.g., an mRNA) of the invention comprising an ORF encoding a functional GALT fragment is sequence optimized.

In some embodiments, the polynucleotide (e.g., a RNA, e.g., an mRNA) of the invention comprises a nucleotide sequence (e.g., an ORF) encoding a GALT fragment that has higher GALT enzymatic activity than the corresponding full length GALT. Thus, in some embodiments the GALT fragment has a GALT activity which is at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100% higher than the GALT activity of the corresponding full length GALT.

In some embodiments, the polynucleotide (e.g., a RNA, e.g., an mRNA) of the invention comprises a nucleotide sequence (e.g., an ORF) encoding a GALT fragment that is at least 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24% or 25% shorter than wild-type isoform 1 or 2 of GALT.

In some embodiments, the polynucleotide (e.g., a RNA, e.g., an mRNA) of the invention comprises a nucleotide sequence (e.g., an ORF) encoding a GALT polypeptide (e.g., the wild-type sequence, functional fragment, or variant thereof), wherein the nucleotide sequence is at least 70%, at least 75%, at least 80%, at least 85%, at least 90%, at least 95%, at least 96%, at least 97%, at least 98%, at least 99%, or 100% identical to the sequence of SEQ ID NO:2 or 4 (see, e.g., panel D in FIGS. 1 and 2, respectively).

In some embodiments, the polynucleotide (e.g., a RNA, e.g., an mRNA) of the invention comprises a nucleotide sequence (e.g., an ORF) encoding a GALT polypeptide (e.g., the wild-type sequence, functional fragment, or variant thereof), wherein the nucleotide sequence has at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to a sequence selected from the group consisting of SEQ ID NOs: 5 to 29 and 113 to 131. See TABLE 2.

In some embodiments, the polynucleotide (e.g., a RNA, e.g., an mRNA) of the invention comprises a nucleotide sequence (e.g., an ORF) encoding a GALT polypeptide (e.g., the wild-type sequence, functional fragment, or variant thereof), wherein the nucleotide sequence has 70% to 100%, 75% to 100%, 80% to 100%, 85% to 100%, 70% to 95%, 80% to 95%, 70% to 85%, 75% to 90%, 80% to 95%, 70% to 75%, 75% to 80%, 80% to 85%, 85% to 90%, 90% to 95%, or 95% to 100%, sequence identity to a sequence selected from the group consisting of SEQ ID NOs: 5 to 29 and 113 to 131. See TABLE 2.

In some embodiments, the polynucleotide (e.g., a RNA, e.g., an mRNA) of the invention comprises an ORF encoding a GALT polypeptide (e.g., the wild-type sequence, functional fragment, or variant thereof), wherein the polynucleotide comprises a nucleic acid sequence having 70% to 100%, 75% to 100%, 80% to 100%, 85% to 100%, 70% to 95%, 80% to 95%, 70% to 85%, 75% to 90%, 80% to 95%, 70% to 75%, 75% to 80%, 80% to 85%, 85% to 90%, 90% to 95%, or 95% to 100%, sequence identity to a sequence selected from the group consisting of SEQ ID NOs: 132-150 e.g., SEQ ID NO: 143 or 145. See TABLE 5.

In some embodiments, the polynucleotide (e.g., a RNA, e.g., an mRNA) of the invention comprises a nucleotide sequence (e.g., an ORF) encoding a GALT polypeptide (e.g., the wild-type sequence, functional fragment, or variant thereof), wherein the nucleotide sequence is at least 75%, at least 76%, at least 77%, at least 78%, at least 79%, least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to the sequence of SEQ ID NO:2 or 4 (see, e.g, panel D in FIGS. 1 and 2, respectively).

In some embodiments the polynucleotide (e.g., a RNA, e.g., an mRNA) of the invention comprises a nucleotide sequence (e.g., an ORF) encoding a GALT polypeptide (e.g., the wild-type sequence, functional fragment, or variant thereof), wherein the nucleotide sequence is between 70% and 90% identical; between 75% and 85% identical; between 76% and 84% identical; between 77% and 83% identical, between 77% and 82% identical, or between 78% and 81% identical to the sequence of SEQ ID NO:2 or 4 (see, e.g., panel D in FIGS. 1 and 2, respectively).

In some embodiments, the polynucleotide (e.g., a RNA, e.g., an mRNA) of the invention comprises from about 900 to about 100,000 nucleotides (e.g., from 900 to 1,000, from 900 to 1,100, from 900 to 1,200, from 900 to 1,300, from 900 to 1,400, from 900 to 1,500, from 1,000 to 1,100, from 1,000 to 1,100, from 1,000 to 1,200, from 1,000 to 1,300, from 1,000 to 1,400, from 1,000 to 1,500, from 1,187 to 1,200, from 1,187 to 1,400, from 1,187 to 1,600, from 1,187 to 1,800, from 1,187 to 2,000, from 1,187 to 3,000, from 1,187 to 5,000, from 1,187 to 7,000, from 1,187 to 10,000, from 1,187 to 25,000, from 1,187 to 50,000, from 1,187 to 70,000, or from 1,187 to 100,000).

In some embodiments, the polynucleotide of the invention (e.g., a RNA, e.g., an mRNA) comprises a nucleotide sequence (e.g., an ORF) encoding a GALT polypeptide (e.g., the wild-type sequence, functional fragment, or variant thereof), wherein the length of the nucleotide sequence (e.g., an ORF) is at least 500 nucleotides in length (e.g., at least or greater than about 500, 600, 700, 80, 900, 1,000, 1,050, 1,100, 1,187, 1,200, 1,300, 1,400, 1,500, 1,600, 1,700, 1,800, 1,900, 2,000, 2,100, 2,200, 2,300, 2,400, 2,500, 2,600, 2,700, 2,800, 2,900, 3,000, 3,100, 3,200, 3,300, 3,400, 3,500, 3,600, 3,700, 3,800, 3,900, 4,000, 4,100, 4,200, 4,300, 4,400, 4,500, 4,600, 4,700, 4,800, 4,900, 5,000, 5,100, 5,200, 5,300, 5,400, 5,500, 5,600, 5,700, 5,800, 5,900, 6,000, 7,000, 8,000, 9,000, 10,000, 20,000, 30,000, 40,000, 50,000, 60,000, 70,000, 80,000, 90,000 or up to and including 100,000 nucleotides).

In some embodiments, the polynucleotide of the invention (e.g., a RNA, e.g., an mRNA) comprises a nucleotide sequence (e.g., an ORF) encoding a GALT polypeptide (e.g., the wild-type sequence, functional fragment, or variant thereof) further comprises at least one nucleic acid sequence that is noncoding, e.g., a microRNA binding site. In some embodiments, the polynucleotide (e.g., a RNA, e.g., an mRNA) of the invention further comprises a 5'-UTR (e.g., selected from the sequences of SEQ ID NOs: 35-52 and 109-111) and a 3'UTR (e.g., selected from the sequences of SEQ ID NOs: 53 to 77, 79, 97, 98, 101 to 108, 112, and 163 to 173). In some embodiments, the polynucleotide (e.g., a RNA, e.g., an mRNA) of the invention comprises a sequence selected from the group consisting of SEQ ID NOs: 132-150, e.g., SEQ ID NO: 143 or 145. In a further embodiment, the polynucleotide (e.g., a RNA, e.g., an mRNA) comprises a 5' terminal cap (e.g., Cap0, Cap1, ARCA, inosine, N1-methyl-guanosine, 2'-fluoro-guanosine, 7-deaza-guanosine, 8-oxo-guanosine, 2-amino-guanosine, LNA-guanosine, 2-azidoguanosine, Cap2, Cap4, 5' methylG cap, or an analog thereof) and a poly-A-tail region (e.g., about 100 nucleotides in length). In a further embodiment, the polynucleotide (e.g., a RNA, e.g., an mRNA) a comprises a 3' UTR comprising a nucleic acid sequence selected from the group consisting of SEQ ID NOs: 98, 163, or 164 or any combination thereof. In some embodiments, the mRNA comprises a 3' UTR comprising a nucleic acid sequence of SEQ ID NO: 163. In some embodiments, the mRNA comprises a 3' UTR comprising a nucleic acid sequence of SEQ ID NO: 164.

In some embodiments, the polynucleotide of the invention (e.g., a RNA, e.g., an mRNA) comprises a nucleotide sequence (e.g., an ORF) encoding a GALT polypeptide is single stranded or double stranded.

In some embodiments, the polynucleotide of the invention comprising a nucleotide sequence (e.g., an ORF) encoding a GALT polypeptide (e.g., the wild-type sequence, functional fragment, or variant thereof) is DNA or RNA. In some embodiments, the polynucleotide of the invention is RNA. In some embodiments, the polynucleotide of the invention is, or functions as, a messenger RNA (mRNA). In some embodiments, the mRNA comprises a nucleotide sequence (e.g., an ORF) that encodes at least one GALT polypeptide, and is capable of being translated to produce the encoded GALT polypeptide in vitro, in vivo, in situ or ex vivo.

In some embodiments, the polynucleotide of the invention (e.g., a RNA, e.g., an mRNA) comprises a sequence-optimized nucleotide sequence (e.g., an ORF) encoding a GALT polypeptide (e.g., the wild-type sequence, functional fragment, or variant thereof), wherein the polynucleotide comprises at least one chemically modified nucleobase, e.g., 5-methoxyuracil. In some embodiments, the polynucleotide further comprises a miRNA binding site, e.g., a miRNA binding site that binds to miR-142 and/or a miRNA binding site that binds to miR-126. In some embodiments, the polynucleotide (e.g., a RNA, e.g., a mRNA) disclosed herein is formulated with a delivery agent comprising, e.g., a compound having the Formula (I), e.g., any of Compounds 1-232, e.g., Compound 18; a compound having the Formula (III), (IV), (V), or (VI), e.g., any of Compounds 233-342, e.g., Compound 236; or a compound having the Formula (VIII), e.g., any of Compounds 419-428, e.g., Compound 428, or any combination thereof. In some embodiments, the delivery agent comprises Compound 18, DSPC, Cholesterol, and Compound 428, e.g., with a mole ratio of about 50:10:38.5:1.5.

3. SIGNAL SEQUENCES

The polynucleotides (e.g., a RNA, e.g., an mRNA) of the invention can also comprise nucleotide sequences that encode additional features that facilitate trafficking of the encoded polypeptides to therapeutically relevant sites. One such feature that aids in protein trafficking is the signal sequence, or targeting sequence. The peptides encoded by these signal sequences are known by a variety of names, including targeting peptides, transit peptides, and signal peptides. In some embodiments, the polynucleotide (e.g., a RNA, e.g., an mRNA) comprises a nucleotide sequence (e.g., an ORF) that encodes a signal peptide operably linked to a nucleotide sequence that encodes a GALT polypeptide described herein.

In some embodiments, the "signal sequence" or "signal peptide" is a polynucleotide or polypeptide, respectively, which is from about 9 to 200 nucleotides (3(i) 70 amino acids) in length that, optionally, is incorporated at the 5' (or N-terminus) of the coding region or the polypeptide, respectively. Addition of these sequences results in trafficking the encoded polypeptide to a desired site, such as the endoplasmic reticulum or the mitochondria through one or more targeting pathways. Some signal peptides are cleaved from the protein, for example by a signal peptidase after the proteins are transported to the desired site.

In some embodiments, the polynucleotide of the invention comprises a nucleotide sequence encoding a GALT polypeptide, wherein the nucleotide sequence further comprises a 5' nucleic acid sequence encoding a heterologous signal peptide.

4. FUSION PROTEINS

In some embodiments, the polynucleotide of the invention (e.g., a RNA, e.g., an mRNA) can comprise more than one nucleic acid sequence (e.g., an ORF) encoding a polypeptide of interest. In some embodiments, polynucleotides of the invention comprise a single ORF encoding a GALT polypeptide, a functional fragment, or a variant thereof. However, in some embodiments, the polynucleotide of the invention can comprise more than one ORF, for example, a first ORF encoding a GALT polypeptide (a first polypeptide of interest), a functional fragment, or a variant thereof, and a second ORF expressing a second polypeptide of interest. In some embodiments, two or more polypeptides of interest can be genetically fused, i.e., two or more polypeptides can be encoded by the same ORF. In some embodiments, the polynucleotide can comprise a nucleic acid sequence encoding a linker (e.g., a G45 peptide linker (SEQ ID NO: 174) or another linker known in the art) between two or more polypeptides of interest.

In some embodiments, a polynucleotide of the invention (e.g., a RNA, e.g., an mRNA) can comprise two, three, four, or more ORFs, each expressing a polypeptide of interest.

In some embodiments, the polynucleotide of the invention (e.g., a RNA, e.g., an mRNA) can comprise a first nucleic acid sequence (e.g., a first ORF) encoding a GALT polypeptide and a second nucleic acid sequence (e.g., a second ORF) encoding a second polypeptide of interest.

5. SEQUENCE OPTIMIZATION OF NUCLEOTIDE SEQUENCE ENCODING A GALT POLYPEPTIDE

In some embodiments, the polynucleotide (e.g., a RNA, e.g., an mRNA) of the invention is sequence optimized. In some embodiments, the polynucleotide (e.g., a RNA, e.g., an mRNA) of the invention comprises a nucleotide sequence (e.g., an ORF) encoding a GALT polypeptide, a nucleotide sequence (e.g, an ORF) encoding another polypeptide of interest, a 5'-UTR, a 3'-UTR, a microRNA binding site, a nucleotide sequence encoding a linker, or any combination thereof) that is sequence optimized.

A sequence-optimized nucleotide sequence, e.g., a codon-optimized mRNA sequence encoding a GALT polypeptide, is a sequence comprising at least one synonymous nucleobase substitution with respect to a reference sequence (e.g., a wild type nucleotide sequence encoding a GALT polypeptide).

A sequence-optimized nucleotide sequence can be partially or completely different in sequence from the reference sequence. For example, a reference sequence encoding polyserine uniformly encoded by TCT codons can be sequence-optimized by having 100% of its nucleobases substituted (for each codon, T in position 1 replaced by A, C in position 2 replaced by G, and T in position 3 replaced by C) to yield a sequence encoding polyserine which would be uniformly encoded by AGC codons. The percentage of sequence identity obtained from a global pairwise alignment between the reference polyserine nucleic acid sequence and the sequence-optimized polyserine nucleic acid sequence would be 0%. However, the protein products from both sequences would be 100% identical.

Some sequence optimization (also sometimes referred to codon optimization) methods are known in the art (and discussed in more detail below) and can be useful to achieve one or more desired results. These results can include, e.g., matching codon frequencies in certain tissue targets and/or host organisms to ensure proper folding; biasing G/C content to increase mRNA stability or reduce secondary structures; minimizing tandem repeat codons or base runs that can impair gene construction or expression; customizing transcriptional and translational control regions; inserting or removing protein trafficking sequences; removing/adding post translation modification sites in an encoded protein (e.g., glycosylation sites); adding, removing or shuffling protein domains; inserting or deleting restriction sites; modifying ribosome binding sites and mRNA degradation sites; adjusting translational rates to allow the various domains of the protein to fold properly; and/or reducing or eliminating problem secondary structures within the polynucleotide. Sequence optimization tools, algorithms and services are known in the art, non-limiting examples include services from GeneArt (Life Technologies), DNA2.0 (Menlo Park Calif.) and/or proprietary methods.

Codon options for each amino acid are given in TABLE 1.

TABLE 1

Codon Options

| Amino Acid | Single Letter Code | Codon Options |
|---|---|---|
| Isoleucine | I | ATT, ATC, ATA |
| Leucine | L | CTT, CTC, CTA, CTG, TTA, TTG |
| Valine | V | GTT, GTC, GTA, GTG |
| Phenylalanine | F | TTT, TTC |
| Methionine | M | ATG |
| Cysteine | C | TGT, TGC |
| Alanine | A | GCT, GCC, GCA, GCG |
| Glycine | G | GGT, GGC, GGA, GGG |
| Proline | P | CCT, CCC, CCA, CCG |
| Threonine | T | ACT, ACC, ACA, ACG |
| Serine | S | TCT, TCC, TCA, TCG, AGT, AGC |
| Tyrosine | Y | TAT, TAC |
| Tryptophan | W | TGG |
| Glutamine | Q | CAA, CAG |
| Asparagine | N | AAT, AAC |
| Histidine | H | CAT, CAC |
| Glutamic acid | E | GAA, GAG |
| Aspartic acid | D | GAT, GAC |
| Lysine | K | AAA, AAG |
| Arginine | R | CGT, CGC, CGA, CGG, AGA, AGG |
| Selenocysteine | Sec | UGA in mRNA in presence of Seleno-cysteine insertion element (SECIS) |
| Stop codons | Stop | TAA, TAG, TGA |

In some embodiments, a polynucleotide (e.g., a RNA, e.g., an mRNA) of the invention comprises a sequence-optimized nucleotide sequence (e.g., an ORF) encoding a GALT polypeptide, a functional fragment, or a variant thereof, wherein the GALT polypeptide, functional fragment, or a variant thereof encoded by the sequence-optimized nucleotide sequence has improved properties (e.g., compared to a GALT polypeptide, functional fragment, or a variant thereof encoded by a reference nucleotide sequence that is not sequence optimized), e.g., improved properties related to expression efficacy after administration in vivo. Such properties include, but are not limited to, improving nucleic acid stability (e.g., mRNA stability), increasing translation efficacy in the target tissue, reducing the number of truncated proteins expressed, improving the folding or prevent misfolding of the expressed proteins, reducing toxicity of the expressed products, reducing cell death caused by the expressed products, increasing and/or decreasing protein aggregation.

In some embodiments, the sequence-optimized nucleotide sequence is codon optimized for expression in human subjects, having structural and/or chemical features that avoid one or more of the problems in the art, for example, features which are useful for optimizing formulation and delivery of nucleic acid-based therapeutics while retaining structural and functional integrity; overcoming a threshold of expression; improving expression rates; half-life and/or protein concentrations; optimizing protein localization; and avoiding deleterious bio-responses such as the immune response and/or degradation pathways.

In some embodiments, the polynucleotides of the invention comprise a nucleotide sequence (e.g., a nucleotide sequence (e.g, an ORF) encoding a GALT polypeptide, a nucleotide sequence (e.g, an ORF) encoding another polypeptide of interest, a 5'-UTR, a 3'-UTR, a microRNA binding site, a nucleic acid sequence encoding a linker, or any combination thereof) that is sequence-optimized according to a method comprising:

(i) substituting at least one codon in a reference nucleotide sequence (e.g., an ORF encoding a GALT polypeptide) with an alternative codon to increase or decrease uridine content to generate a uridine-modified sequence;

(ii) substituting at least one codon in a reference nucleotide sequence (e.g., an ORF encoding a GALT polypeptide) with an alternative codon having a higher codon frequency in the synonymous codon set;

(iii) substituting at least one codon in a reference nucleotide sequence (e.g., an ORF encoding a GALT polypeptide) with an alternative codon to increase G/C content; or (iv) a combination thereof.

In some embodiments, the sequence-optimized nucleotide sequence (e.g., an ORF encoding a GALT polypeptide) has at least one improved property with respect to the reference nucleotide sequence.

In some embodiments, the sequence optimization method is multiparametric and comprises one, two, three, four, or more methods disclosed herein and/or other optimization methods known in the art.

Features, which can be considered beneficial in some embodiments of the invention, can be encoded by or within regions of the polynucleotide and such regions can be upstream (5') to, downstream (3') to, or within the region that encodes the GALT polypeptide. These regions can be incorporated into the polynucleotide before and/or after sequence-optimization of the protein encoding region or open reading frame (ORF). Examples of such features include, but are not limited to, untranslated regions (UTRs), microRNA sequences, Kozak sequences, oligo(dT) sequences, poly-A tail, and detectable tags and can include multiple cloning sites that can have XbaI recognition.

In some embodiments, the polynucleotide of the invention comprises a 5' UTR, a 3' UTR and/or a microRNA binding site. In some embodiments, the polynucleotide comprises two or more 5' UTRs and/or 3' UTRs, which can be the same or different sequences. In some embodiments, the polynucleotide comprises two or more microRNA binding sites, which can be the same or different sequences. Any portion of the 5' UTR, 3' UTR, and/or microRNA binding site, including none, can be sequence-optimized and can independently contain one or more different structural or chemical modifications, before and/or after sequence optimization.

In some embodiments, after optimization, the polynucleotide is reconstituted and transformed into a vector such as, but not limited to, plasmids, viruses, cosmids, and artificial chromosomes. For example, the optimized polynucleotide can be reconstituted and transformed into chemically competent *E. coli*, yeast, *neurospora*, maize, *drosophila*, etc. where high copy plasmid-like or chromosome structures occur by methods described herein.

6. SEQUENCE-OPTIMIZED NUCLEOTIDE SEQUENCES ENCODING GALT POLYPEPTIDES

In some embodiments, the polynucleotide of the invention comprises a sequence-optimized nucleotide sequence encoding a GALT polypeptide disclosed herein. In some embodiments, the polynucleotide of the invention comprises an open reading frame (ORF) encoding a GALT polypeptide, wherein the ORF has been sequence optimized.

Exemplary sequence-optimized nucleotide sequences encoding human GALT isoform 1 are set forth as SEQ ID NOs: 5-29 (GALT-CO01, GALT-CO02, GALT-CO03, GALT-CO04, GALT-CO05, GALT-CO06, GALT-CO07, GALT-CO08, GALT-CO09, GALT-CO10, GALT-CO11, GALT-CO12, GALT-CO13, GALT-CO14, GALT-CO15, GALT-CO16, GALT-CO17, GALT-CO18, GALT-CO19, GALT-CO20, GALT-CO21, GALT-CO22, GALT-CO23, GALT-CO24, and GALT-CO25, respectively). Further exemplary sequence optimized nucleotide sequences encoding GALT isoform 1 are shown in TABLE 2. In some embodiments, the sequence optimized GALT sequences in Table 2, fragments, and variants thereof are used to practice the methods disclosed herein. In some embodiments, the sequence optimized GALT sequences set forth as SEQ ID NOs: 5-29 are shown in Table 2, fragments and variants thereof are combined with or alternatives to the wild-type sequences disclosed in FIGS. 1-2.

Exemplary sequence optimized nucleotide sequences encoding human GALT isoform 1 are set forth as SEQ ID NOs: 113-131 (GALT-CO26, GALT-CO27, GALT-CO28, GALT-CO29, GALT-CO30, GALT-CO31, GALT-CO32, GALT-CO33, GALT-CO34, GALT-CO35, GALT-CO36, GALT-CO37, GALT-CO38, GALT-CO39, GALT-CO40, GALT-CO41, GALT-CO42, GALT-CO43, and GALT-CO44, respectively). Further exemplary sequence optimized nucleotide sequences encoding human GALT isoform 1 are shown in TABLE 2. In some embodiments, the sequence optimized GALT sequences set forth as SEQ ID NOs: 113-131, or shown in TABLE 2, fragments, and variants thereof are used to practice the methods disclosed herein. In some embodiments, the sequence optimized GALT sequences set forth as SEQ ID NOs: 113-131, or shown in TABLE 2, fragments and variants thereof are combined with or alternatives to the wild-type sequences disclosed in FIGS. 1-2.

In some embodiments, a polynucleotide of the present disclosure, for example a polynucleotide comprising an mRNA nucleotide sequence encoding a GALT polypeptide, comprises from 5' to 3' end:

(i) a 5' cap provided herein, for example, Cap1;

(ii) a 5' UTR, such as the sequences provided herein, for example, SEQ ID NO: 35;

(iii) an open reading frame encoding a GALT polypeptide, e.g., a sequence optimized nucleic acid sequence encoding GALT set forth as SEQ ID NOs: 5-29 and 113-131, or shown in TABLE 2;

(iv) at least one stop codon;

(v) a 3' UTR, such as the sequences provided herein, for example, SEQ ID NO: 98, 163, or 164; and (vi) a poly-A tail provided above.

TABLE 2

Sequence optimized sequences for human GALT, isoform 1

| SEQ ID NO | Name | Sequence |
|---|---|---|
| 5 | GALT-CO01 | See Sequence Listing |
| 6 | GALT-CO02 | See Sequence Listing |
| 7 | GALT-CO03 | See Sequence Listing |
| 8 | GALT-CO04 | See Sequence Listing |
| 9 | GALT-CO05 | See Sequence Listing |
| 10 | GALT-CO06 | See Sequence Listing |
| 11 | GALT-CO07 | See Sequence Listing |
| 12 | GALT-CO08 | See Sequence Listing |
| 13 | GALT-CO09 | See Sequence Listing |
| 14 | GALT-CO10 | See Sequence Listing |
| 15 | GALT-CO11 | See Sequence Listing |
| 16 | GALT-CO12 | See Sequence Listing |
| 17 | GALT-CO13 | See Sequence Listing |
| 18 | GALT-CO14 | See Sequence Listing |
| 19 | GALT-CO15 | See Sequence Listing |
| 20 | GALT-CO16 | See Sequence Listing |
| 21 | GALT-CO17 | See Sequence Listing |
| 22 | GALT-CO18 | See Sequence Listing |
| 23 | GALT-CO19 | See Sequence Listing |
| 24 | GALT-CO20 | See Sequence Listing |
| 25 | GALT-CO21 | See Sequence Listing |
| 26 | GALT-CO22 | See Sequence Listing |
| 27 | GALT-CO23 | See Sequence Listing |

TABLE 2-continued

Sequence optimized sequences for human GALT, isoform 1

| SEQ ID NO | Name | Sequence |
|---|---|---|
| 28 | GALT-CO24 | See Sequence Listing |
| 29 | GALT-CO25 | See Sequence Listing |
| 113 | GALT-CO26 | AUGUCUAGGAGCGGGACCGACCCCCAGCAGCGGCAGCAGGCCAGCGAGGCCG<br>ACGCCGCCGCGGCCACCUUCAGGGCCAACGACCAUCAACACAUCAGGUAUAA<br>CCCCCUCCAGGACGAGUGGGUGUUGGUGUCCGCCCAUCGGAUGAAGAGGCCC<br>UGGCAGGGCCAGGUGGAGCCCCAGCUCCUGAAGACCGUGCCCCGGCACGACC<br>CCCUCAACCCCCUGUGCCCCGGCGCGAUCCGCGCCAACGGCGAGGUGAACCC<br>CCAGUAUGACAGCACGUUCCUGUUCGACAACGACUUCCCCGCCCUGCAGCCC<br>GACGCCCCCAGCCCCGGCCCAAGCGACCAUCCCCUGUUCCAGGCCAAGUCCG<br>CCAGGGGCGUGUGUAAGGUGAUGUGCUUCCACCCAUGGUCCGACGUGACCCU<br>GCCCCUGAUGAGCGUGCCCGAGAUCCGCGCCGUGGUGGACGCCUGGGCCAGC<br>GUGACCGAGGAGCUGGGGGCCCAGUACCCUUGGGUGCAAAUCUUCGAGAAUA<br>AGGGCGCCAUGAUGGGCUGCUCCAACCCCCACCCCCACUGUCAGGUGUGGGC<br>CAGCAGUUUCCUGCCCGACAUCGCCCAGCGCGAGGAGCGGUCACAGCAGGCC<br>UACAAGAGCCAACACGGCGAACCUCUGCUCAUGGAGUACAGCAGGCAGGAAC<br>UGCUGCGGAAGGAGAGGCUGGUCCUGACCAGCGAGCACUGGCUGGUGCUGGU<br>GCCCUUCUGGGCCACCUGGCCCUACCAGACACUGCUGCUGCCUAGGCGACAC<br>GUGCGUCGGCUGCCCGAGCUGACCCCUGCCGAAAGGGACGACCUGGCCAGCA<br>UCAUGAAGAAGCUGCUCACCAAGUACGACAACCUGUUUGAAACCAGCUUCCC<br>CUACAGCAUGGGCUGGCACGGCGCACCUACCGGCAGCGAGGCCGGCGCCAAC<br>UGGAACCACUGGCAGCUGCAUGCCCACUACUAUCCGCCCCUCCUCAGGAGCG<br>CCACCGUGCGCAAGUUCAUGGUGGGCUAUGAGAUGCUGGCGCAGGCCCAGCG<br>UGACCUGACCCCCGAGCAGGCCGCCGAGAGGCUGCGUGCCCUGCCUGAGGUG<br>CACUACCACCUGGGGCAGAAGGACAGAGAAACUGCGACCAUCGCC |
| 114 | GALT-CO27 | AUGAGCAGGUCCGGCACCGACCCCCAGCAGAGGCAGCAAGCCUCCGAGGCCG<br>ACGCCGCCGCGGCCACCUUCCGGGCCAACGACCAUCAGCAUAUCAGGUAUAA<br>CCCCCUUCAGGACGAGUGGGUGCUCGUGAGCGCCCACCGGAUGAAGCGCCCC<br>UGGCAGGGGCAGGUCGAGCCCCAGCUGCUGAAGACCGUGCCCAGGCACGAUC<br>CGCUGAACCCGCUGUGCCCCGGGGCCAUCCGGGCCAACGGGGAGGUGAACCC<br>CCAGUACGACAGCACCUUCCUGUUCGACAACGACUUCCCCGCCCUGCAGCCC<br>GAUGCCCCCAGCCCCGGGCCCUCCGACCACCCCCUGUUCCAGGCCAAGAGCG<br>CCAGAGGCGUGUGCAAGGUCAUGUGCUUUCAUCCCUGGAGCGACGUGACCCU<br>GCCCCUGAUGUCCGUGCCCGAGAUCAGAGCUGUCGUGGACGCCUGGGCCUCC<br>GUGACCGAGGAGCUCGGCGCCCAGUACCCCUGGGUGCAGAUCUUCGAGAACA<br>AAGGCGCCAUGAUGGGCUGCAGCAACCCCCACCCACACUGCCAGGUGUGGGC<br>CAGCAGCUUCCUGCCCGACAUCGCCCAGAGAGAGGAGAGGAGCCAGCAGGCC<br>UAUAAGAGCCAGCAUGGCGAGCCCCUGCUGAUGGAGUACAGCAGACAGGAGC<br>UGCUGAGGAAAGAGAGGCUGGUGCUGACAAGCGAGCACUGGCUGGUGCUGGU<br>GCCCUUUUGGGCCACUUGGCCAUACCAGACCCUGCUGCUGCCCCGGCGGCAU<br>GUCAGGAGACUGCCUGAGCUGACUCCCGCCGAGCGGGAUGACCUGGCCAGCA<br>UCAUGAAGAAGCUGCUCACCAAAUACGACAACCUCUUCGAAACCAGCUUCCC<br>CUACAGCAUGGGGUGGCACGGGGCCCCCACCGGCAGCGAAGCCGGAGCCAAU<br>UGGAAUCAUUGGCAGCUCCAUGCCCAUUACUAUCCGCCCCUGCUCAGAAGCG<br>CCACCGUGCGGAAGUUCAUGGUGGGCUACGAGAUGCUCGCCCAGGCCCAGCG<br>GGACCUGACCCCCGAGCAGGCUGCCGAGCGGCUGAGGGCCCUGCCCGAGGUG<br>CACUAUCACCUGGGCCAGAAAGAUAGGGAAACAGCCACUAUCGCC |
| 115 | GALT-CO28 | AUGAGCAGGAGCGGCACCGACCCCCAGCAGAGGCAGCAGGCCAGCGAAGCCG<br>ACGCCGCCGCCGCCACCUUCCGGGCCAACGAUCACCAGCACAUCCGCUACAA<br>CCCUCUCCAGGACGAGUGGGUGCUCGUGAGCGCCCACAGGAUGAAGCGGCCC<br>UGGCAGGGCCAGGUGGAGCCCCAGCUCCUGAAGACCGUGCCCAGACACGACC<br>CCCUGAACCCGCUCUGCCCCGGCGCCAUCAGAGCCAACGGCGAGGUGAACCC<br>CCAGUACGACAGCACCUUCCUGUUCGACAACGACUUCCCCGCCCUCCAGCCC<br>GAUGCCCCCAGCCCCGGUCCCUCCGACCAUCCCCUGUUCCAGGCCAAGUCCG<br>CCAGAGGCGUGUGCAAGGUGAUGUGCUUCCACCCCUGGAGCGACGUGACCCU<br>CCCCCUGAUGUCGGUGCCCGAAAUCAGGGCCGUGGUGGACGCCUGGGCCAGC<br>GUGACCGAGGAGCUGGGGGCCCAGUAUCCCUGGGUCCAGAUCUUCGAGAACA<br>AGGGGGCCAUGAUGGGCUGUAGCAACCCCCACCCACACUGCCAGGUGUGGGC<br>CUCCUCCUUCCUGCCCGACAUCGCCCAAAGGGAGGAGCGGUCCCAGCAAGCC<br>UACAAGUCCCAGCACGGUGAGCCCCUGCUGAUGGAAUAUAGCAGACAGGAGC<br>UGCUGAGGAAGGAGCGCCUGGUCCUGACCAGCGAGCACUGGCUGGUGCUGGU<br>CCCCUUUUGGGCCACCUGGCCCUACCAGACGCUGCUGCUGCCUCGCAGACAU<br>GUGAGGAGGCUGCCGGAGCUGACCCCCGCCGAGCGGGACGACCUGGCAAGCA |

TABLE 2-continued

Sequence optimized sequences for human GALT, isoform 1

| SEQ ID NO | Name | Sequence |
|---|---|---|
| | | UCAUGAAGAAGCUGCUGACCAAGUACGACAACCUGUUCGAGACUUCCUUCCC<br>GUACAGCAUGGGCUGGCACGGCGCCCCGACCGGAAGCGAGGCCGGCGCGAAC<br>UGGAACCACUGGCAGCUGCAUGCGCAUUACUACCCGCCCCUGCUGCGGUCAG<br>CCACCGUCCGCAAGUUCAUGGUGGGCUACGAAAUGCUGGCCCAGGCGCAGAG<br>GGACCUCACCCCCGAGCAGGCCGCCGAAAGACUGCGUGCGCUGCCGGAGGUG<br>CACUACCACCUGGGCCAGAAGGACCGCGAAACCGCGACCAUCGCA |
| 116 | GALT-CO29 | AUGUCACGGAGCGGCACCGACCCGCAGCAGAGGCAGCAGGCCAGCGAGGCAG<br>ACGCCGCCGCCGCCACCUUCAGGGCCAACGACCAUCAGCACAUCAGAUACAA<br>CCCCCUACAGGACGAGUGGGUGCUCGUCAGCGCCCACAGAAUGAAGCGGCCC<br>UGGCAGGGGCAGGUGGAGCCCCAGCUCCUGAAGACCGUGCCCAGGCACGACC<br>CCCUCAAUCCCCUGUGCCCUGGCGCCAUUAGGGCCAACGGCGAGGUGAACCC<br>CCAGUACGACUCAACCUUCCUGUUUGACAACGACUUCCCCGCCCUGCAGCCC<br>GAUGCCCCGAGCCCCGGGCCAGCGACCACCCCCUGUUCCAGGCCAAGUCGG<br>CCAGGGGCGUGUGCAAGGUGAUGUGCUUCCACCCCUGGAGCGAUGUCACCCU<br>GCCCCUGAUGUCGGUGCCCGAGAUCCGCGCCGUGGUGGACGCCUGGGCCAGC<br>GUGACCGAGGAGCUGGGCGCCCAAUACCCCUGGGUGCAGAUCUUUGAGAACA<br>AAGGCGCCAUGAUGGGCUGUAGCAACCCCCACCCCCACUGUCAGGUGUGGGC<br>CAGCAGCUUUCUGCCCGACAUCGCCCAGAGGGAGGAGCGCUCCCAGCAGGCU<br>UACAAGAGCCAGCACGGAGAGCCCCUGCUCAUGGAGUACUCGCGACAGGAGC<br>UGCUCCGGAAGGAACGGCUGGUCCUGACCUCCGAGCACUGGCUCGUGCUGGU<br>GCCGUUCUGGGCCACAUGGCCCUACCAGACCCUGCUGCUACCCCGCAGACAC<br>GUUCGCCGACUGCCCGAGCUGACCCCUGCCGAGAGAGACGACCUGGCGAGCA<br>UCAUGAAGAAGCUGCUCACCAAGUAUGACAACUUAUUCGAAACCUCCUUCCC<br>UUACAGCAUGGGCUGGCACGGCGCCCCCACCGGCAGCGAGGCGGGCGCCAAC<br>UGGAACCACUGGCAGCUGCAUGCCCACUACUACCCACCCCUGCUGCGGAGCG<br>CCACCGUGAGAAAGUUCAUGGUGGGCUACGAGAUGCUGGCCCAGGCCCAACG<br>GGAUCUGACCCCCGAGCAGGCCGCCGAGCGGCUGAGGGCCCUCCCCGAGGUA<br>CACUACCAUCUCGGCCAGAAGGACCGGGAAACCGCCACCAUCGCC |
| 117 | GALT-CO30 | AUGAGCAGAAGCGGCACCGACCCCCAGCAGCGGCAGCAGGCCAGCGAGGCCG<br>ACGCCGCCGCCGCAACCUUCCGCGCCAACGACCACCAGCACAUCAGAUACAA<br>CCCCCUCCAGGACGAGUGGGUCCUCGUGUCCGCCCAUAGAAUGAAGAGGCCA<br>UGGCAGGGCCAGGUAGAACCUCAACUGCUGAAGACCGUCCCCCGGCAUGACC<br>CCCUCAAUCCCCUCUGCCCGGGGGCCAUCCGAGCGAAUGGGGAGGUCAACCC<br>CCAGUACGACAGCACCUUCCUGUUCGACAACGACUUCCCCGCCCUGCAGCCC<br>GACGCCCCGAGCCCCGGACCCAGCGACCACCCCCUGUUCCAGGCCAAAUCCG<br>CCCGGGGCGUCUGCAAGGUGAUGUGCUUUCACCCCUGGUCCGACGUGACCCU<br>GCCCCUCAUGUCCGUGCCCGAGAUCAGGGCCGUGGUGGACGCUUGGGCCAGC<br>GUCACGGAGGAGCUCGGCGCCCAGUACCCCUGGGUCCAGAUCUUCGAGAACA<br>AGGGCGCCAUGAUGGGGUGCUCCAACCCUCACCCCCACUGCCAGGUGUGGGC<br>CAGCAGCUUUCUGCCCGACAUUGCCCAGCGGGAGGAGAGGUCCCAGCAGGCC<br>UACAAGAGUCAGCACGGGGAGCCCCUGCUGAUGGAGUACUCCCGGCAGGAGC<br>UCCUGAGGAAAGAGCGCUUGGUGCUGACAAGCGAGCACUGGCUGGUGCUCGU<br>GCCCUUCUGGGCCACUUGGCCCUACCAGACCCUGCUGCUGCCCAGACGGCAC<br>GUGCGGCGGCUGCCCGAGCUGACACCCGCCGAGAGGGACGAUCUCGCCAGCA<br>UUAUGAAGAAGCUGCUGACCAAGUAUGACAACCUGUUUGAGACUAGCUUUCC<br>CUACAGCAUGGGCUGGCACGGGGCCCCCACGGGCUCCGAGGCCGGCGCCAAC<br>UGGAACCACUGGCAGCUGCACGCCCACUAUUAUCCGCCCCUGCUCCGGAGCG<br>CCACCGUGAGAAAGUUUAUGGUGGGCUAUGAGAUGCUGGCCCAAGCGCAACG<br>GGAUCUGACCCCCGAGCAGGCCGCCGAGCGUCUGAGAGCCCUGCCUGAGGUG<br>CACUAUCACCUGGGGCAGAAGGACCGGGAGACGGCAACCAUCGCC |
| 118 | GALT-CO31 | AUGAGCCGCAGCGGCACCGACCCGCAACAAAGACAGCAGGCCUCCGAGGCCG<br>ACGCCGCCGCCGCUACCUUUAGGGCCAACGACCACCAGCAUAUCCGCUACAA<br>UCCCCUCCAGGACGAGUGGGUGCUCGUGAGCGCCCACCGUAUGAAGAGGCCC<br>UGGCAGGGACAGGUGGAACCCCAGCUGCUGAAGACCGUACCCCGGCACGACC<br>CCCUGAACCCCCUGUGCCCCGGGGCCAUCAGAGCCAAUGGAGAGGUGAACCC<br>CCAGUACGACUCCACCUUCCUGUUCGAUAAUGAUUUUCCGGCCCUGCAGCCC<br>GACGCCCCCAGCCCCGGCCCAAGCGACCACCCUCUGUUCCAGGCCAAGAGCG<br>CCAGGGGCGUUUGCAAGGUCAUGUGCUUCCACCCCUGGAGCGACGUGACCCU<br>GCCCCUGAUGUCGGUGCCCGAGAUCAGGGCCGUGGUGGACGCCUGGGCCAGC<br>GUGACGGAGGAACUCGGCGCCCAGUACCCCUGGGUACAGAUCUUCGAGAACA<br>AGGGUGCCAUGAUGGGCUGCAGCAACCCACAUCCCCACUGUCAGGUGUGGGC<br>CAGCUCAUUCCUGCCUGACAUCGCCCAGCGUGAGGAGAGGAGUCAGCAGGCC<br>UAUAAGAGCCAGCAUGGGGAGCCCCUCCUGAUGGAGUACAGCAGACAAGAGC<br>UGCUCAGGAAGGAGAGACUGGUGCUGACCAGCGAGCAUUGGCUGGUGCUGGU<br>GCCCUUUUGGGCCACAUGGCCCUACCAGACCCUCCUGCUGCCGAGACGCCAC<br>GUGCGCCGGCUGCCCGAGCUGACUCCCGCCGAGAGGGACGACCUCGCUAGCA<br>UCAUGAAGAAACUGCUGACCAAGUACGACAACCUGUUUGAGACAAGCUUUCC<br>CUACUCCAUGGGAUGGCACGGCGCCCCCACCGGCUCCGAGGCCGGCGCCAAC<br>UGGAACCACUGGCAGCUGCACGCCCACUACUAUCCCCCGCUGCUGCGGAGCG |

TABLE 2-continued

Sequence optimized sequences for human GALT, isoform 1

| SEQ ID NO | Name | Sequence |
|---|---|---|
| | | CCACCGUGAGGAAAUUCAUGGUGGGCUACGAGAUGCUCGCUCAGGCCCAACG<br>GGACCUGACCCCCGAGCAGGCGGCCGAGAGGCUCCGAGCUCUGCCCGAGGUG<br>CAUUACCAUCUGGGCCAGAAGGAUAGGGAAACCGCCACCAUCGCC |
| 119 | GALT-CO32 | AUGAGCAGGAGCGGAACCGACCCGCAGCAGAGGCAGCAGGCCAGCGAAGCCG<br>ACGCCGCCGCCGCCACCUUCCGGGCCAACGACCACCAACACAUCAGGUACAA<br>CCCGCUCCAGGACGAGUGGGUGCUCGUUAGCGCCCAUCGCAUGAAGCGGCCG<br>UGGCAAGGCCAGGUGGAGCCGCAGCUGCUGAAGACCGUGCCGCGCCACGACC<br>CGCUGAACCCGCUGUGCCCUGGCGCCAUCCGGGCCAACGGCGAGGUGAACCC<br>UCAGUACGACAGCACCUUCCUGUUCGACAAUGAUUUCCCGGCCUUGCAGCCG<br>GACGCCCCUUCCCCGGGACCGUCCGACCACCCGCUGUUCCAAGCCAAGUCCG<br>CCCGGGGCGUGUGCAAGGUGAUGUGCUUCCACCCGUGGUCCGACGUGACCCU<br>GCCGCUGAUGAGCGUGCCUGAGAUCAGAGCCGUGGUGGACGCCUGGGCCUCC<br>GUGACUGAGGAGCUCGGCGCCCAGUACCCAUGGGUCCAGAUCUUCGAGAACA<br>AGGGUGCCAUGAUGGGCUGCAGCAACCCGCACCCGCACUGCCAAGUGUGGGC<br>CAGCUCCUUCCUGCCGGAUAUUGCCCAGCGGGAGGAGCGGAGCCAGCAAGCA<br>UACAAGAGCCAGCAUGGCGAGCCGCUCUUGAUGGAGUACUCCAGGCAGGAGC<br>UGCUGAGAAAGGAGCGGCUGGUGCUGACCUCUGAGCACUGGCUGGUGCUCGU<br>GCCGUUCUGGGCCACCUGGCCUUACCAGACCCUGCUGCUGCCGAGGCGGCAC<br>GUGCGCCGGCUGCCAGAGCUGACGCCAGCCGAGCGAGACGAUCUGGCCUCCA<br>UCAUGAAGAAGCUACUGACCAAGUAUGACAACCUGUUCGAAACGAGCUUCCC<br>GUACAGCAUGGGCUGGCACGGCGCCCCGACCGGCAGCGAGGCCGGCGCCAAC<br>UGGAAUCACUGGCAGCUGCAUGCCCAUUACUACCCGCCGCUCCUCCGCAGCG<br>CCACCGUGAGGAAGUUCAUGGUGGGCUACGAGAUGCUGGCCCAGGCCCAGCG<br>GGACCUGACCCCGGAGCAGGCGGCCGAGAGACUGAGGGCCCUCCCGGAGGUC<br>CAUUACCACCUGGGCCAGAAGGACCGGGAGACGGCCACCAUCGCC |
| 120 | GALT-CO33 | AUGUCCCGCAGCGGCACGGACCCGCAGCAGCGGCAGCAGGCCAGCGAGGCCG<br>ACGCCGCGGCCGCCACCUUCCGGGCCAACGACCACCAGCACAUCAGGUACAA<br>CCCACUCCAAGACGAGUGGGUGCUCGUGAGCGCCCACCGGAUGAAGAGGCCG<br>UGGCAGGGACAGGUUGAGCCGCAACUGCUGAAGACCGUGCCAAGACACGAUC<br>CGCUGAACCCGCUCUGCCCGGGCGCCAUCCGUGCCAACGGCGAGGUCAACCC<br>ACAGUAUGACAGCACCUUCCUGUUCGACAACGACUUCCCGGCCCUGCAGCCG<br>GACGCGCCUAGCCCUGGACCGUCCGACCACCCGCUGUUCCAGGCCAAGUCCG<br>CUAGGGGCGUGUGCAAGGUGAUGUGCUUCCAUCCGUGGUCCGAUGUCACCCU<br>GCCGCUCAUGUCCGUGCCGGAGAUCCGGGCCGUGGUGGAUGCCUGGGCCAGC<br>GUCACCGAGGAGCUGGGCGCGCAGUACCCUUGGGUCCAGAUCUUCGAGAACA<br>AGGGCGCCAUGAUGGGUUGCAGCAACCCGCACCCACACUGCCAGGUGUGGGC<br>CAGCAGCUUCCUGCCGGACAUCGCACAGAGGGAGGAGCGGAGCCAACAGGCC<br>UACAAGUCCCAGCACGGCGAGCCACUGCUGAUGGAGUACAGCAGGCAGGAGC<br>UGCUGCGGAAGGAGCGGCUGGUGCUCACCUCCGAACAUUGGCUGGUUCUGGU<br>GCCGUUCUGGGCCACCUGGCCUUACCAGACCCUGCUGCUCCCGAGGCGGCAC<br>GUGCGCAGGCUGCCGGAGCUGACACCGGCCGAGCGCGACGACCUGGCCAGCA<br>UCAUGAAGAAGCUGCUCACCAAGUACGAUAACCUGUUCGAGACAUCCUUCCC<br>GUACAGCAUGGGCUGGCACGGCGCCCCUACCGGCUCCGAGGCCGGCGCCAAC<br>UGGAACCACUGGCAGCUGCACGCCCACUACUACCCACCGCUGCUGAGAAGCG<br>CCACCGUCAGAAAGUUCAUGGUGGGAUAUGAGAUGCUGGCCCAGGCUCAGAG<br>AGAUCUGACCCCGGAGCAGGCCGCCGAGAGGCUCCGCGCCCUCCCAGAAGUG<br>CACUACCAUCUGGGCCAGAAGGACAGGGAGACGGCCACCAUCGCC |
| 121 | GALT-CO34 | AUGAGCCGGAGCGGCACCGACCCGCAGCAGCGUCAGCAAGCCAGCGAGGCCG<br>ACGCCGCCGCCGCCACGUUCCGGGCCAACGACCACCAGCACAUUAGGUACAA<br>CCCGCUCCAGGACGAGUGGGUCCUCGUGAGCGCCCACAGGAUGAAGAGGCCA<br>UGGCAGGGACAAGUUGAGCCACAGCUGCUGAAGACCGUGCCACGGCACGACC<br>CGCUCAACCCUCUGUGCCCGGGCGCCAUCCGCGCCAACGGCGAGGUGAACCC<br>ACAGUACGACAGCACCUUCCUGUUCGACAACGACUUCCCUGCCCUCCAGCCG<br>GACGCCCCGAGCCCUGGACCGUCCGACCAUCCGCUGUUCCAGGCCAAGUCCG<br>CGCGGGGCGUGUGCAAGGUGAUGUGCUUCCAUCCGUGGAGCGACGUGACCCU<br>GCCGCUGAUGUCCGUGCCUGAGAUACGGGCCGUGGUGGACGCCUGGGCCAGC<br>GUGACAGAGGAGCUCGGCGCCCAGUACCCUUGGGUGCAGAUCUUCGAGAACA<br>AGGGUGCCAUGAUGGGUUGCAGCAACCCGCACCCGCAUUGCCAGGUGUGGGC<br>CAGCAGCUUCCUGCCUGACAUCGCCCAGCGGGAGGAGCGCAGCCAGCAGGCU<br>UACAAGAGCCAGCACGGCGAGCCGCUGCUGAUGGAGUACUCUAGGCAGGAGC<br>UGCUGAGAAAGGAGAGGCUGGUGCUGACCAGCGAACACUGGCUCGUGCUGGU<br>GCCGUUCUGGGCAACCUGGCCGUACCAGACCCUGCUGCUGCCGAGGCGGCAU<br>GUGAGAAGGCUCCCGGAGCUGACCCCAGCCGAGCGCGACGACCUCGCCAGCA<br>UCAUGAAGAAGCUCCUGACCAAGUACGACAACCUGUUCGAGACGAGCUUCCC<br>GUAUUCCAUGGGCUGGCACGGAGCCCCGACAGGCAGCGAGGCCGGCGCCAAC<br>UGGAAUCACUGGCAGCUGCAUGCCCACUACUACCCGCCGCUCCUGCGGAGCG<br>CCACCGUCCGCAAGUUCAUGGUGGGCUACGAGAUGCUGGCCCAGGCCCAGAG<br>GGACCUCACCCCGGAGCAGGCCGCCGAGAGGCUGCGGGCCCUGCCGGAGGUC<br>CACUACCACCUCGGCCAGAAGGAUAGAGAAACCGCCACGAUCGCG |

TABLE 2-continued

Sequence optimized sequences for human GALT, isoform 1

| SEQ ID NO | Name | Sequence |
| --- | --- | --- |
| 122 | GALT-CO35 | AUGAGCAGGAGCGGCACCGACCCUCAGCAGAGGCAACAGGCCUCCGAGGCCG<br>ACGCGGCGGCCGCCACCUUCAGGGCCAACGACCACCAGCACAUCCGAUACAA<br>CCCGCUCCAAGACGAGUGGGUGCUCGUCUCCGCCCACCGCAUGAAGCGGCCG<br>UGGCAAGGUCAAGUUGAACCACAGCUGCUGAAGACCGUGCCGAGGCACGAUC<br>CGCUGAACCCGCUGUGCCCGGGAGCCAUCCGGGCCAACGGCGAGGUGAACCC<br>UCAGUACGACAGCACAUUCCUGUUCGACAACGACUUCCCGGCCCUGCAGCCG<br>GACGCCCCAAGCCCGGGCCCAAGCGACCAUCCGCUGUUCCAAGCCAAGUCCG<br>CCCGCGGCGUGUGCAAGGUGAUGUGCUUCCACCCGUGGUCCGACGUGACCCU<br>GCCGCUGAUGAGCGUGCCGGAGAUCCGGGCCGUGGUGGAUGCCUGGGCCAGC<br>GUGACCGAGGAAUUAGGCGCCCAGUACCCAUGGGUGCAGAUCUUCGAGAACA<br>AGGGAGCCAUGAUGGGCUGCAGCAACCCGCACCCGCACUGCCAAGUGUGGGC<br>CAGCUCCUUCCUGCCGGACAUCGCCCAGCGCGAGGAGCGGAGCCAGCAGGCC<br>UACAAGAGUCAGCACGGCGAGCCGCUGCUGAUGGAGUACUCUAGGCAGGAGC<br>UGCUCAGGAAGGAGAGGCUGGUGCUGACCAGCGAGCACUGGUUGGUGCUGGU<br>GCCUUUCUGGGCCACCUGGCCAUACCAGACCCUGCUGCUGCCGAGAAGGCAC<br>GUCAGAAGACUGCCGGAACUGACCCCGGCCGAGAGGGACGACCUGGCCUCCA<br>UUAUGAAGAAGCUCCUGACCAAGUACGACAAUCUGUUCGAGACGUCCUUCCC<br>UUACAGCAUGGGUUGGCACGGCGCCCCGACCGGCAGCGAGGCAGGAGCCAAC<br>UGGAACCACUGGCAGCUGCACGCCCACUACUACCCGCCGCUGCUCAGGUCCG<br>CCACCGUUCGGAAGUUCAUGGUGGGCUACGAAAUGCUGGCCCAGGCCCAGCG<br>CGACCUCACCCCAGAGCAGGCCGCCGAGCGGCUGCGGGCCCUGCCGGAGGUG<br>CACUACCACCUGGGCCAGAAGGACCGCGAGACAGCCACCAUCGCU |
| 123 | GALT-CO36 | AUGAGCAGGUCAGGAACCGACCCGCAGCAGCGCCAACAGGCCUCCGAGGCCG<br>ACGCCGCCGCCGCGACCUUCCGAGCCAACGACCAUCAACACAUCAGGUAUAA<br>CCCGUUGCAGGACGAGUGGGUGCUCGUGUCCGCCCAUCGGAUGAAGCGGCCG<br>UGGCAGGGACAGGUGGAGCCGCAGCUGCUCAAGACCGUUCCGCGCCACGACC<br>CGCUCAACCCGCUGUGUCCGGGCGCCAUCCGGGCCAACGGCGAGGUGAACCC<br>GCAGUACGACAGCACCUUCCUGUUCGACAACGAUUUCCCUGCCCUGCAGCCA<br>GAUGCCCCGAGCCCGGGCCCUAGCGAUCACCCGCUGUUCCAGGCCAAGAGCG<br>CCCGGGGCGUCUGUAAGGUGAUGUGCUUCCACCCAUGGAGCGACGUCACCCU<br>GCCGCUGAUGUCCGUGCCAGAGAUCCGCGCCGUGGUGGACGCCUGGGCGAGC<br>GUGACCGAGGAGCUGGGAGCCCAAUACCCUUGGGUGCAGAUCUUCGAGAAUA<br>AGGGCGCUAUGAUGGGCUGCUCCAACCCGCACCCGCACUGCCAGGUGUGGGC<br>CAGCUCCUUCCUCCCGGAUAUCGCCCAGCGGGAGGAGAGAAGCCAGCAGGCC<br>UACAAGUCCCAGCACGGCGAGCCGCUGCUCAUGGAGUAUUCCAGGCAGGAGC<br>UCCUCAGGAAGGAAAGGCUUGUGCUGACGAGCGAGCACUGGCUGGUGCUGGU<br>GCCGUUCUGGGCCACCUGGCCGUACCAGACCCUCCUGCUGCCGCGCCGACAC<br>GUCAGGAGGCUGCCGGAGCUGACCCCGGCCGAGAGGGAUGACCUGGCCUCCA<br>UAAUGAAGAAGUUACUGACUAAGUAUGACAACUUGUUCGAAACCAGCUUCCC<br>UUACAGCAUGGGCUGGCAUGGCGCCCCGACCGGCUCCGAAGCCGGCGCCAAC<br>UGGAACCAUUGGCAACUCCACGCCCACUACUACCCGCCGCUCUUAAGGAGCG<br>CCACCGUGAGGAAGUUCAUGGUGGGAUACGAGAUGCUGGCCCAGGCCCAAAG<br>GGACCUCACCCCGGAGCAGGCCGCGGAGAGGCUGCGUGCCCUGCCUGAGGUC<br>CACUACCACCUGGGCCAGAAGGACAGGGAAACCGCGACCAUCGCC |
| 124 | GALT-CO37 | AUGAGCCGGAGCGGCACCGACCCCCAGCAGCGGCAGCAGGCCAGCGAGGCCG<br>ACGCUGCCGCCGCCACCUUCCGGGCCAACGACCACCAGCACAUCCGGUACAA<br>CCCCCUGCAGGACGAGUGGGUGCUGGUGAGCGCCCACCGGAUGAAGCGGCCC<br>UGGCAGGGCCAGGUGGAGCCCCAGCUGCUGAAGACCGUGCCCCGGCACGACC<br>CCCUGAACCCUCUGUGCCCAGGAGCCAUCCGCGCCAACGGCGAGGUGAAUCC<br>UCAGUACGACAGCACCUUCCUGUUCGACAACGACUUCCCCGCCCUGCAGCCC<br>GACGCCCCCAGCCCCGGCCCCAGCGACCAUCCAUUAUUCCAGGCCAAGAGCG<br>CCCGGGGCGUGUGCAAGGUGAUGUGCUUCCACCCCUGGAGCGACGUGACCCU<br>GCCCCUGAUGAGCGUGCCCGAGAUCAGAGCCGUGGUGGACGCCUGGGCCAGC<br>GUGACCGAGGAGCUGGGCGCCCAGUACCCCUGGGUGCAGAUCUUCGAGAACA<br>AGGGCGCCAUGAUGGGCUGCAGCAACCCCCACCCCCACUGCCAGGUGUGGGC<br>CUCAAGCUUCCUGCCCGACAUCGCCCAGCGGGAGGAGCGGAGCCAACAGGCC<br>UACAAGUCACAGCACGGCGAGCCCCUGCUGAUGGAGUACAGCCGGCAGGAGC<br>UGCUGCGGAAGGAGCGGCUGGUGCUGACCAGCGAGCACUGGCUCGUGCUCGU<br>GCCCUUCUGGGCCACCUGGCCCUACCAGACCCUGCUGCUGCCUAGACGGCAC<br>GUGCGGCGGCUGCCCGAGCUGACCCCCGCCGAGCGGGACGACCUGGCCAGCA<br>UCAUGAAGAAGCUCCUGACCAAGUACGAUAACUUAUUCGAAACAAGCUUCCC<br>CUACAGCAUGGGCUGGCACGGCGCCCCCACCGGCUCAGAGGCCGGCGCUAAC<br>UGGAACCACUGGCAGCUGCACGCCCACUACUACCCGCCUCUGCUGAGAAGCG<br>CCACCGUGCGGAAGUUCAUGGUGGGCUACGAGAUGCUGGCCCAGGCCCAGAG<br>AGACUUAACCCCUGAGCAGGCCGCCGAGAGGCUCCGGGCCUUGCCAGAGGUG<br>CACUACCACCUGGGACAGAAGGACCGGGAGACGGCCACCAUCGCC |
| 125 | GALT-CO38 | AUGAGCCGGAGCGGCACCGACCCCCAGCAGCGGCAGCAGGCCAGCGAGGCCG<br>ACGCAGCCGCCGCUACCUUCCGGGCCAACGACCACCAGCACAUCCGGUACAA<br>CCCCCUGCAGGACGAGUGGGUGCUGGUGAGCGCCCACCGGAUGAAGCGGCCC<br>UGGCAGGGCCAGGUGGAGCCCCAGCUGCUGAAGACCGUGCCCCGGCACGACC |

TABLE 2-continued

Sequence optimized sequences for human GALT, isoform 1

| SEQ ID NO | Name | Sequence |
|---|---|---|
| | | CCCUGAAUCCUCUGUGCCCAGGAGCCAUCAGAGCCAACGGCGAGGUGAACCC<br>UCAGUACGACAGCACCUUCCUGUUCGACAACGACUUCCCCGCCCUGCAGCCC<br>GACGCCCCCAGCCCCGGCCCCAGCGACCAUCCGCUGUUCCAGGCCAAGAGCG<br>CCCGGGGCGUGUGCAAGGUGAUGUGCUUCCACCCCUGGAGCGACGUGACCCU<br>GCCCCUGAUGAGCGUGCCCGAGAUCCGAGCCGUGGUGGACGCCUGGGCCAGC<br>GUGACCGAGGAGCUGGGCGCCCAGUACCCCUGGGUGCAGAUCUUCGAGAACA<br>AGGGCGCCAUGAUGGGCUGCAGCAACCCCCACCCCCACUGCCAGGUGUGGGC<br>CUCGAGCUUCCUGCCCGACAUCGCCCAGCGGGAGGAGCGGAGCCAGCAAGCA<br>UACAAGUCACAGCACGGCGAGCCCCUGCUGAUGGAGUACAGCCGGCAGGAGC<br>UGCUGCGGAAGGAGCGGCUGGUGCUGACCAGCGAGCACUGGCUGGUCCUGGU<br>GCCCUUCUGGGCCACCUGGCCCUACCAGACCCUGCUGUUGCCUAGACGGCAC<br>GUGCGGCGGCUGCCCGAGCUGACCCCCGCCGAGCGGGACGACCUGGCCAGCA<br>UCAUGAAGAAGUUGCUGACAAAGUAUGACAAUCUGUUCGAAACCAGCUUCCC<br>CUACAGCAUGGGCUGGCACGGCGCCCCCACCGGCAGCGAAGCCGGCGCCAAC<br>UGGAACCACUGGCAGCUGCACGCCCACUACUACCCUCCUCUGCUCCGCAGCG<br>CCACCGUGCGGAAGUUCAUGGUGGGCUACGAGAUGCUGGCCCAGGCACAGCG<br>GGACCUGACCCCUGAGCAGGCCGCUGAGAGACUGCGGGCCCUCCCGGAGGUG<br>CACUACCACCUCGGCCAGAAGGACCGGGAAACGGCCACCAUCGCC |
| 126 | GALT-CO39 | AUGAGCCGGAGCGGCACCGACCCCCAGCAGCGGCAGCAGGCCAGCGAGGCCG<br>ACGCAGCCGCCGCGACCUUCCGGGCCAACGACCACCAGCACAUCCGGUACAA<br>CCCCCUGCAGGACGAGUGGGUGCUGGUGAGCGCCCACCGGAUGAAGCGGCCC<br>UGGCAGGGCCAGGUGGAGCCCCAGCUGCUGAAGACCGUGCCCCGGCACGACC<br>CCCUGAACCCUCUGUGCCCAGGAGCCAUUAGAGCCAAUGGCGAGGUGAACCC<br>ACAGUACGACAGCACCUUCCUGUUCGACAACGACUUCCCCGCCCUGCAGCCC<br>GACGCCCCCAGCCCCGGCCCCAGCGACCACCCGCUUUUCCAGGCCAAGAGCG<br>CCCGGGGCGUGUGCAAGGUGAUGUGCUUCCACCCCUGGAGCGACGUGACCCU<br>GCCCCUGAUGAGCGUGCCCGAGAUCAGAGCCGUGGUGGACGCCUGGGCCAGC<br>GUGACCGAGGAGCUGGGCGCCCAGUACCCCUGGGUGCAGAUCUUCGAGAACA<br>AGGGCGCCAUGAUGGGCUGCAGCAACCCCCACCCCCACUGCCAGGUGUGGGC<br>CUCUAGCUUCCUGCCCGACAUCGCCCAGCGGGAGGAGCGGAGCCAGCAAGCC<br>UACAAGUCUCAGCACGGCGAGCCCCUGCUGAUGGAGUACAGCCGGCAGGAGC<br>UGCUGCGGAAGGAGCGGCUGGUGCUGACCAGCGAGCACUGGCUGGUCCUCGU<br>GCCCUUCUGGGCCACCUGGCCCUACCAGACCCUGCUGCUCCCUAGACGGCAC<br>GUGCGGCGGCUGCCCGAGCUGACCCCCGCCGAGCGGGACGACCUGGCCAGCA<br>UCAUGAAGAAGCUGCUCACCAAGUAUGAUAAUCUGUUCGAGACAAGCUUCCC<br>CUACAGCAUGGGCUGGCACGGCGCCCCCACCGGUUCAGAGGCCGGCGCCAAC<br>UGGAACCACUGGCAGCUGCACGCCCACUACUACCCACCUUUGUUGCGUAGCG<br>CCACCGUGCGGAAGUUCAUGGUGGGCUACGAGAUGCUGGCCCAGGCCCAGCG<br>CGAUCUGACCCCAGAGCAGGCCGCCGAGAGGCUGCGGGCCUUACCUGAGGUG<br>CACUACCACCUCGGCCAGAAGGACCGGGAAACCGCCACCAUCGCC |
| 127 | GALT-CO40 | AUGAGCCGGAGCGGCACCGACCCCCAGCAGCGGCAGCAGGCCAGCGAGGCCG<br>ACGCCGCAGCCGCUACCUUCCGGGCCAACGACCACCAGCACAUCCGGUACAA<br>CCCCCUGCAGGACGAGUGGGUGCUGGUGAGCGCCCACCGGAUGAAGCGGCCC<br>UGGCAGGGCCAGGUGGAGCCCCAGCUGCUGAAGACCGUGCCCCGGCACGACC<br>CCCUGAAUCCUCUCUGCCCUGGAGCCAUUAGAGCCAACGGCGAGGUGAACCC<br>ACAGUACGACAGCACCUUCCUGUUCGACAACGACUUCCCCGCCCUGCAGCCC<br>GACGCCCCCAGCCCCGGCCCCAGCGACCACCCUCUGUUCCAGGCCAAGAGCG<br>CCCGGGGCGUGUGCAAGGUGAUGUGCUUCCACCCAUGGAGCGACGUGACCCU<br>GCCCCUGAUGAGCGUGCCCGAGAUCAGAGCUGUGGUGGACGCCUGGGCCAGC<br>GUGACCGAGGAGCUGGGCGCCCAGUACCCCUGGGUGCAGAUCUUCGAGAACA<br>AGGGCGCCAUGAUGGGCUGCAGCAACCCCCACCCCCACUGCCAGGUGUGGGC<br>UUCUAGCUUCCUGCCCGACAUCGCCCAGCGGGAGGAGCGGAGCCAGCAGGCG<br>UACAAGUCCCAGCACGGCGAGCCCCUGCUGAUGGAGUACAGCCGGCAGGAGC<br>UGCUGCGGAAGGAGCGGCUGGUGCUGACCAGCGAGCACUGGCUCGUGUUAGU<br>GCCCUUCUGGGCCACCUGGCCCUACCAGACCCUGCUGCUGCCUCGUCGGCAC<br>GUGCGGCGGCUGCCCGAGCUGACCCCCGCCGAGCGGGACGACCUGGCCAGCA<br>UCAUGAAGAAGCUCCUGACAAAGUAUGACAACCUAUUCGAAACCAGCUUCCC<br>CUACAGCAUGGGCUGGCACGGCGCCCCCACCGGCAGCGAAGCCGGCGCCAAC<br>UGGAACCACUGGCAGCUGCACGCCCACUACUAUCCACCUCUGCUGCGCAGCG<br>CCACCGUGCGGAAGUUCAUGGUGGGCUACGAGAUGCUGGCCCAGGCCCAGCG<br>CGACCUGACCCCUGAGCAGGCUGCCGAACGACUGCGGGCCCUGCCAGAAGUG<br>CACUACCACCUCGGCCAGAAGGACCGGGAGACUGCCACCAUCGCC |
| 128 | GALT-CO41 | AUGAGCCGGAGCGGCACCGACCCCCAGCAGCGGCAGCAGGCCAGCGAGGCCG<br>ACGCUGCAGCCGCCACCUUCCGGGCCAACGACCACCAGCACAUCCGGUACAA<br>CCCCCUGCAGGACGAGUGGGUGCUGGUGAGCGCCCACCGGAUGAAGCGGCCC<br>UGGCAGGGCCAGGUGGAGCCCCAGCUGCUGAAGACCGUGCCCCGGCACGACC<br>CCCUGAACCCUCUGUGCCCUGGUGCCAUCCGAGCCAACGGCGAGGUGAACCC<br>ACAGUACGACAGCACCUUCCUGUUCGACAACGACUUCCCCGCCCUGCAGCCC<br>GACGCCCCCAGCCCCGGCCCCAGCGACCAUCCUCUGUUCCAGGCCAAGAGCG<br>CCCGGGGCGUGUGCAAGGUGAUGUGCUUCCACCCCUGGAGCGACGUGACCCU<br>GCCCCUGAUGAGCGUGCCCGAGAUCAGAGCAGUGGUGGACGCCUGGGCCAGC |

TABLE 2-continued

| SEQ ID NO | Name | Sequence optimized sequences for human GALT, isoform 1<br>Sequence |
|---|---|---|
| | | GUGACCGAGGAGCUGGGCGCCCAGUACCCCUGGGUGCAGAUCUUCGAGAACA AGGGCGCCAUGAUGGGCUGCAGCAACCCCCACCCCCACUGCCAGGUGUGGGC UAGCAGCUUCCUGCCCGACAUCGCCCAGCGGGAGGAGCGGAGCCAGCAGGCU UACAAGUCUCAGCACGGCGAGCCCCUGCUGAUGGAGUACAGCCGGCAGGAGC UGCUGCGGAAGGAGCGGCUGGUGCUGACCAGCGAGCACUGGUUAGUCUUGGU GCCCUUCUGGGCCACCUGGCCCUACCAGACCCUGCUGCUGCCAAGACGGCAC GUGCGGCGGCUGCCCGAGCUGACCCCCGCCGAGCGGGACGACCUGGCCAGCA UCAUGAAGAAGCUCCUGACAAAGUACGAUAACCUUUUCGAGACAAGCUUCCC CUACAGCAUGGGCUGGCACGGCGCCCCAACCGGCUCCGAGGCCGGCGCUAAC UGGAACCACUGGCAGCUGCACGCCCACUACUACCCUCCUCUUUUGAGAAGCG CCACCGUGCGGAAGUUCAUGGUGGGCUACGAGAUGCUGGCCCAGGCCCAGAG GGACCUGACCCCUGAGCAGGCCGCCGAGAGAUUACGGGCUCUCCCAGAGGUG CACUACCACCUGGGACAGAAGGACCGGGAGACAGCCACCAUCGCC |
| 129 | GALT-CO42 | AUGAGCCGGAGCGGCACCGACCCCCAGCAGCGGCAGCAGGCCAGCGAGGCCG ACGCCGCCGCCGCCACCUUCCGGGCCAACGACCACCAGCACAUCCGGUACAA CCCCCUGCAGGACGAGUGGGUGCUGGUGAGCGCCCACCGGAUGAAGCGGCCC UGGCAGGGCCAGGUGGAGCCCCAGCUGCUGAAGACCGUGCCCCGGCACGACC CCCUGAACCCCCUGUGCCCCGGCGCCAUCCGGGCCAACGGCGAGGUGAACCC CCAGUACGACAGCACCUUCCUGUUCGACAACGACUUCCCCGCCCUGCAGCCC GACGCCCCCAGCCCCGGCCCCAGCGACCACCCCCUGUUCCAGGCCAAGAGCG CCCGGGGCGUGUGCAAGGUGAUGUGCUUCCACCCCUGGAGCGACGUGACCCU GCCCCUGAUGAGCGUGCCCGAGAUCCGGGCCGUGGUGGACGCCUGGGCCAGC GUGACCGAGGAGCUGGGCGCCCAGUACCCCUGGGUGCAGAUCUUCGAGAACA AGGGCGCCAUGAUGGGCUGCAGCAACCCCCACCCCCACUGCCAGGUGUGGGC CAGCAGCUUCCUGCCCGACAUCGCCCAGCGGGAGGAGCGGAGCCAGCAGGCC UACAAGAGCCAGCACGGCGAGCCCCUGCUGAUGGAGUACAGCCGGCAGGAGC UGCUGCGGAAGGAGCGGCUGGUGCUGACCAGCGAGCACUGGCUGGUGCUGGU GCCCUUCUGGGCCACCUGGCCCUACCAGACCCUGCUGCUGCCCCGGCGGCAC GUGCGGCGGCUGCCCGAGCUGACCCCCGCCGAGCGGGACGACCUGGCCAGCA UCAUGAAGAAGCUGCUGACCAAGUACGACAACCUGUUCGAGACCAGCUUCCC CUACAGCAUGGGCUGGCACGGCGCCCCCACCGGCAGCGAGGCCGGCGCCAAC UGGAACCACUGGCAGCUGCACGCCCACUACUACCCGCCCCUGCUGCGGAGCG CCACCGUGCGGAAGUUCAUGGUGGGCUACGAGAUGCUGGCCCAGGCCCAGCG GGACCUGACCCCCGAGCAGGCCGCCGAGCGGCUGCGGGCCCUGCCCGAGGUG CACUACCACCUGGGCCAGAAGGACCGGGAGACCGCCACCAUCGCC |
| 130 | GALT-CO43 | AUGAGCCGGAGCGGCACCGACCCCCAGCAGCGGCAGCAGGCCAGCGAGGCCG ACGCCGCCGCCGCCACCUUCCGGGCCAACGACCACCAGCACAUCAGGUACAA CCCGCUGCAGGACGAGUGGGUGCUGGUGAGCGCGCACAGGAUGAAGAGGCCG UGGCAGGGGCAGGUGGAGCCGCAGCUGCUGAAGACGGUGCCGAGGCACGACC CGCUGAACCCGCUGUGCCCGGGGGCGAUCAGGGCGAACGGGGAGGUGAACCC GCAGUACGACAGCACGUUCCUGUUCGACAACGACUUCCCGGCGCUGCAGCCG GACGCGCCGAGCCCGGGGCCGAGCGACCACCCGCUGUUCCAGGCGAAGAGCG CGAGGGGGGUGUGCAAGGUGAUGUGCUUCCACCCGUGGAGCGACGUGACGCU GCCGCUGAUGAGCGUGCCGGAGAUCAGGGCGGUGGUGGACGCGUGGGCGAGC GUGACGGAGGAGCUGGGGGCGCAGUACCCGUGGGUGCAGAUCUUCGAGAACA AGGGGGCGAUGAUGGGGUGCAGCAACCCGCACCCGCACUGCCAGGUGUGGGC GAGCAGCUUCCUGCCGGACAUCGCGCAGAGGGAGGAGAGGAGCCAGCAGGCG UACAAGAGCCAGCACGGGGAGCCGCUGCUGAUGGAGUACAGCAGGCAGGAGC UGCUGAGGAAGGAGAGGCUGGUGCUGACGAGCGAGCACUGGCUGGUGCUGGU GCCGUUCUGGGCGACGUGGCCGUACCAGACGCUGCUGCUGCCGAGGAGGCAC GUGAGGAGGCUGCCGGAGCUGACGCCGGCGGAGAGGGACGACCUGGCGAGCA UCAUGAAGAAGCUGCUGACGAAGUACGACAACCUGUUCGAGACGAGCUUCCC GUACAGCAUGGGGUGGCACGGGGCGCCGACGGGGAGCGAGGCGGGGGCGAAC UGGAACCACUGGCAGCUGCACGCGCACUACUACCCGCCGCUGCUGAGGAGCG CGACGGUGAGGAAGUUCAUGGUGGGGUACGAGAUGCUGGCGCAGGCGCAGAG GGACCUGACGCCGGAGCAGGCGGCGGAGAGGCUGAGGGCGCUGCCGGAGGUG CACUACCACCUGGGGCAGAAGGACAGGGAGACGGCGACGAUCGCG |
| 131 | GALT-CO44 | AUGAGCCGGAGCGGCACCGACCCCCAGCAGCGGCAGCAGGCCAGCGAGGCCG ACGCCGCCGCCGCCACCUUCCGGGCCAACGACCACCAGCACAUCCGCUACAA CCCCCUCCAGGACGAGUGGGUCCUCGUCUCCGCCCACCGCAUGAAGCGCCCC UGGCAGGGCCAGGUCGAGCCCCAGCUCCUCAAGACCGUCCCCCGCCACGACC CCCUCAACCCCCUCUGCCCCGGCGCCAUCCGCGCCAACGGCGAGGUCAACCC CCAGUACGACUCCACCUUCCUCUUCGACAACGACUUCCCCGCCCUCCAGCCC GACGCCCCCUCCCCCGGCCCCUCCGACCACCCCCUCUUCCAGGCCAAGUCCG CCCGCGGCGUCUGCAAGGUCAUGUGCUUCCACCCCUGGUCCGACGUCACCCU CCCCCUCAUGUCCGUCCCCGAGAUCCGCGCCGUCGUCGACGCCUGGGCCUCC GUCACCGAGGAGCUCGGCGCCCAGUACCCCUGGGUCCAGAUCUUCGAGAACA AGGGCGCCAUGAUGGGCUGCUCCAACCCCCACCCCCACUGCCAGGUCUGGGC CUCCUCCUUCCUCCCCGACAUCGCCCAGCGCGAGGAGCGCUCCCAGCAGGCC UACAAGUCCCAGCACGGCGAGCCCCUCCUCAUGGAGUACUCCCGCCAGGAGC UCCUCCGCAAGGAGCGCCUCGUCCUCACCUCCGAGCACUGGCUCGUCCUCGU |

TABLE 2-continued

Sequence optimized sequences for human GALT, isoform 1

| SEQ ID NO | Name | Sequence |
|---|---|---|
| | | CCCCUUCUGGGCCACCUGGCCCUACCAGACCCUCCUCCUCCCCCGCCGCCAC<br>GUCCGCCGCCUCCCCGAGCUCACCCCCGCCGAGCGCGACGACCUCGCCUCCA<br>UCAUGAAGAAGCUCCUCACCAAGUACGACAACCUCUUCGAGACCUCCUUCCC<br>CUACUCCAUGGGCUGGCACGGCGCCCCCACCGGCUCCGAGGCCGGCGCCAAC<br>UGGAACCACUGGCAGCUCCACGCCCACUACUACCCGCCCCUCCUCCGCUCCG<br>CCACCGUCCGCAAGUUCAUGGUCGGCUACGAGAUGCUCGCCCAGGCCCAGCG<br>CGACCUCACCCCCGAGCAGGCCGCCGAGCGCCUCCGCGCCCUCCCCGAGGUC<br>CACUACCACCUCGGCCAGAAGGACCGCGAGACCGCCACCAUCGCC |

The sequence-optimized nucleotide sequences disclosed herein are distinct from the corresponding wild type nucleotide acid sequences and from other known sequence-optimized nucleotide sequences, e.g., these sequence-optimized nucleic acids have unique compositional characteristics.

In some embodiments, the percentage of uracil or thymine nucleobases in a sequence-optimized nucleotide sequence (e.g., encoding a GALT polypeptide, a functional fragment, or a variant thereof) is modified (e.g., reduced) with respect to the percentage of uracil or thymine nucleobases in the reference wild-type nucleotide sequence. Such a sequence is referred to as a uracil-modified or thymine-modified sequence. The percentage of uracil or thymine content in a nucleotide sequence can be determined by dividing the number of uracils or thymines in a sequence by the total number of nucleotides and multiplying by 100. In some embodiments, the sequence-optimized nucleotide sequence has a lower uracil or thymine content than the uracil or thymine content in the reference wild-type sequence. In some embodiments, the uracil or thymine content in a sequence-optimized nucleotide sequence of the invention is greater than the uracil or thymine content in the reference wild-type sequence and still maintain beneficial effects, e.g., increased expression and/or reduced Toll-Like Receptor (TLR) response when compared to the reference wild-type sequence.

The uracil or thymine content of wild-type GALT isoform 1 is about 20%. In some embodiments, the uracil or thymine content of a uracil- or thymine-modified sequence encoding a GALT polypeptide is less than 20%. In some embodiments, the uracil or thymine content of a uracil- or thymine-modified sequence encoding a GALT polypeptide of the invention is less than 19%, less that 18%, less than 17%, less than 16%, less than 15%, less than 14%, less than 13%, less than 12%, or less than 11%. In some embodiments, the uracil or thymine content is not less than 18%, 17%, 16%, 15%, 14%, 13%, 12%, 11%, or 10%. The uracil or thymine content of a sequence disclosed herein, i.er., its total uracil or thymine content is abbreviated herein as % $U_{TL}$ or % $T_{TL}$.

In some embodiments, the uracil or thymine content (% $U_{TL}$ or % $T_{TL}$) of a uracil- or thymine-modified sequence encoding a GALT polypeptide of the invention is between 10% and 20%, between 11% and 20%, between 12% and 20%, between 12% and 19%, between 13% and 19%, between 13% and 18%, between 14% and 17%, between 14% and 16%, or between 14% and 15%.

In some embodiments, the uracil or thymine content (% $U_{TL}$ or % $T_{TL}$) of a uracil- or thymine-modified sequence encoding a GALT polypeptide of the invention is between 13% and 16%, between 13% and 15%, or between 14% and 15%.

In a particular embodiment, the uracil or thymine content (% $U_{TL}$ or % $T_{TL}$) of a uracil- or thymine modified sequence encoding a GALT polypeptide of the invention is between about 14% and about 15%.

A uracil- or thymine-modified sequence encoding a GALT polypeptide of the invention can also be described according to its uracil or thymine content relative to the uracil or thymine content in the corresponding wild-type nucleic acid sequence (% $U_{WT}$ or % $T_{WT}$), or according to its uracil or thymine content relative to the theoretical minimum uracil or thymine content of a nucleic acid encoding the wild-type protein sequence (% $U_{TM}$ or % $T_{TM}$).

The phrases "uracil or thymine content relative to the uracil or thymine content in the wild type nucleic acid sequence," refers to a parameter determined by dividing the number of uracils or thymines in a sequence-optimized nucleic acid by the total number of uracils or thymines in the corresponding wild-type nucleic acid sequence and multiplying by 100. This parameter is abbreviated herein as % $U_{WT}$ or % $T_{WT}$.

In some embodiments, the % $U_{WT}$ or % $T_{WT}$ of a uracil- or thymine-modified sequence encoding a GALT polypeptide of the invention is above 50%, above 55%, above 60%, above 65%, above 70%, above 75%, above 80%, above 85%, above 90%, or above 95%.

In some embodiments, the % $U_{WT}$ or % $T_{WT}$ of a uracil- or thymine modified sequence encoding a GALT polypeptide of the invention is between 58% and 84%, between 59% and 83%, between 60% and 82%, between 61% and 81%, between 62% and 80%, between 63% and 79%, between 64% and 78%, between 65% and 77%, between 66% and 76%, between 67% and 75%, or between 68% and 74%.

In some embodiments, the % $U_{WT}$ or % $T_{WT}$ of a uracil- or thymine-modified sequence encoding a GALT polypeptide of the invention is between 66% and 76%, between 66% and 76%, between 67% and 75%, or between 68% and 74%.

In a particular embodiment, the % $U_{WT}$ or % $T_{WT}$ of a uracil- or thymine-modified sequence encoding a GALT polypeptide of the invention is between about 68% and about 74%.

Uracil- or thymine-content relative to the uracil or thymine theoretical minimum, refers to a parameter determined by dividing the number of uracils or thymines in a sequence-optimized nucleotide sequence by the total number of uracils or thymines in a hypothetical nucleotide sequence in which all the codons in the hypothetical sequence are replaced with synonymous codons having the lowest possible uracil or thymine content and multiplying by 100. This parameter is abbreviated herein as % $U_{TM}$ or % $T_{TM}$ For DNA it is recognized that thymine is present instead of uracil, and one would substitute T where U appears. Thus, all the disclosures related to, e.g., % $U_{TM}$, % $U_{WT}$, or % $U_{TL}$, with respect to RNA are equally applicable to % $T_{TM}$, % $T_{WT}$, or % $T_{TL}$ with respect to DNA.

In some embodiments, the % $U_{TM}$ of a uracil-modified sequence encoding a GALT polypeptide of the invention is below 300%, below 295%, below 290%, below 285%, below 280%, below 275%, below 270%, below 265%, below 260%, below 255%, below 250%, below 245%, below 240%, below 235%, below 230%, below 225%, below 220%, below 215%, below 200%, below 195%, below 190%, below 185%, below 180%, below 175%, below 170%, below 165%, below 160%, below 155%, below 150%, below 145%, below 140%, below 139%, below 138%, below 137%, below 136%, below 135%, below 134%, below 133%, below 132%, below 131%, below 130%, below 129%, below 128%, below 127%, below 126%, below 125%, below 124%, or below 123%.

In some embodiments, the % $U_{TM}$ of a uracil-modified sequence encoding a GALT polypeptide of the invention is above 100%, above 101%, above 102%, above 103%, above 104%, above 105%, above 106%, above 107%, above 108%, above 109%, above 110%, above 111%, above 112%, above 113%, above 114%, above 115%, above 116%, above 117%, above 118%, above 119%, above 120%, above 121%, above 122%, above 123%, above 124%, above 125%, or above 126%, above 127%, above 128%, above 129%, or above 130%, above 135%, above 130%, above 131%, above 132%, or above 133%.

In some embodiments, the % $U_{TM}$ of a uracil-modified sequence encoding a GALT polypeptide of the invention is between 127% and 129%, between 126% and 130%, between 125% and 131%, between 124% and 132%, between 123% and 133%, between 122% and 134%, between 121% and 135%, between 120% and 136%, between 119% and 137%, between 118% and 138%, between 117% and 139%, between 116% and 140%, or between 115% and 141%.

In some embodiments, the % $U_{TM}$ of a uracil-modified sequence encoding a GALT polypeptide of the invention is between about 123% and about 134%.

In some embodiments, a uracil-modified sequence encoding a GALT polypeptide of the invention has a reduced number of consecutive uracils with respect to the corresponding wild-type nucleic acid sequence. For example, two consecutive leucines can be encoded by the sequence CUUUUG, which includes a four uracil cluster. Such a subsequence can be substituted, e.g., with CUGCUC, which removes the uracil cluster.

Phenylalanine can be encoded by UUC or UUU. Thus, even if phenylalanines encoded by UUU are replaced by UUC, the synonymous codon still contains a uracil pair (UU). Accordingly, the number of phenylalanines in a sequence establishes a minimum number of uracil pairs (UU) that cannot be eliminated without altering the number of phenylalanines in the encoded polypeptide. For example, if the polypeptide, e.g., wild type GALT, has 11, 12, 13, or 14 phenylalanines, the absolute minimum number of uracil pairs (UU) in that uracil-modified sequence encoding the polypeptide, e.g., wild type GALT, can contain is 11, 12, 13, or 14, respectively.

Wild type GALT isoform 1 contains 20 uracil pairs (UU), and five uracil triplets (UUU). In some embodiments, a uracil-modified sequence encoding a GALT polypeptide of the invention has a reduced number of uracil triplets (UUU) with respect to the wild-type nucleic acid sequence. In some embodiments, a uracil-modified sequence encoding a GALT polypeptide of the invention contains 5, 4, 3, 2, 1 or no uracil triplets (UUU).

In some embodiments, a uracil-modified sequence encoding a GALT polypeptide has a reduced number of uracil pairs (UU) with respect to the number of uracil pairs (UU) in the wild-type nucleic acid sequence. In some embodiments, a uracil-modified sequence encoding a GALT polypeptide of the invention has a number of uracil pairs (UU) corresponding to the minimum possible number of uracil pairs (UU) in the wild-type nucleic acid sequence, e.g., 12 uracil pairs in the case of wild type GALT isoform 1.

In some embodiments, a uracil-modified sequence encoding a GALT polypeptide of the invention has at least 1, 2, 3, 4, 5, 6, 7, 8, 9, or 10 uracil pairs (UU) less than the number of uracil pairs (UU) in the wild-type nucleic acid sequence. In some embodiments, a uracil-modified sequence encoding a GALT polypeptide of the invention has between 9 and 19 uracil pairs (UU).

The phrase "uracil pairs (UU) relative to the uracil pairs (UU) in the wild type nucleic acid sequence," refers to a parameter determined by dividing the number of uracil pairs (UU) in a sequence-optimized nucleotide sequence by the total number of uracil pairs (UU) in the corresponding wild-type nucleotide sequence and multiplying by 100. This parameter is abbreviated herein as % $UU_{wt}$.

In some embodiments, a uracil-modified sequence encoding a GALT polypeptide of the invention has a % $UU_{wt}$ less than 90%, less than 85%, less than 80%, less than 75%, less than 70%, less than 65%, less than 60%, less than 65%, less than 60%, less than 55%, less than 50%, less than 40%, less than 30%, or less than 20%.

In some embodiments, a uracil-modified sequence encoding a GALT polypeptide has a % $UU_{wt}$ between 40% and 100%. In a particular embodiment, a uracil-modified sequence encoding a GALT polypeptide of the invention has a % $UU_{wt}$ between 45% and 90%.

In some embodiments, the polynucleotide of the invention comprises a uracil-modified sequence encoding a GALT polypeptide disclosed herein. In some embodiments, the uracil-modified sequence encoding a GALT polypeptide comprises at least one chemically modified nucleobase, e.g., 5-methoxyuracil. In some embodiments, at least 95% of a nucleobase (e.g., uracil) in a uracil-modified sequence encoding a GALT polypeptide of the invention are modified nucleobases. In some embodiments, at least 95% of uracil in a uracil-modified sequence encoding a GALT polypeptide is 5-methoxyuracil. In some embodiments, the polynucleotide comprising a uracil-modified sequence further comprises a miRNA binding site, e.g., a miRNA binding site that binds to miR-142 and/or a miRNA binding site that binds to miR-126. In some embodiments, the polynucleotide comprising a uracil-modified sequence is formulated with a delivery agent comprising, e.g., a compound having the Formula (I), e.g., any of Compounds 1-232, e.g., Compound 18; a compound having the Formula (III), (IV), (V), or (VI), e.g., any of Compounds 233-342, e.g., Compound 236; or a compound having the Formula (VIII), e.g., any of Compounds 419-428, e.g., Compound 428, or any combination thereof. In some embodiments, the delivery agent comprises Compound 18, DSPC, Cholesterol, and Compound 428, e.g., with a mole ratio of about 50:10:38.5:1.5.

In some embodiments, the "guanine content of the sequence optimized ORF encoding GALT with respect to the theoretical maximum guanine content of a nucleotide sequence encoding the GALT polypeptide," abbreviated as % $G_{TMX}$ is at least 68%, at least 70%, at least 75%, at least about 80%, at least about 85%, at least about 90%, at least about 95%, or about 100%. In some embodiments, the % $G_{TMX}$ is between about 68% and about 80%, between about 69% and about 78%, between about 70% and about 78%, or between about 70% and about 77%.

In some embodiments, the "cytosine content of the ORF relative to the theoretical maximum cytosine content of a nucleotide sequence encoding the GALT polypeptide," abbreviated as % $C_{TMX}$, is at least 68%, at least 70%, at least about 75%, at least about 80%, at least about 85%, at least about 90%, at least about 95%, or about 100%. In some embodiments, the % $C_{TMX}$ is between about 64% and about 82%, between about 66% and about 80%, between about 68% and about 79%, or between about 70% and about 78%.

In some embodiments, the "guanine and cytosine content (G/C) of the ORF relative to the theoretical maximum G/C content in a nucleotide sequence encoding the GALT polypeptide," abbreviated as % $G/C_{TMX}$ is at least about 89%, at least about 90%, at least about 91%, at least about 95%, or about 100%. The % $G/C_{TMX}$ is between about 80% and about 100%, between about 85% and about 98%, between about 90% and about 96%, or between about 91% and about 95%.

In some embodiments, the "G/C content in the ORF relative to the G/C content in the corresponding wild-type ORF," abbreviated as % $G/C_{WT}$ is at least 104%, at least 105%, at least 106%, at least 107%, at least 108%, at least 109%, at least 111%, at least 113%, at least 115%, or at least 120%.

In some embodiments, the average G/C content in the 3rd codon position in the ORF is at least 20%, at least 21%, at least 22%, at least 23%, at least 24%, or at least 25% higher than the average G/C content in the 3rd codon position in the corresponding wild-type ORF.

In some embodiments, the polynucleotide of the invention comprises an open reading frame (ORF) encoding a GALT polypeptide, wherein the ORF has been sequence optimized, and wherein each of % $U_{TL}$, % $U_{WT}$, % $U_{TM}$, % $G_{TL}$, % $G_{WT}$, % $G_{TMX}$, % $C_{TL}$, % $C_{WT}$, % $C_{TMX}$, % $G/C_{TL}$, % $G/C_{WT}$, or % $G/C_{TMX}$, alone or in a combination thereof is in a range between (i) a maximum corresponding to the parameter's maximum value (MAX) plus about 0.5, 1, 1.5, 2, 2.5, 3, 3.5, 4, 4.5, 5, 5.5, 6, 6.5, 7, 7.5, 8, 8.5, 9, 9.5, or 10 standard deviations (STD DEV), and (ii) a minimum corresponding to the parameter's minimum value (MIN) less 0.5, 1, 1.5, 2, 2.5, 3, 3.5, 4, 4.5, 5, 5.5, 6, 6.5, 7, 7.5, 8, 8.5, 9, 9.5, or 10 standard deviations (STD DEV).

7. METHODS FOR SEQUENCE OPTIMIZATION

In some embodiments, a polynucleotide, e.g. mRNA, of the invention (e.g., a polynucleotide comprising a nucleotide sequence encoding a GALT polypeptide (e.g., the wild-type sequence, functional fragment, or variant thereof) is sequence optimized. A sequence optimized nucleotide sequence (nucleotide sequence is also referred to as "nucleic acid" herein) comprises at least one codon modification with respect to a reference sequence (e.g., a wild-type sequence encoding a GALT polypeptide). Thus, in a sequence optimized nucleic acid, at least one codon is different from a corresponding codon in a reference sequence (e.g., a wild-type sequence).

In general, sequence optimized nucleic acids are generated by at least a step comprising substituting codons in a reference sequence with synonymous codons (i.e., codons that encode the same amino acid). Such substitutions can be effected, for example, by applying a codon substitution map (i.e., a table providing the codons that will encode each amino acid in the codon optimized sequence), or by applying a set of rules (e.g., if glycine is next to neutral amino acid, glycine would be encoded by a certain codon, but if it is next to a polar amino acid, it would be encoded by another codon). In addition to codon substitutions (i.e., "codon optimization") the sequence optimization methods disclosed herein comprise additional optimization steps which are not strictly directed to codon optimization such as the removal of deleterious motifs (destabilizing motif substitution). Compositions and formulations comprising these sequence optimized nucleic acids (e.g., a RNA, e.g., an mRNA) can be administered to a subject in need thereof to facilitate in vivo expression of functionally active GALT.

The recombinant expression of large molecules in cell cultures can be a challenging task with numerous limitations (e.g., poor protein expression levels, stalled translation resulting in truncated expression products, protein misfolding, etc.) These limitations can be reduced or avoided by administering the polynucleotides (e.g., a RNA, e.g., an mRNA), which encode a functionally active GALT or compositions or formulations comprising the same to a patient suffering from Gal-1, so the synthesis and delivery of the GALT polypeptide to treat Gal-1 takes place endogenously.

Changing from an in vitro expression system (e.g., cell culture) to in vivo expression requires the redesign of the nucleic acid sequence encoding the therapeutic agent. Redesigning a naturally occurring gene sequence by choosing different codons without necessarily altering the encoded amino acid sequence can often lead to dramatic increases in protein expression levels (Gustafsson et al., 2004, Journal/Trends Biotechnol 22, 346-53). Variables such as codon adaptation index (CAI), mRNA secondary structures, cis-regulatory sequences, GC content and many other similar variables have been shown to somewhat correlate with protein expression levels (Villalobos et al., 2006, "Journal/BMC Bioinformatics 7, 285). However, due to the degeneracy of the genetic code, there are numerous different nucleic acid sequences that can all encode the same therapeutic agent. Each amino acid is encoded by up to six synonymous codons; and the choice between these codons influences gene expression. In addition, codon usage (i.e., the frequency with which different organisms use codons for expressing a polypeptide sequence) differs among organisms (for example, recombinant production of human or humanized therapeutic antibodies frequently takes place in hamster cell cultures).

In some embodiments, a reference nucleic acid sequence can be sequence optimized by applying a codon map. The skilled artisan will appreciate that the T bases in the codon maps disclosed below are present in DNA, whereas the T bases would be replaced by U bases in corresponding RNAs. For example, a sequence optimized nucleic acid disclosed herein in DNA form, e.g., a vector or an in-vitro translation (IVT) template, would have its T bases transcribed as U based in its corresponding transcribed mRNA. In this respect, both sequence optimized DNA sequences (comprising T) and their corresponding RNA sequences (comprising U) are considered sequence optimized nucleic acid of the present invention. A skilled artisan would also understand that equivalent codon-maps can be generated by replaced one or more bases with non-natural bases. Thus, e.g., a TTC codon (DNA map) would correspond to a UUC codon (RNA map), which in turn can correspond to a ΨΨC codon (RNA map in which U has been replaced with pseudouridine).

In one embodiment, a reference sequence encoding GALT can be optimized by replacing all the codons encoding a certain amino acid with only one of the alternative codons provided in a codon map. For example, all the valines in the optimized sequence would be encoded by GTG or GTC or GTT.

Sequence optimized polynucleotides of the invention can be generated using one or more optimization methods, or a combination thereof. Sequence optimization methods which can be used to sequence optimize nucleic acid sequences are described in detail herein. This list of methods is not comprehensive or limiting.

It will be appreciated that the design principles and rules described for each one of the sequence optimization methods discussed below can be combined in many different ways, for example high G/C content sequence optimization for some regions or uridine content sequence optimization for other regions of the reference nucleic acid sequence, as well as targeted nucleotide mutations to minimize secondary structure throughout the sequence or to eliminate deleterious motifs.

The choice of potential combinations of sequence optimization methods can be, for example, dependent on the specific chemistry used to produce a synthetic polynucleotide. Such a choice can also depend on characteristics of the protein encoded by the sequence optimized nucleic acid, e.g., a full sequence, a functional fragment, or a fusion protein comprising GALT, etc. In some embodiments, such a choice can depend on the specific tissue or cell targeted by the sequence optimized nucleic acid (e.g., a therapeutic synthetic mRNA).

The mechanisms of combining the sequence optimization methods or design rules derived from the application and analysis of the optimization methods can be either simple or complex. For example, the combination can be:

(i) Sequential: Each sequence optimization method or set of design rules applies to a different subsequence of the overall sequence, for example reducing uridine at codon positions 1 to 30 and then selecting high frequency codons for the remainder of the sequence;

(ii) Hierarchical: Several sequence optimization methods or sets of design rules are combined in a hierarchical, deterministic fashion. For example, use the most GC-rich codons, breaking ties (which are common) by choosing the most frequent of those codons.

(iii) Multifactorial/Multiparametric: Machine learning or other modeling techniques are used to design a single sequence that best satisfies multiple overlapping and possibly contradictory requirements. This approach would require the use of a computer applying a number of mathematical techniques, for example, genetic algorithms.

Ultimately, each one of these approaches can result in a specific set of rules which in many cases can be summarized in a single codon table, i.e., a sorted list of codons for each amino acid in the target protein (i.e., GALT), with a specific rule or set of rules indicating how to select a specific codon for each amino acid position.

a. Uridine Content Optimization

The presence of local high concentrations of uridine in a nucleic acid sequence can have detrimental effects on translation, e.g., slow or prematurely terminated translation, especially when modified uridine analogs are used in the production of synthetic mRNAs. Furthermore, high uridine content can also reduce the in vivo half-life of synthetic mRNAs due to TLR activation.

Accordingly, a nucleic acid sequence can be sequence optimized using a method comprising at least one uridine content optimization step. Such a step comprises, e.g., substituting at least one codon in the reference nucleic acid with an alternative codon to generate a uridine-modified sequence, wherein the uridine-modified sequence has at least one of the following properties:

(i) increase or decrease in global uridine content;

(ii) increase or decrease in local uridine content (i.e., changes in uridine content are limited to specific subsequences);

(iii) changes in uridine distribution without altering the global uridine content;

(iv) changes in uridine clustering (e.g., number of clusters, location of clusters, or distance between clusters); or (v) combinations thereof.

In some embodiments, the sequence optimization process comprises optimizing the global uridine content, i.e., optimizing the percentage of uridine nucleobases in the sequence optimized nucleic acid with respect to the percentage of uridine nucleobases in the reference nucleic acid sequence. For example, 30% of nucleobases can be uridines in the reference sequence and 10% of nucleobases can be uridines in the sequence optimized nucleic acid.

In other embodiments, the sequence optimization process comprises reducing the local uridine content in specific regions of a reference nucleic acid sequence, i.e., reducing the percentage of uridine nucleobases in a subsequence of the sequence optimized nucleic acid with respect to the percentage of uridine nucleobases in the corresponding subsequence of the reference nucleic acid sequence. For example, the reference nucleic acid sequence can have a 5'-end region (e.g., 30 codons) with a local uridine content of 30%, and the uridine content in that same region could be reduced to 10% in the sequence optimized nucleic acid.

In specific embodiments, codons can be replaced in the reference nucleic acid sequence to reduce or modify, for example, the number, size, location, or distribution of uridine clusters that could have deleterious effects on protein translation. Although as a general rule it is desirable to reduce the uridine content of the reference nucleic acid sequence, in certain embodiments the uridine content, and in particular the local uridine content, of some subsequences of the reference nucleic acid sequence can be increased.

The reduction of uridine content to avoid adverse effects on translation can be done in combination with other optimization methods disclosed here to achieve other design goals. For example, uridine content optimization can be combined with ramp design, since using the rarest codons for most amino acids will, with a few exceptions, reduce the U content.

In some embodiments, the uridine-modified sequence is designed to induce a lower Toll-Like Receptor (TLR) response when compared to the reference nucleic acid sequence. Several TLRs recognize and respond to nucleic acids. Double-stranded (ds)RNA, a frequent viral constituent, has been shown to activate TLR3. See Alexopoulou et al. (2001) Nature, 413:732-738 and Wang et al. (2004) Nat. Med., 10:1366-1373. Single-stranded (ss)RNA activates TLR7. See Diebold et al. (2004) Science 303:1529-1531. RNA oligonucleotides, for example RNA with phosphorothioate internucleotide linkages, are ligands of human TLR8. See Heil et al. (2004) Science 303:1526-1529. DNA containing unmethylated CpG motifs, characteristic of bacterial and viral DNA, activate TLR9. See Hemmi et al. (2000) Nature, 408: 740-745.

As used herein, the term "TLR response" is defined as the recognition of single-stranded RNA by a TLR7 receptor, and in some embodiments encompasses the degradation of the RNA and/or physiological responses caused by the recognition of the single-stranded RNA by the receptor. Methods to determine and quantitate the binding of an RNA to a TLR7 are known in the art. Similarly, methods to determine whether an RNA has triggered a TLR7-mediated physiological response (e.g., cytokine secretion) are well known in the art. In some embodiments, a TLR response can be mediated by TLR3, TLR8, or TLR9 instead of TLR7.

Suppression of TLR7-mediated response can be accomplished via nucleoside modification. RNA undergoes over hundred different nucleoside modifications in nature (see the RNA Modification Database, available at mods.rna.albany.edu). Human rRNA, for example, has ten times more pseudouridine (Ψ) and 25 times more 2'-O-methylated nucleosides than bacterial rRNA. Bacterial mRNA contains no nucleoside modifications, whereas mammalian mRNAs have modified nucleosides such as 5-methylcytidine (m5C), N6-methyladenosine (m6A), inosine and many 2'-O-methylated nucleosides in addition to N7-methylguanosine (m7G).

Uracil and ribose, the two defining features of RNA, are both necessary and sufficient for TLR7 stimulation, and short single-stranded RNA (ssRNA) act as TLR7 agonists in a sequence-independent manner as long as they contain several uridines in close proximity. See Diebold et al. (2006) Eur. J. Immunol. 36:3256-3267, which is herein incorporated by reference in its entirety. Accordingly, one or more of the optimization methods disclosed herein comprises reducing the uridine content (locally and/or globally) and/or reducing or modifying uridine clustering to reduce or to suppress a TLR7-mediated response.

In some embodiments, the TLR response (e.g., a response mediated by TLR7) caused by the uridine-modified sequence is at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or at least about 100% lower than the TLR response caused by the reference nucleic acid sequence.

In some embodiments, the TLR response caused by the reference nucleic acid sequence is at least about 1-fold, at least about 1.1-fold, at least about 1.2-fold, at least about 1.3-fold, at least about 1.4-fold, at least about 1.5-fold, at least about 1.6-fold, at least about 1.7-fold, at least about 1.8-fold, at least about 1.9-fold, at least about 2-fold, at least about 3-fold, at least about 4-fold, at least about 5-fold, at least about 6-fold, at least about 7-fold, at least about 8-fold, at least about 9-fold, or at least about 10-fold higher than the TLR response caused by the uridine-modified sequence.

In some embodiments, the uridine content (average global uridine content) (absolute or relative) of the uridine-modified sequence is higher than the uridine content (absolute or relative) of the reference nucleic acid sequence. Accordingly, in some embodiments, the uridine-modified sequence contains at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or at least about 100% more uridine that the reference nucleic acid sequence.

In other embodiments, the uridine content (average global uridine content) (absolute or relative) of the uridine-modified sequence is lower than the uridine content (absolute or relative) of the reference nucleic acid sequence. Accordingly, in some embodiments, the uridine-modified sequence contains at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or at least about 100% less uridine that the reference nucleic acid sequence.

In some embodiments, the uridine content (average global uridine content) (absolute or relative) of the uridine-modified sequence is less than 50%, 49%, 48%, 47%, 46%, 45%, 44%, 43%, 42%, 41%, 40%, 39%, 38%, 37%, 36%, 35%, 34%, 33%, 32%, 31%, 30%, 29%, 28%, 27%, 26%, 25%, 24%, 23%, 22%, 21%, 20%, 19%, 18%, 17%, 16%, 15%, 14%, 13%, 12%, 11%, 10%, 9%, 8%, 7%, 6%, 5%, 4%, 3%, 2% or 1% of the total nucleobases in the uridine-modified sequence. In some embodiments, the uridine content of the uridine-modified sequence is between about 10% and about 20%. In some particular embodiments, the uridine content of the uridine-modified sequence is between about 12% and about 16%.

In some embodiments, the uridine content of the reference nucleic acid sequence can be measured using a sliding window. In some embodiments, the length of the sliding window is 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 nucleobases. In some embodiments, the sliding window is over 40 nucleobases in length. In some embodiments, the sliding window is 20 nucleobases in length. Based on the uridine content measured with a sliding window, it is possible to generate a histogram representing the uridine content throughout the length of the reference nucleic acid sequence and sequence optimized nucleic acids.

In some embodiments, a reference nucleic acid sequence can be modified to reduce or eliminate peaks in the histogram that are above or below a certain percentage value. In some embodiments, the reference nucleic acid sequence can be modified to eliminate peaks in the sliding-window representation which are above 65%, 60%, 55%, 50%, 45%, 40%, 35%, or 30% uridine. In another embodiment, the reference nucleic acid sequence can be modified so no peaks are over 30% uridine in the sequence optimized nucleic acid, as measured using a 20 nucleobase sliding window. In some embodiments, the reference nucleic acid sequence can be modified so no more or no less than a predetermined number of peaks in the sequence optimized nucleic sequence, as measured using a 20 nucleobase sliding window, are above or below a certain threshold value. For example, in some embodiments, the reference nucleic acid sequence can be modified so no peaks or no more than 1, 2, 3, 4, 5, 6, 7, 8, 9 or 10 peaks in the sequence optimized nucleic acid are above 10%, 15%, 20%, 25% or 30% uridine. In another embodiment, the sequence optimized nucleic acid contains between 0 peaks and 2 peaks with uridine contents 30% of higher.

In some embodiments, a reference nucleic acid sequence can be sequence optimized to reduce the incidence of consecutive uridines. For example, two consecutive leucines could be encoded by the sequence CUUUUG, which would include a four uridine cluster. Such subsequence could be substituted with CUGCUC, which would effectively remove the uridine cluster. Accordingly, a reference nucleic sequence can be sequence optimized by reducing or eliminating uridine pairs (UU), uridine triplets (UUU) or uridine quadruplets (UUUU). Higher order combinations of U are not considered combinations of lower order combinations. Thus, for example, UUUU is strictly considered a quadruplet, not two consecutive U pairs; or UUUUUU is considered a sextuplet, not three consecutive U pairs, or two consecutive U triplets, etc.

In some embodiments, all uridine pairs (UU) and/or uridine triplets (UUU) and/or uridine quadruplets (UUUU) can be removed from the reference nucleic acid sequence. In other embodiments, uridine pairs (UU) and/or uridine triplets (UUU) and/or uridine quadruplets (UUUU) can be reduced below a certain threshold, e.g., no more than 1, 2, 3, 4, 5, 6, 7, 8, 9, 10, 11, 12, 13, 14, 15, 16, 17, 18, 19, or 20 occurrences in the sequence optimized nucleic acid. In a particular embodiment, the sequence optimized nucleic acid contains less than 20, 19, 18, 17, 16, 15, 14, 13, 12, 11, 10, 9, 8, 7, 6, 5, 4, 3, 2, or 1 uridine pairs. In another particular embodiment, the sequence optimized nucleic acid contains no uridine pairs and/or triplets.

Phenylalanine codons, i.e., UUC or UUU, comprise a uridine pair or triples and therefore sequence optimization to reduce uridine content can at most reduce the phenylalanine U triplet to a phenylalanine U pair. In some embodiments, the occurrence of uridine pairs (UU) and/or uridine triplets (UUU) refers only to non-phenylalanine U pairs or triplets. Accordingly, in some embodiments, non-phenylalanine uridine pairs (UU) and/or uridine triplets (UUU) can be reduced below a certain threshold, e.g., no more than 1, 2, 3, 4, 5, 6, 7, 8, 9, 10, 11, 12, 13, 14, 15, 16, 17, 18, 19, or 20 occurrences in the sequence optimized nucleic acid. In a particular embodiment, the sequence optimized nucleic acid contains less than 20, 19, 18, 17, 16, 15, 14, 13, 12, 11, 10, 9, 8, 7, 6, 5, 4, 3, 2, or 1 non-phenylalanine uridine pairs and/or triplets. In another particular embodiment, the sequence optimized nucleic acid contains no non-phenylalanine uridine pairs and/or triplets.

In some embodiments, the reduction in uridine combinations (e.g., pairs, triplets, quadruplets) in the sequence optimized nucleic acid can be expressed as a percentage reduction with respect to the uridine combinations present in the reference nucleic acid sequence.

In some embodiments, a sequence optimized nucleic acid can contain about 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, or 65% of the total number of uridine pairs present in the reference nucleic acid sequence. In some embodiments, a sequence optimized nucleic acid can contain about 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, or 65% of the total number of uridine triplets present in the reference nucleic acid sequence. In some embodiments, a sequence optimized nucleic acid can contain about 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, or 65% of the total number of uridine quadruplets present in the reference nucleic acid sequence.

In some embodiments, a sequence optimized nucleic acid can contain about 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, or 65% of the total number of non-phenylalanine uridine pairs present in the reference nucleic acid sequence. In some embodiments, a sequence optimized nucleic acid can contain about 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, or 65% of the total number of non-phenylalanine uridine triplets present in the reference nucleic acid sequence.

In some embodiments, the uridine content in the sequence optimized sequence can be expressed with respect to the theoretical minimum uridine content in the sequence. The term "theoretical minimum uridine content" is defined as the uridine content of a nucleic acid sequence as a percentage of the sequence's length after all the codons in the sequence have been replaced with synonymous codon with the lowest uridine content. In some embodiments, the uridine content of the sequence optimized nucleic acid is identical to the theoretical minimum uridine content of the reference sequence (e.g., a wild type sequence). In some aspects, the uridine content of the sequence optimized nucleic acid is about 90%, about 95%, about 100%, about 105%, about 110%, about 115%, about 120%, about 125%, about 130%, about 135%, about 140%, about 145%, about 150%, about 155%, about 160%, about 165%, about 170%, about 175%, about 180%, about 185%, about 190%, about 195% or about 200% of the theoretical minimum uridine content of the reference sequence (e.g., a wild type sequence).

In some embodiments, the uridine content of the sequence optimized nucleic acid is identical to the theoretical minimum uridine content of the reference sequence (e.g., a wild type sequence).

The reference nucleic acid sequence (e.g., a wild type sequence) can comprise uridine clusters which due to their number, size, location, distribution or combinations thereof have negative effects on translation. As used herein, the term "uridine cluster" refers to a subsequence in a reference nucleic acid sequence or sequence optimized nucleic sequence with contains a uridine content (usually described as a percentage) which is above a certain threshold. Thus, in certain embodiments, if a subsequence comprises more than about 10%, 15%, 20%, 25%, 30%, 35%, 40%, 45%, 50%, 55%, 60% or 65% uridine content, such subsequence would be considered a uridine cluster.

The negative effects of uridine clusters can be, for example, eliciting a TLR7 response. Thus, in some implementations of the nucleic acid sequence optimization methods disclosed herein it is desirable to reduce the number of clusters, size of clusters, location of clusters (e.g., close to the 5' and/or 3' end of a nucleic acid sequence), distance between clusters, or distribution of uridine clusters (e.g., a certain pattern of cluster along a nucleic acid sequence, distribution of clusters with respect to secondary structure elements in the expressed product, or distribution of clusters with respect to the secondary structure of an mRNA).

In some embodiments, the reference nucleic acid sequence comprises at least one uridine cluster, wherein said uridine cluster is a subsequence of the reference nucleic acid sequence wherein the percentage of total uridine nucleobases in said subsequence is above a predetermined threshold. In some embodiments, the length of the subsequence is at least about 10, at least about 15, at least about 20, at least about 25, at least about 30, at least about 35, at least about 40, at least about 45, at least about 50, at least about 55, at least about 60, at least about 65, at least about 70, at least about 75, at least about 80, at least about 85, at least about 90, at least about 95, or at least about 100 nucleobases. In some embodiments, the subsequence is longer than 100 nucleobases. In some embodiments, the threshold is 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24% or 25% uridine content. In some embodiments, the threshold is above 25%.

For example, an amino acid sequence comprising A, D, G, S and R could be encoded by the nucleic acid sequence GCU, GAU, GGU, AGU, CGU. Although such sequence does not contain any uridine pairs, triplets, or quadruplets, one third of the nucleobases would be uridines. Such a uridine cluster could be removed by using alternative codons, for example, by using GCC, GAC, GGC, AGC, and CGC, which would contain no uridines.

In other embodiments, the reference nucleic acid sequence comprises at least one uridine cluster, wherein said uridine cluster is a subsequence of the reference nucleic acid sequence wherein the percentage of uridine nucleobases of said subsequence as measured using a sliding window that is above a predetermined threshold. In some embodiments, the length of the sliding window is 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 nucleobases. In some embodiments, the sliding window is over 40 nucleobases in length. In some embodiments, the threshold is 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24% or 25% uridine content. In some embodiments, the threshold is above 25%.

In some embodiments, the reference nucleic acid sequence comprises at least two uridine clusters. In some embodiments, the uridine-modified sequence contains fewer uridine-rich clusters than the reference nucleic acid sequence. In some embodiments, the uridine-modified sequence contains more uridine-rich clusters than the reference nucleic acid sequence. In some embodiments, the uridine-modified sequence contains uridine-rich clusters with are shorter in length than corresponding uridine-rich clusters in the reference nucleic acid sequence. In other embodiments, the uridine-modified sequence contains uridine-rich clusters which are longer in length than the corresponding uridine-rich cluster in the reference nucleic acid sequence.

See, Kariko et al. (2005) Immunity 23:165-175; Kormann et al. (2010) Nature Biotechnology 29:154-157; or Sahin et al. (2014) Nature Reviews Drug Discovery|AOP, published online 19 Sep. 2014m doi:10.1038/nrd4278; all of which are herein incorporated by reference their entireties.

b. Guanine/Cytosine (G/C) Content

A reference nucleic acid sequence can be sequence optimized using methods comprising altering the Guanine/Cytosine (G/C) content (absolute or relative) of the reference nucleic acid sequence. Such optimization can comprise altering (e.g., increasing or decreasing) the global G/C content (absolute or relative) of the reference nucleic acid sequence; introducing local changes in G/C content in the reference nucleic acid sequence (e.g., increase or decrease G/C in selected regions or subsequences in the reference nucleic acid sequence); altering the frequency, size, and distribution of G/C clusters in the reference nucleic acid sequence, or combinations thereof.

In some embodiments, the sequence optimized nucleic acid encoding GALT comprises an overall increase in G/C content (absolute or relative) relative to the G/C content (absolute or relative) of the reference nucleic acid sequence. In some embodiments, the overall increase in G/C content (absolute or relative) is at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or at least about 100% relative to the G/C content (absolute or relative) of the reference nucleic acid sequence.

In some embodiments, the sequence optimized nucleic acid encoding GALT comprises an overall decrease in G/C content (absolute or relative) relative to the G/C content of the reference nucleic acid sequence. In some embodiments, the overall decrease in G/C content (absolute or relative) is at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or at least about 100% relative to the G/C content (absolute or relative) of the reference nucleic acid sequence.

In some embodiments, the sequence optimized nucleic acid encoding GALT comprises a local increase in Guanine/Cytosine (G/C) content (absolute or relative) in a subsequence (i.e., a G/C modified subsequence) relative to the G/C content (absolute or relative) of the corresponding subsequence in the reference nucleic acid sequence. In some embodiments, the local increase in G/C content (absolute or relative) is by at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or at least about 100% relative to the G/C content (absolute or relative) of the corresponding subsequence in the reference nucleic acid sequence.

In some embodiments, the sequence optimized nucleic acid encoding GALT comprises a local decrease in Guanine/Cytosine (G/C) content (absolute or relative) in a subsequence (i.e., a G/C modified subsequence) relative to the G/C content (absolute or relative) of the corresponding subsequence in the reference nucleic acid sequence. In some embodiments, the local decrease in G/C content (absolute or relative) is by at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or at least about 100% relative to the G/C content (absolute or relative) of the corresponding subsequence in the reference nucleic acid sequence.

In some embodiments, the G/C content (absolute or relative) is increased or decreased in a subsequence which is at least about 5, 10, 15, 20, 25, 30, 35, 40, 45, 50, 55, 60, 65, 70, 75, 80, 85, 90, 95, or 100 nucleobases in length.

In some embodiments, the G/C content (absolute or relative) is increased or decreased in a subsequence which is at least about 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, or 1000 nucleobases in length.

In some embodiments, the G/C content (absolute or relative) is increased or decreased in a subsequence which is at least about 1100, 1200, 1300, 1400, 1500, 1600, 1700, 1800, 1900, 2000, 2100, 2200, 2300, 2400, 2500, 2600, 2700, 2800, 2900, 3000, 3100, 3200, 3300, 3400, 3500, 3600, 3700, 3800, 3900, 4000, 4100, 4200, 4300, 4400, 4500, 4600, 4700, 4800, 4900, 5000, 5100, 5200, 5300, 5400, 5500, 5600, 5700, 5800, 5900, 6000, 6100, 6200, 6300, 6400, 6500, 6600, 6700, 6800, 6900, 7000, 7100, 7200, 7300, 7400, 7500, 7600, 7700, 7800, 7900, 8000, 8100, 8200, 8300, 8400, 8500, 8600, 8700, 8800, 8900, 9000, 9100, 9200, 9300, 9400, 9500, 9600, 9700, 9800, 9900, or 10000 nucleobases in length.

The increases or decreases in G and C content (absolute or relative) described herein can be conducted by replacing synonymous codons with low G/C content with synonymous codons having higher G/C content, or vice versa. For example, L has 6 synonymous codons: two of them have 2 G/C (CUC, CUG), 3 have a single G/C (UUG, CUU, CUA), and one has no G/C (UUA). So if the reference nucleic acid had a CUC codon in a certain position, G/C content at that position could be reduced by replacing CUC with any of the codons having a single G/C or the codon with no G/C.

See, U.S. Publ. Nos. US20140228558, US20050032730 A1; Gustafsson et al. (2012) Protein Expression and Purification 83: 37-46; all of which are incorporated herein by reference in their entireties.

c. Codon Frequency—Codon Usage Bias

Numerous codon optimization methods known in the art are based on the substitution of codons in a reference nucleic acid sequence with codons having higher frequencies. Thus, in some embodiments, a nucleic acid sequence encoding GALT disclosed herein can be sequence optimized using methods comprising the use of modifications in the frequency of use of one or more codons relative to other synonymous codons in the sequence optimized nucleic acid with respect to the frequency of use in the non-codon optimized sequence.

As used herein, the term "codon frequency" refers to codon usage bias, i.e., the differences in the frequency of occurrence of synonymous codons in coding DNA/RNA. It is generally acknowledged that codon preferences reflect a balance between mutational biases and natural selection for translational optimization. Optimal codons help to achieve faster translation rates and high accuracy. As a result of these factors, translational selection is expected to be stronger in highly expressed genes. In the field of bioinformatics and computational biology, many statistical methods have been proposed and used to analyze codon usage bias. See, e.g., Comeron & Aguadé (1998) J. Mol. Evol. 47: 268-74. Methods such as the 'frequency of optimal codons' (Fop) (Ikemura (1981) J. Mol. Biol. 151 (3): 389-409), the Relative Codon Adaptation (RCA) (Fox & Eril (2010) DNA Res. 17 (3): 185-96) or the 'Codon Adaptation Index' (CAI) (Sharp & Li (1987) Nucleic Acids Res. 15 (3): 1281-95) are used to predict gene expression levels, while methods such as the 'effective number of codons' (Nc) and Shannon entropy from information theory are used to measure codon usage evenness. Multivariate statistical methods, such as correspondence analysis and principal component analysis, are widely used to analyze variations in codon usage among genes (Suzuki et al. (2008) DNA Res. 15 (6): 357-65; Sandhu et al., In Silico Biol. 2008; 8(2):187-92).

The nucleic acid sequence encoding a GALT polypeptide disclosed herein (e.g., a wild type nucleic acid sequence, a mutant nucleic acid sequence, a chimeric nucleic sequence, etc. which can be, for example, an mRNA), can be codon optimized using methods comprising substituting at least one codon in the reference nucleic acid sequence with an alternative codon having a higher or lower codon frequency in the synonymous codon set; wherein the resulting sequence optimized nucleic acid has at least one optimized property with respect to the reference nucleic acid sequence.

In some embodiments, at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 99%, or 100% of the codons in the reference nucleic acid sequence encoding GALT are substituted with alternative codons, each alternative codon having a codon frequency higher than the codon frequency of the substituted codon in the synonymous codon set.

In some embodiments, at least one codon in the reference nucleic acid sequence encoding GALT is substituted with an alternative codon having a codon frequency higher than the codon frequency of the substituted codon in the synonymous codon set, and at least one codon in the reference nucleic acid sequence is substituted with an alternative codon having a codon frequency lower than the codon frequency of the substituted codon in the synonymous codon set.

In some embodiments, at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, or at least about 75% of the codons in the reference nucleic acid sequence encoding GALT are substituted with alternative codons, each alternative codon having a codon frequency higher than the codon frequency of the substituted codon in the synonymous codon set.

In some embodiments, at least one alternative codon having a higher codon frequency has the highest codon frequency in the synonymous codon set. In other embodiments, all alternative codons having a higher codon frequency have the highest codon frequency in the synonymous codon set.

In some embodiments, at least one alternative codon having a lower codon frequency has the lowest codon frequency in the synonymous codon set. In some embodiments, all alternative codons having a higher codon frequency have the highest codon frequency in the synonymous codon set.

In some specific embodiments, at least one alternative codon has the second highest, the third highest, the fourth highest, the fifth highest or the sixth highest frequency in the synonymous codon set. In some specific embodiments, at least one alternative codon has the second lowest, the third lowest, the fourth lowest, the fifth lowest, or the sixth lowest frequency in the synonymous codon set.

Optimization based on codon frequency can be applied globally, as described above, or locally to the reference nucleic acid sequence encoding a GALT polypeptide. In some embodiments, when applied locally, regions of the reference nucleic acid sequence can modified based on codon frequency, substituting all or a certain percentage of codons in a certain subsequence with codons that have higher or lower frequencies in their respective synonymous codon sets. Thus, in some embodiments, at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 99%, or 100% of the codons in a subsequence of the reference nucleic acid sequence are substituted with alternative codons, each alternative codon having a codon frequency higher than the codon frequency of the substituted codon in the synonymous codon set.

In some embodiments, at least one codon in a subsequence of the reference nucleic acid sequence encoding a GALT polypeptide is substituted with an alternative codon having a codon frequency higher than the codon frequency of the substituted codon in the synonymous codon set, and at least one codon in a subsequence of the reference nucleic acid sequence is substituted with an alternative codon having a codon frequency lower than the codon frequency of the substituted codon in the synonymous codon set.

In some embodiments, at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, or at least about 75% of the codons in a subsequence of the reference nucleic acid sequence encoding a GALT polypeptide are substituted with alternative codons, each alternative codon having a codon frequency higher than the codon frequency of the substituted codon in the synonymous codon set.

In some embodiments, at least one alternative codon substituted in a subsequence of the reference nucleic acid sequence encoding a GALT polypeptide and having a higher codon frequency has the highest codon frequency in the synonymous codon set. In other embodiments, all alternative codons substituted in a subsequence of the reference nucleic acid sequence and having a lower codon frequency have the lowest codon frequency in the synonymous codon set.

In some embodiments, at least one alternative codon substituted in a subsequence of the reference nucleic acid sequence encoding a GALT polypeptide and having a lower codon frequency has the lowest codon frequency in the synonymous codon set. In some embodiments, all alternative codons substituted in a subsequence of the reference nucleic acid sequence and having a higher codon frequency have the highest codon frequency in the synonymous codon set.

In specific embodiments, a sequence optimized nucleic acid encoding a GALT polypeptide can comprise a subsequence having an overall codon frequency higher or lower than the overall codon frequency in the corresponding subsequence of the reference nucleic acid sequence at a specific location, for example, at the 5' end or 3' end of the sequence optimized nucleic acid, or within a predetermined distance from those region (e.g., at least 1, 2, 3, 4, 5, 6, 7, 8, 9, 10, 15, 20, 25, 30, 35, 40, 45, 50, 55, 60, 65, 70, 75, 80, 85, 90, 95 or 100 codons from the 5' end or 3' end of the sequence optimized nucleic acid).

In some embodiments, a sequence optimized nucleic acid encoding a GALT polypeptide can comprise more than one subsequence having an overall codon frequency higher or lower than the overall codon frequency in the corresponding subsequence of the reference nucleic acid sequence. A skilled artisan would understand that subsequences with overall higher or lower overall codon frequencies can be organized in innumerable patterns, depending on whether the overall codon frequency is higher or lower, the length of the subsequence, the distance between subsequences, the location of the subsequences, etc.

See, U.S. Pat. Nos. 5,082,767, 8,126,653, 7,561,973, 8,401,798; U.S. Publ. No. US 20080046192, US 20080076161; Int'l. Publ. No. WO2000018778; Welch et al. (2009) PLoS ONE 4(9): e7002; Gustafsson et al. (2012) Protein Expression and Purification 83: 37-46; Chung et al. (2012) BMC Systems Biology 6:134; all of which are incorporated herein by reference in their entireties.

d. Destabilizing Motif Substitution

There is a variety of motifs that can affect sequence optimization, which fall into various non-exclusive categories, for example:

(i) Primary sequence based motifs: Motifs defined by a simple arrangement of nucleotides.

(ii) Structural motifs: Motifs encoded by an arrangement of nucleotides that tends to form a certain secondary structure.

(iii) Local motifs: Motifs encoded in one contiguous subsequence.

(iv) Distributed motifs: Motifs encoded in two or more disjoint subsequences.

(v) Advantageous motifs: Motifs which improve nucleotide structure or function.

(vi) Disadvantageous motifs: Motifs with detrimental effects on nucleotide structure or function.

There are many motifs that fit into the category of disadvantageous motifs. Some examples include, for example, restriction enzyme motifs, which tend to be relatively short, exact sequences such as the restriction site motifs for Xba1 (TCTAGA), EcoRI (GAATTC), EcoRII (CCWGG, wherein W means A or T, per the IUPAC ambiguity codes), or HindIII (AAGCTT); enzyme sites, which tend to be longer and based on consensus not exact sequence, such in the T7 RNA polymerase (GnnnnWnCRnCTCnCnnWnD (SEQ ID NO: 175), wherein n means any nucleotide, R means A or G, W means A or T, D means A or G or T but not C); structural motifs, such as GGGG repeats (Kim et al. (1991) Nature 351(6324):331-2); or other motifs such as CUG-triplet repeats (Querido et al. (2014) J. Cell Sci. 124:1703-1714).

Accordingly, the nucleic acid sequence encoding a GALT polypeptide disclosed herein can be sequence optimized using methods comprising substituting at least one destabilizing motif in a reference nucleic acid sequence, and removing such disadvantageous motif or replacing it with an advantageous motif In some embodiments, the optimization process comprises identifying advantageous and/or disadvantageous motifs in the reference nucleic sequence, wherein such motifs are, e.g., specific subsequences that can cause a loss of stability in the reference nucleic acid sequence prior or during the optimization process. For example, substitution of specific bases during optimization can generate a subsequence (motif) recognized by a restriction enzyme. Accordingly, during the optimization process the appearance of disadvantageous motifs can be monitored by comparing the sequence optimized sequence with a library of motifs known to be disadvantageous. Then, the identification of disadvantageous motifs could be used as a post-hoc filter, i.e., to determine whether a certain modification which potentially could be introduced in the reference nucleic acid sequence should be actually implemented or not.

In some embodiments, the identification of disadvantageous motifs can be used prior to the application of the sequence optimization methods disclosed herein, i.e., the identification of motifs in the reference nucleic acid sequence encoding a GALT polypeptide and their replacement with alternative nucleic acid sequences can be used as a preprocessing step, for example, before uridine reduction.

In other embodiments, the identification of disadvantageous motifs and their removal is used as an additional sequence optimization technique integrated in a multiparametric nucleic acid optimization method comprising two or more of the sequence optimization methods disclosed herein. When used in this fashion, a disadvantageous motif identified during the optimization process would be removed, for example, by substituting the lowest possible number of nucleobases in order to preserve as closely as possible the original design principle(s) (e.g., low U, high frequency, etc.).

See, e.g., U.S. Publ. Nos. US20140228558, US20050032730, or US20140228558, which are herein incorporated by reference in their entireties.

e. Limited Codon Set Optimization

In some particular embodiments, sequence optimization of a reference nucleic acid sequence encoding a GALT polypeptide can be conducted using a limited codon set, e.g., a codon set wherein less than the native number of codons is used to encode the 20 natural amino acids, a subset of the 20 natural amino acids, or an expanded set of amino acids including, for example, non-natural amino acids.

The genetic code is highly similar among all organisms and can be expressed in a simple table with 64 entries which would encode the 20 standard amino acids involved in protein translation plus start and stop codons. The genetic code is degenerate, i.e., in general, more than one codon specifies each amino acid. For example, the amino acid leucine is specified by the UUA, UUG, CUU, CUC, CUA, or CUG codons, while the amino acid serine is specified by UCA, UCG, UCC, UCU, AGU, or AGC codons (difference in the first, second, or third position). Native genetic codes comprise 62 codons encoding naturally occurring amino acids. Thus, in some embodiments of the methods disclosed herein optimized codon sets (genetic codes) comprising less than 62 codons to encode 20 amino acids can comprise 61, 60, 59, 58, 57, 56, 55, 54, 53, 52, 51, 50, 49, 48, 47, 46, 45, 44, 43, 42, 41, 40, 39, 38, 37, 36, 35, 34, 33, 32, 31, 30, 30, 29, 28, 27, 26, 25, 24, 23, 22, 21, or 20 codons.

In some embodiments, the limited codon set comprises less than 20 codons. For example, if a protein contains less than 20 types of amino acids, such protein could be encoded by a codon set with less than 20 codons. Accordingly, in some embodiments, an optimized codon set comprises as many codons as different types of amino acids are present in the protein encoded by the reference nucleic acid sequence. In some embodiments, the optimized codon set comprises 19, 18, 17, 16, 15, 14, 13, 12, 11, 10, 9, 8, 7, 6, 5, 4, 3, 2 or even 1 codon.

In some embodiments, at least one amino acid selected from the group consisting of Ala, Arg, Asn, Asp, Cys, Gln, Glu, Gly, His, Ile, Leu, Lys, Phe, Pro, Ser, Thr, Tyr, and Val, i.e., amino acids which are naturally encoded by more than one codon, is encoded with less codons than the naturally occurring number of synonymous codons. For example, in some embodiments, Ala can be encoded in the sequence optimized nucleic acid by 3, 2 or 1 codons; Cys can be encoded in the sequence optimized nucleic acid by 1 codon; Asp can be encoded in the sequence optimized nucleic acid by 1 codon; Glu can be encoded in the sequence optimized nucleic acid by 1 codon; Phe can be encoded in the sequence optimized nucleic acid by 1 codon; Gly can be encoded in the sequence optimized nucleic acid by 3 codons, 2 codons or 1 codon; His can be encoded in the sequence optimized nucleic acid by 1 codon; Ile can be encoded in the sequence optimized nucleic acid by 2 codons or 1 codon; Lys can be encoded in the sequence optimized nucleic acid by 1 codon; Leu can be encoded in the sequence optimized nucleic acid by 5 codons, 4 codons, 3 codons, 2 codons or 1 codon; Asn can be encoded in the sequence optimized nucleic acid by 1 codon; Pro can be encoded in the sequence optimized nucleic acid by 3 codons, 2 codons, or 1 codon; Gln can be encoded in the sequence optimized nucleic acid by 1 codon; Arg can be encoded in the sequence optimized nucleic acid by 5 codons, 4 codons, 3 codons, 2 codons, or 1 codon; Ser can be encoded in the sequence optimized nucleic acid by 5 codons, 4 codons, 3 codons, 2 codons, or 1 codon; Thr can be encoded in the sequence optimized nucleic acid by 3 codons, 2 codons, or 1 codon; Val can be encoded in the sequence optimized nucleic acid by 3 codons, 2 codons, or 1 codon; and, Tyr can be encoded in the sequence optimized nucleic acid by 1 codon.

In some embodiments, at least one amino acid selected from the group consisting of Ala, Arg, Asn, Asp, Cys, Gln, Glu, Gly, His, Ile, Leu, Lys, Phe, Pro, Ser, Thr, Tyr, and Val, i.e., amino acids which are naturally encoded by more than one codon, is encoded by a single codon in the limited codon set.

In some specific embodiments, the sequence optimized nucleic acid is a DNA and the limited codon set consists of 20 codons, wherein each codon encodes one of 20 amino acids. In some embodiments, the sequence optimized nucleic acid is a DNA and the limited codon set comprises at least one codon selected from the group consisting of GCT, GCC, GCA, and GCG; at least a codon selected from the group consisting of CGT, CGC, CGA, CGG, AGA, and AGG; at least a codon selected from AAT or ACC; at least a codon selected from GAT or GAC; at least a codon selected from TGT or TGC; at least a codon selected from CAA or CAG; at least a codon selected from GAA or GAG; at least a codon selected from the group consisting of GGT, GGC, GGA, and GGG; at least a codon selected from CAT or CAC; at least a codon selected from the group consisting of ATT, ATC, and ATA; at least a codon selected from the group consisting of TTA, TTG, CTT, CTC, CTA, and CTG; at least a codon selected from AAA or AAG; an ATG codon; at least a codon selected from TTT or TTC; at least a codon selected from the group consisting of CCT, CCC, CCA, and CCG; at least a codon selected from the group consisting of TCT, TCC, TCA, TCG, AGT, and AGC; at least a codon selected from the group consisting of ACT, ACC, ACA, and ACG; a TGG codon; at least a codon selected from TAT or TAC; and, at least a codon selected from the group consisting of GTT, GTC, GTA, and GTG.

In other embodiments, the sequence optimized nucleic acid is an RNA (e.g., an mRNA) and the limited codon set consists of 20 codons, wherein each codon encodes one of 20 amino acids. In some embodiments, the sequence optimized nucleic acid is an RNA and the limited codon set comprises at least one codon selected from the group consisting of GCU, GCC, GCA, and GCG; at least a codon selected from the group consisting of CGU, CGC, CGA, CGG, AGA, and AGG; at least a codon selected from AAU or ACC; at least a codon selected from GAU or GAC; at least a codon selected from UGU or UGC; at least a codon selected from CAA or CAG; at least a codon selected from GAA or GAG; at least a codon selected from the group consisting of GGU, GGC, GGA, and GGG; at least a codon selected from CAU or CAC; at least a codon selected from the group consisting of AUU, AUC, and AUA; at least a codon selected from the group consisting of UUA, UUG, CUU, CUC, CUA, and CUG; at least a codon selected from AAA or AAG; an AUG codon; at least a codon selected from UUU or UUC; at least a codon selected from the group consisting of CCU, CCC, CCA, and CCG; at least a codon selected from the group consisting of UCU, UCC, UCA, UCG, AGU, and AGC; at least a codon selected from the group consisting of ACU, ACC, ACA, and ACG; a UGG codon; at least a codon selected from UAU or UAC; and, at least a codon selected from the group consisting of GUU, GUC, GUA, and GUG.

In some specific embodiments, the limited codon set has been optimized for in vivo expression of a sequence optimized nucleic acid (e.g., a synthetic mRNA) following administration to a certain tissue or cell.

In some embodiments, the optimized codon set (e.g., a 20 codon set encoding 20 amino acids) complies at least with one of the following properties:

(i) the optimized codon set has a higher average G/C content than the original or native codon set; or, (ii) the optimized codon set has a lower average U content than the original or native codon set; or, (iii) the optimized codon set is composed of codons with the highest frequency; or, (iv) the optimized codon set is composed of codons with the lowest frequency; or, (v) a combination thereof.

In some specific embodiments, at least one codon in the optimized codon set has the second highest, the third highest, the fourth highest, the fifth highest or the sixth highest frequency in the synonymous codon set. In some specific embodiments, at least one codon in the optimized codon has the second lowest, the third lowest, the fourth lowest, the fifth lowest, or the sixth lowest frequency in the synonymous codon set.

As used herein, the term "native codon set" refers to the codon set used natively by the source organism to encode the reference nucleic acid sequence. As used herein, the term "original codon set" refers to the codon set used to encode the reference nucleic acid sequence before the beginning of sequence optimization, or to a codon set used to encode an optimized variant of the reference nucleic acid sequence at the beginning of a new optimization iteration when sequence optimization is applied iteratively or recursively.

In some embodiments, 5%, 10%, 15%, 20%, 25%, 30%, 35%, 40%, 45%, 50%, 55%, 60%, 65%, 70%, 75%, 80%, 85%, 90%, 95% or 100% of codons in the codon set are those with the highest frequency. In other embodiments, 5%, 10%, 15%, 20%, 25%, 30%, 35%, 40%, 45%, 50%, 55%, 60%, 65%, 70%, 75%, 80%, 85%, 90%, 95% or 100% of codons in the codon set are those with the lowest frequency.

In some embodiments, 5%, 10%, 15%, 20%, 25%, 30%, 35%, 40%, 45%, 50%, 55%, 60%, 65%, 70%, 75%, 80%, 85%, 90%, 95% or 100% of codons in the codon set are those with the highest uridine content. In some embodiments, 5%, 10%, 15%, 20%, 25%, 30%, 35%, 40%, 45%, 50%, 55%, 60%, 65%, 70%, 75%, 80%, 85%, 90%, 95% or 100% of codons in the codon set are those with the lowest uridine content.

In some embodiments, the average G/C content (absolute or relative) of the codon set is 5%, 10%, 15%, 20%, 25%, 30%, 35%, 40%, 45%, 50%, 55%, 60%, 65%, 70%, 75%, 80%, 85%, 90%, 95% or 100% higher than the average G/C content (absolute or relative) of the original codon set. In some embodiments, the average G/C content (absolute or relative) of the codon set is 5%, 10%, 15%, 20%, 25%, 30%, 35%, 40%, 45%, 50%, 55%, 60%, 65%, 70%, 75%, 80%, 85%, 90%, 95% or 100% lower than the average G/C content (absolute or relative) of the original codon set.

In some embodiments, the uracil content (absolute or relative) of the codon set is 5%, 10%, 15%, 20%, 25%, 30%, 35%, 40%, 45%, 50%, 55%, 60%, 65%, 70%, 75%, 80%, 85%, 90%, 95% or 100% higher than the average uracil content (absolute or relative) of the original codon set. In some embodiments, the uracil content (absolute or relative) of the codon set is 5%, 10%, 15%, 20%, 25%, 30%, 35%, 40%, 45%, 50%, 55%, 60%, 65%, 70%, 75%, 80%, 85%, 90%, 95% or 100% lower than the average uracil content (absolute or relative) of the original codon set.

See also U.S. Appl. Publ. No. 2011/0082055, and Int'l. Publ. No. WO2000018778, both of which are incorporated herein by reference in their entireties.

8. CHARACTERIZATION OF SEQUENCE OPTIMIZED NUCLEIC ACIDS

In some embodiments of the invention, the polynucleotide (e.g., a RNA, e.g., an mRNA) comprising a sequence optimized nucleic acid disclosed herein encoding a GALT polypeptide can be tested to determine whether at least one nucleic acid sequence property (e.g., stability when exposed to nucleases) or expression property has been improved with respect to the non-sequence optimized nucleic acid.

As used herein, "expression property" refers to a property of a nucleic acid sequence either in vivo (e.g., translation efficacy of a synthetic mRNA after administration to a subject in need thereof) or in vitro (e.g., translation efficacy of a synthetic mRNA tested in an in vitro model system). Expression properties include but are not limited to the amount of protein produced by an mRNA encoding a GALT polypeptide after administration, and the amount of soluble or otherwise functional protein produced. In some embodiments, sequence optimized nucleic acids disclosed herein can be evaluated according to the viability of the cells expressing a protein encoded by a sequence optimized nucleic acid sequence (e.g., a RNA, e.g., an mRNA) encoding a GALT polypeptide disclosed herein.

In a particular embodiment, a plurality of sequence optimized nucleic acids disclosed herein (e.g., a RNA, e.g., an mRNA) containing codon substitutions with respect to the non-optimized reference nucleic acid sequence can be characterized functionally to measure a property of interest, for example an expression property in an in vitro model system, or in vivo in a target tissue or cell.

a. Optimization of Nucleic Acid Sequence Intrinsic Properties

In some embodiments of the invention, the desired property of the polynucleotide is an intrinsic property of the nucleic acid sequence. For example, the nucleotide sequence (e.g., a RNA, e.g., an mRNA) can be sequence optimized for in vivo or in vitro stability. In some embodiments, the nucleotide sequence can be sequence optimized for expression in a particular target tissue or cell. In some embodiments, the nucleic acid sequence is sequence optimized to increase its plasma half life by preventing its degradation by endo and exonucleases.

In other embodiments, the nucleic acid sequence is sequence optimized to increase its resistance to hydrolysis in solution, for example, to lengthen the time that the sequence optimized nucleic acid or a pharmaceutical composition comprising the sequence optimized nucleic acid can be stored under aqueous conditions with minimal degradation.

In other embodiments, the sequence optimized nucleic acid can be optimized to increase its resistance to hydrolysis in dry storage conditions, for example, to lengthen the time that the sequence optimized nucleic acid can be stored after lyophilization with minimal degradation.

b. Nucleic Acids Sequence Optimized for Protein Expression

In some embodiments of the invention, the desired property of the polynucleotide is the level of expression of a GALT polypeptide encoded by a sequence optimized sequence disclosed herein. Protein expression levels can be measured using one or more expression systems. In some embodiments, expression can be measured in cell culture systems, e.g., CHO cells or HEK293 cells. In some embodiments, expression can be measured using in vitro expression systems prepared from extracts of living cells, e.g., rabbit reticulocyte lysates, or in vitro expression systems prepared by assembly of purified individual components. In other embodiments, the protein expression is measured in an in vivo system, e.g., mouse, rabbit, monkey, etc.

In some embodiments, protein expression in solution form can be desirable. Accordingly, in some embodiments, a reference sequence can be sequence optimized to yield a sequence optimized nucleic acid sequence having optimized levels of expressed proteins in soluble form. Levels of protein expression and other properties such as solubility, levels of aggregation, and the presence of truncation products (i.e., fragments due to proteolysis, hydrolysis, or defective translation) can be measured according to methods known in the art, for example, using electrophoresis (e.g., native or SDS-PAGE) or chromatographic methods (e.g., HPLC, size exclusion chromatography, etc.).

c. Optimization of Target Tissue or Target Cell Viability

In some embodiments, the expression of heterologous therapeutic proteins encoded by a nucleic acid sequence can have deleterious effects in the target tissue or cell, reducing protein yield, or reducing the quality of the expressed product (e.g., due to the presence of protein fragments or precipitation of the expressed protein in inclusion bodies), or causing toxicity.

Accordingly, in some embodiments of the invention, the sequence optimization of a nucleic acid sequence disclosed herein, e.g., a nucleic acid sequence encoding a GALT polypeptide, can be used to increase the viability of target cells expressing the protein encoded by the sequence optimized nucleic acid.

Heterologous protein expression can also be deleterious to cells transfected with a nucleic acid sequence for autologous or heterologous transplantation. Accordingly, in some embodiments of the present disclosure the sequence optimization of a nucleic acid sequence disclosed herein can be used to increase the viability of target cells expressing the protein encoded by the sequence optimized nucleic acid sequence. Changes in cell or tissue viability, toxicity, and other physiological reaction can be measured according to methods known in the art.

d. Reduction of Immune and/or Inflammatory Response

In some cases, the administration of a sequence optimized nucleic acid encoding GALT polypeptide or a functional fragment thereof can trigger an immune response, which could be caused by (i) the therapeutic agent (e.g., an mRNA encoding a GALT polypeptide), or (ii) the expression product of such therapeutic agent (e.g., the GALT polypeptide encoded by the mRNA), or (iv) a combination thereof. Accordingly, in some embodiments of the present disclosure the sequence optimization of nucleic acid sequence (e.g., an mRNA) disclosed herein can be used to decrease an immune or inflammatory response triggered by the administration of a nucleic acid encoding a GALT polypeptide or by the expression product of GALT encoded by such nucleic acid.

In some aspects, an inflammatory response can be measured by detecting increased levels of one or more inflammatory cytokines using methods known in the art, e.g., ELISA. The term "inflammatory cytokine" refers to cytokines that are elevated in an inflammatory response. Examples of inflammatory cytokines include interleukin-6 (IL-6), CXCL1 (chemokine (C-X-C motif) ligand 1; also known as GROα, interferon-γ (IFNγ), tumor necrosis factor α (TNFα), interferon γ-induced protein 10 (IP-10), or granulocyte-colony stimulating factor (G-CSF). The term inflammatory cytokines includes also other cytokines associated with inflammatory responses known in the art, e.g., interleukin-1 (IL-1), interleukin-8 (IL-8), interleukin-12 (IL-12), interleukin-13 (Il-13), interferon α (IFN-α), etc.

9. MODIFIED NUCLEOTIDE SEQUENCES ENCODING GALT POLYPEPTIDES

In some embodiments, the polynucleotide (e.g., a RNA, e.g., an mRNA) of the invention comprises a chemically modified nucleobase, e.g., 5-methoxyuracil. In some embodiments, the mRNA is a uracil-modified sequence comprising an ORF encoding a GALT polypeptide, wherein the mRNA comprises a chemically modified nucleobase, e.g., 5-methoxyuracil.

In certain aspects of the invention, when the 5-methoxyuracil base is connected to a ribose sugar, as it is in polynucleotides, the resulting modified nucleoside or nucleotide is referred to as 5-methoxyuridine. In some embodiments, uracil in the polynucleotide is at least about 25%, at least about 30%, at least about 40%, at least about 50%, at least about 60%, at least about 70%, at least about 80%, at least 90%, at least 95%, at least 99%, or about 100% 5-methoxyuracil. In one embodiment, uracil in the polynucleotide is at least 95% 5-methoxyuracil. In another embodiment, uracil in the polynucleotide is 100% 5-methoxyuracil.

In embodiments where uracil in the polynucleotide is at least 95% 5-methoxyuracil, overall uracil content can be adjusted such that an mRNA provides suitable protein expression levels while inducing little to no immune response. In some embodiments, the uracil content of the ORF is between about 105% and about 145%, about 105% and about 140%, about 110% and about 140%, about 110% and about 145%, about 115% and about 135%, about 105% and about 135%, about 110% and about 135%, about 115% and about 145%, or about 115% and about 140% of the theoretical minimum uracil content in the corresponding wild-type ORF (% $U_{TM}$). In other embodiments, the uracil content of the ORF is between about 121% and about 136% or between 123% and 134% of the % $U_{TM}$. In some embodiments, the uracil content of the ORF encoding a GALT polypeptide is about 115%, about 120%, about 125%, about 130%, about 135%, about 140%, about 145%, or about 150% of the % $U_{TM}$. In this context, the term "uracil" can refer to 5-methoxyuracil and/or naturally occurring uracil.

In some embodiments, the uracil content in the ORF of the mRNA encoding a GALT polypeptide of the invention is less than about 50%, about 40%, about 30%, about 20%, or about 15% of the total nucleobase content in the ORF. In some embodiments, the uracil content in the ORF is between about 5% and about 20% of the total nucleobase content in the ORF. In other embodiments, the uracil content in the ORF is between about 10% and about 25% of the total nucleobase content in the ORF. In one embodiment, the uracil content in the ORF of the mRNA encoding a GALT polypeptide is less than about 20% of the total nucleobase content in the open reading frame. In this context, the term "uracil" can refer to 5-methoxyuracil and/or naturally occurring uracil.

In further embodiments, the ORF of the mRNA encoding a GALT polypeptide having 5-methoxyuracil and adjusted uracil content has increased Cytosine (C), Guanine (G), or Guanine/Cytosine (G/C) content (absolute or relative). In some embodiments, the overall increase in C, G, or G/C content (absolute or relative) of the ORF is at least about 2%, at least about 3%, at least about 4%, at least about 5%, at least about 6%, at least about 7%, at least about 10%, at least about 15%, at least about 20%, at least about 40%, at least about 50%, at least about 60%, at least about 70%, at least about 80%, at least about 90%, at least about 95%, or at least about 100% relative to the G/C content (absolute or relative) of the wild-type ORF. In some embodiments, the G, the C, or the G/C content in the ORF is less than about 100%, less than about 90%, less than about 85%, or less than about 80% of the theoretical maximum G, C, or G/C content of the corresponding wild type nucleotide sequence encoding the GALT polypeptide (% $G_{TMX}$; % $C_{TMX}$, or % $G/C_{TMX}$). In other embodiments, the G, the C, or the G/C content in the ORF is between about 70% and about 80%, between about 71% and about 79%, between about 71% and about 78%, or between about 71% and about 77% of the % $G_{TMX}$, % $C_{TMX}$, or % $G/C_{TMX}$. In some embodiments, the increases in G and/or C content (absolute or relative) described herein can be conducted by replacing synonymous codons with low G, C, or G/C content with synonymous codons having higher G, C, or G/C content. In other embodiments, the increase in G and/or C content (absolute or relative) is conducted by replacing a codon ending with U with a synonymous codon ending with G or C.

In further embodiments, the ORF of the mRNA encoding a GALT polypeptide of the invention comprises 5-methoxyuracil and has an adjusted uracil content containing less uracil pairs (UU) and/or uracil triplets (UUU) and/or uracil quadruplets (UUUU) than the corresponding wild-type nucleotide sequence encoding the GALT polypeptide. In some embodiments, the ORF of the mRNA encoding a GALT polypeptide of the invention contains no uracil pairs and/or uracil triplets and/or uracil quadruplets. In some embodiments, uracil pairs and/or uracil triplets and/or uracil quadruplets are reduced below a certain threshold, e.g., no more than 1, 2, 3, 4, 5, 6, 7, 8, 9, 10, 11, 12, 13, 14, 15, 16, 17, 18, 19, or 20 occurrences in the ORF of the mRNA encoding the GALT polypeptide. In a particular embodiment, the ORF of the mRNA encoding the GALT polypeptide of the invention contains less than 20, 19, 18, 17, 16, 15, 14, 13, 12, 11, 10, 9, 8, 7, 6, 5, 4, 3, 2, or 1 non-phenylalanine uracil pairs and/or triplets. In another embodiment, the ORF of the mRNA encoding the GALT polypeptide contains no non-phenylalanine uracil pairs and/or triplets.

In further embodiments, the ORF of the mRNA encoding a GALT polypeptide of the invention comprises 5-methoxyuracil and has an adjusted uracil content containing less uracil-rich clusters than the corresponding wild-type nucleotide sequence encoding the GALT polypeptide. In some embodiments, the ORF of the mRNA encoding the GALT polypeptide of the invention contains uracil-rich clusters that are shorter in length than corresponding uracil-rich clusters in the corresponding wild-type nucleotide sequence encoding the GALT polypeptide.

In further embodiments, alternative lower frequency codons are employed. At least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 99%, or 100% of the codons in the GALT polypeptide-encoding ORF of the 5-methoxyuracil-comprising mRNA are substituted with alternative codons, each alternative codon having a codon frequency lower than the codon frequency of the substituted codon in the synonymous codon set. The ORF also has adjusted uracil content, as described above. In some embodiments, at least one codon in the ORF of the mRNA encoding the GALT polypeptide is substituted with an alternative codon having a codon frequency lower than the codon frequency of the substituted codon in the synonymous codon set.

In some embodiments, the adjusted uracil content, GALT polypeptide-encoding ORF of the 5-methoxyuracil-comprising mRNA exhibits expression levels of GALT when administered to a mammalian cell that are higher than expression levels of GALT from the corresponding wild-type mRNA. In other embodiments, the expression levels of GALT when administered to a mammalian cell are increased relative to a corresponding mRNA containing at least 95% 5-methoxyuracil and having a uracil content of about 160%, about 170%, about 180%, about 190%, or about 200% of the theoretical minimum. In yet other embodiments, the expression levels of GALT when administered to a mammalian cell are increased relative to a corresponding mRNA, wherein at least about 50%, at least about 60%, at least about 70%, at least about 80%, at least about 90%, or about 100% of uracils are 1-methylpseudouracil or pseudouracils. In some embodiments, the mammalian cell is a mouse cell, a rat cell, or a rabbit cell. In other embodiments, the mammalian cell is a monkey cell or a human cell. In some embodiments, the human cell is a HeLa cell, a BJ fibroblast cell, or a peripheral blood mononuclear cell (PBMC). In some embodiments, GALT is expressed when the mRNA is administered to a mammalian cell in vivo. In some embodiments, the mRNA is administered to mice, rabbits, rats, monkeys, or humans. In one embodiment, mice are null mice. In some embodiments, the mRNA is administered to mice in an amount of about 0.01 mg/kg, about 0.05 mg/kg, about 0.1 mg/kg, or about 0.15 mg/kg. In some embodiments, the mRNA is administered intravenously or intramuscularly. In other embodiments, the GALT polypeptide is expressed when the mRNA is administered to a mammalian cell in vitro. In some embodiments, the expression is increased by at least about 2-fold, at least about 5-fold, at least about 10-fold, at least about 50-fold, at least about 500-fold, at least about 1500-fold, or at least about 3000-fold. In other embodiments, the expression is increased by at least about 10%, about 20%, about 30%, about 40%, about 50%, 60%, about 70%, about 80%, about 90%, or about 100%.

In some embodiments, adjusted uracil content, GALT polypeptide-encoding ORF of the 5-methoxyuracil-comprising mRNA exhibits increased stability. In some embodiments, the mRNA exhibits increased stability in a cell relative to the stability of a corresponding wild-type mRNA under the same conditions. In some embodiments, the mRNA exhibits increased stability including resistance to nucleases, thermal stability, and/or increased stabilization of secondary structure. In some embodiments, increased stability exhibited by the mRNA is measured by determining the half-life of the mRNA (e.g., in a plasma, serum, cell, or tissue sample) and/or determining the area under the curve (AUC) of the protein expression by the mRNA over time (e.g., in vitro or in vivo). An mRNA is identified as having increased stability if the half-life and/or the AUC is greater than the half-life and/or the AUC of a corresponding wild-type mRNA under the same conditions.

In some embodiments, the mRNA of the present invention induces a detectably lower immune response (e.g., innate or acquired) relative to the immune response induced by a corresponding wild-type mRNA under the same conditions. In other embodiments, the mRNA of the present disclosure induces a detectably lower immune response (e.g., innate or acquired) relative to the immune response induced by an mRNA that encodes for a GALT polypeptide but does not comprise 5-methoxyuracil under the same conditions, or relative to the immune response induced by an mRNA that encodes for a GALT polypeptide and that comprises 5-methoxyuracil but that does not have adjusted uracil content under the same conditions. The innate immune response can be manifested by increased expression of pro-inflammatory cytokines, activation of intracellular PRRs (RIG-I, MDA5, etc), cell death, and/or termination or reduction in protein translation. In some embodiments, a reduction in the innate immune response can be measured by expression or activity level of Type 1 interferons (e.g., IFN-α, IFN-β, IFN-κ, IFN-δ, IFN-ε, IFN-τ, IFN-ω, and IFN-ζ) or the expression of interferon-regulated genes such as the toll-like receptors (e.g., TLR7 and TLR8), and/or by decreased cell death following one or more administrations of the mRNA of the invention into a cell.

In some embodiments, the expression of Type-1 interferons by a mammalian cell in response to the mRNA of the present disclosure is reduced by at least 10%, 20%, 30%, 40%, 50%, 60%, 70%, 80%, 90%, 95%, 99%, 99.9%, or greater than 99.9% relative to a corresponding wild-type mRNA, to an mRNA that encodes a GALT polypeptide but does not comprise 5-methoxyuracil, or to an mRNA that encodes a GALT polypeptide and that comprises 5-methoxyuracil but that does not have adjusted uracil content. In some embodiments, the interferon is IFN-β. In some embodiments, cell death frequency caused by administration of mRNA of the present disclosure to a mammalian cell is 10%, 25%, 50%, 75%, 85%, 90%, 95%, or over 95% less than the cell death frequency observed with a corresponding wild-type mRNA, an mRNA that encodes for a GALT polypeptide but does not comprise 5-methoxyuracil, or an mRNA that encodes for a GALT polypeptide and that comprises 5-methoxyuracil but that does not have adjusted uracil content. In some embodiments, the mammalian cell is a BJ fibroblast cell. In other embodiments, the mammalian cell is a splenocyte. In some embodiments, the mammalian cell is that of a mouse or a rat. In other embodiments, the mammalian cell is that of a human. In one embodiment, the mRNA of the present disclosure does not substantially induce an innate immune response of a mammalian cell into which the mRNA is introduced.

In some embodiments, the polynucleotide is an mRNA that comprises an ORF that encodes a GALT polypeptide, wherein uracil in the mRNA is at least about 95% 5-methoxyuracil, wherein the uracil content of the ORF is between about 115% and about 135% of the theoretical minimum uracil content in the corresponding wild-type ORF, and wherein the uracil content in the ORF encoding the GALT polypeptide is less than about 20% of the total nucleobase content in the ORF. In some embodiments, the ORF that encodes the GALT polypeptide is further modified to increase G/C content of the ORF (absolute or relative) by at least about 40%, as compared to the corresponding wild-type ORF. In yet other embodiments, the ORF encoding the GALT polypeptide contains less than 20 non-phenylalanine uracil pairs and/or triplets. In some embodiments, at least one codon in the ORF of the mRNA encoding the GALT polypeptide is further substituted with an alternative codon having a codon frequency lower than the codon frequency of the substituted codon in the synonymous codon set. In some embodiments, the expression of the GALT polypeptide encoded by an mRNA comprising an ORF wherein uracil in the mRNA is at least about 95% 5-methoxyuracil, and wherein the uracil content of the ORF is between about 115% and about 135% of the theoretical minimum uracil content in the corresponding wild-type ORF, is increased by at least about 10-fold when compared to expression of the GALT polypeptide from the corresponding wild-type mRNA. In some embodiments, the mRNA comprises an open ORF wherein uracil in the mRNA is at least about 95% 5-methoxyuracil, and wherein the uracil content of the ORF is between about 115% and about 135% of the theoretical minimum uracil content in the corresponding wild-type ORF, and wherein the mRNA does not substantially induce an innate immune response of a mammalian cell into which the mRNA is introduced.

10. METHODS FOR MODIFYING POLYNUCLEOTIDES

The invention includes modified polynucleotides comprising a polynucleotide described herein (e.g., a polynucleotide, e.g. mRNA, comprising a nucleotide sequence encoding a GALT polypeptide). The modified polynucleotides can be chemically modified and/or structurally modified. When the polynucleotides of the present invention are chemically and/or structurally modified the polynucleotides can be referred to as "modified polynucleotides."

The present disclosure provides for modified nucleosides and nucleotides of a polynucleotide (e.g., RNA polynucleotides, such as mRNA polynucleotides) encoding a GALT polypeptide. A "nucleoside" refers to a compound containing a sugar molecule (e.g., a pentose or ribose) or a derivative thereof in combination with an organic base (e.g., a purine or pyrimidine) or a derivative thereof (also referred to herein as "nucleobase"). A "nucleotide" refers to a nucleoside including a phosphate group. Modified nucleotides can be synthesized by any useful method, such as, for example, chemically, enzymatically, or recombinantly, to include one or more modified or non-natural nucleosides. Polynucleotides can comprise a region or regions of linked nucleosides. Such regions can have variable backbone linkages. The linkages can be standard phosphodiester linkages, in which case the polynucleotides would comprise regions of nucleotides.

The modified polynucleotides disclosed herein can comprise various distinct modifications. In some embodiments, the modified polynucleotides contain one, two, or more (optionally different) nucleoside or nucleotide modifications. In some embodiments, a modified polynucleotide, introduced to a cell can exhibit one or more desirable properties, e.g., improved protein expression, reduced immunogenicity, or reduced degradation in the cell, as compared to an unmodified polynucleotide.

a. Structural Modifications

In some embodiments, a polynucleotide of the present invention (e.g., a polynucleotide comprising a nucleotide sequence encoding a GALT polypeptide) is structurally modified. As used herein, a "structural" modification is one in which two or more linked nucleosides are inserted, deleted, duplicated, inverted or randomized in a polynucleotide without significant chemical modification to the nucleotides themselves. Because chemical bonds will necessarily be broken and reformed to effect a structural modification, structural modifications are of a chemical nature and hence are chemical modifications. However, structural modifications will result in a different sequence of nucleotides. For example, the polynucleotide "ATCG" can be chemically modified to "AT-5meC-G". The same polynucleotide can be structurally modified from "ATCG" to "ATCCCG". Here, the dinucleotide "CC" has been inserted, resulting in a structural modification to the polynucleotide.

b. Chemical Modifications

In some embodiments, the polynucleotides of the present invention are chemically modified. As used herein in reference to a polynucleotide, the terms "chemical modification" or, as appropriate, "chemically modified" refer to modification with respect to adenosine (A), guanosine (G), uridine (U), thymidine (T) or cytidine (C) ribo- or deoxyribonucleosides in one or more of their position, pattern, percent or population. Generally, herein, these terms are not intended to refer to the ribonucleotide modifications in naturally occurring 5'-terminal mRNA cap moieties.

In some embodiments, the polynucleotides of the present invention can have a uniform chemical modification of all or any of the same nucleoside type or a population of modifications produced by mere downward titration of the same starting modification in all or any of the same nucleoside type, or a measured percent of a chemical modification of all any of the same nucleoside type but with random incorporation, such as where all uridines are replaced by a uridine analog, e.g., pseudouridine or 5-methoxyuridine. In another embodiment, the polynucleotides can have a uniform chemical modification of two, three, or four of the same nucleoside type throughout the entire polynucleotide (such as all uridines and all cytidines, etc. are modified in the same way).

Modified nucleotide base pairing encompasses not only the standard adenosine-thymine, adenosine-uracil, or guanosine-cytosine base pairs, but also base pairs formed between nucleotides and/or modified nucleotides comprising non-standard or modified bases, wherein the arrangement of hydrogen bond donors and hydrogen bond acceptors permits hydrogen bonding between a non-standard base and a standard base or between two complementary non-standard base structures. One example of such non-standard base pairing is the base pairing between the modified nucleotide inosine and adenine, cytosine or uracil. Any combination of base/sugar or linker can be incorporated into polynucleotides of the present disclosure.

The skilled artisan will appreciate that, except where otherwise noted, polynucleotide sequences set forth in the instant application will recite "T"s in a representative DNA sequence but where the sequence represents RNA, the "T"s would be substituted for "U"s.

Modifications of polynucleotides (e.g., RNA polynucleotides, such as mRNA polynucleotides) that are useful in the compositions, methods and synthetic processes of the present disclosure include, but are not limited to the following nucleotides, nucleosides, and nucleobases: 2-methylthio-N6-(cis-hydroxyisopentenyl)adenosine; 2-methylthio-N6-methyladenosine; 2-methylthio-N6-threonyl carbamoyladenosine; N6-glycinylcarbamoyladenosine; N6-isopentenyladenosine; N6-methyladenosine; N6-threonylcarbamoyladenosine; 1,2'-O-dimethyladenosine; 1-methyladenosine; 2'-O-methyladenosine; 2'-O-ribosyladenosine (phosphate); 2-methyladenosine; 2-methylthio-N6 isopentenyladenosine; 2-methylthio-N6-hydroxynorvalyl carbamoyladenosine; 2'-O-methyladenosine; 2'-O-ribosyladenosine (phosphate); Isopentenyladenosine; N6-(cis-hydroxyisopentenyl)adenosine; N6,2'-O-dimethyladenosine; N6,2'-O-dimethyladenosine; N6,N6,2'-O-trimethyladenosine; N6,N6-dimethyladenosine; N6-acetyladenosine; N6-hydroxynorvalylcarbamoyladenosine; N6-methyl-N6-threonylcarbamoyladenosine; 2-methyladenosine; 2-methylthio-N6-isopentenyladenosine; 7-deaza-adenosine; N1-methyl-adenosine; N6,N6 (dimethyl)adenine; N6-cis-hydroxy-isopentenyl-adenosine; α-thio-adenosine; 2 (amino)adenine; 2 (aminopropyl)adenine; 2 (methylthio) N6 (isopentenyl)adenine; 2-(alkyl)adenine; 2-(aminoalkyl)adenine; 2-(aminopropyl)adenine; 2-(halo)adenine; 2-(halo) adenine; 2-(propyl)adenine; 2'-Amino-2'-deoxy-ATP; 2'-Azido-2'-deoxy-ATP; 2'-Deoxy-2'-a-aminoadenosine TP; 2'-Deoxy-2'-a-azidoadenosine TP; 6 (alkyl)adenine; 6 (methyl)adenine; 6-(alkyl)adenine; 6-(methyl)adenine; 7 (deaza)adenine; 8 (alkenyl)adenine; 8 (alkynyl)adenine; 8 (amino)adenine; 8 (thioalkyl)adenine; 8-(alkenyl)adenine; 8-(alkyl)adenine; 8-(alkynyl)adenine; 8-(amino)adenine; 8-(halo)adenine; 8-(hydroxyl)adenine; 8-(thioalkyl)adenine; 8-(thiol)adenine; 8-azido-adenosine; aza adenine; deaza adenine; N6 (methyl)adenine; N6-(isopentyl)adenine; 7-deaza-8-aza-adenosine; 7-methyladenine; 1-Deazaadenosine TP; 2'Fluoro-N6-Bz-deoxyadenosine TP; 2'-OMe-2-Amino-ATP; 2'O-methyl-N6-Bz-deoxyadenosine TP; 2'-a-Ethynyladenosine TP; 2-aminoadenine; 2-Aminoadenosine TP; 2-Amino-ATP; 2'-a-Trifluoromethyladenosine TP; 2-Azidoadenosine TP; 2'-b-Ethynyladenosine TP; 2-Bromoadenosine TP; 2'-b-Trifluoromethyladenosine TP; 2-Chloroadenosine TP; 2'-Deoxy-2',2'-difluoroadenosine TP; 2'-Deoxy-2'-a-mercaptoadenosine TP; 2'-Deoxy-2'-a-thiomethoxyadenosine TP; 2'-Deoxy-2'-b-aminoadenosine TP; 2'-Deoxy-2'-b-azidoadenosine TP; 2'-Deoxy-2'-b-bromoadenosine TP; 2'-Deoxy-2'-b-chloroadenosine TP; 2'-Deoxy-2'-b-fluoroadenosine TP; 2'-Deoxy-2'-b-iodoadenosine TP; 2'-Deoxy-2'-b-mercaptoadenosine TP; 2'-Deoxy-2'-b-thiomethoxyadenosine TP; 2-Fluoroadenosine TP; 2-Iodoadenosine TP; 2-Mercaptoadenosine TP; 2-methoxy-adenine; 2-methylthio-adenine; 2-Trifluoromethyladenosine TP; 3-Deaza-3-bromoadenosine TP; 3-Deaza-3-chloroadenosine TP; 3-Deaza-3-fluoroadenosine TP; 3-Deaza-3-iodoadenosine TP; 3-Deazaadenosine TP; 4'-Azidoadenosine TP; 4'-Carbocyclic adenosine TP; 4'-Ethynyladenosine TP; 5'-Homo-adenosine TP; 8-Aza-ATP; 8-bromo-adenosine TP; 8-Trifluoromethyladenosine TP; 9-Deazaadenosine TP; 2-aminopurine; 7-deaza-2,6-diaminopurine; 7-deaza-8-aza-2,6-diaminopurine; 7-deaza-8-aza-2-aminopurine; 2,6-diaminopurine; 7-deaza-8-aza-adenine, 7-deaza-2-aminopurine; 2-thiocytidine; 3-methylcytidine; 5-formylcytidine; 5-hydroxymethylcytidine; 5-methylcytidine; N4-acetylcytidine; 2'-O-methylcytidine; 2'-O-methylcytidine; 5,2'-O-dimethylcytidine; 5-formyl-2'-O-methylcytidine; Lysidine; N4,2'-O-dimethylcytidine; N4-acetyl-2'-O-methylcytidine; N4-methylcytidine; N4,N4-Dimethyl-2'-OMe-Cytidine TP; 4-methylcytidine; 5-aza-cytidine; Pseudo-iso-cytidine; pyrrolo-cytidine; α-thio-cytidine; 2-(thio)cytosine; 2'-Amino-2'-deoxy-CTP; 2'-Azido-2'-deoxy-CTP; 2'-Deoxy-2'-a-aminocytidine TP; 2'-Deoxy-2'-a-azidocytidine TP; 3 (deaza) 5 (aza)cytosine; 3 (methyl)cytosine; 3-(alkyl)cytosine; 3-(deaza) 5 (aza)cytosine; 3-(methyl)cytidine; 4,2'-0-dimethylcytidine; 5 (halo)cytosine; 5 (methyl)cytosine; 5 (propynyl)cytosine; 5 (trifluoromethyl)cytosine; 5-(alkyl)cytosine; 5-(alkynyl)cytosine; 5-(halo)cytosine; 5-(propynyl) cytosine; 5-(trifluoromethyl)cytosine; 5-bromo-cytidine; 5-iodo-cytidine; 5-propynyl cytosine; 6-(azo)cytosine; 6-aza-cytidine; aza cytosine; deaza cytosine; N4 (acetyl) cytosine; 1-methyl-1-deaza-pseudoisocytidine; 1-methyl-pseudoisocytidine; 2-methoxy-5-methyl-cytidine; 2-methoxy-cytidine; 2-thio-5-methyl-cytidine; 4-methoxy-1-methyl-pseudoisocytidine; 4-methoxy-pseudoisocytidine; 4-thio-1-methyl-1-deaza-pseudoisocytidine; 4-thio-1-methyl-pseudoisocytidine; 4-thio-pseudoisocytidine; 5-aza-zebularine; 5-methyl-zebularine; pyrrolo-pseudoisocytidine; Zebularine; (E)-5-(2-Bromo-vinyl)cytidine TP; 2,2'-anhydro-cytidine TP hydrochloride; 2'Fluor-N4-Bz-cytidine TP; 2'Fluoro-N4-Acetyl-cytidine TP; 2'-O-Methyl-N4-

Acetyl-cytidine TP; 2'O-methyl-N4-Bz-cytidine TP; 2'-a-Ethynylcytidine TP; 2'-a-Trifluoromethylcytidine TP; 2'-b-Ethynylcytidine TP; 2'-b-Trifluoromethylcytidine TP; 2'-Deoxy-2',2'-difluorocytidine TP; 2'-Deoxy-2'-a-mercaptocytidine TP; 2'-Deoxy-2'-a-thiomethoxycytidine TP; 2'-Deoxy-2'-b-aminocytidine TP; 2'-Deoxy-2'-b-azidocytidine TP; 2'-Deoxy-2'-b-bromocytidine TP; 2'-Deoxy-2'-b-chlorocytidine TP; 2'-Deoxy-2'-b-fluorocytidine TP; 2'-Deoxy-2'-b-iodocytidine TP; 2'-Deoxy-2'-b-mercaptocytidine TP; 2'-Deoxy-2'-b-thiomethoxycytidine TP; 2'-O-Methyl-5-(1-propynyl)cytidine TP; 3'-Ethynylcytidine TP; 4'-Azido-cytidine TP; 4'-Carbocyclic cytidine TP; 4'-Ethynylcytidine TP; 5-(1-Propynyl)ara-cytidine TP; 5-(2-Chloro-phenyl)-2-thiocytidine TP; 5-(4-Amino-phenyl)-2-thiocytidine TP; 5-Aminoallyl-CTP; 5-Cyanocytidine TP; 5-Ethynylara-cytidine TP; 5-Ethynylcytidine TP; 5'-Homo-cytidine TP; 5-Methoxycytidine TP; 5-Trifluoromethyl-Cytidine TP; N4-Amino-cytidine TP; N4-Benzoyl-cytidine TP; Pseudoisocytidine; 7-methylguanosine; N2,2'-O-dimethylguanosine; N2-methylguanosine; Wyosine; 1,2'-O-dimethylguanosine; 1-methylguanosine; 2'-O-methylguanosine; 2'-O-ribosylguanosine (phosphate); 2'-O-methylguanosine; 2'-O-ribosylguanosine (phosphate); 7-aminomethyl-7-deazaguanosine; 7-cyano-7-deazaguanosine; Archaeosine; Methylwyosine; N2,7-dimethylguanosine; N2,N2,2'-O-trimethylguanosine; N2,N2,7-trimethylguanosine; N2,N2-dimethylguanosine; N2,7,2'-O-trimethylguanosine; 6-thio-guanosine; 7-deaza-guanosine; 8-oxo-guanosine; N1-methyl-guanosine; α-thio-guanosine; 2 (propyl)guanine; 2-(alkyl)guanine; 2'-Amino-2'-deoxy-GTP; 2'-Azido-2'-deoxy-GTP; 2'-Deoxy-2'-a-aminoguanosine TP; 2'-Deoxy-2'-a-azidoguanosine TP; 6 (methyl)guanine; 6-(alkyl)guanine; 6-(methyl)guanine; 6-methyl-guanosine; 7 (alkyl)guanine; 7 (deaza)guanine; 7 (methyl)guanine; 7-(alkyl)guanine; 7-(deaza)guanine; 7-(methyl)guanine; 8 (alkyl)guanine; 8 (alkynyl)guanine; 8 (halo)guanine; 8 (thioalkyl)guanine; 8-(alkenyl)guanine; 8-(alkyl)guanine; 8-(alkynyl)guanine; 8-(amino)guanine; 8-(halo)guanine; 8-(hydroxyl)guanine; 8-(thioalkyl)guanine; 8-(thiol)guanine; aza guanine; deaza guanine; N (methyl)guanine; N-(methyl)guanine; 1-methyl-6-thio-guanosine; 6-methoxy-guanosine; 6-thio-7-deaza-8-aza-guanosine; 6-thio-7-deaza-guanosine; 6-thio-7-methyl-guanosine; 7-deaza-8-aza-guanosine; 7-methyl-8-oxo-guanosine; N2,N2-dimethyl-6-thio-guanosine; N2-methyl-6-thio-guanosine; 1-Me-GTP; 2'Fluoro-N2-isobutyl-guanosine TP; 2'O-methyl-N2-isobutyl-guanosine TP; 2'-a-Ethynylguanosine TP; 2'-a-Trifluoromethylguanosine TP; 2'-b-Ethynylguanosine TP; 2'-b-Trifluoromethylguanosine TP; 2'-Deoxy-2',2'-difluoroguanosine TP; 2'-Deoxy-2'-a-mercaptoguanosine TP; 2'-Deoxy-2'-a-thiomethoxyguanosine TP; 2'-Deoxy-2'-b-aminoguanosine TP; 2'-Deoxy-2'-b-azidoguanosine TP; 2'-Deoxy-2'-b-bromoguanosine TP; 2'-Deoxy-2'-b-chloroguanosine TP; 2'-Deoxy-2'-b-fluoroguanosine TP; 2'-Deoxy-2'-b-iodoguanosine TP; 2'-Deoxy-2'-b-mercaptoguanosine TP; 2'-Deoxy-2'-b-thiomethoxyguanosine TP; 4'-Azidoguanosine TP; 4'-Carbocyclic guanosine TP; 4'-Ethynylguanosine TP; 5'-Homo-guanosine TP; 8-bromo-guanosine TP; 9-Deazaguanosine TP; N2-isobutyl-guanosine TP; 1-methylinosine; Inosine; 1,2'-O-dimethylinosine; 2'-O-methylinosine; 7-methylinosine; 2'-O-methylinosine; Epoxyqueuosine; galactosyl-queuosine; Mannosylqueuosine; Queuosine; allyamino-thymidine; aza thymidine; deaza thymidine; deoxy-thymidine; 2'-O-methyluridine; 2-thiouridine; 3-methyluridine; 5-carboxymethyluridine; 5-hydroxyuridine; 5-methyluridine; 5-taurinomethyl-2-thiouridine; 5-taurinomethyluridine; Dihydrouridine; Pseudouridine; (3-(3-amino-3-carboxypropyl)uridine; 1-methyl-3-(3-amino-5-carboxypropyl)pseudouridine; 1-methylpseudouridine; 1-ethyl-pseudouridine; 2'-O-methyluridine; 2'-O-methylpseudouridine; 2'-O-methyluridine; 2-thio-2'-O-methyluridine; 3-(3-amino-3-carboxypropyl)uridine; 3,2'-O-dimethyluridine; 3-Methyl-pseudo-Uridine TP; 4-thiouridine; 5-(carboxyhydroxymethyl)uridine; 5-(carboxyhydroxymethyl)uridine methyl ester; 5,2'-O-dimethyluridine; 5,6-dihydro-uridine; 5-aminomethyl-2-thiouridine; 5-carbamoylmethyl-2'-O-methyluridine; 5-carbamoylmethyluridine; 5-carboxyhydroxymethyluridine; 5-carboxyhydroxymethyluridine methyl ester; 5-carboxymethylaminomethyl-2'-O-methyluridine; 5-carboxymethylaminomethyl-2-thiouridine; 5-carboxymethylaminomethyl-2-thiouridine; 5-carboxymethylaminomethyluridine; 5-carboxymethylaminomethyluridine; 5-Carbamoylmethyluridine TP; 5-methoxycarbonylmethyl-2'-O-methyluridine; 5-methoxycarbonylmethyl-2-thiouridine; 5-methoxycarbonylmethyluridine; 5-methyluridine), 5-methoxyuridine; 5-methyl-2-thiouridine; 5-methylaminomethyl-2-selenouridine; 5-methylaminomethyl-2-thiouridine; 5-methylaminomethyluridine; 5-Methyldihydrouridine; 5-Oxyacetic acid-Uridine TP; 5-Oxyacetic acid-methyl ester-Uridine TP; N1-methyl-pseudo-uracil; N1-ethyl-pseudo-uracil; uridine 5-oxyacetic acid; uridine 5-oxyacetic acid methyl ester; 3-(3-Amino-3-carboxypropyl)-Uridine TP; 5-(iso-Pentenylaminomethyl)-2-thiouridine TP; 5-(iso-Pentenylaminomethyl)-2'-O-methyluridine TP; 5-(iso-Pentenylaminomethyl)uridine TP; 5-propynyl uracil; α-thio-uridine; 1 (aminoalkylamino-carbonylethylenyl)-2(thio)-pseudouracil; 1 (aminoalkylaminocarbonylethylenyl)-2,4-(dithio)pseudouracil; 1 (aminoalkylaminocarbonylethylenyl)-4 (thio)pseudouracil; 1 (aminoalkylaminocarbonylethylenyl)-pseudouracil; 1 (aminocarbonylethylenyl)-2(thio)-pseudouracil; 1 (aminocarbonylethylenyl)-2,4-(dithio)pseudouracil; 1 (aminocarbonylethylenyl)-4 (thio)pseudouracil; 1 (aminocarbonylethylenyl)-pseudouracil; 1 substituted 2(thio)-pseudouracil; 1 substituted 2,4-(dithio)pseudouracil; 1 substituted 4 (thio)pseudouracil; 1 substituted pseudouracil; 1-(aminoalkylamino-carbonylethylenyl)-2-(thio)-pseudouracil; 1-Methyl-3-(3-amino-3-carboxypropyl) pseudouridine TP; 1-Methyl-3-(3-amino-3-carboxypropyl) pseudo-UTP; 1-Methyl-pseudo-UTP; 1-Ethyl-pseudo-UTP; 2 (thio)pseudouracil; 2' deoxy uridine; 2' fluorouridine; 2-(thio)uracil; 2,4-(dithio)pseudouracil; 2' methyl, 2'amino, 2'azido, 2'fluro-guanosine; 2'-Amino-2'-deoxy-UTP; 2'-Azido-2'-deoxy-UTP; 2'-Azido-deoxyuridine TP; 2'-O-methylpseudouridine; 2' deoxy uridine; 2' fluorouridine; 2'-Deoxy-2'-a-aminouridine TP; 2'-Deoxy-2'-a-azidouridine TP; 2-methylpseudouridine; 3 (3 amino-3 carboxypropyl) uracil; 4 (thio)pseudouracil; 4-(thio)pseudouracil; 4-(thio) uracil; 4-thiouracil; 5 (1,3-diazole-1-alkyl)uracil; 5 (2-aminopropyl)uracil; 5 (aminoalkyl)uracil; 5 (dimethylaminoalkyl)uracil; 5 (guanidiniumalkyl)uracil; 5 (methoxycarbonylmethyl)-2-(thio)uracil; 5 (methoxycarbonyl-methyl)uracil; 5 (methyl) 2 (thio)uracil; 5 (methyl) 2,4 (dithio)uracil; 5 (methyl) 4 (thio)uracil; 5 (methylaminomethyl)-2 (thio)uracil; 5 (methylaminomethyl)-2,4 (dithio) uracil; 5 (methylaminomethyl)-4 (thio)uracil; 5 (propynyl) uracil; 5 (trifluoromethyl)uracil; 5-(2-aminopropyl)uracil; 5-(alkyl)-2-(thio)pseudouracil; 5-(alkyl)-2,4 (dithio) pseudouracil; 5-(alkyl)-4 (thio)pseudouracil; 5-(alkyl) pseudouracil; 5-(alkyl)uracil; 5-(alkynyl)uracil; 5-(allylamino)uracil; 5-(cyanoalkyl)uracil; 5-(dialkylaminoalkyl) uracil; 5-(dimethylaminoalkyl)uracil; 5-(guanidiniumalkyl) uracil; 5-(halo)uracil; 5-(1,3-diazole-1-alkyl)uracil; 5-(methoxy)uracil; 5-(methoxycarbonylmethyl)-2-(thio)

uracil; 5-(methoxycarbonyl-methyl)uracil; 5-(methyl) 2(thio)uracil; 5-(methyl) 2,4 (dithio)uracil; 5-(methyl) 4 (thio)uracil; 5-(methyl)-2-(thio)pseudouracil; 5-(methyl)-2,4 (dithio)pseudouracil; 5-(methyl)-4 (thio)pseudouracil; 5-(methyl)pseudouracil; 5-(methylaminomethyl)-2 (thio)uracil; 5-(methylaminomethyl)-2,4(dithio)uracil; 5-(methylaminomethyl)-4-(thio)uracil; 5-(propynyl)uracil; 5-(trifluoromethyl)uracil; 5-aminoallyl-uridine; 5-bromo-uridine; 5-iodo-uridine; 5-uracil; 6 (azo)uracil; 6-(azo)uracil; 6-aza-uridine; allyamino-uracil; aza uracil; deaza uracil; N3 (methyl)uracil; Pseudo-UTP-1-2-ethanoic acid; Pseudouracil; 4-Thio-pseudo-UTP; 1-carboxymethyl-pseudouridine; 1-methyl-1-deaza-pseudouridine; 1-propynyl-uridine; 1-taurinomethyl-1-methyl-uridine; 1-taurinomethyl-4-thio-uridine; 1-taurinomethyl-pseudouridine; 2-methoxy-4-thio-pseudouridine; 2-thio-1-methyl-1-deaza-pseudouridine; 2-thio-1-methyl-pseudouridine; 2-thio-5-aza-uridine; 2-thio-dihydropseudouridine; 2-thio-dihydrouridine; 2-thio-pseudouridine; 4-methoxy-2-thio-pseudouridine; 4-methoxy-pseudouridine; 4-thio-1-methyl-pseudouridine; 4-thio-pseudouridine; 5-aza-uridine; Dihydropseudouridine; (±)1-(2-Hydroxypropyl)pseudouridine TP; (2R)-1-(2-Hydroxypropyl)pseudouridine TP; (2S)-1-(2-Hydroxypropyl) pseudouridine TP; (E)-5-(2-Bromo-vinyl)ara-uridine TP; (E)-5-(2-Bromo-vinyl)uridine TP; (Z)-5-(2-Bromo-vinyl) ara-uridine TP; (Z)-5-(2-Bromo-vinyl)uridine TP; 1-(2,2,2-Trifluoroethyl)-pseudo-UTP; Pentafluoropropyl)pseudouridine TP; 1-(2,2-Diethoxyethyl)pseudouridine TP; 1-(2,4,6-Trimethylbenzyl)pseudouridine TP; 1-(2,4,6-Trimethyl-benzyl)pseudo-UTP; 1-(2,4,6-Trimethyl-phenyl)pseudo-UTP; 1-(2-Amino-2-carboxyethyl)pseudo-UTP; 1-(2-Amino-ethyl)pseudo-UTP; 1-(2-Hydroxyethyl) pseudouridine TP; 1-(2-Methoxyethyl)pseudouridine TP; 1-(3,4-Bis-trifluoromethoxybenzyl)pseudouridine TP; 1-(3,4-Dimethoxybenzyl)pseudouridine TP; 1-(3-Amino-3-carboxypropyl)pseudo-UTP; 1-(3-Amino-propyl)pseudo-UTP; 1-(3-Cyclopropyl-prop-2-ynyl)pseudouridine TP; 1-(4-Amino-4-carboxybutyl)pseudo-UTP; 1-(4-Amino-benzyl) pseudo-UTP; 1-(4-Amino-butyl)pseudo-UTP; 1-(4-Amino-phenyl)pseudo-UTP; 1-(4-Azidobenzyl)pseudouridine TP; 1-(4-Bromobenzyl)pseudouridine TP; 1-(4-Chlorobenzyl) pseudouridine TP; 1-(4-Fluorobenzyl)pseudouridine TP; 1-(4-Iodobenzyl)pseudouridine TP; 1-(4-Methanesulfonyl-benzyl)pseudouridine TP; 1-(4-Methoxybenzyl)pseudouridine TP; 1-(4-Methoxy-benzyl)pseudo-UTP; 1-(4-Methoxy-phenyl)pseudo-UTP; 1-(4-Methylbenzyl)pseudouridine TP; 1-(4-Methyl-benzyl)pseudo-UTP; 1-(4-Nitrobenzyl) pseudouridine TP; 1-(4-Nitro-benzyl)pseudo-UTP; 1(4-Nitro-phenyl)pseudo-UTP; 1-(4-Thiomethoxybenzyl) pseudouridine TP; 1-(4-Trifluoromethoxybenzyl) pseudouridine TP; 1-(4-Trifluoromethylbenzyl) pseudouridine TP; 1-(5-Amino-pentyl)pseudo-UTP; 1-(6-Amino-hexyl)pseudo-UTP; 1,6-Dimethyl-pseudo-UTP; 1-[3-(2-{2-[2-(2-Aminoethoxy)-ethoxy]-ethoxy}-ethoxy)-propionyl]pseudouridine TP; 1-{3-[2-(2-Aminoethoxy)-ethoxy]-propionyl}pseudouridine TP; 1-Acetylpseudouridine TP; 1-Alkyl-6-(1-propynyl)-pseudo-UTP; 1-Alkyl-6-(2-propynyl)-pseudo-UTP; 1-Alkyl-6-allyl-pseudo-UTP; 1-Alkyl-6-ethynyl-pseudo-UTP; 1-Alkyl-6-homoallyl-pseudo-UTP; 1-Alkyl-6-vinyl-pseudo-UTP; 1-Allylpseudouridine TP; 1-Aminomethyl-pseudo-UTP; 1-Benzoylpseudouridine TP; 1-Benzyloxymethylpseudouridine TP; 1-Benzyl-pseudo-UTP; 1-Biotinyl-PEG2-pseudouridine TP; 1-Biotinylpseudouridine TP; 1-Butyl-pseudo-UTP; 1-Cyanomethylpseudouridine TP; 1-Cyclobutylmethyl-pseudo-UTP; 1-Cyclobutyl-pseudo-UTP; 1-Cycloheptylmethyl-pseudo-UTP; 1-Cycloheptyl-pseudo-UTP; 1-Cyclohexylmethyl-pseudo-UTP; 1-Cyclohexyl-pseudo-UTP; 1-Cyclooctylmethyl-pseudo-UTP; 1-Cyclooctyl-pseudo-UTP; 1-Cyclopentylmethyl-pseudo-UTP; 1-Cyclopentyl-pseudo-UTP; 1-Cyclopropylmethyl-pseudo-UTP; 1-Cyclopropyl-pseudo-UTP; 1-Ethyl-pseudo-UTP; 1-Hexyl-pseudo-UTP; 1-Homoallylpseudouridine TP; 1-Hydroxymethylpseudouridine TP; 1-iso-propyl-pseudo-UTP; 1-Me-2-thio-pseudo-UTP; 1-Me-4-thio-pseudo-UTP; 1-Me-alpha-thio-pseudo-UTP; 1-Methanesulfonylmethylpseudouridine TP; 1-Methoxymethylpseudouridine TP; 1-Methyl-6-(2,2,2-Trifluoroethyl)pseudo-UTP; 1-Methyl-6-(4-morpholino)-pseudo-UTP; 1-Methyl-6-(4-thiomorpholino)-pseudo-UTP; 1-Methyl-6-(substituted phenyl) pseudo-UTP; 1-Methyl-6-amino-pseudo-UTP; 1-Methyl-6-azido-pseudo-UTP; 1-Methyl-6-bromo-pseudo-UTP; 1-Methyl-6-butyl-pseudo-UTP; 1-Methyl-6-chloro-pseudo-UTP; 1-Methyl-6-cyano-pseudo-UTP; 1-Methyl-6-dimethylamino-pseudo-UTP; 1-Methyl-6-ethoxy-pseudo-UTP; 1-Methyl-6-ethylcarboxylate-pseudo-UTP; 1-Methyl-6-ethyl-pseudo-UTP; 1-Methyl-6-fluoro-pseudo-UTP; 1-Methyl-6-formyl-pseudo-UTP; 1-Methyl-6-hydroxyamino-pseudo-UTP; 1-Methyl-6-hydroxy-pseudo-UTP; 1-Methyl-6-iodo-pseudo-UTP; 1-Methyl-6-iso-propyl-pseudo-UTP; 1-Methyl-6-methoxy-pseudo-UTP; 1-Methyl-6-methylamino-pseudo-UTP; 1-Methyl-6-phenyl-pseudo-UTP; 1-Methyl-6-propyl-pseudo-UTP; 1-Methyl-6-tert-butyl-pseudo-UTP; 1-Methyl-6-trifluoromethoxy-pseudo-UTP; 1-Methyl-6-trifluoromethyl-pseudo-UTP; 1-Morpholinomethylpseudouridine TP; 1-Pentyl-pseudo-UTP; 1-Phenyl-pseudo-UTP; 1-Pivaloylpseudouridine TP; 1-Propargylpseudouridine TP; 1-Propyl-pseudo-UTP; 1-propynyl-pseudouridine; 1-p-tolyl-pseudo-UTP; 1-tert-Butyl-pseudo-UTP; 1-Thiomethoxymethylpseudouridine TP; 1-Thiomorpholinomethylpseudouridine TP; 1-Trifluoroacetylpseudouridine TP; 1-Trifluoromethyl-pseudo-UTP; 1-Vinylpseudouridine TP; 2,2'-anhydro-uridine TP; 2'-bromo-deoxyuridine TP; 2'-F-5-Methyl-2'-deoxy-UTP; 2'-OMe-5-Me-UTP; 2'-OMe-pseudo-UTP; 2'-a-Ethynyluridine TP; 2'-a-Trifluoromethyluridine TP; 2'-b-Ethynyluridine TP; 2'-b-Trifluoromethyluridine TP; 2'-Deoxy-2',2'-difluorouridine TP; 2'-Deoxy-2'-a-mercaptouridine TP; 2'-Deoxy-2'-a-thiomethoxyuridine TP; 2'-Deoxy-2'-b-aminouridine TP; 2'-Deoxy-2'-b-azidouridine TP; 2'-Deoxy-2'-b-bromouridine TP; 2'-Deoxy-2'-b-chlorouridine TP; 2'-Deoxy-2'-b-fluorouridine TP; 2'-Deoxy-2'-b-iodouridine TP; 2'-Deoxy-2'-b-mercaptouridine TP; 2'-Deoxy-2'-b-thiomethoxyuridine TP; 2-methoxy-4-thio-uridine; 2-methoxyuridine; 2'-O-Methyl-5-(1-propynyl)uridine TP; 3-Alkyl-pseudo-UTP; 4'-Azidouridine TP; 4'-Carbocyclic uridine TP; 4'-Ethynyluridine TP; 5-(1-Propynyl)ara-uridine TP; 5-(2-Furanyl)uridine TP; 5-Cyanouridine TP; 5-Dimethylaminouridine TP; 5'-Homo-uridine TP; 5-iodo-2'-fluoro-deoxyuridine TP; 5-Phenylethynyluridine TP; 5-Trideuteromethyl-6-deuterouridine TP; 5-Trifluoromethyl-Uridine TP; 5-Vinylarauridine TP; 6-(2,2,2-Trifluoroethyl)-pseudo-UTP; 6-(4-Morpholino)-pseudo-UTP; 6-(4-Thiomorpholino)-pseudo-UTP; 6-(Substituted-Phenyl)-pseudo-UTP; 6-Amino-pseudo-UTP; 6-Azido-pseudo-UTP; 6-Bromo-pseudo-UTP; 6-Butyl-pseudo-UTP; 6-Chloro-pseudo-UTP; 6-Cyano-pseudo-UTP; 6-Dimethylamino-pseudo-UTP; 6-Ethoxy-pseudo-UTP; 6-Ethylcarboxylate-pseudo-UTP; 6-Ethyl-pseudo-UTP; 6-Fluoro-pseudo-UTP; 6-Formyl-pseudo-UTP; 6-Hydroxyamino-pseudo-UTP; 6-Hydroxy-pseudo-UTP; 6-Iodo-pseudo-UTP; 6-iso-Propyl-pseudo-UTP; 6-Methoxy-pseudo-UTP; 6-Methylamino-pseudo-UTP; 6-Methyl-pseudo-UTP; 6-Phenyl-pseudo-UTP; 6-Phenyl-pseudo-UTP; 6-Propyl-pseudo- UTP; 6-tert-Butyl-pseudo-UTP; 6-Trifluoromethoxy-pseudo-UTP; 6-Trifluoromethyl-pseudo-UTP; Alpha-thio-pseudo-UTP; Pseudouridine 1-(4-methylbenzenesulfonic acid) TP; Pseudouridine 1-(4-methylbenzoic acid) TP; Pseudouridine TP 1-[3-(2-ethoxy)]propionic acid; Pseudouridine TP 1-[3-{2-(2-[2-(2-ethoxy)-ethoxy]-ethoxy)-ethoxyl}]propionic acid; Pseudouridine TP 1-[3-{2-(2-[2-{2 (2-ethoxy)-ethoxy}-ethoxy]-ethoxy)-ethoxyl}]propionic acid; Pseudouridine TP 1-[3-{2-(2-[2-ethoxy]-ethoxy)-ethoxyl}]propionic acid; Pseudouridine TP 1-[3-{2-(2-ethoxy)-ethoxy}]propionic acid; Pseudouridine TP 1-methylphosphonic acid; Pseudouridine TP 1-methylphosphonic acid diethyl ester; Pseudo-UTP-N1-3-propionic acid; Pseudo-UTP-N1-4-butanoic acid; Pseudo-UTP-N1-5-pentanoic acid; Pseudo-UTP-N1-6-hexanoic acid; Pseudo-UTP-N1-7-heptanoic acid; Pseudo-UTP-N1-methyl-p-benzoic acid; Pseudo-UTP-N1-p-benzoic acid; Wybutosine; Hydroxywybutosine; Isowyosine; Peroxywybutosine; undermodified hydroxywybutosine; 4-demethylwyosine; 2,6-(diamino)purine; 1-(aza)-2-(thio)-3-(aza)-phenoxazin-1-yl: 1,3-(diaza)-2-(oxo)-phenthiazin-1-yl; 1,3-(diaza)-2-(oxo)-phenoxazin-1-yl; 1,3,5-(triaza)-2,6-(dioxa)-naphthalene; 2 (amino)purine; 2,4,5-(trimethyl)phenyl; 2' methyl, 2'amino, 2'azido, 2'fluro-cytidine; 2' methyl, 2'amino, 2'azido, 2'fluro-adenine; 2'methyl, 2'amino, 2'azido, 2'fluro-uridine; 2'-amino-2'-deoxyribose; 2-amino-6-Chloro-purine; 2-aza-inosinyl; 2'-azido-2'-deoxyribose; 2'fluoro-2'-deoxyribose; 2'-fluoro-modified bases; 2'-O-methyl-ribose; 2-oxo-7-aminopyridopyrimidin-3-yl; 2-oxo-pyridopyrimidine-3-yl; 2-pyridinone; 3 nitropyrrole; 3-(methyl)-7-(propynyl) isocarbostyrilyl; 3-(methyl)isocarbostyrilyl; 4-(fluoro)-6-(methyl)benzimidazole; 4-(methyl)benzimidazole; 4-(methyl)indolyl; 4,6-(dimethyl)indolyl; 5 nitroindole; 5 substituted pyrimidines; 5-(methyl)isocarbostyrilyl; 5-nitroindole; 6-(aza)pyrimidine; 6-(azo)thymine; 6-(methyl)-7-(aza)indolyl; 6-chloro-purine; 6-phenyl-pyrrolo-pyrimidin-2-on-3-yl; 7-(aminoalkylhydroxy)-1-(aza)-2-(thio)-3-(aza)-phenthiazin-1-yl; 7-(aminoalkylhydroxy)-1-(aza)-2-(thio)-3-(aza)-phenoxazin-1-yl; 7-(aminoalkylhydroxy)-1,3-(diaza)-2-(oxo)-phenoxazin-1-yl; 7-(aminoalkylhydroxy)-1,3-(diaza)-2-(oxo)-phenthiazin-1-yl; 7-(aminoalkylhydroxy)-1,3-(diaza)-2-(oxo)-phenoxazin-1-yl; 7-(aza)indolyl; 7-(guanidiniumalkylhydroxy)-1-(aza)-2-(thio)-3-(aza)-phenoxazinl-yl; 7-(guanidiniumalkylhydroxy)-1-(aza)-2-(thio)-3-(aza)-phenthiazin-1-yl; 7-(guanidiniumalkylhydroxy)-1-(aza)-2-(thio)-3-(aza)-phenoxazin-1-yl; 7-(guanidiniumalkylhydroxy)-1,3-(diaza)-2-(oxo)-phenoxazin-1-yl; 7-(guanidiniumalkyl-hydroxy)-1,3-(diaza)-2-(oxo)-phenthiazin-1-yl; 7-(guanidiniumalkylhydroxy)-1,3-(diaza)-2-(oxo)-phenoxazin-1-yl; 7-(propynyl)isocarbostyrilyl; 7-(propynyl)isocarbostyrilyl, propynyl-7-(aza)indolyl; 7-deaza-inosinyl; 7-substituted 1-(aza)-2-(thio)-3-(aza)-phenoxazin-1-yl; 7-substituted 1,3-(diaza)-2-(oxo)-phenoxazin-1-yl; 9-(methyl)-imidizopyridinyl; Aminoindolyl; Anthracenyl; bis-ortho-(aminoalkylhydroxy)-6-phenyl-pyrrolo-pyrimidin-2-on-3-yl; bis-ortho-substituted-6-phenyl-pyrrolo-pyrimidin-2-on-3-yl; Difluorotolyl; Hypoxanthine; Imidizopyridinyl; Inosinyl; Isocarbostyrilyl; Isoguanisine; N2-substituted purines; N6-methyl-2-amino-purine; N6-substituted purines; N-alkylated derivative; Napthalenyl; Nitrobenzimidazolyl; Nitroimidazolyl; Nitroindazolyl; Nitropyrazolyl; Nubularine; O6-substituted purines; O-alkylated derivative; ortho-(aminoalkylhydroxy)-6-phenyl-pyrrolo-pyrimidin-2-on-3-yl; ortho-substituted-6-phenyl-pyrrolo-pyrimidin-2-on-3-yl; Oxoformycin TP; para-(aminoalkylhydroxy)-6-phenyl-pyrrolo-pyrimidin-2-on-3-yl; para-substituted-6-phenyl-pyrrolo-pyrimidin-2-on-3-yl; Pentacenyl; Phenanthracenyl; Phenyl; propynyl-7-(aza)indolyl; Pyrenyl; pyridopyrimidin-3-yl; pyridopyrimidin-3-yl, 2-oxo-7-amino-pyridopyrimidin-3-yl; pyrrolo-pyrimidin-2-on-3-yl; Pyrrolopyrimidinyl; Pyrrolopyrizinyl; Stilbenzyl; substituted 1,2,4-triazoles; Tetracenyl; Tubercidine; Xanthine; Xanthosine-5'-TP; 2-thio-zebularine; 5-aza-2-thio-zebularine; 7-deaza-2-amino-purine; pyridin-4-one ribonucleoside; 2-Amino-riboside-TP; Formycin A TP; Formycin B TP; Pyrrolosine TP; 2'-OH-ara-adenosine TP; 2'-OH-ara-cytidine TP; 2'-OH-ara-uridine TP; 2'-OH-ara-guanosine TP; 5-(2-carbomethoxyvinyl)uridine TP; and N6-(19-Amino-pentaoxanonadecyl)adenosine TP.

In some embodiments, the polynucleotide (e.g., RNA polynucleotide, such as mRNA polynucleotide) includes a combination of at least two (e.g., 2, 3, 4 or more) of the aforementioned modified nucleobases.

In some embodiments, the mRNA comprises at least one chemically modified nucleoside. In some embodiments, the at least one chemically modified nucleoside is selected from the group consisting of pseudouridine (ψ), 2-thiouridine (s2U), 4'-thiouridine, 5-methylcytosine, 2-thio-1-methyl-1-deaza-pseudouridine, 2-thio-1-methyl-pseudouridine, 2-thio-5-aza-uridine, 2-thio-dihydropseudouridine, 2-thio-dihydrouridine, 2-thio-pseudouridine, 4-methoxy-2-thio-pseudouridine, 4-methoxy-pseudouridine, 4-thio-1-methyl-pseudouridine, 4-thio-pseudouridine, 5-aza-uridine, dihydropseudouridine, 5-methyluridine, 5-methoxyuridine, 2'-O-methyl uridine, 1-methyl-pseudouridine (m1ψ), 1-ethyl-pseudouridine (e1ψ), 5-methoxy-uridine (mo5U), 5-methyl-cytidine (m5C), α-thio-guanosine, α-thio-adenosine, 5-cyano uridine, 4'-thio uridine 7-deaza-adenine, 1-methyl-adenosine (m1A), 2-methyl-adenine (m2A), N6-methyl-adenosine (m6A), and 2,6-Diaminopurine, (I), 1-methyl-inosine (m1I), wyosine (imG), methylwyosine (mimG), 7-deaza-guanosine, 7-cyano-7-deaza-guanosine (preQ0), 7-aminomethyl-7-deaza-guanosine (preQ1), 7-methyl-guanosine (m7G), 1-methyl-guanosine (m1G), 8-oxo-guanosine, 7-methyl-8-oxo-guanosine, 2,8-dimethyladenosine, 2-geranylthiouridine, 2-lysidine, 2-selenouridine, 3-(3-amino-3-carboxypropyl)-5,6-dihydrouridine, 3-(3-amino-3-carboxypropyl)pseudouridine, 3-methylpseudouridine, 5-(carboxyhydroxymethyl)-2'-O-methyluridine methyl ester, 5-aminomethyl-2-geranylthiouridine, 5-aminomethyl-2-selenouridine, 5-aminomethyluridine, 5-carbamoylhydroxymethyluridine, 5-carbamoylmethyl-2-thiouridine, 5-carboxymethyl-2-thiouridine, 5-carboxymethylaminomethyl-2-geranylthiouridine, 5-carboxymethylaminomethyl-2-selenouridine, 5-cyanomethyluridine, 5-hydroxycytidine, 5-methylaminomethyl-2-geranylthiouridine, 7-aminocarboxypropyl-demethylwyosine, 7-aminocarboxypropylwyosine, 7-aminocarboxypropylwyosine methyl ester, 8-methyladenosine, N4,N4-dimethylcytidine, N6-formyladenosine, N6-hydroxymethyladenosine, agmatidine, cyclic N6-threonylcarbamoyladenosine, glutamyl-queuosine, methylated undermodified hydroxywybutosine, N4,N4,2'-O-trimethylcytidine, geranylated 5-methylaminomethyl-2-thiouridine, geranylated 5-carboxymethylaminomethyl-2-thiouridine, Qbase, preQ0base, preQ1base, and two or more combinations thereof. In some embodiments, the at least one chemically modified nucleoside is selected from the group consisting of pseudouridine, 1-methyl-pseudouridine, 1-ethyl-pseudouridine, 5-methylcytosine, 5-methoxyuridine, and a combination thereof. In some embodiments, the polynucleotide (e.g., RNA polynucleotide, such as mRNA polynucleotide) includes a combination of at least two (e.g., 2, 3, 4 or more) of the aforementioned modified nucleobases.

(i) Base Modifications

In certain embodiments, the chemical modification is at nucleobases in the polynucleotides (e.g., RNA polynucleotide, such as mRNA polynucleotide). In some embodiments, modified nucleobases in the polynucleotide (e.g., RNA polynucleotide, such as mRNA polynucleotide) are selected from the group consisting of 1-methyl-pseudouridine (m1ψ), 1-ethyl-pseudouridine (e1ψ), 5-methoxy-uridine (mo5U), 5-methyl-cytidine (m5C), pseudouridine (ψ), α-thio-guanosine and α-thio-adenosine. In some embodiments, the polynucleotide includes a combination of at least two (e.g., 2, 3, 4 or more) of the aforementioned modified nucleobases.

In some embodiments, the polynucleotide (e.g., RNA polynucleotide, such as mRNA polynucleotide) comprises pseudouridine (ψ) and 5-methyl-cytidine (m5C). In some embodiments, the polynucleotide (e.g., RNA polynucleotide, such as mRNA polynucleotide) comprises 1-methyl-pseudouridine (m1ψ). In some embodiments, the polynucleotide (e.g., RNA polynucleotide, such as mRNA polynucleotide) comprises 1-ethyl-pseudouridine (e1ψ). In some embodiments, the polynucleotide (e.g., RNA polynucleotide, such as mRNA polynucleotide) comprises 1-methyl-pseudouridine (m1ψ) and 5-methyl-cytidine (m5C). In some embodiments, the polynucleotide (e.g., RNA polynucleotide, such as mRNA polynucleotide) comprises 1-ethyl-pseudouridine (e1ψ) and 5-methyl-cytidine (m5C). In some embodiments, the polynucleotide (e.g., RNA polynucleotide, such as mRNA polynucleotide) comprises 2-thiouridine (s2U). In some embodiments, the polynucleotide (e.g., RNA polynucleotide, such as mRNA polynucleotide) comprises 2-thiouridine and 5-methyl-cytidine (m5C). In some embodiments, the polynucleotide (e.g., RNA polynucleotide, such as mRNA polynucleotide) comprises methoxy-uridine (mo5U). In some embodiments, the polynucleotide (e.g., RNA polynucleotide, such as mRNA polynucleotide) comprises 5-methoxy-uridine (mo5U) and 5-methyl-cytidine (m5C). In some embodiments, the polynucleotide (e.g., RNA polynucleotide, such as mRNA polynucleotide) comprises 2'-O-methyl uridine. In some embodiments, the polynucleotide (e.g., RNA polynucleotide, such as mRNA polynucleotide) comprises 2'-O-methyl uridine and 5-methyl-cytidine (m5C). In some embodiments, the polynucleotide (e.g., RNA polynucleotide, such as mRNA polynucleotide) comprises N6-methyl-adenosine (m6A). In some embodiments, the polynucleotide (e.g., RNA polynucleotide, such as mRNA polynucleotide) comprises N6-methyl-adenosine (m6A) and 5-methyl-cytidine (m5C).

In some embodiments, the polynucleotide (e.g., RNA polynucleotide, such as mRNA polynucleotide) is uniformly modified (e.g., fully modified, modified throughout the entire sequence) for a particular modification. For example, a polynucleotide can be uniformly modified with 5-methyl-cytidine (m5C), meaning that all cytosine residues in the mRNA sequence are replaced with 5-methyl-cytidine (m5C). Similarly, a polynucleotide can be uniformly modified for any type of nucleoside residue present in the sequence by replacement with a modified residue such as any of those set forth above.

In some embodiments, the chemically modified nucleosides in the open reading frame are selected from the group consisting of uridine, adenine, cytosine, guanine, and any combination thereof.

In some embodiments, the modified nucleobase is a modified cytosine. Examples of nucleobases and nucleosides having a modified cytosine include N4-acetyl-cytidine (ac4C), 5-methyl-cytidine (m5C), 5-halo-cytidine (e.g., 5-iodo-cytidine), 5-hydroxymethyl-cytidine (hm5C), 1-methyl-pseudoisocytidine, 2-thio-cytidine (s2C), 2-thio-5-methyl-cytidine.

In some embodiments, a modified nucleobase is a modified uridine. Example nucleobases and nucleosides having a modified uridine include 5-cyano uridine or 4'-thio uridine.

In some embodiments, a modified nucleobase is a modified adenine. Example nucleobases and nucleosides having a modified adenine include 7-deaza-adenine, 1-methyl-adenosine (m1A), 2-methyl-adenine (m2A), N6-methyl-adenine (m6A), and 2,6-Diaminopurine.

In some embodiments, a modified nucleobase is a modified guanine. Example nucleobases and nucleosides having a modified guanine include inosine (I), 1-methyl-inosine (m1I), wyosine (imG), methylwyosine (mimG), 7-deaza-guanosine, 7-cyano-7-deaza-guanosine (preQ0), 7-aminomethyl-7-deaza-guanosine (preQ1), 7-methyl-guanosine (m7G), 1-methyl-guanosine (m1G), 8-oxo-guanosine, 7-methyl-8-oxo-guanosine.

In some embodiments, the nucleobase modified nucleotides in the polynucleotide (e.g., RNA polynucleotide, such as mRNA polynucleotide) are 5-methoxyuridine.

In some embodiments, the polynucleotide (e.g., RNA polynucleotide, such as mRNA polynucleotide) includes a combination of at least two (e.g., 2, 3, 4 or more) of modified nucleobases.

In some embodiments, at least 95% of a type of nucleobases (e.g., uracil) in a polynucleotide of the invention (e.g., an mRNA polynucleotide encoding GALT) are modified nucleobases. In some embodiments, at least 95% of uracil in a polynucleotide of the present invention (e.g., an mRNA polynucleotide encoding GALT) is 5-methoxyuracil.

In some embodiments, the polynucleotide (e.g., RNA polynucleotide, such as mRNA polynucleotide) comprises 5-methoxyuridine (5mo5U) and 5-methyl-cytidine (m5C).

In some embodiments, the polynucleotide (e.g., RNA polynucleotide, such as mRNA polynucleotide) is uniformly modified (e.g., fully modified, modified throughout the entire sequence) for a particular modification. For example, a polynucleotide can be uniformly modified with 5-methoxyuridine, meaning that substantially all uridine residues in the mRNA sequence are replaced with 5-methoxyuridine. Similarly, a polynucleotide can be uniformly modified for any type of nucleoside residue present in the sequence by replacement with a modified residue such as any of those set forth above.

In some embodiments, the modified nucleobase is a modified cytosine.

In some embodiments, a modified nucleobase is a modified uracil. Example nucleobases and nucleosides having a modified uracil include 5-methoxyuracil.

In some embodiments, a modified nucleobase is a modified adenine.

In some embodiments, a modified nucleobase is a modified guanine.

In some embodiments, the nucleobases, sugar, backbone, or any combination thereof in the open reading frame encoding a GALT polypeptide are chemically modified by at least 10%, at least 20%, at least 30%, at least 40%, at least 50%, at least 60%, at least 70%, at least 80%, at least 90%, at least 95%, at least 99%, or 100%.

In some embodiments, the uridine nucleosides in the open reading frame encoding a GALT polypeptide are chemically modified by at least 10%, at least 20%, at least 30%, at least 40%, at least 50%, at least 60%, at least 70%, at least 80%, at least 90%, at least 95%, at least 99%, or 100%.

In some embodiments, the adenosine nucleosides in the open reading frame encoding a GALT polypeptide are chemically modified by at least 10%, at least 20%, at least 30%, at least 40%, at least 50%, at least 60%, at least 70%, at least 80%, at least 90%, at least 95%, at least 99%, or 100%.

In some embodiments, the cytidine nucleosides in the open reading frame encoding a GALT polypeptide are chemically modified by at least at least 10%, at least 20%, at least 30%, at least 40%, at least 50%, at least 60%, at least 70%, at least 80%, at least 90%, at least 95%, at least 99%, or 100%.

In some embodiments, the guanosine nucleosides in the open reading frame encoding a GALT polypeptide are chemically modified by at least at least 10%, at least 20%, at least 30%, at least 40%, at least 50%, at least 60%, at least 70%, at least 80%, at least 90%, at least 95%, at least 99%, or 100%.

In some embodiments, the polynucleotides can include any useful linker between the nucleosides. Such linkers, including backbone modifications, that are useful in the composition of the present disclosure include, but are not limited to the following: 3'-alkylene phosphonates, 3'-amino phosphoramidate, alkene containing backbones, aminoalkylphosphoramidates, aminoalkylphosphotriesters, boranophosphates, $—CH_2—O—N(CH_3)—CH_2—$, $—CH_2—N(CH_3)—N(CH_3)—CH_2—$, $—CH_2—NH—CH_2—$, chiral phosphonates, chiral phosphorothioates, formacetyl and thioformacetyl backbones, methylene (methylimino), methylene formacetyl and thioformacetyl backbones, methyleneimino and methylenehydrazino backbones, morpholino linkages, $—N(CH_3)—CH_2—CH_2—$, oligonucleosides with heteroatom internucleoside linkage, phosphinates, phosphoramidates, phosphorodithioates, phosphorothioate internucleoside linkages, phosphorothioates, phosphotriesters, PNA, siloxane backbones, sulfamate backbones, sulfide sulfoxide and sulfone backbones, sulfonate and sulfonamide backbones, thionoalkylphosphonates, thionoalkylphosphotriesters, and thionophosphoramidates.

(ii) Sugar Modifications

The modified nucleosides and nucleotides (e.g., building block molecules), which can be incorporated into a polynucleotide (e.g., RNA or mRNA, as described herein), can be modified on the sugar of the ribonucleic acid. For example, the 2' hydroxyl group (OH) can be modified or replaced with a number of different substituents. Exemplary substitutions at the 2'-position include, but are not limited to, H, halo, optionally substituted $C_{1-6}$ alkyl; optionally substituted $C_{1-6}$ alkoxy; optionally substituted $C_{6-10}$ aryloxy; optionally substituted $C_{3-8}$ cycloalkyl; optionally substituted $C_{3-8}$ cycloalkoxy; optionally substituted $C_{6-10}$ aryloxy; optionally substituted $C_{6-10}$ aryl-$C_{1-6}$ alkoxy, optionally substituted $C_{1-12}$ (heterocyclyl)oxy; a sugar (e.g., ribose, pentose, or any described herein); a polyethyleneglycol (PEG), $—O(CH_2CH_2O)_nCH_2CH_2OR$, where R is H or optionally substituted alkyl, and n is an integer from 0 to 20 (e.g., from 0 to 4, from 0 to 8, from 0 to 10, from 0 to 16, from 1 to 4, from 1 to 8, from 1 to 10, from 1 to 16, from 1 to 20, from 2 to 4, from 2 to 8, from 2 to 10, from 2 to 16, from 2 to 20, from 4 to 8, from 4 to 10, from 4 to 16, and from 4 to 20); "locked" nucleic acids (LNA) in which the 2'-hydroxyl is connected by a $C_{1-6}$ alkylene or $C_{1-6}$ heteroalkylene bridge to the 4'-carbon of the same ribose sugar, where exemplary bridges included methylene, propylene, ether, or amino bridges; aminoalkyl, as defined herein; aminoalkoxy, as defined herein; amino as defined herein; and amino acid, as defined herein Generally, RNA includes the sugar group ribose, which is a 5-membered ring having an oxygen. Exemplary, non-limiting modified nucleotides include replacement of the oxygen in ribose (e.g., with S, Se, or alkylene, such as methylene or ethylene); addition of a double bond (e.g., to replace ribose with cyclopentenyl or cyclohexenyl); ring contraction of ribose (e.g., to form a 4-membered ring of cyclobutane or oxetane); ring expansion of ribose (e.g., to form a 6- or 7-membered ring having an additional carbon or heteroatom, such as for anhydrohexitol, altritol, mannitol, cyclohexanyl, cyclohexenyl, and morpholino that also has a phosphoramidate backbone); multicyclic forms (e.g., tricyclo; and "unlocked" forms, such as glycol nucleic acid (GNA) (e.g., R-GNA or S-GNA, where ribose is replaced by glycol units attached to phosphodiester bonds), threose nucleic acid (TNA, where ribose is replace with α-L-threofuranosyl-(3'→2')), and peptide nucleic acid (PNA, where 2-amino-ethyl-glycine linkages replace the ribose and phosphodiester backbone). The sugar group can also contain one or more carbons that possess the opposite stereochemical configuration than that of the corresponding carbon in ribose. Thus, a polynucleotide molecule can include nucleotides containing, e.g., arabinose, as the sugar. Such sugar modifications are taught International Patent Publication Nos. WO2013052523 and WO2014093924, the contents of each of which are incorporated herein by reference in their entireties.

(iii) Combinations of Modifications

The polynucleotides of the invention (e.g., a polynucleotide comprising a nucleotide sequence encoding a GALT polypeptide or a functional fragment or variant thereof) can include a combination of modifications to the sugar, the nucleobase, and/or the internucleoside linkage. These combinations can include any one or more modifications described herein.

Combinations of modified nucleotides can be used to form the polynucleotides of the invention. Unless otherwise noted, the modified nucleotides can be completely substituted for the natural nucleotides of the polynucleotides of the invention. As a non-limiting example, the natural nucleotide uridine can be substituted with a modified nucleoside described herein. In another non-limiting example, the natural nucleotide uridine can be partially substituted or replaced (e.g., about 0%, 1%, 5%, 10%, 15%, 20%, 25%, 30%, 35%, 40%, 45%, 50%, 55%, 60%, 65%, 70%, 75%, 80%, 85%, 90%, 95% or 99%) with at least one of the modified nucleoside disclosed herein. Any combination of base/sugar or linker can be incorporated into the polynucleotides of the invention and such modifications are taught in International Patent Publications WO2013052523 and WO2014093924, and U.S. Publ. Nos. US 20130115272 and US20150307542, the contents of each of which are incorporated herein by reference in its entirety.

11. UNTRANSLATED REGIONS (UTRS)

Untranslated regions (UTRs) are nucleic acid sections of a polynucleotide before a start codon (5' UTR) and after a stop codon (3' UTR) that are not translated. In some embodiments, a polynucleotide (e.g., a ribonucleic acid (RNA), e.g., a messenger RNA (mRNA)) of the invention comprising an open reading frame (ORF) encoding a GALT polypeptide further comprises UTR (e.g., a 5'UTR or functional fragment thereof, a 3'UTR or functional fragment thereof, or a combination thereof).

A UTR can be homologous or heterologous to the coding region in a polynucleotide. In some embodiments, the UTR is homologous to the ORF encoding the GALT polypeptide. In some embodiments, the UTR is heterologous to the ORF encoding the GALT polypeptide. In some embodiments, the polynucleotide comprises two or more 5'UTRs or functional fragments thereof, each of which has the same or different nucleotide sequences. In some embodiments, the polynucleotide comprises two or more 3'UTRs or functional fragments thereof, each of which has the same or different nucleotide sequences.

In some embodiments, the 5'UTR or functional fragment thereof, 3' UTR or functional fragment thereof, or any combination thereof is sequence optimized.

In some embodiments, the 5'UTR or functional fragment thereof, 3' UTR or functional fragment thereof, or any combination thereof comprises at least one chemically modified nucleobase, e.g., 1-methylpseudouridine or 5-methoxyuracil.

UTRs can have features that provide a regulatory role, e.g., increased or decreased stability, localization and/or translation efficiency. A polynucleotide comprising a UTR can be administered to a cell, tissue, or organism, and one or more regulatory features can be measured using routine methods. In some embodiments, a functional fragment of a 5' UTR or 3' UTR comprises one or more regulatory features of a full length 5' or 3' UTR, respectively.

Natural 5'UTRs bear features that play roles in translation initiation. They harbor signatures like Kozak sequences that are commonly known to be involved in the process by which the ribosome initiates translation of many genes. Kozak sequences have the consensus CCR(A/G)CCAUGG, where R is a purine (adenine or guanine) three bases upstream of the start codon (AUG), which is followed by another 'G'. 5'UTRs also have been known to form secondary structures that are involved in elongation factor binding.

By engineering the features typically found in abundantly expressed genes of specific target organs, one can enhance the stability and protein production of a polynucleotide. For example, introduction of 5'UTR of liver-expressed mRNA, such as albumin, serum amyloid A, Apolipoprotein A/B/E, transferrin, alpha fetoprotein, erythropoietin, or Factor VIII, can enhance expression of polynucleotides in hepatic cell lines or liver. Likewise, use of 5'UTR from other tissue-specific mRNA to improve expression in that tissue is possible for muscle (e.g., MyoD, Myosin, Myoglobin, Myogenin, Herculin), for endothelial cells (e.g., Tie-1, CD36), for myeloid cells (e.g., C/EBP, AML1, G-CSF, GM-CSF, CD11b, MSR, Fr-1, i-NOS), for leukocytes (e.g., CD45, CD18), for adipose tissue (e.g., CD36, GLUT4, ACRP30, adiponectin) and for lung epithelial cells (e.g., SP-A/B/C/D).

In some embodiments, UTRs are selected from a family of transcripts whose proteins share a common function, structure, feature or property. For example, an encoded polypeptide can belong to a family of proteins (i.e., that share at least one function, structure, feature, localization, origin, or expression pattern), which are expressed in a particular cell, tissue or at some time during development. The UTRs from any of the genes or mRNA can be swapped for any other UTR of the same or different family of proteins to create a new polynucleotide.

In some embodiments, the 5' UTR and the 3' UTR can be heterologous. In some embodiments, the 5' UTR can be derived from a different species than the 3' UTR. In some embodiments, the 3' UTR can be derived from a different species than the 5' UTR.

Co-owned International Patent Application No. PCT/US2014/021522 (Publ. No. WO/2014/164253, incorporated herein by reference in its entirety) provides a listing of exemplary UTRs that can be utilized in the polynucleotide of the present invention as flanking regions to an ORF.

Exemplary UTRs of the application include, but are not limited to, one or more 5'UTR and/or 3'UTR derived from the nucleic acid sequence of: a globin, such as an α- or β-globin (e.g., a *Xenopus*, mouse, rabbit, or human globin); a strong Kozak translational initiation signal; a CYBA (e.g., human cytochrome b-245 α polypeptide); an albumin (e.g., human albumin7); a HSD17B4 (hydroxysteroid (17-β) dehydrogenase); a virus (e.g., a tobacco etch virus (TEV), a Venezuelan equine encephalitis virus (VEEV), a Dengue virus, a cytomegalovirus (CMV) (e.g., CMV immediate early 1 (IE1)), a hepatitis virus (e.g., hepatitis B virus), a sindbis virus, or a PAV barley yellow dwarf virus); a heat shock protein (e.g., hsp70); a translation initiation factor (e.g., elF4G); a glucose transporter (e.g., hGLUT1 (human glucose transporter 1)); an actin (e.g., human α or β actin); a GAPDH; a tubulin; a histone; a citric acid cycle enzyme; a topoisomerase (e.g., a 5'UTR of a TOP gene lacking the 5' TOP motif (the oligopyrimidine tract)); a ribosomal protein Large 32 (L32); a ribosomal protein (e.g., human or mouse ribosomal protein, such as, for example, rps9); an ATP synthase (e.g., ATP5A1 or the β subunit of mitochondrial $H^+$-ATP synthase); a growth hormone e (e.g., bovine (bGH) or human (hGH)); an elongation factor (e.g., elongation factor 1 α1 (EEF1A1)); a manganese superoxide dismutase (MnSOD); a myocyte enhancer factor 2A (MEF2A); a β-F1-ATPase, a creatine kinase, a myoglobin, a granulocyte-colony stimulating factor (G-CSF); a collagen (e.g., collagen type I, alpha 2 (Col1A2), collagen type I, alpha 1 (Col1A1), collagen type VI, alpha 2 (Col6A2), collagen type VI, alpha 1 (Col6A1)); a ribophorin (e.g., ribophorin I (RPNI)); a low density lipoprotein receptor-related protein (e.g., LRP1); a cardiotrophin-like cytokine factor (e.g., Nnt1); calreticulin (Calr); a procollagen-lysine, 2-oxoglutarate 5-dioxygenase 1 (Plod1); and a nucleobindin (e.g., Nucb1).

In some embodiments, the 5' UTR is selected from the group consisting of a β-globin 5' UTR; a 5'UTR containing a strong Kozak translational initiation signal; a cytochrome b-245 α polypeptide (CYBA) 5' UTR; a hydroxysteroid (17-β) dehydrogenase (HSD17B4) 5' UTR; a Tobacco etch virus (TEV) 5' UTR; a Venezuelen equine encephalitis virus (TEEV) 5' UTR; a 5' proximal open reading frame of rubella virus (RV) RNA encoding nonstructural proteins; a Dengue virus (DEN) 5' UTR; a heat shock protein 70 (Hsp70) 5' UTR; a eIF4G 5' UTR; a GLUT1 5' UTR; functional fragments thereof and any combination thereof.

In some embodiments, the 3' UTR is selected from the group consisting of a β-globin 3' UTR; a CYBA 3' UTR; an albumin 3' UTR; a growth hormone (GH) 3' UTR; a VEEV 3' UTR; a hepatitis B virus (HBV) 3' UTR; α-globin 3'UTR; a DEN 3' UTR; a PAV barley yellow dwarf virus (BYDV-PAV) 3' UTR; an elongation factor 1 α1 (EEF1A1) 3' UTR; a manganese superoxide dismutase (MnSOD) 3' UTR; a β subunit of mitochondrial H(+)-ATP synthase (β-mRNA) 3' UTR; a GLUT1 3' UTR; a MEF2A 3' UTR; a β-F1-ATPase 3' UTR; functional fragments thereof and combinations thereof.

Wild-type UTRs derived from any gene or mRNA can be incorporated into the polynucleotides of the invention. In some embodiments, a UTR can be altered relative to a wild type or native UTR to produce a variant UTR, e.g., by changing the orientation or location of the UTR relative to the ORF; or by inclusion of additional nucleotides, deletion of nucleotides, swapping or transposition of nucleotides. In some embodiments, variants of 5' or 3' UTRs can be utilized, for example, mutants of wild type UTRs, or variants wherein one or more nucleotides are added to or removed from a terminus of the UTR.

Additionally, one or more synthetic UTRs can be used in combination with one or more non-synthetic UTRs. See, e.g., Mandal and Rossi, Nat. Protoc. 2013 8(3):568-82, the contents of which are incorporated herein by reference in their entirety, and sequences available at www.addgene.org/Derrick_Rossi/.

UTRs or portions thereof can be placed in the same orientation as in the transcript from which they were selected or can be altered in orientation or location. Hence, a 5' and/or 3' UTR can be inverted, shortened, lengthened, or combined with one or more other 5' UTRs or 3' UTRs.

In some embodiments, the polynucleotide comprises multiple UTRs, e.g., a double, a triple or a quadruple 5' UTR or 3' UTR. For example, a double UTR comprises two copies of the same UTR either in series or substantially in series. For example, a double beta-globin 3'UTR can be used (see US2010/0129877, the contents of which are incorporated herein by reference in its entirety).

In certain embodiments, the polynucleotides of the invention comprise a 5' UTR and/or a 3' UTR selected from any of the UTRs disclosed herein. In some embodiments, the 5' UTR comprises:

5' UTR-001 (Upstream UTR)
(SEQ ID NO. 35)
(GGGAAAUAAGAGAGAAAAGAAGAGUAAGAAGAAAUAUAAGAGCCACC);

5' UTR-002 (Upstream UTR)
(SEQ ID NO. 36)
(GGGAGAUCAGAGAGAAAAGAAGAGUAAGAAGAAAUAUAAGAGCCACC);

5' UTR-003 (Upstream UTR) (See SEQ ID NO. 37);

5' UTR-004 (Upstream UTR)
(SEQ ID NO. 38)
(GGGAGACAAGCUUGGCAUUCCGGUACUGUUGGUAAAGCCACC);

5' UTR-005 (Upstream UTR)
(SEQ ID NO. 39)
(GGGAGAUCAGAGAGAAAAGAAGAGUAAGAAGAAAUAUAAGAGCCACC);

5' UTR-006 (Upstream UTR) (See SEQ ID NO. 40);

5' UTR-007 (Upstream UTR)
(SEQ ID NO. 41)
(GGGAGACAAGCUUGGCAUUCCGGUACUGUUGGUAAAGCCACC);

5' UTR-008 (Upstream UTR)
(SEQ ID NO. 42)
(GGGAAUUAACAGAGAAAAGAAGAGUAAGAAGAAAUAUAAGAGCCACC);

5' UTR-009 (Upstream UTR)
(SEQ ID NO. 43)
(GGGAAAUUAGACAGAAAAGAAGAGUAAGAAGAAAUAUAAGAGCCACC);

5' UTR-010, Upstream
(SEQ ID NO. 44)
(GGGAAAUAAGAGAGUAAAGAACAGUAAGAAGAAAUAUAAGAGCCACC);

5' UTR-011 (Upstream UTR)
(SEQ ID NO. 45)
(GGGAAAAAAGAGAGAAAAGAAGACUAAGAAGAAAUAUAAGAGCCACC);

-continued

5' UTR-012 (Upstream UTR)
(SEQ ID NO. 46)
(GGGAAAUAAGAGAGAAAAGAAGAGUAAGAAGAUAUAUAAGAGCCACC);

5' UTR-013 (Upstream UTR)
(SEQ ID NO. 47)
(GGGAAAUAAGAGACAAAACAAGAGUAAGAAGAAAUAUAAGAGCCACC);

5' UTR-014 (Upstream UTR)
(SEQ ID NO. 48)
(GGGAAAUUAGAGAGUAAAGAACAGUAAGUAGAAUUAAAAGAGCCACC);

5' UTR-15 (Upstream UTR)
(SEQ ID NO. 49)
(GGGAAAUAAGAGAGAAUAGAAGAGUAAGAAGAAAUAUAAGAGCCACC);

5' UTR-016 (Upstream UTR)
(SEQ ID NO. 50)
(GGGAAAUAAGAGAGAAAAGAAGAGUAAGAAGAAAAUUAAGAGCCACC);

5' UTR-017 (Upstream UTR); or
(SEQ ID NO. 51)
(GGGAAAUAAGAGAGAAAAGAAGAGUAAGAAGAAAUUUAAGAGCCACC);

5' UTR-018 (Upstream UTR) 5' UTR
(SEQ ID NO. 52)
(UCAAGCUUUUGGACCCUCGUACAGAAGCUAAUACGACUCACUAUAGGGA
AAUAAGAGAGAAAAGAAGAGUAAGAAGAAAUAUAAGAGCCACC).

In some embodiments, the 3' UTR comprises:

142-3p 3' UTR (UTR including miR142-3p binding site)
(SEQ ID NO. 53)
(UGAUAAUAGUCCAUAAAGUAGGAAACACUACAGCUGGAGCCUCGGUGGC
CAUGCUUCUUGCCCCUUGGGCCUCCCCCCAGCCCCUCCUCCCCUUCCUGC
ACCCGUACCCCCGUGGUCUUUGAAUAAAGUCUGAGUGGGCGGC);

142-3p 3' UTR (UTR including miR142-3p binding site)
(SEQ ID NO. 54)
(UGAUAAUAGGCUGGAGCCUCGGUGGCUCCAUAAAGUAGGAAACACUACA
CAUGCUUCUUGCCCCUUGGGCCUCCCCCCAGCCCCUCCUCCCCUUCCUGC
ACCCGUACCCCCGUGGUCUUUGAAUAAAGUCUGAGUGGGCGGC);
or 142-3p 3' UTR (UTR including miR142-3p binding site)
(SEQ ID NO. 55)
(UGAUAAUAGGCUGGAGCCUCGGUGGCCAUGCUUCUUGCCCCUUCCAUAA
AGUAGGAAACACUACAUGGGCCUCCCCCCAGCCCCUCCUCCCCUUCCUGC
ACCCGUACCCCCGUGGUCUUUGAAUAAAGUCUGAGUGGGCGGC);

142-3p 3' UTR (UTR including miR142-3p binding site)
(SEQ ID NO. 56)
(UGAUAAUAGGCUGGAGCCUCGGUGGCCAUGCUUCUUGCCCCUUGGGCCU
CCCCCCAGUCCAUAAAGUAGGAAACACUACACCCCUCCUCCCCUUCCUGC
ACCCGUACCCCCGUGGUCUUUGAAUAAAGUCUGAGUGGGCGGC);

142-3p 3' UTR (UTR including miR142-3p binding site)
(SEQ ID NO. 57)
(UGAUAAUAGGCUGGAGCCUCGGUGGCCAUGCUUCUUGCCCCUUGGGCCU
CCCCCCAGCCCCUCCUCCCCUUCUCCAUAAAGUAGGAAACACUACACUGC
ACCCGUACCCCCGUGGUCUUUGAAUAAAGUCUGAGUGGGCGGC);

-continued 142-3p 3' UTR (UTR including miR142-3p binding site)

(SEQ ID NO. 58)

(UGAUAAUAGGCUGGAGCCUCGGUGGCCAUGCUUCUUGCCCCUUGGGCCU

CCCCCCAGCCCCUCCUCCCCUUCCUGCACCCGUACCCCCUCCAUAAAGUA

GGAAACACUACAGUGGUCUUUGAAUAAAGUCUGAGUGGGCGGC).

142-3p 3' UTR (UTR including miR142-3p binding site)

(SEQ ID NO. 59)

(UGAUAAUAGGCUGGAGCCUCGGUGGCCAUGCUUCUUGCCCCUUGGGCCU

CCCCCCAGCCCCUCCUCCCCUUCCUGCACCCGUACCCCCGUGGUCUUUGA

AUAAAGUUCCAUAAAGUAGGAAACACUACACUGAGUGGGCGGC);

(See SEQ ID NO. 60)

3' UTR-001 (Creatine Kinase UTR);

(See SEQ ID NO. 61)

3' UTR-002 (Myoglobin UTR);

(See SEQ ID NO. 62)

3' UTR-003 (a-actin UTR);

(See SEQ ID NO. 63)

3' UTR-004 (Albumin UTR);

(See SEQ ID NO. 64)

3' UTR-005 (a-globin UTR);

(See SEQ ID NO. 65)

3' UTR-006 (G-CSF UTR);

(See SEQ ID NO. 66)

3' UTR-007 (Col1a2; collagen, type I, alpha 2 UTR);

(See SEQ ID NO. 67)

3' UTR-008 (Col6a2; collagen, type VI, alpha 2 UTR);

(See SEQ ID NO. 68)

3' UTR-009 (RPN1; ribophorin I UTR);

(See SEQ ID NO. 69)

3' UTR-010 (LRP1; low density lipoprotein receptor-related protein 1 UTR);

(See SEQ ID NO. 70)

3' UTR-011 (Nnt1; cardiotrophin-like cytokine factor 1 UTR);

(See SEQ ID NO. 71)

3' UTR-012 (Col6a1; collagen, type VI, alpha 1 UTR);

(See SEQ ID NO. 72)

3' UTR-013 (Calr; calreticulin UTR);

(See SEQ ID NO. 73)

3' UTR-014 (Col1a1; collagen, type I, alpha 1 UTR);

(See SEQ ID NO. 74)

3' UTR-015 (Plod1; procollagen-lysine, 2-oxoglutarate 5-dioxygenase 1 UTR);

(See SEQ ID NO. 75)

3' UTR-016 (Nucb1; nucleobindin 1 UTR);

(See SEQ ID NO. 76)

3' UTR-017 (α-globin);

(See SEQ ID NO. 77)

3' UTR-018;

-continued

3' UTR (miR142 and miR126 binding sites variant 1)

(SEQ ID NO. 98)

(UGAUAAUAGUCCAUAAAGUAGGAAACACUACAGCUGGAGCCUCGGUGGC

CAUGCUUCUUGCCCCUUGGGCCUCCCCCCAGCCCCUCCUCCCCUUCCUGC

ACCCGUACCCCCCGCAUUAUUACUCACGGUACGAGUGGUCUUUGAAUAAA

GUCUGAGUGGGCGGC)

3' UTR (miR142 and miR126 binding sites variant 2)

(SEQ ID NO. 163)

(UGAUAAUAGUCCAUAAAGUAGGAAACACUACAGCUGGAGCCUCGGUGGC

CUAGCUUCUUGCCCCUUGGGCCUCCCCCCAGCCCCUCCUCCCCUUCCUGC

ACCCGUACCCCCCGCAUUAUUACUCACGGUACGAGUGGUCUUUGAAUAAA

GUCUGAGUGGGCGGC);

or

3'UTR (miR142-3p binding site variant 3)

(SEQ ID NO. 164)

UGAUAAUAGGCUGGAGCCUCGGUGGCCUAGCUUCUUGCCCCUUGGGCCUC

CCCCCAGCCCCUCCUCCCCUUCCUGCACCCGUACCCCCUCCAUAAAGUAG

GAAACACUACAGUGGUCUUUGAAUAAAGUCUGAGUGGGCGGC.

In certain embodiments, the 5' UTR and/or 3' UTR sequence of the invention comprises a nucleotide sequence at least about 60%, at least about 70%, at least about 80%, at least about 90%, at least about 95%, at least about 96%, at least about 97%, at least about 98%, at least about 99%, or about 100% identical to a sequence selected from the group consisting of 5' UTR sequences comprising any of SEQ ID NOs: 35-52 or 109-111 and/or 3' UTR sequences comprises any of SEQ ID NOs: 53 to 77, 79, 97, 98, 101 to 108, 112, and 163 to 173, and any combination thereof.

The polynucleotides of the invention can comprise combinations of features. For example, the ORF can be flanked by a 5'UTR that comprises a strong Kozak translational initiation signal and/or a 3'UTR comprising an oligo(dT) sequence for templated addition of a poly-A tail. A 5'UTR can comprise a first polynucleotide fragment and a second polynucleotide fragment from the same and/or different UTRs (see, e.g., US2010/0293625, herein incorporated by reference in its entirety).

Other non-UTR sequences can be used as regions or subregions within the polynucleotides of the invention. For example, introns or portions of intron sequences can be incorporated into the polynucleotides of the invention. Incorporation of intronic sequences can increase protein production as well as polynucleotide expression levels. In some embodiments, the polynucleotide of the invention comprises an internal ribosome entry site (IRES) instead of or in addition to a UTR (see, e.g., Yakubov et al., Biochem. Biophys. Res. Commun. 2010 394(1):189-193, the contents of which are incorporated herein by reference in their entirety). In some embodiments, the polynucleotide comprises an IRES instead of a 5' UTR sequence. In some embodiments, the polynucleotide comprises an ORF and a viral capsid sequence. In some embodiments, the polynucleotide comprises a synthetic 5' UTR in combination with a non-synthetic 3' UTR.

In some embodiments, the UTR can also include at least one translation enhancer polynucleotide, translation enhancer element, or translational enhancer elements (collectively, "TEE," which refers to nucleic acid sequences that increase the amount of polypeptide or protein produced from a polynucleotide. As a non-limiting example, the TEE can include those described in US2009/0226470, incorporated herein by reference in its entirety, and others known in the art. As a non-limiting example, the TEE can be located between the transcription promoter and the start codon. In some embodiments, the 5' UTR comprises a TEE.

In one aspect, a TEE is a conserved element in a UTR that can promote translational activity of a nucleic acid such as, but not limited to, cap-dependent or cap-independent translation.

In one non-limiting example, the TEE comprises the TEE sequence in the 5'-leader of the Gtx homeodomain protein. See Chappell et al., PNAS 2004 101:9590-9594, incorporated herein by reference in its entirety.

In some embodiments, the polynucleotide of the invention comprises one or multiple copies of a TEE. The TEE in a translational enhancer polynucleotide can be organized in one or more sequence segments. A sequence segment can harbor one or more of the TEEs provided herein, with each TEE being present in one or more copies. When multiple sequence segments are present in a translational enhancer polynucleotide, they can be homogenous or heterogeneous. Thus, the multiple sequence segments in a translational enhancer polynucleotide can harbor identical or different types of the TEE provided herein, identical or different number of copies of each of the TEE, and/or identical or different organization of the TEE within each sequence segment. In one embodiment, the polynucleotide of the invention comprises a translational enhancer polynucleotide sequence. Non-limiting examples of TEE sequences are described in U.S. Publication 2014/0200261, the contents of which are incorporated herein by reference in their entirety.

12. MICRORNA (MIRNA) BINDING SITES

Polynucleotides of the invention can include regulatory elements, for example, microRNA (miRNA) binding sites, transcription factor binding sites, structured mRNA sequences and/or motifs, artificial binding sites engineered to act as pseudo-receptors for endogenous nucleic acid binding molecules, and combinations thereof. In some embodiments, polynucleotides including such regulatory elements are referred to as including "sensor sequences". Non-limiting examples of sensor sequences are described in U.S. Publication 2014/0200261, the contents of which are incorporated herein by reference in their entirety.

In some embodiments, a polynucleotide (e.g., a ribonucleic acid (RNA), e.g., a messenger RNA (mRNA)) of the invention comprises an open reading frame (ORF) encoding a polypeptide of interest and further comprises one or more miRNA binding site(s). Inclusion or incorporation of miRNA binding site(s) provides for regulation of polynucleotides of the invention, and in turn, of the polypeptides encoded therefrom, based on tissue-specific and/or cell-type specific expression of naturally-occurring miRNAs.

The present invention also provides pharmaceutical compositions and formulations that comprise any of the polynucleotides described above. In some embodiments, the composition or formulation further comprises a delivery agent.

In some embodiments, the composition or formulation can contain a polynucleotide comprising a sequence optimized nucleic acid sequence disclosed herein which encodes a polypeptide. In some embodiments, the composition or formulation can contain a polynucleotide (e.g., a RNA, e.g., an mRNA) comprising a polynucleotide (e.g., an ORF) having significant sequence identity to a sequence optimized nucleic acid sequence disclosed herein which encodes a polypeptide. In some embodiments, the polynucleotide further comprises a miRNA binding site, e.g., a miRNA binding site that binds A miRNA, e.g., a natural-occurring miRNA, is a 19-25 nucleotide long noncoding RNA that binds to a polynucleotide and down-regulates gene expression either by reducing stability or by inhibiting translation of the polynucleotide. A miRNA sequence comprises a "seed" region, i.e., a sequence in the region of positions 2-8 of the mature miRNA. A miRNA seed can comprise positions 2-8 or 2-7 of the mature miRNA. In some embodiments, a miRNA seed can comprise 7 nucleotides (e.g., nucleotides 2-8 of the mature miRNA), wherein the seed-complementary site in the corresponding miRNA binding site is flanked by an adenosine (A) opposed to miRNA position 1. In some embodiments, a miRNA seed can comprise 6 nucleotides (e.g., nucleotides 2-7 of the mature miRNA), wherein the seed-complementary site in the corresponding miRNA binding site is flanked by an adenosine (A) opposed to miRNA position 1. See, for example, Grimson A, Farh K K, Johnston W K, Garrett-Engele P, Lim L P, Bartel D P; Mol Cell. 2007 Jul. 6; 27(1):91-105. miRNA profiling of the target cells or tissues can be conducted to determine the presence or absence of miRNA in the cells or tissues. In some embodiments, a polynucleotide (e.g., a ribonucleic acid (RNA), e.g., a messenger RNA (mRNA)) of the invention comprises one or more microRNA binding sites, microRNA target sequences, microRNA complementary sequences, or microRNA seed complementary sequences. Such sequences can correspond to, e.g., have complementarity to, any known microRNA such as those taught in US Publication US2005/0261218 and US Publication US2005/0059005, the contents of each of which are incorporated herein by reference in their entirety.

microRNAs derive enzymatically from regions of RNA transcripts that fold back on themselves to form short hairpin structures often termed a pre-miRNA (precursor-miRNA). A pre-miRNA typically has a two-nucleotide overhang at its 3' end, and has 3' hydroxyl and 5' phosphate groups. This precursor-mRNA is processed in the nucleus and subsequently transported to the cytoplasm where it is further processed by DICER (a RNase III enzyme), to form a mature microRNA of approximately 22 nucleotides. The mature microRNA is then incorporated into a ribonuclear particle to form the RNA-induced silencing complex, RISC, which mediates gene silencing. Art-recognized nomenclature for mature miRNAs typically designates the arm of the pre-miRNA from which the mature miRNA derives; "5p" means the microRNA is from the 5 prime arm of the pre-miRNA hairpin and "3p" means the microRNA is from the 3 prime end of the pre-miRNA hairpin. A miR referred to by number herein can refer to either of the two mature microRNAs originating from opposite arms of the same pre-miRNA (e.g., either the 3p or 5p microRNA). All miRs referred to herein are intended to include both the 3p and 5p arms/sequences, unless particularly specified by the 3p or 5p designation.

As used herein, the term "microRNA (miRNA or miR) binding site" refers to a sequence within a polynucleotide, e.g., within a DNA or within an RNA transcript, including in the 5'UTR and/or 3'UTR, that has sufficient complementarity to all or a region of a miRNA to interact with, associate with or bind to the miRNA. In some embodiments, a polynucleotide of the invention comprising an ORF encoding a polypeptide of interest and further comprises one or more miRNA binding site(s). In exemplary embodiments, a 5' UTR and/or 3' UTR of the polynucleotide (e.g., a ribonucleic acid (RNA), e.g., a messenger RNA (mRNA)) comprises the one or more miRNA binding site(s).

A miRNA binding site having sufficient complementarity to a miRNA refers to a degree of complementarity sufficient to facilitate miRNA-mediated regulation of a polynucleotide, e.g., miRNA-mediated translational repression or degradation of the polynucleotide. In exemplary aspects of the invention, a miRNA binding site having sufficient complementarity to the miRNA refers to a degree of complementarity sufficient to facilitate miRNA-mediated degradation of the polynucleotide, e.g., miRNA-guided RNA-induced silencing complex (RISC)-mediated cleavage of mRNA. The miRNA binding site can have complementarity to, for example, a 19-25 nucleotide long miRNA sequence, to a 19-23 nucleotide long miRNA sequence, or to a 22 nucleotide long miRNA sequence. A miRNA binding site can be complementary to only a portion of a miRNA, e.g., to a portion less than 1, 2, 3, or 4 nucleotides of the full length of a naturally-occurring miRNA sequence, or to a portion less than 1, 2, 3, or 4 nucleotides shorter than a naturally-occurring miRNA sequence. Full or complete complementarity (e.g., full complementarity or complete complementarity over all or a significant portion of the length of a naturally-occurring miRNA) is preferred when the desired regulation is mRNA degradation.

In some embodiments, a miRNA binding site includes a sequence that has complementarity (e.g., partial or complete complementarity) with an miRNA seed sequence. In some embodiments, the miRNA binding site includes a sequence that has complete complementarity with a miRNA seed sequence. In some embodiments, a miRNA binding site includes a sequence that has complementarity (e.g., partial or complete complementarity) with an miRNA sequence. In some embodiments, the miRNA binding site includes a sequence that has complete complementarity with a miRNA sequence. In some embodiments, a miRNA binding site has complete complementarity with a miRNA sequence but for 1, 2, or 3 nucleotide substitutions, terminal additions, and/or truncations.

In some embodiments, the miRNA binding site is the same length as the corresponding miRNA. In other embodiments, the miRNA binding site is one, two, three, four, five, six, seven, eight, nine, ten, eleven or twelve nucleotide(s) shorter than the corresponding miRNA at the 5' terminus, the 3' terminus, or both. In still other embodiments, the microRNA binding site is two nucleotides shorter than the corresponding microRNA at the 5' terminus, the 3' terminus, or both. The miRNA binding sites that are shorter than the corresponding miRNAs are still capable of degrading the mRNA incorporating one or more of the miRNA binding sites or preventing the mRNA from translation.

In some embodiments, the miRNA binding site binds the corresponding mature miRNA that is part of an active RISC containing Dicer. In another embodiment, binding of the miRNA binding site to the corresponding miRNA in RISC degrades the mRNA containing the miRNA binding site or prevents the mRNA from being translated. In some embodiments, the miRNA binding site has sufficient complementarity to miRNA so that a RISC complex comprising the miRNA cleaves the polynucleotide comprising the miRNA binding site. In other embodiments, the miRNA binding site has imperfect complementarity so that a RISC complex comprising the miRNA induces instability in the polynucleotide comprising the miRNA binding site. In another embodiment, the miRNA binding site has imperfect complementarity so that a RISC complex comprising the miRNA represses transcription of the polynucleotide comprising the miRNA binding site.

In some embodiments, the miRNA binding site has one, two, three, four, five, six, seven, eight, nine, ten, eleven or twelve mismatch(es) from the corresponding miRNA.

In some embodiments, the miRNA binding site has at least about ten, at least about eleven, at least about twelve, at least about thirteen, at least about fourteen, at least about fifteen, at least about sixteen, at least about seventeen, at least about eighteen, at least about nineteen, at least about twenty, or at least about twenty-one contiguous nucleotides complementary to at least about ten, at least about eleven, at least about twelve, at least about thirteen, at least about fourteen, at least about fifteen, at least about sixteen, at least about seventeen, at least about eighteen, at least about nineteen, at least about twenty, or at least about twenty-one, respectively, contiguous nucleotides of the corresponding miRNA.

By engineering one or more miRNA binding sites into a polynucleotide of the invention, the polynucleotide can be targeted for degradation or reduced translation, provided the miRNA in question is available. This can reduce off-target effects upon delivery of the polynucleotide. For example, if a polynucleotide of the invention is not intended to be delivered to a tissue or cell but ends up is said tissue or cell, then a miRNA abundant in the tissue or cell can inhibit the expression of the gene of interest if one or multiple binding sites of the miRNA are engineered into the 5'UTR and/or 3'UTR of the polynucleotide. Thus, in some embodiments, incorporation of one or more miRNA binding sites into an mRNA of the disclosure may reduce the hazard of off-target effects upon nucleic acid molecule delivery and/or enable tissue-specific regulation of expression of a polypeptide encoded by the mRNA. In yet other embodiments, incorporation of one or more miRNA binding sites into an mRNA of the disclosure can modulate immune responses upon nucleic acid delivery in vivo. In further embodiments, incorporation of one or more miRNA binding sites into an mRNA of the disclosure can modulate accelerated blood clearance (ABC) of lipid-comprising compounds and compositions described herein.

Conversely, miRNA binding sites can be removed from polynucleotide sequences in which they naturally occur in order to increase protein expression in specific tissues. For example, a binding site for a specific miRNA can be removed from a polynucleotide to improve protein expression in tissues or cells containing the miRNA.

Regulation of expression in multiple tissues can be accomplished through introduction or removal of one or more miRNA binding sites, e.g., one or more distinct miRNA binding sites. The decision whether to remove or insert a miRNA binding site can be made based on miRNA expression patterns and/or their profilings in tissues and/or cells in development and/or disease. Identification of miRNAs, miRNA binding sites, and their expression patterns and role in biology have been reported (e.g., Bonauer et al., Curr Drug Targets 2010 11:943-949; Anand and Cheresh Curr Opin Hematol 2011 18:171-176; Contreras and Rao Leukemia 2012 26:404-413 (2011 Dec. 20. doi: 10.1038/leu.2011.356); Bartel Cell 2009 136:215-233; Landgraf et al, Cell, 2007 129:1401-1414; Gentner and Naldini, Tissue Antigens. 2012 80:393-403 and all references therein; each of which is incorporated herein by reference in its entirety).

miRNAs and miRNA binding sites can correspond to any known sequence, including non-limiting examples described in U.S. Publication Nos. 2014/0200261, 2005/

0261218, and 2005/0059005, each of which are incorporated herein by reference in their entirety.

Examples of tissues where miRNA are known to regulate mRNA, and thereby protein expression, include, but are not limited to, liver (miR-122), muscle (miR-133, miR-206, miR-208), endothelial cells (miR-17-92, miR-126), myeloid cells (miR-142-3p, miR-142-5p, miR-16, miR-21, miR-223, miR-24, miR-27), adipose tissue (let-7, miR-30c), heart (miR-1d, miR-149), kidney (miR-192, miR-194, miR-204), and lung epithelial cells (let-7, miR-133, miR-126).

Specifically, miRNAs are known to be differentially expressed in immune cells (also called hematopoietic cells), such as antigen presenting cells (APCs) (e.g., dendritic cells and macrophages), macrophages, monocytes, B lymphocytes, T lymphocytes, granulocytes, natural killer cells, etc. Immune cell specific miRNAs are involved in immunogenicity, autoimmunity, the immune-response to infection, inflammation, as well as unwanted immune response after gene therapy and tissue/organ transplantation. Immune cells specific miRNAs also regulate many aspects of development, proliferation, differentiation and apoptosis of hematopoietic cells (immune cells). For example, miR-142 and miR-146 are exclusively expressed in immune cells, particularly abundant in myeloid dendritic cells. It has been demonstrated that the immune response to a polynucleotide can be shut-off by adding miR-142 binding sites to the 3'-UTR of the polynucleotide, enabling more stable gene transfer in tissues and cells. miR-142 efficiently degrades exogenous polynucleotides in antigen presenting cells and suppresses cytotoxic elimination of transduced cells (e.g., Annoni A et al., blood, 2009, 114, 5152-5161; Brown B D, et al., Nat med. 2006, 12(5), 585-591; Brown B D, et al., blood, 2007, 110(13): 4144-4152, each of which is incorporated herein by reference in its entirety).

An antigen-mediated immune response can refer to an immune response triggered by foreign antigens, which, when entering an organism, are processed by the antigen presenting cells and displayed on the surface of the antigen presenting cells. T cells can recognize the presented antigen and induce a cytotoxic elimination of cells that express the antigen.

Introducing a miR-142 binding site into the 5' UTR and/or 3'UTR of a polynucleotide of the invention can selectively repress gene expression in antigen presenting cells through miR-142 mediated degradation, limiting antigen presentation in antigen presenting cells (e.g., dendritic cells) and thereby preventing antigen-mediated immune response after the delivery of the polynucleotide. The polynucleotide is then stably expressed in target tissues or cells without triggering cytotoxic elimination.

In one embodiment, binding sites for miRNAs that are known to be expressed in immune cells, in particular, antigen presenting cells, can be engineered into a polynucleotide of the invention to suppress the expression of the polynucleotide in antigen presenting cells through miRNA mediated RNA degradation, subduing the antigen-mediated immune response. Expression of the polynucleotide is maintained in non-immune cells where the immune cell specific miRNAs are not expressed. For example, in some embodiments, to prevent an immunogenic reaction against a liver specific protein, any miR-122 binding site can be removed and a miR-142 (and/or mirR-146) binding site can be engineered into the 5' UTR and/or 3' UTR of a polynucleotide of the invention.

To further drive the selective degradation and suppression in APCs and macrophage, a polynucleotide of the invention can include a further negative regulatory element in the 5' UTR and/or 3' UTR, either alone or in combination with miR-142 and/or miR-146 binding sites. As a non-limiting example, the further negative regulatory element is a Constitutive Decay Element (CDE).

Immune cell specific miRNAs include, but are not limited to, hsa-let-7a-2-3p, hsa-let-7a-3p, hsa-7a-5p, hsa-let-7c, hsa-let-7e-3p, hsa-let-7e-5p, hsa-let-7g-3p, hsa-let-7g-5p, hsa-let-7i-3p, hsa-let-7i-5p, miR-10a-3p, miR-10a-5p, miR-1184, hsa-let-7f-1-3p, hsa-let-7f-2-5p, hsa-let-7f-5p, miR-125b-1-3p, miR-125b-2-3p, miR-125b-5p, miR-1279, miR-130a-3p, miR-130a-5p, miR-132-3p, miR-132-5p, miR-142-3p, miR-142-5p, miR-143-3p, miR-143-5p, miR-146a-3p, miR-146a-5p, miR-146b-3p, miR-146b-5p, miR-147a, miR-147b, miR-148a-5p, miR-148a-3p, miR-150-3p, miR-150-5p, miR-151b, miR-155-3p, miR-155-5p, miR-15a-3p, miR-15a-5p, miR-15b-5p, miR-15b-3p, miR-16-1-3p, miR-16-2-3p, miR-16-5p, miR-17-5p, miR-181a-3p, miR-181a-5p, miR-181a-2-3p, miR-182-3p, miR-182-5p, miR-197-3p, miR-197-5p, miR-21-5p, miR-21-3p, miR-214-3p, miR-214-5p, miR-223-3p, miR-223-5p, miR-221-3p, miR-221-5p, miR-23b-3p, miR-23b-5p, miR-24-1-5p, miR-24-2-5p, miR-24-3p, miR-26a-1-3p, miR-26a-2-3p, miR-26a-5p, miR-26b-3p, miR-26b-5p, miR-27a-3p, miR-27a-5p, miR-27b-3p, miR-27b-5p, miR-28-3p, miR-28-5p, miR-2909, miR-29a-3p, miR-29a-5p, miR-29b-1-5p, miR-29b-2-5p, miR-29c-3p, miR-29c-5p, miR-30e-3p, miR-30e-5p, miR-331-5p, miR-339-3p, miR-339-5p, miR-345-3p, miR-345-5p, miR-346, miR-34a-3p, miR-34a-5p, miR-363-3p, miR-363-5p, miR-372, miR-377-3p, miR-377-5p, miR-493-3p, miR-493-5p, miR-542, miR-548b-5p, miR548c-5p, miR-548i, miR-548j, miR-548n, miR-574-3p, miR-598, miR-718, miR-935, miR-99a-3p, miR-99a-5p, miR-99b-3p, and miR-99b-5p. Furthermore, novel miRNAs can be identified in immune cell through micro-array hybridization and microtome analysis (e.g., Jima D D et al, Blood, 2010, 116:e118-e127; Vaz C et al., BMC Genomics, 2010, 11,288, the content of each of which is incorporated herein by reference in its entirety.)

miRNAs that are known to be expressed in the liver include, but are not limited to, miR-107, miR-122-3p, miR-122-5p, miR-1228-3p, miR-1228-5p, miR-1249, miR-129-5p, miR-1303, miR-151a-3p, miR-151a-5p, miR-152, miR-194-3p, miR-194-5p, miR-199a-3p, miR-199a-5p, miR-199b-3p, miR-199b-5p, miR-296-5p, miR-557, miR-581, miR-939-3p, and miR-939-5p. MiRNA binding sites from any liver specific miRNA can be introduced to or removed from a polynucleotide of the invention to regulate expression of the polynucleotide in the liver. Liver specific miRNA binding sites can be engineered alone or further in combination with immune cell (e.g., APC) miRNA binding sites in a polynucleotide of the invention.

miRNAs that are known to be expressed in the lung include, but are not limited to, let-7a-2-3p, let-7a-3p, let-7a-5p, miR-126-3p, miR-126-5p, miR-127-3p, miR-127-5p, miR-130a-3p, miR-130a-5p, miR-130b-3p, miR-130b-5p, miR-133a, miR-133b, miR-134, miR-18a-3p, miR-18a-5p, miR-18b-3p, miR-18b-5p, miR-24-1-5p, miR-24-2-5p, miR-24-3p, miR-296-3p, miR-296-5p, miR-32-3p, miR-337-3p, miR-337-5p, miR-381-3p, and miR-381-5p. miRNA binding sites from any lung specific miRNA can be introduced to or removed from a polynucleotide of the invention to regulate expression of the polynucleotide in the lung. Lung specific miRNA binding sites can be engineered alone or further in combination with immune cell (e.g., APC) miRNA binding sites in a polynucleotide of the invention.

miRNAs that are known to be expressed in the heart include, but are not limited to, miR-1, miR-133a, miR-133b, miR-149-3p, miR-149-5p, miR-186-3p, miR-186-5p, miR-208a, miR-208b, miR-210, miR-296-3p, miR-320, miR-451a, miR-451b, miR-499a-3p, miR-499a-5p, miR-499b-3p, miR-499b-5p, miR-744-3p, miR-744-5p, miR-92b-3p, and miR-92b-5p. mMiRNA binding sites from any heart specific microRNA can be introduced to or removed from a polynucleotide of the invention to regulate expression of the polynucleotide in the heart. Heart specific miRNA binding sites can be engineered alone or further in combination with immune cell (e.g., APC) miRNA binding sites in a polynucleotide of the invention.

miRNAs that are known to be expressed in the nervous system include, but are not limited to, miR-124-5p, miR-125a-3p, miR-125a-5p, miR-125b-1-3p, miR-125b-2-3p, miR-125b-5p, miR-1271-3p, miR-1271-5p, miR-128, miR-132-5p, miR-135a-3p, miR-135a-5p, miR-135b-3p, miR-135b-5p, miR-137, miR-139-5p, miR-139-3p, miR-149-3p, miR-149-5p, miR-153, miR-181c-3p, miR-181c-5p, miR-183-3p, miR-183-5p, miR-190a, miR-190b, miR-212-3p, miR-212-5p, miR-219-1-3p, miR-219-2-3p, miR-23a-3p, miR-23a-5p, miR-30a-5p, miR-30b-3p, miR-30b-5p, miR-30c-1-3p, miR-30c-2-3p, miR-30c-5p, miR-30d-3p, miR-30d-5p, miR-329, miR-342-3p, miR-3665, miR-3666, miR-380-3p, miR-380-5p, miR-383, miR-410, miR-425-3p, miR-425-5p, miR-454-3p, miR-454-5p, miR-483, miR-510, miR-516a-3p, miR-548b-5p, miR-548c-5p, miR-571, miR-7-1-3p, miR-7-2-3p, miR-7-5p, miR-802, miR-922, miR-9-3p, and miR-9-5p. miRNAs enriched in the nervous system further include those specifically expressed in neurons, including, but not limited to, miR-132-3p, miR-132-3p, miR-148b-3p, miR-148b-5p, miR-151a-3p, miR-151a-5p, miR-212-3p, miR-212-5p, miR-320b, miR-320e, miR-323a-3p, miR-323a-5p, miR-324-5p, miR-325, miR-326, miR-328, miR-922 and those specifically expressed in glial cells, including, but not limited to, miR-1250, miR-219-1-3p, miR-219-2-3p, miR-219-5p, miR-23a-3p, miR-23a-5p, miR-3065-3p, miR-3065-5p, miR-30e-3p, miR-30e-5p, miR-32-5p, miR-338-5p, and miR-657. miRNA binding sites from any CNS specific miRNA can be introduced to or removed from a polynucleotide of the invention to regulate expression of the polynucleotide in the nervous system. Nervous system specific miRNA binding sites can be engineered alone or further in combination with immune cell (e.g., APC) miRNA binding sites in a polynucleotide of the invention.

miRNAs that are known to be expressed in the pancreas include, but are not limited to, miR-105-3p, miR-105-5p, miR-184, miR-195-3p, miR-195-5p, miR-196a-3p, miR-196a-5p, miR-214-3p, miR-214-5p, miR-216a-3p, miR-216a-5p, miR-30a-3p, miR-33a-3p, miR-33a-5p, miR-375, miR-7-1-3p, miR-7-2-3p, miR-493-3p, miR-493-5p, and miR-944. MiRNA binding sites from any pancreas specific miRNA can be introduced to or removed from a polynucleotide of the invention to regulate expression of the polynucleotide in the pancreas. Pancreas specific miRNA binding sites can be engineered alone or further in combination with immune cell (e.g. APC) miRNA binding sites in a polynucleotide of the invention.

miRNAs that are known to be expressed in the kidney include, but are not limited to, miR-122-3p, miR-145-5p, miR-17-5p, miR-192-3p, miR-192-5p, miR-194-3p, miR-194-5p, miR-20a-3p, miR-20a-5p, miR-204-3p, miR-204-5p, miR-210, miR-216a-3p, miR-216a-5p, miR-296-3p, miR-30a-3p, miR-30a-5p, miR-30b-3p, miR-30b-5p, miR-30c-1-3p, miR-30c-2-3p, miR30c-5p, miR-324-3p, miR-335-3p, miR-335-5p, miR-363-3p, miR-363-5p, and miR-562. miRNA binding sites from any kidney specific miRNA can be introduced to or removed from a polynucleotide of the invention to regulate expression of the polynucleotide in the kidney. Kidney specific miRNA binding sites can be engineered alone or further in combination with immune cell (e.g., APC) miRNA binding sites in a polynucleotide of the invention.

miRNAs that are known to be expressed in the muscle include, but are not limited to, let-7g-3p, let-7g-5p, miR-1, miR-1286, miR-133a, miR-133b, miR-140-3p, miR-143-3p, miR-143-5p, miR-145-3p, miR-145-5p, miR-188-3p, miR-188-5p, miR-206, miR-208a, miR-208b, miR-25-3p, and miR-25-5p. MiRNA binding sites from any muscle specific miRNA can be introduced to or removed from a polynucleotide of the invention to regulate expression of the polynucleotide in the muscle. Muscle specific miRNA binding sites can be engineered alone or further in combination with immune cell (e.g., APC) miRNA binding sites in a polynucleotide of the invention.

miRNAs are also differentially expressed in different types of cells, such as, but not limited to, endothelial cells, epithelial cells, and adipocytes.

miRNAs that are known to be expressed in endothelial cells include, but are not limited to, let-7b-3p, let-7b-5p, miR-100-3p, miR-100-5p, miR-101-3p, miR-101-5p, miR-126-3p, miR-126-5p, miR-1236-3p, miR-1236-5p, miR-130a-3p, miR-130a-5p, miR-17-5p, miR-17-3p, miR-18a-3p, miR-18a-5p, miR-19a-3p, miR-19a-5p, miR-19b-1-5p, miR-19b-2-5p, miR-19b-3p, miR-20a-3p, miR-20a-5p, miR-217, miR-210, miR-21-3p, miR-21-5p, miR-221-3p, miR-221-5p, miR-222-3p, miR-222-5p, miR-23a-3p, miR-23a-5p, miR-296-5p, miR-361-3p, miR-361-5p, miR-421, miR-424-3p, miR-424-5p, miR-513a-5p, miR-92a-1-5p, miR-92a-2-5p, miR-92a-3p, miR-92b-3p, and miR-92b-5p. Many novel miRNAs are discovered in endothelial cells from deep-sequencing analysis (e.g., Voellenkle C et al., RNA, 2012, 18, 472-484, herein incorporated by reference in its entirety). miRNA binding sites from any endothelial cell specific miRNA can be introduced to or removed from a polynucleotide of the invention to regulate expression of the polynucleotide in the endothelial cells.

miRNAs that are known to be expressed in epithelial cells include, but are not limited to, let-7b-3p, let-7b-5p, miR-1246, miR-200a-3p, miR-200a-5p, miR-200b-3p, miR-200b-5p, miR-200c-3p, miR-200c-5p, miR-338-3p, miR-429, miR-451a, miR-451b, miR-494, miR-802 and miR-34a, miR-34b-5p, miR-34c-5p, miR-449a, miR-449b-3p, miR-449b-5p specific in respiratory ciliated epithelial cells, let-7 family, miR-133a, miR-133b, miR-126 specific in lung epithelial cells, miR-382-3p, miR-382-5p specific in renal epithelial cells, and miR-762 specific in corneal epithelial cells. miRNA binding sites from any epithelial cell specific miRNA can be introduced to or removed from a polynucleotide of the invention to regulate expression of the polynucleotide in the epithelial cells.

In addition, a large group of miRNAs are enriched in embryonic stem cells, controlling stem cell self-renewal as well as the development and/or differentiation of various cell lineages, such as neural cells, cardiac, hematopoietic cells, skin cells, osteogenic cells and muscle cells (e.g., Kuppusamy K T et al., Curr. Mol Med, 2013, 13(5), 757-764; Vidigal J A and Ventura A, Semin Cancer Biol. 2012, 22(5-6), 428-436; Goff L A et al., PLoS One, 2009, 4:e7192; Morin R D et al., Genome Res, 2008,18, 610-621; Yoo J K et al., Stem Cells Dev. 2012, 21(11), 2049-2057, each of which is herein incorporated by reference in its entirety).

MiRNAs abundant in embryonic stem cells include, but are not limited to, let-7a-2-3p, let-a-3p, let-7a-5p, let7d-3p, let-7d-5p, miR-103a-2-3p, miR-103a-5p, miR-106b-3p, miR-106b-5p, miR-1246, miR-1275, miR-138-1-3p, miR-138-2-3p, miR-138-5p, miR-154-3p, miR-154-5p, miR-200c-3p, miR-200c-5p, miR-290, miR-301a-3p, miR-301a-5p, miR-302a-3p, miR-302a-5p, miR-302b-3p, miR-302b-5p, miR-302c-3p, miR-302c-5p, miR-302d-3p, miR-302d-5p, miR-302e, miR-367-3p, miR-367-5p, miR-369-3p, miR-369-5p, miR-370, miR-371, miR-373, miR-380-5p, miR-423-3p, miR-423-5p, miR-486-5p, miR-520c-3p, miR-548e, miR-548f, miR-548g-3p, miR-548g-5p, miR-548i, miR-548k, miR-548l, miR-548m, miR-548n, miR-548o-3p, miR-548o-5p, miR-548p, miR-664a-3p, miR-664a-5p, miR-664b-3p, miR-664b-5p, miR-766-3p, miR-766-5p, miR-885-3p, miR-885-5p, miR-93-3p, miR-93-5p, miR-941, miR-96-3p, miR-96-5p, miR-99b-3p and miR-99b-5p. Many predicted novel miRNAs are discovered by deep sequencing in human embryonic stem cells (e.g., Morin R D et al., Genome Res, 2008, 18, 610-621; Goff L A et al., PLoS One, 2009, 4:e7192; Bar M et al., Stem cells, 2008, 26, 2496-2505, the content of each of which is incorporated herein by reference in its entirety).

In some embodiments, miRNAs are selected based on expression and abundance in immune cells of the hematopoietic lineage, such as B cells, T cells, macrophages, dendritic cells, and cells that are known to express TLR7/TLR8 and/or able to secrete cytokines such as endothelial cells and platelets. In some embodiments, the miRNA set thus includes miRs that may be responsible in part for the immunogenicity of these cells, and such that a corresponding miR-site incorporation in polynucleotides of the present invention (e.g., mRNAs) could lead to destabilization of the mRNA and/or suppression of translation from these mRNAs in the specific cell type. Non-limiting representative examples include miR-142, miR-144, miR-150, miR-155 and miR-223, which are specific for many of the hematopoietic cells; miR-142, miR150, miR-16 and miR-223, which are expressed in B cells; miR-223, miR-451, miR-26a, miR-16, which are expressed in progenitor hematopoietic cells; and miR-126, which is expressed in plasmacytoid dendritic cells, platelets and endothelial cells. For further discussion of tissue expression of miRs see e.g., Teruel-Montoya, R. et al. (2014) PLoS One 9:e102259; Landgraf, P. et al. (2007) Cell 129:1401-1414; Bissels, U. et al. (2009) RNA 15:2375-2384. Any one miR-site incorporation in the 3' UTR and/or 5' UTR may mediate such effects in multiple cell types of interest (e.g., miR-142 is abundant in both B cells and dendritic cells).

In some embodiments, it may be beneficial to target the same cell type with multiple miRs and to incorporate binding sites to each of the 3p and 5p arm if both are abundant (e.g., both miR-142-3p and miR142-5p are abundant in hematopoietic stem cells). Thus, in certain embodiments, polynucleotides of the invention contain two or more (e.g., two, three, four or more) miR bindings sites from: (i) the group consisting of miR-142, miR-144, miR-150, miR-155 and miR-223 (which are expressed in many hematopoietic cells); or (ii) the group consisting of miR-142, miR150, miR-16 and miR-223 (which are expressed in B cells); or the group consisting of miR-223, miR-451, miR-26a, miR-16 (which are expressed in progenitor hematopoietic cells).

In some embodiments, it may also be beneficial to combine various miRs such that multiple cell types of interest are targeted at the same time (e.g., miR-142 and miR-126 to target many cells of the hematopoietic lineage and endothelial cells). Thus, for example, in certain embodiments, polynucleotides of the invention comprise two or more (e.g., two, three, four or more) miRNA bindings sites, wherein: (i) at least one of the miRs targets cells of the hematopoietic lineage (e.g., miR-142, miR-144, miR-150, miR-155 or miR-223) and at least one of the miRs targets plasmacytoid dendritic cells, platelets or endothelial cells (e.g., miR-126); or (ii) at least one of the miRs targets B cells (e.g., miR-142, miR150, miR-16 or miR-223) and at least one of the miRs targets plasmacytoid dendritic cells, platelets or endothelial cells (e.g., miR-126); or (iii) at least one of the miRs targets progenitor hematopoietic cells (e.g., miR-223, miR-451, miR-26a or miR-16) and at least one of the miRs targets plasmacytoid dendritic cells, platelets or endothelial cells (e.g., miR-126); or (iv) at least one of the miRs targets cells of the hematopoietic lineage (e.g., miR-142, miR-144, miR-150, miR-155 or miR-223), at least one of the miRs targets B cells (e.g., miR-142, miR150, miR-16 or miR-223) and at least one of the miRs targets plasmacytoid dendritic cells, platelets or endothelial cells (e.g., miR-126); or any other possible combination of the foregoing four classes of miR binding sites (i.e., those targeting the hematopoietic lineage, those targeting B cells, those targeting progenitor hematopoietic cells and/or those targeting plamacytoid dendritic cells/platelets/endothelial cells).

In one embodiment, to modulate immune responses, polynucleotides of the present invention can comprise one or more miRNA binding sequences that bind to one or more miRs that are expressed in conventional immune cells or any cell that expresses TLR7 and/or TLR8 and secrete pro-inflammatory cytokines and/or chemokines (e.g., in immune cells of peripheral lymphoid organs and/or splenocytes and/or endothelial cells). It has now been discovered that incorporation into an mRNA of one or more miRs that are expressed in conventional immune cells or any cell that expresses TLR7 and/or TLR8 and secrete pro-inflammatory cytokines and/or chemokines (e.g., in immune cells of peripheral lymphoid organs and/or splenocytes and/or endothelial cells) reduces or inhibits immune cell activation (e.g., B cell activation, as measured by frequency of activated B cells) and/or cytokine production (e.g., production of IL-6, IFN-γ and/or TNFα). Furthermore, it has now been discovered that incorporation into an mRNA of one or more miRs that are expressed in conventional immune cells or any cell that expresses TLR7 and/or TLR8 and secrete pro-inflammatory cytokines and/or chemokines (e.g., in immune cells of peripheral lymphoid organs and/or splenocytes and/or endothelial cells) can reduce or inhibit an anti-drug antibody (ADA) response against a protein of interest encoded by the mRNA.

In another embodiment, to modulate accelerated blood clearance of an polynucleotide delivered in a lipid-comprising compound or composition, polynucleotides of the invention can comprise one or more miR binding sequences that bind to one or more miRNAs expressed in conventional immune cells or any cell that expresses TLR7 and/or TLR8 and secrete pro-inflammatory cytokines and/or chemokines (e.g., in immune cells of peripheral lymphoid organs and/or splenocytes and/or endothelial cells). It has now been discovered that incorporation into an mRNA of one or more miR binding sites reduces or inhibits accelerated blood clearance (ABC) of the lipid-comprising compound or composition for use in delivering the mRNA.

Furthermore, it has now been discovered that incorporation of one or more miR binding sites into an mRNA reduces serum levels of anti-PEG anti-IgM (e.g, reduces or inhibits the acute production of IgMs that recognize polyethylene glycol (PEG) by B cells) and/or reduces or inhibits proliferation and/or activation of plasmacytoid dendritic cells following administration of a lipid-comprising compound or composition comprising the mRNA.

In some embodiments, miR sequences may correspond to any known microRNA expressed in immune cells, including but not limited to those taught in US Publication US2005/0261218 and US Publication US2005/0059005, the contents of which are incorporated herein by reference in their entirety. Non-limiting examples of miRs expressed in immune cells include those expressed in spleen cells, myeloid cells, dendritic cells, plasmacytoid dendritic cells, B cells, T cells and/or macrophages. For example, miR-142-3p, miR-142-5p, miR-16, miR-21, miR-223, miR-24 and miR-27 are expressed in myeloid cells, miR-155 is expressed in dendritic cells, B cells and T cells, miR-146 is upregulated in macrophages upon TLR stimulation and miR-126 is expressed in plasmacytoid dendritic cells. In certain embodiments, the miR(s) is expressed abundantly or preferentially in immune cells. For example, miR-142 (miR-142-3p and/or miR-142-5p), miR-126 (miR-126-3p and/or miR-126-5p), miR-146 (miR-146-3p and/or miR-146-5p) and miR-155 (miR-155-3p and/or miR155-5p) are expressed abundantly in immune cells. These microRNA sequences are known in the art and, thus, one of ordinary skill in the art can readily design binding sequences or target sequences to which these microRNAs will bind based upon Watson-Crick complementarity.

Accordingly, in various embodiments, polynucleotides of the present invention comprise at least one microRNA binding site for a miR selected from the group consisting of miR-142, miR-146, miR-155, miR-126, miR-16, miR-21, miR-223, miR-24 and miR-27. In another embodiment, the mRNA comprises at least two miR binding sites for microRNAs expressed in immune cells. In various embodiments, the polynucleotide of the invention comprises 1-4, one, two, three or four miR binding sites for microRNAs expressed in immune cells. In another embodiment, the polynucleotide of the invention comprises three miR binding sites. These miR binding sites can be for microRNAs selected from the group consisting of miR-142, miR-146, miR-155, miR-126, miR-16, miR-21, miR-223, miR-24, miR-27, and combinations thereof. In one embodiment, the polynucleotide of the invention comprises two or more (e.g., two, three, four) copies of the same miR binding site expressed in immune cells, e.g., two or more copies of a miR binding site selected from the group of miRs consisting of miR-142, miR-146, miR-155, miR-126, miR-16, miR-21, miR-223, miR-24, miR-27.

In one embodiment, the polynucleotide of the invention comprises three copies of the same miRNA binding site. In certain embodiments, use of three copies of the same miR binding site can exhibit beneficial properties as compared to use of a single miRNA binding site. Non-limiting examples of sequences for 3' UTRs containing three miRNA bindings sites are shown in SEQ ID NO: 101 (three miR-142-3p binding sites) and SEQ ID NO: 103 (three miR-142-5p binding sites).

In another embodiment, the polynucleotide of the invention comprises two or more (e.g., two, three, four) copies of at least two different miR binding sites expressed in immune cells. Non-limiting examples of sequences of 3' UTRs containing two or more different miR binding sites are shown in SEQ ID NO: 98 (one miR-142-3p binding site and one miR-126-3p binding site), SEQ ID NO: 104 (two miR-142-5p binding sites and one miR-142-3p binding sites), and SEQ ID NO: 107 (two miR-155-5p binding sites and one miR-142-3p binding sites).

In another embodiment, the polynucleotide of the invention comprises at least two miR binding sites for microRNAs expressed in immune cells, wherein one of the miR binding sites is for miR-142-3p. In various embodiments, the polynucleotide of the invention comprises binding sites for miR-142-3p and miR-155 (miR-155-3p or miR-155-5p), miR-142-3p and miR-146 (miR-146-3 or miR-146-5p), or miR-142-3p and miR-126 (miR-126-3p or miR-126-5p).

In another embodiment, the polynucleotide of the invention comprises at least two miR binding sites for microRNAs expressed in immune cells, wherein one of the miR binding sites is for miR-126-3p. In various embodiments, the polynucleotide of the invention comprises binding sites for miR-126-3p and miR-155 (miR-155-3p or miR-155-5p), miR-126-3p and miR-146 (miR-146-3p or miR-146-5p), or miR-126-3p and miR-142 (miR-142-3p or miR-142-5p).

In another embodiment, the polynucleotide of the invention comprises at least two miR binding sites for microRNAs expressed in immune cells, wherein one of the miR binding sites is for miR-142-5p. In various embodiments, the polynucleotide of the invention comprises binding sites for miR-142-5p and miR-155 (miR-155-3p or miR-155-5p), miR-142-5p and miR-146 (miR-146-3 or miR-146-5p), or miR-142-5p and miR-126 (miR-126-3p or miR-126-5p).

In yet another embodiment, the polynucleotide of the invention comprises at least two miR binding sites for microRNAs expressed in immune cells, wherein one of the miR binding sites is for miR-155-5p. In various embodiments, the polynucleotide of the invention comprises binding sites for miR-155-5p and miR-142 (miR-142-3p or miR-142-5p), miR-155-5p and miR-146 (miR-146-3 or miR-146-5p), or miR-155-5p and miR-126 (miR-126-3p or miR-126-5p).

miRNA can also regulate complex biological processes such as angiogenesis (e.g., miR-132) (Anand and Cheresh Curr Opin Hematol 2011 18:171-176). In the polynucleotides of the invention, miRNA binding sites that are involved in such processes can be removed or introduced, in order to tailor the expression of the polynucleotides to biologically relevant cell types or relevant biological processes. In this context, the polynucleotides of the invention are defined as auxotrophic polynucleotides.

In some embodiments, a polynucleotide of the invention comprises a miRNA binding site, wherein the miRNA binding site comprises one or more nucleotide sequences selected from Table 3, including one or more copies of any one or more of the miRNA binding site sequences. In some embodiments, a polynucleotide of the invention further comprises at least one, two, three, four, five, six, seven, eight, nine, ten, or more of the same or different miRNA binding sites selected from Table 3, including any combination thereof.

In some embodiments, the miRNA binding site binds to miR-142 or is complementary to miR-142. In some embodiments, the miR-142 comprises SEQ ID NO:30. In some embodiments, the miRNA binding site binds to miR-142-3p or miR-142-5p. In some embodiments, the miR-142-3p binding site comprises SEQ ID NO:32. In some embodiments, the miR-142-5p binding site comprises SEQ ID NO:34. In some embodiments, the miRNA binding site comprises a nucleotide sequence at least 80%, at least 85%, at least 90%, at least 95%, or 100% identical to SEQ ID NO:32 or SEQ ID NO:34.

In some embodiments, the miRNA binding site binds to miR-126 or is complementary to miR-126. In some embodiments, the miR-126 comprises SEQ ID NO: 155. In some embodiments, the miRNA binding site binds to miR-126-3p or miR-126-5p. In some embodiments, the miR-126-3p binding site comprises SEQ ID NO: 96. In some embodiments, the miR-126-5p binding site comprises SEQ ID NO: 156. In some embodiments, the miRNA binding site comprises a nucleotide sequence at least 80%, at least 85%, at least 90%, at least 95%, or 100% identical to SEQ ID NO: 96 or SEQ ID NO: 156.

In one embodiment, the 3' UTR comprises two miRNA binding sites, wherein a first miRNA binding site binds to miR-142 and a second miRNA binding site binds to miR-126. In a specific embodiment, the 3' UTR binding to miR-142 and miR-126 comprises, consists, or consists essentially of the sequence of SEQ ID NO: 98 or 163.

TABLE 3 miR-142, miR-126, and miR-142 and miR-126 binding sites

| SEQ ID NO. | Description | Sequence |
|---|---|---|
| 30 | miR-142 | GACAGUGCAGUCACCCAUAAAGUAGAAAGCACUACUAACAGCACUGGAGGGUGUAGUGUUUCCUACUUUAUGGAUGAGUGUACUGUG |
| 31 | miR-142-3p | UGUAGUGUUUCCUACUUUAUGGA |
| 32 | miR-142-3p binding site | UCCAUAAAGUAGGAAACACUACA |
| 33 | miR-142-5p | CAUAAAGUAGAAAGCACUACU |
| 34 | miR-142-5p binding site | AGUAGUGCUUUCUACUUUAUG |
| 155 | miR-126 | CGCUGGCGACGGGACAUUAUUACUUUUGGUACGCGCUGUGACACUUCAAACUCGUACCGUGAGUAAUAAUGCGCCGUCCACGGCA |
| 84 | miR-126-3p | UCGUACCGUGAGUAAUAAUGCG |
| 96 | miR-126-3p binding site | CGCAUUAUUACUCACGGUACGA |
| 85 | miR-126-5p | CAUUAUUACUUUUGGUACGCG |
| 156 | miR-126-5p binding site | CGCGUACCAAAAGUAAUAAUG |

In some embodiments, a miRNA binding site is inserted in the polynucleotide of the invention in any position of the polynucleotide (e.g., the 5' UTR and/or 3' UTR). In some embodiments, the 5' UTR comprises a miRNA binding site. In some embodiments, the 3' UTR comprises a miRNA binding site. In some embodiments, the 5' UTR and the 3' UTR comprise a miRNA binding site. The insertion site in the polynucleotide can be anywhere in the polynucleotide as long as the insertion of the miRNA binding site in the polynucleotide does not interfere with the translation of a functional polypeptide in the absence of the corresponding miRNA; and in the presence of the miRNA, the insertion of the miRNA binding site in the polynucleotide and the binding of the miRNA binding site to the corresponding miRNA are capable of degrading the polynucleotide or preventing the translation of the polynucleotide.

In some embodiments, a miRNA binding site is inserted in at least about 30 nucleotides downstream from the stop codon of an ORF in a polynucleotide of the invention comprising the ORF. In some embodiments, a miRNA binding site is inserted in at least about 10 nucleotides, at least about 15 nucleotides, at least about 20 nucleotides, at least about 25 nucleotides, at least about 30 nucleotides, at least about 35 nucleotides, at least about 40 nucleotides, at least about 45 nucleotides, at least about 50 nucleotides, at least about 55 nucleotides, at least about 60 nucleotides, at least about 65 nucleotides, at least about 70 nucleotides, at least about 75 nucleotides, at least about 80 nucleotides, at least about 85 nucleotides, at least about 90 nucleotides, at least about 95 nucleotides, or at least about 100 nucleotides downstream from the stop codon of an ORF in a polynucleotide of the invention. In some embodiments, a miRNA binding site is inserted in about 10 nucleotides to about 100 nucleotides, about 20 nucleotides to about 90 nucleotides, about 30 nucleotides to about 80 nucleotides, about 40 nucleotides to about 70 nucleotides, about 50 nucleotides to about 60 nucleotides, about 45 nucleotides to about 65 nucleotides downstream from the stop codon of an ORF in a polynucleotide of the invention.

In some embodiments, a miRNA binding site is inserted within the 3' UTR immediately following the stop codon of the coding region within the polynucleotide of the invention, e.g., mRNA. In some embodiments, if there are multiple copies of a stop codon in the construct, a miRNA binding site is inserted immediately following the final stop codon. In some embodiments, a miRNA binding site is inserted further downstream of the stop codon, in which case there are 3' UTR bases between the stop codon and the miR binding site(s). In some embodiments, three non-limiting examples of possible insertion sites for a miR in a 3' UTR are shown in SEQ ID NOs: 53, 54, and 108, which show a 3' UTR sequence with a miR-142-3p site inserted in one of three different possible insertion sites, respectively, within the 3' UTR.

In some embodiments, one or more miRNA binding sites can be positioned within the 5' UTR at one or more possible insertion sites. For example, three non-limiting examples of possible insertion sites for a miR in a 5' UTR are shown in SEQ ID NOs: 109, 110, and 111, which show a 5' UTR sequence with a miR-142-3p site inserted into one of three different possible insertion sites, respectively, within the 5' UTR.

In one embodiment, a codon optimized open reading frame encoding a polypeptide of interest comprises a stop codon and the at least one microRNA binding site is located within the 3' UTR 1-100 nucleotides after the stop codon. In one embodiment, the codon optimized open reading frame encoding the polypeptide of interest comprises a stop codon and the at least one microRNA binding site for a miR expressed in immune cells is located within the 3' UTR 30-50 nucleotides after the stop codon. In another embodiment, the codon optimized open reading frame encoding the polypeptide of interest comprises a stop codon and the at least one microRNA binding site for a miR expressed in immune cells is located within the 3' UTR at least 50 nucleotides after the stop codon. In other embodiments, the codon optimized open reading frame encoding the polypeptide of interest comprises a stop codon and the at least one microRNA binding site for a miR expressed in immune cells is located within the 3' UTR immediately after the stop codon, or within the 3' UTR 15-20 nucleotides after the stop codon or within the 3' UTR 70-80 nucleotides after the stop codon. In other embodiments, the 3' UTR comprises more than one miRNA bindingsite (e.g., 2-4 miRNA binding sites), wherein there can be a spacer region (e.g., of 10-100, 20-70 or 30-50 nucleotides in length) between each miRNA bindingsite. In another embodiment, the 3' UTR comprises a spacer region between the end of the miRNA bindingsite(s) and the poly A tail nucleotides. For example, a spacer region of 10-100, 20-70 or 30-50 nucleotides in length can be situated between the end of the miRNA bindingsite(s) and the beginning of the poly A tail.

In one embodiment, a codon optimized open reading frame encoding a polypeptide of interest comprises a start codon and the at least one microRNA binding site is located within the 5' UTR 1-100 nucleotides before (upstream of) the start codon. In one embodiment, the codon optimized open reading frame encoding the polypeptide of interest comprises a start codon and the at least one microRNA binding site for a miR expressed in immune cells is located within the 5' UTR 10-50 nucleotides before (upstream of) the start codon. In another embodiment, the codon optimized open reading frame encoding the polypeptide of interest comprises a start codon and the at least one microRNA binding site for a miR expressed in immune cells is located within the 5' UTR at least 25 nucleotides before (upstream of) the start codon. In other embodiments, the codon optimized open reading frame encoding the polypeptide of interest comprises a start codon and the at least one microRNA binding site for a miR expressed in immune cells is located within the 5' UTR immediately before the start codon, or within the 5' UTR 15-20 nucleotides before the start codon or within the 5' UTR 70-80 nucleotides before the start codon. In other embodiments, the 5' UTR comprises more than one miRNA bindingsite (e.g., 2-4 miRNA binding sites), wherein there can be a spacer region (e.g., of 10-100, 20-70 or 30-50 nucleotides in length) between each miRNA bindingsite.

In one embodiment, the 3' UTR comprises more than one stop codon, wherein at least one miRNA bindingsite is positioned downstream of the stop codons. For example, a 3' UTR can comprise 1, 2 or 3 stop codons. Non-limiting examples of triple stop codons that can be used include: UGAUAAUAG, UGAUAGUAA, UAAUGAUAG, UGAUAAUAA, UGAUAGUAG, UAAUGAUGA, UAAUAGUAG, UGAUGAUGA, UAAUAAUAA, and UAGUAGUAG. Within a 3' UTR, for example, 1, 2, 3 or 4 miRNA binding sites, e.g., miR-142-3p binding sites, can be positioned immediately adjacent to the stop codon(s) or at any number of nucleotides downstream of the final stop codon. When the 3' UTR comprises multiple miRNA binding sites, these binding sites can be positioned directly next to each other in the construct (i.e., one after the other) or, alternatively, spacer nucleotides can be positioned between each binding site.

In one embodiment, the 3' UTR comprises three stop codons with a single miR-142-3p binding site located downstream of the 3rd stop codon. Non-limiting examples of sequences of 3' UTR having three stop codons and a single miR-142-3p binding site located at different positions downstream of the final stop codon are shown in SEQ ID NOs: 58, 53, 54, and 108.

TABLE 4

5' UTRs, 3' UTRs, miR sequences, and miR binding sites

| SEQ ID NO: | Sequence |
|---|---|
| 79 | GCUGGAGCCUCGGUGGCCAUGCUUCUUGCCCCUUGGGCCUCCCCCCAGCCCCUCCUCCCCUUCCUGCACCCGUACCCCCUCCAUAAAGUAGGAAACACUACAGUGGUCUUUGAAUAAAGUCUGAGUGGGCGGC (3' UTR with miR 142-3p binding site) |

TABLE 4-continued

5' UTRs, 3' UTRs, miR sequences, and miR binding sites

| SEQ ID NO: | Sequence |
|---|---|
| 32 | UCCAUAAAGUAGGAAACACUACA (miR 142-3p binding site) |
| 31 | UGUAGUGUUUCCUACUUUAUGGA (miR 142-3p sequence) |
| 33 | CAUAAAGUAGAAAGCACUACU (miR 142-5p sequence) |
| 80 | CCUCUGAAAUUCAGUUCUUCAG (miR 146-3p sequence) |
| 81 | UGAGAACUGAAUUCCAUGGGUU (miR 146-5p sequence) |
| 82 | CUCCUACAUAUUAGCAUUAACA (miR 155-3p sequence) |
| 83 | UUAAUGCUAAUCGUGAUAGGGGU (miR 155-5p sequence) |
| 84 | UCGUACCGUGAGUAAUAAUGCG (miR 126-3p sequence) |
| 85 | CAUUAUUACUUUUGGUACGCG (miR 126-5p sequence) |
| 86 | CCAGUAUUAACUGUGCUGCUGA (miR 16-3p sequence) |
| 87 | UAGCAGCACGUAAAUAUUGGCG (miR 16-5p sequence) |
| 88 | CAACACCAGUCGAUGGGCUGU (miR 21-3p sequence) |
| 89 | UAGCUUAUCAGACUGAUGUUGA (miR 21-5p sequence) |
| 90 | UGUCAGUUUGUCAAAUACCCCA (miR 223-3p sequence) |
| 91 | CGUGUAUUUGACAAGCUGAGUU (miR 223-5p sequence) |
| 92 | UGGCUCAGUUCAGCAGGAACAG (miR 24-3p sequence) |
| 93 | UGCCUACUGAGCUGAUAUCAGU (miR 24-5p sequence) |
| 94 | UUCACAGUGGCUAAGUUCCGC (miR 27-3p sequence) |
| 95 | AGGGCUUAGCUGCUUGUGAGCA (miR 27-5p sequence) |
| 96 | CGCAUUAUUACUCACGGUACGA (miR 126-3p binding site) |
| 97 | **UGAUAAUAG**GCUGGAGCCUCGGUGGCCAUGCUUCUUGCCCCUUGGGCCUCCCCCCAGCCCCUCCUCCCCUUCCUGCACCCGUACCCCCCGCAUUAUUACUCACGGUACGAGUGGUCUUUGAAUAAAGUCUGAGUGGGCGGC (3' UTR with miR 126-3p binding site) |
| 77 | **UGAUAAUAG**GCUGGAGCCUCGGUGGCCAUGCUUCUUGCCCCUUGGGCCUCCCCCCAGCCCCUCCUCCCCUUCCUGCACCCGUACCCCCGUGGUCUUUGAAUAAAGUCUGAGUGGGCGGC (3' UTR, no miR binding sites) |

TABLE 4-continued

5' UTRs, 3' UTRs, miR sequences, and miR binding sites

| SEQ ID NO: | Sequence |
|---|---|
| 58 | **UGAUAAUAG**GCUGGAGCCUCGGUGGCCAUGCUUCUUGCCCCUUGGGCCUCCCCCCAGCCCCUCCUCCCCUUCCUGCACCCGUACCCCCUCCAUAAAGUAGGAAACACUACAGUGGUCUUUGAAUAAAGUCUGAGUGGGCGGC<br>(3' UTR with miR 142-3p binding site) |
| 98 | **UGAUAAUAG**UCCAUAAAGUAGGAAACACUACAGCUGGAGCCUCGGUGGCCAUGCUUCUUGCCCCUUGGGCCUCCCCCCAGCCCCUCCUCCCCUUCCUGCACCCGUACCCCCGCAUUAUUACUCACGGUACGAGUGGUCUUUGAAUAAAGUCUGAGUGGGCGGC<br>(3' UTR with miR 142-3p and miR 126-3p binding sites variant 1) |
| 99 | UUAAUGCUAAUUGUGAUAGGGGU<br>(miR 155-5p sequence) |
| 100 | ACCCCUAUCACAAUUAGCAUUAA<br>(miR 155-5p binding site) |
| 101 | **UGAUAAUAG**UCCAUAAAGUAGGAAACACUACAGCUGGAGCCUCGGUGGCCAUGCUUCUUGCCCCUUGGGCCUCCAUAAAGUAGGAAACACUACAUCCCCCCAGCCCCUCCUCCCCUUCCUGCACCCGUACCCCCUCCAUAAAGUAGGAAACACUACAGUGGUCUUUGAAUAAAGUCUGAGUGGGCGGC<br>(3' UTR with 3 miR 142-3p binding sites) |
| 102 | **UGAUAAUAG**GCUGGAGCCUCGGUGGCCAUGCUUCUUGCCCCUUGGGCCUCCCCCCAGCCCCUCCUCCCCUUCCUGCACCCGUACCCCCAGUAGUGCUUUCUACUUUAUGGUGGUCUUUGAAUAAAGUCUGAGUGGGCGGC<br>(3' UTR with miR 142-5p binding site) |
| 103 | **UGAUAAUAG**AGUAGUGCUUUCUACUUUAUGGCUGGAGCCUCGGUGGCCAUGCUUCUUGCCCCUUGGGCCAGUAGUGCUUUCUACUUUAUGUCCCCCCAGCCCCUCCUCCCCUUCCUGCACCCGUACCCCCAGUAGUGCUUUCUACUUUAUGGUGGUCUUUGAAUAAAGUCUGAGUGGGCGGC<br>(3' UTR with 3 miR 142-5p binding sites) |
| 104 | **UGAUAAUAG**AGUAGUGCUUUCUACUUUAUGGCUGGAGCCUCGGUGGCCAUGCUUCUUGCCCCUUGGGCCUCCAUAAAGUAGGAAACACUACAUCCCCCCAGCCCCUCCUCCCCUUCCUGCACCCGUACCCCCAGUAGUGCUUUCUACUUUAUGGUGGUCUUUGAAUAAAGUCUGAGUGGGCGGC<br>(3' UTR with 2 miR 142-5p binding sites and 1 miR 142-3p binding site) |
| 105 | **UGAUAAUAG**GCUGGAGCCUCGGUGGCCAUGCUUCUUGCCCCUUGGGCCUCCCCCCAGCCCCUCCUCCCCUUCCUGCACCCGUACCCCCACCCCUAUCACAAUUAGCAUUAAGUGGUCUUUGAAUAAAGUCUGAGUGGGCGGC<br>(3' UTR with miR 155-5p binding site) |
| 106 | **UGAUAAUAG**ACCCCUAUCACAAUUAGCAUUAAGCUGGAGCCUCGGUGGCCAUGCUUCUUGCCCCUUGGGCCACCCCUAUCACAAUUAGCAUUAAUCCCCCCAGCCCCUCCUCCCCUUCCUGCACCCGUACCCCCACCCCUAUCACAAUUAGCAUUAAGUGGUCUUUGAAUAAAGUCUGAGUGGGCGGC<br>(3' UTR with 3 miR 155-5p binding sites) |
| 107 | **UGAUAAUAG**ACCCCUAUCACAAUUAGCAUUAAGCUGGAGCCUCGGUGGCCAUGCUUCUUGCCCCUUGGGCCUCCAUAAAGUAGGAAACACUACAUCCCCCCAGCCCCUCCUCCCCUUCCUGCACCCGUACCCCCACCCCUAUCACAAUUAGCAUUAAGUGGUCUUUGAAUAAAGUCUGAGUGGGCGGC<br>(3' UTR with 2 miR 155-5p binding sites and 1 miR 142-3p binding site) |
| 53 | **UGAUAAUAG**UCCAUAAAGUAGGAAACACUACAGCUGGAGCCUCGGUGGCCAUGCUUCUUGCCCCUUGGGCCUCCCCCCAGCCCCUCCUCCCCUUCCUGCACCCGUACCCCCGUGGUCUUUGAAUAAAGUCUGAGUGGGCGGC<br>(3' UTR with miR 142-3p binding site, P1 insertion) |
| 54 | **UGAUAAUAG**GCUGGAGCCUCGGUGGCUCCAUAAAGUAGGAAACACUACACAUGCUUCUUGCCCCUUGGGCCUCCCCCCAGCCCCUCCUCCCCUUCCUGCACCCGUACCCCCGUGGUCUUUGAAUAAAGUCUGAGUGGGCGGC<br>(3' UTR with miR 142-3p binding site, P2 insertion) |
| 108 | **UGAUAAUAG**GCUGGAGCCUCGGUGGCCAUGCUUCUUGCCCCUUGGGCCUCCAUAAAGUAGGAAACACUACAUCCCCCCAGCCCCUCCUCCCCUUCCUGCACCCGUACCCCCGUGGUCUUUGAAUAAAGUCUGAGUGGGCGGC<br>(3' UTR with miR 142-3p binding site, P3 insertion) |
| 34 | AGUAGUGCUUUCUACUUUAUG<br>(miR-142-5p binding site) |
| 30 | GACAGUGCAGUCACCCAUAAAGUAGAAAGCACUACUAACAGCACUGGAGGGUGUAGUGUUUCCUACUUUAUGGAUGAGUGUACUGUG<br>(miR-142) |
| 35 | GGGAAAUAAGAGAGAAAAGAAGAGUAAGAAGAAAUAUAAGAGCCACC<br>(5' UTR) |
| 109 | GGGAAAUAAGAGUCCAUAAAGUAGGAAACACUACAAGAAAAGAAGAGUAAGAAGAAAUAUAAGAGCCACC<br>(5' UTR with miR142-3p binding site at position p1) |
| 110 | GGGAAAUAAGAGAGAAAAGAAGAGUAAUCCAUAAAGUAGGAAACACUACAGAAGAAAUAUAAGAGCCACC<br>(5' UTR with miR142-3p binding site at position p2) |
| 111 | GGGAAAUAAGAGAGAAAAGAAGAGUAAGAAGAAAUAUAAUCCAUAAAGUAGGAAACACUACAGAGCCACC<br>(5' UTR with miR142-3p binding site at position p3) |
| 100 | ACCCCUAUCACAAUUAGCAUUAA<br>(miR 155-5p binding site) |
| 112 | **UGAUAAUAG**AGUAGUGCUUUCUACUUUAUGGCUGGAGCCUCGGUGGCCAUGCUUCUUGCCCCUUGGGCCAGUAGUGCUUUCUACUUUAUGUCCCCCCAGCCCCUCUCCCCUUCCUGCACCCGUACCCCCAGUAGUGCUUUCUACUUUAUGGUGGUCUUUGAAUAAAGUCUGAGUGGGCGGC<br>(3' UTR with 3 miR 142-5p binding sites) |
| 55 | **UGAUAAUAG**GCUGGAGCCUCGGUGGCCAUGCUUCUUGCCCCUUCCAUAAAGUAGGAAACACUACAUGGGCCUCCCCCCAGCCCCUCCUCCCCUUCCUGCACCCGUACCCCCGUGGUCUUUGAAUAAAGUCUGAGUGGGCGGC<br>(3' UTR including miR142-3p binding site) |
| 56 | **UGAUAAUAG**GCUGGAGCCUCGGUGGCCAUGCUUCUUGCCCCUUGGGCCUCCCCCCAGUCCAUAAAGUAGGAAACACUACACCCCUCCUCCCCUUCCUGCACCCGUACCCCCGUGGUCUUUGAAUAAAGUCUGAGUGGGCGGC<br>(3' UTR including miR142-3p binding site) |
| 57 | **UGAUAAUAG**GCUGGAGCCUCGGUGGCCAUGCUUCUUGCCCCUUGGGCCUCCCCCCAGCCCCUCCUCCCCUUCUCCAUAAAGUAGGA |

TABLE 4-continued

5' UTRs, 3' UTRs, miR sequences, and miR binding sites

| SEQ ID NO: | Sequence |
|---|---|
| | AACACUACACUGCACCCGUACCCCCGUGGUCUUUGAAUAAAGU<br>CUGAGUGGGCGGC<br>(3' UTR including including miR142-3p binding site) |
| 59 | **UGAUAAUAG**GCUGGAGCCUCGGUGGCCAUGCUUCUUGCCCCUU<br>GGGCCUCCCCCCAGCCCCUCCUCCCCUUCCUGCACCCGUACCC<br>CCGUGGUCUUUGAAUAAAGUUCCAUAAAGUAGGAAACACUACA<br>CUGAGUGGGCGGC<br>(3' UTR including including miR142-3p binding site) |
| 163 | **UGAUAAUAG**UCCAUAAAGUAGGAAACACUACAGCUGGAGCCUC<br>GGUGGCCUAGCUUCUUGCCCCUUGGGCCUCCCCCCAGCCCCUC<br>CUCCCCUUCCUGCACCCGUACCCCCGCAUUAUUACUCACGGU<br>ACGAGUGGUCUUUGAAUAAAGUCUGAGUGGGCGGC<br>(3' UTR with miR 142-3p and miR 126-3p binding sites variant 2) |
| 165 | **UGAUAAUAG**GCUGGAGCCUCGGUGGCCUAGCUUCUUGCCCCUU<br>GGGCCUCCCCCCAGCCCCUCCUCCCCUUCCUGCACCCGUACCC<br>CCGUGGUCUUUGAAUAAAGUCUGAGUGGGCGGC<br>(3' UTR, no miR binding sites variant 2) |
| 164 | **UGAUAAUAG**GCUGGAGCCUCGGUGGCCUAGCUUCUUGCCCCUU<br>GGGCCUCCCCCCAGCCCCUCCUCCCCUUCCUGCACCCGUACCC<br>CCUCCAUAAAGUAGGAAACACUACAGUGGUCUUUGAAUAAAGU<br>CUGAGUGGGCGGC<br>(3' UTR with miR 142-3p binding site variant 3) |
| 166 | **UGAUAAUAG**GCUGGAGCCUCGGUGGCCUAGCUUCUUGCCCCUU<br>GGGCCUCCCCCCAGCCCCUCCUCCCCUUCCUGCACCCGUACCC<br>CCCGCAUUAUUACUCACGGUACGAGUGGUCUUUGAAUAAAGUC<br>UGAGUGGGCGGC<br>(3' UTR with miR 126-3p binding site variant 3) |
| 167 | **UGAUAAUAG**UCCAUAAAGUAGGAAACACUACAGCUGGAGCCUC<br>GGUGGCCUAGCUUCUUGCCCCUUGGGCCUCCAUAAAGUAGGAA<br>ACACUACAUCCCCCCAGCCCCUCCUCCCCUUCCUGCACCCGUA<br>CCCCCUCCAUAAAGUAGGAAACACUACAGUGGUCUUUGAAUAA<br>AGUCUGAGUGGGCGGC<br>(3' UTR with 3 miR 142-3p binding sites variant 2) |
| 168 | **UGAUAAUAG**UCCAUAAAGUAGGAAACACUACAGCUGGAGCCUC<br>GGUGGCCUAGCUUCUUGCCCCUUGGGCCUCCCCCCAGCCCCUC<br>CUCCCCUUCCUGCACCCGUACCCCCGUGGUCUUUGAAUAAAGU<br>CUGAGUGGGCGGC<br>(3' UTR with miR 142-3p binding site, P1 insertion variant 2) |
| 169 | **UGAUAAUAG**GCUGGAGCCUCGGUGGCUCCAUAAAGUAGGAAAC<br>ACUACACUAGCUUCUUGCCCCUUGGGCCUCCCCCCAGCCCCUC<br>CUCCCCUUCCUGCACCCGUACCCCCGUGGUCUUUGAAUAAAGU<br>CUGAGUGGGCGGC<br>(3' UTR with miR 142-3p binding site, P2 insertion variant 2) |
| 170 | **UGAUAAUAG**GCUGGAGCCUCGGUGGCCUAGCUUCUUGCCCCUU<br>GGGCCUCCAUAAAGUAGGAAACACUACAUCCCCCCAGCCCCUC<br>CUCCCCUUCCUGCACCCGUACCCCCGUGGUCUUUGAAUAAAGU<br>CUGAGUGGGCGGC<br>(3' UTR with miR 142-3p binding site, P3 insertion variant 2) |
| 171 | **UGAUAAUAG**GCUGGAGCCUCGGUGGCCUAGCUUCUUGCCCCUU<br>GGGCCUCCCCCCAGCCCCUCCUCCCCUUCCUGCACCCGUACCC<br>CCACCCCUAUCACAAUUAGCAUUAAGUGGUCUUUGAAUAAAGU<br>CUGAGUGGGCGGC<br>(3' UTR with miR 155-5p binding site variant 2) |
| 172 | **UGAUAAUAG**ACCCCUAUCACAAUUAGCAUUAAGCUGGAGCCUC<br>GGUGGCCUAGCUUCUUGCCCCUUGGGCCACCCCUAUCACAAUU<br>AGCAUUAAUCCCCCCAGCCCCUCCUCCCCUUCCUGCACCCGUA<br>CCCCCACCCCUAUCACAAUUAGCAUUAAGUGGUCUUUGAAUAA<br>AGUCUGAGUGGGCGGC<br>(3' UTR with 3 miR 155-5p binding sites variant 2) |
| 173 | **UGAUAAUAG**ACCCCUAUCACAAUUAGCAUUAAGCUGGAGCCUC<br>GGUGGCCUAGCUUCUUGCCCCUUGGGCCUCCAUAAAGUAGGAA<br>ACACUACAUCCCCCCAGCCCCUCCUCCCCUUCCUGCACCCGUA<br>CCCCCACCCCUAUCACAAUUAGCAUUAAGUGGUCUUUGAAUAA<br>AGUCUGAGUGGGCGGC<br>(3' UTR with 2 miR 155-5p binding sites and 1 miR 142-3p binding site variant 2) |

Stop codon = bold
miR 142-3p binding site = underline
miR 126-3p binding site = bold underline
miR 155-5p binding site = shaded
miR 142-5p binding site = shaded and bold underline In one embodiment, the polynucleotide of the invention comprises a 5' UTR, a codon optimized open reading frame encoding a polypeptide of interest, a 3' UTR comprising the at least one miRNA binding site for a miR expressed in immune cells, and a 3' tailing region of linked nucleosides. In various embodiments, the 3' UTR comprises 1-4, at least two, one, two, three or four miRNA binding sites for miRs expressed in immune cells, preferably abundantly or preferentially expressed in immune cells.

In one embodiment, the at least one miRNA expressed in immune cells is a miR-142-3p microRNA binding site. In one embodiment, the miR-142-3p microRNA binding site comprises the sequence shown in SEQ ID NO: 32. In one embodiment, the 3' UTR of the mRNA comprising the miR-142-3p microRNA binding site comprises the sequence shown in SEQ ID NO: 79.

In one embodiment, the at least one miRNA expressed in immune cells is a miR-126 microRNA binding site. In one embodiment, the miR-126 binding site is a miR-126-3p binding site. In one embodiment, the miR-126-3p microRNA binding site comprises the sequence shown in SEQ ID NO: 96. In one embodiment, the 3' UTR of the mRNA of the invention comprising the miR-126-3p microRNA binding site comprises the sequence shown in SEQ ID NO: 97.

Non-limiting exemplary sequences for miRs to which a microRNA binding site(s) of the disclosure can bind include the following: miR-142-3p (SEQ ID NO: 31), miR-142-5p (SEQ ID NO: 33), miR-146-3p (SEQ ID NO: 80), miR-146-5p (SEQ ID NO: 81), miR-155-3p (SEQ ID NO: 82), miR-155-5p (SEQ ID NO: 83), miR-126-3p (SEQ ID NO: 84), miR-126-5p (SEQ ID NO: 85), miR-16-3p (SEQ ID NO: 86), miR-16-5p (SEQ ID NO: 87), miR-21-3p (SEQ ID NO: 88), miR-21-5p (SEQ ID NO: 89), miR-223-3p (SEQ ID NO: 90), miR-223-5p (SEQ ID NO: 91), miR-24-3p (SEQ ID NO: 92), miR-24-5p (SEQ ID NO: 93), miR-27-3p (SEQ ID NO: 94) and miR-27-5p (SEQ ID NO: 95). Other suitable miR sequences expressed in immune cells (e.g., abundantly or preferentially expressed in immune cells) are known and available in the art, for example at the University of Manchester's microRNA database, miRBase. Sites that bind any of the aforementioned miRs can be designed based on Watson-Crick complementarity to the miR, typically 100% complementarity to the miR, and inserted into an mRNA construct of the disclosure as described herein.

In another embodiment, a polynucleotide of the present invention (e.g., and mRNA, e.g., the 3' UTR thereof) can comprise at least one miRNA bindingsite to thereby reduce or inhibit accelerated blood clearance, for example by reducing or inhibiting production of IgMs, e.g., against PEG, by B cells and/or reducing or inhibiting proliferation and/or activation of pDCs, and can comprise at least one miRNA bindingsite for modulating tissue expression of an encoded protein of interest.

miRNA gene regulation can be influenced by the sequence surrounding the miRNA such as, but not limited to, the species of the surrounding sequence, the type of sequence (e.g., heterologous, homologous, exogenous, endogenous, or artificial), regulatory elements in the surrounding sequence and/or structural elements in the surrounding sequence. The miRNA can be influenced by the 5'UTR and/or 3'UTR. As a non-limiting example, a non-human 3'UTR can increase the regulatory effect of the miRNA sequence on the expression of a polypeptide of interest compared to a human 3'UTR of the same sequence type.

In one embodiment, other regulatory elements and/or structural elements of the 5'UTR can influence miRNA mediated gene regulation. One example of a regulatory element and/or structural element is a structured IRES (Internal Ribosome Entry Site) in the 5'UTR, which is necessary for the binding of translational elongation factors to initiate protein translation. EIF4A2 binding to this secondarily structured element in the 5'-UTR is necessary for miRNA mediated gene expression (Meijer H A et al., Science, 2013, 340, 82-85, herein incorporated by reference in its entirety). The polynucleotides of the invention can further include this structured 5'UTR in order to enhance microRNA mediated gene regulation.

At least one miRNA binding site can be engineered into the 3'UTR of a polynucleotide of the invention. In this context, at least two, at least three, at least four, at least five, at least six, at least seven, at least eight, at least nine, at least ten, or more miRNA binding sites can be engineered into a 3'UTR of a polynucleotide of the invention. For example, 1 to 10, 1 to 9, 1 to 8, 1 to 7, 1 to 6, 1 to 5, 1 to 4, 1 to 3, 2, or 1 miRNA binding sites can be engineered into the 3'UTR of a polynucleotide of the invention. In one embodiment, miRNA binding sites incorporated into a polynucleotide of the invention can be the same or can be different miRNA sites. A combination of different miRNA binding sites incorporated into a polynucleotide of the invention can include combinations in which more than one copy of any of the different miRNA sites are incorporated. In another embodiment, miRNA binding sites incorporated into a polynucleotide of the invention can target the same or different tissues in the body. As a non-limiting example, through the introduction of tissue-, cell-type-, or disease-specific miRNA binding sites in the 3'-UTR of a polynucleotide of the invention, the degree of expression in specific cell types (e.g., myeloid cells, endothelial cells, etc.) can be reduced.

In one embodiment, a miRNA binding site can be engineered near the 5' terminus of the 3'UTR, about halfway between the 5' terminus and 3' terminus of the 3'UTR and/or near the 3' terminus of the 3'UTR in a polynucleotide of the invention. As a non-limiting example, a miRNA binding site can be engineered near the 5' terminus of the 3'UTR and about halfway between the 5' terminus and 3' terminus of the 3'UTR. As another non-limiting example, a miRNA binding site can be engineered near the 3' terminus of the 3'UTR and about halfway between the 5' terminus and 3' terminus of the 3'UTR. As yet another non-limiting example, a miRNA binding site can be engineered near the 5' terminus of the 3'UTR and near the 3' terminus of the 3'UTR.

In another embodiment, a 3'UTR can comprise 1, 2, 3, 4, 5, 6, 7, 8, 9, or 10 miRNA binding sites. The miRNA binding sites can be complementary to a miRNA, miRNA seed sequence, and/or miRNA sequences flanking the seed sequence.

In some embodiments, the expression of a polynucleotide of the invention can be controlled by incorporating at least one sensor sequence in the polynucleotide and formulating the polynucleotide for administration. As a non-limiting example, a polynucleotide of the invention can be targeted to a tissue or cell by incorporating a miRNA binding site and formulating the polynucleotide in a lipid nanoparticle comprising a ionizable lipid, including any of the lipids described herein.

A polynucleotide of the invention can be engineered for more targeted expression in specific tissues, cell types, or biological conditions based on the expression patterns of miRNAs in the different tissues, cell types, or biological conditions. Through introduction of tissue-specific miRNA binding sites, a polynucleotide of the invention can be designed for optimal protein expression in a tissue or cell, or in the context of a biological condition.

In some embodiments, a polynucleotide of the invention can be designed to incorporate miRNA binding sites that either have 100% identity to known miRNA seed sequences or have less than 100% identity to miRNA seed sequences. In some embodiments, a polynucleotide of the invention can be designed to incorporate miRNA binding sites that have at least: 60%, 65%, 70%, 75%, 80%, 85%, 90%, 95%, 96%, 97%, 98%, or 99% identity to known miRNA seed sequences. The miRNA seed sequence can be partially mutated to decrease miRNA binding affinity and as such result in reduced downmodulation of the polynucleotide. In essence, the degree of match or mis-match between the miRNA binding site and the miRNA seed can act as a rheostat to more finely tune the ability of the miRNA to modulate protein expression. In addition, mutation in the non-seed region of a miRNA binding site can also impact the ability of a miRNA to modulate protein expression.

In one embodiment, a miRNA sequence can be incorporated into the loop of a stem loop.

In another embodiment, a miRNA seed sequence can be incorporated in the loop of a stem loop and a miRNA binding site can be incorporated into the 5' or 3' stem of the stem loop.

In one embodiment, a translation enhancer element (TEE) can be incorporated on the 5'end of the stem of a stem loop and a miRNA seed can be incorporated into the stem of the stem loop. In another embodiment, a TEE can be incorporated on the 5' end of the stem of a stem loop, a miRNA seed can be incorporated into the stem of the stem loop and a miRNA binding site can be incorporated into the 3' end of the stem or the sequence after the stem loop. The miRNA seed and the miRNA binding site can be for the same and/or different miRNA sequences.

In one embodiment, the incorporation of a miRNA sequence and/or a TEE sequence changes the shape of the stem loop region which can increase and/or decrease translation. (see e.g, Kedde et al., "A Pumilio-induced RNA structure switch in p27-3'UTR controls miR-221 and miR-22 accessibility." Nature Cell Biology. 2010, incorporated herein by reference in its entirety).

In one embodiment, the 5'-UTR of a polynucleotide of the invention can comprise at least one miRNA sequence. The miRNA sequence can be, but is not limited to, a 19 or 22 nucleotide sequence and/or a miRNA sequence without the seed.

In one embodiment the miRNA sequence in the 5'UTR can be used to stabilize a polynucleotide of the invention described herein.

In another embodiment, a miRNA sequence in the 5'UTR of a polynucleotide of the invention can be used to decrease the accessibility of the site of translation initiation such as, but not limited to a start codon. See, e.g., Matsuda et al., PLoS One. 2010 11(5):e15057; incorporated herein by reference in its entirety, which used antisense locked nucleic acid (LNA) oligonucleotides and exon junction complexes (EJCs) around a start codon (−4 to +37 where the A of the AUG codons is +1) in order to decrease the accessibility to the first start codon (AUG). Matsuda showed that altering the sequence around the start codon with an LNA or EJC affected the efficiency, length and structural stability of a polynucleotide. A polynucleotide of the invention can comprise a miRNA sequence, instead of the LNA or EJC sequence described by Matsuda et al, near the site of translation initiation in order to decrease the accessibility to the site of translation initiation. The site of translation initiation can be prior to, after or within the miRNA sequence. As a non-limiting example, the site of translation initiation can be located within a miRNA sequence such as a seed sequence or binding site.

In some embodiments, a polynucleotide of the invention can include at least one miRNA in order to dampen the antigen presentation by antigen presenting cells. The miRNA can be the complete miRNA sequence, the miRNA seed sequence, the miRNA sequence without the seed, or a combination thereof. As a non-limiting example, a miRNA incorporated into a polynucleotide of the invention can be specific to the hematopoietic system. As another non-limiting example, a miRNA incorporated into a polynucleotide of the invention to dampen antigen presentation is miR-142-3p.

In some embodiments, a polynucleotide of the invention can include at least one miRNA in order to dampen expression of the encoded polypeptide in a tissue or cell of interest. As a non-limiting example a polynucleotide of the invention can include at least one miR-142-3p binding site, miR-142-3p seed sequence, miR-142-3p binding site without the seed, miR-142-5p binding site, miR-142-5p seed sequence, miR-142-5p binding site without the seed, miR-146 binding site, miR-146 seed sequence and/or miR-146 binding site without the seed sequence.

In some embodiments, a polynucleotide of the invention can comprise at least one miRNA binding site in the 3'UTR in order to selectively degrade mRNA therapeutics in the immune cells to subdue unwanted immunogenic reactions caused by therapeutic delivery. As a non-limiting example, the miRNA binding site can make a polynucleotide of the invention more unstable in antigen presenting cells. Non-limiting examples of these miRNAs include mir-142-5p, mir-142-3p, mir-146a-5p, and mir-146-3p.

In one embodiment, a polynucleotide of the invention comprises at least one miRNA sequence in a region of the polynucleotide that can interact with a RNA binding protein.

In some embodiments, the polynucleotide of the invention (e.g., a RNA, e.g., an mRNA) comprising (i) a sequence-optimized nucleotide sequence (e.g., an ORF) encoding a GALT polypeptide (e.g., the wild-type sequence, functional fragment, or variant thereof) and (ii) a miRNA binding site (e.g., a miRNA binding site that binds to miR-142) and/or a miRNA binding site that binds to miR-126.

In some embodiments, the polynucleotide of the invention comprises a uracil-modified sequence encoding a polypeptide disclosed herein and a miRNA binding site disclosed herein, e.g., a miRNA binding site that binds to miR-126, miR-142, miR-144, miR-146, miR-150, miR-155, miR-16, miR-21, miR-223, miR-24, miR-27 or miR-26a. In some embodiments, the miRNA binding site binds to miR126-3p, miR-142-3p, miR-142-5p, or miR-155. In some embodiments, the polynucleotide of the invention comprises a uracil-modified sequence encoding a polypeptide disclosed herein and at least two different microRNA binding sites, wherein the microRNA is expressed in an immune cell of hematopoietic lineage or a cell that expresses TLR7 and/or TLR8 and secretes pro-inflammatory cytokines and/or chemokines, and wherein the polynucleotide comprises one or more modified nucleobases. In some embodiments, the uracil-modified sequence encoding a GALT polypeptide comprises at least one chemically modified nucleobase, e.g., 5-methoxyuracil. In some embodiments, at least 95% of a type of nucleobase (e.g., uracil) in a uracil-modified sequence encoding a GALT polypeptide of the invention are modified nucleobases. In some embodiments, at least 95% of uricil in a uracil-modified sequence encoding a GALT polypeptide is 5-methoxyuridine. In some embodiments, the polynucleotide (e.g., a RNA, e.g., an mRNA) disclosed herein, e.g., comprising an miRNA binding site, is formulated with a delivery agent comprising, e.g., a compound having the Formula (I), e.g., any of Compounds 1-232, e.g., Compound 18; a compound having the Formula (III), (IV), (V), or (VI), e.g., any of Compounds 233-342, e.g., Compound 236; or a compound having the Formula (VIII), e.g., any of Compounds 419-428, e.g., Compound 428, or any combination thereof. In some embodiments, the delivery agent comprises Compound 18, DSPC, Cholesterol, and Compound 428, e.g., with a mole ratio of about 50:10:38.5:1.5.

In some embodiments, the polynucleotide of the invention comprises a uracil-modified sequence encoding a GALT polypeptide disclosed herein and a miRNA binding site disclosed herein, e.g., a miRNA binding site that binds to miR-142. In some embodiments, the uracil-modified sequence encoding a GALT polypeptide comprises at least one chemically modified nucleobase, e.g., 5-methoxyuracil. In some embodiments, at least 95% of a type of nucleobase (e.g., uricil) in a uracil-modified sequence encoding a GALT polypeptide of the invention are modified nucleobases. In some embodiments, at least 95% of uricil in a uracil-modified sequence encoding a GALT polypeptide is 5-methoxyuridine. In some embodiments, the polynucleotide comprising a nucleotide sequence encoding a GALT polypeptide disclosed herein and a miRNA binding site is formulated with a delivery agent, e.g., a compound having the Formula (I), (III), (IV), (V), (VI), or (VIII) e.g., any of Compounds 1-342, or any of Compounds 1-147, or any of Compounds 233-342, or any of Compounds 419-428, or any of Compounds 18, 236, or any combination thereof, e.g., Compound 428.

13. 3' UTRS

In certain embodiments, a polynucleotide of the present invention (e.g., a polynucleotide comprising a nucleotide sequence encoding a GALT polypeptide of the invention) further comprises a 3' UTR.

3'-UTR is the section of mRNA that immediately follows the translation termination codon and often contains regulatory regions that post-transcriptionally influence gene expression. Regulatory regions within the 3'-UTR can influence polyadenylation, translation efficiency, localization, and stability of the mRNA. In one embodiment, the 3'-UTR useful for the invention comprises a binding site for regulatory proteins or microRNAs.

In certain embodiments, the 3' UTR useful for the polynucleotides of the invention comprises a 3' UTR selected from the group consisting of SEQ ID NO: 53 to 77, 79, 97, 98, 101 to 108, 112, and 163 to 173, or any combination thereof. In some embodiments, the 3' UTR comprises a nucleic acid sequence selected from the group consisting of SEQ ID NOs: 98, 163, or 164 or any combination thereof. In some embodiments, the 3' UTR comprises a nucleic acid sequence of SEQ ID NO: 98. In some embodiments, the 3' UTR comprises a nucleic acid sequence of SEQ ID NO: 163. In some embodiments, the 3' UTR comprises a nucleic acid sequences of SEQ ID NO: 164.

In certain embodiments, the 3' UTR sequence useful for the invention comprises a nucleotide sequence at least about 60%, at least about 70%, at least about 80%, at least about 90%, at least about 95%, at least about 96%, at least about 97%, at least about 98%, at least about 99%, or about 100% identical to a sequence selected from the group consisting of 3' UTR sequences selected from the group consisting of SEQ ID NOs: 53 to 77, 79, 97, 98, 101 to 108, 112, and 163 to 173, or any combination thereof.

14. REGIONS HAVING A 5' CAP

The invention also includes a polynucleotide that comprises both a 5' Cap and a polynucleotide of the present invention (e.g., a polynucleotide comprising a nucleotide sequence encoding a GALT polypeptide).

The 5' cap structure of a natural mRNA is involved in nuclear export, increasing mRNA stability and binds the mRNA Cap Binding Protein (CBP), which is responsible for mRNA stability in the cell and translation competency through the association of CBP with poly(A) binding protein to form the mature cyclic mRNA species. The cap further assists the removal of 5' proximal introns during mRNA splicing.

Endogenous mRNA molecules can be 5'-end capped generating a 5'-ppp-5'-triphosphate linkage between a terminal guanosine cap residue and the 5'-terminal transcribed sense nucleotide of the mRNA molecule. This 5'-guanylate cap can then be methylated to generate an N7-methyl-guanylate residue. The ribose sugars of the terminal and/or anteterminal transcribed nucleotides of the 5' end of the mRNA can optionally also be 2'-O-methylated. 5'-decapping through hydrolysis and cleavage of the guanylate cap structure can target a nucleic acid molecule, such as an mRNA molecule, for degradation.

In some embodiments, the polynucleotides of the present invention (e.g., a polynucleotide comprising a nucleotide sequence encoding a GALT polypeptide) incorporate a cap moiety.

In some embodiments, polynucleotides of the present invention (e.g., a polynucleotide comprising a nucleotide sequence encoding a GALT polypeptide) comprise a non-hydrolyzable cap structure preventing decapping and thus increasing mRNA half-life. Because cap structure hydrolysis requires cleavage of 5'-ppp-5' phosphorodiester linkages, modified nucleotides can be used during the capping reaction. For example, a Vaccinia Capping Enzyme from New England Biolabs (Ipswich, Mass.) can be used with α-thio-guanosine nucleotides according to the manufacturer's instructions to create a phosphorothioate linkage in the 5'-ppp-5' cap. Additional modified guanosine nucleotides can be used such as α-methyl-phosphonate and seleno-phosphate nucleotides.

Additional modifications include, but are not limited to, 2'-O-methylation of the ribose sugars of 5'-terminal and/or 5'-anteterminal nucleotides of the polynucleotide (as mentioned above) on the 2'-hydroxyl group of the sugar ring. Multiple distinct 5'-cap structures can be used to generate the 5'-cap of a nucleic acid molecule, such as a polynucleotide that functions as an mRNA molecule. Cap analogs, which herein are also referred to as synthetic cap analogs, chemical caps, chemical cap analogs, or structural or functional cap analogs, differ from natural (i.e., endogenous, wild-type or physiological) 5'-caps in their chemical structure, while retaining cap function. Cap analogs can be chemically (i.e., non-enzymatically) or enzymatically synthesized and/or linked to the polynucleotides of the invention.

For example, the Anti-Reverse Cap Analog (ARCA) cap contains two guanines linked by a 5'-5'-triphosphate group, wherein one guanine contains an N7 methyl group as well as a 3'-O-methyl group (i.e., N7,3'-O-dimethyl-guanosine-5'-triphosphate-5'-guanosine ($m^7$G-3'mppp-G; which can equivalently be designated 3' O-Me-m7G(5')ppp(5')G). The 3'-O atom of the other, unmodified, guanine becomes linked to the 5'-terminal nucleotide of the capped polynucleotide. The N7- and 3'-O-methlyated guanine provides the terminal moiety of the capped polynucleotide.

Another exemplary cap is mCAP, which is similar to ARCA but has a 2'-O-methyl group on guanosine (i.e., N7,2'-O-dimethyl-guanosine-5'-triphosphate-5'-guanosine, m7Gm-ppp-G).

In some embodiments, the cap is a dinucleotide cap analog. As a non-limiting example, the dinucleotide cap analog can be modified at different phosphate positions with a boranophosphate group or a phosphoroselenoate group such as the dinucleotide cap analogs described in U.S. Pat. No. 8,519,110, the contents of which are herein incorporated by reference in its entirety.

In another embodiment, the cap is a cap analog is a N7-(4-chlorophenoxyethyl) substituted dinucleotide form of a cap analog known in the art and/or described herein. Non-limiting examples of a N7-(4-chlorophenoxyethyl) substituted dinucleotide form of a cap analog include a N7-(4-chlorophenoxyethyl)-G(5')ppp(5')G and a N7-(4-chlorophenoxyethyl)-$m^{3'-O}$G(5)ppp(5')G cap analog (See, e.g., the various cap analogs and the methods of synthesizing cap analogs described in Kore et al. Bioorganic & Medicinal Chemistry 2013 21:4570-4574; the contents of which are herein incorporated by reference in its entirety). In another embodiment, a cap analog of the present invention is a 4-chloro/bromophenoxyethyl analog.

While cap analogs allow for the concomitant capping of a polynucleotide or a region thereof, in an in vitro transcription reaction, up to 20% of transcripts can remain uncapped. This, as well as the structural differences of a cap analog from an endogenous 5'-cap structures of nucleic acids produced by the endogenous, cellular transcription machinery, can lead to reduced translational competency and reduced cellular stability.

Polynucleotides of the invention (e.g., a polynucleotide comprising a nucleotide sequence encoding a GALT polypeptide) can also be capped post-manufacture (whether IVT or chemical synthesis), using enzymes, in order to generate more authentic 5'-cap structures. As used herein, the phrase “more authentic” refers to a feature that closely mirrors or mimics, either structurally or functionally, an endogenous or wild type feature. That is, a “more authentic” feature is better representative of an endogenous, wild-type, natural or physiological cellular function and/or structure as compared to synthetic features or analogs, etc., of the prior art, or which outperforms the corresponding endogenous, wild-type, natural or physiological feature in one or more respects. Non-limiting examples of more authentic 5'cap structures of the present invention are those that, among other things, have enhanced binding of cap binding proteins, increased half-life, reduced susceptibility to 5' endonucleases and/or reduced 5'decapping, as compared to synthetic 5'cap structures known in the art (or to a wild-type, natural or physiological 5'cap structure). For example, recombinant Vaccinia Virus Capping Enzyme and recombinant 2'-O-methyltransferase enzyme can create a canonical 5'-5'-triphosphate linkage between the 5'-terminal nucleotide of a polynucleotide and a guanine cap nucleotide wherein the cap guanine contains an N7 methylation and the 5'-terminal nucleotide of the mRNA contains a 2'-O-methyl. Such a structure is termed the Cap1 structure. This cap results in a higher translational-competency and cellular stability and a reduced activation of cellular pro-inflammatory cytokines, as compared, e.g., to other 5'cap analog structures known in the art. Cap structures include, but are not limited to, 7mG(5')ppp(5')N, pN2p (cap 0), 7mG(5')ppp(5')NlmpNp (cap 1), and 7mG(5')-ppp(5')NlmpN2mp (cap 2).

As a non-limiting example, capping chimeric polynucleotides post-manufacture can be more efficient as nearly 100% of the chimeric polynucleotides can be capped. This is in contrast to ~80% when a cap analog is linked to a chimeric polynucleotide in the course of an in vitro transcription reaction.

According to the present invention, 5' terminal caps can include endogenous caps or cap analogs. According to the present invention, a 5' terminal cap can comprise a guanine analog. Useful guanine analogs include, but are not limited to, inosine, N1-methyl-guanosine, 2'fluoro-guanosine, 7-deaza-guanosine, 8-oxo-guanosine, 2-amino-guanosine, LNA-guanosine, and 2-azido-guanosine.

15. POLY-A TAILS

In some embodiments, the polynucleotides of the present disclosure (e.g., a polynucleotide comprising a nucleotide sequence encoding a GALT polypeptide) further comprise a poly-A tail. In further embodiments, terminal groups on the poly-A tail can be incorporated for stabilization. In other embodiments, a poly-A tail comprises des-3' hydroxyl tails.

During RNA processing, a long chain of adenine nucleotides (poly-A tail) can be added to a polynucleotide such as an mRNA molecule in order to increase stability. Immediately after transcription, the 3' end of the transcript can be cleaved to free a 3' hydroxyl. Then poly-A polymerase adds a chain of adenine nucleotides to the RNA. The process, called polyadenylation, adds a poly-A tail that can be between, for example, approximately 80 to approximately 250 residues long, including approximately 80, 90, 100, 110, 120, 130, 140, 150, 160, 170, 180, 190, 200, 210, 220, 230, 240 or 250 residues long.

PolyA tails can also be added after the construct is exported from the nucleus.

According to the present invention, terminal groups on the poly A tail can be incorporated for stabilization. Polynucleotides of the present invention can include des-3' hydroxyl tails. They can also include structural moieties or 2'-Omethyl modifications as taught by Junjie Li, et al. (Current Biology, Vol. 15, 1501-1507, Aug. 23, 2005, the contents of which are incorporated herein by reference in its entirety).

The polynucleotides of the present invention can be designed to encode transcripts with alternative polyA tail structures including histone mRNA. According to Norbury, “Terminal uridylation has also been detected on human replication-dependent histone mRNAs. The turnover of these mRNAs is thought to be important for the prevention of potentially toxic histone accumulation following the completion or inhibition of chromosomal DNA replication. These mRNAs are distinguished by their lack of a 3' poly(A) tail, the function of which is instead assumed by a stable stem-loop structure and its cognate stem-loop binding protein (SLBP); the latter carries out the same functions as those of PABP on polyadenylated mRNAs” (Norbury, “Cytoplasmic RNA: a case of the tail wagging the dog,” Nature Reviews Molecular Cell Biology; AOP, published online 29 Aug. 2013; doi:10.1038/nrm3645) the contents of which are incorporated herein by reference in its entirety.

Unique poly-A tail lengths provide certain advantages to the polynucleotides of the present invention. Generally, the length of a poly-A tail, when present, is greater than 30 nucleotides in length. In another embodiment, the poly-A tail is greater than 35 nucleotides in length (e.g., at least or greater than about 35, 40, 45, 50, 55, 60, 70, 80, 90, 100, 120, 140, 160, 180, 200, 250, 300, 350, 400, 450, 500, 600, 700, 800, 900, 1,000, 1,100, 1,200, 1,300, 1,400, 1,500, 1,600, 1,700, 1,800, 1,900, 2,000, 2,500, and 3,000 nucleotides).

In some embodiments, the polynucleotide or region thereof includes from about 30 to about 3,000 nucleotides (e.g., from 30 to 50, from 30 to 100, from 30 to 250, from 30 to 500, from 30 to 750, from 30 to 1,000, from 30 to 1,500, from 30 to 2,000, from 30 to 2,500, from 50 to 100, from 50 to 250, from 50 to 500, from 50 to 750, from 50 to 1,000, from 50 to 1,500, from 50 to 2,000, from 50 to 2,500, from 50 to 3,000, from 100 to 500, from 100 to 750, from 100 to 1,000, from 100 to 1,500, from 100 to 2,000, from 100 to 2,500, from 100 to 3,000, from 500 to 750, from 500 to 1,000, from 500 to 1,500, from 500 to 2,000, from 500 to 2,500, from 500 to 3,000, from 1,000 to 1,500, from 1,000 to 2,000, from 1,000 to 2,500, from 1,000 to 3,000, from 1,500 to 2,000, from 1,500 to 2,500, from 1,500 to 3,000, from 2,000 to 3,000, from 2,000 to 2,500, and from 2,500 to 3,000).

In some embodiments, the poly-A tail is designed relative to the length of the overall polynucleotide or the length of a particular region of the polynucleotide. This design can be based on the length of a coding region, the length of a particular feature or region or based on the length of the ultimate product expressed from the polynucleotides.

In this context, the poly-A tail can be 10, 20, 30, 40, 50, 60, 70, 80, 90, or 100% greater in length than the polynucleotide or feature thereof. The poly-A tail can also be designed as a fraction of the polynucleotides to which it belongs. In this context, the poly-A tail can be 10, 20, 30, 40, 50, 60, 70, 80, or 90% or more of the total length of the construct, a construct region or the total length of the construct minus the poly-A tail. Further, engineered binding sites and conjugation of polynucleotides for Poly-A binding protein can enhance expression.

Additionally, multiple distinct polynucleotides can be linked together via the PABP (Poly-A binding protein) through the 3'-end using modified nucleotides at the 3'-terminus of the poly-A tail. Transfection experiments can be conducted in relevant cell lines at and protein production can be assayed by ELISA at 12 hr, 24 hr, 48 hr, 72 hr and day 7 post-transfection.

In some embodiments, the polynucleotides of the present invention are designed to include a polyA-G Quartet region. The G-quartet is a cyclic hydrogen bonded array of four guanine nucleotides that can be formed by G-rich sequences in both DNA and RNA. In this embodiment, the G-quartet is incorporated at the end of the poly-A tail. The resultant polynucleotide is assayed for stability, protein production and other parameters including half-life at various time points. It has been discovered that the polyA-G quartet results in protein production from an mRNA equivalent to at least 75% of that seen using a poly-A tail of 120 nucleotides alone (SEQ ID NO: 176).

16. START CODON REGION

The invention also includes a polynucleotide that comprises both a start codon region and the polynucleotide described herein (e.g., a polynucleotide comprising a nucleotide sequence encoding a GALT polypeptide). In some embodiments, the polynucleotides of the present invention can have regions that are analogous to or function like a start codon region.

In some embodiments, the translation of a polynucleotide can initiate on a codon that is not the start codon AUG. Translation of the polynucleotide can initiate on an alternative start codon such as, but not limited to, ACG, AGG, AAG, CTG/CUG, GTG/GUG, ATA/AUA, ATT/AUU, TTG/UUG (see Touriol et al. Biology of the Cell 95 (2003) 169-178 and Matsuda and Mauro PLoS ONE, 2010 5:11; the contents of each of which are herein incorporated by reference in its entirety).

As a non-limiting example, the translation of a polynucleotide begins on the alternative start codon ACG. As another non-limiting example, polynucleotide translation begins on the alternative start codon CTG or CUG. As yet another non-limiting example, the translation of a polynucleotide begins on the alternative start codon GTG or GUG.

Nucleotides flanking a codon that initiates translation such as, but not limited to, a start codon or an alternative start codon, are known to affect the translation efficiency, the length and/or the structure of the polynucleotide. (See, e.g., Matsuda and Mauro PLoS ONE, 2010 5:11; the contents of which are herein incorporated by reference in its entirety). Masking any of the nucleotides flanking a codon that initiates translation can be used to alter the position of translation initiation, translation efficiency, length and/or structure of a polynucleotide.

In some embodiments, a masking agent can be used near the start codon or alternative start codon in order to mask or hide the codon to reduce the probability of translation initiation at the masked start codon or alternative start codon. Non-limiting examples of masking agents include antisense locked nucleic acids (LNA) polynucleotides and exon junction complexes (EJCs) (See, e.g., Matsuda and Mauro describing masking agents LNA polynucleotides and EJCs (PLoS ONE, 2010 5:11); the contents of which are herein incorporated by reference in its entirety).

In another embodiment, a masking agent can be used to mask a start codon of a polynucleotide in order to increase the likelihood that translation will initiate on an alternative start codon. In some embodiments, a masking agent can be used to mask a first start codon or alternative start codon in order to increase the chance that translation will initiate on a start codon or alternative start codon downstream to the masked start codon or alternative start codon.

In some embodiments, a start codon or alternative start codon can be located within a perfect complement for a miRNA binding site. The perfect complement of a miRNA binding site can help control the translation, length and/or structure of the polynucleotide similar to a masking agent. As a non-limiting example, the start codon or alternative start codon can be located in the middle of a perfect complement for a miRNA binding site. The start codon or alternative start codon can be located after the first nucleotide, second nucleotide, third nucleotide, fourth nucleotide, fifth nucleotide, sixth nucleotide, seventh nucleotide, eighth nucleotide, ninth nucleotide, tenth nucleotide, eleventh nucleotide, twelfth nucleotide, thirteenth nucleotide, fourteenth nucleotide, fifteenth nucleotide, sixteenth nucleotide, seventeenth nucleotide, eighteenth nucleotide, nineteenth nucleotide, twentieth nucleotide or twenty-first nucleotide.

In another embodiment, the start codon of a polynucleotide can be removed from the polynucleotide sequence in order to have the translation of the polynucleotide begin on a codon that is not the start codon. Translation of the polynucleotide can begin on the codon following the removed start codon or on a downstream start codon or an alternative start codon. In a non-limiting example, the start codon ATG or AUG is removed as the first 3 nucleotides of the polynucleotide sequence in order to have translation initiate on a downstream start codon or alternative start codon. The polynucleotide sequence where the start codon was removed can further comprise at least one masking agent for the downstream start codon and/or alternative start codons in order to control or attempt to control the initiation of translation, the length of the polynucleotide and/or the structure of the polynucleotide.

17. STOP CODON REGION

The invention also includes a polynucleotide that comprises both a stop codon region and the polynucleotide described herein (e.g., a polynucleotide comprising a nucleotide sequence encoding a GALT polypeptide). In some embodiments, the polynucleotides of the present invention can include at least two stop codons before the 3' untranslated region (UTR). The stop codon can be selected from TGA, TAA and TAG in the case of DNA, or from UGA, UAA and UAG in the case of RNA. In some embodiments, the polynucleotides of the present invention include the stop codon TGA in the case or DNA, or the stop codon UGA in the case of RNA, and one additional stop codon. In a further embodiment the addition stop codon can be TAA or UAA. In another embodiment, the polynucleotides of the present invention include three consecutive stop codons, four stop codons, or more.

18. INSERTIONS AND SUBSTITUTIONS

The invention also includes a polynucleotide of the present disclosure that further comprises insertions and/or substitutions.

In some embodiments, the 5' UTR of the polynucleotide can be replaced by the insertion of at least one region and/or string of nucleosides of the same base. The region and/or string of nucleotides can include, but is not limited to, at least 3, at least 4, at least 5, at least 6, at least 7 or at least 8 nucleotides and the nucleotides can be natural and/or unnatural. As a non-limiting example, the group of nucleotides can include 5-8 adenine, cytosine, thymine, a string of any of the other nucleotides disclosed herein and/or combinations thereof.

In some embodiments, the 5' UTR of the polynucleotide can be replaced by the insertion of at least two regions and/or strings of nucleotides of two different bases such as, but not limited to, adenine, cytosine, thymine, any of the other nucleotides disclosed herein and/or combinations thereof. For example, the 5' UTR can be replaced by inserting 5-8 adenine bases followed by the insertion of 5-8 cytosine bases. In another example, the 5' UTR can be replaced by inserting 5-8 cytosine bases followed by the insertion of 5-8 adenine bases.

In some embodiments, the polynucleotide can include at least one substitution and/or insertion downstream of the transcription start site that can be recognized by an RNA polymerase. As a non-limiting example, at least one substitution and/or insertion can occur downstream of the transcription start site by substituting at least one nucleic acid in the region just downstream of the transcription start site (such as, but not limited to, +1 to +6). Changes to region of nucleotides just downstream of the transcription start site can affect initiation rates, increase apparent nucleotide triphosphate (NTP) reaction constant values, and increase the dissociation of short transcripts from the transcription complex curing initial transcription (Brieba et al, Biochemistry (2002) 41: 5144-5149; herein incorporated by reference in its entirety). The modification, substitution and/or insertion of at least one nucleoside can cause a silent mutation of the sequence or can cause a mutation in the amino acid sequence.

In some embodiments, the polynucleotide can include the substitution of at least 1, at least 2, at least 3, at least 4, at least 5, at least 6, at least 7, at least 8, at least 9, at least 10, at least 11, at least 12 or at least 13 guanine bases downstream of the transcription start site.

In some embodiments, the polynucleotide can include the substitution of at least 1, at least 2, at least 3, at least 4, at least 5 or at least 6 guanine bases in the region just downstream of the transcription start site. As a non-limiting example, if the nucleotides in the region are GGGAGA, the guanine bases can be substituted by at least 1, at least 2, at least 3 or at least 4 adenine nucleotides. In another non-limiting example, if the nucleotides in the region are GGGAGA the guanine bases can be substituted by at least 1, at least 2, at least 3 or at least 4 cytosine bases. In another non-limiting example, if the nucleotides in the region are GGGAGA the guanine bases can be substituted by at least 1, at least 2, at least 3 or at least 4 thymine, and/or any of the nucleotides described herein.

In some embodiments, the polynucleotide can include at least one substitution and/or insertion upstream of the start codon. For the purpose of clarity, one of skill in the art would appreciate that the start codon is the first codon of the protein coding region whereas the transcription start site is the site where transcription begins. The polynucleotide can include, but is not limited to, at least 1, at least 2, at least 3, at least 4, at least 5, at least 6, at least 7 or at least 8 substitutions and/or insertions of nucleotide bases. The nucleotide bases can be inserted or substituted at 1, at least 1, at least 2, at least 3, at least 4 or at least 5 locations upstream of the start codon. The nucleotides inserted and/or substituted can be the same base (e.g., all A or all C or all T or all G), two different bases (e.g., A and C, A and T, or C and T), three different bases (e.g., A, C and T or A, C and T) or at least four different bases.

As a non-limiting example, the guanine base upstream of the coding region in the polynucleotide can be substituted with adenine, cytosine, thymine, or any of the nucleotides described herein. In another non-limiting example the substitution of guanine bases in the polynucleotide can be designed so as to leave one guanine base in the region downstream of the transcription start site and before the start codon (see Esvelt et al. Nature (2011) 472(7344):499-503; the contents of which is herein incorporated by reference in its entirety). As a non-limiting example, at least 5 nucleotides can be inserted at 1 location downstream of the transcription start site but upstream of the start codon and the at least 5 nucleotides can be the same base type.

19. POLYNUCLEOTIDE COMPRISING AN MRNA ENCODING A GALT POLYPEPTIDE

In certain embodiments, a polynucleotide of the present disclosure, for example a polynucleotide comprising an mRNA nucleotide sequence encoding a GALT polypeptide, comprises from 5' to 3' end:

(i) a 5' cap provided above;

(ii) a 5' UTR, such as the sequences provided above;

(iii) an open reading frame encoding a GALT polypeptide, e.g., a sequence optimized nucleic acid sequence encoding GALT disclosed herein;

(iv) at least one stop codon;

(v) a 3' UTR, such as the sequences provided above; and (vi) a poly-A tail provided above.

In some embodiments, the polynucleotide further comprises a miRNA binding site, e.g, a miRNA binding site that binds to miRNA-142. In some embodiments, the 5' UTR comprises the miRNA binding site.

In some embodiments, a polynucleotide of the present disclosure comprises a nucleotide sequence encoding a polypeptide sequence at least 70%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to the protein sequence of a wild type GALT (e.g, isoform 1 or 2).

In some embodiments, a polynucleotide of the present disclosure, for example a polynucleotide comprising an mRNA nucleotide sequence encoding a polypeptide, comprises (1) a 5' cap provided above, for example, CAP1, (2) a nucleotide sequence selected form the group consisting of SEQ ID NOs:143 and 145, and (3) a poly-A tail provided above, for example, a poly-A tail of about 100 residues, wherein SEQ ID NO: 143 comprises from 5' to 3' end: 5' UTR of SEQ ID NO:35, GALT polypeptide ORF of SEQ ID NO: 124, and 3' UTR of SEQ ID NO: 98;

SEQ ID NO: 145 comprises from 5' to 3' end: 5' UTR of SEQ ID NO:35, GALT polypeptide ORF of SEQ ID NO: 126, and 3' UTR of SEQ ID NO: 98;

In some embodiments, a polynucleotide of the present disclosure, for example a polynucleotide comprising an mRNA nucleotide sequence encoding a GALT polypeptide, comprises (1) a 5' cap provided above, for example, CAP1, (2) a nucleotide sequence selected form the group consisting of SEQ ID NO: 132 to 142, 144, and 146 to 150, and (3) a poly-A tail provided above, for example, a poly A tail of ~100 residues, wherein SEQ ID NO: 132 comprises from 5' to 3' end: 5' UTR of SEQ ID NO: 35, GALT polypeptide ORF of SEQ ID NO: 113, and 3'UTR of SEQ ID NO: 98;

SEQ ID NO: 133 comprises from 5' to 3' end: 5' UTR of SEQ ID NO: 35, GALT polypeptide ORF of SEQ ID NO: 114, and 3'UTR of SEQ ID NO: 98;

SEQ ID NO: 134 comprises from 5' to 3' end: 5' UTR of SEQ ID NO:35, GALT polypeptide ORF of SEQ ID NO: 115, and 3'UTR of SEQ ID NO: 98;

SEQ ID NO: 135 comprises from 5' to 3' end: 5' UTR of SEQ ID NO:35, GALT polypeptide ORF of SEQ ID NO: 116, and 3'UTR of SEQ ID NO: 98;

SEQ ID NO: 136 comprises from 5' to 3' end: 5' UTR of SEQ ID NO:35, GALT polypeptide ORF of SEQ ID NO: 117, and 3'UTR of SEQ ID NO: 98;

SEQ ID NO: 137 comprises from 5' to 3' end: 5' UTR of SEQ ID NO:35, GALT polypeptide ORF of SEQ ID NO: 118, and 3'UTR of SEQ ID NO: 98;

SEQ ID NO: 138 comprises from 5' to 3' end: 5' UTR of SEQ ID NO:35, GALT polypeptide ORF of SEQ ID NO: 119, and 3'UTR of SEQ ID NO: 98;

SEQ ID NO: 139 comprises from 5' to 3' end: 5' UTR of SEQ ID NO:35, GALT polypeptide ORF of SEQ ID NO: 120, and 3'UTR of SEQ ID NO: 98;

SEQ ID NO: 140 comprises from 5' to 3' end: 5' UTR of SEQ ID NO:35, GALT polypeptide ORF of SEQ ID NO: 121, and 3'UTR of SEQ ID NO: 98;

SEQ ID NO: 141 comprises from 5' to 3' end: 5' UTR of SEQ ID NO:35, GALT polypeptide ORF of SEQ ID NO: 122, and 3'UTR of SEQ ID NO: 98;

SEQ ID NO: 142 comprises from 5' to 3' end: 5' UTR of SEQ ID NO:35, GALT polypeptide ORF of SEQ ID NO: 123, and 3'UTR of SEQ ID NO: 98;

SEQ ID NO: 144 comprises from 5' to 3' end: 5' UTR of SEQ ID NO:35, GALT polypeptide ORF of SEQ ID NO: 125, and 3'UTR of SEQ ID NO: 98;

SEQ ID NO: 146 comprises from 5' to 3' end: 5' UTR of SEQ ID NO:35, GALT polypeptide ORF of SEQ ID NO: 127, and 3'UTR of SEQ ID NO: 98;

SEQ ID NO: 147 comprises from 5' to 3' end: 5' UTR of SEQ ID NO:35, GALT polypeptide ORF of SEQ ID NO: 128, and 3'UTR of SEQ ID NO: 98;

SEQ ID NO: 148 comprises from 5' to 3' end: 5' UTR of SEQ ID NO:35, GALT polypeptide ORF of SEQ ID NO: 129, and 3'UTR of SEQ ID NO: 98;

SEQ ID NO: 149 comprises from 5' to 3' end: 5' UTR of SEQ ID NO:35, GALT polypeptide ORF of SEQ ID NO: 130, and 3'UTR of SEQ ID NO: 98; and SEQ ID NO: 150 comprises from 5' to 3' end: 5' UTR of SEQ ID NO:35, GALT polypeptide ORF of SEQ ID NO: 131, and 3'UTR of SEQ ID NO: 98.

TABLE 5 mRNA Constructs

| SEQ ID NO | Construct | Sequence (5' UTR = bold underline: 3' UTR comprimising a stop codon = bold italics) |
|---|---|---|
| 132 | #1 | **GGGAAAUAAGAGAGAAAAGAAGAGUAAGAAGAAAUAUAAGAGCCA**<br>**CC**AUGUCUAGGAGCGGGACCGACCCCCAGCAGCGGCAGCAGGCCAGC<br>GAGGCCGACGCCGCCGCGGCCACCUUCAGGGCCAACGACCAUCAACA<br>CAUCAGGUAUAACCCCCUCCAGGACGAGUGGGUGUUGGUGUCCGCCC<br>AUCGGAUGAAGAGGCCCUGGCAGGGCCAGGUGGAGCCCCAGCUCCUG<br>AAGACCGUGCCCCGGCACGACCCCCUCAACCCCCUGUGCCCCGGCGC<br>GAUCCGCGCCAACGGCGAGGUGAACCCCCAGUAUGACAGCACGUUCC<br>UGUUCGACAACGACULCCCCGCCCUGCAGCCCGACGCCCCCAGCCCC<br>GGCCCAAGCGACCAUCCCCUGUUCCAGGCCAAGUCCGCCAGGGGCGU<br>GUGUAAGGUGAUGUGCUUCCACCCAUGGUCCGACGUGACCCUGCCCC<br>UGAUGAGCGUGCCCGAGAUCCGCGCCGUGGUGGACGCCUGGGCCAGC<br>GUGACCGAGGAGCUGGGGGCCCAGUACCCUUGGGUGCAAAUCUUCG<br>AGAAUAAGGGCGCCAUGAUGGGCUGCUCCAACCCCCACCCCCACUGU<br>CAGGUGUGGGCCAGCAGUUUCCUGCCCGACAUCGCCCAGCGCGAGGA<br>GCGGUCACAGCAGGCCUACAAGAGCCAACACGGCGAACCUCUGCUCA<br>UGGAGUACAGCAGGCAGGAACUGCUGCGGAAGGAGAGGCUGGUCCU<br>GACCAGCGAGCACUGGCUGGUGCUGGUGCCCUUCUGGGCCACCUGGC<br>CCUACCAGACACUGCUGCUGCCUAGGCGACACGUGCGUCGGCUGCCC<br>GAGCUGACCCCUGCCGAAAGGGACGACCUGGCCAGCAUCAUGAAGAA<br>GCUGCUCACCAAGUACGACAACCUGUUUGAAACCAGCUUCCCCUACA<br>GCAUGGGCUGGCACGGCGCACCUACCGGCAGCGAGGCCGGCGCCAAC<br>UGGAACCACUGGCAGCUGCAUGCCCACUACUAUCCGCCCCUCCUCAG<br>GAGCGCCACCGUGCGCAAGUUCAUGGUGGGCUAUGAGAUGCUGGCG<br>CAGGCCCAGCGUGACCUGACCCCCGAGCAGGCCGCCGAGAGGCUGCG<br>UGCCCUGCCUGAGGUGCACUACCACCUGGGGCAGAAGGACAGAGAAA<br>CUGCGACCAUCGCC***UGAUAAUAGUCCAUAAAGUAGGAAACACUACAGC***<br>***UGGAGCCUCGGUGGCCAUGCUUCUUGCCCCUUGGGCCUCCCCCCAGC***<br>***CCCUCCUCCCCUUCCUGCACCCGUACCCCCGCAUUAUUACUCACGGU***<br>***ACGAGUGGUCUUUGAAUAAAGUCUGAGUGGGCGGC*** |
| 133 | #2 | **GGGAAAUAAGAGAGAAAAGAAGAGUAAGAAGAAAUAUAAGAGCCA**<br>**CC**AUGAGCAGGUCCGGCACCGACCCCCAGCAGAGGCAGCAAGCCUCC<br>GGGAAAUAAGAGAGAAAAGAAGAGUAAGAAGAAAUAUAAGAGCCA<br>CCAUGAGCAGGUCCGGCACCGACCCCCAGCAGAGGCAGCAAGCCUCC<br>GAGGCCGACGCCGCCGCGGCCACCUUCCGGGCCAACGACCAUCAGCA<br>UAUCAGGUAUAACCCCCUUCAGGACGAGUGGGUGCUCGUGAGCGCCC<br>ACCGGAUGAAGCGCCCCUGGCAGGGGCAGGUCGAGCCCCAGCUGCUG<br>AAGACCGUGCCCAGGCACGAUCCGCUGAACCCGCUGUGCCCCGGGGC<br>CAUCCGGGCCAACGGGGAGGUGAACCCCCAGUACGACAGCACCUUCC<br>UGUUCGACAACGACUUCCCCGCCCUGCAGCCCGAUGCCCCCAGCCCC<br>GGGCCCUCCGACCACCCCCUGUUCCAGGCCAAGAGCGCCAGAGGCGU<br>GUGCAAGGUCAUGUGCUUUCAUCCCUGGAGCGACGUGACCCUGCCCC<br>UGAUGUCCGUGCCCGAGAUCAGAGCUGUCGUGGACGCCUGGGCCUCC<br>GUGACCGAGGAGCUCGGCGCCCAGUACCCCUGGGUGCAGAUCUUCGA |

TABLE 5-continued

| mRNA Constructs | | |
|---|---|---|
| SEQ ID NO | Construct | Sequence (5' UTR = bold underline: 3' UTR comprimising a stop codon = bold italics) |
| | | GAACAAAGGCGCCAUGAUGGGCUGCAGCAACCCCCACCCACACUGCC<br>AGGUGUGGGCCAGCAGCUUCCUGCCCGACAUCGCCCAGAGAGAGGAG<br>AGGAGCCAGCAGGCCUAUAAGAGCCAGCAUGGCGAGCCCCUGCUGAU<br>GGAGUACAGCAGACAGGAGCUGCUGAGGAAAGAGAGGCUGGUGCUG<br>ACAAGCGAGCACUGGCUGGUGCUGGUGCCCUUUUGGGCCACUUGGCC<br>AUACCAGACCCUGCUGCUGCCCCGGCGGCAUGUCAGGAGACUGCCUG<br>AGCUGACUCCCGCCGAGCGGGAUGACCUGGCCAGCAUCAUGAAGAAG<br>CUGCUCACCAAAUACGACAACCUCUUCGAAACCAGCUUCCCCUACAG<br>CAUGGGGUGGCACGGGGCCCCCACCGGCAGCGAAGCCGGAGCCAAUU<br>GGAAUCAUUGGCAGCUCCAUGCCCAUUACUAUCCGCCCCUGCUCAGA<br>AGCGCCACCGUGCGGAAGUUCAUGGUGGGCUACGAGAUGCUCGCCCA<br>GGCCCAGCGGGACCUGACCCCCGAGCAGGCUGCCGAGCGGCUGAGGG<br>CCCUGCCCGAGGUGCACUAUCACCUGGGCCAGAAAGAUAGGGAAACA<br>GCCACUAUCGCC***UGAUAAUAGUCCAUAAAGUAGGAAACACUACAGCUG<br>GAGCCUCGGUGGCCAUGCUUCUUGCCCCUUGGGCCUCCCCCCAGCCCC<br>UCCUCCCCUUCCUGCACCCGUACCCCCCGCAUUAUUACUCACGGUACG<br>AGUGGUCUUUGAAUAAAGUCUGAGUGGGCGGC*** |
| 134 | #3 | **GGGAAAUAAGAGAGAAAAGAAGAGUAAGAAGAAAUAUAAGAGCCA<br>CC**AUGAGCAGGAGCGGCACCGACCCCCAGCAGAGGCAGCAGGCCAGC<br>GAAGCCGACGCCGCCGCCGCCACCUUCCGGGCCAACGAUCACCAGCA<br>CAUCCGCUACAACCCUCUCCAGGACGAGUGGGUGCUCGUGAGCGCCC<br>ACAGGAUGAAGCGGCCCUGGCAGGGCCAGGUGGAGCCCCAGCUCCUG<br>AAGACCGUGCCCAGACACGACCCCCUGAACCCGCUCUGCCCCGGCGC<br>CAUCAGAGCCAACGGCGAGGUGAACCCCCAGUACGACAGCACCUUCC<br>UGUUCGACAACGACUUCCCCGCCCUCCAGCCCGAUGCCCCCAGCCCC<br>GGUCCCUCCGACCAUCCCCUGUUCCAGGCCAAGUCCGCCAGAGGCGU<br>GUGCAAGGUGAUGUGCUUCCACCCCUGGAGCGACGUGACCCUCCCCC<br>UGAUGUCGGUGCCCGAAAUCAGGGCCGUGGUGGACGCCUGGGCCAGC<br>GUGACCGAGGAGCUGGGGGCCCAGUAUCCCUGGGUCCAGAUCUUCGA<br>GAACAAGGGGGCCAUGAUGGGCUGUAGCAACCCCCACCCACACUGCC<br>AGGUGUGGGCCUCCUCCUUCCUGCCCGACAUCGCCCAAAGGGAGGAG<br>CGGUCCCAGCAAGCCUACAAGUCCCAGCACGGUGAGCCCCUGCUGAU<br>GGAAUAUAGCAGACAGGAGCUGCUGAGGAAGGAGCGCCUGGUCCUG<br>ACCAGCGAGCACUGGCUGGUGCUGGUCCCCUUUUGGGCCACCUGGCC<br>CUACCAGACGCUGCUGCUGCCUCGCAGACAUGUGAGGAGGCUGCCGG<br>AGCUGACCCCCGCCGAGCGGGACGACCUGGCAAGCAUCAUGAAGAAG<br>CUGCUGACCAAGUACGACAACCUGUUCGAGACUUCCUUCCCGUACAG<br>CAUGGGCUGGCACGGCGCCCCGACCGGAAGCGAGGCCGGCGCGAACU<br>GGAACCACUGGCAGCUGCAUGCGCAUUACUACCCGCCCCUGCUGCGG<br>UCAGCCACCGUCCGCAAGUUCAUGGUGGGCUACGAAAUGCUGGCCCA<br>GGCGCAGAGGGACCUCACCCCCGAGCAGGCCGCCGAAAGACUGCGUG<br>CGCUGCCGGAGGUGCACUACCACCUGGGCCAGAAGGACCGCGAAACC<br>GCGACCAUCGCA***UGAUAAUAGUCCAUAAAGUAGGAAACACUACAGCUG<br>GAGCCUCGGUGGCCAUGCUUCUUGCCCCUUGGGCCUCCCCCCAGCCCC<br>UCCUCCCCUUCCUGCACCCGUACCCCCCGCAUUAUUACUCACGGUACG<br>AGUGGUCUUUGAAUAAAGUCUGAGUGGGCGGC*** |
| 135 | #4 | **GGGAAAUAAGAGAGAAAAGAAGAGUAAGAAGAAAUAUAAGAGCCA<br>CC**AUGUCACGGAGCGGCACCGACCCGCAGCAGAGGCAGCAGGCCAGC<br>GAGGCAGACGCCGCCGCCGCCACCUUCAGGGCCAACGACCAUCAGCA<br>CAUCAGAUACAACCCCCUACAGGACGAGUGGGUGCUCGUCAGCGCCC<br>ACAGAAUGAAGCGGCCCUGGCAGGGGCAGGUGGAGCCCCAGCUCCUG<br>AAGACCGUGCCCAGGCACGACCCCCUCAAUCCCCUGUGCCCUGGCGC<br>CAUUAGGGCCAACGGCGAGGUGAACCCCCAGUACGACUCAACCUUCC<br>UGUUUGACAACGACUUCCCCGCCCUGCAGCCCGAUGCCCCGAGCCCC<br>GGGCCCAGCGACCACCCCCUGUUCCAGGCCAAGUCGGCCAGGGGCGU<br>GUGCAAGGUGAUGUGCUUCCACCCCUGGAGCGAUGUCACCCUGCCCC<br>UGAUGUCGGUGCCCGAGAUCCGCGCCGUGGUGGACGCCUGGGCCAGC<br>GUGACCGAGGAGCUGGGCGCCCAAUACCCCUGGGUGCAGAUCUUUGA<br>GAACAAAGGCGCCAUGAUGGGCUGUAGCAACCCCCACCCCCACUGUC<br>AGGUGUGGGCCAGCAGCUUUCUGCCCGACAUCGCCCAGAGGGAGGAG<br>CGCUCCCAGCAGGCUUACAAGAGCCAGCACGGAGAGCCCCUGCUCAU<br>GGAGUACUCGCGACAGGAGCUGCUCCGGAAGGAACGGCUGGUCCUG<br>ACCUCCGAGCACUGGCUCGUGCUGGUGCCGUUCUGGGCCACAUGGCC<br>CUACCAGACCCUGCUGCUACCCCGCAGACACGUUCGCCGACUGCCCG<br>AGCUGACCCCUGCCGAGAGAGACGACCUGGCGAGCAUCAUGAAGAAG<br>CUGCUCACCAAGUAUGACAACUUAUUCGAAACCUCCUUCCCUUACAG<br>CAUGGGCUGGCACGGCGCCCCCACCGGCAGCGAGGCGGGCGCCAACU<br>GGAACCACUGGCAGCUGCAUGCCCACUACUACCCACCCCUGCUGCGG<br>AGCGCCACCGUGAGAAAGUUCAUGGUGGGCUACGAGAUGCUGGCCC<br>AGGCCCAACGGGAUCUGACCCCCGAGCAGGCCGCCGAGCGGCUGAGG<br>GCCCUCCCCGAGGUACACUACCAUCUCGGCCAGAAGGACCGGGAAAC<br>CGCCACCAUCGCC***UGAUAAUAGUCCAUAAAGUAGGAAACACUACAGCU<br>GGAGCCUCGGUGGCCAUGCUUCUUGCCCCUUGGGCCUCCCCCCAGCC*** |

TABLE 5-continued mRNA Constructs

| SEQ ID NO | Construct | Sequence (5' UTR = bold underline: 3' UTR comprimising a stop codon = bold italics) |
|---|---|---|
| | | ***CCUCCUCCCCUUCCUGCACCCGUACCCCCCGCAUUAUUACUCACGGUA<br>CGAGUGGUCUUUGAAUAAAGUCUGAGUGGGCGGC*** |
| 136 | #5 | **GGGAAAUAAGAGAGAAAAGAAGAGUAAGAAGAAAUAUAAGAGCCA<br>CC**AUGAGCAGAAGCGGCACCGACCCCCAGCAGCGGCAGCAGGCCAGC<br>GAGGCCGACGCCGCCGCCGCAACCUUCCGCGCCAACGACCACCAGCA<br>CAUCAGAUACAACCCCCUCCAGGACGAGUGGGUCCUCGUGUCCGCCC<br>AUAGAAUGAAGAGGCCAUGGCAGGGCCAGGUAGAACCUCAACUGCU<br>GAAGACCGUCCCCCGGCAUGACCCCCUCAAUCCCCUCUGCCCGGGGG<br>CCAUCCGAGCGAAUGGGGAGGUCAACCCCCAGUACGACAGCACCUUC<br>CUGUUCGACAACGACUUCCCCGCCCUGCAGCCCGACGCCCCGAGCCC<br>CGGACCCAGCGACCACCCCCUGUUCCAGGCCAAAUCCGCCCGGGGCG<br>UCUGCAAGGUGAUGUGCUUUCACCCCUGGUCCGACGUGACCCUGCCC<br>CUCAUGUCCGUGCCCGAGAUCAGGGCCGUGGUGGACGCUUGGGCCAG<br>CGUCACGGAGGAGCUCGGCGCCCAGUACCCCUGGGUCCAGAUCUUCG<br>AGAACAAGGGCGCCAUGAUGGGGUGCUCCAACCCUCACCCCCACUGC<br>CAGGUGUGGGCCAGCAGCUUUCUGCCCGACAUUGCCCAGCGGGAGGA<br>GAGGUCCCAGCAGGCCUACAAGAGUCAGCACGGGGAGCCCCUGCUGA<br>UGGAGUACUCCCGGCAGGAGCUCCUGAGGAAAGAGCGCUUGGUGCU<br>GACAAGCGAGCACUGGCUGGUGCUCGUGCCCUUCUGGGCCACUUGGC<br>CCUACCAGACCCUGCUGCUGCCCAGACGGCACGUGCGGCGGCUGCCC<br>GAGCUGACACCCGCCGAGAGGGACGAUCUCGCCAGCAUUAUGAAGAA<br>GCUGCUGACCAAGUAUGACAACCUGUUUGAGACUAGCUUUCCCUACA<br>GCAUGGGCUGGCACGGGGCCCCCACGGGCUCCGAGGCCGGCGCCAAC<br>UGGAACCACUGGCAGCUGCACGCCCACUAUUAUCCGCCCCUGCUCCG<br>GAGCGCCACCGUGAGAAAGUUUAUGGUGGGCUAUGAGAUGCUGGCC<br>CAAGCGCAACGGGAUCUGACCCCCGAGCAGGCCGCCGAGCGUCUGAG<br>AGCCCUGCCUGAGGUGCACUAUCACCUGGGGCAGAAGGACCGGGAGA<br>CGGCAACCAUCGCC***UGAUAAUAGUCCAUAAAGUAGGAAACACUACAGC<br>UGGAGCCUCGGUGGCCAUGCUUCUUGCCCCUUGGGCCUCCCCCCAGC<br>CCCUCCUCCCCUUCCUGCACCCGUACCCCCCGCAUUAUUACUCACGGU<br>ACGAGUGGUCUUUGAAUAAAGUCUGAGUGGGCGGC*** |
| 137 | #6 | **GGGAAAUAAGAGAGAAAAGAAGAGUAAGAAGAAAUAUAAGAGCCA<br>CC**AUGAGCCGCAGCGGCACCGACCCGCAACAAAGACAGCAGGCCUCC<br>GAGGCCGACGCCGCCGCCGCUACCUUUAGGGCCAACGACCACCAGCA<br>UAUCCGCUACAAUCCCCUCCAGGACGAGUGGGUGCUCGUGAGCGCCC<br>ACCGUAUGAAGAGGCCCUGGCAGGGACAGGUGGAACCCCAGCUGCUG<br>AAGACCGUACCCCGGCACGACCCCCUGAACCCCCUGUGCCCCGGGGC<br>CAUCAGAGCCAAUGGAGAGGUGAACCCCCAGUACGACUCCACCUUCC<br>UGUUCGAUAAUGAUUUUCCGGCCCUGCAGCCCGACGCCCCCAGCCCC<br>GGCCCAAGCGACCACCCUCUGUUCCAGGCCAAGAGCGCCAGGGGCGU<br>UUGCAAGGUCAUGUGCUUCCACCCCUGGAGCGACGUGACCCUGCCCC<br>UGAUGUCGGUGCCCGAGAUCAGGGCCGUGGUGGACGCCUGGGCCAGC<br>GUGACGGAGGAACUCGGCGCCCAGUACCCCUGGGUACAGAUCUUCGA<br>GAACAAGGGUGCCAUGAUGGGCUGCAGCAACCCACAUCCCCACUGUC<br>AGGUGUGGGCCAGCUCAUUCCUGCCUGACAUCGCCCAGCGUGAGGAG<br>AGGAGUCAGCAGGCCUAUAAGAGCCAGCAUGGGGAGCCCCUCCUGAU<br>GGAGUACAGCAGACAAGAGCUGCUCAGGAAGGAGAGACUGGUGCUG<br>ACCAGCGAGCAUUGGCUGGUGCUGGUGCCCUUUUGGGCCACAUGGCC<br>CUACCAGACCCUCCUGCUGCCGAGACGCCACGUGCGCCGGCUGCCCG<br>AGCUGACUCCCGCCGAGAGGGACGACCUCGCUAGCAUCAUGAAGAAA<br>CUGCUGACCAAGUACGACAACCUGUUUGAGACAAGCUUUCCCUACUC<br>CAUGGGAUGGCACGGCGCCCCCACCGGCUCCGAGGCCGGCGCCAACU<br>GGAACCACUGGCAGCUGCACGCCCACUACUAUCCCCCGCUGCUGCGG<br>AGCGCCACCGUGAGGAAAUUCAUGGUGGGCUACGAGAUGCUCGCUC<br>AGGCCCAACGGGACCUGACCCCCGAGCAGGCGGCCGAGAGGCUCCGA<br>GCUCUGCCCGAGGUGCAUUACCAUCUGGGCCAGAAGGAUAGGGAAA<br>CCGCCACCAUCGCC***UGAUAAUAGUCCAUAAAGUAGGAAACACUACAGC<br>UGGAGCCUCGGUGGCCAUGCUUCUUGCCCCUUGGGCCUCCCCCCAGC<br>CCCUCCUCCCCUUCCUGCACCCGUACCCCCCGCAUUAUUACUCACGGU<br>ACGAGUGGUCUUUGAAUAAAGUCUGAGUGGGCGGC*** |
| 138 | #7 | **GGGAAAUAAGAGAGAAAAGAAGAGUAAGAAGAAAUAUAAGAGCCA<br>CC**AUGAGCAGGAGCGGAACCGACCCGCAGCAGAGGCAGCAGGCCAGC<br>GAAGCCGACGCCGCCGCCGCCACCUUCCGGGCCAACGACCACCAACA<br>CAUCAGGUACAACCCGCUCCAGGACGAGUGGGUGCUCGUUAGCGCCC<br>AUCGCAUGAAGCGGCCGUGGCAAGGCCAGGUGGAGCCGCAGCUGCUG<br>AAGACCGUGCCGCGCCACGACCCGCUGAACCCGCUGUGCCCUGGCGC<br>CAUCCGGGCCAACGGCGAGGUGAACCCUCAGUACGACAGCACCUUCC<br>UGUUCGACAAUGAUUUCCCGGCCUUGCAGCCGGACGCCCCUUCCCCG<br>GGACCGUCCGACCACCCGCUGUUCCAAGCCAAGUCCGCCCGGGGCGU<br>GUGCAAGGUGAUGUGCUUCCACCCGUGGUCCGACGUGACCCUGCCGC<br>UGAUGAGCGUGCCUGAGAUCAGAGCCGUGGUGGACGCCUGGGCCUCC<br>GUGACUGAGGAGCUCGGCGCCCAGUACCCAUGGGUCCAGAUCUUCGA |

TABLE 5-continued

| mRNA Constructs | | |
|---|---|---|
| SEQ ID NO | Construct | Sequence (5' UTR = bold underline: 3' UTR comprimising a stop codon = bold italics) |
| | | GAACAAGGGUGCCAUGAUGGGCUGCAGCAACCCGCACCCGCACUGCC<br>AAGUGUGGGCCAGCUCCUUCCUGCCGGAUAUUGCCCAGCGGGAGGAG<br>CGGAGCCAGCAAGCAUACAAGAGCCAGCAUGGCGAGCCGCUCUUGAU<br>GGAGUACUCCAGGCAGGAGCUGCUGAGAAAGGAGCGGCUGGUGCUG<br>ACCUCUGAGCACUGGCUGGUGCUCGUGCCGUUCUGGGCCACCUGGCC<br>UUACCAGACCCUGCUGCUGCCGAGGCGGCACGUGCGCCGGCUGCCAG<br>AGCUGACGCCAGCCGAGCGAGACGAUCUGGCCUCCAUCAUGAAGAAG<br>CUACUGACCAAGUAUGACAACCUGUUCGAAACGAGCUUCCCCGUACAG<br>CAUGGGCUGGCACGGCGCCCCGACCGGCAGCGAGGCCGGCGCCAACU<br>GGAAUCACUGGCAGCUGCAUGCCCAUUACUACCCGCCGCUCCUCCGC<br>AGCGCCACCGUGAGGAAGUUCAUGGUGGGCUACGAGAUGCUGGCCC<br>AGGCCCAGCGGGACCUGACCCCGGAGCAGGCGGCCGAGAGACUGAGG<br>GCCCUCCCGGAGGUCCAUUACCACCUGGGCCAGAAGGACCGGGAGAC<br>GGCCACCAUCGCC***UGAUAAUAGUCCAUAAAGUAGGAAACACUACAGCU***<br>***GGAGCCUCGGUGGCCAUGCUUCUUGCCCCUUGGGCCUCCCCCCAGCC***<br>***CCUCCUCCCCUUCCUGCACCCGUACCCCCCGCAUUAUUACUCACGGUA***<br>***CGAGUGGUCUUUGAAUAAAGUCUGAGUGGGCGGC*** |
| 139 | #8 | **GGGAAAUAAGAGAGAAAAGAAGAGUAAGAAGAAAUAUAAGAGCCA**<br>**CC**AUGUCCCGCAGCGGCACGGACCCGCAGCAGCGGCAGCAGGCCAGC<br>GAGGCCGACGCCGCGGCCGCCACCUUCCGGGCCAACGACCACCAGCA<br>CAUCAGGUACAACCCACUCCAAGACGAGUGGGUGCUCGUGAGCGCCC<br>ACCGGAUGAAGAGGCCGUGGCAGGGACAGGUUGAGCCGCAACUGCU<br>GAAGACCGUGCCAAGACACGAUCCGCUGAACCCGCUCUGCCCGGGCG<br>CCAUCCGUGCCAACGGCGAGGUCAACCCACAGUAUGACAGCACCUUC<br>CUGUUCGACAACGACUUCCCGGCCCUGCAGCCGGACGCGCCUAGCCC<br>UGGACCGUCCGACCACCCGCUGUUCCAGGCCAAGUCCGCUAGGGGCG<br>UGUGCAAGGUGAUGUGCUUCCAUCCGUGGUCCGAUGUCACCCUGCCG<br>CUCAUGUCCGUGCCGGAGAUCCGGGCCGUGGUGGAUGCCUGGGCCAG<br>CGUCACCGAGGAGCUGGGCGCGCAGUACCCUUGGGUCCAGAUCUUCG<br>AGAACAAGGGCGCCAUGAUGGGUUGCAGCAACCCGCACCCACACUGC<br>CAGGUGUGGGCCAGCAGCUUCCUGCCGGACAUCGCACAGAGGGAGGA<br>GCGGAGCCAACAGGCCUACAAGUCCCAGCACGGCGAGCCACUGCUGA<br>UGGAGUACAGCAGGCAGGAGCUGCUGCGGAAGGAGCGGCUGGUGCU<br>CACCUCCGAACAUUGGCUGGUUCUGGUGCCGUUCUGGGCCACCUGGC<br>CUUACCAGACCCUGCUGCUCCCGAGGCGGCACGUGCGCAGGCUGCCG<br>GAGCUGACACCGGCCGAGCGCGACGACCUGGCCAGCAUCAUGAAGAA<br>GCUGCUCACCAAGUACGAUAACCUGUUCGAGACAUCCUUCCCGUACA<br>GCAUGGGCUGGCACGGCGCCCCUACCGGCUCCGAGGCCGGCGCCAAC<br>UGGAACCACUGGCAGCUGCACGCCCACUACUACCCACCGCUGCUGAG<br>AAGCGCCACCGUCAGAAAGUUCAUGGUGGGAUAUGAGAUGCUGGCC<br>CAGGCUCAGAGAGAUCUGACCCCGGAGCAGGCCGCCGAGAGGCUCCG<br>CGCCCUCCCAGAAGUGCACUACCAUCUGGGCCAGAAGGACAGGGAGA<br>CGGCCACCAUCGCC***UGAUAAUAGUCCAUAAAGUAGGAAACACUACAGC***<br>***UGGAGCCUCGGUGGCCAUGCUUCUUGCCCCUUGGGCCUCCCCCCAGC***<br>***CCCUCCUCCCCUUCCUGCACCCGUACCCCCCGCAUUAUUACUCACGGU***<br>***ACGAGUGGUCUUUGAAUAAAGUCUGAGUGGGCGGC*** |
| 140 | #9 | **GGGAAAUAAGAGAGAAAAGAAGAGUAAGAAGAAAUAUAAGAGCCA**<br>**CC**AUGAGCCGGAGCGGCACCGACCCGCAGCAGCGUCAGCAAGCCAGC<br>GAGGCCGACGCCGCCGCCGCCACGUUCCGGGCCAACGACCACCAGCA<br>CAUUAGGUACAACCCGCUCCAGGACGAGUGGGUCCUCGUGAGCGCCC<br>ACAGGAUGAAGAGGCCAUGGCAGGGACAAGUUGAGCCACAGCUGCU<br>GAAGACCGUGCCACGGCACGACCCGCUCAACCCUCUGUGCCCGGGCG<br>CCAUCCGCGCCAACGGCGAGGUGAACCCACAGUACGACAGCACCUUC<br>CUGUUCGACAACGACUUCCCUGCCCUCCAGCCGGACGCCCCGAGCCC<br>UGGACCGUCCGACCAUCCGCUGUUCCAGGCCAAGUCCGCGCGGGGCG<br>UGUGCAAGGUGAUGUGCUUCCAUCCGUGGAGCGACGUGACCCUGCCG<br>CUGAUGUCCGUGCCUGAGAUACGGGCCGUGGUGGACGCCUGGGCCAG<br>CGUGACAGAGGAGCUCGGCGCCCAGUACCCUUGGGUGCAGAUCUUCG<br>AGAACAAGGGUGCCAUGAUGGGUUGCAGCAACCCGCACCCGCAUUGC<br>CAGGUGUGGGCCAGCAGCUUCCUGCCUGACAUCGCCCAGCGGGAGGA<br>GCGCAGCCAGCAGGCUUACAAGAGCCAGCACGGCGAGCCGCUGCUGA<br>UGGAGUACUCUAGGCAGGAGCUGCUGAGAAAGGAGAGGCUGGUGCU<br>GACCAGCGAACACUGGCUCGUGCUGGUGCCGUUCUGGGCAACCUGGC<br>CGUACCAGACCCUGCUGCUGCCGAGGCGGCAUGUGAGAAGGCUCCCG<br>GAGCUGACCCCAGCCGAGCGCGACGACCUCGCCAGCAUCAUGAAGAA<br>GCUCCUGACCAAGUACGACAACCUGUUCGAGACGAGCUUCCCGUAUU<br>CCAUGGGCUGGCACGGAGCCCCGACAGGCAGCGAGGCCGGCGCCAAC<br>UGGAAUCACUGGCAGCUGCAUGCCCACUACUACCCGCCGCUCCUGCG<br>GAGCGCCACCGUCCGCAAGUUCAUGGUGGGCUACGAGAUGCUGGCCC<br>AGGCCCAGAGGGACCUCACCCCGGAGCAGGCCGCCGAGAGGCUGCGG<br>GCCCUGCCGGAGGUCCACUACCACCUCGGCCAGAAGGAUAGAGAAAC<br>CGCCACGAUCGCG***UGAUAAUAGUCCAUAAAGUAGGAAACACUACAGCU***<br>***GGAGCCUCGGUGGCCAUGCUUCUUGCCCCUUGGGCCUCCCCCCAGCC*** |

TABLE 5-continued

| mRNA Constructs | | |
|---|---|---|
| SEQ ID NO | Construct | Sequence (5' UTR = bold underline: 3' UTR comprimising a stop codon = bold italics) |
| | | ***CCUCCUCCCCUUCCUGCACCCGUACCCCCCGCAUUAUUACUCACGGUA<br>CGAGUGGUCUUUGAAUAAAGUCUGAGUGGGCGGC*** |
| 141 | #10 | **GGGAAAUAAGAGAGAAAAGAAGAGUAAGAAGAAAUAUAAGAGCCA<br>CC**AUGAGCAGGAGCGGCACCGACCCUCAGCAGAGGCAACAGGCCUCC<br>GAGGCCGACGCGGCGGCCGCCACCUUCAGGGCCAACGACCACCAGCA<br>CAUCCGAUACAACCCGCUCCAAGACGAGUGGGUGCUCGUCUCCGCCC<br>ACCGCAUGAAGCGGCCGUGGCAAGGUCAAGUUGAACCACAGCUGCUG<br>AAGACCGUGCCGAGGCACGAUCCGCUGAACCCGCUGUGCCCGGGAGC<br>CAUCCGGGCCAACGGCGAGGUGAACCCUCAGUACGACAGCACAUUCC<br>UGUUCGACAACGACUUCCCGGCCCUGCAGCCGGACGCCCCAAGCCCG<br>GGCCCAAGCGACCAUCCGCUGUUCCAAGCCAAGUCCGCCCGCGGCGU<br>GUGCAAGGUGAUGUGCUUCCACCCGUGGUCCGACGUGACCCUGCCGC<br>UGAUGAGCGUGCCGGAGAUCCGGGCCGUGGUGGAUGCCUGGGCCAG<br>CGUGACCGAGGAAUUAGGCGCCCAGUACCCAUGGGUGCAGAUCUUCG<br>AGAACAAGGGAGCCAUGAUGGGCUGCAGCAACCCGCACCCGCACUGC<br>CAAGUGUGGGCCAGCUCCUUCCUGCCGGACAUCGCCCAGCGCGAGGA<br>GCGGAGCCAGCAGGCCUACAAGAGUCAGCACGGCGAGCCGCUGCUGA<br>UGGAGUACUCUAGGCAGGAGCUGCUCAGGAAGGAGAGGCUGGUGCU<br>GACCAGCGAGCACUGGUUGGUGCUGGUGCCUUUCUGGGCCACCUGGC<br>CAUACCAGACCCUGCUGCUGCCGAGAAGGCACGUCAGAAGACUGCCG<br>GAACUGACCCCGGCCGAGAGGGACGACCUGGCCUCCAUUAUGAAGAA<br>GCUCCUGACCAAGUACGACAAUCUGUUCGAGACGUCCUUCCCUUACA<br>GCAUGGGUUGGCACGGCGCCCCGACCGGCAGCGAGGCAGGAGCCAAC<br>UGGAACCACUGGCAGCUGCACGCCCACUACUACCCGCCGCUGCUCAG<br>GUCCGCCACCGUUCGGAAGUUCAUGGUGGGCUACGAAAUGCUGGCCC<br>AGGCCCAGCGCGACCUCACCCCAGAGCAGGCCGCCGAGCGGCUGCGG<br>GCCCUGCCGGAGGUGCACUACCACCUGGGCCAGAAGGACCGCGAGAC<br>AGCCACCAUCGCU***UGAUAAUAGUCCAUAAAGUAGGAAACACUACAGCU<br>GGAGCCUCGGUGGCCAUGCUUCUUGCCCCUUGGGCCUCCCCCCAGCC<br>CCUCCUCCCCUUCCUGCACCCGUACCCCCCGCAUUAUUACUCACGGUA<br>CGAGUGGUCUUUGAAUAAAGUCUGAGUGGGCGGC*** |
| 142 | #11 | **GGGAAAUAAGAGAGAAAAGAAGAGUAAGAAGAAAUAUAAGAGCCA<br>CC**AUGAGCAGGUCAGGAACCGACCCGCAGCAGCGCCAACAGGCCUCC<br>GAGGCCGACGCCGCCGCCGCGACCUUCCGAGCCAACGACCAUCAACA<br>CAUCAGGUAUAACCCGUUGCAGGACGAGUGGGUGCUCGUGUCCGCCC<br>AUCGGAUGAAGCGGCCGUGGCAGGGACAGGUGGAGCCGCAGCUGCU<br>CAAGACCGUUCCGCGCCACGACCCGCUCAACCCGCUGUGUCCGGGCG<br>CCAUCCGGGCCAACGGCGAGGUGAACCCGCAGUACGACAGCACCUUC<br>CUGUUCGACAACGAUUUCCCUGCCCUGCAGCCAGAUGCCCCGAGCCC<br>GGGCCCUAGCGAUCACCCGCUGUUCCAGGCCAAGAGCGCCCGGGGCG<br>UCUGUAAGGUGAUGUGCUUCCACCCAUGGAGCGACGUCACCCUGCCG<br>CUGAUGUCCGUGCCAGAGAUCCGCGCCGUGGUGGACGCCUGGGCGAG<br>CGUGACCGAGGAGCUGGGAGCCCAAUACCCUUGGGUGCAGAUCUUCG<br>AGAAUAAGGGCGCUAUGAUGGGCUGCUCCAACCCGCACCCGCACUGC<br>CAGGUGUGGGCCAGCUCCUUCCUCCCGGAUAUCGCCCAGCGGGAGGA<br>GAGAAGCCAGCAGGCCUACAAGUCCCAGCACGGCGAGCCGCUGCUCA<br>UGGAGUAUUCCAGGCAGGAGCUCCUCAGGAAGGAAAGGCUUGUGCU<br>GACGAGCGAGCACUGGCUGGUGCUGGUGCCGUUCUGGGCCACCUGGC<br>CGUACCAGACCCUCCUGCUGCCGCGCCGACACGUCAGGAGGCUGCCG<br>GAGCUGACCCCGGCCGAGAGGGAUGACCUGGCCUCCAUAAUGAAGAA<br>GUUACUGACUAAGUAUGACAACUUGUUCGAAACCAGCUUCCCUUAC<br>AGCAUGGGCUGGCAUGGCGCCCCGACCGGCUCCGAAGCCGGCGCCAA<br>CUGGAACCAUUGGCAACUCCACGCCCACUACUACCCGCCGCUCUUAA<br>GGAGCGCCACCGUGAGGAAGUUCAUGGUGGGAUACGAGAUGCUGGC<br>CCAGGCCCAAAGGGACCUCACCCCGGAGCAGGCCGCGGAGAGGCUGC<br>GUGCCCUGCCUGAGGUCCACUACCACCUGGGCCAGAAGGACAGGGAA<br>ACCGCGACCAUCGCC***UGAUAAUAGUCCAUAAAGUAGGAAACACUACAG<br>CUGGAGCCUCGGUGGCCAUGCUUCUUGCCCCUUGGGCCUCCCCCCAG<br>CCCCUCCUCCCCUUCCUGCACCCGUACCCCCCGCAUUAUUACUCACGG<br>UACGAGUGGUCUUUGAAUAAAGUCUGAGUGGGCGGC*** |
| 143 | #12 | **GGGAAAUAAGAGAGAAAAGAAGAGUAAGAAGAAAUAUAAGAGCCA<br>CC**AUGAGCCGGAGCGGCACCGACCCCCAGCAGCGGCAGCAGGCCAGC<br>GAGGCCGACGCUGCCGCCGCCACCUUCCGGGCCAACGACCACCAGCA<br>CAUCCGGUACAACCCCCUGCAGGACGAGUGGGUGCUGGUGAGCGCCC<br>ACCGGAUGAAGCGGCCCUGGCAGGGCCAGGUGGAGCCCCAGCUGCUG<br>AAGACCGUGCCCCGGCACGACCCCCUGAACCCUCUGUGCCCAGGAGC<br>CAUCCGCGCCAACGGCGAGGUGAAUCCUCAGUACGACAGCACCUUCC<br>UGUUCGACAACGACUUCCCCGCCCUGCAGCCCGACGCCCCCAGCCCC<br>GGCCCCAGCGACCAUCCAUUAUUCCAGGCCAAGAGCGCCCGGGGCGU<br>GUGCAAGGUGAUGUGCUUCCACCCCUGGAGCGACGUGACCCUGCCCC<br>UGAUGAGCGUGCCCGAGAUCAGAGCCGUGGUGGACGCCUGGGCCAGC<br>GUGACCGAGGAGCUGGGCGCCCAGUACCCCUGGGUGCAGAUCUUCGA |

TABLE 5-continued mRNA Constructs

| SEQ ID NO | Construct | Sequence (5' UTR = bold underline: 3' UTR comprimising a stop codon = bold italics) |
|---|---|---|
| | | GAACAAGGGCGCCAUGAUGGGCUGCAGCAACCCCCACCCCCACUGCC<br>AGGUGUGGGCCUCAAGCUUCCUGCCCGACAUCGCCCAGCGGGAGGAG<br>CGGAGCCAACAGGCCUACAAGUCACAGCACGGCGAGCCCCUGCUGAU<br>GGAGUACAGCCGGCAGGAGCUGCUGCGGAAGGAGCGGCUGGUGCUG<br>ACCAGCGAGCACUGGCUCGUGCUCGUGCCCUUCUGGGCCACCUGGCC<br>CUACCAGACCCUGCUGCUGCCUAGACGGCACGUGCGGCGGCUGCCCG<br>AGCUGACCCCCGCCGAGCGGGACGACCUGGCCAGCAUCAUGAAGAAG<br>CUCCUGACCAAGUACGAUAACUUAUUCGAAACAAGCUUCCCCUACAG<br>CAUGGGCUGGCACGGCGCCCCCACCGGCUCAGAGGCCGGCGCUAACU<br>GGAACCACUGGCAGCUGCACGCCCACUACUACCCGCCUCUGCUGAGA<br>AGCGCCACCGUGCGGAAGUUCAUGGUGGGCUACGAGAUGCUGGCCCA<br>GGCCCAGAGAGACUUAACCCCUGAGCAGGCCGCCGAGAGGCUCCGGG<br>CCUUGCCAGAGGUGCACUACCACCUGGGACAGAAGGACCGGGAGACG<br>GCCACCAUCGCC***UGAUAAUAGUCCAUAAAGUAGGAAACACUACAGCUG***<br>***GAGCCUCGGUGGCCAUGCUUCUUGCCCCUUGGGCCUCCCCCCAGCCCC***<br>***UCCUCCCCUUCCUGCACCCGUACCCCCCGCAUUAUUACUCACGGUACG***<br>***AGUGGUCUUUGAAUAAAGUCUGAGUGGGCGGC*** |
| 144 | #13 | **GGGAAAUAAGAGAGAAAAGAAGAGUAAGAAGAAAUAUAAGAGCCA**<br>**CC**AUGAGCCGGAGCGGCACCGACCCCCAGCAGCGGCAGCAGGCCAGC<br>GAGGCCGACGCAGCCGCCGCUACCUUCCGGGCCAACGACCACCAGCA<br>CAUCCGGUACAACCCCCUGCAGGACGAGUGGGUGCUGGUGAGCGCCC<br>ACCGGAUGAAGCGGCCCUGGCAGGGCCAGGUGGAGCCCCAGCUGCUG<br>AAGACCGUGCCCCGGCACGACCCCCUGAAUCCUCUGUGCCCAGGAGC<br>CAUCAGAGCCAACGGCGAGGUGAACCCUCAGUACGACAGCACCUUCC<br>UGUUCGACAACGACUUCCCCGCCCUGCAGCCCGACGCCCCCAGCCCC<br>GGCCCCAGCGACCAUCCGCUGUUCCAGGCCAAGAGCGCCCGGGGCGU<br>GUGCAAGGUGAUGUGCUUCCACCCCUGGAGCGACGUGACCCUGCCCC<br>UGAUGAGCGUGCCCGAGAUCCGAGCCGUGGUGGACGCCUGGGCCAGC<br>GUGACCGAGGAGCUGGGCGCCCAGUACCCCUGGGUGCAGAUCUUCGA<br>GAACAAGGGCGCCAUGAUGGGCUGCAGCAACCCCCACCCCCACUGCC<br>AGGUGUGGGCCUCGAGCUUCCUGCCCGACAUCGCCCAGCGGGAGGAG<br>CGGAGCCAGCAAGCAUACAAGUCACAGCACGGCGAGCCCCUGCUGAU<br>GGAGUACAGCCGGCAGGAGCUGCUGCGGAAGGAGCGGCUGGUGCUG<br>ACCAGCGAGCACUGGCUGGUCCUGGUGCCCUUCUGGGCCACCUGGCC<br>CUACCAGACCCUGCUGUUGCCUAGACGGCACGUGCGGCGGCUGCCCG<br>AGCUGACCCCCGCCGAGCGGGACGACCUGGCCAGCAUCAUGAAGAAG<br>UUGCUGACAAAGUAUGACAAUCUGUUCGAAACCAGCUUCCCCUACAG<br>CAUGGGCUGGCACGGCGCCCCCACCGGCAGCGAAGCCGGCGCCAACU<br>GGAACCACUGGCAGCUGCACGCCCACUACUACCCUCCUCUGCUCCGC<br>AGCGCCACCGUGCGGAAGUUCAUGGUGGGCUACGAGAUGCUGGCCCA<br>GGCACAGCGGGACCUGACCCCUGAGCAGGCCGCUGAGAGACUGCGGG<br>CCCUCCCGGAGGUGCACUACCACCUCGGCCAGAAGGACCGGGAAACG<br>GCCACCAUCGCC***UGAUAAUAGUCCAUAAAGUAGGAAACACUACAGCUG***<br>***GAGCCUCGGUGGCCAUGCUUCUUGCCCCUUGGGCCUCCCCCCAGCCCC***<br>***UCCUCCCCUUCCUGCACCCGUACCCCCCGCAUUAUUACUCACGGUACG***<br>***AGUGGUCUUUGAAUAAAGUCUGAGUGGGCGGC*** |
| 145 | #14 | **GGGAAAUAAGAGAGAAAAGAAGAGUAAGAAGAAAUAUAAGAGCCA**<br>**CC**AUGAGCCGGAGCGGCACCGACCCCCAGCAGCGGCAGCAGGCCAGC<br>GAGGCCGACGCAGCCGCCGCGACCUUCCGGGCCAACGACCACCAGCA<br>CAUCCGGUACAACCCCCUGCAGGACGAGUGGGUGCUGGUGAGCGCCC<br>ACCGGAUGAAGCGGCCCUGGCAGGGCCAGGUGGAGCCCCAGCUGCUG<br>AAGACCGUGCCCCGGCACGACCCCCUGAACCCUCUGUGCCCAGGAGC<br>CAUUAGAGCCAAUGGCGAGGUGAACCCACAGUACGACAGCACCUUCC<br>UGUUCGACAACGACUUCCCCGCCCUGCAGCCCGACGCCCCCAGCCCC<br>GGCCCCAGCGACCACCCGCUUUUCCAGGCCAAGAGCGCCCGGGGCGU<br>GUGCAAGGUGAUGUGCUUCCACCCCUGGAGCGACGUGACCCUGCCCC<br>UGAUGAGCGUGCCCGAGAUCAGAGCCGUGGUGGACGCCUGGGCCAGC<br>GUGACCGAGGAGCUGGGCGCCCAGUACCCCUGGGUGCAGAUCUUCGA<br>GAACAAGGGCGCCAUGAUGGGCUGCAGCAACCCCCACCCCCACUGCC<br>AGGUGUGGGCCUCUAGCUUCCUGCCCGACAUCGCCCAGCGGGAGGAG<br>CGGAGCCAGCAAGCCUACAAGUCUCAGCACGGCGAGCCCCUGCUGAU<br>GGAGUACAGCCGGCAGGAGCUGCUGCGGAAGGAGCGGCUGGUGCUG<br>ACCAGCGAGCACUGGCUGGUCCUCGUGCCCUUCUGGGCCACCUGGCC<br>CUACCAGACCCUGCUGCUCCCUAGACGGCACGUGCGGCGGCUGCCCG<br>AGCUGACCCCCGCCGAGCGGGACGACCUGGCCAGCAUCAUGAAGAAG<br>CUGCUCACCAAGUAUGAUAAUCUGUUCGAGACAAGCUUCCCCUACAG<br>CAUGGGCUGGCACGGCGCCCCCACCGGUUCAGAGGCCGGCGCCAACU<br>GGAACCACUGGCAGCUGCACGCCCACUACUACCCACCUUUGUUGCGU<br>AGCGCCACCGUGCGGAAGUUCAUGGUGGGCUACGAGAUGCUGGCCCA<br>GGCCCAGCGCGAUCUGACCCCAGAGCAGGCCGCCGAGAGGCUGCGGG<br>CCUUACCUGAGGUGCACUACCACCUCGGCCAGAAGGACCGGGAAACC<br>GCCACCAUCGCC***UGAUAAUAGUCCAUAAAGUAGGAAACACUACAGCUG***<br>***GAGCCUCGGUGGCCAUGCUUCUUGCCCCUUGGGCCUCCCCCCAGCCCC*** |

TABLE 5-continued mRNA Constructs

| SEQ ID NO | Construct | Sequence (5' UTR = bold underline: 3' UTR comprimising a stop codon = bold italics) |
|---|---|---|
| | | ***UCCUCCCCUUCCUGCACCCGUACCCCCCGCAUUAUUACUCACGGUACG<br>AGUGGUCUUUGAAUAAAGUCUGAGUGGGCGGC*** |
| 146 | #15 | **GGGAAAUAAGAGAGAAAAGAAGAGUAAGAAGAAAUAUAAGAGCCA<br>CC**AUGAGCCGGAGCGGCACCGACCCCCAGCAGCGGCAGCAGGCCAGC<br>GAGGCCGACGCCGCAGCCGCUACCUUCCGGGCCAACGACCACCAGCA<br>CAUCCGGUACAACCCCCUGCAGGACGAGUGGGUGCUGGUGAGCGCCC<br>ACCGGAUGAAGCGGCCCUGGCAGGGCCAGGUGGAGCCCCAGCUGCUG<br>AAGACCGUGCCCCGGCACGACCCCCUGAAUCCUCUCUGCCCUGGAGC<br>CAUUAGAGCCAACGGCGAGGUGAACCCACAGUACGACAGCACCUUCC<br>UGUUCGACAACGACUUCCCCGCCCUGCAGCCCGACGCCCCCAGCCCC<br>GGCCCCAGCGACCACCCUCUGUUCCAGGCCAAGAGCGCCCGGGGCGU<br>GUGCAAGGUGAUGUGCUUCCACCCAUGGAGCGACGUGACCCUGCCCC<br>UGAUGAGCGUGCCCGAGAUCAGAGCUGUGGUGGACGCCUGGGCCAG<br>CGUGACCGAGGAGCUGGGCGCCCAGUACCCCUGGGUGCAGAUCUUCG<br>AGAACAAGGGCGCCAUGAUGGGCUGCAGCAACCCCCACCCCCACUGC<br>CAGGUGUGGGCUUCUAGCUUCCUGCCCGACAUCGCCCAGCGGGAGGA<br>GCGGAGCCAGCAGGCGUACAAGUCCCAGCACGGCGAGCCCCUGCUGA<br>UGGAGUACAGCCGGCAGGAGCUGCUGCGGAAGGAGCGGCUGGUGCU<br>GACCAGCGAGCACUGGCUCGUGUUAGUGCCCUUCUGGGCCACCUGGC<br>CCUACCAGACCCUGCUGCUGCCUCGUCGGCACGUGCGGCGGCUGCCC<br>GAGCUGACCCCCGCCGAGCGGGACGACCUGGCCAGCAUCAUGAAGAA<br>GCUCCUGACAAAGUAUGACAACCUAUUCGAAACCAGCUUCCCCUACA<br>GCAUGGGCUGGCACGGCGCCCCCACCGGCAGCGAAGCCGGCGCCAAC<br>UGGAACCACUGGCAGCUGCACGCCCACUACUAUCCACCUCUGCUGCG<br>CAGCGCCACCGUGCGGAAGUUCAUGGUGGGCUACGAGAUGCUGGCCC<br>AGGCCCAGCGCGACCUGACCCCUGAGCAGGCUGCCGAACGACUGCGG<br>GCCCUGCCAGAAGUGCACUACCACCUCGGCCAGAAGGACCGGGAGAC<br>UGCCACCAUCGCC***UGAUAAUAGUCCAUAAAGUAGGAAACACUACAGCU<br>GGAGCCUCGGUGGCCAUGCUUCUUGCCCCUUGGGCCUCCCCCCAGCC<br>CCUCCUCCCCUUCCUGCACCCGUACCCCCGCAUUAUUACUCACGGUA<br>CGAGUGGUCUUUGAAUAAAGUCUGAGUGGGCGGC*** |
| 147 | #16 | **GGGAAAUAAGAGAGAAAAGAAGAGUAAGAAGAAAUAUAAGAGCCA<br>CC**AUGAGCCGGAGCGGCACCGACCCCCAGCAGCGGCAGCAGGCCAGC<br>GAGGCCGACGCUGCAGCCGCCACCUUCCGGGCCAACGACCACCAGCA<br>CAUCCGGUACAACCCCCUGCAGGACGAGUGGGUGCUGGUGAGCGCCC<br>ACCGGAUGAAGCGGCCCUGGCAGGGCCAGGUGGAGCCCCAGCUGCUG<br>AAGACCGUGCCCCGGCACGACCCCCUGAACCCUCUGUGCCCUGGUGC<br>CAUCCGAGCCAACGGCGAGGUGAACCCACAGUACGACAGCACCUUCC<br>UGUUCGACAACGACUUCCCCGCCCUGCAGCCCGACGCCCCCAGCCCC<br>GGCCCCAGCGACCAUCCUCUGUUCCAGGCCAAGAGCGCCCGGGGCGU<br>GUGCAAGGUGAUGUGCUUCCACCCCUGGAGCGACGUGACCCUGCCCC<br>UGAUGAGCGUGCCCGAGAUCAGAGCAGUGGUGGACGCCUGGGCCAG<br>CGUGACCGAGGAGCUGGGCGCCCAGUACCCCUGGGUGCAGAUCUUCG<br>AGAACAAGGGCGCCAUGAUGGGCUGCAGCAACCCCCACCCCCACUGC<br>CAGGUGUGGGCUAGCAGCUUCCUGCCCGACAUCGCCCAGCGGGAGGA<br>GCGGAGCCAGCAGGCUUACAAGUCUCAGCACGGCGAGCCCCUGCUGA<br>UGGAGUACAGCCGGCAGGAGCUGCUGCGGAAGGAGCGGCUGGUGCU<br>GACCAGCGAGCACUGGUUAGUCUUGGUGCCCUUCUGGGCCACCUGGC<br>CCUACCAGACCCUGCUGCUGCCAAGACGGCACGUGCGGCGGCUGCCC<br>GAGCUGACCCCCGCCGAGCGGGACGACCUGGCCAGCAUCAUGAAGAA<br>GCUCCUGACAAAGUACGAUAACCUUUUCGAGACAAGCUUCCCCUACA<br>GCAUGGGCUGGCACGGCGCCCCAACCGGCUCCGAGGCCGGCGCUAAC<br>UGGAACCACUGGCAGCUGCACGCCCACUACUACCCUCCUCUUUUGAG<br>AAGCGCCACCGUGCGGAAGUUCAUGGUGGGCUACGAGAUGCUGGCCC<br>AGGCCCAGAGGGACCUGACCCCUGAGCAGGCCGCCGAGAGAUUACGG<br>GCUCUCCCAGAGGUGCACUACCACCUGGGACAGAAGGACCGGGAGAC<br>AGCCACCAUCGCC***UGAUAAUAGUCCAUAAAGUAGGAAACACUACAGCU<br>GGAGCCUCGGUGGCCAUGCUUCUUGCCCCUUGGGCCUCCCCCCAGCC<br>CCUCCUCCCCUUCCUGCACCCGUACCCCCCGCAUUAUUACUCACGGUA<br>CGAGUGGUCUUUGAAUAAAGUCUGAGUGGGCGGC*** |
| 148 | #17 | **GGGAAAUAAGAGAGAAAAGAAGAGUAAGAAGAAAUAUAAGAGCCA<br>CC**AUGAGCCGGAGCGGCACCGACCCCCAGCAGCGGCAGCAGGCCAGC<br>GAGGCCGACGCCGCCGCCGCCACCUUCCGGGCCAACGACCACCAGCA<br>CAUCCGGUACAACCCCCUGCAGGACGAGUGGGUGCUGGUGAGCGCCC<br>ACCGGAUGAAGCGGCCCUGGCAGGGCCAGGUGGAGCCCCAGCUGCUG<br>AAGACCGUGCCCCGGCACGACCCCCUGAACCCCCUGUGCCCCGGCGC<br>CAUCCGGGCCAACGGCGAGGUGAACCCCCAGUACGACAGCACCUUCC<br>UGUUCGACAACGACUUCCCCGCCCUGCAGCCCGACGCCCCCAGCCCC<br>GGCCCCAGCGACCACCCCCUGUUCCAGGCCAAGAGCGCCCGGGGCGU<br>GUGCAAGGUGAUGUGCUUCCACCCCUGGAGCGACGUGACCCUGCCCC<br>UGAUGAGCGUGCCCGAGAUCCGGGCCGUGGUGGACGCCUGGGCCAGC<br>GUGACCGAGGAGCUGGGCGCCCAGUACCCCUGGGUGCAGAUCUUCGA |

TABLE 5-continued

| mRNA Constructs | | |
|---|---|---|
| SEQ ID NO | Construct | Sequence (5' UTR = bold underline: 3' UTR comprimising a stop codon = bold italics) |
| | | GAACAAGGGCGCCAUGAUGGGCUGCAGCAACCCCCACCCCCACUGCC<br>AGGUGUGGGCCAGCAGCUUCCUGCCCGACAUCGCCCAGCGGGAGGAG<br>CGGAGCCAGCAGGCCUACAAGAGCCAGCACGGCGAGCCCCUGCUGAU<br>GGAGUACAGCCGGCAGGAGCUGCUGCGGAAGGAGCGGCUGGUGCUG<br>ACCAGCGAGCACUGGCUGGUGCUGGUGCCCUUCUGGGCCACCUGGCC<br>CUACCAGACCCUGCUGCUGCCCCGGCGGCACGUGCGGCGGCUGCCCG<br>AGCUGACCCCCGCCGAGCGGGACGACCUGGCCAGCAUCAUGAAGAAG<br>CUGCUGACCAAGUACGACAACCUGUUCGAGACCAGCUUCCCCUACAG<br>CAUGGGCUGGCACGGCGCCCCCACCGGCAGCGAGGCCGGCGCCAACU<br>GGAACCACUGGCAGCUGCACGCCCACUACUACCCGCCCCUGCUGCGG<br>AGCGCCACCGUGCGGAAGUUCAUGGUGGGCUACGAGAUGCUGGCCCA<br>GGCCCAGCGGGACCUGACCCCCGAGCAGGCCGCCGAGCGGCUGCGGG<br>CCCUGCCCGAGGUGCACUACCACCUGGGCCAGAAGGACCGGGAGACC<br>GCCACCAUCGCC***UGAUAAUAGUCCAUAAAGUAGGAAACACUACAGCUG<br>GAGCCUCGGUGGCCAUGCUUCUUGCCCCUUGGGCCUCCCCCCAGCCCC<br>UCCUCCCCUUCCUGCACCCGUACCCCCGCAUUAUUACUCACGGUACG<br>AGUGGUCUUUGAAUAAAGUCUGAGUGGGCGGC*** |
| 149 | #18 | **GGGAAAUAAGAGAGAAAAGAAGAGUAAGAAGAAAUAUAAGAGCCA<br>CC**AUGAGCCGGAGCGGCACCGACCCCCAGCAGCGGCAGCAGGCCAGC<br>GAGGCCGACGCCGCCGCCGCCACCUUCCGGGCCAACGACCACCAGCA<br>CAUCAGGUACAACCCGCUGCAGGACGAGUGGGUGCUGGUGAGCGCGC<br>ACAGGAUGAAGAGGCCGUGGCAGGGGCAGGUGGAGCCGCAGCUGCU<br>GAAGACGGUGCCGAGGCACGACCCGCUGAACCCGCUGUGCCCGGGGG<br>CGAUCAGGGCGAACGGGGAGGUGAACCCGCAGUACGACAGCACGUUC<br>CUGUUCGACAACGACUUCCCGGCGCUGCAGCCGGACGCGCCGAGCCC<br>GGGGCCGAGCGACCACCCGCUGUUCCAGGCGAAGAGCGCGAGGGGG<br>UGUGCAAGGUGAUGUGCUUCCACCCGUGGAGCGACGUGACGCUGCCG<br>CUGAUGAGCGUGCCGGAGAUCAGGGCGGUGGUGGACGCGUGGGCGA<br>GCGUGACGGAGGAGCUGGGGGCGCAGUACCCGUGGGUGCAGAUCUU<br>CGAGAACAAGGGGGCGAUGAUGGGGUGCAGCAACCCGCACCCGCACU<br>GCCAGGUGUGGGCGAGCAGCUUCCUGCCGGACAUCGCGCAGAGGGAG<br>GAGAGGAGCCAGCAGGCGUACAAGAGCCAGCACGGGGAGCCGCUGCU<br>GAUGGAGUACAGCAGGCAGGAGCUGCUGAGGAAGGAGAGGCUGGUG<br>CUGACGAGCGAGCACUGGCUGGUGCUGGUGCCGUUCUGGGCGACGU<br>GGCCGUACCAGACGCUGCUGCUGCCGAGGAGGCACGUGAGGAGGCUG<br>CCGGAGCUGACGCCGGCGGAGAGGGACGACCUGGCGAGCAUCAUGAA<br>GAAGCUGCUGACGAAGUACGACAACCUGUUCGAGACGAGCUUCCCGU<br>ACAGCAUGGGGUGGCACGGGGCGCCGACGGGGAGCGAGGCGGGGGC<br>GAACUGGAACCACUGGCAGCUGCACGCGCACUACUACCCGCCGCUGC<br>UGAGGAGCGCGACGGUGAGGAAGUUCAUGGUGGGGUACGAGAUGCU<br>GGCGCAGGCGCAGAGGGACCUGACGCCGGAGCAGGCGGCGGAGAGGC<br>UGAGGGCGCUGCCGGAGGUGCACUACCACCUGGGGCAGAAGGACAG<br>GGAGACGGCGACGAUCGCG***UGAUAAUAGUCCAUAAAGUAGGAAACAC<br>UACAGCUGGAGCCUCGGUGGCCAUGCUUCUUGCCCCUUGGGCCUCCC<br>CCCAGCCCCUCCUCCCCUUCCUGCACCCGUACCCCCGCAUUAUUACU<br>CACGGUACGAGUGGUCUUUGAAUAAAGUCUGAGUGGGCGGC*** |
| 150 | #19 | **GGGAAAUAAGAGAGAAAAGAAGAGUAAGAAGAAAUAUAAGAGCCA<br>CC**AUGAGCCGGAGCGGCACCGACCCCCAGCAGCGGCAGCAGGCCAGC<br>GAGGCCGACGCCGCCGCCGCCACCUUCCGGGCCAACGACCACCAGCA<br>CAUCCGCUACAACCCCCUCCAGGACGAGUGGGUCCUCGUCUCCGCCC<br>ACCGCAUGAAGCGCCCCUGGCAGGGCCAGGUCGAGCCCCAGCUCCUC<br>AAGACCGUCCCCCGCCACGACCCCCUCAACCCCCUCUGCCCCGGCGCC<br>AUCCGCGCCAACGGCGAGGUCAACCCCCAGUACGACUCCACCUUCCU<br>CUUCGACAACGACUUCCCCGCCCUCCAGCCCGACGCCCCCUCCCCCGG<br>CCCCUCCGACCACCCCCUCUUCCAGGCCAAGUCCGCCCGCGGCGUCUG<br>CAAGGUCAUGUGCUUCCACCCCUGGUCCGACGUCACCCUCCCCCUCA<br>UGUCCGUCCCCGAGAUCCGCGCCGUCGUCGACGCCUGGGCCUCCGUC<br>ACCGAGGAGCUCGGCGCCCAGUACCCCUGGGUCCAGAUCUUCGAGAA<br>CAAGGGCGCCAUGAUGGGCUGCUCCAACCCCCACCCCCACUGCCAGG<br>UCUGGGCCUCCUCCUUCCUCCCCGACAUCGCCCAGCGCGAGGAGCGC<br>UCCCAGCAGGCCUACAAGUCCCAGCACGGCGAGCCCCUCCUCAUGGA<br>GUACUCCCGCCAGGAGCUCCUCCGCAAGGAGCGCCUCGUCCUCACCU<br>CCGAGCACUGGCUCGUCCUCGUCCCCUUCUGGGCCACCUGGCCCUAC<br>CAGACCCUCCUCCUCCCCCGCCGCCACGUCCGCCGCCUCCCCGAGCUC<br>ACCCCCGCCGAGCGCGACGACCUCGCCUCCAUCAUGAAGAAGCUCCU<br>CACCAAGUACGACAACCUCUUCGAGACCUCCUUCCCCUACUCCAUGG<br>GCUGGCACGGCGCCCCCACCGGCUCCGAGGCCGGCGCCAACUGGAAC<br>CACUGGCAGCUCCACGCCCACUACUACCCGCCCCUCCUCCGCUCCGCC<br>ACCGUCCGCAAGUUCAUGGUCGGCUACGAGAUGCUCGCCCAGGCCCA<br>GCGCGACCUCACCCCCGAGCAGGCCGCCGAGCGCCUCCGCGCCCUCCC<br>CGAGGUCCACUACCACCUCGGCCAGAAGGACCGCGAGACCGCCACCA<br>UCGCC***UGAUAAUAGUCCAUAAAGUAGGAAACACUACAGCUGGAGCCUC<br>GGUGGCCAUGCUUCUUGCCCCUUGGGCCUCCCCCCAGCCCCUCCUCCC*** |

TABLE 5-continued mRNA Constructs

| SEQ ID NO | Construct | Sequence (5' UTR = bold underline: 3' UTR comprimising a stop codon = bold italics) |
|---|---|---|
| | | ***CUUCCUGCACCCGUACCCCCCGCAUUAUUACUCACGGUACGAGUGGUC<br>UUUGAAUAAAGUCUGAGUGGGCGGC*** |
| 158 | #20 | **GGGAAAUAAGAGAGAAAAGAAGAGUAAGAAGAAAUAUAAGAGCCA<br>CC**AUGUCGCGCAGUGGAACCGAUCCUCAGCAACGCCAGCAGGCGUCA<br>GAGGCGGACGCCGCAGCAGCAACCUUCCGGGCAAACGACCAUCAGCA<br>UAUCCGCUACAACCCGCUGCAGGAUGAGUGGGUGCUGGUGUCAGCUC<br>ACCGCAUGAAGCGGCCCUGGCAGGGUCAAGUGGAGCCCCAGCUUCUG<br>AAGACAGUGCCCCGCCAUGACCCUCUCAACCCUCUGUGUCCUGGGGC<br>CAUCCGAGCCAACGGAGAGGUGAAUCCCCAGUACGAUAGCACCUUCC<br>UGUUUGACAACGACUUCCCAGCUCUGCAGCCUGAUGCCCCCAGUCCA<br>GGACCCAGUGAUCAUCCCCUUUUCCAAGCAAAGUCUGCUCGAGGAGU<br>CUGUAAGGUCAUGUGCUUCCACCCCUGGUCGGAUGUAACGCUGCCAC<br>UCAUGUCGGUCCCUGAGAUCCGGGCUGUUGUUGAUGCAUGGGCCUC<br>AGUCACAGAGGAGCUGGGUGCCCAGUACCCUUGGGUGCAGAUCUUU<br>GAAAACAAAGGUGCCAUGAUGGGCUGUUCUAACCCCCACCCCCACUG<br>CCAGGUAUGGGCCAGCAGUUUCCUGCCAGAUAUUGCCCAGCGUGAGG<br>AGCGAUCUCAGCAGGCCUAUAAGAGUCAGCAUGGAGAGCCCCUGCUA<br>AUGGAGUACAGCCGCCAGGAGCUACUCAGGAAGGAACGUCUGGUCC<br>UAACCAGUGAGCACUGGUUAGUACUGGUCCCCUUCUGGGCAACAUG<br>GCCCUACCAGACACUGCUGCUGCCCCGUCGGCAUGUGCGGCGGCUAC<br>CUGAGCUGACCCCUGCUGAGCGUGAUGAUCUAGCCUCCAUCAUGAAG<br>AAGCUCUUGACCAAGUAUGACAACCUCUUUGAGACGUCCUUUCCCUA<br>CUCCAUGGGCUGGCAUGGGGCUCCCACAGGAUCAGAGGCUGGGGCCA<br>ACUGGAACCAUUGGCAGCUGCACGCUCAUUACUACCCUCCGCUCCUG<br>CGCUCUGCCACUGUCCGGAAAUUCAUGGUUGGCUACGAAAUGCUUGC<br>UCAGGCUCAGAGGGACCUCACCCCUGAGCAGGCUGCAGAGAGACUAA<br>GGGCACUUCCUGAGGUUCAUUACCACCUGGGGCAGAAGGACAGGGA<br>GACAGCAACCAUCGCC***UGAUAAUAGGCUGGAGCCUCGGUGGCCAUGC<br>UUCUUGCCCCUUGGGCCUCCCCCCAGCCCCUCCUCCCCUUCCUGCACC<br>CGUACCCCCGUGGUCUUUGAAUAAAGUCUGAGUGGGCGGC*** |
| 159 | #21 | **GGGAAAUAAGAGAGAAAAGAAGAGUAAGAAGAAAUAUAAGAGCCA<br>CC**AUGGCAGCGACCUUCCGGGCGAGCGAACACCAGCAUAUUCGCUAC<br>AACCCGCUCCAGGACGAGUGGGUGUUAGUGUCGGCUCAUCGCAUGA<br>AGCGGCCCUGGCAAGGACAAGUGGAGCCCCAGCUUCUGAAGACAGUG<br>CCCCGCCACGACCCACUCAACCCUCUGUGUCCCGGGGCCACACGAGC<br>UAAUGGGGAGGUGAAUCCCCACUAUGAUGGUACCUUUCUGUUUGAC<br>AAUGACUUCCCGGCUCUGCAGCCCGAUGCUCCGGAUCCAGGACCCAG<br>UGACCACCCUCUCUUCCGAGCAGAGGCCGCCAGAGGAGUUUGUAAGG<br>UCAUGUGCUUCCACCCCUGGUCGGAUGUGACGCUGCCACUCAUGUCU<br>GUCCCUGAGAUCCGAGCUGUCAUCGAUGCAUGGGCCUCAGUCACAGA<br>GGAGCUGGGUGCCCAGUACCCUUGGGUGCAGAUCUUUGAAAAUAAA<br>GGAGCCAUGAUGGGCUGUUCUAACCCCCAUCCCCACUGCCAGGUUUG<br>GGCUAGCAGCUUCCUGCCAGAUAUCGCCCAGCGUGAAGAGCGAUCCC<br>AGCAGACCUAUCACAGCCAGCAUGGAAAACCUUUGUUAUUGGAAUA<br>UGGUCACCAAGAGCUCCUCAGGAAGGAACGUCUGGUCCUAACCAGUG<br>AGCACUGGAUAGUUCUGGUCCCCUUCUGGGCAGUGUGGCCUUUCCAG<br>ACACUUCUGCUGCCCCGGCGGCACGUGCGGCGGCUACCUGAGCUGAA<br>CCCCGCUGAGCGUGAUGAUCUCGCCUCCAUCAUGAAGAAGCUCUUGA<br>CCAAGUACGACAAUCUAUUUGAGACAUCCUUUCCCUACUCCAUGGGC<br>UGGCAUGGGGCUCCCACGGGAUUAAAGACUGGAGCCACCUGUGACCA<br>CUGGCAGCUCCACGCCCACUACUACCCCCCACUUCUGCGAUCCGCAA<br>CUGUCCGGAAGUUCAUGGUUGGCUAUGAAAUGCUUGCCCAGGCCCA<br>GCGUGACCUCACUCCCGAACAGGCCGCAGAAAGAUUAAGGGCGCUUC<br>CCGAGGUACACUAUUGCCUGGCGCAGAAAGACAAGGAAACGGCAGCC<br>AUUGCU***UGAUAAUAGGCUGGAGCCUCGGUGGCCAUGCUUCUUGCCCC<br>UUGGGCCUCCCCCCAGCCCCUCCUCCCCUUCCUGCACCCGUACCCCCG<br>UGGUCUUUGAAUAAAGUCUGAGUGGGCGGC*** |
| 160 | #22 | **GGGAAAUAAGAGAGAAAAGAAGAGUAAGAAGAAAUAUAAGACAGC<br>GCGUCAACAUUGCCGAAUCGCCGGGACUCAUCACAAUCUGCCUCU<br>UGGGUUAUCUCUUGUCGGCAGAUACCUUCUUGGAUCACGAAAACG<br>CGAACAAAAUUCUUAAUCGCCCGAAGCGGUAUAACUCCGGGAAAC<br>UUGAGGAGUUUCAGGGCAAUCUUGAACGAGACGAGGAGAACUCC<br>UUUGAGGAGGCGAGGGAAUUUGAAAACACAGAGCGAACAACGGA<br>GUUUUGGAAGCAAUACGUAGGGGACCAGUCGAAUCCCCUCAGGG<br>GAUCUAAAGACAUCAAUAGCUACUGCCCGUUUGGGUUUGAAGGGA<br>AGAACUAGCUGACCAACAUCAAAAACGGACGCUAGCAGUUUUGUA<br>AGAACUCGGCUGACAAUAAGGUAGUCUCCACAGAGGGAUACCGGC<br>UGGCGGAGAACCAAAAAUCCGAGCCCGCAGUCCCGUUCCCUUGGA<br>GGAGCUCACAGACUAGCAAGUUGACGAGAGCGGAGACUGUAUUC<br>CCCGACGACUACGUCAACAGCACCGAAGCCGAAACAAUCCUCGAU<br>AACAUCACGCAGAGCACUCAGUCCUUCAACUUUACGAGGGUCGUA<br>GAGGACGCGAAACCCGGUCAGUUCCCCUGGCAGGUAUUGAACGG** |

TABLE 5-continued

| mRNA Constructs | | |
|---|---|---|
| SEQ ID NO | Construct | Sequence (5' UTR = bold underline: 3' UTR comprimising a stop codon = bold italics) |
| | | **AAAAGUCGCCUUUUGAGGUUCCAUUGUCAACGAGAAGAUUGUCAC**<br>**AGCGGCACACUGCGUAGAAACAGGAAAAAUCACGGUAGCGGGAG**<br>**AGCAUAACAUUGAAGAGACAGAGCACACGGAACAAAAGCGAAUCA**<br>**UCAGAAUCAUUCCACACCAUAACUAUAACGCGGCAAUCAAUAAGU**<br>**ACAAUCACGACAUCGCACUUUUGGAGCUUGACGAACCUUUGCUUA**<br>**AUUCGUACGUCACCCCUAUUUGUAUUGCCGACAAAGAGUAUACAA**<br>**ACAUCUUCUUGAAAUUCGGCUCCGGGUACGUAUCGGGCUGGGGC**<br>**AGAUUCCAUAAGGGUAGAUCCGCACUGUUGCAAUACCUCAGGCCC**<br>**CUCGAUCGAGCCACUUGUCUGCGGUCCACCAAAUUCACAAUCUAC**<br>**AACAAUUUCUCGGGAUUCCAAGGGAGAGAUAGCUGCCAGGGAGA**<br>**CUCAGGGGGUCCCCACACGGAAGUCGAGGGGACGUCAUUUCUGA**<br>**CGGGAAUUAUCUCGGGAGAGGCGAAGGGGAACAUCUACACUAAA**<br>**UCACGGUUCAAUUGGAUCAAGGAAAAGACGAAACUCACGUGAUAA**<br>**UAGGCUGGAGCCUCGGUGGCC**AUGCUUCUUGCCCCUUGGGCCUCCC<br>CCCAGCCCCUCCUCCCCUUCCUGCACCCGUACCCCCGUGGUCUU***UGAA***<br>***UAAAGUCUGAGUGGGCGGC*** |
| 161 | #23 | **GGGAAAUAAGAGAGAAAAGAAGAGUAAGAAGAAAUAUAAGAGCCA**<br>**CC**AUGACCCUCUCAACCCUCUGUGUCCUGGGGCCAUCCGAGCCAACG<br>GAGAGUAAGGUCAUGUGCUUCCACCCCUGGUCGGAUGUAACGCUGCC<br>ACUCAUGUCGGUCCCUGAGAUCCGGGCUGUUGUUGAUGCAUGGGCC<br>UCAGUCACAGAGGAGCUGGGUGCCCAGUACCCUUGGGUGCAGAUCU<br>UUGAAAACAAAGGUGCCAUGAUGGGCUGUUCUAACCCCCACCCCCAC<br>UGCCAGGUAUGGGCCAGCAGUUUCCUGCCAGAUAUUGCCCAGCGUGA<br>GGAGCGAUCUCAGCAGGCCUAUAAGAGUCAGCAUGGAGAGCCCCUGC<br>UAAUGGAGUACAGCCGCCAGGAGCUACUCAGGAAGGAACGUCUGGU<br>CCUAACCAGUGAGCACUGGUUAGUACUGGUCCCCUUCUGGGCAACAU<br>GGCCCUACCAGACACUGCUGCUGCCCCGUCGGCAUGUGCGGCGGCUA<br>CCUGAGCUGACCCCUGCUGAGCGUGAUGAUCUAGCCUCCAUCAUGAA<br>GAAGCUCUUGACCAAGUAUGACAACCUCUUUGAGACGUCCUUUCCCU<br>ACUCCAUGGGCUGGCAUGGGGCUCCCACAGGAUCAGAGGCUGGGGCC<br>AACUGGAACCAUUGGCAGCUGCACGCUCAUUACUACCCUCCGCUCCU<br>GCGCUCUGCCACUGUCCGGAAAUUCAUGGUUGGCUACGAAAUGCUU<br>GCUCAGGCUCAGAGGGACCUCACCCCUGAGCAGGCUGCAGAGAGACU<br>AAGGGCACUUCCUGAGGUUCAUUACCACCUGGGGCAGAAGGACAGG<br>GAGACAGCAACCAUCGCC***UGAUAAUAGGCUGGAGCCUCGGUGGCCAU***<br>***GCUUCUUGCCCCUUGGGCCUCCCCCCAGCCCCUCCUCCCCUUCCUGCA***<br>***CCCGUACCCCCGUGGUCUUUGAAUAAAGUCUGAGUGGGCGGC*** |
| 162 | #24 | **GGGAAAUAAGAGAGAAAAGAAGAGUAAGAAGAAAUAUAAGAGCCA**<br>**CC**AUGAUGGGCUGUUCUAACCCCCAUCCCCACUGCCAGGUUUGGGCU<br>AGCAGCUUCCUGCCAGAUAUCGCCCAGCGUGAAGAGCGAUCCCAGCA<br>GACCUAUCACAGCCAGCAUGGAAAACCUUUGUUAUUGGAAUAUGGU<br>CACCAAGAGCUCCUCAGGAAGGAACGUCUGGUCCUAACCAGUGAGCA<br>CUGGAUAGUUCUGGUCCCCUUCUGGGCAGUGUGGCCUUUCCAGACAC<br>UUCUGCUGCCCCGGCGGCACGUGCGGCGGCUACCUGAGCUGAACCCC<br>GCUGAGCGUGAUGAUCUCGCCUCCAUCAUGAAGAAGCUCUUGACCAA<br>GUACGACAAUCUAUUUGAGACAUCCUUUCCCUACUCCAUGGGCUGGC<br>AUGGGGCUCCCACGGGAUUAAAGACUGGAGCCACCUGUGACCACUGG<br>CAGCUCCACGCCCACUACUACCCCCCACUUCUGCGAUCCGCAACUGU<br>CCGGAAGUUCAUGGUUGGCUAUGAAAUGCUUGCCCAGGCCCAGCGU<br>GACCUCACUCCCGAACAGGCCGCAGAAAGAUUAAGGGCGCUUCCCGA<br>GGUACACUAUUGCCUGGCGCAGAAAGACAAGGAAACGGCAGCCAUU<br>GCU***UGAUAAUAGGCUGGAGCCUCGGUGGCCAUGCUUCUUGCCCCUUG***<br>***GGCCUCCCCCCAGCCCCUCCUCCCCUUCCUGCACCCGUACCCCCGUGG***<br>***UCUUUGAAUAAAGUCUGAGUGGGCGGC*** |

Additional mRNA (ORF) sequences used in the Examples are listed in Table 6.

TABLE 6

| ORF Sequences Encoding Wild-type GALT Isoforms | | |
|---|---|---|
| 151 | Human GALT isoform 2 | AUGACCCUCUCAACCCUCUGUGUCCUGGGGCCAUC<br>CGAGCCAACGGAGAGUAAGGUCAUGUGCUUCCACC<br>CCUGGUCGGAUGUAACGCUGCCACUCAUGUCGGUC<br>CCUGAGAUCCGGGCUGUUGUUGAUGCAUGGGCCUC<br>AGUCACAGAGGAGCUGGGUGCCCAGUACCCUUGGG<br>UGCAGAUCUUUGAAAACAAAGGUGCCAUGAUGGGC<br>UGUUCUAACCCCCACCCCCACUGCCAGGUAUGGGC |

TABLE 6-continued

| ORF Sequences Encoding Wild-type GALT Isoforms | | |
|---|---|---|
| | | CAGCAGUUUCCUGCCAGAUAUUGCCCAGCGUGAGG<br>AGCGAUCUCAGCAGGCCUAUAAGAGUCAGCAUGGA<br>GAGCCCCUGCUAAUGGAGUACAGCCGCCAGGAGCU<br>ACUCAGGAAGGAACGUCUGGUCCUAACCAGUGAGC<br>ACUGGUUAGUACUGGUCCCCUUCUGGGCAACAUGG<br>CCCUACCAGACACUGCUGCUGCCCCGUCGGCAUGU<br>GCGGCGGCUACCUGAGCUGACCCCUGCUGAGCGUG<br>AUGAUCUAGCCUCCAUCAUGAAGAAGCUCUUGACC<br>AAGUAUGACAACCUCUUUGAGACGUCCUUUCCCUA<br>CUCCAUGGGCUGGCAUGGGGCUCCCACAGGAUCAG |

TABLE 6-continued

| | | ORF Sequences Encoding Wild-type GALT Isoforms |
|---|---|---|
| | | AGGCUGGGGCCAACUGGAACCAUUGGCAGCUGCAC<br>GCUCAUUACUACCCUCCGCUCCUGCGCUCUGCCAC<br>UGUCCGGAAAUUCAUGGUUGGCUACGAAAUGCUUG<br>CUCAGGCUCAGAGGGACCUCACCCCUGAGCAGGCU<br>GCAGAGAGACUAAGGGCACUUCCUGAGGUUCAUUA<br>CCACCUGGGGCAGAAGGACAGGGAGACAGCAACCA<br>UCGCC |
| 152 | Mouse GALT isoform 2 | AUGAUGGGCUGUUCUAACCCCCAUCCCCACUGCCA<br>GGUUUGGGCUAGCAGCUUCCUGCCAGAUAUCGCCC<br>AGCGUGAAGAGCGAUCCCAGCAGACCUAUCACAGC<br>CAGCAUGGAAAACCUUUGUUAUUGGAAUAUGGUCA<br>CCAAGAGCUCCUCAGGAAGGAACGUCUGGUCCUAA<br>CCAGUGAGCACUGGAUAGUUCUGGUCCCCUUCUGG<br>GCAGUGUGGCCUUUCCAGACACUUCUGCUGCCCCG<br>GCGGCACGUGCGGCGGCUACCUGAGCUGAACCCCG<br>CUGAGCGUGAUGAUCUCGCCUCCAUCAUGAAGAAG<br>CUCUUGACCAAGUACGACAAUCUAUUUGAGACAUC<br>CUUUCCCUACUCCAUGGGCUGGCAUGGGGCUCCCA<br>CGGGAUUAAAGACUGGAGCCACCUGUGACCACUGG<br>CAGCUCCACGCCCACUACUACCCCCCACUUCUGCG<br>AUCCGCAACUGUCCGGAAGUUCAUGGUUGGCUAUG<br>AAAUGCUUGCCCAGGCCCAGCGUGACCUCACUCCC<br>GAACAGGCCGCAGAAAGAUUAAGGGCGCUUCCCGA<br>GGUACACUAUUGCCUGGCGCAGAAAGACAAGGAAA<br>CGGCAGCCAUUGCU |
| 153 | Human GALT isoform 1 | AUGUCGCGCAGUGGAACCGAUCCUCAGCAACGCCA<br>GCAGGCGUCAGAGGCGGACGCCGCAGCAGCAACCU<br>UCCGGGCAAACGACCAUCAGCAUAUCCGCUACAAC<br>CCGCUGCAGGAUGAGUGGGUGCUGGUGUCAGCUCA<br>CCGCAUGAAGCGGCCCUGGCAGGGUCAAGUGGAGC<br>CCCAGCUUCUGAAGACAGUGCCCCGCCAUGACCCU<br>CUCAACCCUCUGUGUCCUGGGGCCAUCCGAGCCAA<br>CGGAGAGGUGAAUCCCCAGUACGAUAGCACCUUCC<br>UGUUUGACAACGACUUCCCAGCUCUGCAGCCUGAU<br>GCCCCCAGUCCAGGACCCAGUGAUCAUCCCCUUUU<br>CCAAGCAAAGUCUGCUCGAGGAGUCUGUAAGGUCA<br>UGUGCUUCCACCCCUGGUCGGAUGUAACGCUGCCA<br>CUCAUGUCGGUCCCUGAGAUCCGGGCUGUUGUUGA<br>UGCAUGGGCCUCAGUCACAGAGGAGCUGGGUGCCC<br>AGUACCCUUGGGUGCAGAUCUUUGAAAACAAAGGU<br>GCCAUGAUGGGCUGUUCUAACCCCCACCCCCACUG<br>CCAGGUAUGGGCCAGCAGUUUCCUGCCAGAUAUUG<br>CCCAGCGUGAGGAGCGAUCUCAGCAGGCCUAUAAG<br>AGUCAGCAUGGAGAGCCCCUGCUAAUGGAGUACAG<br>CCGCCAGGAGCUACUCAGGAAGGAACGUCUGGUCC<br>UAACCAGUGAGCACUGGUUAGUACUGGUCCCCUUC<br>UGGGCAACAUGGCCCUACCAGACACUGCUGCUGCC<br>CCGUCGGCAUGUGCGGCGGCUACCUGAGCUGACCC<br>CUGCUGAGCGUGAUGAUCUAGCCUCCAUCAUGAAG<br>AAGCUCUUGACCAAGUAUGACAACCUCUUUGAGAC<br>GUCCUUUCCCUACUCCAUGGGCUGGCAUGGGGCUC<br>CCACAGGAUCAGAGGCUGGGGCCAACUGGAACCAU<br>UGGCAGCUGCACGCUCAUUACUACCCUCCGCUCCU<br>GCGCUCUGCCACUGUCCGGAAAUUCAUGGUUGGCU<br>ACGAAAUGCUUGCUCAGGCUCAGAGGGACCUCACC<br>CCUGAGCAGGCUGCAGAGAGACUAAGGGCACUUCC<br>UGAGGUUCAUUACCACCUGGGGCAGAAGGACAGGG<br>AGACAGCAACCAUCGCC |
| 154 | Mouse GALT isoform 1 | AUGGCAGCGACCUUCCGGGCGAGCGAACACCAGCA<br>UAUUCGCUACAACCCGCUCCAGGACGAGUGGGUGU<br>UAGUGUCGGCUCAUCGCAUGAAGCGGCCCUGGCAA<br>GGACAAGUGGAGCCCCAGCUUCUGAAGACAGUGCC<br>CCGCCACGACCCACUCAACCCUCUGUGUCCCGGGG<br>CCACACGAGCUAAUGGGGAGGUGAAUCCCCACUAU<br>GAUGGUACCUUUCUGUUUGACAAUGACUUCCCGGC<br>UCUGCAGCCCGAUGCUCCGGAUCCAGGACCCAGUG<br>ACCACCCUCUCUUCCGAGCAGAGGCCGCCAGAGGA<br>GUUUGUAAGGUCAUGUGCUUCCACCCCUGGUCGGA<br>UGUGACGCUGCCACUCAUGUCUGUCCCUGAGAUCC<br>GAGCUGUCAUCGAUGCAUGGGCCUCAGUCACAGAG<br>GAGCUGGGUGCCCAGUACCCUUGGGUGCAGAUCUU<br>UGAAAAUAAAGGAGCCAUGAUGGGCUGUUCUAACC<br>CCCAUCCCCACUGCCAGGUUUGGGCUAGCAGCUUC<br>CUGCCAGAUAUCGCCCAGCGUGAAGAGCGAUCCCA<br>GCAGACCUAUCACAGCCAGCAUGGAAAACCUUUGU<br>UAUUGGAAUAUGGUCACCAAGAGCUCCUCAGGAAG<br>GAACGUCUGGUCCUAACCAGUGAGCACUGGAUAGU<br>UCUGGUCCCCUUCUGGGCAGUGUGGCCUUUCCAGA<br>CACUUCUGCUGCCCCGGCGGCACGUGCGGCGGCUA<br>CCUGAGCUGAACCCCGCUGAGCGUGAUGAUCUCGC<br>CUCCAUCAUGAAGAAGCUCUUGACCAAGUACGACA<br>AUCUAUUUGAGACAUCCUUUCCCUACUCCAUGGGC<br>UGGCAUGGGGCUCCCACGGGAUUAAAGACUGGAGC<br>CACCUGUGACCACUGGCAGCUCCACGCCCACUACU<br>ACCCCCCACUUCUGCGAUCCGCAACUGUCCGGAAG<br>UUCAUGGUUGGCUAUGAAAUGCUUGCCCAGGCCCA<br>GCGUGACCUCACUCCCGAACAGGCCGCAGAAAGAU<br>UAAGGGCGCUUCCCGAGGUACACUAUUGCCUGGCG<br>CAGAAAGACAAGGAAACGGCAGCCAUUGCU |

20. METHODS OF MAKING POLYNUCLEOTIDES

The present disclosure also provides methods for making a polynucleotide of the invention (e.g., a polynucleotide comprising a nucleotide sequence encoding a GALT polypeptide) or a complement thereof.

In some aspects, a polynucleotide (e.g., a RNA, e.g., an mRNA) disclosed herein, and encoding a GALT polypeptide, can be constructed using in vitro transcription. In other aspects, a polynucleotide (e.g., a RNA, e.g., an mRNA) disclosed herein, and encoding a GALT polypeptide, can be constructed by chemical synthesis using an oligonucleotide synthesizer.

In other aspects, a polynucleotide (e.g., a RNA, e.g., an mRNA) disclosed herein, and encoding a GALT polypeptide is made by using a host cell. In certain aspects, a polynucleotide (e.g., a RNA, e.g., an mRNA) disclosed herein, and encoding a GALT polypeptide is made by one or more combination of the IVT, chemical synthesis, host cell expression, or any other methods known in the art.

Naturally occurring nucleosides, non-naturally occurring nucleosides, or combinations thereof, can totally or partially naturally replace occurring nucleosides present in the candidate nucleotide sequence and can be incorporated into a sequence-optimized nucleotide sequence (e.g., a RNA, e.g., an mRNA) encoding a GALT polypeptide. The resultant polynucleotides, e.g., mRNAs, can then be examined for their ability to produce protein and/or produce a therapeutic outcome.

a. In Vitro Transcription/Enzymatic Synthesis

The polynucleotides of the present invention disclosed herein (e.g., a polynucleotide comprising a nucleotide sequence encoding a GALT polypeptide) can be transcribed using an in vitro transcription (IVT) system. The system typically comprises a transcription buffer, nucleotide triphosphates (NTPs), an RNase inhibitor and a polymerase. The NTPs can be selected from, but are not limited to, those described herein including natural and unnatural (modified) NTPs. The polymerase can be selected from, but is not limited to, T7 RNA polymerase, T3 RNA polymerase and mutant polymerases such as, but not limited to, polymerases able to incorporate polynucleotides disclosed herein. See U.S. Publ. No. US20130259923, which is herein incorporated by reference in its entirety.

Any number of RNA polymerases or variants can be used in the synthesis of the polynucleotides of the present invention. RNA polymerases can be modified by inserting or deleting amino acids of the RNA polymerase sequence. As a non-limiting example, the RNA polymerase can be modified to exhibit an increased ability to incorporate a 2'-modified nucleotide triphosphate compared to an unmodified RNA polymerase (see International Publication WO2008078180 and U.S. Pat. No. 8,101,385; herein incorporated by reference in their entireties).

Variants can be obtained by evolving an RNA polymerase, optimizing the RNA polymerase amino acid and/or nucleic acid sequence and/or by using other methods known in the art. As a non-limiting example, T7 RNA polymerase variants can be evolved using the continuous directed evolution system set out by Esvelt et al. (Nature 472:499-503 (2011); herein incorporated by reference in its entirety) where clones of T7 RNA polymerase can encode at least one mutation such as, but not limited to, lysine at position 93 substituted for threonine (K93T), I4M, A7T, E63V, V64D, A65E, D66Y, T76N, C125R, S128R, A136T, N165S, G175R, H176L, Y178H, F182L, L196F, G198V, D208Y, E222K, S228A, Q239R, T243N, G259D, M267I, G280C, H300R, D351A, A354S, E356D, L360P, A383V, Y385C, D388Y, S397R, M401T, N410S, K450R, P451T, G452V, E484A, H523L, H524N, G542V, E565K, K577E, K577M, N601S, S684Y, L699I, K713E, N748D, Q754R, E775K, A827V, D851N or L864F. As another non-limiting example, T7 RNA polymerase variants can encode at least mutation as described in U.S. Pub. Nos. 20100120024 and 20070117112; herein incorporated by reference in their entireties. Variants of RNA polymerase can also include, but are not limited to, substitutional variants, conservative amino acid substitution, insertional variants, and/or deletional variants.

In one aspect, the polynucleotide can be designed to be recognized by the wild type or variant RNA polymerases. In doing so, the polynucleotide can be modified to contain sites or regions of sequence changes from the wild type or parent chimeric polynucleotide.

Polynucleotide or nucleic acid synthesis reactions can be carried out by enzymatic methods utilizing polymerases. Polymerases catalyze the creation of phosphodiester bonds between nucleotides in a polynucleotide or nucleic acid chain. Currently known DNA polymerases can be divided into different families based on amino acid sequence comparison and crystal structure analysis. DNA polymerase I (pol I) or A polymerase family, including the Klenow fragments of *E. coli, Bacillus* DNA polymerase I, *Thermus aquaticus* (Taq) DNA polymerases, and the T7 RNA and DNA polymerases, is among the best studied of these families. Another large family is DNA polymerase a (pol a) or B polymerase family, including all eukaryotic replicating DNA polymerases and polymerases from phages T4 and RB69. Although they employ similar catalytic mechanism, these families of polymerases differ in substrate specificity, substrate analog-incorporating efficiency, degree and rate for primer extension, mode of DNA synthesis, exonuclease activity, and sensitivity against inhibitors.

DNA polymerases are also selected based on the optimum reaction conditions they require, such as reaction temperature, pH, and template and primer concentrations. Sometimes a combination of more than one DNA polymerases is employed to achieve the desired DNA fragment size and synthesis efficiency. For example, Cheng et al. increase pH, add glycerol and dimethyl sulfoxide, decrease denaturation times, increase extension times, and utilize a secondary thermostable DNA polymerase that possesses a 3' to 5' exonuclease activity to effectively amplify long targets from cloned inserts and human genomic DNA. (Cheng et al., PNAS 91:5695-5699 (1994), the contents of which are incorporated herein by reference in their entirety). RNA polymerases from bacteriophage T3, T7, and SP6 have been widely used to prepare RNAs for biochemical and biophysical studies. RNA polymerases, capping enzymes, and poly-A polymerases are disclosed in the co-pending International Publication No. WO2014028429, the contents of which are incorporated herein by reference in their entirety.

In one aspect, the RNA polymerase which can be used in the synthesis of the polynucleotides of the present invention is a Syn5 RNA polymerase. (see Zhu et al. Nucleic Acids Research 2013, doi:10.1093/nar/gkt1193, which is herein incorporated by reference in its entirety). The Syn5 RNA polymerase was recently characterized from marine cyanophage Syn5 by Zhu et al. where they also identified the promoter sequence (see Zhu et al. Nucleic Acids Research 2013, the contents of which is herein incorporated by reference in its entirety). Zhu et al. found that Syn5 RNA polymerase catalyzed RNA synthesis over a wider range of temperatures and salinity as compared to T7 RNA polymerase. Additionally, the requirement for the initiating nucleotide at the promoter was found to be less stringent for Syn5 RNA polymerase as compared to the T7 RNA polymerase making Syn5 RNA polymerase promising for RNA synthesis.

In one aspect, a Syn5 RNA polymerase can be used in the synthesis of the polynucleotides described herein. As a non-limiting example, a Syn5 RNA polymerase can be used in the synthesis of the polynucleotide requiring a precise 3'-terminus.

In one aspect, a Syn5 promoter can be used in the synthesis of the polynucleotides. As a non-limiting example, the Syn5 promoter can be 5'-ATTGGGCACCCGTAAGGG-3' (SEQ ID NO: 78 as described by Zhu et al. (Nucleic Acids Research 2013).

In one aspect, a Syn5 RNA polymerase can be used in the synthesis of polynucleotides comprising at least one chemical modification described herein and/or known in the art (see e.g., the incorporation of pseudo-UTP and 5Me-CTP described in Zhu et al. Nucleic Acids Research 2013).

In one aspect, the polynucleotides described herein can be synthesized using a Syn5 RNA polymerase which has been purified using modified and improved purification procedure described by Zhu et al. (Nucleic Acids Research 2013).

Various tools in genetic engineering are based on the enzymatic amplification of a target gene which acts as a template. For the study of sequences of individual genes or specific regions of interest and other research needs, it is necessary to generate multiple copies of a target gene from a small sample of polynucleotides or nucleic acids. Such methods can be applied in the manufacture of the polynucleotides of the invention. For example, polymerase chain reaction (PCR), strand displacement amplification (SDA), nucleic acid sequence-based amplification (NASBA), also called transcription mediated amplification (TMA), and/or rolling-circle amplification (RCA) can be utilized in the manufacture of one or more regions of the polynucleotides of the present invention. Assembling polynucleotides or nucleic acids by a ligase is also widely used.

b. Chemical Synthesis

Standard methods can be applied to synthesize an isolated polynucleotide sequence encoding an isolated polypeptide of interest, such as a polynucleotide of the invention (e.g., a polynucleotide comprising a nucleotide sequence encoding a GALT polypeptide). For example, a single DNA or RNA oligomer containing a codon-optimized nucleotide sequence coding for the particular isolated polypeptide can be synthesized. In other aspects, several small oligonucleotides coding for portions of the desired polypeptide can be synthesized and then ligated. In some aspects, the individual oligonucleotides typically contain 5' or 3' overhangs for complementary assembly.

A polynucleotide disclosed herein (e.g., a RNA, e.g., an mRNA) can be chemically synthesized using chemical synthesis methods and potential nucleobase substitutions known in the art. See, for example, International Publication Nos. WO2014093924, WO2013052523; WO2013039857, WO2012135805, WO2013151671; U.S. Publ. No. US20130115272; or U.S. Pat. No. 8,999,380 or 8,710,200, all of which are herein incorporated by reference in their entireties.

c. Purification of Polynucleotides Encoding GALT

Purification of the polynucleotides described herein (e.g., a polynucleotide comprising a nucleotide sequence encoding a GALT polypeptide) can include, but is not limited to, polynucleotide clean-up, quality assurance and quality control. Clean-up can be performed by methods known in the arts such as, but not limited to, AGENCOURT® beads (Beckman Coulter Genomics, Danvers, Mass.), poly-T beads, LNA™ oligo-T capture probes (EXIQON® Inc., Vedbaek, Denmark) or HPLC based purification methods such as, but not limited to, strong anion exchange HPLC, weak anion exchange HPLC, reverse phase HPLC (RP-HPLC), and hydrophobic interaction HPLC (HIC-HPLC).

The term "purified" when used in relation to a polynucleotide such as a "purified polynucleotide" refers to one that is separated from at least one contaminant. As used herein, a "contaminant" is any substance that makes another unfit, impure or inferior. Thus, a purified polynucleotide (e.g., DNA and RNA) is present in a form or setting different from that in which it is found in nature, or a form or setting different from that which existed prior to subjecting it to a treatment or purification method.

In some embodiments, purification of a polynucleotide of the invention (e.g., a polynucleotide comprising a nucleotide sequence encoding a GALT polypeptide) removes impurities that can reduce or remove an unwanted immune response, e.g., reducing cytokine activity.

In some embodiments, the polynucleotide of the invention (e.g., a polynucleotide comprising a nucleotide sequence encoding a GALT polypeptide) is purified prior to administration using column chromatography (e.g., strong anion exchange HPLC, weak anion exchange HPLC, reverse phase HPLC (RP-HPLC), and hydrophobic interaction HPLC (HIC-HPLC), or (LCMS)).

In some embodiments, the polynucleotide of the invention (e.g., a polynucleotide comprising a nucleotide sequence a GALT polypeptide) purified using column chromatography (e.g., strong anion exchange HPLC, weak anion exchange HPLC, reverse phase HPLC (RP-HPLC, hydrophobic interaction HPLC (HIC-HPLC), or (LCMS)) presents increased expression of the encoded GALT protein compared to the expression level obtained with the same polynucleotide of the present disclosure purified by a different purification method.

In some embodiments, a column chromatography (e.g., strong anion exchange HPLC, weak anion exchange HPLC, reverse phase HPLC (RP-HPLC), hydrophobic interaction HPLC (HIC-HPLC), or (LCMS)) purified polynucleotide comprises a nucleotide sequence encoding a GALT polypeptide comprising one or more of the point mutations known in the art.

In some embodiments, the use of RP-HPLC purified polynucleotide increases GALT protein expression levels in cells when introduced into those cells, e.g., by 10-100%, i.e., at least about 10%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 90%, at least about 95%, or at least about 100% with respect to the expression levels of GALT protein in the cells before the RP-HPLC purified polynucleotide was introduced in the cells, or after a non-RP-HPLC purified polynucleotide was introduced in the cells.

In some embodiments, the use of RP-HPLC purified polynucleotide increases functional GALT protein expression levels in cells when introduced into those cells, e.g., by 10-100%, i.e., at least about 10%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 90%, at least about 95%, or at least about 100% with respect to the functional expression levels of GALT protein in the cells before the RP-HPLC purified polynucleotide was introduced in the cells, or after a non-RP-HPLC purified polynucleotide was introduced in the cells.

In some embodiments, the use of RP-HPLC purified polynucleotide increases detectable GALT activity in cells when introduced into those cells, e.g., by 10-100%, i.e., at least about 10%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 90%, at least about 95%, or at least about 100% with respect to the activity levels of functional GALT in the cells before the RP-HPLC purified polynucleotide was introduced in the cells, or after a non-RP-HPLC purified polynucleotide was introduced in the cells.

In some embodiments, the purified polynucleotide is at least about 80% pure, at least about 85% pure, at least about 90% pure, at least about 95% pure, at least about 96% pure, at least about 97% pure, at least about 98% pure, at least about 99% pure, or about 100% pure.

A quality assurance and/or quality control check can be conducted using methods such as, but not limited to, gel electrophoresis, UV absorbance, or analytical HPLC. In another embodiment, the polynucleotide can be sequenced by methods including, but not limited to reverse-transcriptase-PCR.

d. Quantification of Expressed Polynucleotides Encoding GALT

In some embodiments, the polynucleotides of the present invention (e.g., a polynucleotide comprising a nucleotide sequence encoding a GALT polypeptide), their expression products, as well as degradation products and metabolites can be quantified according to methods known in the art.

In some embodiments, the polynucleotides of the present invention can be quantified in exosomes or when derived from one or more bodily fluid. As used herein "bodily fluids" include peripheral blood, serum, plasma, ascites, urine, cerebrospinal fluid (CSF), sputum, saliva, bone marrow, synovial fluid, aqueous humor, amniotic fluid, cerumen, breast milk, broncheoalveolar lavage fluid, semen, prostatic fluid, cowper's fluid or pre-ejaculatory fluid, sweat, fecal matter, hair, tears, cyst fluid, pleural and peritoneal fluid, pericardial fluid, lymph, chyme, chyle, bile, interstitial fluid, menses, pus, sebum, vomit, vaginal secretions, mucosal secretion, stool water, pancreatic juice, lavage fluids from sinus cavities, bronchopulmonary aspirates, blastocyl cavity fluid, and umbilical cord blood. Alternatively, exosomes can be retrieved from an organ selected from the group consisting of lung, heart, pancreas, stomach, intestine, bladder, kidney, ovary, testis, skin, colon, breast, prostate, brain, esophagus, liver, and placenta.

In the exosome quantification method, a sample of not more than 2 mL is obtained from the subject and the exosomes isolated by size exclusion chromatography, density gradient centrifugation, differential centrifugation, nanomembrane ultrafiltration, immunoabsorbent capture, affinity purification, microfluidic separation, or combinations thereof. In the analysis, the level or concentration of a polynucleotide can be an expression level, presence, absence, truncation or alteration of the administered construct. It is advantageous to correlate the level with one or more clinical phenotypes or with an assay for a human disease biomarker.

The assay can be performed using construct specific probes, cytometry, qRT-PCR, real-time PCR, PCR, flow cytometry, electrophoresis, mass spectrometry, or combinations thereof while the exosomes can be isolated using immunohistochemical methods such as enzyme linked immunosorbent assay (ELISA) methods. Exosomes can also be isolated by size exclusion chromatography, density gradient centrifugation, differential centrifugation, nanomembrane ultrafiltration, immunoabsorbent capture, affinity purification, microfluidic separation, or combinations thereof.

These methods afford the investigator the ability to monitor, in real time, the level of polynucleotides remaining or delivered. This is possible because the polynucleotides of the present invention differ from the endogenous forms due to the structural or chemical modifications.

In some embodiments, the polynucleotide can be quantified using methods such as, but not limited to, ultraviolet visible spectroscopy (UV/Vis). A non-limiting example of a UV/Vis spectrometer is a NANODROP® spectrometer (ThermoFisher, Waltham, Mass.). The quantified polynucleotide can be analyzed in order to determine if the polynucleotide can be of proper size, check that no degradation of the polynucleotide has occurred. Degradation of the polynucleotide can be checked by methods such as, but not limited to, agarose gel electrophoresis, HPLC based purification methods such as, but not limited to, strong anion exchange HPLC, weak anion exchange HPLC, reverse phase HPLC (RP-HPLC), and hydrophobic interaction HPLC (HIC-HPLC), liquid chromatography-mass spectrometry (LCMS), capillary electrophoresis (CE) and capillary gel electrophoresis (CGE).

21. PHARMACEUTICAL COMPOSITIONS AND FORMULATIONS

The present invention provides pharmaceutical compositions and formulations that comprise any of the polynucleotides described above. In some embodiments, the composition or formulation further comprises a delivery agent.

In some embodiments, the composition or formulation can contain a polynucleotide comprising a sequence optimized nucleic acid sequence disclosed herein which encodes a GALT polypeptide. In some embodiments, the composition or formulation can contain a polynucleotide (e.g., a RNA, e.g., an mRNA) comprising a polynucleotide (e.g., an ORF) having significant sequence identity to a sequence optimized nucleic acid sequence disclosed herein which encodes a GALT polypeptide. In some embodiments, the polynucleotide further comprises a miRNA binding site, e.g., a miRNA binding site that binds miR-126, miR-142, miR-144, miR-146, miR-150, miR-155, miR-16, miR-21, miR-223, miR-24, miR-27 and miR-26a.

Pharmaceutical compositions or formulation can optionally comprise one or more additional active substances, e.g., therapeutically and/or prophylactically active substances. Pharmaceutical compositions or formulation of the present invention can be sterile and/or pyrogen-free. General considerations in the formulation and/or manufacture of pharmaceutical agents can be found, for example, in *Remington: The Science and Practice of Pharmacy* $21^{st}$ ed., Lippincott Williams & Wilkins, 2005 (incorporated herein by reference in its entirety). In some embodiments, compositions are administered to humans, human patients or subjects. For the purposes of the present disclosure, the phrase "active ingredient" generally refers to polynucleotides to be delivered as described herein.

Formulations and pharmaceutical compositions described herein can be prepared by any method known or hereafter developed in the art of pharmacology. In general, such preparatory methods include the step of associating the active ingredient with an excipient and/or one or more other accessory ingredients, and then, if necessary and/or desirable, dividing, shaping and/or packaging the product into a desired single- or multi-dose unit.

A pharmaceutical composition or formulation in accordance with the present disclosure can be prepared, packaged, and/or sold in bulk, as a single unit dose, and/or as a plurality of single unit doses. As used herein, a "unit dose" refers to a discrete amount of the pharmaceutical composition comprising a predetermined amount of the active ingredient. The amount of the active ingredient is generally equal to the dosage of the active ingredient that would be administered to a subject and/or a convenient fraction of such a dosage such as, for example, one-half or one-third of such a dosage.

Relative amounts of the active ingredient, the pharmaceutically acceptable excipient, and/or any additional ingredients in a pharmaceutical composition in accordance with the present disclosure can vary, depending upon the identity, size, and/or condition of the subject being treated and further depending upon the route by which the composition is to be administered.

In some embodiments, the compositions and formulations described herein can contain at least one polynucleotide of the invention. As a non-limiting example, the composition or formulation can contain 1, 2, 3, 4 or 5 polynucleotides of the invention. In some embodiments, the compositions or formulations described herein can comprise more than one type of polynucleotide. In some embodiments, the composition or formulation can comprise a polynucleotide in linear and circular form. In another embodiment, the composition or formulation can comprise a circular polynucleotide and an in vitro transcribed (IVT) polynucleotide. In yet another embodiment, the composition or formulation can comprise an IVT polynucleotide, a chimeric polynucleotide and a circular polynucleotide.

Although the descriptions of pharmaceutical compositions and formulations provided herein are principally directed to pharmaceutical compositions and formulations that are suitable for administration to humans, it will be understood by the skilled artisan that such compositions are generally suitable for administration to any other animal, e.g., to non-human animals, e.g. non-human mammals.

The present invention provides pharmaceutical formulations that comprise a polynucleotide described herein (e.g., a polynucleotide comprising a nucleotide sequence encoding a GALT polypeptide). The polynucleotides described herein can be formulated using one or more excipients to: (1) increase stability; (2) increase cell transfection; (3) permit the sustained or delayed release (e.g., from a depot formulation of the polynucleotide); (4) alter the biodistribution (e.g., target the polynucleotide to specific tissues or cell types); (5) increase the translation of encoded protein in vivo; and/or (6) alter the release profile of encoded protein in vivo. In some embodiments, the pharmaceutical formulation further comprises a delivery agent comprising, e.g., a compound having the Formula (I), e.g., any of Compounds 1-232, e.g., Compound 18; a compound having the Formula (III), (IV), (V), or (VI), e.g., any of Compounds 233-342, e.g., Compound 236; or a compound having the Formula (VIII), e.g., any of Compounds 419-428, e.g., Compound 428, or any combination thereof. In some embodiments, the delivery agent comprises Compound 18, DSPC, Cholesterol, and Compound 428, e.g., with a mole ratio of about 50:10:38.5:1.5.

A pharmaceutically acceptable excipient, as used herein, includes, but are not limited to, any and all solvents, dispersion media, or other liquid vehicles, dispersion or suspension aids, diluents, granulating and/or dispersing agents, surface active agents, isotonic agents, thickening or emulsifying agents, preservatives, binders, lubricants or oil, coloring, sweetening or flavoring agents, stabilizers, antioxidants, antimicrobial or antifungal agents, osmolality adjusting agents, pH adjusting agents, buffers, chelants, cyoprotectants, and/or bulking agents, as suited to the particular dosage form desired. Various excipients for formulating pharmaceutical compositions and techniques for preparing the composition are known in the art (see Remington: The Science and Practice of Pharmacy, 21st Edition, A. R. Gennaro (Lippincott, Williams & Wilkins, Baltimore, Md., 2006; incorporated herein by reference in its entirety).

Exemplary diluents include, but are not limited to, calcium or sodium carbonate, calcium phosphate, calcium hydrogen phosphate, sodium phosphate, lactose, sucrose, cellulose, microcrystalline cellulose, kaolin, mannitol, sorbitol, etc., and/or combinations thereof.

Exemplary granulating and/or dispersing agents include, but are not limited to, starches, pregelatinized starches, or microcrystalline starch, alginic acid, guar gum, agar, poly (vinyl-pyrrolidone), (providone), cross-linked poly(vinyl-pyrrolidone) (crospovidone), cellulose, methylcellulose, carboxymethyl cellulose, cross-linked sodium carboxymethyl cellulose (croscarmellose), magnesium aluminum silicate (VEEGUM®), sodium lauryl sulfate, etc., and/or combinations thereof.

Exemplary surface active agents and/or emulsifiers include, but are not limited to, natural emulsifiers (e.g., acacia, agar, alginic acid, sodium alginate, tragacanth, chondrux, cholesterol, xanthan, pectin, gelatin, egg yolk, casein, wool fat, cholesterol, wax, and lecithin), sorbitan fatty acid esters (e.g., polyoxyethylene sorbitan monooleate [TWEEN®80], sorbitan monopalmitate [SPAN®40], glyceryl monooleate, polyoxyethylene esters, polyethylene glycol fatty acid esters (e.g., CREMOPHOR®), polyoxyethylene ethers (e.g., polyoxyethylene lauryl ether [BRIJ®30]), PLUORINC®F 68, POLOXAMER®188, etc. and/or combinations thereof.

Exemplary binding agents include, but are not limited to, starch, gelatin, sugars (e.g., sucrose, glucose, dextrose, dextrin, molasses, lactose, lactitol, mannitol), amino acids (e.g., glycine), natural and synthetic gums (e.g., acacia, sodium alginate), ethylcellulose, hydroxyethylcellulose, hydroxypropyl methylcellulose, etc., and combinations thereof.

Oxidation is a potential degradation pathway for mRNA, especially for liquid mRNA formulations. In order to prevent oxidation, antioxidants can be added to the formulations. Exemplary antioxidants include, but are not limited to, alpha tocopherol, ascorbic acid, ascorbyl palmitate, benzyl alcohol, butylated hydroxyanisole, m-cresol, methionine, butylated hydroxytoluene, monothioglycerol, sodium or potassium metabisulfite, propionic acid, propyl gallate, sodium ascorbate, etc., and combinations thereof.

Exemplary chelating agents include, but are not limited to, ethylenediaminetetraacetic acid (EDTA), citric acid monohydrate, disodium edetate, fumaric acid, malic acid, phosphoric acid, sodium edetate, tartaric acid, trisodium edetate, etc., and combinations thereof.

Exemplary antimicrobial or antifungal agents include, but are not limited to, benzalkonium chloride, benzethonium chloride, methyl paraben, ethyl paraben, propyl paraben, butyl paraben, benzoic acid, hydroxybenzoic acid, potassium or sodium benzoate, potassium or sodium sorbate, sodium propionate, sorbic acid, etc., and combinations thereof.

Exemplary preservatives include, but are not limited to, vitamin A, vitamin C, vitamin E, beta-carotene, citric acid, ascorbic acid, butylated hydroxyanisol, ethylenediamine, sodium lauryl sulfate (SLS), sodium lauryl ether sulfate (SLES), etc., and combinations thereof.

In some embodiments, the pH of polynucleotide solutions are maintained between pH 5 and pH 8 to improve stability. Exemplary buffers to control pH can include, but are not limited to sodium phosphate, sodium citrate, sodium succinate, histidine (or histidine-HCl), sodium malate, sodium carbonate, etc., and/or combinations thereof.

Exemplary lubricating agents include, but are not limited to, magnesium stearate, calcium stearate, stearic acid, silica, talc, malt, hydrogenated vegetable oils, polyethylene glycol, sodium benzoate, sodium or magnesium lauryl sulfate, etc., and combinations thereof.

The pharmaceutical composition or formulation described here can contain a cryoprotectant to stabilize a polynucleotide described herein during freezing. Exemplary cryoprotectants include, but are not limited to mannitol, sucrose, trehalose, lactose, glycerol, dextrose, etc., and combinations thereof.

The pharmaceutical composition or formulation described here can contain a bulking agent in lyophilized polynucleotide formulations to yield a "pharmaceutically elegant" cake, stabilize the lyophilized polynucleotides during long term (e.g., 36 month) storage. Exemplary bulking agents of the present invention can include, but are not limited to sucrose, trehalose, mannitol, glycine, lactose, raffinose, and combinations thereof.

In some embodiments, the pharmaceutical composition or formulation further comprises a delivery agent. The delivery agent of the present disclosure can include, without limitation, liposomes, lipid nanoparticles, lipidoids, polymers, lipoplexes, microvesicles, exosomes, peptides, proteins, cells transfected with polynucleotides, hyaluronidase, nanoparticle mimics, nanotubes, conjugates, and combinations thereof.

22. DELIVERY AGENTS a. Lipid Compound

The present disclosure provides pharmaceutical compositions with advantageous properties. The lipid compositions described herein may be advantageously used in lipid nanoparticle compositions for the delivery of therapeutic and/or prophylactic agents, e.g., mRNAs, to mammalian cells or organs. For example, the lipids described herein have little or no immunogenicity. For example, the lipid compounds disclosed herein have a lower immunogenicity as compared to a reference lipid (e.g., MC3, KC2, or DLinDMA). For example, a formulation comprising a lipid disclosed herein and a therapeutic or prophylactic agent, e.g., mRNA, has an increased therapeutic index as compared to a corresponding formulation which comprises a reference lipid (e.g., MC3, KC2, or DLinDMA) and the same therapeutic or prophylactic agent.

In certain embodiments, the present application provides pharmaceutical compositions comprising:

(a) a polynucleotide comprising a nucleotide sequence encoding a GALT polypeptide; and (b) a delivery agent.

In some embodiments, the delivery agent comprises a lipid compound having the Formula (I)

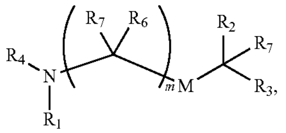

(I)

wherein $R_1$ is selected from the group consisting of $C_{5-30}$ alkyl, $C_{5-20}$ alkenyl, —R*YR", —YR", and —R"M'R';

$R_2$ and $R_3$ are independently selected from the group consisting of H, $C_{1-14}$ alkyl, $C_{2-14}$ alkenyl, —R*YR", —YR", and —R*OR", or $R_2$ and $R_3$, together with the atom to which they are attached, form a heterocycle or carbocycle;

$R_4$ is selected from the group consisting of a $C_{3-6}$ carbocycle, $—(CH_2)_nQ$, $—(CH_2)_nCHQR$, —CHQR, $—CQ(R)_2$, and unsubstituted $C_{1-6}$ alkyl, where Q is selected from a carbocycle, heterocycle, —OR, $—O(CH_2)_nN(R)_2$, —C(O)OR, —OC(O)R, $—CX_3$, $—CX_2H$, $—CXH_2$, —CN, $—N(R)_2$, $—C(O)N(R)_2$, —N(R)C(O)R, $—N(R)S(O)_2R$, $—N(R)C(O)N(R)_2$, $—N(R)C(S)N(R)_2$, $—N(R)R_8$, $—O(CH_2)_nOR$, $—N(R)C(═NR_9)N(R)_2$, $—N(R)C(═CHR_9)N(R)_2$, $—OC(O)N(R)_2$, —N(R)C(O)OR, —N(OR)C(O)R, $—N(OR)S(O)_2R$, —N(OR)C(O)OR, $—N(OR)C(O)N(R)_2$, $—N(OR)C(S)N(R)_2$, $—N(OR)C(═NR_9)N(R)_2$, $—N(OR)C(═CHR_9)N(R)_2$, $—C(═NR_9)N(R)_2$, $—C(═NR_9)R$, —C(O)N(R)OR, and $—C(R)N(R)_2C(O)OR$, and each n is independently selected from 1, 2, 3, 4, and 5;

each $R_5$ is independently selected from the group consisting of $C_{1-3}$ alkyl, $C_{2-3}$ alkenyl, and H;

each $R_6$ is independently selected from the group consisting of $C_{1-3}$ alkyl, $C_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, $—S(O)_2—$, —S—S—, an aryl group, and a heteroaryl group;

$R_7$ is selected from the group consisting of $C_{1-3}$ alkyl, $C_{2-3}$ alkenyl, and H;

$R_8$ is selected from the group consisting of $C_{3-6}$ carbocycle and heterocycle;

$R_9$ is selected from the group consisting of H, CN, $NO_2$, $C_{1-6}$ alkyl, —OR, $—S(O)_2R$, $—S(O)_2N(R)_2$, $C_{2-6}$ alkenyl, $C_{3-6}$ carbocycle and heterocycle;

each R is independently selected from the group consisting of $C_{1-3}$ alkyl, $C_{2-3}$ alkenyl, and H;

each R' is independently selected from the group consisting of $C_{1-18}$ alkyl, $C_{2-18}$ alkenyl, —R*YR", —YR", and H;

each R" is independently selected from the group consisting of $C_{3-14}$ alkyl and $C_{3-14}$ alkenyl;

each R* is independently selected from the group consisting of $C_{1-12}$ alkyl and $C_{2-12}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13, or salts or stereoisomers thereof.

In some embodiments, a subset of compounds of Formula (I) includes those in which $R_1$ is selected from the group consisting of $C_{5-20}$ alkyl, $C_{5-20}$ alkenyl, —R*YR", —YR", and —R"M'R';

$R_2$ and $R_3$ are independently selected from the group consisting of H, $C_{1-14}$ alkyl, $C_{2-14}$ alkenyl, —R*YR", —YR", and —R*OR", or $R_2$ and $R_3$, together with the atom to which they are attached, form a heterocycle or carbocycle;

$R_4$ is selected from the group consisting of a $C_{3-6}$ carbocycle, $—(CH_2)_nQ$, $—(CH_2)_nCHQR$, —CHQR, $—CQ(R)_2$, and unsubstituted $C_{1-6}$ alkyl, where Q is selected from a carbocycle, heterocycle, —OR, $—O(CH_2)_nN(R)_2$, —C(O)OR, —OC(O)R, $—CX_3$, $—CX_2H$, $—CXH_2$, —CN, $—N(R)_2$, $—C(O)N(R)_2$, —N(R)C(O)R, $—N(R)S(O)_2R$, $—N(R)C(O)N(R)_2$, $—N(R)C(S)N(R)_2$, and $—C(R)N(R)_2C(O)OR$, and each n is independently selected from 1, 2, 3, 4, and 5;

each $R_5$ is independently selected from the group consisting of $C_{1-3}$ alkyl, $C_{2-3}$ alkenyl, and H;

each $R_6$ is independently selected from the group consisting of $C_{1-3}$ alkyl, $C_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, $—S(O)_2—$, an aryl group, and a heteroaryl group;

$R_7$ is selected from the group consisting of $C_{1-3}$ alkyl, $C_{2-3}$ alkenyl, and H;

each R is independently selected from the group consisting of $C_{1-3}$ alkyl, $C_{2-3}$ alkenyl, and H;

each R' is independently selected from the group consisting of $C_{1-18}$ alkyl, $C_{2-18}$ alkenyl, —R*YR", —YR", and H;

each R" is independently selected from the group consisting of $C_{3-14}$ alkyl and $C_{3-14}$ alkenyl;

each R* is independently selected from the group consisting of $C_{1-12}$ alkyl and $C_{2-12}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13, or salts or stereoisomers thereof, wherein alkyl and alkenyl groups may be linear or branched.

In some embodiments, a subset of compounds of Formula (I) includes those in which when $R_4$ is $—(CH_2)_nQ$, $—(CH_2)_nCHQR$, —CHQR, or $—CQ(R)_2$, then (i) Q is not $—N(R)_2$ when n is 1, 2, 3, 4 or 5, or (ii) Q is not 5, 6, or 7-membered heterocycloalkyl when n is 1 or 2.

In another embodiments, another subset of compounds of Formula (I) includes those in which $R_1$ is selected from the group consisting of $C_{5-30}$ alkyl, $C_{5-20}$ alkenyl, —R*YR", —YR", and —R"M'R';

$R_2$ and $R_3$ are independently selected from the group consisting of H, $C_{1-14}$ alkyl, $C_{2-14}$ alkenyl, —R*YR", —YR", and —R*OR", or $R_2$ and $R_3$, together with the atom to which they are attached, form a heterocycle or carbocycle;

$R_4$ is selected from the group consisting of a $C_{3-6}$ carbocycle, $—(CH_2)_nQ$, $—(CH_2)_nCHQR$, —CHQR, $—CQ(R)_2$, and unsubstituted $C_{1-6}$ alkyl, where Q is selected from a $C_{3-6}$ carbocycle, a 5- to 14-membered heteroaryl having one or more heteroatoms selected from N, O, and S, —OR, —$O(CH_2)_nN(R)_2$, —C(O)OR, —OC(O)R, —$CX_3$, —$CX_2H$, —$CXH_2$, —CN, —$C(O)N(R)_2$, —N(R)C(O)R, —$N(R)S(O)_2R$, —$N(R)C(O)N(R)_2$, —$N(R)C(S)N(R)_2$, —$CRN(R)_2C(O)OR$, —$N(R)R_8$, —$O(CH_2)_nOR$, —N(R)C(=$NR_9$)$N(R)_2$, —N(R)C(=$CHR_9$)$N(R)_2$, —$OC(O)N(R)_2$, —N(R)C(O)OR, —N(OR)C(O)R, —$N(OR)S(O)_2R$, —N(OR)C(O)OR, —$N(OR)C(O)N(R)_2$, —$N(OR)C(S)N(R)_2$, —N(OR)C(=$NR_9$)$N(R)_2$, —N(OR)C(=$CHR_9$)$N(R)_2$, —C(=$NR_9$)$N(R)_2$, —C(=$NR_9$)R, —C(O)N(R)OR, and a 5- to 14-membered heterocycloalkyl having one or more heteroatoms selected from N, O, and S which is substituted with one or more substituents selected from oxo (=O), OH, amino, and $C_{1-3}$ alkyl, and each n is independently selected from 1, 2, 3, 4, and 5;

each $R_5$ is independently selected from the group consisting of $C_{1-3}$ alkyl, $C_{2-3}$ alkenyl, and H;

each $R_6$ is independently selected from the group consisting of $C_{1-3}$ alkyl, $C_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —$S(O)_2$—, an aryl group, and a heteroaryl group;

$R_7$ is selected from the group consisting of $C_{1-3}$ alkyl, $C_{2-3}$ alkenyl, and H;

$R_8$ is selected from the group consisting of $C_{3-6}$ carbocycle and heterocycle;

$R_9$ is selected from the group consisting of H, CN, $NO_2$, $C_{1-6}$ alkyl, —OR, —$S(O)_2R$, —$S(O)_2N(R)_2$, $C_{2-6}$ alkenyl, $C_{3-6}$ carbocycle and heterocycle;

each R is independently selected from the group consisting of $C_{1-3}$ alkyl, $C_{2-3}$ alkenyl, and H;

each R' is independently selected from the group consisting of $C_{1-18}$ alkyl, $C_{2-18}$ alkenyl, —R*YR", —YR", and H;

each R" is independently selected from the group consisting of $C_{3-14}$ alkyl and $C_{3-14}$ alkenyl;

each R* is independently selected from the group consisting of $C_{1-12}$ alkyl and $C_{2-12}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13, or salts or stereoisomers thereof.

In another embodiments, another subset of compounds of Formula (I) includes those in which $R_1$ is selected from the group consisting of $C_{5-20}$ alkyl, $C_{5-20}$ alkenyl, —R*YR", —YR", and —R"M'R';

$R_2$ and $R_3$ are independently selected from the group consisting of H, $C_{1-14}$ alkyl, $C_{2-14}$ alkenyl, —R*YR", —YR", and —R*OR", or $R_2$ and $R_3$, together with the atom to which they are attached, form a heterocycle or carbocycle;

$R_4$ is selected from the group consisting of a $C_{3-6}$ carbocycle, —$(CH_2)_nQ$, —$(CH_2)_nCHQR$, —CHQR, —$CQ(R)_2$, and unsubstituted $C_{1-6}$ alkyl, where Q is selected from a $C_{3-6}$ carbocycle, a 5- to 14-membered heteroaryl having one or more heteroatoms selected from N, O, and S, —OR, —$O(CH_2)_nN(R)_2$, —C(O)OR, —OC(O)R, —$CX_3$, —$CX_2H$, —$CXH_2$, —CN, —$C(O)N(R)_2$, —N(R)C(O)R, —$N(R)S(O)_2R$, —$N(R)C(O)N(R)_2$, —$N(R)C(S)N(R)_2$, —$CRN(R)_2C(O)OR$, and a 5- to 14-membered heterocycloalkyl having one or more heteroatoms selected from N, O, and S which is substituted with one or more substituents selected from oxo (=O), OH, amino, and $C_{1-3}$ alkyl, and each n is independently selected from 1, 2, 3, 4, and 5;

each $R_5$ is independently selected from the group consisting of $C_{1-3}$ alkyl, $C_{2-3}$ alkenyl, and H;

each $R_6$ is independently selected from the group consisting of $C_{1-3}$ alkyl, $C_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —$S(O)_2$—, an aryl group, and a heteroaryl group;

$R_7$ is selected from the group consisting of $C_{1-3}$ alkyl, $C_{2-3}$ alkenyl, and H; each R is independently selected from the group consisting of $C_{1-3}$ alkyl, $C_{2-3}$ alkenyl, and H;

each R' is independently selected from the group consisting of $C_{1-18}$ alkyl, $C_{2-18}$ alkenyl, —R*YR", —YR", and H;

each R" is independently selected from the group consisting of $C_{3-14}$ alkyl and $C_{3-14}$ alkenyl;

each R* is independently selected from the group consisting of $C_{1-12}$ alkyl and $C_{2-12}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13, or salts or stereoisomers thereof.

In yet another embodiments, another subset of compounds of Formula (I) includes those in which $R_1$ is selected from the group consisting of $C_{5-30}$ alkyl, $C_{5-20}$ alkenyl, —R*YR", —YR", and —R"M'R';

$R_2$ and $R_3$ are independently selected from the group consisting of H, $C_{1-14}$ alkyl, $C_{2-14}$ alkenyl, —R*YR", —YR", and —R*OR", or $R_2$ and $R_3$, together with the atom to which they are attached, form a heterocycle or carbocycle;

$R_4$ is selected from the group consisting of a $C_{3-6}$ carbocycle, —$(CH_2)_nQ$, —$(CH_2)_nCHQR$, —CHQR, —$CQ(R)_2$, and unsubstituted $C_{1-6}$ alkyl, where Q is selected from a $C_{3-6}$ carbocycle, a 5- to 14-membered heterocycle having one or more heteroatoms selected from N, O, and S, —OR, —$O(CH_2)_nN(R)_2$, —C(O)OR, —OC(O)R, —$CX_3$, —$CX_2H$, —$CXH_2$, —CN, —$C(O)N(R)_2$, —N(R)C(O)R, —$N(R)S(O)_2R$, —$N(R)C(O)N(R)_2$, —$N(R)C(S)N(R)_2$, —$CRN(R)_2C(O)OR$, —$N(R)R_8$, —$O(CH_2)_nOR$, —N(R)C(=$NR_9$)$N(R)_2$, —N(R)C(=$CHR_9$)$N(R)_2$, —$OC(O)N(R)_2$, —N(R)C(O)OR, —N(OR)C(O)R, —$N(OR)S(O)_2R$, —N(OR)C(O)OR, —$N(OR)C(O)N(R)_2$, —$N(OR)C(S)N(R)_2$, —N(OR)C(=$NR_9$)$N(R)_2$, —N(OR) C(=$CHR_9$)$N(R)_2$, —C(=$NR_9$)R, —C(O)N(R)OR, and —C(=$NR_9$)$N(R)_2$, and each n is independently selected from 1, 2, 3, 4, and 5; and when Q is a 5- to 14-membered heterocycle and (i) $R_4$ is —$(CH_2)_nQ$ in which n is 1 or 2, or (ii) $R_4$ is —$(CH_2)_nCHQR$ in which n is 1, or (iii) R4 is —CHQR, and —$CQ(R)_2$, then Q is either a 5- to 14-membered heteroaryl or 8- to 14-membered heterocycloalkyl;

each $R_5$ is independently selected from the group consisting of $C_{1-3}$ alkyl, $C_{2-3}$ alkenyl, and H;

each $R_6$ is independently selected from the group consisting of $C_{1-3}$ alkyl, $C_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —$S(O)_2$—, —S—S—, an aryl group, and a heteroaryl group;

$R_7$ is selected from the group consisting of $C_{1-3}$ alkyl, $C_{2-3}$ alkenyl, and H;

$R_8$ is selected from the group consisting of $C_{3-6}$ carbocycle and heterocycle;

$R_9$ is selected from the group consisting of H, CN, $NO_2$, $C_{1-6}$ alkyl, —OR, —$S(O)_2R$, —$S(O)_2N(R)_2$, $C_{2-6}$ alkenyl, $C_{3-6}$ carbocycle and heterocycle;

each R is independently selected from the group consisting of $C_{1-3}$ alkyl, $C_{2-3}$ alkenyl, and H;

each R' is independently selected from the group consisting of $C_{1-18}$ alkyl, $C_{2-18}$ alkenyl, —R*YR", —YR", and H;

each R" is independently selected from the group consisting of $C_{3-14}$ alkyl and $C_{3-14}$ alkenyl;

each R* is independently selected from the group consisting of $C_{1-12}$ alkyl and $C_{2-12}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13, or salts or stereoisomers thereof.

In yet another embodiments, another subset of compounds of Formula (I) includes those in which $R_1$ is selected from the group consisting of $C_{5-20}$ alkyl, $C_{5-20}$ alkenyl, —R*YR", —YR", and —R"M'R';

$R_2$ and $R_3$ are independently selected from the group consisting of H, $C_{1-14}$ alkyl, $C_{2-14}$ alkenyl, —R*YR", —YR", and —R*OR", or $R_2$ and $R_3$, together with the atom to which they are attached, form a heterocycle or carbocycle;

$R_4$ is selected from the group consisting of a $C_{3-6}$ carbocycle, $—(CH_2)_nQ$, $—(CH_2)_nCHQR$, —CHQR, $—CQ(R)_2$, and unsubstituted $C_{1-6}$ alkyl, where Q is selected from a $C_{3-6}$ carbocycle, a 5- to 14-membered heterocycle having one or more heteroatoms selected from N, O, and S, —OR, $—O(CH_2)_nN(R)_2$, —C(O)OR, —OC(O)R, $—CX_3$, $—CX_2H$, $—CXH_2$, —CN, $—C(O)N(R)_2$, —N(R)C(O)R, $—N(R)S(O)_2R$, $—N(R)C(O)N(R)_2$, $—N(R)C(S)N(R)_2$, $—CRN(R)_2C(O)OR$, and each n is independently selected from 1, 2, 3, 4, and 5; and when Q is a 5- to 14-membered heterocycle and (i) $R_4$ is $—(CH_2)_nQ$ in which n is 1 or 2, or (ii) $R_4$ is $—(CH_2)_nCHQR$ in which n is 1, or (iii) $R_4$ is —CHQR, and $—CQ(R)_2$, then Q is either a 5- to 14-membered heteroaryl or 8- to 14-membered heterocycloalkyl;

each $R_5$ is independently selected from the group consisting of $C_{1-3}$ alkyl, $C_{2-3}$ alkenyl, and H;

each $R_6$ is independently selected from the group consisting of $C_{1-3}$ alkyl, $C_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, $—S(O)_2—$, an aryl group, and a heteroaryl group;

$R_7$ is selected from the group consisting of $C_{1-3}$ alkyl, $C_{2-3}$ alkenyl, and H; each R is independently selected from the group consisting of $C_{1-3}$ alkyl, $C_{2-3}$ alkenyl, and H;

each R' is independently selected from the group consisting of $C_{1-18}$ alkyl, $C_{2-18}$ alkenyl, —R*YR", —YR", and H;

each R" is independently selected from the group consisting of $C_{3-14}$ alkyl and $C_{3-14}$ alkenyl;

each R* is independently selected from the group consisting of $C_{1-12}$ alkyl and $C_{2-12}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13, or salts or stereoisomers thereof.

In still another embodiments, another subset of compounds of Formula (I) includes those in which $R_1$ is selected from the group consisting of $C_{5-30}$ alkyl, $C_{5-20}$ alkenyl, —R*YR", —YR", and —R"M'R';

$R_2$ and $R_3$ are independently selected from the group consisting of H, $C_{1-14}$ alkyl, $C_{2-14}$ alkenyl, —R*YR", —YR", and —R*OR", or $R_2$ and $R_3$, together with the atom to which they are attached, form a heterocycle or carbocycle;

$R_4$ is selected from the group consisting of a $C_{3-6}$ carbocycle, $—(CH_2)_nQ$, $—(CH_2)_nCHQR$, —CHQR, $—CQ(R)_2$, and unsubstituted $C_{1-6}$ alkyl, where Q is selected from a $C_{3-6}$ carbocycle, a 5- to 14-membered heteroaryl having one or more heteroatoms selected from N, O, and S, —OR, $—O(CH_2)_nN(R)_2$, —C(O)OR, —OC(O)R, $—CX_3$, $—CX_2H$, $—CXH_2$, —CN, $—C(O)N(R)_2$, —N(R)C(O)R, $—N(R)S(O)_2R$, $—N(R)C(O)N(R)_2$, $—N(R)C(S)N(R)_2$, $—CRN(R)_2C(O)OR$, $—N(R)R_5$, $—O(CH_2)_nOR$, $—N(R)C(=NR_9)N(R)_2$, $—N(R)C(=CHR_9)N(R)_2$, $—OC(O)N(R)_2$, —N(R)C(O)OR, —N(OR)C(O)R, $—N(OR)S(O)_2R$, —N(OR)C(O)OR, $—N(OR)C(O)N(R)_2$, $—N(OR)C(S)N(R)_2$, $—N(OR)C(=NR_9)N(R)_2$, $—N(OR)C(=CHR_9)N(R)_2$, $—C(=NR_9)R$, —C(O)N(R)OR, and $—C(=NR_9)N(R)_2$, and each n is independently selected from 1, 2, 3, 4, and 5;

each $R_5$ is independently selected from the group consisting of $C_{1-3}$ alkyl, $C_{2-3}$ alkenyl, and H;

each $R_6$ is independently selected from the group consisting of $C_{1-3}$ alkyl, $C_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, $—S(O)_2—$, S—S—, an aryl group, and a heteroaryl group;

$R_7$ is selected from the group consisting of $C_{1-3}$ alkyl, $C_{2-3}$ alkenyl, and H;

$R_8$ is selected from the group consisting of $C_{3-6}$ carbocycle and heterocycle;

$R_9$ is selected from the group consisting of H, CN, $NO_2$, $C_{1-6}$ alkyl, —OR, $—S(O)_2R$, $—S(O)_2N(R)_2$, $C_{2-6}$ alkenyl, $C_{3-6}$ carbocycle and heterocycle;

each R is independently selected from the group consisting of $C_{1-3}$ alkyl, $C_{2-3}$ alkenyl, and H;

each R' is independently selected from the group consisting of $C_{1-18}$ alkyl, $C_{2-18}$ alkenyl, —R*YR", —YR", and H;

each R" is independently selected from the group consisting of $C_{3-14}$ alkyl and $C_{3-14}$ alkenyl;

each R* is independently selected from the group consisting of $C_{1-12}$ alkyl and $C_{2-12}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13, or salts or stereoisomers thereof.

In still another embodiments, another subset of compounds of Formula (I) includes those in which $R_1$ is selected from the group consisting of $C_{5-20}$ alkyl, $C_{5-20}$ alkenyl, —R*YR", —YR", and —R"M'R';

$R_2$ and $R_3$ are independently selected from the group consisting of H, $C_{1-14}$ alkyl, $C_{2-14}$ alkenyl, —R*YR", —YR", and —R*OR", or $R_2$ and $R_3$, together with the atom to which they are attached, form a heterocycle or carbocycle;

$R_4$ is selected from the group consisting of a $C_{3-6}$ carbocycle, $—(CH_2)_nQ$, $—(CH_2)_nCHQR$, —CHQR, $—CQ(R)_2$, and unsubstituted $C_{1-6}$ alkyl, where Q is selected from a $C_{3-6}$ carbocycle, a 5- to 14-membered heteroaryl having one or more heteroatoms selected from N, O, and S, —OR, $—O(CH_2)_nN(R)_2$, —C(O)OR, —OC(O)R, $—CX_3$, $—CX_2H$, $—CXH_2$, —CN, $—C(O)N(R)_2$, —N(R)C(O)R, $—N(R)S(O)_2R$, $—N(R)C(O)N(R)_2$, $—N(R)C(S)N(R)_2$, $—CRN(R)_2C(O)OR$, and each n is independently selected from 1, 2, 3, 4, and 5;

each $R_5$ is independently selected from the group consisting of $C_{1-3}$ alkyl, $C_{2-3}$ alkenyl, and H;

each $R_6$ is independently selected from the group consisting of $C_{1-3}$ alkyl, $C_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —$S(O)_2$—, an aryl group, and a heteroaryl group;

$R_7$ is selected from the group consisting of $C_{1-3}$ alkyl, $C_{2-3}$ alkenyl, and H; each R is independently selected from the group consisting of $C_{1-3}$ alkyl, $C_{2-3}$ alkenyl, and H;

each R' is independently selected from the group consisting of $C_{1-18}$ alkyl, $C_{2-18}$ alkenyl, —R*YR", —YR", and H;

each R" is independently selected from the group consisting of $C_{3-14}$ alkyl and $C_{3-14}$ alkenyl;

each R* is independently selected from the group consisting of $C_{1-12}$ alkyl and $C_{2-12}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13, or salts or stereoisomers thereof.

In yet another embodiments, another subset of compounds of Formula (I) includes those in which $R_1$ is selected from the group consisting of $C_{5-30}$ alkyl, $C_{5-20}$ alkenyl, —R*YR", —YR", and —R"M'R';

$R_2$ and $R_3$ are independently selected from the group consisting of H, $C_{2-14}$ alkyl, $C_{2-14}$ alkenyl, —R*YR", —YR", and —R*OR", or $R_2$ and $R_3$, together with the atom to which they are attached, form a heterocycle or carbocycle;

$R_4$ is —$(CH_2)_n$Q or —$(CH_2)_n$CHQR, where Q is —$N(R)_2$, and n is selected from 3, 4, and 5;

each $R_5$ is independently selected from the group consisting of $C_{1-3}$ alkyl, $C_{2-3}$ alkenyl, and H;

each $R_6$ is independently selected from the group consisting of $C_{1-3}$ alkyl, $C_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —$S(O)_2$—, —S—S—, an aryl group, and a heteroaryl group;

$R_7$ is selected from the group consisting of $C_{1-3}$ alkyl, $C_{2-3}$ alkenyl, and H;

each R is independently selected from the group consisting of $C_{1-3}$ alkyl, $C_{2-3}$ alkenyl, and H;

each R' is independently selected from the group consisting of $C_{1-18}$ alkyl, $C_{2-18}$ alkenyl, —R*YR", —YR", and H;

each R" is independently selected from the group consisting of $C_{3-14}$ alkyl and $C_{3-14}$ alkenyl;

each R* is independently selected from the group consisting of $C_{1-12}$ alkyl and $C_{1-12}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13, or salts or stereoisomers thereof.

In yet another embodiments, another subset of compounds of Formula (I) includes those in which $R_1$ is selected from the group consisting of $C_{5-20}$ alkyl, $C_{5-20}$ alkenyl, —R*YR", —YR", and —R"M'R';

$R_2$ and $R_3$ are independently selected from the group consisting of H, $C_{2-14}$ alkyl, $C_{2-14}$ alkenyl, —R*YR", —YR", and —R*OR", or $R_2$ and $R_3$, together with the atom to which they are attached, form a heterocycle or carbocycle;

$R_4$ is —$(CH_2)_n$Q or —$(CH_2)_n$CHQR, where Q is —$N(R)_2$, and n is selected from 3, 4, and 5;

each $R_5$ is independently selected from the group consisting of $C_{1-3}$ alkyl, $C_{2-3}$ alkenyl, and H;

each $R_6$ is independently selected from the group consisting of $C_{1-3}$ alkyl, $C_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —$S(O)_2$—, an aryl group, and a heteroaryl group;

$R_7$ is selected from the group consisting of $C_{1-3}$ alkyl, $C_{2-3}$ alkenyl, and H; each R is independently selected from the group consisting of $C_{1-3}$ alkyl, $C_{2-3}$ alkenyl, and H;

each R' is independently selected from the group consisting of $C_{1-18}$ alkyl, $C_{2-18}$ alkenyl, —R*YR", —YR", and H;

each R" is independently selected from the group consisting of $C_{3-14}$ alkyl and $C_{3-14}$ alkenyl;

each R* is independently selected from the group consisting of $C_{1-12}$ alkyl and $C_{1-12}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13, or salts or stereoisomers thereof.

In still other embodiments, another subset of compounds of Formula (I) includes those in which $R_1$ is selected from the group consisting of $C_{5-30}$ alkyl, $C_{5-20}$ alkenyl, —R*YR", —YR", and —R"M'R';

$R_2$ and $R_3$ are independently selected from the group consisting of $C_{1-14}$ alkyl, $C_{2-14}$ alkenyl, —R*YR", —YR", and —R*OR", or $R_2$ and $R_3$, together with the atom to which they are attached, form a heterocycle or carbocycle;

$R_4$ is selected from the group consisting of —$(CH_2)_n$Q, —$(CH_2)_n$CHQR, —CHQR, and —$CQ(R)_2$, where Q is —$N(R)_2$, and n is selected from 1, 2, 3, 4, and 5;

each $R_5$ is independently selected from the group consisting of $C_{1-3}$ alkyl, $C_{2-3}$ alkenyl, and H;

each $R_6$ is independently selected from the group consisting of $C_{1-3}$ alkyl, $C_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —$S(O)_2$—, —S—S—, an aryl group, and a heteroaryl group;

$R_7$ is selected from the group consisting of $C_{1-3}$ alkyl, $C_{2-3}$ alkenyl, and H;

each R is independently selected from the group consisting of $C_{1-3}$ alkyl, $C_{2-3}$ alkenyl, and H;

each R' is independently selected from the group consisting of $C_{1-18}$ alkyl, $C_{2-18}$ alkenyl, —R*YR", —YR", and H;

each R" is independently selected from the group consisting of $C_{3-14}$ alkyl and $C_{3-14}$ alkenyl;

each R* is independently selected from the group consisting of $C_{1-12}$ alkyl and $C_{1-12}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13, or salts or stereoisomers thereof.

In still other embodiments, another subset of compounds of Formula (I) includes those in which $R_1$ is selected from the group consisting of $C_{5-20}$ alkyl, $C_{5-20}$ alkenyl, —R*YR", —YR", and —R"M'R';

$R_2$ and $R_3$ are independently selected from the group consisting of $C_{1-14}$ alkyl, $C_{2-14}$ alkenyl, —R*YR", —YR", and —R*OR", or $R_2$ and $R_3$, together with the atom to which they are attached, form a heterocycle or carbocycle;

$R_4$ is selected from the group consisting of —$(CH_2)_n$Q, —$(CH_2)_n$CHQR, —CHQR, and —$CQ(R)_2$, where Q is —$N(R)_2$, and n is selected from 1, 2, 3, 4, and 5;

each $R_5$ is independently selected from the group consisting of $C_{1-3}$ alkyl, $C_{2-3}$ alkenyl, and H;

each $R_6$ is independently selected from the group consisting of $C_{1-3}$ alkyl, $C_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —$S(O)_2$—, an aryl group, and a heteroaryl group;

$R_7$ is selected from the group consisting of $C_{1-3}$ alkyl, $C_{2-3}$ alkenyl, and H;

each R is independently selected from the group consisting of $C_{1-3}$ alkyl, $C_{2-3}$ alkenyl, and H;

each R' is independently selected from the group consisting of $C_{1-18}$ alkyl, $C_{2-18}$ alkenyl, —R*YR", —YR", and H;

each R" is independently selected from the group consisting of $C_{3-14}$ alkyl and $C_{3-14}$ alkenyl;

each R* is independently selected from the group consisting of $C_{1-12}$ alkyl and $C_{1-12}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13, or salts or stereoisomers thereof.

In certain embodiments, a subset of compounds of Formula (I) includes those of Formula (IA):

(IA)

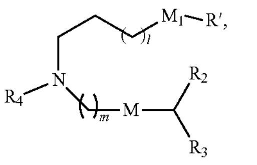

or a salt or stereoisomer thereof, wherein l is selected from 1, 2, 3, 4, and 5; m is selected from 5, 6, 7, 8, and 9; $M_1$ is a bond or M'; $R_4$ is unsubstituted $C_{1-3}$ alkyl, or —$(CH_2)_n$Q, in which Q is OH, —NHC(S)N$(R)_2$, —NHC(O)N$(R)_2$, —N(R)C(O)R, —N(R)$S(O)_2$R, —N(R)$R_8$, —NHC(═$NR_9$)N$(R)_2$, —NHC(═$CHR_9$)N$(R)_2$, —OC(O)N$(R)_2$, —N(R)C(O)OR, heteroaryl or heterocycloalkyl; M and M' are independently selected from —C(O)O—, —OC(O)—, —C(O)N(R')—, —P(O)(OR')O—, —S—S— an aryl group, and a heteroaryl group; and $R_2$ and $R_3$ are independently selected from the group consisting of H, $C_{1-14}$ alkyl, and $C_{2-14}$ alkenyl.

In some embodiments, a subset of compounds of Formula (I) includes those of Formula (IA), or a salt or stereoisomer thereof, wherein l is selected from 1, 2, 3, 4, and 5; m is selected from 5, 6, 7, 8, and 9;

$M_1$ is a bond or M';

$R_4$ is unsubstituted $C_{1-3}$ alkyl, or —$(CH_2)_n$Q, in which Q is OH, —NHC(S)N$(R)_2$, or —NHC(O)N$(R)_2$;

M and M' are independently selected from —C(O)O—, —OC(O)—, —C(O)N(R')—, —P(O)(OR')O—, an aryl group, and a heteroaryl group; and $R_2$ and $R_3$ are independently selected from the group consisting of H, $C_{1-14}$ alkyl, and $C_{2-14}$ alkenyl.

In certain embodiments, a subset of compounds of Formula (I) includes those of Formula (II):

(II)

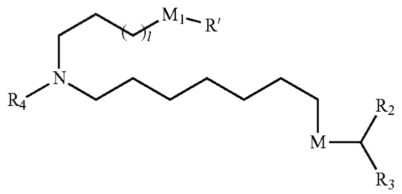

or a salt or stereoisomer thereof, wherein l is selected from 1, 2, 3, 4, and 5; $M_1$ is a bond or M'; $R_4$ is unsubstituted $C_{1-3}$ alkyl, or —$(CH_2)_n$Q, in which n is 2, 3, or 4, and Q is OH, —NHC(S)N$(R)_2$, —NHC(O)N$(R)_2$, —N(R)C(O)R, —N(R)$S(O)_2$R, —N(R)$R_8$, —NHC(═$NR_9$)N$(R)_2$, —NHC(═$CHR_9$)N$(R)_2$, —OC(O)N$(R)_2$, —N(R)C(O)OR, heteroaryl or heterocycloalkyl; M and M' are independently selected from —C(O)O—, —OC(O)—, —C(O)N(R')—, —P(O)(OR')O—, —S—S—, an aryl group, and a heteroaryl group; and $R_2$ and $R_3$ are independently selected from the group consisting of H, $C_{1-14}$ alkyl, and $C_{2-14}$ alkenyl.

In some embodiments, a subset of compounds of Formula (I) includes those of Formula (II), or a salt or stereoisomer thereof, wherein l is selected from 1, 2, 3, 4, and 5;

$M_1$ is a bond or M';

$R_4$ is unsubstituted $C_{1-3}$ alkyl, or —$(CH_2)_n$Q, in which n is 2, 3, or 4, and Q is OH, —NHC(S)N$(R)_2$, or —NHC(O)N$(R)_2$;

M and M' are independently selected from —C(O)O—, —OC(O)—, —C(O)N(R')—, —P(O)(OR')O—, —S—S, an aryl group, and a heteroaryl group; and $R_2$ and $R_3$ are independently selected from the group consisting of H, $C_{1-14}$ alkyl, and $C_{2-14}$ alkenyl.

In some embodiments, the compound of Formula (I) is of the Formula (IIa), (IIa)

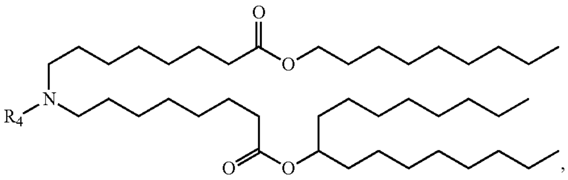

or a salt thereof, wherein $R_4$ is as described above.

In some embodiments, the compound of Formula (I) is of the Formula (IIb), (IIb)

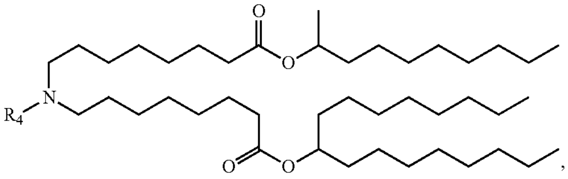

or a salt thereof, wherein $R_4$ is as described above.

In some embodiments, the compound of Formula (I) is of the Formula (IIc), (IIc)

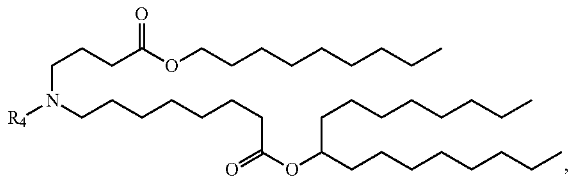

or a salt thereof, wherein $R_4$ is as described above.

In some embodiments, the compound of Formula (I) is of the Formula (IIe):

(IIe)

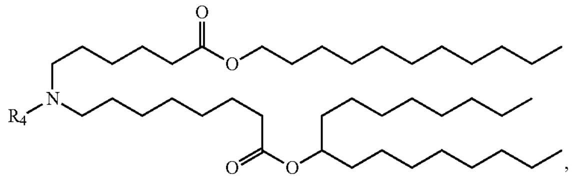

or a salt thereof, wherein R4 is as described above.

In some embodiments, the compound of Formula (IIa), (IIb), (IIc), or (IIe) comprises an $R_4$ which is selected from $-(CH_2)_nQ$ and $-(CH_2)_nCHQR$, wherein Q, R and n are as defined above.

In some embodiments, Q is selected from the group consisting of —OR, —OH, $-O(CH_2)_nN(R)_2$, —OC(O)R, $-CX_3$, —CN, —N(R)C(O)R, —N(H)C(O)R, $-N(R)S(O)_2R$, $-N(H)S(O)_2R$, $-N(R)C(O)N(R)_2$, $-N(H)C(O)N(R)_2$, —N(H)C(O)N(H)(R), $-N(R)C(S)N(R)_2$, $-N(H)C(S)N(R)_2$, —N(H)C(S)N(H)(R), and a heterocycle, wherein R is as defined above. In some aspects, n is 1 or 2. In some embodiments, Q is OH, $-NHC(S)N(R)_2$, or $-NHC(O)N(R)_2$.

In some embodiments, the compound of Formula (I) is of the Formula (IId), (IId)

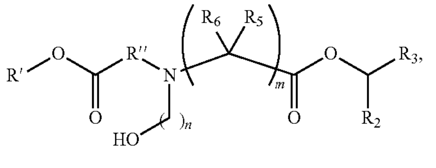

or a salt thereof, wherein $R_2$ and $R_3$ are independently selected from the group consisting of $C_{5-14}$ alkyl and $C_{5-14}$ alkenyl, n is selected from 2, 3, and 4, and R', R", $R_5$, $R_6$ and m are as defined above.

In some aspects of the compound of Formula (IId), $R_2$ is $C_8$ alkyl. In some aspects of the compound of Formula (IId), $R_3$ is $C_5$-$C_9$ alkyl. In some aspects of the compound of Formula (IId), m is 5, 7, or 9. In some aspects of the compound of Formula (IId), each $R_5$ is H. In some aspects of the compound of Formula (IId), each $R_6$ is H.

In another aspect, the present application provides a lipid composition (e.g., a lipid nanoparticle (LNP)) comprising: (1) a compound having the Formula (I); (2) optionally a helper lipid (e.g. a phospholipid); (3) optionally a structural lipid (e.g. a sterol); and (4) optionally a lipid conjugate (e.g. a PEG-lipid). In exemplary embodiments, the lipid composition (e.g., LNP) further comprises a polynucleotide encoding a GALT polypeptide, e.g., a polynucleotide encapsulated therein.

As used herein, the term "alkyl" or "alkyl group" means a linear or branched, saturated hydrocarbon including one or more carbon atoms (e.g., one, two, three, four, five, six, seven, eight, nine, ten, eleven, twelve, thirteen, fourteen, fifteen, sixteen, seventeen, eighteen, nineteen, twenty, or more carbon atoms).

The notation "$C_{1-14}$ alkyl" means a linear or branched, saturated hydrocarbon including 1-14 carbon atoms. An alkyl group can be optionally substituted.

As used herein, the term "alkenyl" or "alkenyl group" means a linear or branched hydrocarbon including two or more carbon atoms (e.g., two, three, four, five, six, seven, eight, nine, ten, eleven, twelve, thirteen, fourteen, fifteen, sixteen, seventeen, eighteen, nineteen, twenty, or more carbon atoms) and at least one double bond.

The notation "$C_{2-14}$ alkenyl" means a linear or branched hydrocarbon including 2-14 carbon atoms and at least one double bond. An alkenyl group can include one, two, three, four, or more double bonds. For example, $C_{18}$ alkenyl can include one or more double bonds. A $C_{18}$ alkenyl group including two double bonds can be a linoleyl group. An alkenyl group can be optionally substituted.

As used herein, the term "carbocycle" or "carbocyclic group" means a mono- or multi-cyclic system including one or more rings of carbon atoms. Rings can be three, four, five, six, seven, eight, nine, ten, eleven, twelve, thirteen, fourteen, or fifteen membered rings.

The notation "$C_{3-6}$ carbocycle" means a carbocycle including a single ring having 3-6 carbon atoms. Carbocycles can include one or more double bonds and can be aromatic (e.g., aryl groups). Examples of carbocycles include cyclopropyl, cyclopentyl, cyclohexyl, phenyl, naphthyl, and 1,2-dihydronaphthyl groups. Carbocycles can be optionally substituted.

As used herein, the term "heterocycle" or "heterocyclic group" means a mono- or multi-cyclic system including one or more rings, where at least one ring includes at least one heteroatom. Heteroatoms can be, for example, nitrogen, oxygen, or sulfur atoms. Rings can be three, four, five, six, seven, eight, nine, ten, eleven, or twelve membered rings. Heterocycles can include one or more double bonds and can be aromatic (e.g., heteroaryl groups). Examples of heterocycles include imidazolyl, imidazolidinyl, oxazolyl, oxazolidinyl, thiazolyl, thiazolidinyl, pyrazolidinyl, pyrazolyl, isoxazolidinyl, isoxazolyl, isothiazolidinyl, isothiazolyl, morpholinyl, pyrrolyl, pyrrolidinyl, furyl, tetrahydrofuryl, thiophenyl, pyridinyl, piperidinyl, quinolyl, and isoquinolyl groups. Heterocycles can be optionally substituted.

As used herein, a "biodegradable group" is a group that can facilitate faster metabolism of a lipid in a subject. A biodegradable group can be, but is not limited to, —C(O)O—, —OC(O)—, —C(O)N(R')—, —N(R')C(O)—, —C(O)—, —C(S)—, —C(S)S—, —SC(S)—, —CH(OH)—, —P(O)(OR')O—, $-S(O)_2-$, an aryl group, and a heteroaryl group.

As used herein, an "aryl group" is a carbocyclic group including one or more aromatic rings. Examples of aryl groups include phenyl and naphthyl groups.

As used herein, a "heteroaryl group" is a heterocyclic group including one or more aromatic rings. Examples of heteroaryl groups include pyrrolyl, furyl, thiophenyl, imidazolyl, oxazolyl, and thiazolyl. Both aryl and heteroaryl groups can be optionally substituted. For example, M and M' can be selected from the non-limiting group consisting of optionally substituted phenyl, oxazole, and thiazole. In the formulas herein, M and M' can be independently selected from the list of biodegradable groups above.

Alkyl, alkenyl, and cyclyl (e.g., carbocyclyl and heterocyclyl) groups can be optionally substituted unless otherwise specified. Optional substituents can be selected from the group consisting of, but are not limited to, a halogen atom (e.g., a chloride, bromide, fluoride, or iodide group), a carboxylic acid (e.g., —C(O)OH), an alcohol (e.g., a hydroxyl, —OH), an ester (e.g., —C(O)OR or —OC(O)R), an aldehyde (e.g., —C(O)H), a carbonyl (e.g., —C(O)R, alternatively represented by C═O), an acyl halide (e.g., —C(O)X, in which X is a halide selected from bromide, fluoride, chloride, and iodide), a carbonate (e.g., —OC(O)OR), an alkoxy (e.g., —OR), an acetal (e.g., $—C(OR)_2R''''$, in which each OR are alkoxy groups that can be the same or different and R'''' is an alkyl or alkenyl group), a phosphate (e.g., $P(O)_4^{3-}$), a thiol (e.g., —SH), a sulfoxide (e.g., —S(O)R), a sulfuric acid (e.g., —S(O)OH), a sulfonic acid (e.g., $—S(O)_2OH$), a thial (e.g., —C(S)H), a sulfate (e.g., $S(O)_4^{2-}$), a sulfonyl (e.g., $—S(O)_2—$), an amide (e.g., $—C(O)NR_2$, or —N(R)C(O)R), an azido (e.g., $—N_3$), a nitro (e.g., $—NO_2$), a cyano (e.g., —CN), an isocyano (e.g., —NC), an acyloxy (e.g., —OC(O)R), an amino (e.g., $—NR_2$, —NRH, or $—NH_2$), a carbamoyl (e.g., $—OC(O)NR_2$, —OC(O)NRH, or $—OC(O)NH_2$), a sulfonamide (e.g., $—S(O)_2NR_2$, $—S(O)_2NRH$, $—S(O)_2NH_2$, $—N(R)S(O)_2R$, $—N(H)S(O)_2R$, $—N(R)S(O)_2H$, or $—N(H)S(O)_2H$), an alkyl group, an alkenyl group, and a cyclyl (e.g., carbocyclyl or heterocyclyl) group.

In any of the preceding, R is an alkyl or alkenyl group, as defined herein. In some embodiments, the substituent groups themselves can be further substituted with, for example, one, two, three, four, five, or six substituents as defined herein. For example, a $C_{1-6}$ alkyl group can be further substituted with one, two, three, four, five, or six substituents as described herein.

The compounds of any one of Formulae (I), (IA), (II), (IIa), (IIb), (IIc), (IId), and (IIe) include one or more of the following features when applicable.

In some embodiments, $R_4$ is selected from the group consisting of a $C_{3-6}$ carbocycle, $—(CH_2)_nQ$, $—(CH_2)_nCHQR$, —CHQR, and $—CQ(R)_2$, where Q is selected from a $C_{3-6}$ carbocycle, 5- to 14-membered aromatic or non-aromatic heterocycle having one or more heteroatoms selected from N, O, S, and P, —OR, $—O(CH_2)_nN(R)_2$, —C(O)OR, —OC(O)R, $—CX_3$, $—CX_2H$, $—CXH_2$, —CN, $—N(R)_2$, $—C(O)N(R)_2$, —N(R)C(O)R, $—N(R)S(O)_2R$, $—N(R)C(O)N(R)_2$, $—N(R)C(S)N(R)_2$, and $—C(R)N(R)_2C(O)OR$, and each n is independently selected from 1, 2, 3, 4, and 5.

In another embodiment, $R_4$ is selected from the group consisting of a $C_{3-6}$ carbocycle, $—(CH_2)_nQ$, $—(CH_2)_nCHQR$, —CHQR, and $—CQ(R)_2$, where Q is selected from a $C_{3-6}$ carbocycle, a 5- to 14-membered heteroaryl having one or more heteroatoms selected from N, O, and S, —OR, $—O(CH_2)_nN(R)_2$, —C(O)OR, —OC(O)R, $—CX_3$, $—CX_2H$, $—CXH_2$, —CN, $—C(O)N(R)_2$, —N(R)C(O)R, $—N(R)S(O)_2R$, $—N(R)C(O)N(R)_2$, $—N(R)C(S)N(R)_2$, $—C(R)N(R)_2C(O)OR$, and a 5- to 14-membered heterocycloalkyl having one or more heteroatoms selected from N, O, and S which is substituted with one or more substituents selected from oxo (═O), OH, amino, and $C_{1-3}$ alkyl, and each n is independently selected from 1, 2, 3, 4, and 5.

In another embodiment, $R_4$ is selected from the group consisting of a $C_{3-6}$ carbocycle, $—(CH_2)_nQ$, $—(CH_2)_nCHQR$, —CHQR, and $—CQ(R)_2$, where Q is selected from a $C_{3-6}$ carbocycle, a 5- to 14-membered heterocycle having one or more heteroatoms selected from N, O, and S, —OR, $—O(CH_2)_nN(R)_2$, —C(O)OR, —OC(O)R, $—CX_3$, $—CX_2H$, $—CXH_2$, —CN, $—C(O)N(R)_2$, —N(R)C(O)R, $—N(R)S(O)_2R$, $—N(R)C(O)N(R)_2$, $—N(R)C(S)N(R)_2$, $—C(R)N(R)_2C(O)OR$, and each n is independently selected from 1, 2, 3, 4, and 5; and when Q is a 5- to 14-membered heterocycle and (i) $R_4$ is $—(CH_2)_nQ$ in which n is 1 or 2, or (ii) $R_4$ is $—(CH_2)_nCHQR$ in which n is 1, or (iii) $R_4$ is —CHQR, and $—CQ(R)_2$, then Q is either a 5- to 14-membered heteroaryl or 8- to 14-membered heterocycloalkyl.

In another embodiment, $R_4$ is selected from the group consisting of a $C_{3-6}$ carbocycle, $—(CH_2)_nQ$, $—(CH_2)_nCHQR$, —CHQR, and $—CQ(R)_2$, where Q is selected from a $C_{3-6}$ carbocycle, a 5- to 14-membered heteroaryl having one or more heteroatoms selected from N, O, and S, —OR, $—O(CH_2)_nN(R)_2$, —C(O)OR, —OC(O)R, $—CX_3$, $—CX_2H$, $—CXH_2$, —CN, $—C(O)N(R)_2$, —N(R)C(O)R, $—N(R)S(O)_2R$, $—N(R)C(O)N(R)_2$, $—N(R)C(S)N(R)_2$, $—C(R)N(R)_2C(O)OR$, and each n is independently selected from 1, 2, 3, 4, and 5.

In another embodiment, $R_4$ is unsubstituted $C_{1-4}$ alkyl, e.g., unsubstituted methyl.

In certain embodiments, the disclosure provides a compound having the Formula (I), wherein $R_4$ is $—(CH_2)_nQ$ or $—(CH_2)_nCHQR$, where Q is $—N(R)_2$, and n is selected from 3, 4, and 5.

In certain embodiments, the disclosure provides a compound having the Formula (I), wherein $R_4$ is selected from the group consisting of $—(CH_2)_nQ$, $—(CH_2)_nCHQR$, —CHQR, and $—CQ(R)_2$, where Q is $—N(R)_2$, and n is selected from 1, 2, 3, 4, and 5.

In certain embodiments, the disclosure provides a compound having the Formula (I), wherein $R_2$ and $R_3$ are independently selected from the group consisting of $C_{2-14}$ alkyl, $C_{2-14}$ alkenyl, —R*YR'', —YR'', and —R*OR'', or $R_2$ and $R_3$, together with the atom to which they are attached, form a heterocycle or carbocycle, and $R_4$ is $—(CH_2)_nQ$ or $—(CH_2)_nCHQR$, where Q is $—N(R)_2$, and n is selected from 3, 4, and 5.

In certain embodiments, $R_2$ and $R_3$ are independently selected from the group consisting of $C_{2-14}$ alkyl, $C_{2-14}$ alkenyl, —R*YR'', —YR'', and —R*OR'', or $R_2$ and $R_3$, together with the atom to which they are attached, form a heterocycle or carbocycle.

In some embodiments, $R_1$ is selected from the group consisting of $C_{5-20}$ alkyl and $C_{5-20}$ alkenyl.

In other embodiments, $R_1$ is selected from the group consisting of —R*YR'', —YR'', and —R''M'R'.

In certain embodiments, $R_1$ is selected from —R*YR'' and —YR''. In some embodiments, Y is a cyclopropyl group. In some embodiments, R* is $C_8$ alkyl or $C_8$ alkenyl. In certain embodiments, R'' is $C_{3-12}$ alkyl. For example, R'' can be $C_3$ alkyl. For example, R'' can be $C_{4-8}$ alkyl (e.g., $C_4$, $C_5$, $C_6$, $C_7$, or $C_8$ alkyl).

In some embodiments, $R_1$ is $C_{5-20}$ alkyl. In some embodiments, $R_1$ is $C_6$ alkyl. In some embodiments, $R_1$ is $C_8$ alkyl. In other embodiments, $R_1$ is $C_9$ alkyl. In certain embodiments, $R_1$ is $C_{14}$ alkyl. In other embodiments, $R_1$ is $C_{18}$ alkyl.

In some embodiments, $R_1$ is $C_{5-20}$ alkenyl. In certain embodiments, $R_1$ is $C_{18}$ alkenyl. In some embodiments, $R_1$ is linoleyl.

In certain embodiments, $R_1$ is branched (e.g., decan-2-yl, undecan-3-yl, dodecan-4-yl, tridecan-5-yl, tetradecan-6-yl, 2-methylundecan-3-yl, 2-methyldecan-2-yl, 3-methylundecan-3-yl, 4-methyldodecan-4-yl, or heptadeca-9-yl). In certain embodiments, $R_1$ is

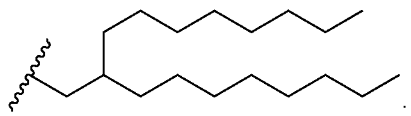 [SMILES: *CC(CCCCCCCC)CCCCCCCC]

In certain embodiments, $R_1$ is unsubstituted $C_{5-20}$ alkyl or $C_{5-20}$ alkenyl. In certain embodiments, R' is substituted $C_{5-20}$ alkyl or $C_{5-20}$ alkenyl (e.g., substituted with a $C_{3-6}$ carbocycle such as 1-cyclopropylnonyl).

In other embodiments, $R_1$ is —R"M'R'.

In some embodiments, R' is selected from —R*YR" and —YR". In some embodiments, Y is $C_{3-8}$ cycloalkyl. In some embodiments, Y is $C_{6-10}$ aryl. In some embodiments, Y is a cyclopropyl group. In some embodiments, Y is a cyclohexyl group. In certain embodiments, R* is $C_1$ alkyl.

In some embodiments, R" is selected from the group consisting of $C_{3-12}$ alkyl and $C_{3-12}$ alkenyl. In some embodiments, R" adjacent to Y is $C_1$ alkyl. In some embodiments, R" adjacent to Y is $C_{4-9}$ alkyl (e.g., $C_4$, $C_5$, $C_6$, $C_7$ or $C_8$ or $C_9$ alkyl).

In some embodiments, R' is selected from $C_4$ alkyl and $C_4$ alkenyl. In certain embodiments, R' is selected from $C_5$ alkyl and $C_5$ alkenyl. In some embodiments, R' is selected from $C_6$ alkyl and $C_6$ alkenyl. In some embodiments, R' is selected from $C_7$ alkyl and $C_7$ alkenyl. In some embodiments, R' is selected from $C_9$ alkyl and $C_9$ alkenyl.

In other embodiments, R' is selected from $C_{11}$ alkyl and $C_{11}$ alkenyl. In other embodiments, R' is selected from $C_{12}$ alkyl, $C_{12}$ alkenyl, $C_{13}$ alkyl, $C_{13}$ alkenyl, $C_{14}$ alkyl, $C_{14}$ alkenyl, $C_{15}$ alkyl, $C_{15}$ alkenyl, $C_{16}$ alkyl, $C_{16}$ alkenyl, $C_{17}$ alkyl, $C_{17}$ alkenyl, $C_{18}$ alkyl, and $C_{18}$ alkenyl. In certain embodiments, R' is branched (e.g., decan-2-yl, undecan-3-yl, dodecan-4-yl, tridecan-5-yl, tetradecan-6-yl, 2-methylundecan-3-yl, 2-methyldecan-2-yl, 3-methylundecan-3-yl, 4-methyldodecan-4-yl or heptadeca-9-yl). In certain embodiments, R' is

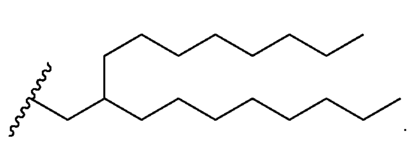 [SMILES: *CC(CCCCCCCC)CCCCCCCC]

In certain embodiments, R' is unsubstituted $C_{1-18}$ alkyl. In certain embodiments, R' is substituted $C_{1-18}$ alkyl (e.g., $C_{1-15}$ alkyl substituted with a $C_{3-6}$ carbocycle such as 1-cyclopropylnonyl).

In some embodiments, R" is selected from the group consisting of $C_{3-14}$ alkyl and $C_{3-14}$ alkenyl. In some embodiments, R" is $C_3$ alkyl, $C_4$ alkyl, $C_5$ alkyl, $C_6$ alkyl, $C_7$ alkyl, or $C_8$ alkyl. In some embodiments, R" is $C_9$ alkyl, $C_{10}$ alkyl, $C_{11}$ alkyl, $C_{12}$ alkyl, $C_{13}$ alkyl, or $C_{14}$ alkyl.

In some embodiments, M' is —C(O)O—. In some embodiments, M' is —OC(O)—.

In other embodiments, M' is an aryl group or heteroaryl group. For example, M' can be selected from the group consisting of phenyl, oxazole, and thiazole.

In some embodiments, M is —C(O)O— In some embodiments, M is —OC(O)—. In some embodiments, M is —C(O)N(R')—. In some embodiments, M is —P(O)(OR')O—.

In other embodiments, M is an aryl group or heteroaryl group. For example, M can be selected from the group consisting of phenyl, oxazole, and thiazole.

In some embodiments, M is the same as M'. In other embodiments, M is different from M'.

In some embodiments, each $R_5$ is H. In certain such embodiments, each $R_6$ is also H.

In some embodiments, $R_7$ is H. In other embodiments, $R_7$ is $C_{1-3}$ alkyl (e.g., methyl, ethyl, propyl, or i-propyl).

In some embodiments, $R_2$ and $R_3$ are independently $C_{5-14}$ alkyl or $C_{5-14}$ alkenyl.

In some embodiments, $R_2$ and $R_3$ are the same. In some embodiments, $R_2$ and $R_3$ are $C_8$ alkyl. In certain embodiments, $R_2$ and $R_3$ are $C_2$ alkyl. In other embodiments, $R_2$ and $R_3$ are $C_3$ alkyl. In some embodiments, $R_2$ and $R_3$ are $C_4$ alkyl. In certain embodiments, $R_2$ and $R_3$ are $C_5$ alkyl. In other embodiments, $R_2$ and $R_3$ are $C_6$ alkyl. In some embodiments, $R_2$ and $R_3$ are $C_7$ alkyl.

In other embodiments, $R_2$ and $R_3$ are different. In certain embodiments, $R_2$ is $C_8$ alkyl. In some embodiments, $R_3$ is $C_{1-7}$ (e.g., $C_1$, $C_2$, $C_3$, $C_4$, $C_5$, $C_6$, or $C_7$ alkyl) or $C_9$ alkyl.

In some embodiments, $R_7$ and $R_3$ are H.

In certain embodiments, $R_2$ is H.

In some embodiments, m is 5, 7, or 9.

In some embodiments, $R_4$ is selected from $-(CH_2)_nQ$ and $-(CH_2)_nCHQR$.

In some embodiments, Q is selected from the group consisting of —OR, —OH, $-O(CH_2)_nN(R)_2$, —OC(O)R, $-CX_3$, —CN, —N(R)C(O)R, —N(H)C(O)R, $-N(R)S(O)_2R$, $-N(H)S(O)_2R$, $-N(R)C(O)N(R)_2$, $-N(H)C(O)N(R)_2$, —N(H)C(O)N(H)(R), $-N(R)C(S)N(R)_2$, $-N(H)C(S)N(R)_2$, —N(H)C(S)N(H)(R), $-C(R)N(R)_2C(O)OR$, a carbocycle, and a heterocycle.

In certain embodiments, Q is —OH.

In certain embodiments, Q is a substituted or unsubstituted 5- to 10-membered heteroaryl, e.g., Q is an imidazole, a pyrimidine, a purine, 2-amino-1,9-dihydro-6H-purin-6-one-9-yl (or guanin-9-yl), adenin-9-yl, cytosin-1-yl, or uracil-1-yl. In certain embodiments, Q is a substituted 5- to 14-membered heterocycloalkyl, e.g., substituted with one or more substituents selected from oxo (═O), OH, amino, and $C_{1-3}$ alkyl. For example, Q is 4-methylpiperazinyl, 4-(4-methoxybenzyl)piperazinyl, or isoindolin-2-yl-1,3-dione.

In certain embodiments, Q is an unsubstituted or substituted $C_{6-10}$ aryl (such as phenyl) or $C_{3-6}$ cycloalkyl.

In some embodiments, n is 1. In other embodiments, n is 2. In further embodiments, n is 3. In certain other embodiments, n is 4. For example, $R_4$ can be $-(CH_2)_2OH$. For example, $R_4$ can be $-(CH_2)_3OH$. For example, $R_4$ can be $-(CH_2)_4OH$. For example, $R_4$ can be benzyl. For example, $R_4$ can be 4-methoxybenzyl.

In some embodiments, $R_4$ is a $C_{3-6}$ carbocycle. In some embodiments, $R_4$ is a $C_{3-6}$ cycloalkyl. For example, $R_4$ can be cyclohexyl optionally substituted with e.g., OH, halo, $C_{1-6}$ alkyl, etc. For example, $R_4$ can be 2-hydroxycyclohexyl.

In some embodiments, R is H.

In some embodiments, R is unsubstituted $C_{1-3}$ alkyl or unsubstituted $C_{2-3}$ alkenyl. For example, $R_4$ can be $-CH_2CH(OH)CH_3$ or $-CH_2CH(OH)CH_2CH_3$.

In some embodiments, R is substituted $C_{1-3}$ alkyl, e.g., $CH_2OH$. For example, $R_4$ can be $-CH_2CH(OH)CH_2OH$.

In some embodiments, $R_2$ and $R_3$, together with the atom to which they are attached, form a heterocycle or carbocycle. In some embodiments, $R_2$ and $R_3$, together with the atom to which they are attached, form a 5- to 14-membered aromatic or non-aromatic heterocycle having one or more heteroatoms selected from N, O, S, and P. In some embodiments, $R_2$ and $R_3$, together with the atom to which they are attached, form an optionally substituted $C_{3-20}$ carbocycle (e.g., $C_{3-18}$ carbocycle, $C_{3-15}$ carbocycle, $C_{3-12}$ carbocycle, or $C_{3-10}$ carbocycle), either aromatic or non-aromatic. In some embodiments, $R_2$ and $R_3$, together with the atom to which they are attached, form a $C_{3-6}$ carbocycle. In other embodiments, $R_2$ and $R_3$, together with the atom to which they are attached, form a $C_6$ carbocycle, such as a cyclohexyl or phenyl group. In certain embodiments, the heterocycle or $C_{3-6}$ carbocycle is substituted with one or more alkyl groups (e.g., at the same ring atom or at adjacent or non-adjacent ring atoms). For example, $R_2$ and $R_3$, together with the atom to which they are attached, can form a cyclohexyl or phenyl group bearing one or more $C_5$ alkyl substitutions. In certain embodiments, the heterocycle or $C_{3-6}$ carbocycle formed by $R_2$ and $R_3$, is substituted with a carbocycle groups. For example, $R_2$ and $R_3$, together with the atom to which they are attached, can form a cyclohexyl or phenyl group that is substituted with cyclohexyl. In some embodiments, $R_2$ and $R_3$, together with the atom to which they are attached, form a $C_{7-15}$ carbocycle, such as a cycloheptyl, cyclopentadecanyl, or naphthyl group.

In some embodiments, $R_4$ is selected from —$(CH_2)_nQ$ and —$(CH_2)_nCHQR$. In some embodiments, Q is selected from the group consisting of —OR, —OH, —$O(CH_2)_nN(R)_2$, —OC(O)R, —$CX_3$, —CN, —N(R)C(O)R, —N(H)C(O)R, —$N(R)S(O)_2R$, —$N(H)S(O)_2R$, —$N(R)C(O)N(R)_2$, —$N(H)C(O)N(R)_2$, —N(H)C(O)N(H)(R), —$N(R)C(S)N(R)_2$, —$N(H)C(S)N(R)_2$, —N(H)C(S)N(H)(R), and a heterocycle. In other embodiments, Q is selected from the group consisting of an imidazole, a pyrimidine, and a purine.

In some embodiments, $R_2$ and $R_3$, together with the atom to which they are attached, form a heterocycle or carbocycle. In some embodiments, $R_2$ and $R_3$, together with the atom to which they are attached, form a $C_{3-6}$ carbocycle, such as a phenyl group. In certain embodiments, the heterocycle or $C_{3-6}$ carbocycle is substituted with one or more alkyl groups (e.g., at the same ring atom or at adjacent or non-adjacent ring atoms). For example, $R_2$ and $R_3$, together with the atom to which they are attached, can form a phenyl group bearing one or more $C_5$ alkyl substitutions.

In some embodiments, the pharmaceutical compositions of the present disclosure, the compound of Formula (I) is selected from the group consisting of:

(Compound 1)

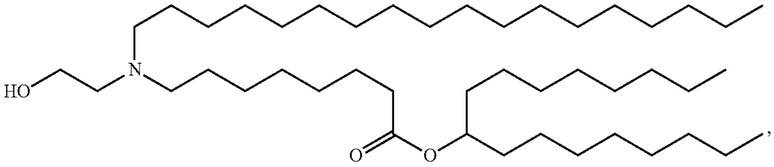, (Compound 2)

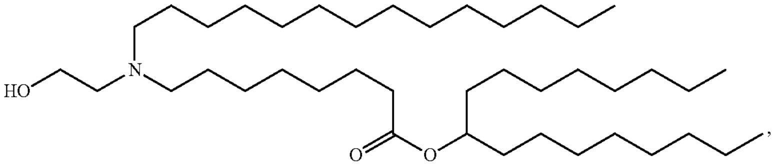, (Compound 3)

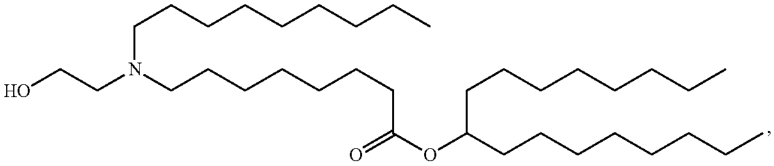, (Compound 4)

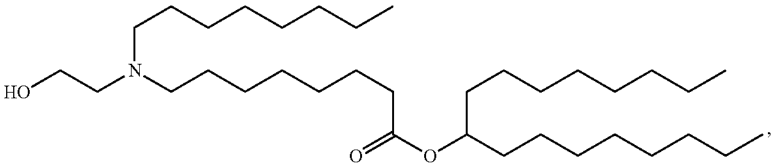, (Compound 5)

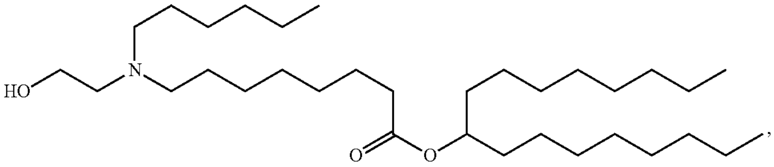,

-continued
(Compound 6)
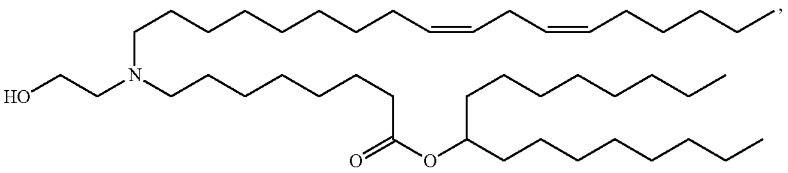
(Compound 8)
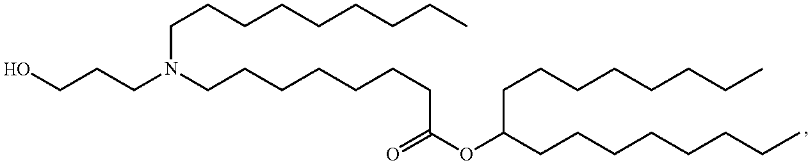
(Compound 8)
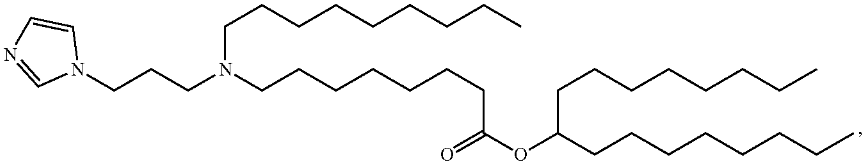
(Compound 9)
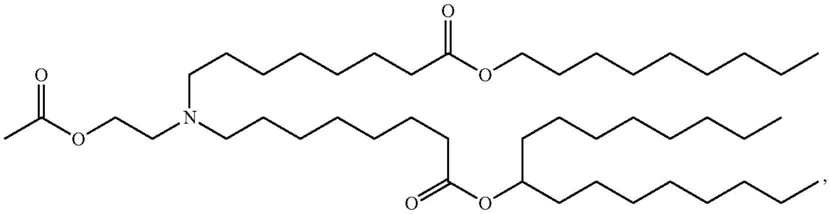
(Compound 10)
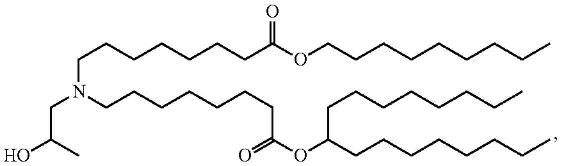
(Compound 11)
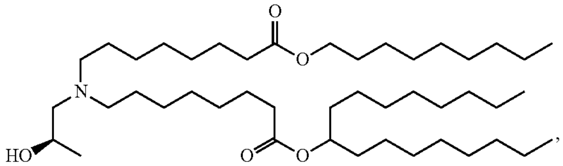
(Compound 12)
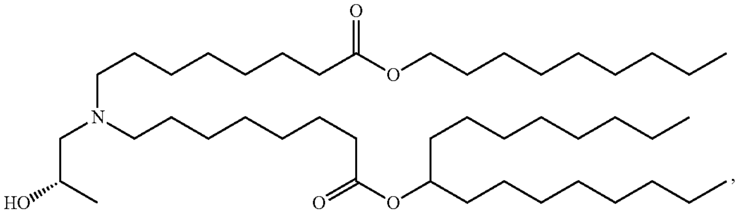
(Compound 13)
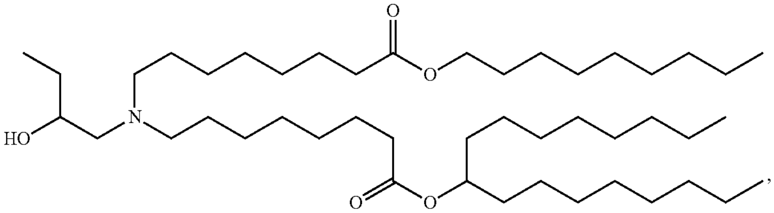
(Compound 14)
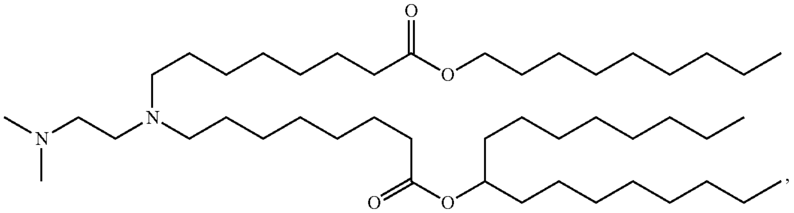

-continued
(Compound 15)
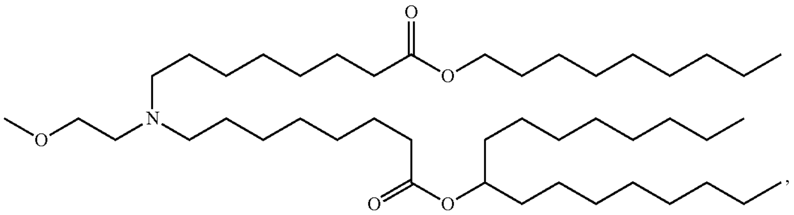
(Compound 16)
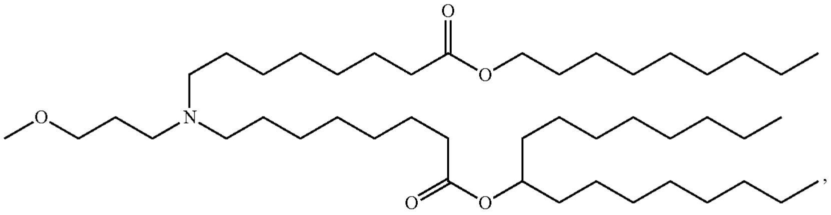
(Compound 17)
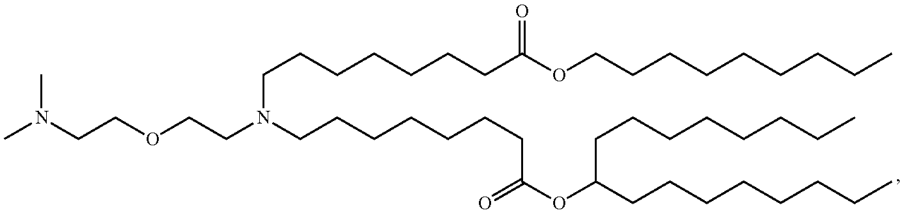
(Compound 18)
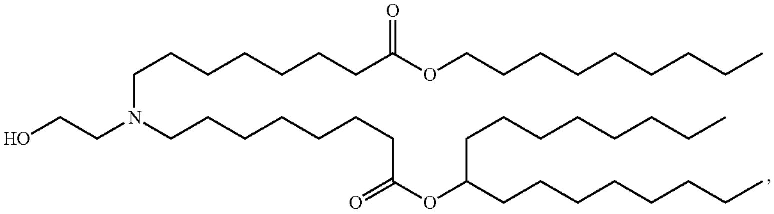
(Compound 19)
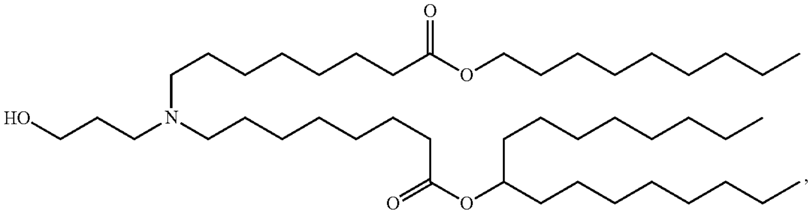
(Compound 20)
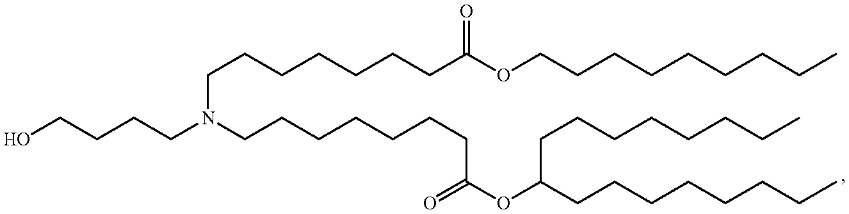
(Compound 21)
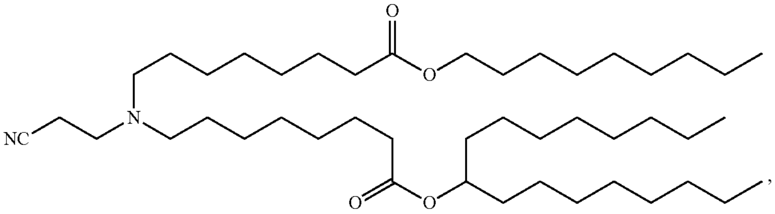

-continued
(Compound 22)
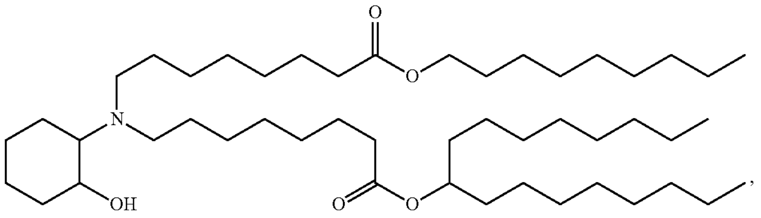
,
(Compound 23)
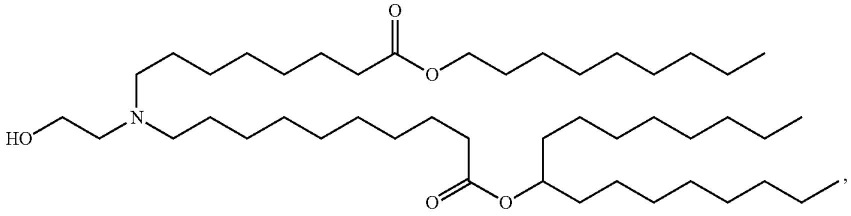
,
(Compound 24)
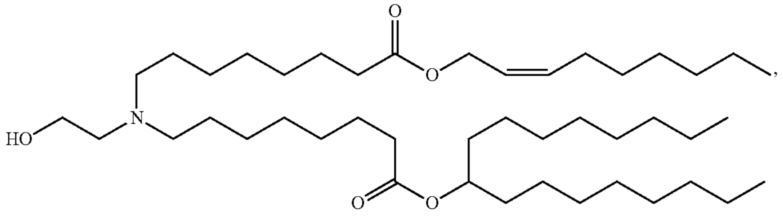
,
(Compound 25)
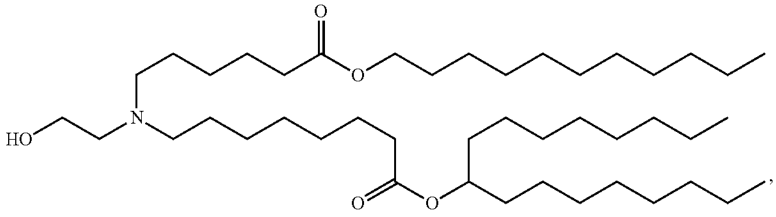
,
(Compound 26)
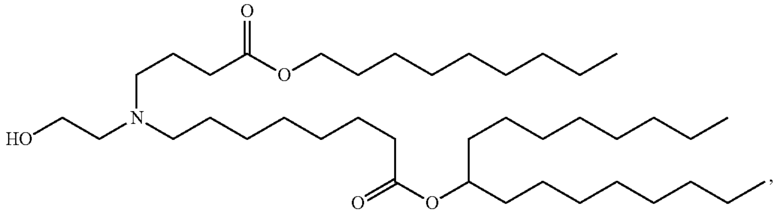
,
(Compound 27)
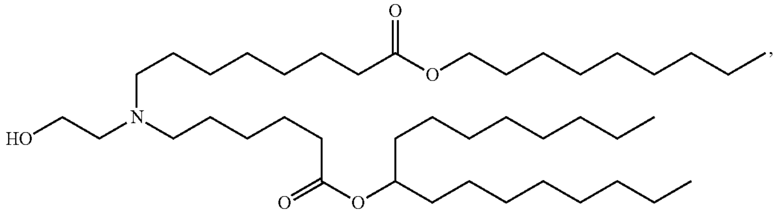
,
(Compound 28)
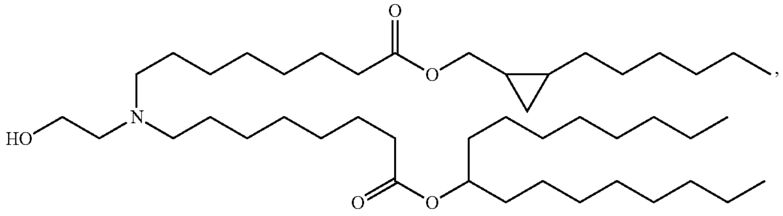
, -continued
(Compound 29)
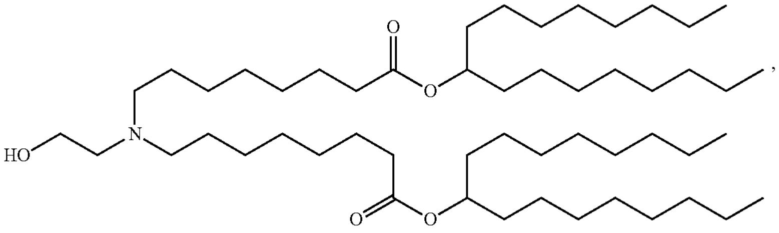
,
(Compound 30)
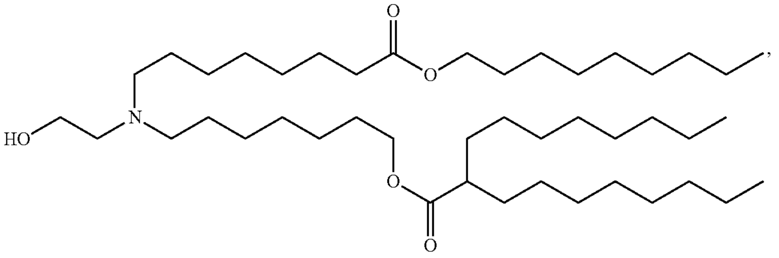
,
(Compound 31)
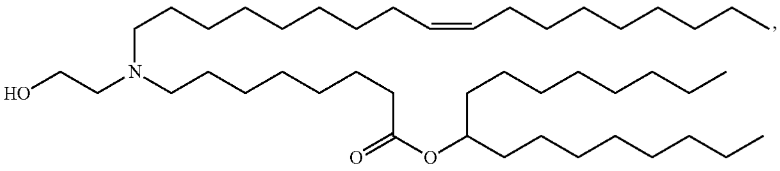
,
(Compound 32)
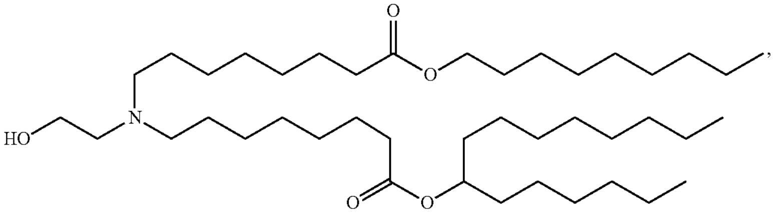
,
(Compound 33)
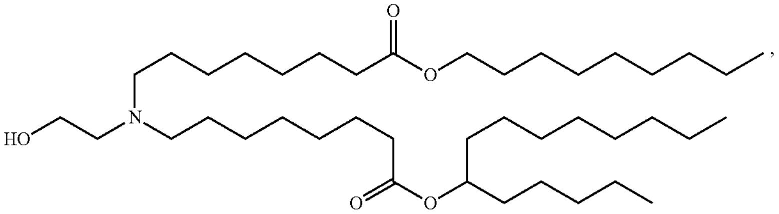
,
(Compound 34)
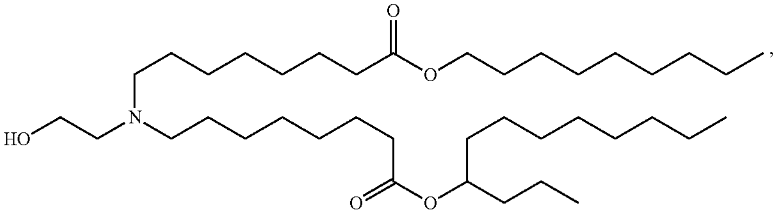
,
(Compound 35)
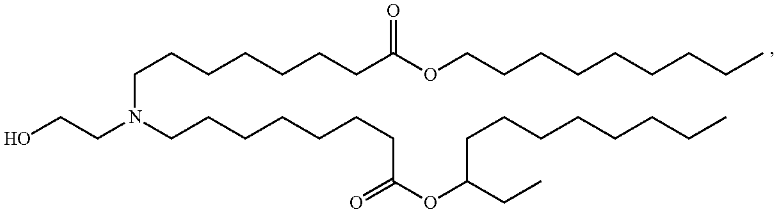
, -continued
(Compound 36)
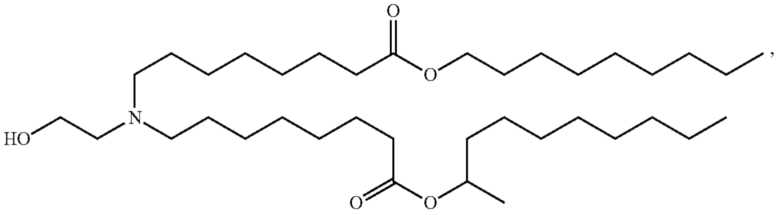
(Compound 37)
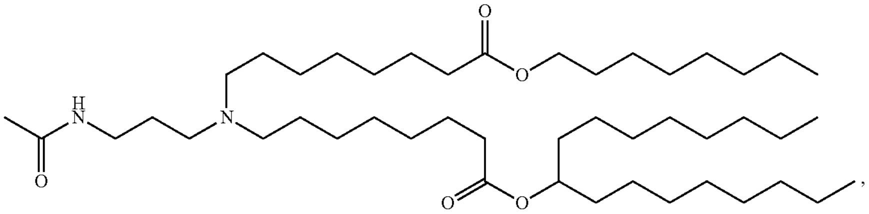
(Compound 38)
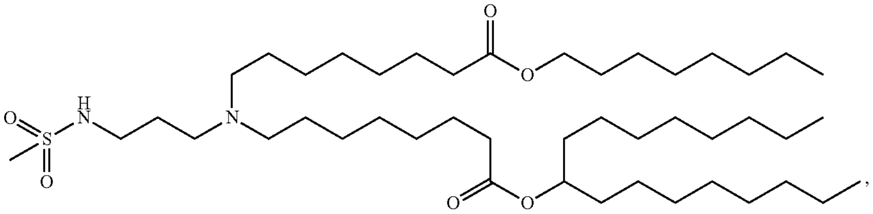
(Compound 39)
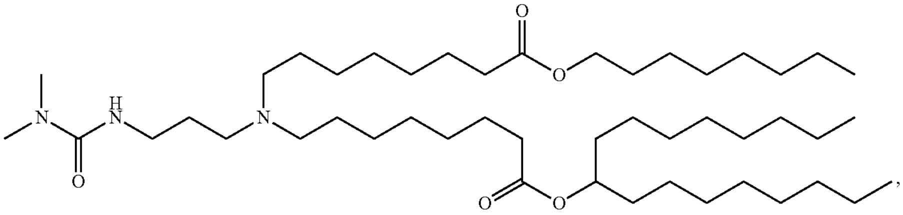
(Compound 40)
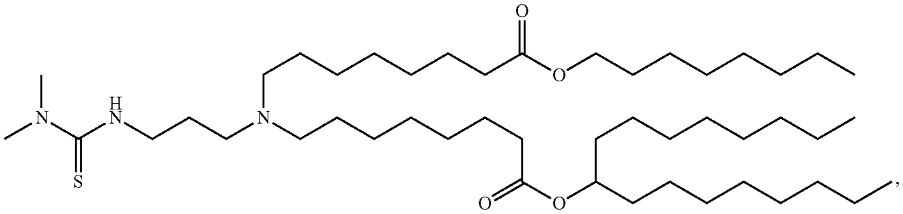
(Compound 41)
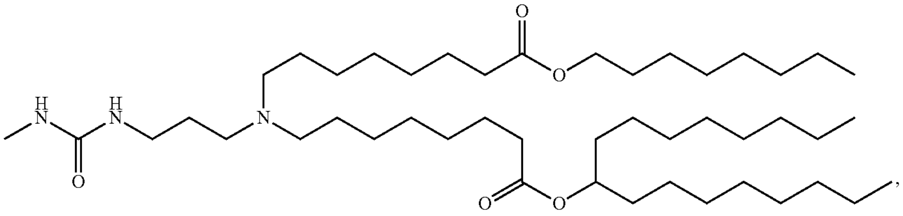
(Compound 42)
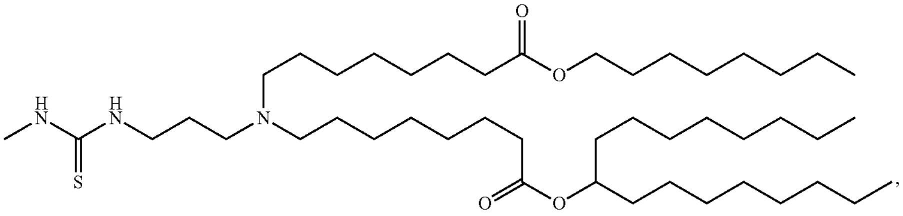

-continued
(Compound 43)
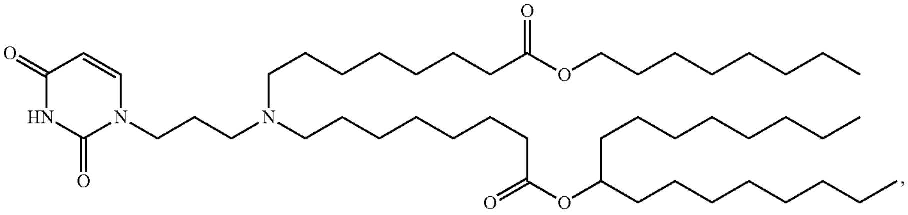,
(Compound 44)
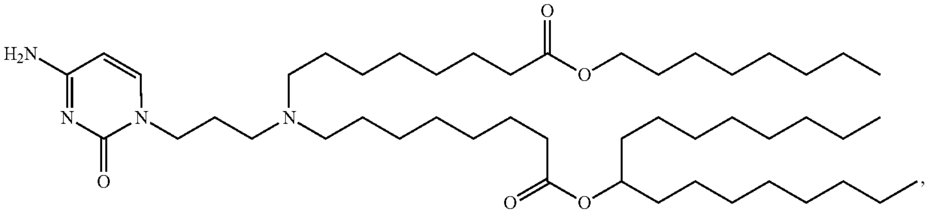,
(Compound 45)
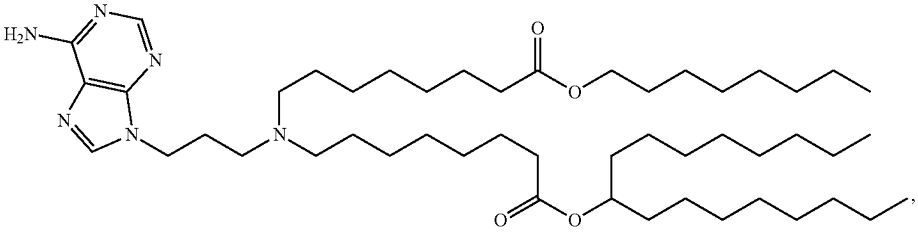,
(Compound 46)
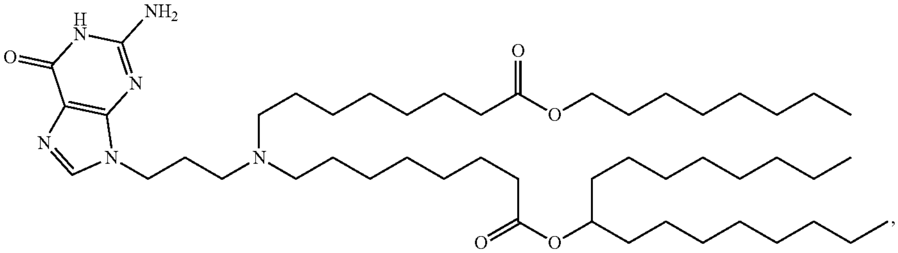,
(Compound 47)
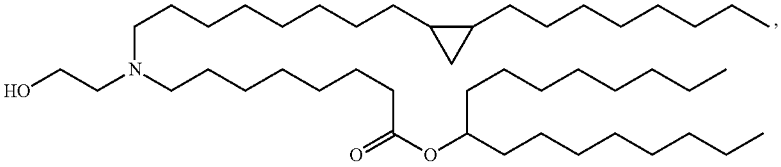,
(Compound 48)
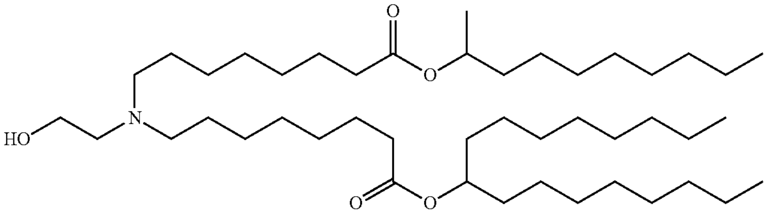,
(Compound 49)
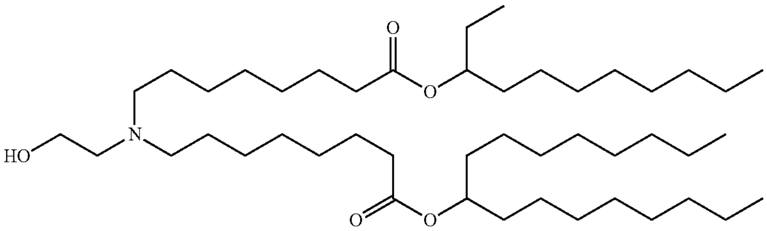, -continued
(Compound 50)
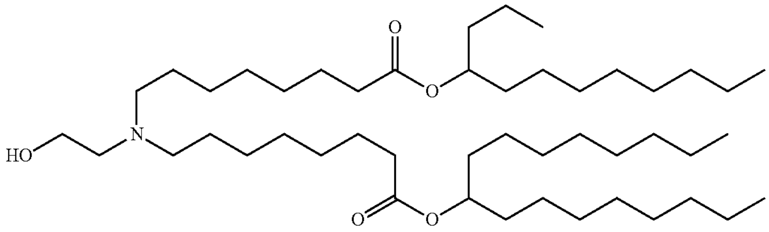,
(Compound 51)
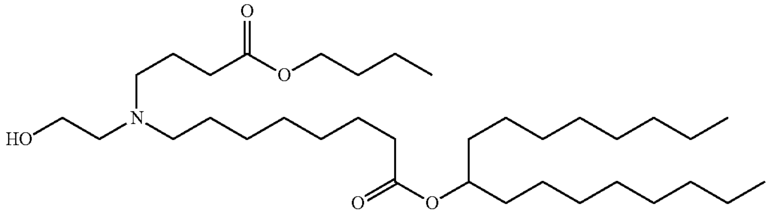,
(Compound 52)
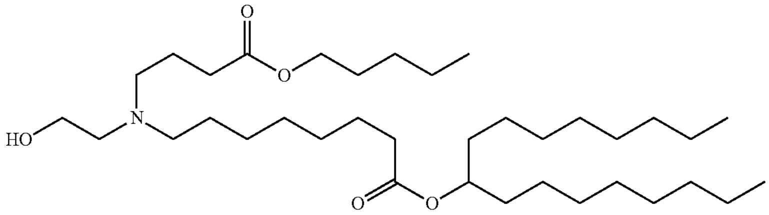,
(Compound 53)
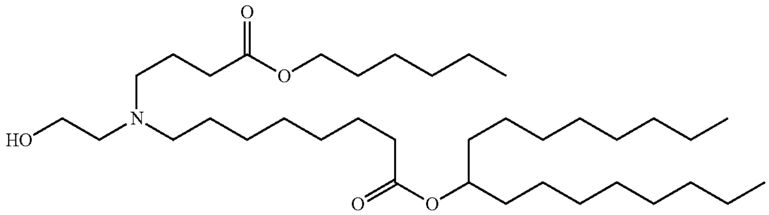,
(Compound 54)
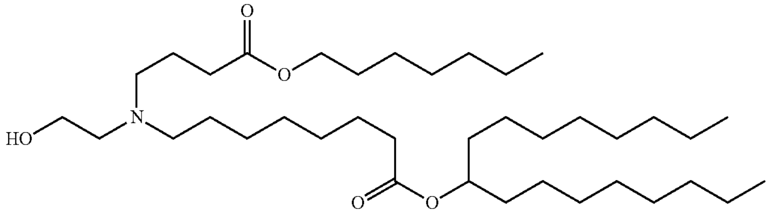,
(Compound 55)
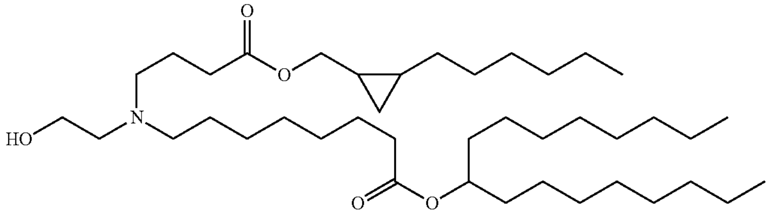,
(Compound 56)
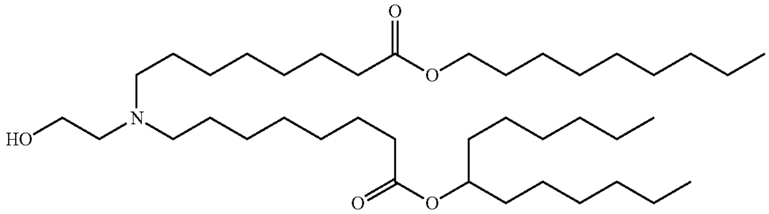, -continued
(Compound 57)
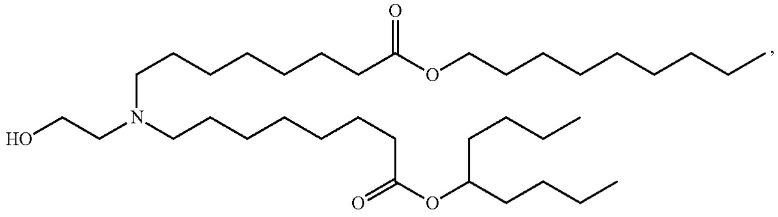,
(Compound 58)
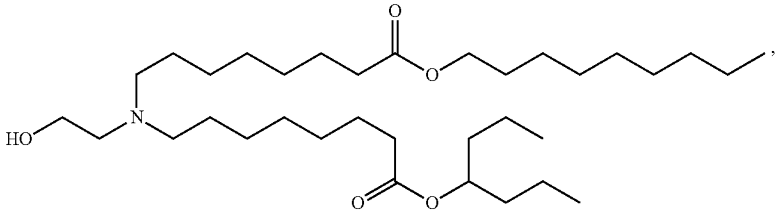,
(Compound 59)
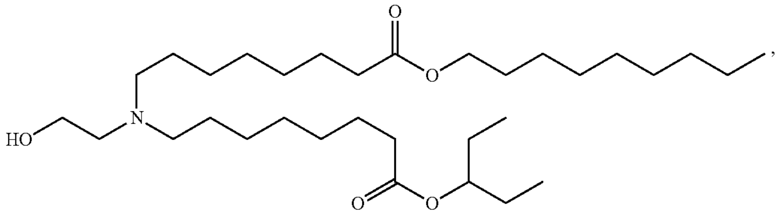,
(Compound 60)
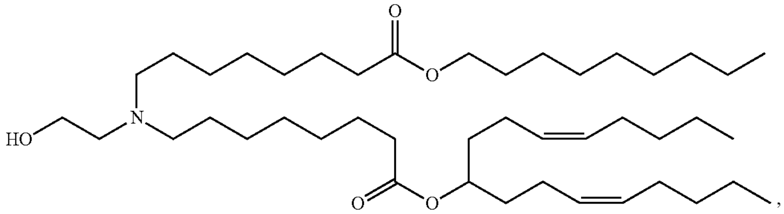,
(Compound 61)
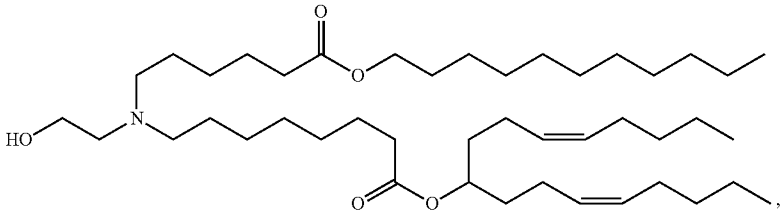,
(Compound 62)
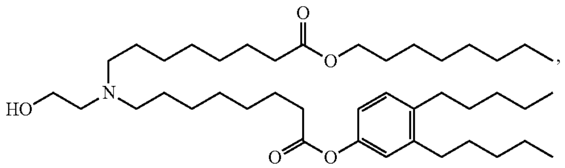,
(Compound 63)
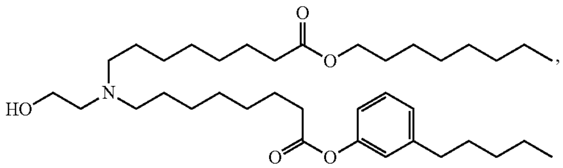,
(Compound 64)
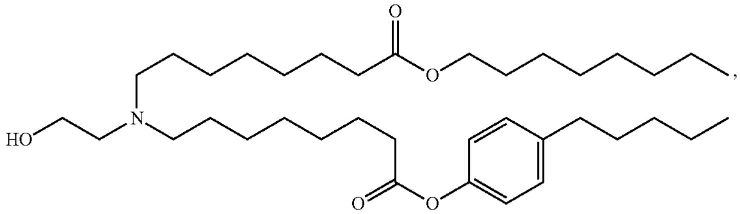, -continued
(Compound 65)
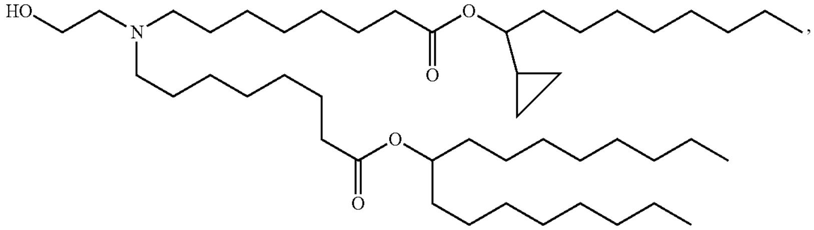
,
(Compound 66)
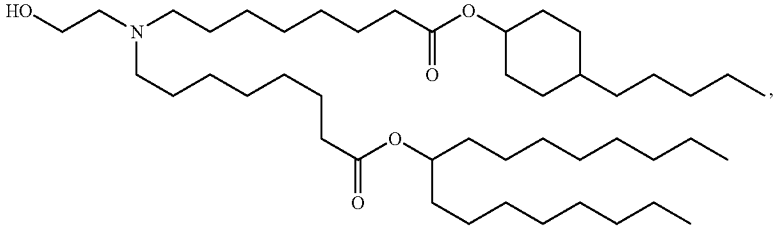
,
(Compound 67)
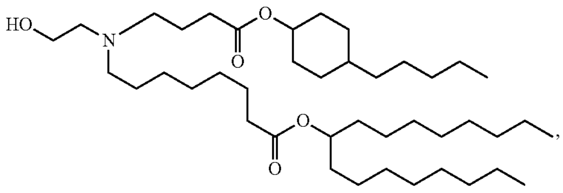
,
(Compound 68)
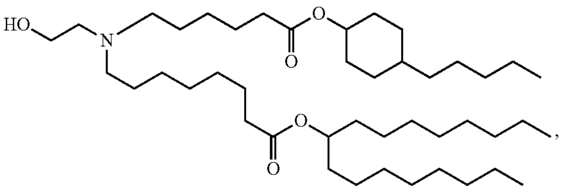
,
(Compound 69)
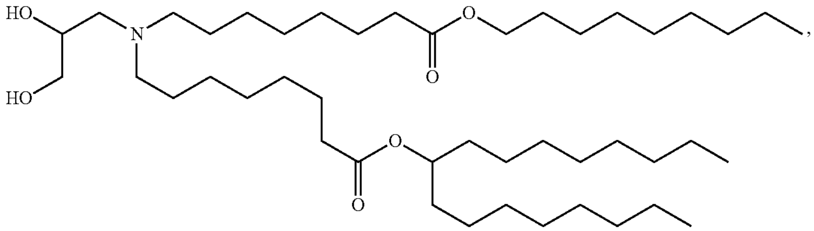
,
(Compound 70)
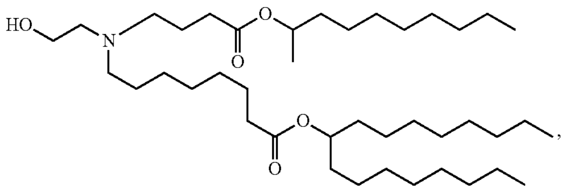
,
(Compound 71)
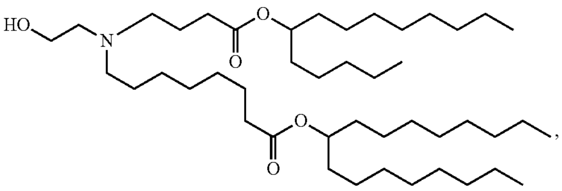
,
(Compound 72)
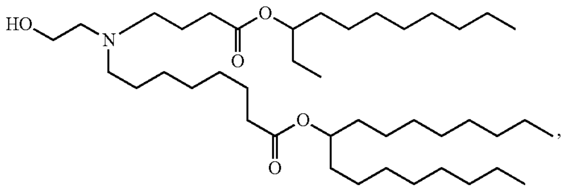
,
(Compound 73)
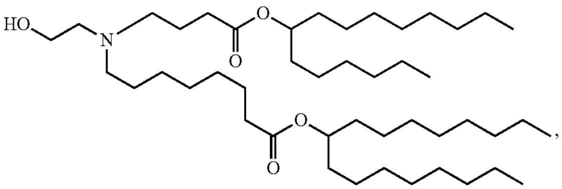
,
(Compound 74)
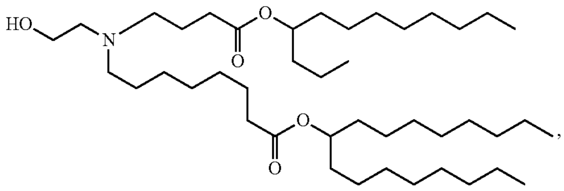
,
(Compound 75)
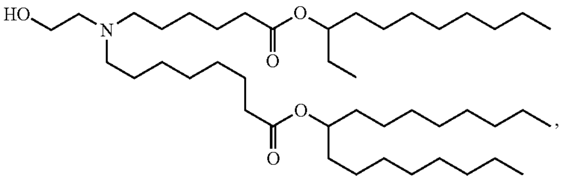
, -continued
(Compound 76)
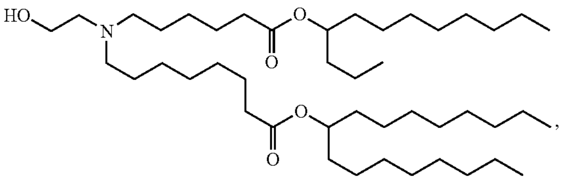
(Compound 77)
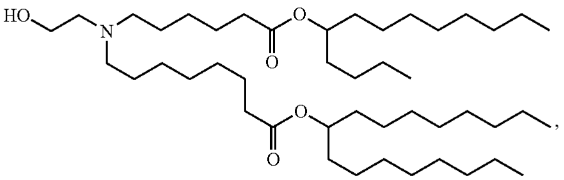
(Compound 78)
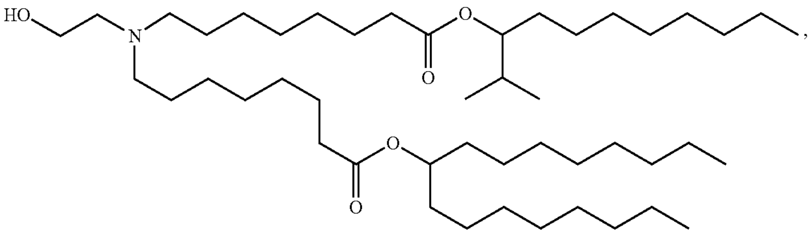
(Compound 79)
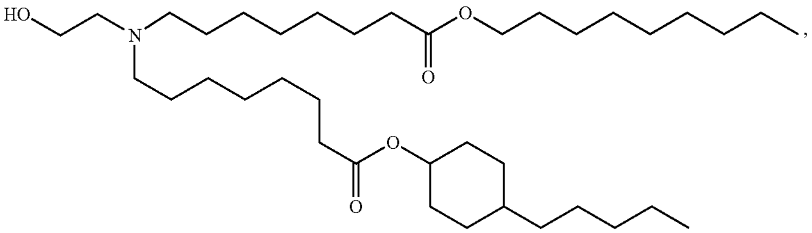
(Compound 80)
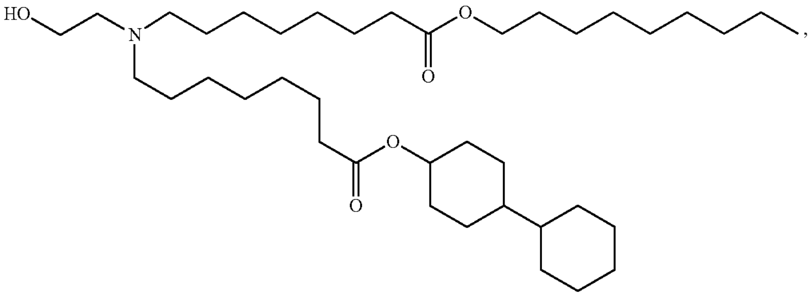
(Compound 81)
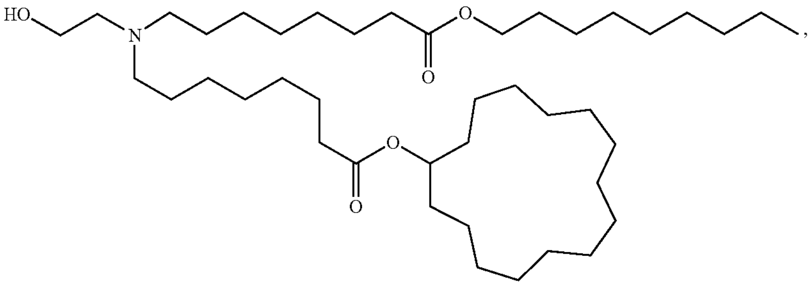
(Compound 82)
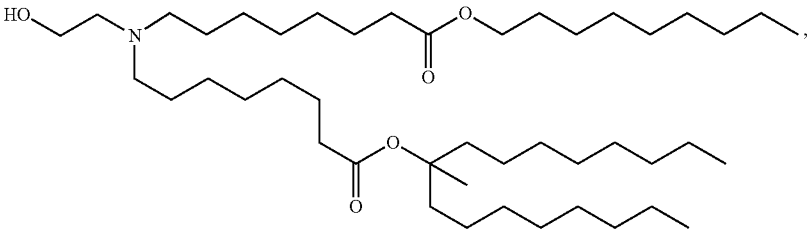

-continued
(Compound 83)
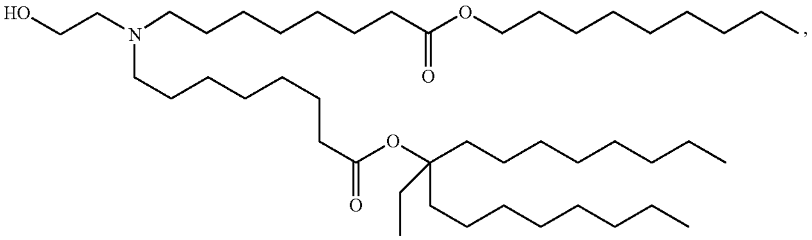
(Compound 84)
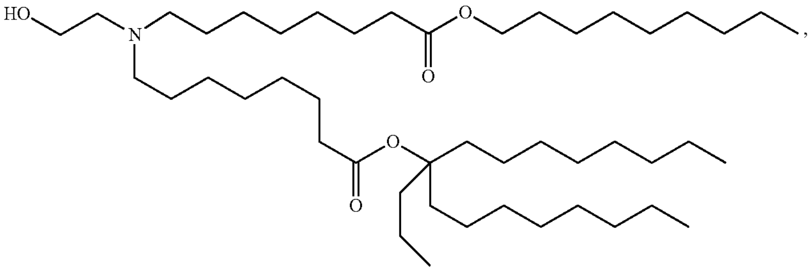
(Compound 85)
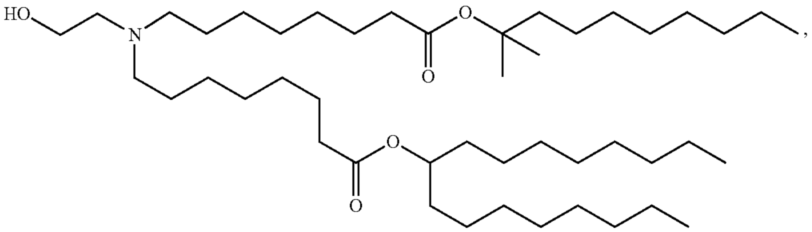
(Compound 86)
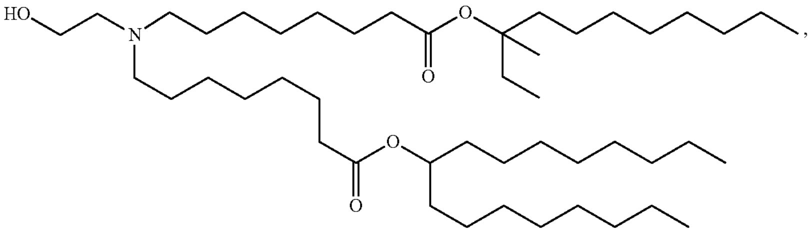
(Compound 87)
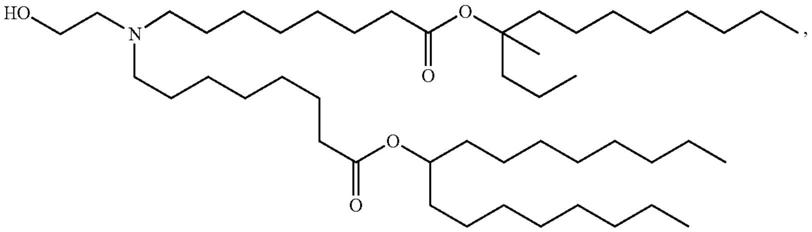
(Compound 88)
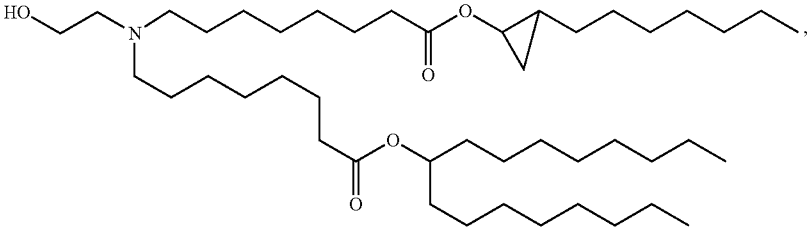

-continued
(Compound 89)
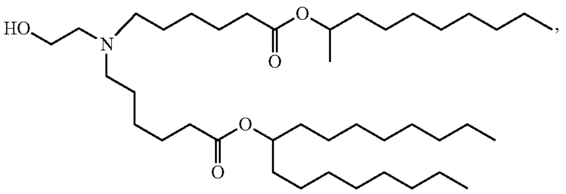
(Compound 90)
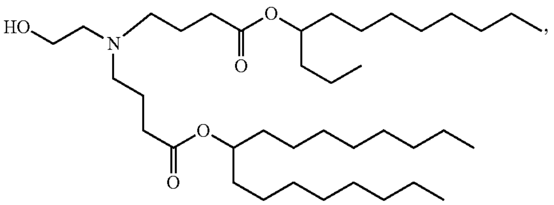
(Compound 91)
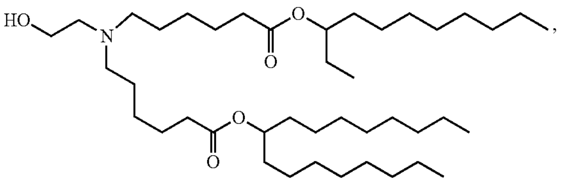
(Compound 92)
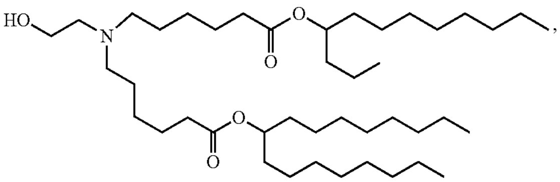
(Compound 93)
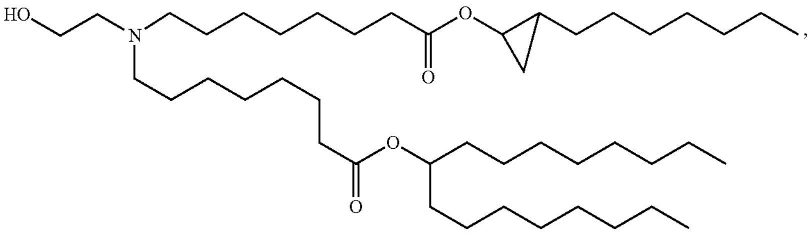
(Compound 94)
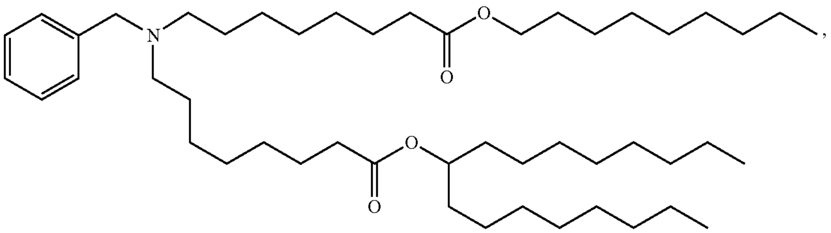
(Compound 95)
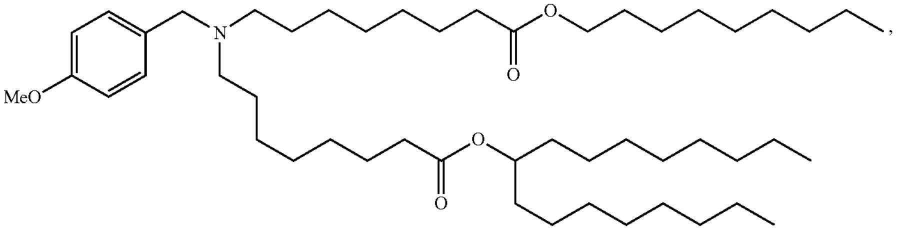
(Compound 96)
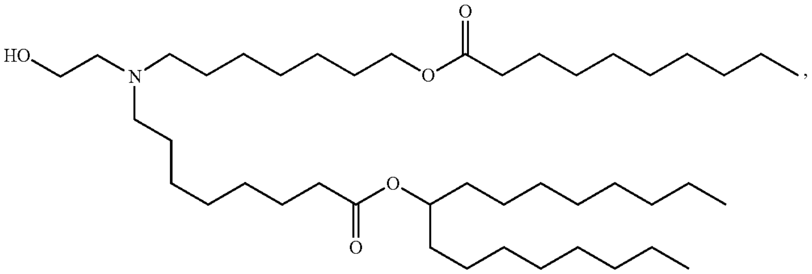

-continued
(Compound 97)
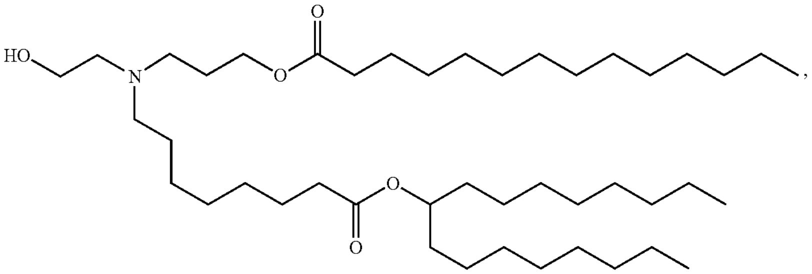
(Compound 98)
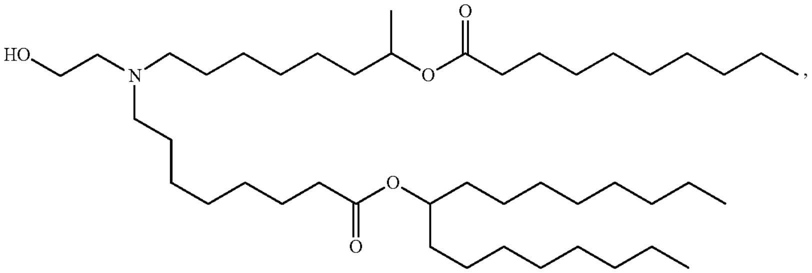
(Compound 99)
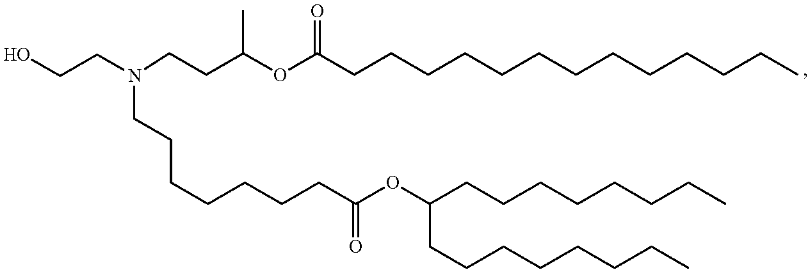
(Compound 100)
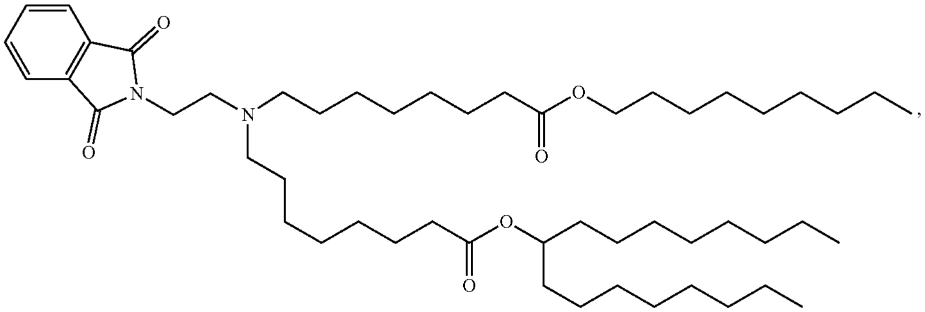
(Compound 101)
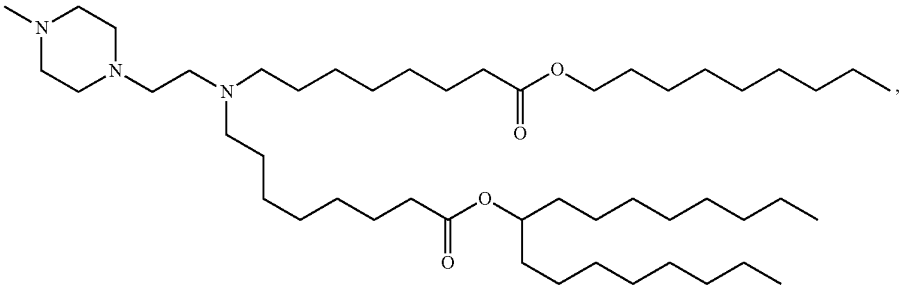

-continued
(Compound 102)
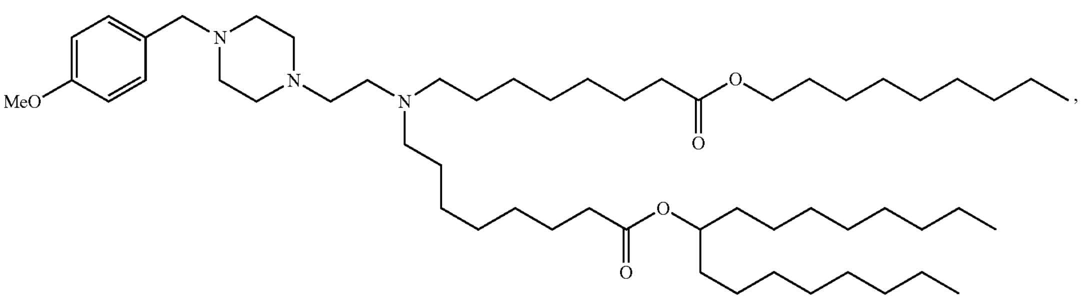
(Compound 103)
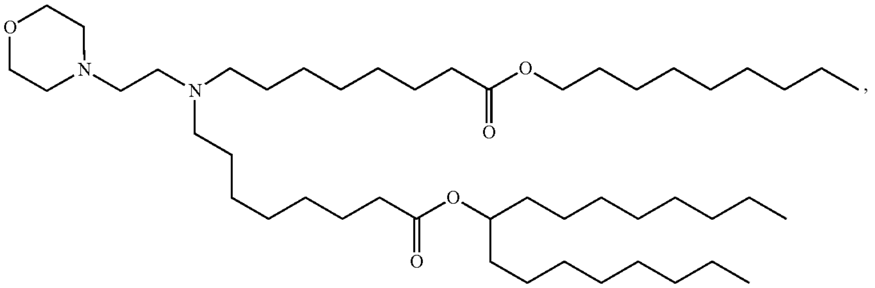
(Compound 104)
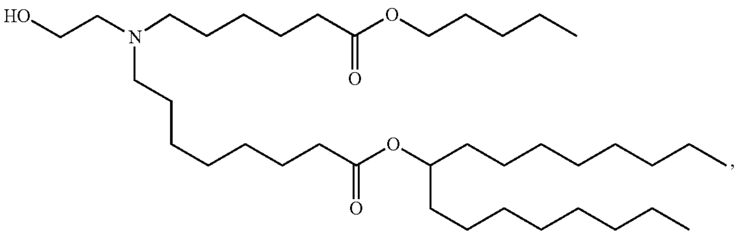
(Compound 105)
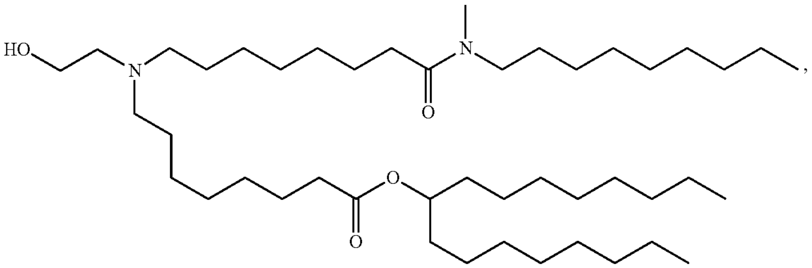
(Compound 106)
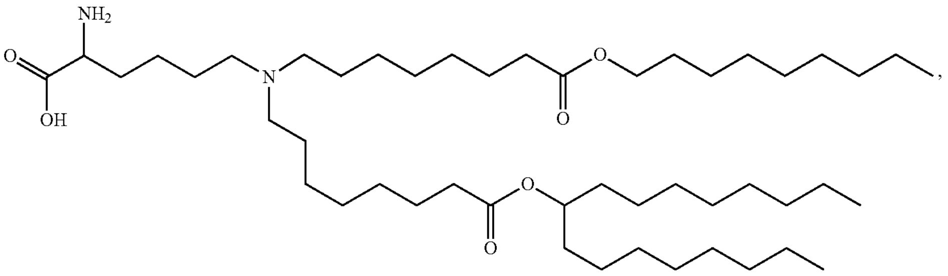
(Compound 107)
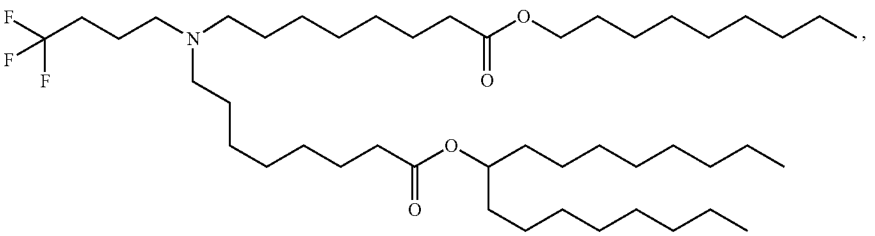

-continued
(Compound 108)
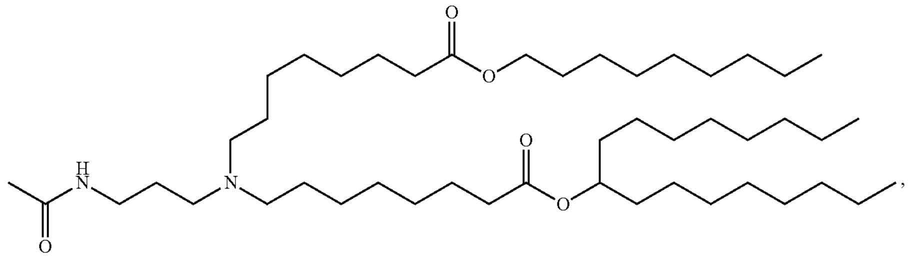
(Compound 109)
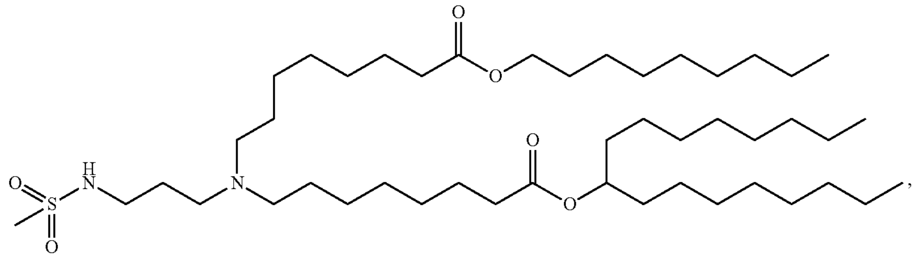
(Compound 110)
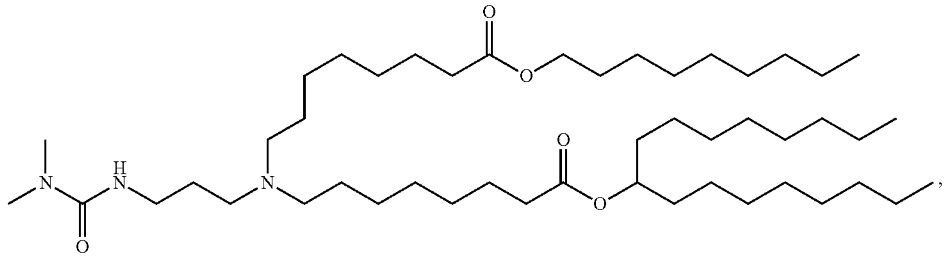
(Compound 111)
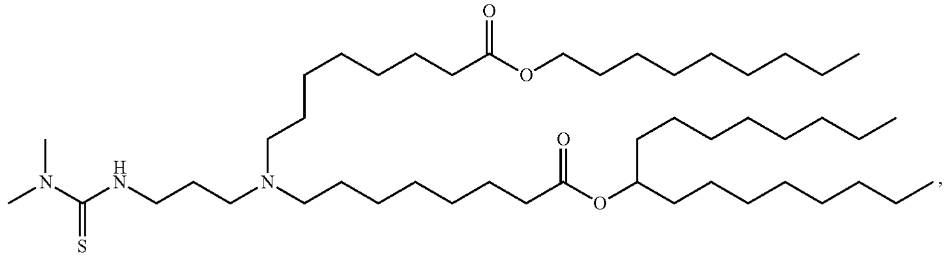
(Compound 112)
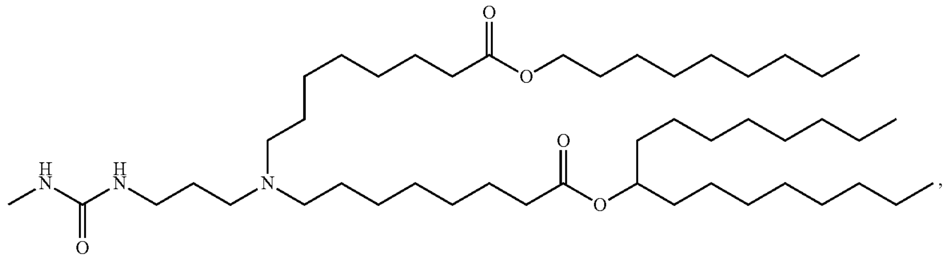
(Compound 113)
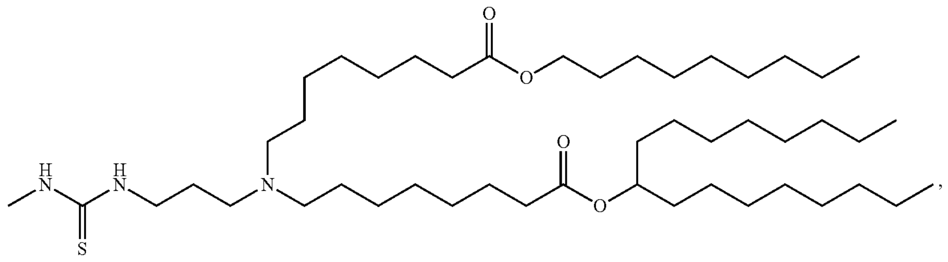

-continued
(Compound 114)
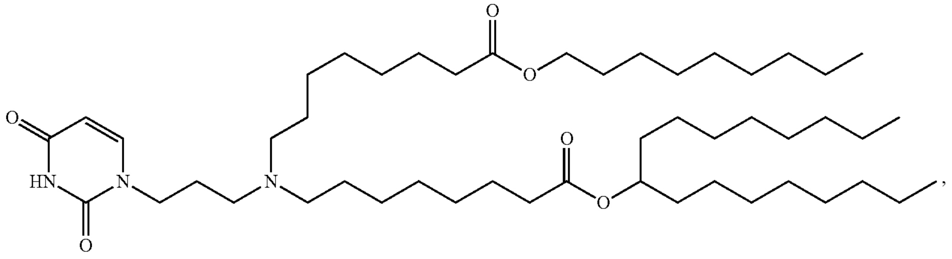
(Compound 115)
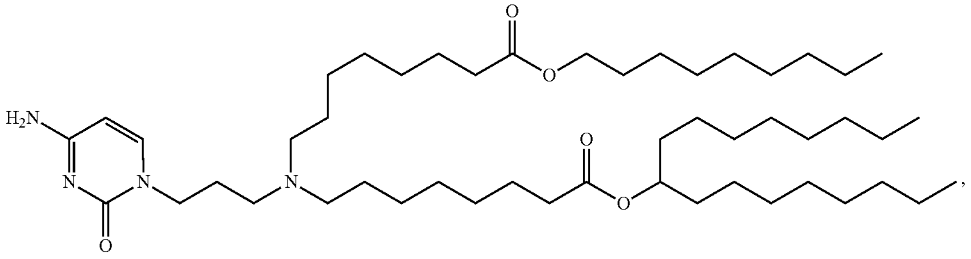
(Compound 116)
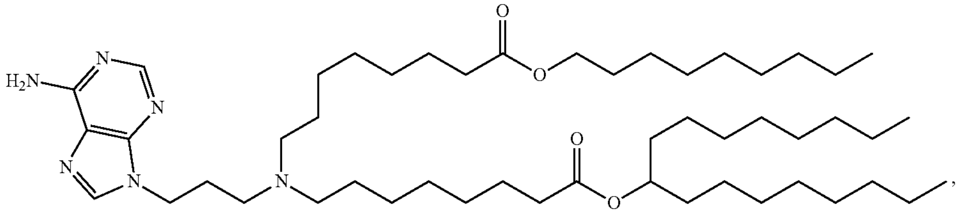
(Compound 117)
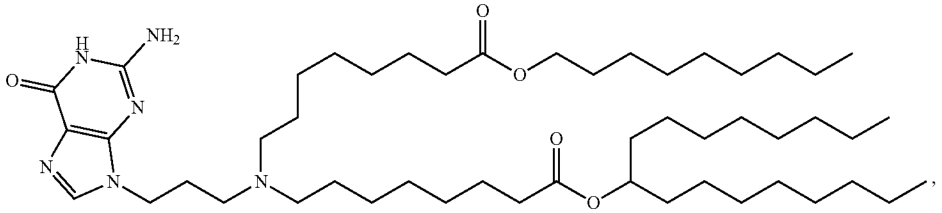
(Compound 118)
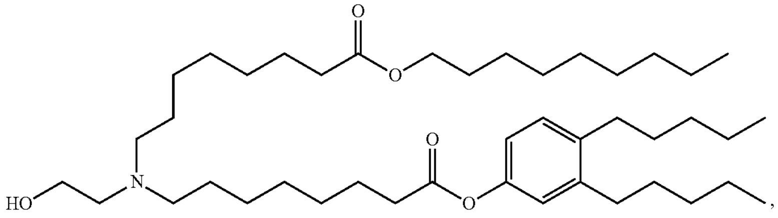
(Compound 119)
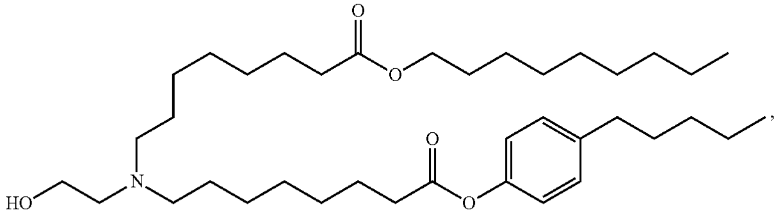
(Compound 120)
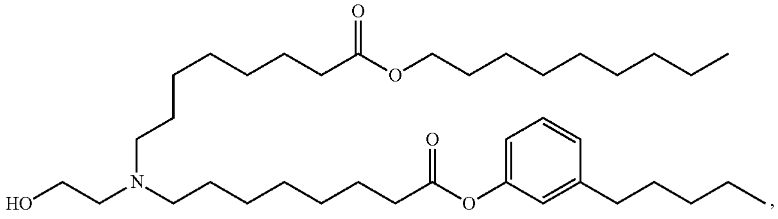

-continued
(Compound 121)
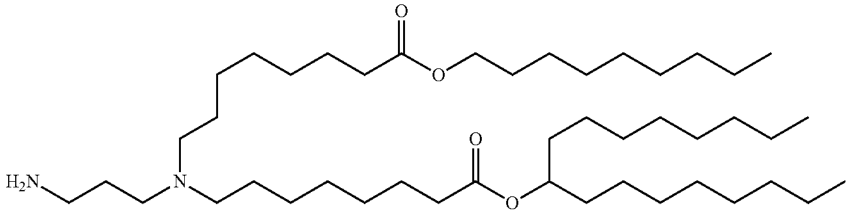
,
(Compound 122)
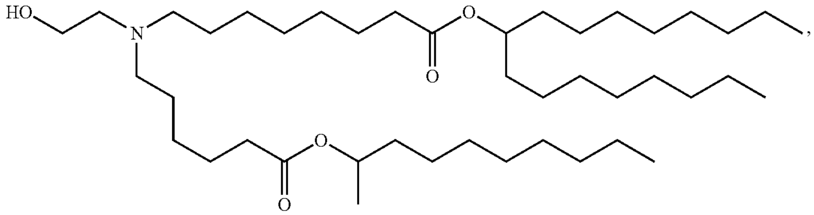
,
(Compound 123)
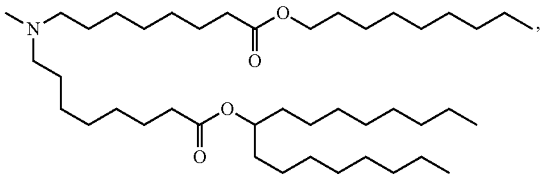
,
(Compound 124)
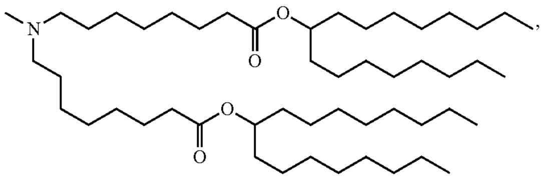
,
(Compound 125)
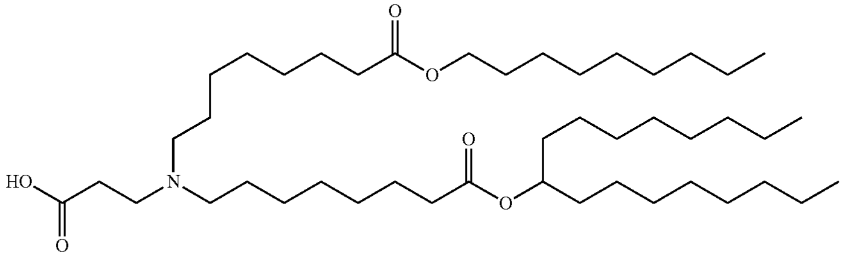
,
(Compound 126)
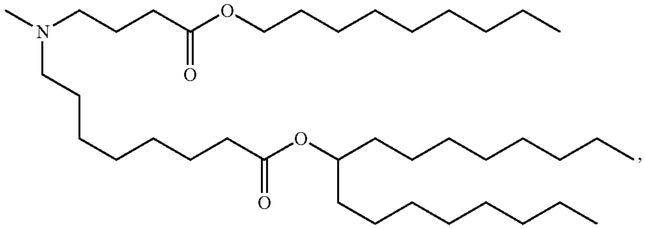
,
(Compound 127)
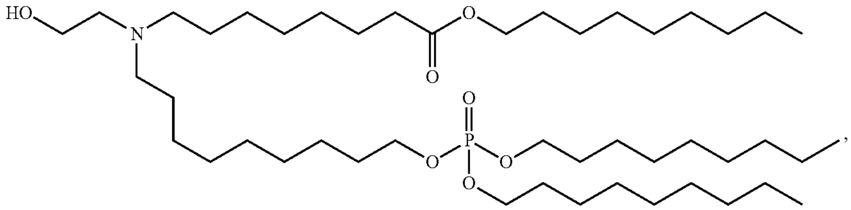
,
(Compound 128)
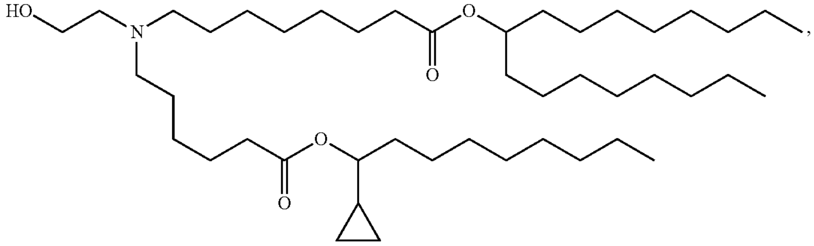
, -continued
(Compound 129)
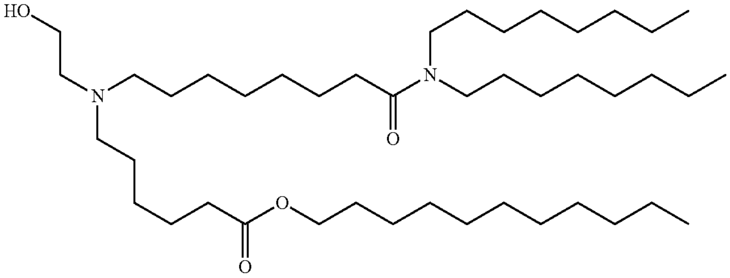
,
(Compound 130)
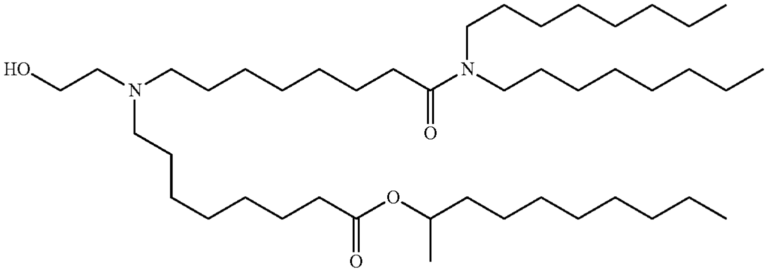
,
(Compound 131)
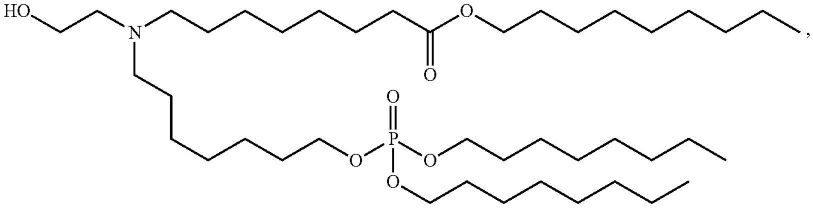
,
(Compound 132)
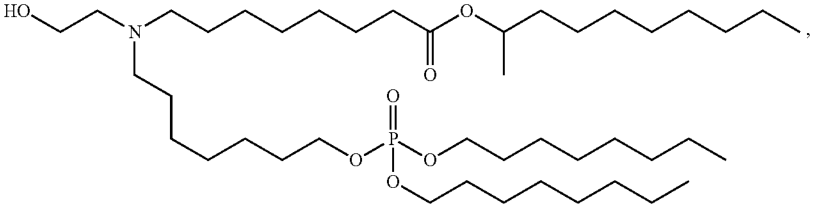
,
(Compound 133)
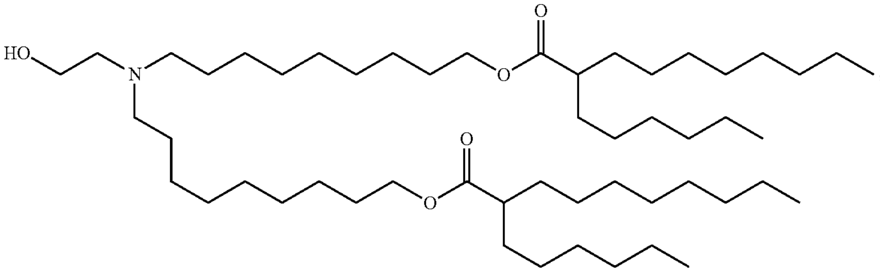
,
(Compound 134)
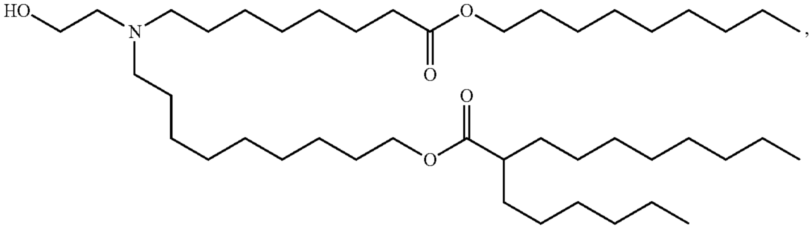
, -continued
(Compound 135)
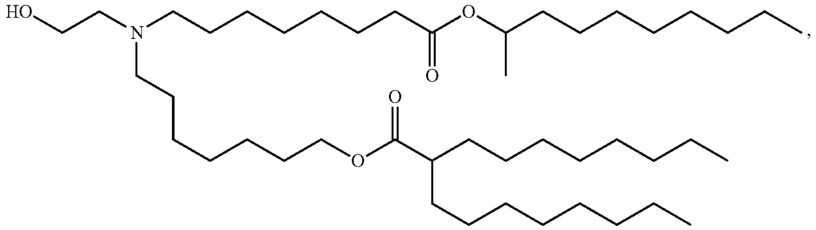
(Compound 136)
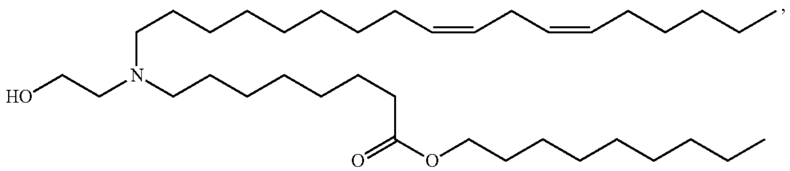
(Compound 137)
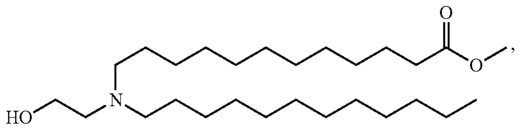
(Compound 138)
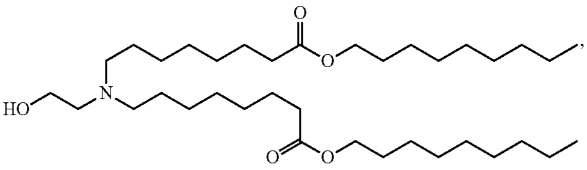
(Compound 139)
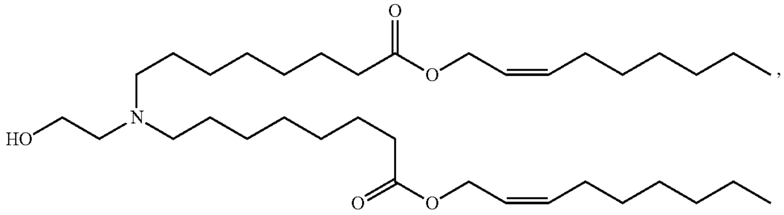
(Compound 140)
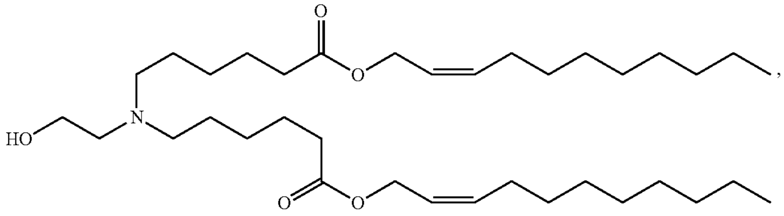
(Compound 141)
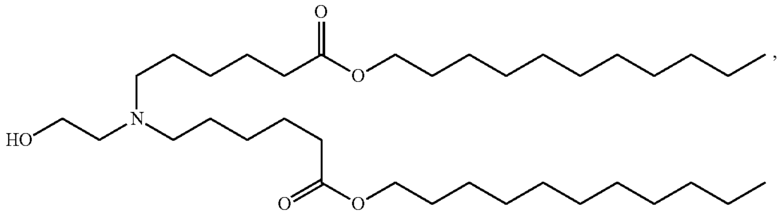
(Compound 142)
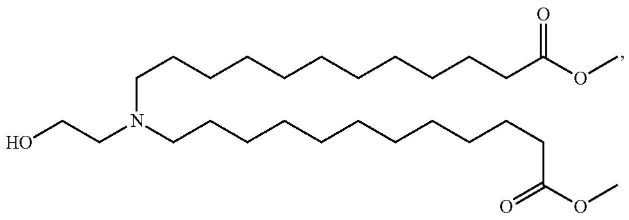

-continued
(Compound 143)
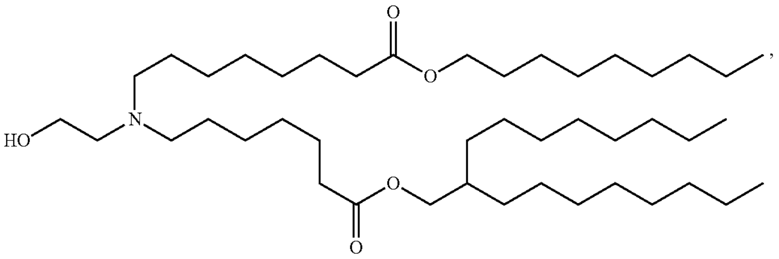
(Compound 144)
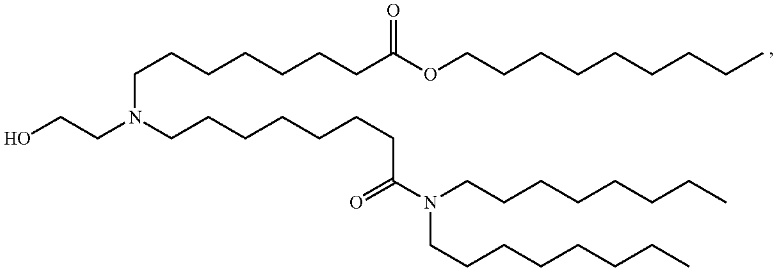
(Compound 145)
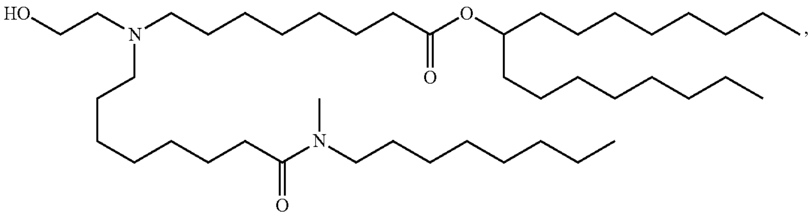
(Compound 146)
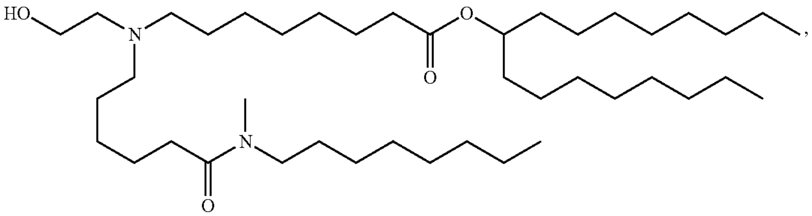
(Compound 147)
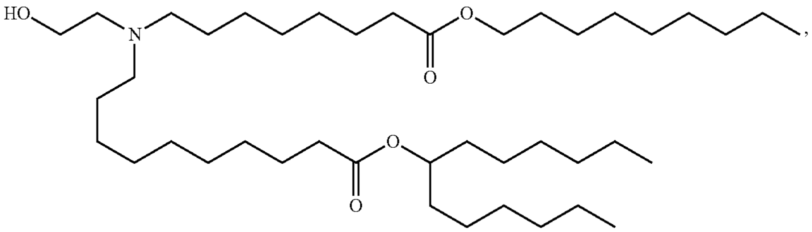
(Compound 148)
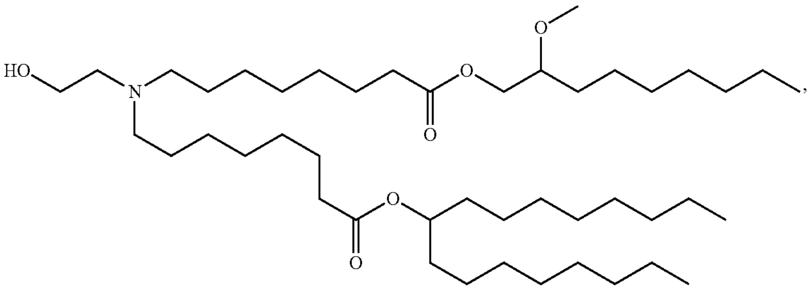

-continued
(Compound 149)
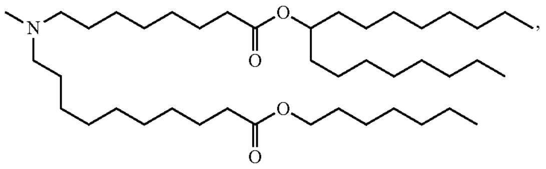
(Compound 150)
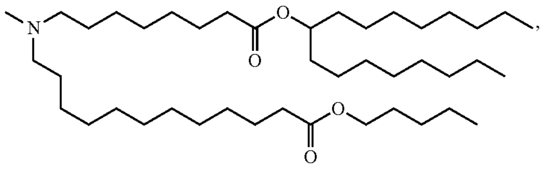
(Compound 151)
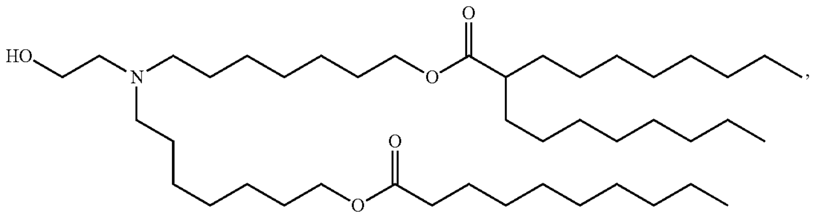
(Compound 152)
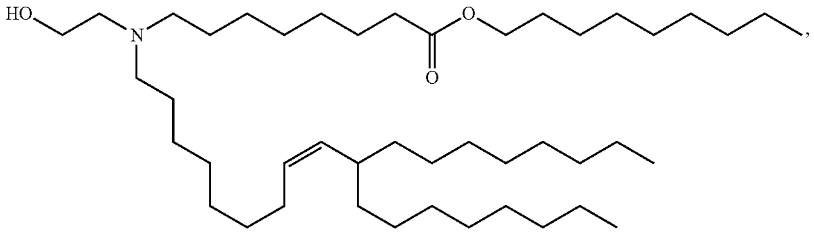
(Compound 153)
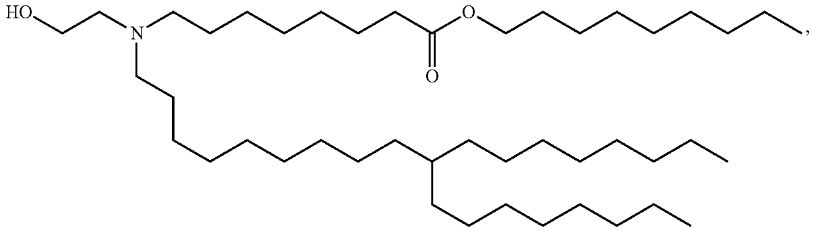
(Compound 154)
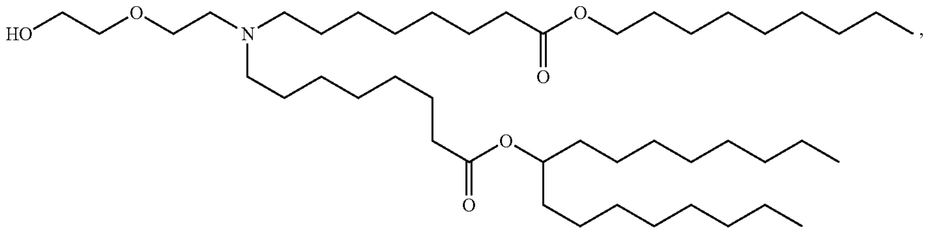
(Compound 155)
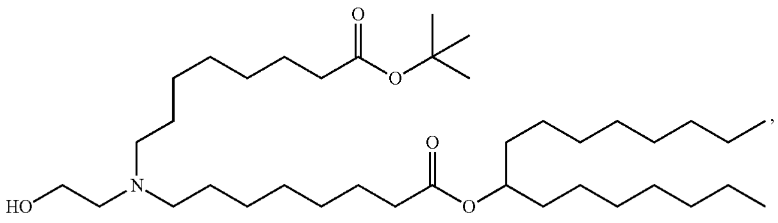

-continued
(Compound 156)
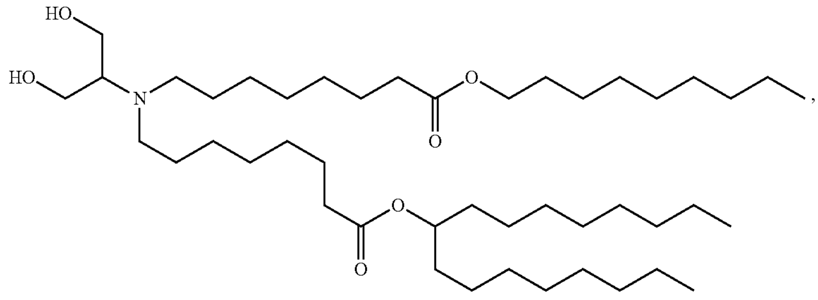
,
(Compound 157)
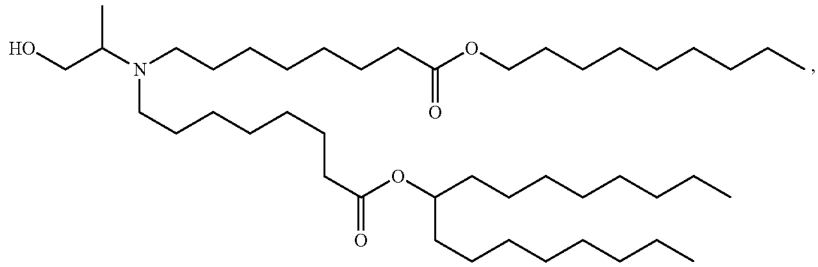
,
(Compound 158)
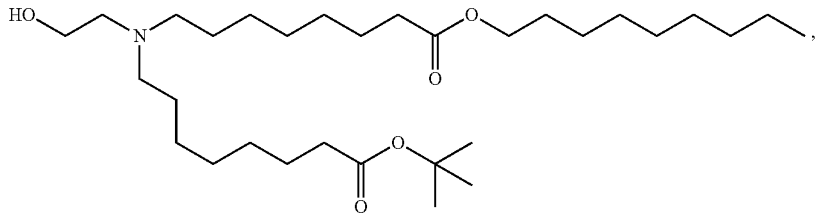
,
(Compound 159)
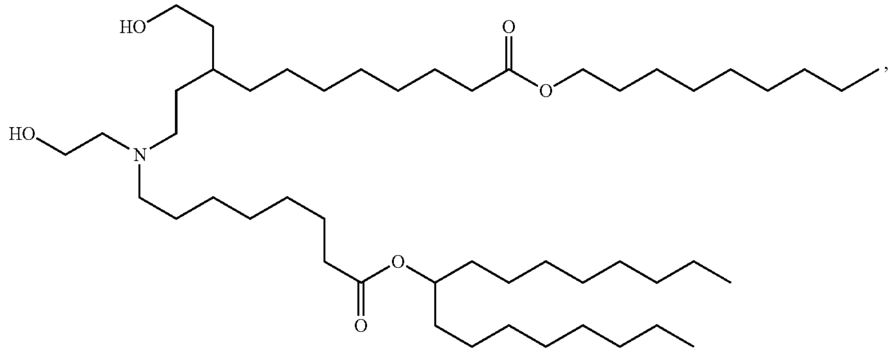
, -continued
(Compound 160)
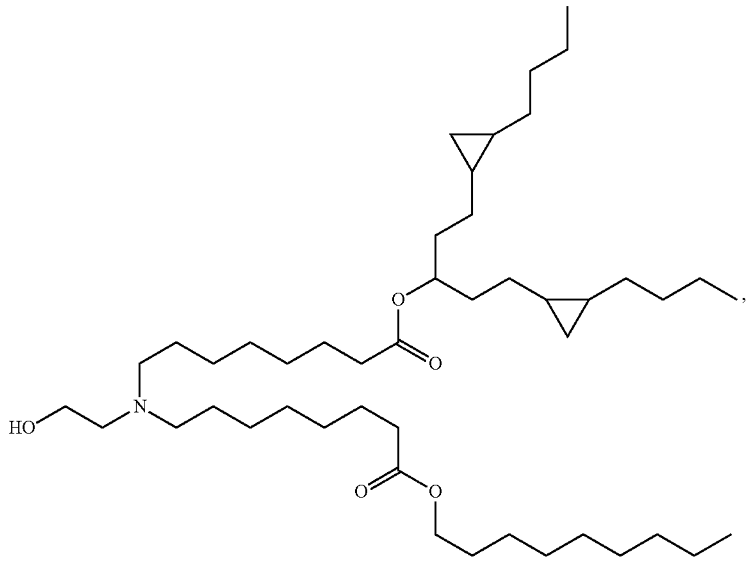
(Compound 161)
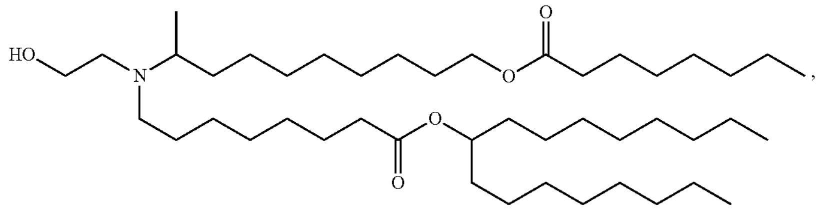
(Compound 162)
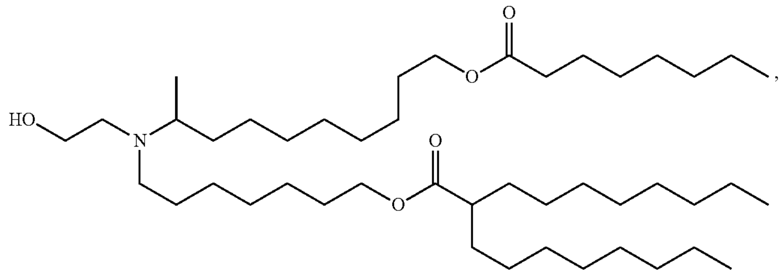
(Compound 163)
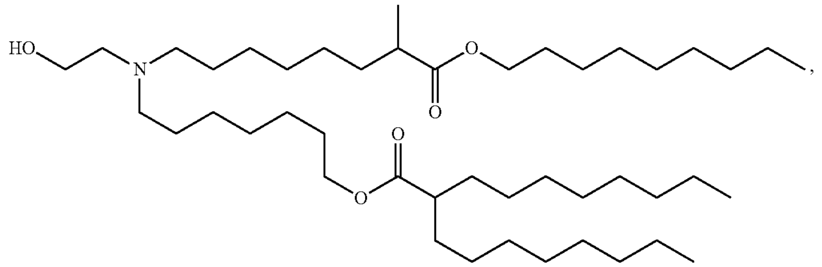
(Compound 164)
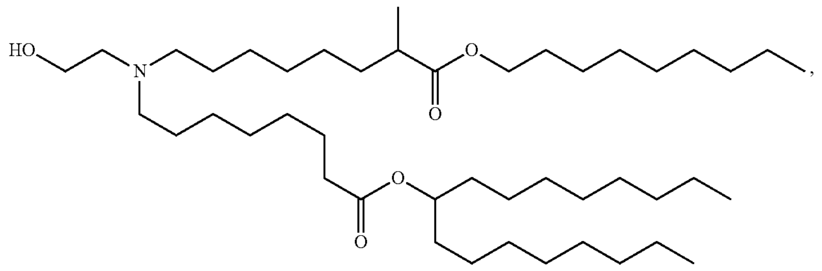

-continued
(Compound 165)
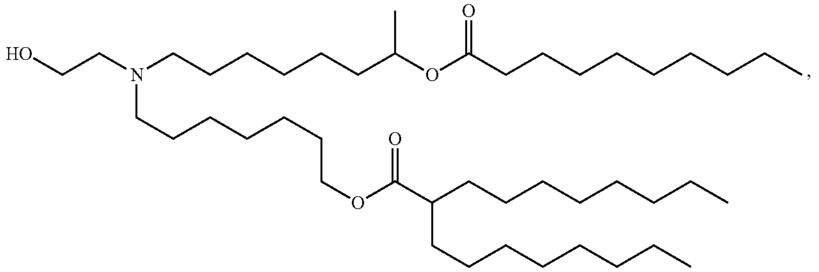
(Compound 166)
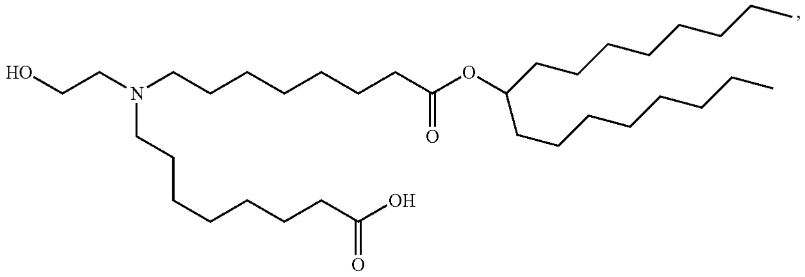
(Compound 167)
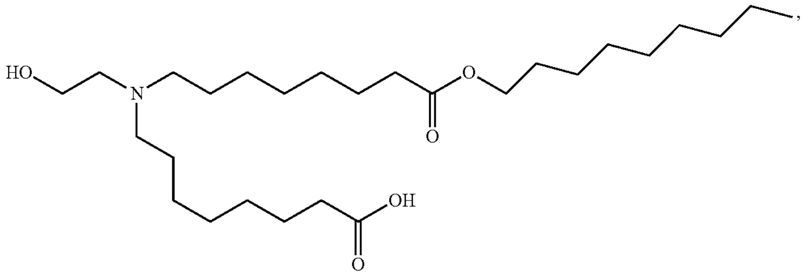
(Compound 168)
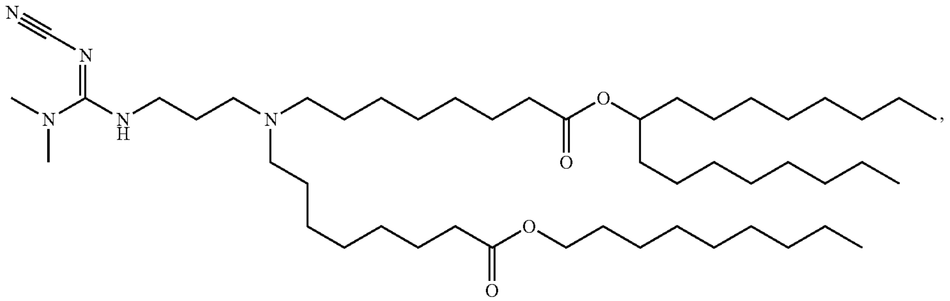
(Compound 169)
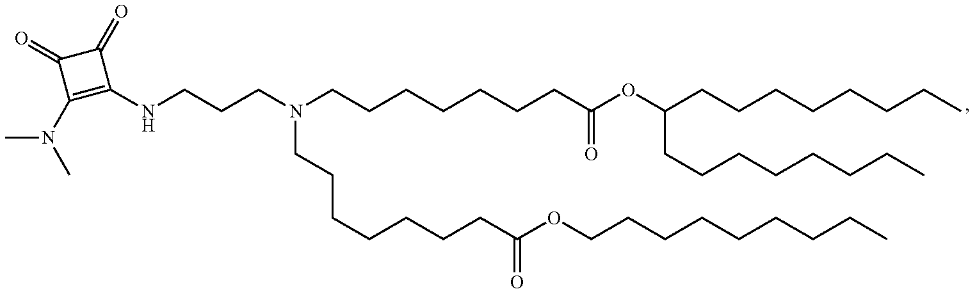

-continued
(Compound 170)
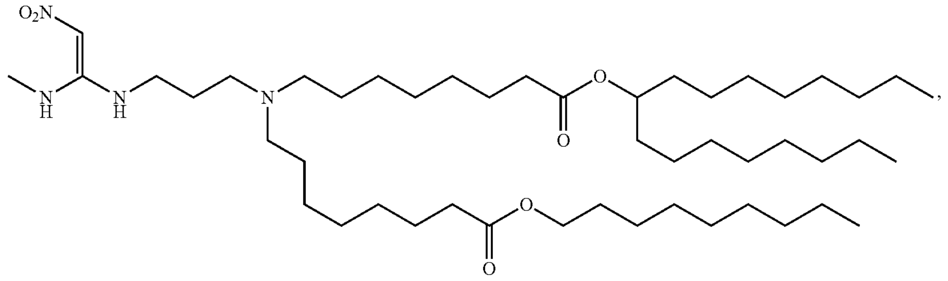
(Compound 171)
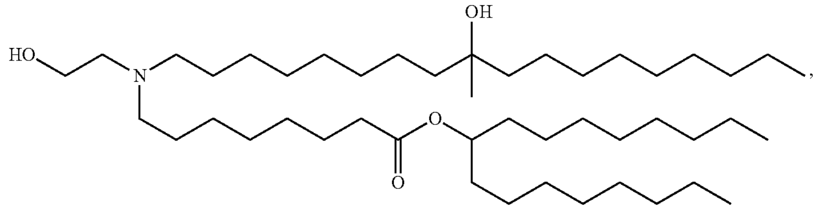
(Compound 172)
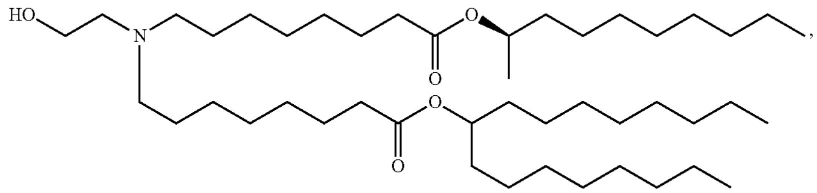
(Compound 173)
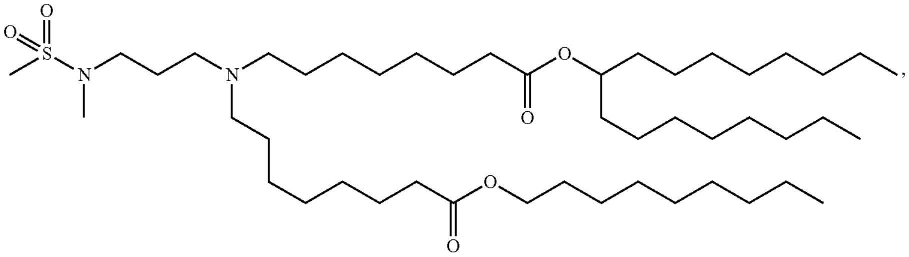
(Compound 174)
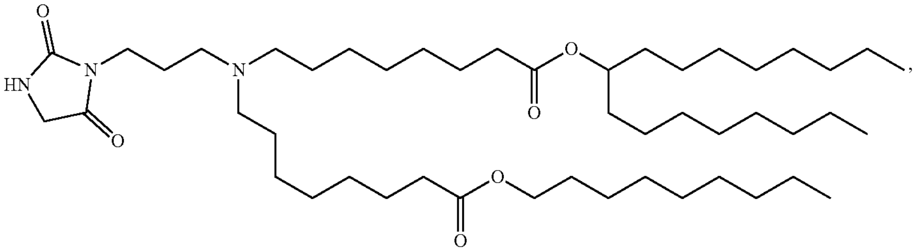
(Compound 175)
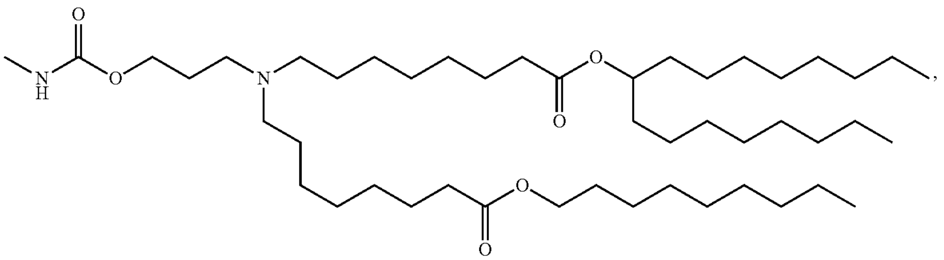

-continued
(Compound 176)
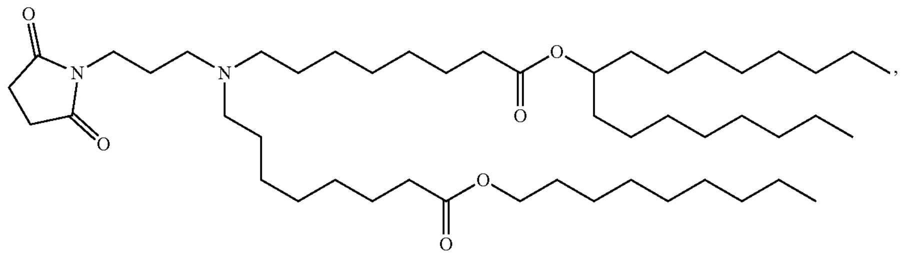
,
(Compound 177)
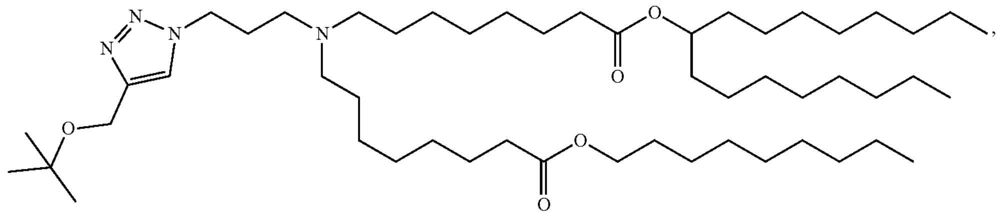
,
(Compound 178)
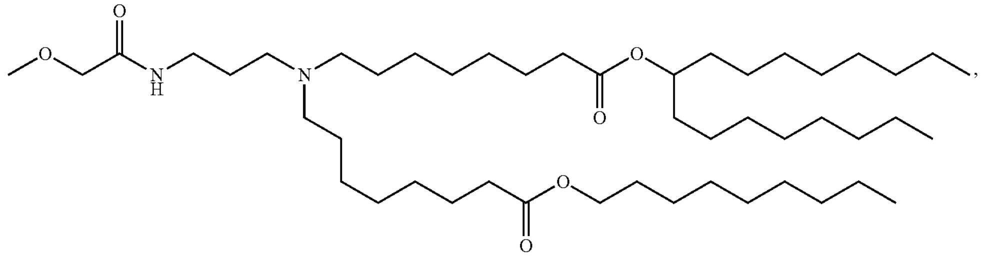
,
(Compound 179)
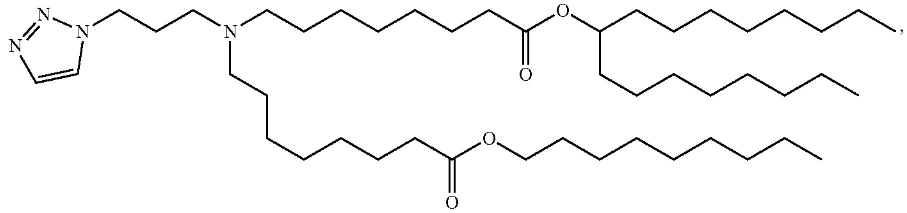
,
(Compound 180)
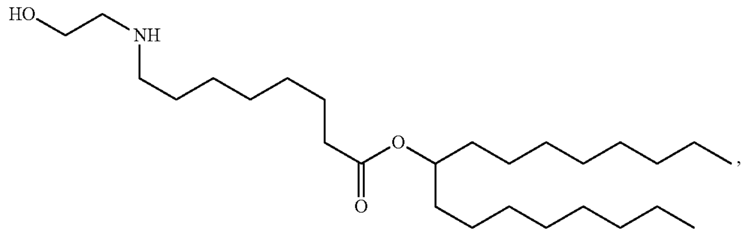
,
(Compound 181)
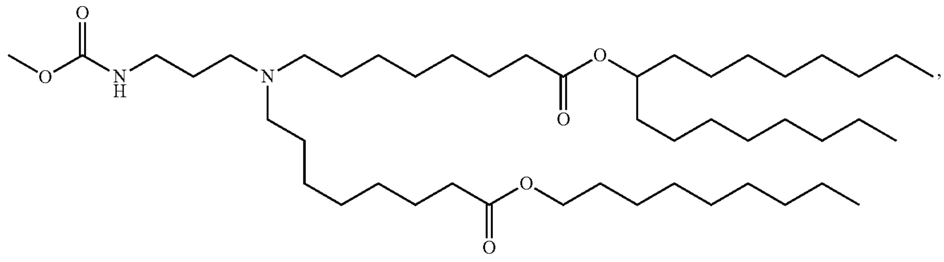
, -continued
(Compound 182)
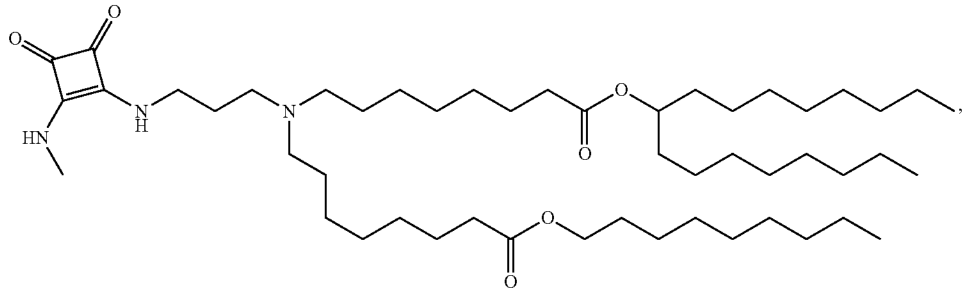
(Compound 183)
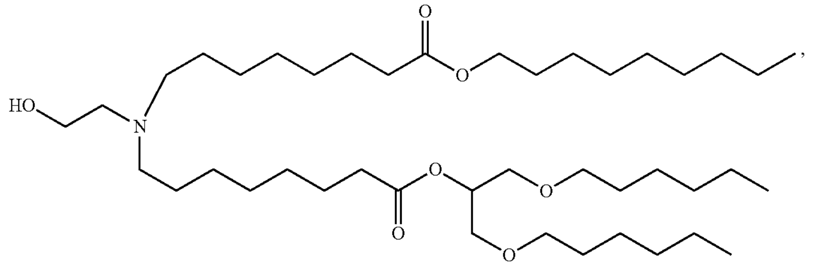
(Compound 184)
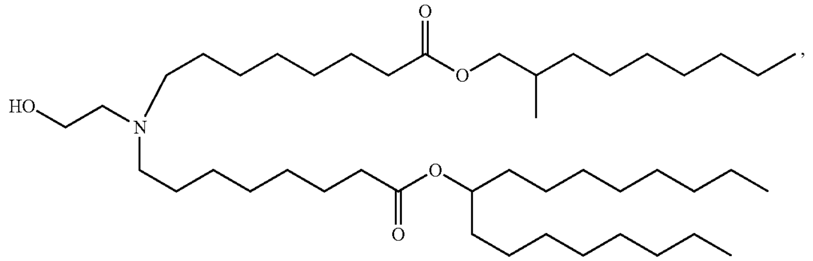
(Compound 185)
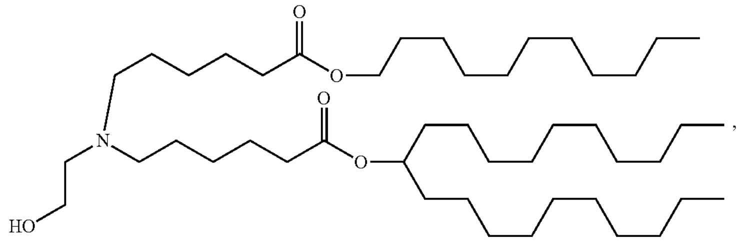
(Compound 186)
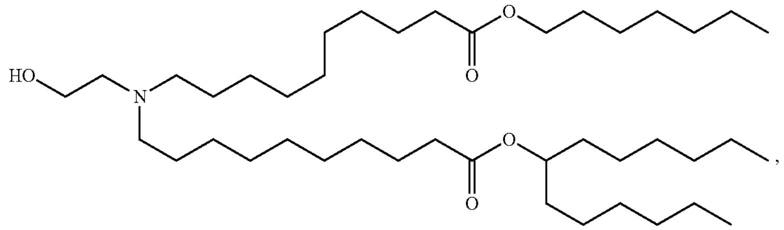
(Compound 187)
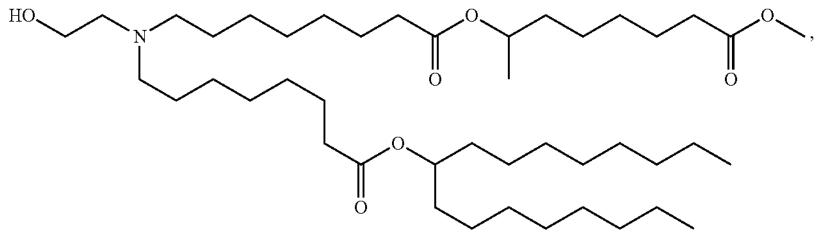

-continued
(Compound 188)
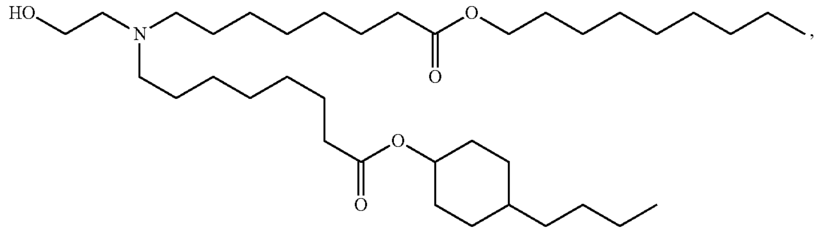
(Compound 189)
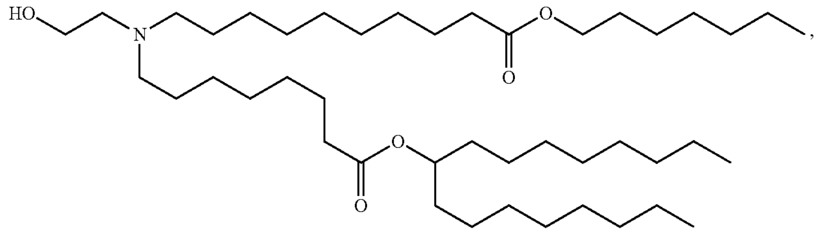
(Compound 190)
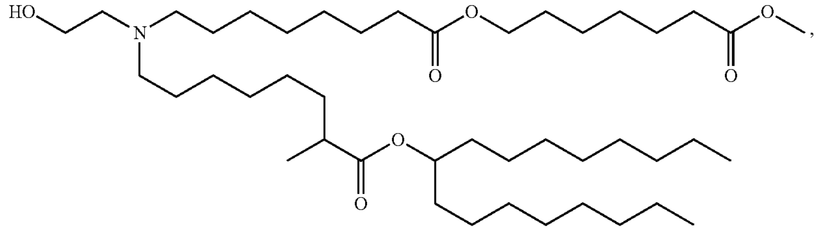
(Compound 191)
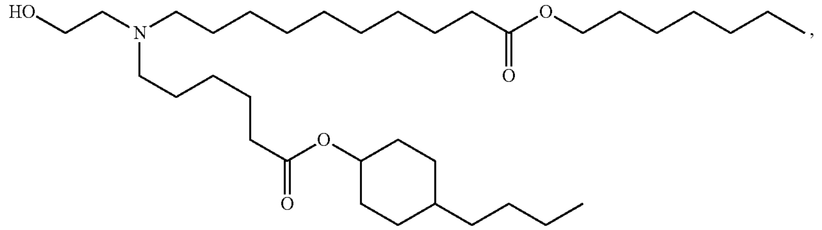
(Compound 192)
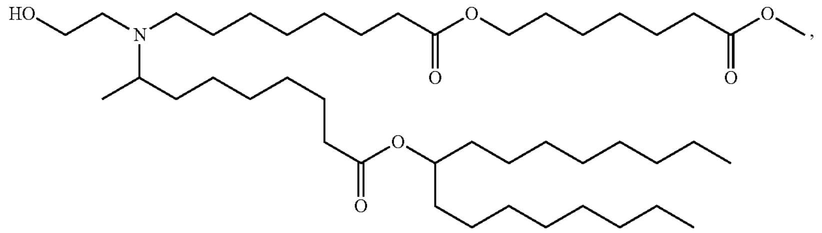
(Compound 193)
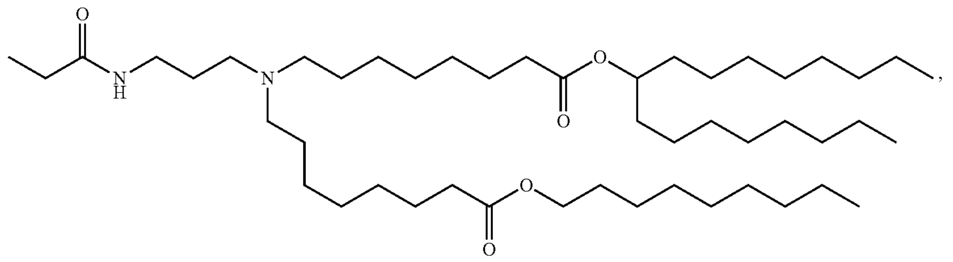

-continued
(Compound 194)
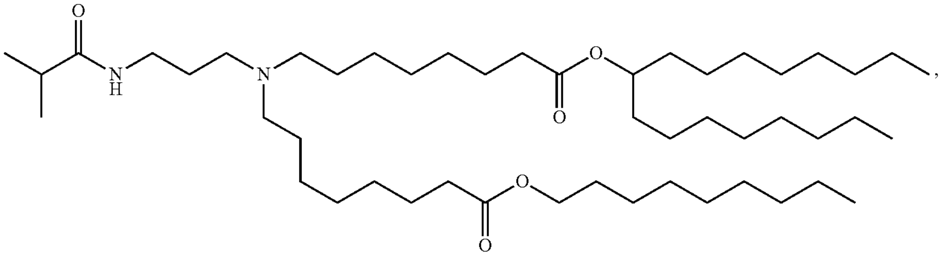
(Compound 195)
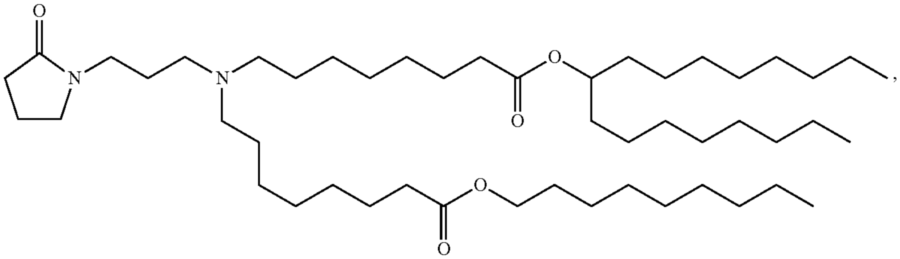
(Compound 196)
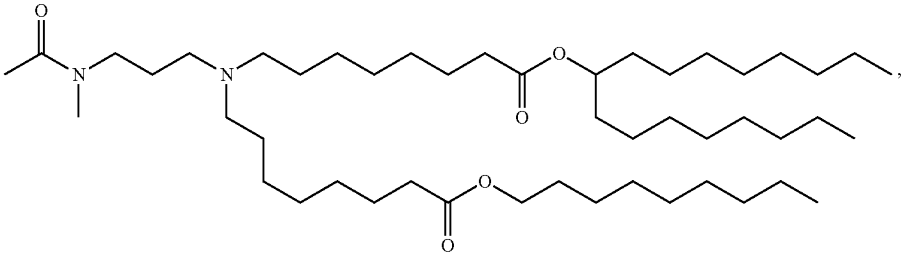
(Compound 197)
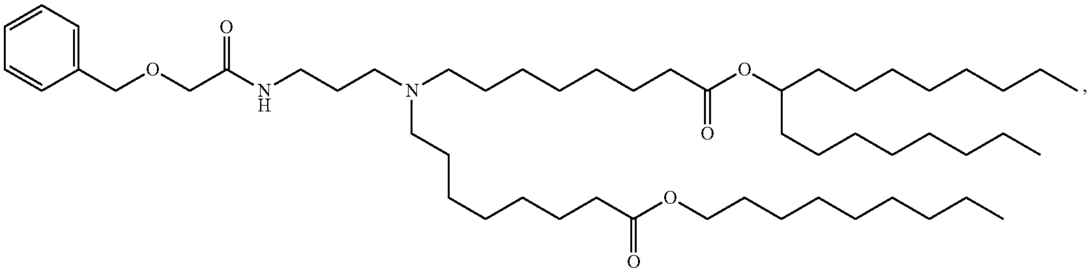
(Compound 198)
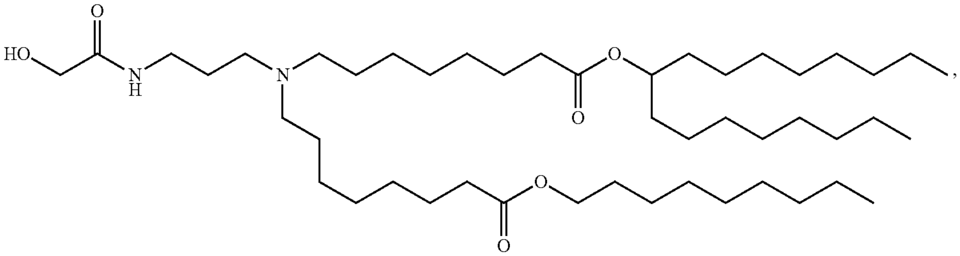
(Compound 199)
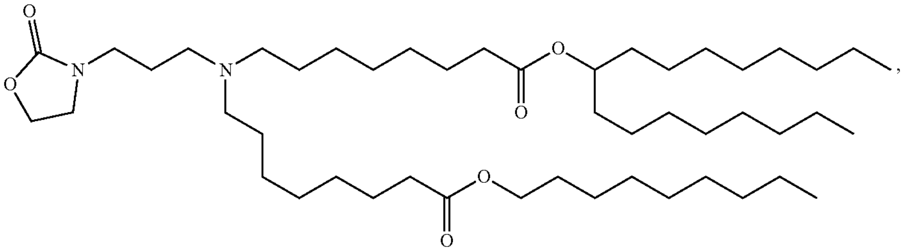

-continued
(Compound 200)
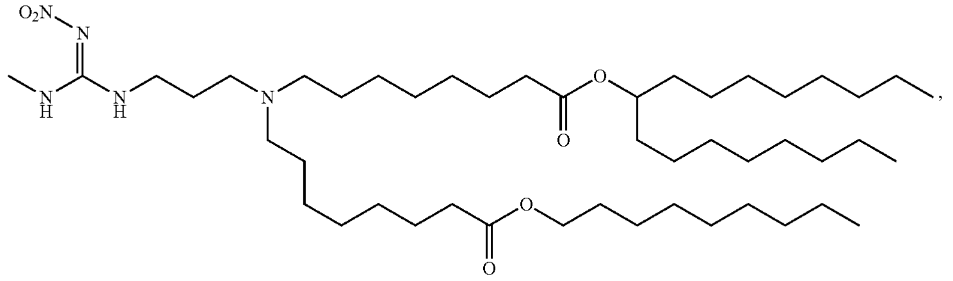
(Compound 201)
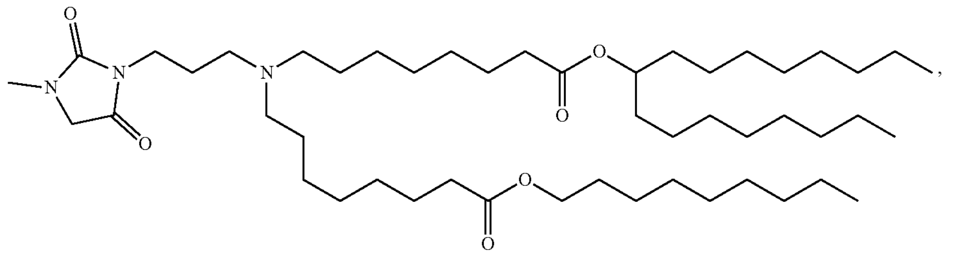
(Compound 202)
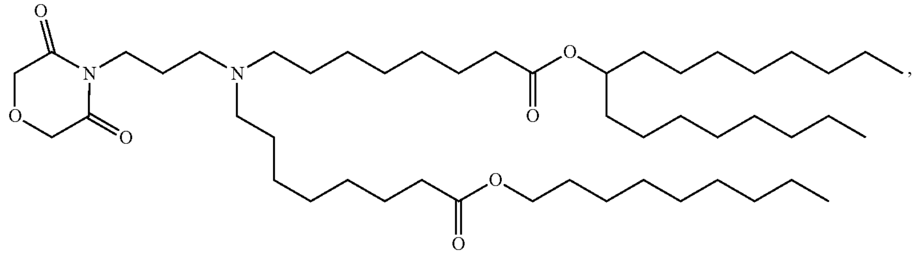
(Compound 203)
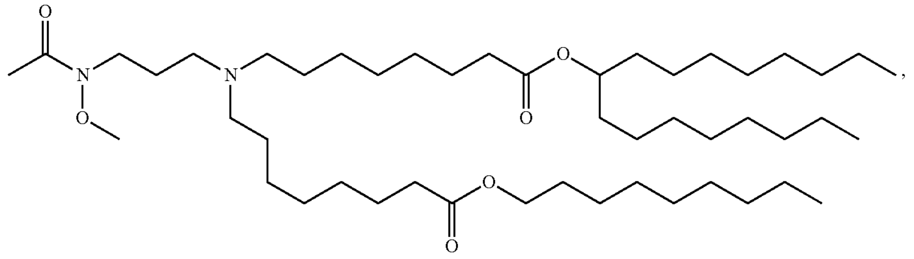
(Compound 204)
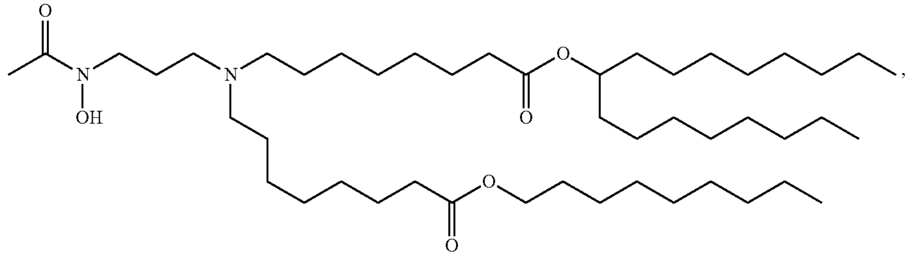
(Compound 205)
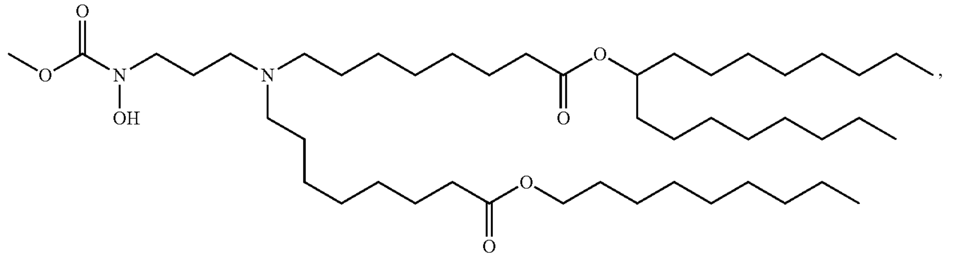

-continued
(Compound 206)
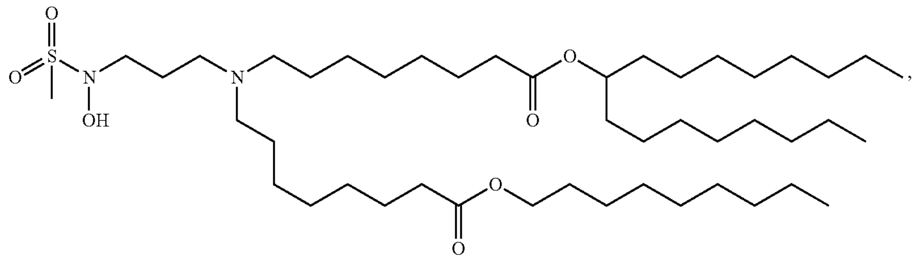
(Compound 207)
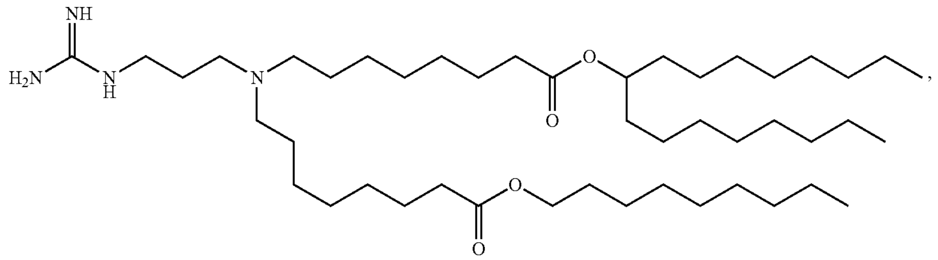
(Compound 208)
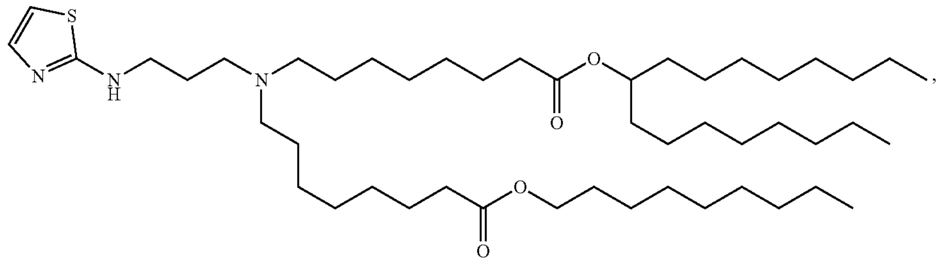
(Compound 209)
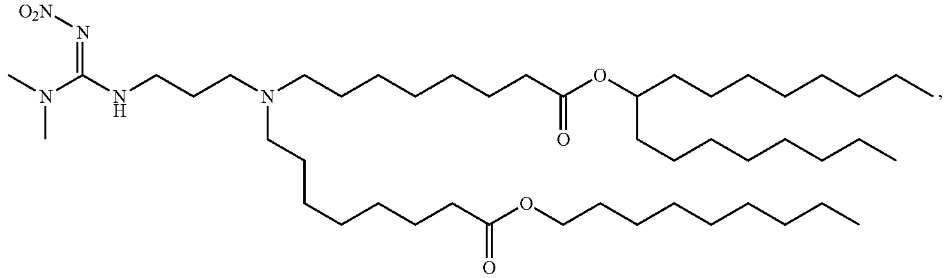
(Compound 210)
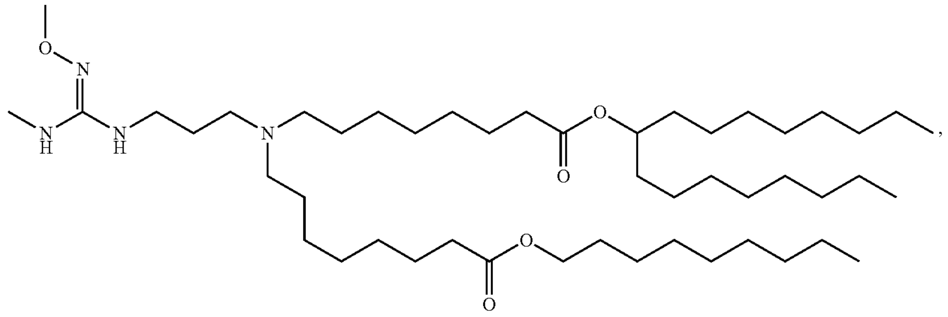

-continued
(Compound 211)
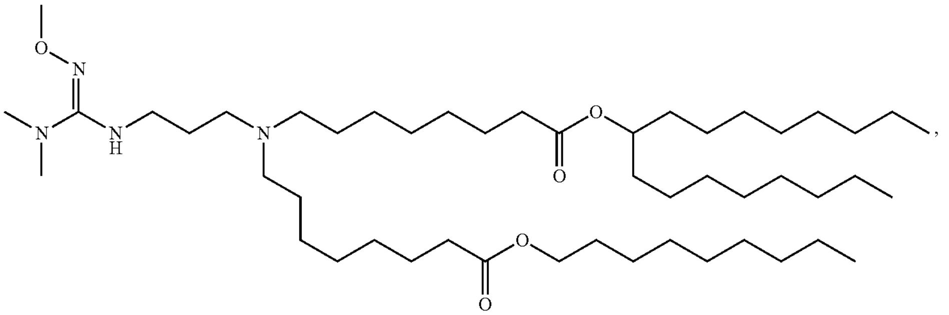
(Compound 212)
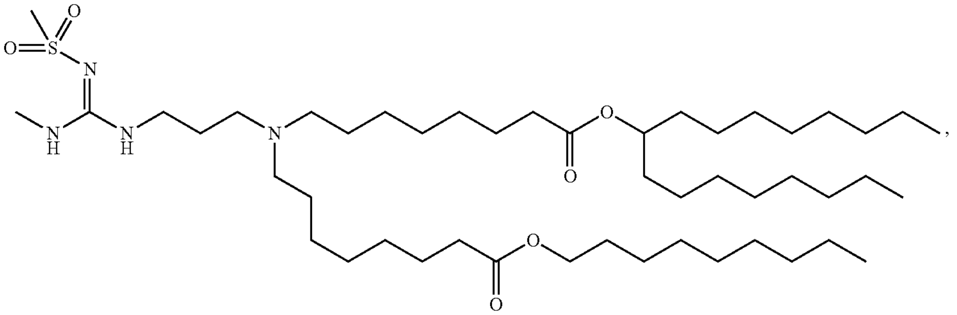
(Compound 213)
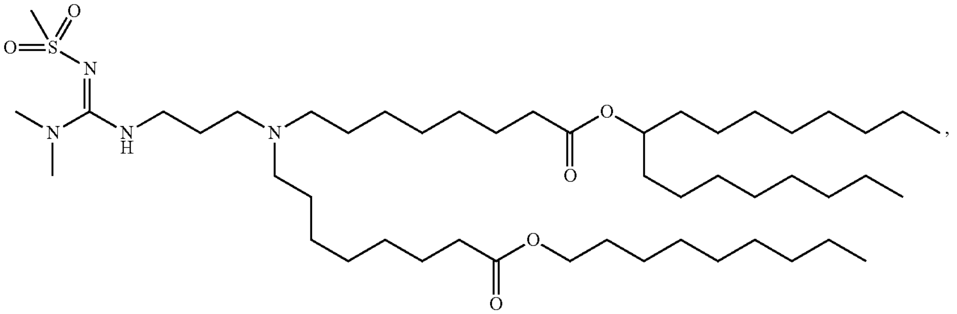
(Compound 214)
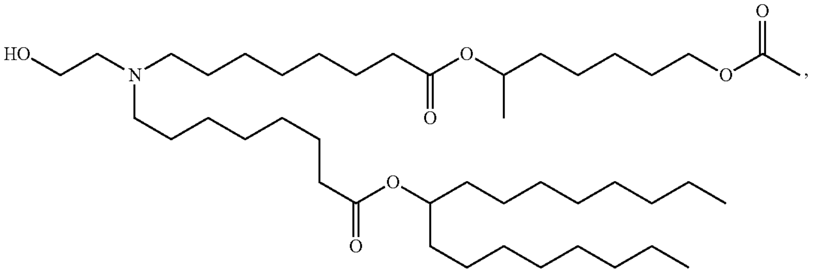
(Compound 215)
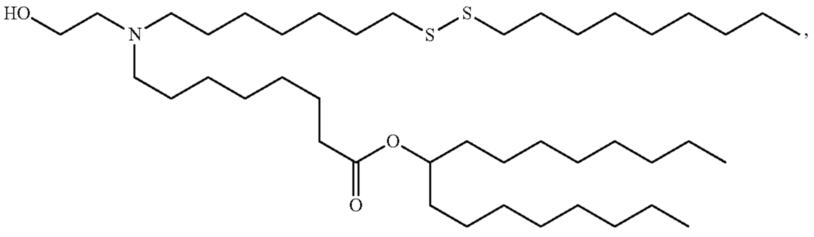

-continued
(Compound 216)
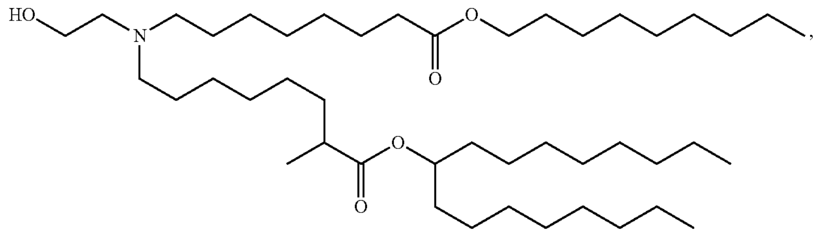
(Compound 217)
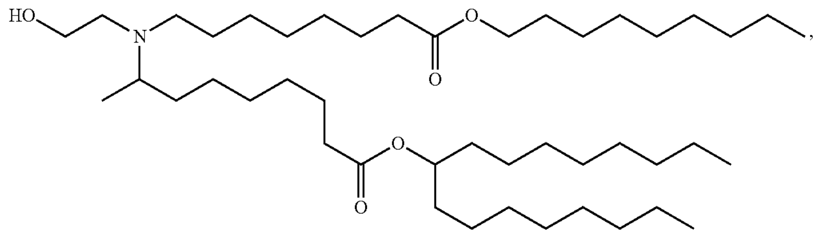
(Compound 218)
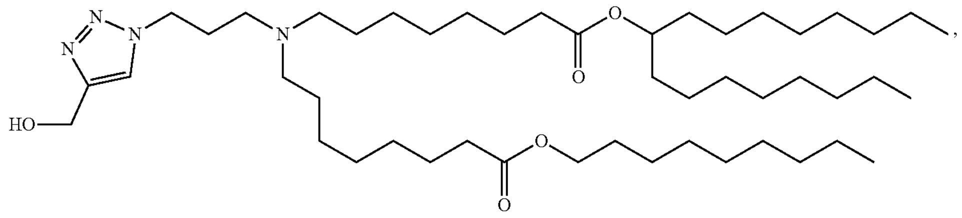
(Compound 219)
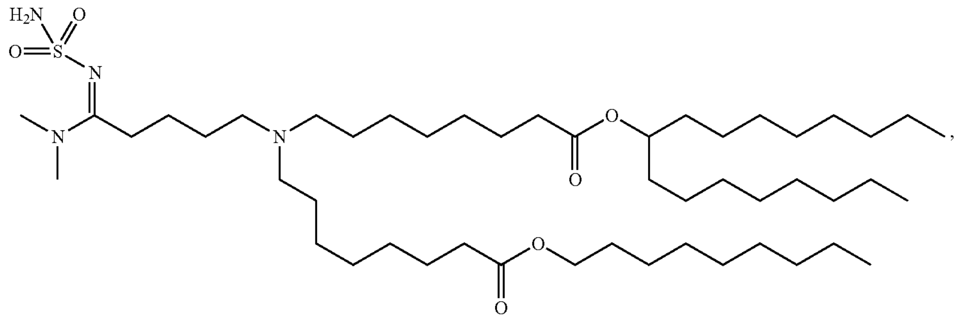
(Compound 220)
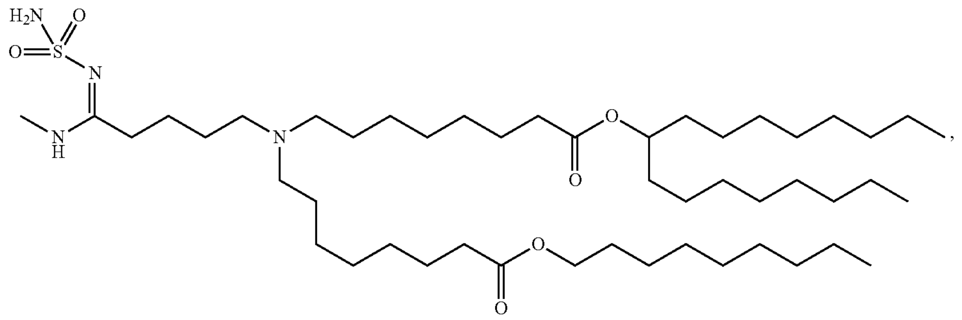

-continued
(Compound 221)
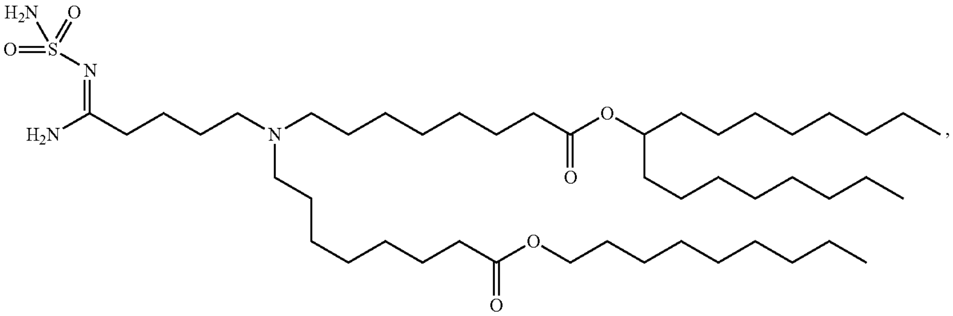
(Compound 222)
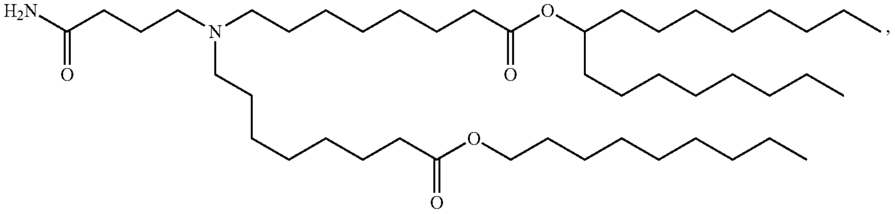
(Compound 223)
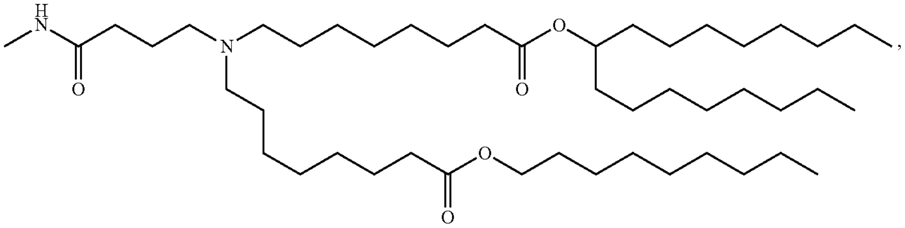
(Compound 224)
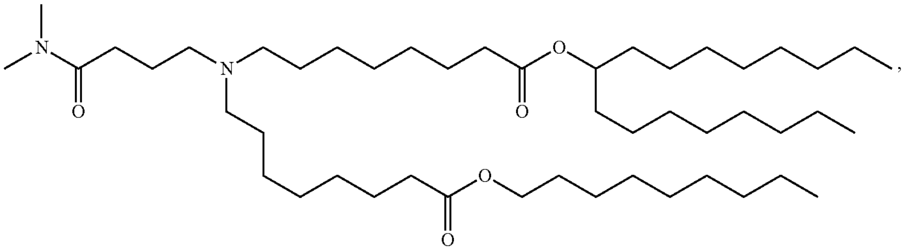
(Compound 225)
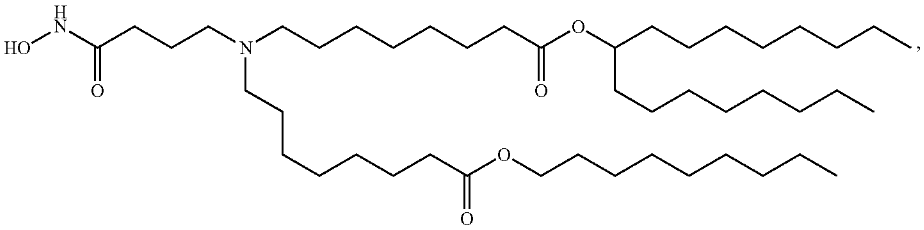
(Compound 226)
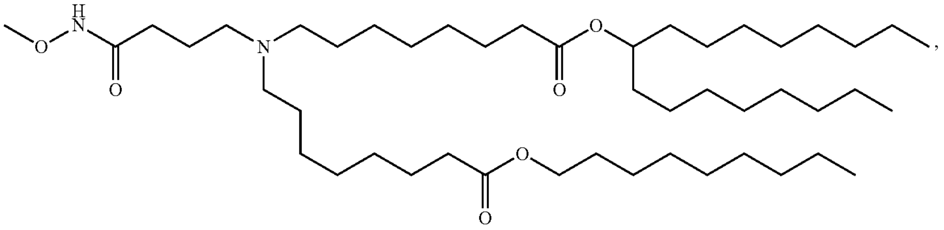

-continued (Compound 227)

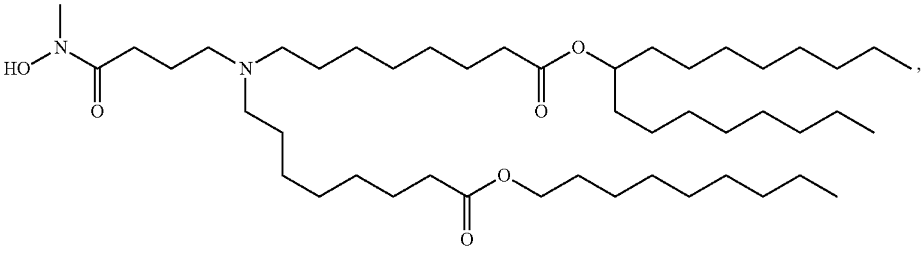

(Compound 228)

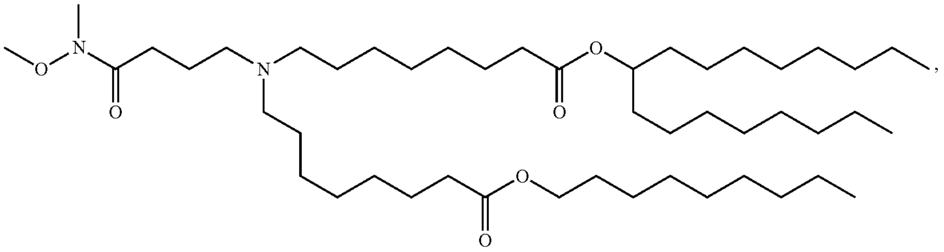

(Compound 229)

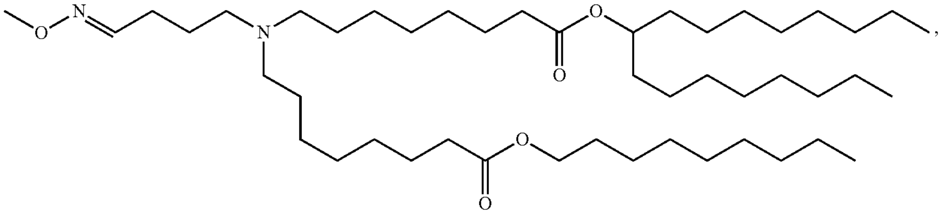

(Compound 230)

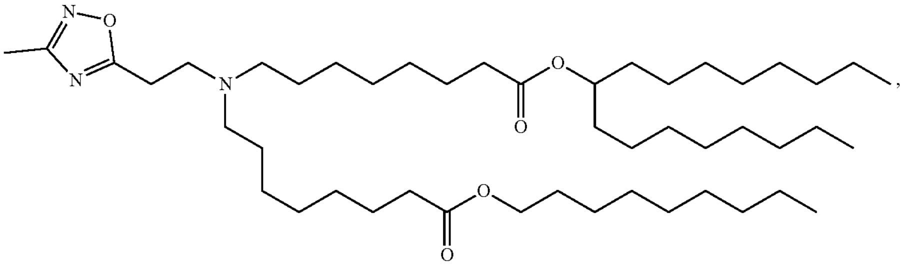

(Compound 231)

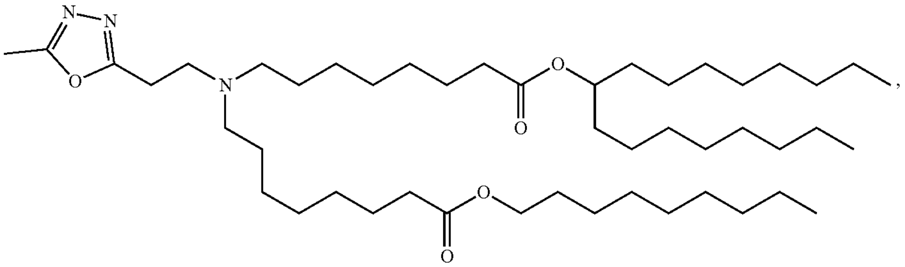

(Compound 232)

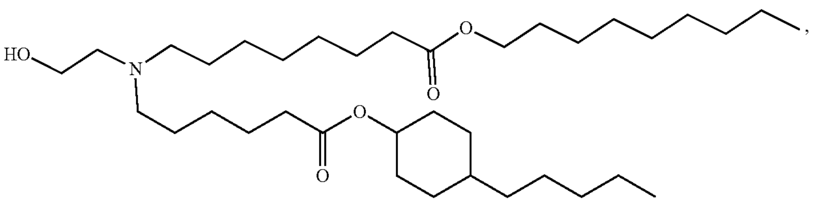

and salts or stereoisomers thereof.

In other embodiments, the compound of Formula (I) is selected from the group consisting of Compound 1-Compound 147, or salt or stereoisomers thereof.

In some embodiments ionizable lipids including a central piperazine moiety are provided.

In some embodiments, the delivery agent comprises a lipid compound having the Formula (III)

(III)

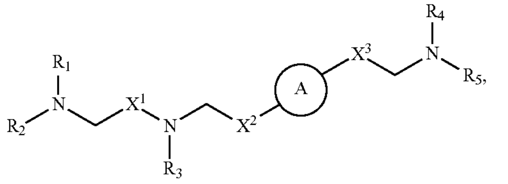

or salts or stereoisomers thereof, wherein ring A is

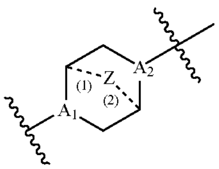

or

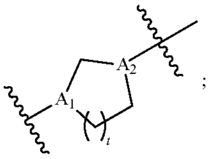

;

t is 1 or 2;

$A_1$ and $A_2$ are each independently selected from CH or N;

Z is $CH_2$ or absent wherein when Z is $CH_2$, the dashed lines (1) and (2) each represent a single bond; and when Z is absent, the dashed lines (1) and (2) are both absent;

$R_1$, $R_2$, $R_3$, $R_4$, and $R_5$ are independently selected from the group consisting of $C_{5-20}$ alkyl, $C_{5-20}$ alkenyl, —R"MR', —R*YR", —YR", and —R*OR";

each M is independently selected from the group consisting of —C(O)O—, —OC(O)—, —OC(O)O—, —C(O)N(R')—, —N(R')C(O)—, —C(O)—, —C(S)—, —C(S)S—, —SC(S)—, —CH(OH)—, —P(O)(OR')O—, —$S(O)_2$—, an aryl group, and a heteroaryl group;

$X^1$, $X^2$, and $X^3$ are independently selected from the group consisting of a bond, —$CH_2$—, —$(CH_2)_2$—, —CHR—, —CHY—, —C(O)—, —C(O)O—, —OC(O)—, —C(O)—$CH_2$—, —$CH_2$—C(O)—, —C(O)O—$CH_2$—, —OC(O)—$CH_2$—, —$CH_2$—C(O)O—, —$CH_2$—OC(O)—, —CH(OH)—, —C(S)—, and —CH(SH)—;

each Y is independently a $C_{3-6}$ carbocycle;

each R* is independently selected from the group consisting of $C_{1-12}$ alkyl and $C_{2-12}$ alkenyl;

each R is independently selected from the group consisting of $C_{1-3}$ alkyl and a $C_{3-6}$ carbocycle;

each R' is independently selected from the group consisting of $C_{1-12}$ alkyl, $C_{2-12}$ alkenyl, and H; and each R" is independently selected from the group consisting of $C_{3-12}$ alkyl and $C_{3-12}$ alkenyl, wherein when ring A is then

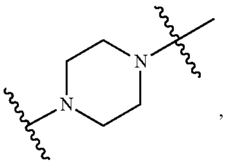 [SMILES: *N1CCN(*)CC1]

, i) at least one of $X^1$, $X^2$, and $X^3$ is not —$CH_2$—; and/or ii) at least one of $R_1$, $R_2$, $R_3$, $R_4$, and $R_5$ is —R"MR'.

In some embodiments, the compound is of any of Formulae (IIIa1)-(IIIa6):

(IIIa1)

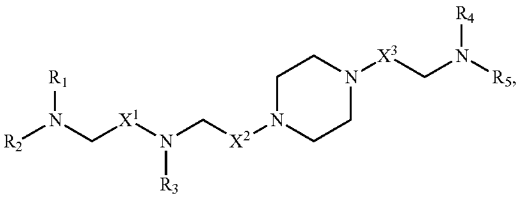

(IIIa2)

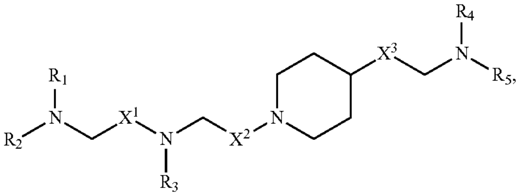

(IIIa3)

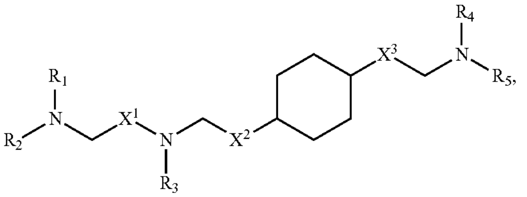

(IIIa4)

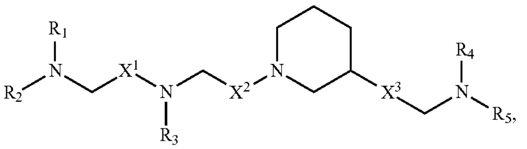

(IIIa5)

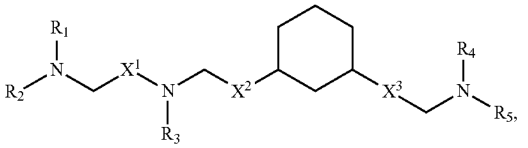

or (IIIa6)

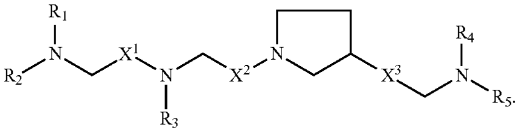

The compounds of Formula (III) or any of (IIIa1)-(IIIa6) include one or more of the following features when applicable.

In some embodiments, ring A is

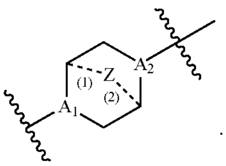

.

In some embodiments, ring A is

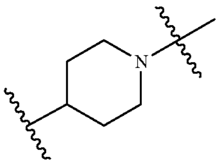

or

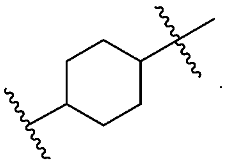

In some embodiments, ring A is

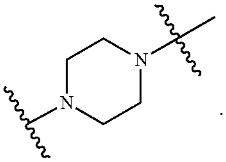 [SMILES: *N1CCN(*)CC1]

In some embodiments, ring A is

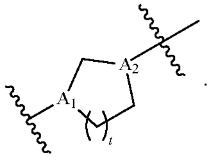

In some embodiments, ring A is

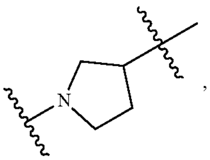

,

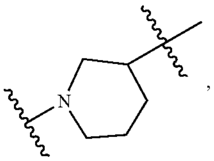

, or

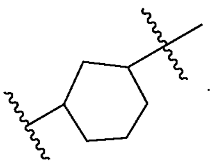

In some embodiments, ring A is

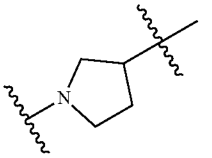

or

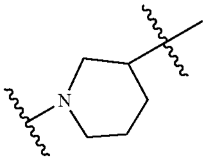

wherein ring, in which the N atom is connected with $X^2$.

In some embodiments, Z is $CH_2$.

In some embodiments, Z is absent.

In some embodiments, at least one of $A_1$ and $A_2$ is N.

In some embodiments, each of $A_1$ and $A_2$ is N.

In some embodiments, each of $A_1$ and $A_2$ is CH.

In some embodiments, $A_1$ is N and $A_2$ is CH.

In some embodiments, $A_1$ is CH and $A_2$ is N.

In some embodiments, at least one of $X^1$, $X^2$, and $X^3$ is not —$CH_2$—. For example, in certain embodiments, $X^1$ is not —$CH_2$—. In some embodiments, at least one of $X^1$, $X^2$, and $X^3$ is —C(O)—.

In some embodiments, $X^2$ is —C(O)—, —C(O)O—, —OC(O)—, —C(O)—$CH_2$—, —$CH_2$—C(O)—, —C(O)O—$CH_2$—, —OC(O)—$CH_2$—, —$CH_2$—C(O)O—, or —$CH_2$—OC(O)—.

In some embodiments, $X^3$ is —C(O)—, —C(O)O—, —OC(O)—, —C(O)—$CH_2$—, —$CH_2$—C(O)—, —C(O)O—$CH_2$—, —OC(O)—$CH_2$—, —$CH_2$—C(O)O—, or —$CH_2$—OC(O)—. In other embodiments, $X^3$ is —$CH_2$—.

In some embodiments, $X^3$ is a bond or —$(CH_2)_2$—.

In some embodiments, $R_1$ and $R_2$ are the same. In certain embodiments, $R_1$, $R_2$, and $R_3$ are the same. In some embodiments, $R_4$ and $R_5$ are the same. In certain embodiments, $R_1$, $R_2$, $R_3$, $R_4$, and $R_5$ are the same.

In some embodiments, at least one of $R_1$, $R_2$, $R_3$, $R_4$, and $R_5$ is —R"MR'. In some embodiments, at most one of $R_1$, $R_2$, $R_3$, $R_4$, and $R_5$ is —R"MR'. For example, at least one of $R_1$, $R_2$, and $R_3$ may be —R"MR', and/or at least one of $R_4$ and $R_5$ is —R"MR'. In certain embodiments, at least one M is —C(O)O—. In some embodiments, each M is —C(O)O—. In some embodiments, at least one M is —OC(O)—. In some embodiments, each M is —OC(O)—. In some embodiments, at least one M is —OC(O)O—. In some embodiments, each M is —OC(O)O—. In some embodiments, at least one R" is $C_3$ alkyl. In certain embodiments, each R" is $C_3$ alkyl. In some embodiments, at least one R" is $C_5$ alkyl. In certain embodiments, each R" is $C_5$ alkyl. In some embodiments, at least one R" is $C_6$ alkyl. In certain embodiments, each R" is $C_6$ alkyl. In some embodiments, at least one R" is $C_7$ alkyl. In certain embodiments, each R" is $C_7$ alkyl. In some embodiments, at least one R' is $C_5$ alkyl. In certain embodiments, each R' is $C_5$ alkyl. In other embodiments, at least one R' is $C_1$ alkyl. In certain embodiments, each R' is $C_1$ alkyl. In some embodiments, at least one R' is $C_2$ alkyl. In certain embodiments, each R' is $C_2$ alkyl.

In some embodiments, at least one of $R_1$, $R_2$, $R_3$, $R_4$, and $R_5$ is $C_{12}$ alkyl. In certain embodiments, each of $R_1$, $R_2$, $R_3$, $R_4$, and $R_5$ are $C_{12}$ alkyl.

In certain embodiments, the compound is selected from the group consisting of:

(Compound 233)
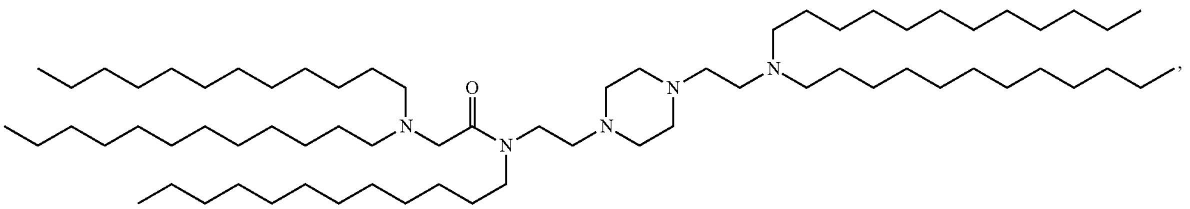
(Compound 234)
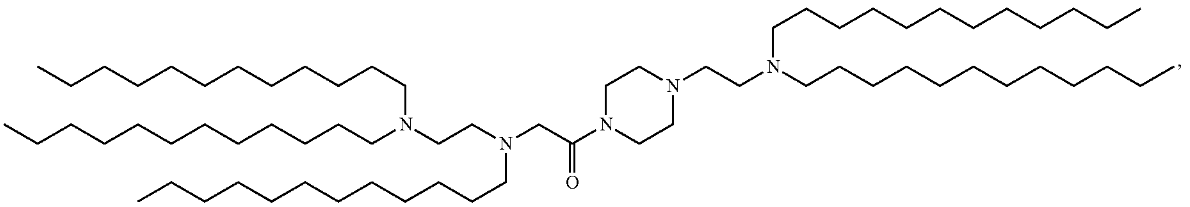
(Compound 235)
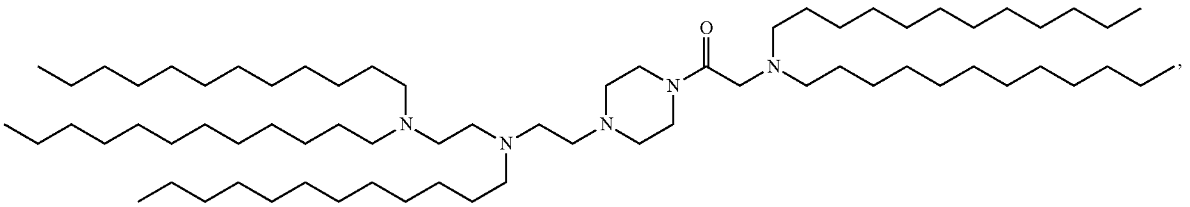
(Compound 236)
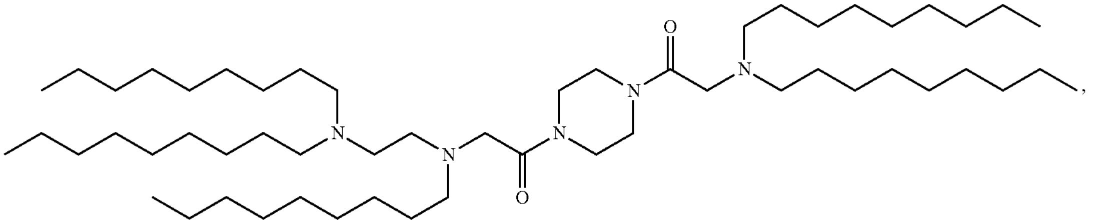
(Compound 237)
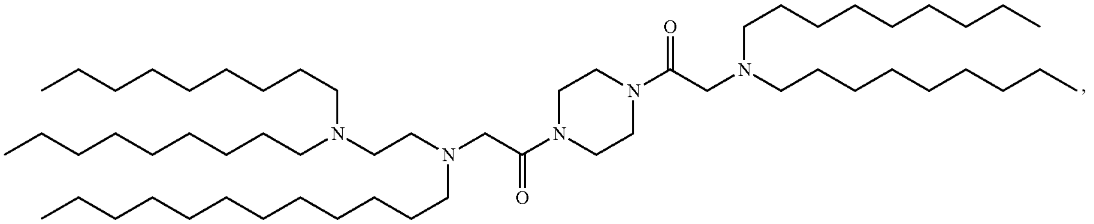
(Compound 238)
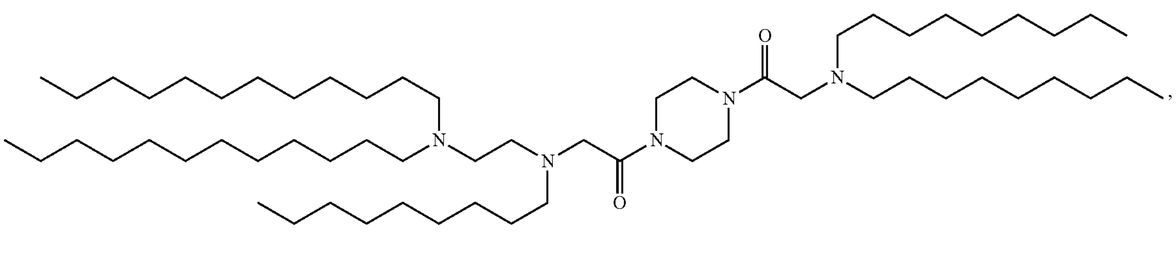

-continued
(Compound 239)
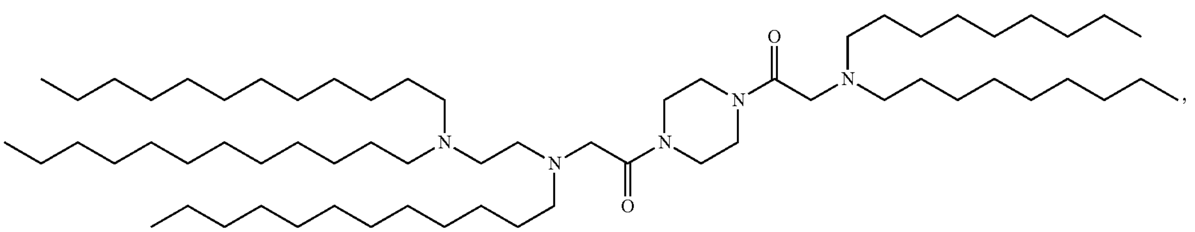
(Compound 240)
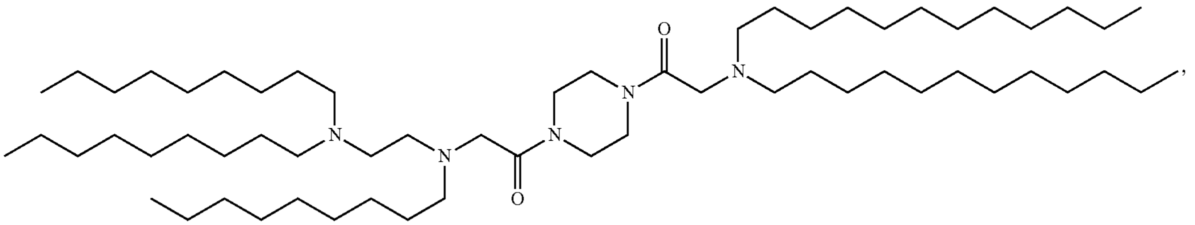
(Compound 241)
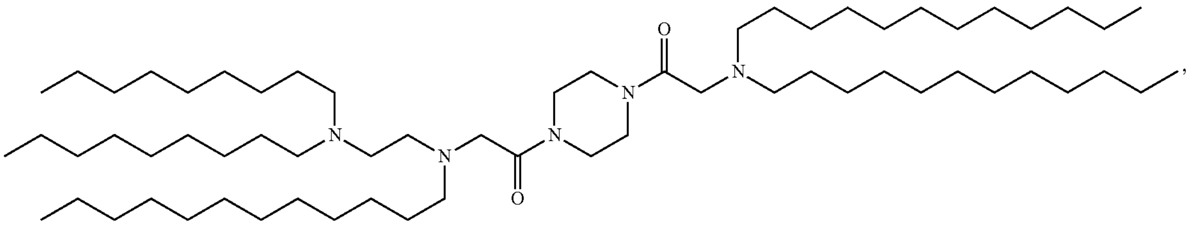
(Compound 242)
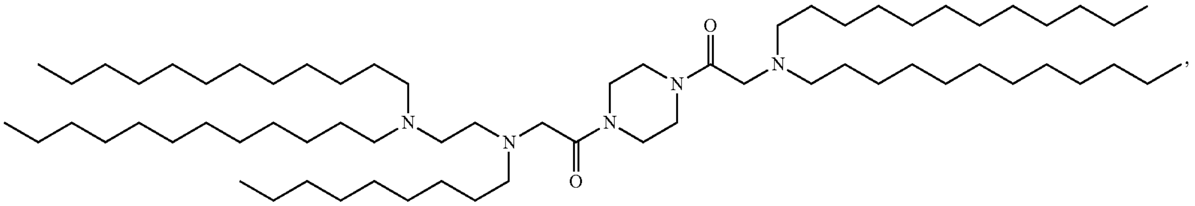
(Compound 243)
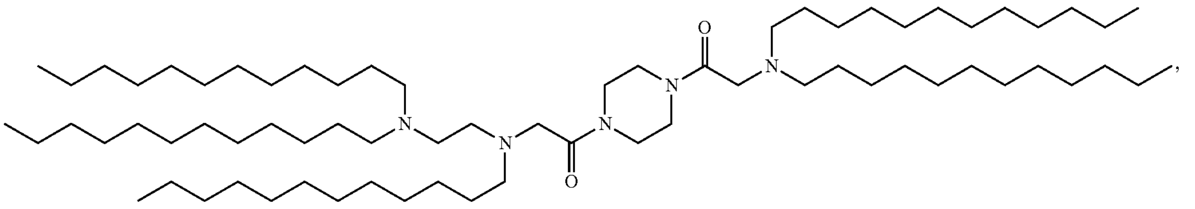
(Compound 244)
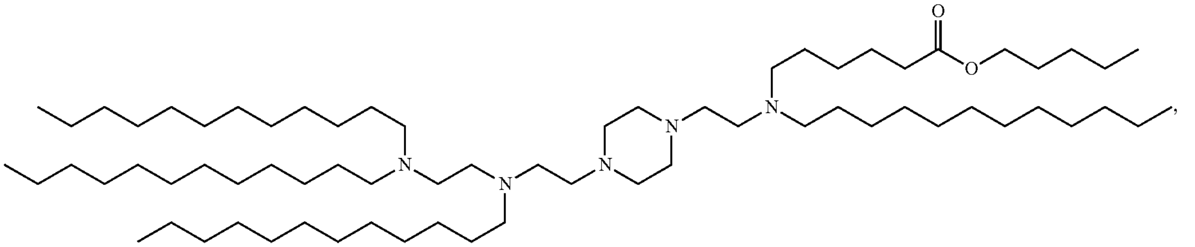

-continued
(Compound 245)
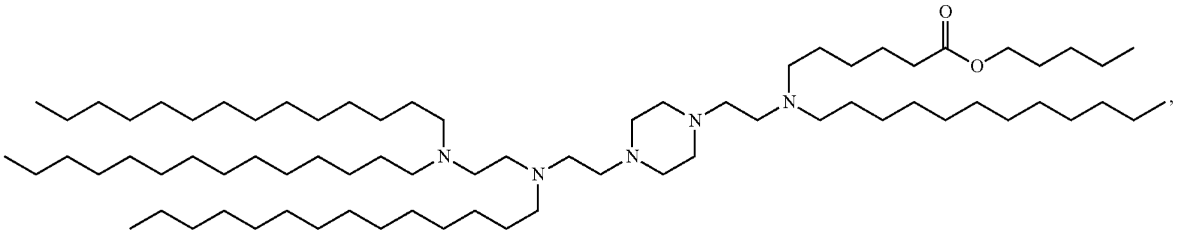
(Compound 246)
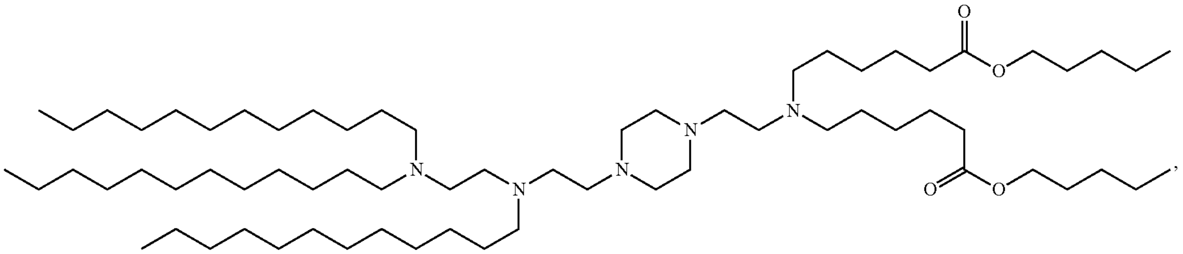
(Compound 247)
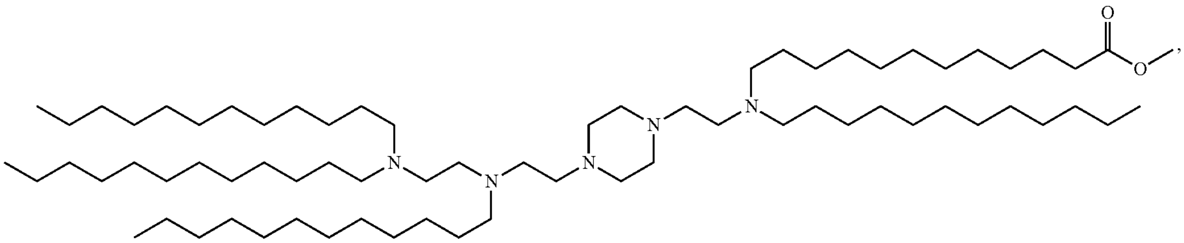
(Compound 248)
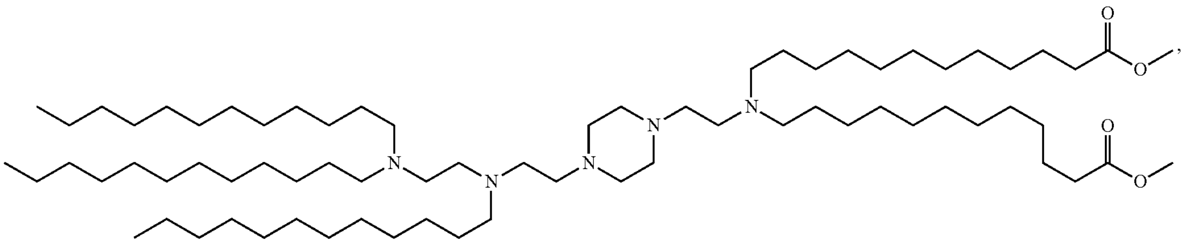
(Compound 274)
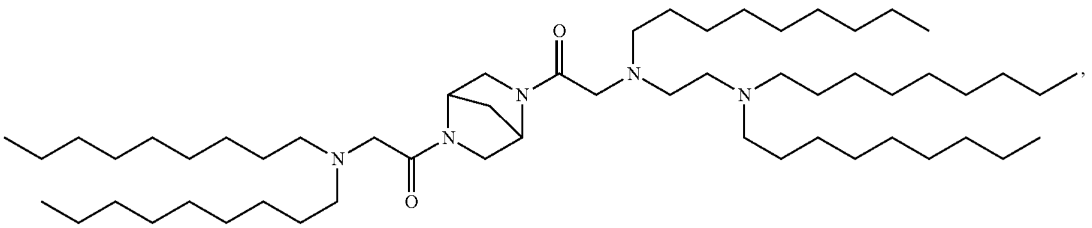
(Compound 275)
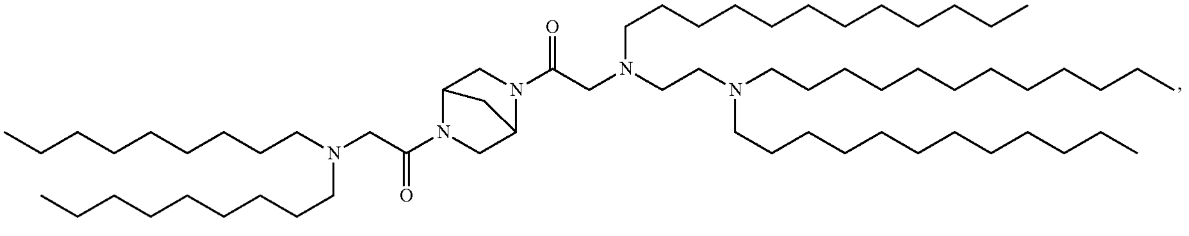

-continued
(Compound 276)
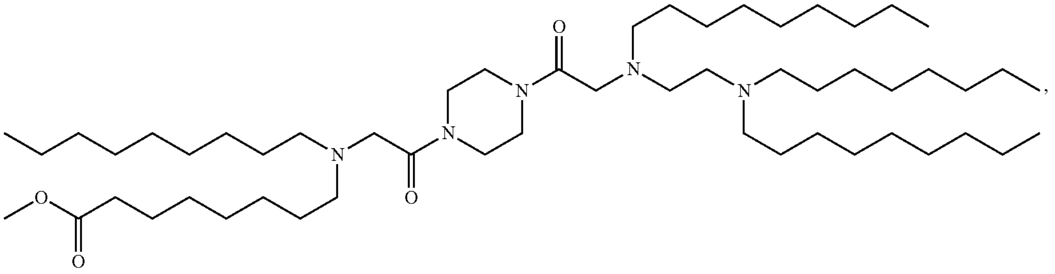
(Compound 277)
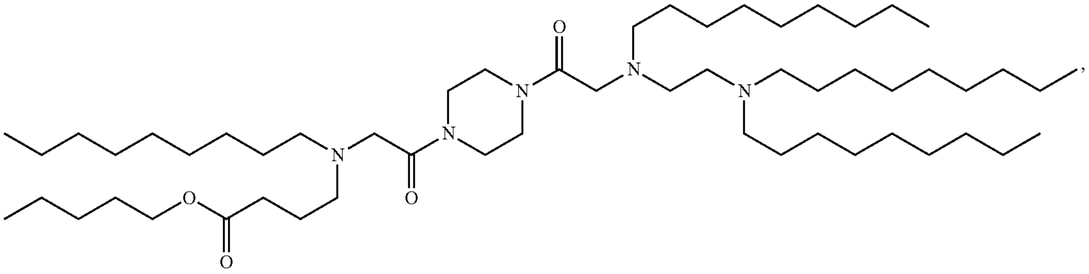
(Compound 278)
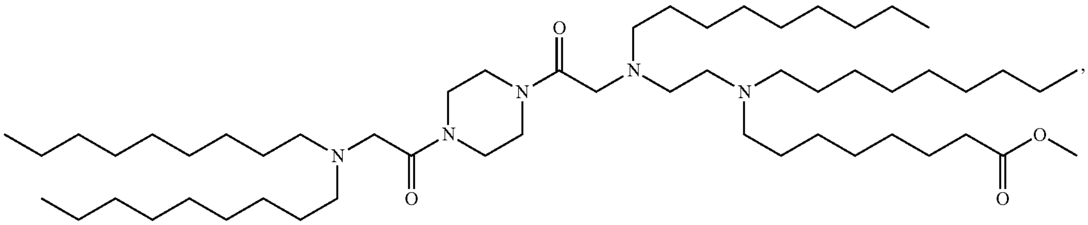
(Compound 279)
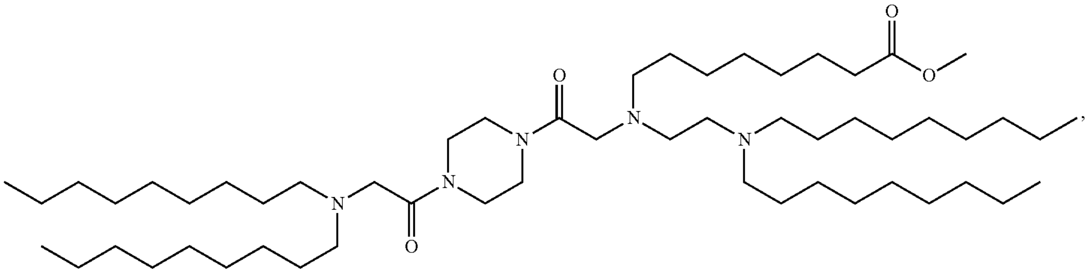
(Compound 280)
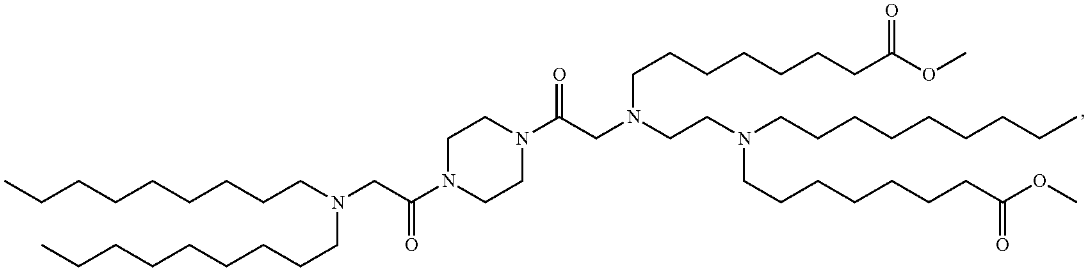

-continued
(Compound 281)
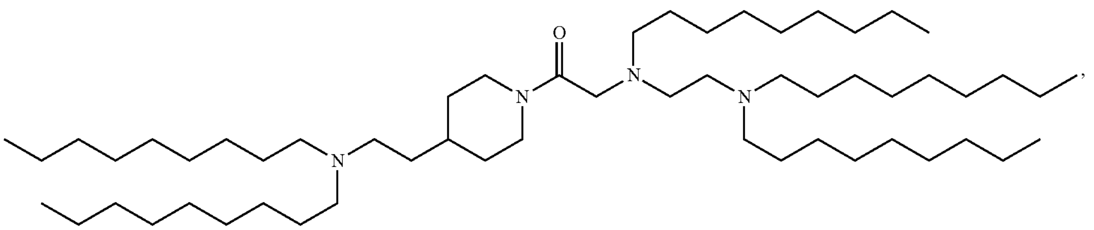
(Compound 282)
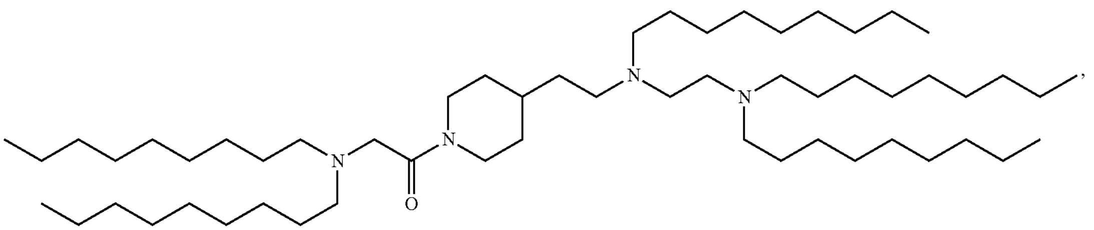
(Compound 283)
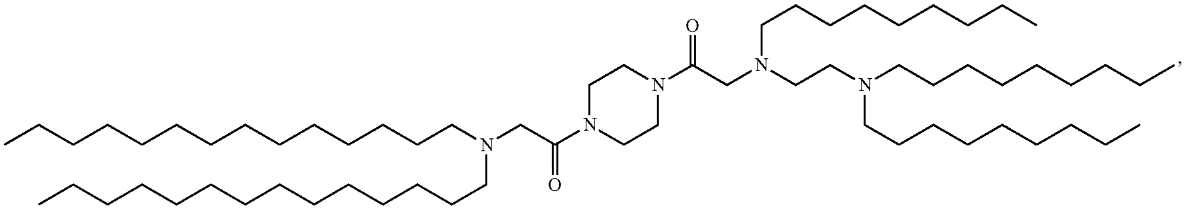
(Compound 284)
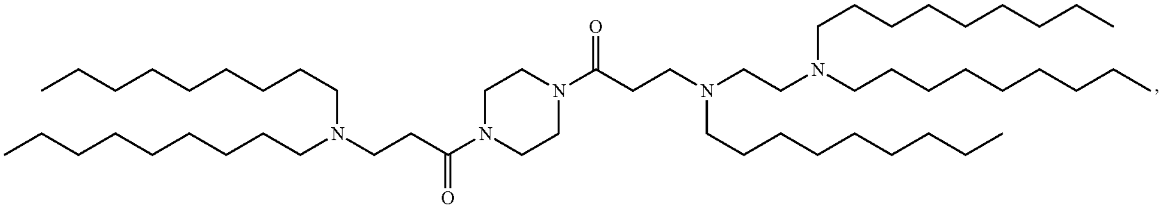
(Compound 285)
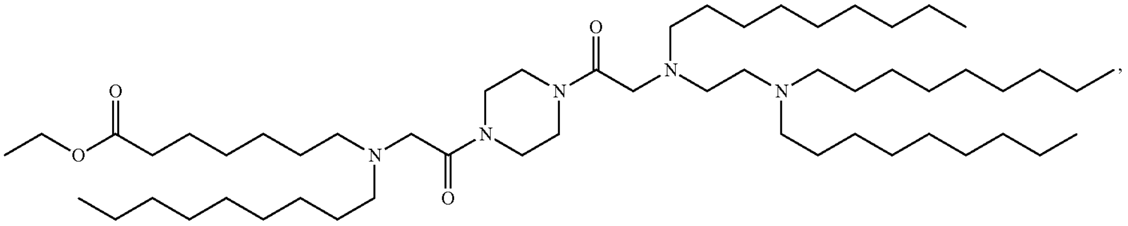
(Compound 286)
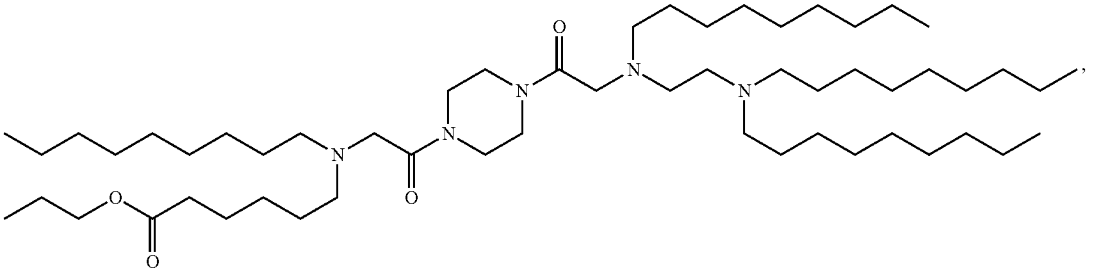

-continued
(Compound 287)
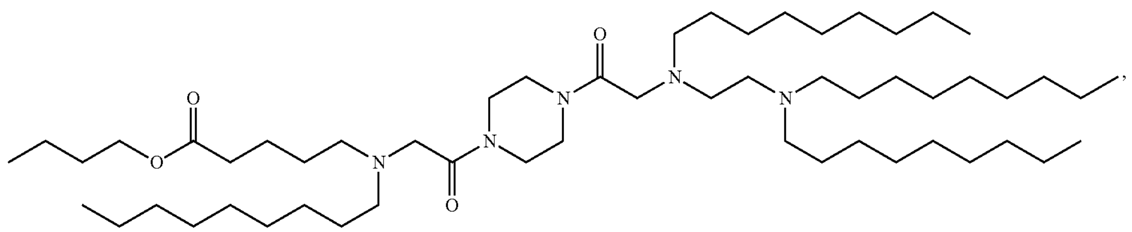
(Compound 288)
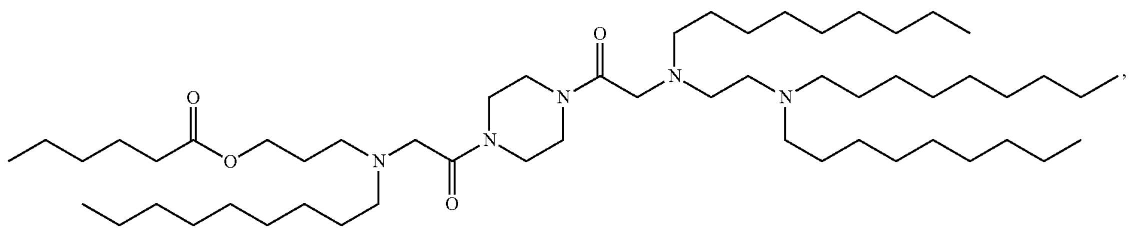
(Compound 289)
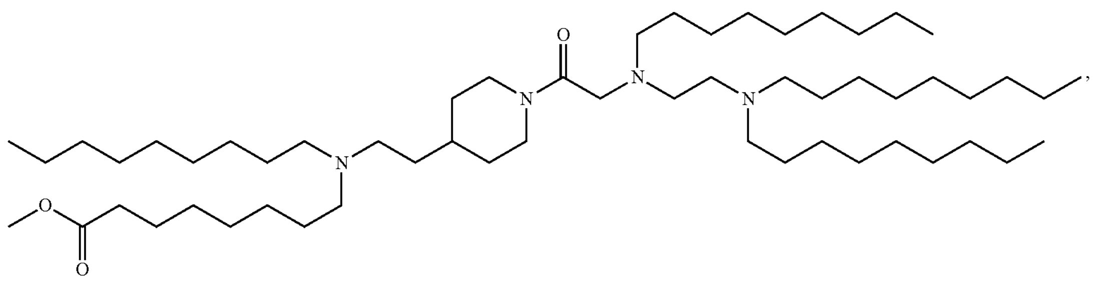
(Compound 290)
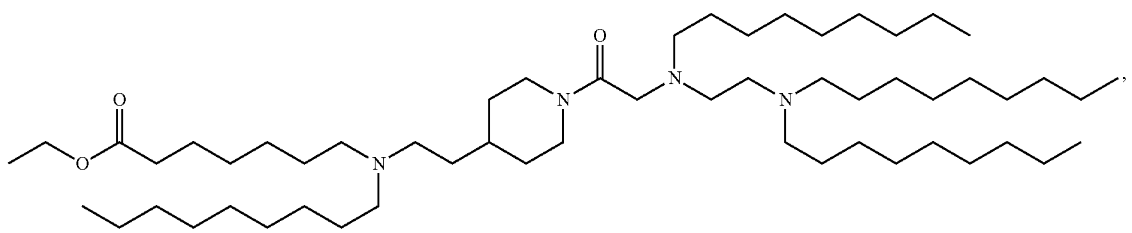
(Compound 291)
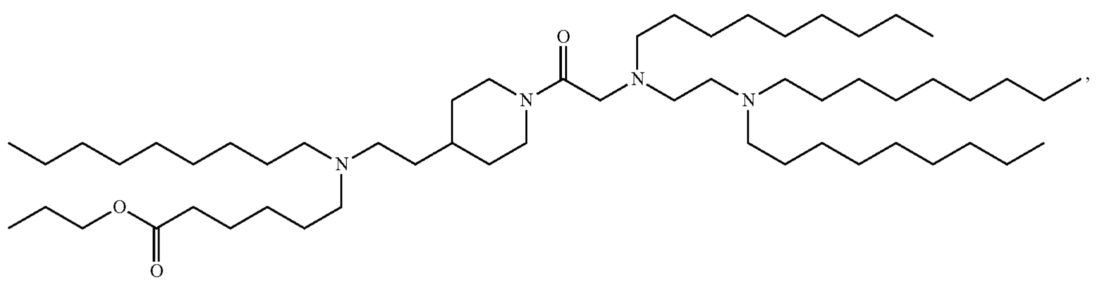
(Compound 292)
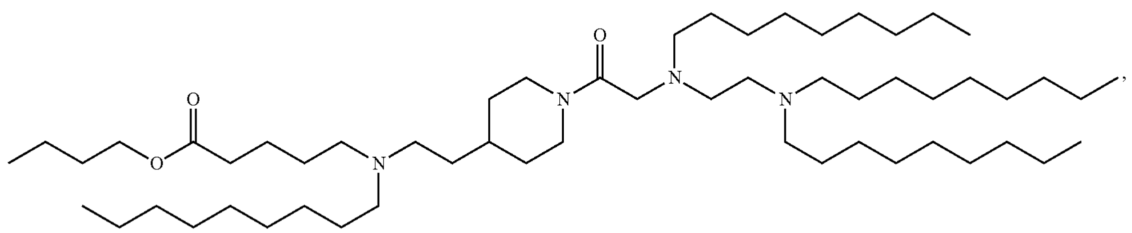

-continued
(Compound 293)
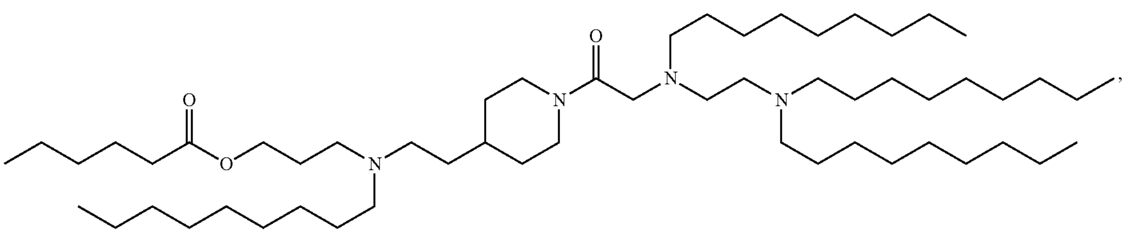
(Compound 294)
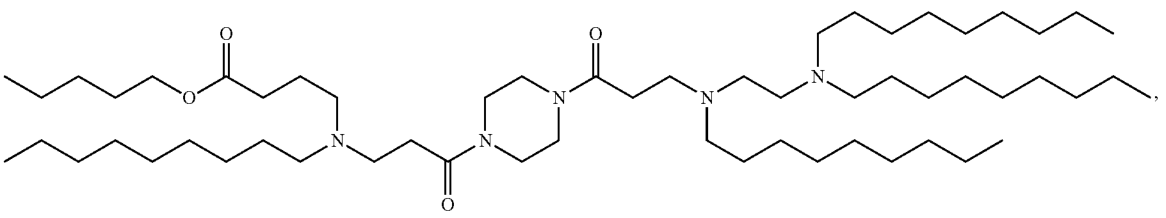
(Compound 295)
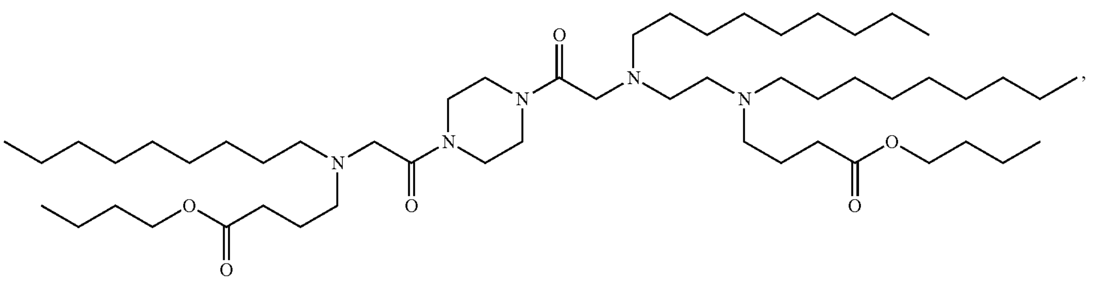
(Compound 296)
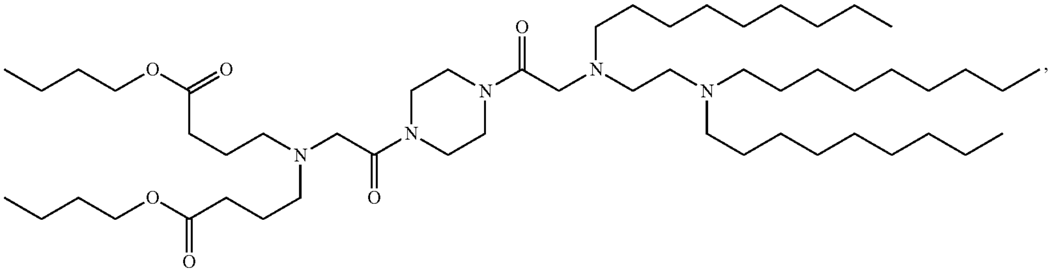
(Compound 297)
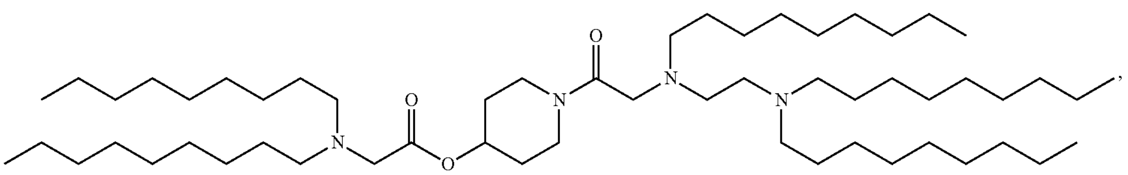
(Compound 298)
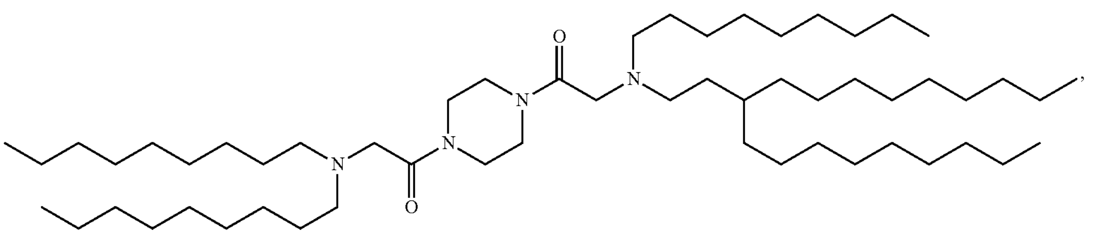

-continued
(Compound 300)
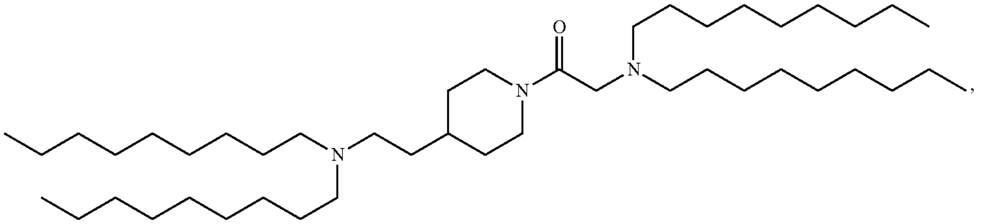
(Compound 301)
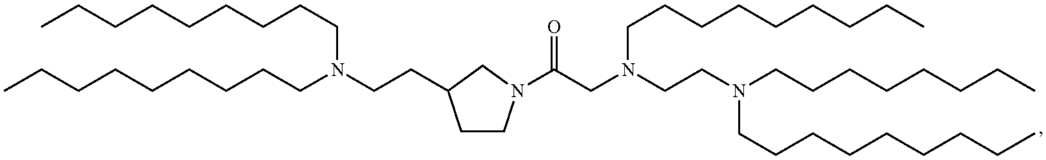
(Compound 302)
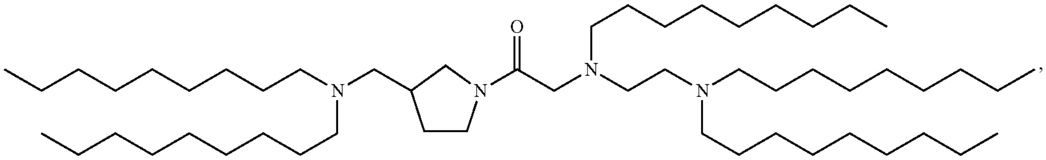
(Compound 303)
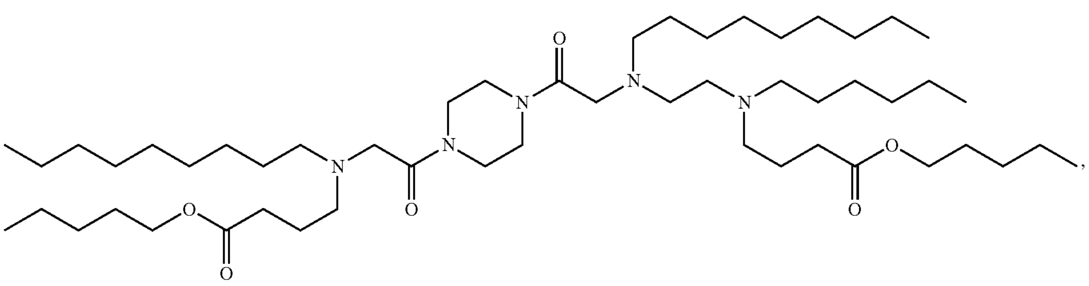
(Compound 304)
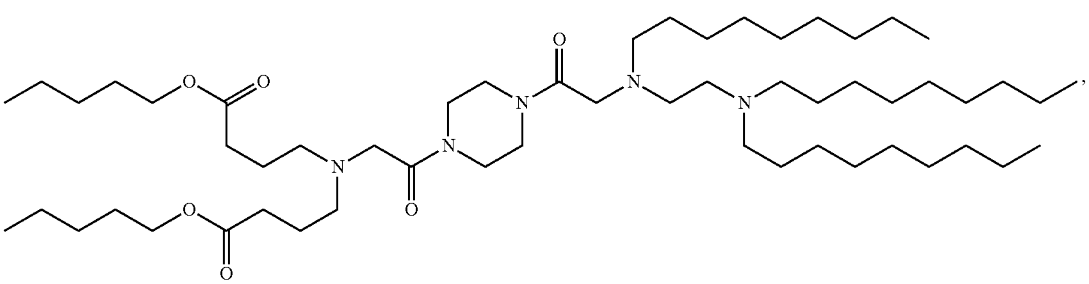
(Compound 305)
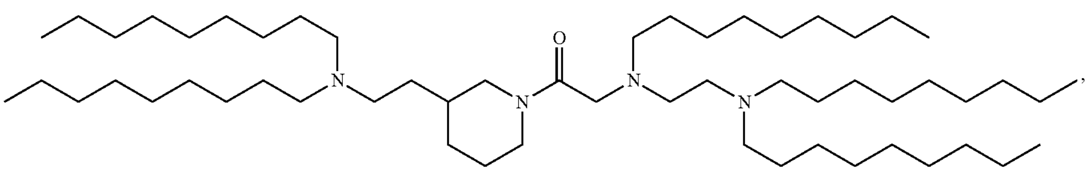
(Compound 306)
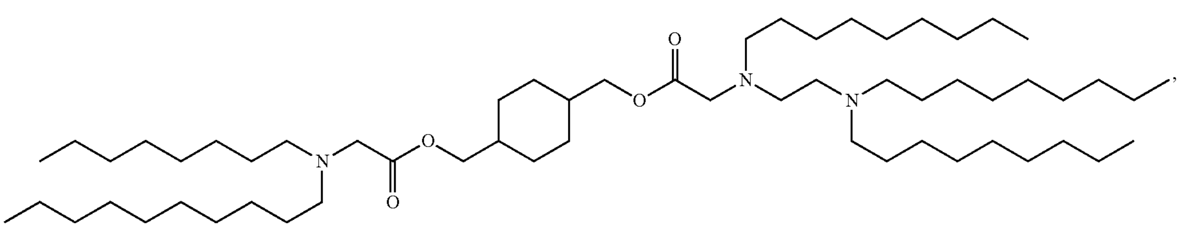

-continued
(Compound 307)
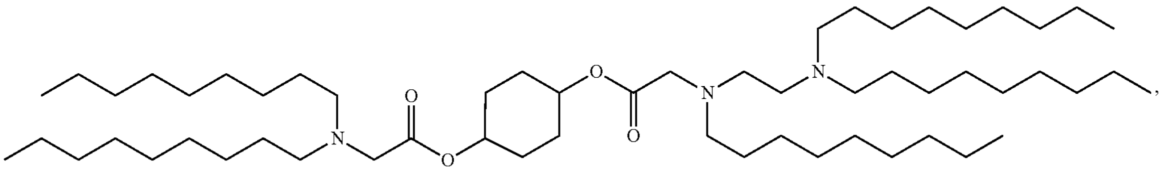
(Compound 308)
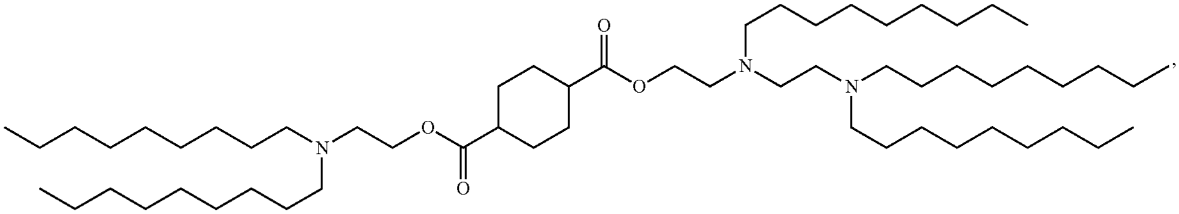
(Compound 310)
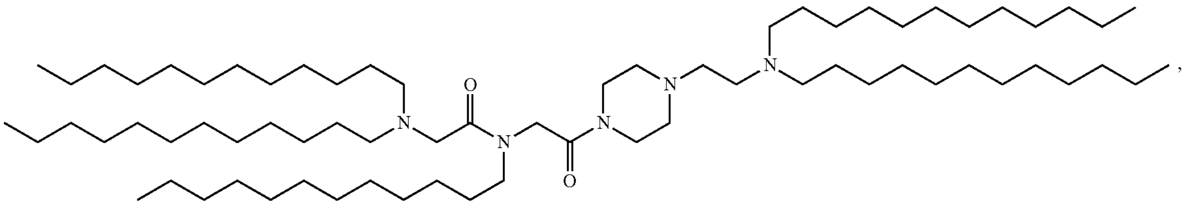
(Compound 311)
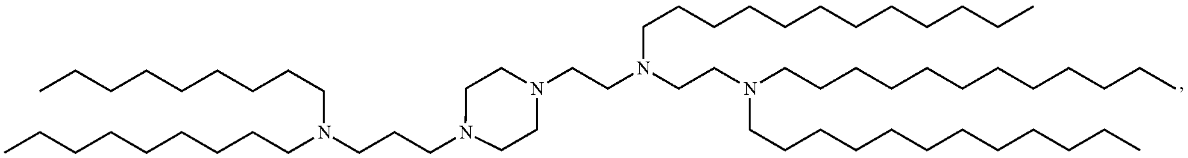
(Compound 312)
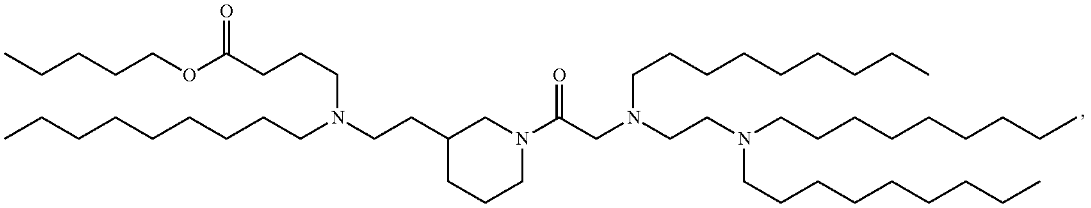
(Compound 313)
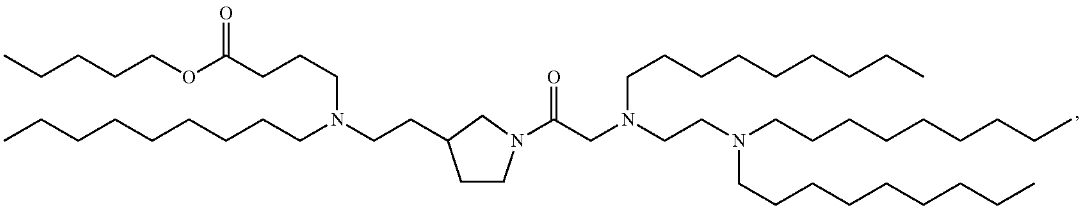
(Compound 314)
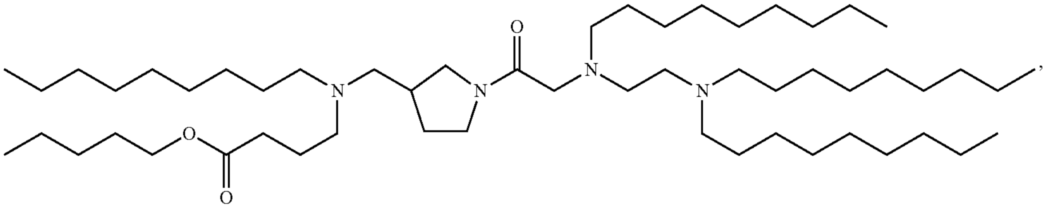

-continued
(Compound 315)
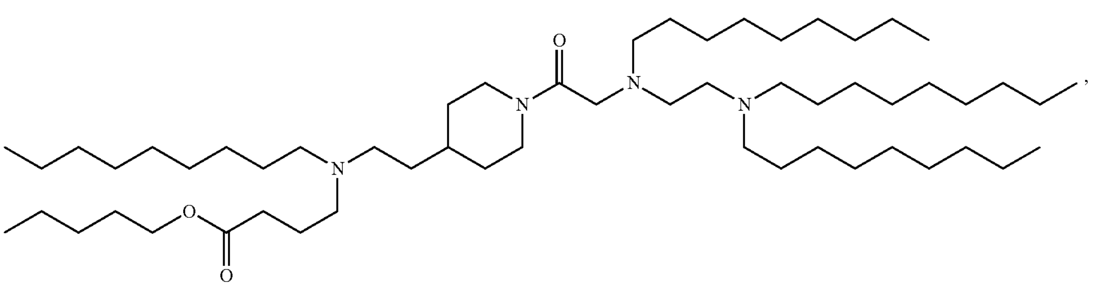
(Compound 316)
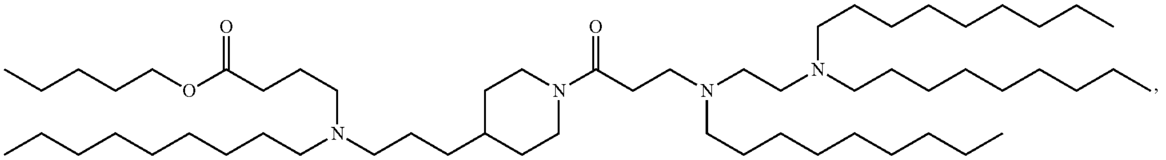
(Compound 317)
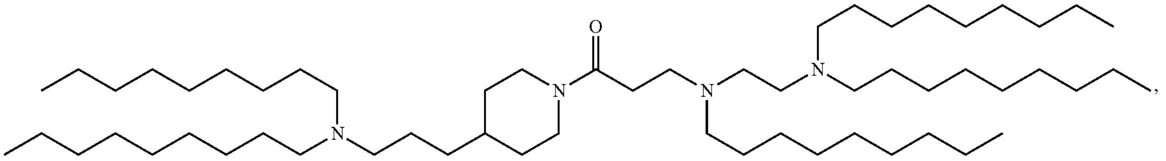
(Compound 318)
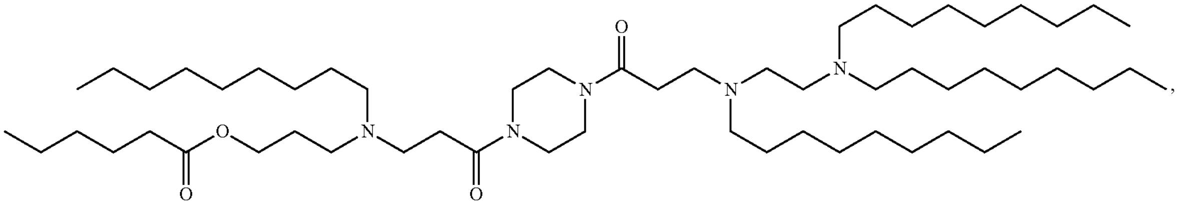
(Compound 319)
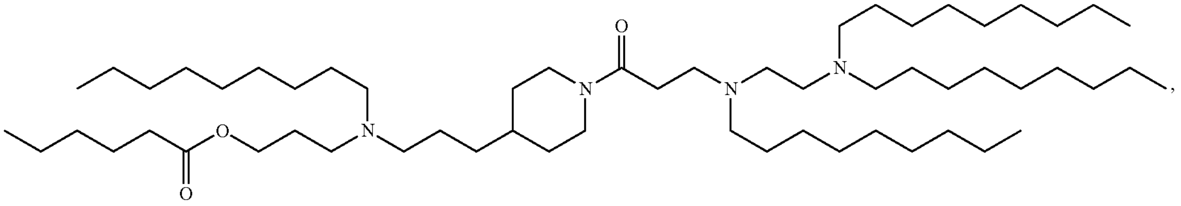
(Compound 320)
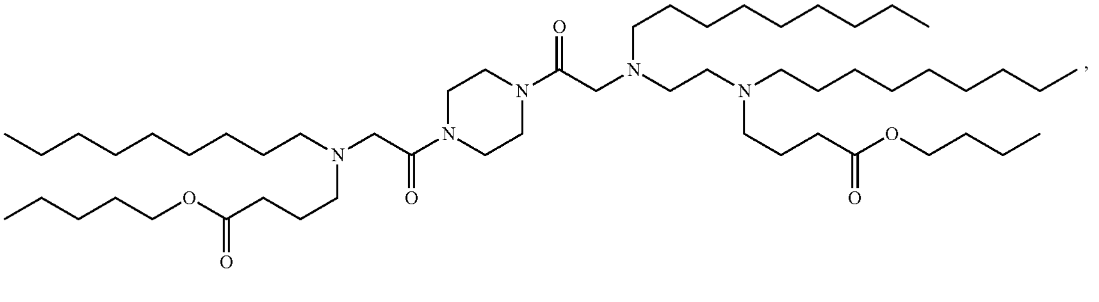

-continued
(Compound 321)
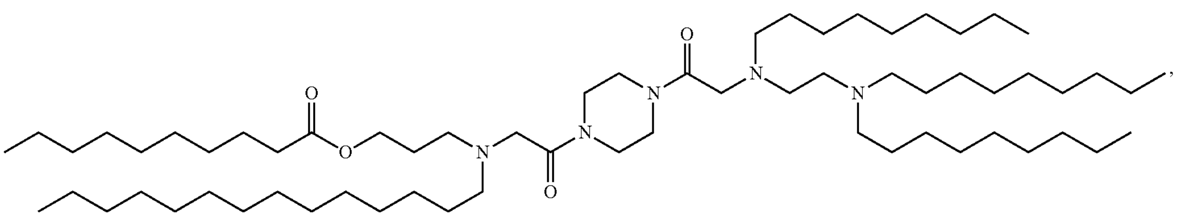
(Compound 322)
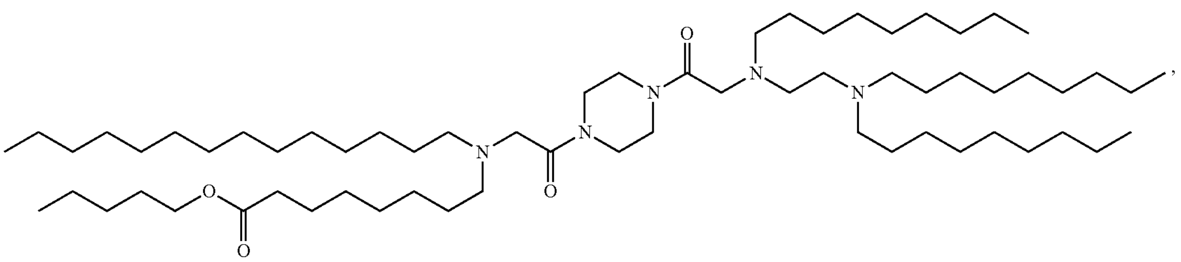
(Compound 323)
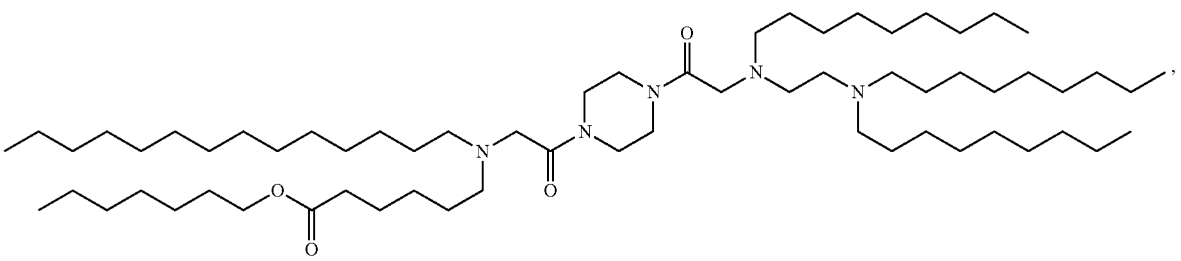
(Compound 324)
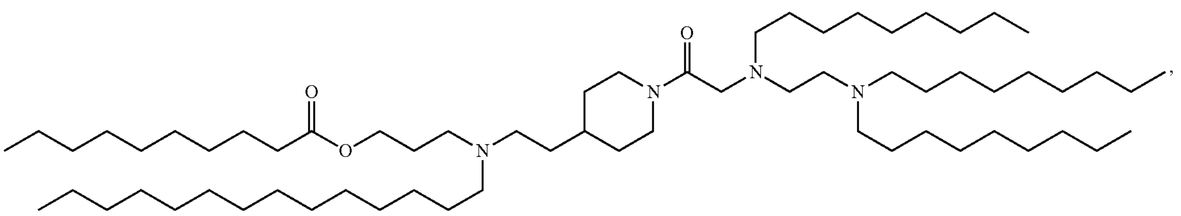
(Compound 325)
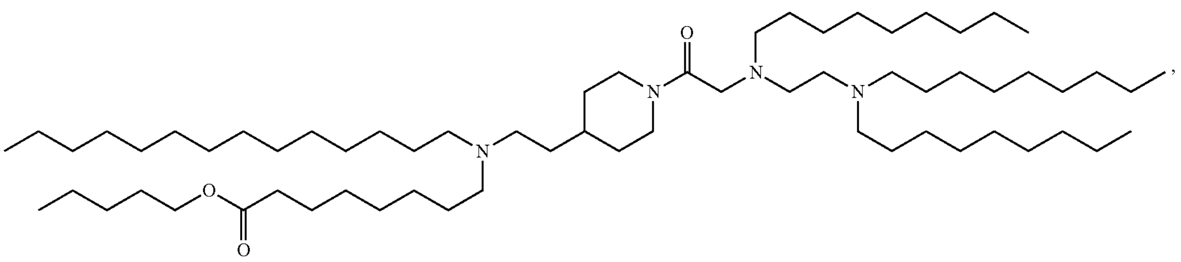
(Compound 326)
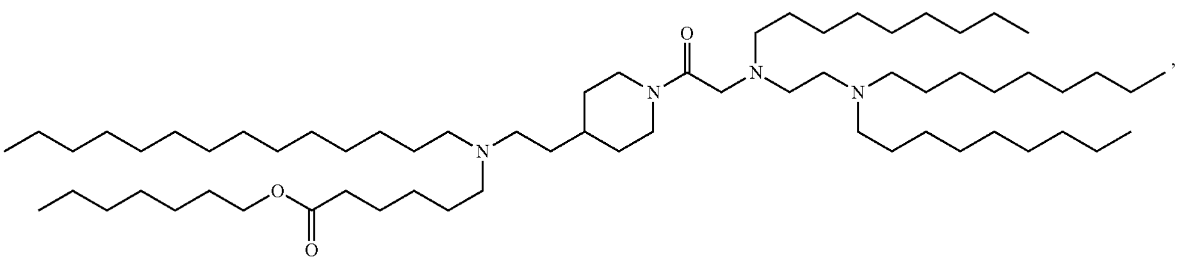

-continued
(Compound 327)
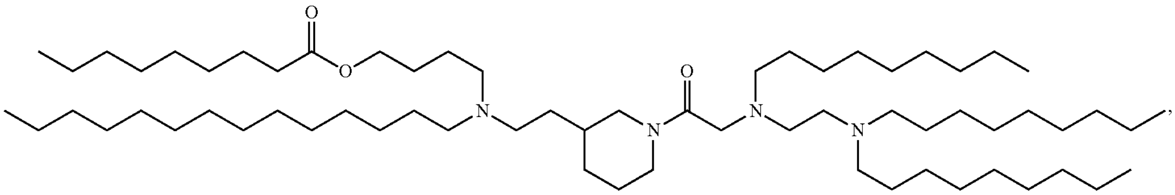
,
(Compound 328)
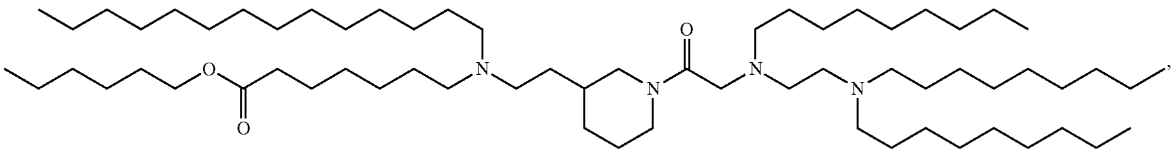
,
(Compound 329)
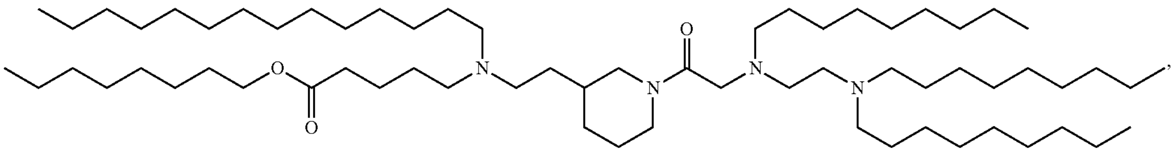
,
(Compound 330)
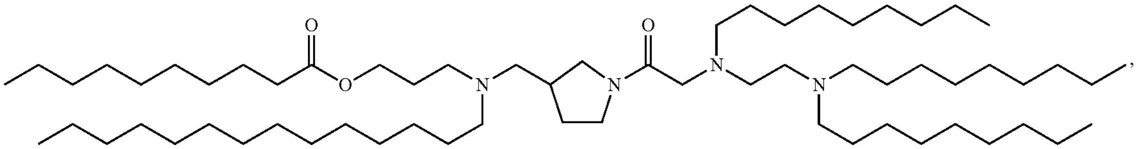
,
(Compound 331)
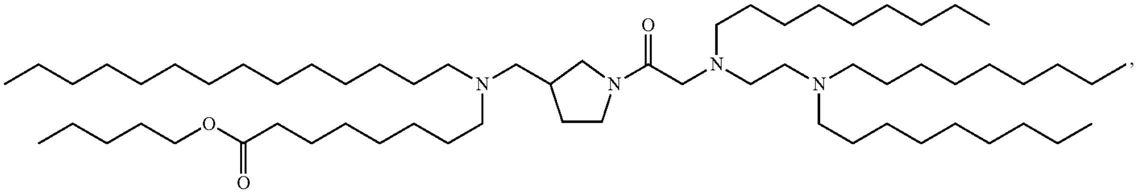
,
(Compound 332)
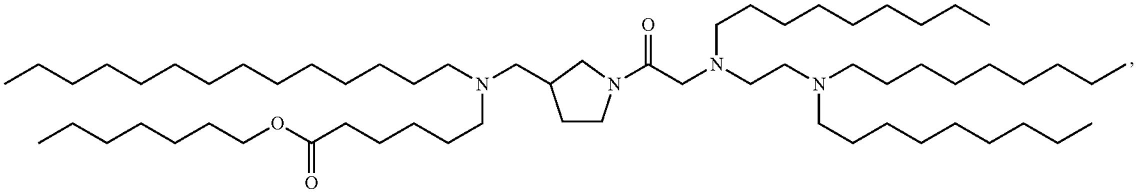
,
(Compound 333)
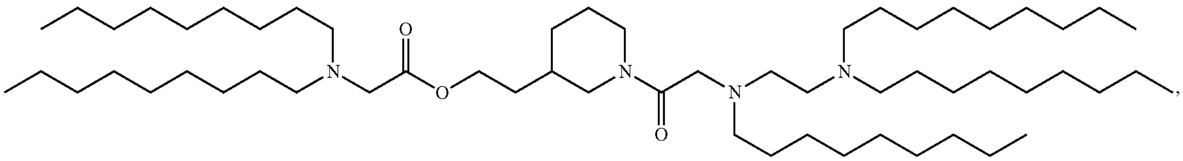
,
(Compound 334)
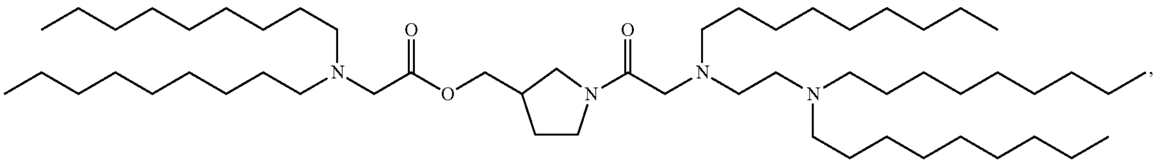
, -continued
(Compound 335)
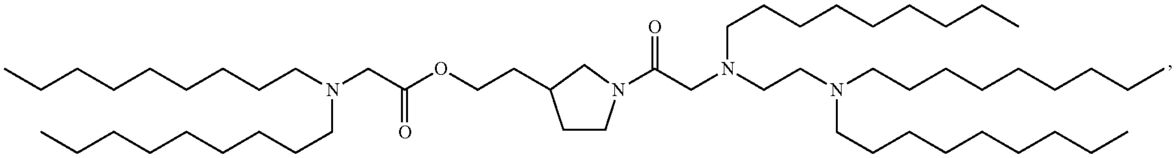
(Compound 336)
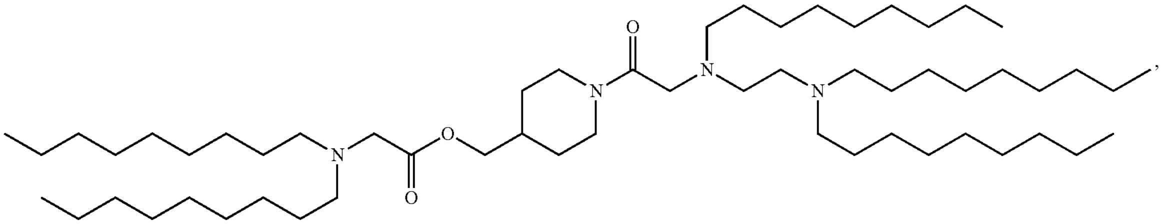
(Compound 337)
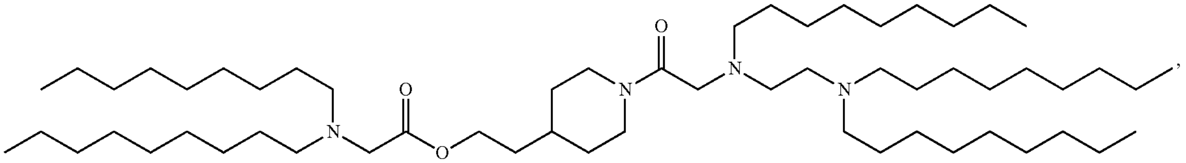
(Compound 338)
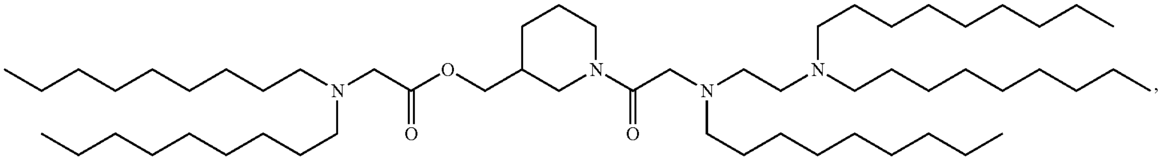
(Compound 339)
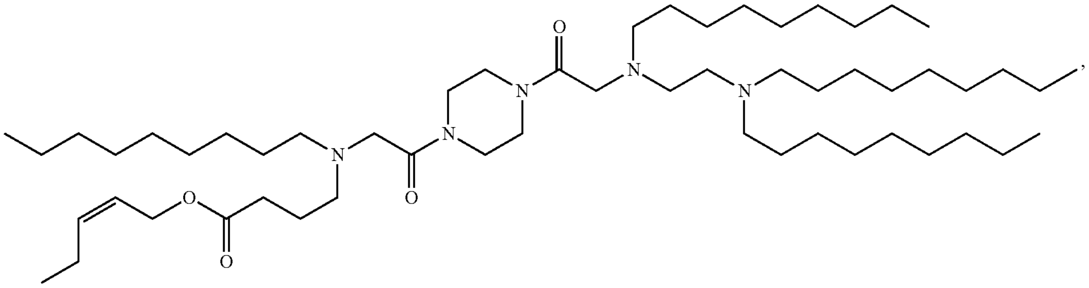
(Compound 340)
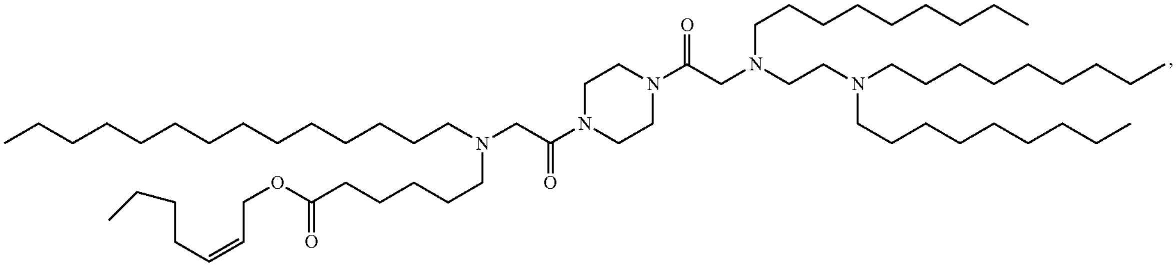

-continued and (Compound 341)

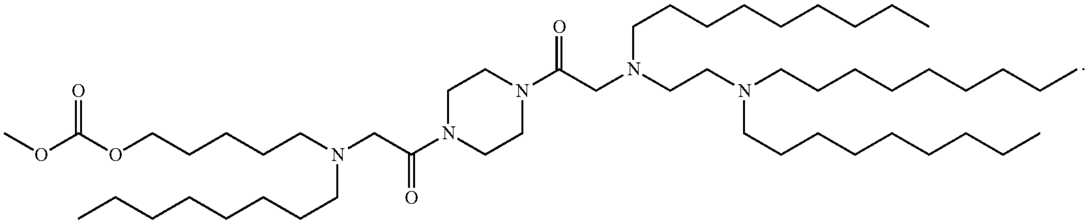

In some embodiments, the delivery agent comprises Compound 236.

In some embodiments, the delivery agent comprises a compound having the Formula (IV)

(IV)

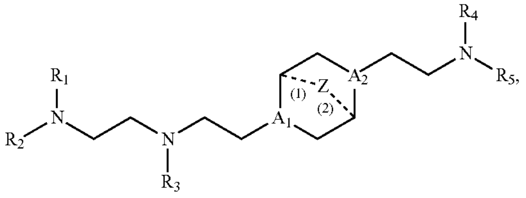

or salts or stereoisomer thereof, wherein $A_1$ and $A_2$ are each independently selected from CH or N and at least one of $A_1$ and $A_2$ is N;

Z is $CH_2$ or absent wherein when Z is $CH_2$, the dashed lines (1) and (2) each represent a single bond; and when Z is absent, the dashed lines (1) and (2) are both absent;

$R_1$, $R_2$, $R_3$, $R_4$, and $R_5$ are independently selected from the group consisting of $C_{6-20}$ alkyl and $C_{6-20}$ alkenyl; wherein when ring A is

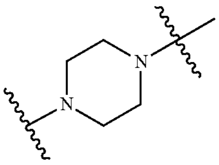

, then i) $R_1$, $R_2$, $R_3$, $R_4$, and $R_5$ are the same, wherein $R_1$ is not $C_{12}$ alkyl, $C_{18}$ alkyl, or $C_{18}$ alkenyl;

ii) only one of $R_1$, $R_2$, $R_3$, $R_4$, and $R_5$ is selected from $C_{6-20}$ alkenyl;

iii) at least one of $R_1$, $R_2$, $R_3$, $R_4$, and $R_5$ have a different number of carbon atoms than at least one other of $R_1$, $R_2$, $R_3$, $R_4$, and $R_5$;

iv) $R_1$, $R_2$, and $R_3$ are selected from $C_{6-20}$ alkenyl, and $R_4$ and $R_5$ are selected from $C_{6-20}$ alkyl; or v) $R_1$, $R_2$, and $R_3$ are selected from $C_{6-20}$ alkyl, and $R_4$ and $R_5$ are selected from $C_{6-20}$ alkenyl.

In some embodiments, the compound is of Formula (IVa):

(IVa)

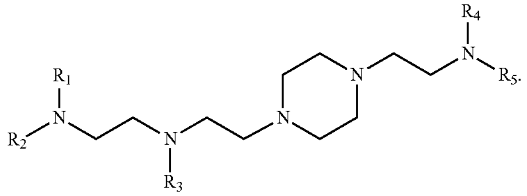

The compounds of Formula (IV) or (IVa) include one or more of the following features when applicable.

In some embodiments, Z is $CH_2$.

In some embodiments, Z is absent.

In some embodiments, at least one of $A_1$ and $A_2$ is N.

In some embodiments, each of $A_1$ and $A_2$ is N.

In some embodiments, each of $A_1$ and $A_2$ is CH.

In some embodiments, $A_1$ is N and $A_2$ is CH.

In some embodiments, $A_1$ is CH and $A_2$ is N.

In some embodiments, $R_1$, $R_2$, $R_3$, $R_4$, and $R_5$ are the same, and are not $C_{12}$ alkyl, $C_{18}$ alkyl, or $C_{18}$ alkenyl. In some embodiments, $R_1$, $R_2$, $R_3$, $R_4$, and $R_5$ are the same and are $C_9$ alkyl or $C_{14}$ alkyl.

In some embodiments, only one of $R_1$, $R_2$, $R_3$, $R_4$, and $R_5$ is selected from $C_{6-20}$ alkenyl. In certain such embodiments, $R_1$, $R_2$, $R_3$, $R_4$, and $R_5$ have the same number of carbon atoms. In some embodiments, $R_4$ is selected from $C_{5-20}$ alkenyl. For example, $R_4$ may be $C_{12}$ alkenyl or $C_{18}$ alkenyl.

In some embodiments, at least one of $R_1$, $R_2$, $R_3$, $R_4$, and $R_5$ have a different number of carbon atoms than at least one other of $R_1$, $R_2$, $R_3$, $R_4$, and $R_5$.

In certain embodiments, $R_1$, $R_2$, and $R_3$ are selected from $C_{6-20}$ alkenyl, and $R_4$ and $R_5$ are selected from $C_{6-20}$ alkyl. In other embodiments, $R_1$, $R_2$, and $R_3$ are selected from $C_{6-20}$ alkyl, and $R_4$ and $R_5$ are selected from $C_{6-20}$ alkenyl. In some embodiments, $R_1$, and $R_3$ have the same number of carbon atoms, and/or $R_4$ and $R_5$ have the same number of carbon atoms. For example, $R_1$, $R_2$, and $R_3$, or $R_4$ and $R_5$, may have 6, 8, 9, 12, 14, or 18 carbon atoms. In some embodiments, $R_1$, $R_2$, and $R_3$, or $R_4$ and $R_5$, are $C_{18}$ alkenyl (e.g., linoleyl). In some embodiments, $R_1$, $R_2$, and $R_3$, or $R_4$ and $R_5$, are alkyl groups including 6, 8, 9, 12, or 14 carbon atoms.

In some embodiments, $R_1$ has a different number of carbon atoms than $R_2$, $R_3$, $R_4$, and $R_5$. In other embodiments, $R_3$ has a different number of carbon atoms than $R_1$, $R_2$, $R_4$, and $R_5$. In further embodiments, $R_4$ has a different number of carbon atoms than $R_1$, $R_2$, $R_3$, and $R_5$.

In some embodiments, the compound is selected from the group consisting of:
(Compound 249)
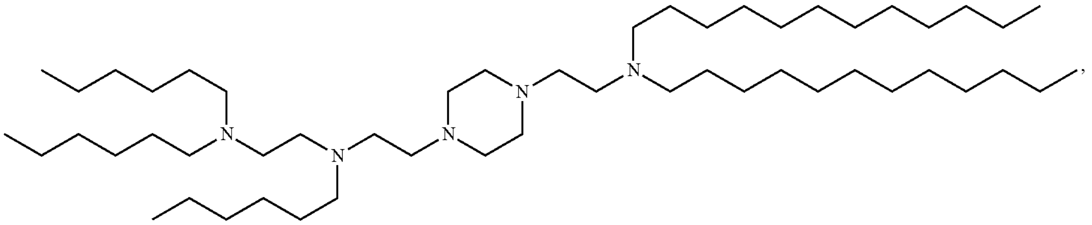
(Compound 250)
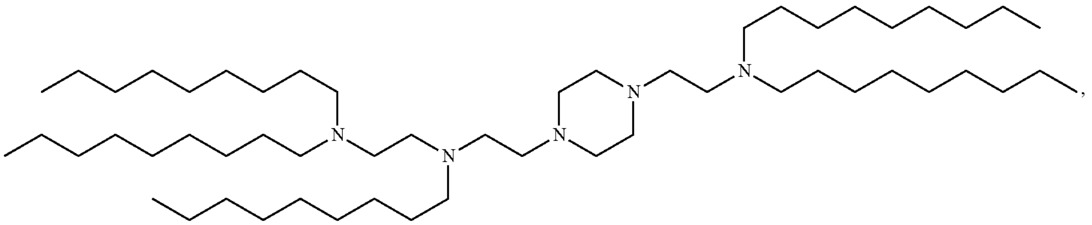
(Compound 251)
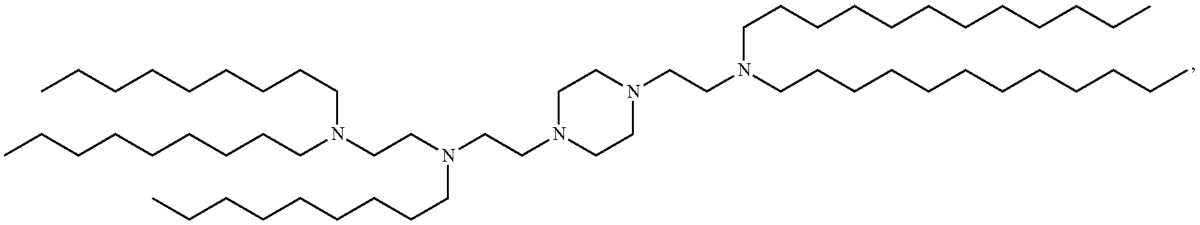
(Compound 252)
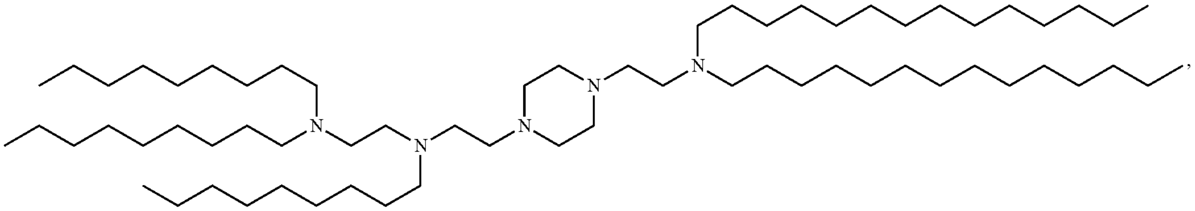
(Compound 253)
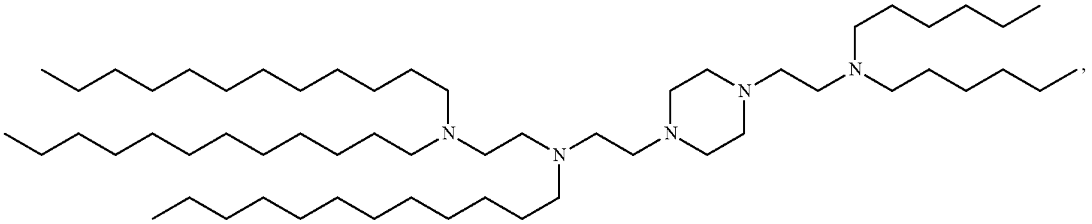
(Compound 254)
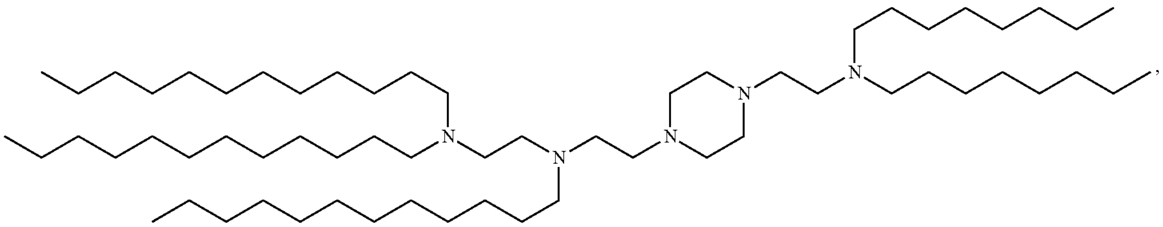

-continued
(Compound 255)
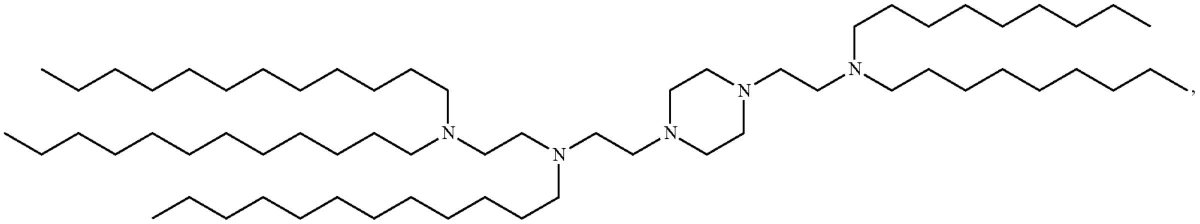
(Compound 256)
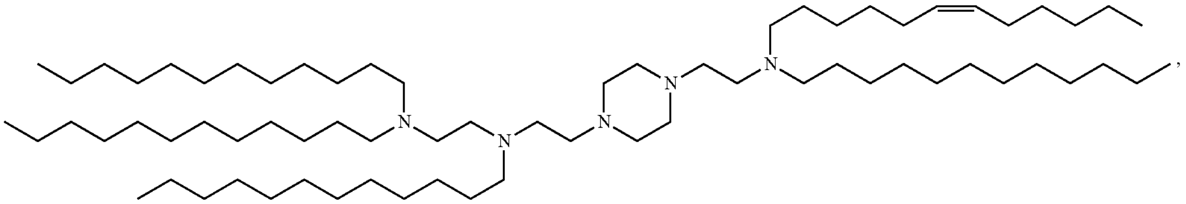
(Compound 257)
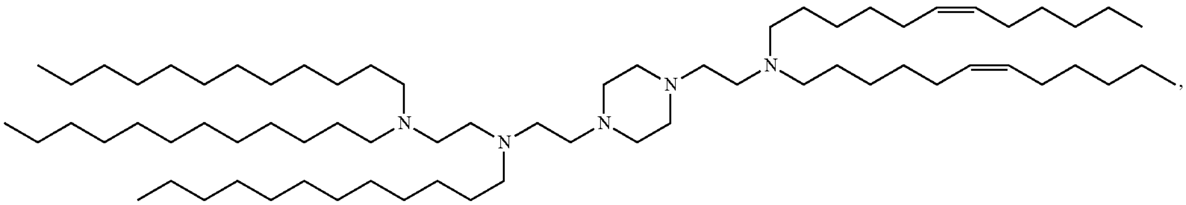
(Compound 258)
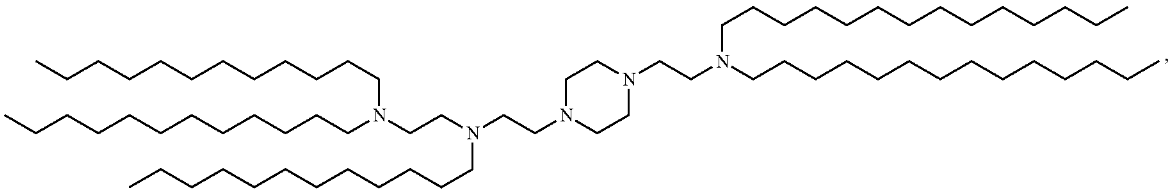
(Compound 259)
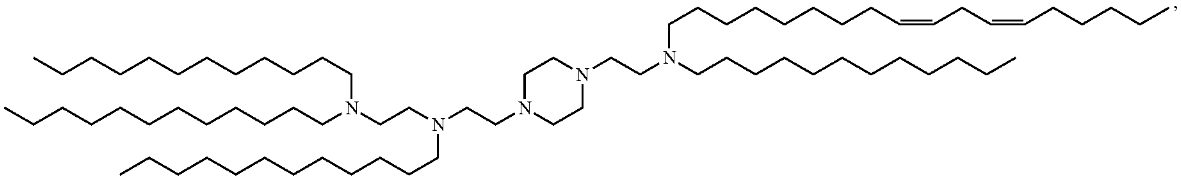
(Compound 260)
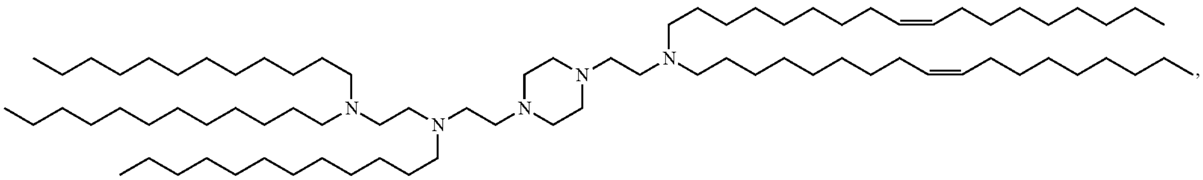
(Compound 261)
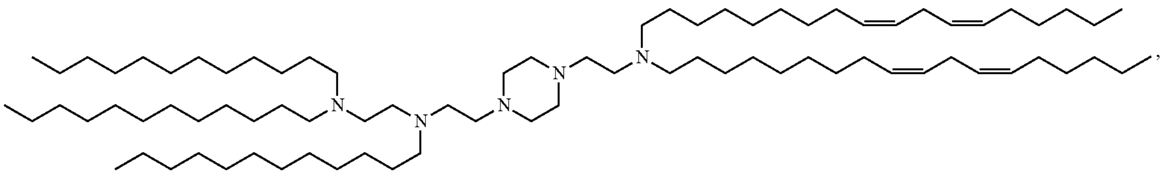

-continued (Compound 262)

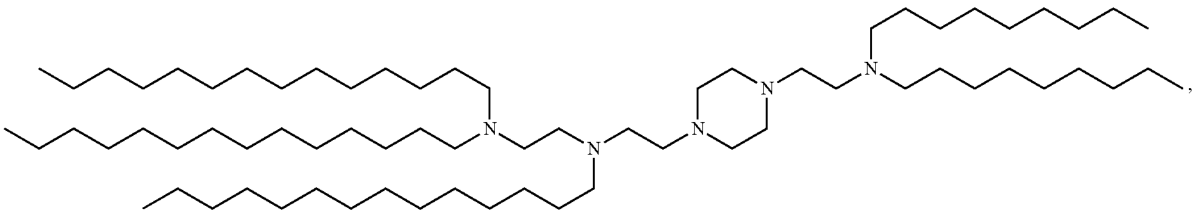

(Compound 263)

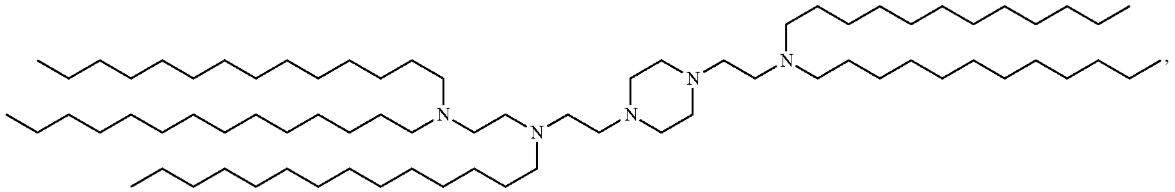

(Compound 264)

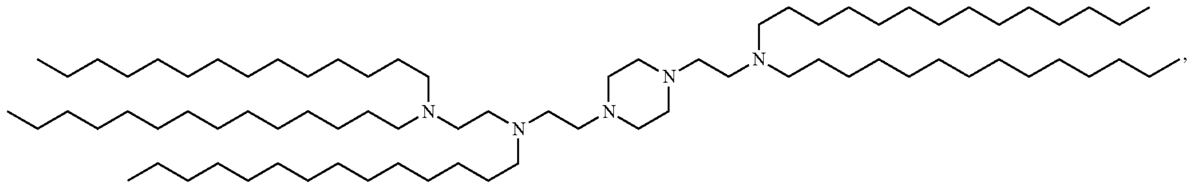

(Compound 265)

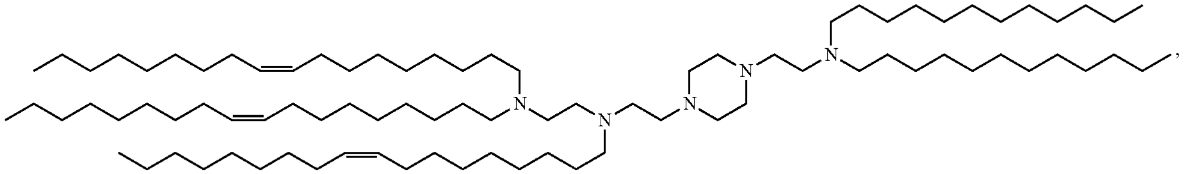

and (Compound 266)

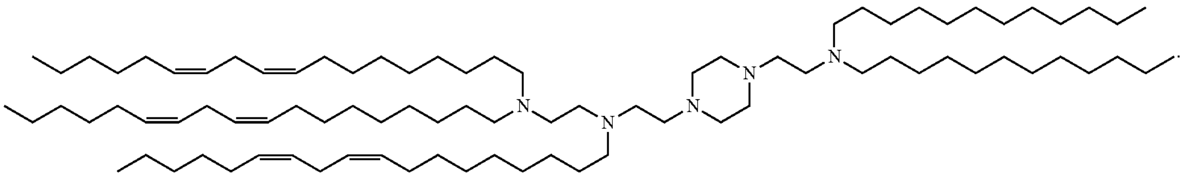

In other embodiments, the delivery agent comprises a compound having the Formula (V)

(V)

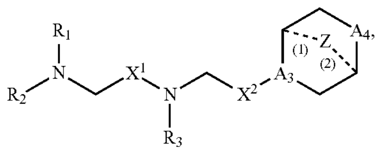

or salts or stereoisomers thereof, in which $A_3$ is CH or N;

$A_4$ is $CH_2$ or NH; and at least one of $A_3$ and $A_4$ is N or NH;

Z is $CH_2$ or absent wherein when Z is $CH_2$, the dashed lines (1) and (2) each represent a single bond; and when Z is absent, the dashed lines (1) and (2) are both absent;

$R_1$, $R_2$, and $R_3$ are independently selected from the group consisting of $C_{5-20}$ alkyl, $C_{5-20}$ alkenyl, —R"MR', —R*YR", —YR", and —R*OR";

each M is independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —$S(O)_2$—, an aryl group, and a heteroaryl group;

$X^1$ and $X^2$ are independently selected from the group consisting of —$CH_2$—, —$(CH_2)_2$—, —CHR—, —CHY—, —C(O)—, —C(O)O—, —OC(O)—, —C(O)—$CH_2$—, —$CH_2$—C(O)—, —C(O)O—$CH_2$—, —OC(O)—$CH_2$—, —$CH_2$—C(O)O—, —$CH_2$—OC(O)—, —CH(OH)—, —C(S)—, and —CH(SH)—;

each Y is independently a $C_{3-6}$ carbocycle;

each R* is independently selected from the group consisting of $C_{1-12}$ alkyl and $C_{2-12}$ alkenyl;

each R is independently selected from the group consisting of $C_{1-3}$ alkyl and a $C_{3-6}$ carbocycle;

each R' is independently selected from the group consisting of $C_{1-12}$ alkyl, $C_{2-12}$ alkenyl, and H; and each R'' is independently selected from the group consisting of $C_{3-12}$ alkyl and $C_{3-12}$ alkenyl.

In some embodiments, the compound is of Formula (Va):

(Va)

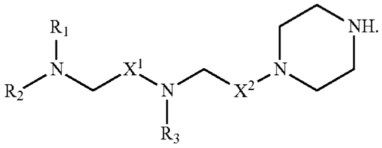

The compounds of Formula (V) or (Va) include one or more of the following features when applicable.

In some embodiments, Z is $CH_2$.

In some embodiments, Z is absent.

In some embodiments, at least one of $A_3$ and $A_4$ is N or NH.

In some embodiments, $A_3$ is N and $A_4$ is NH.

In some embodiments, $A_3$ is N and $A_4$ is $CH_2$.

In some embodiments, $A_3$ is CH and $A_4$ is NH.

In some embodiments, at least one of $X^1$ and $X^2$ is not $—CH_2—$. For example, in certain embodiments, $X^1$ is not $—CH_2—$. In some embodiments, at least one of $X^1$ and $X^2$ is —C(O)—.

In some embodiments, $X^2$ is —C(O)—, —C(O)O—, —OC(O)—, $—C(O)—CH_2—$, $—CH_2—C(O)—$, $—C(O)O—CH_2—$, $—OC(O)—CH_2—$, $—CH_2—C(O)O—$, or $—CH_2—OC(O)—$.

In some embodiments, $R_1$, $R_2$, and $R_3$ are independently selected from the group consisting of $C_{5-20}$ alkyl and $C_{5-20}$ alkenyl. In some embodiments, $R_1$, $R_2$, and $R_3$ are the same. In certain embodiments, $R_1$, $R_2$, and $R_3$ are $C_6$, $C_9$, $C_{12}$, or $C_{14}$ alkyl. In other embodiments, $R_1$, $R_2$, and $R_3$ are $C_{18}$ alkenyl. For example, $R_1$, $R_2$, and $R_3$ may be linoleyl.

In some embodiments, the compound is selected from the group consisting of:

(Compound 1)

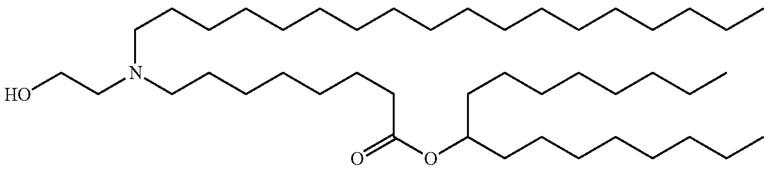

, (Compound 2)

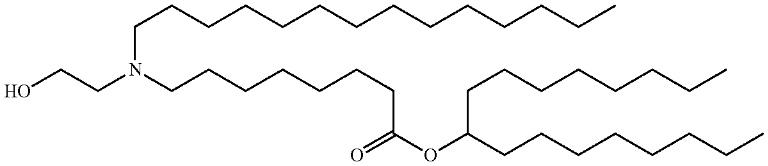

, (Compound 3)

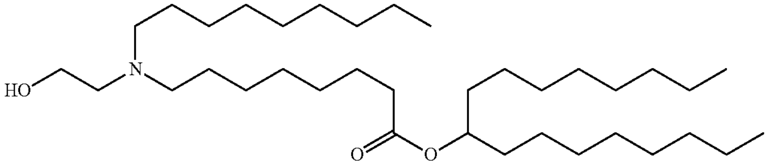

, (Compound 4)

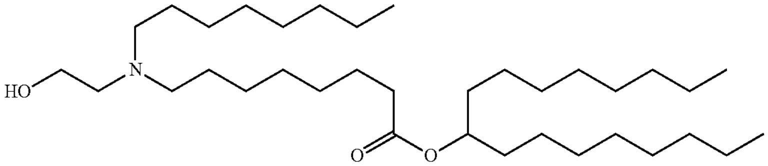

, (Compound 5)

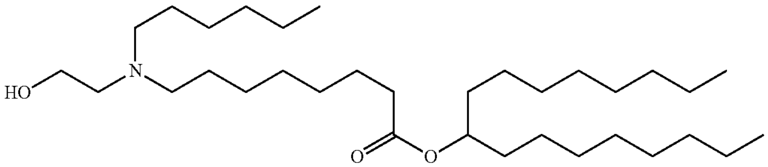

, (Compound 6)

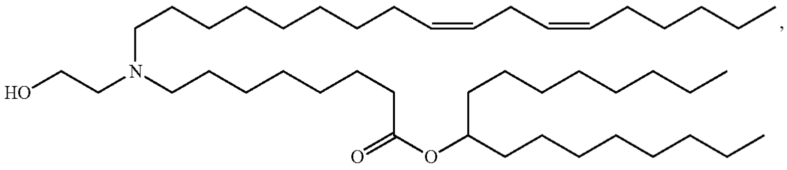

,

-continued
(Compound 7)
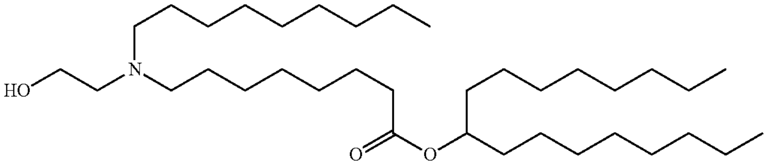
,
(Compound 8)
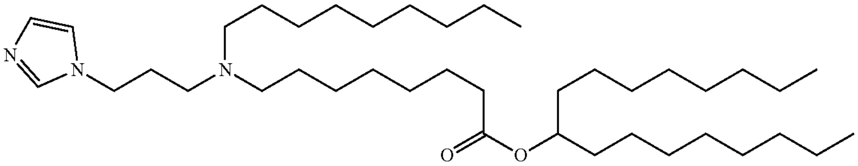
,
(Compound 9)
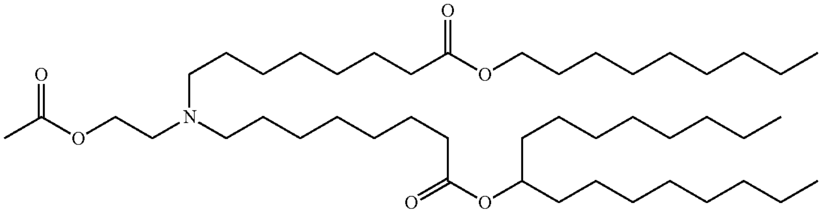
,
(Compound 10)
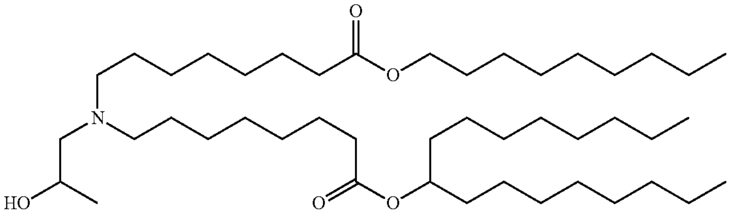
,
(Compound 11)
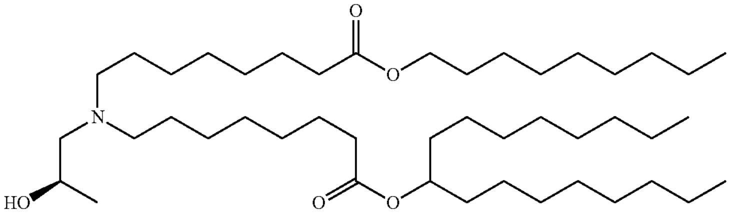
,
(Compound 12)
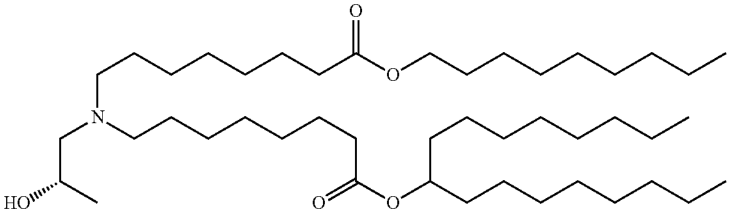
,
(Compound 13)
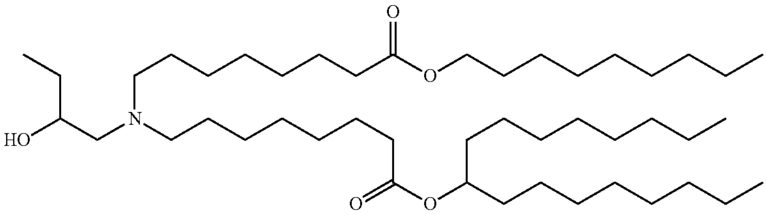
, -continued
(Compound 14)
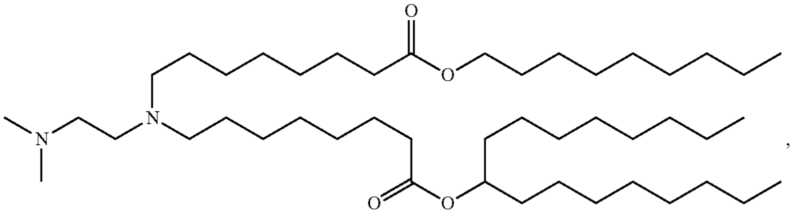
,
(Compound 15)
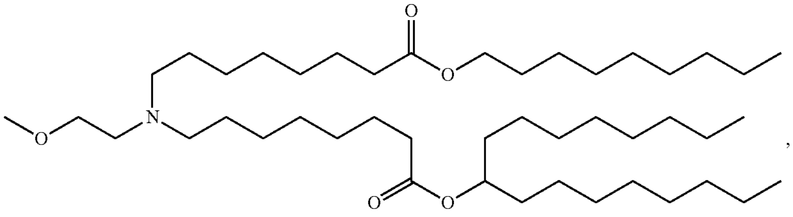
,
(Compound 16)
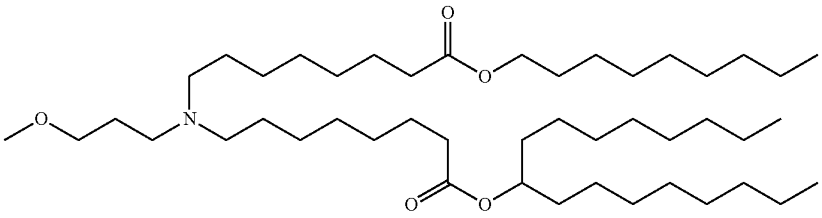
,
(Compound 17)
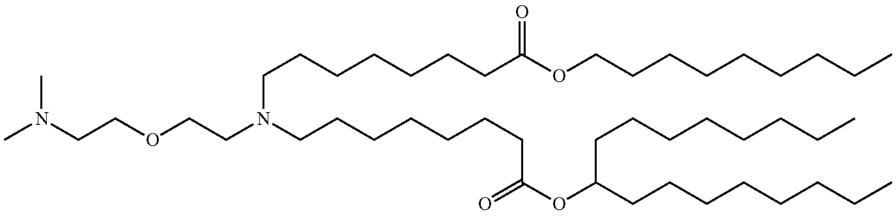
,
(Compound 18)
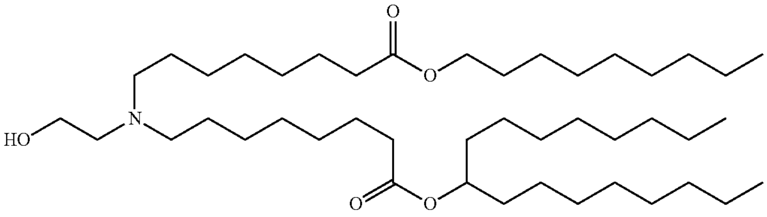
,
(Compound 19)
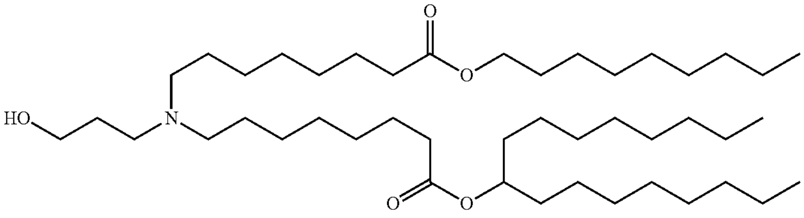
,
(Compound 20)
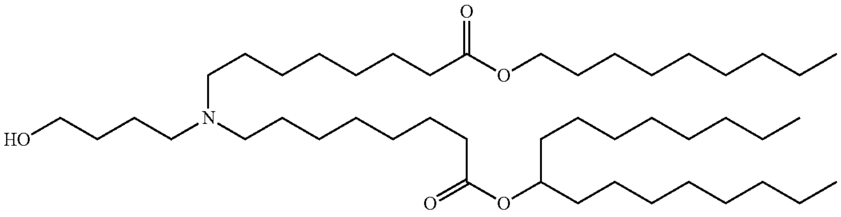
, -continued
(Compound 21)
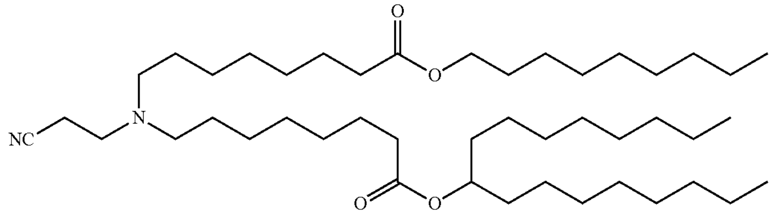
,
(Compound 22)
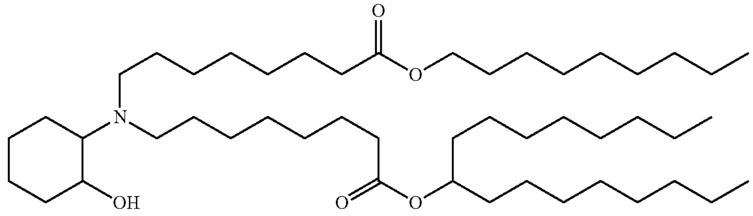
,
(Compound 23)
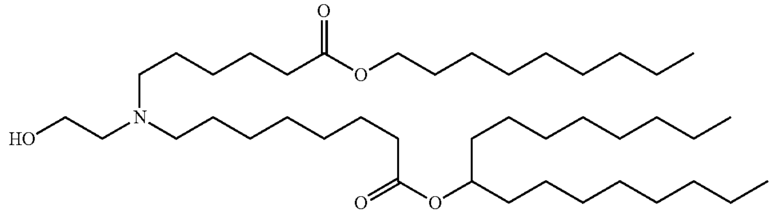
,
(Compound 24)
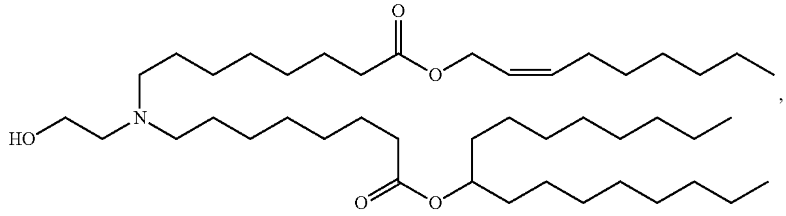
,
(Compound 25)
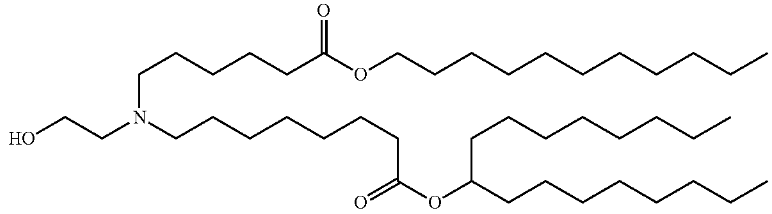
,
(Compound 26)
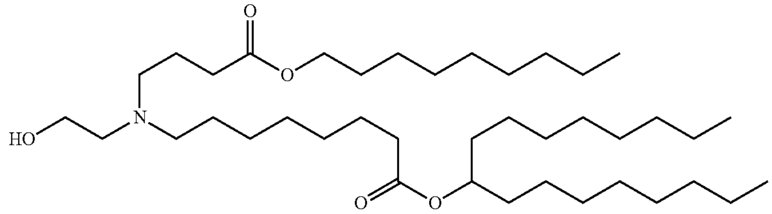
,
(Compound 27)
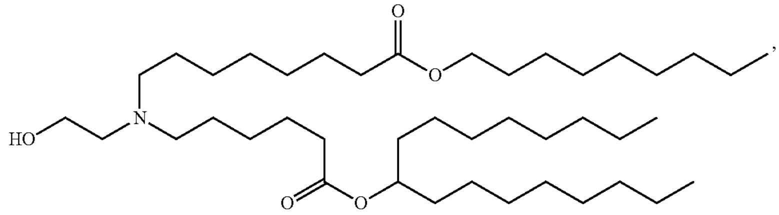
, -continued
(Compound 28)
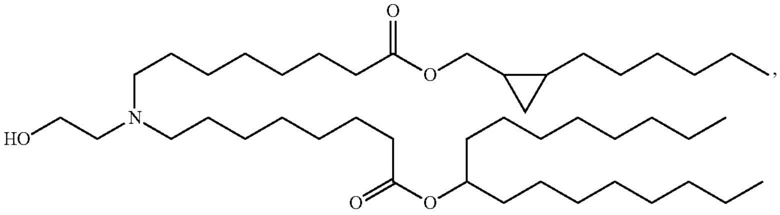
,
(Compound 29)
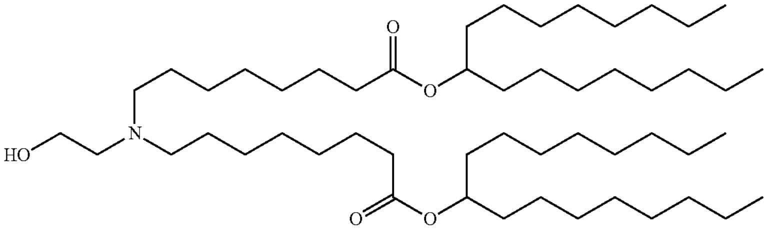
,
(Compound 30)
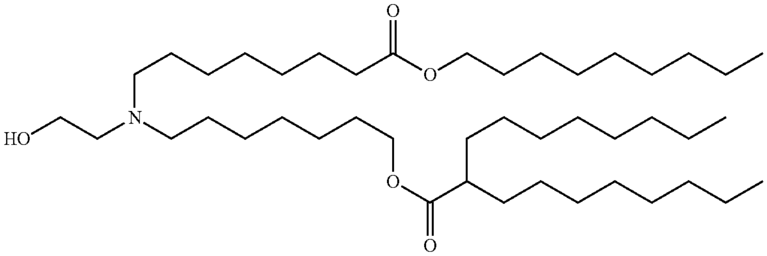
,
(Compound 31)
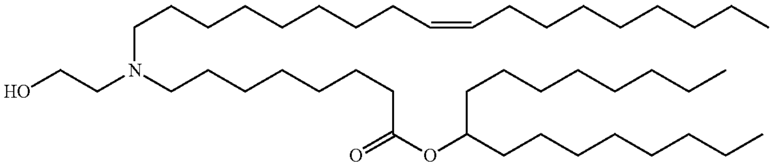
,
(Compound 32)
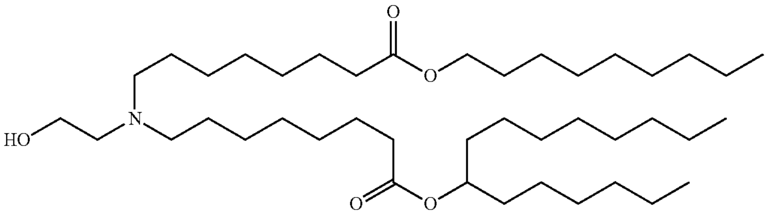
,
(Compound 33)
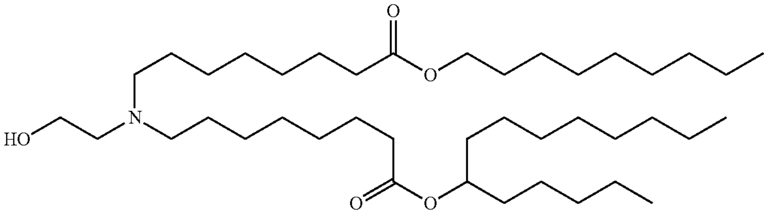
,
(Compound 34)
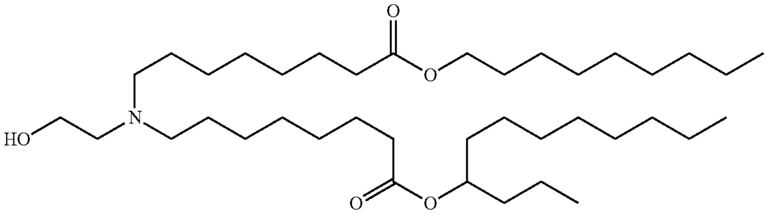
, -continued
(Compound 35)
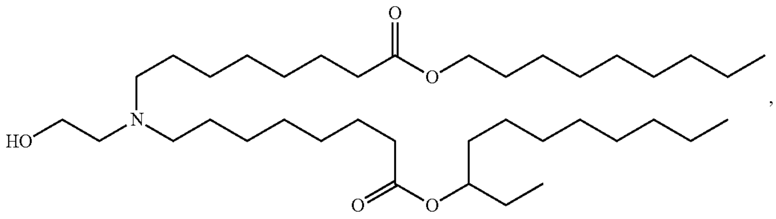
,
(Compound 36)
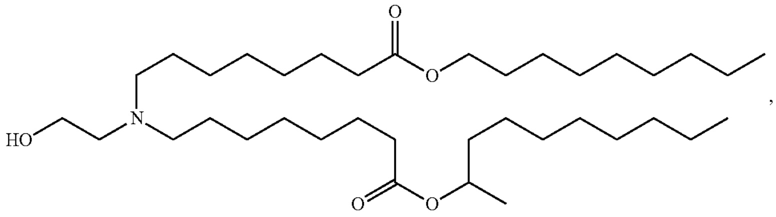
,
(Compound 37)
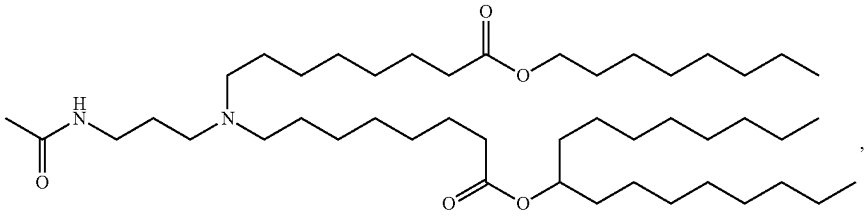
,
(Compound 38)
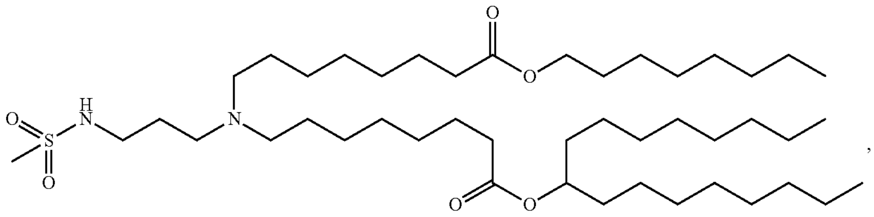
,
(Compound 39)
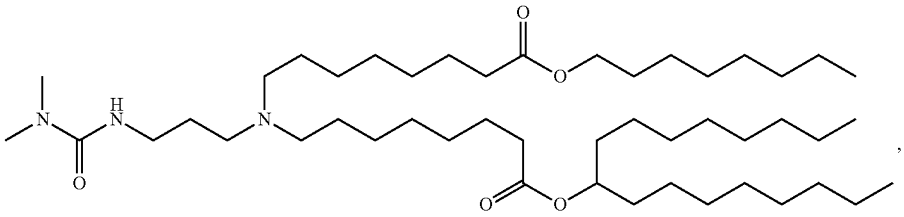
,
(Compound 40)
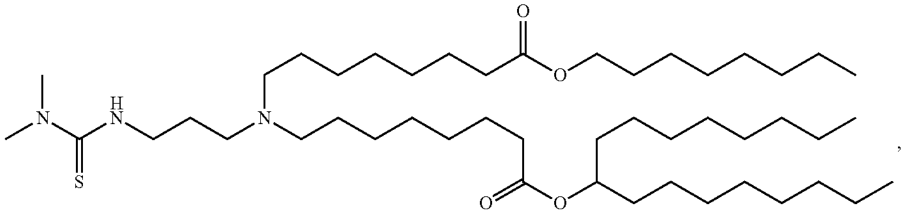
,
(Compound 41)
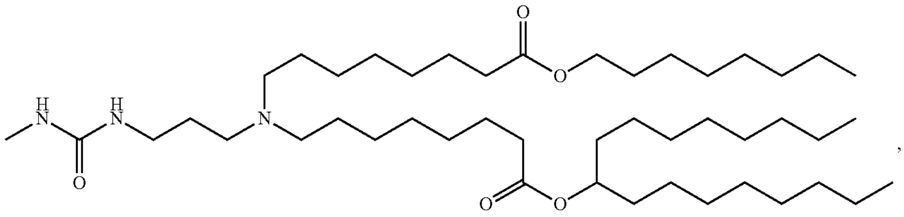
, -continued
(Compound 42)
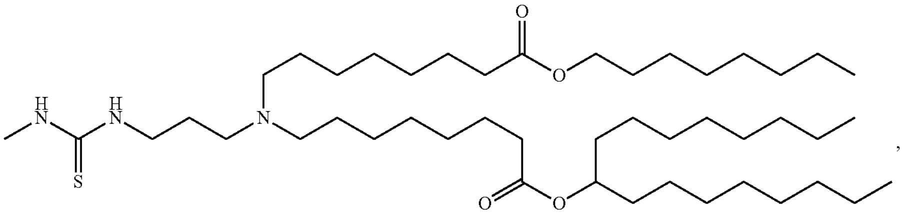
,
(Compound 43)
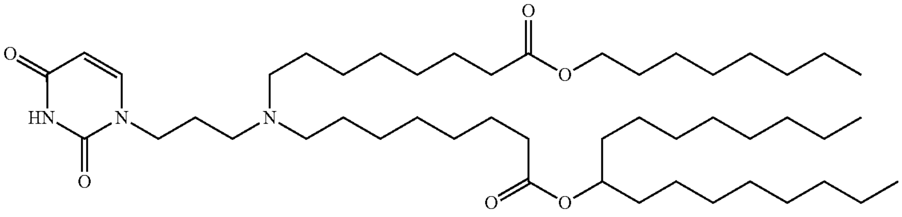
,
(Compound 44)
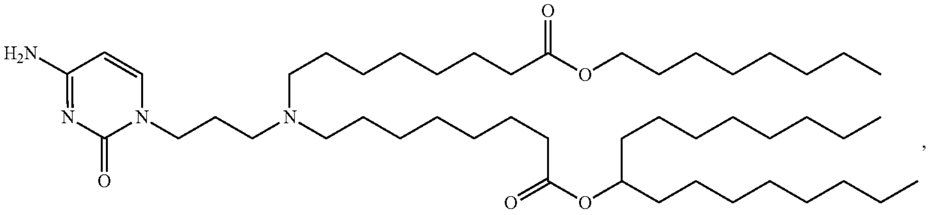
,
(Compound 45)
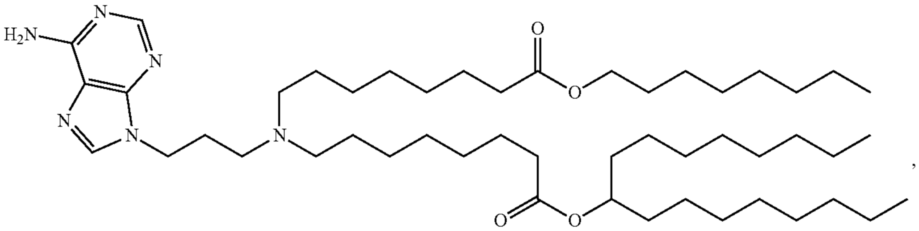
,
(Compound 46)
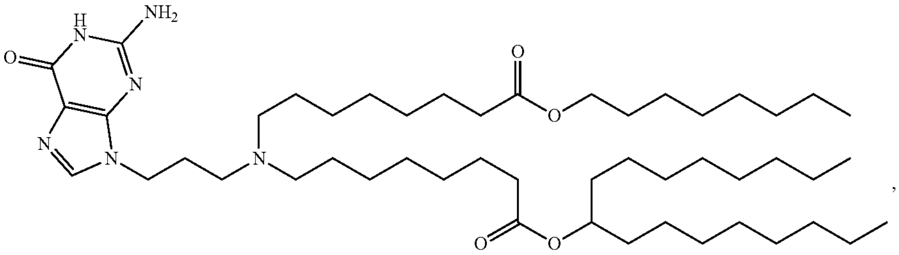
,
(Compound 47)
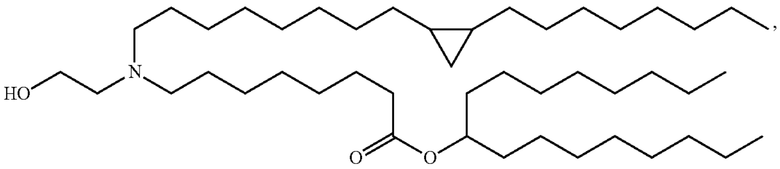
,
(Compound 48)
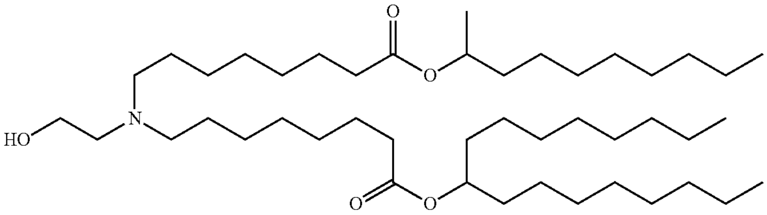
, -continued
(Compound 49)
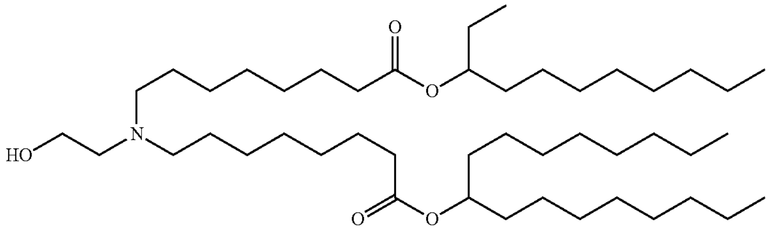
,
(Compound 50)
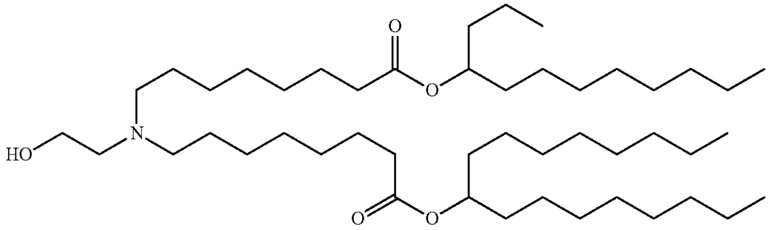
,
(Compound 51)
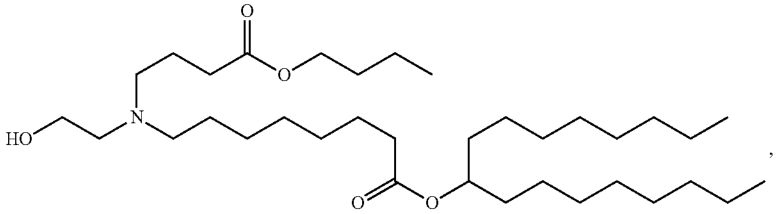
,
(Compound 52)
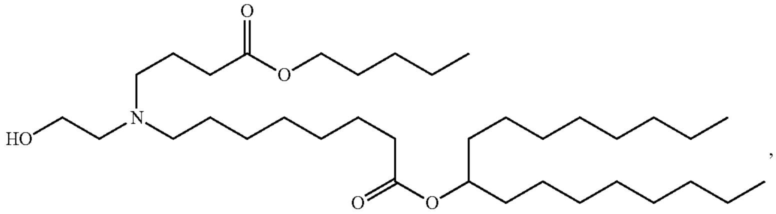
,
(Compound 53)
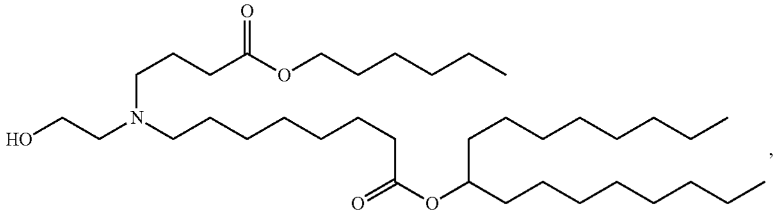
,
(Compound 54)
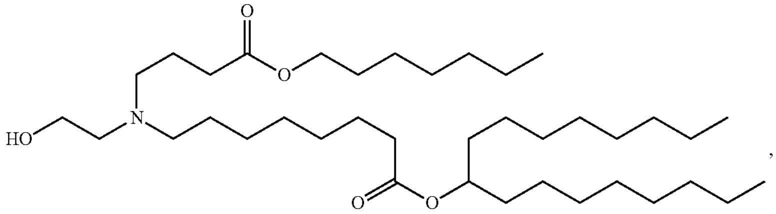
,
(Compound 55)
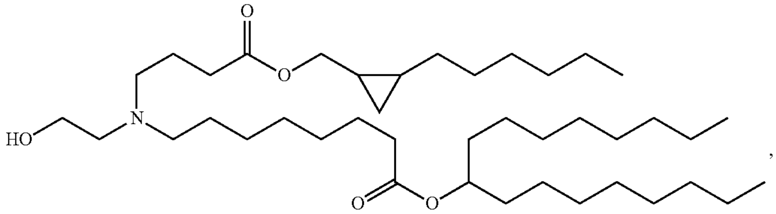
, -continued
(Compound 56)
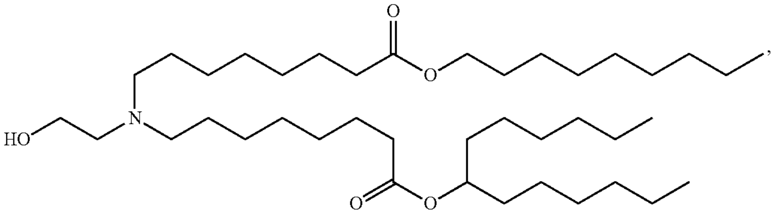
(Compound 57)
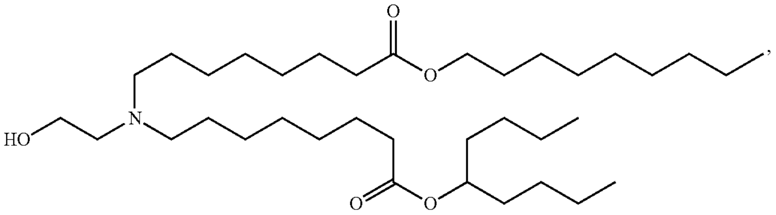
(Compound 58)
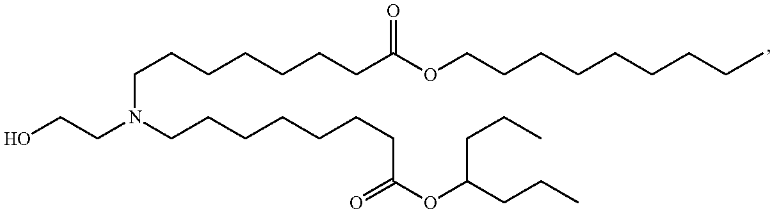
(Compound 59)
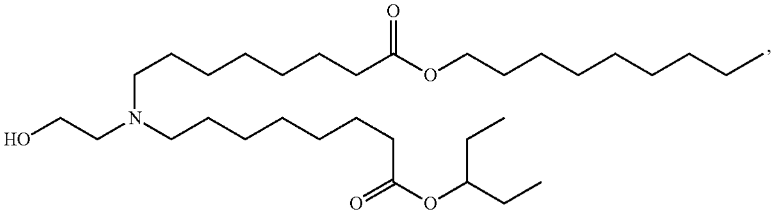
(Compound 60)
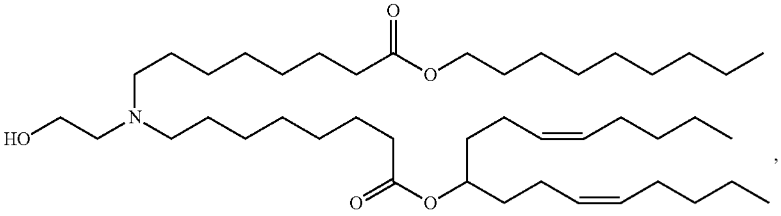
(Compound 61)
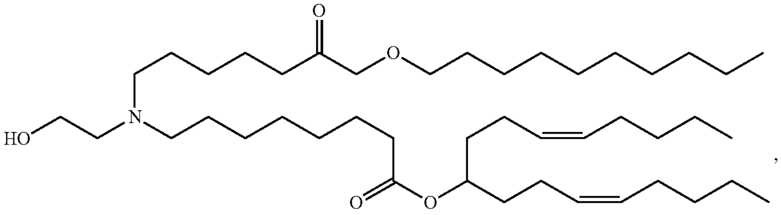
(Compound 62)
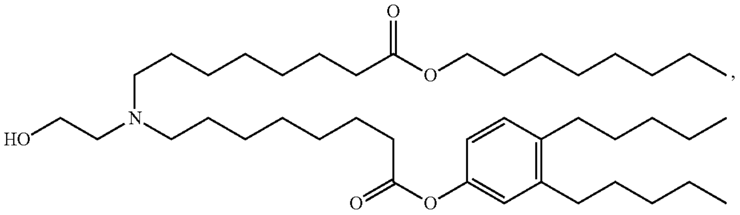

-continued
(Compound 63)
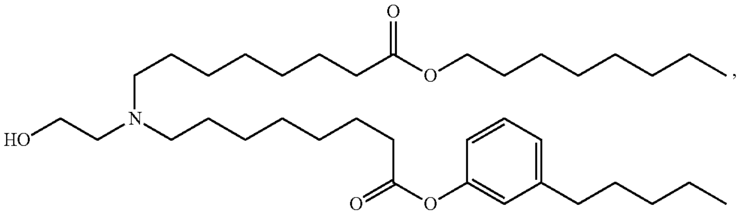
(Compound 64)
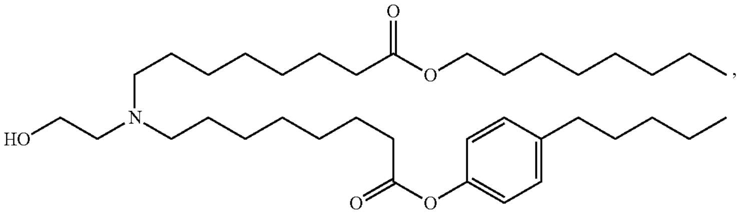
(Compound 65)
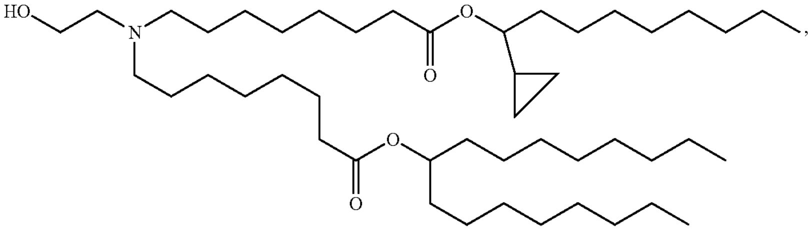
(Compound 66)
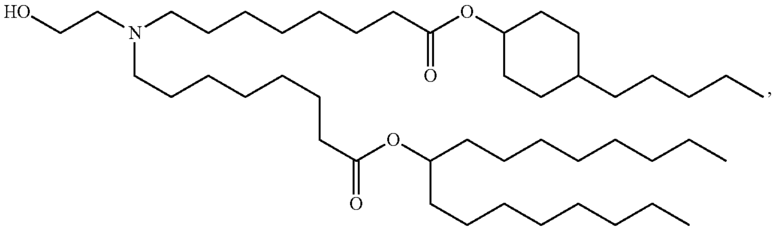
(Compound 67)
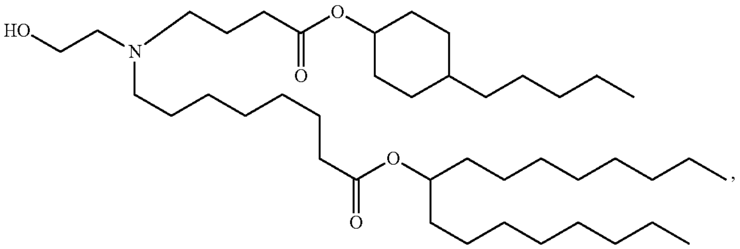
(Compound 68)
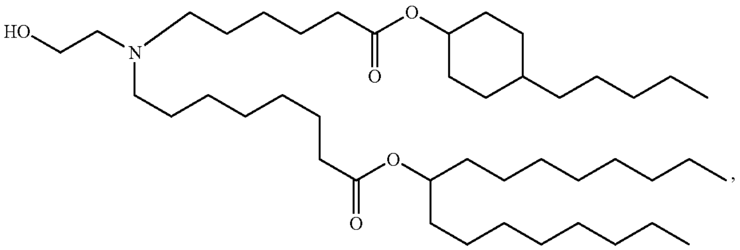

-continued
(Compound 69)
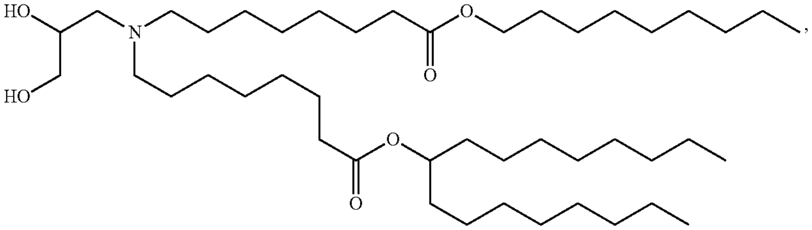
(Compound 70)
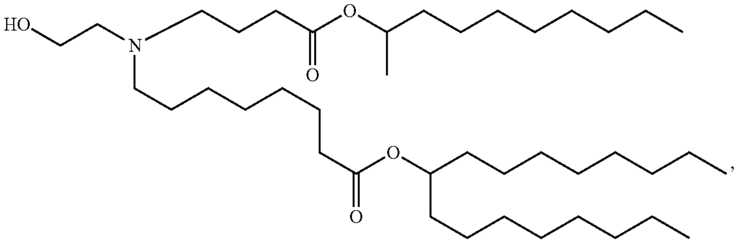
(Compound 71)
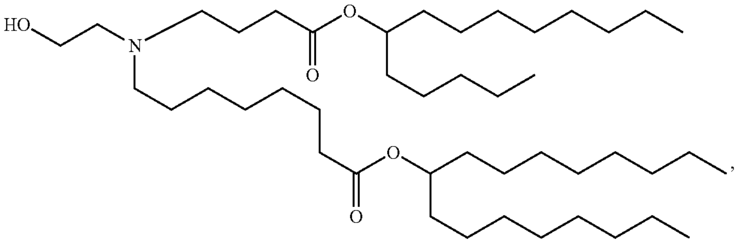
(Compound 72)
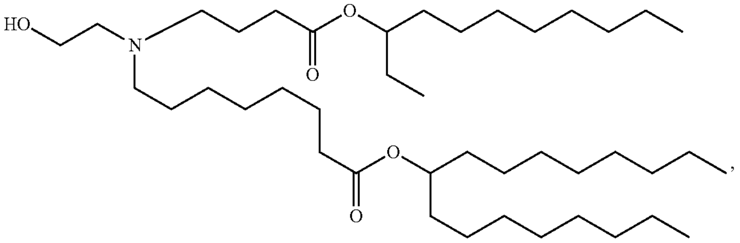
(Compound 73)
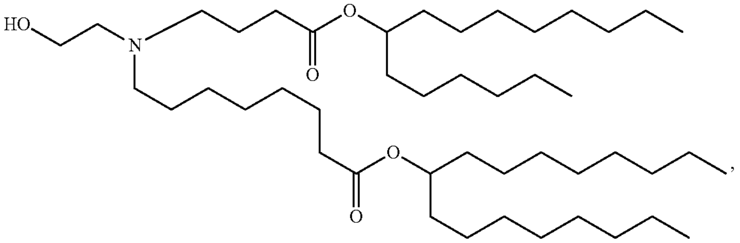
(Compound 74)
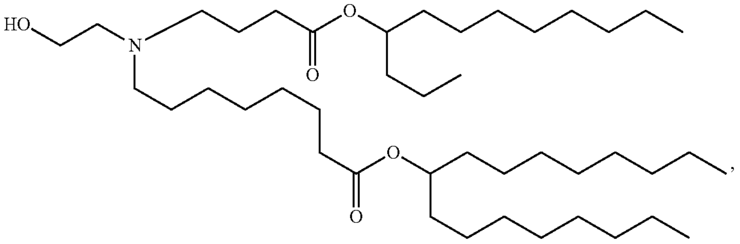

-continued
(Compound 75)
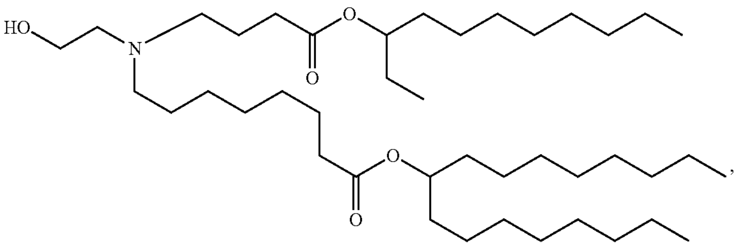
,
(Compound 76)
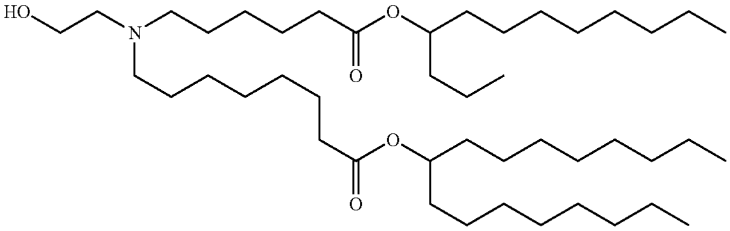
,
(Compound 77)
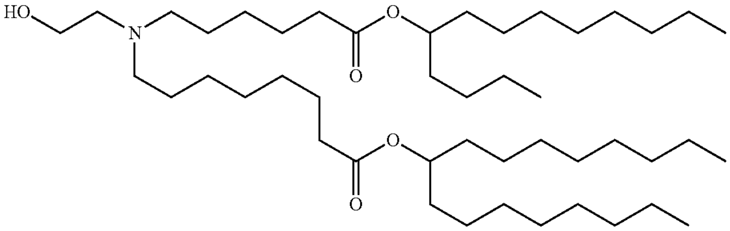
,
(Compound 78)
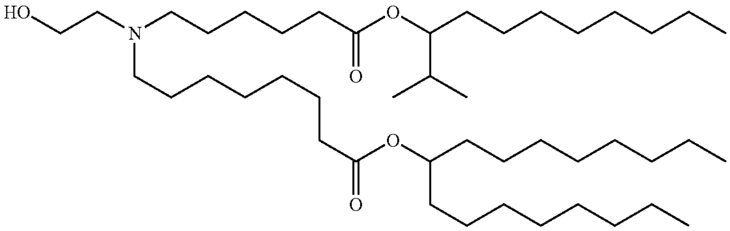
,
(Compound 79)
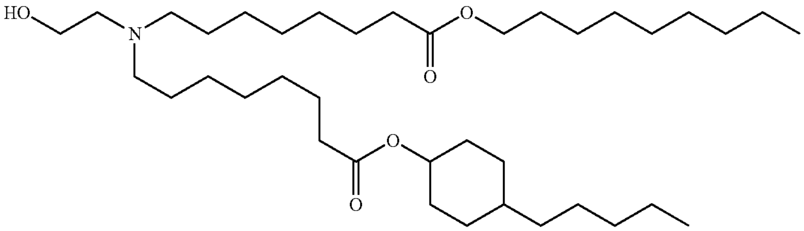
,
(Compound 80)
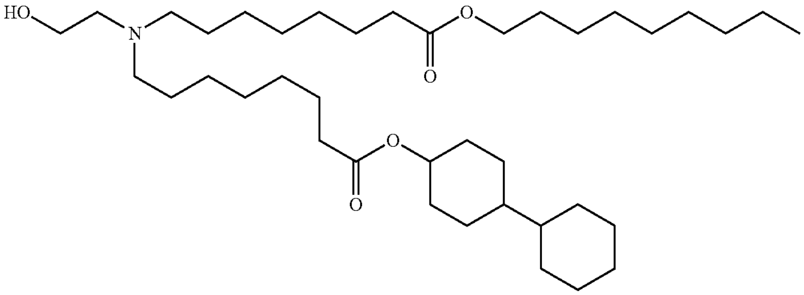
, -continued
(Compound 81)
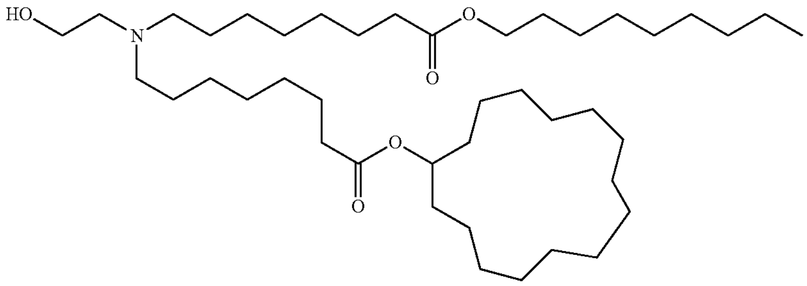,
(Compound 82)
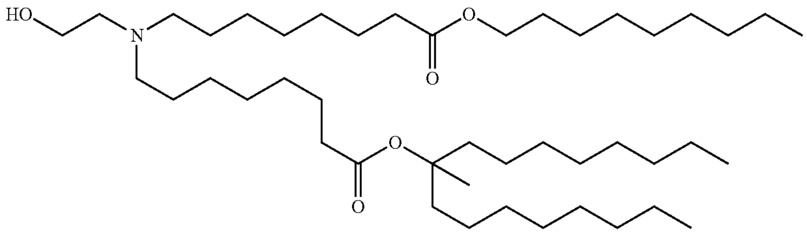,
(Compound 83)
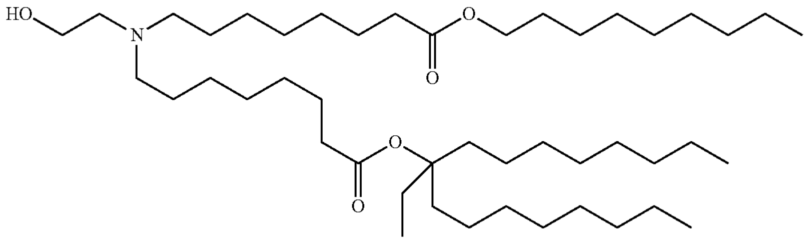,
(Compound 84)
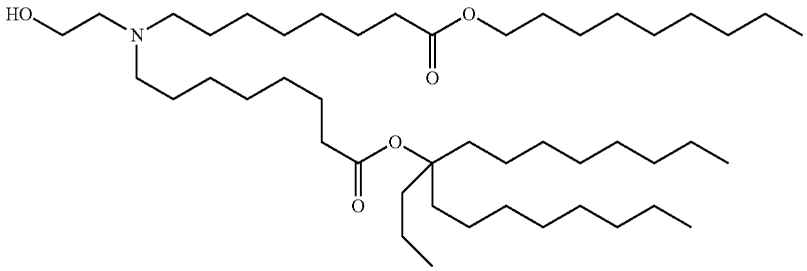,
(Compound 85)
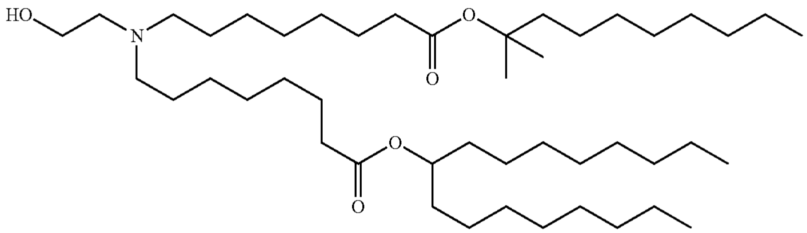,
(Compound 86)
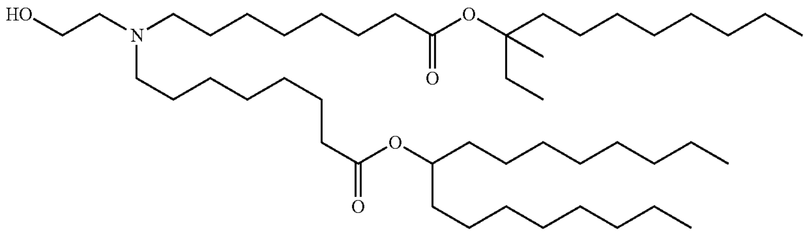, -continued
(Compound 87)
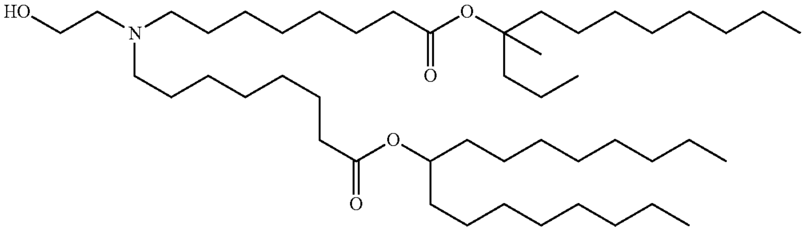
,
(Compound 88)
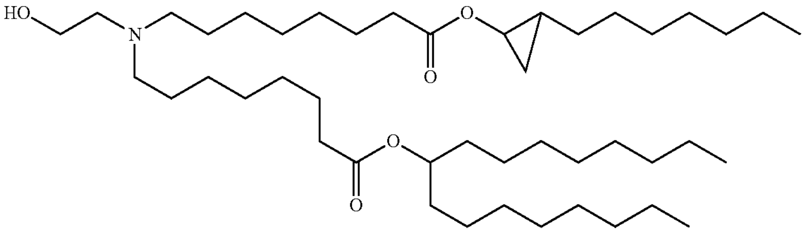
,
(Compound 89)
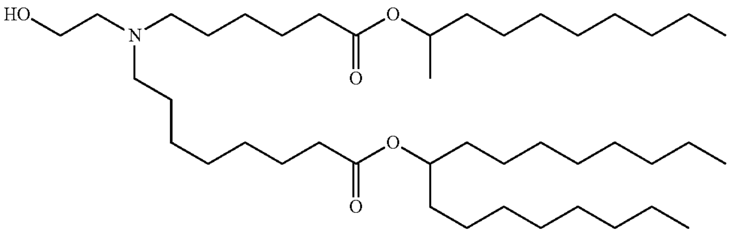
,
(Compound 90)
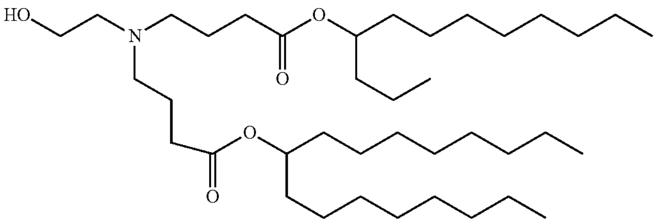
,
(Compound 91)
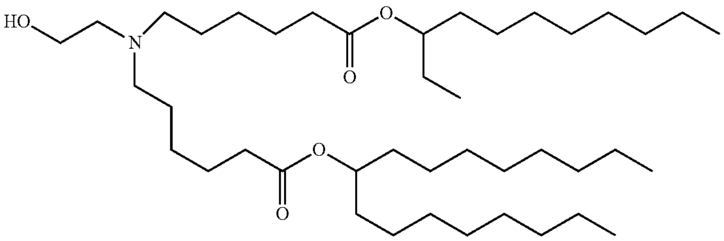
,
(Compound 92)
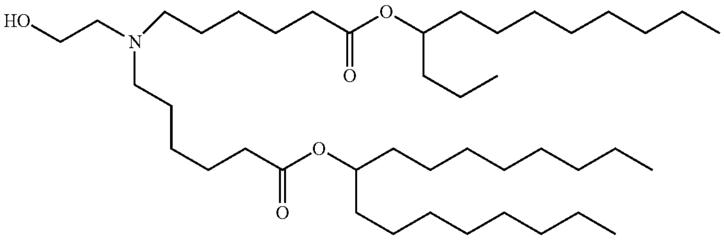
, -continued
(compound 93)
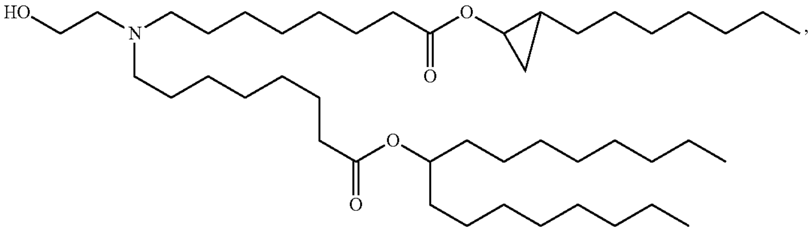
(Compound 94)
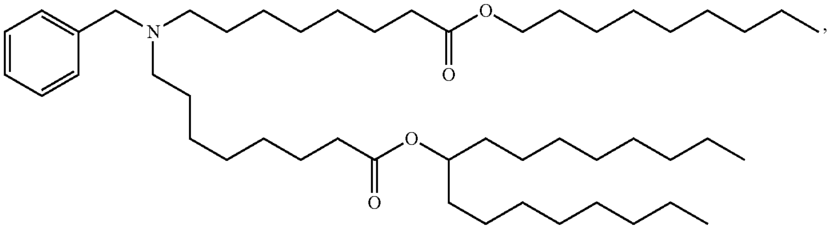
(Compound 95)
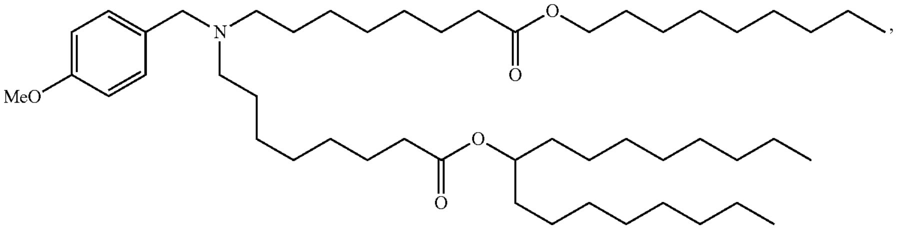
(Compound 96)
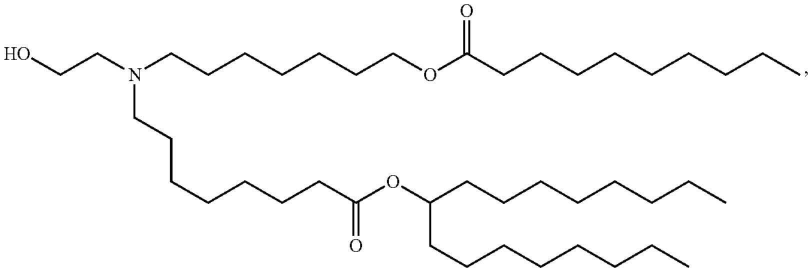
(Compound 97)
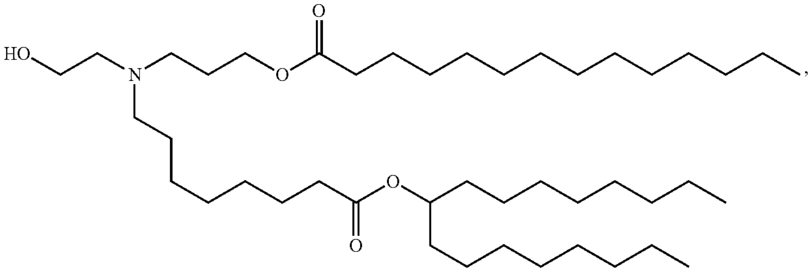
(Compound 98)
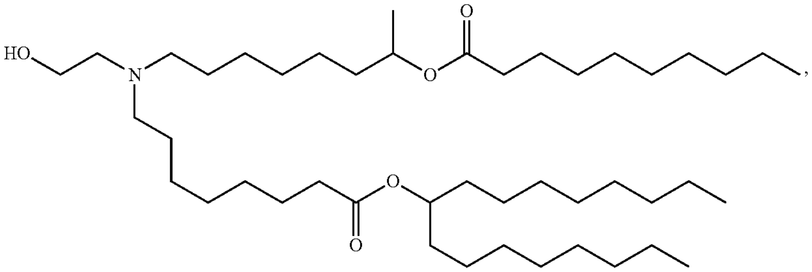

-continued
(Compound 99)
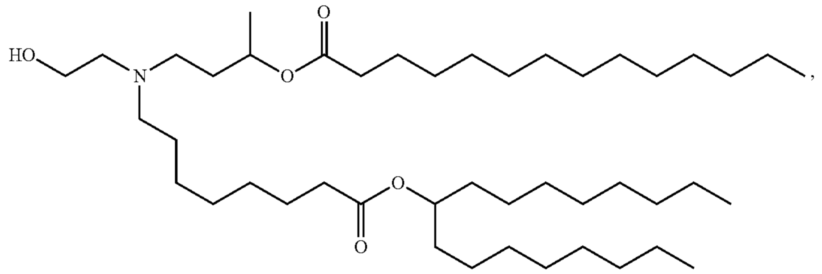
(Compound 100)
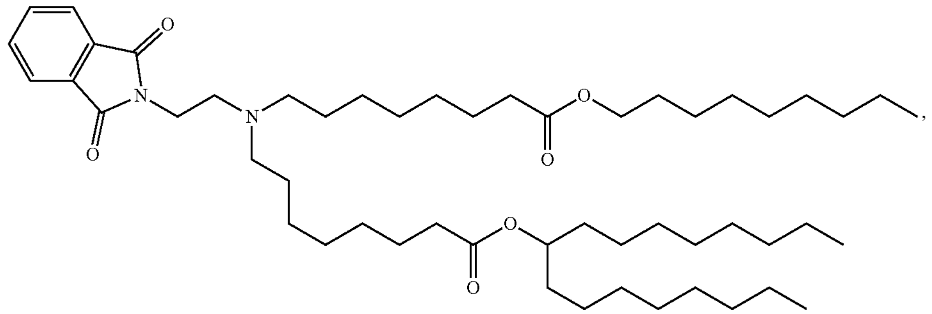
(Compound 101)
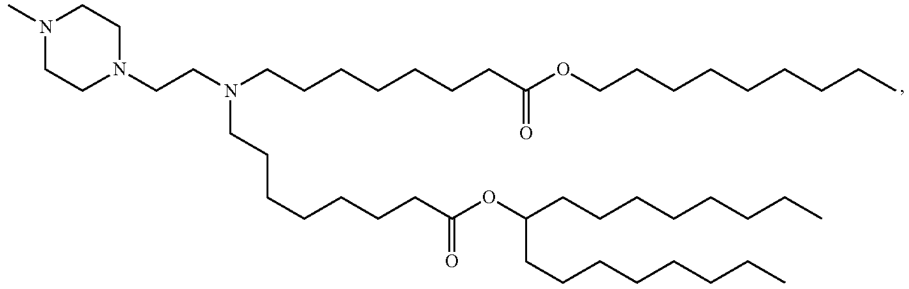
(Compound 102)
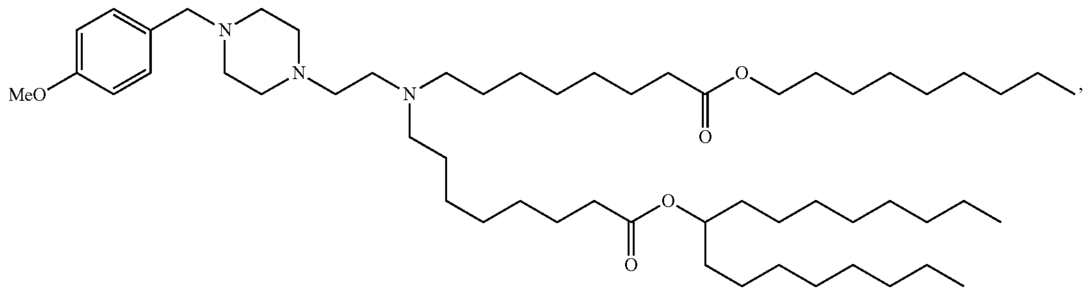
(Compound 103)
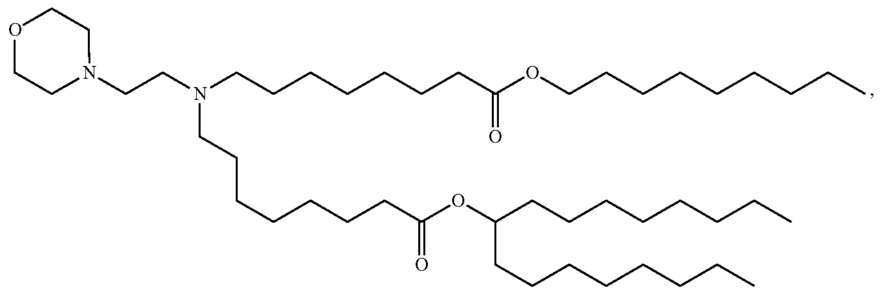

-continued
(Compound 104)
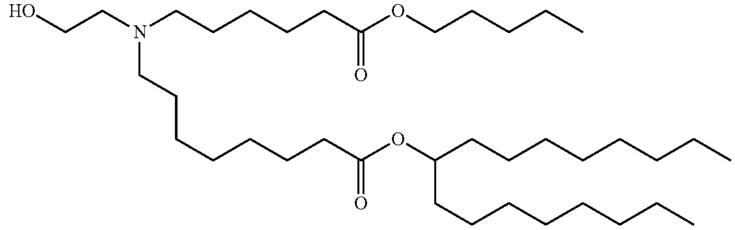
,
(Compound 105)
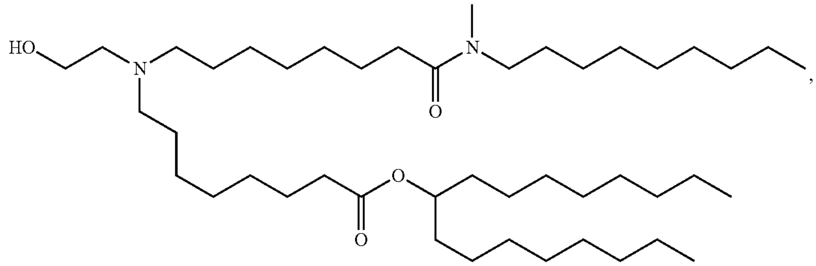
,
(Compound 106)
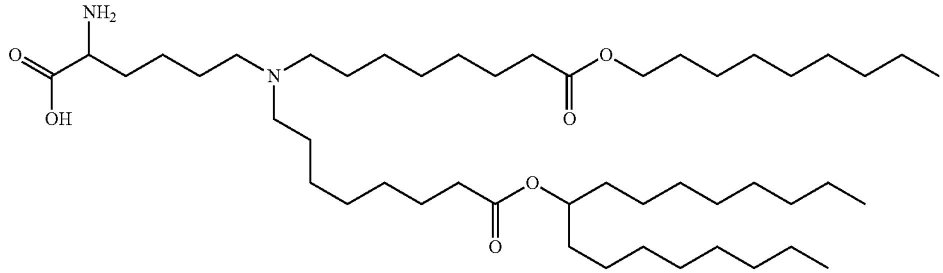
,
(Compound 107)
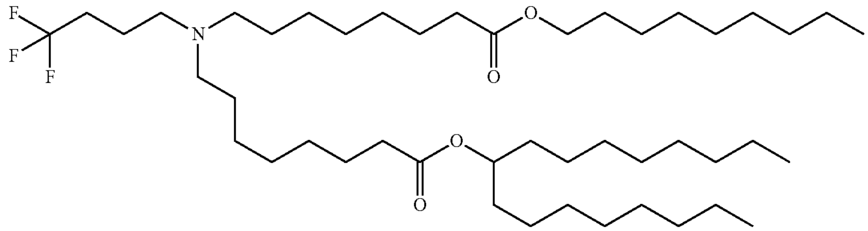
,
(Compound 108)
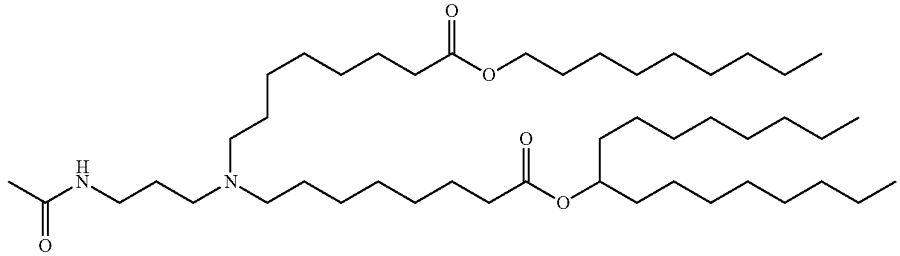
,
(Compound 109)
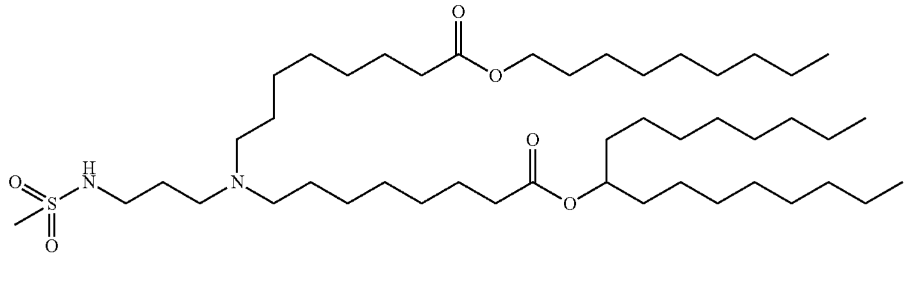
, -continued
(Compound 110)
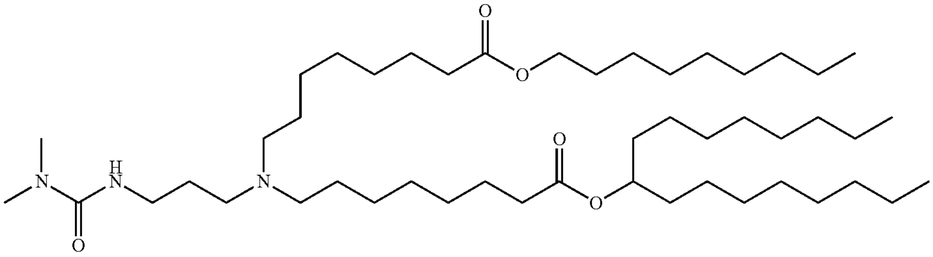
,
(Compound 111)
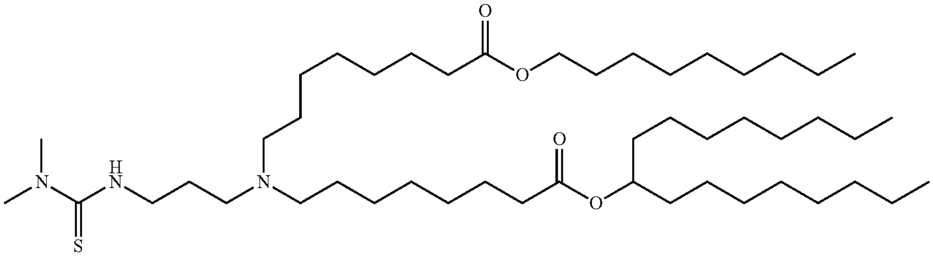
,
(Compound 112)
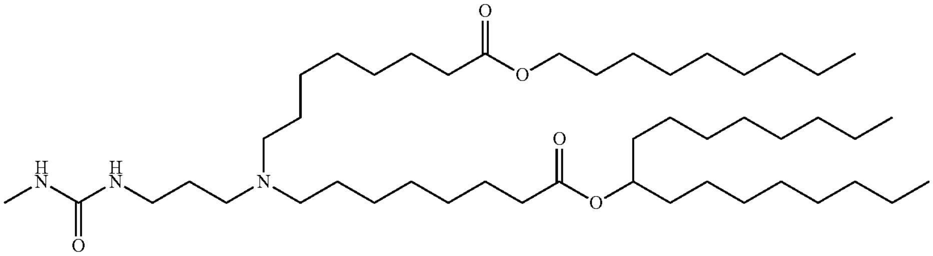
,
(Compound 113)
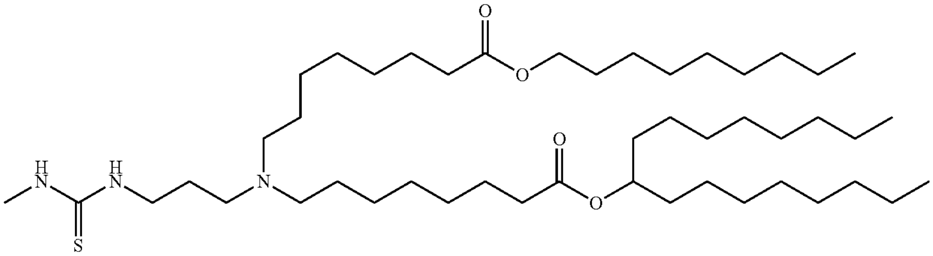
,
(Compound 114)
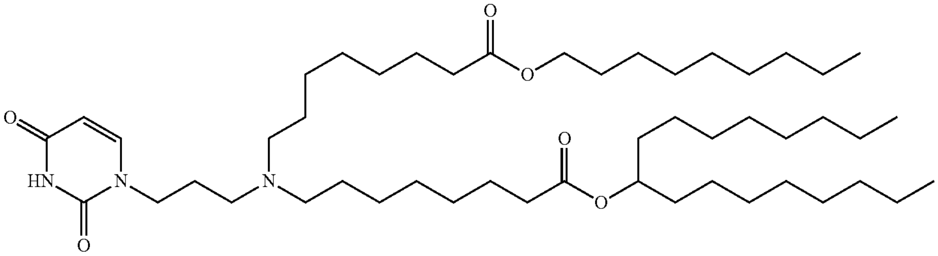
,
(Compound 115)
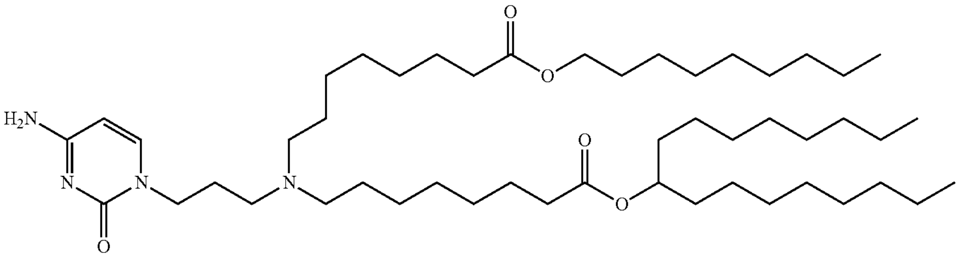
, -continued
(Compound 116)
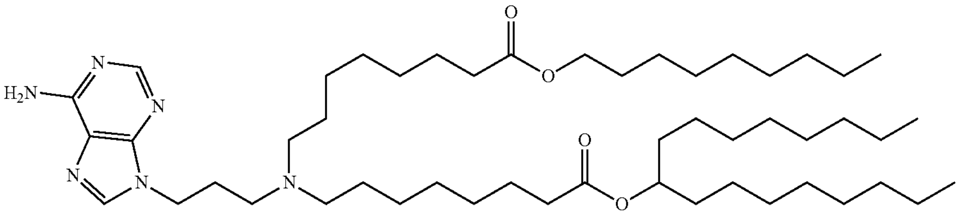
,
(Compound 117)
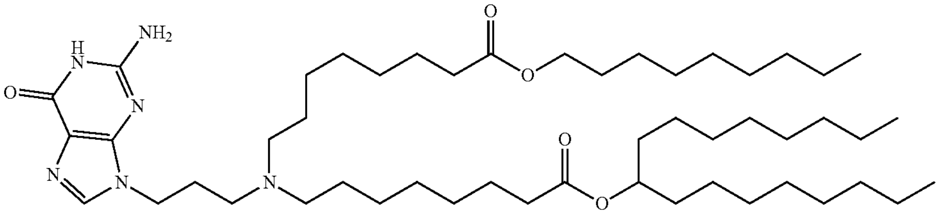
,
(Compound 118)
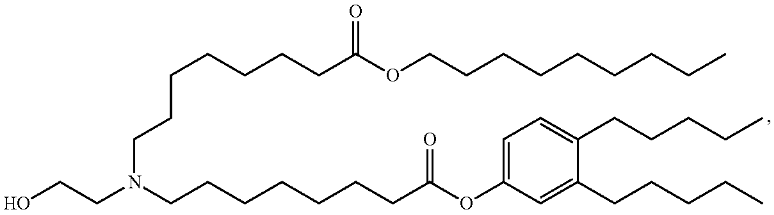
,
(Compound 119)
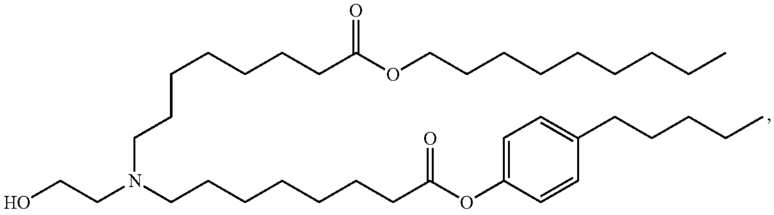
,
(Compound 120)
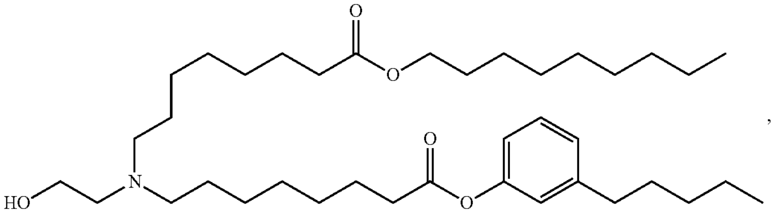
,
(Compound 121)
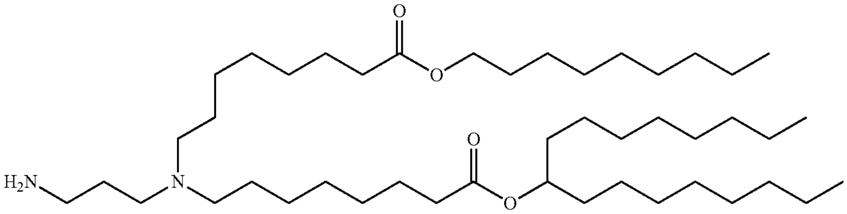
,
(Compound 122)
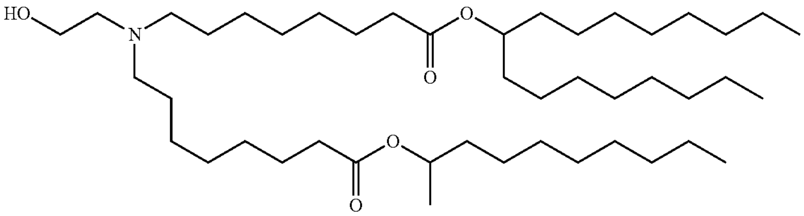
, -continued
(Compound 123)
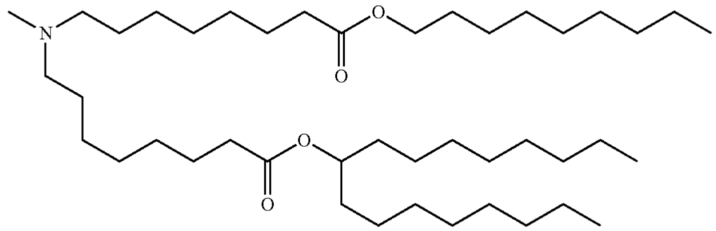
,
(Compound 124)
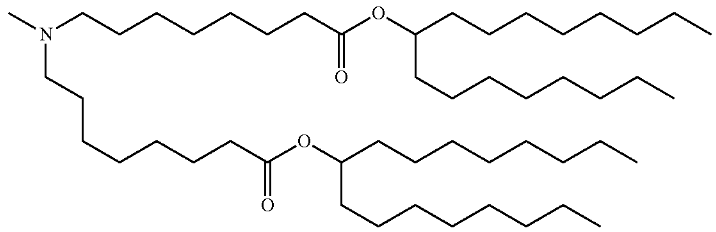
,
(Compound 125)
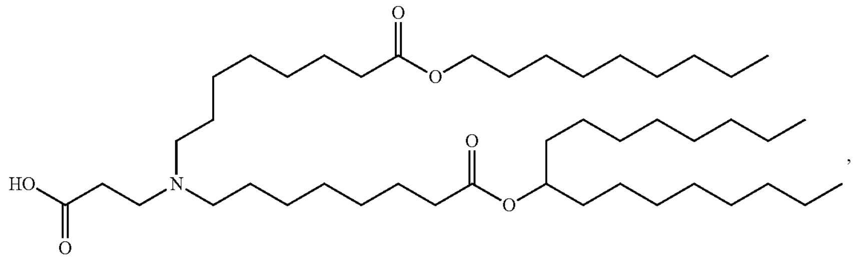
,
(Compound 126)
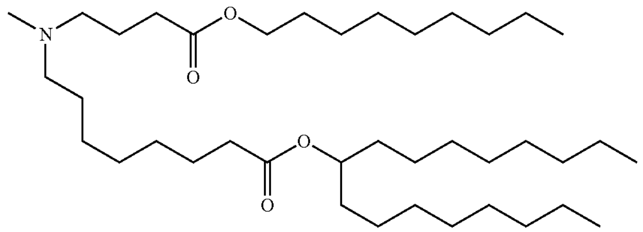
,
(Compound 127)
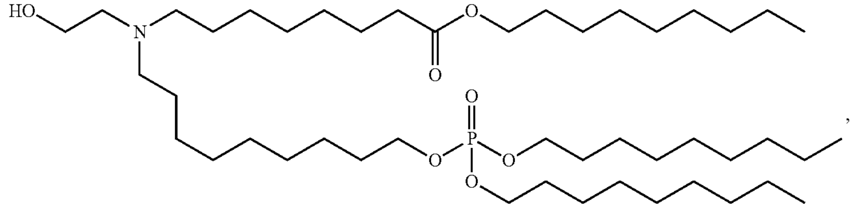
,
(Compound 128)
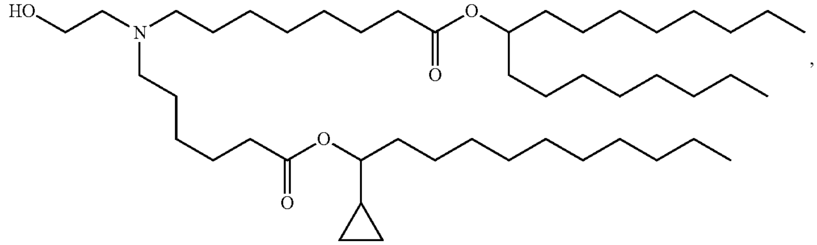
, -continued
(Compound 129)
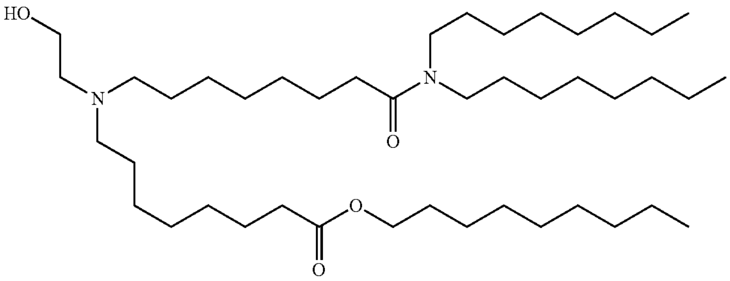,
(Compound 130)
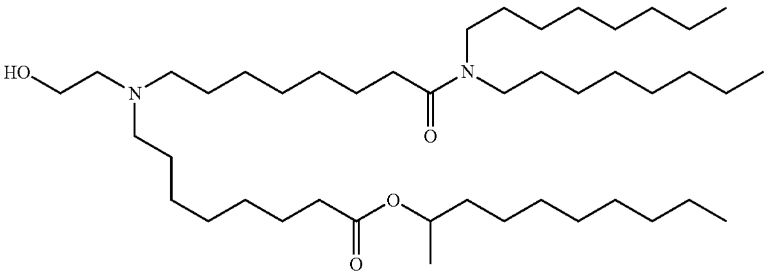,
(Compound 131)
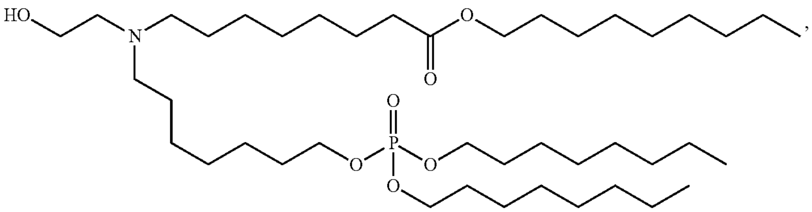,
(Compound 132)
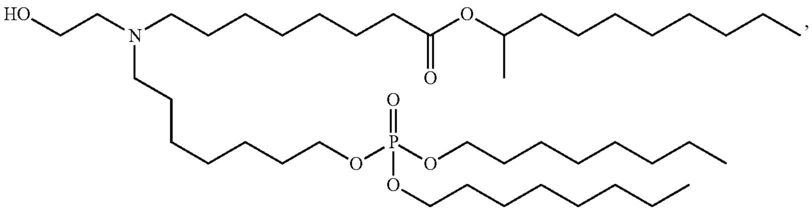,
(Compound 133)
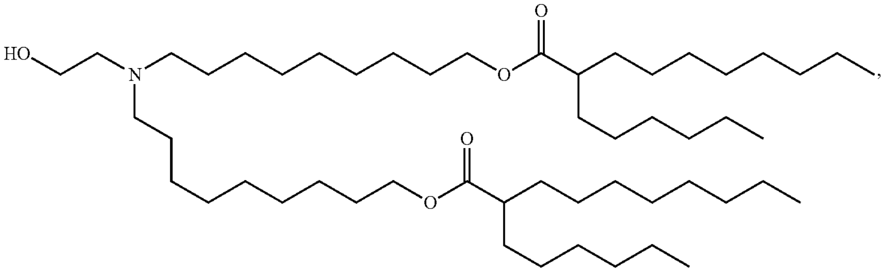,
(Compound 134)
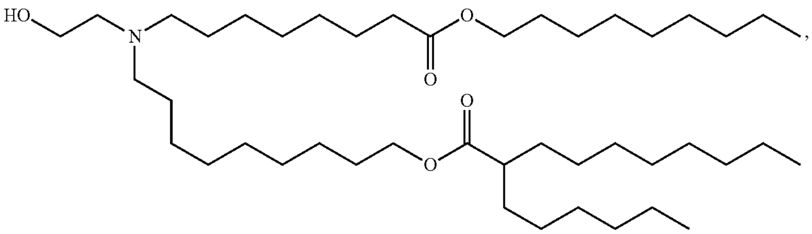, -continued
(Compound 135)
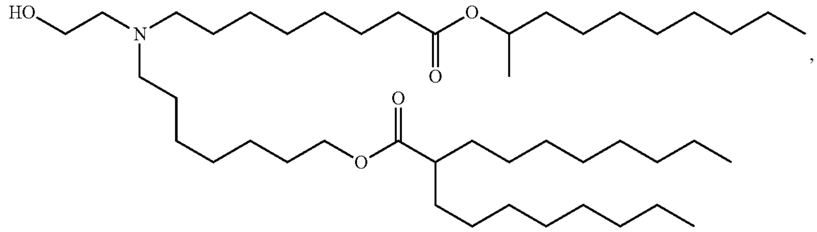
,
(Compound 136)
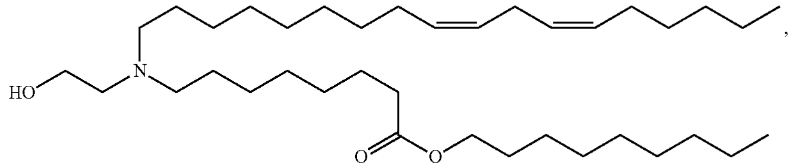
,
(Compound 137)
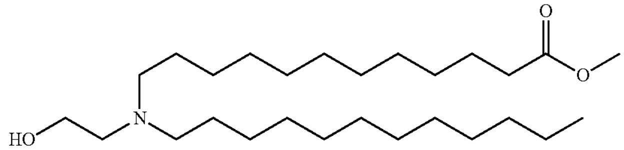
,
(Compound 138)
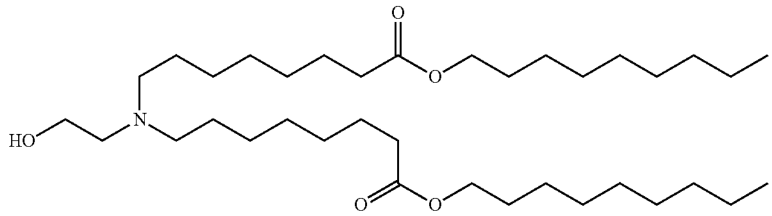
,
(Compound 139)
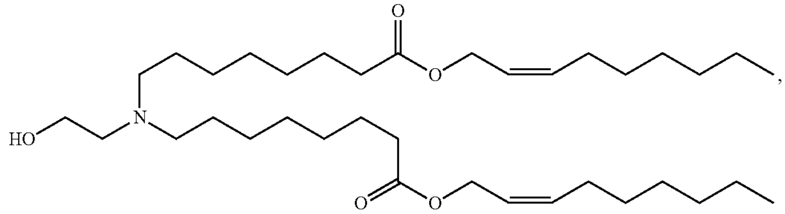
,
(Compound 140)
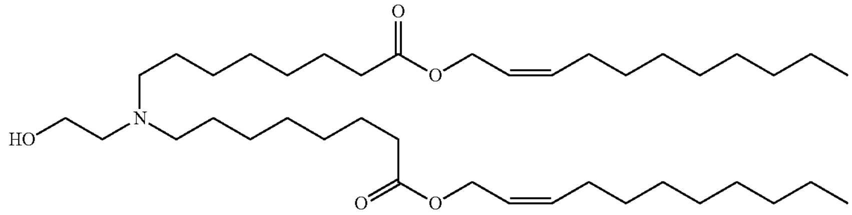
,
(Compound 141)
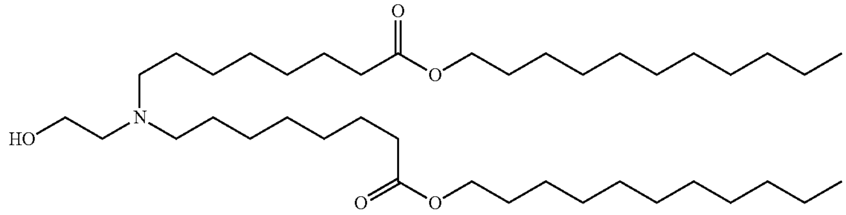
, -continued
(Compound 142)
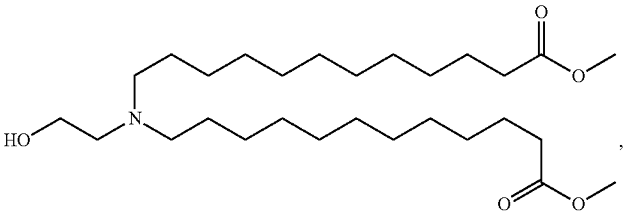
,
(Compound 143)
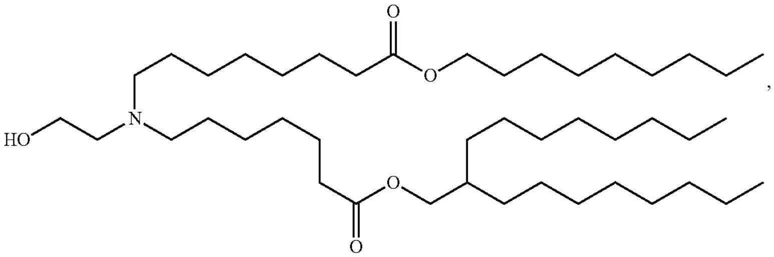
,
(Compound 144)
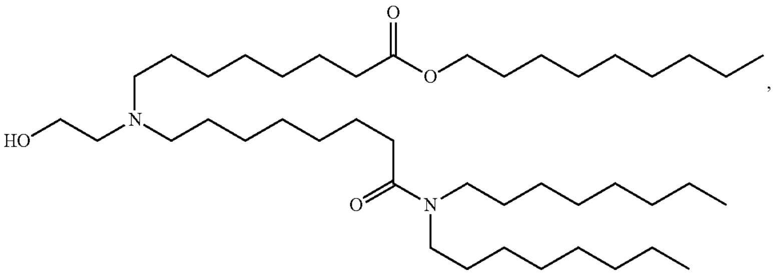
,
(Compound 145)
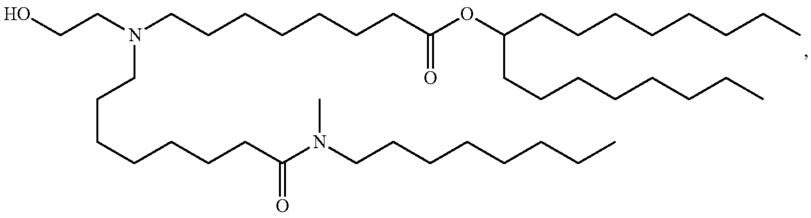
,
(Compound 146)
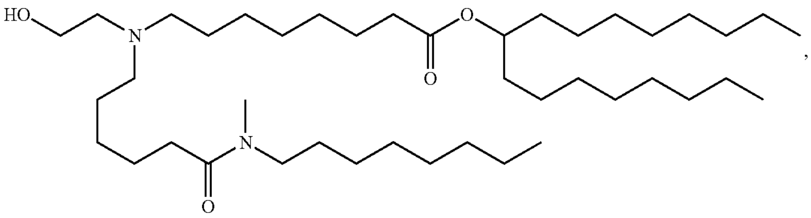
,
(Compound 147)
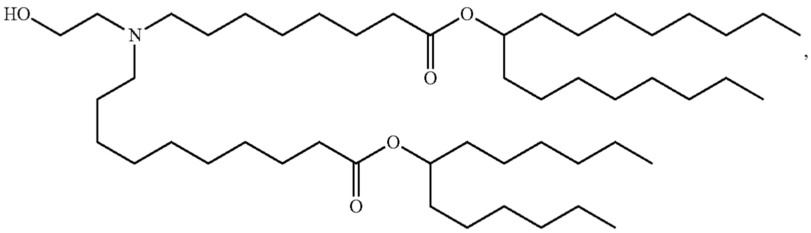
, -continued
(Compound 148)
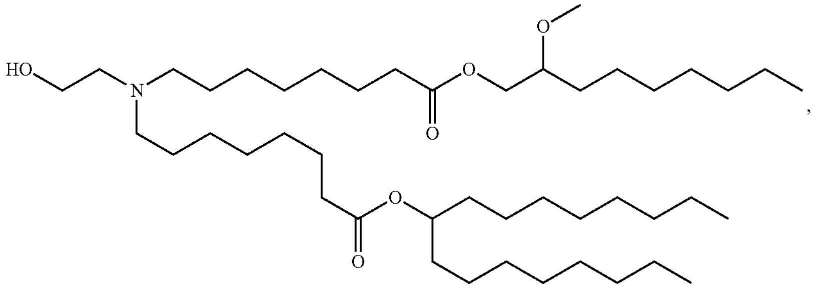
,
(Compound 149)
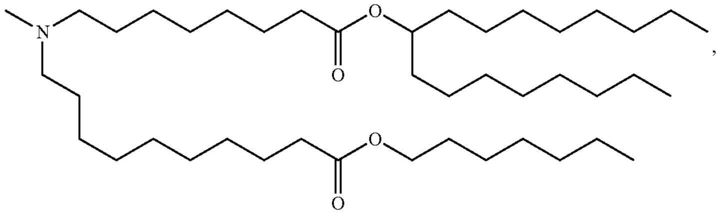
,
(Compound 150)
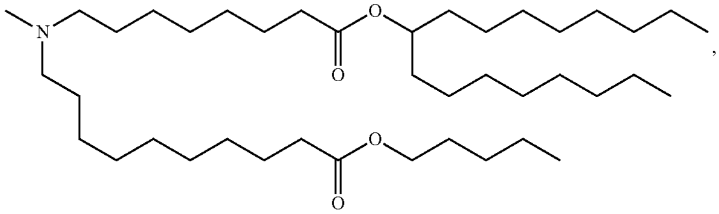
,
(Compound 151)
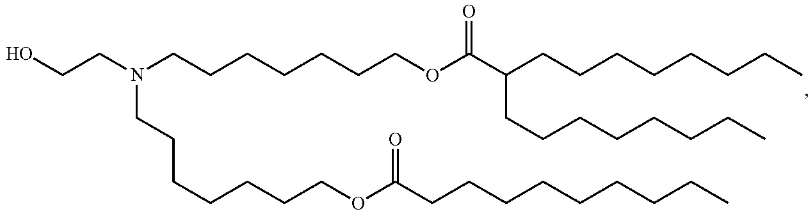
,
(Compound 152)
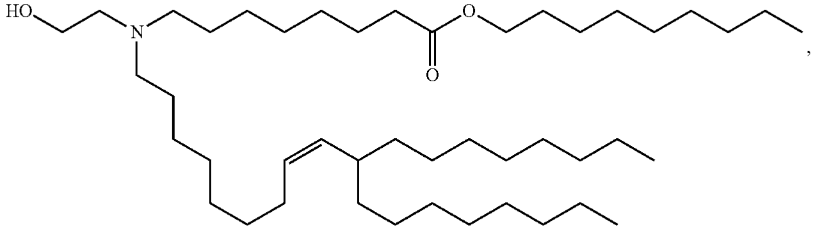
,
(Compound 153)
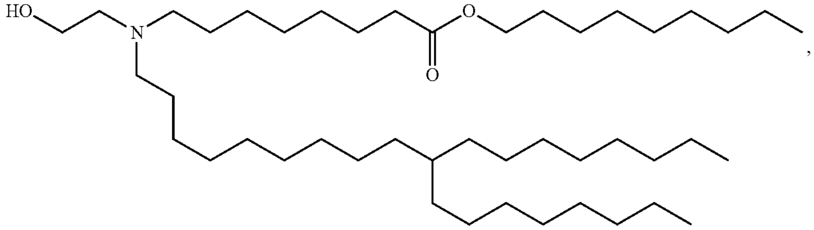
, -continued
(Compound 154)
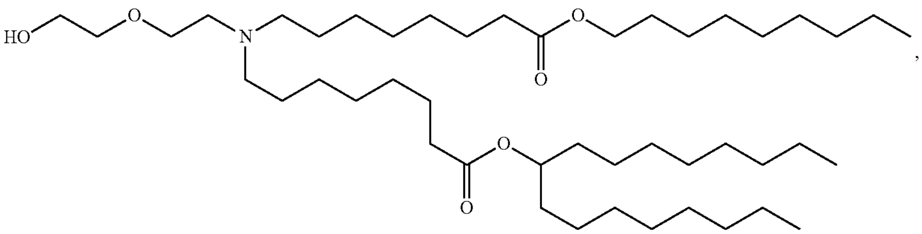
,
(Compound 155)
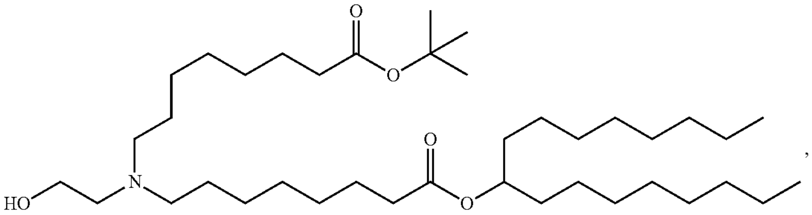
,
(Compound 156)
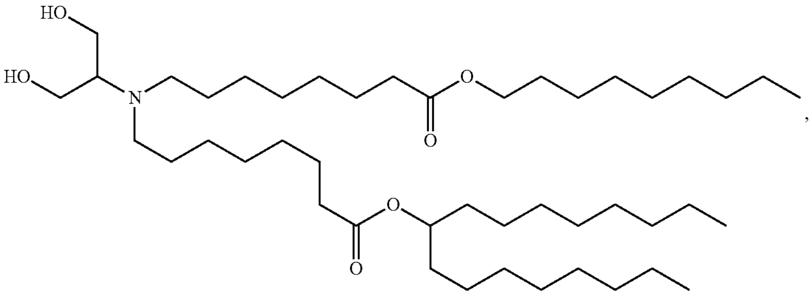
,
(Compound 157)
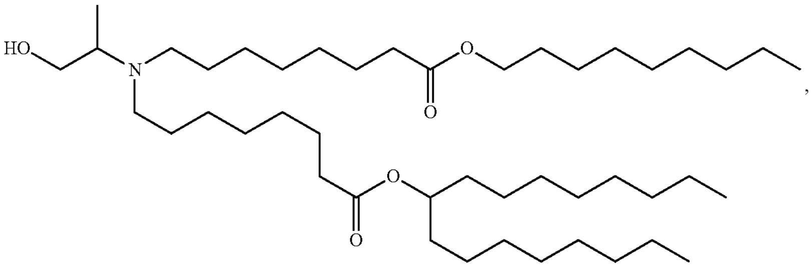
,
(Compound 158)
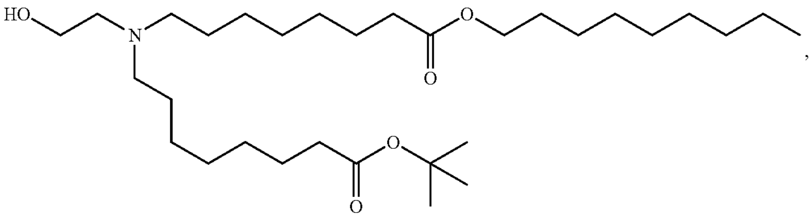
,
(Compound 159)
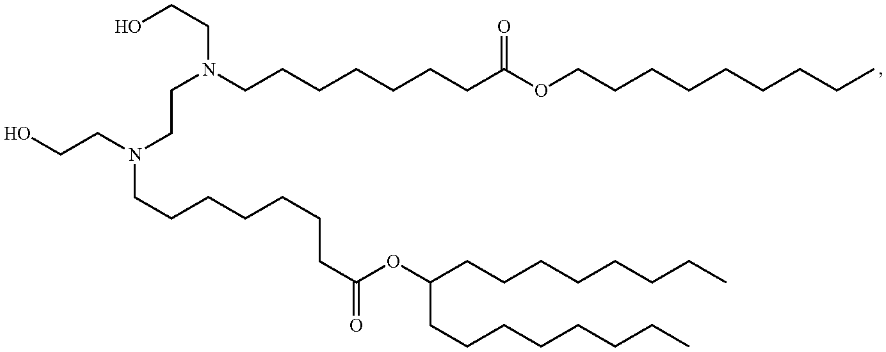
, -continued
(Compound 160)
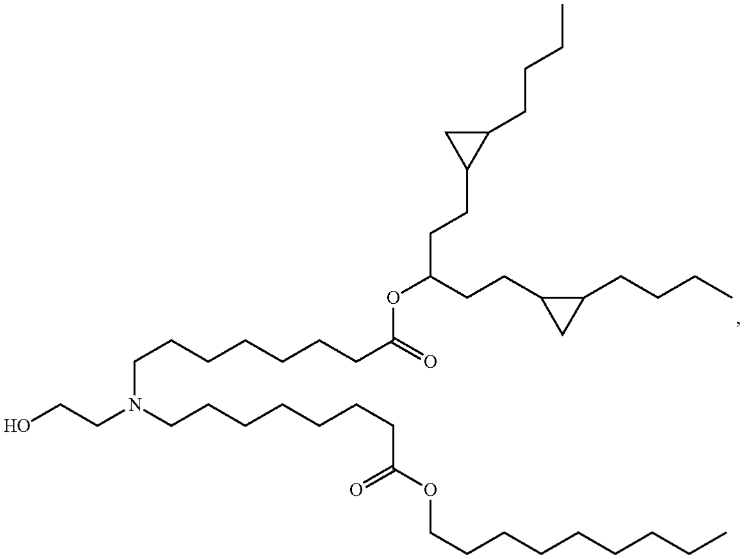
(Compound 161)
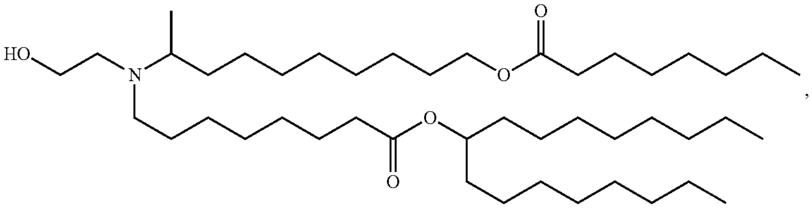
(Compound 162)
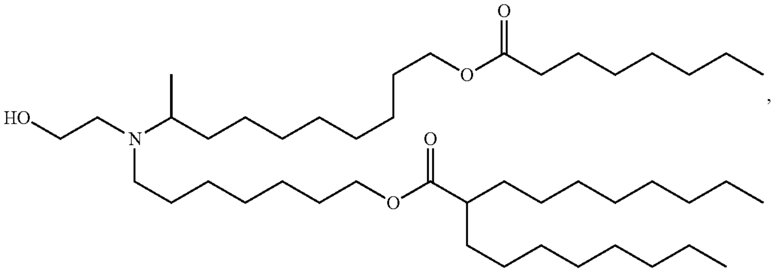
(Compound 163)
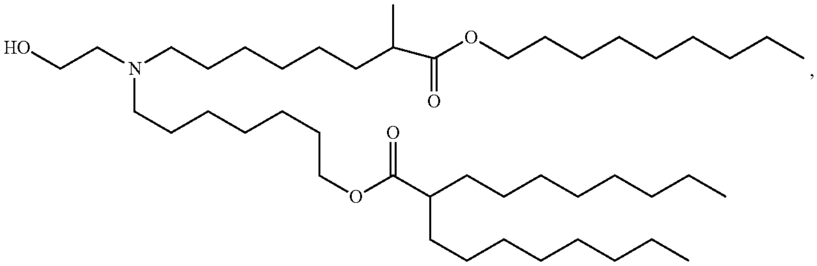
(Compound 164)
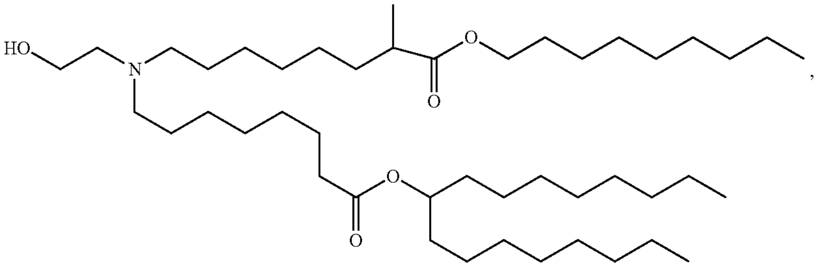

-continued
(Compound 165)
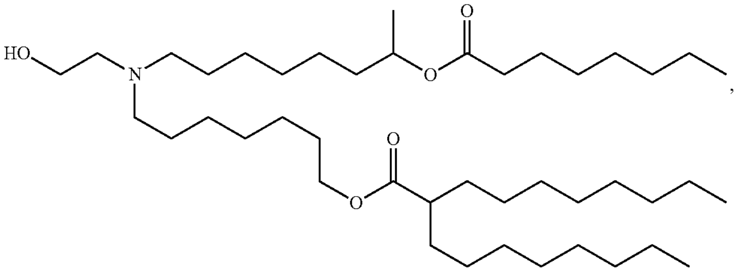
(Compound 166)
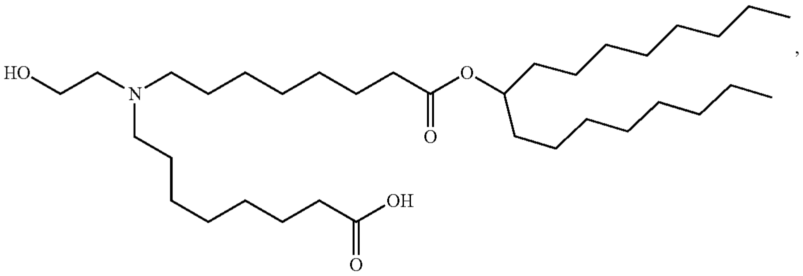
(Compound 167)
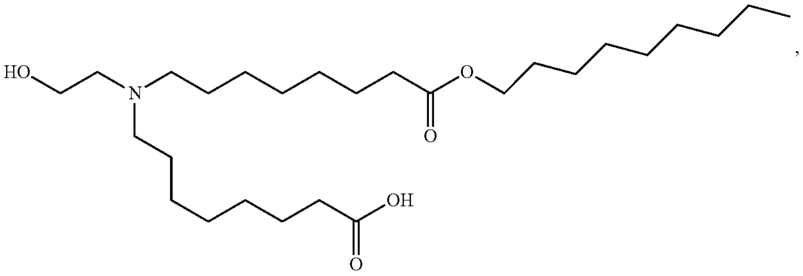
(Compound 168)
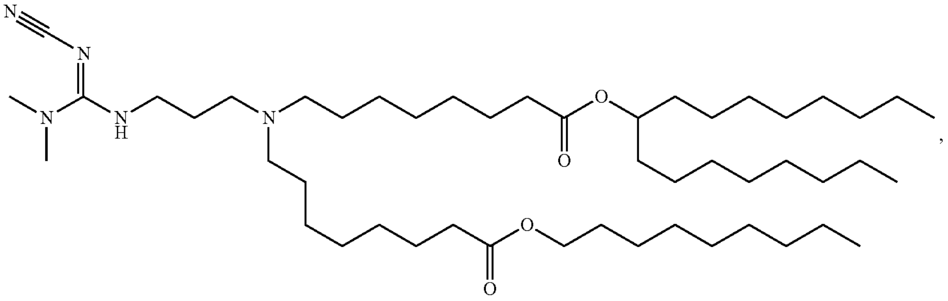
(Compound 169)
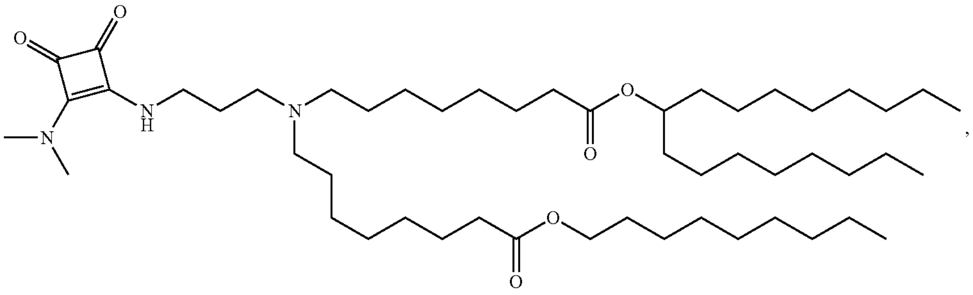

-continued
(Compound 170)
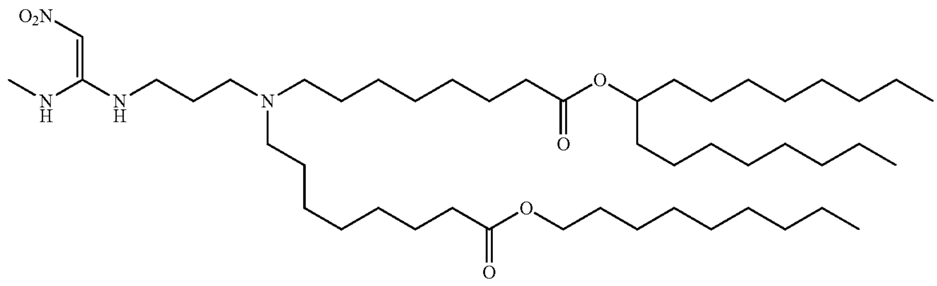
,
(Compound 171)
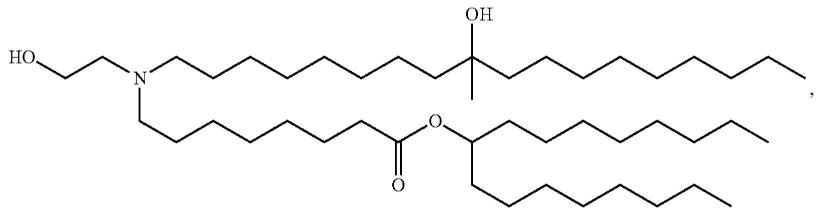
,
(Compound 172)
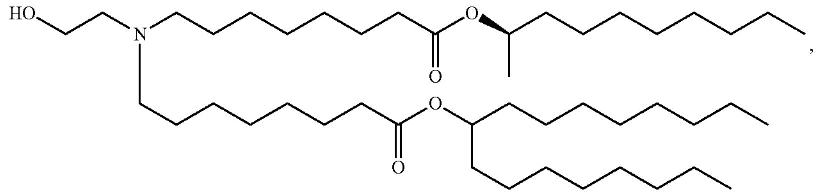
,
(Compound 173)
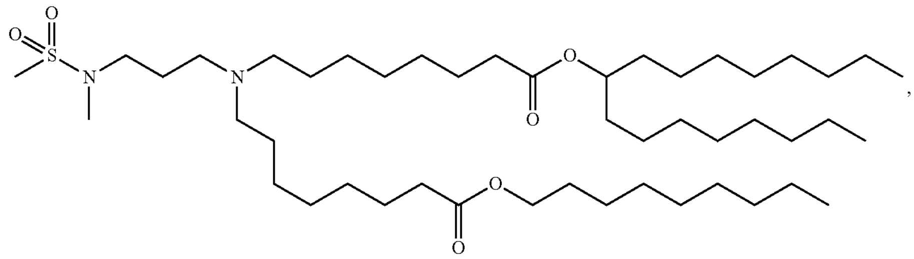
,
(Compound 174)
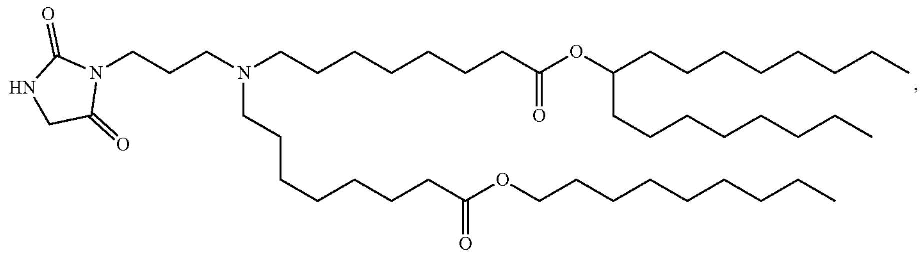
,
(Compound 175)
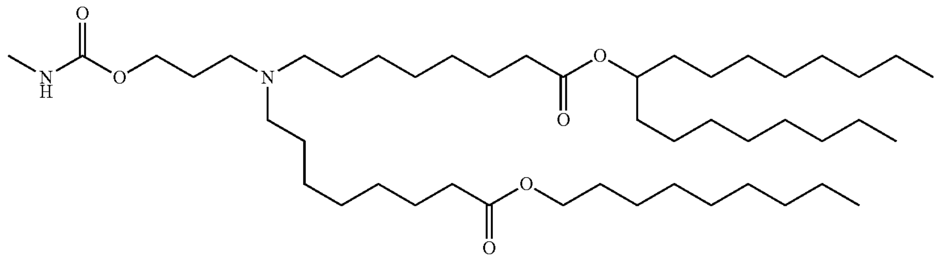
, -continued
(Compound 176)
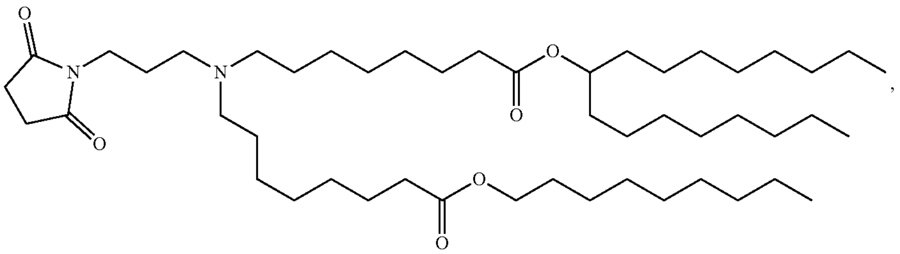
(Compound 177)
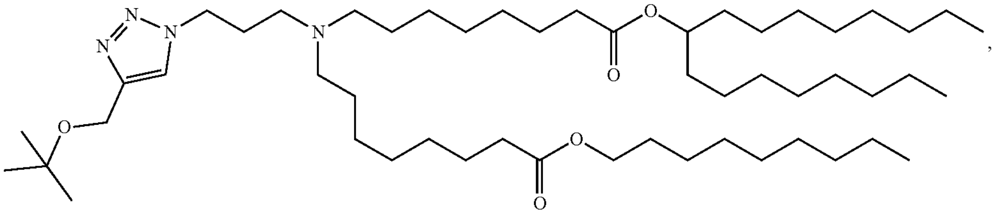
(Compound 178)
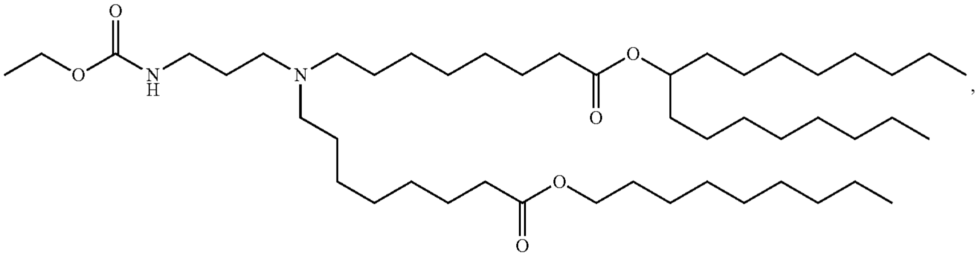
(Compound 179)
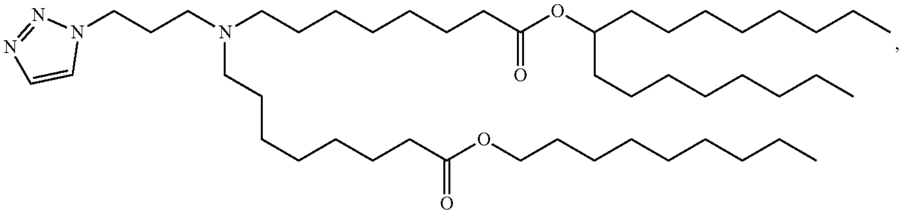
(Compound 180)
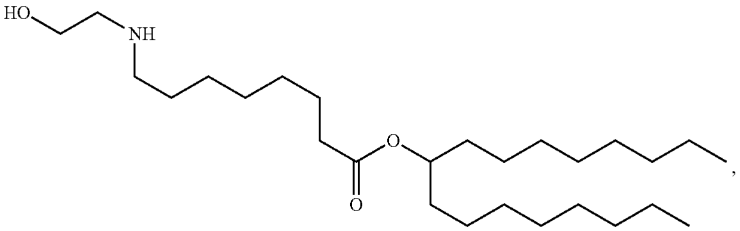
(Compound 181)
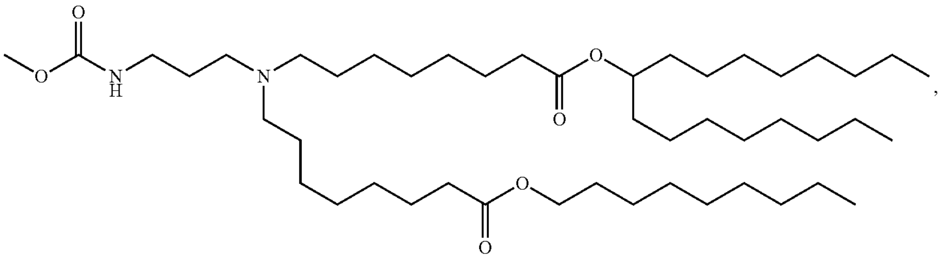

-continued
(Compound 182)
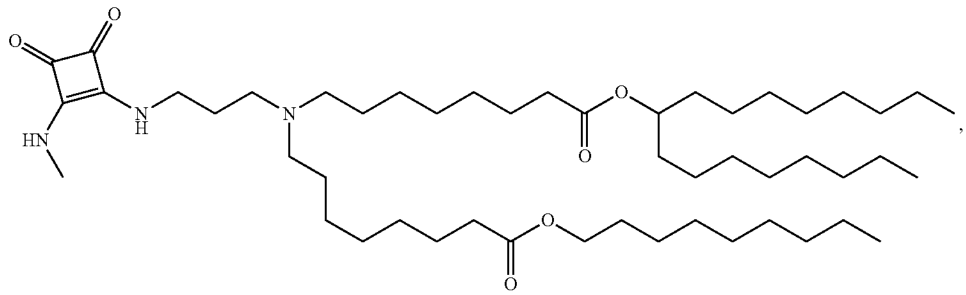
,
(Compound 183)
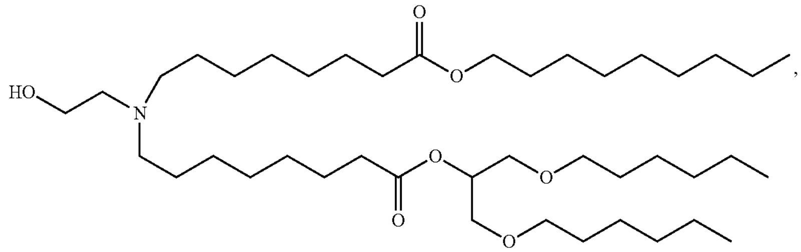
,
(Compound 184)
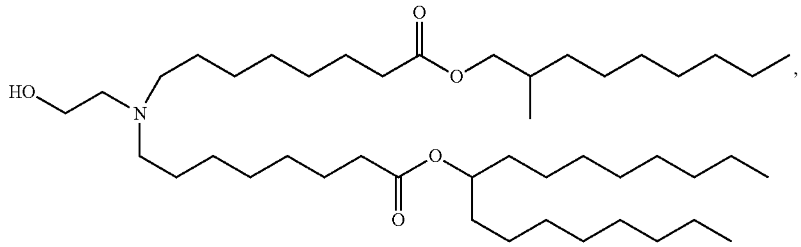
,
(Compound 185)
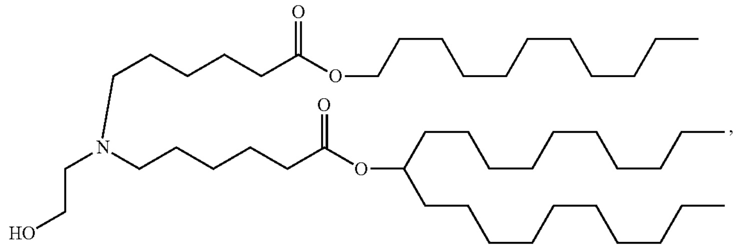
,
(Compound 186)
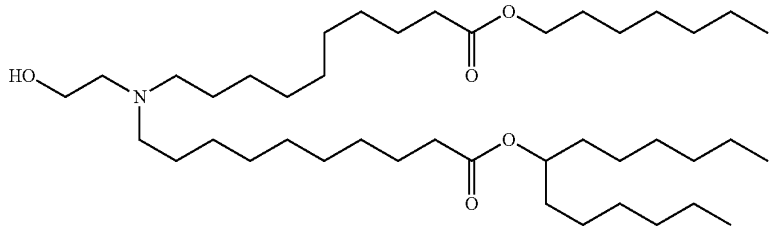
,
(Compound 187)
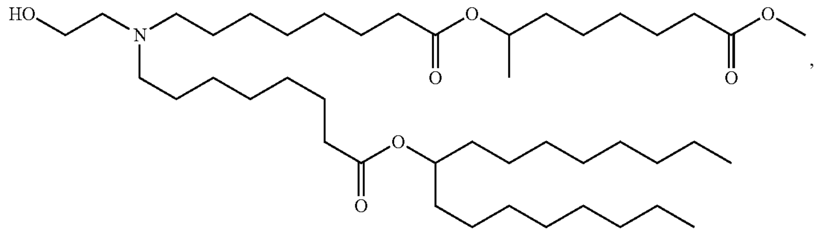
, -continued
(Compound 188)
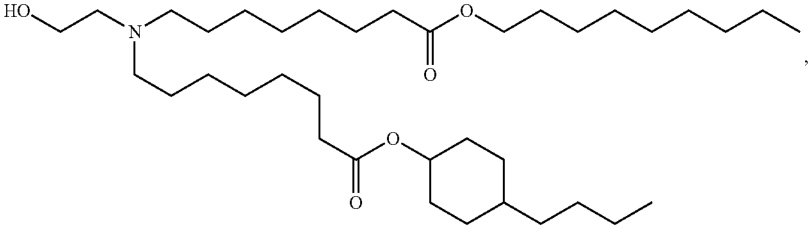
(Compound 189)
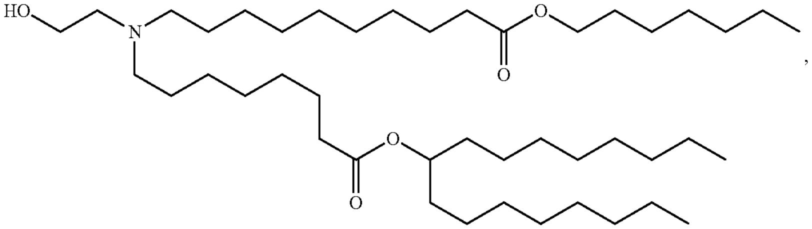
(Compound 190)
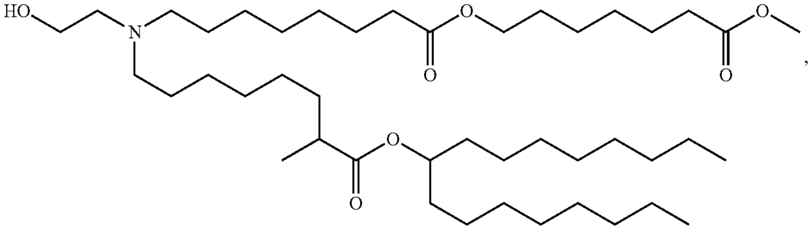
(Compound 191)
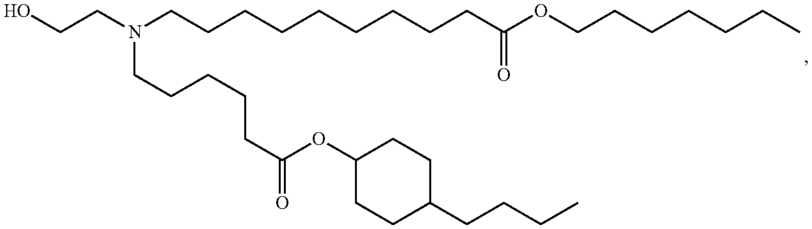
(Compound 192)
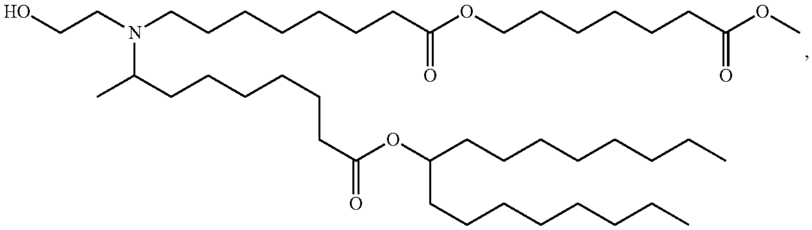
(Compound 193)
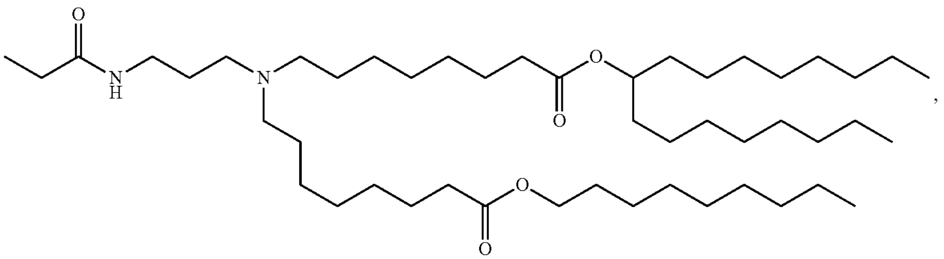

-continued
(Compound 194)
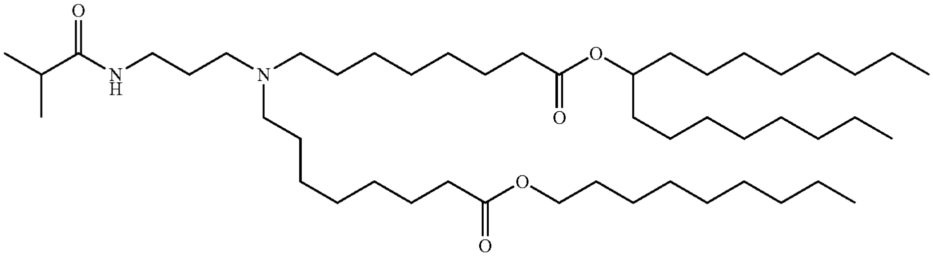
,
(Compound 195)
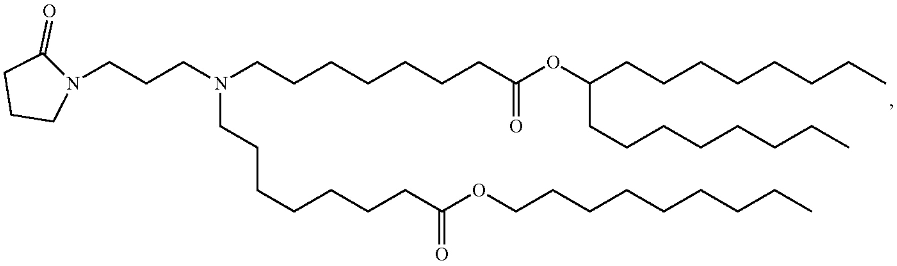
,
(Compound 196)
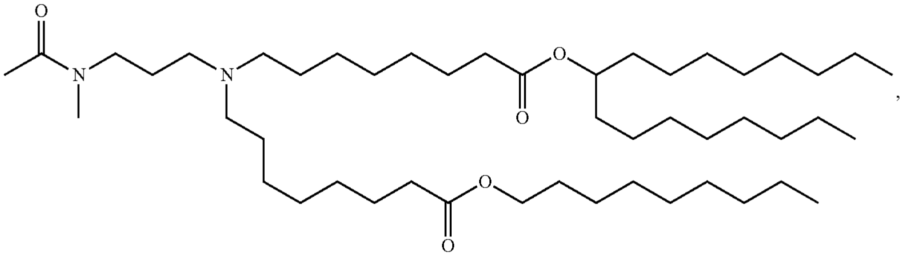
,
(Compound 197)
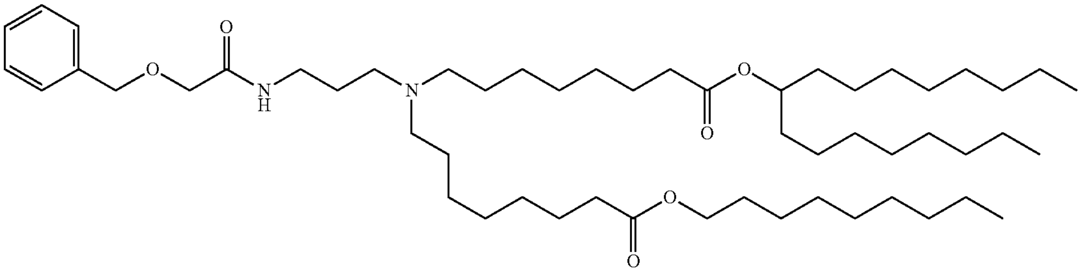
,
(Compound 198)
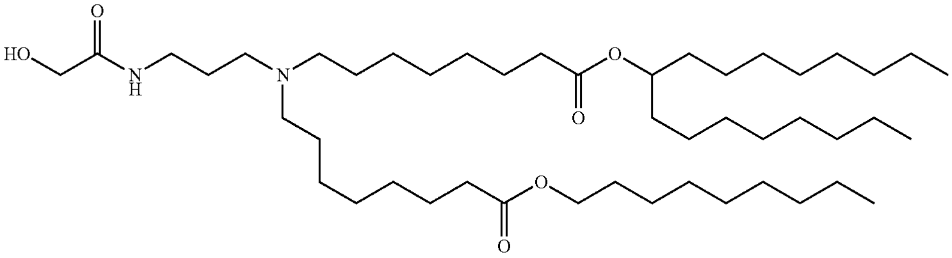
,
(Compound 199)
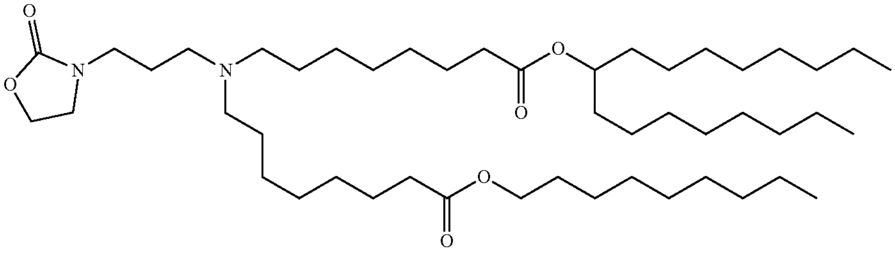
, -continued
(Compound 200)
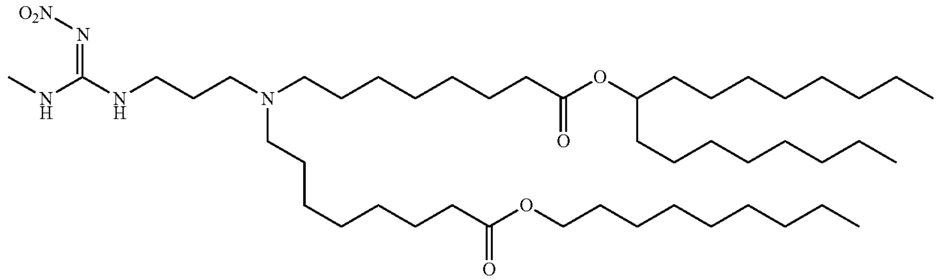
,
(Compound 201)
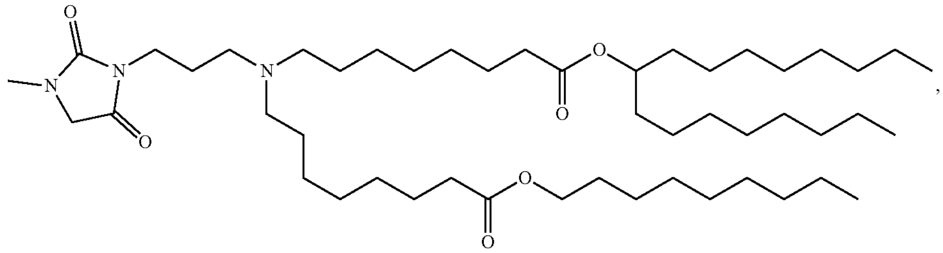
,
(Compound 202)
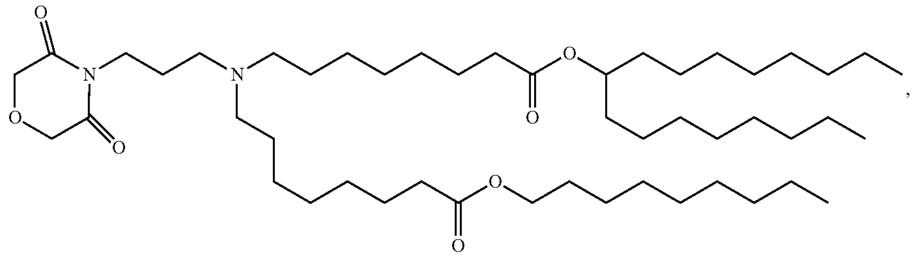
,
(Compound 203)
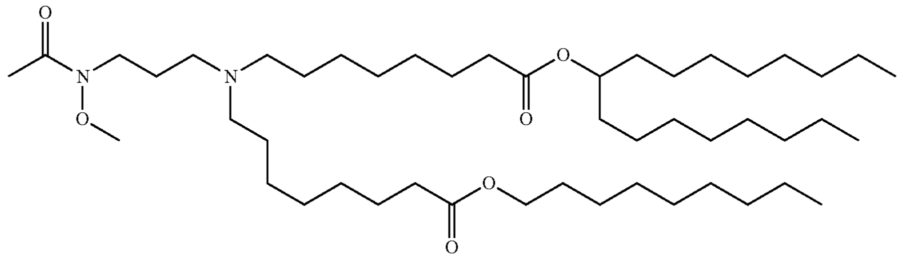
,
(Compound 204)
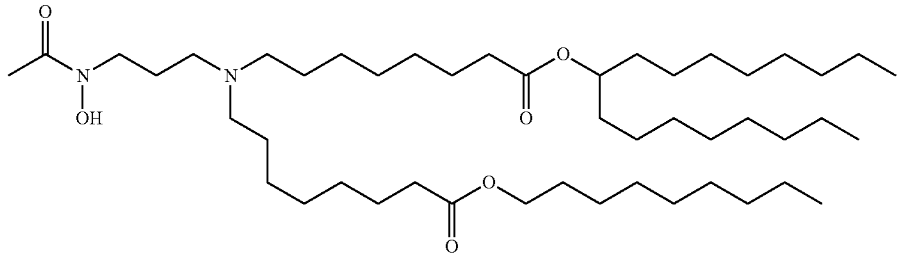
,
(Compound 205)
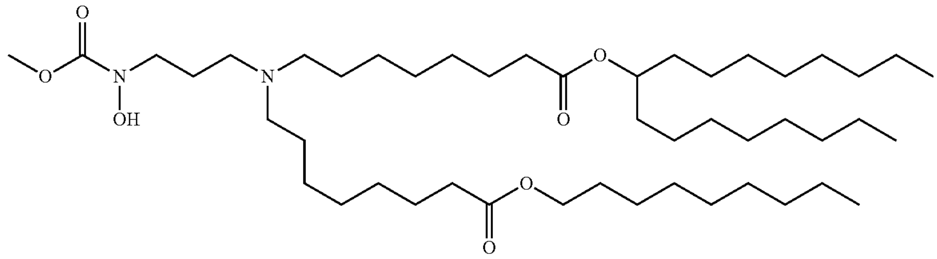
, -continued
(Compound 206)
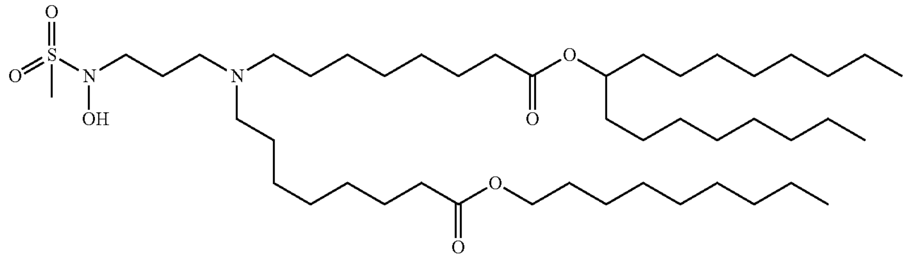
,
(Compound 207)
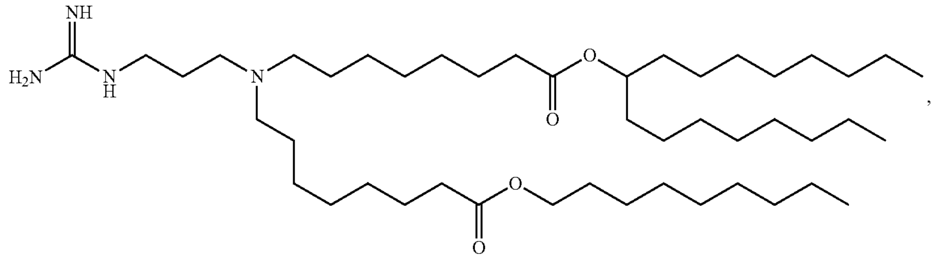
,
(Compound 208)
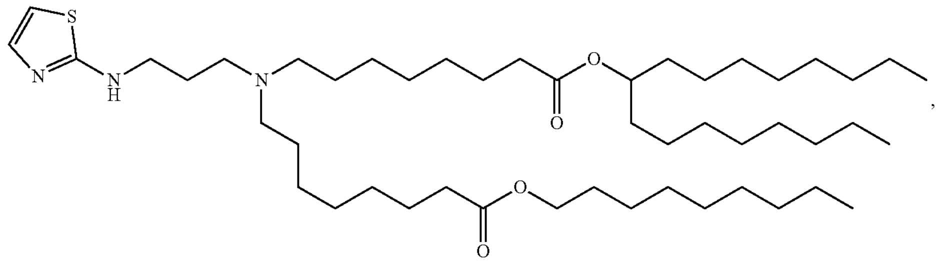
,
(Compound 209)
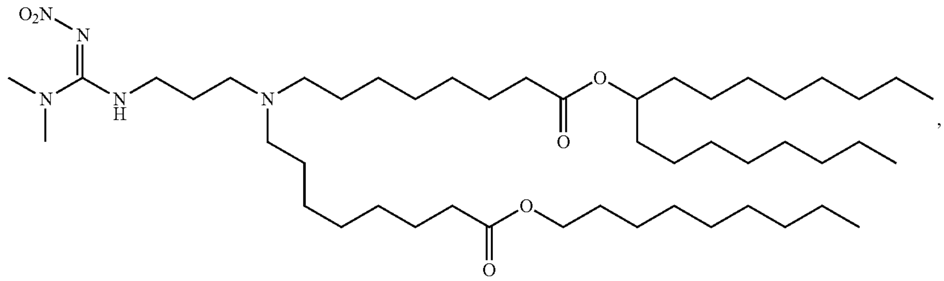
,
(Compound 210)
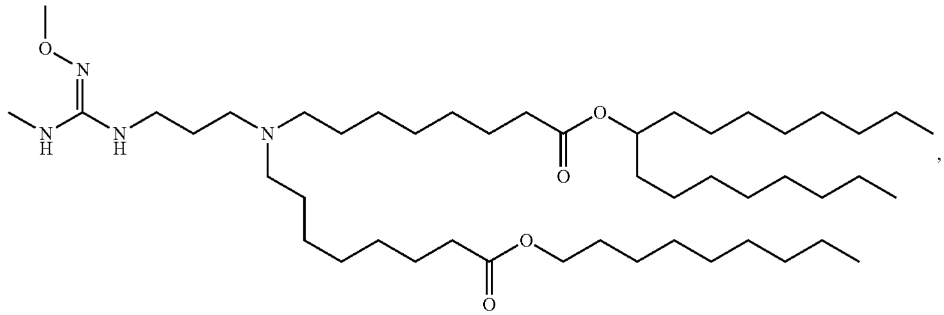
, -continued
(Compound 211)
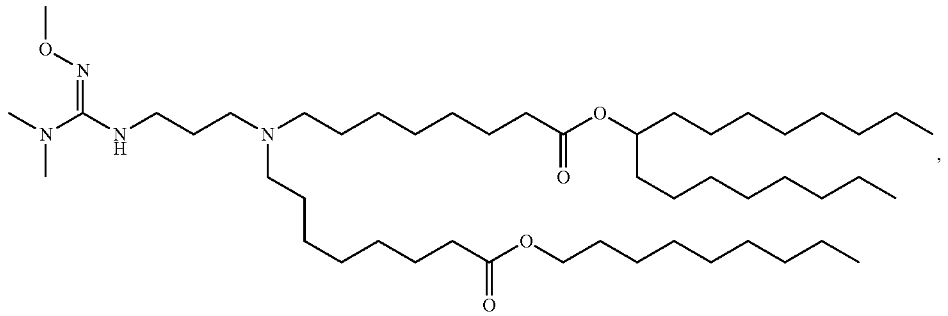
(Compound 212)
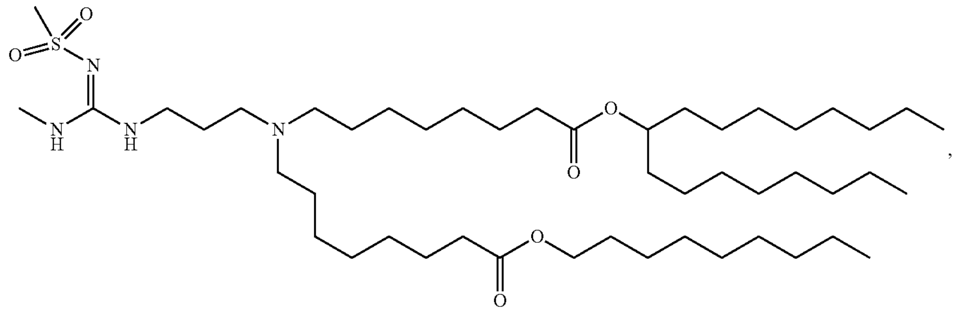
(Compound 213)
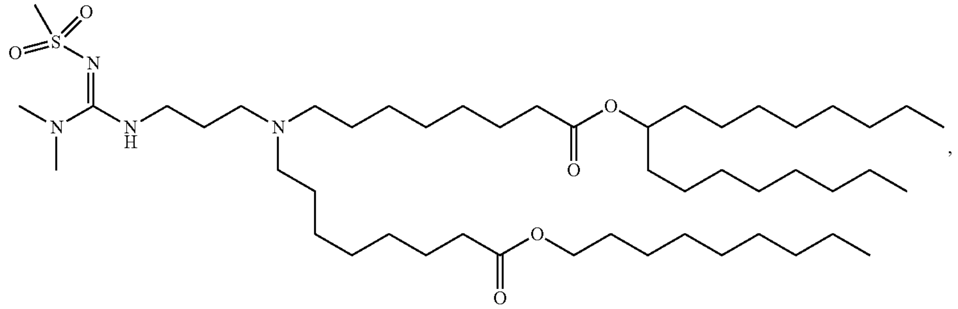
(Compound 214)
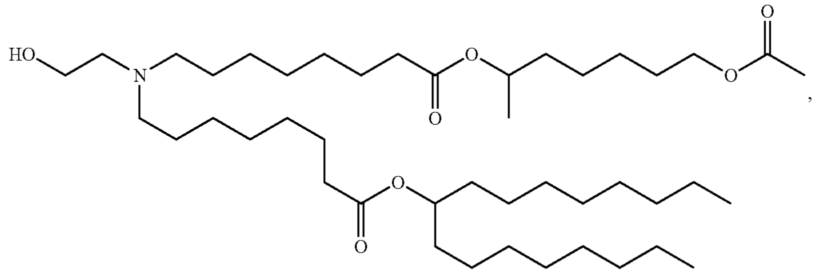
(Compound 215)
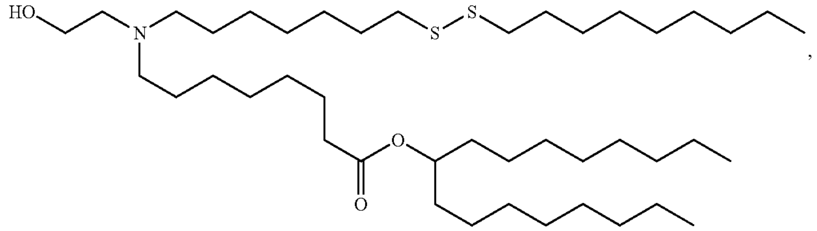

-continued
(Compound 216)
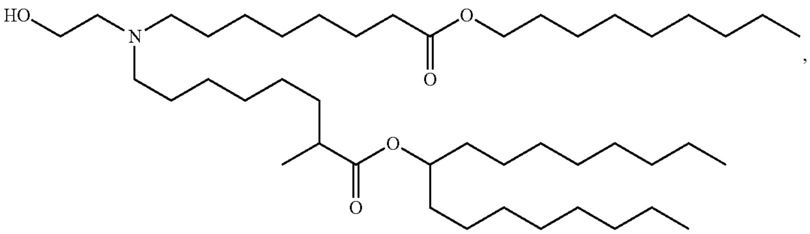
,
(Compound 217)
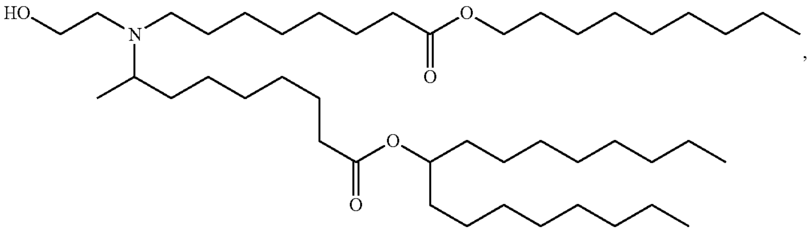
,
(Compound 218)
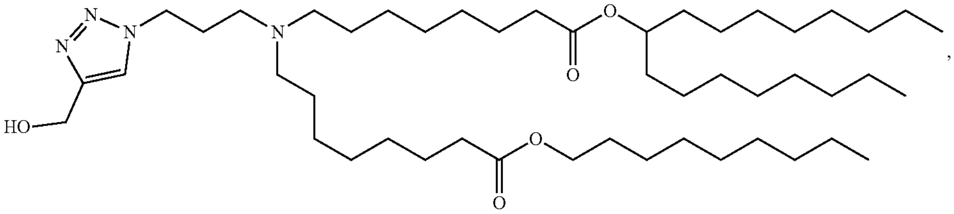
,
(Compound 219)
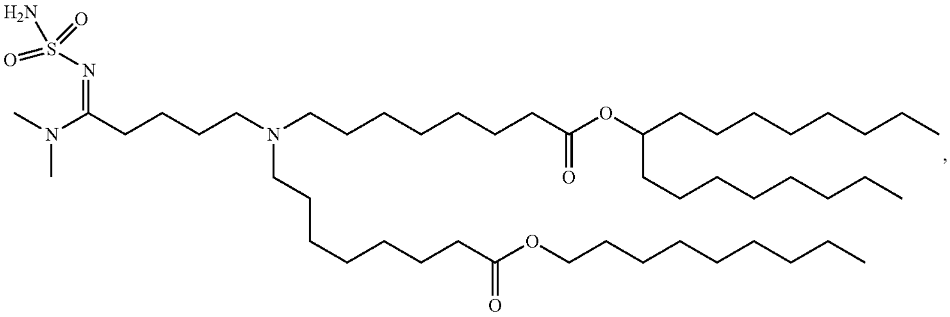
,
(Compound 220)
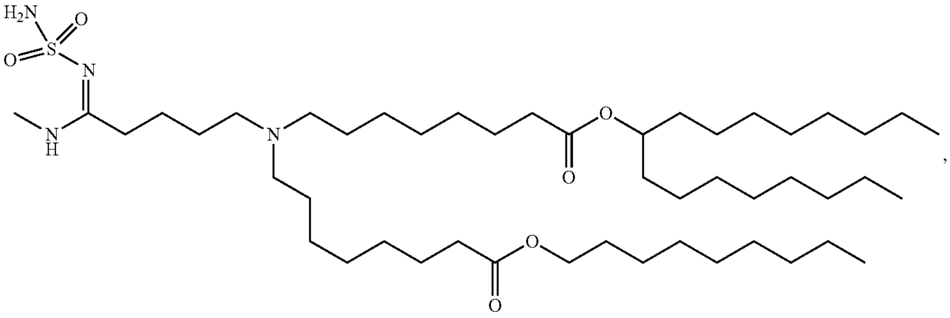
, -continued
(Compound 221)
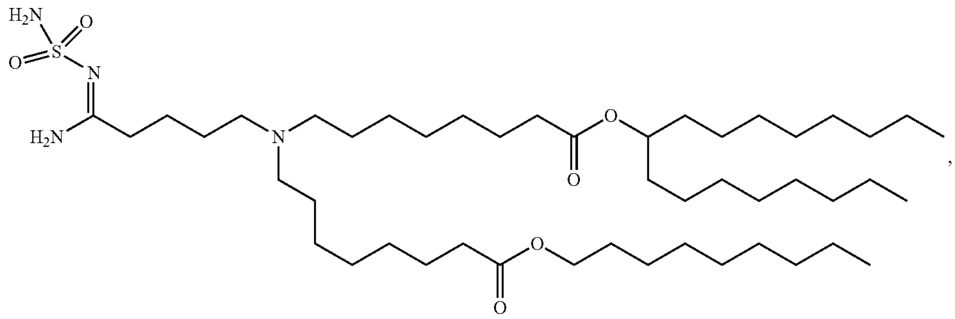
,
(Compound 222)
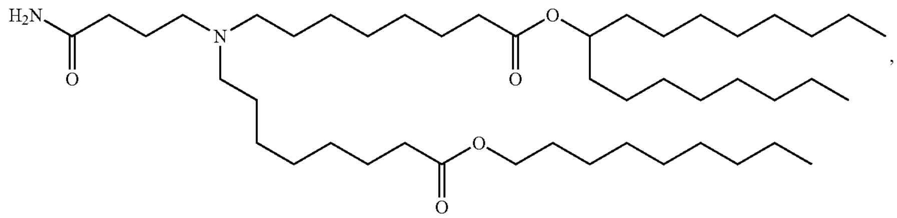
,
(Compound 223)
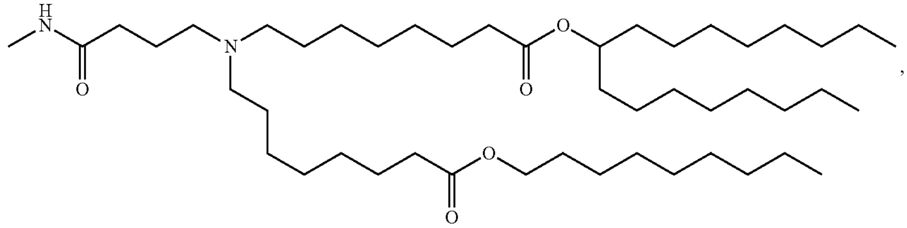
,
(Compound 224)
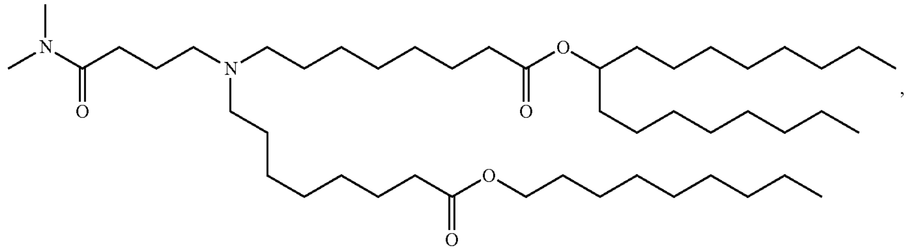
,
(Compound 225)
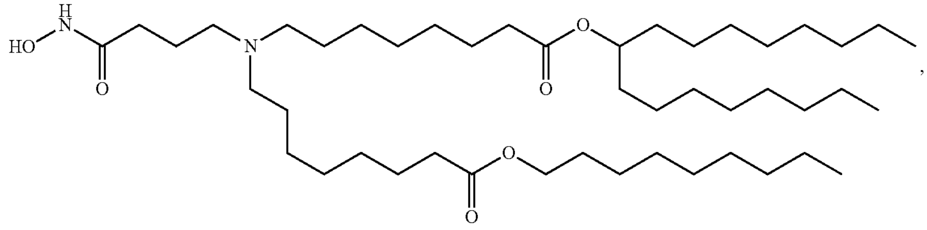
,
(Compound 226)
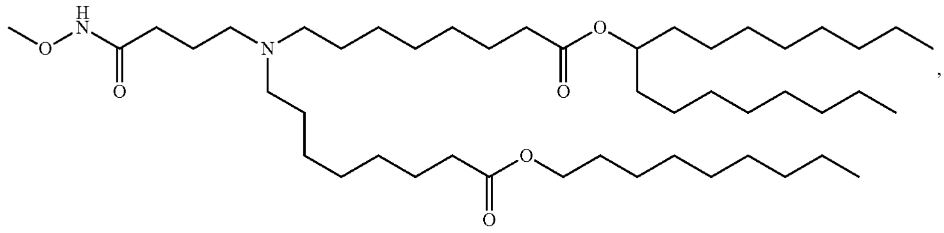
, -continued
(Compound 227)
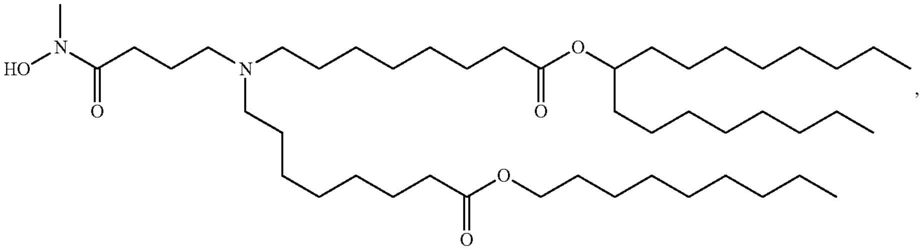
,
(Compound 228)
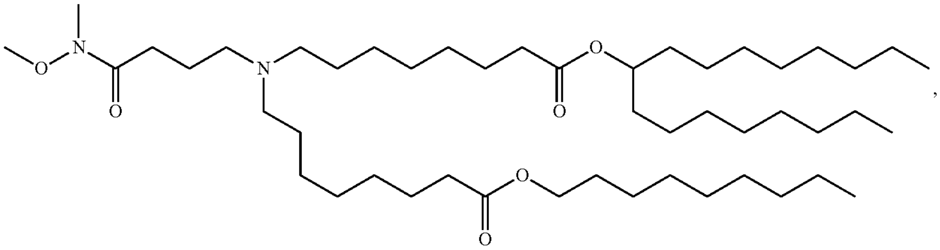
,
(Compound 229)
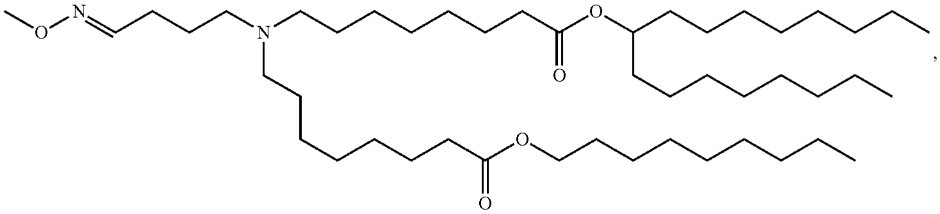
,
(Compound 230)
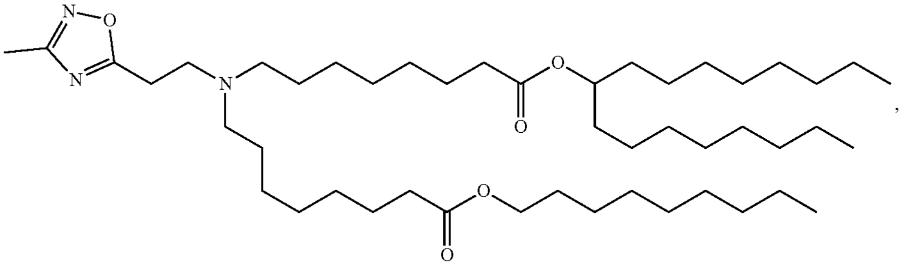
,
(Compound 231)
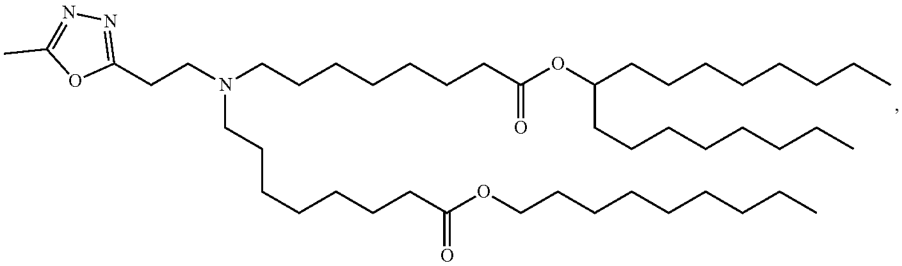
, and
(Compound 323)
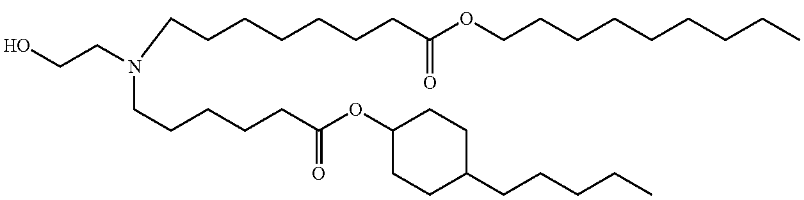
, In other embodiments, the delivery agent comprises a compound having the Formula (VI):

(VI)

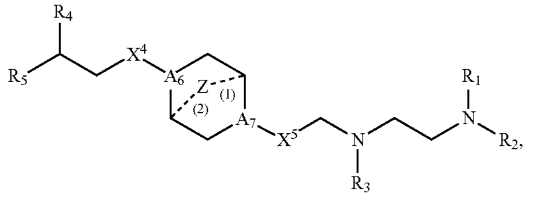

or salts or stereoisomers thereof, in which $A_6$ and $A_7$ are each independently selected from CH or N, wherein at least one of $A_6$ and $A_7$ is N;

Z is $CH_2$ or absent wherein when Z is $CH_2$, the dashed lines (1) and (2) each represent a single bond; and when Z is absent, the dashed lines (1) and (2) are both absent;

$X^4$ and $X^5$ are independently selected from the group consisting of —$CH_2$—, —$(CH_2)_2$—, —CHR—, —CHY—, —C(O)—, —C(O)O—, —OC(O)—, —C(O)—$CH_2$—, —$CH_2$—C(O)—, —C(O)O—$CH_2$—, —OC(O)—$CH_2$—, —$CH_2$—C(O)O—, —$CH_2$—OC(O)—, —CH(OH)—, —C(S)—, and —CH(SH)—;

$R_1$, $R_2$, $R_3$, $R_4$, and $R_5$ each are independently selected from the group consisting of $C_{5-20}$ alkyl, $C_{5-20}$ alkenyl, —R"MR', —R*YR", —YR", and —R*OR";

each M is independently selected from the group consisting of —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —$S(O)_2$—, an aryl group, and a heteroaryl group;

each Y is independently a $C_{3-6}$ carbocycle;

each R* is independently selected from the group consisting of $C_{1-12}$ alkyl and $C_{2-12}$ alkenyl;

each R is independently selected from the group consisting of $C_{1-3}$ alkyl and a $C_{3-6}$ carbocycle;

each R' is independently selected from the group consisting of $C_{1-12}$ alkyl, $C_{2-12}$ alkenyl, and H; and each R" is independently selected from the group consisting of $C_{3-12}$ alkyl and $C_{3-12}$ alkenyl.

In some embodiments, $R_1$, $R_2$, $R_3$, $R_4$, and $R_5$ each are independently selected from the group consisting of $C_{6-20}$ alkyl and $C_{6-20}$ alkenyl.

In some embodiments, $R_1$ and $R_2$ are the same. In certain embodiments, $R_1$, $R_2$, and $R_3$ are the same. In some embodiments, $R_4$ and $R_5$ are the same. In certain embodiments, $R_1$, $R_2$, $R_3$, $R_4$, and $R_5$ are the same.

In some embodiments, at least one of $R_1$, $R_2$, $R_3$, $R_4$, and $R_5$ is $C_{9-12}$ alkyl. In certain embodiments, each of $R_1$, $R_2$, $R_3$, $R_4$, and $R_5$ independently is $C_9$, $C_{12}$ or $C_{14}$ alkyl. In certain embodiments, each of $R_1$, $R_2$, $R_3$, $R_4$, and $R_5$ is $C_9$ alkyl.

In some embodiments, $A_6$ is N and $A_7$ is N. In some embodiments, $A_6$ is CH and $A_7$ is N.

In some embodiments, $X^4$ is —$CH_2$— and $X^5$ is —C(O)—. In some embodiments, $X^4$ and $X^5$ are —C(O)—.

In some embodiments, when $A_6$ is N and $A_7$ is N, at least one of $X^4$ and $X^5$ is not —$CH_2$—, e.g., at least one of $X^4$ and $X^5$ is —C(O)—. In some embodiments, when $A_6$ is N and $A_7$ is N, at least one of $R_1$, $R_2$, $R_3$, $R_4$, and $R_5$ is —R"MR'.

In some embodiments, at least one of $R_1$, $R_2$, $R_3$, $R_4$, and $R_5$ is not —R"MR'.

In some embodiments, the compound is (Compound 299)

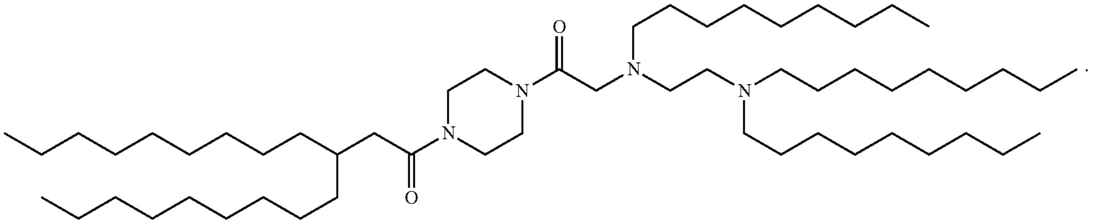

In other embodiments, the delivery agent comprises a compound having the formula:

(Compound 342)

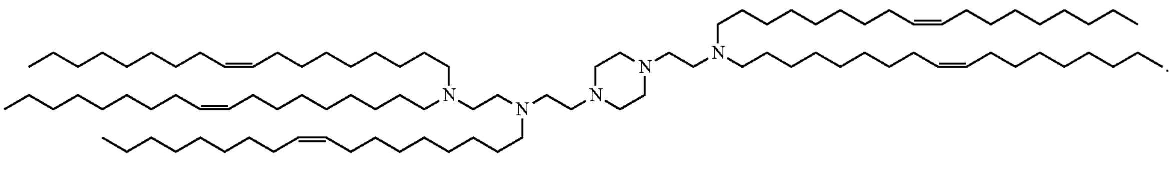

Amine moieties of the lipid compounds disclosed herein can be protonated under certain conditions. For example, the central amine moiety of a lipid according to Formula (I) is typically protonated (i.e., positively charged) at a pH below the pKa of the amino moiety and is substantially not charged at a pH above the pKa. Such lipids can be referred to ionizable amino lipids.

In one specific embodiment, the ionizable amino lipid is Compound 18. In another embodiment, the ionizable amino lipid is Compound 236.

In some embodiments, the amount the ionizable amino lipid, e.g., compound of Formula (I) ranges from about 1 mol % to 99 mol % in the lipid composition.

In one embodiment, the amount of the ionizable amino lipid, e.g., compound of Formula (I) is at least about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99 mol % in the lipid composition.

In one embodiment, the amount of the ionizable amino lipid, e.g., compound of Formula (I) ranges from about 30 mol % to about 70 mol %, from about 35 mol % to about 65 mol %, from about 40 mol % to about 60 mol %, and from about 45 mol % to about 55 mol % in the lipid composition.

In one specific embodiment, the amount of the ionizable amino lipid, e.g., compound of Formula (I) is about 50 mol % in the lipid composition.

In addition to the ionizable amino lipid disclosed herein, e.g., compound of Formula (I), the lipid composition of the pharmaceutical compositions disclosed herein can comprise additional components such as phospholipids, structural lipids, PEG-lipids, and any combination thereof.

b. Additional Components in the Lipid Composition (i) Phospholipids

The lipid composition of the pharmaceutical composition disclosed herein can comprise one or more phospholipids, for example, one or more saturated or (poly)unsaturated phospholipids or a combination thereof. In general, phospholipids comprise a phospholipid moiety and one or more fatty acid moieties.

A phospholipid moiety can be selected, for example, from the non-limiting group consisting of phosphatidyl choline, phosphatidyl ethanolamine, phosphatidyl glycerol, phosphatidyl serine, phosphatidic acid, 2-lysophosphatidyl choline, and a sphingomyelin.

A fatty acid moiety can be selected, for example, from the non-limiting group consisting of lauric acid, myristic acid, myristoleic acid, palmitic acid, palmitoleic acid, stearic acid, oleic acid, linoleic acid, alpha-linolenic acid, erucic acid, phytanoic acid, arachidic acid, arachidonic acid, eicosapentaenoic acid, behenic acid, docosapentaenoic acid, and docosahexaenoic acid.

Particular phospholipids can facilitate fusion to a membrane. For example, a cationic phospholipid can interact with one or more negatively charged phospholipids of a membrane (e.g., a cellular or intracellular membrane). Fusion of a phospholipid to a membrane can allow one or more elements (e.g., a therapeutic agent) of a lipid-containing composition (e.g., LNPs) to pass through the membrane permitting, e.g., delivery of the one or more elements to a target tissue.

Non-natural phospholipid species including natural species with modifications and substitutions including branching, oxidation, cyclization, and alkynes are also contemplated. For example, a phospholipid can be functionalized with or cross-linked to one or more alkynes (e.g., an alkenyl group in which one or more double bonds is replaced with a triple bond). Under appropriate reaction conditions, an alkyne group can undergo a copper-catalyzed cycloaddition upon exposure to an azide. Such reactions can be useful in functionalizing a lipid bilayer of a nanoparticle composition to facilitate membrane permeation or cellular recognition or in conjugating a nanoparticle composition to a useful component such as a targeting or imaging moiety (e.g., a dye).

Phospholipids include, but are not limited to, glycerophospholipids such as phosphatidylcholines, phosphatidylethanolamines, phosphatidylserines, phosphatidylinositols, phosphatidy glycerols, and phosphatidic acids. Phospholipids also include phosphosphingolipid, such as sphingomyelin. Examples of phospholipids include, but are not limited to, the following:

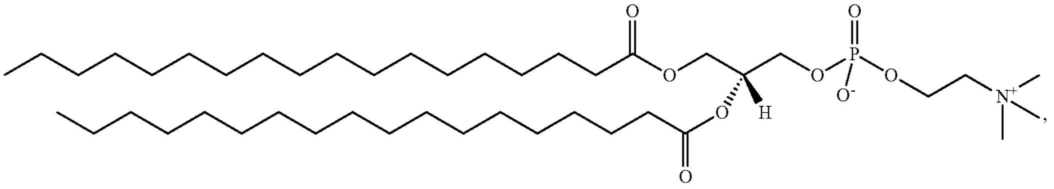

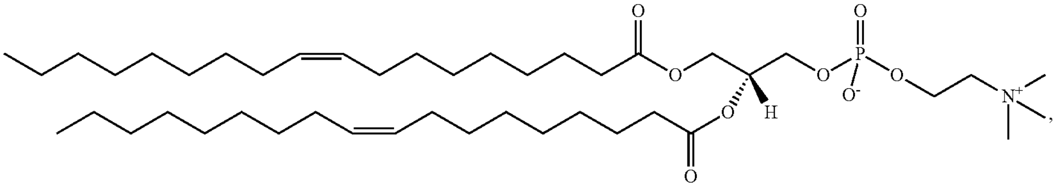

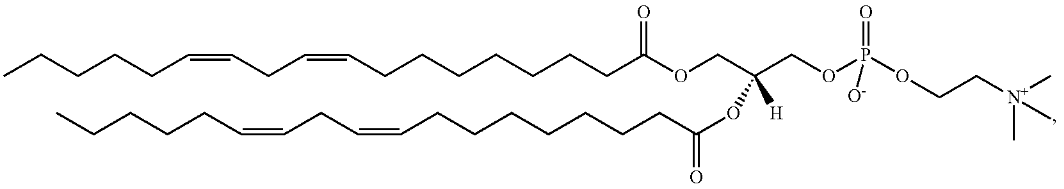

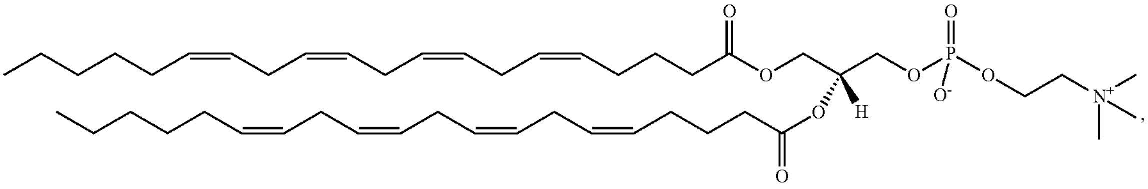

-continued
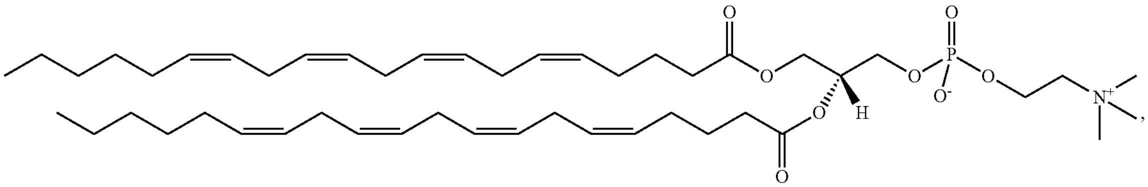,
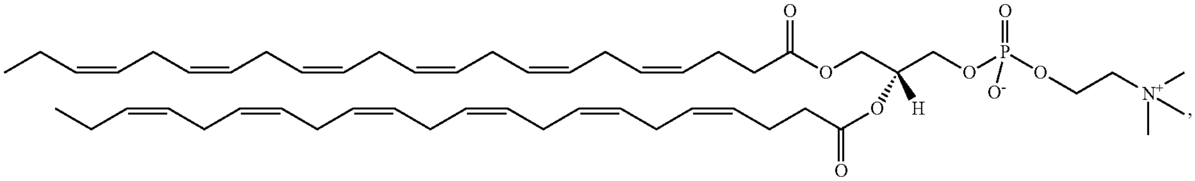,
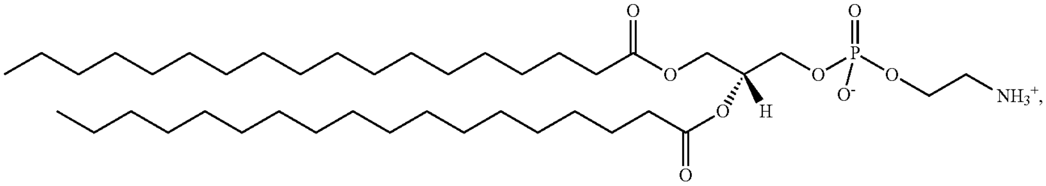,
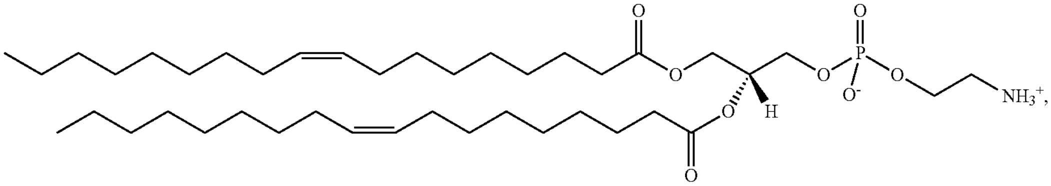,
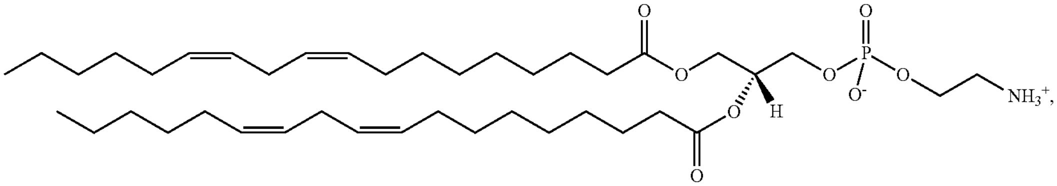,
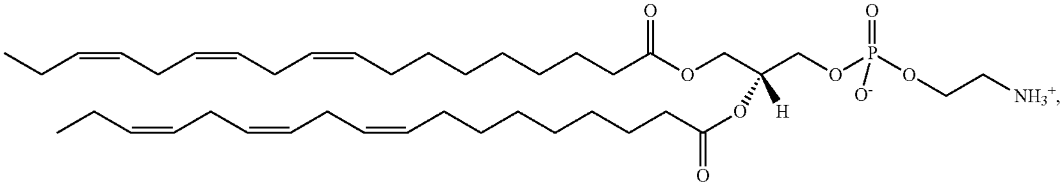,
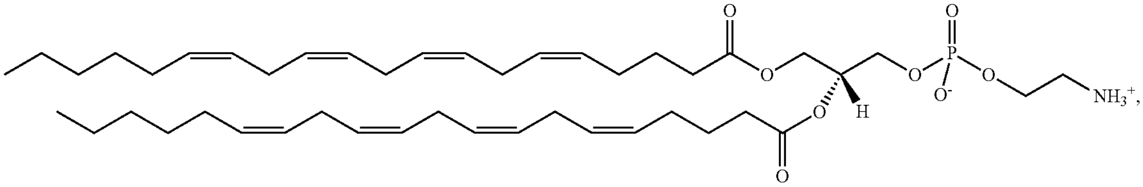,
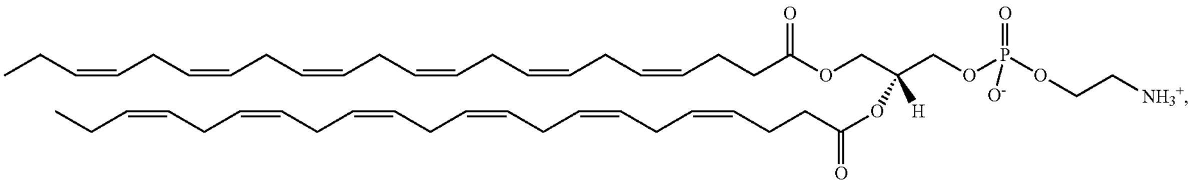,
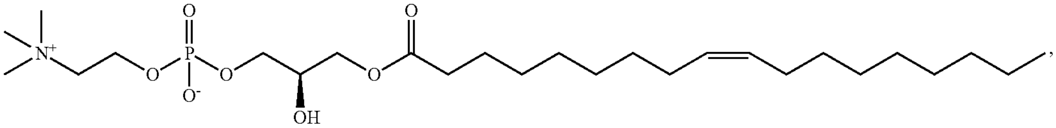, -continued

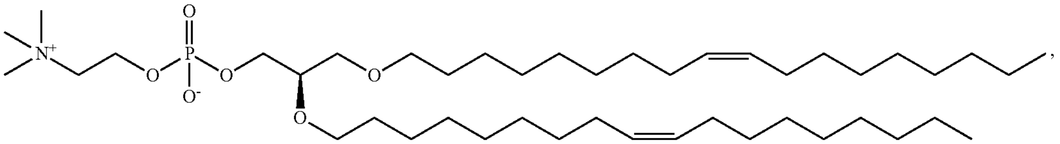

,

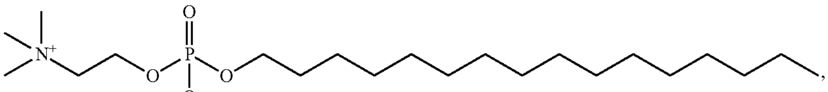

,

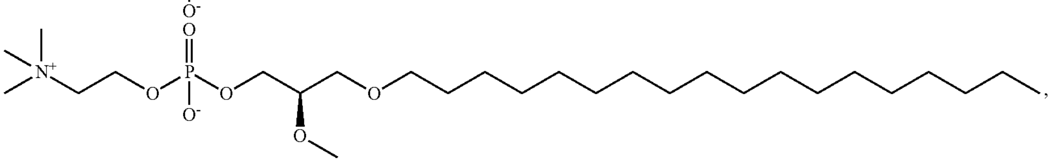

, and

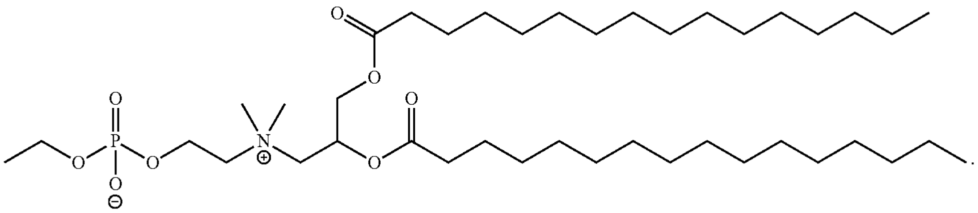

.

In certain embodiments, a phospholipid useful or potentially useful in the present invention is an analog or variant of DSPC. In certain embodiments, a phospholipid useful or potentially useful in the present invention is a compound of Formula (IX):

(IX)

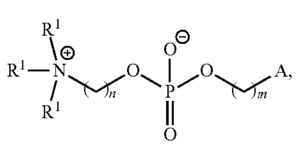

or a salt thereof, wherein:

each $R^1$ is independently optionally substituted alkyl; or optionally two $R^1$ are joined together with the intervening atoms to form optionally substituted monocyclic carbocyclyl or optionally substituted monocyclic heterocyclyl; or optionally three $R^1$ are joined together with the intervening atoms to form optionally substituted bicyclic carbocyclyl or optionally substitute bicyclic heterocyclyl;

n is 1, 2, 3, 4, 5, 6, 7, 8, 9, or 10;

m is 0, 1, 2, 3, 4, 5, 6, 7, 8, 9, or 10;

A is of the formula:

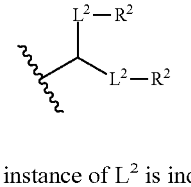

or

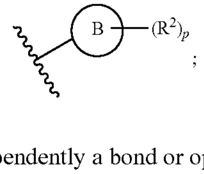

;

each instance of $L^2$ is independently a bond or optionally substituted $C_{1-6}$ alkylene, wherein one methylene unit of the optionally substituted $C_{1-6}$ alkylene is optionally replaced with —O—, —N($R^N$)—, —S—, —C(O)—, —C(O)N($R^N$)—, —NR$^N$C(O)—, —C(O)O—, —OC(O)—, —OC(O)O—, —OC(O)N($R^N$)—, —NR$^N$C(O)O—, or —NR$^N$C(O)N($R^N$)—;

each instance of $R^2$ is independently optionally substituted $C_{1-30}$ alkyl, optionally substituted $C_{1-30}$ alkenyl, or optionally substituted $C_{1-30}$ alkynyl; optionally wherein one or more methylene units of $R^2$ are independently replaced with optionally substituted carbocyclylene, optionally substituted heterocyclylene, optionally substituted arylene, optionally substituted heteroarylene, —N($R^N$)—, —O—, —S—, —C(O)—, —C(O)N($R^N$)—, —NR$^N$C(O)—, —NR$^N$C(O)N($R^N$)—, —C(O)O—, —OC(O)—, —OC(O)O—, —OC(O)N($R^N$)—, —NR$^N$C(O)O—, —C(O)S—, —SC(O)—, —C(=NR$^N$)—, —C(=NR$^N$)N($R^N$)—, —NR$^N$C(=NR$^N$)—, —NR$^N$C(=NR$^N$)N($R^N$)—, —C(S)—, —C(S)N($R^N$)—, —NR$^N$C(S)—, —NR$^N$C(S)N($R^N$)—, —S(O)—, —OS(O)—, —S(O)O—, —OS(O)O—, —OS(O)$_2$—, —S(O)$_2$O—, —OS(O)$_2$O—, —N($R^N$)S(O)—, —S(O)N($R^N$)—, —N($R^N$)S(O)N($R^N$)—, —OS(O)N($R^N$)—, —N($R^N$)S(O)O—, —S(O)$_2$—, —N($R^N$)S(O)$_2$—, —S(O)$_2$N($R^N$)—, —N($R^N$)S(O)$_2$N($R^N$)—, —OS(O)$_2$N($R^N$)—, or —N($R^N$)S(O)$_2$O—;

each instance of $R^N$ is independently hydrogen, optionally substituted alkyl, or a nitrogen protecting group;

Ring B is optionally substituted carbocyclyl, optionally substituted heterocyclyl, optionally substituted aryl, or optionally substituted heteroaryl; and p is 1 or 2;

provided that the compound is not of the formula:

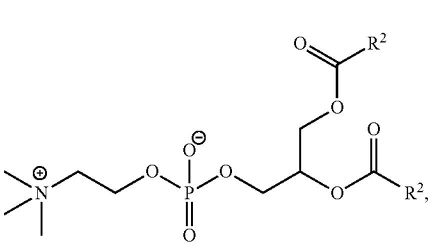

wherein each instance of $R^2$ is independently unsubstituted alkyl, unsubstituted alkenyl, or unsubstituted alkynyl.

Phospholipid Head Modifications

In certain embodiments, a phospholipid useful or potentially useful in the present invention comprises a modified phospholipid head (e.g., a modified choline group). In certain embodiments, a phospholipid with a modified head is DSPC, or analog thereof, with a modified quaternary amine. For example, in embodiments of Formula (IX), at least one of $R^1$ is not methyl. In certain embodiments, at least one of $R^1$ is not hydrogen or methyl. In certain embodiments, the compound of Formula (IX) is of one of the following formulae:

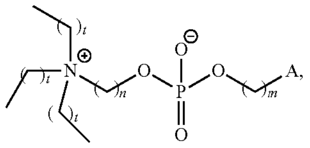

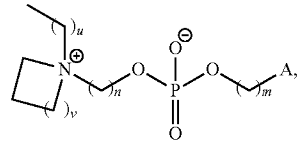

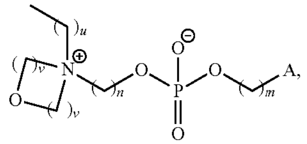

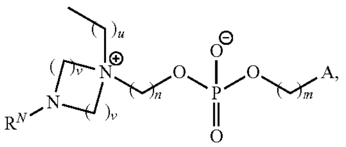

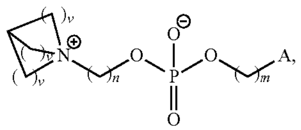

or a salt thereof, wherein:

each t is independently 1, 2, 3, 4, 5, 6, 7, 8, 9, or 10;

each u is independently 0, 1, 2, 3, 4, 5, 6, 7, 8, 9, or 10; and each v is independently 1, 2, or 3.

In certain embodiments, the compound of Formula (IX) is of one of the following formulae:

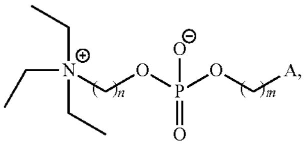

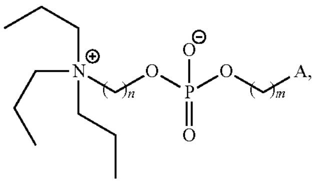

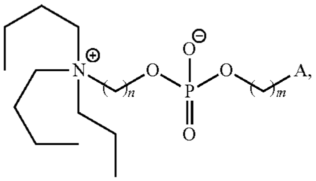

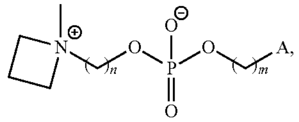

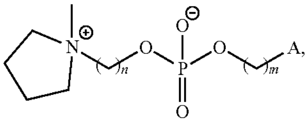

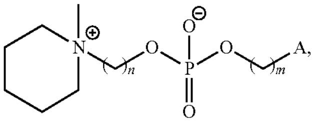

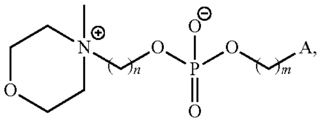

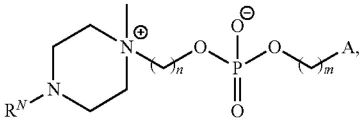

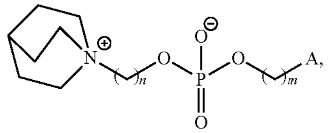

or a salt thereof.

In certain embodiments, a compound of Formula (IX) is one of the following:

(Compound 400)

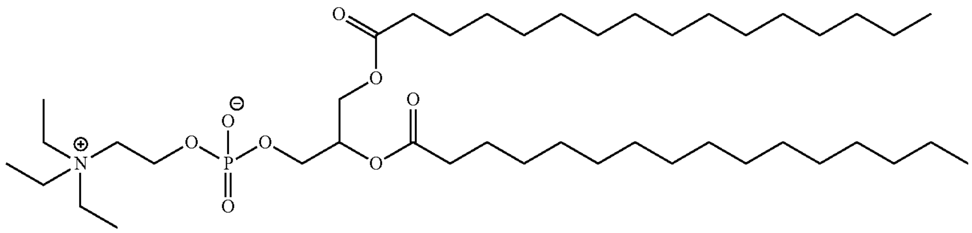

-continued
(Compound 401)
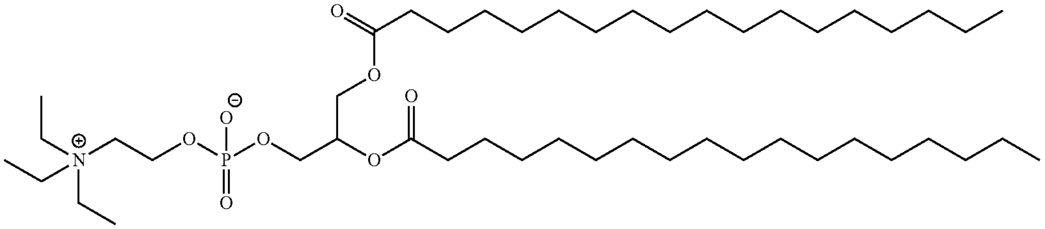
(Compound 402)
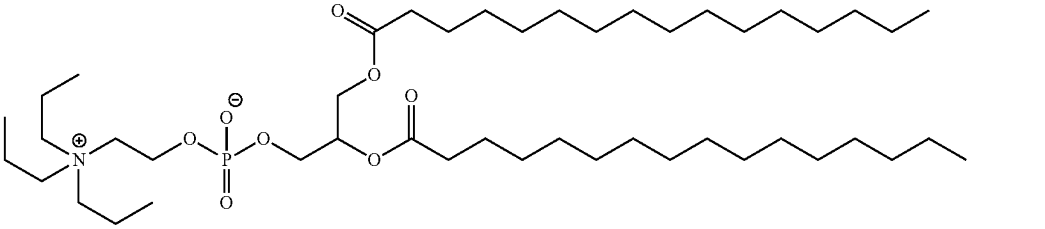
(Compound 403)
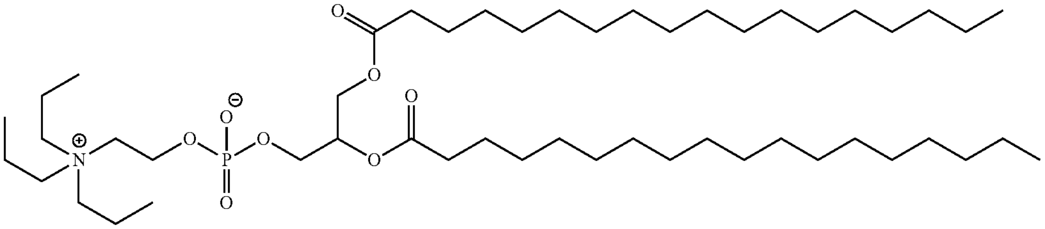
(Compound 404)
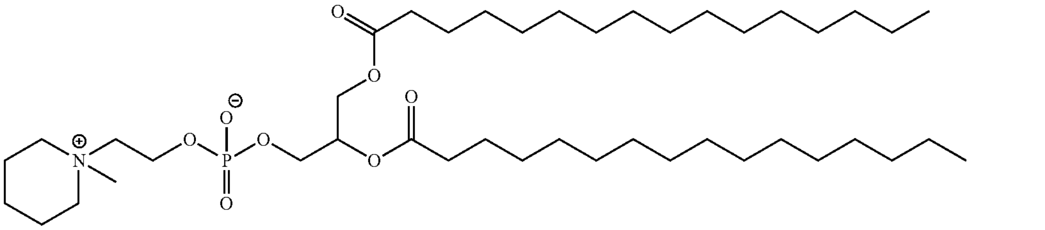
(Compound 405)
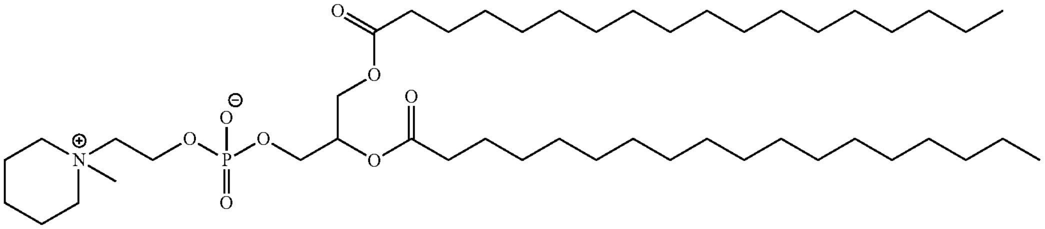
(Compound 406)
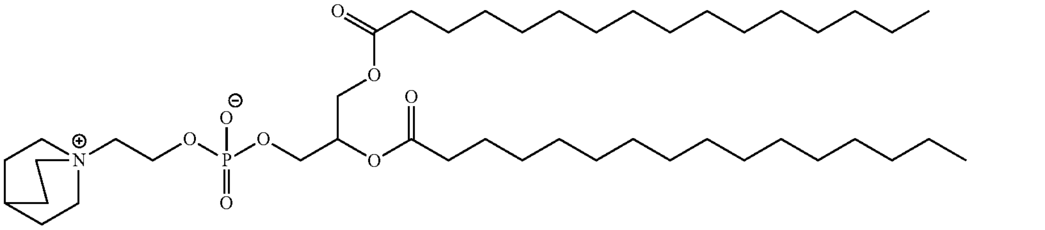

-continued (Compound 407)

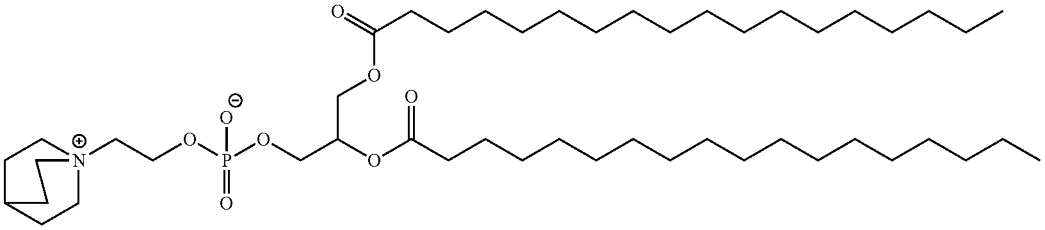

(Compound 408)

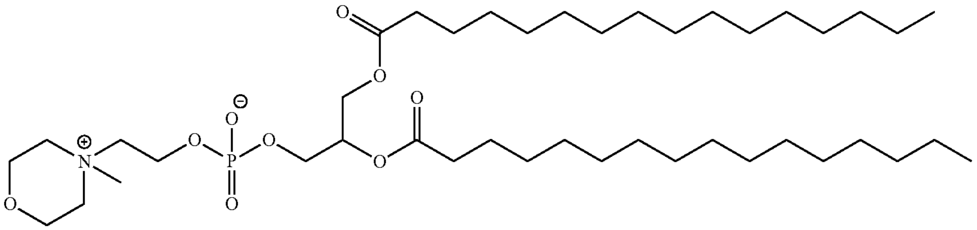

(Compound 409)

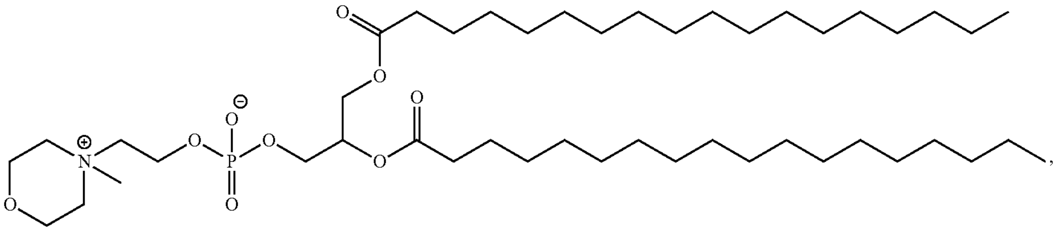

or a salt thereof.

In certain embodiments, a compound of Formula (IX) is of Formula (IX-a):

(IX-a)

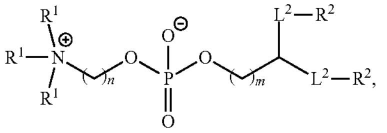

or a salt thereof.

In certain embodiments, phospholipids useful or potentially useful in the present invention comprise a modified core. In certain embodiments, a phospholipid with a modified core described herein is DSPC, or analog thereof, with a modified core structure. For example, in certain embodiments of Formula (IX-a), group A is not of the following formula:

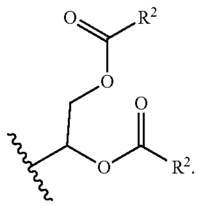

In certain embodiments, the compound of Formula (IX-a) is of one of the following formulae:

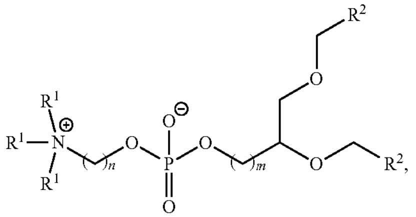

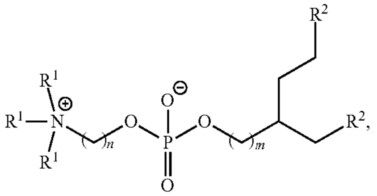

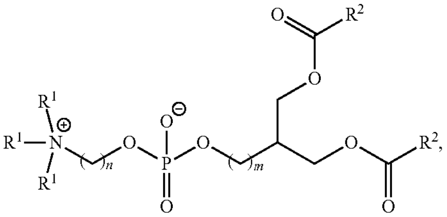

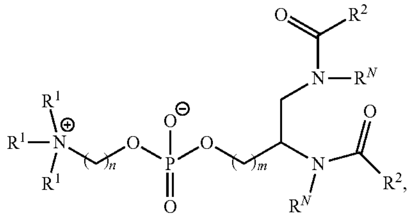

-continued

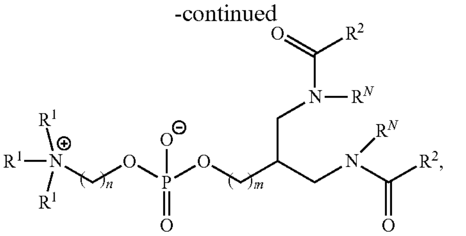

or a salt thereof.

In certain embodiments, a compound of Formula (IX) is one of the following:

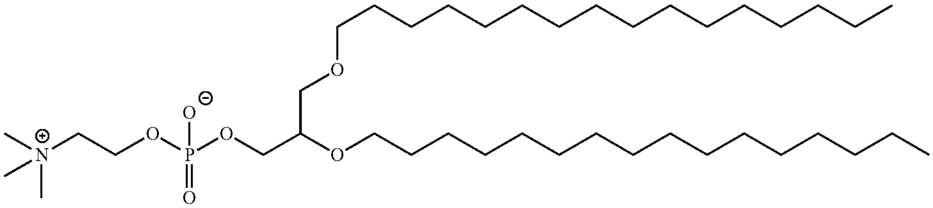

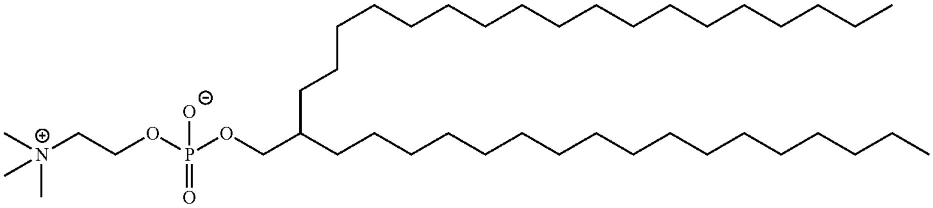

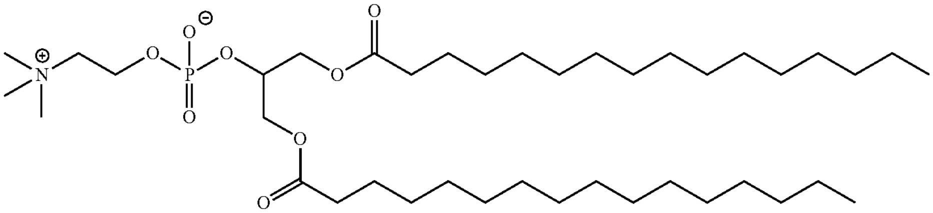

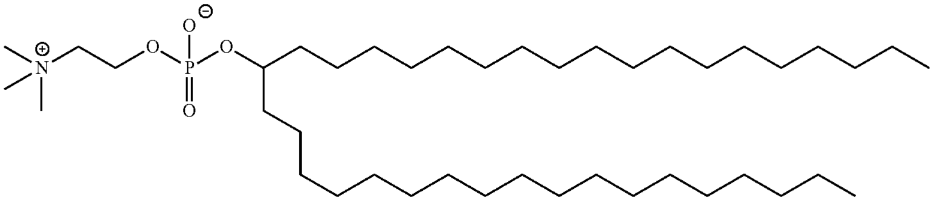

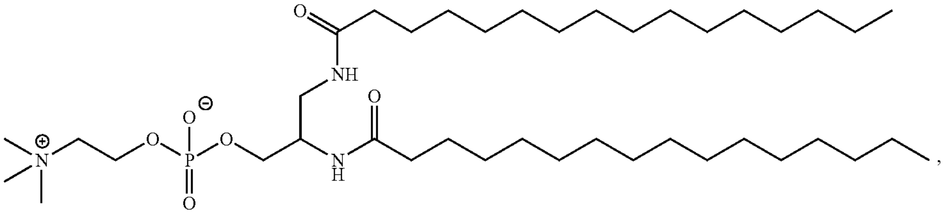

or salts thereof.

In certain embodiments, a phospholipid useful or potentially useful in the present invention comprises a cyclic moiety in place of the glyceride moiety. In certain embodiments, a phospholipid useful in the present invention is DSPC, or analog thereof, with a cyclic moiety in place of the glyceride moiety. In certain embodiments, the compound of Formula (IX) is of Formula (IX-b):

(IX-b)

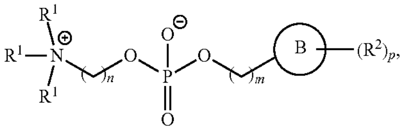

or a salt thereof.

In certain embodiments, the compound of Formula (IX-b) is of Formula (IX-b-1):

(IX-b-1)

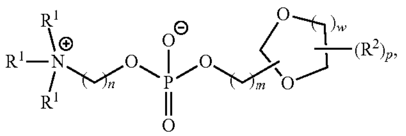

or a salt thereof, wherein.

w is 0, 1, 2, or 3.

(IX-b-3)

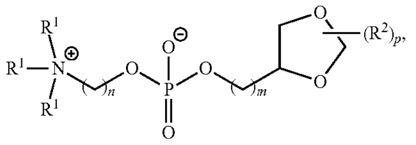

or a salt thereof.

In certain embodiments, the compound of Formula (IX-b) is of Formula (IX-b-4):

(IX-b-4)

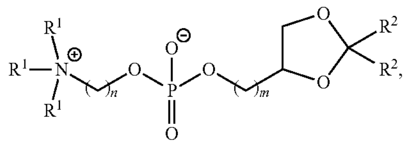

or a salt thereof.

In certain embodiments, the compound of Formula (IX-b) is one of the following:

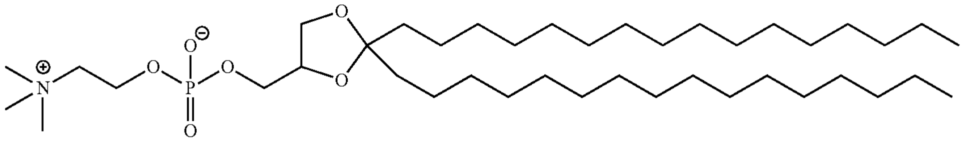

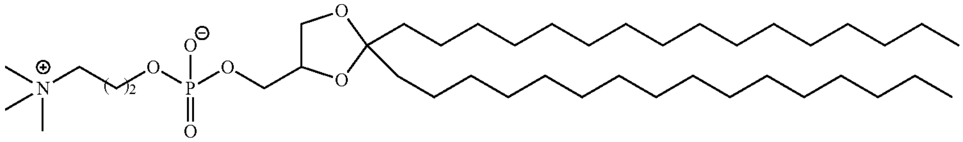

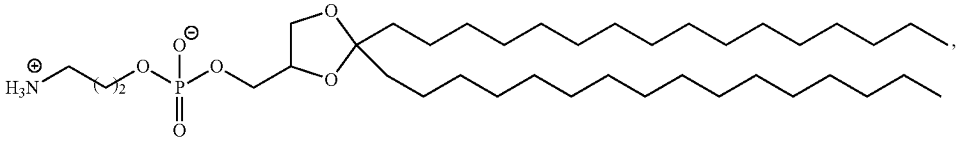,

In certain embodiments, the compound of Formula (IX-b) is of Formula (IX-b-2):

(IX-b-2)

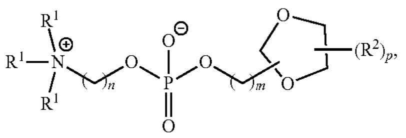

or a salt thereof.

In certain embodiments, the compound of Formula (IX-b) is of Formula (IX-b-3):

or salts thereof

Phospholipid Tail Modifications

In certain embodiments, a phospholipid useful or potentially useful in the present invention comprises a modified tail. In certain embodiments, a phospholipid useful or potentially useful in the present invention is DSPC, or analog thereof, with a modified tail. As described herein, a "modified tail" may be a tail with shorter or longer aliphatic chains, aliphatic chains with branching introduced, aliphatic chains with substituents introduced, aliphatic chains wherein one or more methylenes are replaced by cyclic or heteroatom groups, or any combination thereof. For example, in certain embodiments, the compound of (IX) is of Formula (IX-a), or a salt thereof, wherein at least one instance of $R^2$ is each instance of $R^2$ is optionally substituted $C_{1-30}$ alkyl, wherein one or more methylene units of $R^2$ are independently replaced with optionally substituted carbocyclylene, optionally substituted heterocyclylene, optionally substituted arylene, optionally substituted heteroarylene, —$N(R^N)$—, —O—, —S—, —C(O)—, —$C(O)N(R^N)$—, —$NR^NC(O)$—, —$NR^NC(O)N(R^N)$—, —C(O)O—, —OC(O)—, —OC(O)O—, —$OC(O)N(R^N)$—, —$NR^NC(O)O$—, —C(O)S—, —SC(O)—, —C(=$NR^N$)—, —C(=$N^RN$)N($R^N$)—, —$NR^N$C(=$N^RN$)—, —$NR^N$C(=$NR^N$)N($R^N$)—, —C(S)—, —C(S)N($R^N$)—, —$NR^N$C(S)—, —$NR^N$C(S)N($R^N$)—, —S(O)—, —OS(O)—, —S(O)O—, —OS(O)O—, —OS$(O)_2$—, —S$(O)_2$O—, —OS$(O)_2$O—, —N($R^N$)S(O)—, —S(O)N($R^N$)—, —N($R^N$)S(O)N($R^N$)—, —OS(O)N($R^N$)—, —N($R^N$)S(O)O—, —S$(O)_2$—, —N($R^N$)S$(O)_2$—, —S$(O)_2$N($R^N$)—, —N($R^N$)S$(O)_2$N($R^N$)—, —OS$(O)_2$N($R^N$)—, or —N($R^N$)S$(O)_2$O—.

In certain embodiments, the compound of Formula (IX) is of Formula (IX-c):

(IX-c)

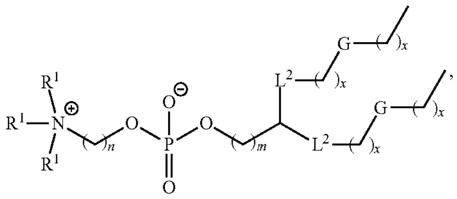

or a salt thereof, wherein:

each x is independently an integer between 0-30, inclusive; and each instance is G is independently selected from the group consisting of optionally substituted carbocyclylene, optionally substituted heterocyclylene, optionally substituted arylene, optionally substituted heteroarylene, —N($R^N$), —O—, —S—, —C(O)—, —C(O)N($R^N$)—, —$NR^N$C(O)—, —$NR^N$C(O)N($R^N$)—, —C(O)O—, —OC(O)—, —OC(O)O—, —OC(O)N($R^N$)—, —$NR^N$C(O)O—, —C(O)S—, —SC(O)—, —C(=$NR^N$)—, —C(=$NR^N$)N($R^N$)—, —$NR^N$C(=$NR^N$)—, —$NR^N$C(=$NR^N$)N($R^N$)—, —C(S)—, —C(S)N($R^N$)—, —$NR^N$C(S)—, —$NR^N$C(S)N($R^N$)—, —S(O)—, —OS(O)—, —S(O)O—, —OS(O)O—, —OS$(O)_2$—, —S$(O)_2$O—, —OS$(O)_2$O—, —N($R^N$)S(O)—, —S(O)N($R^N$)—, —N($R^N$)S(O)N($R^N$)—, —OS(O)N($R^N$)—, —N($R^N$)S(O)O—, —S$(O)_2$—, —N($R^N$)S$(O)_2$—, —S$(O)_2$N($R^N$)—, —N($R^N$)S$(O)_2$N($R^N$)—, —OS$(O)_2$N($R^N$)—, or —N($R^N$)S$(O)_2$O—. Each possibility represents a separate embodiment of the present invention.

In certain embodiments, the compound of Formula (IX-c) is of Formula (IX-c-1):

(IX-c-1)

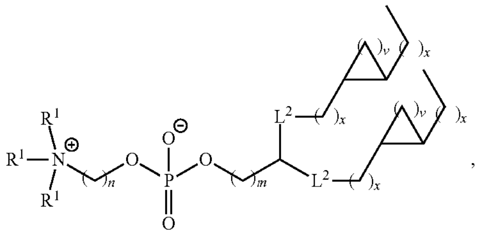

or salt thereof, wherein:

each instance of v is independently 1, 2, or 3.

In certain embodiments, the compound of Formula (IX-c) is of Formula (IX-c-2):

(IX-c-2)

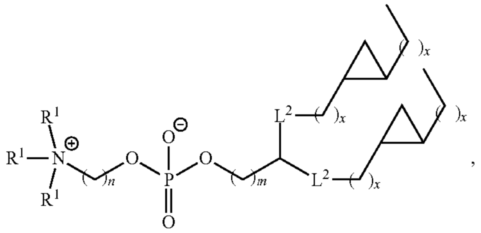

or a salt thereof.

In certain embodiments, the compound of Formula (IX-c) is of the following formula:

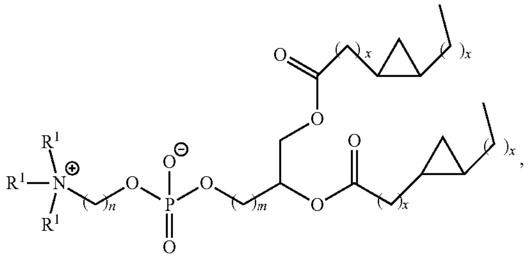

or a salt thereof.

In certain embodiments, the compound of Formula (IX-c) is the following:

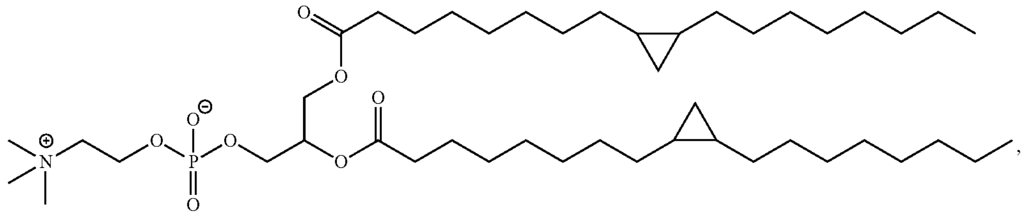 [SMILES: CCCCCCCCC1CC1CCCCCCCC(=O)OCC(COP(=O)([O-])OCC[N+](C)(C)C)OC(=O)CCCCCCCC1CC1CCCCCCCC]

or a salt thereof.

In certain embodiments, the compound of Formula (IX-c) is of Formula (IX-c-3):

(IX-c-3)

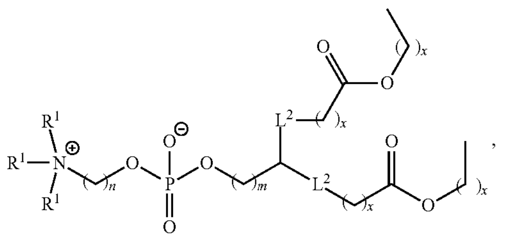

or a salt thereof.

In certain embodiments, the compound of Formula (IX-c) is of the following formulae:

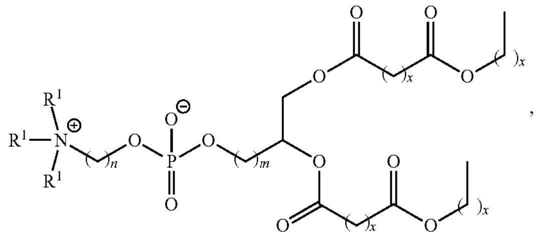

or a salt thereof.

In certain embodiments, the compound of Formula (IX-c) is the following:

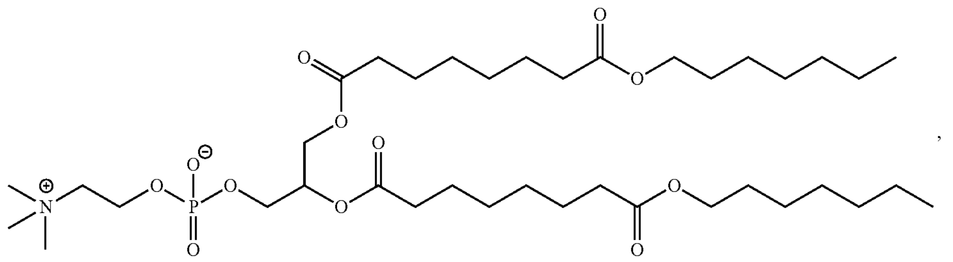 [SMILES: CCCCCCCOC(=O)CCCCCCC(=O)OCC(COP(=O)([O-])OCC[N+](C)(C)C)OC(=O)CCCCCCC(=O)OCCCCCCC]

or a salt thereof.

In certain embodiments, a phospholipid useful or potentially useful in the present invention comprises a modified phosphocholine moiety, wherein the alkyl chain linking the quaternary amine to the phosphoryl group is not ethylene (e.g., n is not 2). Therefore, in certain embodiments, a phospholipid useful or potentially useful in the present invention is a compound of Formula (IX), wherein n is 1, 3, 4, 5, 6, 7, 8, 9, or 10. For example, in certain embodiments, a compound of Formula (IX) is of one of the following formulae:
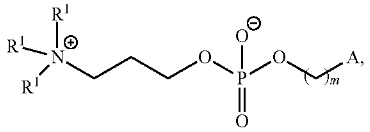
-continued
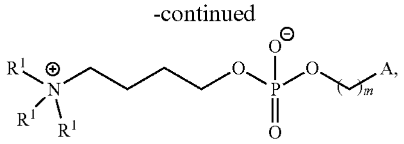
or a salt thereof.
In certain embodiments, a compound of Formula (IX) is one of the following:
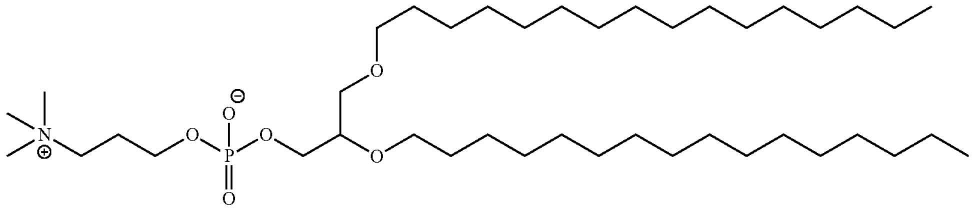
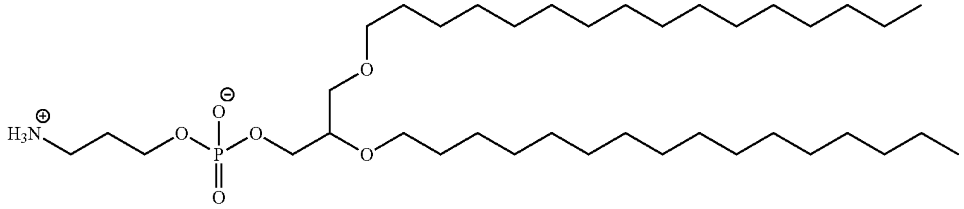
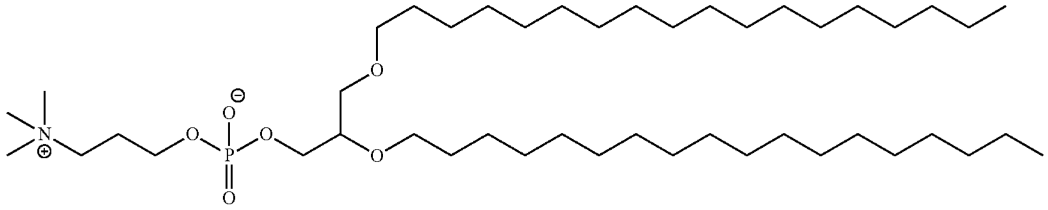
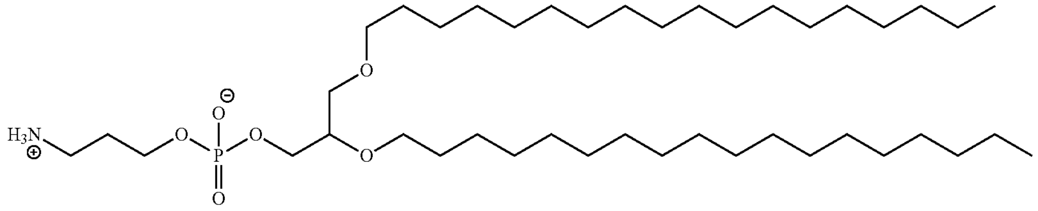
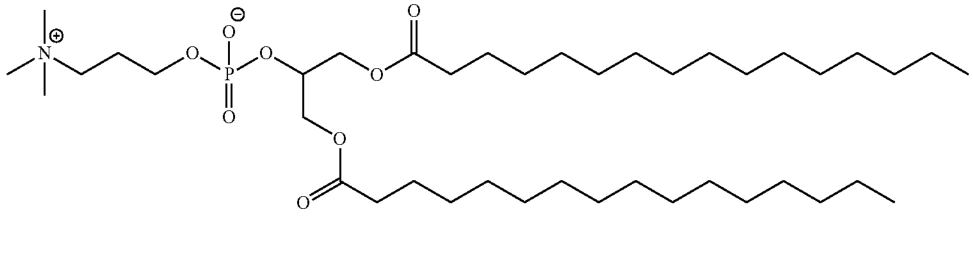
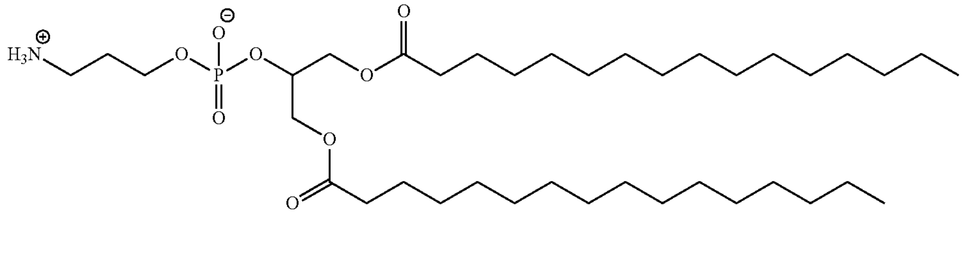

-continued
(Compound 411)
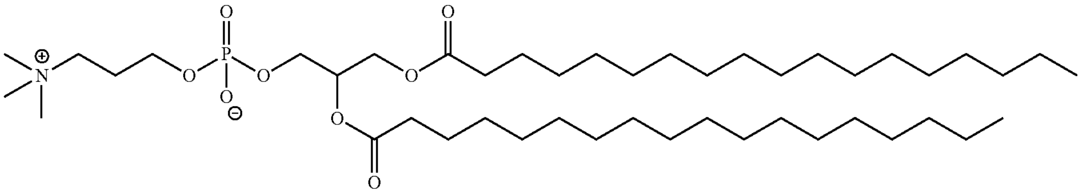
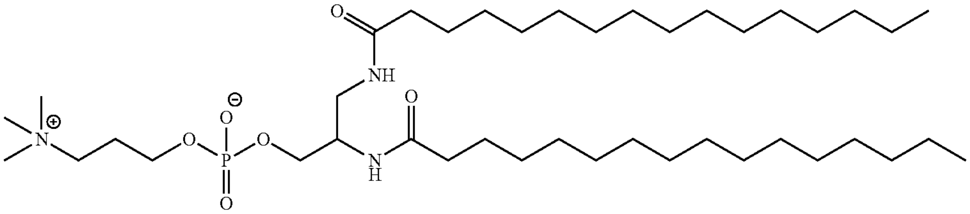
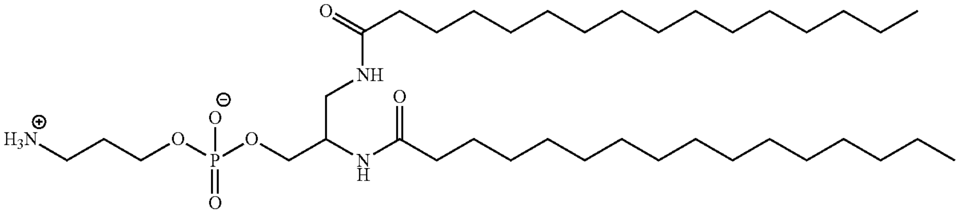
(Compound 412)
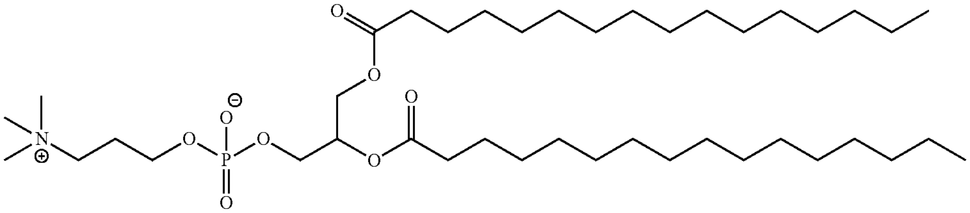
(Compound 413)
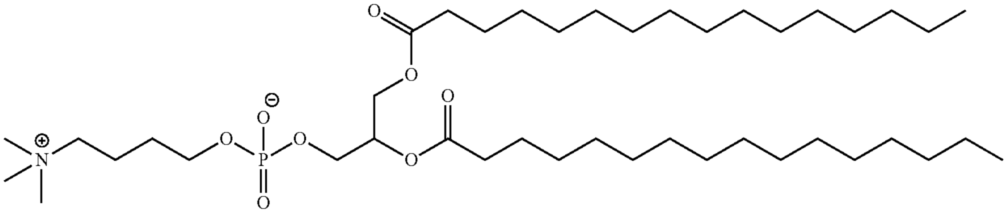
(Compound 414)
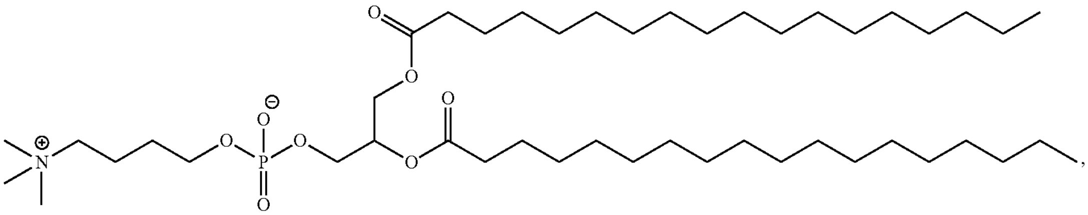
,
or salts thereof.
(ii) Alternative Lipids
In certain embodiments, an alternative lipid is used in place of a phospholipid of the invention. Non-limiting examples of such alternative lipids include the following:

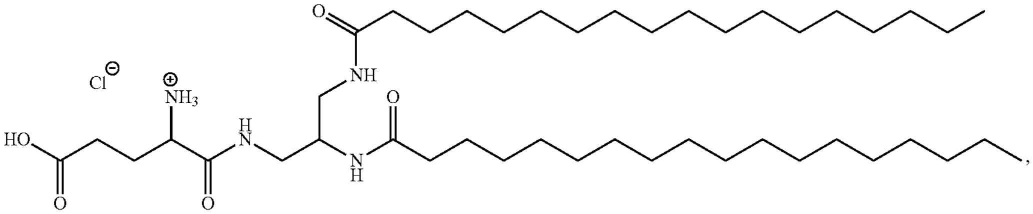,

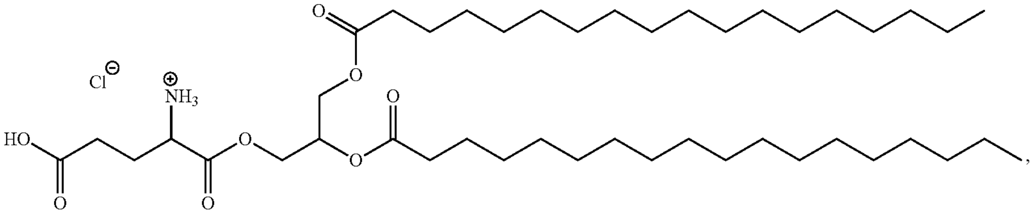,

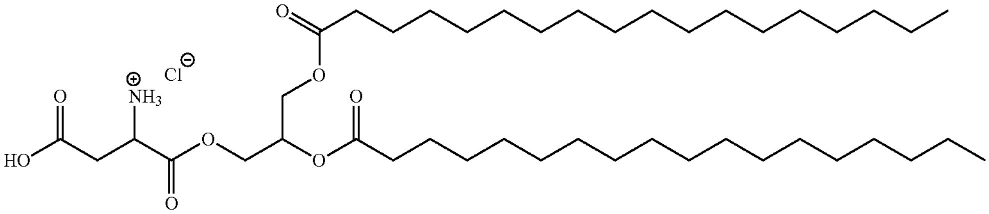,

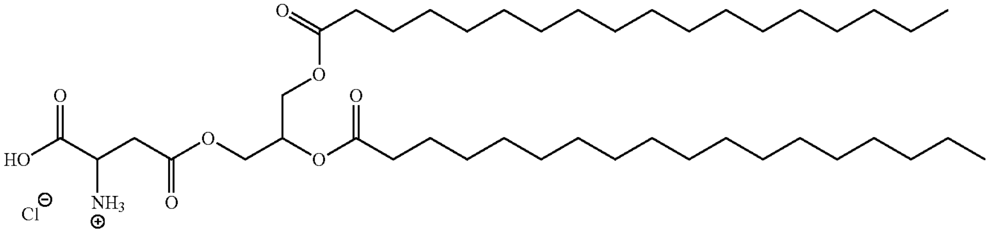,

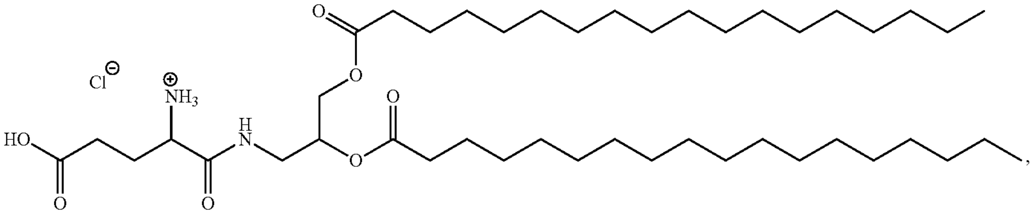,

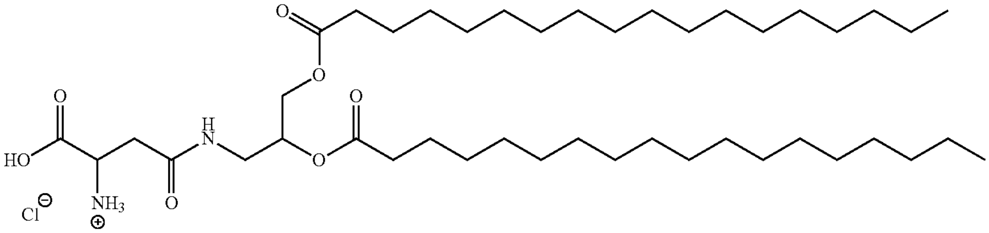, and

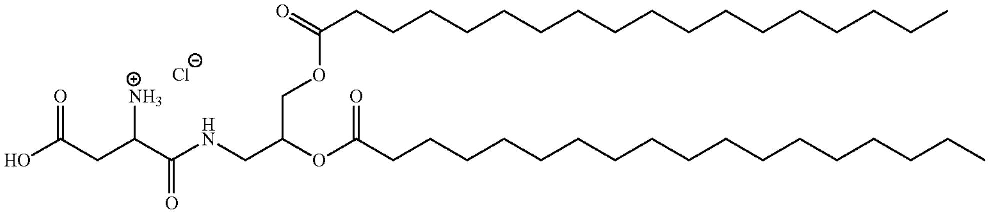

(iii) Structural Lipids

The lipid composition of a pharmaceutical composition disclosed herein can comprise one or more structural lipids. As used herein, the term "structural lipid" refers to sterols and also to lipids containing sterol moieties.

Incorporation of structural lipids in the lipid nanoparticle may help mitigate aggregation of other lipids in the particle. Structural lipids can be selected from the group including but not limited to, cholesterol, fecosterol, sitosterol, ergosterol, campesterol, stigmasterol, brassicasterol, tomatidine, tomatine, ursolic acid, alpha-tocopherol, hopanoids, phytosterols, steroids, and mixtures thereof. In some embodiments, the structural lipid is a sterol. As defined herein, "sterols" are a subgroup of steroids consisting of steroid alcohols. In certain embodiments, the structural lipid is a steroid. In certain embodiments, the structural lipid is cholesterol. In certain embodiments, the structural lipid is an analog of cholesterol. In certain embodiments, the structural lipid is alpha-tocopherol. Examples of structural lipids include, but are not limited to, the following:

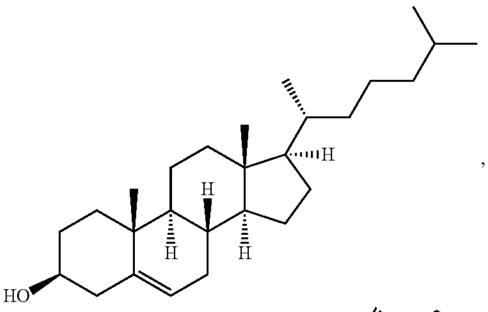

,

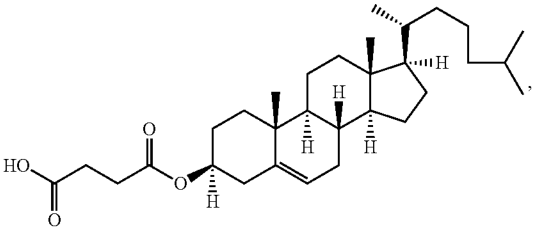

, and

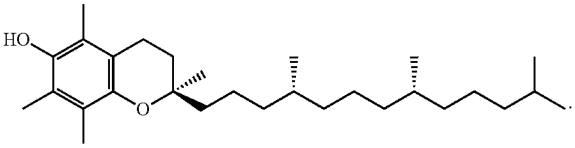

.

In one embodiment, the amount of the structural lipid (e.g., an sterol such as cholesterol) in the lipid composition of a pharmaceutical composition disclosed herein ranges from about 20 mol % to about 60 mol %, from about 25 mol % to about 55 mol %, from about 30 mol % to about 50 mol %, or from about 35 mol % to about 45 mol %.

In one embodiment, the amount of the structural lipid (e.g., an sterol such as cholesterol) in the lipid composition disclosed herein ranges from about 25 mol % to about 30 mol %, from about 30 mol % to about 35 mol %, or from about 35 mol % to about 40 mol %.

In one embodiment, the amount of the structural lipid (e.g., a sterol such as cholesterol) in the lipid composition disclosed herein is about 24 mol %, about 29 mol %, about 34 mol %, or about 39 mol %.

In some embodiments, the amount of the structural lipid (e.g., an sterol such as cholesterol) in the lipid composition disclosed herein is at least about 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60 mol %.

(iv) Polyethylene Glycol (PEG)-Lipids

The lipid composition of a pharmaceutical composition disclosed herein can comprise one or more a polyethylene glycol (PEG) lipid.

As used herein, the term "PEG-lipid" refers to polyethylene glycol (PEG)-modified lipids. Non-limiting examples of PEG-lipids include PEG-modified phosphatidylethanolamine and phosphatidic acid, PEG-ceramide conjugates (e.g., PEG-CerC14 or PEG-CerC20), PEG-modified dialkylamines and PEG-modified 1,2-diacyloxypropan-3-amines. Such lipids are also referred to as PEGylated lipids. For example, a PEG lipid can be PEG-c-DOMG, PEG-DMG, PEG-DLPE, PEG-DMPE, PEG-DPPC, or a PEG-DSPE lipid.

In some embodiments, the PEG-lipid includes, but not limited to 1,2-dimyristoyl-sn-glycerol methoxypolyethylene glycol (PEG-DMG), 1,2-distearoyl-sn-glycero-3-phosphoethanolamine-N-[amino(polyethylene glycol)] (PEG-DSPE), PEG-disteryl glycerol (PEG-DSG), PEG-dipalmetoleyl, PEG-dioleyl, PEG-distearyl, PEG-diacylglycamide (PEG-DAG), PEG-dipalmitoyl phosphatidylethanolamine (PEG-DPPE), or PEG-1,2-dimyristyloxlpropyl-3-amine (PEG-c-DMA).

In one embodiment, the PEG-lipid is selected from the group consisting of a PEG-modified phosphatidylethanolamine, a PEG-modified phosphatidic acid, a PEG-modified ceramide, a PEG-modified dialkylamine, a PEG-modified diacylglycerol, a PEG-modified dialkylglycerol, and mixtures thereof.

In some embodiments, the lipid moiety of the PEG-lipids includes those having lengths of from about $C_{14}$ to about $C_{22}$, preferably from about $C_{14}$ to about $C_{16}$. In some embodiments, a PEG moiety, for example an mPEG-$NH_2$, has a size of about 1000, 2000, 5000, 10,000, 15,000 or 20,000 daltons. In one embodiment, the PEG-lipid is PEG2k-DMG.

In one embodiment, the lipid nanoparticles described herein can comprise a PEG lipid which is a non-diffusible PEG. Non-limiting examples of non-diffusible PEGs include PEG-DSG and PEG-DSPE.

PEG-lipids are known in the art, such as those described in U.S. Pat. No. 8,158,601 and International Publ. No. WO 2015/130584 A2, which are incorporated herein by reference in their entirety.

In general, some of the other lipid components (e.g., PEG lipids) of various formulae, described herein may be synthesized as described International Patent Application No. PCT/US2016/000129, filed Dec. 10, 2016, entitled "Compositions and Methods for Delivery of Therapeutic Agents," which is incorporated by reference in its entirety.

The lipid component of a lipid nanoparticle composition may include one or more molecules comprising polyethylene glycol, such as PEG or PEG-modified lipids. Such species may be alternately referred to as PEGylated lipids. A PEG lipid is a lipid modified with polyethylene glycol. A PEG lipid may be selected from the non-limiting group including PEG-modified phosphatidylethanolamines, PEG-modified phosphatidic acids, PEG-modified ceramides, PEG-modified dialkylamines, PEG-modified diacylglycerols, PEG-modified dialkylglycerols, and mixtures thereof. For example, a PEG lipid may be PEG-c-DOMG, PEG-DMG, PEG-DLPE, PEG-DMPE, PEG-DPPC, or a PEG-DSPE lipid.

In some embodiments the PEG-modified lipids are a modified form of PEG DMG. PEG-DMG has the following structure:

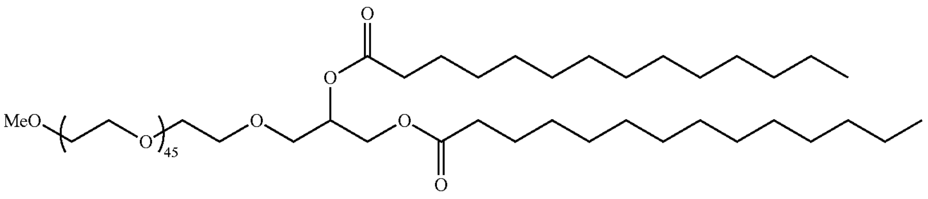

In one embodiment, PEG lipids useful in the present invention can be PEGylated lipids described in International Publication No. WO2012099755, the contents of which is herein incorporated by reference in its entirety. Any of these exemplary PEG lipids described herein may be modified to comprise a hydroxyl group on the PEG chain. In certain embodiments, the PEG lipid is a PEG-OH lipid. As generally defined herein, a "PEG-OH lipid" (also referred to herein as "hydroxy-PEGylated lipid") is a PEGylated lipid having one or more hydroxyl (—OH) groups on the lipid. In certain embodiments, the PEG-OH lipid includes one or more hydroxyl groups on the PEG chain. In certain embodiments, a PEG-OH or hydroxy-PEGylated lipid comprises an —OH group at the terminus of the PEG chain. Each possibility represents a separate embodiment of the present invention.

In certain embodiments, a PEG lipid useful in the present invention is a compound of Formula (VII). Provided herein are compounds of Formula (VII):

(VII)

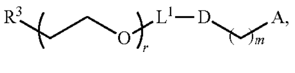

or salts thereof, wherein:

$R^3$ is —$OR^O$;

$R^O$ is hydrogen, optionally substituted alkyl, or an oxygen protecting group;

r is an integer between 1 and 100, inclusive;

$L^1$ is optionally substituted $C_{1-10}$ alkylene, wherein at least one methylene of the optionally substituted $C_{1-10}$ alkylene is independently replaced with optionally substituted carbocyclylene, optionally substituted heterocyclylene, optionally substituted arylene, optionally substituted heteroarylene, —O—, —$N(R^N)$—, —S—, —C(O)—, —$C(O)N(R^N)$—, —$NR^NC(O)$—, —C(O)O—, —OC(O)—, —OC(O)O—, —$OC(O)N(R^N)$—, —$NR^NC(O)O$—, or —$NR^NC(O)N(R^N)$—;

D is a moiety obtained by click chemistry or a moiety cleavable under physiological conditions;

m is 0, 1, 2, 3, 4, 5, 6, 7, 8, 9, or 10;

A is of the formula:

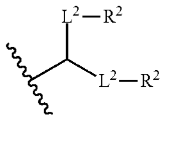 or 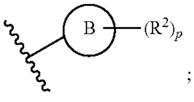 ;

each instance of $L^2$ is independently a bond or optionally substituted $C_{1-6}$ alkylene, wherein one methylene unit of the optionally substituted $C_{1-6}$ alkylene is optionally replaced with —O—, —$N(R^N)$—, —S—, —C(O)—, —$C(O)N(R^N)$—, —$NR^NC(O)$—, —C(O)O—, —OC(O)—, —OC(O)O—, —$OC(O)N(R^N)$—, —$NR^NC(O)O$—, or —$NR^NC(O)N(R^N)$—;

each instance of $R^2$ is independently optionally substituted $C_{1-30}$ alkyl, optionally substituted $C_{1-30}$ alkenyl, or optionally substituted $C_{1-30}$ alkynyl; optionally wherein one or more methylene units of $R^2$ are independently replaced with optionally substituted carbocyclylene, optionally substituted heterocyclylene, optionally substituted arylene, optionally substituted heteroarylene, —$N(R^N)$—, —O—, —S—, —C(O)—, —$C(O)N(R^N)$—, —$NR^NC(O)$—, —$NR^NC(O)N(R^N)$—, —C(O)O—, —OC(O)—, —OC(O)O—, —$OC(O)N(R^N)$—, —$NR^NC(O)O$—, —C(O)S—, —SC(O)—, —$C(=NR^N)$—, —$C(=NR^N)N(R^N)$—, —$NR^NC(=NR^N)$—, —$NR^NC(=NR^N)N(R^N)$—, —C(S)—, —$C(S)N(R^N)$—, —$NR^NC(S)$—, —$NR^NC(S)N(R^N)$—, —S(O)—, —OS(O)—, —S(O)O—, —OS(O)O—, —$OS(O)_2$—, —$S(O)_2O$—, —$OS(O)_2O$—, —$N(R^N)S(O)$—, —$S(O)N(R^N)$—, —$N(R^N)S(O)N(R^N)$—, —$OS(O)N(R^N)$—, —$N(R^N)S(O)O$—, —$S(O)_2$—, —$N(R^N)S(O)_2$—, —$S(O)_2N(R^N)$—, —$N(R^N)S(O)_2N(R^N)$—, —$OS(O)_2N(R^N)$—, or —$N(R^N)S(O)_2O$—;

each instance of $R^N$ is independently hydrogen, optionally substituted alkyl, or a nitrogen protecting group;

Ring B is optionally substituted carbocyclyl, optionally substituted heterocyclyl, optionally substituted aryl, or optionally substituted heteroaryl; and p is 1 or 2.

In certain embodiments, the compound of Formula (VII) is a PEG-OH lipid (i.e., $R^3$ is —$OR^O$, and $R^O$ is hydrogen). In certain embodiments, the compound of Formula (VII) is of Formula (VII-OH):

(VII-OH)

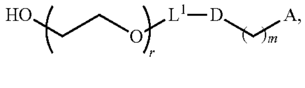

or a salt thereof.

In certain embodiments, D is a moiety obtained by click chemistry (e.g., triazole).

In certain embodiments, the compound of Formula (VII) is of Formula (VII-a-1) or (VII-a-2):

(VII-a-1)

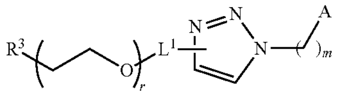 or (VII-a-2)

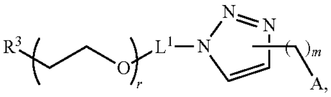

or a salt thereof.

In certain embodiments, the compound of Formula (VII) is of one of the following formulae:

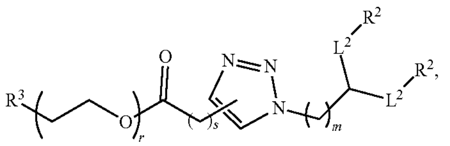

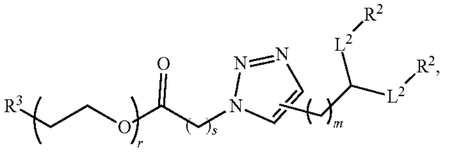

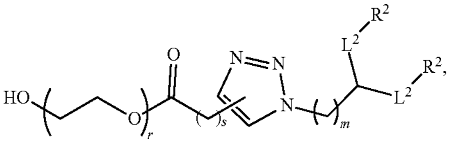

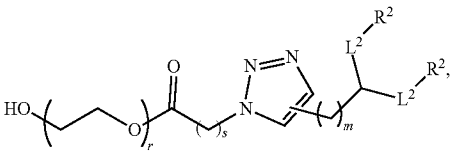

or a salt thereof, wherein s is 0, 1, 2, 3, 4, 5, 6, 7, 8, 9, or 10.

In certain embodiments, the compound of Formula (VII) is of one of the following formulae:

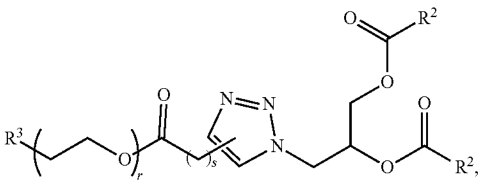

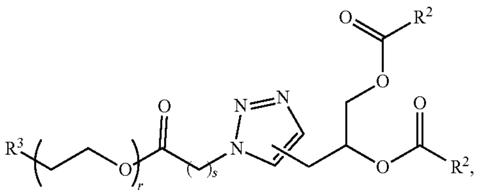

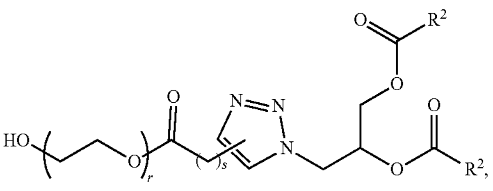

-continued

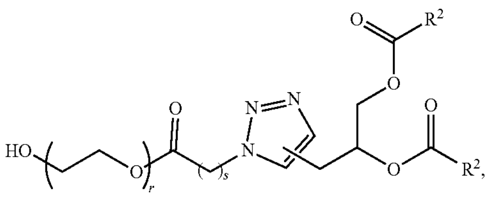

or a salt thereof.

In certain embodiments, a compound of Formula (VII) is of one of the following formulae:

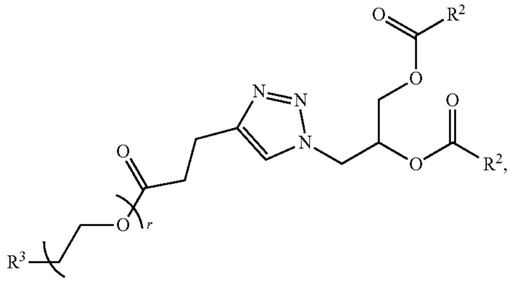

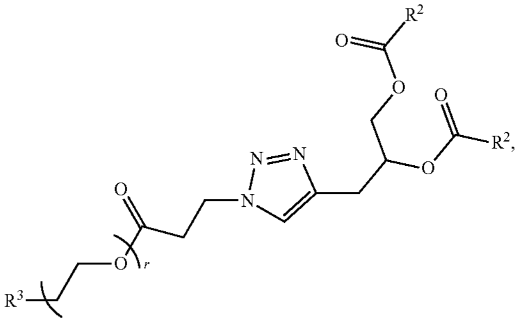

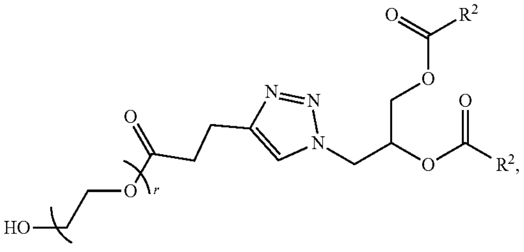

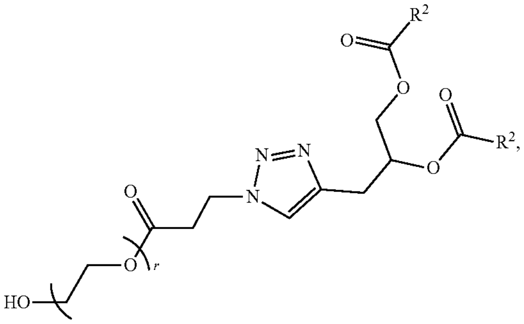

or a salt thereof.

In certain embodiments, a compound of Formula (VII) is of one of the following formulae:

(Compound 415)

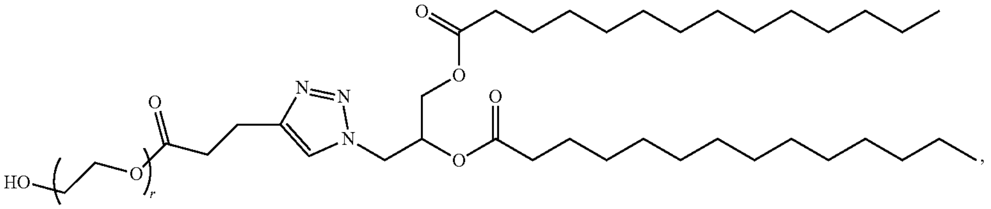

(Compound 416)

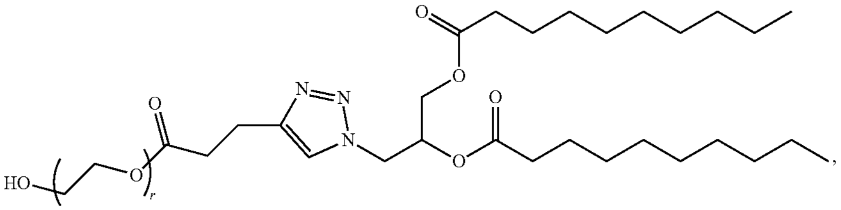

(Compound 417)

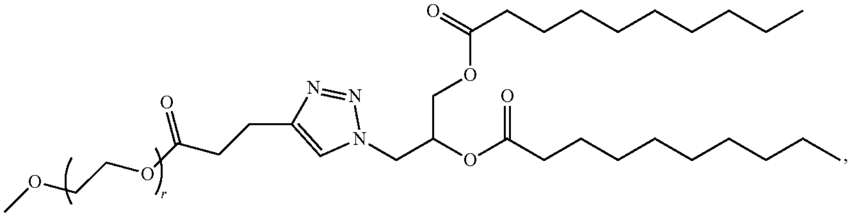

(Compound 418)

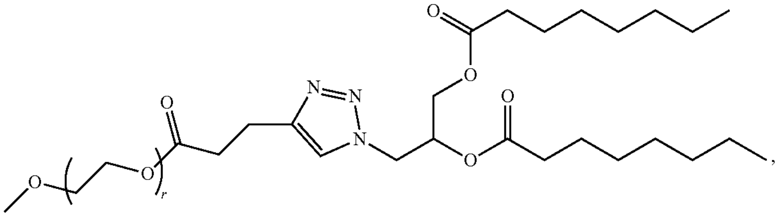

or a salt thereof.

In certain embodiments, D is a moiety cleavable under physiological conditions (e.g., ester, amide, carbonate, carbamate, urea). In certain embodiments, a compound of Formula (VII) is of Formula (VII-b-1) or (VII-b-2):

(VII-b-1)

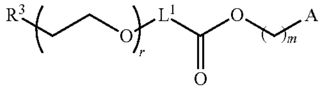

(VII-b-2)

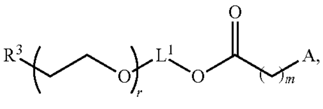

or a salt thereof.

In certain embodiments, a compound of Formula (VII) is of Formula (VII-b-1-OH) or (VII-b-2-OH):

(VII-b-1-OH)

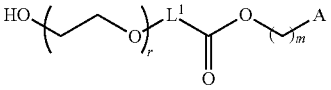

-continued (VII-b-2-OH)

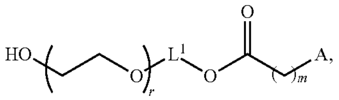

or a salt thereof.

In certain embodiments, the compound of Formula (VII) is of one of the following formulae:

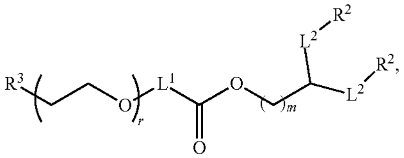

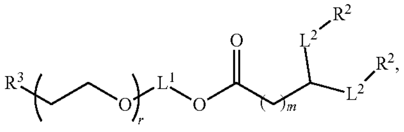

-continued
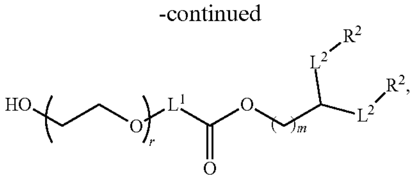
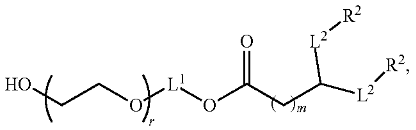
or a salt thereof.
In certain embodiments, a compound of Formula (VII) is of one of the following formulae:
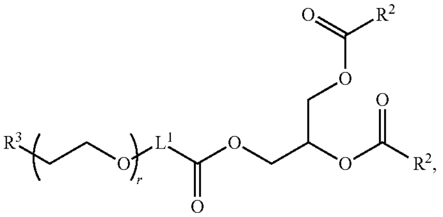
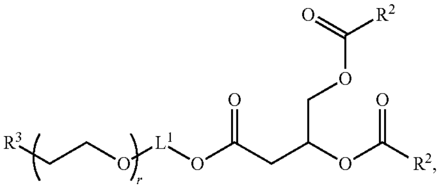
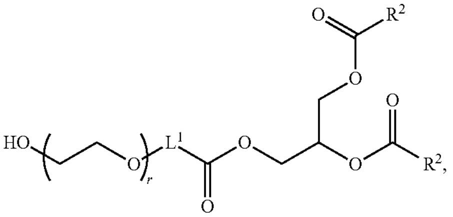
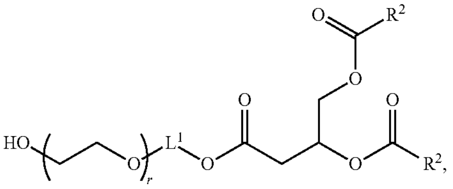
or a salt thereof.
In certain embodiments, a compound of Formula (VII) is of one of the following formulae:
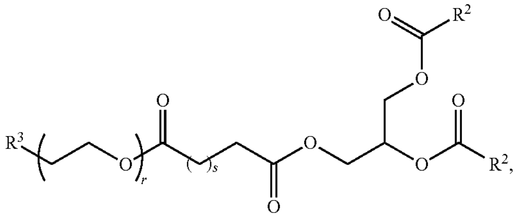
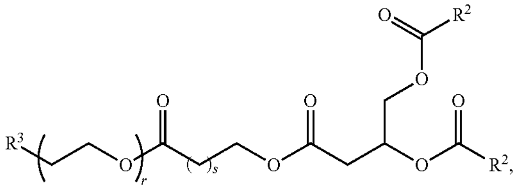
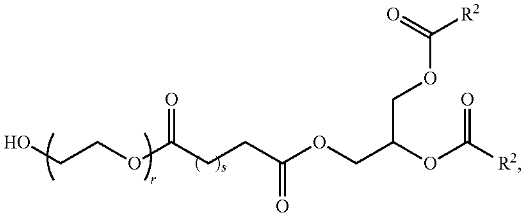
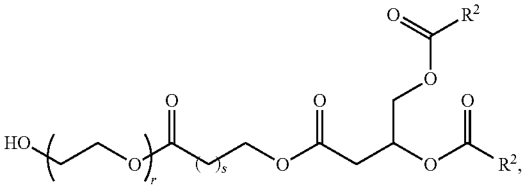
or a salt thereof.
In certain embodiments, a compound of Formula (VII) is of one of the following formulae:
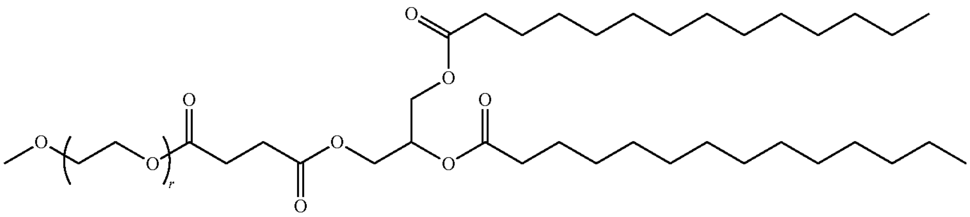
, -continued

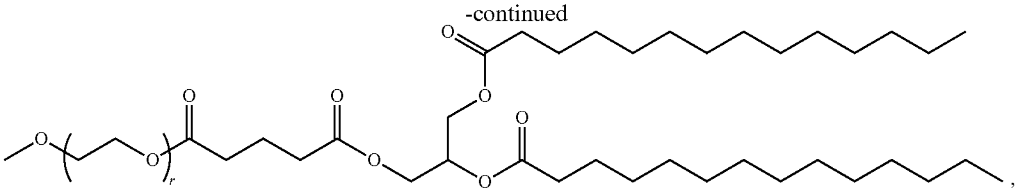

or salts thereof.

In certain embodiments, a PEG lipid useful in the present invention is a PEGylated fatty acid. In certain embodiments, a PEG lipid useful in the present invention is a compound of Formula (VIII). Provided herein are compounds of Formula (VIII):

(VIII)

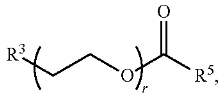

or a salts thereof, wherein:

$R^3$ is —$OR^O$;

$R^O$ is hydrogen, optionally substituted alkyl or an oxygen protecting group;

r is an integer between 1 and 100, inclusive;

$R^5$ is optionally substituted $C_{10-40}$ alkyl, optionally substituted $C_{10-40}$ alkenyl, or optionally substituted $C_{10-40}$ alkynyl; and optionally one or more methylene groups of $R^5$ are replaced with optionally substituted carbocyclylene, optionally substituted heterocyclylene, optionally substituted arylene, optionally substituted heteroarylene, —$N(R^N)$—, —O—, —S—, —C(O)—, —$C(O)N(R^N)$—, —$NR^NC(O)$—, —$NR^NC(O)N(R^N)$—, —C(O)O—, —OC(O)—, —OC(O)O—, —$OC(O)N(R^N)$—, —$NR^NC(O)O$—, —C(O)S—, —SC(O)—, —$C(=NR^N)$—, —$C(=NR^N)N(R^N)$—, —$NR^NC(=NR^N)$—, —$NR^NC(=NR^N)N(R^N)$—, —C(S)—, —$C(S)N(R^N)$—, —$NR^NC(S)$—, —$NR^NC(S)N(R^N)$—, —S(O)—, —OS(O)—, —S(O)O—, —OS(O)O—, —$OS(O)_2$—, —$S(O)_2O$—, —$OS(O)_2O$—, —$N(R^N)S(O)$—, —$S(O)N(R^N)$—, —$N(R^N)S(O)N(R^N)$—, —$OS(O)N(R^N)$—, —$N(R^N)S(O)O$—, —$S(O)_2$—, —$N(R^N)S(O)_2$—, —$S(O)_2N(R^N)$—, —$N(R^N)S(O)_2N(R^N)$—, —$OS(O)_2N(R^N)$—, or —$N(R^N)S(O)_2O$—; and each instance of $R^N$ is independently hydrogen, optionally substituted alkyl, or a nitrogen protecting group.

In certain embodiments, the compound of Formula (VIII) is of Formula (VIII-OH):

(VIII-OH)

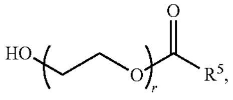

or a salt thereof. In some embodiments, r is 45.

In certain embodiments, a compound of Formula (VIII) is of one of the following formulae:

(Compound 419)

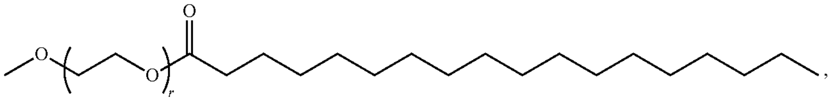

(Compound 420)

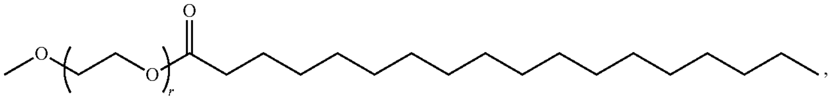

(Compound 421)

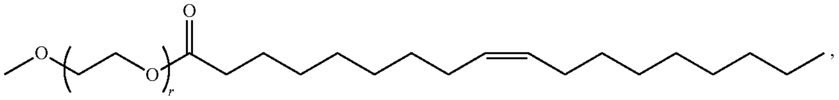

(Compound 422)

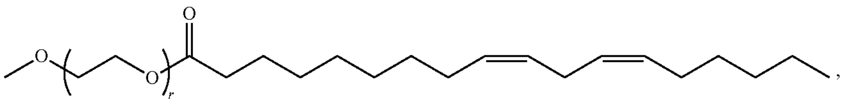

(Compound 423)

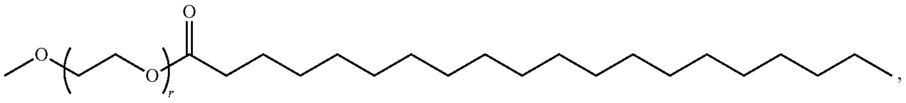

(Compound 424)

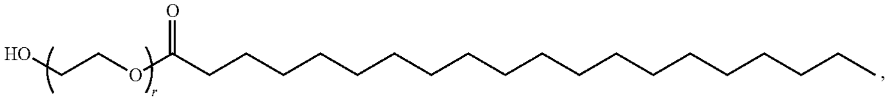

-continued (Compound 425)

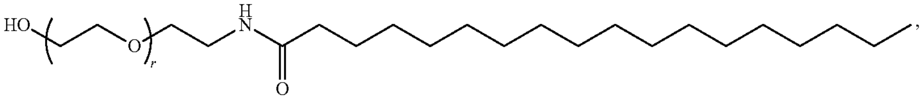

(Compound 426)

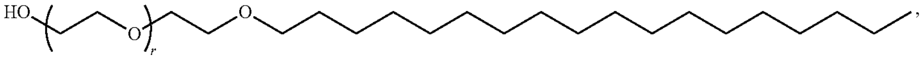

or a salt thereof. In some embodiments, r is 45.

In yet other embodiments the compound of Formula (VIII) is:

(Compound 427)

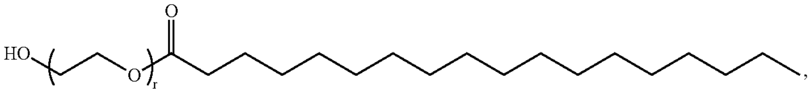

or a salt thereof.

In one embodiment, the compound of Formula (VIII) is (Compound 428)

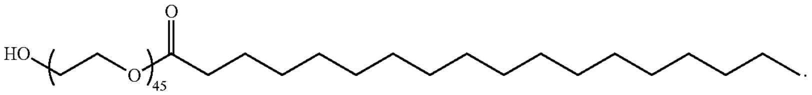

In one embodiment, the amount of PEG-lipid in the lipid composition of a pharmaceutical composition disclosed herein ranges from about 0.1 mol % to about 5 mol %, from about 0.5 mol % to about 5 mol %, from about 1 mol % to about 5 mol %, from about 1.5 mol % to about 5 mol %, from about 2 mol % to about 5 mol % mol %, from about 0.1 mol % to about 4 mol %, from about 0.5 mol % to about 4 mol %, from about 1 mol % to about 4 mol %, from about 1.5 mol % to about 4 mol %, from about 2 mol % to about 4 mol %, from about 0.1 mol % to about 3 mol %, from about 0.5 mol % to about 3 mol %, from about 1 mol % to about 3 mol %, from about 1.5 mol % to about 3 mol %, from about 2 mol % to about 3 mol %, from about 0.1 mol % to about 2 mol %, from about 0.5 mol % to about 2 mol %, from about 1 mol % to about 2 mol %, from about 1.5 mol % to about 2 mol %, from about 0.1 mol % to about 1.5 mol %, from about 0.5 mol % to about 1.5 mol %, or from about 1 mol % to about 1.5 mol %.

In one embodiment, the amount of PEG-lipid in the lipid composition disclosed herein is about 2 mol %. In one embodiment, the amount of PEG-lipid in the lipid composition disclosed herein is about 1.5 mol %.

In one embodiment, the amount of PEG-lipid in the lipid composition disclosed herein is at least about 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, or 5 mol %.

In some aspects, the lipid composition of the pharmaceutical compositions disclosed herein does not comprise a PEG-lipid.

(v) Other Ionizable Amino Lipids

The lipid composition of the pharmaceutical composition disclosed herein can comprise one or more ionizable amino lipids in addition to a lipid according to Formula (I), (III), (IV), (V), or (VI).

Ionizable lipids can be selected from the non-limiting group consisting of 3-(didodecylamino)-N1,N1,4-tridodecyl-1-piperazineethanamine (KL10), N1-[2-(didodecylamino)ethyl]-N1,N4,N4-tridodecyl-1,4-piperazinediethanamine (KL22), 14,25-ditridecyl-15,18,21,24-tetraaza-octatriacontane (KL25), 1,2-dilinoleyloxy-N,N-dimethylaminopropane (DLin-DMA), 2,2-dilinoleyl-4-dimethylaminomethyl-[1,3]-dioxolane (DLin-K-DMA), heptatriaconta-6,9,28,31-tetraen-19-yl 4-(dimethylamino) butanoate (DLin-MC3-DMA), 2,2-dilinoleyl-4-(2-dimethylaminoethyl)-[1,3]-dioxolane (DLin-KC2-DMA), 1,2-dioleyloxy-N,N-dimethylaminopropane (DODMA), (13Z, 165Z)—N,N-dimethyl-3-nonydocosa-13-16-dien-1-amine (L608), 2-({8-[(3β)-cholest-5-en-3-yloxy]octyl}oxy)-N,N-dimethyl-3-[(9Z,12Z)-octadeca-9,12-dien-1-yloxy]propan-1-amine (Octyl-CLinDMA), (2R)-2-({8-[(3β)-cholest-5-en-3-yloxy]octyl}oxy)-N,N-dimethyl-3-[(9Z,12Z)-octadeca-9,12-dien-1-yloxy]propan-1-amine (Octyl-CLinDMA (2R)), and (2S)-2-({8-[(3β)-cholest-5-en-3-yloxy]octyl}oxy)-N,N-dimethyl-3-[(9Z,12Z)-octadeca-9,12-dien-1-yloxy]propan-1-amine (Octyl-CLinDMA (2S)). In addition to these, an ionizable amino lipid can also be a lipid including a cyclic amine group.

Ionizable lipids can also be the compounds disclosed in International Publication No. WO 2017/075531 A1, hereby incorporated by reference in its entirety. For example, the ionizable amino lipids include, but not limited to:

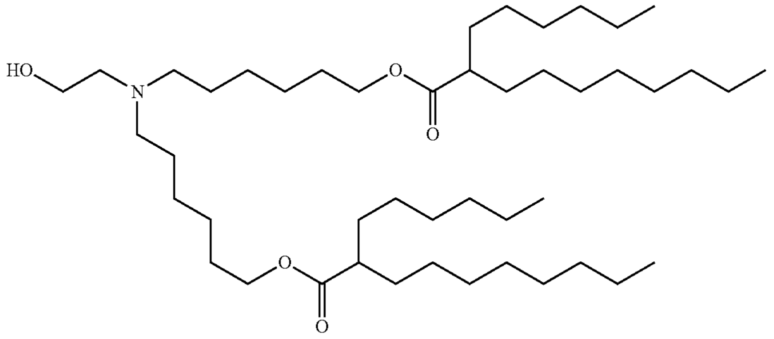

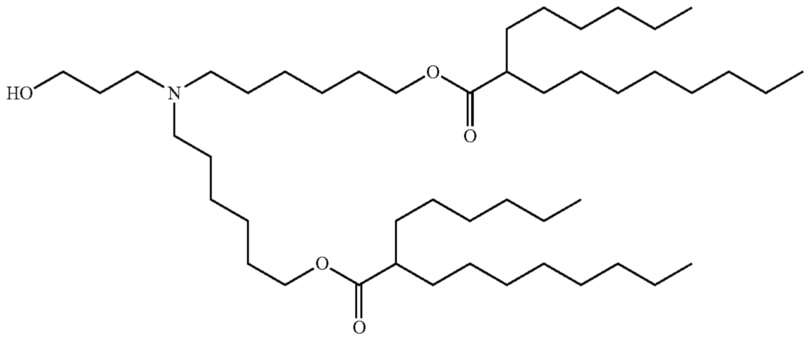

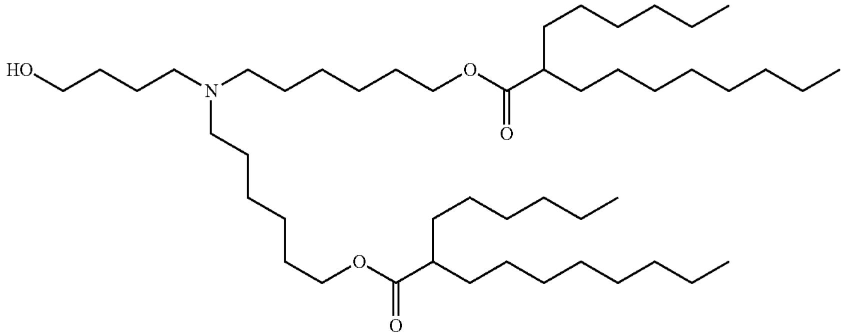

and any combination thereof.

Ionizable lipids can also be the compounds disclosed in International Publication No. WO 2015/199952 A1, hereby incorporated by reference in its entirety. For example, the ionizable amino lipids include, but not limited to:

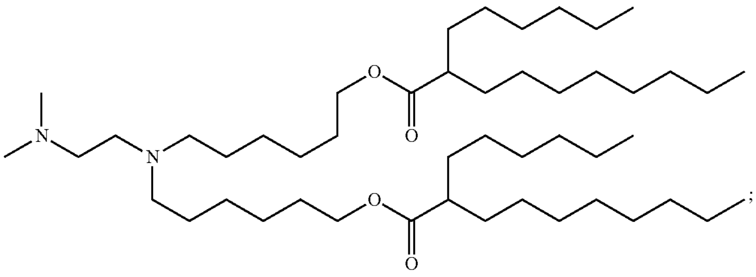
;
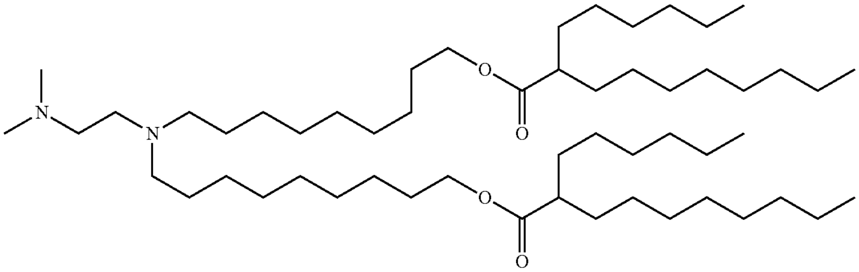
;
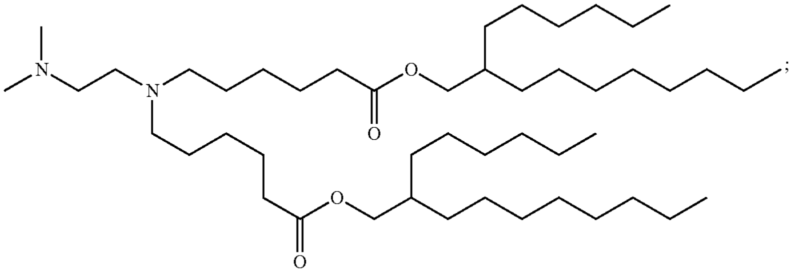
;
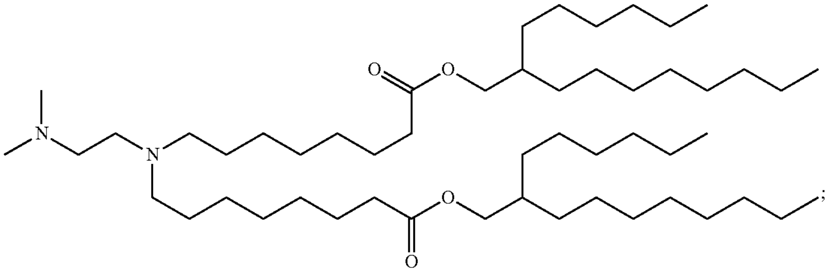
;
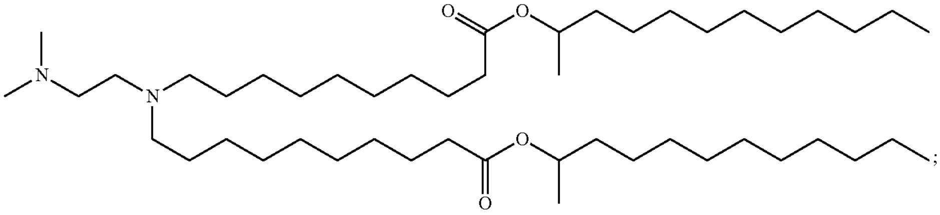
;
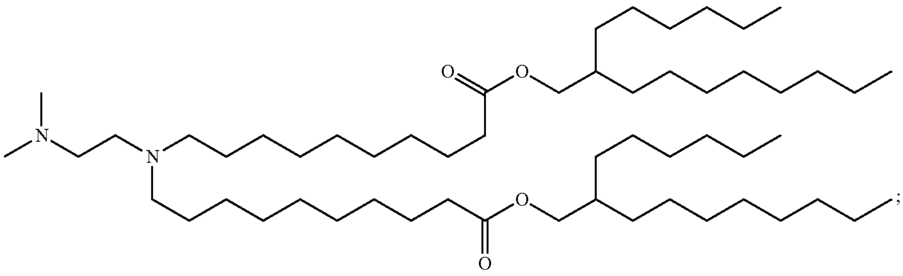
;

-continued
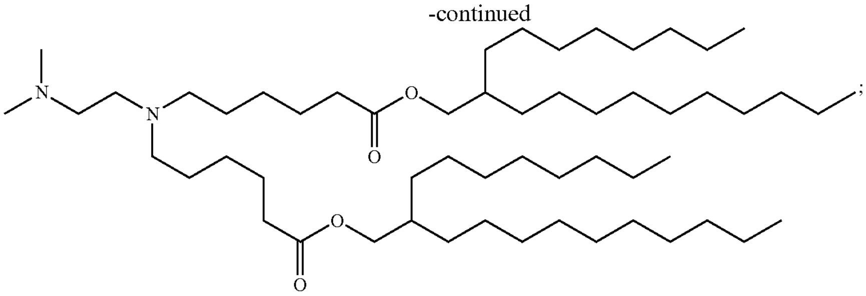
;
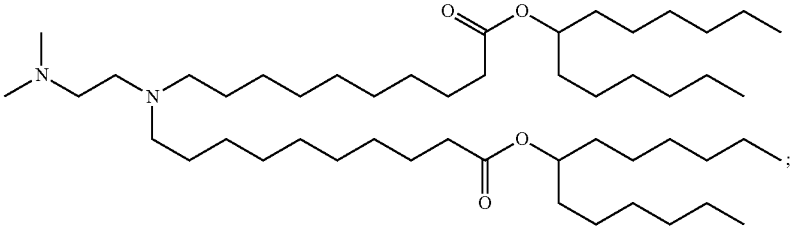
;
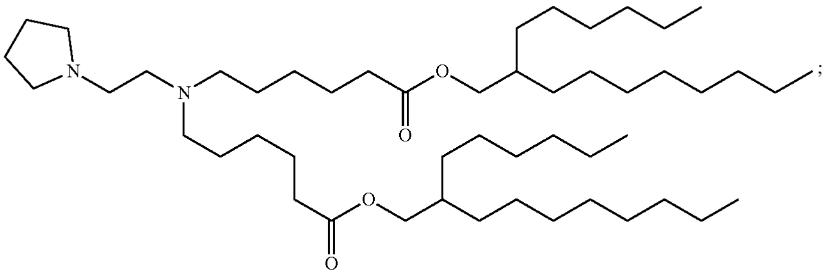
;
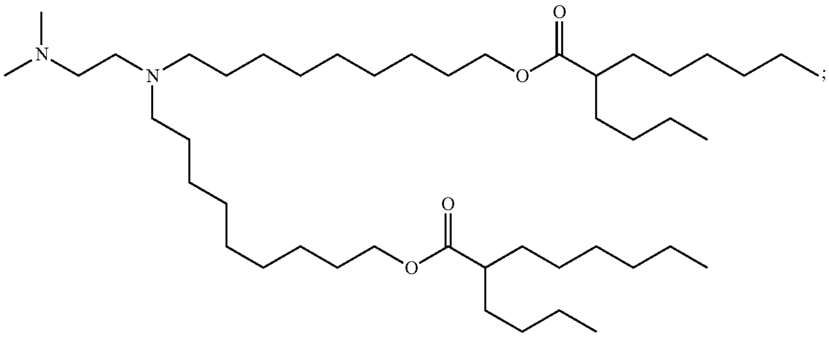
;
and any combination thereof.
Ionizable lipids can further include, but are not limited to:
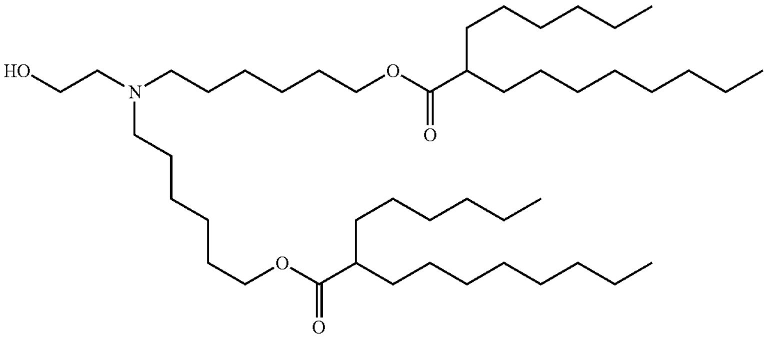

-continued

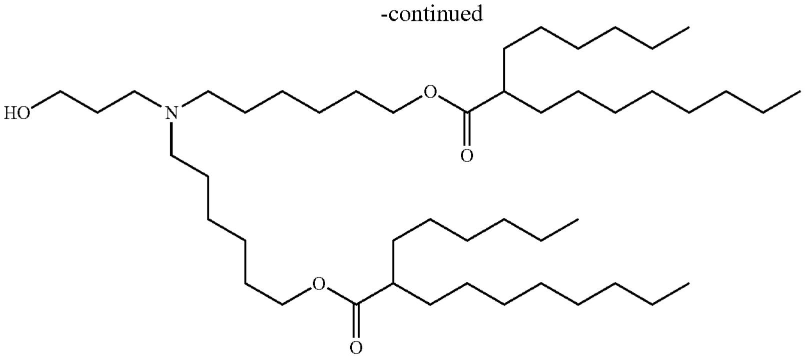

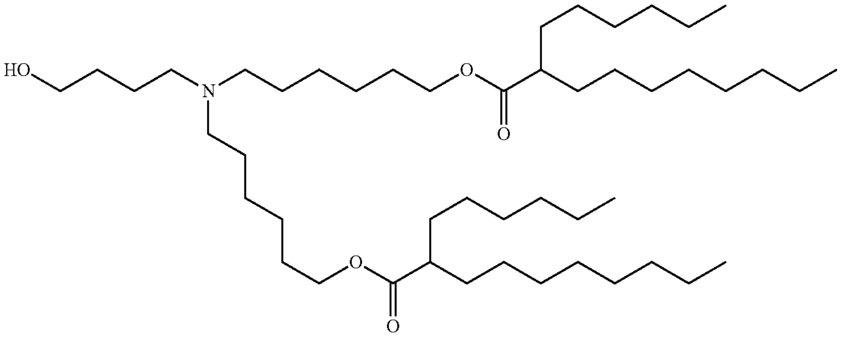

and any combination thereof.

(vi) Other Lipid Composition Components

The lipid composition of a pharmaceutical composition disclosed herein can include one or more components in addition to those described above. For example, the lipid composition can include one or more permeability enhancer molecules, carbohydrates, polymers, surface altering agents (e.g., surfactants), or other components. For example, a permeability enhancer molecule can be a molecule described by U.S. Patent Application Publication No. 2005/0222064. Carbohydrates can include simple sugars (e.g., glucose) and polysaccharides (e.g., glycogen and derivatives and analogs thereof).

A polymer can be included in and/or used to encapsulate or partially encapsulate a pharmaceutical composition disclosed herein (e.g., a pharmaceutical composition in lipid nanoparticle form). A polymer can be biodegradable and/or biocompatible. A polymer can be selected from, but is not limited to, polyamines, polyethers, polyamides, polyesters, polycarbamates, polyureas, polycarbonates, polystyrenes, polyimides, polysulfones, polyurethanes, polyacetylenes, polyethylenes, polyethyleneimines, polyisocyanates, polyacrylates, polymethacrylates, polyacrylonitriles, and polyarylates.

The ratio between the lipid composition and the polynucleotide range can be from about 10:1 to about 60:1 (wt/wt).

In some embodiments, the ratio between the lipid composition and the polynucleotide can be about 10:1, 11:1, 12:1, 13:1, 14:1, 15:1, 16:1, 17:1, 18:1, 19:1, 20:1, 21:1, 22:1, 23:1, 24:1, 25:1, 26:1, 27:1, 28:1, 29:1, 30:1, 31:1, 32:1, 33:1, 34:1, 35:1, 36:1, 37:1, 38:1, 39:1, 40:1, 41:1, 42:1, 43:1, 44:1, 45:1, 46:1, 47:1, 48:1, 49:1, 50:1, 51:1, 52:1, 53:1, 54:1, 55:1, 56:1, 57:1, 58:1, 59:1 or 60:1 (wt/wt). In some embodiments, the wt/wt ratio of the lipid composition to the polynucleotide encoding a therapeutic agent is about 20:1 or about 15:1.

In some embodiments, the pharmaceutical composition disclosed herein can contain more than one polypeptides. For example, a pharmaceutical composition disclosed herein can contain two or more polynucleotides (e.g., RNA, e.g., mRNA).

In one embodiment, the lipid nanoparticles described herein can comprise polynucleotides (e.g., mRNA) in a lipid:polynucleotide weight ratio of 5:1, 10:1, 15:1, 20:1, 25:1, 30:1, 35:1, 40:1, 45:1, 50:1, 55:1, 60:1 or 70:1, or a range or any of these ratios such as, but not limited to, 5:1 to about 10:1, from about 5:1 to about 15:1, from about 5:1 to about 20:1, from about 5:1 to about 25:1, from about 5:1 to about 30:1, from about 5:1 to about 35:1, from about 5:1 to about 40:1, from about 5:1 to about 45:1, from about 5:1 to about 50:1, from about 5:1 to about 55:1, from about 5:1 to about 60:1, from about 5:1 to about 70:1, from about 10:1 to about 15:1, from about 10:1 to about 20:1, from about 10:1 to about 25:1, from about 10:1 to about 30:1, from about 10:1 to about 35:1, from about 10:1 to about 40:1, from about 10:1 to about 45:1, from about 10:1 to about 50:1, from about 10:1 to about 55:1, from about 10:1 to about 60:1, from about 10:1 to about 70:1, from about 15:1 to about 20:1, from about 15:1 to about 25:1, from about 15:1 to about 30:1, from about 15:1 to about 35:1, from about 15:1 to about 40:1, from about 15:1 to about 45:1, from about 15:1 to about 50:1, from about 15:1 to about 55:1, from about 15:1 to about 60:1 or from about 15:1 to about 70:1.

In one embodiment, the lipid nanoparticles described herein can comprise the polynucleotide in a concentration from approximately 0.1 mg/ml to 2 mg/ml such as, but not limited to, 0.1 mg/ml, 0.2 mg/ml, 0.3 mg/ml, 0.4 mg/ml, 0.5 mg/ml, 0.6 mg/ml, 0.7 mg/ml, 0.8 mg/ml, 0.9 mg/ml, 1.0 mg/ml, 1.1 mg/ml, 1.2 mg/ml, 1.3 mg/ml, 1.4 mg/ml, 1.5 mg/ml, 1.6 mg/ml, 1.7 mg/ml, 1.8 mg/ml, 1.9 mg/ml, 2.0 mg/ml or greater than 2.0 mg/ml.

(vii) Nanoparticle Compositions

In some embodiments, the pharmaceutical compositions disclosed herein are formulated as lipid nanoparticles (LNP). Accordingly, the present disclosure also provides nanoparticle compositions comprising (i) a lipid composition comprising a delivery agent such as compound of Formula (I) or (III) as described herein, and (ii) a polynucleotide encoding a GALT polypeptide. In such nanoparticle composition, the lipid composition disclosed herein can encapsulate the polynucleotide encoding a GALT polypeptide.

Nanoparticle compositions are typically sized on the order of micrometers or smaller and can include a lipid bilayer. Nanoparticle compositions encompass lipid nanoparticles (LNPs), liposomes (e.g., lipid vesicles), and lipoplexes. For example, a nanoparticle composition can be a liposome having a lipid bilayer with a diameter of 500 nm or less.

Nanoparticle compositions include, for example, lipid nanoparticles (LNPs), liposomes, and lipoplexes. In some embodiments, nanoparticle compositions are vesicles including one or more lipid bilayers. In certain embodiments, a nanoparticle composition includes two or more concentric bilayers separated by aqueous compartments. Lipid bilayers can be functionalized and/or crosslinked to one another. Lipid bilayers can include one or more ligands, proteins, or channels.

In some embodiments, the nanoparticle compositions of the present disclosure comprise at least one compound according to Formula (I), (III), (IV), (V), or (VI). For example, the nanoparticle composition can include one or more of Compounds 1-147, or one or more of Compounds 1-342. Nanoparticle compositions can also include a variety of other components. For example, the nanoparticle composition can include one or more other lipids in addition to a lipid according to Formula (I), (III), (IV), (V), or (VI) such as (i) at least one phospholipid, (ii) at least one structural lipid, (iii) at least one PEG-lipid, or (iv) any combination thereof. Inclusion of structural lipid can be optional, for example when lipids according to Formula (III) are used in the lipid nanoparticle compositions of the invention.

In some embodiments, the nanoparticle composition comprises a compound of Formula (I), (e.g., Compounds 18, 25, 26 or 48). In some embodiments, the nanoparticle composition comprises a compound of Formula (I) (e.g., Compounds 18, 25, 26 or 48) and a phospholipid (e.g., DSPC).

In some embodiments, the nanoparticle composition comprises a compound of Formula (III) (e.g., Compound 236). In some embodiments, the nanoparticle composition comprises a compound of Formula (III) (e.g., Compound 236) and a phospholipid (e.g., DOPE or DSPC).

In some embodiments, the nanoparticle composition comprises a lipid composition consisting or consisting essentially of compound of Formula (I) (e.g., Compounds 18, 25, 26 or 48). In some embodiments, the nanoparticle composition comprises a lipid composition consisting or consisting essentially of a compound of Formula (I) (e.g., Compounds 18, 25, 26 or 48) and a phospholipid (e.g., DSPC).

In some embodiments, the nanoparticle composition comprises a lipid composition consisting or consisting essentially of compound of Formula (III) (e.g., Compound 236). In some embodiments, the nanoparticle composition comprises a lipid composition consisting or consisting essentially of a compound of Formula (III) (e.g., Compound 236) and a phospholipid (e.g., DOPE or DSPC).

In one embodiment, a lipid nanoparticle comprises an ionizable lipid, a structural lipid, a phospholipid, and mRNA. In some embodiments, the LNP comprises an ionizable lipid, a PEG-modified lipid, a sterol and a structural lipid. In some embodiments, the LNP has a molar ratio of about 20-60% ionizable lipid:about 5-25% structural lipid: about 25-55% sterol; and about 0.5-15% PEG-modified lipid. In some embodiments, the LNP comprises a molar ratio of about 50% ionizable lipid, about 1.5% PEG-modified lipid, about 38.5% cholesterol and about 10% structural lipid. In some embodiments, the LNP comprises a molar ratio of about 55% ionizable lipid, about 2.5% PEG lipid, about 32.5% cholesterol and about 10% structural lipid. In some embodiments, the ionizable lipid is an ionizable amino lipid and the structural lipid is a neutral lipid, and the sterol is a cholesterol. In some embodiments, the LNP has a molar ratio of 50:38.5:10:1.5 of ionizable lipid:cholesterol:DSPC: PEG lipid. In some embodiments, the ionizable lipid is Compound 18 or Compound 236, and the PEG lipid is Compound 428.

In some embodiments, the LNP has a molar ratio of 50:38.5:10:1.5 of Compound 18: Cholesterol:Phospholipid: Compound 428. In some embodiments, the LNP has a molar ratio of 50:38.5:10:1.5 of Compound 18:Cholesterol:DSPC: Compound 428.

In some embodiments, the LNP has a molar ratio of 50:38.5:10:1.5 of Compound 236:Cholesterol:Phospholipid: Compound 428. In some embodiments, the LNP has a molar ratio of 50:38.5:10:1.5 of Compound 236:Cholesterol:D-SPC:Compound 428.

In some embodiments, the LNP has a polydispersity value of less than 0.4. In some embodiments, the LNP has a net neutral charge at a neutral pH. In some embodiments, the LNP has a mean diameter of 50-150 nm. In some embodiments, the LNP has a mean diameter of 80-100 nm.

As generally defined herein, the term "lipid" refers to a small molecule that has hydrophobic or amphiphilic properties. Lipids may be naturally occurring or synthetic. Examples of classes of lipids include, but are not limited to, fats, waxes, sterol-containing metabolites, vitamins, fatty acids, glycerolipids, glycerophospholipids, sphingolipids, saccharolipids, and polyketides, and prenol lipids. In some instances, the amphiphilic properties of some lipids leads them to form liposomes, vesicles, or membranes in aqueous media.

In some embodiments, a lipid nanoparticle (LNP) may comprise an ionizable lipid. As used herein, the term "ionizable lipid" has its ordinary meaning in the art and may refer to a lipid comprising one or more charged moieties. In some embodiments, an ionizable lipid may be positively charged or negatively charged. An ionizable lipid may be positively charged, in which case it can be referred to as "cationic lipid". In certain embodiments, an ionizable lipid molecule may comprise an amine group, and can be referred to as an ionizable amino lipid. As used herein, a "charged moiety" is a chemical moiety that carries a formal electronic charge, e.g., monovalent (+1, or −1), divalent (+2, or −2), trivalent (+3, or −3), etc. The charged moiety may be anionic (i.e., negatively charged) or cationic (i.e., positively charged). Examples of positively-charged moieties include amine groups (e.g., primary, secondary, and/or tertiary amines), ammonium groups, pyridinium group, guanidine groups, and imidazolium groups. In a particular embodiment, the charged moieties comprise amine groups. Examples of negatively-charged groups or precursors thereof, include carboxylate groups, sulfonate groups, sulfate groups, phosphonate groups, phosphate groups, hydroxyl groups, and the like. The charge of the charged moiety may vary, in some cases, with the environmental conditions, for example, changes in pH may alter the charge of the moiety, and/or cause the moiety to become charged or uncharged. In general, the charge density of the molecule may be selected as desired.

It should be understood that the terms "charged" or "charged moiety" does not refer to a "partial negative charge" or "partial positive charge" on a molecule. The terms "partial negative charge" and "partial positive charge" are given its ordinary meaning in the art. A "partial negative charge" may result when a functional group comprises a bond that becomes polarized such that electron density is pulled toward one atom of the bond, creating a partial negative charge on the atom. Those of ordinary skill in the art will, in general, recognize bonds that can become polarized in this way.

In some embodiments, the ionizable lipid is an ionizable amino lipid, sometimes referred to in the art as an "ionizable cationic lipid". In one embodiment, the ionizable amino lipid may have a positively charged hydrophilic head and a hydrophobic tail that are connected via a linker structure.

In addition to these, an ionizable lipid may also be a lipid including a cyclic amine group.

In one embodiment, the ionizable lipid may be selected from, but not limited to, a ionizable lipid described in International Publication Nos. WO2013086354 and WO2013116126; the contents of each of which are herein incorporated by reference in their entirety.

In yet another embodiment, the ionizable lipid may be selected from, but not limited to, formula CLI-CLXXXXII of U.S. Pat. No. 7,404,969; each of which is herein incorporated by reference in their entirety.

In one embodiment, the lipid may be a cleavable lipid such as those described in International Publication No. WO2012170889, herein incorporated by reference in its entirety. In one embodiment, the lipid may be synthesized by methods known in the art and/or as described in International Publication Nos. WO2013086354; the contents of each of which are herein incorporated by reference in their entirety.

Nanoparticle compositions can be characterized by a variety of methods. For example, microscopy (e.g., transmission electron microscopy or scanning electron microscopy) can be used to examine the morphology and size distribution of a nanoparticle composition. Dynamic light scattering or potentiometry (e.g., potentiometric titrations) can be used to measure zeta potentials. Dynamic light scattering can also be utilized to determine particle sizes. Instruments such as the Zetasizer Nano ZS (Malvern Instruments Ltd, Malvern, Worcestershire, UK) can also be used to measure multiple characteristics of a nanoparticle composition, such as particle size, polydispersity index, and zeta potential.

The size of the nanoparticles can help counter biological reactions such as, but not limited to, inflammation, or can increase the biological effect of the polynucleotide.

As used herein, "size" or "mean size" in the context of nanoparticle compositions refers to the mean diameter of a nanoparticle composition.

In one embodiment, the polynucleotide encoding a GALT polypeptide are formulated in lipid nanoparticles having a diameter from about 10 to about 100 nm such as, but not limited to, about 10 to about 20 nm, about 10 to about 30 nm, about 10 to about 40 nm, about 10 to about 50 nm, about 10 to about 60 nm, about 10 to about 70 nm, about 10 to about 80 nm, about 10 to about 90 nm, about 20 to about 30 nm, about 20 to about 40 nm, about 20 to about 50 nm, about 20 to about 60 nm, about 20 to about 70 nm, about 20 to about 80 nm, about 20 to about 90 nm, about 20 to about 100 nm, about 30 to about 40 nm, about 30 to about 50 nm, about 30 to about 60 nm, about 30 to about 70 nm, about 30 to about 80 nm, about 30 to about 90 nm, about 30 to about 100 nm, about 40 to about 50 nm, about 40 to about 60 nm, about 40 to about 70 nm, about 40 to about 80 nm, about 40 to about 90 nm, about 40 to about 100 nm, about 50 to about 60 nm, about 50 to about 70 nm, about 50 to about 80 nm, about 50 to about 90 nm, about 50 to about 100 nm, about 60 to about 70 nm, about 60 to about 80 nm, about 60 to about 90 nm, about 60 to about 100 nm, about 70 to about 80 nm, about 70 to about 90 nm, about 70 to about 100 nm, about 80 to about 90 nm, about 80 to about 100 nm and/or about 90 to about 100 nm.

In one embodiment, the nanoparticles have a diameter from about 10 to 500 nm. In one embodiment, the nanoparticle has a diameter greater than 100 nm, greater than 150 nm, greater than 200 nm, greater than 250 nm, greater than 300 nm, greater than 350 nm, greater than 400 nm, greater than 450 nm, greater than 500 nm, greater than 550 nm, greater than 600 nm, greater than 650 nm, greater than 700 nm, greater than 750 nm, greater than 800 nm, greater than 850 nm, greater than 900 nm, greater than 950 nm or greater than 1000 nm.

In some embodiments, the largest dimension of a nanoparticle composition is 1 μm or shorter (e.g., 1 μm, 900 nm, 800 nm, 700 nm, 600 nm, 500 nm, 400 nm, 300 nm, 200 nm, 175 nm, 150 nm, 125 nm, 100 nm, 75 nm, 50 nm, or shorter).

A nanoparticle composition can be relatively homogenous. A polydispersity index can be used to indicate the homogeneity of a nanoparticle composition, e.g., the particle size distribution of the nanoparticle composition. A small (e.g., less than 0.3) polydispersity index generally indicates a narrow particle size distribution. A nanoparticle composition can have a polydispersity index from about 0 to about 0.25, such as 0.01, 0.02, 0.03, 0.04, 0.05, 0.06, 0.07, 0.08, 0.09, 0.10, 0.11, 0.12, 0.13, 0.14, 0.15, 0.16, 0.17, 0.18, 0.19, 0.20, 0.21, 0.22, 0.23, 0.24, or 0.25. In some embodiments, the polydispersity index of a nanoparticle composition disclosed herein can be from about 0.10 to about 0.20.

The zeta potential of a nanoparticle composition can be used to indicate the electrokinetic potential of the composition. For example, the zeta potential can describe the surface charge of a nanoparticle composition. Nanoparticle compositions with relatively low charges, positive or negative, are generally desirable, as more highly charged species can interact undesirably with cells, tissues, and other elements in the body. In some embodiments, the zeta potential of a nanoparticle composition disclosed herein can be from about −10 mV to about +20 mV, from about −10 mV to about +15 mV, from about 10 mV to about +10 mV, from about −10 mV to about +5 mV, from about −10 mV to about 0 mV, from about −10 mV to about −5 mV, from about −5 mV to about +20 mV, from about −5 mV to about +15 mV, from about −5 mV to about +10 mV, from about −5 mV to about +5 mV, from about −5 mV to about 0 mV, from about 0 mV to about +20 mV, from about 0 mV to about +15 mV, from about 0 mV to about +10 mV, from about 0 mV to about +5 mV, from about +5 mV to about +20 mV, from about +5 mV to about +15 mV, or from about +5 mV to about +10 mV.

In some embodiments, the zeta potential of the lipid nanoparticles can be from about 0 mV to about 100 mV, from about 0 mV to about 90 mV, from about 0 mV to about 80 mV, from about 0 mV to about 70 mV, from about 0 mV to about 60 mV, from about 0 mV to about 50 mV, from about 0 mV to about 40 mV, from about 0 mV to about 30 mV, from about 0 mV to about 20 mV, from about 0 mV to about 10 mV, from about 10 mV to about 100 mV, from about 10 mV to about 90 mV, from about 10 mV to about 80 mV, from about 10 mV to about 70 mV, from about 10 mV to about 60 mV, from about 10 mV to about 50 mV, from about 10 mV to about 40 mV, from about 10 mV to about 30 mV, from about 10 mV to about 20 mV, from about 20 mV to about 100 mV, from about 20 mV to about 90 mV, from about 20 mV to about 80 mV, from about 20 mV to about 70 mV, from about 20 mV to about 60 mV, from about 20 mV to about 50 mV, from about 20 mV to about 40 mV, from about 20 mV to about 30 mV, from about 30 mV to about 100 mV, from about 30 mV to about 90 mV, from about 30 mV to about 80 mV, from about 30 mV to about 70 mV, from about 30 mV to about 60 mV, from about 30 mV to about 50 mV, from about 30 mV to about 40 mV, from about 40 mV to about 100 mV, from about 40 mV to about 90 mV, from about 40 mV to about 80 mV, from about 40 mV to about 70 mV, from about 40 mV to about 60 mV, and from about 40 mV to about 50 mV. In some embodiments, the zeta potential of the lipid nanoparticles can be from about 10 mV to about 50 mV, from about 15 mV to about 45 mV, from about 20 mV to about 40 mV, and from about 25 mV to about 35 mV. In some embodiments, the zeta potential of the lipid nanoparticles can be about 10 mV, about 20 mV, about 30 mV, about 40 mV, about 50 mV, about 60 mV, about 70 mV, about 80 mV, about 90 mV, and about 100 mV.

The term "encapsulation efficiency" of a polynucleotide describes the amount of the polynucleotide that is encapsulated by or otherwise associated with a nanoparticle composition after preparation, relative to the initial amount provided. As used herein, "encapsulation" can refer to complete, substantial, or partial enclosure, confinement, surrounding, or encasement.

Encapsulation efficiency is desirably high (e.g., close to 100%). The encapsulation efficiency can be measured, for example, by comparing the amount of the polynucleotide in a solution containing the nanoparticle composition before and after breaking up the nanoparticle composition with one or more organic solvents or detergents.

Fluorescence can be used to measure the amount of free polynucleotide in a solution. For the nanoparticle compositions described herein, the encapsulation efficiency of a polynucleotide can be at least 50%, for example 50%, 55%, 60%, 65%, 70%, 75%, 80%, 85%, 90%, 91%, 92%, 93%, 94%, 95%, 96%, 97%, 98%, 99%, or 100%. In some embodiments, the encapsulation efficiency can be at least 80%. In certain embodiments, the encapsulation efficiency can be at least 90%.

The amount of a polynucleotide present in a pharmaceutical composition disclosed herein can depend on multiple factors such as the size of the polynucleotide, desired target and/or application, or other properties of the nanoparticle composition as well as on the properties of the polynucleotide.

For example, the amount of an mRNA useful in a nanoparticle composition can depend on the size (expressed as length, or molecular mass), sequence, and other characteristics of the mRNA. The relative amounts of a polynucleotide in a nanoparticle composition can also vary.

The relative amounts of the lipid composition and the polynucleotide present in a lipid nanoparticle composition of the present disclosure can be optimized according to considerations of efficacy and tolerability. For compositions including an mRNA as a polynucleotide, the N:P ratio can serve as a useful metric.

As the N:P ratio of a nanoparticle composition controls both expression and tolerability, nanoparticle compositions with low N:P ratios and strong expression are desirable. N:P ratios vary according to the ratio of lipids to RNA in a nanoparticle composition.

In general, a lower N:P ratio is preferred. The one or more RNA, lipids, and amounts thereof can be selected to provide an N:P ratio from about 2:1 to about 30:1, such as 2:1, 3:1, 4:1, 5:1, 6:1, 7:1, 8:1, 9:1, 10:1, 12:1, 14:1, 16:1, 18:1, 20:1, 22:1, 24:1, 26:1, 28:1, or 30:1. In certain embodiments, the N:P ratio can be from about 2:1 to about 8:1. In other embodiments, the N:P ratio is from about 5:1 to about 8:1. In certain embodiments, the N:P ratio is between 5:1 and 6:1. In one specific aspect, the N:P ratio is about is about 5.67:1.

In addition to providing nanoparticle compositions, the present disclosure also provides methods of producing lipid nanoparticles comprising encapsulating a polynucleotide. Such method comprises using any of the pharmaceutical compositions disclosed herein and producing lipid nanoparticles in accordance with methods of production of lipid nanoparticles known in the art. See, e.g., Wang et al. (2015) "Delivery of oligonucleotides with lipid nanoparticles" Adv. Drug Deliv. Rev. 87:68-80; Silva et al. (2015) "Delivery Systems for Biopharmaceuticals. Part I: Nanoparticles and Microparticles" Curr. Pharm. Technol. 16: 940-954; Naseri et al. (2015) "Solid Lipid Nanoparticles and Nanostructured Lipid Carriers: Structure, Preparation and Application" Adv. Pharm. Bull. 5:305-13; Silva et al. (2015) "Lipid nanoparticles for the delivery of biopharmaceuticals" Curr. Pharm. Biotechnol. 16:291-302, and references cited therein.

23. OTHER DELIVERY AGENTS a. Liposomes, Lipoplexes, and Lipid Nanoparticles

In some embodiments, the compositions or formulations of the present disclosure comprise a delivery agent, e.g., a liposome, a lioplexes, a lipid nanoparticle, or any combination thereof. The polynucleotides described herein (e.g., a polynucleotide comprising a nucleotide sequence encoding a GALT polypeptide) can be formulated using one or more liposomes, lipoplexes, or lipid nanoparticles. Liposomes, lipoplexes, or lipid nanoparticles can be used to improve the efficacy of the polynucleotides directed protein production as these formulations can increase cell transfection by the polynucleotide; and/or increase the translation of encoded protein. The liposomes, lipoplexes, or lipid nanoparticles can also be used to increase the stability of the polynucleotides.

Liposomes are artificially-prepared vesicles that can primarily be composed of a lipid bilayer and can be used as a delivery vehicle for the administration of pharmaceutical formulations. Liposomes can be of different sizes. A multilamellar vesicle (MLV) can be hundreds of nanometers in diameter, and can contain a series of concentric bilayers separated by narrow aqueous compartments. A small unicellular vesicle (SUV) can be smaller than 50 nm in diameter, and a large unilamellar vesicle (LUV) can be between 50 and 500 nm in diameter. Liposome design can include, but is not limited to, opsonins or ligands to improve the attachment of liposomes to unhealthy tissue or to activate events such as, but not limited to, endocytosis. Liposomes can contain a low or a high pH value in order to improve the delivery of the pharmaceutical formulations.

The formation of liposomes can depend on the pharmaceutical formulation entrapped and the liposomal ingredients, the nature of the medium in which the lipid vesicles are dispersed, the effective concentration of the entrapped substance and its potential toxicity, any additional processes involved during the application and/or delivery of the vesicles, the optimal size, polydispersity and the shelf-life of the vesicles for the intended application, and the batch-to-batch reproducibility and scale up production of safe and efficient liposomal products, etc.

As a non-limiting example, liposomes such as synthetic membrane vesicles can be prepared by the methods, apparatus and devices described in U.S. Pub. Nos. US20130177638, US20130177637, US20130177636, US20130177635, US20130177634, US20130177633, US20130183375, US20130183373, and US20130183372. In some embodiments, the polynucleotides described herein can be encapsulated by the liposome and/or it can be contained in an aqueous core that can then be encapsulated by the liposome as described in, e.g., Intl. Pub. Nos. WO2012031046, WO2012031043, WO2012030901, WO2012006378, and WO2013086526; and U.S. Pub. Nos. US20130189351, US20130195969 and US20130202684. Each of the references in herein incorporated by reference in its entirety.

In some embodiments, the polynucleotides described herein can be formulated in a cationic oil-in-water emulsion where the emulsion particle comprises an oil core and a cationic lipid that can interact with the polynucleotide anchoring the molecule to the emulsion particle. In some embodiments, the polynucleotides described herein can be formulated in a water-in-oil emulsion comprising a continuous hydrophobic phase in which the hydrophilic phase is dispersed. Exemplary emulsions can be made by the methods described in Intl. Pub. Nos. WO2012006380 and WO201087791, each of which is herein incorporated by reference in its entirety.

In some embodiments, the polynucleotides described herein can be formulated in a lipid-polycation complex. The formation of the lipid-polycation complex can be accomplished by methods as described in, e.g., U.S. Pub. No. US20120178702. As a non-limiting example, the polycation can include a cationic peptide or a polypeptide such as, but not limited to, polylysine, polyornithine and/or polyarginine and the cationic peptides described in Intl. Pub. No. WO2012013326 or U.S. Pub. No. US20130142818. Each of the references is herein incorporated by reference in its entirety.

In some embodiments, the polynucleotides described herein can be formulated in a lipid nanoparticle (LNP) such as those described in Intl. Pub. Nos. WO2013123523, WO2012170930, WO2011127255 and WO2008103276; and U.S. Pub. No. US20130171646, each of which is herein incorporated by reference in its entirety.

Lipid nanoparticle formulations typically comprise one or more lipids. In some embodiments, the lipid is an ionizable lipid (e.g., an ionizable amino lipid), sometimes referred to in the art as an "ionizable cationic lipid". In some embodiments, lipid nanoparticle formulations further comprise other components, including a phospholipid, a structural lipid, and a molecule capable of reducing particle aggregation, for example a PEG or PEG-modified lipid.

Exemplary ionizable lipids include, but not limited to, any one of Compounds 1-342 disclosed herein, DLin-MC3-DMA (MC3), DLin-DMA, DLenDMA, DLin-D-DMA, DLin-K-DMA, DLin-M-C2-DMA, DLin-K-DMA, DLin-KC2-DMA, DLin-KC3-DMA, DLin-KC4-DMA, DLin-C2K-DMA, DLin-MP-DMA, DODMA, 98N12-5, C12-200, DLin-C-DAP, DLin-DAC, DLinDAP, DLinAP, DLin-EG-DMA, DLin-2-DMAP, KL10, KL22, KL25, Octyl-CLinDMA, Octyl-CLinDMA (2R), Octyl-CLinDMA (2S), and any combination thereof. Other exemplary ionizable lipids include, (13Z,16Z)—N,N-dimethyl-3-nonyldocosa-13,16-dien-1-amine (L608), (20Z,23Z)—N,N-dimethyl-nonacosa-20,23-dien-10-amine, (17Z,20Z)—N,N-dimemyl-hexacosa-17,20-dien-9-amine, (16Z,19Z)-N5N-dimethylpentacosa-16,19-dien-8-amine, (13Z,16Z)—N,N-dimethyldocosa-13,16-dien-5-amine, (12Z,15Z)—N,N-dimethylhenicosa-12,15-dien-4-amine, (14Z,17Z)—N,N-dimethyltricosa-14,17-dien-6-amine, (15Z,18Z)—N,N-dimethyltetracosa-15,18-dien-7-amine, (18Z,21Z)—N,N-dimethylheptacosa-18,21-dien-10-amine, (15Z,18Z)—N,N-dimethyltetracosa-15,18-dien-5-amine, (14Z,17Z)—N,N-dimethyltricosa-14,17-dien-4-amine, (19Z,22Z)—N,N-dimeihyloctacosa-19,22-dien-9-amine, (18Z,21Z)—N,N-dimethylheptacosa-18,21-dien-8-amine, (17Z,20Z)—N,N-dimethylhexacosa-17,20-dien-7-amine, (16Z,19Z)—N,N-dimethylpentacosa-16,19-dien-6-amine, (22Z,25Z)—N,N-dimethylhentriaconta-22,25-dien-10-amine, (21Z,24Z)—N,N-dimethyltriaconta-21,24-dien-9-amine, (18Z)—N,N-dimetylheptacos-18-en-10-amine, (17Z)—N,N-dimethylhexacos-17-en-9-amine, (19Z,22Z)—N,N-dimethyloctacosa-19,22-dien-7-amine, N,N-dimethylheptacosan-10-amine, (20Z,23Z)-N-ethyl-N-methylnonacosa-20,23-dien-10-amine, 1-[(11Z,14Z)-1-nonylicosa-11,14-dien-1-yl]pyrrolidine, (20Z)—N,N-dimethylheptacos-20-en-10-amine, (15Z)—N,N-dimethyl eptacos-15-en-10-amine, (14Z)—N,N-dimethylnonacos-14-en-10-amine, (17Z)—N,N-dimethylnonacos-17-en-10-amine, (24Z)—N,N-dimethyltritriacont-24-en-10-amine, (20Z)—N,N-dimethylnonacos-20-en-10-amine, (22Z)—N,N-dimethylhentriacont-22-en-10-amine, (16Z)—N,N-dimethylpentacos-16-en-8-amine, (12Z,15Z)—N,N-dimethyl-2-nonylhenicosa-12,15-dien-1-amine, N,N-dimethyl-1-[(1S,2R)-2-octylcyclopropyl]eptadecan-8-amine, 1-[(1S,2R)-2-hexylcyclopropyl]-N,N-dimethylnonadecan-10-amine, N,N-dimethyl-1-[(1S,2R)-2-octylcyclopropyl]nonadecan-10-amine, N,N-dimethyl-21-[(1S,2R)-2-octylcyclopropyl]henicosan-10-amine, N,N-dimethyl-1-[(1S,2S)-2-{[(1R,2R)-2-pentylcyclopropyl]methyl}cyclopropyl]nonadecan-10-amine, N,N-dimethyl-1-[(1S,2R)-2-octylcyclopropyl]hexadecan-8-amine, N,N-dimethyl-[(1R,2S)-2-undecylcyclopropyl]tetradecan-5-amine, N,N-dimethyl-3-{7-[(1S,2R)-2-octylcyclopropyl]heptyl}dodecan-1-amine, 1-[(1R,2S)-2-heptylcyclopropyl]-N,N-dimethyloctadecan-9-amine, 1-[(1S,2R)-2-decylcyclopropyl]-N,N-dimethylpentadecan-6-amine, N,N-dimethyl-1-[(1S,2R)-2-octylcyclopropyl]pentadecan-8-amine, R-N,N-dimethyl-1-[(9Z,12Z)-octadeca-9,12-dien-1-yloxy]-3-(octyloxy)propan-2-amine, S—N,N-dimethyl-1-[(9Z,12Z)-octadeca-9,12-dien-1-yloxy]-3-(octyloxy)propan-2-amine, 1-{2-[(9Z,12Z)-octadeca-9,12-dien-1-yloxy]-1-[(octyloxy)methyl]ethyl}pyrrolidine, (2S)—N,N-dimethyl-1-[(9Z,12Z)-octadeca-9,12-dien-1-yloxy]-3-[(5Z)-oct-5-en-1-yloxy]propan-2-amine, 1-{2-[(9Z,12Z)-octadeca-9,12-dien-1-yloxy]-1-[(octyloxy)methyl]ethyl}azetidine, (2S)-1-(hexyloxy)-N,N-dimethyl-3-[(9Z,12Z)-octadeca-9,12-dien-1-yloxy]propan-2-amine, (2S)-1-(heptyloxy)-N,N-dimethyl-3-[(9Z,12Z)-octadeca-9,12-dien-1-yloxy]propan-2-amine, N,N-dimethyl-1-(nonyloxy)-3-[(9Z,12Z)-octadeca-9,12-dien-1-yloxy]propan-2-amine, N,N-dimethyl-1-[(9Z)-octadec-9-en-1-yloxy]-3-(octyloxy)propan-2-amine; (2S)—N,N-dimethyl-1-[(6Z,9Z,12Z)-octadeca-6,9,12-trien-1-yloxy]-3-(octyloxy)propan-2-amine, (2S)-1-[(11Z,14Z)-icosa-11,14-dien-1-yloxy]-N,N-dimethyl-3-(pentyloxy)propan-2-amine, (2S)-1-(hexyloxy)-3-[(11Z,14Z)-icosa-11,14-dien-1-yloxy]-N,N-dimethylpropan-2-amine, 1-[(11Z,14Z)-icosa-11,14-dien-1-yloxy]-N,N-dimethyl-3-(octyloxy)propan-2-amine, 1-[(13Z,16Z)- docosa-13,16-dien-1-yloxy]-N,N-dimethyl-3-(octyloxy) propan-2-amine, (2S)-1-[(13Z,16Z)-docosa-13,16-dien-1-yloxy]-3-(hexyloxy)-N,N-dimethylpropan-2-amine, (2S)-1-[(13Z)-docos-13-en-1-yloxy]-3-(hexyloxy)-N,N-dimethylpropan-2-amine, 1-[(13Z)-docos-13-en-1-yloxy]-N,N-dimethyl-3-(octyloxy)propan-2-amine, 1-[(9Z)-hexadec-9-en-1-yloxy]-N,N-dimethyl-3-(octyloxy)propan-2-amine, (2R)—N,N-dimethyl-H(1-metoyloctyl)oxyl-3-[(9Z,12Z)-octadeca-9,12-dien-1-yloxy]propan-2-amine, (2R)-1-[(3,7-dimethyloctyl)oxy]-N,N-dimethyl-3-[(9Z,12Z)-octadeca-9,12-dien-1-yloxy]propan-2-amine, N,N-dimethyl-1-(octyloxy)-3-({8-[(1S,2S)-2-{[(1R,2R)-2-pentylcyclopropyl]methyl}cyclopropyl]octyl}oxy)propan-2-amine, N,N-dimethyl-1-{[8-(2-oclylcyclopropyl)octyl]oxy}-3-(octyloxy)propan-2-amine, and (11E,20Z,23Z)—N,N-dimethylnonacosa-11,20,2-trien-10-amine, and any combination thereof.

Phospholipids include, but are not limited to, glycerophospholipids such as phosphatidylcholines, phosphatidylethanolamines, phosphatidylserines, phosphatidylinositols, phosphatidy glycerols, and phosphatidic acids. Phospholipids also include phosphosphingolipid, such as sphingomyelin. In some embodiments, the phospholipids are DLPC, DMPC, DOPC, DPPC, DSPC, DUPC, 18:0 Diether PC, DLnPC, DAPC, DHAPC, DOPE, 4ME 16:0 PE, DSPE, DLPE, DLnPE, DAPE, DHAPE, DOPG, and any combination thereof. In some embodiments, the phospholipids are MPPC, MSPC, PMPC, PSPC, SMPC, SPPC, DHAPE, DOPG, and any combination thereof. In some embodiments, the amount of phospholipids (e.g., DSPC) in the lipid composition ranges from about 1 mol % to about 20 mol %.

The structural lipids include sterols and lipids containing sterol moieties. In some embodiments, the structural lipids include cholesterol, fecosterol, sitosterol, ergosterol, campesterol, stigmasterol, brassicasterol, tomatidine, tomatine, ursolic acid, alpha-tocopherol, and mixtures thereof. In some embodiments, the structural lipid is cholesterol. In some embodiments, the amount of the structural lipids (e.g., cholesterol) in the lipid composition ranges from about 20 mol % to about 60 mol %.

The PEG-modified lipids include PEG-modified phosphatidylethanolamine and phosphatidic acid, PEG-ceramide conjugates (e.g., PEG-CerC14 or PEG-CerC20), PEG-modified dialkylamines and PEG-modified 1,2-diacyloxypropan-3-amines. Such lipids are also referred to as PEGylated lipids. For example, a PEG lipid can be PEG-c-DOMG, PEG-DMG, PEG-DLPE, PEG DMPE, PEG-DPPC, or a PEG-DSPE lipid. In some embodiments, the PEG-lipid are 1,2-dimyristoyl-sn-glycerol methoxypolyethylene glycol (PEG-DMG), 1,2-distearoyl-sn-glycero-3-phosphoethanolamine-N-[amino(polyethylene glycol)] (PEG-DSPE), PEG-disteryl glycerol (PEG-DSG), PEG-dipalmetoleyl, PEG-dioleyl, PEG-distearyl, PEG-diacylglycamide (PEG-DAG), PEG-dipalmitoyl phosphatidylethanolamine (PEG-DPPE), or PEG-1,2-dimyristyloxlpropyl-3-amine (PEG-c-DMA). In some embodiments, the PEG moiety has a size of about 1000, 2000, 5000, 10,000, 15,000 or 20,000 daltons. In some embodiments, the amount of PEG-lipid in the lipid composition ranges from about 0 mol % to about 5 mol %.

In some embodiments, the LNP formulations described herein can additionally comprise a permeability enhancer molecule. Non-limiting permeability enhancer molecules are described in U.S. Pub. No. US20050222064, herein incorporated by reference in its entirety.

The LNP formulations can further contain a phosphate conjugate. The phosphate conjugate can increase in vivo circulation times and/or increase the targeted delivery of the nanoparticle. Phosphate conjugates can be made by the methods described in, e.g., Intl. Pub. No. WO2013033438 or U.S. Pub. No. US20130196948. The LNP formulation can also contain a polymer conjugate (e.g., a water soluble conjugate) as described in, e.g., U.S. Pub. Nos. US20130059360, US20130196948, and US20130072709. Each of the references is herein incorporated by reference in its entirety.

The LNP formulations can comprise a conjugate to enhance the delivery of nanoparticles of the present invention in a subject. Further, the conjugate can inhibit phagocytic clearance of the nanoparticles in a subject. In some embodiments, the conjugate can be a "self" peptide designed from the human membrane protein CD47 (e.g., the "self" particles described by Rodriguez et al, Science 2013 339, 971-975, herein incorporated by reference in its entirety). As shown by Rodriguez et al. the self peptides delayed macrophage-mediated clearance of nanoparticles which enhanced delivery of the nanoparticles.

The LNP formulations can comprise a carbohydrate carrier. As a non-limiting example, the carbohydrate carrier can include, but is not limited to, an anhydride-modified phytoglycogen or glycogen-type material, phytoglycogen octenyl succinate, phytoglycogen beta-dextrin, anhydride-modified phytoglycogen beta-dextrin (e.g., Intl. Pub. No. WO2012109121, herein incorporated by reference in its entirety).

The LNP formulations can be coated with a surfactant or polymer to improve the delivery of the particle. In some embodiments, the LNP can be coated with a hydrophilic coating such as, but not limited to, PEG coatings and/or coatings that have a neutral surface charge as described in U.S. Pub. No. US20130183244, herein incorporated by reference in its entirety.

The LNP formulations can be engineered to alter the surface properties of particles so that the lipid nanoparticles can penetrate the mucosal barrier as described in U.S. Pat. No. 8,241,670 or Intl. Pub. No. WO2013110028, each of which is herein incorporated by reference in its entirety.

The LNP engineered to penetrate mucus can comprise a polymeric material (i.e., a polymeric core) and/or a polymer-vitamin conjugate and/or a tri-block co-polymer. The polymeric material can include, but is not limited to, polyamines, polyethers, polyamides, polyesters, polycarbamates, polyureas, polycarbonates, poly(styrenes), polyimides, polysulfones, polyurethanes, polyacetylenes, polyethylenes, polyethyeneimines, polyisocyanates, polyacrylates, polymethacrylates, polyacrylonitriles, and polyarylates.

LNP engineered to penetrate mucus can also include surface altering agents such as, but not limited to, polynucleotides, anionic proteins (e.g., bovine serum albumin), surfactants (e.g., cationic surfactants such as for example dimethyldioctadecyl-ammonium bromide), sugars or sugar derivatives (e.g., cyclodextrin), nucleic acids, polymers (e.g., heparin, polyethylene glycol and poloxamer), mucolytic agents (e.g., N-acetylcysteine, mugwort, bromelain, papain, clerodendrum, acetylcysteine, bromhexine, carbocisteine, eprazinone, mesna, ambroxol, sobrerol, domiodol, letosteine, stepronin, tiopronin, gelsolin, thymosin β4 dornase alfa, neltenexine, erdosteine) and various DNases including rhDNase.

In some embodiments, the mucus penetrating LNP can be a hypotonic formulation comprising a mucosal penetration enhancing coating. The formulation can be hypotonic for the epithelium to which it is being delivered. Non-limiting examples of hypotonic formulations can be found in, e.g., Intl. Pub. No. WO2013110028, herein incorporated by reference in its entirety.

In some embodiments, the polynucleotide described herein is formulated as a lipoplex, such as, without limitation, the ATUPLEX™ system, the DACC system, the DBTC system and other siRNA-lipoplex technology from Silence Therapeutics (London, United Kingdom), STEMFECT™ from STEMGENT® (Cambridge, Mass.), and polyethylenimine (PEI) or protamine-based targeted and non-targeted delivery of nucleic acids (Aleku et al. Cancer Res. 2008 68:9788-9798; Strumberg et al. Int J Clin Pharmacol Ther 2012 50:76-78; Santel et al., Gene Ther 2006 13:1222-1234; Santel et al., Gene Ther 2006 13:1360-1370; Gutbier et al., Pulm Pharmacol. Ther. 2010 23:334-344; Kaufmann et al. Microvasc Res 2010 80:286-293 Weide et al. J Immunother. 2009 32:498-507; Weide et al. J Immunother. 2008 31:180-188; Pascolo Expert Opin. Biol. Ther. 4:1285-1294; Fotin-Mleczek et al., 2011 J. Immunother. 34:1-15; Song et al., Nature Biotechnol. 2005, 23:709-717; Peer et al., Proc Natl Acad Sci USA. 2007 6; 104:4095-4100; deFougerolles Hum Gene Ther. 2008 19:125-132; all of which are incorporated herein by reference in its entirety).

In some embodiments, the polynucleotides described herein are formulated as a solid lipid nanoparticle (SLN), which can be spherical with an average diameter between 10 to 1000 nm. SLN possess a solid lipid core matrix that can solubilize lipophilic molecules and can be stabilized with surfactants and/or emulsifiers. Exemplary SLN can be those as described in Intl. Pub. No. WO2013105101, herein incorporated by reference in its entirety.

In some embodiments, the polynucleotides described herein can be formulated for controlled release and/or targeted delivery. As used herein, "controlled release" refers to a pharmaceutical composition or compound release profile that conforms to a particular pattern of release to effect a therapeutic outcome. In one embodiment, the polynucleotides can be encapsulated into a delivery agent described herein and/or known in the art for controlled release and/or targeted delivery. As used herein, the term "encapsulate" means to enclose, surround or encase. As it relates to the formulation of the compounds of the invention, encapsulation can be substantial, complete or partial. The term "substantially encapsulated" means that at least greater than 50, 60, 70, 80, 85, 90, 95, 96, 97, 98, 99, or greater than 99% of the pharmaceutical composition or compound of the invention can be enclosed, surrounded or encased within the delivery agent. "Partially encapsulation" means that less than 10, 10, 20, 30, 40 50 or less of the pharmaceutical composition or compound of the invention can be enclosed, surrounded or encased within the delivery agent.

Advantageously, encapsulation can be determined by measuring the escape or the activity of the pharmaceutical composition or compound of the invention using fluorescence and/or electron micrograph. For example, at least 1, 5, 10, 20, 30, 40, 50, 60, 70, 80, 85, 90, 95, 96, 97, 98, 99, 99.9, or greater than 99% of the pharmaceutical composition or compound of the invention are encapsulated in the delivery agent.

In some embodiments, the polynucleotide controlled release formulation can include at least one controlled release coating (e.g., OPADRY®, EUDRAGIT RL®, EUDRAGIT RS® and cellulose derivatives such as ethylcellulose aqueous dispersions (AQUACOAT® and SURELEASE®)). In some embodiments, the polynucleotide controlled release formulation can comprise a polymer system as described in U.S. Pub. No. US20130130348, or a PEG and/or PEG related polymer derivative as described in U.S. Pat. No. 8,404,222, each of which is incorporated by reference in its entirety.

In some embodiments, the polynucleotides described herein can be encapsulated in a therapeutic nanoparticle, referred to herein as "therapeutic nanoparticle polynucleotides." Therapeutic nanoparticles can be formulated by methods described in, e.g., Intl. Pub. Nos. WO2010005740, WO2010030763, WO2010005721, WO2010005723, and WO2012054923; and U.S. Pub. Nos. US20110262491, US20100104645, US20100087337, US20100068285, US20110274759, US20100068286, US20120288541, US20120140790, US20130123351 and US20130230567; and U.S. Pat. Nos. 8,206,747, 8,293,276, 8,318,208 and 8,318,211, each of which is herein incorporated by reference in its entirety.

In some embodiments, the therapeutic nanoparticle polynucleotide can be formulated for sustained release. As used herein, "sustained release" refers to a pharmaceutical composition or compound that conforms to a release rate over a specific period of time. The period of time can include, but is not limited to, hours, days, weeks, months and years. As a non-limiting example, the sustained release nanoparticle of the polynucleotides described herein can be formulated as disclosed in Intl. Pub. No. WO2010075072 and U.S. Pub. Nos. US20100216804, US20110217377, US20120201859 and US20130150295, each of which is herein incorporated by reference in their entirety.

In some embodiments, the therapeutic nanoparticle polynucleotide can be formulated to be target specific, such as those described in Intl. Pub. Nos. WO2008121949, WO2010005726, WO2010005725, WO2011084521 and WO2011084518; and U.S. Pub. Nos. US20100069426, US20120004293 and US20100104655, each of which is herein incorporated by reference in its entirety.

The LNPs can be prepared using microfluidic mixers or micromixers. Exemplary microfluidic mixers can include, but are not limited to, a slit interdigital micromixer including, but not limited to those manufactured by Microinnova (Allerheiligen bei Wildon, Austria) and/or a staggered herringbone micromixer (SHM) (see Zhigaltsevet al., "Bottom-up design and synthesis of limit size lipid nanoparticle systems with aqueous and triglyceride cores using millisecond microfluidic mixing," Langmuir 28:3633-40 (2012); Belliveau et al., "Microfluidic synthesis of highly potent limit-size lipid nanoparticles for in vivo delivery of siRNA," Molecular Therapy-Nucleic Acids. 1:e37 (2012); Chen et al., "Rapid discovery of potent siRNA-containing lipid nanoparticles enabled by controlled microfluidic formulation," J. Am. Chem. Soc. 134(16):6948-51 (2012); each of which is herein incorporated by reference in its entirety). Exemplary micromixers include Slit Interdigital Microstructured Mixer (SIMM-V2) or a Standard Slit Interdigital Micro Mixer (SSIMM) or Caterpillar (CPMM) or Impinging-jet (IJMM,) from the Institut fur Mikrotechnik Mainz GmbH, Mainz Germany. In some embodiments, methods of making LNP using SHM further comprise mixing at least two input streams wherein mixing occurs by microstructure-induced chaotic advection (MICA). According to this method, fluid streams flow through channels present in a herringbone pattern causing rotational flow and folding the fluids around each other. This method can also comprise a surface for fluid mixing wherein the surface changes orientations during fluid cycling. Methods of generating LNPs using SHM include those disclosed in U.S. Pub. Nos. US20040262223 and US20120276209, each of which is incorporated herein by reference in their entirety.

In some embodiments, the polynucleotides described herein can be formulated in lipid nanoparticles using microfluidic technology (see Whitesides, George M., "The Origins and the Future of Microfluidics," Nature 442: 368-373 (2006); and Abraham et al., "Chaotic Mixer for Microchannels," Science 295: 647-651 (2002); each of which is herein incorporated by reference in its entirety). In some embodiments, the polynucleotides can be formulated in lipid nanoparticles using a micromixer chip such as, but not limited to, those from Harvard Apparatus (Holliston, Mass.) or Dolomite Microfluidics (Royston, UK). A micromixer chip can be used for rapid mixing of two or more fluid streams with a split and recombine mechanism.

In some embodiments, the polynucleotides described herein can be formulated in lipid nanoparticles having a diameter from about 1 nm to about 100 nm such as, but not limited to, about 1 nm to about 20 nm, from about 1 nm to about 30 nm, from about 1 nm to about 40 nm, from about 1 nm to about 50 nm, from about 1 nm to about 60 nm, from about 1 nm to about 70 nm, from about 1 nm to about 80 nm, from about 1 nm to about 90 nm, from about 5 nm to about from 100 nm, from about 5 nm to about 10 nm, about 5 nm to about 20 nm, from about 5 nm to about 30 nm, from about 5 nm to about 40 nm, from about 5 nm to about 50 nm, from about 5 nm to about 60 nm, from about 5 nm to about 70 nm, from about 5 nm to about 80 nm, from about 5 nm to about 90 nm, about 10 to about 20 nm, about 10 to about 30 nm, about 10 to about 40 nm, about 10 to about 50 nm, about 10 to about 60 nm, about 10 to about 70 nm, about 10 to about 80 nm, about 10 to about 90 nm, about 20 to about 30 nm, about 20 to about 40 nm, about 20 to about 50 nm, about 20 to about 60 nm, about 20 to about 70 nm, about 20 to about 80 nm, about 20 to about 90 nm, about 20 to about 100 nm, about 30 to about 40 nm, about 30 to about 50 nm, about 30 to about 60 nm, about 30 to about 70 nm, about 30 to about 80 nm, about 30 to about 90 nm, about 30 to about 100 nm, about 40 to about 50 nm, about 40 to about 60 nm, about 40 to about 70 nm, about 40 to about 80 nm, about 40 to about 90 nm, about 40 to about 100 nm, about 50 to about 60 nm, about 50 to about 70 nm about 50 to about 80 nm, about 50 to about 90 nm, about 50 to about 100 nm, about 60 to about 70 nm, about 60 to about 80 nm, about 60 to about 90 nm, about 60 to about 100 nm, about 70 to about 80 nm, about 70 to about 90 nm, about 70 to about 100 nm, about 80 to about 90 nm, about 80 to about 100 nm and/or about 90 to about 100 nm.

In some embodiments, the lipid nanoparticles can have a diameter from about 10 to 500 nm. In one embodiment, the lipid nanoparticle can have a diameter greater than 100 nm, greater than 150 nm, greater than 200 nm, greater than 250 nm, greater than 300 nm, greater than 350 nm, greater than 400 nm, greater than 450 nm, greater than 500 nm, greater than 550 nm, greater than 600 nm, greater than 650 nm, greater than 700 nm, greater than 750 nm, greater than 800 nm, greater than 850 nm, greater than 900 nm, greater than 950 nm or greater than 1000 nm.

In some embodiments, the polynucleotides can be delivered using smaller LNPs. Such particles can comprise a diameter from below 0.1 μm up to 100 nm such as, but not limited to, less than 0.1 μm, less than 1.0 μm, less than 5 μm, less than 10 μm, less than 15 um, less than 20 um, less than 25 um, less than 30 um, less than 35 um, less than 40 um, less than 50 um, less than 55 um, less than 60 um, less than 65 um, less than 70 um, less than 75 um, less than 80 um, less than 85 um, less than 90 um, less than 95 um, less than 100 um, less than 125 um, less than 150 um, less than 175 um, less than 200 um, less than 225 um, less than 250 um, less than 275 um, less than 300 um, less than 325 um, less than 350 um, less than 375 um, less than 400 um, less than 425 um, less than 450 um, less than 475 um, less than 500 um, less than 525 um, less than 550 um, less than 575 um, less than 600 um, less than 625 um, less than 650 um, less than 675 um, less than 700 um, less than 725 um, less than 750 um, less than 775 um, less than 800 um, less than 825 um, less than 850 um, less than 875 um, less than 900 um, less than 925 um, less than 950 um, or less than 975 um.

The nanoparticles and microparticles described herein can be geometrically engineered to modulate macrophage and/or the immune response. The geometrically engineered particles can have varied shapes, sizes and/or surface charges to incorporate the polynucleotides described herein for targeted delivery such as, but not limited to, pulmonary delivery (see, e.g., Intl. Pub. No. WO2013082111, herein incorporated by reference in its entirety). Other physical features the geometrically engineering particles can include, but are not limited to, fenestrations, angled arms, asymmetry and surface roughness, charge that can alter the interactions with cells and tissues.

In some embodiment, the nanoparticles described herein are stealth nanoparticles or target-specific stealth nanoparticles such as, but not limited to, those described in U.S. Pub. No. US20130172406, herein incorporated by reference in its entirety. The stealth or target-specific stealth nanoparticles can comprise a polymeric matrix, which can comprise two or more polymers such as, but not limited to, polyethylenes, polycarbonates, polyanhydrides, polyhydroxyacids, polypropylfumerates, polycaprolactones, polyamides, polyacetals, polyethers, polyesters, poly(orthoesters), polycyanoacrylates, polyvinyl alcohols, polyurethanes, polyphosphazenes, polyacrylates, polymethacrylates, polycyanoacrylates, polyureas, polystyrenes, polyamines, polyesters, polyanhydrides, polyethers, polyurethanes, polymethacrylates, polyacrylates, polycyanoacrylates, or combinations thereof.

b. Lipidoids

In some embodiments, the compositions or formulations of the present disclosure comprise a delivery agent, e.g., a lipidoid. The polynucleotides described herein (e.g., a polynucleotide comprising a nucleotide sequence encoding a GALT polypeptide) can be formulated with lipidoids. Complexes, micelles, liposomes or particles can be prepared containing these lipidoids and therefore to achieve an effective delivery of the polynucleotide, as judged by the production of an encoded protein, following the injection of a lipidoid formulation via localized and/or systemic routes of administration. Lipidoid complexes of polynucleotides can be administered by various means including, but not limited to, intravenous, intramuscular, or subcutaneous routes.

The synthesis of lipidoids is described in literature (see Mahon et al., Bioconjug. Chem. 2010 21:1448-1454; Schroeder et al., J Intern Med. 2010 267:9-21; Akinc et al., Nat Biotechnol. 2008 26:561-569; Love et al., Proc Natl Acad Sci USA. 2010 107:1864-1869; Siegwart et al., Proc Natl Acad Sci USA. 2011 108:12996-3001; all of which are incorporated herein in their entireties).

Formulations with the different lipidoids, including, but not limited to penta[3-(1-laurylaminopropionyl)]-triethylenetetramine hydrochloride (TETA-SLAP; also known as 98N12-5, see Murugaiah et al., Analytical Biochemistry, 401:61 (2010)), C12-200 (including derivatives and variants), and MD1, can be tested for in vivo activity. The lipidoid "98N12-5" is disclosed by Akinc et al., Mol Ther. 2009 17:872-879. The lipidoid "C12-200" is disclosed by Love et al., Proc Natl Acad Sci USA. 2010 107:1864-1869 and Liu and Huang, Molecular Therapy. 2010 669-670. Each of the references is herein incorporated by reference in its entirety.

In one embodiment, the polynucleotides described herein can be formulated in an aminoalcohol lipidoid. Aminoalcohol lipidoids can be prepared by the methods described in U.S. Pat. No. 8,450,298 (herein incorporated by reference in its entirety).

The lipidoid formulations can include particles comprising either 3 or 4 or more components in addition to polynucleotides. Lipidoids and polynucleotide formulations comprising lipidoids are described in Intl. Pub. No. WO 2015051214 (herein incorporated by reference in its entirety.

c. Hyaluronidase

In some embodiments, the polynucleotides described herein (e.g., a polynucleotide comprising a nucleotide sequence encoding a GALT polypeptide) and hyaluronidase for injection (e.g., intramuscular or subcutaneous injection). Hyaluronidase catalyzes the hydrolysis of hyaluronan, which is a constituent of the interstitial barrier. Hyaluronidase lowers the viscosity of hyaluronan, thereby increases tissue permeability (Frost, Expert Opin. Drug Deliv. (2007) 4:427-440). Alternatively, the hyaluronidase can be used to increase the number of cells exposed to the polynucleotides administered intramuscularly, or subcutaneously.

d. Nanoparticle Mimics

In some embodiments, the polynucleotides described herein (e.g., a polynucleotide comprising a nucleotide sequence encoding a GALT polypeptide) is encapsulated within and/or absorbed to a nanoparticle mimic. A nanoparticle mimic can mimic the delivery function organisms or particles such as, but not limited to, pathogens, viruses, bacteria, fungus, parasites, prions and cells. As a non-limiting example, the polynucleotides described herein can be encapsulated in a non-viron particle that can mimic the delivery function of a virus (see e.g., Intl. Pub. No. WO2012006376 and U.S. Pub. Nos. US20130171241 and US20130195968, each of which is herein incorporated by reference in its entirety).

e. Nanotubes

In some embodiments, the compositions or formulations of the present disclosure comprise the polynucleotides described herein (e.g., a polynucleotide comprising a nucleotide sequence encoding a GALT polypeptide) attached or otherwise bound to (e.g., through steric, ionic, covalent and/or other forces) at least one nanotube, such as, but not limited to, rosette nanotubes, rosette nanotubes having twin bases with a linker, carbon nanotubes and/or single-walled carbon nanotubes. Nanotubes and nanotube formulations comprising a polynucleotide are described in, e.g., Intl. Pub. No. WO2014152211, herein incorporated by reference in its entirety.

f. Self-Assembled Nanoparticles, or Self-Assembled Macromolecules

In some embodiments, the compositions or formulations of the present disclosure comprise the polynucleotides described herein (e.g., a polynucleotide comprising a nucleotide sequence encoding a GALT polypeptide) in self-assembled nanoparticles, or amphiphilic macromolecules (AMs) for delivery. AMs comprise biocompatible amphiphilic polymers that have an alkylated sugar backbone covalently linked to poly(ethylene glycol). In aqueous solution, the AMs self-assemble to form micelles. Nucleic acid self-assembled nanoparticles are described in Intl. Appl. No. PCT/US2014/027077, and AMs and methods of forming AMs are described in U.S. Pub. No. US20130217753, each of which is herein incorporated by reference in its entirety.

g. Inorganic Nanoparticles, Semi-Conductive and Metallic Nanoparticles

In some embodiments, the compositions or formulations of the present disclosure comprise the polynucleotides described herein (e.g., a polynucleotide comprising a nucleotide sequence encoding a GALT polypeptide) in inorganic nanoparticles, or water-dispersible nanoparticles comprising a semiconductive or metallic material. The inorganic nanoparticles can include, but are not limited to, clay substances that are water swellable. The water-dispersible nanoparticles can be hydrophobic or hydrophilic nanoparticles. As a non-limiting example, the inorganic, semiconductive and metallic nanoparticles are described in, e.g., U.S. Pat. Nos. 5,585,108 and 8,257,745; and U.S. Pub. Nos. US20120228565, US 20120265001 and US 20120283503, each of which is herein incorporated by reference in their entirety.

h. Surgical Sealants: Gels and Hydrogels

In some embodiments, the compositions or formulations of the present disclosure comprise the polynucleotides described herein (e.g., a polynucleotide comprising a nucleotide sequence encoding a GALT polypeptide) in a surgical sealant. Surgical sealants such as gels and hydrogels are described in Intl. Appl. No. PCT/US2014/027077, herein incorporated by reference in its entirety.

i. Suspension Formulations

In some embodiments, the compositions or formulations of the present disclosure comprise the polynucleotides described herein (e.g., a polynucleotide comprising a nucleotide sequence encoding a GALT polypeptide) in suspensions. In some embodiments, suspensions comprise a polynucleotide, water immiscible oil depots, surfactants and/or co-surfactants and/or co-solvents. Suspensions can be formed by first preparing an aqueous solution of a polynucleotide and an oil-based phase comprising one or more surfactants, and then mixing the two phases (aqueous and oil-based).

Exemplary oils for suspension formulations can include, but are not limited to, sesame oil and Miglyol (comprising esters of saturated coconut and palmkernel oil-derived caprylic and capric fatty acids and glycerin or propylene glycol), corn oil, soybean oil, peanut oil, beeswax and/or palm seed oil. Exemplary surfactants can include, but are not limited to Cremophor, polysorbate 20, polysorbate 80, polyethylene glycol, transcutol, Capmul®, labrasol, isopropyl myristate, and/or Span 80. In some embodiments, suspensions can comprise co-solvents including, but not limited to ethanol, glycerol and/or propylene glycol.

In some embodiments, suspensions can provide modulation of the release of the polynucleotides into the surrounding environment by diffusion from a water immiscible depot followed by resolubilization into a surrounding environment (e.g., an aqueous environment).

In some embodiments, the polynucleotides can be formulated such that upon injection, an emulsion forms spontaneously (e.g., when delivered to an aqueous phase), which can provide a high surface area to volume ratio for release of polynucleotides from an oil phase to an aqueous phase. In some embodiments, the polynucleotide is formulated in a nanoemulsion, which can comprise a liquid hydrophobic core surrounded by or coated with a lipid or surfactant layer. Exemplary nanoemulsions and their preparations are described in, e.g., U.S. Pat. No. 8,496,945, herein incorporated by reference in its entirety.

j. Cations and Anions

In some embodiments, the compositions or formulations of the present disclosure comprise the polynucleotides described herein (e.g., a polynucleotide comprising a nucleotide sequence encoding a GALT polypeptide) and a cation or anion, such as Zn2+, Ca2+, Cu2+, Mg2+ and combinations thereof. Exemplary formulations can include polymers and a polynucleotide complexed with a metal cation as described in, e.g., U.S. Pat. Nos. 6,265,389 and 6,555,525, each of which is herein incorporated by reference in its entirety. In some embodiments, cationic nanoparticles can contain a combination of divalent and monovalent cations. The delivery of polynucleotides in cationic nanoparticles or in one or more depot comprising cationic nanoparticles can improve polynucleotide bioavailability by acting as a long-acting depot and/or reducing the rate of degradation by nucleases.

k. Molded Nanoparticles and Microparticles

In some embodiments, the compositions or formulations of the present disclosure comprise the polynucleotides described herein (e.g., a polynucleotide comprising a nucleotide sequence encoding a GALT polypeptide) in molded nanoparticles in various sizes, shapes and chemistry. For example, the nanoparticles and/or microparticles can be made using the PRINT® technology by LIQUIDA TECHNOLOGIES® (Morrisville, N.C.) (e.g., International Pub. No. WO2007024323, herein incorporated by reference in its entirety).

In some embodiments, the polynucleotides described herein (e.g., a polynucleotide comprising a nucleotide sequence encoding a GALT polypeptide) is formulated in microparticles. The microparticles can contain a core of the polynucleotide and a cortex of a biocompatible and/or biodegradable polymer, including but not limited to, poly (a-hydroxy acid), a polyhydroxy butyric acid, a polycaprolactone, a polyorthoester and a polyanhydride. The microparticle can have adsorbent surfaces to adsorb polynucleotides. The microparticles can have a diameter of from at least 1 micron to at least 100 microns (e.g., at least 1 micron, at least 10 micron, at least 20 micron, at least 30 micron, at least 50 micron, at least 75 micron, at least 95 micron, and at least 100 micron). In some embodiment, the compositions or formulations of the present disclosure are microemulsions comprising microparticles and polynucleotides. Exemplary microparticles, microemulsions and their preparations are described in, e.g., U.S. Pat. Nos. 8,460,709, 8,309,139 and 8,206,749; U.S. Pub. Nos. US20130129830, US2013195923 and US20130195898; and Intl. Pub. No. WO2013075068, each of which is herein incorporated by reference in its entirety.

l. NanoJackets and NanoLiposomes

In some embodiments, the compositions or formulations of the present disclosure comprise the polynucleotides described herein (e.g., a polynucleotide comprising a nucleotide sequence encoding a GALT polypeptide) in NanoJackets and NanoLiposomes by Keystone Nano (State College, Pa.). NanoJackets are made of materials that are naturally found in the body including calcium, phosphate and can also include a small amount of silicates. Nanojackets can have a size ranging from 5 to 50 nm.

NanoLiposomes are made of lipids such as, but not limited to, lipids that naturally occur in the body. NanoLiposomes can have a size ranging from 60-80 nm. In some embodiments, the polynucleotides disclosed herein are formulated in a NanoLiposome such as, but not limited to, Ceramide NanoLiposomes.

m. Cells or Minicells

In some embodiments, the compositions or formulations of the present disclosure comprise the polynucleotides described herein (e.g., a polynucleotide comprising a nucleotide sequence encoding a GALT polypeptide) that is transfected ex vivo into cells, which are subsequently transplanted into a subject. Cell-based formulations of the polynucleotide disclosed herein can be used to ensure cell transfection (e.g., in the cellular carrier), alter the biodistribution of the polynucleotide (e.g., by targeting the cell carrier to specific tissues or cell types), and/or increase the translation of encoded protein.

Exemplary cells include, but are not limited to, red blood cells, virosomes, and electroporated cells (see e.g., Godfrin et al., Expert Opin Biol Ther. 2012 12:127-133; Fang et al., Expert Opin Biol Ther. 2012 12:385-389; Hu et al., Proc Natl Acad Sci USA. 2011 108:10980-10985; Lund et al., Pharm Res. 2010 27:400-420; Huckriede et al., J Liposome Res. 2007; 17:39-47; Cusi, Hum Vaccin. 2006 2:1-7; de Jonge et al., Gene Ther. 2006 13:400-411; all of which are herein incorporated by reference in its entirety).

A variety of methods are known in the art and are suitable for introduction of nucleic acid into a cell, including viral and non-viral mediated techniques. Examples of typical non-viral mediated techniques include, but are not limited to, electroporation, calcium phosphate mediated transfer, nucleofection, sonoporation, heat shock, magnetofection, liposome mediated transfer, microinjection, microprojectile mediated transfer (nanoparticles), cationic polymer mediated transfer (DEAE-dextran, polyethylenimine, polyethylene glycol (PEG) and the like) or cell fusion.

In some embodiments, the polynucleotides described herein can be delivered in synthetic virus-like particles (VLPs) synthesized by the methods as described in Intl. Pub Nos. WO2011085231 and WO2013116656; and U.S. Pub. No. 20110171248, each of which is herein incorporated by reference in its entirety.

The technique of sonoporation, or cellular sonication, is the use of sound (e.g., ultrasonic frequencies) for modifying the permeability of the cell plasma membrane. Sonoporation methods are known to deliver nucleic acids in vivo (Yoon and Park, Expert Opin Drug Deliv. 2010 7:321-330; Postema and Gilja, Curr Pharm Biotechnol. 2007 8:355-361; Newman and Bettinger, Gene Ther. 2007 14:465-475; U.S. Pub. Nos. US20100196983 and US20100009424; all herein incorporated by reference in their entirety).

In some embodiments, the polynucleotides described herein can be delivered by electroporation. Electroporation techniques are known to deliver nucleic acids in vivo and clinically (Andre et al., Curr Gene Ther. 2010 10:267-280; Chiarella et al., Curr Gene Ther. 2010 10:281-286; Hojman, Curr Gene Ther. 2010 10:128-138; all herein incorporated by reference in their entirety). Electroporation devices are sold by many companies worldwide including, but not limited to BTX® Instruments (Holliston, Mass.) (e.g., the AgilePulse In Vivo System) and Inovio (Blue Bell, Pa.) (e.g., Inovio SP-5P intramuscular delivery device or the CELLECTRA® 3000 intradermal delivery device).

In some embodiments, the cells are selected from the group consisting of mammalian cells, bacterial cells, plant, microbial, algal and fungal cells. In some embodiments, the cells are mammalian cells, such as, but not limited to, human, mouse, rat, goat, horse, rabbit, hamster or cow cells. In a further embodiment, the cells can be from an established cell line, including, but not limited to, HeLa, NS0, SP2/0, KEK 293T, Vero, Caco, Caco-2, MDCK, COS-1, COS-7, K562, Jurkat, CHO-K1, DG44, CHOK1SV, CHO-S, Huvec, CV-1, Huh-7, NIH3T3, HEK293, 293, A549, HepG2, IMR-90, MCF-7, U-20S, Per.C6, SF9, SF21 or Chinese Hamster Ovary (CHO) cells.

In certain embodiments, the cells are fungal cells, such as, but not limited to, *Chrysosporium* cells, *Aspergillus* cells, *Trichoderma* cells, *Dictyostelium* cells, *Candida* cells, *Saccharomyces* cells, *Schizosaccharomyces* cells, and *Penicillium* cells.

In certain embodiments, the cells are bacterial cells such as, but not limited to, *E. coli, B. subtilis*, or BL21 cells. Primary and secondary cells to be transfected by the methods of the invention can be obtained from a variety of tissues and include, but are not limited to, all cell types that can be maintained in culture. The primary and secondary cells include, but are not limited to, fibroblasts, keratinocytes, epithelial cells (e.g., mammary epithelial cells, intestinal epithelial cells), endothelial cells, glial cells, neural cells, formed elements of the blood (e.g., lymphocytes, bone marrow cells), muscle cells and precursors of these somatic cell types. Primary cells can also be obtained from a donor of the same species or from another species (e.g., mouse, rat, rabbit, cat, dog, pig, cow, bird, sheep, goat, horse).

In some embodiments, the compositions or formulations of the present disclosure comprise the polynucleotides described herein in bacterial minicells. As a non-limiting example, bacterial minicells can be those described in Intl. Pub. No. WO2013088250 or U.S. Pub. No. US20130177499, each of which is herein incorporated by reference in its entirety.

n. Semi-Solid Compositions

In some embodiments, the compositions or formulations of the present disclosure comprise the polynucleotides described herein (e.g., a polynucleotide comprising a nucleotide sequence encoding a GALT polypeptide) in a hydrophobic matrix to form a semi-solid or paste-like composition. As a non-limiting example, the semi-solid or paste-like composition can be made by the methods described in Intl. Pub. No. WO201307604, herein incorporated by reference in its entirety.

o. Exosomes

In some embodiments, the compositions or formulations of the present disclosure comprise the polynucleotides described herein (e.g., a polynucleotide comprising a nucleotide sequence encoding a GALT polypeptide) in exosomes, which can be loaded with at least one polynucleotide and delivered to cells, tissues and/or organisms. As a non-limiting example, the polynucleotides can be loaded in the exosomes as described in Intl. Pub. No. WO2013084000, herein incorporated by reference in its entirety.

p. Silk-Based Delivery

In some embodiments, the compositions or formulations of the present disclosure comprise the polynucleotides described herein (e.g., a polynucleotide comprising a nucleotide sequence encoding a GALT polypeptide) that is formulated for silk-based delivery. The silk-based delivery system can be formed by contacting a silk fibroin solution with a polynucleotide described herein. As a non-limiting example, a sustained release silk-based delivery system and methods of making such system are described in U.S. Pub. No. US20130177611, herein incorporated by reference in its entirety.

q. Amino Acid Lipids

In some embodiments, the compositions or formulations of the present disclosure comprise the polynucleotides described herein (e.g., a polynucleotide comprising a nucleotide sequence encoding a GALT polypeptide) that is formulation with an amino acid lipid. Amino acid lipids are lipophilic compounds comprising an amino acid residue and one or more lipophilic tails. Non-limiting examples of amino acid lipids and methods of making amino acid lipids are described in U.S. Pat. No. 8,501,824. The amino acid lipid formulations can deliver a polynucleotide in releasable form that comprises an amino acid lipid that binds and releases the polynucleotides. As a non-limiting example, the release of the polynucleotides described herein can be provided by an acid-labile linker as described in, e.g., U.S. Pat. Nos. 7,098,032, 6,897,196, 6,426,086, 7,138,382, 5,563,250, and 5,505,931, each of which is herein incorporated by reference in its entirety.

r. Microvesicles

In some embodiments, the compositions or formulations of the present disclosure comprise the polynucleotides described herein (e.g., a polynucleotide comprising a nucleotide sequence encoding a GALT polypeptide) in a microvesicle formulation. Exemplary microvesicles include those described in U.S. Pub. No. US20130209544 (herein incorporated by reference in its entirety). In some embodiments, the microvesicle is an ARRDC1-mediated microvesicles (ARMMs) as described in Intl. Pub. No. WO2013119602 (herein incorporated by reference in its entirety).

s. Interpolyelectrolyte Complexes

In some embodiments, the compositions or formulations of the present disclosure comprise the polynucleotides described herein (e.g., a polynucleotide comprising a nucleotide sequence encoding a GALT polypeptide) in an interpolyelectrolyte complex. Interpolyelectrolyte complexes are formed when charge-dynamic polymers are complexed with one or more anionic molecules. Non-limiting examples of charge-dynamic polymers and interpolyelectrolyte complexes and methods of making interpolyelectrolyte complexes are described in U.S. Pat. No. 8,524,368, herein incorporated by reference in its entirety.

t. Crystalline Polymeric Systems

In some embodiments, the compositions or formulations of the present disclosure comprise the polynucleotides described herein (e.g., a polynucleotide comprising a nucleotide sequence encoding a GALT polypeptide) in crystalline polymeric systems. Crystalline polymeric systems are polymers with crystalline moieties and/or terminal units comprising crystalline moieties. Exemplary polymers are described in U.S. Pat. No. 8,524,259 (herein incorporated by reference in its entirety).

u. Polymers, Biodegradable Nanoparticles, and Core-Shell Nanoparticles

In some embodiments, the compositions or formulations of the present disclosure comprise the polynucleotides described herein (e.g., a polynucleotide comprising a nucleotide sequence encoding a GALT polypeptide) and a natural and/or synthetic polymer. The polymers include, but not limited to, polyethenes, polyethylene glycol (PEG), poly(l-lysine)(PLL), PEG grafted to PLL, cationic lipopolymer, biodegradable cationic lipopolymer, polyethyleneimine (PEI), cross-linked branched poly(alkylene imines), a polyamine derivative, a modified poloxamer, elastic biodegradable polymer, biodegradable copolymer, biodegradable polyester copolymer, biodegradable polyester copolymer, multiblock copolymers, poly[α-(4-aminobutyl)-L-glycolic acid) (PAGA), biodegradable cross-linked cationic multiblock copolymers, polycarbonates, polyanhydrides, polyhydroxyacids, polypropylfumerates, polycaprolactones, polyamides, polyacetals, polyethers, polyesters, poly (orthoesters), polycyanoacrylates, polyvinyl alcohols, polyurethanes, polyphosphazenes, polyureas, polystyrenes, polyamines, polylysine, poly(ethylene imine), poly(serine ester), poly(L-lactide-co-L-lysine), poly(4-hydroxy-L-proline ester), amine-containing polymers, dextran polymers, dextran polymer derivatives or combinations thereof.

Exemplary polymers include, DYNAMIC POLYCONJUGATE® (Arrowhead Research Corp., Pasadena, Calif.) formulations from MIRUS® Bio (Madison, Wis.) and Roche Madison (Madison, Wis.), PHASERX™ polymer formulations such as, without limitation, SMARTT POLYMER TECHNOLOGY™ (PHASERX®, Seattle, Wash.), DMRI/DOPE, poloxamer, VAXFECTIN® adjuvant from Vical (San Diego, Calif.), chitosan, cyclodextrin from Calando Pharmaceuticals (Pasadena, Calif.), dendrimers and poly (lactic-co-glycolic acid) (PLGA) polymers. RONDEL™ (RNAi/Oligonucleotide Nanoparticle Delivery) polymers (Arrowhead Research Corporation, Pasadena, Calif.) and pH responsive co-block polymers such as PHASERX® (Seattle, Wash.).

The polymer formulations allow a sustained or delayed release of the polynucleotide (e.g., following intramuscular or subcutaneous injection). The altered release profile for the polynucleotide can result in, for example, translation of an encoded protein over an extended period of time. The polymer formulation can also be used to increase the stability of the polynucleotide. Sustained release formulations can include, but are not limited to, PLGA microspheres, ethylene vinyl acetate (EVAc), poloxamer, GELSITE® (Nanotherapeutics, Inc. Alachua, Fla.), HYLENEX® (Halozyme Therapeutics, San Diego Calif.), surgical sealants such as fibrinogen polymers (Ethicon Inc. Cornelia, Ga.), TISSELL® (Baxter International, Inc. Deerfield, Ill.), PEG-based sealants, and COSEAL® (Baxter International, Inc. Deerfield, Ill.).

As a non-limiting example modified mRNA can be formulated in PLGA microspheres by preparing the PLGA microspheres with tunable release rates (e.g., days and weeks) and encapsulating the modified mRNA in the PLGA microspheres while maintaining the integrity of the modified mRNA during the encapsulation process. EVAc are non-biodegradable, biocompatible polymers that are used extensively in pre-clinical sustained release implant applications (e.g., extended release products Ocusert a pilocarpine ophthalmic insert for glaucoma or progestasert a sustained release progesterone intrauterine device; transdermal delivery systems Testoderm, Duragesic and Selegiline; catheters). Poloxamer F-407 NF is a hydrophilic, non-ionic surfactant triblock copolymer of polyoxyethylene-polyoxypropylene-polyoxyethylene having a low viscosity at temperatures less than 5° C. and forms a solid gel at temperatures greater than 15° C.

As a non-limiting example, the polynucleotides described herein can be formulated with the polymeric compound of PEG grafted with PLL as described in U.S. Pat. No. 6,177,274. As another non-limiting example, the polynucleotides described herein can be formulated with a block copolymer such as a PLGA-PEG block copolymer (see e.g., U.S. Pub. No. US20120004293 and U.S. Pat. Nos. 8,236,330 and 8,246,968), or a PLGA-PEG-PLGA block copolymer (see e.g., U.S. Pat. No. 6,004,573). Each of the references is herein incorporated by reference in its entirety.

In some embodiments, the polynucleotides described herein can be formulated with at least one amine-containing polymer such as, but not limited to polylysine, polyethylene imine, poly(amidoamine) dendrimers, poly(amine-co-esters) or combinations thereof. Exemplary polyamine polymers and their use as delivery agents are described in, e.g., U.S. Pat. Nos. 8,460,696, 8,236,280, each of which is herein incorporated by reference in its entirety.

In some embodiments, the polynucleotides described herein can be formulated in a biodegradable cationic lipopolymer, a biodegradable polymer, or a biodegradable copolymer, a biodegradable polyester copolymer, a biodegradable polyester polymer, a linear biodegradable copolymer, PAGA, a biodegradable cross-linked cationic multi-block copolymer or combinations thereof as described in, e.g., U.S. Pat. Nos. 6,696,038, 6,517,869, 6,267,987, 6,217,912, 6,652,886, 8,057,821, and 8,444,992; U.S. Pub. Nos. US20030073619, US20040142474, US20100004315, US2012009145 and US20130195920; and Intl Pub. Nos. WO2006063249 and WO2013086322, each of which is herein incorporated by reference in its entirety.

In some embodiments, the polynucleotides described herein can be formulated in or with at least one cyclodextrin polymer as described in U.S. Pub. No. US20130184453. In some embodiments, the polynucleotides described herein can be formulated in or with at least one crosslinked cation-binding polymers as described in Intl. Pub. Nos. WO2013106072, WO2013106073 and WO2013106086. In some embodiments, the polynucleotides described herein can be formulated in or with at least PEGylated albumin polymer as described in U.S. Pub. No. US20130231287. Each of the references is herein incorporated by reference in its entirety.

In some embodiments, the polynucleotides disclosed herein can be formulated as a nanoparticle using a combination of polymers, lipids, and/or other biodegradable agents, such as, but not limited to, calcium phosphate. Components can be combined in a core-shell, hybrid, and/or layer-by-layer architecture, to allow for fine-tuning of the nanoparticle for delivery (Wang et al., Nat Mater. 2006 5:791-796; Fuller et al., Biomaterials. 2008 29:1526-1532; DeKoker et al., Adv Drug Deliv Rev. 2011 63:748-761; Endres et al., Biomaterials. 2011 32:7721-7731; Su et al., Mol Pharm. 2011 Jun. 6; 8(3):774-87; herein incorporated by reference in their entireties). As a non-limiting example, the nanoparticle can comprise a plurality of polymers such as, but not limited to hydrophilic-hydrophobic polymers (e.g., PEG-PLGA), hydrophobic polymers (e.g., PEG) and/or hydrophilic polymers (Intl. Pub. No. WO20120225129, herein incorporated by reference in its entirety).

The use of core-shell nanoparticles has additionally focused on a high-throughput approach to synthesize cationic cross-linked nanogel cores and various shells (Siegwart et al., Proc Natl Acad Sci USA. 2011 108:12996-13001; herein incorporated by reference in its entirety). The complexation, delivery, and internalization of the polymeric nanoparticles can be precisely controlled by altering the chemical composition in both the core and shell components of the nanoparticle. For example, the core-shell nanoparticles can efficiently deliver siRNA to mouse hepatocytes after they covalently attach cholesterol to the nanoparticle.

In some embodiments, a hollow lipid core comprising a middle PLGA layer and an outer neutral lipid layer containing PEG can be used to delivery of the polynucleotides as described herein. In some embodiments, the lipid nanoparticles can comprise a core of the polynucleotides disclosed herein and a polymer shell, which is used to protect the polynucleotides in the core. The polymer shell can be any of the polymers described herein and are known in the art. The polymer shell can be used to protect the polynucleotides in the core.

Core-shell nanoparticles for use with the polynucleotides described herein are described in U.S. Pat. No. 8,313,777 or Intl. Pub. No. WO2013124867, each of which is herein incorporated by reference in their entirety.

v. Peptides and Proteins

In some embodiments, the compositions or formulations of the present disclosure comprise the polynucleotides described herein (e.g., a polynucleotide comprising a nucleotide sequence encoding a GALT polypeptide) that is formulated with peptides and/or proteins to increase transfection of cells by the polynucleotide, and/or to alter the biodistribution of the polynucleotide (e.g., by targeting specific tissues or cell types), and/or increase the translation of encoded protein (e.g., Intl. Pub. Nos. WO2012110636 and WO2013123298. In some embodiments, the peptides can be those described in U.S. Pub. Nos. US20130129726, US20130137644 and US20130164219. Each of the references is herein incorporated by reference in its entirety.

w. Conjugates

In some embodiments, the compositions or formulations of the present disclosure comprise the polynucleotides described herein (e.g., a polynucleotide comprising a nucleotide sequence encoding a GALT polypeptide) that is covalently linked to a carrier or targeting group, or including two encoding regions that together produce a fusion protein (e.g., bearing a targeting group and therapeutic protein or peptide) as a conjugate. The conjugate can be a peptide that selectively directs the nanoparticle to neurons in a tissue or organism, or assists in crossing the blood-brain barrier.

The conjugates include a naturally occurring substance, such as a protein (e.g., human serum albumin (HSA), low-density lipoprotein (LDL), high-density lipoprotein (HDL), or globulin); an carbohydrate (e.g., a dextran, pullulan, chitin, chitosan, inulin, cyclodextrin or hyaluronic acid); or a lipid. The ligand can also be a recombinant or synthetic molecule, such as a synthetic polymer, e.g., a synthetic polyamino acid, an oligonucleotide (e.g., an aptamer). Examples of polyamino acids include polyamino acid is a polylysine (PLL), poly L-aspartic acid, poly L-glutamic acid, styrene-maleic acid anhydride copolymer, poly (L-lactide-co-glycolied) copolymer, divinyl ether-maleic anhydride copolymer, N-(2-hydroxypropyl)methacrylamide copolymer (HMPA), polyethylene glycol (PEG), polyvinyl alcohol (PVA), polyurethane, poly(2-ethylacryllic acid), N-isopropylacrylamide polymers, or polyphosphazine. Example of polyamines include: polyethylenimine, polylysine (PLL), spermine, spermidine, polyamine, pseudopeptide-polyamine, peptidomimetic polyamine, dendrimer polyamine, arginine, amidine, protamine, cationic lipid, cationic porphyrin, quaternary salt of a polyamine, or an alpha helical peptide.

In some embodiments, the conjugate can function as a carrier for the polynucleotide disclosed herein. The conjugate can comprise a cationic polymer such as, but not limited to, polyamine, polylysine, polyalkylenimine, and polyethylenimine that can be grafted to with poly(ethylene glycol). Exemplary conjugates and their preparations are described in U.S. Pat. No. 6,586,524 and U.S. Pub. No. US20130211249, each of which herein is incorporated by reference in its entirety.

The conjugates can also include targeting groups, e.g., a cell or tissue targeting agent, e.g., a lectin, glycoprotein, lipid or protein, e.g., an antibody, that binds to a specified cell type such as a kidney cell. A targeting group can be a thyrotropin, melanotropin, lectin, glycoprotein, surfactant protein A, Mucin carbohydrate, multivalent lactose, multivalent galactose, N-acetyl-galactosamine, N-acetyl-glucosamine multivalent mannose, multivalent fucose, glycosylated polyaminoacids, multivalent galactose, transferrin, bisphosphonate, polyglutamate, polyaspartate, a lipid, cholesterol, a steroid, bile acid, folate, vitamin B12, biotin, an RGD peptide, an RGD peptide mimetic or an aptamer.

Targeting groups can be proteins, e.g., glycoproteins, or peptides, e.g., molecules having a specific affinity for a co-ligand, or antibodies e.g., an antibody, that binds to a specified cell type such as an endothelial cell or bone cell. Targeting groups can also include hormones and hormone receptors. They can also include non-peptidic species, such as lipids, lectins, carbohydrates, vitamins, cofactors, multivalent lactose, multivalent galactose, N-acetyl-galactosamine, N-acetyl-glucosamine multivalent mannose, multivalent fructose, or aptamers. The ligand can be, for example, a lipopolysaccharide, or an activator of p38 MAP kinase.

The targeting group can be any ligand that is capable of targeting a specific receptor. Examples include, without limitation, folate, GalNAc, galactose, mannose, mannose-6P, apatamers, integrin receptor ligands, chemokine receptor ligands, transferrin, biotin, serotonin receptor ligands, PSMA, endothelin, GCPII, somatostatin, LDL, and HDL ligands. In particular embodiments, the targeting group is an aptamer. The aptamer can be unmodified or have any combination of modifications disclosed herein. As a non-limiting example, the targeting group can be a glutathione receptor (GR)-binding conjugate for targeted delivery across the blood-central nervous system barrier as described in, e.g., U.S. Pub. No. US2013021661012 (herein incorporated by reference in its entirety).

In some embodiments, the conjugate can be a synergistic biomolecule-polymer conjugate, which comprises a long-acting continuous-release system to provide a greater therapeutic efficacy. The synergistic biomolecule-polymer conjugate can be those described in U.S. Pub. No. US20130195799. In some embodiments, the conjugate can be an aptamer conjugate as described in Intl. Pat. Pub. No. WO2012040524. In some embodiments, the conjugate can be an amine containing polymer conjugate as described in U.S. Pat. No. 8,507,653. Each of the references is herein incorporated by reference in its entirety. In some embodiments, the polynucleotides can be conjugated to SMARTT POLYMER TECHNOLOGY® (PHASERX®, Inc. Seattle, Wash.).

In some embodiments, the polynucleotides described herein are covalently conjugated to a cell penetrating polypeptide, which can also include a signal sequence or a targeting sequence. The conjugates can be designed to have increased stability, and/or increased cell transfection; and/or altered the biodistribution (e.g., targeted to specific tissues or cell types).

In some embodiments, the polynucleotides described herein can be conjugated to an agent to enhance delivery. In some embodiments, the agent can be a monomer or polymer such as a targeting monomer or a polymer having targeting blocks as described in Intl. Pub. No. WO2011062965. In some embodiments, the agent can be a transport agent covalently coupled to a polynucleotide as described in, e.g., U.S. Pat. Nos. 6,835,393 and 7,374,778. In some embodiments, the agent can be a membrane barrier transport enhancing agent such as those described in U.S. Pat. Nos. 7,737,108 and 8,003,129. Each of the references is herein incorporated by reference in its entirety.

x. Micro-Organs

In some embodiments, the compositions or formulations of the present disclosure comprise the polynucleotides described herein (e.g., a polynucleotide comprising a nucleotide sequence encoding a GALT polypeptide) in a micro-organ that can then express an encoded polypeptide of interest in a long-lasting therapeutic formulation. Exemplary micro-organs and formulations are described in Intl. Pub. No. WO2014152211 (herein incorporated by reference in its entirety).

y. Pseudovirions

In some embodiments, the compositions or formulations of the present disclosure comprise the polynucleotides described herein (e.g., a polynucleotide comprising a nucleotide sequence encoding a GALT polypeptide) in pseudovirions (e.g., pseudovirions developed by Aura Biosciences, Cambridge, Mass.).

In some embodiments, the pseudovirion used for delivering the polynucleotides can be derived from viruses such as, but not limited to, herpes and papillomaviruses as described in, e.g., U.S. Pub. Nos. US20130012450, US20130012566, US21030012426 and US20120207840; and Intl. Pub. No. WO2013009717, each of which is herein incorporated by reference in its entirety.

The pseudovirion can be a virus-like particle (VLP) prepared by the methods described in U.S. Pub. Nos. US20120015899 and US20130177587, and Intl. Pub. Nos. WO2010047839, WO2013116656, WO2013106525 and WO2013122262. In one aspect, the VLP can be bacteriophages MS, Qβ, R17, fr, GA, Sp, MI, I, MXI, NL95, AP205, f2, PP7, and the plant viruses Turnip crinkle virus (TCV), Tomato bushy stunt virus (TBSV), Southern bean mosaic virus (SBMV) and members of the genus Bromovirus including Broad bean mottle virus, Brome mosaic virus, *Cassia* yellow blotch virus, Cowpea chlorotic mottle virus (CCMV), Melandrium yellow fleck virus, and Spring beauty latent virus. In another aspect, the VLP can be derived from the influenza virus as described in U.S. Pub. No. US20130177587 and U.S. Pat. No. 8,506,967. In one aspect, the VLP can comprise a B7-1 and/or B7-2 molecule anchored to a lipid membrane or the exterior of the particle such as described in Intl. Pub. No. WO2013116656. In one aspect, the VLP can be derived from norovirus, rotavirus recombinant VP6 protein or double layered VP2/VP6 such as the VLP as described in Intl. Pub. No. WO2012049366. Each of the references is herein incorporated by reference in its entirety.

In some embodiments, the pseudovirion can be a human papilloma virus-like particle as described in Intl. Pub. No. WO2010120266 and U.S. Pub. No. US20120171290. In some embodiments, the virus-like particle (VLP) can be a self-assembled particle. In one aspect, the pseudovirions can be virion derived nanoparticles as described in U.S. Pub. Nos. US20130116408 and US20130115247; and Intl. Pub. No. WO2013119877. Each of the references is herein incorporated by reference in their entirety.

Non-limiting examples of formulations and methods for formulating the polynucleotides described herein are also provided in Intl. Pub. No WO2013090648 (incorporated herein by reference in their entirety).

24. ACCELERATED BLOOD CLEARANCE

The invention provides compounds, compositions and methods of use thereof for reducing the effect of ABC on a repeatedly administered active agent such as a biologically active agent. As will be readily apparent, reducing or eliminating altogether the effect of ABC on an administered active agent effectively increases its half-life and thus its efficacy.

In some embodiments the term reducing ABC refers to any reduction in ABC in comparison to a positive reference control ABC inducing LNP such as an MC3 LNP. ABC inducing LNPs cause a reduction in circulating levels of an active agent upon a second or subsequent administration within a given time frame. Thus a reduction in ABC refers to less clearance of circulating agent upon a second or subsequent dose of agent, relative to a standard LNP. The reduction may be, for instance, at least 10%, 15%, 20%, 25%, 30%, 35%, 40%, 45%, 50%, 55%, 60%, 65%, 70%, 75%, 80%, 85%, 90%, 95%, 98%, or 100%. In some embodiments the reduction is 10-100%, 10-50%, 20-100%, 20-50%, 30-100%, 30-50%, 40%-100%, 40-80%, 50-90%, or 50-100%. Alternatively the reduction in ABC may be characterized as at least a detectable level of circulating agent following a second or subsequent administration or at least a 2 fold, 3 fold, 4 fold, 5 fold increase in circulating agent relative to circulating agent following administration of a standard LNP. In some embodiments the reduction is a 2-100 fold, 2-50 fold, 3-100 fold, 3-50 fold, 3-20 fold, 4-100 fold, 4-50 fold, 4-40 fold, 4-30 fold, 4-25 fold, 4-20 fold, 4-15 fold, 4-10 fold, 4-5 fold, 5-100 fold, 5-50 fold, 5-40 fold, 5-30 fold, 5-25 fold, 5-20 fold, 5-15 fold, 5-10 fold, 6-100 fold, 6-50 fold, 6-40 fold, 6-30 fold, 6-25 fold, 6-20 fold, 6-15 fold, 6-10 fold, 8-100 fold, 8-50 fold, 8-40 fold, 8-30 fold, 8-25 fold, 8-20 fold, 8-15 fold, 8-10 fold, 10-100 fold, 10-50 fold, 10-40 fold, 10-30 fold, 10-25 fold, 10-20 fold, 10-15 fold, 20-100 fold, 20-50 fold, 20-40 fold, 20-30 fold, or 20-25 fold.

The disclosure provides lipid-comprising compounds and compositions that are less susceptible to clearance and thus have a longer half-life in vivo. This is particularly the case where the compositions are intended for repeated including chronic administration, and even more particularly where such repeated administration occurs within days or weeks.

Significantly, these compositions are less susceptible or altogether circumvent the observed phenomenon of accelerated blood clearance (ABC). ABC is a phenomenon in which certain exogenously administered agents are rapidly cleared from the blood upon second and subsequent administrations. This phenomenon has been observed, in part, for a variety of lipid-containing compositions including but not limited to lipidated agents, liposomes or other lipid-based delivery vehicles, and lipid-encapsulated agents. Heretofore, the basis of ABC has been poorly understood and in some cases attributed to a humoral immune response and accordingly strategies for limiting its impact in vivo particularly in a clinical setting have remained elusive.

This disclosure provides compounds and compositions that are less susceptible, if at all susceptible, to ABC. In some important aspects, such compounds and compositions are lipid-comprising compounds or compositions. The lipid-containing compounds or compositions of this disclosure, surprisingly, do not experience ABC upon second and subsequent administration in vivo. This resistance to ABC renders these compounds and compositions particularly suitable for repeated use in vivo, including for repeated use within short periods of time, including days or 1-2 weeks. This enhanced stability and/or half-life is due, in part, to the inability of these compositions to activate B1a and/or B1b cells and/or conventional B cells, pDCs and/or platelets.

This disclosure therefore provides an elucidation of the mechanism underlying accelerated blood clearance (ABC). It has been found, in accordance with this disclosure and the inventions provided herein, that the ABC phenomenon at least as it relates to lipids and lipid nanoparticles is mediated, at least in part an innate immune response involving B1a and/or B1b cells, pDC and/or platelets. B1a cells are normally responsible for secreting natural antibody, in the form of circulating IgM. This IgM is poly-reactive, meaning that it is able to bind to a variety of antigens, albeit with a relatively low affinity for each.

It has been found in accordance with the invention that some lipidated agents or lipid-comprising formulations such as lipid nanoparticles administered in vivo trigger and are subject to ABC. It has now been found in accordance with the invention that upon administration of a first dose of the LNP, one or more cells involved in generating an innate immune response (referred to herein as sensors) bind such agent, are activated, and then initiate a cascade of immune factors (referred to herein as effectors) that promote ABC and toxicity. For instance, B1a and B1b cells may bind to LNP, become activated (alone or in the presence of other sensors such as pDC and/or effectors such as IL6) and secrete natural IgM that binds to the LNP. Pre-existing natural IgM in the subject may also recognize and bind to the LNP, thereby triggering complement fixation. After administration of the first dose, the production of natural IgM begins within 1-2 hours of administration of the LNP. Typically by about 2-3 weeks the natural IgM is cleared from the system due to the natural half-life of IgM. Natural IgG is produced beginning around 96 hours after administration of the LNP. The agent, when administered in a naïve setting, can exert its biological effects relatively unencumbered by the natural IgM produced post-activation of the B1a cells or B1b cells or natural IgG. The natural IgM and natural IgG are non-specific and thus are distinct from anti-PEG IgM and anti-PEG IgG.

Although Applicant is not bound by mechanism, it is proposed that LNPs trigger ABC and/or toxicity through the following mechanisms. It is believed that when an LNP is administered to a subject the LNP is rapidly transported through the blood to the spleen. The LNPs may encounter immune cells in the blood and/or the spleen. A rapid innate immune response is triggered in response to the presence of the LNP within the blood and/or spleen. Applicant has shown herein that within hours of administration of an LNP several immune sensors have reacted to the presence of the LNP. These sensors include but are not limited to immune cells involved in generating an immune response, such as B cells, pDC, and platelets. The sensors may be present in the spleen, such as in the marginal zone of the spleen and/or in the blood. The LNP may physically interact with one or more sensors, which may interact with other sensors. In such a case the LNP is directly or indirectly interacting with the sensors. The sensors may interact directly with one another in response to recognition of the LNP. For instance many sensors are located in the spleen and can easily interact with one another. Alternatively one or more of the sensors may interact with LNP in the blood and become activated. The activated sensor may then interact directly with other sensors or indirectly (e.g., through the stimulation or production of a messenger such as a cytokine e.g., IL6).

In some embodiments the LNP may interact directly with and activate each of the following sensors: pDC, B1a cells, B1b cells, and platelets. These cells may then interact directly or indirectly with one another to initiate the production of effectors which ultimately lead to the ABC and/or toxicity associated with repeated doses of LNP. For instance, Applicant has shown that LNP administration leads to pDC activation, platelet aggregation and activation and B cell activation. In response to LNP platelets also aggregate and are activated and aggregate with B cells. pDC cells are activated. LNP has been found to interact with the surface of platelets and B cells relatively quickly. Blocking the activation of any one or combination of these sensors in response to LNP is useful for dampening the immune response that would ordinarily occur. This dampening of the immune response results in the avoidance of ABC and/or toxicity.

The sensors once activated produce effectors. An effector, as used herein, is an immune molecule produced by an immune cell, such as a B cell. Effectors include but are not limited to immunoglobulin such as natural IgM and natural IgG and cytokines such as IL6. B1a and B1b cells stimulate the production of natural IgMs within 2-6 hours following administration of an LNP. Natural IgG can be detected within 96 hours. IL6 levels are increased within several hours. The natural IgM and IgG circulate in the body for several days to several weeks. During this time the circulating effectors can interact with newly administered LNPs, triggering those LNPs for clearance by the body. For instance, an effector may recognize and bind to an LNP. The Fc region of the effector may be recognized by and trigger uptake of the decorated LNP by macrophage. The macrophage are then transported to the spleen. The production of effectors by immune sensors is a transient response that correlates with the timing observed for ABC.

If the administered dose is the second or subsequent administered dose, and if such second or subsequent dose is administered before the previously induced natural IgM and/or IgG is cleared from the system (e.g., before the 2-3 window time period), then such second or subsequent dose is targeted by the circulating natural IgM and/or natural IgG or Fc which trigger alternative complement pathway activation and is itself rapidly cleared. When LNP are administered after the effectors have cleared from the body or are reduced in number, ABC is not observed.

Thus, it is useful according to aspects of the invention to inhibit the interaction between LNP and one or more sensors, to inhibit the activation of one or more sensors by LNP (direct or indirect), to inhibit the production of one or more effectors, and/or to inhibit the activity of one or more effectors. In some embodiments the LNP is designed to limit or block interaction of the LNP with a sensor. For instance the LNP may have an altered PC and/or PEG to prevent interactions with sensors. Alternatively or additionally an agent that inhibits immune responses induced by LNPs may be used to achieve any one or more of these effects.

It has also been determined that conventional B cells are also implicated in ABC. Specifically, upon first administration of an agent, conventional B cells, referred to herein as CD19(+), bind to and react against the agent. Unlike B1a and B1b cells though, conventional B cells are able to mount first an IgM response (beginning around 96 hours after administration of the LNPs) followed by an IgG response (beginning around 14 days after administration of the LNPs) concomitant with a memory response. Thus conventional B cells react against the administered agent and contribute to IgM (and eventually IgG) that mediates ABC. The IgM and IgG are typically anti-PEG IgM and anti-PEG IgG.

It is contemplated that in some instances, the majority of the ABC response is mediated through B1a cells and B1a-mediated immune responses. It is further contemplated that in some instances, the ABC response is mediated by both IgM and IgG, with both conventional B cells and B1a cells mediating such effects. In yet still other instances, the ABC response is mediated by natural IgM molecules, some of which are capable of binding to natural IgM, which may be produced by activated B1a cells. The natural IgMs may bind to one or more components of the LNPs, e.g., binding to a phospholipid component of the LNPs (such as binding to the PC moiety of the phospholipid) and/or binding to a PEG-lipid component of the LNPs (such as binding to PEG- DMG, in particular, binding to the PEG moiety of PEG-DMG). Since B1a expresses CD36, to which phosphatidylcholine is a ligand, it is contemplated that the CD36 receptor may mediate the activation of B1a cells and thus production of natural IgM. In yet still other instances, the ABC response is mediated primarily by conventional B cells.

It has been found in accordance with the invention that the ABC phenomenon can be reduced or abrogated, at least in part, through the use of compounds and compositions (such as agents, delivery vehicles, and formulations) that do not activate B1a cells. Compounds and compositions that do not activate B1a cells may be referred to herein as B1a inert compounds and compositions. It has been further found in accordance with the invention that the ABC phenomenon can be reduced or abrogated, at least in part, through the use of compounds and compositions that do not activate conventional B cells. Compounds and compositions that do not activate conventional B cells may in some embodiments be referred to herein as CD19-inert compounds and compositions. Thus, in some embodiments provided herein, the compounds and compositions do not activate B1a cells and they do not activate conventional B cells. Compounds and compositions that do not activate B1a cells and conventional B cells may in some embodiments be referred to herein as B1a/CD19-inert compounds and compositions.

These underlying mechanisms were not heretofore understood, and the role of B1a and B1b cells and their interplay with conventional B cells in this phenomenon was also not appreciated.

Accordingly, this disclosure provides compounds and compositions that do not promote ABC. These may be further characterized as not capable of activating B1a and/or B1b cells, platelets and/or pDC, and optionally conventional B cells also. These compounds (e.g., agents, including biologically active agents such as prophylactic agents, therapeutic agents and diagnostic agents, delivery vehicles, including liposomes, lipid nanoparticles, and other lipid-based encapsulating structures, etc.) and compositions (e.g., formulations, etc.) are particularly desirable for applications requiring repeated administration, and in particular repeated administrations that occur within with short periods of time (e.g., within 1-2 weeks). This is the case, for example, if the agent is a nucleic acid based therapeutic that is provided to a subject at regular, closely-spaced intervals. The findings provided herein may be applied to these and other agents that are similarly administered and/or that are subject to ABC.

Of particular interest are lipid-comprising compounds, lipid-comprising particles, and lipid-comprising compositions as these are known to be susceptible to ABC. Such lipid-comprising compounds particles, and compositions have been used extensively as biologically active agents or as delivery vehicles for such agents. Thus, the ability to improve their efficacy of such agents, whether by reducing the effect of ABC on the agent itself or on its delivery vehicle, is beneficial for a wide variety of active agents.

Also provided herein are compositions that do not stimulate or boost an acute phase response (ARP) associated with repeat dose administration of one or more biologically active agents.

The composition, in some instances, may not bind to IgM, including but not limited to natural IgM.

The composition, in some instances, may not bind to an acute phase protein such as but not limited to C-reactive protein.

The composition, in some instances, may not trigger a CD5(+) mediated immune response. As used herein, a CD5(+) mediated immune response is an immune response that is mediated by B1a and/or B1b cells. Such a response may include an ABC response, an acute phase response, induction of natural IgM and/or IgG, and the like.

The composition, in some instances, may not trigger a CD19(+) mediated immune response. As used herein, a CD19(+) mediated immune response is an immune response that is mediated by conventional CD19(+), CD5(−) B cells. Such a response may include induction of IgM, induction of IgG, induction of memory B cells, an ABC response, an anti-drug antibody (ADA) response including an anti-protein response where the protein may be encapsulated within an LNP, and the like.

B1a cells are a subset of B cells involved in innate immunity. These cells are the source of circulating IgM, referred to as natural antibody or natural serum antibody. Natural IgM antibodies are characterized as having weak affinity for a number of antigens, and therefore they are referred to as “poly-specific” or “poly-reactive”, indicating their ability to bind to more than one antigen. B1a cells are not able to produce IgG. Additionally, they do not develop into memory cells and thus do not contribute to an adaptive immune response. However, they are able to secrete IgM upon activation. The secreted IgM is typically cleared within about 2-3 weeks, at which point the immune system is rendered relatively naïve to the previously administered antigen. If the same antigen is presented after this time period (e.g., at about 3 weeks after the initial exposure), the antigen is not rapidly cleared. However, significantly, if the antigen is presented within that time period (e.g., within 2 weeks, including within 1 week, or within days), then the antigen is rapidly cleared. This delay between consecutive doses has rendered certain lipid-containing therapeutic or diagnostic agents unsuitable for use.

In humans, B1a cells are CD19(+), CD20(+), CD27(+), CD43(+), CD70(−) and CD5(+). In mice, B1a cells are CD19(+), CD5(+), and CD45 B cell isoform B220(+). It is the expression of CD5 which typically distinguishes B1a cells from other convention B cells. B1a cells may express high levels of CD5, and on this basis may be distinguished from other B-1 cells such as B-1b cells which express low or undetectable levels of CD5. CD5 is a pan-T cell surface glycoprotein. B1a cells also express CD36, also known as fatty acid translocase. CD36 is a member of the class B scavenger receptor family. CD36 can bind many ligands, including oxidized low density lipoproteins, native lipoproteins, oxidized phospholipids, and long-chain fatty acids.

B1b cells are another subset of B cells involved in innate immunity. These cells are another source of circulating natural IgM. Several antigens, including PS, are capable of inducing T cell independent immunity through B1b activation. CD27 is typically upregulated on B1b cells in response to antigen activation. Similar to B1a cells, the B1b cells are typically located in specific body locations such as the spleen and peritoneal cavity and are in very low abundance in the blood. The B1b secreted natural IgM is typically cleared within about 2-3 weeks, at which point the immune system is rendered relatively naïve to the previously administered antigen. If the same antigen is presented after this time period (e.g., at about 3 weeks after the initial exposure), the antigen is not rapidly cleared. However, significantly, if the antigen is presented within that time period (e.g., within 2 weeks, including within 1 week, or within days), then the antigen is rapidly cleared. This delay between consecutive doses has rendered certain lipid-containing therapeutic or diagnostic agents unsuitable for use.

In some embodiments it is desirable to block B1a and/or B1b cell activation. One strategy for blocking B1a and/or B1b cell activation involves determining which components of a lipid nanoparticle promote B cell activation and neutralizing those components. It has been discovered herein that at least PEG and phosphatidylcholine (PC) contribute to B1a and B1b cell interaction with other cells and/or activation. PEG may play a role in promoting aggregation between B1 cells and platelets, which may lead to activation. PC (a helper lipid in LNPs) is also involved in activating the B1 cells, likely through interaction with the CD36 receptor on the B cell surface. Numerous particles have PEG-lipid alternatives, PEG-less, and/or PC replacement lipids (e.g. oleic acid or analogs thereof) have been designed and tested. Applicant has established that replacement of one or more of these components within an LNP that otherwise would promote ABC upon repeat administration, is useful in preventing ABC by reducing the production of natural IgM and/or B cell activation. Thus, the invention encompasses LNPs that have reduced ABC as a result of a design which eliminates the inclusion of B cell triggers.

Another strategy for blocking B1a and/or B1b cell activation involves using an agent that inhibits immune responses induced by LNPs. These types of agents are discussed in more detail below. In some embodiments these agents block the interaction between B1a/B1b cells and the LNP or platelets or pDC. For instance the agent may be an antibody or other binding agent that physically blocks the interaction. An example of this is an antibody that binds to CD36 or CD6. The agent may also be a compound that prevents or disables the B1a/B1b cell from signaling once activated or prior to activation. For instance, it is possible to block one or more components in the B1a/B1b signaling cascade the results from B cell interaction with LNP or other immune cells. In other embodiments the agent may act one or more effectors produced by the B1a/B1b cells following activation. These effectors include for instance, natural IgM and cytokines.

It has been demonstrated according to aspects of the invention that when activation of pDC cells is blocked, B cell activation in response to LNP is decreased. Thus, in order to avoid ABC and/or toxicity, it may be desirable to prevent pDC activation. Similar to the strategies discussed above, pDC cell activation may be blocked by agents that interfere with the interaction between pDC and LNP and/or B cells/platelets. Alternatively agents that act on the pDC to block its ability to get activated or on its effectors can be used together with the LNP to avoid ABC.

Platelets may also play an important role in ABC and toxicity. Very quickly after a first dose of LNP is administered to a subject platelets associate with the LNP, aggregate and are activated. In some embodiments it is desirable to block platelet aggregation and/or activation. One strategy for blocking platelet aggregation and/or activation involves determining which components of a lipid nanoparticle promote platelet aggregation and/or activation and neutralizing those components. It has been discovered herein that at least PEG contribute to platelet aggregation, activation and/or interaction with other cells. Numerous particles have PEG-lipid alternatives and PEG-less have been designed and tested. Applicant has established that replacement of one or more of these components within an LNP that otherwise would promote ABC upon repeat administration, is useful in preventing ABC by reducing the production of natural IgM and/or platelet aggregation. Thus, the invention encompasses LNPs that have reduced ABC as a result of a design which eliminates the inclusion of platelet triggers. Alternatively agents that act on the platelets to block its activity once it is activated or on its effectors can be used together with the LNP to avoid ABC.

(i) Measuring ABC Activity and Related Activities

Various compounds and compositions provided herein, including LNPs, do not promote ABC activity upon administration in vivo. These LNPs may be characterized and/or identified through any of a number of assays, such as but not limited to those described below, as well as any of the assays disclosed in the Examples section, include the methods subsection of the Examples.

In some embodiments the methods involve administering an LNP without producing an immune response that promotes ABC. An immune response that promotes ABC involves activation of one or more sensors, such as B1 cells, pDC, or platelets, and one or more effectors, such as natural IgM, natural IgG or cytokines such as IL6. Thus administration of an LNP without producing an immune response that promotes ABC, at a minimum involves administration of an LNP without significant activation of one or more sensors and significant production of one or more effectors. Significant used in this context refers to an amount that would lead to the physiological consequence of accelerated blood clearance of all or part of a second dose with respect to the level of blood clearance expected for a second dose of an ABC triggering LNP. For instance, the immune response should be dampened such that the ABC observed after the second dose is lower than would have been expected for an ABC triggering LNP.

(ii) B1a or B1b Activation Assay

Certain compositions provided in this disclosure do not activate B cells, such as B1a or B1b cells (CD19+CD5+) and/or conventional B cells (CD19+CD5−). Activation of B1a cells, B1b cells, or conventional B cells may be determined in a number of ways, some of which are provided below. B cell population may be provided as fractionated B cell populations or unfractionated populations of splenocytes or peripheral blood mononuclear cells (PBMC). If the latter, the cell population may be incubated with the LNP of choice for a period of time, and then harvested for further analysis. Alternatively, the supernatant may be harvested and analyzed.

(iii) Upregulation of Activation Marker Cell Surface Expression

Activation of B1a cells, B1b cells, or conventional B cells may be demonstrated as increased expression of B cell activation markers including late activation markers such as CD86. In an exemplary non-limiting assay, unfractionated B cells are provided as a splenocyte population or as a PBMC population, incubated with an LNP of choice for a particular period of time, and then stained for a standard B cell marker such as CD19 and for an activation marker such as CD86, and analyzed using for example flow cytometry. A suitable negative control involves incubating the same population with medium, and then performing the same staining and visualization steps. An increase in CD86 expression in the test population compared to the negative control indicates B cell activation.

(iv) Pro-Inflammatory Cytokine Release

B cell activation may also be assessed by cytokine release assay. For example, activation may be assessed through the production and/or secretion of cytokines such as IL-6 and/or TNF-alpha upon exposure with LNPs of interest.

Such assays may be performed using routine cytokine secretion assays well known in the art. An increase in cytokine secretion is indicative of B cell activation.

(v) LNP Binding/Association to and/or Uptake by B Cells

LNP association or binding to B cells may also be used to assess an LNP of interest and to further characterize such LNP. Association/binding and/or uptake/internalization may be assessed using a detectably labeled, such as fluorescently labeled, LNP and tracking the location of such LNP in or on B cells following various periods of incubation.

The invention further contemplates that the compositions provided herein may be capable of evading recognition or detection and optionally binding by downstream mediators of ABC such as circulating IgM and/or acute phase response mediators such as acute phase proteins (e.g., C-reactive protein (CRP).

(vi) Methods of Use for Reducing ABC

Also provided herein are methods for delivering LNPs, which may encapsulate an agent such as a therapeutic agent, to a subject without promoting ABC.

In some embodiments, the method comprises administering any of the LNPs described herein, which do not promote ABC, for example, do not induce production of natural IgM binding to the LNPs, do not activate B1a and/or B1b cells. As used herein, an LNP that "does not promote ABC" refers to an LNP that induces no immune responses that would lead to substantial ABC or a substantially low level of immune responses that is not sufficient to lead to substantial ABC. An LNP that does not induce the production of natural IgMs binding to the LNP refers to LNPs that induce either no natural IgM binding to the LNPs or a substantially low level of the natural IgM molecules, which is insufficient to lead to substantial ABC. An LNP that does not activate B1a and/or B1b cells refer to LNPs that induce no response of B1a and/or B1b cells to produce natural IgM binding to the LNPs or a substantially low level of B1a and/or B1b responses, which is insufficient to lead to substantial ABC.

In some embodiments the terms do not activate and do not induce production are a relative reduction to a reference value or condition. In some embodiments the reference value or condition is the amount of activation or induction of production of a molecule such as IgM by a standard LNP such as an MC3 LNP. In some embodiments the relative reduction is a reduction of at least 30%, for example at least 30%, 35%, 40%, 45%, 50%, 55%, 60%, 65%, 70%, 75%, 80%, 85%, 90%, 91%, 92%, 93%, 94%, 95%, 96%, 97%, 98%, 99%, or 100%. In other embodiments the terms do not activate cells such as B cells and do not induce production of a protein such as IgM may refer to an undetectable amount of the active cells or the specific protein.

(vii) Platelet Effects and Toxicity

The invention is further premised in part on the elucidation of the mechanism underlying dose-limiting toxicity associated with LNP administration. Such toxicity may involve coagulopathy, disseminated intravascular coagulation (DIC, also referred to as consumptive coagulopathy), whether acute or chronic, and/or vascular thrombosis. In some instances, the dose-limiting toxicity associated with LNPs is acute phase response (APR) or complement activation-related psudoallergy (CARPA).

As used herein, coagulopathy refers to increased coagulation (blood clotting) in vivo. The findings reported in this disclosure are consistent with such increased coagulation and significantly provide insight on the underlying mechanism. Coagulation is a process that involves a number of different factors and cell types, and heretofore the relationship between and interaction of LNPs and platelets has not been understood in this regard. This disclosure provides evidence of such interaction and also provides compounds and compositions that are modified to have reduced platelet effect, including reduced platelet association, reduced platelet aggregation, and/or reduced platelet aggregation. The ability to modulate, including preferably down-modulate, such platelet effects can reduce the incidence and/or severity of coagulopathy post-LNP administration. This in turn will reduce toxicity relating to such LNP, thereby allowing higher doses of LNPs and importantly their cargo to be administered to patients in need thereof.

CARPA is a class of acute immune toxicity manifested in hypersensitivity reactions (HSRs), which may be triggered by nanomedicines and biologicals. Unlike allergic reactions, CARPA typically does not involve IgE but arises as a consequence of activation of the complement system, which is part of the innate immune system that enhances the body's abilities to clear pathogens. One or more of the following pathways, the classical complement pathway (CP), the alternative pathway (AP), and the lectin pathway (LP), may be involved in CARPA. Szebeni, Molecular Immunology, 61:163-173 (2014).

The classical pathway is triggered by activation of the C1-complex, which contains. C1q, C1r, C1s, or C1qr2s2. Activation of the C1-complex occurs when C1q binds to IgM or IgG complexed with antigens, or when C1q binds directly to the surface of the pathogen. Such binding leads to conformational changes in the C1q molecule, which leads to the activation of C1r, which in turn, cleave C1s. The C1r2s2 component now splits C4 and then C2, producing C4a, C4b, C2a, and C2b. C4b and C2b bind to form the classical pathway C3-convertase (C4b2b complex), which promotes cleavage of C3 into C3a and C3b. C3b then binds the C3 convertase to from the C5 convertase (C4b2b3b complex). The alternative pathway is continuously activated as a result of spontaneous C3 hydrolysis. Factor P (properdin) is a positive regulator of the alternative pathway. Oligomerization of properdin stabilizes the C3 convertase, which can then cleave much more C3. The C3 molecules can bind to surfaces and recruit more B, D, and P activity, leading to amplification of the complement activation.

Acute phase response (APR) is a complex systemic innate immune responses for preventing infection and clearing potential pathogens. Numerous proteins are involved in APR and C-reactive protein is a well-characterized one.

It has been found, in accordance with the invention, that certain LNP are able to associate physically with platelets almost immediately after administration in vivo, while other LNP do not associate with platelets at all or only at background levels. Significantly, those LNPs that associate with platelets also apparently stabilize the platelet aggregates that are formed thereafter. Physical contact of the platelets with certain LNPs correlates with the ability of such platelets to remain aggregated or to form aggregates continuously for an extended period of time after administration. Such aggregates comprise activated platelets and also innate immune cells such as macrophages and B cells.

25. METHODS OF USE

The polynucleotides, pharmaceutical compositions and formulations described herein are used in the preparation, manufacture and therapeutic use of to treat and/or prevent GALT-related diseases, disorders or conditions. In some embodiments, the polynucleotides, compositions and formulations of the invention are used to treat and/or prevent Gal-1.

In some embodiments, the polynucleotides, pharmaceutical compositions and formulations of the invention are used in methods for reducing the levels of galactose in a subject in need thereof. For instance, one aspect of the invention provides a method of alleviating the symptoms of Gal-1 in a subject comprising the administration of a composition or formulation comprising a polynucleotide encoding GALT to that subject (e.g, an mRNA encoding a GALT polypeptide).

In some embodiments, the polynucleotides, pharmaceutical compositions and formulations of the invention are used to reduce the level of a metabolite associated with Gal-1 (e.g., the substrate or product, i.e., galactose), the method comprising administering to the subject an effective amount of a polynucleotide encoding a GALT polypeptide.

In some embodiments, the administration of an effective amount of a polynucleotide, pharmaceutical composition or formulation of the invention reduces the levels of a biomarker of Gal-1, e.g., galactose-1-phosphate, galactose, galactitol, galactonate, 8-hydroxy-2-desoxyguanosine, and or any combination thereof. In some embodiments, the administration of the polynucleotide, pharmaceutical composition or formulation of the invention results in reduction in the level of one or more biomarkers of Gal-1, e.g., galactose-1-phosphate, galactitol, galactonate, 8-hydroxy-2-desoxyguanosine, and/or galactose, within a short period of time (e.g., within about 6 hours, within about 8 hours, within about 12 hours, within about 16 hours, within about 20 hours, or within about 24 hours) after administration of the polynucleotide, pharmaceutical composition or formulation of the invention.

Replacement therapy is a potential treatment for Gal-1. Thus, in certain aspects of the invention, the polynucleotides, e.g., mRNA, disclosed herein comprise one or more sequences encoding a GALT polypeptide that is suitable for use in gene replacement therapy for Gal-1. In some embodiments, the present disclosure treats a lack of GALT or GALT activity, or decreased or abnormal GALT activity in a subject by providing a polynucleotide, e.g., mRNA, that encodes a GALT polypeptide to the subject. In some embodiments, the polynucleotide is sequence-optimized. In some embodiments, the polynucleotide (e.g., an mRNA) comprises a nucleic acid sequence (e.g., an ORF) encoding a GALT polypeptide, wherein the nucleic acid is sequence-optimized, e.g., by modifying its G/C, uridine, or thymidine content, and/or the polynucleotide comprises at least one chemically modified nucleoside. In some embodiments, the polynucleotide comprises a miRNA binding site, e.g., a miRNA binding site that binds miRNA-142 and/or a miRNA binding site that binds miRNA-126.

In some embodiments, the administration of a composition or formulation comprising polynucleotide, pharmaceutical composition or formulation of the invention to a subject results in a decrease in galactose in cells to a level at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or to 100% lower than the level observed prior to the administration of the composition or formulation.

In some embodiments, the administration of the polynucleotide, pharmaceutical composition or formulation of the invention results in expression of GALT in cells of the subject. In some embodiments, administering the polynucleotide, pharmaceutical composition or formulation of the invention results in an increase of GALT expression and/or enzymatic activity in the subject. For example, in some embodiments, the polynucleotides of the present invention are used in methods of administering a composition or formulation comprising an mRNA encoding a GALT polypeptide to a subject, wherein the method results in an increase of GALT expression and/or enzymatic activity in at least some cells of a subject.

In some embodiments, the administration of a composition or formulation comprising an mRNA encoding a GALT polypeptide to a subject results in an increase of GALT expression and/or enzymatic activity in cells subject to a level at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or to 100% or more of the expression and/or activity level expected in a normal subject, e.g., a human not suffering from Gal-1.

In some embodiments, the administration of the polynucleotide, pharmaceutical composition or formulation of the invention results in expression of GALT protein in at least some of the cells of a subject that persists for a period of time sufficient to allow significant galactose metabolism to occur.

In some embodiments, the expression of the encoded polypeptide is increased. In some embodiments, the polynucleotide increases GALT expression and/or enzymatic activity levels in cells when introduced into those cells, e.g., by at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or to 100% with respect to the GALT expression and/or enzymatic activity level in the cells before the polypeptide is introduced in the cells.

In some embodiments, the method or use comprises administering a polynucleotide, e.g., mRNA, comprising a nucleotide sequence having sequence similarity to a polynucleotide selected from the group of SEQ ID NOs: 5 to 29 and 113 to 131, e.g., 124 or 126 (See Table 2) or a polynucleotide selected from the group of SEQ ID NOs: 132 to 150, e.g., 143 or 145 (See Table 5), wherein the polynucleotide encodes an GALT polypeptide.

Other aspects of the present disclosure relate to transplantation of cells containing polynucleotides to a mammalian subject. Administration of cells to mammalian subjects is known to those of ordinary skill in the art, and includes, but is not limited to, local implantation (e.g., topical or subcutaneous administration), organ delivery or systemic injection (e.g., intravenous injection or inhalation), and the formulation of cells in pharmaceutically acceptable carriers.

In some embodiments, the polynucleotides (e.g., mRNA), pharmaceutical compositions and formulations used in the methods of the invention comprise a uracil-modified sequence encoding a GALT polypeptide disclosed herein and a miRNA binding site disclosed herein, e.g., a miRNA binding site that binds to miR-142 and/or a miRNA binding site that binds to miR-126. In some embodiments, the uracil-modified sequence encoding a GALT polypeptide comprises at least one chemically modified nucleobase, e.g., 5-methoxyuracil. In some embodiments, at least 95% of a type of nucleobase (e.g., uracil) in a uracil-modified sequence encoding a GALT polypeptide of the invention are modified nucleobases. In some embodiments, at least 95% of uricil in a uracil-modified sequence encoding a GALT polypeptide is 5-methoxyuridine. In some embodiments, the polynucleotide comprising a nucleotide sequence encoding a GALT polypeptide disclosed herein and a miRNA binding site is formulated with a delivery agent comprising, e.g., a compound having the Formula (I), e.g., any of Compounds 1-232, e.g., Compound 18; a compound having the Formula (III), (IV), (V), or (VI), e.g., any of Compounds 233-342, e.g., Compound 236; or a compound having the Formula (VIII), e.g., any of Compounds 419-428, e.g., Compound 428, or any combination thereof. In some embodiments, the delivery agent comprises Compound 18, DSPC, Cholesterol, and Compound 428, e.g., with a mole ratio of about 50:10:38.5:1.5.

The skilled artisan will appreciate that the therapeutic effectiveness of a drug or a treatment of the instant invention can be characterized or determined by measuring the level of expression of an encoded protein (e.g., enzyme) in a sample or in samples taken from a subject (e.g., from a preclinical test subject (rodent, primate, etc.) or from a clinical subject (human). Likewise, the therapeutic effectiveness of a drug or a treatment of the instant invention can be characterized or determined by measuring the level of activity of an encoded protein (e.g., enzyme) in a sample or in samples taken from a subject (e.g., from a preclinical test subject (rodent, primate, etc.) or from a clinical subject (human). Furthermore, the therapeutic effectiveness of a drug or a treatment of the instant invention can be characterized or determined by measuring the level of an appropriate biomarker in sample(s) taken from a subject. Levels of protein and/or biomarkers can be determined post-administration with a single dose of an mRNA therapeutic of the invention or can be determined and/or monitored at several time points following administration with a single dose or can be determined and/or monitored throughout a course of treatment, e.g., a multi-dose treatment.

Gal-1 is associated with an impaired ability to convert UDP-glucose and galactose-1-phosphate to glucose-1-phosphate and UDP-galactose. Accordingly, Gal-1 patients commonly show high levels of galactose-1-phosphate in their blood.

Gal-1 is an autosomal recessive metabolic disorder characterized by the inability to convert UDP-glucose and galactose-1-phosphate to glucose-1-phosphate and UDP-galactose. Accordingly, Gal-1 patients can be asymptomatic carriers of the disorder or suffer from the various symptoms associated with the disease. Gal-1 patients commonly show high levels of galactose-1-phosphate, galactose, 8-hydroxy-2-desoxyguanosine, and/or galactitol and galactonate (produced via alternative pathways when galactose metabolism is impaired) in their plasma, serum, red blood cells (RBC), urine, and/or tissue (e.g., liver). Unless otherwise specified, the methods of treating Gal-1 patients or human subjects disclosed herein include treatment of both asymptomatic carriers and those individuals with abnormal levels of biomarkers, e.g., galactose-1-phosphate, galactose, galactitol, galactonate, and/or 8-hydroxy-2-desoxyguanosine.

GALT Protein Expression Levels

Certain aspects of the invention feature measurement, determination and/or monitoring of the expression level or levels of galactose-1-phosphate uridylyltransferase (GALT) protein in a subject, for example, in an animal (e.g., rodents, primates, and the like) or in a human subject. Animals include normal, healthy or wildtype animals, as well as animal models for use in understanding galactosemia type 1 (Gal-1) and treatments thereof. Exemplary animal models include rodent models, for example, GALT deficient mice also referred to as GALT mice.

GALT protein expression levels can be measured or determined by any art-recognized method for determining protein levels in biological samples, e.g., from blood samples or a needle biopsy. The term "level" or "level of a protein" as used herein, preferably means the weight, mass or concentration of the protein within a sample or a subject. It will be understood by the skilled artisan that in certain embodiments the sample may be subjected, e.g., to any of the following: purification, precipitation, separation, e.g. centrifugation and/or HPLC, and subsequently subjected to determining the level of the protein, e.g., using mass and/or spectrometric analysis. In exemplary embodiments, enzyme-linked immunosorbent assay (ELISA) can be used to determine protein expression levels. In other exemplary embodiments, protein purification, separation and LC-MS can be used as a means for determining the level of a protein according to the invention. In some embodiments, an mRNA therapy of the invention (e.g., a single intravenous dose) results in increased GALT protein expression levels in the liver tissue of the subject (e.g., 2-fold, 3-fold, 4-fold, 5-fold, 6-fold, 7-fold, 8-fold, 9-fold, 10-fold, 20-fold, 30-fold, 40-fold, 50-fold increase and/or increased to at least 50%, at least 60%, at least 70%, at least 75%, 80%, at least 85%, at least 90%, at least 95%, or at least 100% of normal levels) for at least 6 hours, at least 12 hours, at least 24 hours, at least 36 hours, at least 48 hours, at least 60 hours, at least 72 hours, at least 84 hours, at least 96 hours, at least 108 hours, at least 122 hours after administration of a single dose of the mRNA therapy.

GALT Protein Activity

In Gal-1 patients, galactose-1-phosphate uridylyltransferase (GALT) enzymatic activity is reduced compared to a normal physiological activity level. Further aspects of the invention feature measurement, determination and/or monitoring of the activity level(s) (i.e., enzymatic activity level(s)) of GALT protein in a subject, for example, in an animal (e.g., rodent, primate, and the like) or in a human subject. Activity levels can be measured or determined by any art-recognized method for determining enzymatic activity levels in biological samples. The term "activity level" or "enzymatic activity level" as used herein, preferably means the activity of the enzyme per volume, mass or weight of sample or total protein within a sample. In exemplary embodiments, the "activity level" or "enzymatic activity level" is described in terms of units per milliliter of fluid (e.g., bodily fluid, e.g., serum, plasma, urine and the like) or is described in terms of units per weight of tissue or per weight of protein (e.g., total protein) within a sample. Units ("U") of enzyme activity can be described in terms of weight or mass of substrate hydrolyzed per unit time. In certain embodiments of the invention feature GALT activity described in terms of U/ml plasma or U/mg protein (tissue), where units ("U") are described in terms of nmol substrate hydrolyzed per hour (or nmol/hr).

In certain embodiments, an mRNA therapy of the invention features a pharmaceutical composition comprising a dose of mRNA effective to result in at least 5 U/mg, at least 10 U/mg, at least 20 U/mg, at least 30 U/mg, at least 40 U/mg, at least 50 U/mg, at least 60 U/mg, at least 70 U/mg, at least 80 U/mg, at least 90 U/mg, at least 100 U/mg, or at least 150 U/mg of GALT activity in tissue (e.g., liver) between 6 and 12 hours, or between 12 and 24, between 24 and 48, or between 48 and 72 hours post administration (e.g., at 48 or at 72 hours post administration).

In exemplary embodiments, an mRNA therapy of the invention features a pharmaceutical composition comprising a single intravenous dose of mRNA that results in the above-described levels of activity. In another embodiment, an mRNA therapy of the invention features a pharmaceutical composition which can be administered in multiple single unit intravenous doses of mRNA that maintain the above-described levels of activity.

GALT Biomarkers

Further aspects of the invention feature determining the level (or levels) of a biomarker, e.g., galactose-1-phosphate, galactose, galactitol, galactonate, and/or 8-hydroxy-2-desoxyguanosine, determined in a sample as compared to a level (e.g., a reference level) of the same or another biomarker in another sample, e.g., from the same patient, from another patient, from a control and/or from the same or different time points, and/or a physiologic level, and/or an elevated level, and/or a supraphysiologic level, and/or a level of a control. The skilled artisan will be familiar with physiologic levels of biomarkers, for example, levels in normal or wildtype animals, normal or healthy subjects, and the like, in particular, the level or levels characteristic of subjects who are healthy and/or normal functioning. As used herein, the phrase “elevated level” means amounts greater than normally found in a normal or wildtype preclinical animal or in a normal or healthy subject, e.g. a human subject. As used herein, the term “supraphysiologic” means amounts greater than normally found in a normal or wild-type preclinical animal or in a normal or healthy subject, e.g. a human subject, optionally producing a significantly enhanced physiologic response. As used herein, the term “comparing” or “compared to” preferably means the mathematical comparison of the two or more values, e.g., of the levels of the biomarker(s). It will thus be readily apparent to the skilled artisan whether one of the values is higher, lower or identical to another value or group of values if at least two of such values are compared with each other. Comparing or comparison to can be in the context, for example, of comparing to a control value, e.g., as compared to a reference red blood cells (RBC) and/or tissue (e.g., liver) Gal-1-P level, a serum, plasma, and/or urinary 8-hydroxy-2desoxyguanosine level, a blood plasma, serum, and/or urinary galactose level, urinary, serum, and/or plasma galactitol level, and/or a reference urinary serum, and/or plasma galactonate level in said subject prior to administration (e.g., in a person suffering from Gal-1) or in a normal or healthy subject. Comparing or comparison to can also be in the context, for example, of comparing to a control value, e.g., as compared to a reference RBC and/or tissue (e.g., liver) galactose-1-phosphate, plasma, serum, and/or urinary galactose, urinary, serum, and/or plasma galactitol, serum, plasma, and/or urinary 8-hydroxy-desoxyguanosine, and/or urinary, serum, and/or plasma galactonate excretion level in said subject prior to administration (e.g., in a person suffering from Gal-1) or in a normal or healthy subject.

As used herein, a “control” is preferably a sample from a subject wherein the Gal-1 status of said subject is known. In one embodiment, a control is a sample of a healthy patient. In another embodiment, the control is a sample from at least one subject having a known Gal-1 status, for example, a severe, mild, or healthy Gal-1 status, e.g. a control patient. In another embodiment, the control is a sample from a subject not being treated for Gal-1. In a still further embodiment, the control is a sample from a single subject or a pool of samples from different subjects and/or samples taken from the subject(s) at different time points.

The term “level” or “level of a biomarker” as used herein, preferably means the mass, weight or concentration of a biomarker of the invention within a sample or a subject. Biomarkers of the invention include, for example, galactose-1-phosphate (e.g., reference RBC levels: 5-49 μg/g of hemoglobin (<1 mg/dL)), galactitol (e.g., reference urinary excretion levels in individuals 18 years and older: <13 mmol/mol creatinine), galactonate (e.g., reference urinary excretion levels: not detectable), galactose (e.g. reference serum levels: <4-5 mg/dL) and/or 8-hydroxy-2-desoxyguanosine (e.g., reference serum levels: <about 0.25 ng/mL). It will be understood by the skilled artisan that in certain embodiments the sample may be subjected to, e.g., one or more of the following: substance purification, precipitation, separation, e.g. centrifugation and/or HPLC and subsequently subjected to determining the level of the biomarker, e.g. using mass spectrometric analysis. In certain embodiments, LC-MS can be used as a means for determining the level of a biomarker according to the invention.

The term “determining the level” of a biomarker as used herein can mean methods which include quantifying an amount of at least one substance in a sample from a subject, for example, in a bodily fluid from the subject (e.g., serum, plasma, urine, RBC, lymph, fecal, etc.) or in a tissue of the subject (e.g., liver, heart, spleen kidney, etc.).

The term “reference level” as used herein can refer to levels (e.g., of a biomarker) in a subject prior to administration of an mRNA therapy of the invention (e.g., in a person suffering from Gal-1) or in a normal or healthy subject.

As used herein, the term “normal subject” or “healthy subject” refers to a subject not suffering from symptoms associated with Gal-1. Moreover, a subject will be considered to be normal (or healthy) if it has no mutation of the functional portions or domains of the galactose-1-phosphate uridylytransferase (GALT) gene and/or no mutation of the GALT gene resulting in a reduction of or deficiency of the enzyme GALT (also known as galactose-1-phosphate uridylytransferase) or the activity thereof, resulting in symptoms associated with Gal-1. Said mutations will be detected if a sample from the subject is subjected to a genetic testing for such GALT mutations. In certain embodiments of the present invention, a sample from a healthy subject is used as a control sample, or the known or standardized value for the level of biomarker from samples of healthy or normal subjects is used as a control.

In some embodiments, comparing the level of the biomarker in a sample from a subject in need of treatment for Gal-1 or in a subject being treated for Gal-1 to a control level of the biomarker comprises comparing the level of the biomarker in the sample from the subject (in need of treatment or being treated for Gal-1) to a baseline or reference level, wherein if a level of the biomarker in the sample from the subject (in need of treatment or being treated for Gal-1) is elevated, increased or higher compared to the baseline or reference level, this is indicative that the subject is suffering from Gal-1 and/or is in need of treatment; and/or wherein if a level of the biomarker in the sample from the subject (in need of treatment or being treated for Gal-1) is decreased or lower compared to the baseline level this is indicative that the subject is not suffering from, is successfully being treated for Gal-1, or is not in need of treatment for Gal-1. The stronger the reduction (e.g., at least 2-fold, at least 3-fold, at least 4-fold, at least 5-fold, at least 6-fold, at least 7-fold, at least 8-fold, at least 10-fold, at least 20-fold, at least-30 fold, at least 40-fold, at least 50-fold reduction and/or at least 10%, at least 20%, at least 30% at least 40%, at least 50%, at least 60%, at least 70%, at least 80%, at least 90%, or at least 100% reduction) of the level of a biomarker, e.g., galactose-1-phosphate, galactose, galactitol, galactonate, and/or 8-hydroxy-2-desoxyguanosine, within a certain time period, e.g., within 6 hours, within 12 hours, 24 hours, 36 hours, 48 hours, 60 hours, or 72 hours, and/or for a certain duration of time, e.g., 48 hours, 72 hours, 96 hours, 120 hours, 144 hours, 1 week, 2 weeks, 3 weeks, 4 weeks, 1 month, 2 months, 3 months, 4 months, 5 months, 6 months, 7 months, 8 months, 9 months, 10 months, 11 months, 12 months, 18 months, 24 months, etc. the more successful is a therapy, such as for example an mRNA therapy of the invention (e.g., a single dose or a multiple regimen).

A reduction of at least about 20%, at least about 30%, at least about 40%, at least about 50%, at least about 60%, at least about 70%, at least about 80%, at least about 90%, at least 100% or more of the level of biomarker, in particular, in bodily fluid (e.g., plasma, serum, red blood cells (RBC), urine, e.g., urinary sediment) or in tissue(s) in a subject (e.g., liver), for example a galactose-1-phosphate, galactose, galactitol, galactonate, and/or 8-hydroxy-2-desoxyguanosine, within 1, 2, 3, 4, 5, 6 or more days following administration is indicative of a dose suitable for successful treatment Gal-1, wherein reduction as used herein, preferably means that the level of biomarker determined at the end of a specified time period (e.g., post-administration, for example, of a single intravenous dose) is compared to the level of the same biomarker determined at the beginning of said time period (e.g., pre-administration of said dose). Exemplary time periods include 12, 24, 48, 72, 96, 120 or 144 hours post administration, in particular 24, 48, 72 or 96 hours post administration.

A sustained reduction in substrate levels (e.g., biomarkers such as galactose-1-phosphate, galactose, galactitol, galactonate, and/or 8-hydroxy-2-desoxyguanosine) is particularly indicative of mRNA therapeutic dosing and/or administration regimens successful for treatment of Gal-1. Such sustained reduction can be referred to herein as "duration" of effect. In exemplary embodiments, a reduction of at least about 20%, at least about 30%, at least about 40%, at least about 50%, at least about 60%, at least about 65%, at least about 70%, at least about 75%, at least about 80%, at least about 85%, at least about 90%, or at least about 95% at least about 96%, at least about 97%, at least about 98%, at least about 99%, at least about 100% or more of the level of biomarker, in particular, in a bodily fluid (e.g., plasma, serum, RBC, urine, e.g., urinary sediment) or in tissue(s) in a subject (e.g., liver), for example galactose-1-phosphate, galactose, galactitol, galactonate, and/or 8-hydroxy-2-desoxyguanosine, within 1, 2, 3, 4, 5, 6, 7, 8 or more days following administration is indicative of a successful therapeutic approach. In exemplary embodiments, sustained reduction in substrate (e.g., biomarker) levels in one or more samples (e.g., fluids and/or tissues) is preferred. For example, mRNA therapies resulting in sustained reduction in galactose-1-phosphate, galactose, galactitol, galactonate, and/or 8-hydroxy-2-desoxyguanosine (as defined herein), optionally in combination with sustained reduction of said biomarker in at least one tissue, preferably two, three, four, five or more tissues, is indicative of successful treatment.

In some embodiments, a single dose of an mRNA therapy of the invention is about 0.2 to about 0.8 mpk. about 0.3 to about 0.7 mpk, about 0.4 to about 0.8 mpk, or about 0.5 mpk. In another embodiment, a single dose of an mRNA therapy of the invention is less than 1.5 mpk, less than 1.25 mpk, less than 1 mpk, or less than 0.75 mpk.

26. COMPOSITIONS AND FORMULATIONS FOR USE

Certain aspects of the invention are directed to compositions or formulations comprising any of the polynucleotides disclosed above.

In some embodiments, the composition or formulation comprises:

(i) a polynucleotide (e.g., a RNA, e.g., an mRNA) comprising a sequence-optimized nucleotide sequence (e.g., an ORF) encoding a GALT polypeptide (e.g., the wild-type sequence, functional fragment, or variant thereof), wherein the polynucleotide comprises at least one chemically modified nucleobase, e.g., 5-methoxyuracil (e.g., wherein at least about 25%, at least about 30%, at least about 40%, at least about 50%, at least about 60%, at least about 70%, at least about 80%, at least about 90%, at least about 95%, at least about 99%, or 100% of the uracils are 5-methoxyuracils), and wherein the polynucleotide further comprises a miRNA binding site, e.g., a miRNA binding site that binds to miR-142 (e.g., a miR-142-3p or miR-142-5p binding site) and/or a miRNA binding site that binds to miR-126 (e.g., a miR-126-3p or miR-126-5p binding site); and (ii) a delivery agent comprising, e.g., a compound having the Formula (I), e.g., any of Compounds 1-232, e.g., Compound 18; a compound having the Formula (III), (IV), (V), or (VI), e.g., any of Compounds 233-342, e.g., Compound 236; or a compound having the Formula (VIII), e.g., any of Compounds 419-428, e.g., Compound 428, or any combination thereof. In some embodiments, the delivery agent is a lipid nanoparticle comprising Compound 18, Compound 236, a salt or a stereoisomer thereof, or any combination thereof. In some embodiments, the lipid nanoparticle or the delivery agent comprises Compound 18, DSPC, Cholesterol, and Compound 428, e.g., with a mole ratio of about 50:10:38.5:1.5.

In some embodiments, the uracil or thymine content of the ORF relative to the theoretical minimum uracil or thymine content of a nucleotide sequence encoding the GALT polypeptide (% $U_{TM}$ or % $T_{TM}$), is between about 100% and about 150%.

In some embodiments, the polynucleotides, compositions or formulations above are used to treat and/or prevent a GALT-related diseases, disorders or conditions, e.g., Gal-1.

27. FORMS OF ADMINISTRATION

The polynucleotides, pharmaceutical compositions and formulations of the invention described above can be administered by any route that results in a therapeutically effective outcome. These include, but are not limited to enteral (into the intestine), gastroenteral, epidural (into the dura matter), oral (by way of the mouth), transdermal, peridural, intracerebral (into the cerebrum), intracerebroventricular (into the cerebral ventricles), epicutaneous (application onto the skin), intradermal, (into the skin itself), subcutaneous (under the skin), nasal administration (through the nose), intravenous (into a vein), intravenous bolus, intravenous drip, intraarterial (into an artery), intramuscular (into a muscle), intracardiac (into the heart), intraosseous infusion (into the bone marrow), intrathecal (into the spinal canal), intraperitoneal, (infusion or injection into the peritoneum), intravesical infusion, intravitreal, (through the eye), intracavernous injection (into a pathologic cavity) intracavitary (into the base of the penis), intravaginal administration, intrauterine, extra-amniotic administration, transdermal (diffusion through the intact skin for systemic distribution), transmucosal (diffusion through a mucous membrane), transvaginal, insufflation (snorting), sublingual, sublabial, enema, eye drops (onto the conjunctiva), in ear drops, auricular (in or by way of the ear), buccal (directed toward the cheek), conjunctival, cutaneous, dental (to a tooth or teeth), electro-osmosis, endocervical, endosinusial, endotracheal, extracorporeal, hemodialysis, infiltration, interstitial, intra-abdominal, intra-amniotic, intra-articular, intrabiliary, intrabronchial, intrabursal, intracartilaginous (within a cartilage), intracaudal (within the cauda equine), intracisternal (within the cisterna magna cerebellomedularis), intracorneal (within the cornea), dental intracornal, intracoronary (within the coronary arteries), intracorporus cavernosum (within the dilatable spaces of the corporus cavernosa of the penis), intradiscal (within a disc), intraductal (within a duct of a gland), intraduodenal (within the duodenum), intradural (within or beneath the dura), intraepidermal (to the epidermis), intraesophageal (to the esophagus), intragastric (within the stomach), intragingival (within the gingivae), intraileal (within the distal portion of the small intestine), intralesional (within or introduced directly to a localized lesion), intraluminal (within a lumen of a tube), intralymphatic (within the lymph), intramedullary (within the marrow cavity of a bone), intrameningeal (within the meninges), intraocular (within the eye), intraovarian (within the ovary), intrapericardial (within the pericardium), intrapleural (within the pleura), intraprostatic (within the prostate gland), intrapulmonary (within the lungs or its bronchi), intrasinal (within the nasal or periorbital sinuses), intraspinal (within the vertebral column), intrasynovial (within the synovial cavity of a joint), intratendinous (within a tendon), intratesticular (within the testicle), intrathecal (within the cerebrospinal fluid at any level of the cerebrospinal axis), intrathoracic (within the thorax), intratubular (within the tubules of an organ), intratympanic (within the aurus media), intravascular (within a vessel or vessels), intraventricular (within a ventricle), iontophoresis (by means of electric current where ions of soluble salts migrate into the tissues of the body), irrigation (to bathe or flush open wounds or body cavities), laryngeal (directly upon the larynx), nasogastric (through the nose and into the stomach), occlusive dressing technique (topical route administration that is then covered by a dressing that occludes the area), ophthalmic (to the external eye), oropharyngeal (directly to the mouth and pharynx), parenteral, percutaneous, periarticular, peridural, perineural, periodontal, rectal, respiratory (within the respiratory tract by inhaling orally or nasally for local or systemic effect), retrobulbar (behind the pons or behind the eyeball), intramyocardial (entering the myocardium), soft tissue, subarachnoid, subconjunctival, submucosal, topical, transplacental (through or across the placenta), transtracheal (through the wall of the trachea), transtympanic (across or through the tympanic cavity), ureteral (to the ureter), urethral (to the urethra), vaginal, caudal block, diagnostic, nerve block, biliary perfusion, cardiac perfusion, photopheresis or spinal. In specific embodiments, compositions can be administered in a way that allows them cross the blood-brain barrier, vascular barrier, or other epithelial barrier. In some embodiments, a formulation for a route of administration can include at least one inactive ingredient.

The polynucleotides of the present invention (e.g., a polynucleotide comprising a nucleotide sequence encoding a GALT polypeptide or a functional fragment or variant thereof) can be delivered to a cell naked. As used herein in, “naked” refers to delivering polynucleotides free from agents that promote transfection. The naked polynucleotides can be delivered to the cell using routes of administration known in the art and described herein.

The polynucleotides of the present invention (e.g., a polynucleotide comprising a nucleotide sequence encoding a GALT polypeptide or a functional fragment or variant thereof) can be formulated, using the methods described herein. The formulations can contain polynucleotides that can be modified and/or unmodified. The formulations can further include, but are not limited to, cell penetration agents, a pharmaceutically acceptable carrier, a delivery agent, a bioerodible or biocompatible polymer, a solvent, and a sustained-release delivery depot. The formulated polynucleotides can be delivered to the cell using routes of administration known in the art and described herein.

A pharmaceutical composition for parenteral administration can comprise at least one inactive ingredient. Any or none of the inactive ingredients used can have been approved by the US Food and Drug Administration (FDA). A non-exhaustive list of inactive ingredients for use in pharmaceutical compositions for parenteral administration includes hydrochloric acid, mannitol, nitrogen, sodium acetate, sodium chloride and sodium hydroxide.

Injectable preparations, for example, sterile injectable aqueous or oleaginous suspensions can be formulated according to the known art using suitable dispersing agents, wetting agents, and/or suspending agents. Sterile injectable preparations can be sterile injectable solutions, suspensions, and/or emulsions in nontoxic parenterally acceptable diluents and/or solvents, for example, as a solution in 1,3-butanediol. Among the acceptable vehicles and solvents that can be employed are water, Ringer's solution, U.S.P., and isotonic sodium chloride solution. Sterile, fixed oils are conventionally employed as a solvent or suspending medium. For this purpose any bland fixed oil can be employed including synthetic mono- or diglycerides. Fatty acids such as oleic acid can be used in the preparation of injectables. The sterile formulation can also comprise adjuvants such as local anesthetics, preservatives and buffering agents.

Injectable formulations can be sterilized, for example, by filtration through a bacterial-retaining filter, and/or by incorporating sterilizing agents in the form of sterile solid compositions that can be dissolved or dispersed in sterile water or other sterile injectable medium prior to use.

Injectable formulations can be for direct injection into a region of a tissue, organ and/or subject. As a non-limiting example, a tissue, organ and/or subject can be directly injected a formulation by intramyocardial injection into the ischemic region. (See, e.g., Zangi et al. Nature Biotechnology 2013; the contents of which are herein incorporated by reference in its entirety).

In order to prolong the effect of an active ingredient, it is often desirable to slow the absorption of the active ingredient from subcutaneous or intramuscular injection. This can be accomplished by the use of a liquid suspension of crystalline or amorphous material with poor water solubility. The rate of absorption of the drug then depends upon its rate of dissolution which, in turn, can depend upon crystal size and crystalline form. Alternatively, delayed absorption of a parenterally administered drug form is accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides). Depot injectable formulations are prepared by entrapping the drug in liposomes or microemulsions that are compatible with body tissues.

28. KITS AND DEVICES a. Kits

The invention provides a variety of kits for conveniently and/or effectively using the claimed nucleotides of the present invention. Typically kits will comprise sufficient amounts and/or numbers of components to allow a user to perform multiple treatments of a subject(s) and/or to perform multiple experiments.

In one aspect, the present invention provides kits comprising the molecules (polynucleotides) of the invention.

Said kits can be for protein production, comprising a first polynucleotides comprising a translatable region. The kit can further comprise packaging and instructions and/or a delivery agent to form a formulation composition. The delivery agent can comprise a saline, a buffered solution, a lipidoid or any delivery agent disclosed herein.

In some embodiments, the buffer solution can include sodium chloride, calcium chloride, phosphate and/or EDTA. In another embodiment, the buffer solution can include, but is not limited to, saline, saline with 2 mM calcium, 5% sucrose, 5% sucrose with 2 mM calcium, 5% Mannitol, 5% Mannitol with 2 mM calcium, Ringer's lactate, sodium chloride, sodium chloride with 2 mM calcium and mannose (See, e.g., U.S. Pub. No. 20120258046; herein incorporated by reference in its entirety). In a further embodiment, the buffer solutions can be precipitated or it can be lyophilized. The amount of each component can be varied to enable consistent, reproducible higher concentration saline or simple buffer formulations. The components can also be varied in order to increase the stability of modified RNA in the buffer solution over a period of time and/or under a variety of conditions. In one aspect, the present invention provides kits for protein production, comprising: a polynucleotide comprising a translatable region, provided in an amount effective to produce a desired amount of a protein encoded by the translatable region when introduced into a target cell; a second polynucleotide comprising an inhibitory nucleic acid, provided in an amount effective to substantially inhibit the innate immune response of the cell; and packaging and instructions.

In one aspect, the present invention provides kits for protein production, comprising a polynucleotide comprising a translatable region, wherein the polynucleotide exhibits reduced degradation by a cellular nuclease, and packaging and instructions.

In one aspect, the present invention provides kits for protein production, comprising a polynucleotide comprising a translatable region, wherein the polynucleotide exhibits reduced degradation by a cellular nuclease, and a mammalian cell suitable for translation of the translatable region of the first nucleic acid.

b. Devices

The present invention provides for devices that can incorporate polynucleotides that encode polypeptides of interest. These devices contain in a stable formulation the reagents to synthesize a polynucleotide in a formulation available to be immediately delivered to a subject in need thereof, such as a human patient Devices for administration can be employed to deliver the polynucleotides of the present invention according to single, multi- or split-dosing regimens taught herein. Such devices are taught in, for example, International Application Publ. No. WO2013151666, the contents of which are incorporated herein by reference in their entirety.

Method and devices known in the art for multi-administration to cells, organs and tissues are contemplated for use in conjunction with the methods and compositions disclosed herein as embodiments of the present invention. These include, for example, those methods and devices having multiple needles, hybrid devices employing for example lumens or catheters as well as devices utilizing heat, electric current or radiation driven mechanisms.

According to the present invention, these multi-administration devices can be utilized to deliver the single, multi- or split doses contemplated herein. Such devices are taught for example in, International Application Publ. No. WO2013151666, the contents of which are incorporated herein by reference in their entirety.

In some embodiments, the polynucleotide is administered subcutaneously or intramuscularly via at least 3 needles to three different, optionally adjacent, sites simultaneously, or within a 60 minutes period (e.g., administration to 4, 5, 6, 7, 8, 9, or 10 sites simultaneously or within a 60 minute period).

c. Methods and Devices Utilizing Catheters and/or Lumens

Methods and devices using catheters and lumens can be employed to administer the polynucleotides of the present invention on a single, multi- or split dosing schedule. Such methods and devices are described in International Application Publication No. WO2013151666, the contents of which are incorporated herein by reference in their entirety.

d. Methods and Devices Utilizing Electrical Current

Methods and devices utilizing electric current can be employed to deliver the polynucleotides of the present invention according to the single, multi- or split dosing regimens taught herein. Such methods and devices are described in International Application Publication No. WO2013151666, the contents of which are incorporated herein by reference in their entirety.

29. DEFINITIONS

In order that the present disclosure can be more readily understood, certain terms are first defined. As used in this application, except as otherwise expressly provided herein, each of the following terms shall have the meaning set forth below. Additional definitions are set forth throughout the application.

The invention includes embodiments in which exactly one member of the group is present in, employed in, or otherwise relevant to a given product or process. The invention includes embodiments in which more than one, or all of the group members are present in, employed in, or otherwise relevant to a given product or process.

In this specification and the appended claims, the singular forms "a", "an" and "the" include plural referents unless the context clearly dictates otherwise. The terms "a" (or "an"), as well as the terms "one or more," and "at least one" can be used interchangeably herein. In certain aspects, the term "a" or "an" means "single." In other aspects, the term "a" or "an" includes "two or more" or "multiple."

Furthermore, "and/or" where used herein is to be taken as specific disclosure of each of the two specified features or components with or without the other. Thus, the term "and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following aspects: A, B, and C; A, B, or C; A or C; A or B; B or C; A and C; A and B; B and C; A (alone); B (alone); and C (alone).

Unless defined otherwise, all technical and scientific terms used herein have the same meaning as commonly understood by one of ordinary skill in the art to which this disclosure is related. For example, the Concise Dictionary of Biomedicine and Molecular Biology, Juo, Pei-Show, 2nd ed., 2002, CRC Press; The Dictionary of Cell and Molecular Biology, 3rd ed., 1999, Academic Press; and the Oxford Dictionary Of Biochemistry And Molecular Biology, Revised, 2000, Oxford University Press, provide one of skill with a general dictionary of many of the terms used in this disclosure.

Wherever aspects are described herein with the language "comprising," otherwise analogous aspects described in terms of "consisting of" and/or "consisting essentially of" are also provided.

Units, prefixes, and symbols are denoted in their Systeme International de Unites (SI) accepted form. Numeric ranges are inclusive of the numbers defining the range. Where a range of values is recited, it is to be understood that each intervening integer value, and each fraction thereof, between the recited upper and lower limits of that range is also specifically disclosed, along with each subrange between such values. The upper and lower limits of any range can independently be included in or excluded from the range, and each range where either, neither or both limits are included is also encompassed within the invention. Where a value is explicitly recited, it is to be understood that values which are about the same quantity or amount as the recited value are also within the scope of the invention. Where a combination is disclosed, each subcombination of the elements of that combination is also specifically disclosed and is within the scope of the invention. Conversely, where different elements or groups of elements are individually disclosed, combinations thereof are also disclosed. Where any element of an invention is disclosed as having a plurality of alternatives, examples of that invention in which each alternative is excluded singly or in any combination with the other alternatives are also hereby disclosed; more than one element of an invention can have such exclusions, and all combinations of elements having such exclusions are hereby disclosed.

Nucleotides are referred to by their commonly accepted single-letter codes. Unless otherwise indicated, nucleic acids are written left to right in 5' to 3' orientation. Nucleobases are referred to herein by their commonly known one-letter symbols recommended by the IUPAC-IUB Biochemical Nomenclature Commission. Accordingly, A represents adenine, C represents cytosine, G represents guanine, T represents thymine, U represents uracil.

Amino acids are referred to herein by either their commonly known three letter symbols or by the one-letter symbols recommended by the IUPAC-IUB Biochemical Nomenclature Commission. Unless otherwise indicated, amino acid sequences are written left to right in amino to carboxy orientation.

About: The term "about" as used in connection with a numerical value throughout the specification and the claims denotes an interval of accuracy, familiar and acceptable to a person skilled in the art, such interval of accuracy is ±10%.

Where ranges are given, endpoints are included. Furthermore, unless otherwise indicated or otherwise evident from the context and understanding of one of ordinary skill in the art, values that are expressed as ranges can assume any specific value or subrange within the stated ranges in different embodiments of the invention, to the tenth of the unit of the lower limit of the range, unless the context clearly dictates otherwise.

Administered in combination: As used herein, the term "administered in combination" or "combined administration" means that two or more agents are administered to a subject at the same time or within an interval such that there can be an overlap of an effect of each agent on the patient. In some embodiments, they are administered within about 60, 30, 15, 10, 5, or 1 minute of one another. In some embodiments, the administrations of the agents are spaced sufficiently closely together such that a combinatorial (e.g., a synergistic) effect is achieved.

Amino acid substitution: The term "amino acid substitution" refers to replacing an amino acid residue present in a parent or reference sequence (e.g., a wild type GALT sequence) with another amino acid residue. An amino acid can be substituted in a parent or reference sequence (e.g., a wild type GALT polypeptide sequence), for example, via chemical peptide synthesis or through recombinant methods known in the art. Accordingly, a reference to a "substitution at position X" refers to the substitution of an amino acid present at position X with an alternative amino acid residue. In some aspects, substitution patterns can be described according to the schema AnY, wherein A is the single letter code corresponding to the amino acid naturally or originally present at position n, and Y is the substituting amino acid residue. In other aspects, substitution patterns can be described according to the schema An(YZ), wherein A is the single letter code corresponding to the amino acid residue substituting the amino acid naturally or originally present at position X, and Y and Z are alternative substituting amino acid residue.

In the context of the present disclosure, substitutions (even when they referred to as amino acid substitution) are conducted at the nucleic acid level, i.e., substituting an amino acid residue with an alternative amino acid residue is conducted by substituting the codon encoding the first amino acid with a codon encoding the second amino acid.

Animal: As used herein, the term "animal" refers to any member of the animal kingdom. In some embodiments, "animal" refers to humans at any stage of development. In some embodiments, "animal" refers to non-human animals at any stage of development. In certain embodiments, the non-human animal is a mammal (e.g., a rodent, a mouse, a rat, a rabbit, a monkey, a dog, a cat, a sheep, cattle, a primate, or a pig). In some embodiments, animals include, but are not limited to, mammals, birds, reptiles, amphibians, fish, and worms. In some embodiments, the animal is a transgenic animal, genetically-engineered animal, or a clone.

Approximately: As used herein, the term "approximately," as applied to one or more values of interest, refers to a value that is similar to a stated reference value. In certain embodiments, the term "approximately" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Associated with: As used herein with respect to a disease, the term "associated with" means that the symptom, measurement, characteristic, or status in question is linked to the diagnosis, development, presence, or progression of that disease. As association can, but need not, be causatively linked to the disease. For example, symptoms, sequelae, or any effects causing a decrease in the quality of life of a patient of Gal-1 are considered associated with Gal-1 and in some embodiments of the present invention can be treated, ameliorated, or prevented by administering the polynucleotides of the present invention to a subject in need thereof.

When used with respect to two or more moieties, the terms "associated with," "conjugated," "linked," "attached," and "tethered," when used with respect to two or more moieties, means that the moieties are physically associated or connected with one another, either directly or via one or more additional moieties that serves as a linking agent, to form a structure that is sufficiently stable so that the moieties remain physically associated under the conditions in which the structure is used, e.g., physiological conditions. An "association" need not be strictly through direct covalent chemical bonding. It can also suggest ionic or hydrogen bonding or a hybridization based connectivity sufficiently stable such that the "associated" entities remain physically associated.

Bifunctional: As used herein, the term "bifunctional" refers to any substance, molecule or moiety that is capable of or maintains at least two functions. The functions can affect the same outcome or a different outcome. The structure that produces the function can be the same or different. For example, bifunctional modified RNAs of the present invention can encode a GALT peptide (a first function) while those nucleosides that comprise the encoding RNA are, in and of themselves, capable of extending the half-life of the RNA (second function). In this example, delivery of the bifunctional modified RNA to a subject suffering from a protein deficiency would produce not only a peptide or protein molecule that can ameliorate or treat a disease or conditions, but would also maintain a population modified RNA present in the subject for a prolonged period of time. In other aspects, a bifunction modified mRNA can be a chimeric or quimeric molecule comprising, for example, an RNA encoding a GALT peptide (a first function) and a second protein either fused to first protein or co-expressed with the first protein.

Biocompatible: As used herein, the term "biocompatible" means compatible with living cells, tissues, organs or systems posing little to no risk of injury, toxicity or rejection by the immune system.

Biodegradable: As used herein, the term "biodegradable" means capable of being broken down into innocuous products by the action of living things.

Biologically active: As used herein, the phrase "biologically active" refers to a characteristic of any substance that has activity in a biological system and/or organism. For instance, a substance that, when administered to an organism, has a biological effect on that organism, is considered to be biologically active. In particular embodiments, a polynucleotide of the present invention can be considered biologically active if even a portion of the polynucleotide is biologically active or mimics an activity considered biologically relevant.

Chimera: As used herein, "chimera" is an entity having two or more incongruous or heterogeneous parts or regions. For example, a chimeric molecule can comprise a first part comprising a GALT polypeptide, and a second part (e.g., genetically fused to the first part) comprising a second therapeutic protein (e.g., a protein with a distinct enzymatic activity, an antigen binding moiety, or a moiety capable of extending the plasma half life of GALT, for example, an Fc region of an antibody).

Sequence Optimization: The term "sequence optimization" refers to a process or series of processes by which nucleobases in a reference nucleic acid sequence are replaced with alternative nucleobases, resulting in a nucleic acid sequence with improved properties, e.g., improved protein expression or decreased immunogenicity.

In general, the goal in sequence optimization is to produce a synonymous nucleotide sequence than encodes the same polypeptide sequence encoded by the reference nucleotide sequence. Thus, there are no amino acid substitutions (as a result of codon optimization) in the polypeptide encoded by the codon optimized nucleotide sequence with respect to the polypeptide encoded by the reference nucleotide sequence.

Codon substitution: The terms "codon substitution" or "codon replacement" in the context of sequence optimization refer to replacing a codon present in a reference nucleic acid sequence with another codon. A codon can be substituted in a reference nucleic acid sequence, for example, via chemical peptide synthesis or through recombinant methods known in the art. Accordingly, references to a "substitution" or "replacement" at a certain location in a nucleic acid sequence (e.g., an mRNA) or within a certain region or subsequence of a nucleic acid sequence (e.g., an mRNA) refer to the substitution of a codon at such location or region with an alternative codon.

As used herein, the terms "coding region" and "region encoding" and grammatical variants thereof, refer to an Open Reading Frame (ORF) in a polynucleotide that upon expression yields a polypeptide or protein.

Compound: As used herein, the term "compound," is meant to include all stereoisomers and isotopes of the structure depicted. As used herein, the term "stereoisomer" means any geometric isomer (e.g., cis- and trans-isomer), enantiomer, or diastereomer of a compound. The present disclosure encompasses any and all stereoisomers of the compounds described herein, including stereomerically pure forms (e.g., geometrically pure, enantiomerically pure, or diastereomerically pure) and enantiomeric and stereoisomeric mixtures, e.g., racemates. Enantiomeric and stereometric mixtures of compounds and means of resolving them into their component enantiomers or stereoisomers are well-known. "Isotopes" refers to atoms having the same atomic number but different mass numbers resulting from a different number of neutrons in the nuclei. For example, isotopes of hydrogen include tritium and deuterium. Further, a compound, salt, or complex of the present disclosure can be prepared in combination with solvent or water molecules to form solvates and hydrates by routine methods.

Contacting: As used herein, the term "contacting" means establishing a physical connection between two or more entities. For example, contacting a mammalian cell with a nanoparticle composition means that the mammalian cell and a nanoparticle are made to share a physical connection. Methods of contacting cells with external entities both in vivo and ex vivo are well known in the biological arts. For example, contacting a nanoparticle composition and a mammalian cell disposed within a mammal can be performed by varied routes of administration (e.g., intravenous, intramuscular, intradermal, and subcutaneous) and can involve varied amounts of nanoparticle compositions. Moreover, more than one mammalian cell can be contacted by a nanoparticle composition.

Conservative amino acid substitution: A "conservative amino acid substitution" is one in which the amino acid residue in a protein sequence is replaced with an amino acid residue having a similar side chain. Families of amino acid residues having similar side chains have been defined in the art, including basic side chains (e.g., lysine, arginine, or histidine), acidic side chains (e.g., aspartic acid or glutamic acid), uncharged polar side chains (e.g., glycine, asparagine, glutamine, serine, threonine, tyrosine, or cysteine), nonpolar side chains (e.g., alanine, valine, leucine, isoleucine, proline, phenylalanine, methionine, or tryptophan), beta-branched side chains (e.g., threonine, valine, isoleucine) and aromatic side chains (e.g., tyrosine, phenylalanine, tryptophan, or histidine). Thus, if an amino acid in a polypeptide is replaced with another amino acid from the same side chain family, the amino acid substitution is considered to be conservative. In another aspect, a string of amino acids can be conservatively replaced with a structurally similar string that differs in order and/or composition of side chain family members.

Non-conservative amino acid substitution: Non-conservative amino acid substitutions include those in which (i) a residue having an electropositive side chain (e.g., Arg, His or Lys) is substituted for, or by, an electronegative residue (e.g., Glu or Asp), (ii) a hydrophilic residue (e.g., Ser or Thr) is substituted for, or by, a hydrophobic residue (e.g., Ala, Leu, Ile, Phe or Val), (iii) a cysteine or proline is substituted for, or by, any other residue, or (iv) a residue having a bulky hydrophobic or aromatic side chain (e.g., Val, His, Ile or Trp) is substituted for, or by, one having a smaller side chain (e.g., Ala or Ser) or no side chain (e.g., Gly).

Other amino acid substitutions can be readily identified by workers of ordinary skill. For example, for the amino acid alanine, a substitution can be taken from any one of D-alanine, glycine, beta-alanine, L-cysteine and D-cysteine. For lysine, a replacement can be any one of D-lysine, arginine, D-arginine, homo-arginine, methionine, D-methionine, ornithine, or D-ornithine. Generally, substitutions in functionally important regions that can be expected to induce changes in the properties of isolated polypeptides are those in which (i) a polar residue, e.g., serine or threonine, is substituted for (or by) a hydrophobic residue, e.g., leucine, isoleucine, phenylalanine, or alanine; (ii) a cysteine residue is substituted for (or by) any other residue; (iii) a residue having an electropositive side chain, e.g., lysine, arginine or histidine, is substituted for (or by) a residue having an electronegative side chain, e.g., glutamic acid or aspartic acid; or (iv) a residue having a bulky side chain, e.g., phenylalanine, is substituted for (or by) one not having such a side chain, e.g., glycine. The likelihood that one of the foregoing non-conservative substitutions can alter functional properties of the protein is also correlated to the position of the substitution with respect to functionally important regions of the protein: some non-conservative substitutions can accordingly have little or no effect on biological properties.

Conserved: As used herein, the term "conserved" refers to nucleotides or amino acid residues of a polynucleotide sequence or polypeptide sequence, respectively, that are those that occur unaltered in the same position of two or more sequences being compared. Nucleotides or amino acids that are relatively conserved are those that are conserved amongst more related sequences than nucleotides or amino acids appearing elsewhere in the sequences.

In some embodiments, two or more sequences are said to be "completely conserved" if they are 100% identical to one another. In some embodiments, two or more sequences are said to be "highly conserved" if they are at least 70% identical, at least 80% identical, at least 90% identical, or at least 95% identical to one another. In some embodiments, two or more sequences are said to be "highly conserved" if they are about 70% identical, about 80% identical, about 90% identical, about 95%, about 98%, or about 99% identical to one another. In some embodiments, two or more sequences are said to be "conserved" if they are at least 30% identical, at least 40% identical, at least 50% identical, at least 60% identical, at least 70% identical, at least 80% identical, at least 90% identical, or at least 95% identical to one another. In some embodiments, two or more sequences are said to be "conserved" if they are about 30% identical, about 40% identical, about 50% identical, about 60% identical, about 70% identical, about 80% identical, about 90% identical, about 95% identical, about 98% identical, or about 99% identical to one another. Conservation of sequence can apply to the entire length of an polynucleotide or polypeptide or can apply to a portion, region or feature thereof.

Controlled Release: As used herein, the term "controlled release" refers to a pharmaceutical composition or compound release profile that conforms to a particular pattern of release to effect a therapeutic outcome.

Cyclic or Cyclized: As used herein, the term "cyclic" refers to the presence of a continuous loop. Cyclic molecules need not be circular, only joined to form an unbroken chain of subunits. Cyclic molecules such as the engineered RNA or mRNA of the present invention can be single units or multimers or comprise one or more components of a complex or higher order structure.

Cytotoxic: As used herein, "cytotoxic" refers to killing or causing injurious, toxic, or deadly effect on a cell (e.g., a mammalian cell (e.g., a human cell)), bacterium, virus, fungus, protozoan, parasite, prion, or a combination thereof.

Delivering: As used herein, the term "delivering" means providing an entity to a destination. For example, delivering a polynucleotide to a subject can involve administering a nanoparticle composition including the polynucleotide to the subject (e.g., by an intravenous, intramuscular, intradermal, or subcutaneous route). Administration of a nanoparticle composition to a mammal or mammalian cell can involve contacting one or more cells with the nanoparticle composition.

Delivery Agent: As used herein, "delivery agent" refers to any substance that facilitates, at least in part, the in vivo, in vitro, or ex vivo delivery of a polynucleotide to targeted cells.

Destabilized: As used herein, the term "destable," "destabilize," or "destabilizing region" means a region or molecule that is less stable than a starting, wild-type or native form of the same region or molecule.

Diastereomer: As used herein, the term "diastereomer," means stereoisomers that are not mirror images of one another and are non-superimposable on one another.

Digest: As used herein, the term "digest" means to break apart into smaller pieces or components. When referring to polypeptides or proteins, digestion results in the production of peptides.

Distal: As used herein, the term "distal" means situated away from the center or away from a point or region of interest.

Domain: As used herein, when referring to polypeptides, the term "domain" refers to a motif of a polypeptide having one or more identifiable structural or functional characteristics or properties (e.g., binding capacity, serving as a site for protein-protein interactions).

Dosing regimen: As used herein, a "dosing regimen" or a "dosing regimen" is a schedule of administration or physician determined regimen of treatment, prophylaxis, or palliative care.

Effective Amount: As used herein, the term "effective amount" of an agent is that amount sufficient to effect beneficial or desired results, for example, clinical results, and, as such, an "effective amount" depends upon the context in which it is being applied. For example, in the context of administering an agent that treats a protein deficiency (e.g., a GALT deficiency), an effective amount of an agent is, for example, an amount of mRNA expressing sufficient GALT to ameliorate, reduce, eliminate, or prevent the symptoms associated with the GALT deficiency, as compared to the severity of the symptom observed without administration of the agent. The term "effective amount" can be used interchangeably with "effective dose," "therapeutically effective amount," or "therapeutically effective dose."

Enantiomer: As used herein, the term "enantiomer" means each individual optically active form of a compound of the invention, having an optical purity or enantiomeric excess (as determined by methods standard in the art) of at least 80% (i.e., at least 90% of one enantiomer and at most 10% of the other enantiomer), at least 90%, or at least 98%.

Encapsulate: As used herein, the term "encapsulate" means to enclose, surround or encase.

Encapsulation Efficiency: As used herein, "encapsulation efficiency" refers to the amount of a polynucleotide that becomes part of a nanoparticle composition, relative to the initial total amount of polynucleotide used in the preparation of a nanoparticle composition. For example, if 97 mg of polynucleotide are encapsulated in a nanoparticle composition out of a total 100 mg of polynucleotide initially provided to the composition, the encapsulation efficiency can be given as 97%. As used herein, "encapsulation" can refer to complete, substantial, or partial enclosure, confinement, surrounding, or encasement.

Encoded protein cleavage signal: As used herein, "encoded protein cleavage signal" refers to the nucleotide sequence that encodes a protein cleavage signal.

Engineered: As used herein, embodiments of the invention are "engineered" when they are designed to have a feature or property, whether structural or chemical, that varies from a starting point, wild type or native molecule.

Enhanced Delivery: As used herein, the term "enhanced delivery" means delivery of more (e.g., at least 1.5 fold more, at least 2-fold more, at least 3-fold more, at least 4-fold more, at least 5-fold more, at least 6-fold more, at least 7-fold more, at least 8-fold more, at least 9-fold more, at least 10-fold more) of a polynucleotide by a nanoparticle to a target tissue of interest (e.g., mammalian liver) compared to the level of delivery of a polynucleotide by a control nanoparticle to a target tissue of interest (e.g., MC3, KC2, or DLinDMA). The level of delivery of a nanoparticle to a particular tissue can be measured by comparing the amount of protein produced in a tissue to the weight of said tissue, comparing the amount of polynucleotide in a tissue to the weight of said tissue, comparing the amount of protein produced in a tissue to the amount of total protein in said tissue, or comparing the amount of polynucleotide in a tissue to the amount of total polynucleotide in said tissue. It will be understood that the enhanced delivery of a nanoparticle to a target tissue need not be determined in a subject being treated, it can be determined in a surrogate such as an animal model (e.g., a rat model).

Exosome: As used herein, "exosome" is a vesicle secreted by mammalian cells or a complex involved in RNA degradation.

Expression: As used herein, "expression" of a nucleic acid sequence refers to one or more of the following events: (1) production of an mRNA template from a DNA sequence (e.g., by transcription); (2) processing of an mRNA transcript (e.g., by splicing, editing, 5' cap formation, and/or 3' end processing); (3) translation of an mRNA into a polypeptide or protein; and (4) post-translational modification of a polypeptide or protein.

Ex Vivo: As used herein, the term "ex vivo" refers to events that occur outside of an organism (e.g., animal, plant, or microbe or cell or tissue thereof). Ex vivo events can take place in an environment minimally altered from a natural (e.g., in vivo) environment.

Feature: As used herein, a "feature" refers to a characteristic, a property, or a distinctive element. When referring to polypeptides, "features" are defined as distinct amino acid sequence-based components of a molecule. Features of the polypeptides encoded by the polynucleotides of the present invention include surface manifestations, local conformational shape, folds, loops, half-loops, domains, half-domains, sites, termini or any combination thereof.

Formulation: As used herein, a "formulation" includes at least a polynucleotide and one or more of a carrier, an excipient, and a delivery agent.

Fragment: A "fragment," as used herein, refers to a portion. For example, fragments of proteins can comprise polypeptides obtained by digesting full-length protein isolated from cultured cells. In some embodiments, a fragment is a subsequences of a full length protein (e.g., GALT) wherein N-terminal, and/or C-terminal, and/or internal subsequences have been deleted. In some preferred aspects of the present invention, the fragments of a protein of the present invention are functional fragments.

Functional: As used herein, a "functional" biological molecule is a biological molecule in a form in which it exhibits a property and/or activity by which it is characterized. Thus, a functional fragment of a polynucleotide of the present invention is a polynucleotide capable of expressing a functional GALT fragment. As used herein, a functional fragment of GALT refers to a fragment of wild type GALT (i.e., a fragment of any of its naturally occurring isoforms), or a mutant or variant thereof, wherein the fragment retains a least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, or at least about 95% of the biological activity of the corresponding full length protein.

GALT Associated Disease: As use herein the terms "GALT-associated disease" or

"GALT-associated disorder" refer to diseases or disorders, respectively, which result from aberrant GALT activity (e.g., decreased activity or increased activity). As a non-limiting example, galactosemia type 1 is a GALT associated disease. Numerous clinical variants of galactosemia type 1 are know in the art. See, e.g., http://omim.org/entry/606999.

The terms "GALT enzymatic activity," "GALT activity," "UDP-glucose-hexose-1-phosphate uridylyltransferase activity," and "Gal-1-P Uridylyltransferase activity" are used interchangeably in the present disclosure and refer to GALT's ability to convert UDP-glucose and galactose-1-phosphate to glucose-1-phosphate and UDP-galactose as part of the Leloir pathway. Accordingly, a fragment or variant retaining or having GALT enzymatic activity or GALT activity refers to a fragment or variant that has measurable enzymatic activity in catalyzing the convsion of UDP-glucose and galactose-1-phosphate to glucose-1-phosphate and UDP-galactose.

Helper Lipid: As used herein, the term "helper lipid" refers to a compound or molecule that includes a lipidic moiety (for insertion into a lipid layer, e.g., lipid bilayer) and a polar moiety (for interaction with physiologic solution at the surface of the lipid layer). Typically the helper lipid is a phospholipid. A function of the helper lipid is to "complement" the amino lipid and increase the fusogenicity of the bilayer and/or to help facilitate endosomal escape, e.g., of nucleic acid delivered to cells. Helper lipids are also believed to be a key structural component to the surface of the LNP.

Homology: As used herein, the term "homology" refers to the overall relatedness between polymeric molecules, e.g. between nucleic acid molecules (e.g. DNA molecules and/or RNA molecules) and/or between polypeptide molecules. Generally, the term "homology" implies an evolutionary relationship between two molecules. Thus, two molecules that are homologous will have a common evolutionary ancestor. In the context of the present invention, the term homology encompasses both to identity and similarity.

In some embodiments, polymeric molecules are considered to be "homologous" to one another if at least 25%, 30%, 35%, 40%, 45%, 50%, 55%, 60%, 65%, 70%, 75%, 80%, 85%, 90%, 95%, or 99% of the monomers in the molecule are identical (exactly the same monomer) or are similar (conservative substitutions). The term "homologous" necessarily refers to a comparison between at least two sequences (polynucleotide or polypeptide sequences).

Identity: As used herein, the term "identity" refers to the overall monomer conservation between polymeric molecules, e.g., between polynucleotide molecules (e.g. DNA molecules and/or RNA molecules) and/or between polypeptide molecules. Calculation of the percent identity of two polynucleotide sequences, for example, can be performed by aligning the two sequences for optimal comparison purposes (e.g., gaps can be introduced in one or both of a first and a second nucleic acid sequences for optimal alignment and non-identical sequences can be disregarded for comparison purposes). In certain embodiments, the length of a sequence aligned for comparison purposes is at least 30%, at least 40%, at least 50%, at least 60%, at least 70%, at least 80%, at least 90%, at least 95%, or 100% of the length of the reference sequence. The nucleotides at corresponding nucleotide positions are then compared. When a position in the first sequence is occupied by the same nucleotide as the corresponding position in the second sequence, then the molecules are identical at that position. The percent identity between the two sequences is a function of the number of identical positions shared by the sequences, taking into account the number of gaps, and the length of each gap, which needs to be introduced for optimal alignment of the two sequences. The comparison of sequences and determination of percent identity between two sequences can be accomplished using a mathematical algorithm. When comparing DNA and RNA, thymine (T) and uracil (U) can be considered equivalent.

Suitable software programs are available from various sources, and for alignment of both protein and nucleotide sequences. One suitable program to determine percent sequence identity is bl2seq, part of the BLAST suite of program available from the U.S. government's National Center for Biotechnology Information BLAST web site (blast.ncbi.nlm.nih.gov). Bl2seq performs a comparison between two sequences using either the BLASTN or BLASTP algorithm. BLASTN is used to compare nucleic acid sequences, while BLASTP is used to compare amino acid sequences. Other suitable programs are, e.g., Needle, Stretcher, Water, or Matcher, part of the EMBOSS suite of bioinformatics programs and also available from the European Bioinformatics Institute (EBI) at www.ebi.ac.uk/Tools/psa.

Sequence alignments can be conducted using methods known in the art such as MAFFT, Clustal (ClustalW, Clustal X or Clustal Omega), MUSCLE, etc.

Different regions within a single polynucleotide or polypeptide target sequence that aligns with a polynucleotide or polypeptide reference sequence can each have their own percent sequence identity. It is noted that the percent sequence identity value is rounded to the nearest tenth. For example, 80.11, 80.12, 80.13, and 80.14 are rounded down to 80.1, while 80.15, 80.16, 80.17, 80.18, and 80.19 are rounded up to 80.2. It also is noted that the length value will always be an integer.

In certain aspects, the percentage identity "% ID" of a first amino acid sequence (or nucleic acid sequence) to a second amino acid sequence (or nucleic acid sequence) is calculated as % ID=100×(Y/Z), where Y is the number of amino acid residues (or nucleobases) scored as identical matches in the alignment of the first and second sequences (as aligned by visual inspection or a particular sequence alignment program) and Z is the total number of residues in the second sequence. If the length of a first sequence is longer than the second sequence, the percent identity of the first sequence to the second sequence will be higher than the percent identity of the second sequence to the first sequence.

One skilled in the art will appreciate that the generation of a sequence alignment for the calculation of a percent sequence identity is not limited to binary sequence-sequence comparisons exclusively driven by primary sequence data. It will also be appreciated that sequence alignments can be generated by integrating sequence data with data from heterogeneous sources such as structural data (e.g., crystallographic protein structures), functional data (e.g., location of mutations), or phylogenetic data. A suitable program that integrates heterogeneous data to generate a multiple sequence alignment is T-Coffee, available at www.tcoffee.org, and alternatively available, e.g., from the EBI. It will also be appreciated that the final alignment used to calculate percent sequence identity can be curated either automatically or manually.

Immune response: The term "immune response" refers to the action of, for example, lymphocytes, antigen presenting cells, phagocytic cells, granulocytes, and soluble macromolecules produced by the above cells or the liver (including antibodies, cytokines, and complement) that results in selective damage to, destruction of, or elimination from the human body of invading pathogens, cells or tissues infected with pathogens, cancerous cells, or, in cases of autoimmunity or pathological inflammation, normal human cells or tissues. In some cases, the administration of a nanoparticle comprising a lipid component and an encapsulated therapeutic agent can trigger an immune response, which can be caused by (i) the encapsulated therapeutic agent (e.g., an mRNA), (ii) the expression product of such encapsulated therapeutic agent (e.g., a polypeptide encoded by the mRNA), (iii) the lipid component of the nanoparticle, or (iv) a combination thereof.

Inflammatory response: "Inflammatory response" refers to immune responses involving specific and non-specific defense systems. A specific defense system reaction is a specific immune system reaction to an antigen. Examples of specific defense system reactions include antibody responses. A non-specific defense system reaction is an inflammatory response mediated by leukocytes generally incapable of immunological memory, e.g., macrophages, eosinophils and neutrophils. In some aspects, an immune response includes the secretion of inflammatory cytokines, resulting in elevated inflammatory cytokine levels.

Inflammatory cytokines: The term "inflammatory cytokine" refers to cytokines that are elevated in an inflammatory response. Examples of inflammatory cytokines include interleukin-6 (IL-6), CXCL1 (chemokine (C-X-C motif) ligand 1; also known as GROα, interferon-γ (IFNγ), tumor necrosis factor α (TNFα), interferon γ-induced protein 10 (IP-10), or granulocyte-colony stimulating factor (G-CSF). The term inflammatory cytokines includes also other cytokines associated with inflammatory responses known in the art, e.g., interleukin-1 (IL-1), interleukin-8 (IL-8), interleukin-12 (IL-12), interleukin-13 (Il-13), interferon α (IFN-α), etc.

In Vitro: As used herein, the term "in vitro" refers to events that occur in an artificial environment, e.g., in a test tube or reaction vessel, in cell culture, in a Petri dish, etc., rather than within an organism (e.g., animal, plant, or microbe).

In Vivo: As used herein, the term "in vivo" refers to events that occur within an organism (e.g., animal, plant, or microbe or cell or tissue thereof).

Insertional and deletional variants: "Insertional variants" when referring to polypeptides are those with one or more amino acids inserted immediately adjacent to an amino acid at a particular position in a native or starting sequence. "Immediately adjacent" to an amino acid means connected to either the alpha-carboxy or alpha-amino functional group of the amino acid. "Deletional variants" when referring to polypeptides are those with one or more amino acids in the native or starting amino acid sequence removed. Ordinarily, deletional variants will have one or more amino acids deleted in a particular region of the molecule.

Intact: As used herein, in the context of a polypeptide, the term "intact" means retaining an amino acid corresponding to the wild type protein, e.g., not mutating or substituting the wild type amino acid. Conversely, in the context of a nucleic acid, the term "intact" means retaining a nucleobase corresponding to the wild type nucleic acid, e.g., not mutating or substituting the wild type nucleobase.

Ionizable amino lipid: The term "ionizable amino lipid" includes those lipids having one, two, three, or more fatty acid or fatty alkyl chains and a pH-titratable amino head group (e.g., an alkylamino or dialkylamino head group). An ionizable amino lipid is typically protonated (i.e., positively charged) at a pH below the pKa of the amino head group and is substantially not charged at a pH above the pKa. Such ionizable amino lipids include, but are not limited to DLin-MC3-DMA (MC3) and (13Z,165Z)—N,N-dimethyl-3-nonydocosa-13-16-dien-1-amine (L608).

Isolated: As used herein, the term "isolated" refers to a substance or entity that has been separated from at least some of the components with which it was associated (whether in nature or in an experimental setting). Isolated substances (e.g., polynucleotides or polypeptides) can have varying levels of purity in reference to the substances from which they have been isolated. Isolated substances and/or entities can be separated from at least about 10%, about 20%, about 30%, about 40%, about 50%, about 60%, about 70%, about 80%, about 90%, or more of the other components with which they were initially associated. In some embodiments, isolated substances are more than about 80%, about 85%, about 90%, about 91%, about 92%, about 93%, about 94%, about 95%, about 96%, about 97%, about 98%, about 99%, or more than about 99% pure. As used herein, a substance is "pure" if it is substantially free of other components.

Substantially isolated: By "substantially isolated" is meant that the compound is substantially separated from the environment in which it was formed or detected. Partial separation can include, for example, a composition enriched in the compound of the present disclosure. Substantial separation can include compositions containing at least about 50%, at least about 60%, at least about 70%, at least about 80%, at least about 90%, at least about 95%, at least about 97%, or at least about 99% by weight of the compound of the present disclosure, or salt thereof.

A polynucleotide, vector, polypeptide, cell, or any composition disclosed herein which is "isolated" is a polynucleotide, vector, polypeptide, cell, or composition which is in a form not found in nature. Isolated polynucleotides, vectors, polypeptides, or compositions include those which have been purified to a degree that they are no longer in a form in which they are found in nature. In some aspects, a polynucleotide, vector, polypeptide, or composition which is isolated is substantially pure.

Isomer: As used herein, the term "isomer" means any tautomer, stereoisomer, enantiomer, or diastereomer of any compound of the invention. It is recognized that the compounds of the invention can have one or more chiral centers and/or double bonds and, therefore, exist as stereoisomers, such as double-bond isomers (i.e., geometric E/Z isomers) or diastereomers (e.g., enantiomers (i.e., (+) or (−)) or cis/trans isomers). According to the invention, the chemical structures depicted herein, and therefore the compounds of the invention, encompass all of the corresponding stereoisomers, that is, both the stereomerically pure form (e.g., geometrically pure, enantiomerically pure, or diastereomerically pure) and enantiomeric and stereoisomeric mixtures, e.g., racemates. Enantiomeric and stereoisomeric mixtures of compounds of the invention can typically be resolved into their component enantiomers or stereoisomers by well-known methods, such as chiral-phase gas chromatography, chiral-phase high performance liquid chromatography, crystallizing the compound as a chiral salt complex, or crystallizing the compound in a chiral solvent. Enantiomers and stereoisomers can also be obtained from stereomerically or enantiomerically pure intermediates, reagents, and catalysts by well-known asymmetric synthetic methods.

Linker: As used herein, a "linker" refers to a group of atoms, e.g., 10-1,000 atoms, and can be comprised of the atoms or groups such as, but not limited to, carbon, amino, alkylamino, oxygen, sulfur, sulfoxide, sulfonyl, carbonyl, and imine. The linker can be attached to a modified nucleoside or nucleotide on the nucleobase or sugar moiety at a first end, and to a payload, e.g., a detectable or therapeutic agent, at a second end. The linker can be of sufficient length as to not interfere with incorporation into a nucleic acid sequence. The linker can be used for any useful purpose, such as to form polynucleotide multimers (e.g., through linkage of two or more chimeric polynucleotides molecules or IVT polynucleotides) or polynucleotides conjugates, as well as to administer a payload, as described herein. Examples of chemical groups that can be incorporated into the linker include, but are not limited to, alkyl, alkenyl, alkynyl, amido, amino, ether, thioether, ester, alkylene, heteroalkylene, aryl, or heterocyclyl, each of which can be optionally substituted, as described herein. Examples of linkers include, but are not limited to, unsaturated alkanes, polyethylene glycols (e.g., ethylene or propylene glycol monomeric units, e.g., diethylene glycol, dipropylene glycol, triethylene glycol, tripropylene glycol, tetraethylene glycol, or tetraethylene glycol), and dextran polymers and derivatives thereof, Other examples include, but are not limited to, cleavable moieties within the linker, such as, for example, a disulfide bond (—S—S—) or an azo bond (—N═N—), which can be cleaved using a reducing agent or photolysis. Non-limiting examples of a selectively cleavable bond include an amido bond can be cleaved for example by the use of tris(2-carboxyethyl)phosphine (TCEP), or other reducing agents, and/or photolysis, as well as an ester bond can be cleaved for example by acidic or basic hydrolysis.

Methods of Administration: As used herein, "methods of administration" can include intravenous, intramuscular, intradermal, subcutaneous, or other methods of delivering a composition to a subject. A method of administration can be selected to target delivery (e.g., to specifically deliver) to a specific region or system of a body.

Modified: As used herein "modified" refers to a changed state or structure of a molecule of the invention. Molecules can be modified in many ways including chemically, structurally, and functionally. In some embodiments, the mRNA molecules of the present invention are modified by the introduction of non-natural nucleosides and/or nucleotides, e.g., as it relates to the natural ribonucleotides A, U, G, and C. Noncanonical nucleotides such as the cap structures are not considered "modified" although they differ from the chemical structure of the A, C, G, U ribonucleotides.

Mucus: As used herein, "mucus" refers to the natural substance that is viscous and comprises mucin glycoproteins.

Nanoparticle Composition: As used herein, a "nanoparticle composition" is a composition comprising one or more lipids. Nanoparticle compositions are typically sized on the order of micrometers or smaller and can include a lipid bilayer. Nanoparticle compositions encompass lipid nanoparticles (LNPs), liposomes (e.g., lipid vesicles), and lipoplexes. For example, a nanoparticle composition can be a liposome having a lipid bilayer with a diameter of 500 nm or less.

Naturally occurring: As used herein, "naturally occurring" means existing in nature without artificial aid.

Non-human vertebrate: As used herein, a "non-human vertebrate" includes all vertebrates except *Homo sapiens*, including wild and domesticated species. Examples of non-human vertebrates include, but are not limited to, mammals, such as alpaca, banteng, bison, camel, cat, cattle, deer, dog, donkey, gayal, goat, guinea pig, horse, llama, mule, pig, rabbit, reindeer, sheep water buffalo, and yak.

Nucleic acid sequence: The terms "nucleic acid sequence," "nucleotide sequence," or "polynucleotide sequence" are used interchangeably and refer to a contiguous nucleic acid sequence. The sequence can be either single stranded or double stranded DNA or RNA, e.g., an mRNA.

The term "nucleic acid," in its broadest sense, includes any compound and/or substance that comprises a polymer of nucleotides. These polymers are often referred to as polynucleotides. Exemplary nucleic acids or polynucleotides of the invention include, but are not limited to, ribonucleic acids (RNAs), deoxyribonucleic acids (DNAs), threose nucleic acids (TNAs), glycol nucleic acids (GNAs), peptide nucleic acids (PNAs), locked nucleic acids (LNAs, including LNA having a β-D-ribo configuration, α-LNA having an α-L-ribo configuration (a diastereomer of LNA), 2'-amino-LNA having a 2'-amino functionalization, and 2'-amino-α-LNA having a 2'-amino functionalization), ethylene nucleic acids (ENA), cyclohexenyl nucleic acids (CeNA) or hybrids or combinations thereof.

The phrase "nucleotide sequence encoding" refers to the nucleic acid (e.g., an mRNA or DNA molecule) coding sequence which encodes a polypeptide. The coding sequence can further include initiation and termination signals operably linked to regulatory elements including a promoter and polyadenylation signal capable of directing expression in the cells of an individual or mammal to which the nucleic acid is administered. The coding sequence can further include sequences that encode signal peptides.

Off-target: As used herein, "off target" refers to any unintended effect on any one or more target, gene, or cellular transcript.

Open reading frame: As used herein, "open reading frame" or "ORF" refers to a sequence which does not contain a stop codon in a given reading frame.

Operably linked: As used herein, the phrase "operably linked" refers to a functional connection between two or more molecules, constructs, transcripts, entities, moieties or the like.

Optionally substituted: Herein a phrase of the form "optionally substituted X" (e.g., optionally substituted alkyl) is intended to be equivalent to "X, wherein X is optionally substituted" (e.g., "alkyl, wherein said alkyl is optionally substituted"). It is not intended to mean that the feature "X" (e.g., alkyl) per se is optional.

Part: As used herein, a "part" or "region" of a polynucleotide is defined as any portion of the polynucleotide that is less than the entire length of the polynucleotide.

Patient: As used herein, "patient" refers to a subject who can seek or be in need of treatment, requires treatment, is receiving treatment, will receive treatment, or a subject who is under care by a trained professional for a particular disease or condition. In some embodiments, the treatment is needed, required, or received to prevent or decrease the risk of developing acute disease, i.e., it is a prophylactic treatment.

Pharmaceutically acceptable: The phrase "pharmaceutically acceptable" is employed herein to refer to those compounds, materials, compositions, and/or dosage forms that are, within the scope of sound medical judgment, suitable for use in contact with the tissues of human beings and animals without excessive toxicity, irritation, allergic response, or other problem or complication, commensurate with a reasonable benefit/risk ratio.

Pharmaceutically acceptable excipients: The phrase "pharmaceutically acceptable excipient," as used herein, refers any ingredient other than the compounds described herein (for example, a vehicle capable of suspending or dissolving the active compound) and having the properties of being substantially nontoxic and non-inflammatory in a patient. Excipients can include, for example: antiadherents, antioxidants, binders, coatings, compression aids, disintegrants, dyes (colors), emollients, emulsifiers, fillers (diluents), film formers or coatings, flavors, fragrances, glidants (flow enhancers), lubricants, preservatives, printing inks, sorbents, suspending or dispersing agents, sweeteners, and waters of hydration. Exemplary excipients include, but are not limited to: butylated hydroxytoluene (BHT), calcium carbonate, calcium phosphate (dibasic), calcium stearate, croscarmellose, crosslinked polyvinyl pyrrolidone, citric acid, crospovidone, cysteine, ethylcellulose, gelatin, hydroxypropyl cellulose, hydroxypropyl methylcellulose, lactose, magnesium stearate, maltitol, mannitol, methionine, methylcellulose, methyl paraben, microcrystalline cellulose, polyethylene glycol, polyvinyl pyrrolidone, povidone, pregelatinized starch, propyl paraben, retinyl palmitate, shellac, silicon dioxide, sodium carboxymethyl cellulose, sodium citrate, sodium starch glycolate, sorbitol, starch (corn), stearic acid, sucrose, talc, titanium dioxide, vitamin A, vitamin E, vitamin C, and xylitol.

Pharmaceutically acceptable salts: The present disclosure also includes pharmaceutically acceptable salts of the compounds described herein. As used herein, "pharmaceutically acceptable salts" refers to derivatives of the disclosed compounds wherein the parent compound is modified by converting an existing acid or base moiety to its salt form (e.g., by reacting the free base group with a suitable organic acid). Examples of pharmaceutically acceptable salts include, but are not limited to, mineral or organic acid salts of basic residues such as amines; alkali or organic salts of acidic residues such as carboxylic acids; and the like. Representative acid addition salts include acetate, acetic acid, adipate, alginate, ascorbate, aspartate, benzenesulfonate, benzene sulfonic acid, benzoate, bisulfate, borate, butyrate, camphorate, camphorsulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, valerate salts, and the like. Representative alkali or alkaline earth metal salts include sodium, lithium, potassium, calcium, magnesium, and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine, and the like. The pharmaceutically acceptable salts of the present disclosure include the conventional non-toxic salts of the parent compound formed, for example, from non-toxic inorganic or organic acids. The pharmaceutically acceptable salts of the present disclosure can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are used. Lists of suitable salts are found in *Remington's Pharmaceutical Sciences,* 17th ed., Mack Publishing Company, Easton, Pa., 1985, p. 1418, *Pharmaceutical Salts: Properties, Selection, and Use*, P. H. Stahl and C. G. Wermuth (eds.), Wiley-VCH, 2008, and Berge et al., *Journal of Pharmaceutical Science,* 66, 1-19 (1977), each of which is incorporated herein by reference in its entirety.

Pharmaceutically acceptable solvate: The term "pharmaceutically acceptable solvate," as used herein, means a compound of the invention wherein molecules of a suitable solvent are incorporated in the crystal lattice. A suitable solvent is physiologically tolerable at the dosage administered. For example, solvates can be prepared by crystallization, recrystallization, or precipitation from a solution that includes organic solvents, water, or a mixture thereof. Examples of suitable solvents are ethanol, water (for example, mono-, di-, and tri-hydrates), N-methylpyrrolidinone (NMP), dimethyl sulfoxide (DMSO), N,N'-dimethylformamide (DMF), N,N'-dimethylacetamide (DMAC), 1,3-dimethyl-2-imidazolidinone (DMEU), 1,3-dimethyl-3,4,5,6-tetrahydro-2-(1H)-pyrimidinone (DMPU), acetonitrile (ACN), propylene glycol, ethyl acetate, benzyl alcohol, 2-pyrrolidone, benzyl benzoate, and the like. When water is the solvent, the solvate is referred to as a "hydrate."

Pharmacokinetic: As used herein, "pharmacokinetic" refers to any one or more properties of a molecule or compound as it relates to the determination of the fate of substances administered to a living organism. Pharmacokinetics is divided into several areas including the extent and rate of absorption, distribution, metabolism and excretion. This is commonly referred to as ADME where: (A) Absorption is the process of a substance entering the blood circulation; (D) Distribution is the dispersion or dissemination of substances throughout the fluids and tissues of the body; (M) Metabolism (or Biotransformation) is the irreversible transformation of parent compounds into daughter metabolites; and (E) Excretion (or Elimination) refers to the elimination of the substances from the body. In rare cases, some drugs irreversibly accumulate in body tissue.

Physicochemical: As used herein, "physicochemical" means of or relating to a physical and/or chemical property.

Polynucleotide: The term "polynucleotide" as used herein refers to polymers of nucleotides of any length, including ribonucleotides, deoxyribonucleotides, analogs thereof, or mixtures thereof. This term refers to the primary structure of the molecule. Thus, the term includes triple-, double- and single-stranded deoxyribonucleic acid ("DNA"), as well as triple-, double- and single-stranded ribonucleic acid ("RNA"). It also includes modified, for example by alkylation, and/or by capping, and unmodified forms of the polynucleotide. More particularly, the term "polynucleotide" includes polydeoxyribonucleotides (containing 2-deoxy-D-ribose), polyribonucleotides (containing D-ribose), including tRNA, rRNA, hRNA, siRNA and mRNA, whether spliced or unspliced, any other type of polynucleotide which is an N- or C-glycoside of a purine or pyrimidine base, and other polymers containing normucleotidic backbones, for example, polyamide (e.g., peptide nucleic acids "PNAs") and polymorpholino polymers, and other synthetic sequence-specific nucleic acid polymers providing that the polymers contain nucleobases in a configuration which allows for base pairing and base stacking, such as is found in DNA and RNA. In particular aspects, the polynucleotide comprises an mRNA. In other aspect, the mRNA is a synthetic mRNA. In some aspects, the synthetic mRNA comprises at least one unnatural nucleobase. In some aspects, all nucleobases of a certain class have been replaced with unnatural nucleobases (e.g., all uridines in a polynucleotide disclosed herein can be replaced with an unnatural nucleobase, e.g., 5-methoxyuridine). In some aspects, the polynucleotide (e.g., a synthetic RNA or a synthetic DNA) comprises only natural nucleobases, i.e., A (adenosine), G (guanosine), C (cytidine), and T (thymidine) in the case of a synthetic DNA, or A, C, G, and U (uridine) in the case of a synthetic RNA.

The skilled artisan will appreciate that the T bases in the codon maps disclosed herein are present in DNA, whereas the T bases would be replaced by U bases in corresponding RNAs. For example, a codon-nucleotide sequence disclosed herein in DNA form, e.g., a vector or an in-vitro translation (IVT) template, would have its T bases transcribed as U based in its corresponding transcribed mRNA. In this respect, both codon-optimized DNA sequences (comprising T) and their corresponding mRNA sequences (comprising U) are considered codon-optimized nucleotide sequence of the present invention. A skilled artisan would also understand that equivalent codon-maps can be generated by replaced one or more bases with non-natural bases. Thus, e.g., a TTC codon (DNA map) would correspond to a UUC codon (RNA map), which in turn would correspond to a ΨΨC codon (RNA map in which U has been replaced with pseudouridine).

Standard A-T and G-C base pairs form under conditions which allow the formation of hydrogen bonds between the N3-H and C4-oxy of thymidine and the N1 and C6-NH2, respectively, of adenosine and between the C2-oxy, N3 and C4-NH2, of cytidine and the C2-NH2, N'—H and C6-oxy, respectively, of guanosine. Thus, for example, guanosine (2-amino-6-oxy-9-β-D-ribofuranosyl-purine) can be modified to form isoguanosine (2-oxy-6-amino-9-β-D-ribofuranosyl-purine). Such modification results in a nucleoside base which will no longer effectively form a standard base pair with cytosine. However, modification of cytosine (1-β-D-ribofuranosyl-2-oxy-4-amino-pyrimidine) to form isocytosine (1-β-D-ribofuranosyl-2-amino-4-oxy-pyrimidine-) results in a modified nucleotide which will not effectively base pair with guanosine but will form a base pair with isoguanosine (U.S. Pat. No. 5,681,702 to Collins et al.). Isocytosine is available from Sigma Chemical Co. (St. Louis, Mo.); isocytidine can be prepared by the method described by Switzer et al. (1993) Biochemistry 32:10489-10496 and references cited therein; 2'-deoxy-5-methyl-isocytidine can be prepared by the method of Tor et al., 1993, J. Am. Chem. Soc. 115:4461-4467 and references cited therein; and isoguanine nucleotides can be prepared using the method described by Switzer et al., 1993, supra, and Mantsch et al., 1993, Biochem. 14:5593-5601, or by the method described in U.S. Pat. No. 5,780,610 to Collins et al. Other nonnatural base pairs can be synthesized by the method described in Piccirilli et al., 1990, Nature 343:33-37, for the synthesis of 2,6-diaminopyrimidine and its complement (1-methylpyrazolo-[4,3]pyrimidine-5,7-(4H,6H)-dione. Other such modified nucleotide units which form unique base pairs are known, such as those described in Leach et al. (1992) J. Am. Chem. Soc. 114:3675-3683 and Switzer et al., supra.

Polypeptide: The terms "polypeptide," "peptide," and "protein" are used interchangeably herein to refer to polymers of amino acids of any length. The polymer can comprise modified amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids such as homocysteine, ornithine, p-acetylphenylalanine, D-amino acids, and creatine), as well as other modifications known in the art.

The term, as used herein, refers to proteins, polypeptides, and peptides of any size, structure, or function. Polypeptides include encoded polynucleotide products, naturally occurring polypeptides, synthetic polypeptides, homologs, orthologs, paralogs, fragments and other equivalents, variants, and analogs of the foregoing. A polypeptide can be a monomer or can be a multi-molecular complex such as a dimer, trimer or tetramer. They can also comprise single chain or multichain polypeptides. Most commonly disulfide linkages are found in multichain polypeptides. The term polypeptide can also apply to amino acid polymers in which one or more amino acid residues are an artificial chemical analogue of a corresponding naturally occurring amino acid. In some embodiments, a "peptide" can be less than or equal to 50 amino acids long, e.g., about 5, 10, 15, 20, 25, 30, 35, 40, 45, or 50 amino acids long.

Polypeptide variant: As used herein, the term "polypeptide variant" refers to molecules that differ in their amino acid sequence from a native or reference sequence. The amino acid sequence variants can possess substitutions, deletions, and/or insertions at certain positions within the amino acid sequence, as compared to a native or reference sequence. Ordinarily, variants will possess at least about 50% identity, at least about 60% identity, at least about 70% identity, at least about 80% identity, at least about 90% identity, at least about 95% identity, at least about 99% identity to a native or reference sequence. In some embodiments, they will be at least about 80%, or at least about 90% identical to a native or reference sequence.

Polypeptide per unit drug (PUD): As used herein, a PUD or product per unit drug, is defined as a subdivided portion of total daily dose, usually 1 mg, pg, kg, etc., of a product (such as a polypeptide) as measured in body fluid or tissue, usually defined in concentration such as pmol/mL, mmol/mL, etc. divided by the measure in the body fluid.

Preventing: As used herein, the term "preventing" refers to partially or completely delaying onset of an infection, disease, disorder and/or condition; partially or completely delaying onset of one or more symptoms, features, or clinical manifestations of a particular infection, disease, disorder, and/or condition; partially or completely delaying onset of one or more symptoms, features, or manifestations of a particular infection, disease, disorder, and/or condition; partially or completely delaying progression from an infection, a particular disease, disorder and/or condition; and/or decreasing the risk of developing pathology associated with the infection, the disease, disorder, and/or condition.

Proliferate: As used herein, the term "proliferate" means to grow, expand or increase or cause to grow, expand or increase rapidly. "Proliferative" means having the ability to proliferate. "Anti-proliferative" means having properties counter to or inapposite to proliferative properties.

Prophylactic: As used herein, "prophylactic" refers to a therapeutic or course of action used to prevent the spread of disease.

Prophylaxis: As used herein, a "prophylaxis" refers to a measure taken to maintain health and prevent the spread of disease. An "immune prophylaxis" refers to a measure to produce active or passive immunity to prevent the spread of disease.

Protein cleavage site: As used herein, "protein cleavage site" refers to a site where controlled cleavage of the amino acid chain can be accomplished by chemical, enzymatic or photochemical means.

Protein cleavage signal: As used herein "protein cleavage signal" refers to at least one amino acid that flags or marks a polypeptide for cleavage.

Protein of interest: As used herein, the terms "proteins of interest" or "desired proteins" include those provided herein and fragments, mutants, variants, and alterations thereof.

Proximal: As used herein, the term "proximal" means situated nearer to the center or to a point or region of interest.

Pseudouridine: As used herein, pseudouridine (w) refers to the C-glycoside isomer of the nucleoside uridine. A "pseudouridine analog" is any modification, variant, isoform or derivative of pseudouridine. For example, pseudouridine analogs include but are not limited to 1-carboxymethyl-pseudouridine, 1-propynyl-pseudouridine, 1-taurinomethyl-pseudouridine, 1-taurinomethyl-4-thio-pseudouridine, 1-methylpseudouridine ($m^1\psi$), 1-methyl-4-thio-pseudouridine ($m^1s^4\psi$), 4-thio-1-methyl-pseudouridine, 3-methyl-pseudouridine ($m^3\psi$), 2-thio-1-methyl-pseudouridine, 1-methyl-1-deaza-pseudouridine, 2-thio-1-methyl-1-deaza-pseudouridine, dihydropseudouridine, 2-thio-dihydropseudouridine, 2-methoxyuridine, 2-methoxy-4-thio-uridine, 4-methoxy-pseudouridine, 4-methoxy-2-thio-pseudouridine, N1-methyl-pseudouridine, 1-methyl-3-(3-amino-3-carboxypropyl)pseudouridine ($acp^3\psi$), and 2'-O-methyl-pseudouridine ($\psi$m).

Purified: As used herein, "purify," "purified," "purification" means to make substantially pure or clear from unwanted components, material defilement, admixture or imperfection.

Reference Nucleic Acid Sequence: The term "reference nucleic acid sequence" or "reference nucleic acid" or "reference nucleotide sequence" or "reference sequence" refers to a starting nucleic acid sequence (e.g., a RNA, e.g., an mRNA sequence) that can be sequence optimized. In some embodiments, the reference nucleic acid sequence is a wild type nucleic acid sequence, a fragments or a variant thereof. In some embodiments, the reference nucleic acid sequence is a previously sequence optimized nucleic acid sequence.

Salts: In some aspects, the pharmaceutical composition for delivery disclosed herein and comprises salts of some of their lipid constituents. The term "salt" includes any anionic and cationic complex. Non-limiting examples of anions include inorganic and organic anions, e.g., fluoride, chloride, bromide, iodide, oxalate (e.g., hemioxalate), phosphate, phosphonate, hydrogen phosphate, dihydrogen phosphate, oxide, carbonate, bicarbonate, nitrate, nitrite, nitride, bisulfite, sulfide, sulfite, bisulfate, sulfate, thiosulfate, hydrogen sulfate, borate, formate, acetate, benzoate, citrate, tartrate, lactate, acrylate, polyacrylate, fumarate, maleate, itaconate, glycolate, gluconate, malate, mandelate, tiglate, ascorbate, salicylate, polymethacrylate, perchlorate, chlorate, chlorite, hypochlorite, bromate, hypobromite, iodate, an alkylsulfonate, an arylsulfonate, arsenate, arsenite, chromate, dichromate, cyanide, cyanate, thiocyanate, hydroxide, peroxide, permanganate, and mixtures thereof.

Sample: As used herein, the term "sample" or "biological sample" refers to a subset of its tissues, cells or component parts (e.g., body fluids, including but not limited to blood, mucus, lymphatic fluid, synovial fluid, cerebrospinal fluid, saliva, amniotic fluid, amniotic cord blood, urine, vaginal fluid and semen). A sample further can include a homogenate, lysate or extract prepared from a whole organism or a subset of its tissues, cells or component parts, or a fraction or portion thereof, including but not limited to, for example, plasma, serum, spinal fluid, lymph fluid, the external sections of the skin, respiratory, intestinal, and genitourinary tracts, tears, saliva, milk, blood cells, tumors, organs. A sample further refers to a medium, such as a nutrient broth or gel, which can contain cellular components, such as proteins or nucleic acid molecule.

Signal Sequence: As used herein, the phrases "signal sequence," "signal peptide," and "transit peptide" are used interchangeably and refer to a sequence that can direct the transport or localization of a protein to a certain organelle, cell compartment, or extracellular export. The term encompasses both the signal sequence polypeptide and the nucleic acid sequence encoding the signal sequence. Thus, references to a signal sequence in the context of a nucleic acid refer in fact to the nucleic acid sequence encoding the signal sequence polypeptide.

Signal transduction pathway: A "signal transduction pathway" refers to the biochemical relationship between a variety of signal transduction molecules that play a role in the transmission of a signal from one portion of a cell to another portion of a cell. As used herein, the phrase "cell surface receptor" includes, for example, molecules and complexes of molecules capable of receiving a signal and the transmission of such a signal across the plasma membrane of a cell.

Similarity: As used herein, the term "similarity" refers to the overall relatedness between polymeric molecules, e.g. between polynucleotide molecules (e.g. DNA molecules and/or RNA molecules) and/or between polypeptide molecules. Calculation of percent similarity of polymeric molecules to one another can be performed in the same manner as a calculation of percent identity, except that calculation of percent similarity takes into account conservative substitutions as is understood in the art.

Single unit dose: As used herein, a "single unit dose" is a dose of any therapeutic administered in one dose/at one time/single route/single point of contact, i.e., single administration event.

Split dose: As used herein, a "split dose" is the division of single unit dose or total daily dose into two or more doses.

Specific delivery: As used herein, the term "specific delivery," "specifically deliver," or "specifically delivering" means delivery of more (e.g., at least 1.5 fold more, at least 2-fold more, at least 3-fold more, at least 4-fold more, at least 5-fold more, at least 6-fold more, at least 7-fold more, at least 8-fold more, at least 9-fold more, at least 10-fold more) of a polynucleotide by a nanoparticle to a target tissue of interest (e.g., mammalian liver) compared to an off-target tissue (e.g., mammalian spleen). The level of delivery of a nanoparticle to a particular tissue can be measured by comparing the amount of protein produced in a tissue to the weight of said tissue, comparing the amount of polynucleotide in a tissue to the weight of said tissue, comparing the amount of protein produced in a tissue to the amount of total protein in said tissue, or comparing the amount of polynucleotide in a tissue to the amount of total polynucleotide in said tissue. For example, for renovascular targeting, a polynucleotide is specifically provided to a mammalian kidney as compared to the liver and spleen if 1.5, 2-fold, 3-fold, 5-fold, 10-fold, 15 fold, or 20 fold more polynucleotide per 1 g of tissue is delivered to a kidney compared to that delivered to the liver or spleen following systemic administration of the polynucleotide. It will be understood that the ability of a nanoparticle to specifically deliver to a target tissue need not be determined in a subject being treated, it can be determined in a surrogate such as an animal model (e.g., a rat model).

Stable: As used herein "stable" refers to a compound that is sufficiently robust to survive isolation to a useful degree of purity from a reaction mixture, and in some cases capable of formulation into an efficacious therapeutic agent.

Stabilized: As used herein, the term "stabilize," "stabilized," "stabilized region" means to make or become stable.

Stereoisomer: As used herein, the term "stereoisomer" refers to all possible different isomeric as well as conformational forms that a compound can possess (e.g., a compound of any formula described herein), in particular all possible stereochemically and conformationally isomeric forms, all diastereomers, enantiomers and/or conformers of the basic molecular structure. Some compounds of the present invention can exist in different tautomeric forms, all of the latter being included within the scope of the present invention.

Subject: By "subject" or "individual" or "animal" or "patient" or "mammal," is meant any subject, particularly a mammalian subject, for whom diagnosis, prognosis, or therapy is desired. Mammalian subjects include, but are not limited to, humans, domestic animals, farm animals, zoo animals, sport animals, pet animals such as dogs, cats, guinea pigs, rabbits, rats, mice, horses, cattle, cows; primates such as apes, monkeys, orangutans, and chimpanzees; canids such as dogs and wolves; felids such as cats, lions, and tigers; equids such as horses, donkeys, and zebras; bears, food animals such as cows, pigs, and sheep; ungulates such as deer and giraffes; rodents such as mice, rats, hamsters and guinea pigs; and so on. In certain embodiments, the mammal is a human subject. In other embodiments, a subject is a human patient. In a particular embodiment, a subject is a human patient in need of treatment.

Substantially: As used herein, the term "substantially" refers to the qualitative condition of exhibiting total or near-total extent or degree of a characteristic or property of interest. One of ordinary skill in the biological arts will understand that biological and chemical characteristics rarely, if ever, go to completion and/or proceed to completeness or achieve or avoid an absolute result. The term "substantially" is therefore used herein to capture the potential lack of completeness inherent in many biological and chemical characteristics.

Substantially equal: As used herein as it relates to time differences between doses, the term means plus/minus 2%.

Substantially simultaneous: As used herein and as it relates to plurality of doses, the term means within 2 seconds.

Suffering from: An individual who is "suffering from" a disease, disorder, and/or condition has been diagnosed with or displays one or more symptoms of the disease, disorder, and/or condition.

Susceptible to: An individual who is "susceptible to" a disease, disorder, and/or condition has not been diagnosed with and/or cannot exhibit symptoms of the disease, disorder, and/or condition but harbors a propensity to develop a disease or its symptoms. In some embodiments, an individual who is susceptible to a disease, disorder, and/or condition (for example, Gal-1) can be characterized by one or more of the following: (1) a genetic mutation associated with development of the disease, disorder, and/or condition; (2) a genetic polymorphism associated with development of the disease, disorder, and/or condition; (3) increased and/or decreased expression and/or activity of a protein and/or nucleic acid associated with the disease, disorder, and/or condition; (4) habits and/or lifestyles associated with development of the disease, disorder, and/or condition; (5) a family history of the disease, disorder, and/or condition; and (6) exposure to and/or infection with a microbe associated with development of the disease, disorder, and/or condition. In some embodiments, an individual who is susceptible to a disease, disorder, and/or condition will develop the disease, disorder, and/or condition. In some embodiments, an individual who is susceptible to a disease, disorder, and/or condition will not develop the disease, disorder, and/or condition.

Sustained release: As used herein, the term "sustained release" refers to a pharmaceutical composition or compound release profile that conforms to a release rate over a specific period of time.

Synthetic: The term "synthetic" means produced, prepared, and/or manufactured by the hand of man. Synthesis of polynucleotides or other molecules of the present invention can be chemical or enzymatic.

Targeted Cells: As used herein, "targeted cells" refers to any one or more cells of interest. The cells can be found in vitro, in vivo, in situ or in the tissue or organ of an organism. The organism can be an animal, for example a mammal, a human, a subject or a patient.

Target tissue: As used herein "target tissue" refers to any one or more tissue types of interest in which the delivery of a polynucleotide would result in a desired biological and/or pharmacological effect. Examples of target tissues of interest include specific tissues, organs, and systems or groups thereof. In particular applications, a target tissue can be a liver, a kidney, a lung, a spleen, or a vascular endothelium in vessels (e.g., intra-coronary or intra-femoral). An "off-target tissue" refers to any one or more tissue types in which the expression of the encoded protein does not result in a desired biological and/or pharmacological effect.

The presence of a therapeutic agent in an off-target issue can be the result of: (i) leakage of a polynucleotide from the administration site to peripheral tissue or distant off-target tissue via diffusion or through the bloodstream (e.g., a polynucleotide intended to express a polypeptide in a certain tissue would reach the off-target tissue and the polypeptide would be expressed in the off-target tissue); or (ii) leakage of an polypeptide after administration of a polynucleotide encoding such polypeptide to peripheral tissue or distant off-target tissue via diffusion or through the bloodstream (e.g., a polynucleotide would expressed a polypeptide in the target tissue, and the polypeptide would diffuse to peripheral tissue).

Targeting sequence: As used herein, the phrase "targeting sequence" refers to a sequence that can direct the transport or localization of a protein or polypeptide.

Terminus: As used herein the terms "termini" or "terminus," when referring to polypeptides, refers to an extremity of a peptide or polypeptide. Such extremity is not limited only to the first or final site of the peptide or polypeptide but can include additional amino acids in the terminal regions. The polypeptide based molecules of the invention can be characterized as having both an N-terminus (terminated by an amino acid with a free amino group ($NH_2$)) and a C-terminus (terminated by an amino acid with a free carboxyl group (COOH)). Proteins of the invention are in some cases made up of multiple polypeptide chains brought together by disulfide bonds or by non-covalent forces (multimers, oligomers). These sorts of proteins will have multiple N- and C-termini. Alternatively, the termini of the polypeptides can be modified such that they begin or end, as the case can be, with a non-polypeptide based moiety such as an organic conjugate.

Therapeutic Agent: The term "therapeutic agent" refers to an agent that, when administered to a subject, has a therapeutic, diagnostic, and/or prophylactic effect and/or elicits a desired biological and/or pharmacological effect. For example, in some embodiments, an mRNA encoding a GALT polypeptide can be a therapeutic agent.

Therapeutically effective amount: As used herein, the term "therapeutically effective amount" means an amount of an agent to be delivered (e.g., nucleic acid, drug, therapeutic agent, diagnostic agent, prophylactic agent, etc.) that is sufficient, when administered to a subject suffering from or susceptible to an infection, disease, disorder, and/or condition, to treat, improve symptoms of, diagnose, prevent, and/or delay the onset of the infection, disease, disorder, and/or condition.

Therapeutically effective outcome: As used herein, the term "therapeutically effective outcome" means an outcome that is sufficient in a subject suffering from or susceptible to an infection, disease, disorder, and/or condition, to treat, improve symptoms of, diagnose, prevent, and/or delay the onset of the infection, disease, disorder, and/or condition.

Total daily dose: As used herein, a "total daily dose" is an amount given or prescribed in 24 hr. period. The total daily dose can be administered as a single unit dose or a split dose.

Transcription factor: As used herein, the term "transcription factor" refers to a DNA-binding protein that regulates transcription of DNA into RNA, for example, by activation or repression of transcription. Some transcription factors effect regulation of transcription alone, while others act in concert with other proteins. Some transcription factor can both activate and repress transcription under certain conditions. In general, transcription factors bind a specific target sequence or sequences highly similar to a specific consensus sequence in a regulatory region of a target gene. Transcription factors can regulate transcription of a target gene alone or in a complex with other molecules.

Transcription: As used herein, the term "transcription" refers to methods to produce mRNA (e.g., an mRNA sequence or template) from DNA (e.g., a DNA template or sequence)

Transfection: As used herein, "transfection" refers to the introduction of a polynucleotide (e.g., exogenous nucleic acids) into a cell wherein a polypeptide encoded by the polynucleotide is expressed (e.g., mRNA) or the polypeptide modulates a cellular function (e.g., siRNA, miRNA). As used herein, "expression" of a nucleic acid sequence refers to translation of a polynucleotide (e.g., an mRNA) into a polypeptide or protein and/or post-translational modification of a polypeptide or protein. Methods of transfection include, but are not limited to, chemical methods, physical treatments and cationic lipids or mixtures.

Treating, treatment, therapy: As used herein, the term "treating" or "treatment" or "therapy" refers to partially or completely alleviating, ameliorating, improving, relieving, delaying onset of, inhibiting progression of, reducing severity of, and/or reducing incidence of one or more symptoms or features of a disease, e.g., galactosemia type 1. For example, "treating" galactosemia type 1 can refer to diminishing symptoms associate with the disease, prolong the lifespan (increase the survival rate) of patients, reducing the severity of the disease, preventing or delaying the onset of the disease, etc. Treatment can be administered to a subject who does not exhibit signs of a disease, disorder, and/or condition and/or to a subject who exhibits only early signs of a disease, disorder, and/or condition for the purpose of decreasing the risk of developing pathology associated with the disease, disorder, and/or condition.

Unmodified: As used herein, "unmodified" refers to any substance, compound or molecule prior to being changed in some way. Unmodified can, but does not always, refer to the wild type or native form of a biomolecule. Molecules can undergo a series of modifications whereby each modified molecule can serve as the "unmodified" starting molecule for a subsequent modification.

Uracil: Uracil is one of the four nucleobases in the nucleic acid of RNA, and it is represented by the letter U. Uracil can be attached to a ribose ring, or more specifically, a ribofuranose via a $\beta$-$N_1$-glycosidic bond to yield the nucleoside uridine. The nucleoside uridine is also commonly abbreviated according to the one letter code of its nucleobase, i.e., U. Thus, in the context of the present disclosure, when a monomer in a polynucleotide sequence is U, such U is designated interchangeably as a "uracil" or a "uridine."

Uridine Content: The terms "uridine content" or "uracil content" are interchangeable and refer to the amount of uracil or uridine present in a certain nucleic acid sequence. Uridine content or uracil content can be expressed as an absolute value (total number of uridine or uracil in the sequence) or relative (uridine or uracil percentage respect to the total number of nucleobases in the nucleic acid sequence).

Uridine Modified Sequence: The terms "uridine-modified sequence" refers to a sequence optimized nucleic acid (e.g., a synthetic mRNA sequence) with a different overall or local uridine content (higher or lower uridine content) or with different uridine patterns (e.g., gradient distribution or clustering) with respect to the uridine content and/or uridine patterns of a candidate nucleic acid sequence. In the content of the present disclosure, the terms "uridine-modified sequence" and "uracil-modified sequence" are considered equivalent and interchangeable.

A "high uridine codon" is defined as a codon comprising two or three uridines, a "low uridine codon" is defined as a codon comprising one uridine, and a "no uridine codon" is a codon without any uridines. In some embodiments, a uridine-modified sequence comprises substitutions of high uridine codons with low uridine codons, substitutions of high uridine codons with no uridine codons, substitutions of low uridine codons with high uridine codons, substitutions of low uridine codons with no uridine codons, substitution of no uridine codons with low uridine codons, substitutions of no uridine codons with high uridine codons, and combinations thereof. In some embodiments, a high uridine codon can be replaced with another high uridine codon. In some embodiments, a low uridine codon can be replaced with another low uridine codon. In some embodiments, a no uridine codon can be replaced with another no uridine codon. A uridine-modified sequence can be uridine enriched or uridine rarefied.

Uridine Enriched: As used herein, the terms "uridine enriched" and grammatical variants refer to the increase in uridine content (expressed in absolute value or as a percentage value) in an sequence optimized nucleic acid (e.g., a synthetic mRNA sequence) with respect to the uridine content of the corresponding candidate nucleic acid sequence. Uridine enrichment can be implemented by substituting codons in the candidate nucleic acid sequence with synonymous codons containing less uridine nucleobases. Uridine enrichment can be global (i.e., relative to the entire length of a candidate nucleic acid sequence) or local (i.e., relative to a subsequence or region of a candidate nucleic acid sequence).

Uridine Rarefied: As used herein, the terms "uridine rarefied" and grammatical variants refer to a decrease in uridine content (expressed in absolute value or as a percentage value) in an sequence optimized nucleic acid (e.g., a synthetic mRNA sequence) with respect to the uridine content of the corresponding candidate nucleic acid sequence. Uridine rarefication can be implemented by substituting codons in the candidate nucleic acid sequence with synonymous codons containing less uridine nucleobases. Uridine rarefication can be global (i.e., relative to the entire length of a candidate nucleic acid sequence) or local (i.e., relative to a subsequence or region of a candidate nucleic acid sequence).

Variant: The term variant as used in present disclosure refers to both natural variants (e.g, polymorphisms, isoforms, etc) and artificial variants in which at least one amino acid residue in a native or starting sequence (e.g., a wild type sequence) has been removed and a different amino acid inserted in its place at the same position. These variants can de described as "substitutional variants." The substitutions can be single, where only one amino acid in the molecule has been substituted, or they can be multiple, where two or more amino acids have been substituted in the same molecule. If amino acids are inserted or deleted, the resulting variant would be an "insertional variant" or a "deletional variant" respectively.

30. EMBODIMENTS

Throughout this section, the term embodiment is abbreviated as 'E' followed by an ordinal. For example, E1 is equivalent to Embodiment 1.

E1. A polynucleotide comprising an open reading frame (ORF) encoding a galactose-1-phosphate uridylyltransferase (GALT) polypeptide, wherein the uracil or thymine content of the ORF relative to the theoretical minimum uracil or thymine content of a nucleotide sequence encoding the GALT polypeptide (% $U_{TM}$ or % $T_{TM}$) is between 100% and about 150%.

E2. The polynucleotide of E1, wherein the % $U_{TM}$ or % $T_{TM}$ is between about 105% and about 145%, about 105% and about 140%, about 110% and about 140%, about 110% and about 145%, about 115% and about 135%, about 105% and about 135%, about 110% and about 135%, about 115% and about 145%, or about 115% and about 140%.

E3. The polynucleotide of E2, wherein the % $U_{TM}$ or % $T_{TM}$ is between (i) 110%, 111%, 112%, 113%, 114%, 115%, 116%, 117%, 118%, 119%, 120%, 121%, 122%, or 123% and (ii) 134%, 135%, 136%, 137%, 138%, 139%, or 140%.

E4. The polynucleotide of any one of E1 to E3, wherein the uracil or thymine content in the ORF relative to the uracil or thymine content of the corresponding wild-type ORF (% $U_{WT}$ or % $T_{WT}$) is less than 100%.

E5. The polynucleotide of E4, wherein the % $U_{WT}$ or % $T_{WT}$ is less than about 95%, less than about 90%, less than about 85%, less than 80%, less than 79%, less than 78%, less than 77%, less than 76%, less than 75%, or less than 74% of the % $U_{WT}$ or % $T_{WT}$.

E6. The polynucleotide of E4, wherein the % $U_{WT}$ or % $T_{WT}$ is between 68% and 74%.

E7. The polynucleotide of any one of E1 to E6, wherein the uracil or thymine content in the ORF is less than about 50%, less than about 40%, less than about 30%, or less than about 20% of the total nucleotide content in the ORF.

E8. The polynucleotide of E7, wherein the uracil or thymine content in the ORF relative to the total nucleotide content in the ORF (% $U_{TL}$ or % $T_{TL}$) is less than about 20%.

E9. The polynucleotide of any one of E1 to E8, wherein the % $U_{TL}$ or % $T_{TL}$ is between about 13% and about 15%.

E10. The polynucleotide of any one of E1 to E9, wherein the guanine content of the ORF with respect to the theoretical maximum guanine content of a nucleotide sequence encoding the GALT polypeptide (% $G_{TMX}$) is less than 100%, less than about 90%, less than about 85%, or less than about 80%.

E11. The polynucleotide of E10, wherein the % $G_{TMX}$ is between about 69% and about 80%, between about 70% and about 79%, between about 70% and about 78%, or between about 70% and about 77%.

E12. The polynucleotide of any one of E1 to E11, wherein the cytosine content of the ORF relative to the theoretical maximum cytosine content of a nucleotide sequence encoding the GALT polypeptide (% $C_{TMX}$) is less than 95%.

E13. The polynucleotide of E12, wherein the % $C_{TMX}$ is between about 60% and about 80%, between about 65% and about 80%, between about 68% and about 79%, or between about 70% and about 78%.

E14. The polynucleotide of any one of E1 to E13, wherein the guanine and cytosine content (G/C) of the ORF relative to the theoretical maximum G/C content in a nucleotide sequence encoding the GALT polypeptide (% $G/C_{TMX}$) is at least about 69%, at least about 70%, at least about 75%, at least about 80%, at least about 85%, at least about 90%, at least about 95%, or about 100%.

E15. The polynucleotide of any one of E1 to E13, wherein the % G/C is between about 80% and about 100%, between about 85% and about 99%, between about 90% and about 97%, or between about 91% and about 95%.

E16. The polynucleotide of any one of E1 to E15, wherein the % G/C is at least 2%, at least 3%, at least 4%, at least 5%, at least 6%, at least 7%, at least about 10%, or at least about 11% higher.

E17. The polynucleotide of any one of E1 to E15, wherein the average G/C content in the 3rd codon position in the ORF is at least 20%, at least 21%, at least 22%, at least 23%, at least 24%, at least 25%, at least 26%, at least 27%, at least 28%, at least 29%, or at least 30% higher than the average G/C content in the 3rd codon position in the corresponding wild-type ORF.

E18. The polynucleotide of any one of E1 to E17, wherein the ORF further comprises at least one low-frequency codon.

E19. The polynucleotide of any one of E1 to E18, (i) wherein the ORF is at least 88%, at least 89%, at least 90%, at least 91%, at least 92%, at least 93%, at least 94%, at least 95%, at least 96%, at least 97%, at least 98%, at least 99%, or 100% identical to GALT-CO10;

(ii) wherein the ORF is at least 89%, at least 90%, at least 91%, at least 92%, at least 93%, at least 94%, at least 95%, at least 96%, at least 97%, at least 98%, at least 99%, or 100% identical to: GALT-CO01, GALT-CO07, GALT-CO19, GALT-CO20, or GALT-CO24;

(iii) wherein the ORF is at least 90%, at least 91%, at least 92%, at least 93%, at least 94%, at least 95%, at least 96%, at least 97%, at least 98%, at least 99%, or 100% identical to: GALT-CO05, GALT-CO09, GALT-CO10, GALT-CO12, GALT-CO15, GALT-CO17, GALT-CO18, GALT-CO19, GALT-CO20, GALT-CO21, or GALT-CO22; or (iv) wherein the ORF is at least 91%, at least 92%, at least 93%, at least 94%, at least 95%, at least 96%, at least 97%, at least 98%, at least 99%, or 100% identical to: GALT-CO02, GALT-CO04, GALT-CO06, GALT-CO15, GALT-CO16, GALT-CO17, GALT-CO18, or GALT-CO23.

E20. A polynucleotide comprising an ORF, (i) wherein the ORF is at least 88%, at least 89%, at least 90%, at least 91%, at least 92%, at least 93%, at least 94%, at least 95%, at least 96%, at least 97%, at least 98%, at least 99%, or 100% identical to GALT-CO10;

(ii) wherein the ORF is at least 89%, at least 90%, at least 91%, at least 92%, at least 93%, at least 94%, at least 95%, at least 96%, at least 97%, at least 98%, at least 99%, or 100% identical to: GALT-CO01, GALT-CO07, GALT-CO19, GALT-CO20, or GALT-CO24;

(iii) wherein the ORF is at least 90%, at least 91%, at least 92%, at least 93%, at least 94%, at least 95%, at least 96%, at least 97%, at least 98%, at least 99%, or 100% identical to: GALT-CO05, GALT-CO09, GALT-CO10, GALT-CO12, GALT-CO15, GALT-CO17, GALT-CO18, GALT-CO19, GALT-CO20, GALT-CO21, or GALT-CO22; or (iv) wherein the ORF is at least 91%, at least 92%, at least 93%, at least 94%, at least 95%, at least 96%, at least 97%, at least 98%, at least 99%, or 100% identical to: GALT-CO02, GALT-CO04, GALT-CO06, GALT-CO15, GALT-CO16, GALT-CO17, GALT-CO18, or GALT-CO23.

E21. The polynucleotide of any one of E1 to E20, wherein the ORF has at least 79%, at least 80%, at least 90%, at least 91%, at least 92%, at least 93%, at least 94%, at least 95%, at least 96%, at least 97%, at least 98%, at least 99%, or 100% sequence identity to SEQ ID NO: 5-29.

E22. The polynucleotide of E21, wherein the GALT polypeptide is a variant, derivative, or mutant having a galactose-1-phosphate uridylyltransferase activity.

E23. The polynucleotide of any one of E1 to E22, wherein the polynucleotide sequence further comprises a nucleotide sequence encoding a transit peptide.

E24. The polynucleotide of any one of E1 to E23, wherein the polynucleotide is single stranded.

E25. The polynucleotide of any one of E1 to E23, wherein the polynucleotide is double stranded.

E26. The polynucleotide of any one of claims 1 to 25, wherein the polynucleotide is DNA.

E27. The polynucleotide of any one of E1 to E25, wherein the polynucleotide is RNA.

E28. The polynucleotide of E27, wherein the polynucleotide is mRNA.

E29. The polynucleotide of any one of E1 to E28, wherein the polynucleotide comprises at least one chemically modified nucleobase, sugar, backbone, or any combination thereof.

E30. The polynucleotide of E29, wherein the at least one chemically modified nucleobase is selected from the group consisting of pseudouracil (ψ), N1-methylpseudouracil (m1ψ), 2-thiouracil (s2U), 4'-thiouracil, 5-methylcytosine, 5-methyluracil, and any combinations thereof.

E31. The polynucleotide of E29, wherein the at least one chemically modified nucleobase is 5-methoxyuracil.

E32. The polynucleotide of E31, wherein at least about 25%, at least about 30%, at least about 40%, at least about 50%, at least about 60%, at least about 70%, at least about 80%, at least about 90%, at least about 95%, at least about 99%, or 100% of the uracils are 5-methoxyuracils.

E33. The polynucleotide of any one of E1 to E32, wherein the polynucleotide further comprises a miRNA binding site.

E34. The polynucleotide of E33, wherein the miRNA binding site comprises one or more nucleotide sequences selected from Table 4.

E35. The polynucleotide of E33, wherein the miRNA binding site binds to miR-142.

E36. The polynucleotide of E34 or E35, wherein the miRNA binding site binds to miR-142-3p or miR-142-5p.

E37. The polynucleotide of E35 or E36, wherein the miR-142 comprises SEQ ID NO: 30.

E38. The polynucleotide of any one of E1 to E37, wherein the polynucleotide further comprises a 5' UTR.

E39. The polynucleotide of E38, wherein the 5' UTR comprises a nucleic acid sequence at least 90%, at least about 95%, at least about 96%, at least about 97%, at least about 98%, at least about 99%, or about 100% identical to a 5' UTR sequence selected from the group consisting of SEQ ID NO: 35-59 and 109-111, or any combination thereof.

E40. The polynucleotide of any one of E1 to E39, wherein the polynucleotide further comprises a 3' UTR.

E41. The polynucleotide of E40, wherein the 3' UTR comprises a nucleic acid sequence at least about 90%, at least about 95%, at least about 96%, at least about 97%, at least about 98%, at least about 99%, or about 100% identical to a 3' UTR sequence selected from the group consisting of SEQ ID NO: 53, 54, 58, 60 to 77, 79, 97, 98, 101 to 107, 108, 112, and 163, or any combination thereof.

E42. The polynucleotide of E40 or E41, wherein the miRNA binding site is located within the 3' UTR.

E43. The polynucleotide of any one of E1 to E42, wherein the polynucleotide further comprises a 5' terminal cap.

E44. The polynucleotide of E43, wherein the 5' terminal cap comprises a Cap0, Cap1, ARCA, inosine, N1-methyl-guanosine, 2'-fluoro-guanosine, 7-deaza-guanosine, 8-oxo-guanosine, 2-amino-guanosine, LNA-guanosine, 2-azido-guanosine, Cap2, Cap4, 5' methylG cap, or an analog thereof.

E45. The polynucleotide of any one of E1 to E44, wherein the polynucleotide further comprises a poly-A region.

E46. The polynucleotide of E45, wherein the poly-A region is at least about 10, at least about 20, at least about 30, at least about 40, at least about 50, at least about 60, at least about 70, at least about 80, or at least about 90 nucleotides in length.

E47. The polynucleotide of E46, wherein the poly-A region has about 10 to about 200, about 20 to about 180, about 50 to about 160, about 70 to about 140, or about 80 to about 120 nucleotides in length.

E48. The polynucleotide of any one of E1 to E47, wherein the polynucleotide encodes a GALT polypeptide that is fused to one or more heterologous polypeptides.

E49. The polynucleotide of E48, wherein the one or more heterologous polypeptides increase a pharmacokinetic property of the GALT polypeptide.

E50. The polynucleotide of any one of E1 to E49, wherein upon administration to a subject, the polynucleotide has:

(i) a longer plasma half-life;

(ii) increased expression of a GALT polypeptide encoded by the ORF;

(iii) a lower frequency of arrested translation resulting in an expression fragment;

(iv) greater structural stability; or (v) any combination thereof, relative to a corresponding polynucleotide comprising SEQ ID NO: 2 or 4.

E51. The polynucleotide of any one of E1 to E50, wherein the polynucleotide comprises:

(i) a 5'-terminal cap;

(ii) a 5'-UTR;

(iii) an ORF encoding a GALT polypeptide;

(iv) a 3'-UTR; and (v) a poly-A region.

E52. The polynucleotide of E51, wherein the 3'-UTR comprises a miRNA binding site.

E53. A method of producing the polynucleotide of any one of E1 to E52, the method comprising modifying an ORF encoding a GALT polypeptide by substituting at least one uracil nucleobase with an adenine, guanine, or cytosine nucleobase, or by substituting at least one adenine, guanine, or cytosine nucleobase with a uracil nucleobase, wherein all the substitutions are synonymous substitutions.

E54. The method of E53, wherein the method further comprises replacing at least about 90%, at least about 95%, at least about 99%, or about 100% of uracils with 5-methoxyuracils.

E55. A composition comprising the polynucleotide of any one of E1 to E52; and a delivery agent.

E56. The composition of E55, wherein the delivery agent comprises a lipidoid, a liposome, a lipoplex, a lipid nanoparticle, a polymeric compound, a peptide, a protein, a cell, a nanoparticle mimic, a nanotube, or a conjugate.

E57. The composition of E55, wherein the delivery agent comprises a lipid nanoparticle.

E58. The composition of E57, wherein the lipid nanoparticle comprises a lipid selected from the group consisting of 3-(didodecylamino)-N1,N1,4-tridodecyl-1-piperazineethanamine (KL10), N1-[2-(didodecylamino)ethyl]-N1,N4,N4-tridodecyl-1,4-piperazinediethanamine (KL22), 14,25-ditridecyl-15,18,21,24-tetraaza-octatriacontane (KL25), 1,2-dilinoleyloxy-N,N-dimethylaminopropane (DLin-DMA), 2,2-dilinoleyl-4-dimethylaminomethyl-[1,3]-dioxolane (DLin-K-DMA), heptatriaconta-6,9,28,31-tetraen-19-yl 4-(dimethylamino)butanoate (DLin-MC3-DMA), 2,2-dilinoleyl-4-(2-dimethylaminoethyl)-[1,3]-dioxolane (DLin-KC2-DMA), 1,2-dioleyloxy-N,N-dimethylaminopropane (DODMA), (13Z,165Z)—N,N- dimethyl-3-nonydocosa-13-16-dien-1-amine (L608), 2-({8-[(3β)-cholest-5-en-3-yloxy]octyl}oxy)-N,N-dimethyl-3-[(9Z,12Z)-octadeca-9,12-dien-1-yloxy]propan-1-amine (Octyl-CLinDMA), (2R)-2-({8-[(3β)-cholest-5-en-3-yloxy]octyl}oxy)-N,N-dimethyl-3-[(9Z,12Z)-octadeca-9,12-dien-1-yloxy]propan-1-amine (Octyl-CLinDMA (2R)), (2S)-2-({8-[(3β)-cholest-5-en-3-yloxy]octyl}oxy)-N,N-dimethyl-3-[(9Z,12Z)-octadeca-9,12-dien-1-yloxy]propan-1-amine (Octyl-CLinDMA (2S)), and any combinations thereof.

E59. The composition of any one of E55 to E58, wherein the delivery agent comprises a compound having the Formula (I)

(I)

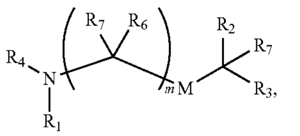

or a salt or stereoisomer thereof, wherein $R_1$ is selected from the group consisting of $C_{5-20}$ alkyl, $C_{5-20}$ alkenyl, —R*YR", —YR", and —R"M'R';

$R_2$ and $R_3$ are independently selected from the group consisting of H, $C_{1-14}$ alkyl, $C_{2-14}$ alkenyl, —R*YR", —YR", and —R*OR", or $R_2$ and $R_3$, together with the atom to which they are attached, form a heterocycle or carbocycle;

$R_4$ is selected from the group consisting of a $C_{3-6}$ carbocycle, $—(CH_2)_nQ$, $—(CH_2)_nCHQR$, —CHQR, $—CQ(R)_2$, and unsubstituted $C_{1-6}$ alkyl, where Q is selected from a carbocycle, heterocycle, —OR, $—O(CH_2)_nN(R)_2$, —C(O)OR, —OC(O)R, $—CX_3$, $—CX_2H$, $—CXH_2$, —CN, $—N(R)_2$, $—C(O)N(R)_2$, —N(R)C(O)R, $—N(R)S(O)_2R$, $—N(R)C(O)N(R)_2$, $—N(R)C(S)N(R)_2$, and $—C(R)N(R)_2C(O)OR$, and each n is independently selected from 1, 2, 3, 4, and 5;

each $R_5$ is independently selected from the group consisting of $C_{1-3}$ alkyl, $C_{2-3}$ alkenyl, and H;

each $R_6$ is independently selected from the group consisting of $C_{1-3}$ alkyl, $C_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, $—S(O)_2—$, an aryl group, and a heteroaryl group;

$R_7$ is selected from the group consisting of $C_{1-3}$ alkyl, $C_{2-3}$ alkenyl, and H;

each R is independently selected from the group consisting of $C_{1-3}$ alkyl, $C_{2-3}$ alkenyl, and H;

each R' is independently selected from the group consisting of $C_{1-18}$ alkyl, $C_{2-18}$ alkenyl, —R*YR", —YR", and H;

each R" is independently selected from the group consisting of $C_{3-14}$ alkyl and $C_{3-14}$ alkenyl;

each R* is independently selected from the group consisting of $C_{1-12}$ alkyl and $C_{2-12}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13; and provided when $R_4$ is $—(CH_2)_nQ$, $—(CH_2)_nCHQR$, —CHQR, or $—CQ(R)_2$, then (i) Q is not $—N(R)_2$ when n is 1, 2, 3, 4 or 5, or (ii) Q is not 5, 6, or 7-membered heterocycloalkyl when n is 1 or 2.

E60. A composition comprising a nucleotide sequence encoding a GALT polypeptide and a delivery agent, wherein the delivery agent comprises a compound having the Formula (I)

(I)

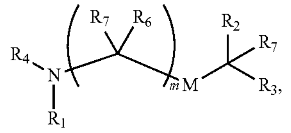

or a salt or stereoisomer thereof, wherein $R_1$ is selected from the group consisting of $C_{5-20}$ alkyl, $C_{5-20}$ alkenyl, —R*YR", —YR", and —R"M'R';

$R_2$ and $R_3$ are independently selected from the group consisting of H, $C_{1-14}$ alkyl, $C_{2-14}$ alkenyl, —R*YR", —YR", and —R*OR", or $R_2$ and $R_3$, together with the atom to which they are attached, form a heterocycle or carbocycle;

$R_4$ is selected from the group consisting of a $C_{3-6}$ carbocycle, $—(CH_2)_nQ$, $—(CH_2)_nCHQR$, —CHQR, $—CQ(R)_2$, and unsubstituted $C_{1-6}$ alkyl, where Q is selected from a carbocycle, heterocycle, —OR, $—O(CH_2)_nN(R)_2$, —C(O)OR, —OC(O)R, $—CX_3$, $—CX_2H$, $—CXH_2$, —CN, $—N(R)_2$, $—C(O)N(R)_2$, —N(R)C(O)R, $—N(R)S(O)_2R$, $—N(R)C(O)N(R)_2$, $—N(R)C(S)N(R)_2$, and $—C(R)N(R)_2C(O)OR$, and each n is independently selected from 1, 2, 3, 4, and 5;

each $R_5$ is independently selected from the group consisting of $C_{1-3}$ alkyl, $C_{2-3}$ alkenyl, and H;

each $R_6$ is independently selected from the group consisting of $C_{1-3}$ alkyl, $C_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, $—S(O)_2—$, an aryl group, and a heteroaryl group;

$R_7$ is selected from the group consisting of $C_{1-3}$ alkyl, $C_{2-3}$ alkenyl, and H; each R is independently selected from the group consisting of $C_{1-3}$ alkyl, $C_{2-3}$ alkenyl, and H;

each R' is independently selected from the group consisting of $C_{1-18}$ alkyl, $C_{2-18}$ alkenyl, —R*YR", —YR", and H;

each R" is independently selected from the group consisting of $C_{3-14}$ alkyl and $C_{3-14}$ alkenyl;

each R* is independently selected from the group consisting of $C_{1-12}$ alkyl and $C_{2-12}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13; and provided when $R_4$ is $—(CH_2)_nQ$, $—(CH_2)_nCHQR$, —CHQR, or $—CQ(R)_2$, then (i) Q is not $—N(R)_2$ when n is 1, 2, 3, 4 or 5, or (ii) Q is not 5, 6, or 7-membered heterocycloalkyl when n is 1 or 2.

E61. The composition of E59 or E60, wherein the compound is of Formula (IA):

(IA)

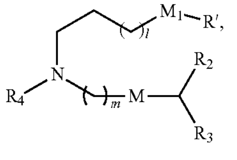

or a salt or stereoisomer thereof, wherein l is selected from 1, 2, 3, 4, and 5;

m is selected from 5, 6, 7, 8, and 9;

$M_1$ is a bond or M';

$R_4$ is unsubstituted $C_{1-3}$ alkyl, or $-(CH_2)_nQ$, in which n is 1, 2, 3, 4, or 5 and Q is OH, $-NHC(S)N(R)_2$, or $-NHC(O)N(R)_2$;

M and M' are independently selected from —C(O)O—, —OC(O)—, —C(O)N(R')—, —P(O)(OR')O—, an aryl group, and a heteroaryl group; and $R_2$ and $R_3$ are independently selected from the group consisting of H, $C_{1-14}$ alkyl, and $C_{2-14}$ alkenyl.

E62. The composition of any one of E59 to E61, wherein m is 5, 7, or 9.

E63. The composition of any one of E59 to E62, wherein the compound is of Formula (II):

(II)

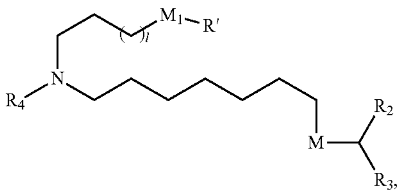

or a salt or stereoisomer thereof, wherein l is selected from 1, 2, 3, 4, and 5;

$M_1$ is a bond or M';

$R_4$ is unsubstituted $C_{1-3}$ alkyl, or $-(CH_2)_nQ$, in which n is 2, 3, or 4 and Q is OH, $-NHC(S)N(R)_2$, or $-NHC(O)N(R)_2$;

M and M' are independently selected from —C(O)O—, —OC(O)—, —C(O)N(R')—, —P(O)(OR')O—, an aryl group, and a heteroaryl group; and $R_2$ and $R_3$ are independently selected from the group consisting of H, $C_{1-14}$ alkyl, and $C_{2-14}$ alkenyl.

E64. The composition of any one of E61 to E63, wherein $M_1$ is M'.

E65. The composition of E64, wherein M and M' are independently —C(O)O— or —OC(O)—.

E66. The composition of any one of E61 to E65, wherein 1 is 1, 3, or 5.

E67. The composition of E59 or E60, wherein the compound is selected from the group consisting of Compound 1 to Compound 147, salts and stereoisomers thereof, and any combination thereof.

E68. The composition of E59 or E60, wherein the compound is of the Formula (IIa), (IIa)

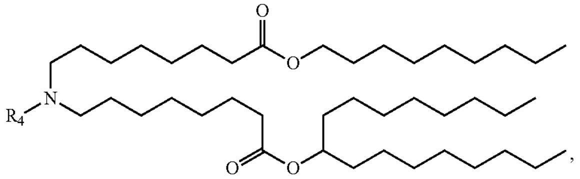

or a salt or stereoisomer thereof.

E69. The composition of E59 or E60, wherein the compound is of the Formula (IIb), (IIb)

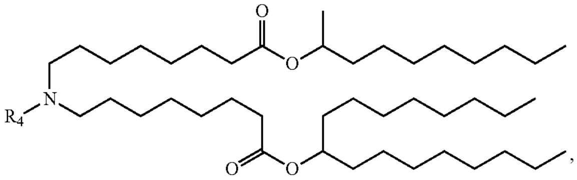

or a salt or stereoisomer thereof.

E70. The composition of E59 or E60, wherein the compound is of the Formula (IIc) or (IIe), (IIc)

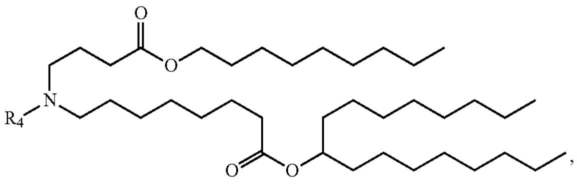

(IIe)

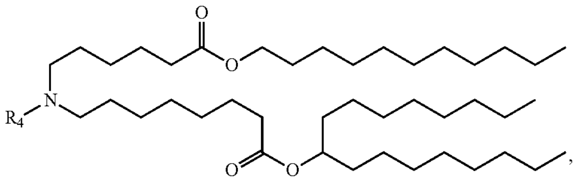

or a salt or stereoisomer thereof.

E71. The composition of any one of E68 to E70, wherein $R_4$ is selected from $-(CH_2)_nQ$ and $-(CH_2)_nCHQR$.

E72. The composition of E59 or E60, wherein the compound is of the Formula (IId)

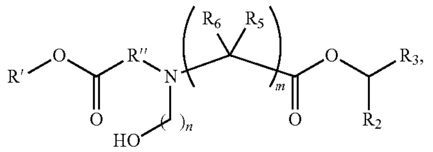

or a salt or stereoisomer thereof, wherein $R_2$ and $R_3$ are independently selected from the group consisting of $C_{5-14}$ alkyl and $C_{5-14}$ alkenyl, n is selected from 2, 3, and 4, and R', R", R5, R6 and m are as defined in E59 or E60.

E73. The composition of E72, wherein $R_2$ is $C_8$ alkyl.

E74. The composition of E73, wherein $R_3$ is $C_5$ alkyl, $C_6$ alkyl, $C_7$ alkyl, $C_8$ alkyl, or $C_9$ alkyl.

E75. The composition of any one of E72 to E74, wherein m is 5, 7, or 9.

E76. The composition of any one of E72 to E75, wherein each $R_5$ is H.

E77. The composition of E76, wherein each R6 is H.

E78. The composition of any one of E59 to E77, which is a nanoparticle composition.

E79. The composition of E78, wherein the delivery agent further comprises a phospholipid.

E80. The composition of E79, wherein the phospholipid is selected from the group consisting of 1,2-dilinoleoyl-snglycero-3-phosphocholine (DLPC), 1,2-dimyristoyl-sn-glycero-phosphocholine (DMPC), 1,2-dioleoyl-sn-glycero-3-phosphocholine (DOPC), 1,2-dipalmitoyl-sn-glycero-3-phosphocholine (DPPC), 1,2-distearoyl-sn-glycero-3-phosphocholine (DSPC), 1,2-diundecanoyl-sn-glycero-phosphocholine (DUPC), 1-palmitoyl-2-oleoyl-sn-glycero-3-phosphocholine (POPC), 1,2-di-O-octadecenyl-sn-glycero-3-phosphocholine (18:0 Diether PC), 1-oleoyl-2-cholesterylhemisuccinoyl-sn-glycero-3-phosphocholine (OChemsPC), 1-hexadecyl-sn-glycero-3-phosphocholine (C16 Lyso PC), 1,2-dilinolenoyl-sn-glycero-3-phosphocholine, 1,2-diarachidonoyl-sn-glycero-3-phosphocholine, 1,2-didocosahexaenoyl-sn-glycero-3-phosphocholine, 1,2-dioleoyl-sn-glycero-3-phosphoethanolamine (DOPE), 1,2-diphytanoyl-sn-glycero-3-phosphoethanolamine (ME 16:0 PE), 1,2-distearoyl-sn-glycero-3-phosphoethanolamine, 1,2-dilinoleoyl-sn-glycero-3-phosphoethanolamine, 1,2-dilinolenoyl-sn-glycero-3-phosphoethanolamine, 1,2-diarachidonoyl-sn-glycero-3-phosphoethanolamine, 1,2-didocosahexaenoyl-sn-glycero-3-phosphoethanolamine, 1,2-dioleoyl-sn-glycero-3-phospho-rac-(1-glycerol) sodium salt (DOPG), sphingomyelin, and any mixtures thereof.

E81. The composition of any one of E59 to E80, wherein the delivery agent further comprises a structural lipid.

E82. The composition of E81, wherein the structural lipid is selected from the group consisting of cholesterol, fecosterol, sitosterol, ergosterol, campesterol, stigmasterol, brassicasterol, tomatidine, ursolic acid, alpha-tocopherol, and any mixtures thereof.

E83. The composition of any one of E59 to E82, wherein the delivery agent further comprises a PEG lipid.

E84. The composition of E83, wherein the PEG lipid is selected from the group consisting of a PEG-modified phosphatidylethanolamine, a PEG-modified phosphatidic acid, a PEG-modified ceramide, a PEG-modified dialkylamine, a PEG-modified diacylglycerol, a PEG-modified dialkylglycerol, and any mixtures thereof.

E85. The composition of any one of E59 to E84, wherein the delivery agent further comprises an ionizable lipid selected from the group consisting of 3-(didodecylamino)-N1,N1,4-tridodecyl-1-piperazineethanamine (KL10), N1-[2-(didodecylamino)ethyl]-N1,N4,N4-tridodecyl-1,4-piperazinediethanamine (KL22), 14,25-ditridecyl-15,18,21,24-tetraaza-octatriacontane (KL25), 1,2-dilinoleyloxy-N,N-dimethylaminopropane (DLin-DMA), 2,2-dilinoleyl-4-dimethylaminomethyl-[1,3]-dioxolane (DLin-K-DMA), heptatriaconta-6,9,28,31-tetraen-19-yl 4-(dimethylamino) butanoate (DLin-MC3-DMA), 2,2-dilinoleyl-4-(2-dimethylaminoethyl)-[1,3]-dioxolane (DLin-KC2-DMA), 1,2-dioleyloxy-N,N-dimethylaminopropane (DODMA), 2-({8-[(3β)-cholest-5-en-3-yloxy]octyl}oxy)-N,N-dimethyl-3-[(9Z,12Z)-octadeca-9,12-di en-1-yloxy]propan-1-amine (Octyl-CLinDMA), (2R)-2-({8-[(3β)-cholest-5-en-3-yloxy]octyl}oxy)-N,N-dimethyl-3-[(9Z,12Z)-octadeca-9,12-dien-1-yloxy]propan-1-amine (Octyl-CLinDMA (2R)), and (2S)-2-({8-[(3β)-cholest-5-en-3-yloxy]octyl}oxy)-N,N-dimethyl-3-[(9Z,12Z)-octadeca-9,12-dien-1-yloxy]propan-1-amine (Octyl-CLinDMA (2S)).

E86. The composition of any one of E59 to E85, wherein the delivery agent further comprises a phospholipid, a structural lipid, a PEG lipid, or any combination thereof.

E87. The composition of any one of E59 to E86, wherein the composition is formulated for in vivo delivery.

E88. The composition according any one of E59 to E87, which is formulated for intramuscular, subcutaneous, or intradermal delivery.

E89. A host cell comprising the polynucleotide of any one of E1 to E52.

E90. The host cell of E89, wherein the host cell is a eukaryotic cell.

E91. A vector comprising the polynucleotide of any one of E1 to E52.

E92. A method of making a polynucleotide comprising enzymatically or chemically synthesizing the polynucleotide of any one of E1 to E52.

E93. A polypeptide encoded by the polynucleotide of any one of E1 to E52, the composition of any one of E55 to E88, the host cell of E89 or E90, or the vector of E91 or produced by the method of E92.

E94. A method of expressing in vivo an active GALT polypeptide in a subject in need thereof comprising administering to the subject an effective amount of the polynucleotide of any one of E1 to E52, the composition of any one of E55 to E88, the host cell of E89 or E90, or the vector of E91.

E95. A method of treating galactosemia type 1 (Gal-1) in a subject in need thereof comprising administering to the subject a therapeutically effective amount of the polynucleotide of any one of E1 to E52, the composition of any one of E55 to E88, the host cell of E89 or E90, or the vector of E91, wherein the administration alleviates the signs or symptoms of Gal-1 in the subject.

E96. A method to prevent or delay the onset of Gal-1 signs or symptoms in a subject in need thereof comprising administering to the subject a prophylactically effective amount of the polynucleotide of any one of E1 to E52, the composition of any one of E55 to E88, the host cell of E89 or E90, or the vector of E91 before Gal-1 signs or symptoms manifest, wherein the administration prevents or delays the onset of Gal-1 signs or symptoms in the subject.

E97. A method to ameliorate the signs or symptoms of Gal-1 in a subject in need thereof comprising administering to the subject a therapeutically effective amount of the polynucleotide of any one of E1 to E52, the composition of any one of E55 to E88, the host cell of E89 or E90, or the vector of E91 before Gal-1 signs or symptoms manifest, wherein the administration ameliorates Gal-1 signs or symptoms in the subject.

31. EQUIVALENTS AND SCOPE

Those skilled in the art will recognize, or be able to ascertain using no more than routine experimentation, many equivalents to the specific embodiments in accordance with the invention described herein. The scope of the present invention is not intended to be limited to the above Description, but rather is as set forth in the appended claims.

In the claims, articles such as "a," "an," and "the" can mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

It is also noted that the term "comprising" is intended to be open and permits but does not require the inclusion of additional elements or steps. When the term "comprising" is used herein, the term "consisting of" is thus also encompassed and disclosed.

Where ranges are given, endpoints are included. Furthermore, it is to be understood that unless otherwise indicated or otherwise evident from the context and understanding of one of ordinary skill in the art, values that are expressed as ranges can assume any specific value or subrange within the stated ranges in different embodiments of the invention, to the tenth of the unit of the lower limit of the range, unless the context clearly dictates otherwise.

In addition, it is to be understood that any particular embodiment of the present invention that falls within the prior art can be explicitly excluded from any one or more of the claims. Since such embodiments are deemed to be known to one of ordinary skill in the art, they can be excluded even if the exclusion is not set forth explicitly herein. Any particular embodiment of the compositions of the invention (e.g., any nucleic acid or protein encoded thereby; any method of production; any method of use; etc.) can be excluded from any one or more claims, for any reason, whether or not related to the existence of prior art.

All cited sources, for example, references, publications, databases, database entries, and art cited herein, are incorporated into this application by reference, even if not expressly stated in the citation. In case of conflicting statements of a cited source and the instant application, the statement in the instant application shall control.

Section and table headings are not intended to be limiting.

EXAMPLES

Example 1

Chimeric Polynucleotide Synthesis

A. Triphosphate Route

Two regions or parts of a chimeric polynucleotide can be joined or ligated using triphosphate chemistry. According to this method, a first region or part of 100 nucleotides or less can be chemically synthesized with a 5' monophosphate and terminal 3'desOH or blocked OH. If the region is longer than 80 nucleotides, it can be synthesized as two strands for ligation.

If the first region or part is synthesized as a non-positionally modified region or part using in vitro transcription (IVT), conversion the 5'monophosphate with subsequent capping of the 3' terminus can follow. Monophosphate protecting groups can be selected from any of those known in the art.

The second region or part of the chimeric polynucleotide can be synthesized using either chemical synthesis or IVT methods. IVT methods can include an RNA polymerase that can utilize a primer with a modified cap. Alternatively, a cap of up to 80 nucleotides can be chemically synthesized and coupled to the IVT region or part.

It is noted that for ligation methods, ligation with DNA T4 ligase, followed by treatment with DNAse should readily avoid concatenation.

The entire chimeric polynucleotide need not be manufactured with a phosphate-sugar backbone. If one of the regions or parts encodes a polypeptide, then such region or part can comprise a phosphate-sugar backbone.

Ligation can then be performed using any known click chemistry, orthoclick chemistry, solulink, or other bioconjugate chemistries known to those in the art.

B. Synthetic Route

The chimeric polynucleotide can be made using a series of starting segments. Such segments include:

(a) Capped and protected 5' segment comprising a normal 3'OH (SEG. 1)

(b) 5' triphosphate segment which can include the coding region of a polypeptide and comprising a normal 3'OH (SEG. 2)

(c) 5' monophosphate segment for the 3' end of the chimeric polynucleotide (e.g., the tail) comprising cordycepin or no 3'OH (SEG. 3)

After synthesis (chemical or IVT), segment 3 (SEG. 3) can be treated with cordycepin and then with pyrophosphatase to create the 5'monophosphate.

Segment 2 (SEG. 2) can then be ligated to SEG. 3 using RNA ligase. The ligated polynucleotide can then be purified and treated with pyrophosphatase to cleave the diphosphate. The treated SEG.2-SEG. 3 construct is then purified and SEG. 1 is ligated to the 5' terminus. A further purification step of the chimeric polynucleotide can be performed.

Where the chimeric polynucleotide encodes a polypeptide, the ligated or joined segments can be represented as: 5' UTR (SEG. 1), open reading frame or ORF (SEG. 2) and 3' UTR+PolyA (SEG. 3).

The yields of each step can be as much as 90-95%.

Example 2

PCR for cDNA Production

PCR procedures for the preparation of cDNA can be performed using 2×KAPA HIFI™ HotStart ReadyMix by Kapa Biosystems (Woburn, Mass.). This system includes 2× KAPA ReadyMix 12.5 µl; Forward Primer (10 µM) 0.75 µl; Reverse Primer (10 µM) 0.75 µl; Template cDNA −100 ng; and $dH_2O$ diluted to 25.0 µl. The PCR reaction conditions can be: at 95° C. for 5 min. and 25 cycles of 98° C. for 20 sec, then 58° C. for 15 sec, then 72° C. for 45 sec, then 72° C. for 5 min. then 4° C. to termination.

The reverse primer of the instant invention can incorporate a poly-$T_{120}$ (SEQ ID NO: 177) for a poly-$A_{120}$ (SEQ ID NO: 176) in the mRNA. Other reverse primers with longer or shorter poly(T) tracts can be used to adjust the length of the poly(A) tail in the polynucleotide mRNA.

The reaction can be cleaned up using Invitrogen's PURELINK™ PCR Micro Kit (Carlsbad, Calif.) per manufacturer's instructions (up to 5 µg). Larger reactions will require a cleanup using a product with a larger capacity. Following the cleanup, the cDNA can be quantified using the NANODROP™ and analyzed by agarose gel electrophoresis to confirm the cDNA is the expected size. The cDNA can then be submitted for sequencing analysis before proceeding to the in vitro transcription reaction.

Example 3

In Vitro Transcription (IVT)

The in vitro transcription reactions can generate polynucleotides containing uniformly modified polynucleotides. Such uniformly modified polynucleotides can comprise a region or part of the polynucleotides of the invention. The input nucleotide triphosphate (NTP) mix can be made using natural and un-natural NTPs.

A typical in vitro transcription reaction can include the following:

1 Template cDNA—1.0

2 10× transcription buffer (400 mM Tris-HCl pH 8.0, 190 mM $MgCl_2$, 50 mM DTT, 10 mM Spermidine)—2.0 μl 3 Custom NTPs (25 mM each)—7.2 μl 4 RNase Inhibitor—20 U 5 T7 RNA polymerase—3000 U 6 $dH_2O$—Up to 20.0 μl. and 7 Incubation at 37° C. for 3 hr-5 hrs.

The crude IVT mix can be stored at 4° C. overnight for cleanup the next day. 1 U of RNase-free DNase can then be used to digest the original template. After 15 minutes of incubation at 37° C., the mRNA can be purified using Ambion's MEGACLEAR™ Kit (Austin, Tex.) following the manufacturer's instructions. This kit can purify up to 500 μg of RNA. Following the cleanup, the RNA can be quantified using the NanoDrop and analyzed by agarose gel electrophoresis to confirm the RNA is the proper size and that no degradation of the RNA has occurred.

Example 4

Enzymatic Capping

Capping of a polynucleotide can be performed with a mixture includes: IVT RNA 60 μg-180 μg and $dH_2O$ up to 72 μl. The mixture can be incubated at 65° C. for 5 minutes to denature RNA, and then can be transferred immediately to ice.

The protocol can then involve the mixing of 10× Capping Buffer (0.5 M Tris-HCl (pH 8.0), 60 mM KCl, 12.5 mM $MgCl_2$) (10.0 μl); 20 mM GTP (5.0 μl); 20 mM S-Adenosyl Methionine (2.5 μl); RNase Inhibitor (100 U); 2'-O-Methyltransferase (400U); Vaccinia capping enzyme (Guanylyl transferase) (40 U); $dH_2O$ (Up to 28 μl); and incubation at 37° C. for 30 minutes for 60 μg RNA or up to 2 hours for 180 μg of RNA.

The polynucleotide can then be purified using Ambion's MEGACLEAR™ Kit (Austin, Tex.) following the manufacturer's instructions. Following the cleanup, the RNA can be quantified using the NANODROP™ (ThermoFisher, Waltham, Mass.) and analyzed by agarose gel electrophoresis to confirm the RNA is the proper size and that no degradation of the RNA has occurred. The RNA product can also be sequenced by running a reverse-transcription-PCR to generate the cDNA for sequencing.

Example 5

PolyA Tailing Reaction

Without a poly-T in the cDNA, a poly-A tailing reaction must be performed before cleaning the final product. This can be done by mixing Capped IVT RNA (100 μl); RNase Inhibitor (20 U); 10× Tailing Buffer (0.5 M Tris-HCl (pH 8.0), 2.5 M NaCl, 100 mM $MgCl_2$)(12.0 μl); 20 mM ATP (6.0 μl); Poly-A Polymerase (20 U); $dH_2O$ up to 123.5 μl and incubating at 37° C. for 30 min. If the poly-A tail is already in the transcript, then the tailing reaction can be skipped and proceed directly to cleanup with Ambion's MEGACLEAR™ kit (Austin, Tex.) (up to 500 μg). Poly-A Polymerase is, in some cases, a recombinant enzyme expressed in yeast.

It should be understood that the processivity or integrity of the polyA tailing reaction does not always result in an exact size polyA tail. Hence polyA tails of approximately between 40-200 nucleotides, e.g., about 40, 50, 60, 70, 80, 90, 91, 92, 93, 94, 95, 96, 97, 98, 99, 100, 101, 102, 103, 104, 105, 106, 107, 108, 109, 110, 150-165, 155, 156, 157, 158, 159, 160, 161, 162, 163, 164 or 165 are within the scope of the invention.

Example 6

Natural 5' Caps and 5' Cap Analogues

5'-capping of polynucleotides can be completed concomitantly during the in vitro-transcription reaction using the following chemical RNA cap analogs to generate the 5'-guanosine cap structure according to manufacturer protocols: 3'-O-Me-m7G(5')ppp(5') G [the ARCA cap]; G(5')ppp(5')A; G(5')ppp(5')G; m7G(5')ppp(5')A; m7G(5')ppp(5')G (New England BioLabs, Ipswich, Mass.). 5'-capping of modified RNA can be completed post-transcriptionally using a Vaccinia Virus Capping Enzyme to generate the "Cap 0" structure: m7G(5')ppp(5')G (New England BioLabs, Ipswich, Mass.). Cap 1 structure can be generated using both Vaccinia Virus Capping Enzyme and a 2'-O methyl-transferase to generate: m7G(5')ppp(5')G-2'-O-methyl. Cap 2 structure can be generated from the Cap 1 structure followed by the 2'-O-methylation of the 5'-antepenultimate nucleotide using a 2'-O methyl-transferase. Cap 3 structure can be generated from the Cap 2 structure followed by the 2'-O-methylation of the 5'-preantepenultimate nucleotide using a 2'-O methyl-transferase. Enzymes can be derived from a recombinant source.

When transfected into mammalian cells, the modified mRNAs can have a stability of between 12-18 hours or more than 18 hours, e.g., 24, 36, 48, 60, 72 or greater than 72 hours.

Example 7

Capping Assays

A. Protein Expression Assay

Polynucleotides encoding a polypeptide, containing any of the caps taught herein, can be transfected into cells at equal concentrations. After 6, 12, 24 and 36 hours post-transfection, the amount of protein secreted into the culture medium can be assayed by ELISA. Synthetic polynucleotides that secrete higher levels of protein into the medium would correspond to a synthetic polynucleotide with a higher translationally-competent Cap structure.

B. Purity Analysis Synthesis

Polynucleotides encoding a polypeptide, containing any of the caps taught herein, can be compared for purity using denaturing Agarose-Urea gel electrophoresis or HPLC analysis. Polynucleotides with a single, consolidated band by electrophoresis correspond to the higher purity product compared to polynucleotides with multiple bands or streaking bands. Synthetic polynucleotides with a single HPLC peak would also correspond to a higher purity product. The capping reaction with a higher efficiency would provide a more pure polynucleotide population.

C. Cytokine Analysis

Polynucleotides encoding a polypeptide, containing any of the caps taught herein, can be transfected into cells at multiple concentrations. After 6, 12, 24 and 36 hours post-transfection the amount of pro-inflammatory cytokines such as TNF-alpha and IFN-beta secreted into the culture medium can be assayed by ELISA. Polynucleotides resulting in the secretion of higher levels of pro-inflammatory cytokines into the medium would correspond to polynucleotides containing an immune-activating cap structure.

D. Capping Reaction Efficiency

Polynucleotides encoding a polypeptide, containing any of the caps taught herein, can be analyzed for capping reaction efficiency by LC-MS after nuclease treatment. Nuclease treatment of capped polynucleotides would yield a mixture of free nucleotides and the capped 5'-5-triphosphate cap structure detectable by LC-MS. The amount of capped product on the LC-MS spectra can be expressed as a percent of total polynucleotide from the reaction and would correspond to capping reaction efficiency. The cap structure with higher capping reaction efficiency would have a higher amount of capped product by LC-MS.

Example 8

Agarose Gel Electrophoresis of Modified RNA or RT PCR Products

Individual polynucleotides (200-400 ng in a 20 μl volume) or reverse transcribed PCR products (200-400 ng) can be loaded into a well on a non-denaturing 1.2% Agarose E-Gel (Invitrogen, Carlsbad, Calif.) and run for 12-15 minutes according to the manufacturer protocol.

Example 9

Nanodrop Modified RNA Quantification and UV Spectral Data

Modified polynucleotides in TE buffer (1 μl) can be used for Nanodrop UV absorbance readings to quantitate the yield of each polynucleotide from an chemical synthesis or in vitro transcription reaction.

Example 10

Formulation of Modified mRNA Using Lipidoids

Polynucleotides can be formulated for in vitro experiments by mixing the polynucleotides with the lipidoid at a set ratio prior to addition to cells. In vivo formulation can require the addition of extra ingredients to facilitate circulation throughout the body. To test the ability of these lipidoids to form particles suitable for in vivo work, a standard formulation process used for siRNA-lipidoid formulations can be used as a starting point. After formation of the particle, polynucleotide can be added and allowed to integrate with the complex. The encapsulation efficiency can be determined using a standard dye exclusion assays.

Example 11

Method of Screening for Protein Expression

A. Electrospray Ionization

A biological sample that can contain proteins encoded by a polynucleotide administered to the subject can be prepared and analyzed according to the manufacturer protocol for electrospray ionization (ESI) using 1, 2, 3 or 4 mass analyzers. A biologic sample can also be analyzed using a tandem ESI mass spectrometry system.

Patterns of protein fragments, or whole proteins, can be compared to known controls for a given protein and identity can be determined by comparison.

B. Matrix-Assisted Laser Desorption/Ionization

A biological sample that can contain proteins encoded by one or more polynucleotides administered to the subject can be prepared and analyzed according to the manufacturer protocol for matrix-assisted laser desorption/ionization (MALDI).

Patterns of protein fragments, or whole proteins, can be compared to known controls for a given protein and identity can be determined by comparison.

C. Liquid Chromatography-Mass Spectrometry-Mass Spectrometry

A biological sample, which can contain proteins encoded by one or more polynucleotides, can be treated with a trypsin enzyme to digest the proteins contained within. The resulting peptides can be analyzed by liquid chromatography-mass spectrometry-mass spectrometry (LC/MS/MS). The peptides can be fragmented in the mass spectrometer to yield diagnostic patterns that can be matched to protein sequence databases via computer algorithms. The digested sample can be diluted to achieve 1 ng or less starting material for a given protein. Biological samples containing a simple buffer background (e.g., water or volatile salts) are amenable to direct in-solution digest; more complex backgrounds (e.g., detergent, non-volatile salts, glycerol) require an additional clean-up step to facilitate the sample analysis.

Patterns of protein fragments, or whole proteins, can be compared to known controls for a given protein and identity can be determined by comparison.

Example 12

Synthesis of mRNA Encoding GALT

Sequence optimized polynucleotides encoding GALT polypeptides, i.e., SEQ ID NOs: 1 or 3, are synthesized and characterized as described in Examples 1 to 11. mRNA's encoding both human GALT isoforms were prepared for the Examples described below, and were synthesized and characterized as described in Examples 1 to 11.

An mRNA encoding human GALT can be constructed, e.g., by using the ORF sequence provided in SEQ ID NO: 2 or 4. The mRNA sequence includes both 5' and 3' UTR regions (see, e.g., SEQ ID NOs: 52 and 77, respectively). In a construct, the 5' UTR and 3' UTR sequences are SEQ ID NO: 52 and SEQ ID NOs: 77 or 98, respectively (see Table 5). 5' UTR

```
                                        (SEQ ID NO: 52)
5' UTR UCAAGCUUUUGGACCCUCGUACAGAAGCUAAUACGACUCACUAU

AGGGAAAUAAGAGAGAAAAGAAGAGUAAGAAGAAAUAUAAGAGCCACC

                                        (SEQ ID NO: 77)
3' UTR UGAUAAUAGGCUGGAGCCUCGGUGGCCAUGCUUCUUGCCCCUUG

GGCCUCCCCCCAGCCCCUCCUCCCCUUCCUGCACCCGUACCCCCGUGGUCU

UUGAAUAAAGUCUGAGUGGGCGGC
```

The GALT mRNA sequence was prepared as modified mRNA. Specifically, during in vitro translation, modified mRNA can be generated using 5-methoxy-UTP to ensure that the mRNAs contain 100% 5-methoxy-uridine instead of uridine. Further, GALT-mRNA can be synthesized with a primer that introduces a polyA-tail, and a Cap 1 structure is generated on both mRNAs using Vaccinia Virus Capping Enzyme and a 2'-O methyl-transferase to generate: m7G(5) ppp(5')G-2'-O-methyl.

Example 13

Detecting Endogenous GALT Expression In Vitro

GALT expression is characterized in a variety of cell lines derived from both mice and human sources. Cell are cultured in standard conditions and cell extracts are obtained by placing the cells in lysis buffer. For comparison purposes, appropriate controls are also prepared. To analyze GALT expression, lysate samples are prepared from the tested cells and mixed with lithium dodecyl sulfate sample loading buffer and subjected to standard Western blot analysis. For detection of GALT, the antibody used is a commercial anti-GALT antibody. For detection of a load control, the antibody used is anti-citrase synthase (rabbit polyclonal; PAS-22126; Thermo-Fisher Scientific®). To examine the localization of endogenous GALT, immunofluorescence analysis is performed on cells. GALT expression is detected using a commercial anti-GALT. The location of specific organelles can be detected with existing commercial products. For example, mitochondria can be detected using Mitotracker, and the nucleus can be stained with DAPI. Image analysis is performed on a Zeiss ELYRA imaging system.

Endogenous GALT expression can be used as a base line to determine changes in GALT expression resulting from transfection with mRNAs comprising nucleic acids encoding GALT.

Example 14

In Vitro Expression of GALT in HeLa Cells

To measure in vitro expression of human GALT in HeLa cells, those cells are seeded on 12-well plates (BD Biosciences, San Jose, USA) one day prior to transfection. mRNA formulations comprising human GALT or a GFP control are transfected using 800 ng mRNA and 2 μL Lipofectamin 2000 in 60 μL OPTI-MEM per well and incubated.

After 24 hours, the cells in each well are lysed using a consistent amount of lysis buffer. Appropriate controls are used. Protein concentrations of each are determined using a BCA assay according to manufacturer's instructions. To analyze GALT expression, equal loads of each lysate (24 μg) are prepared in a loading buffer and subjected to standard Western blot analysis. For detection of GALT, a commercial anti-GALT antibody is used according to the manufacturer's instructions.

Example 15

In Vitro GALT Activity in HeLa Cells

An in vitro GALT activity assay is performed to determine whether GALT exogenously-expressed after introduction of mRNA comprising a GALT sequence is active.

A. Expression Assay

HeLa cells are transfected with mRNA formulations comprising human GALT or a GFP control. Cells are transfected with Lipofectamin 2000 and lysed as described in Example 14 above. Appropriate controls are also prepared.

B. Activity Assay

To assess whether exogenous GALT can function, an in vitro activity assay is performed using transfected HeLa cell lysates as the source of enzymatic activity. To begin, lysate is mixed GALT substrate. The reaction is stopped by adding 100 g/L TCA and vortexing. The reaction tubes are then centrifuged at 13,000 g for 1 min, and the supernatant is analyzed for the presence of labeled enzymatic products resulting from the activity of GALT using HPLC-based separation and quantification. Specifically, 20 μL of each activity reaction supernatant are analyzed using a HPLC system equipped with a Quaternary-Pump, a Multi-sampler, a Thermostated Column-Compartment, a Poroshell EC-C18 120 HPLC-column and a Radiometric Detector controlled by OpenLAB Chromatography Data System, all used according to the manufacturers' recommendations.

Example 16

Measuring In Vitro Expression of GALT in Cells

Cells from normal subjects and galactosemia type 1 patients are examined for their capacity to express exogenous GALT. Cells are transfected with mRNA formulations comprising human GALT, mouse GALT, or a GFP control via electroporation using a standard protocol. Each construct is tested separately. After incubation, cells are lysed and protein concentration in each lysate is measured using a suitable assay, e.g., by BCA assay. To analyze GALT expression, equal loads of each lysate are prepared in a loading buffer and subjected to standard Western blot analysis. For detection of GALT, an anti-GALT is used. For detection of a load control, the antibody used is anti-citrase synthase (rabbit polyclonal; MA5-17625; Pierce®).

Example 17

Measuring In Vitro GALT Activity in Lysates

A. Expression

Cells from normal human subjects and galactosemia type 1 patients are cultured. Cells are transfected with mRNA formulations comprising human GALT, mouse GALT, or a GFP control via electroporation using a standard protocol.

B. Activity Assay

To assess whether exogenous GALT function, an in vitro activity assay is performed using transfected cell lysates as the source of enzymatic activity. Lysate containing expressed GALT protein is incubated with labeled GALT substrate, and the activity of GALT is quantified by measuring the levels of labeled products resulting from the enzymatic activity of GALT.

Example 18

In Vivo GALT Expression in Animal Models

To assess the ability of GALT-containing mRNA's to facilitate GALT expression in vivo, mRNA encoding human GALT is introduced into C57B/L6 mice. C57B/L6 mice are injected intravenously with either control mRNA (NT-FIX) or human GALT mRNA. The mRNA is formulated in lipid nanoparticles for delivery into the mice. Mice are sacrificed after 24 or 48 hrs. and GALT protein levels in liver lysates are determined by capillary electrophoresis (CE). Citrate synthase expression is examined for use as a load control. For control NT-FIX injections, 4 mice are tested for each time point. For human GALT mRNA injections, 6 mice are tested for each time point. Treatment with mRNA encoding GALT is expected to reliably induce expression of GALT.

Example 19

Human GALT Mutant and Chimeric Constructs

A polynucleotide of the present invention can comprise at least a first region of linked nucleosides encoding human GALT, which can be constructed, expressed, and characterized according to the examples above. Similarly, the polynucleotide sequence can contain one or more mutations that results in the expression of a GALT with increased or decreased activity. Furthermore, the polynucleotide sequence encoding GALT can be part of a construct encoding a chimeric fusion protein.

Example 20

Production of Nanoparticle Compositions

A. Production of Nanoparticle Compositions

Nanoparticles can be made with mixing processes such as microfluidics and T-junction mixing of two fluid streams, one of which contains the polynucleotide and the other has the lipid components.

Lipid compositions are prepared by combining an ionizable amino lipid disclosed herein, e.g., a lipid according to Formula (I) such as Compound 18 or a lipid according to Formula (III) such as Compound 236, a phospholipid (such as DOPE or DSPC, obtainable from Avanti Polar Lipids, Alabaster, Ala.), a PEG lipid (such as 1,2-dimyristoyl-sn-glycerol methoxypolyethylene glycol, also known as PEG-DMG, obtainable from Avanti Polar Lipids, Alabaster, Ala.), and a structural lipid (such as cholesterol, obtainable from Sigma-Aldrich, Taufkirchen, Germany, or a corticosteroid (such as prednisolone, dexamethasone, prednisone, and hydrocortisone), or a combination thereof) at concentrations of about 50 mM in ethanol. Solutions should be refrigerated for storage at, for example, −20° C. Lipids are combined to yield desired molar ratios and diluted with water and ethanol to a final lipid concentration of between about 5.5 mM and about 25 mM.

Nanoparticle compositions including a polynucleotide and a lipid composition are prepared by combining the lipid solution with a solution including the a polynucleotide at lipid composition to polynucleotide wt:wt ratios between about 5:1 and about 50:1. The lipid solution is rapidly injected using a NanoAssemblr microfluidic based system at flow rates between about 10 ml/min and about 18 ml/min into the polynucleotide solution to produce a suspension with a water to ethanol ratio between about 1:1 and about 4:1.

For nanoparticle compositions including an RNA, solutions of the RNA at concentrations of 0.1 mg/ml in deionized water are diluted in 50 mM sodium citrate buffer at a pH between 3 and 4 to form a stock solution.

Nanoparticle compositions can be processed by dialysis to remove ethanol and achieve buffer exchange. Formulations are dialyzed twice against phosphate buffered saline (PBS), pH 7.4, at volumes 200 times that of the primary product using Slide-A-Lyzer cassettes (Thermo Fisher Scientific Inc., Rockford, Ill.) with a molecular weight cutoff of 10 kD. The first dialysis is carried out at room temperature for 3 hours. The formulations are then dialyzed overnight at 4° C. The resulting nanoparticle suspension is filtered through 0.2 μm sterile filters (Sarstedt, Nümbrecht, Germany) into glass vials and sealed with crimp closures. Nanoparticle composition solutions of 0.01 mg/ml to 0.10 mg/ml are generally obtained.

The method described above induces nano-precipitation and particle formation. Alternative processes including, but not limited to, T-junction and direct injection, can be used to achieve the same nano-precipitation.

B. Characterization of Nanoparticle Compositions

A Zetasizer Nano ZS (Malvern Instruments Ltd, Malvern, Worcestershire, UK) can be used to determine the particle size, the polydispersity index (PDI) and the zeta potential of the nanoparticle compositions in 1×PBS in determining particle size and 15 mM PBS in determining zeta potential.

Ultraviolet-visible spectroscopy can be used to determine the concentration of a polynucleotide (e.g., RNA) in nanoparticle compositions. 100 μL of the diluted formulation in 1×PBS is added to 900 μL of a 4:1 (v/v) mixture of methanol and chloroform. After mixing, the absorbance spectrum of the solution is recorded, for example, between 230 nm and 330 nm on a DU 800 spectrophotometer (Beckman Coulter, Beckman Coulter, Inc., Brea, Calif.). The concentration of polynucleotide in the nanoparticle composition can be calculated based on the extinction coefficient of the polynucleotideused in the composition and on the difference between the absorbance at a wavelength of, for example, 260 nm and the baseline value at a wavelength of, for example, 330 nm.

For nanoparticle compositions including an RNA, a QUANT-IT™ RIBOGREEN® RNA assay (Invitrogen Corporation Carlsbad, Calif.) can be used to evaluate the encapsulation of an RNA by the nanoparticle composition. The samples are diluted to a concentration of approximately 5 μg/mL in a TE buffer solution (10 mM Tris-HCl, 1 mM EDTA, pH 7.5). 50 μL of the diluted samples are transferred to a polystyrene 96 well plate and either 50 μL of TE buffer or 50 μL of a 2% Triton X-100 solution is added to the wells. The plate is incubated at a temperature of 37° C. for 15 minutes. The RIBOGREEN® reagent is diluted 1:100 in TE buffer, and 100 μL of this solution is added to each well. The fluorescence intensity can be measured using a fluorescence plate reader (Wallac Victor 1420 Multilablel Counter; Perkin Elmer, Waltham, Mass.) at an excitation wavelength of, for example, about 480 nm and an emission wavelength of, for example, about 520 nm. The fluorescence values of the reagent blank are subtracted from that of each of the samples and the percentage of free RNA is determined by dividing the fluorescence intensity of the intact sample (without addition of Triton X-100) by the fluorescence value of the disrupted sample (caused by the addition of Triton X-100).

Exemplary formulations of the nanoparticle compositions are presented in the Table 7 below. The term “Compound” refers to an ionizable lipid such as MC3, Compound 18, or Compound 236. “Phospholipid” can be DSPC or DOPE. “PEG-lipid” can be PEG-DMG or Compound 428.

TABLE 7

Exemplary Formulations of Nanoparticles

| Composition (mol %) | Components |
|---|---|
| 40:20:38.5:1.5 | Compound:Phospholipid:Chol:PEG-lipid |
| 45:15:38.5:1.5 | Compound:Phospholipid:Chol:PEG-lipid |
| 50:10:38.5:1.5 | Compound:Phospholipid:Chol:PEG-lipid |
| 55:5:38.5:1.5 | Compound:Phospholipid:Chol:PEG-lipid |
| 60:5:33.5:1.5 | Compound:Phospholipid:Chol:PEG-lipid |
| 45:20:33.5:1.5 | Compound:Phospholipid:Chol:PEG-lipid |
| 50:20:28.5:1.5 | Compound:Phospholipid:Chol:PEG-lipid |

TABLE 7-continued

| Exemplary Formulations of Nanoparticles | |
|---|---|
| Composition (mol %) | Components |
| 55:20:23.5:1.5 | Compound:Phospholipid:Chol:PEG-lipid |
| 60:20:18.5:1.5 | Compound:Phospholipid:Chol:PEG-lipid |
| 40:15:43.5:1.5 | Compound:Phospholipid:Chol:PEG-lipid |
| 50:15:33.5:1.5 | Compound:Phospholipid:Chol:PEG-lipid |
| 55:15:28.5:1.5 | Compound:Phospholipid:Chol:PEG-lipid |
| 60:15:23.5:1.5 | Compound:Phospholipid:Chol:PEG-lipid |
| 40:10:48.5:1.5 | Compound:Phospholipid:Chol:PEG-lipid |
| 45:10:43.5:1.5 | Compound:Phospholipid:Chol:PEG-lipid |
| 55:10:33.5:1.5 | Compound:Phospholipid:Chol:PEG-lipid |
| 60:10:28.5:1.5 | Compound:Phospholipid:Chol:PEG-lipid |
| 40:5:53.5:1.5 | Compound:Phospholipid:Chol:PEG-lipid |
| 45:5:48.5:1.5 | Compound:Phospholipid:Chol:PEG-lipid |
| 50:5:43.5:1.5 | Compound:Phospholipid:Chol:PEG-lipid |
| 40:20:40:0 | Compound:Phospholipid:Chol:PEG-lipid |
| 45:20:35:0 | Compound:Phospholipid:Chol:PEG-lipid |
| 50:20:30:0 | Compound:Phospholipid:Chol:PEG-lipid |
| 55:20:25:0 | Compound:Phospholipid:Chol:PEG-lipid |
| 60:20:20:0 | Compound:Phospholipid:Chol:PEG-lipid |
| 40:15:45:0 | Compound:Phospholipid:Chol:PEG-lipid |
| 45:15:40:0 | Compound:Phospholipid:Chol:PEG-lipid |
| 50:15:35:0 | Compound:Phospholipid:Chol:PEG-lipid |
| 55:15:30:0 | Compound:Phospholipid:Chol:PEG-lipid |
| 60:15:25:0 | Compound:Phospholipid:Chol:PEG-lipid |
| 40:10:50:0 | Compound:Phospholipid:Chol:PEG-lipid |
| 45:10:45:0 | Compound:Phospholipid:Chol:PEG-lipid |
| 50:10:40:0 | Compound:Phospholipid:Chol:PEG-lipid |
| 55:10:35:0 | Compound:Phospholipid:Chol:PEG-lipid |
| 60:10:30:0 | Compound:Phospholipid:Chol:PEG-lipid |

Example 21

Figure 8B:
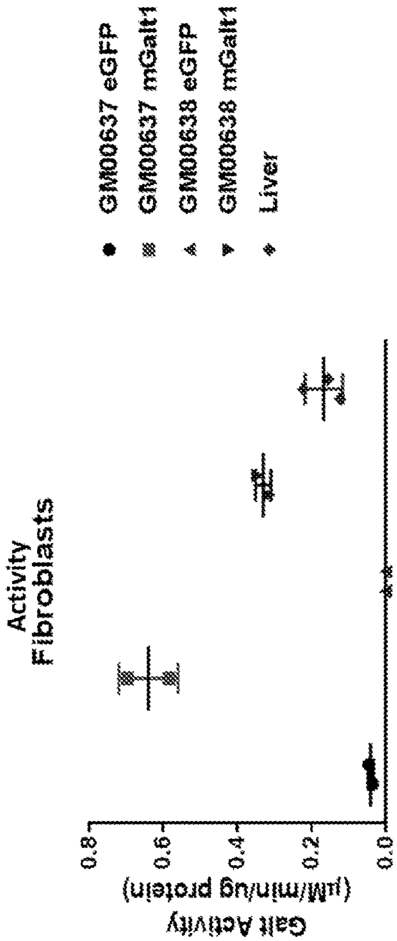
FIG. 8B shows GALT activity levels in normal fibroblasts (GM0637) and type 1 galactosemia patient fibroblasts (GM0638) after administration of mRNA encoding mouse GALT isoform 1 (mGalt1) or a control mRNA encoding eGFP.
Figure 8A:
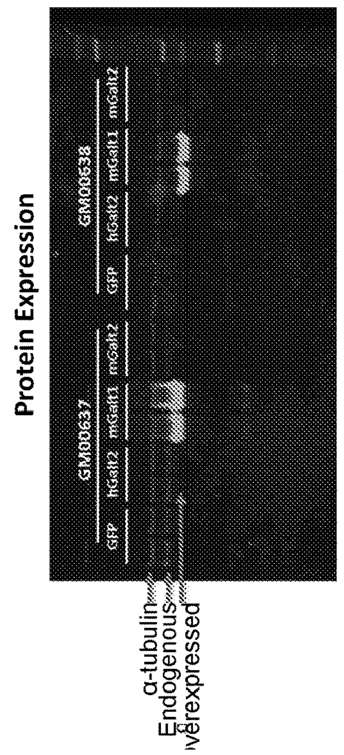
FIG. 8C shows type 1 galactosemia patient fibroblasts grown in: (i) culture medium containing glucose (left panel), (ii) culture medium containing galactose after administration of mRNA encoding eGFP control (center panel), or (iii) culture medium containing galactose after administration of mRNA encoding mouse GALT isoform 1 (mGALT1).

In Vitro GALT Protein Expression, Activity, and Function in Galactosemia Patient Fibroblasts GALT protein expression was determined for normal fibroblasts (GM00637) and type 1 galactosemia patient fibroblasts (GM00638) after transfection of mRNA encoding human GALT isoform 2 (hGalt2; Construct #23), mouse GALT isoform 1 (mGalt1; Construct #21), mouse GALT isoform 2 (mGalt2; Construct #24) or control GFP to the cells. GALT protein expression was determined by Western Blot analysis (Abcam, AB178406). GALT enzymatic activity (μM/min/μg protein) was determined by a HPLC-based assay as described previously in Lindhout M, et al., *Clinica chimica Acta,* 411(13-14):980-983, 2010. Transfection of mRNA encoding mGalt1 resulted in GALT overexpression in both normal fibroblasts (GM00637) and type 1 galactosemia patient fibroblasts (GM00638) (FIG. 8A). GALT activity was detected by HPLC in both normal and patient fibroblasts administered mRNA encoding mGalt1 (FIG. 8B).

Figure 8C:
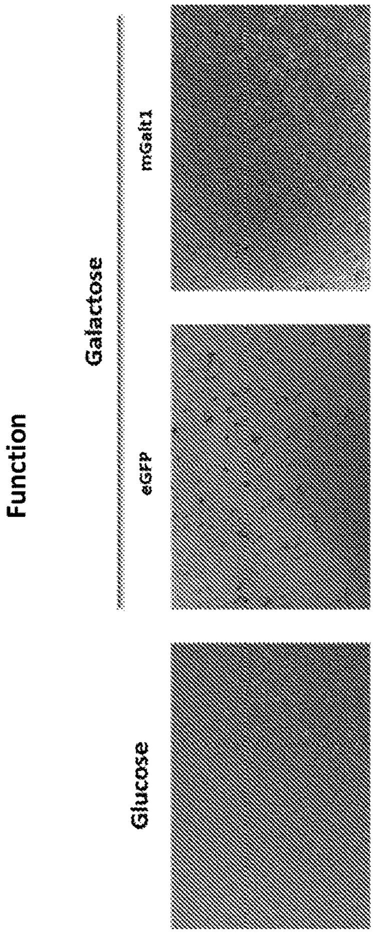

As shown in FIG. 8C, type 1 galactosemia fibroblasts (GM00638) proliferated normally in glucose-containing medium (FIG. 8C, left panel). However, patient fibroblasts administered control eGFP died within 5 days when cultured in galactose-containing medium (FIG. 8C, center panel). Administration of mRNA encoding mGalt1 partially rescued (about 50%) of galactose-induced death in the fibroblasts isolated from patients with galactosemia (FIG. 8C, right panel).

Example 22

In Vivo GALT Protein Expression and Activity in Wild-Type Mice Administered mRNA Encoding mGalt1

Figure 9A:
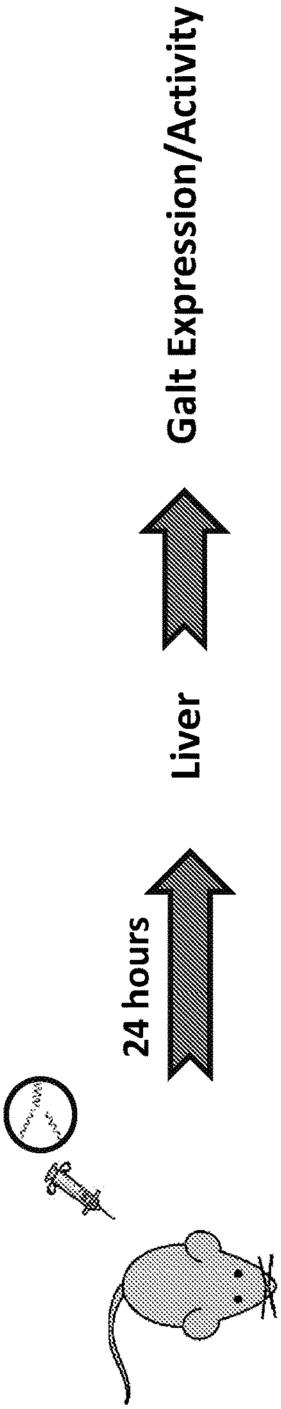
FIG. 9A is an experimental design diagram showing that wild-type mice were IV administered a single dose of mRNA encoding mouse Galt1 or a control mRNA encoding NTFIX (non-translated Factor IX), and after 24 hours GALT protein expression and activity were measured in liver.
Figure 9B:
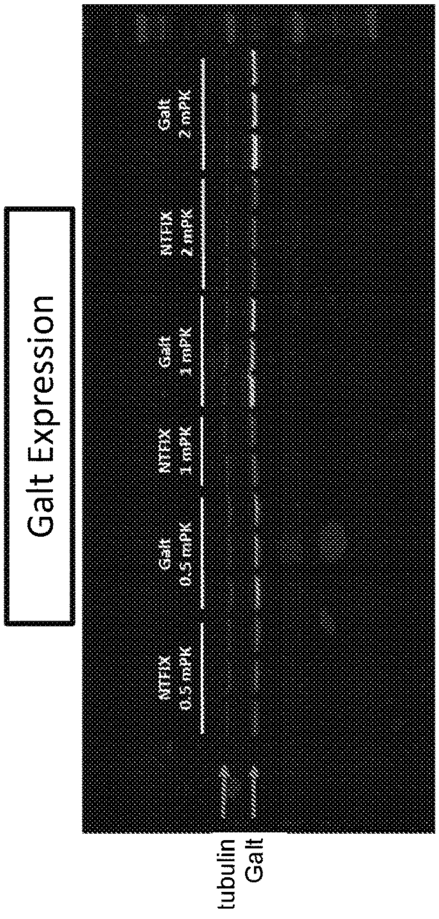
FIG. 9B shows GALT protein expression in liver 24 hours after a single IV administration of a 0.5 mg/kg, 1 mg/kg, or 2 mg/kg dose of mRNA encoding mouse Galt1 to wild-type mice. Mice administered 0.5 mg/kg, 1 mg/kg, or 2 mg/kg of mRNA encoding NTFIX were used as controls.
Figure 9C:
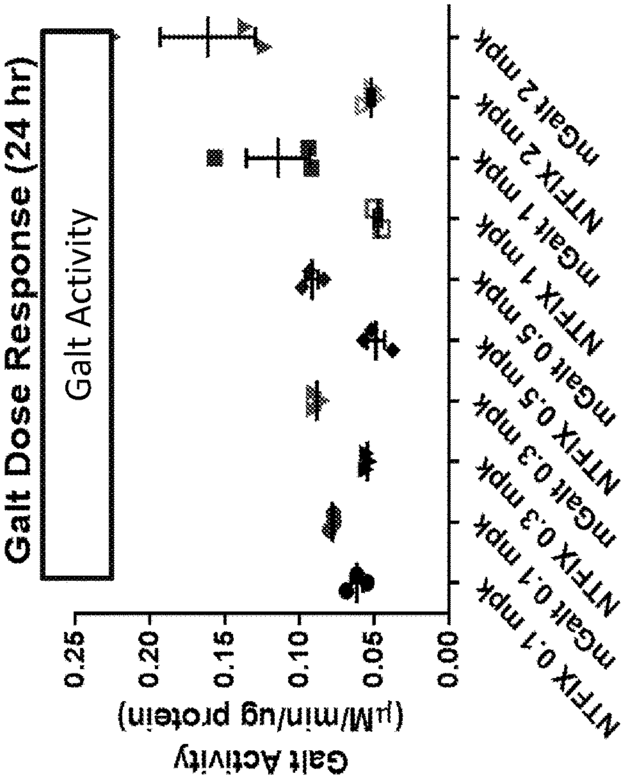
FIG. 9C shows GALT activity in liver 24 hours after a single IV administration of a 0.1 mg/kg, 0.3 mg/kg, 0.5 mg/kg, 1 mg/kg, or 2 mg/kg dose of mRNA encoding mouse Galt1 to wild-type mice. mRNA encoding NTFIX was used as control.

GALT activity and protein expression in liver were measured 24 hours after a single administration of 1-methyl-pseudouridine modified mRNA encoding mouse Galt1 (mGalt1; Construct #21) or control mRNA encoding NTFIX (non-translated Factor IX; Construct #22) formulated in lipid nanoparticle (MC3) to wild-type mice (FIG. 9A). The single doses were administered as 0.1 mg/kg, 0.3 mg/kg, 0.5 mg/kg, 1 mg/kg, and 2 mg/kg intravenous injections. Administration of modified mRNA encoding mGalt1 resulted in a dose-dependent increase in GALT protein expression (FIG. 9B) and activity (FIG. 9C) in liver of wild-type mice.

In a further study, wild-type mice were administered 1-methyl-pseudouridine modified mRNA encoding mGalt1 or control mRNA encoding NTFIX formulated in lipid nanoparticle (MC3) as single 0.3 mg/kg intravenous injection, and GALT activity in liver was measured 1 day, 3 days, and 7 days post-administration (FIG. 10A). GALT enzymatic activity was determined by an HPLC-based assay. Elevated GALT activity in the liver was detected 1, 3, and 7 days after a single intravenous injection of modified mRNA encoding mGalt1 at 0.3 mg/kg (FIG. 10B). These results show that GALT activity was still elevated (about 10%) in the liver at least 1 week after a single administration of modified mRNA encoding mGalt1.

Example 23

In Vivo GALT Protein Expression, Activity, and Function in GALT Knock-Out Mice Administered mRNA Encoding mGalt1 or hGalt1

GALT protein expression, GALT activity, and biomarker (Gal-1-P) level in liver as well as biomarker (Gal-1-P) level in red blood cells from GALT knock-out mice (KO mice) measured 24 hours after intravenous (IV) administration of 1-methyl-pseudouridine modified mRNA encoding mouse Galt1 (Construct #21) and human GALT isoform 1 (hGalt1; Construct #20) or control mRNA encoding NTFIX (non-translated Factor IX; Construct #22) formulated in lipid nanoparticle (MC3). GALT protein expression and activity were determined 24 hours after administration of a single IV dose of 0.1 mg/kg, 0.3 mg/kg, or 0.5 mg/kg modified mRNA. Galactose-1-phosphate (Gal-1-P) levels in liver and red blood cells (RBC) were determined for samples taken 24 hours after administration of a IV single dose of 0.5 mg/kg modified mRNA using gas chromatography-mass spectrometry (GC-MS) as descrived previously (Chen J et al., *Clinical Chemistry,* 48(4):604-12, 2002).

A single IV administration of modified mRNA encoding either mGalt or hGalt resulted in dose dependent expression of GALT protein in livers of KO mice (FIG. 11A). GALT protein expression was normalized to endogenous GALT protein expression in wild-type mice. At the 0.5 mg/kg dose, modified mRNA encoding mGalt resulted in expression of GALT protein in KO mice that was close to (about 80-90%) the endogenous level of GALT protein expression in wild-type mice. GALT activity correlated with the protein expression levels (FIG. 11B). In GALT knock-out mice, administration of the 0.5 mg/kg dose of modified mRNA encoding either mGalt or hGalt lowered galactose-1-phosphate levels in red blood cells by about 80% compared to control (FIG. 11C) and in liver by about 80% compared to control (FIG. 11D) at 24 hours.

Example 24

In Vivo Duration of GALT Protein Expression, Activity, and Function in GALT Knock-Out Mice Administered a Single Dose of mRNA Encoding mGalt1

GALT protein expression, GALT activity, and biomarker (Gal-1-P) level in liver as well as biomarker (Gal-1-P) level in red blood cells from GALT knock-out mice (KO mice, male) was measured 2, 6, 10, and 14 days after intravenous (IV) administration of 1-methyl-pseudouridine modified mRNA encoding mouse Galt1 (mGalt1; Construct #21) or control mRNA encoding NTFIX (non-translated Factor IX; Construct #22) formulated in lipid nanoparticle (MC3). GALT protein expression in liver at each time point was determined by Western blot, and GALT enzymatic activity was determined by an HPLC-based assay (the same methods as described in Example 21). Galactose-1-phosphate levels in liver and red blood cells were measured for each time point using GC-MS (the same method as described in Example 23)

Expression of GALT protein in KO mice relative to endogenous GALT protein expression in WT mice is shown in FIG. 12A. GALT protein expression in KO mice administered mRNA encoding GALT was highest two days post-injection (about 59.7% endogenous WT levels), but GALT protein was still detected 14 days post injection (about 7% endogenous WT levels) (FIG. 12A). The protein expression levels correlated with GALT activity. GALT activity in liver was detected at least 10 days after a single injection of GALT mRNA in KO mice (FIG. 12B).

A significant decrease in galactose-1-phosphate (Gal-1-P) levels in red blood cells (RBC) of GALT KO mice was observed two weeks after a single intravenous injection of mRNA encoding GALT. Prior to administration of mRNA encoding GALT, the Gal-1-P levels in RBCs from untreated KO mice were similar (FIG. 13A). After administration of a single dose of mRNA encoding GALT, Gal-1-P levels in KO mice decreased, while Gal-1-P levels in KO mice administered control mRNA remained elevated (FIG. 13B). In KO mice administered GALT mRNA, an up to 70% reduction in galactose-1-phosphate in red blood cells was observed around day 6 (FIG. 13C). Gal-1-P levels remained lower in GALT mRNA treated mice compared to NTFIX mRNA control mice at 14 days.

Gal-1-P levels in liver decreased by 60% in GALT KO mice administered GALT mRNA, and Gal-1-P was maintained at low levels in these mice compared to Gal-1-P levels in control mice for at least 14 days (FIG. 14). These results indicated that a single dose of mRNA encoding GALT can decrease Gal-1-P levels in RBCs and liver of KO mice for at least two weeks.

Example 25

GALT Protein Expression and Activity in Wild-Type Mice Administered a Single Dose of mRNA Encoding Human Galt1

GALT protein expression and GALT activity in liver were measured 24 hours after a single administration of 5-methoxyuridine modified mRNA encoding human Galt1 (hGalt1) (Constructs #1-#19), 1-methyl-pseudouridine modified mRNA encoding human Galt1 (hGalt1) (hGALT1-ModRNA, construct #20), 1-methyl-pseudouridine modified mRNA encoding mouse Galt1 (mGalt1) (mGALT1-ModRNA, construct #21), or control mRNA encoding NTFIX (non-translated Factor IX) (Construct #22) formulated in MC3 lipid nanoparticle to wild-type CD1 mice (n=3/group). The constructs are shown in Table 8.

TABLE 8

Modified mRNA constructs including ORFs encoding human or mouse GALT(each of constructs #1 to #21 comprises a Cap1 5' terminal cap and a 3' terminal Poly A region)

| GALT mRNA construct | 5' UTR SEQ ID NO | GALT ORF Name | GALT ORF SEQ ID NO | 3' UTR SEQ ID NO: |
|---|---|---|---|---|
| #1 (SEQ ID NO: 132) | 35 | GALT-CO26 | 113 | 98 |
| #2 (SEQ ID NO: 133) | 35 | GALT-CO27 | 114 | 98 |
| #3 (SEQ ID NO: 134) | 35 | GALT-CO28 | 115 | 98 |
| #4 (SEQ ID NO: 135) | 35 | GALT-CO29 | 116 | 98 |
| #5 (SEQ ID NO: 136) | 35 | GALT-CO30 | 117 | 98 |
| #6 (SEQ ID NO: 137) | 35 | GALT-CO31 | 118 | 98 |
| #7 (SEQ ID NO: 138) | 35 | GALT-CO32 | 119 | 98 |
| #8 (SEQ ID NO: 139) | 35 | GALT-CO33 | 120 | 98 |
| #9 (SEQ ID NO: 140) | 35 | GALT-CO34 | 121 | 98 |
| #10 (SEQ ID NO: 141) | 35 | GALT-CO35 | 122 | 98 |
| #11 (SEQ ID NO: 142) | 35 | GALT-CO36 | 123 | 98 |
| #12 (SEQ ID NO: 143) | 35 | GALT-CO37 | 124 | 98 |
| #13 (SEQ ID NO: 144) | 35 | GALT-CO38 | 125 | 98 |
| #14 (SEQ ID NO: 145) | 35 | GALT-CO39 | 126 | 98 |
| #15 (SEQ ID NO: 146) | 35 | GALT-CO40 | 127 | 98 |
| #16 (SEQ ID NO: 147) | 35 | GALT-CO41 | 128 | 98 |
| #17 (SEQ ID NO: 148) | 35 | GALT-CO42 | 129 | 98 |
| #18 (SEQ ID NO: 149) | 35 | GALT-CO43 | 130 | 98 |
| #19 (SEQ ID NO: 150) | 35 | GALT-CO44 | 131 | 98 |

The single dose was administered as 0.5 mg/kg tail vein injection. GALT protein expression was determined by Western blot, and GALT enzymatic activity was determined by a HPLC-based assay (the same methods as described in Example 21). The results for each mouse are shown in TABLE 9 (protein expression) and TABLE 10 (activity).

TABLE 9

GALT Protein Expression for mRNA Constructs Encoding GALT

| SEQ ID NO of ORF: | Construct# | Description | Mouse #1 | Mouse #2 | Mouse #3 | Average |
|---|---|---|---|---|---|---|
| 153 | 20 | hGALT; 1-methyl-pseudouridine | 1.27 | 0.85 | 0.88 | 1.00 |
| 113 | 1 | hGALT; 5-methoxyuridine | 0.48 | 0.43 | 0.51 | 0.47 |
| 114 | 2 | hGALT; 5-methoxyuridine | 0.30 | 0.47 | 0.36 | 0.38 |
| 115 | 3 | hGALT; 5-methoxyuridine | 0.34 | 0.50 | 0.55 | 0.46 |
| 116 | 4 | hGALT; 5-methoxyuridine | 0.51 | 0.54 | 0.53 | 0.53 |
| 117 | 5 | hGALT; 5-methoxyuridine | 0.46 | 0.37 | 0.30 | 0.37 |
| 118 | 6 | hGALT; 5-methoxyuridine | 0.49 | 0.53 | 0.49 | 0.50 |
| 119 | 7 | hGALT; 5-methoxyuridine | 1.07 | 0.92 | 0.68 | 0.89 |
| 120 | 8 | hGALT; 5-methoxyuridine | 0.56 | 0.52 | 0.51 | 0.53 |
| 121 | 9 | hGALT; 5-methoxyuridine | 0.37 | 0.46 | 0.37 | 0.40 |
| 122 | 10 | hGALT; 5-methoxyuridine | 1.16 | 0.83 | 0.95 | 0.98 |
| 123 | 11 | hGALT; 5-methoxyuridine | 0.76 | 0.75 | 0.55 | 0.69 |

TABLE 9-continued

GALT Protein Expression for mRNA Constructs Encoding GALT

| SEQ ID NO of ORF: | Construct# | Description | Mouse #1 | Mouse #2 | Mouse #3 | Average |
|---|---|---|---|---|---|---|
| 124 | 12 | hGALT; 5-methoxyuridine | 0.89 | 1.20 | 1.54 | 1.21 |
| 125 | 13 | hGALT; 5-methoxyuridine | 1.04 | 1.00 | 0.95 | 1.00 |
| 126 | 14 | hGALT; 5-methoxyuridine | 1.01 | 1.12 | 1.33 | 1.16 |
| 127 | 15 | hGALT; 5-methoxyuridine | 0.72 | 0.70 | 0.66 | 0.70 |
| 128 | 16 | hGALT; 5-methoxyuridine | 0.69 | 0.64 | 0.69 | 0.68 |
| 129 | 17 | hGALT; 5-methoxyuridine | 0.82 | 0.65 | 0.86 | 0.78 |
| 130 | 18 | hGALT; 5-methoxyuridine | 0.93 | 0.87 | 0.61 | 0.80 |
| 131 | 19 | hGALT; 5-methoxyuridine | 0.60 | 0.65 | 0.74 | 0.66 |

TABLE 10

GALT Activity

| SEQ ID NO of ORF: | Construct # | Description | Mouse #1 | Mouse #2 | Mouse #3 | Average |
|---|---|---|---|---|---|---|
| 157 | 22 | NTFIX | 6.83 | 6.86 | 7.15 | 6.95 |
| 154 | 21 | mGALT; 1-methyl-pseudouridine | 15.84 | 18.18 | 13.61 | 15.88 |
| 153 | 20 | hGALT; 1-methyl-pseudouridine | 19.76 | 14.43 | 14.59 | 16.26 |
| 113 | 1 | hGALT; 5-methoxyuridine | 11.16 | 8.99 | 9.80 | 9.99 |
| 114 | 2 | hGALT; 5-methoxyuridine | 11.54 | 11.27 | 8.99 | 10.60 |
| 119 | 7 | hGALT; 5-methoxyuridine | 14.59 | 12.25 | 12.14 | 12.99 |
| 122 | 10 | hGALT; 5-methoxyuridine | 10.78 | | 10.95 | 10.86 |
| 124 | 12 | hGALT; 5-methoxyuridine | 15.19 | 18.29 | 18.94 | 17.47 |
| 125 | 13 | hGALT; 5-methoxyuridine | 15.30 | 17.47 | 13.23 | 15.33 |
| 126 | 14 | hGALT; 5-methoxyuridine | 17.58 | 20.35 | 16.76 | 18.23 |
| 129 | 17 | hGALT; 5-methoxyuridine | 15.24 | 15.46 | 15.13 | 15.28 |
| 130 | 18 | hGALT; 5-methoxyuridine | 13.45 | 13.94 | 13.66 | 13.68 |

Administration of the modified mRNAs encoding hGalt1 resulted in a increased GALT protein expression and activity in liver of wild-type mice. The protein expression for each construct corresponded to GALT activity level, with constructs #12 and #14 having the highest GALT protein expression (FIG. 15A) and activity (FIG. 15B).

In a further study, GALT protein expression and GALT activity in liver were measured 24 hours after a single administration of 5-methoxyuridine modified mRNA encoding human Galt1 (hGalt1) (constructs #12 and #14, respectively), 1-methyl-pseudouridine modified mRNA encoding human Galt1 (hGalt1) (Construct #20), or control mRNA encoding NTFIX (non-translated Factor IX, Construct #22) formulated in Compound 18 lipid nanoparticle to wild-type CD1 mice (n=3/group). The single dose was administered as 0.5 mg/kg tail vein injection. Both constructs #12 and #14 had higher protein expression (FIG. 15C) and activity (FIG. 15D) than the construct encoding hGalt1 (Construct #20). GALT protein expression and activity level with construct #12 were higher than construct #14. Construct #12 was used for the studies described in Examples 27-28 below.

Example 26

Multi-Dose mRNA Encoding Human Gala Efficacy Study in GALT KO Mice

GALT protein expression and biomarker (Gal-1-P) levels in red blood cells (RBC), and liver from GALT knock-out mice (KO mice, male & female) were measured 24 hours after the last tail vein intravenous administration of 5-methoxyuridine modified mRNA encoding human Galt1 (hGalt1) (Construct #12) or control mRNA encoding NTFIX (non-translated Factor IX, Construct #22) formulated in Compound 18 lipid nanoparticle. GALT KO mice (n=8/group) were administered with hGalt1 mRNA at 0.2 mg/kg biweekly for 4 doses. GALT protein expression in liver at each time point was determined by Western blot, and Gal-1-P levels in RBC and liver were measured for each time point using GC-MS (the same methods as described in Examples 24).

After 4 doses, administration of mRNA encoding hGalt1 resulted in increased GALT protein expression in liver of GALT KO mice compared to PBS and NTFIX mRNA controls (FIG. 16). Also, administration of the mRNA encoding hGalt1 resulted in lower Gal-1-P and galactose levels in RBC or plasmas from GALT KO mice after each of the 4 doses compared to PBS and NTFIX mRNA controls (FIGS. 17A, 17B, and 17C). Administration of hGalt1 mRNA resulted in about 70% reduction in Gal-1-P in RBC from KO mice compared to PBS, and about 50% reduction in Gal-1-P in RBC from KO mice compared to NTFIX mRNA. The statistical significance analysis for the data in FIG. 17B is presented in TABLE 11.

TABLE 11

Statistical Significance Summary

| Tukey's multi* comparisons test | Mean Diff. | 95.00% Cl of diff. | Significant? | Summary | Adjusted P Value |
|---|---|---|---|---|---|
| $1^{st}$ Dose | | | | | |
| PBS vs. NTFIX | 61.01 | 20.04 to 102 | Yes | ** | 0.0019 |
| PBS vs. GALT | 115.5 | 74.51 to 156.4 | Yes | **** | <0.0001 |
| NTFIX vs. GALT | 54.47 | 24.21 to 84.73 | Yes | *** | 0.0002 |
| $2^{nd}$ Dose | | | | | |
| PBS vs. NTFIX | 72.82 | 31.85 to 113.8 | Yes | *** | 0.0002 |
| PBS vs. GALT | 107.8 | 66.83 to 148.8 | Yes | **** | <0.0001 |
| NTFIX vs. GALT | 34.97 | 4.715 to 66.23 | Yes | * | 0.0196 |
| $3^{rd}$ Dose | | | | | |
| PBS vs. NTFIX | 72.53 | 31.57 to 113.5 | Yes | *** | 0.0002 |
| PBS vs. GALT | 111.3 | 70.37 to 152.3 | Yes | **** | <0.0001 |
| NTFIX vs. GALT | 38.8 | 8.644 to 69.06 | Yes | ** | 0.0085 |
| $4^{th}$ Dose | | | | | |
| PBS vs. NTFIX | 47.27 | 6.305 to 88.24 | Yes | * | 0.0199 |
| PBS vs. GALT | 116.8 | 75.84 to 157.8 | Yes | **** | <0.0001 |
| NTFIX vs. GALT | 69.54 | 39.28 to 99.8 | Yes | **** | <0.0001 |

Administering mRNA encoding hGalt1 to KO mice also lowered Gal-1-P levels in liver (FIG. 18).

Example 27

Rescue Study in KO Neonatal Mice Administered mRNA Encoding hGalt1

Survival and body weight for neonatal GALT KO mice (n=8-16 group) following administration of a single 0.5 mg/kg, 1 mg/kg, or 2 mg/kg intraperitoneal dose of 5-methoxyuridine modified mRNA encoding hGalt1 (Construct #12) or control mRNA encoding NTFIX was determined out to at least 21 days. mRNA was formulated in Compound 18 lipid nanoparticle. PBS was used as a control.

Administration of a single dose of mRNA encoding hGalt1 prolonged survival of GALT KO mice neonates compared to controls in a dose dependent manner (FIG. 19). Administration of a single dose of the hGalt1 mRNA also increased body weight in GALT KO neonates compared to controls at each dose tested, i.e., 0.5 mg/kg, 1 mg/kg, and 2 mg/kg (FIG. 20A-C).

It is to be appreciated that the Detailed Description section, and not the Summary and Abstract sections, is intended to be used to interpret the claims. The Summary and Abstract sections can set forth one or more but not all exemplary embodiments of the present invention as contemplated by the inventor(s), and thus, are not intended to limit the present invention and the appended claims in any way.

The present invention has been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present invention should not be limited by any of the above-described exemplary embodiments, but should be defined only in accordance with the following claims and their equivalents.

All publications, patent applications, patents, and other references mentioned herein are incorporated by reference in their entirety. In case of conflict, the present specification, including definitions, will control.

What is claimed is:

1. A pharmaceutical composition comprising a lipid nanoparticle, wherein the lipid nanoparticle comprises a compound having the Formula (I)

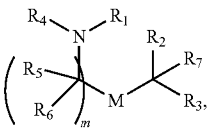

or a salt or stereoisomer thereof, wherein $R_1$ is selected from the group consisting of $C_{5-30}$ alkyl, $C_{5-20}$ alkenyl, —R*YR″, —YR″, and —R″M′R′;

$R_2$ and $R_3$ are independently selected from the group consisting of H, $C_{1-14}$ alkyl, $C_{2-14}$ alkenyl, —R*YR″, —YR″, and —R*OR″, or $R_2$ and $R_3$, together with the atom to which they are attached, form a heterocycle or carbocycle;

$R_4$ is selected from the group consisting of a $C_{3-6}$ carbocycle, —(CH$_2$)$_n$Q, —(CH$_2$)$_n$CHQR, —CHQR, —CQ(R)$_2$, and unsubstituted $C_{1-6}$ alkyl, where Q is selected from a carbocycle, heterocycle, —OR, —O(CH$_2$)$_n$N(R)$_2$, —C(O)OR, —OC(O)R, —CX$_3$, —CX$_2$H, —CXH$_2$, —CN, —N(R)$_2$, —C(O)N(R)$_2$, —N(R)C(O)R, —N(R)S(O)$_2$R, —N(R)C(O)N(R)$_2$, —N(R)C(S)N(R)$_2$, —N(R)R$_8$, —O(CH$_2$)$_n$OR, —N(R)C(=NR$_9$)N(R)$_2$, —N(R)C(=CHR$_9$)N(R)$_2$, —OC(O)N(R)$_2$, —N(R)C(O)OR, —N(OR)C(O)R, —N(OR)S(O)$_2$R, —N(OR)C(O)OR, —N(OR)C(O)N(R)$_2$, —N(OR)C(S)N(R)$_2$, —N(OR)C(=NR$_9$)N(R)$_2$, —N(OR)C(=CHR$_9$)N(R)$_2$, —C(=NR$_9$)N(R)$_2$, —C(=NR$_9$)R, —C(O)N(R)OR, and —C(R)N(R)$_2$C(O)OR, and each n is independently selected from 1, 2, 3, 4, and 5;

each $R_5$ is independently selected from the group consisting of $C_{1-3}$ alkyl, $C_{2-3}$ alkenyl, and H;

each $R_6$ is independently selected from the group consisting of $C_{1-3}$ alkyl, $C_{2-3}$ alkenyl, and H;

M and M′ are independently selected from —C(O)O—, —OC(O)—, —C(O)N(R′)—, —N(R′)C(O)—, —C(O)—, —C(S)—, —C(S)S—, —SC(S)—, —CH(OH)—, —P(O)(OR′)O—, —S(O)$_2$—, —S—S—, an aryl group, and a heteroaryl group;

$R_7$ is selected from the group consisting of $C_{1-3}$ alkyl, $C_{2-3}$ alkenyl, and H;

$R_8$ is selected from the group consisting of $C_{3-6}$ carbocycle and heterocycle;

$R_9$ is selected from the group consisting of H, CN, NO$_2$, $C_{1-6}$ alkyl, —OR, —S(O)$_2$R, —S(O)$_2$N(R)$_2$, $C_{2-6}$ alkenyl, $C_{3-6}$ carbocycle and heterocycle;

each R is independently selected from the group consisting of $C_{1-3}$ alkyl, $C_{2-3}$ alkenyl, and H;

each R′ is independently selected from the group consisting of $C_{1-18}$ alkyl, $C_{2-18}$ alkenyl, —R*YR″, —YR″, and H;

each R″ is independently selected from the group consisting of $C_{3-14}$ alkyl and $C_{3-14}$ alkenyl;

each R* is independently selected from the group consisting of $C_{1-12}$ alkyl and $C_{2-12}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13; and provided that when $R_4$ is —(CH$_2$)$_n$Q, —(CH$_2$)$_n$CHQR, —CHQR, or —CQ(R)$_2$, then (i) Q is not —N(R)$_2$ when n is 1, 2, 3, 4 or 5, or (ii) Q is not 5, 6, or 7-membered heterocycloalkyl when n is 1 or 2, wherein the lipid nanoparticle comprises an mRNA that comprises an open reading frame (ORF) encoding a galactose-1-phosphate uridylyltransferase (GALT)

polypeptide, wherein the composition is suitable for administration to a human subject in need of treatment for galactosemia type 1 (Gal-1).

2. The pharmaceutical composition of claim 1, wherein the compound is of Formula (IA):

(IA)

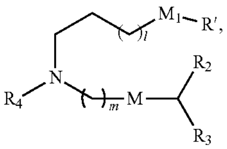

or a salt or stereoisomer thereof, wherein l is selected from 1, 2, 3, 4, and 5;

m is selected from 5, 6, 7, 8, and 9;

$M_1$ is a bond or M';

$R_4$ is unsubstituted $C_{1-3}$ alkyl, or —$(CH_2)_nQ$, in which Q is OH, —NHC(S)N$(R)_2$, —NHC(O)N$(R)_2$, —N(R)C(O)R, —N(R)S$(O)_2$R, —N(R)$R_8$, —NHC(=N$R_9$)N$(R)_2$, —NHC(=CH$R_9$)N$(R)_2$, —OC(O)N$(R)_2$, —N(R)C(O)OR, heteroaryl or heterocycloalkyl;

M and M' are independently selected from —C(O)O—, —OC(O)—, —C(O)N(R')—, —P(O)(OR')O—, —S—S—, an aryl group, and a heteroaryl group; and $R_2$ and $R_3$ are independently selected from the group consisting of H, $C_{1-14}$ alkyl, and $C_{2-14}$ alkenyl.

3. The pharmaceutical composition of claim 1, wherein m is 5, 7, or 9.

4. The pharmaceutical composition of claim 1, wherein the compound is of Formula (II)

(II)

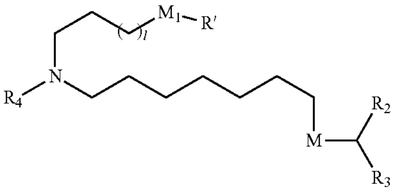

or a salt or stereoisomer thereof, wherein l is selected from 1, 2, 3, 4, and 5;

$M_1$ is a bond or M';

$R_4$ is unsubstituted $C_{1-3}$ alkyl, or —$(CH_2)_nQ$, in which n is 2, 3, or 4, and Q is OH, —NHC(S)N$(R)_2$, —NHC(O)N$(R)_2$, —N(R)C(O)R, —N(R)S$(O)_2$R, —N(R)$R_8$, —NHC(=N$R_9$)N$(R)_2$, —NHC(=CH$R_9$)N$(R)_2$, —OC(O)N$(R)_2$, —N(R)C(O)OR, heteroaryl, or heterocycloalkyl;

M and M' are independently selected from —C(O)O—, —OC(O)—, —C(O)N(R')—, —P(O)(OR')O—, —S—S—, an aryl group, and a heteroaryl group; and $R_2$ and $R_3$ are independently selected from the group consisting of H, $C_{1-14}$ alkyl, and $C_{2-14}$ alkenyl.

5. The pharmaceutical composition of claim 2, wherein $M_1$ is M'.

6. The pharmaceutical composition of claim 5, wherein M and M' are independently —C(O)O— or —OC(O)—.

7. The pharmaceutical composition of claim 2, wherein 1 is 1, 3, or 5.

8. The pharmaceutical composition of claim 1, wherein the compound is selected from the group consisting of: or a salt or stereoisomer thereof.

9. The pharmaceutical composition of claim 8, wherein the compound is selected from the group consisting of:

(Compound 1)

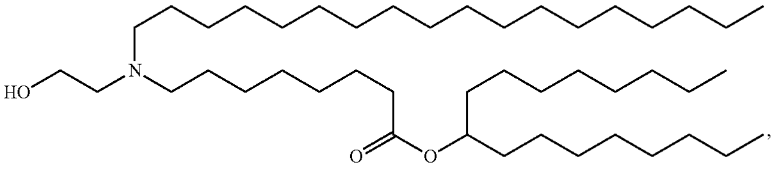

, (Compound 2)

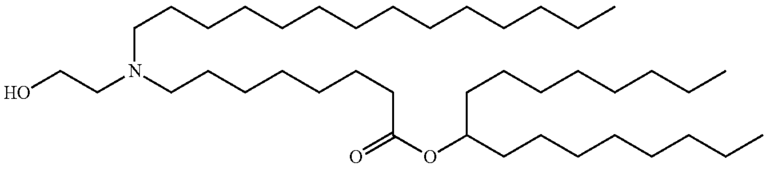

, (Compound 3)

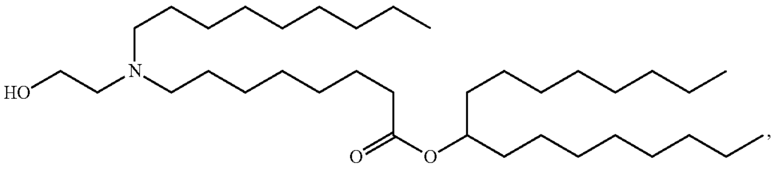

,

-continued
(Compound 4)
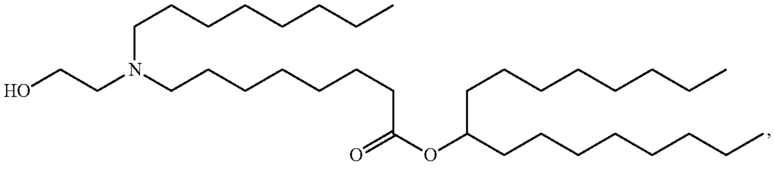
,
(Compound 5)
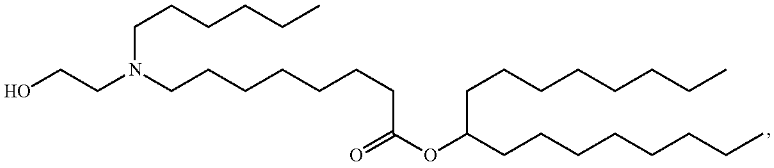
,
(Compound 6)
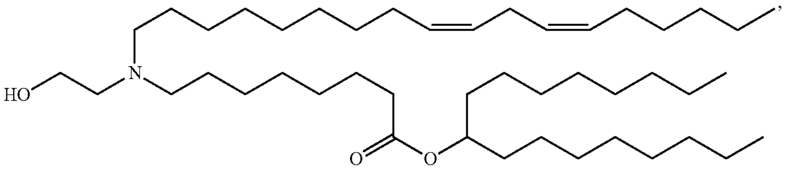
,
(Compound 7)
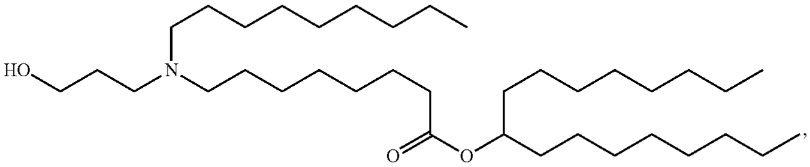
,
(Compound 8)
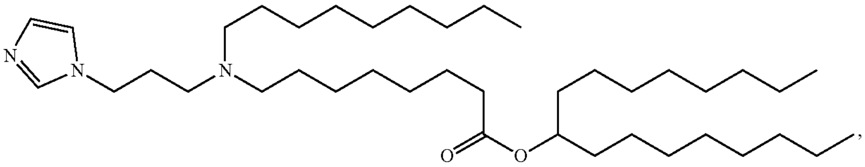
,
(Compound 9)
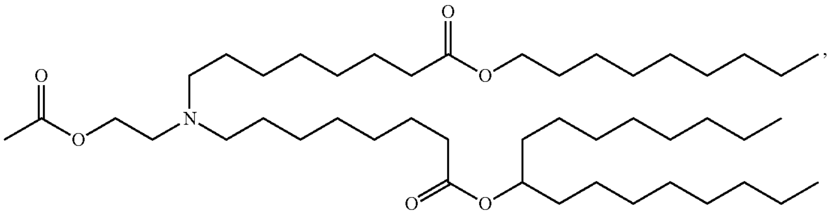
,
(Compound 10)
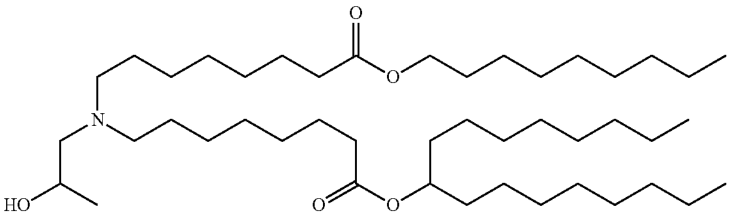
,
(Compound 11)
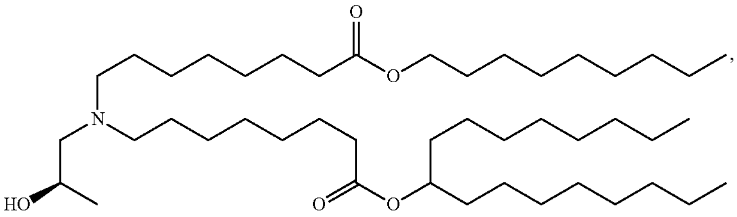
, -continued
(Compound 12)
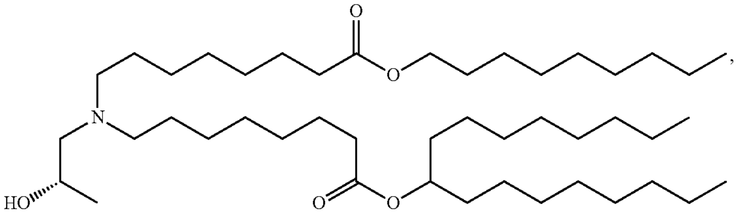
,
(Compound 13)
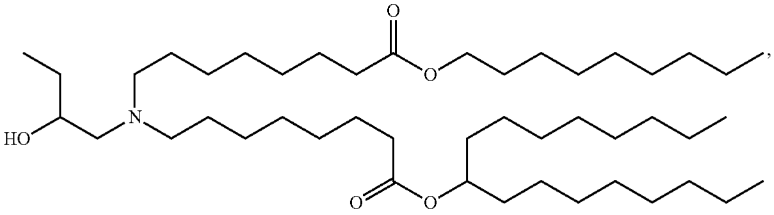
,
(Compound 14)
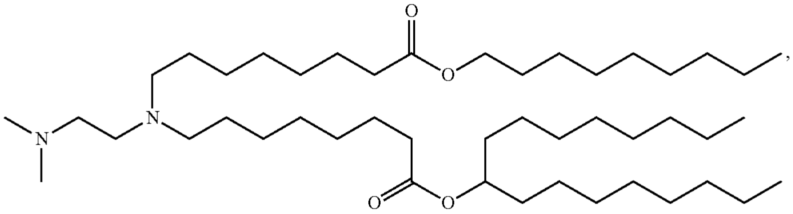
,
(Compound 15)
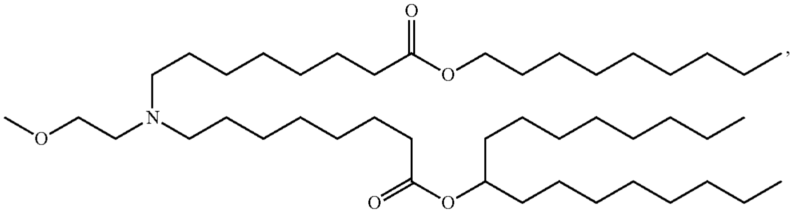
,
(Compound 16)
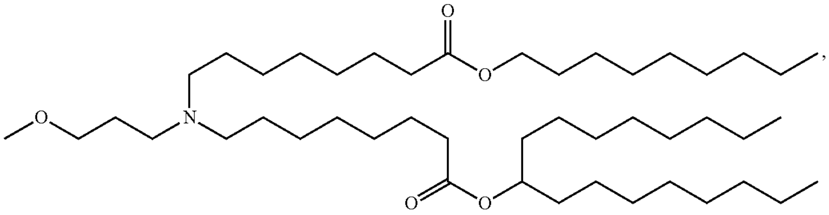
,
(Compound 17)
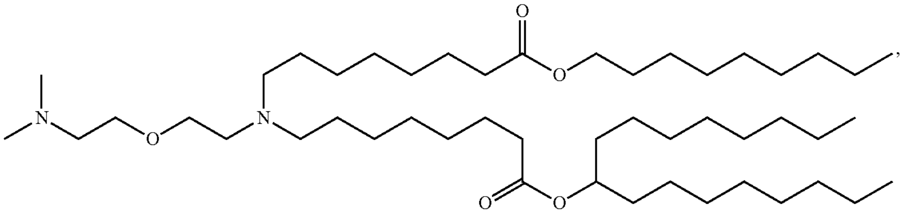
,
(Compound 18)
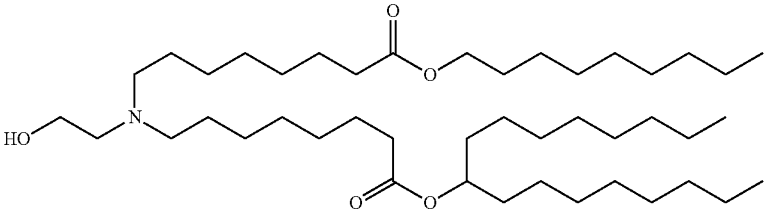
, -continued
(Compound 19)
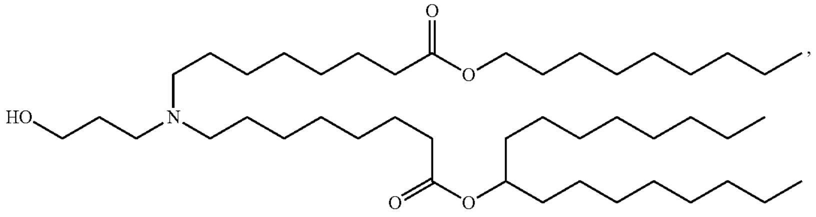
(Compound 20)
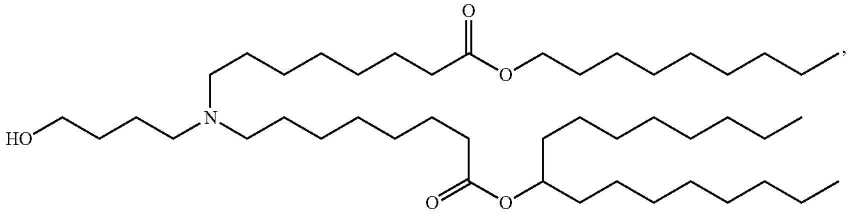
(Compound 21)
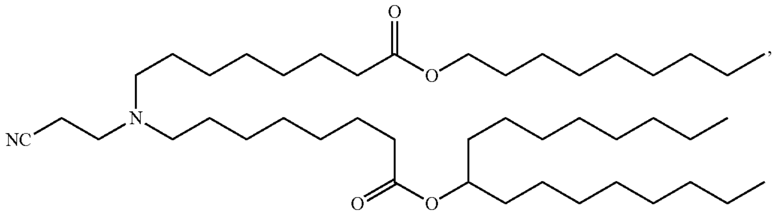
(Compound 22)
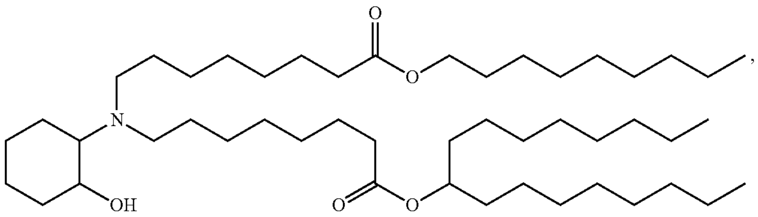
(Compound 23)
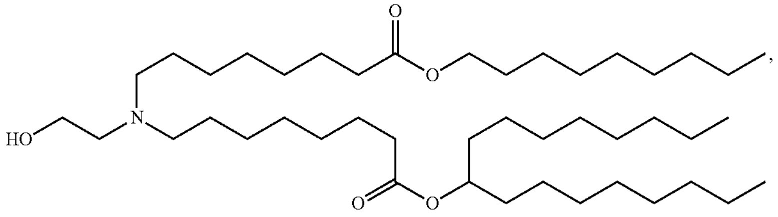
(Compound 24)
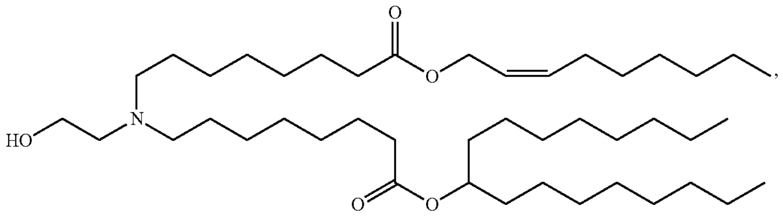
(Compound 25)
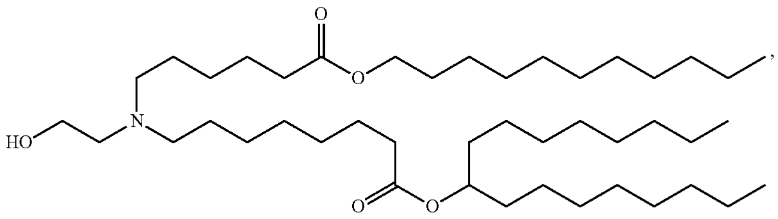

-continued
(Compound 26)
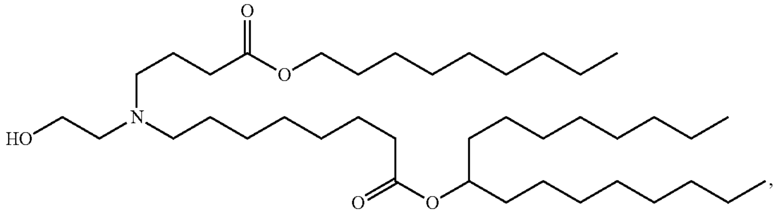
,
(Compound 27)
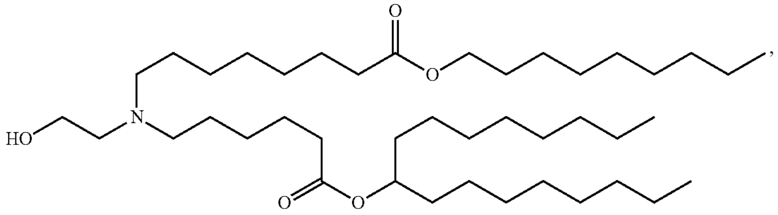
,
(Compound 28)
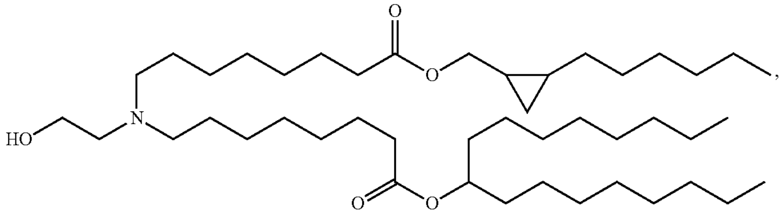
,
(Compound 29)
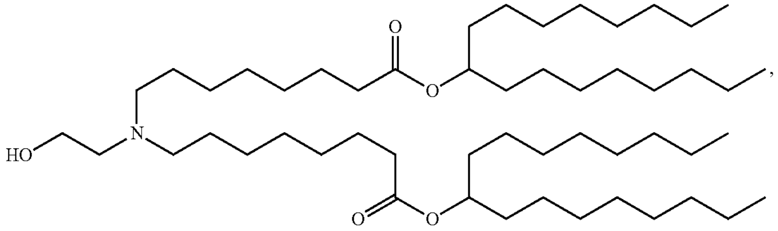
,
(Compound 30)
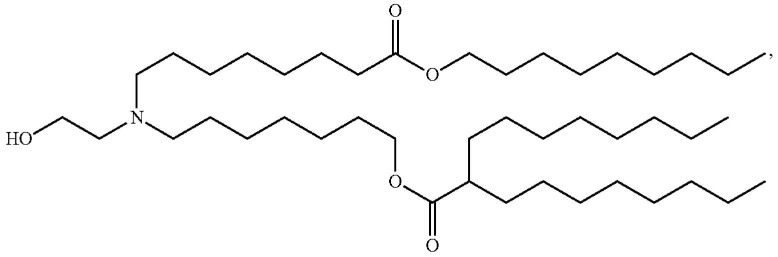
,
(Compound 31)
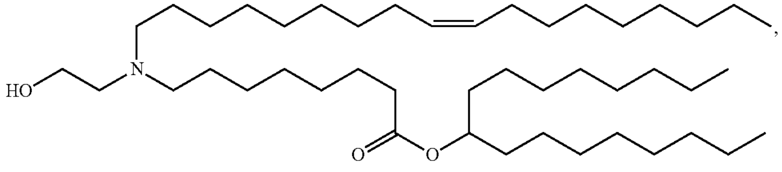
,
(Compound 32)
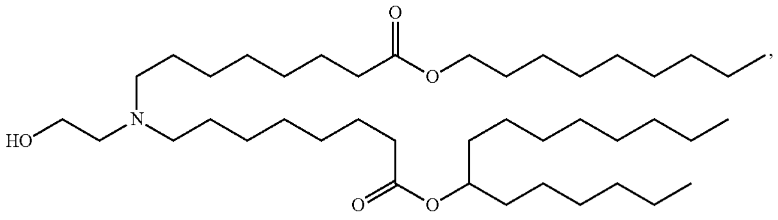
, -continued
(Compound 33)
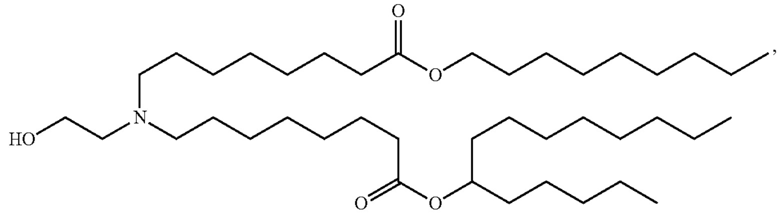
(Compound 34)
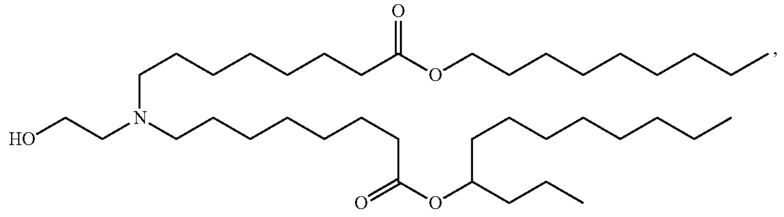
(Compound 35)
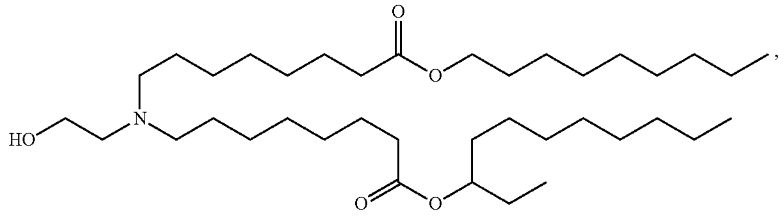
(Compound 36)
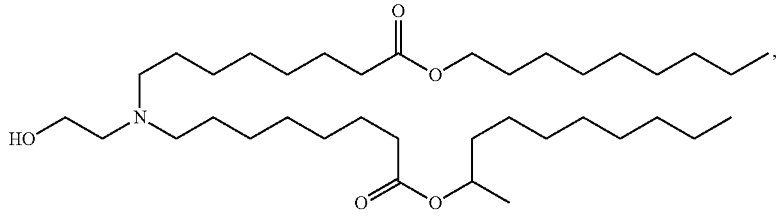
(Compound 37)
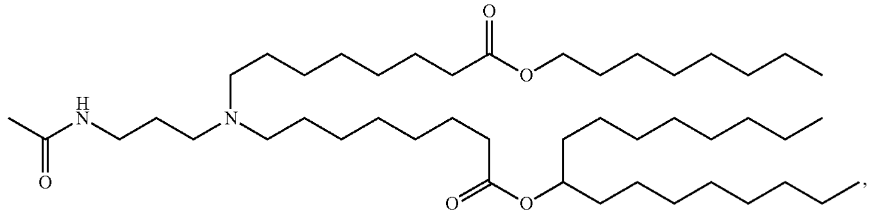
(Compound 38)
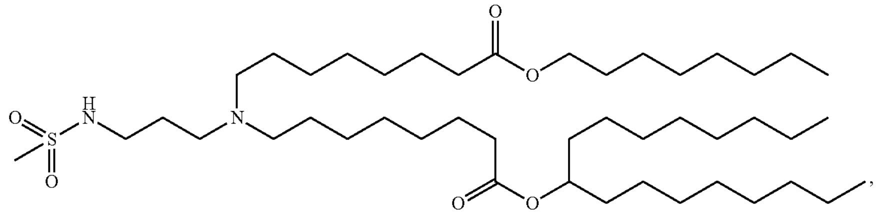
(Compound 39)
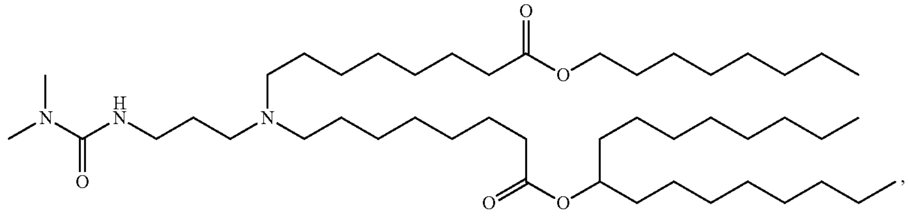

-continued
(Compound 40)
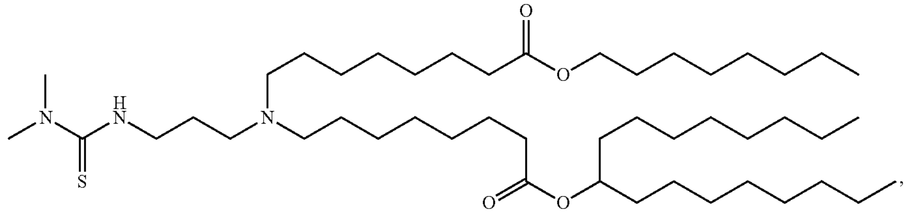
(Compound 41)
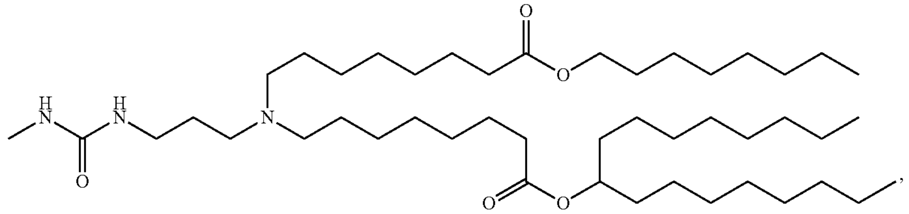
(Compound 42)
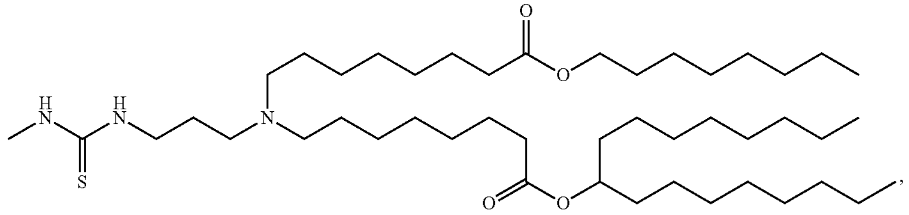
(Compound 43)
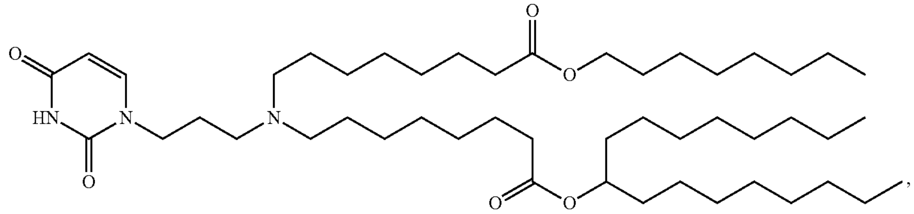
(Compound 44)
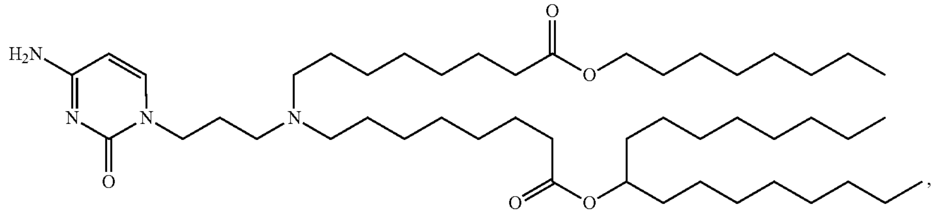
(Compound 45)
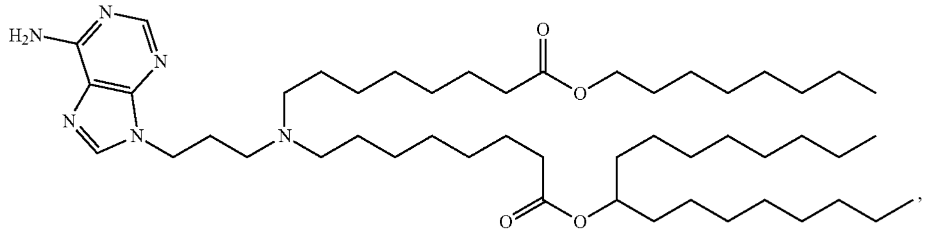
(Compound 46)
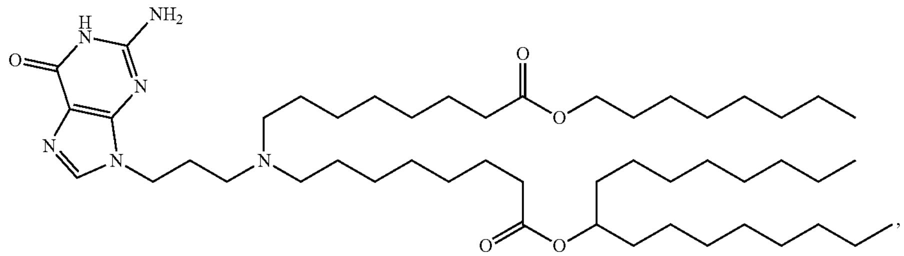

-continued
(Compound 47)
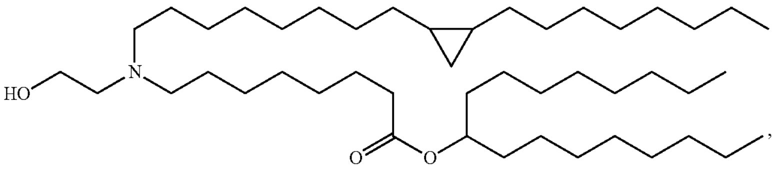,
(Compound 48)
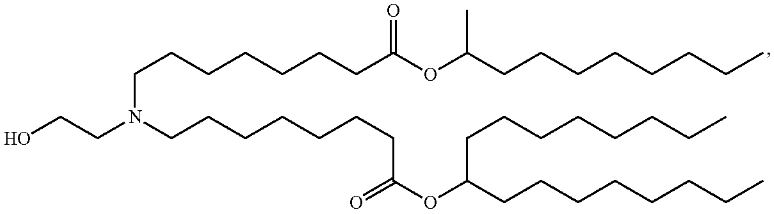,
(Compound 49)
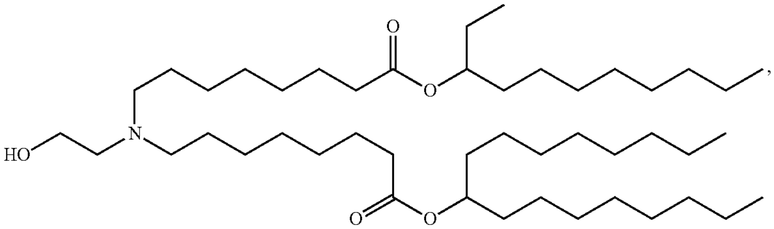,
(Compound 50)
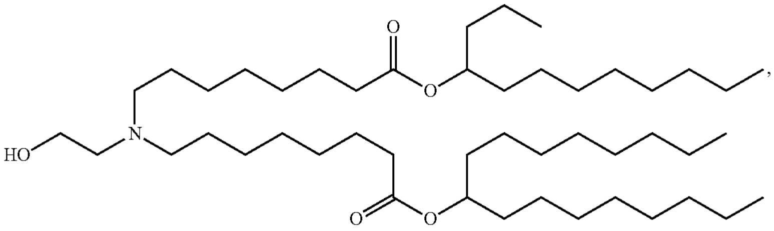,
(Compound 51)
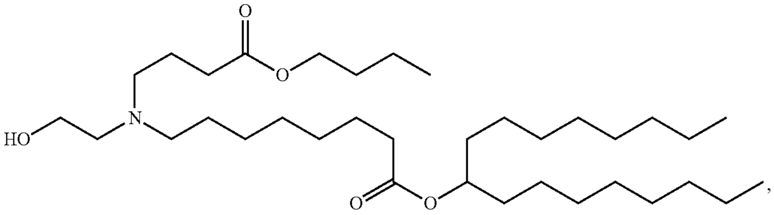,
(Compound 52)
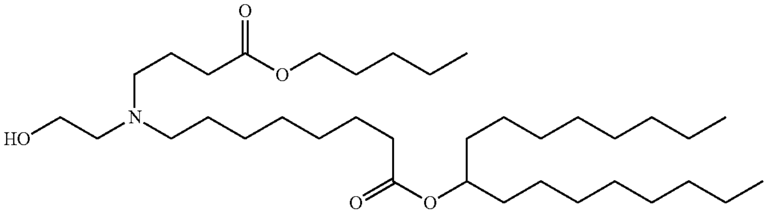,
(Compound 53)
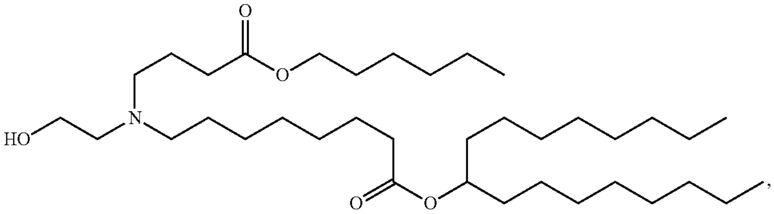, -continued
(Compound 54)
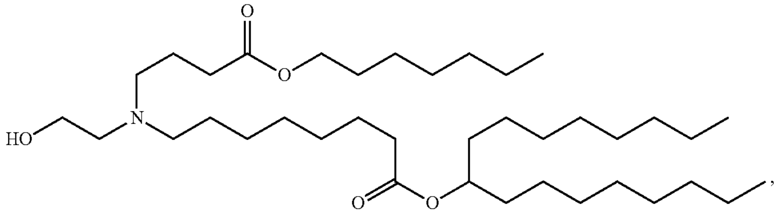
(Compound 55)
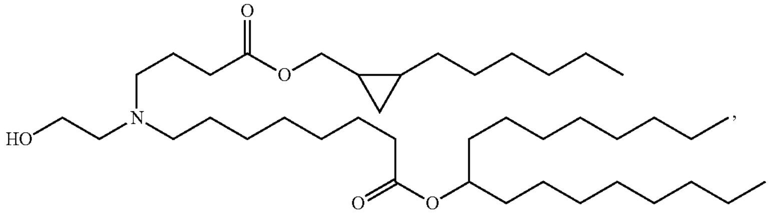
(Compound 56)
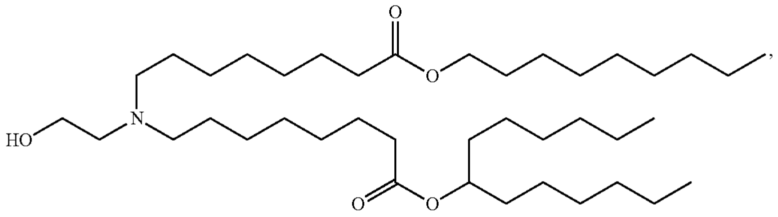
(Compound 57)
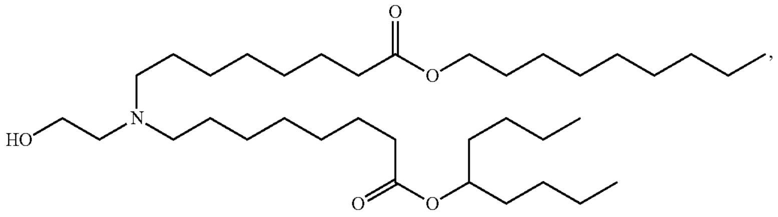
(Compound 58)
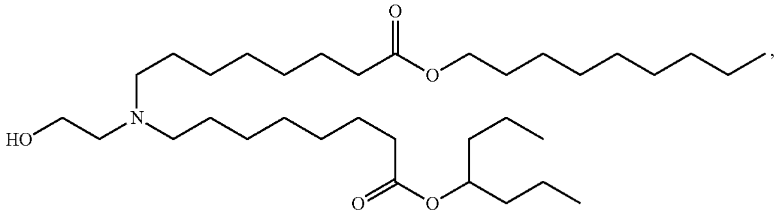
(Compound 59)
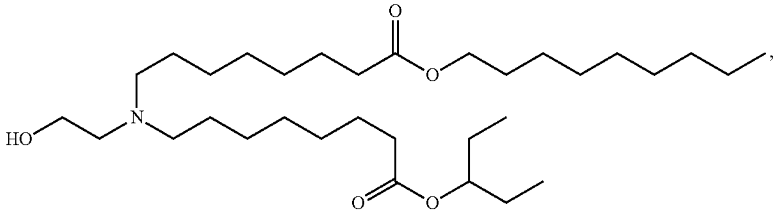
(Compound 60)
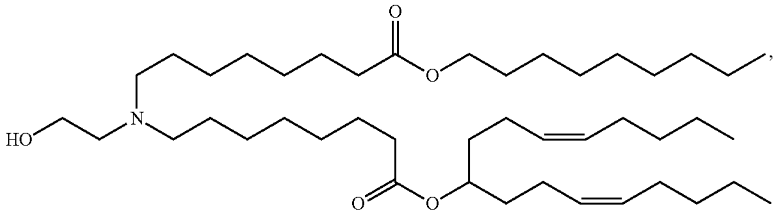

-continued
(Compound 61)
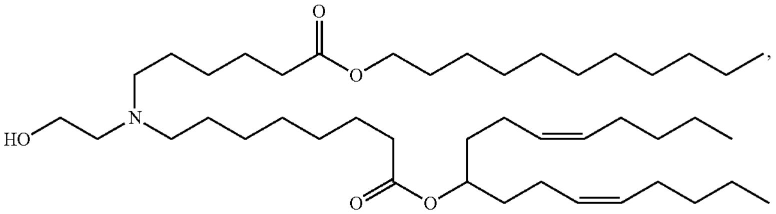
(Compound 62)
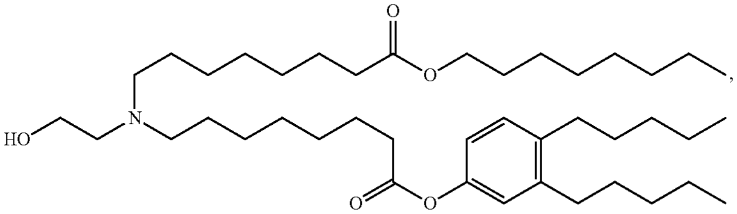
(Compound 63)
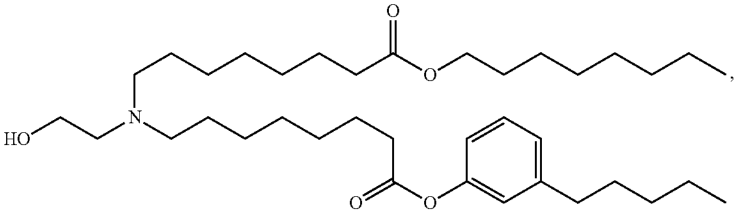
(Compound 64)
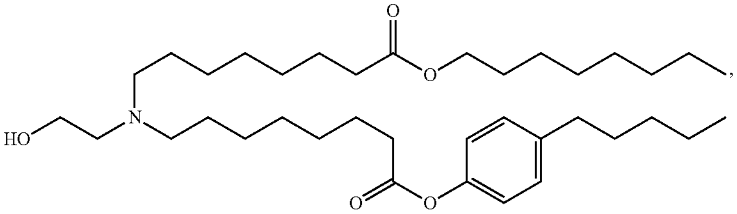
(Compound 65)
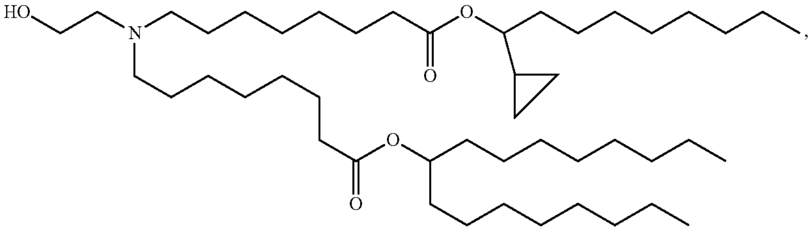
(Compound 66)
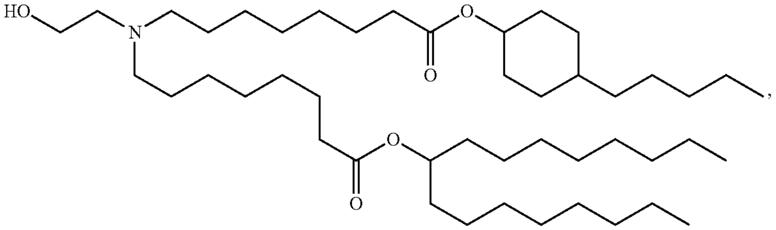
(Compound 67)
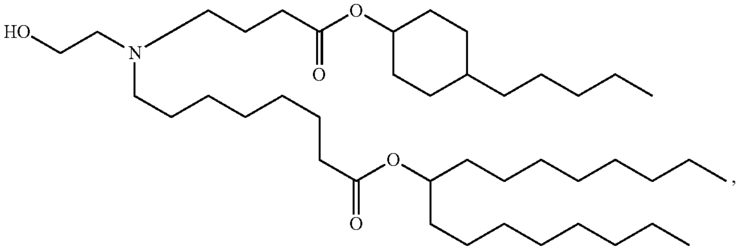

-continued
(Compound 68)
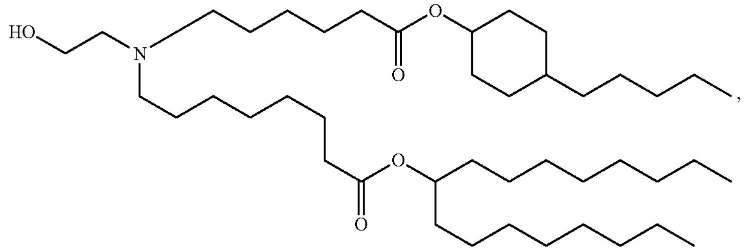
(Compound 69)
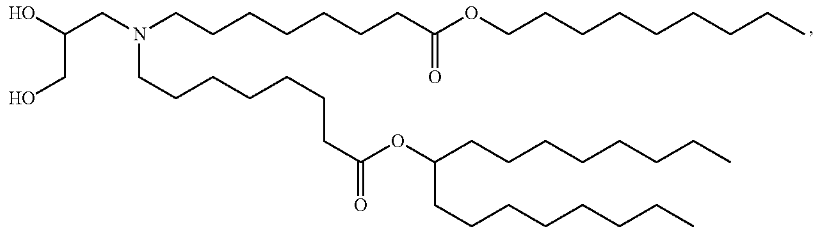
(Compound 70)
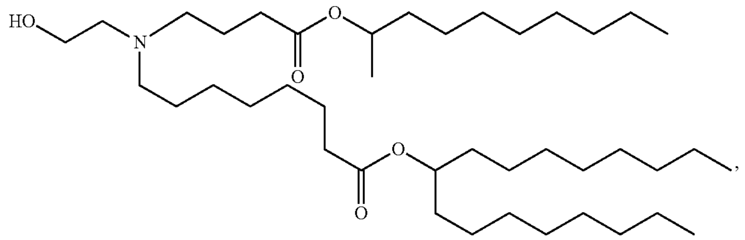
(Compound 71)
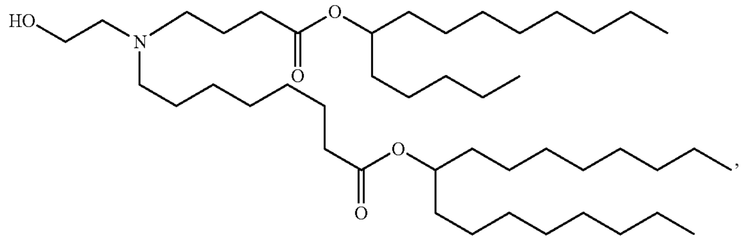
(Compound 72)
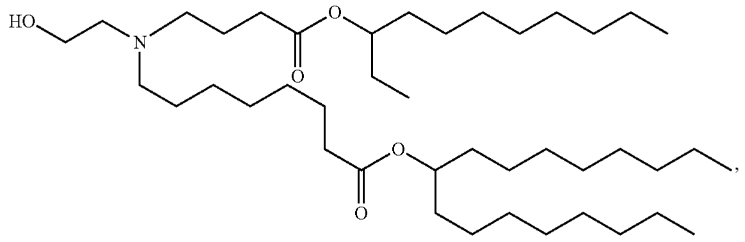
(Compound 73)
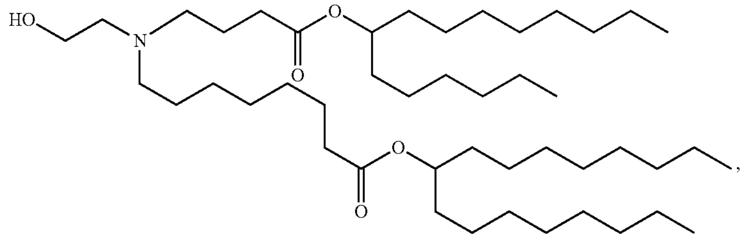

-continued
(Compound 74)
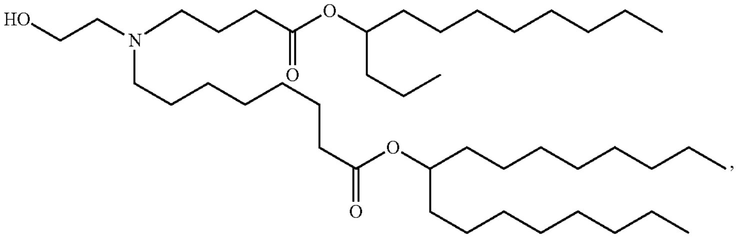
,
(Compound 75)
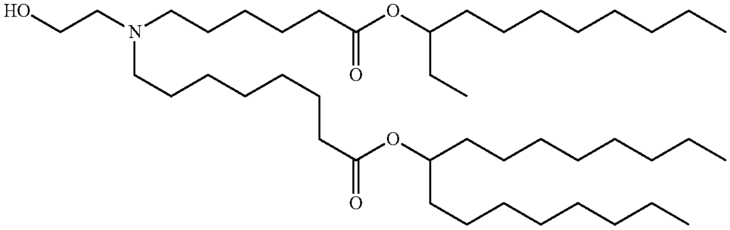
,
(Compound 76)
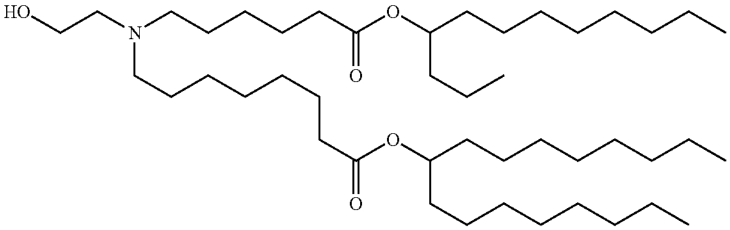
,
(Compound 77)
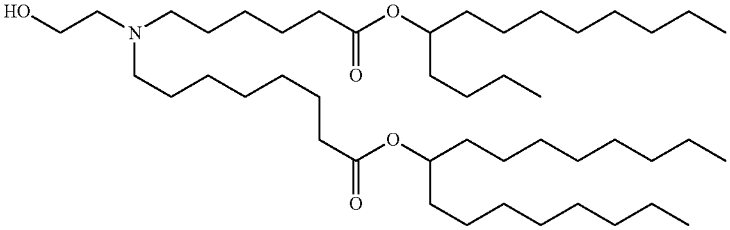
,
(Compound 78)
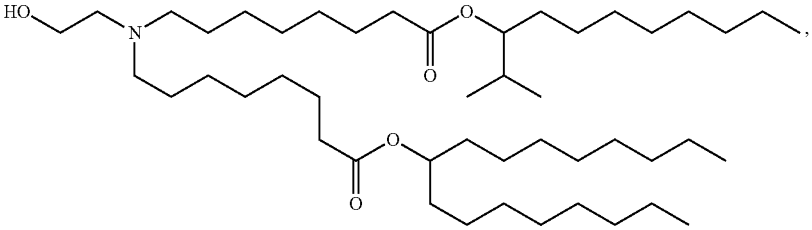
,
(Compound 79)
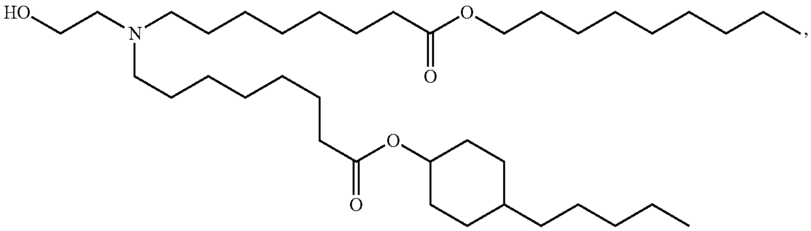
, -continued
(Compound 80)
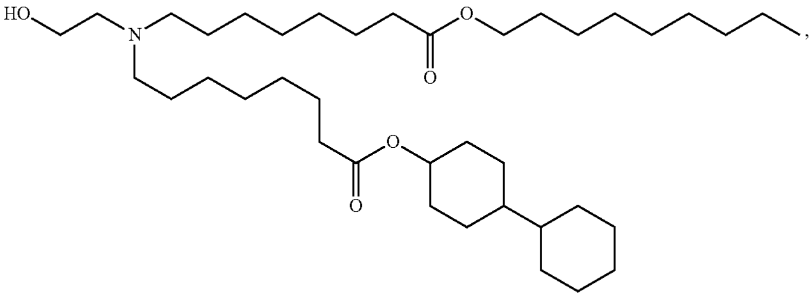
(Compound 81)
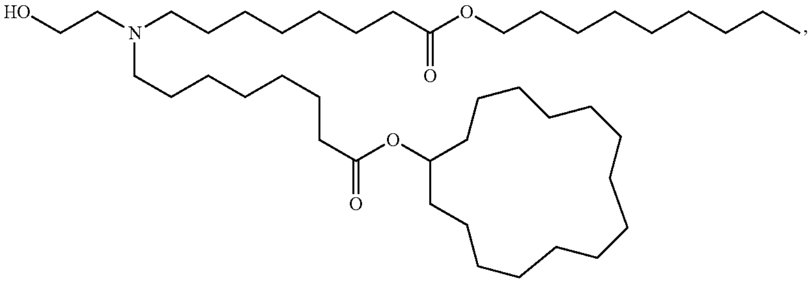
(Compound 82)
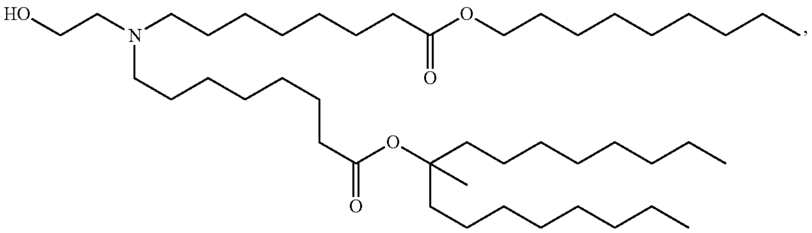
(Compound 83)
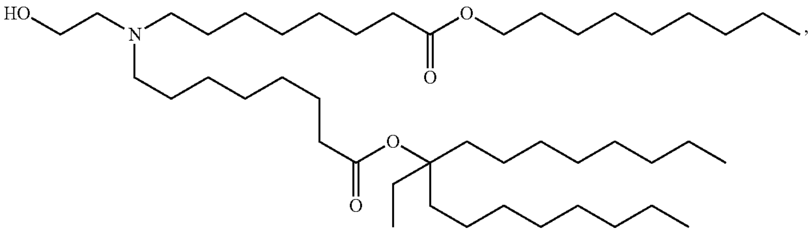
(Compound 84)
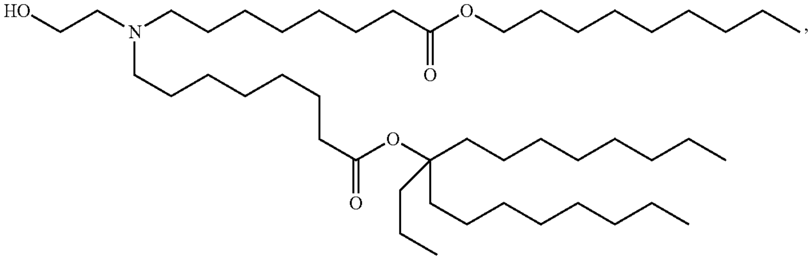
(Compound 85)
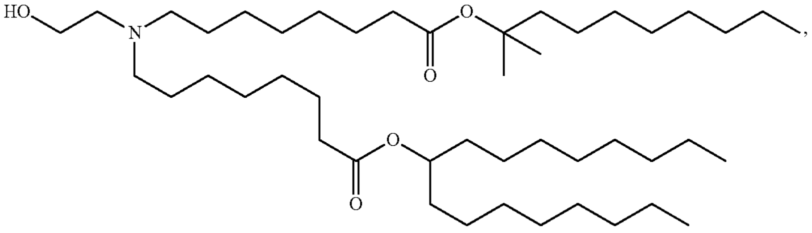

-continued
(Compound 86)
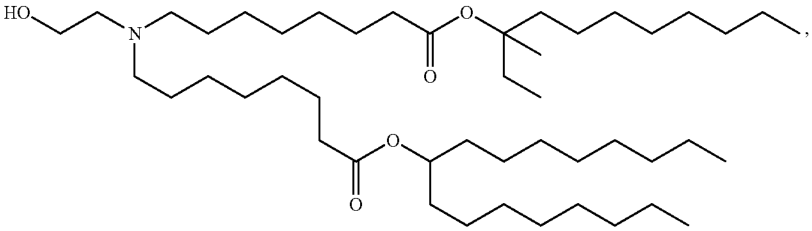
(Compound 87)
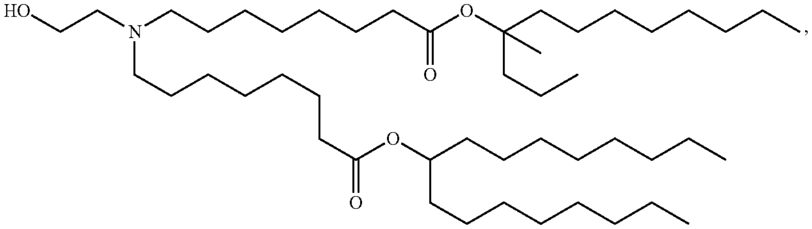
(Compound 88)
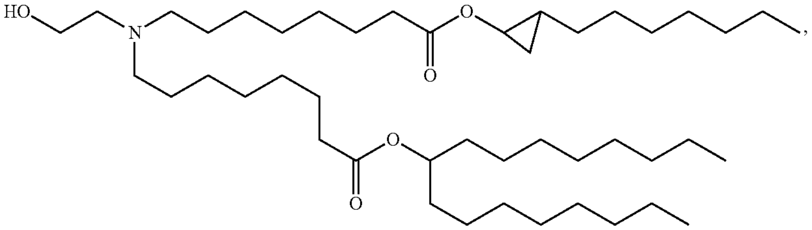
(Compound 89)
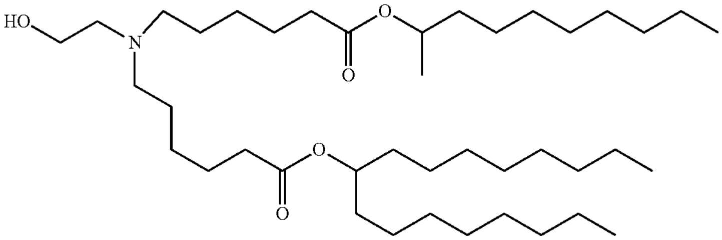
(Compound 90)
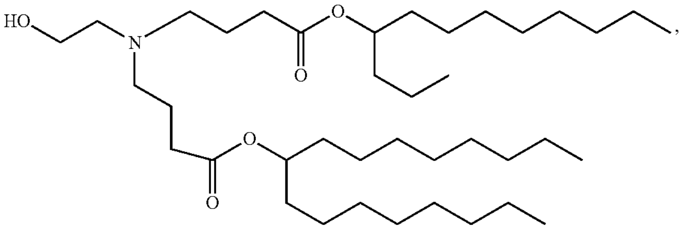
(Compound 91)
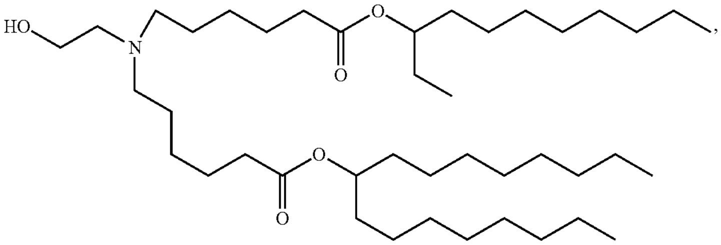

-continued
(Compound 92)
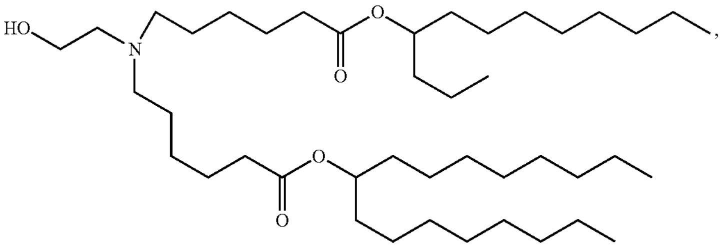
(Compound 93)
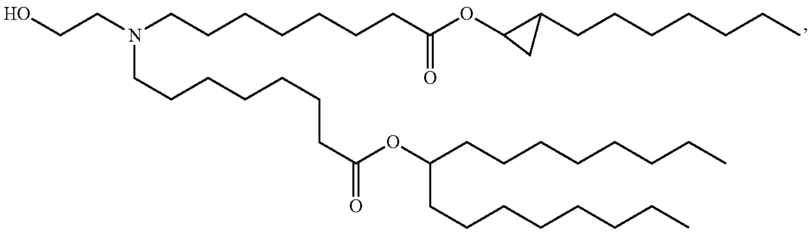
(Compound 94)
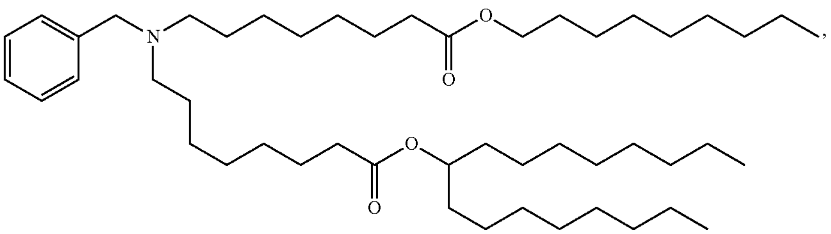
(Compound 95)
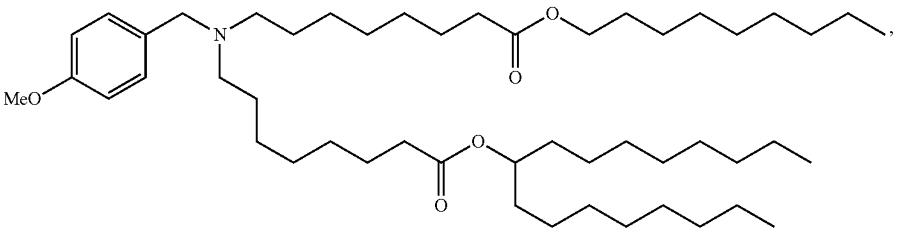
(Compound 96)
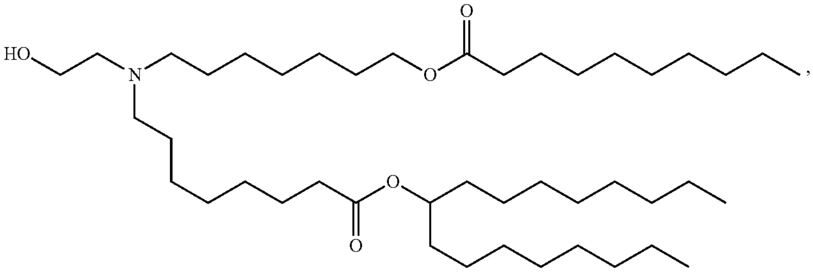
(Compound 97)
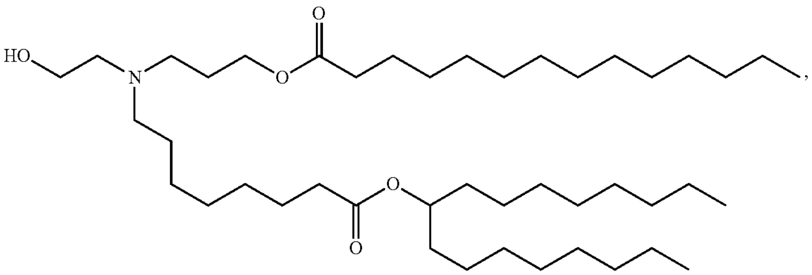

-continued
(Compound 98)
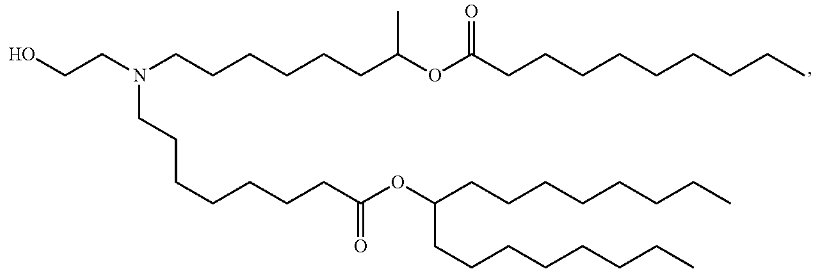
(Compound 99)
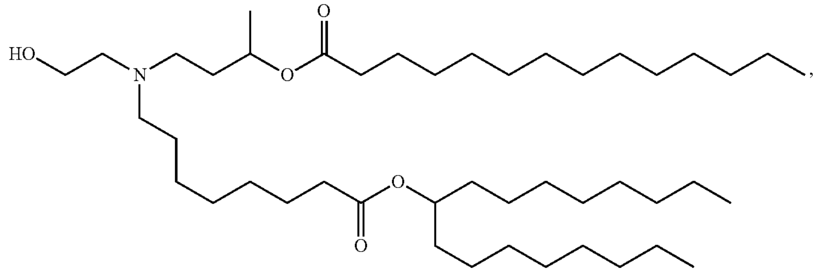
(Compound 100)
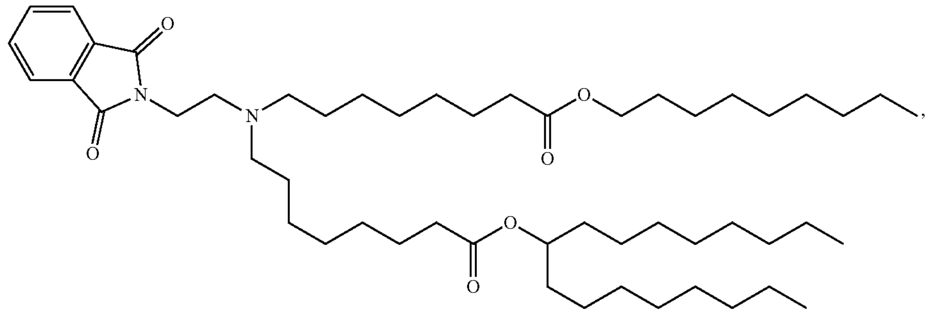
(Compound 101)
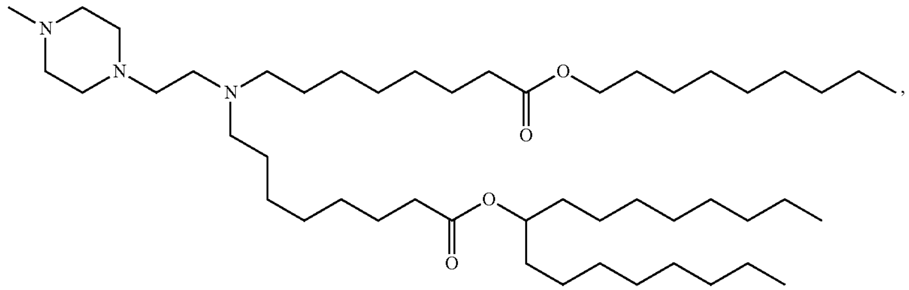
(Compound 102)
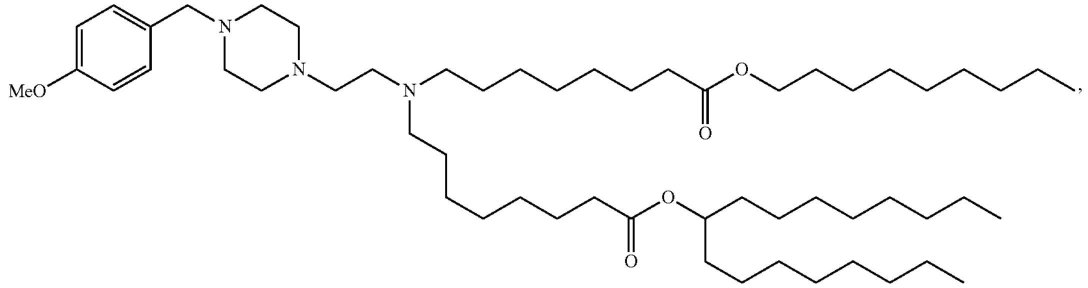

-continued
(Compound 103)
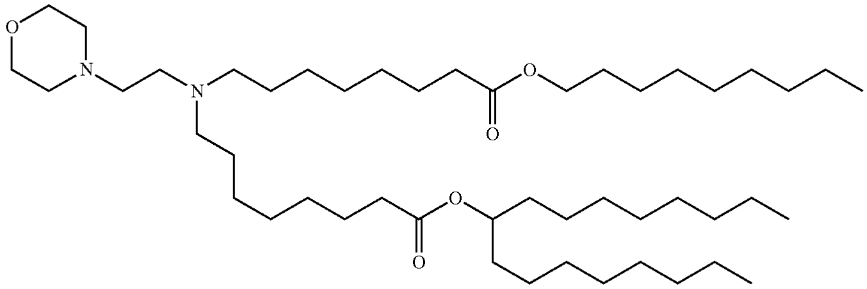
(Compound 104)
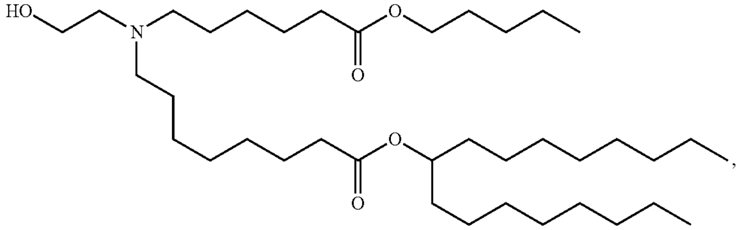
,
(Compound 105)
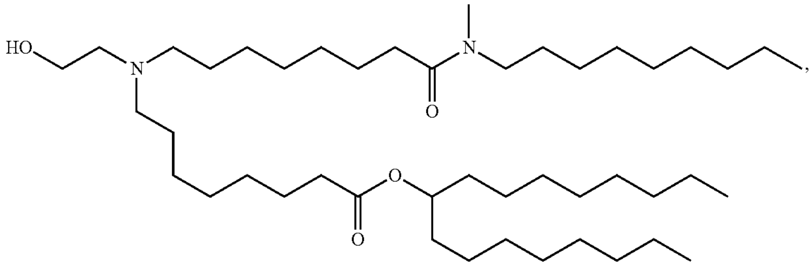
,
(Compound 106)
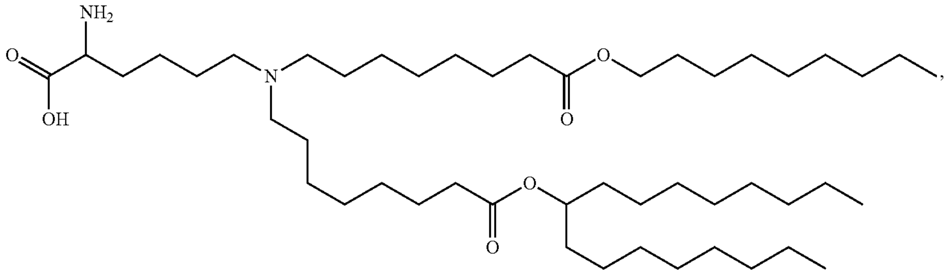
,
(Compound 107)
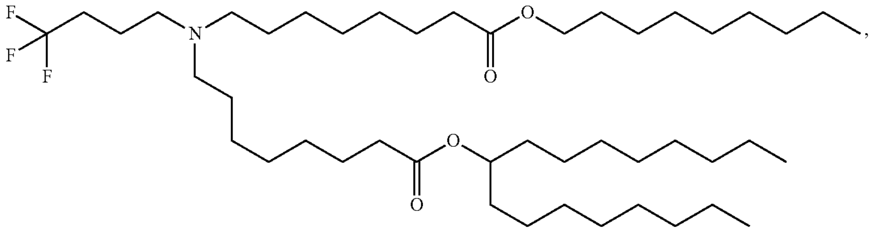
,
(Compound 108)
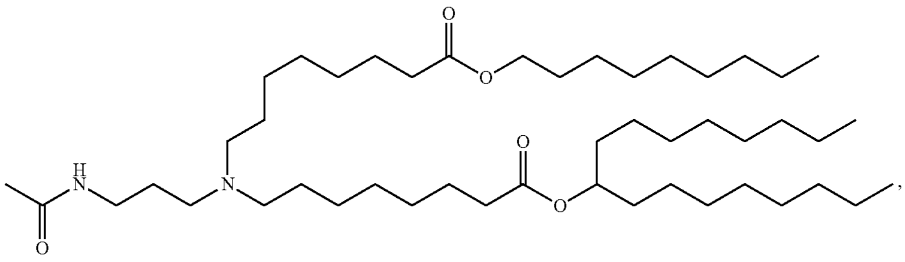
, -continued
(Compound 109)
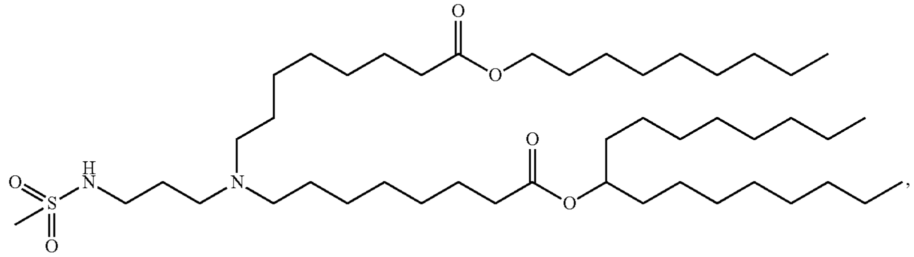
(Compound 110)
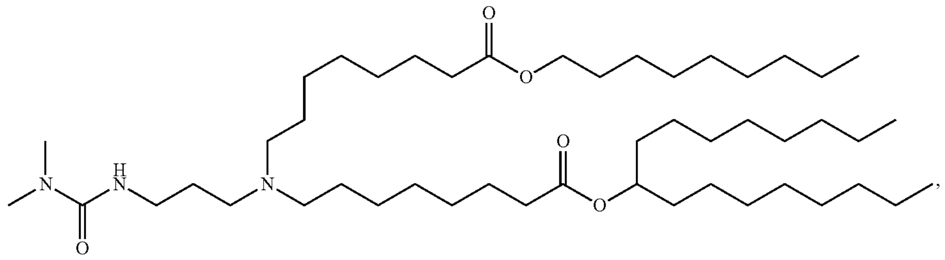
(Compound 111)
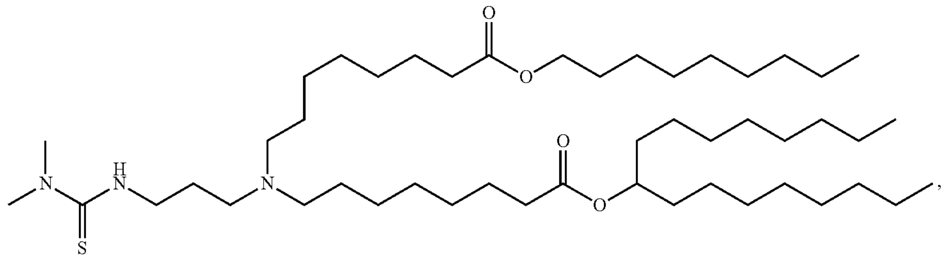
(Compound 112)
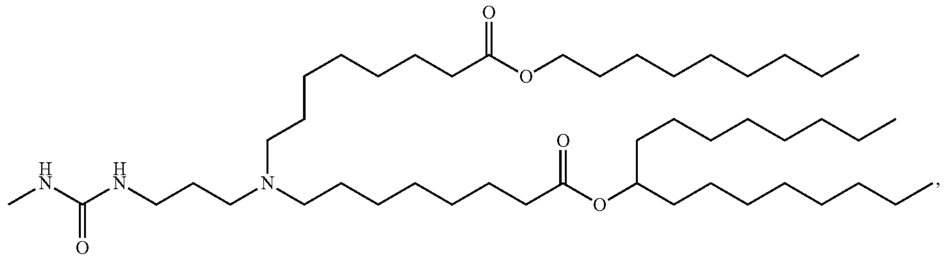
(Compound 113)
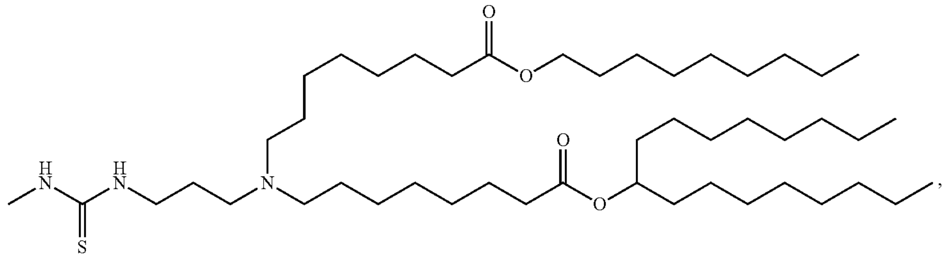
(Compound 114)
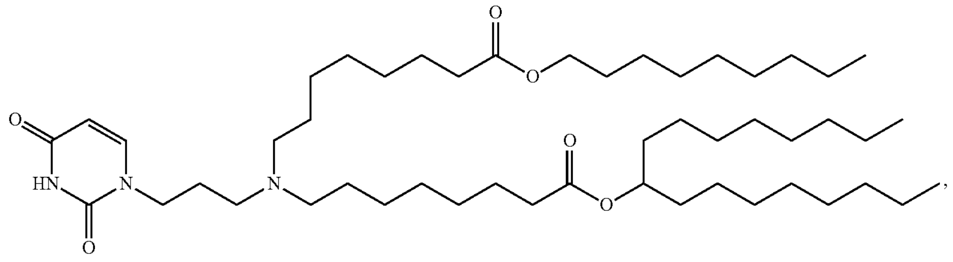

-continued
(Compound 115)
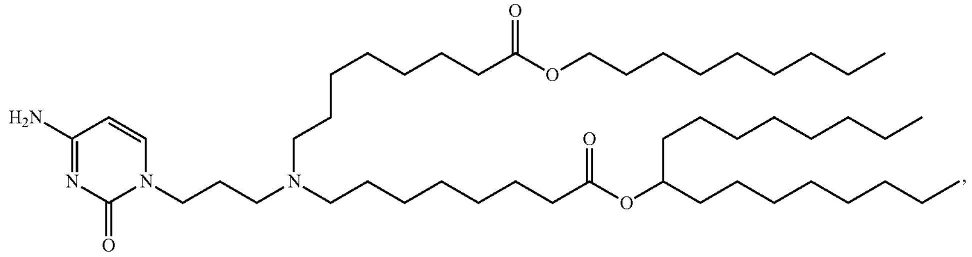
(Compound 116)
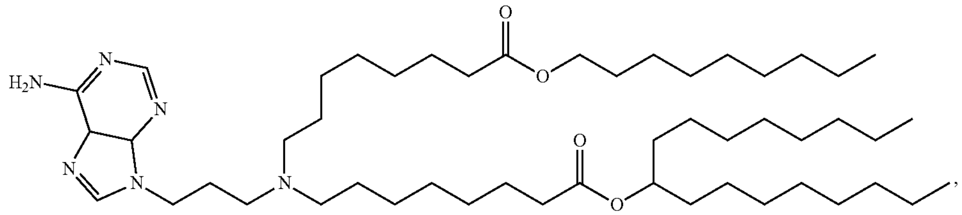
(Compound 117)
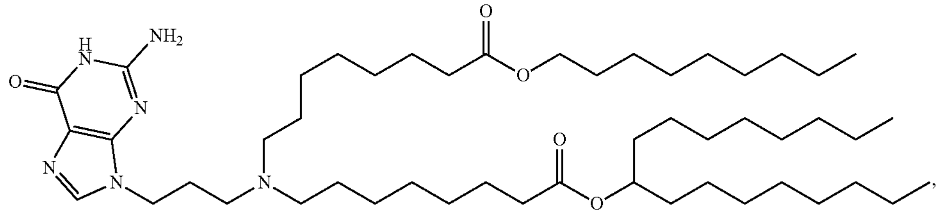
(Compound 118)
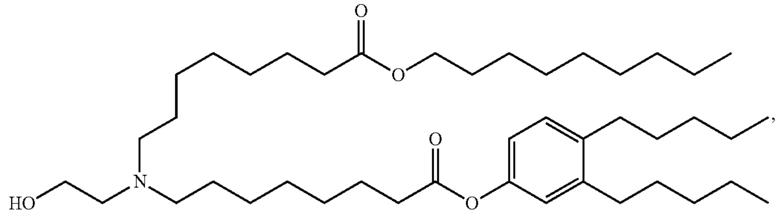
(Compound 119)
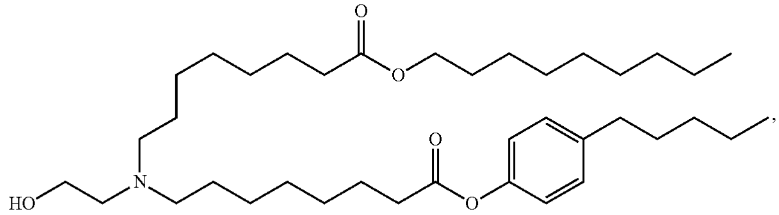
(Compound 120)
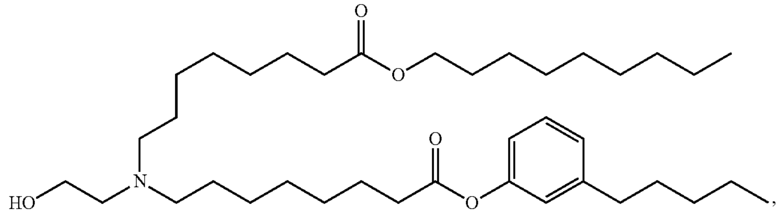
(Compound 121)
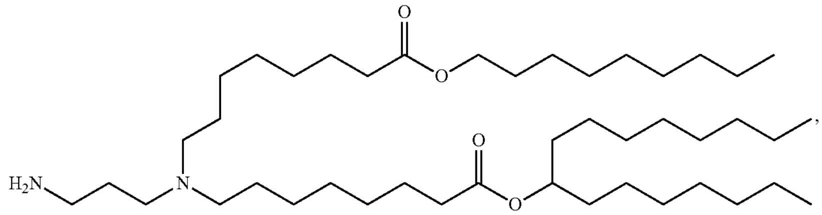

-continued
(Compound 122)
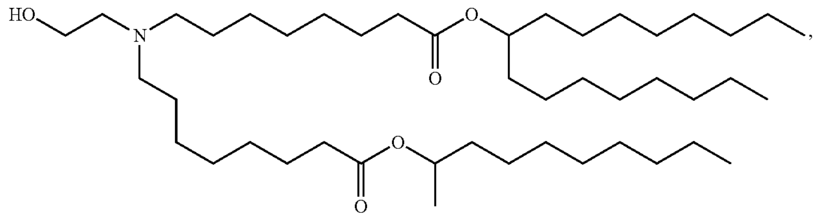
(Compound 123)
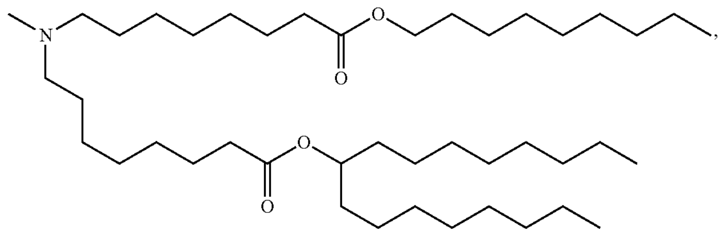
(Compound 124)
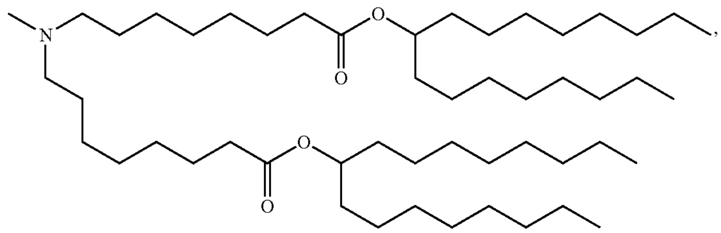
(Compound 125)
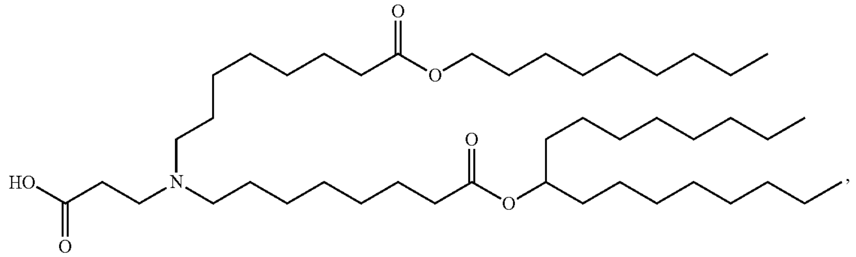
(Compound 126)
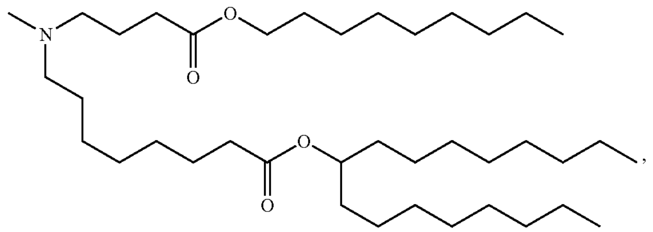
(Compound 127)
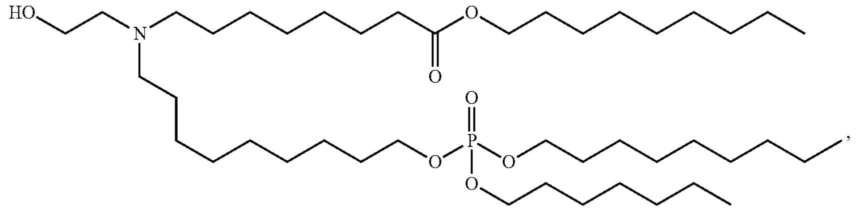

-continued
(Compound 128)
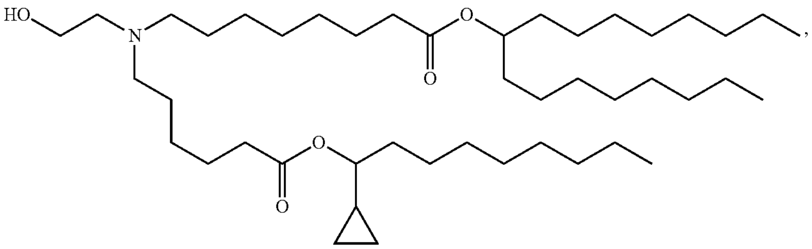
(Compound 129)
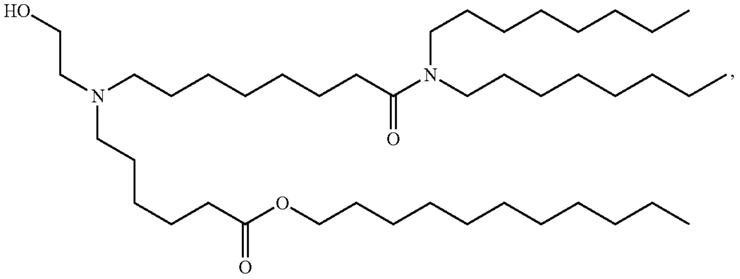
(Compound 130)
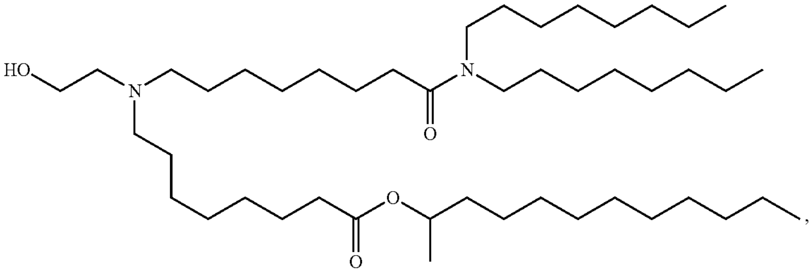
(Compound 131)
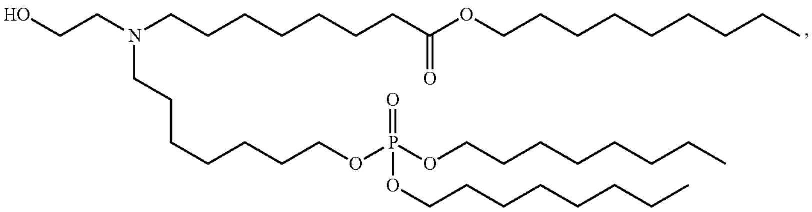
(Compound 132)
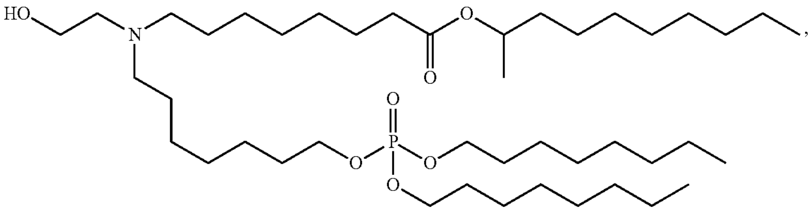
(Compound 133)
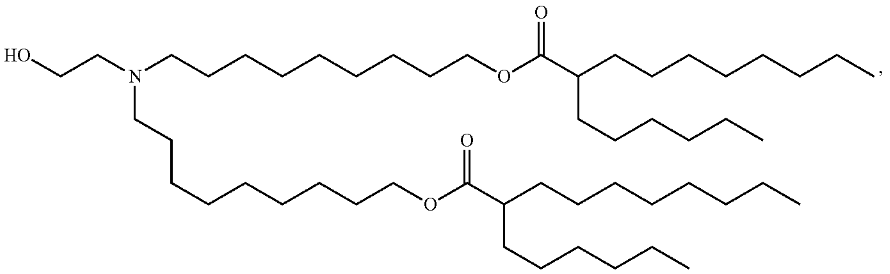

-continued
(Compound 134)
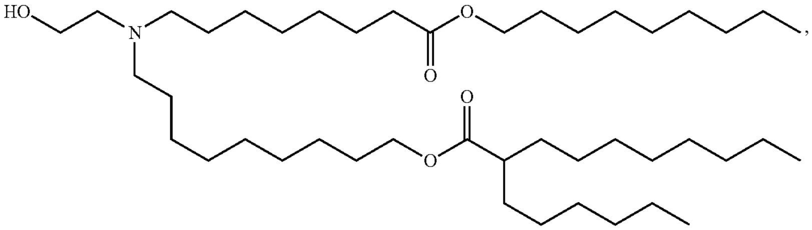
,
(Compound 135)
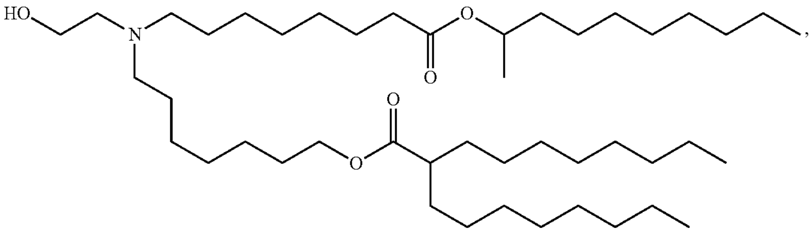
,
(Compound 136)
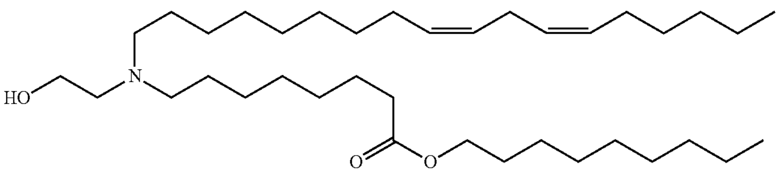
,
(Compound 137)
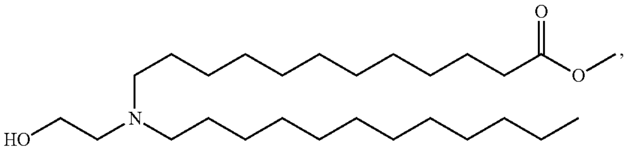
,
(Compound 138)
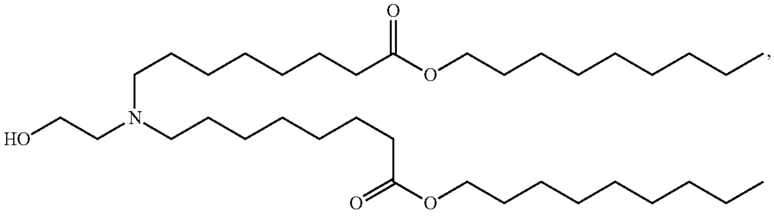
,
(Compound 139)
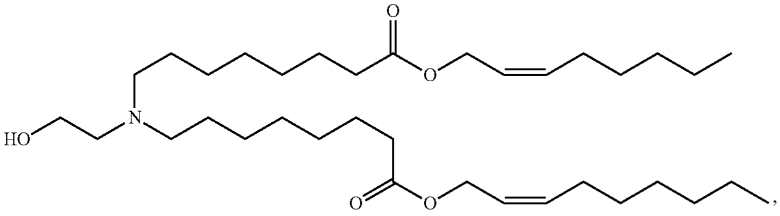
,
(Compound 140)
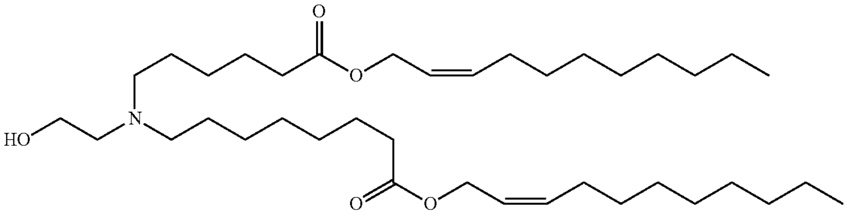
, -continued
(Compound 141)
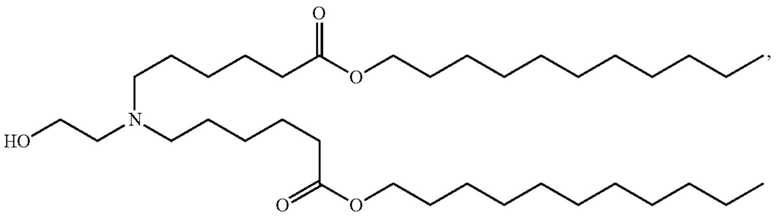
(Compound 142)
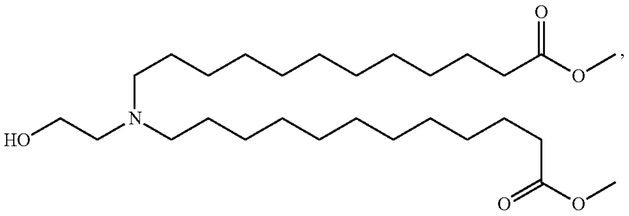
(Compound 143)
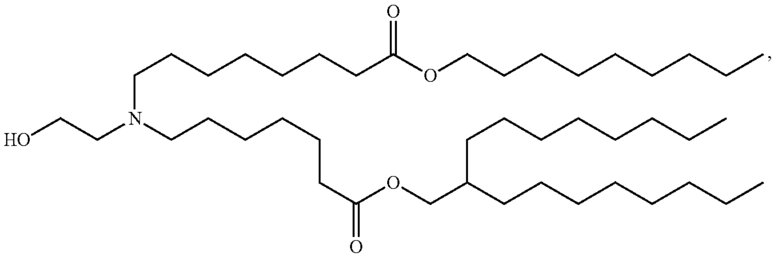
(Compound 144)
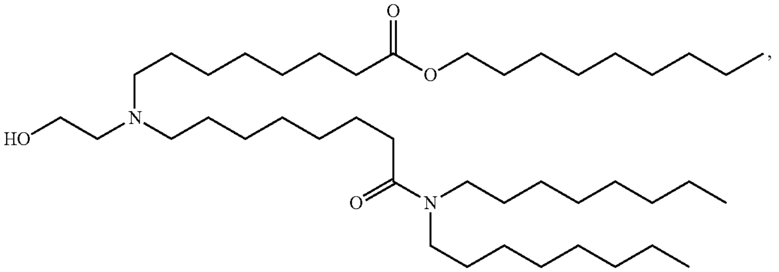
(Compound 145)
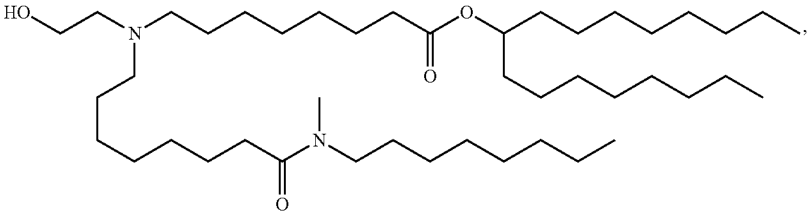
(Compound 146)
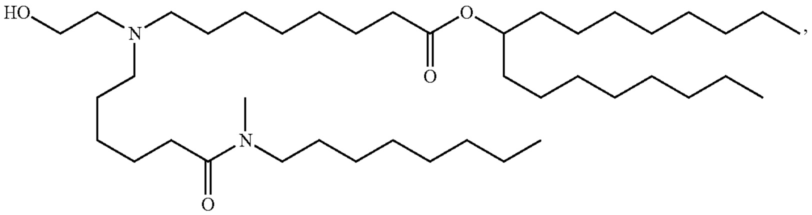

-continued (Compound 147)

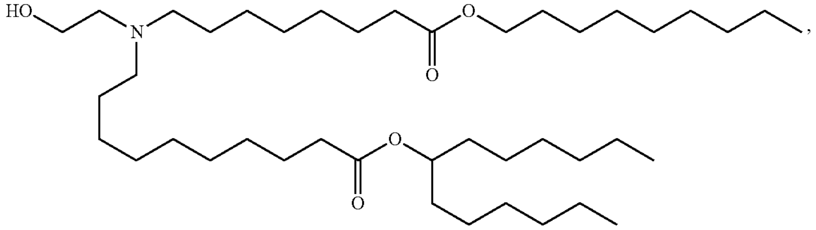

or a salt or stereoisomer thereof.

10. The pharmaceutical composition of claim 9, wherein the compound is (Compound 18)

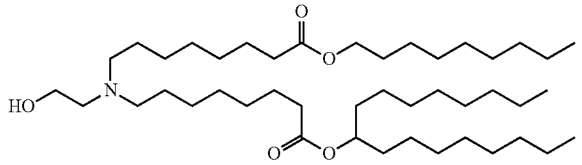

or a salt or stereoisomer thereof.

11. The pharmaceutical composition of claim 1, wherein the lipid nanoparticle comprises Compound 18, DSPC, Cholesterol, and Compound 428 with a mole ratio of about 50:10:38.5:1.5, wherein Compound 18 is

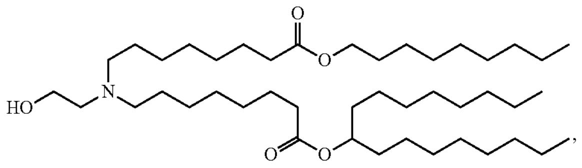 [SMILES: CCCCCCCCCOC(=O)CCCCCCCN(CCO)CCCCCCCC(=O)OC(CCCCCCCC)CCCCCCCC]

and wherein Compound 428 is

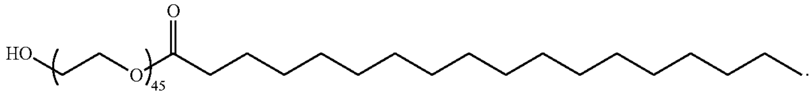

12. The pharmaceutical composition of claim 1, wherein the lipid nanoparticle comprises from about 45 mol % to about 55 mol % of ionizable lipid.

13. The pharmaceutical composition of claim 1, wherein the lipid nanoparticle comprises from about 1 mol % to about 20 mol % of phophsolipid.

14. The pharmaceutical composition of claim 1, wherein the lipid nanoparticle comprises from about 35 mol % to about 40 mol % of structural lipid.

15. The pharmaceutical composition of claim 1, wherein the lipid nanoparticle comprises from about 2 mol % to about 4 mol % of PEG lipid.

16. A method of expressing a GALT polypeptide in a human subject in need thereof comprising administering to the subject an effective amount of the pharmaceutical composition of claim 1, wherein the pharmaceutical composition is suitable for administrating as a single dose or as a plurality of single unit doses to the subject.

17. A method of treating, preventing or delaying the onset and/or progression of Gal-1 signs or symptoms in a human subject in need thereof comprising administering to the subject an effective amount of the pharmaceutical composition of claim 1, wherein the administration treats, prevents or delays the onset and/or progression of one or more of the signs or symptoms of Gal-1 in the subject.

18. A method for the treatment of Gal-1, comprising administering to a human subject suffering from Gal-1 a single dose or as a plurality of single unit doses of the pharmaceutical composition of claim 1.

19. A method of reducing a galactose-1-phosphate (Gal-1-P) and/or galactose blood level in a human subject in need thereof comprising administering to the subject an effective amount of the pharmaceutical composition of claim 1, wherein the administration reduces the Gal-1-P and/or galactose blood level in the subject.

20. The method of claim 16, wherein (i) the Gal-1-P red blood cell (RBC) and/or liver level is reduced at least 20%, at least 30%, at least 40%, at least 50%, at least 60%, at least 70%, at least 80%, at least 90%, or at least 100% as compared to the subject's baseline Gal-1-P RBC and/or liver level or a reference Gal-1-P RBC and/or liver level in a patient with Gal-1, for at least 24 hours, at least 48 hours, at least 72 hours, at least 96 hours, at least 120 hours, 6 days, 1 week, 8 days, 9 days, 10 days, 11 days, or 12 days post-administration, and/or (ii) the galactose plasma, serum, and/or urine level is reduced at least 20%, at least 30%, at least 40%, at least 30%, at least 40%, at least 50%, at least 60%, at least 70%, at least 80%, at least 90%, or at least 100% as compared to the subject's baseline galactose plasma, serum, and/or urine level or a reference galactose plasma, serum, and/or urine level in a patient with Gal-1, for at least 24 hours, at least 48 hours, at least 72 hours, at least 96 hours, at least 120 hours, 6 days, 1 week, 8 days, 9 days, 10 days, 11 days, or 12 days post-administration.

21. A method of increasing GALT activity in a human subject in need thereof comprising administering to the subject an effective amount of the pharmaceutical composition of claim 1, wherein the administration increases GALT activity in the subject.

22. A method of treating Gal-1 in a human subject in need thereof, comprising administering to the human subject an effective amount of the pharmaceutical composition of claim 1.

23. A method of reducing a Gal-1-P and/or galactose blood level in a human subject in need thereof comprising administering to the subject an effective amount of the pharmaceutical composition of claim 4, wherein the administration reduces the Gal-1-P and/or galactose blood level in the subject.

24. A method of increasing GALT activity in a human subject in need thereof comprising administering to the subject an effective amount of the pharmaceutical composition of claim 4, wherein the administration increases GALT activity in the subject.

25. A method of treating Gal-1 in a human subject in need thereof, comprising administering to the human subject an effective amount of the pharmaceutical composition of claim 4.

26. A method of reducing a Gal-1-P and/or galactose blood level in a human subject in need thereof comprising administering to the subject an effective amount of the pharmaceutical composition of claim 10, wherein the administration reduces the Gal-1-P and/or galactose blood level in the subject.

27. A method of increasing GALT activity in a human subject in need thereof comprising administering to the subject an effective amount of the pharmaceutical composition of claim 10, wherein the administration increases GALT activity in the subject.

28. A method of treating Gal-1 in a human subject in need thereof, comprising administering to the human subject an effective amount of the pharmaceutical composition of claim 10.

29. A method of reducing a Gal-1-P and/or galactose blood level in a human subject in need thereof comprising administering to the subject an effective amount of the pharmaceutical composition of claim 11, wherein the administration reduces the Gal-1-P and/or galactose blood level in the subject.

30. A method of increasing GALT activity in a human subject in need thereof comprising administering to the subject an effective amount of the pharmaceutical composition of claim 11, wherein the administration increases GALT activity in the subject.

31. A method of treating Gal-1 in a human subject in need thereof, comprising administering to the human subject an effective amount of the pharmaceutical composition of claim 11.

32. The pharmaceutical composition of claim 1, wherein the GALT polypeptide comprises SEQ ID NO:1 or SEQ ID NO:3.

33. The pharmaceutical composition of claim 2, wherein the GALT polypeptide comprises SEQ ID NO:1 or SEQ ID NO:3.

34. The pharmaceutical composition of claim 4, wherein the GALT polypeptide comprises SEQ ID NO:1 or SEQ ID NO:3.

35. The pharmaceutical composition of claim 8, wherein the GALT polypeptide comprises SEQ ID NO:1 or SEQ ID NO:3.

36. The pharmaceutical composition of claim 9, wherein the GALT polypeptide comprises SEQ ID NO:1 or SEQ ID NO:3.

37. The pharmaceutical composition of claim 10, wherein the GALT polypeptide comprises SEQ ID NO:1 or SEQ ID NO:3.

38. The pharmaceutical composition of claim 11, wherein the GALT polypeptide comprises SEQ ID NO:1 or SEQ ID NO:3.

39. The method of claim 19, wherein the GALT polypeptide comprises SEQ ID NO:1 or SEQ ID NO:3.

40. The method of claim 21, wherein the GALT polypeptide comprises SEQ ID NO:1 or SEQ ID NO:3.

41. The method of claim 22, wherein the GALT polypeptide comprises SEQ ID NO:1 or SEQ ID NO:3.

42. The method of claim 23, wherein the GALT polypeptide comprises SEQ ID NO:1 or SEQ ID NO:3.

43. The method of claim 24, wherein the GALT polypeptide comprises SEQ ID NO:1 or SEQ ID NO:3.

44. The method of claim 25, wherein the GALT polypeptide comprises SEQ ID NO:1 or SEQ ID NO:3.

45. The method of claim 26, wherein the GALT polypeptide comprises SEQ ID NO:1 or SEQ ID NO:3.

46. The method of claim 27, wherein the GALT polypeptide comprises SEQ ID NO:1 or SEQ ID NO:3.

47. The method of claim 28, wherein the GALT polypeptide comprises SEQ ID NO:1 or SEQ ID NO:3.

48. The method of claim 29, wherein the GALT polypeptide comprises SEQ ID NO:1 or SEQ ID NO:3.

49. The method of claim 30, wherein the GALT polypeptide comprises SEQ ID NO:1 or SEQ ID NO:3.

50. The method of claim 31, wherein the GALT polypeptide comprises SEQ ID NO:1 or SEQ ID NO:3.

* * * * *

SEQUENCE LISTING

```
<160> NUMBER OF SEQ ID NOS: 179

<210> SEQ ID NO 1
<211> LENGTH: 379
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: wild-type isoform 1 of human GALT

<400> SEQUENCE: 1

Met Ser Arg Ser Gly Thr Asp Pro Gln Gln Arg Gln Gln Ala Ser Glu
1               5                   10                  15

Ala Asp Ala Ala Ala Ala Thr Phe Arg Ala Asn Asp His Gln His Ile
            20                  25                  30

Arg Tyr Asn Pro Leu Gln Asp Glu Trp Val Leu Val Ser Ala His Arg
        35                  40                  45

Met Lys Arg Pro Trp Gln Gly Gln Val Glu Pro Gln Leu Leu Lys Thr
    50                  55                  60

Val Pro Arg His Asp Pro Leu Asn Pro Leu Cys Pro Gly Ala Ile Arg
65                  70                  75                  80

Ala Asn Gly Glu Val Asn Pro Gln Tyr Asp Ser Thr Phe Leu Phe Asp
                85                  90                  95

Asn Asp Phe Pro Ala Leu Gln Pro Asp Ala Pro Ser Pro Gly Pro Ser
            100                 105                 110

Asp His Pro Leu Phe Gln Ala Lys Ser Ala Arg Gly Val Cys Lys Val
        115                 120                 125

Met Cys Phe His Pro Trp Ser Asp Val Thr Leu Pro Leu Met Ser Val
```

```
    130                 135                 140

Pro Glu Ile Arg Ala Val Val Asp Ala Trp Ala Ser Val Thr Glu Glu
145                 150                 155                 160

Leu Gly Ala Gln Tyr Pro Trp Val Gln Ile Phe Glu Asn Lys Gly Ala
                165                 170                 175

Met Met Gly Cys Ser Asn Pro His Pro His Cys Gln Val Trp Ala Ser
            180                 185                 190

Ser Phe Leu Pro Asp Ile Ala Gln Arg Glu Glu Arg Ser Gln Gln Ala
        195                 200                 205

Tyr Lys Ser Gln His Gly Glu Pro Leu Leu Met Glu Tyr Ser Arg Gln
    210                 215                 220

Glu Leu Leu Arg Lys Glu Arg Leu Val Leu Thr Ser Glu His Trp Leu
225                 230                 235                 240

Val Leu Val Pro Phe Trp Ala Thr Trp Pro Tyr Gln Thr Leu Leu Leu
                245                 250                 255

Pro Arg Arg His Val Arg Arg Leu Pro Glu Leu Thr Pro Ala Glu Arg
            260                 265                 270

Asp Asp Leu Ala Ser Ile Met Lys Lys Leu Leu Thr Lys Tyr Asp Asn
        275                 280                 285

Leu Phe Glu Thr Ser Phe Pro Tyr Ser Met Gly Trp His Gly Ala Pro
    290                 295                 300

Thr Gly Ser Glu Ala Gly Ala Asn Trp Asn His Trp Gln Leu His Ala
305                 310                 315                 320

His Tyr Tyr Pro Pro Leu Leu Arg Ser Ala Thr Val Arg Lys Phe Met
                325                 330                 335

Val Gly Tyr Glu Met Leu Ala Gln Ala Gln Arg Asp Leu Thr Pro Glu
            340                 345                 350

Gln Ala Ala Glu Arg Leu Arg Ala Leu Pro Glu Val His Tyr His Leu
        355                 360                 365

Gly Gln Lys Asp Arg Glu Thr Ala Thr Ile Ala
    370                 375
```

<210> SEQ ID NO 2
<211> LENGTH: 1137
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: nucleotide sequence of wild type PBGD, isoform
      1

<400> SEQUENCE: 2

```
atgtcgcgca gtggaaccga tcctcagcaa cgccagcagg cgtcagaggc ggacgccgca     60

gcagcaacct tccgggcaaa cgaccatcag catatccgct acaacccgct gcaggatgag    120

tgggtgctgg tgtcagctca ccgcatgaag cggccctggc agggtcaagt ggagccccag    180

cttctgaaga cagtgccccg ccatgaccct ctcaaccctc tgtgtcctgg ggccatccga    240

gccaacggag aggtgaatcc ccagtacgat agcaccttcc tgtttgacaa cgacttccca    300

gctctgcagc ctgatgcccc cagtccagga cccagtgatc atccccttt ccaagcaaag     360

tctgctcgag gagtctgtaa ggtcatgtgc ttccacccct ggtcggatgt aacgctgcca    420

ctcatgtcgg tccctgagat ccgggctgtt gttgatgcat gggcctcagt cacagaggag    480

ctgggtgccc agtacccttg ggtgcagatc tttgaaaaca aaggtgccat gatgggctgt    540
```

```
tctaaccccc acccccactg ccaggtatgg gccagcagtt tcctgccaga tattgcccag    600

cgtgaggagc gatctcagca ggcctataag agtcagcatg gagagcccct gctaatggag    660

tacagccgcc aggagctact caggaaggaa cgtctggtcc taaccagtga gcactggtta    720

gtactggtcc ccttctgggc aacatggccc taccagacac tgctgctgcc ccgtcggcat    780

gtgcggcggc tacctgagct gacccctgct gagcgtgatg atctagcctc catcatgaag    840

aagctcttga ccaagtatga caacctcttt gagacgtcct ttccctactc catgggctgg    900

catggggctc ccacaggatc agaggctggg gccaactgga accattggca gctgcacgct    960

cattactacc ctccgctcct gcgctctgcc actgtccgga aattcatggt tggctacgaa   1020

atgcttgctc aggctcagag ggacctcacc cctgagcagg ctgcagagag actaagggca   1080

cttcctgagg ttcattacca cctggggcag aaggacaggg agacagcaac catcgcc      1137
```

```
<210> SEQ ID NO 3
<211> LENGTH: 270
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: wild-type isoform 2 of human GALT

<400> SEQUENCE: 3

Met Thr Leu Ser Thr Leu Cys Val Leu Gly Pro Ser Glu Pro Thr Glu
1               5                   10                  15

Ser Lys Val Met Cys Phe His Pro Trp Ser Asp Val Thr Leu Pro Leu
            20                  25                  30

Met Ser Val Pro Glu Ile Arg Ala Val Val Asp Ala Trp Ala Ser Val
        35                  40                  45

Thr Glu Glu Leu Gly Ala Gln Tyr Pro Trp Val Gln Ile Phe Glu Asn
    50                  55                  60

Lys Gly Ala Met Met Gly Cys Ser Asn Pro His Pro His Cys Gln Val
65                  70                  75                  80

Trp Ala Ser Ser Phe Leu Pro Asp Ile Ala Gln Arg Glu Glu Arg Ser
                85                  90                  95

Gln Gln Ala Tyr Lys Ser Gln His Gly Glu Pro Leu Leu Met Glu Tyr
            100                 105                 110

Ser Arg Gln Glu Leu Leu Arg Lys Glu Arg Leu Val Leu Thr Ser Glu
        115                 120                 125

His Trp Leu Val Leu Val Pro Phe Trp Ala Thr Trp Pro Tyr Gln Thr
    130                 135                 140

Leu Leu Leu Pro Arg Arg His Val Arg Arg Leu Pro Glu Leu Thr Pro
145                 150                 155                 160

Ala Glu Arg Asp Asp Leu Ala Ser Ile Met Lys Lys Leu Leu Thr Lys
                165                 170                 175

Tyr Asp Asn Leu Phe Glu Thr Ser Phe Pro Tyr Ser Met Gly Trp His
            180                 185                 190

Gly Ala Pro Thr Gly Ser Glu Ala Gly Ala Asn Trp Asn His Trp Gln
        195                 200                 205

Leu His Ala His Tyr Tyr Pro Pro Leu Leu Arg Ser Ala Thr Val Arg
    210                 215                 220

Lys Phe Met Val Gly Tyr Glu Met Leu Ala Gln Ala Gln Arg Asp Leu
225                 230                 235                 240

Thr Pro Glu Gln Ala Ala Glu Arg Leu Arg Ala Leu Pro Glu Val His
```

-continued 245 250 255

Tyr His Leu Gly Gln Lys Asp Arg Glu Thr Ala Thr Ile Ala
260 265 270

<210> SEQ ID NO 4
<211> LENGTH: 810
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: wild type isoform

<400> SEQUENCE: 4
atgaccctct caaccctctg tgtcctgggg ccatccgagc caacggagag taaggtcatg 60
tgcttccacc cctggtcgga tgtaacgctg ccactcatgt cggtccctga gatccgggct 120
gttgttgatg catgggcctc agtcacagag gagctgggtg cccagtaccc ttgggtgcag 180
atctttgaaa acaaaggtgc catgatgggc tgttctaacc cccacccccca ctgccaggta 240 tgggccagca gtttcctgcc agatattgcc cagcgtgagg agcgatctca gcaggcctat 300
aagagtcagc atggagagcc cctgctaatg gagtacagcc gccaggagct actcaggaag 360
gaacgtctgg tcctaaccag tgagcactgg ttagtactgg tccccttctg ggcaacatgg 420
ccctaccaga cactgctgct gccccgtcgg catgtgcggc ggctacctga gctgacccct 480
gctgagcgtg atgatctagc ctccatcatg aagaagctct tgaccaagta tgacaacctc 540
tttgagacgt cctttcccta ctccatgggc tggcatgggg ctcccacagg atcagaggct 600
ggggccaact ggaaccattg gcagctgcac gctcattact accctccgct cctgcgctct 660
gccactgtcc ggaaattcat ggttggctac gaaatgcttg ctcaggctca gagggacctc 720
acccctgagc aggctgcaga gagactaagg gcacttcctg aggttcatta ccacctgggg 780
cagaaggaca gggagacagc aaccatcgcc 810

<210> SEQ ID NO 5
<211> LENGTH: 1137
<212> TYPE: RNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: GALT-CO01

<400> SEQUENCE: 5
augagcaggu ccgggaccga uccccagcag aggcagcagg ccuccgaggc ggacgccgcc 60
gccgccaccu uucgcgccaa cgaccaccag cauaucaggu acaaccccuu gcaagacgag 120
uggguccuag ugagcgccca caggaugaag cggcccuggc agggccaggu ggagccccag 180
cugcugaaga ccgugccucg ccacgacccc cugaaccccc ugugccccgg ggccaucagg 240
gccaacggug aggugaaccc acaauacgau ucgaccuucc uauucgacaa cgauuucccc 300
gcccuccagc ccgaugcccc cagccccggc ccguccgacc auccgcuguu ccaggccaag 360
uccgccaggg gagugugaa ggugaugugc uuucaccccu gguccgaugu gacccucccg 420
cugaugagcg ugcccgagau cagggcagug gucgacgccu gggcgagcgu gaccgaagag 480
cucggugccc aguacccgug ggugcagauc uucgagaaua agggcgccau gaugggcugc 540
agcaaccccc auccccacug ccaagugugg gcaagcagcu uccugcccga caucgcccag 600
agggaggagc gcucccagca ggccuacaaa agccagcacg gcgaaccccu ucugauggag 660
uacagccggc aggagcugcu caggaaagag aggcuggugc ugacaagcga gcacuggcuc 720
gugcuggugc cguucugggc caccuggccc uaccagaccc ugcugcugcc caggaggcac 780
gugaggcguc uucccgaacu cacgcccgcc gagagggaug aucuggccuc caucaugaag 840
aagcugcuga ccaaauacga caaucucuuc gagaccuccu uccccuacag caugggaugg 900
cacggcgccc cgaccggcuc cgaggccggc gccaauugga accacuggca gcuccacgcc 960
cacuacuacc ccccccuccu gagguccgcc accgugcgua aguucauggu aggcuaugag 1020
augcuggccc aggcccagcg ggaccugacc ccggagcagg ccgccgagcg gcugcgggcc 1080
cuccccgagg uccacuauca ccucggccag aaagacaggg agaccgccac caucgcc 1137

<210> SEQ ID NO 6
<211> LENGTH: 1137
<212> TYPE: RNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: GALT-CO02

<400> SEQUENCE: 6
augucccgaa gcggcaccga uccgcagcag cggcagcagg caucagaggc cgacgccgcc 60
gccgccaccu uucgugccaa cgaccaccag cacauuaggu acaaucccu gcaagacgag 120 ugggugcugg ugagcgccca ccggaugaaa aggcccuggc agggccaggu cgagccccag 180
cuacucaaga ccgucccag gcacgacccc cugaaccccc ucugccccgg cgcgauccgg 240
gccaauggcg aggugaaccc ccaguacgau uccaccuucc uguucgacaa cgacuucccc 300
gcccugcagc ccgaugcccc gagccccggc cccagcgacc acccccuguu ccaggccaaa 360
uccgccagag gugugugcaa ggugaugugc uuccacccu ggagcgacgu gacccugccc 420
cucaugagcg uccccgagau ccgcgcagug guggacgccu gggcguccgu gaccgaggag 480
cugggggccc aguaccccug ggugcagauc uuugagaaua agggcgccau gaugggcugu 540
agcaaccccc acccccacug ucaggugugg gccagcagcu uccugcccga caucgcccag 600
agggaagagc gcagccagca ggccuauaag agccagcaug ggagccccu gcucauggaa 660 uacucccguc aggagcugcu gcggaaggag aggcuggugc ugacuagcga gcauuggcug 720
gugcuggugc ccuucugggc caccuggccu uaccagaccc ugcugcuccc ccggaggcac 780
gugcgaaggc ugcccgagcu gacccccgcc gagcgcgacg accuggccuc aaucaugaag 840
aagcugcuga ccaaguacga caaccuuuuc gagaccuccu ucccguauag caugggcugg 900
cacggcgccc ccaccggcag cgaggccggc gccaacugga accacuggca gcugcacgcg 960
cacuacuacc cuccccugcu caggagcgcc accgugcgga aguucauggu gggcuacgaa 1020
augcuggccc aagcgcagcg cgaccucacc cccgagcagg ccgccgaaag gcuccgugcc 1080
cugccagagg ugcacuacca ccugggucaa aaggaucggg agaccgccac caucgcc 1137

<210> SEQ ID NO 7
<211> LENGTH: 1137
<212> TYPE: RNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: GALT-CO03

<400> SEQUENCE: 7
augagcagga gcgguaccga cccccagcaa cggcagcagg ccuccgaggc cgacgcagcc 60
gccgccaccu uccgcgccaa cgaccaucag cauauccgcu acaacccccu gcaggacgag 120
ugggugcugg uguccgccca caggaugaag cggcccuggc agggccaggu ggagccccag 180
cugcugaaaa ccgugccgcg acacgacccc cuuaaccccc ucugucccgg ugccauccgc 240
gccaacggcg aggugaaccc acaguacgac agcacauucc uguuugacaa cgacuuuccc 300
gcucuccagc ccgacgcccc cagccccggc cccagcgacc auccccucuu ccaggccaag 360
agugcgcggg gcgugugcaa ggugaugugu uuccaccccu gguccgacgu gacccugccu 420
cugaugagcg ugcccgagau cagggccgug gucgacgccu gggccucggu gaccgaggag 480
cugggcgccc aauaccccug gguccagauc uucgaaaaca agggcgccau gaugggcugc 540
agcaaccccc acccucacug ucaggugugg gccuccuccu uccuccccga caucgcccag 600
agggaagaaa ggagccagca ggccuacaag ucacaacacg gcgagccgcu gcugauggag 660
uacuccaggc aggagcugcu gaggaaggag cggcuggugc ugaccagcga gcacuggcug 720
guccuggugc ccuucugggc caccuggccg uaccagaccu ugcugcugcc caggaggcau 780
gugaggaggc ugccagagcu cacccccgcc gaacgggacg accuggccuc uaucaugaag 840
aagcugcuga ccaaguauga caaccuguuc gaaacgagcu ucccauacag caugggcugg 900
cacggggcac ccaccggcag cgaggccggc gccaacugga accacuggca gcugcacgcc 960
cauuacuacc cgccccugcu gcggagcgcc accguccgga aguucauggu gggcuacgag 1020
augcuggcac aggcgcagag ggaccugacc cccgagcagg ccgcagagcg gcuccgggcc 1080
cugcccgagg ugcacuacca ccucggccag aaggauaggg agaccgccac caucgcc 1137

<210> SEQ ID NO 8
<211> LENGTH: 1137
<212> TYPE: RNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: GALT-CO04

<400> SEQUENCE: 8
augagccgga gcggcaccga cccccaacag cgccagcagg ccuccgaagc cgacgccgcc 60
gccgccaccu uccgcgccaa cgaccaccag cauauccggu auaacccccu gcaggacgag 120
ugggugcugg ugagcgccca cagaaugaag aggcccuggc agggccaggu ugaaccccaa 180
cugcugaaga ccgugcccag gcacgacccc cugaacccgc ugugcccggg agccaucagg 240
gccaacggcg aggucaaccc ccaguacgau agcacguucc uguuugacaa ugacuuccca 300
gcccugcaac ccgaugcccc aucccccggg ccauccgacc acccccuguu ccaggccaag 360
uccgcccgag gcgucugcaa ggugaugugc uuucaccccu ggagcgacgu gacccugccc 420
cugaugagcg ugccggagau ccgcgccgug guggacgccu gggcguccgu gaccgaagaa 480
cugggcgccc aauaccccug ggugcagauc uucgagaaca agggcgccau gaugggaugc 540
uccaaccccc acccccauug ccaggugugg gccagcagcu uccugcccga caucgcccag 600
agggaagaga ggagccagca ggccuacaag ucacagcacg gugagccccu gcucauggaa 660
uacagcaggc aggagcugcu gcgcaaggag cgccuggugc ucaccagcga gcauuggcug 720
gugcuggugc ccuucugggc cacauggccc uaccagaccc ugcugcuccc caggaggcac 780
gugaggcggc ugcccgagcu cacgccggcg gagagggacg accuggcgag caucaugaag 840
aagcugcuga ccaaauacga caaccucuuu gagaccagcu uucccuauag caugggcugg 900
cacggcgccc ccaccgggag cgaagccggc gccaacugga accauuggca gcugcacgcc 960
cacuacuacc ccccccugcu gagaagcgcc accgugcgaa aguucauggu gggcuaugag 1020
augcuggccc aagcccagcg cgaccugacc ccggaacagg ccgccgagag acugcgcgcc 1080
cugcccgagg uccacuacca ccucggacag aaggacaggg agaccgccac cauugcc 1137

<210> SEQ ID NO 9
<211> LENGTH: 1137
<212> TYPE: RNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: GALT-CO05

<400> SEQUENCE: 9
auguccaggu ccggcaccga uccccaacaa aggcagcagg ccuccgaggc cgacgccgcc 60
gccgcgaccu ucagggccaa cgaccaccag cacaucaggu auaacccccu ccaggacgag 120
ugggugcugg ugagcgccca caggaugaag cgccccuggc agggccaggu cgaaccccag 180
cuccugaaga ccgugccccg ccacgacccc cugaaccccc ucugcccggg cgccauccgg 240
gccaacggug aggugaaccc ccaguacgac agcacguuuc uguuugacaa cgacuucccc 300
gccuugcagc ccgacgcccc cagccccggc cccagcgacc auccccuguu ucaagccaaa 360
agcgcacggg gcgugugcaa ggugaugugc uuccacccgu ggagcgacgu gacacugccg 420
cugaugucgg ugccggagau cagggccguc guggacgcgu gggccuccgu gaccgaggag 480
cugggggccc aguaccccug ggugcagauc uucgagaaca agggagccau gaugggcugc 540
agcaaucccc acccccacug ccaggucugg gccagcagcu uucugcccga caucgcccaa 600
cgggaggaac gcagccaaca ggccuacaag agccagcaug gcgaaccgcu gcugauggag 660
uacagccgcc aggagcugcu gcggaaggaa aggcuggugc ugacauccga acacuggcug 720
gugcuggugc ccuucugggc caccuggccc uaccagaccc ugcugcugcc caggcgccac 780
gugaggaggc ugcccgagcu gaccccccgcc gagagggacg aucuggcgag caucaugaag 840
aagcuccuca ccaaguacga caaccuuuuc gagaccagcu uucccuacag caugggguugg 900 cacggcgccc ccaccggcag cgaggccggu gccaacugga accacuggca acugcacgcg 960
cacuacuacc ccccccugcu gagguccgcc accgugcgua aguucauggu cggauaugaa 1020
augcuggccc aagcgcagag ggaccucacc cccgagcagg ccgccgagcg ccugagggcc 1080
cugcccgagg ugcauuacca ccuggggcag aaggacaggg agacggccac caucgcc 1137

<210> SEQ ID NO 10
<211> LENGTH: 1137
<212> TYPE: RNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: GALT-CO06

<400> SEQUENCE: 10
augagcagga gcgguacgga cccgcagcaa aggcagcagg ccagcgaggc cgacgccgcc 60
gccgccaccu uccgggccaa cgaccaccaa cacauccggu acaaccccu gcaggacgag 120 ugggugcugg ugagcgcaca ccggaugaag aggcccuggc agggccaggu ggagccccaa 180
cugcugaaga ccgugcccag gcacgacccg cugaaucccc ugugucccgg ugccauuagg 240
gccaaugggg aggugaaccc gcaguacgau agcacguucc uguucgauaa ugacuucccc 300
gcccugcagc cggacgcccc gucccccggc cccagcgacc acccgcucuu ucaggccaag 360
agcgccaggg gcgugugcaa ggugaugugu uuucaccccu ggagcgacgu gacccugccc 420
cugauguccg ugcccgagau ccgcgccgug guggacgcau gggccagcgu gaccgaggaa 480
cugggggccc aguaccccug ggugcagaua uucgagaaca aaggcgccau gaugggcugc 540
agcaaccccc acccccacug ccaggugugg gccucgucgu uucuccccga uaucgcccaa 600
agggaggaga ggucccagca ggccuauaag agccagcaug gcgaaccccu gcugauggag 660
uacagcaggc aggagcugcu gcggaaagaa aggcuggucc ugaccagcga gcauuggcug 720
gugcuggugc ccuucugggc caccuggccc uaccagacgc ugcugcugcc caggaggcac 780
gucaggcgcc ugcccgaacu gacccccgcc gagcgcgaug accucgcuag cauaaugaag 840
aagcugcuga ccaaguacga caaccuguuu gaaaccagcu ucccguacuc aaugggcugg 900
cauggcgccc cgacggguag cgaggcgggc gccaacugga accacuggca gcugcacgcc 960
cacuacuacc ccccccugcu caggagcgcc accgugagga aguuuauggu gggcuacgag 1020
augcuggccc aggcgcagag ggaccugacc cccgagcagg cggccgagag gcugcgagcc 1080
cugcccgagg uccauuacca ccugggccag aaggacaggg aaacggccac gauugcc 1137

<210> SEQ ID NO 11
<211> LENGTH: 1137
<212> TYPE: RNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: GALT-CO07

<400> SEQUENCE: 11
augagcagga gcggcaccga uccccagcag aggcagcagg ccagcgaggc cgacgccgcc 60
gccgccacgu ucagggccaa cgaucaccag cacaucaggu acaacccacu gcaggacgag 120
ugggugcugg ugagcgcgca ucggaugaaa cgccccuggc agggccaggu cgagccgcaa 180
cuccugaaga ccgugccaag gcacgacccc cugaaccccc uaugccccgg cgcgaucagg 240
gccaacggcg aggugaaccc ccaguacgau ucgaccuuuc ucuucgauaa cgacuucccc 300
gcccugcaac ccgacgcccc cagccccggg cccuccgacc acccgcucuu ccaggccaag 360
uccgcccgcg gcgucuguaa ggugaugugc uuccaccccu ggucggacgu gacccucccg 420
cucaugagcg uccccgaaau ccgagccgug guggacgccu gggccucggu gacggaggag 480
cugggcgccc aauaccccug ggugcagauu uuugagaaca agggggcgau gaugggcugc 540
agcaaccccc acccacacug ccaggucugg gccaguagcu uucugcccga uaucgcgcaa 600
agggaagaga ggagccagca ggcauauaaa agccagcaug gcgagccccu gcuuauggag 660
uacuccaggc aggagcugcu gaggaaggag aggcucgugc uaaccagcga gcauuggcug 720
guccuggugc ccuucugggc caccuggcca uaccagaccu ugcugcugcc ccgccggcac 780
guccgcagac ugcccgagcu cacgcccgcc gagagggaug aucuggccag caucaugaag 840
aagcugcuca ccaaauacga uaaccuguuc gagaccagcu ucccguacag caugggggugg 900 cacggcgcgc ccaccggcag cgaggccggc gccaauugga aucacuggca gcugcaugcc 960
cacuacuacc ccccccuccu gcggucggcc accgugagga aauucauggu gggcuaugag 1020
augcuggccc aggcgcagag ggaccugacc cccgaacagg ccgccgaacg acugagggcc 1080
cuccccgagg ugcacuauca ccucgggcaa aaagacaggg agaccgccac caucgcc 1137

<210> SEQ ID NO 12
<211> LENGTH: 1137
<212> TYPE: RNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: GALT-CO08

<400> SEQUENCE: 12
augagccgga gcgggaccga cccacagcag cggcagcagg ccagcgaggc ggacgccgcc 60
gccgccacau uccgcgccaa cgaucaccag cacauccgcu auaaucccccu gcaggacgag 120 uggguccugg ugagcgcuca caggaugaag cgucccuggc aaggccaggu ggagccccag 180
cugcugaaaa ccgugccgag gcacgacccg cuaaacccgu uauguccogg cgccauccga 240 gccaacggcg aagugaaucc gcaguacgac agcaccuucc ucuuugacaa cgacuucccc 300
gcgcugcagc ccgacgcccc cucccccggc cccagcgacc acccgcuguu ccaggccaag 360
agcgcccgag gcgugugcaa agucaugugc uuccaccccu ggagcgacgu gacucugccc 420
cugaugagcg ugcccgagau ccgcgccgug guggacgccu gggccagcgu cacggaagag 480
cugggcgcgc aauaccccug ggugcagauc uucgagaaca agggggccau gaugggggugc 540 agcaaucccc acccccacug ccaggugugg gccagcagcu uccugccgga caucgcucag 600
cgggaggaga ggagccaaca ggccuacaaa agccaacacg gggagccccu gcugauggag 660
uacagcaggc aggagcugcu caggaaagag cggcuggugc ugaccuccga gcauuggcug 720
gugcucguac ccuucugggc caccuggccc uaccagacuc ugcugcugcc gcgccggcac 780
gugcgaaggc uccccgagcu uaccccggcc gaacgggacg accucgccag caucaugaaa 840
aagcugcuga ccaaguacga uaaucuguuc gaaaccagcu uuccauacag uaugggcugg 900
cacggcgccc ccaccgguag cgaggccggc gcgaacugga accauuggca gcugcacgcc 960
cacuacuacc cuccccuccu gcguuccgcc accgugagga aguucauggu gggcuacgag 1020
augcuggccc aggcccaacg ggaucugacc cccgagcagg ccgccgagcg gcuccgggcc 1080
cugcccgagg ugcacuacca ccugggccag aaggaccggg agaccgccac gaucgcc 1137

<210> SEQ ID NO 13
<211> LENGTH: 1137
<212> TYPE: RNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: GALT-CO09

<400> SEQUENCE: 13
augagccggu ccggcaccga cccccagcag aggcagcagg ccagcgaggc cgacgccgcc 60
gccgcgaccu uucgggccaa cgaccaccag cacaucagau acaacccgcu ccaggacgag 120
ugggugcugg ugagcgccca caggaugaag aggccguggc aggggcaagu ggaaccccag 180
cuacugaaga ccgugcccag gcacgauccc cugaaccccc ugugcccggg agccauccgg 240
gcaaacgggg aggugaaccc ccaguacgac agcaccuuuc uguuugacaa cgacuucccg 300
gcccuccagc cggacgcccc cucccccggc ccgagcgacc acccccuguu ccaggccaaa 360
uccgccaggg gcgugugcaa ggugaugugu uuccacccau gguccgaugu gacgcugccc 420
cugaugagcg uccccgagau cagggccgug guggaugccu gggccagcgu gaccgaggag 480
cugggggccc aguaccccug ggugcaaauc uuugagaaca agggggccau gaugggcugc 540
agcaaccccc acccccacug ucaggugugg gccuccagcu uucuccccga cauugcccag 600
agggaggagc guagccagca ggccuacaag agccagcacg gggagccccu gcugauggag 660
uacucccggc aagagcuccu ccggaaggag aggcuugugc ugacgucgga gcauuggcug 720
guacuggugc ccuucugggc caccuggccc uaccagacuc ugcugcuccc ccggcggcac 780
gugcguaggc ugcccgagcu gacccccgcc gagcgggacg accucgccag caucaugaag 840
aagcuccuga caaaguacga caaucuguuc gagacuuccu uccccuacuc cauggggugg 900
cacggcgccc ccaccggcag cgaggccggg gccaacugga accacuggca acugcaugcc 960
cacuauuacc cccccuucu gcguagcgcg accgugcgga aguucauggu cggcuacgag 1020
augcuggccc aggcccagag ggaccugacg cccgaacagg ccgccgagcg gcugagggcc 1080
cugcccgagg ugcacuacca ccuggggcag aaagaccgcg agaccgccac uaucgcc 1137

<210> SEQ ID NO 14
<211> LENGTH: 1137
<212> TYPE: RNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: GALT-CO10

<400> SEQUENCE: 14
augagccgga gcggcaccga cccccaacag aggcagcaag ccagcgaggc cgacgccgcc 60
gcggccaccu uucgagccaa cgaccaccag cacauccggu acaacccgcu gcaggacgag 120
uggguucugg ucucggccca ccgaaugaag cgccccuggc agggccaggu cgagccgcag 180
cugcugaaga cgguucccag gcacgacccc cucaaccccc ugugccccgg cgccauccgg 240
gcaaaugggg aggugaaucc ccaguacgac agcaccuucc uguucgacaa cgauuucccc 300
gcccugcagc ccgacgcccc auccccagga cccuccgacc acccccucuu ucaggccaaa 360
uccgcgcgag gcgugugcaa ggucaugugc uuucaccccu gguccgaugu gacacugccg 420
cuuaugucag uccccgagau ccgggcggug guggaugccu gggccagcgu gaccgaggag 480
cucggcgccc aauaccccug ggugcagauc uucgaaaaca aaggcgccau gaugggcugc 540
uccaaucccc acccccacug ccaggugugg gcuagcuccu uccugccgga caucgcgcag 600
cgggaagagc ggucccagca ggccuauaag agucagcacg gcgagccccu gcugauggaa 660
uacagcaggc aggagcugcu gcggaaagag cgccuggugc ugaccagcga acacuggcug 720
guacugyucc ccuuuugggc cacuuggccg uaccaaaccc uccugcuccc caggcggcac 780
gugcgcaggc ugccugagcu gaccccggcc gagagggacg accuggcauc aaucaugaag 840
aagcugcuga cgaaguacga caaucucuuc gaaaccagcu uccccuacag cauggggugg 900
cauggcgccc cgacggggag cgaggccggc gccaacugga aucauuggca gcugcacgcc 960
cacuauuacc cccccugcu gaggagcgcc accgugagga aauucauggu cggcuacgaa 1020
augcuggccc aggcccagcg ggaucugacg ccugagcaag ccgccgagag gcugcgggcc 1080
cugccagagg ugcacuacca ucucggccag aaagaccgcg agaccgcgac cauagcc 1137

<210> SEQ ID NO 15
<211> LENGTH: 1137
<212> TYPE: RNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: GALT-CO11

<400> SEQUENCE: 15
auguccaggu ccggcacgga cccccagcag cgccagcaag ccagcgaggc cgacgccgcc 60
gcggcgaccu uccgggccaa cgaccaccag cacaucaggu acaacccgcu gcaggacgag 120
ugggugcugg ugagcgccca caggaugaag cggcccuggc agggccaggu agagccccaa 180
cugcugaaga ccgugcccag gcacgacccg cugaaccccc ugugccccgg cgccauccgc 240
gccaacggcg aggugaaccc acaguacgau agcaccuuuc ucuucgacaa ugauuucccc 300
gcccugcagc ccgacgcccc aagccccggc cccucagacc acccccuguu ccaagccaag 360
agcgcgaggg gcguguguaa ggugaugugc uuccaccccu ggagcgaugu gacgcugccc 420
cugaugagcg ucccggagau cagggccgug gucgacgccu gggcguccgu gaccgaggag 480
cugggggccc aguaccccug gguccagauc uucgagaaca agggcgccau gaugggcugc 540
agcaaucccc acccccauug ccaggugugg gccucuagcu uccugcccga caucgcccag 600
agggaggaga ggagccagca agccuauaag agccagcacg gggagccgcu gcugauggag 660
uacucccgcc aggagcuccu caggaaggag cggcuggugc ugacaagcga gcacuggcug 720
gugcucgugc ccuuuugggc aacauggccc uaccagaccc ugcugcugcc ccggcggcac 780
gugaggaggc ugcccgagcu gacccccgcc gaaagggaug aucuggccuc caucaugaag 840
aagcuccuga ccaaguacga caaccucuuc gaaacaucgu uccccuacag caugggcugg 900
cacggugccc cgacaggcuc cgaagccggc gccaacugga accacuggca gcugcacgcg 960
cacuacuacc ccccccugcu gaggagugcu accgugcgaa aguuuauggu gggcuacgag 1020
augcuggcgc aggcccagag ggaccugaca cccgaacagg ccgccgagcg gcugcgggcc 1080
cugcccgagg uccacuacca ccucggccag aaggaccggg agaccgccac gauagcc 1137

<210> SEQ ID NO 16
<211> LENGTH: 1137
<212> TYPE: RNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: GALT-CO12

<400> SEQUENCE: 16
augagcagga gcggcaccga cccccagcag cggcagcaag cguccgaggc cgacgccgcc 60
gccgccacau uccgugccaa cgaucaccaa cacauacggu acaacccgcu gcaggacgag 120
ugggugcugg ugagcgccca ccgcaugaag aggcccuggc agggccaggu ggagccccag 180
cugcugaaga ccgugccucg gcacgacccc cugaaccccc ucugccccgg ggccaucagg 240
gccaacggcg aggugaaccc gcaauacgac agcaccuucc uguucgacaa cgacuucccc 300
gcccugcaac ccgacgcacc cagccccggc ccgagcgauc acccgcucuu ccaggcgaag 360

-continued

```
agcgccaggg gcgugugcaa ggugaugugc uuccauccgu ggagcgaugu gacccugccc    420

cugaugagcg ucccugaaau cagggccgug guggacgccu gggccucugu gaccgaggag    480

cucggggccc aguauccgug ggugcagauc uucgagaaca agggugccau gaugggcugc    540

agcaaccccc auccccacug ccaggugugg gccuccagcu uccuacccga cauugcacag    600

cgagaggagc ggagccaaca ggcguacaag agccaacaug gcgagccccu gcucauggag    660

uacucgaggc aagagcugcu gcggaaggag aggcucgucc ugaccagcga gcacuggcug    720

gugcuugugc ccuucugggc aaccuggccc uaccagaccc ugcugcugcc aaggaggcac    780

gugcgcaggc ucccggagcu gaccccccgcc gagagagaug accuggccuc caucaugaag    840

aaacugcuga caaaguauga caaccuguuc gagacgucgu uccccuacuc caugggggugg    900

cacggcgccc ccacgggcag cgaggccggc gccaacugga aucacuggca gcugcaugcc    960

cacuacuauc ccccccugcu gcguagcgcg accgucagga aauucauggu cggcuacgag   1020

augcuggccc aggcccagag ggaccugacc cccgagcagg ccgccgagag gcugcgggcc   1080

cugcccgagg uccacuauca ccucggccag aaggaccggg aaaccgccac gaucgcg      1137
```

<210> SEQ ID NO 17
<211> LENGTH: 1137
<212> TYPE: RNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: GALT-CO13

<400> SEQUENCE: 17

```
auguccagga gcggcaccga cccccagcag aggcagcagg cuuccgaggc cgacgccgcc     60

gccgccaccu ucagggccaa cgaccaccag cacauccguu acaacccgcu gcaagacgag    120

uggguccuag uguccgccca ccggaugaaa cgccccuggc agggccaggu ggagccccag    180

uugcugaaga ccguacccag gcacgacccc cugaacccgc ucugccccgg cgccaucagg    240

gccaacggcg aggugaaccc ccaauacgac agcaccuucc uguucgacaa cgacuucccc    300

gcccuccagc cugaugcccc cagcccgggc cccagcgacc acccacuguu ccaggccaaa    360

agcgccaggg gcgugugcaa ggucaugugc uuccaccccu ggucggacgu gacgcugccc    420

cucauguccg ugcccgagau ccgcgccgug guggacgccu gggccagcgu gaccgaggag    480

cugggcgcuc aguaucccug ggugcagauc uuugagaaca agggggccau gaugggcugu    540

agcaaccccc accccccacug ccaggugugg gccagcuccu uccugccaga caucgcccag    600

cgugaggagc guucccagca ggccuacaaa agccagcacg gugagccgcu gcucauggaa    660

uacagccggc aggaacugcu gcggaaggag cgucucgugc ugacguccga gcacuggcug    720

gugcugguuc cguucugggc caccuggccc uaccagaccc ugcuccugcc caggcggcac    780

gucagaaggc ucccggagcu gacccccgcc gagcgggacg accuggcgag caucaugaag    840

aagcugcuga ccaaguacga caaccuguuc gagaccucau uccccuacag caugggcugg    900

cacggggccc ccaccgggag cgaggccggc gcuaauugga accacuggca gcugcacgcc    960

cacuacuacc ccccccugcu gagguccgcc accguccgaa aguucauggu aggcuacgaa   1020

augcuggccc aggcccaacg agaccugacc cccgagcaag ccgccgaacg cuugagggcc   1080

cugcccgagg uccacuacca ccugggccag aaggaccggg agacugccac caucgcc      1137
```

<210> SEQ ID NO 18

<211> LENGTH: 1137
<212> TYPE: RNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: GALT-CO14

<400> SEQUENCE: 18
augagcaggu ccggcaccga cccucagcag aggcagcagg ccagcgaggc cgacgccgcc 60
gccgccacau uccgcgccaa cgaucaccag cacauccgcu acaacccccu gcaggacgag 120
ugggugcugg ucagugcgca caggaugaag aggccguggc agggccaggu ugagccccag 180
cuccugaaga cggugccacg ucacgacccc cucaaccccc ugugccccgg cgcgauccgg 240
gcuaacggcg aggucaaucc ccaauacgac agcaccuucc uguucgacaa cgacuucccc 300
gcacugcagc cggacgcccc aagccccggg cccagcgacc acccccuguu ucaagccaaa 360
agcgccaggg gcgucugcaa ggugaugugc uuccaccccu gguccgaugu gacccugccc 420
uugaugagcg uccccgagau ccgugccgug guggaugccu gggccuccgu uaccgaggag 480
cugggcgccc aauacccaug ggugcaaaua uucgagaaca agggcgcgau gaugggcugc 540
agcaaccccc auccccauug ucaggugugg gccagcagcu uccuccccga caucgcccag 600
cgcgaggaaa ggagucagca ggccuacaag agccagcacg gcgagccacu gcugauggag 660
uacagccgac aggagcugcu gcggaaggag aggcuugugc ucaccagcga gcacuggcug 720 gugcugguccc ccuucugggc caccuggccc uaccaaacgc uccugcuccc ccggaggcau 780
gugcgccguc ugccagagcu cacccccgcc gagagggaug accuggcgag cauuaugaag 840
aagcugcuga ccaaguauga uaaccuguuu gagacgagcu uccccuacag caugggaugg 900
cacggcgccc ccaccggcuc cgaggccggc gccaauugga accacuggca gcugcacgcc 960
cauuacuacc ccccgcugcu gcgguccgcc accgugagga aauucauggu gggguacgaa 1020
augcuggccc aggcucagag ggaccugacc cccgagcaag cggccgagcg gcugagggcg 1080
cugccugagg ugcacuacca ucugggccaa aaggacaggg aaaccgcaac caucgcc 1137

<210> SEQ ID NO 19
<211> LENGTH: 1137
<212> TYPE: RNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: GALT-CO15

<400> SEQUENCE: 19
augagccggu ccggaaccga cccccagcag aggcagcagg caagcgaggc cgacgccgcc 60
gcggccaccu uccgcgccaa cgaucaccag cacauccgcu acaacccccu gcaggacgag 120
ugggugcugg ugagcgccca caggaugaag cgccccuggc aggggcaggu ggagccgcag 180
cugcugaaga ccgugccccg gcaugauccc cugaaccccc ucugucccgg cgccauaagg 240
gcgaauggcg aggucaaccc ccaguacgac agcacauucc uguucgacaa cgacuucccc 300
gcccugcagc ccgacgcccc cagccccggc ccaagcgauc auccccucuu ccaggccaag 360
agcgcccggg gggugugcaa agugaugugc uuccaccccu gguccgacgu gacccucccc 420
cucaugagcg ugccugagau uagggccgug guggacgccu gggccagcgu gaccgaagag 480
cugggagccc aguaccccug ggugcagauc uucgaaaaca agggcgccau gaugggcugu 540

```
uccaacccccc aucccccacug ucaggugugg gccagcagcu uucugcccga uaucgcccag    600

agggaagaga ggagccagca ggccuacaag ucccagcacg gagagccccu gcugauggag    660

uacagcaggc aagaacugcu gaggaaggag cggcuggugc ugaccagcga gcauuggcug    720

guccuggugc ccuucugggc caccuggcca uaccagaccc ugcugcugcc ccgacggcac    780

guccgcaggc ugcccgagcu gacccccgcc gaaagggacg accuggccag caucaugaag    840

aagcugcuga cgaaguacga caaccuguuu gagaccagcu uccccuacag caugggcugg    900

cacggcgccc ccacgggcag cgaggccggc gccaauugga aucacuggca gcugcacgcc    960

cauuauuacc cccccuccu gagguccgcc accgugcgaa aguuuauggu cggcuacgag   1020

augcuggccc aggcgcagcg agaucugacc cccgagcagg ccgccgagag gcugagggcc   1080

cugcccgaag ugcacuacca ccugggccag aaggacaggg aaaccgccac gaucgcc      1137
```

<210> SEQ ID NO 20
<211> LENGTH: 1137
<212> TYPE: RNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: GALT-CO16

<400> SEQUENCE: 20

```
augagccgga gcgggaccga uccccagcag aggcagcagg ccagcgaagc cgacgcagca     60

gccgcaaccu uccgggccaa cgaccaccag cauaucaggu auaaucccuu gcaagacgag    120

ugggugcucg ucagcgccca ccggaugaag aggcccuggc aggggcaagu ggagccccag    180

cugcucaaga ccgugccuag gcacgacccc cucaacccgc ugugcccugg cgccaucagg    240

gccaacggcg aggucaaccc ccaguaugac agcaccuucc uguucgacaa cgacuucccc    300

gcucuccagc ccgacgcccc aagccccggc ccguccgacc acccccucuu ccaggccaag    360

ucagcccggg gcgucugcaa ggugaugugc uuccaccccu ggagcgacgu cacgcugccc    420

cugaugagcg ugcccgagau ccgggccgug guggacgccu gggccagcgu gaccgaggag    480

cugggcgccc aauaucccug gguccagauc uuugagaaca agggcgccau gaugggaugc    540

agcaaccccc acccccacug ccaggucugg gccagcagcu uccugcccga caucgcccag    600

agggaagaga ggagccagca agccuacaag ucccagcacg gcgagccucu gcugauggag    660

uacuccaggc aggagcugcu caggaaggag cggcuggugc ucaccagcga acacuggcug    720

gugcuggugc ccuuuugggc cacauggccc uaccagacgc ugcugcuccc ccgccgacau    780

gugaggaggc ugcccgagcu gaccccagcg gaaagggacg accuggccag caucaugaag    840

aagcuccuga ccaaguacga caaccuguuc gagaccagcu uccccuacag cauggggugg    900

cauggcgcgc ccaccggcag cgaggccggc gccaacugga aucacuggca acugcacgcc    960

cacuacuacc cccccugcu ccggagugcc accgugagga aguuuauggu gggcuaugag   1020

augcuggccc aggcccagcg ugaccugacc ccggaacagg cggccgagcg ccugcgggcc   1080

cugcccgagg ugcacuauca ccucggccag aaggacaggg agacagccac caucgcc      1137
```

<210> SEQ ID NO 21
<211> LENGTH: 1137
<212> TYPE: RNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: GALT-CO17

<400> SEQUENCE: 21
augagccguu ccggcaccga cccccagcag agacagcagg ccagcgaggc cgacgccgcc 60
gccgccacau uccgcgccaa cgaccaccag cacaucaggu acaaucccccu gcaagacgag 120
ugggugcugg ugagcgccca ucggaugaag cggccauggc agggccaggu ggagccccag 180
cuccugaaga cggugcccag gcaugaucca cugaacccccc ucugccccgg cgccauccgg 240
gccaacggcg aggucaaccc gcaguacgac agcaccuucc uguucgauaa cgacuucccc 300
gcccugcagc ccgacgcccc cuccccgggc ccgagcgauc auccccuguu ccaggccaag 360
agcgccaggg gggugugcaa agugaugugc uuccacccgu ggagcgacgu cacccugccc 420
cugaugagcg ugcccgagau ccgugccgug guggacgccu gggccagcgu cacggaggag 480
cucggggccc aguaccccug ggugcagauc uucgaaaaca aaggcgcgau gauggggugc 540
agcaacccac aucccacug ccaggugugg gccagcagcu uccucccccga cauagcccag 600
agggaggaga ggucucagca ggccuauaag ucccagcacg gggaaccccu gcucauggag 660
uacagccggc aggaacugcu ccggaaggag aggcuggucc ugaccuccga gcacuggcuc 720
gugcucgugc ccuucugggc gaccuggccc uaccagaccc ugcugcugcc ccggaggcac 780
gugaggaggc ugccggagcu gaccccggcc gagcgggacg accuggccag caucaugaag 840
aagcugcuga ccaaguacga uaaccuguuc gagaccaguu uucccuacag cauggggugg 900
cacggcgccc ccaccggcag cgaggccggg gccaacugga aucauuggca gcugcacgcc 960
cacuauuacc ccccccugcu gaggucagcc acggugagga aguucauggu gggguaugag 1020
augcuggccc aggcccagcg ggaccugacc cccgagcagg ccgccgagag acugagggcc 1080
cuccccgaag ugcacuacca ccuggggcag aaggaccgcg agaccgccac cauagcc 1137

<210> SEQ ID NO 22
<211> LENGTH: 1137
<212> TYPE: RNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: GALT-CO18

<400> SEQUENCE: 22
augagucgga gcggcaccga cccccagcag aggcagcagg ccagcgaggc cgacgccgcc 60
gccgccaccu ucagggccaa cgaucaccag cacauccgcu acaacccccu gcaggacgag 120
ugggugcugg ugagcgcgca caggaugaaa aggcccuggc agggccaggu ggagccccag 180
cugcugaaga ccgucccgag gcacgacccg cugaaccccc ugugccccgg ggcgaucagg 240
gcgaauggcg aggugaaccc ccaguacgac agcaccuuuc uguuugacaa ugauuuccca 300
gcccugcagc ccgacgcccc cucccccggc cccagcgacc acccccuguu ccaggccaag 360
agcgccaggg gcgugugcaa ggucaugugc uuccaccccu ggagcgacgu gacccugccc 420
uuaaugagcg ugcccgaaau cagggccgug guggaugccu gggcgagcgu cacggaggaa 480
cugggcgccc aauaucccug gguacagauc uuugagaaca agggggccau gaugggcugc 540
agcaaucccc acccccacug ccaagucugg gcaagcagcu uccugcccga caucgcgcag 600
agggaggagc guagccagca ggcauacaag agccagcacg gcgagccccu gcugauggag 660
uacagcaggc aggagcugcu gagaaaggag cgucuggugc ugaccagcga gcacuggcug 720
gugcucgucc ccuucugggc caccuggccc uaccagaccc uccugcugcc caggcggcac 780
gugcgcaggc ugcccgagcu gacccccgcc gaaagggacg acuuagccag caucaugaag 840
aaacuccuga ccaaguauga caaucuguuc gagacguccu uccccuauuc caugggcugg 900
cauggcgcac cgaccggaag cgaagccggg gccaacugga accauuggca gcuccaugcg 960
cacuacuacc ccccccuccu cagguccgcc accgugagga aguucauggu cggguacgag 1020
augcuggccc aggcccagag ggaccugacg cccgaacagg ccgccgaacg ccugagggcc 1080
cugcccgagg uacacuacca ccugggccag aaggacaggg agaccgccac caucgcc 1137

<210> SEQ ID NO 23
<211> LENGTH: 1137
<212> TYPE: RNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: GALT-CO19

<400> SEQUENCE: 23
augucccgca gcggcacgga cccccagcag cggcagcagg cgagcgaggc cgacgcugcc 60
gccgccaccu uucgcgcaaa cgaccaucag cacaucaggu auaacccacu ccaggacgag 120
uggguccugg uguccgccca uaggaugaag cgacccuggc aggggcaggu ggagccccag 180
cugcugaaaa ccgugcccag gcacgacccc cugaaucccu uaugccccgg cgccauccgg 240
gccaacggcg aggugaaccc acaguaugac uccaccuuuc uguucgacaa cgauuucccc 300
gccuuacagc ccgacgcccc cagccccggu ccgagcgauc acccccucuu ccaggccaag 360
agcgcgcgcg gggugugcaa ggugaugugc uuccaccccu ggucggaugu gacgcugccc 420
cucaugagcg ugccggaaau cagggcggug guggacgcau gggccagcgu gacagaggag 480
cugggcgccc aauaccccug ggugcagauc uucgagaaca agggcgcaau gaugggcugc 540
agcaaccccc acccccauug ccaggugugg gcgagcagcu uccugcccga caucgcccag 600
agggaggaga gguccccagca agccuauaaa ucccagcaug gugaaccccu gcugauggag 660
uacuccaggc aggagcugcu gcggaaggag cgccuggucc ugaccuccga acauuggcug 720
gugcugguac cguucugggc caccuggccc uaccagaccc ugcugcuccc ccgccgacac 780
gugcggaggc ugccggagcu gacccccgcc gaacgggacg accuggccuc cauaaugaag 840
aagcugcuga ccaaguacga caaccuguuc gagaccuccu uccccuauag caugggaugg 900
cacggggccc ccaccggcag cgaggccggc gccaacugga accacuggca gcugcacgcc 960
cacuacuacc ccccccugcu gcgauccgcc accguccgga aguucauggu gggcuacgag 1020
augcuggccc aagcgcagcg ggaccugacg cccgagcagg ccgcggagcg ucugcgcgcc 1080
cuacccgagg ugcacuacca ccugggccag aaagacaggg agaccgccac aauagcc 1137

<210> SEQ ID NO 24
<211> LENGTH: 1137
<212> TYPE: RNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: GALT-CO20

<400> SEQUENCE: 24

```
augucccgca gcggcaccga cccccagcaa cgacaacaag ccagcgaggc cgacgcggcc     60

gccgcaaccu uccgcgccaa cgaccaucag cacauccgcu acaaucccccu ccaagacgag   120

ugggugcugg ucagcgccca uaggaugaag cgcccguggc agggccaggu ggaaccgcag   180

cuucugaaga ccgugccgcg acacgacccc cucaaccccc ugugccccgg cgccaucagg   240

gcaaauggcg aggugaaccc ccaguacgac ucgacguuuc uguucgacaa cgacuuuccc   300

gcccugcagc ccgacgcccc cucgcccggu cccagcgacc acccccuguu ccaggccaag   360

agcgcccgcg gcgugugcaa ggugaugugc uuucaucccu gguccgacgu gacccugccc   420

cuuauguccg ugccggagau ccgcgccgug guggacgccu gggccagcgu caccgaggag   480

cugggggccc aguacccaug ggugcagauc uucgaaaaca aaggugcaau gauggggugc   540

agcaacccuc acccccacug ccaagucugg gcgagcagcu ucccucccgga cauagcccag   600

agggaggagc ggucccagca ggccuacaag agccagcacg gagagccccu gcugauggag   660

uacagccgcc aggagcuccu gcgcaaggag aggcuggucc ugaccagcga gcauuggcug   720

gugcuggugc ccuucugggc caccuggccc uaccagaccc uccugcugcc ccggaggcac   780

gugcggcggc ugcccgaguu gacccccgcg gagcgcgaug aucuggccag caucaugaag   840

aaacugcuga ccaaguacga caaucuguuu gagacauccu uccccuacag caugggcugg   900

cauggcgccc ccacuggcag cgaggccggc gcgaacugga accauuggca gcugcacgcc   960

cacuacuacc caccccugcu ccggagcgcc acggugagga aguucauggu cggcuacgag  1020

augcuggccc aggcccagag ggaccugacg cccgagcagg ccgcggaaag gcuucgcgcc  1080

cugcccgagg ugcacuacca ccuaggccaa aaggaucggg agaccgccac caucgcc     1137
```

```
<210> SEQ ID NO 25
<211> LENGTH: 1137
<212> TYPE: RNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: GALT-CO21

<400> SEQUENCE: 25
```

```
augagcagga gcggcaccga cccccaacag agacagcaag ccagcgaagc cgacgccgca     60

gccgcuaccu uccgggcuaa cgaucaccag cacaucaggu acaacccccu ccaggacgag   120

ugggugcucg uguccgccca uaggaugaag cgcccccuggc aaggccaggu ggagccccag   180

cugcugaaga ccgugcccag gcacgacccc cugaaucccc ugugccccgg cgccauacgg   240

gccaacgggg aggugaaccc gcaguacgac agcaccuucc uguucgauaa cgacuucccc   300

gcccugcagc cggacgcccc aucccccggc cccagcgauc acccccuguu ccaggccaag   360

uccgccaggg gcgugugcaa ggugaugugu uuccaccccu gguccgacgu gacccugccc   420

cuuauguccg ugccagagau cagggccguu guugacgccu gggcguccgu gaccgaggag   480

cugggagccc aguaccccug ggugcagauc uucgagaaca agggcgccau gaugggcugu   540

agcaaccccc acccgcauug ccaagucugg gccuccagcu uccugcccga caucgcgcag   600

cgagaggagc ggagccaaca agccuacaag agccagcacg gugagcccuu gcugauggag   660

uacagccggc aggagcuccu gaggaaagag aggcucguuc ugaccuccga gcacuggcug   720

guguuagugc ccuucugggc caccuggccc uaccagaccc ugcugcugcc ccguaggcac   780

gugcgccggc ugcccgagcu gacccccgcc gagcgggaug aucuggccuc caucaugaaa   840
```

aagcugcuga ccaaguacga caaucuguuc gagaccagcu uccccuacag cauggggugg 900
cacggcgccc ccaccggcuc cgaagccggc gccaacugga accacuggca gcuucacgcc 960
cacuauuauc cgccccugcu ccggagcgcc accguccgca aauucauggu gggcuacgag 1020
augcuggcuc aagcgcaacg cgaccugacc cccgagcagg ccgccgagag gcugagggcc 1080
cugcccgagg ugcacuacca ccugggccag aaagauaggg agacggccac caucgcc 1137

<210> SEQ ID NO 26
<211> LENGTH: 1137
<212> TYPE: RNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: GALT-CO22

<400> SEQUENCE: 26
auguccaggu ccggcaccga uccccaacag aggcagcagg ccuccgaagc cgacgccgcc 60
gccgccaccu ucagggccaa cgaccaucag cacauccgcu acaacccccu gcaggacgag 120
ugggugcugg ucagcgccca uaggaugaaa cgcccguggc aggggcaggu agagccacag 180
cuccugaaga ccgugccgag gcacgaucca cucaaccccc ugugccccgg cgccaucagg 240
gccaacgggg aagugaaccc ccaguacgac uccaccuuuc ucuucgacaa cgauuucccc 300
gcccugcagc cagacgcccc gagccccggc ccaagcgauc acccccuguu ccaggccaag 360
agcgcccgug gcgugugcaa ggugaugugu uuccaccccu ggagcgacgu gacccugccc 420
cugaugagcg ugcccgaaau ccgcgcggug gucgaugccu gggcaucagu gaccgaggag 480
cugggcgccc aauacccgug gguacagauc uucgagaaca agggcgccau gaugggcugu 540
agcaaccccc auccccacug ccaggugugg gccagcucau uccuccccga caucgcccag 600
agggaggaga ggucgcagca ggccuacaag ucccagcacg gggagccccu ucugauggag 660
uacagccggc aggaacugcu gcggaaggaa cggcuggugc ugaccagcga gcacuggcug 720
gugcuggugc ccuuuugggc caccuggccc uaccagaccc ugcuacuccc ccggcggcac 780
guccggcggc ugcccgagcu cacccccgcc gagagagacg accuggccuc caucaugaag 840
aagcugcuca ccaaauacga caaucuguuc gagaccagcu uccccuauag caugggcugg 900
cacggcgcgc ccaccggcag cgaggccggg gcgaacugga accauuggca acuccacgcc 960
cacuacuauc ccccccugcu gaggagcgcc acggugagga aauucauggu agguuaugag 1020
augcuggccc aggcccagag ggaccugacc cccgagcagg ccgccgagag gcugagggcc 1080
cugcccgagg ugcauuacca ccuggggcag aaggacaggg agaccgccac cauagcc 1137

<210> SEQ ID NO 27
<211> LENGTH: 1137
<212> TYPE: RNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: GALT-CO23

<400> SEQUENCE: 27
augucccggu caggcaccga cccacaacag cgccagcagg ccagcgaggc cgacgccgcc 60
gccgcgaccu ucagggccaa cgaccaccag cacaucaggu acaacccccu gcaggacgag 120
ugggugcugg ugagcgccca caggaugaag cgacccuggc agggucaggu ggagccccag 180
cugcugaaga ccguacccag gcacgacccc cugaaccccc ucugcccggg ggccaucagg 240
gccaacggag aggugaaccc ccaguacgac uccaccuucc uguuugauaa cgacuuuccc 300
gcccugcagc cugaugcccc cagcccuggg cccagcgauc acccccuguu ccaggccaaa 360
agcgccaggg gagugugcaa agugaugugc uuccacccgu ggagcgaugu gacccucccc 420
cugauguccg ucccegagau ccgagcagug guggacgccu gggcgagcgu gacggaggag 480
cugggcgcgc aauaccccug gguccagauc uucgagaaca agggcgccau gauggggugc 540
uccaacccca acccccacug ccaggugugg gcuuccuccu uccuccccga caucgcccaa 600
agggaggaga ggagccagca ggccuacaag agccagcacg gggagccucu gcugauggag 660
uacagcaggc aggaacugcu gaggaaggag aggcuggugc uuaccuccga gcacuggcug 720
gugcucguac ccuucugggc caccuggccc uaccagaccc ugcugcugcc ccggaggcac 780
gugcggaggc ugcccgaacu gacccccgca gagcgagacg accucgccag uaucaugaag 840
aaacugcuga ccaaguauga caaccuguuc gagaccuccu uccccuacag caugggcugg 900
cacggcgccc ccacgggcag cgaggccggu gcuaacugga accacuggca gcugcacgcc 960
cacuacuacc ccccccugcu gaggagcgcc accgugagga aguucauggu gggguaugag 1020
augcuggccc aggcccaacg ugaccugacg cccgaacagg ccgcagaacg gcucagggcc 1080
cugcccgagg ugcacuacca ccugggccag aaggacaggg agaccgccac caucgcc 1137

<210> SEQ ID NO 28
<211> LENGTH: 1137
<212> TYPE: RNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: GALT-CO24

<400> SEQUENCE: 28
augagccggu ccggcaccga cccccagcag cggcagcagg cauccgaggc cgacgccgcc 60
gccgccaccu uccgggccaa cgaccaucag cacauccguu auaacccacu gcaagacgag 120
uggguguugg ugagcgcgca ucgcaugaaa aggccguggc aggggcaggu ggagccccag 180
cugcugaaga ccguccccccg gcacgacccc cugaacccuc ugugccccgg cgccauccgg 240
gccaacggcg aggugaaccc gcaauacgac agcacguucc uguucgauaa cgacuucccc 300
gcgcugcagc ccgacgcccc cagcccgggc cccucggacc acccccuguu ccaggccaag 360
agcgcccgug gcgucugcaa ggucaugugc uuccaccccu gguccgacgu gacccucccc 420
cugaugagcg ugcccgagau ccgcgccgug guggacgccu gggccuccgu gaccgaggaa 480
cucggcgcgc aguaccccug ggugcagaua uucgagaaca aaggcgccau gaugggcugc 540
uccaacccca acccccacug ucaggucugg gccucaagcu uccugcccga uaucgcccag 600
cgcgaagagc ggagccagca ggccuacaag agccagcacg ggaacccccu gcugauggag 660
uacagccggc aggagcuccu acggaaggag aggcuggugc ugaccuccga gcacuggcug 720
gugcuggugc ccuucugggc gaccuggccc uaucagaccc ugcuacugcc ccgcaggcac 780
gugaggaggc ugcccgaacu gacccccgcc gaaagggacg accuggccuc cauaaugaaa 840
aagcugcuga ccaaguacga caaucuguuc gagaccagcu uccccuacag caugggcugg 900
cacggugccc ccaccggguc cgaggccggc gccaauugga aucacuggca gcugcaugcc 960

```
cauuauuacc ccccccuccu gcgaagcgcc accguccgca aguucauggu gggguacgaa   1020

augcuggccc aggcacagcg ggaccugacc cccgagcagg ccgccgagag gcugagggcg   1080

cugcccgagg ugcacuacca ccuggggcaa aaggaccggg agaccgccac gaucgcc      1137
```

<210> SEQ ID NO 29
<211> LENGTH: 1137
<212> TYPE: RNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: GALT-CO25

<400> SEQUENCE: 29

```
augucccgga gcggcaccga cccccaacag cggcagcagg cgagcgaagc cgacgccgcc     60

gccgcaaccu uccgggccaa cgaccaccag cacaucaggu auaaauccuu acaggacgag    120

uggguccugg ugagcgccca caggaugaag cggcccuggc aaggccaggu ggagccccag    180

cugcugaaga ccgugccgcg ucacgacccc uugaacccuc ugugccccgg cgccaucagg    240

gccaacggcg aggugaaucc ccaguacgac agcaccuucc uguucgacaa cgacuucccc    300

gcccugcagc cagacgcccc cucccccggg cccagcgacc auccccuguu ccaggccaaa    360

agcgcgcggg gcgugugcaa ggugaugugc uuucaccccu ggagcgacgu gacccugccg    420

cugaugagcg ugcccgagau ccgcgccguc gucgacgcgu gggccagcgu gaccgaggag    480

cugggcgccc aauacccgug ggugcagauc uucgagaaca agggcgccau gauggggugc    540

agcaacccgc acccccacug ccaggugugg gccagcagcu uccugcccga caucgcgcaa    600

agggaggaga ggagccagca ggccuacaag agccagcacg gugagccacu gcugauggaa    660

uauagcaggc aggaacugcu gaggaaagag aggcuggugc ugaccuccga gcauuggcug    720

gugcuggucc cuuuuugggc caccuggccc uaccagacac uccugcuccc caggaggcac    780

gugcgcaggc ugcccgagcu gaccccagcc gagcgggacg accucgccuc caucaugaaa    840

aagcuccuga ccaaguacga caaccuguuc gagaccuccu uuccguauag caugggaugg    900

cacggcgccc ccaccggcuc cgaggccggc gccaacugga accacuggca acugcaugcc    960

cauuacuacc caccccugcu gcguuccgcc accgugcgga aguucauggu ggguuacgag   1020

augcucgccc aggcccagag ggaucugacc cccgagcagg ccgccgagag gcugagggcc   1080

cugcccgagg uccacuacca ccuggggcaa aaggacaggg agacugccac cauugcc      1137
```

<210> SEQ ID NO 30
<211> LENGTH: 87
<212> TYPE: RNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: miR-142

<400> SEQUENCE: 30

```
gacagugcag ucacccauaa aguagaaagc acuacuaaca gcacuggagg guguaguguu     60

uccuacuuua uggaugagug uacugug                                          87
```

<210> SEQ ID NO 31
<211> LENGTH: 23
<212> TYPE: RNA
<213> ORGANISM: Artificial Sequence -continued
<220> FEATURE:
<223> OTHER INFORMATION: Description of Artificial Sequence: Synthetic
oligonucleotide
<220> FEATURE:
<223> OTHER INFORMATION: miR-142-3p

<400> SEQUENCE: 31
uguaguguuu ccuacuuuau gga 23

<210> SEQ ID NO 32
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: miR-142-3p binding site

<400> SEQUENCE: 32
uccauaaagu aggaaacacu aca 23

<210> SEQ ID NO 33
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: miR-142-5p

<400> SEQUENCE: 33
cauaaaguag aaagcacuac u 21

<210> SEQ ID NO 34
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: miR-142-5p binding site

<400> SEQUENCE: 34
aguagugcuu ucuacuuuau g 21

<210> SEQ ID NO 35
<211> LENGTH: 47
<212> TYPE: RNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: 5' UTR-001 (Upstream UTR)

<400> SEQUENCE: 35
gggaaauaag agagaaaaga agaguaagaa gaaauauaag agccacc 47

<210> SEQ ID NO 36
<211> LENGTH: 47
<212> TYPE: RNA
<213> ORGANISM: Artificial Sequence
<220> FEATURE:
<223> OTHER INFORMATION: Description of Artificial Sequence: Synthetic
oligonucleotide
<220> FEATURE:

<223> OTHER INFORMATION: 5' UTR-002 (Upstream UTR)

<400> SEQUENCE: 36
gggagaucag agagaaaaga agaguaagaa gaaauauaag agccacc 47

<210> SEQ ID NO 37
<211> LENGTH: 145
<212> TYPE: RNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: 5' UTR-003

<400> SEQUENCE: 37
ggaauaaaag ucucaacaca acauauacaa aacaaacgaa ucucaagcaa ucaagcauuc 60
uacuucuauu gcagcaauuu aaaucauuuc uuuuaaagca aaagcaauuu ucugaaaauu 120
uucaccauuu acgaacgaua gcaac 145

<210> SEQ ID NO 38
<211> LENGTH: 42
<212> TYPE: RNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: 5' UTR-004

<400> SEQUENCE: 38
gggagacaag cuuggcauuc cgguacuguu gguaaagcca cc 42

<210> SEQ ID NO 39
<211> LENGTH: 47
<212> TYPE: RNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: 5' UTR-005 (Upstream UTR)

<400> SEQUENCE: 39
gggagaucag agagaaaaga agaguaagaa gaaauauaag agccacc 47

<210> SEQ ID NO 40
<211> LENGTH: 145
<212> TYPE: RNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: 5' UTR-006

<400> SEQUENCE: 40
ggaauaaaag ucucaacaca acauauacaa aacaaacgaa ucucaagcaa ucaagcauuc 60
uacuucuauu gcagcaauuu aaaucauuuc uuuuaaagca aaagcaauuu ucugaaaauu 120
uucaccauuu acgaacgaua gcaac 145

<210> SEQ ID NO 41
<211> LENGTH: 42
<212> TYPE: RNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: 5' UTR-007

<400> SEQUENCE: 41
gggagacaag cuuggcauuc cgguacuguu gguaaagcca cc 42

<210> SEQ ID NO 42
<211> LENGTH: 47
<212> TYPE: RNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: 5' UTR-008

<400> SEQUENCE: 42
gggaauuaac agagaaaaga agaguaagaa gaaauauaag agccacc 47

<210> SEQ ID NO 43
<211> LENGTH: 47
<212> TYPE: RNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: 5' UTR-009

<400> SEQUENCE: 43
gggaaauuag acagaaaaga agaguaagaa gaaauauaag agccacc 47

<210> SEQ ID NO 44
<211> LENGTH: 47
<212> TYPE: RNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: 5' UTR-010

<400> SEQUENCE: 44
gggaaauaag agaguaaaga acaguaagaa gaaauauaag agccacc 47

<210> SEQ ID NO 45
<211> LENGTH: 47
<212> TYPE: RNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: 5' UTR-011

<400> SEQUENCE: 45
gggaaaaaag agagaaaaga agacuaagaa gaaauauaag agccacc 47

<210> SEQ ID NO 46
<211> LENGTH: 47
<212> TYPE: RNA
<213> ORGANISM: Artificial Sequence
<220> FEATURE:
<223> OTHER INFORMATION: Description of Artificial Sequence: Synthetic
oligonucleotide
<220> FEATURE:

```
<223> OTHER INFORMATION: 5' UTR-012

<400> SEQUENCE: 46

gggaaauaag agagaaaaga agaguaagaa gauauauaag agccacc                 47


<210> SEQ ID NO 47
<211> LENGTH: 47
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 5' UTR-013

<400> SEQUENCE: 47

gggaaauaag agacaaaaca agaguaagaa gaaauauaag agccacc                 47


<210> SEQ ID NO 48
<211> LENGTH: 47
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 5' UTR-014

<400> SEQUENCE: 48

gggaaauuag agaguaaaga acaguaagua gaauuaaaag agccacc                 47


<210> SEQ ID NO 49
<211> LENGTH: 47
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 5' UTR-15 (Upstream UTR)

<400> SEQUENCE: 49

gggaaauaag agagaauaga agaguaagaa gaaauauaag agccacc                 47


<210> SEQ ID NO 50
<211> LENGTH: 47
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 5' UTR-016 (Upstream UTR)

<400> SEQUENCE: 50

gggaaauaag agagaaaaga agaguaagaa gaaaauuaag agccacc                 47


<210> SEQ ID NO 51
<211> LENGTH: 47
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 5' UTR-017 (Upstream UTR)

<400> SEQUENCE: 51
```

gggaaauaag agagaaaaga agaguaagaa gaaauuuaag agccacc 47

<210> SEQ ID NO 52
<211> LENGTH: 92
<212> TYPE: RNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: 5' UTR-018 (Upstream UTR)

<400> SEQUENCE: 52
ucaagcuuuu ggacccucgu acagaagcua auacgacuca cuauagggaa auaagagaga 60
aaagaagagu aagaagaaau auaagagcca cc 92

<210> SEQ ID NO 53
<211> LENGTH: 142
<212> TYPE: RNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: 142-3p 3'UTR (UTR including miR142-3p binding
site)

<400> SEQUENCE: 53
ugauaauagu ccauaaagua ggaaacacua cagcuggagc cucgguggcc augcuucuug 60
ccccuugggc cucccccag ccccuccucc ccuuccugca cccguacccc cguggucuuu 120
gaauaaaguc ugagugggcg gc 142

<210> SEQ ID NO 54
<211> LENGTH: 142
<212> TYPE: RNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: 142-3p 3'UTR (UTR including miR142-3p binding
site)

<400> SEQUENCE: 54
ugauaauagg cuggagccuc gguggcucca uaaaguagga aacacuacac augcuucuug 60
ccccuugggc cucccccag ccccuccucc ccuuccugca cccguacccc cguggucuuu 120
gaauaaaguc ugagugggcg gc 142

<210> SEQ ID NO 55
<211> LENGTH: 142
<212> TYPE: RNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: 142-3p 3'UTR (UTR including miR142-3p binding
site)

<400> SEQUENCE: 55
ugauaauagg cuggagccuc gguggccaug cuucuugccc cuuccauaaa guaggaaaca 60
cuacaugggc cucccccag ccccuccucc ccuuccugca cccguacccc cguggucuuu 120
gaauaaaguc ugagugggcg gc 142

```
<210> SEQ ID NO 56
<211> LENGTH: 142
<212> TYPE: RNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: 142-3p 3'UTR (UTR including miR142-3p binding
      site)

<400> SEQUENCE: 56

ugauaauagg cuggagccuc gguggccaug cuucuugccc cuugggccuc cccccagucc     60

auaaaguagg aaacacuaca ccccuccucc ccuuccugca cccguacccc cgugguculu    120

gaauaaaguc ugagugggcg gc                                             142


<210> SEQ ID NO 57
<211> LENGTH: 142
<212> TYPE: RNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: 142-3p 3'UTR (UTR including miR142-3p binding
      site)

<400> SEQUENCE: 57

ugauaauagg cuggagccuc gguggccaug cuucuugccc cuugggccuc cccccagccc     60

cuccuccccu ucuccauaaa guaggaaaca cuacacugca cccguacccc cguggucuuu    120

gaauaaaguc ugagugggcg gc                                             142


<210> SEQ ID NO 58
<211> LENGTH: 142
<212> TYPE: RNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: 142-3p 3'UTR (UTR including miR142-3p binding
      site)

<400> SEQUENCE: 58

ugauaauagg cuggagccuc gguggccaug cuucuugccc cuugggccuc cccccagccc     60

cuccuccccu uccugcaccc guacccccuc cauaaaguag gaaacacuac aguggucuuu    120

gaauaaaguc ugagugggcg gc                                             142


<210> SEQ ID NO 59
<211> LENGTH: 142
<212> TYPE: RNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: 142-3p 3'UTR (UTR including miR142-3p binding
      site)

<400> SEQUENCE: 59

ugauaauagg cuggagccuc gguggccaug cuucuugccc cuugggccuc cccccagccc     60

cuccuccccu uccugcaccc guacccccgu ggucuuugaa uaaaguucca uaaaguagga    120

aacacuacac ugagugggcg gc                                             142
```

<210> SEQ ID NO 60
<211> LENGTH: 371
<212> TYPE: RNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: 3' UTR-001

<400> SEQUENCE: 60
gcgccugccc accugccacc gacugcugga acccagccag ugggagggcc uggcccacca 60
gaguccugcu cccucacucc ucgccccgcc cccugucccca gagucccacc ugggggcucu 120
cuccacccuu cucagaguuc caguuucaac cagaguucca accaaugggc uccauccucu 180
ggauucuggc caaugaaaua ucucccuggc aggguccucu ucuuuuccca gagcuccacc 240
ccaaccagga gcucuaguua auggagagcu cccagcacac ucggagcuug ugcuuugucu 300
ccacgcaaag cgauaaauaa aagcauuggu ggccuuuggu cuuugaauaa agccugagua 360
ggaagucuag a 371

<210> SEQ ID NO 61
<211> LENGTH: 568
<212> TYPE: RNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: 3' UTR-002

<400> SEQUENCE: 61
gccccugccg cucccacccc cacccaucug ggccccgggu ucaagagaga gcggggucug 60
aucucgugua gccauauaga guuugcuucu gagugucugc uuuguuuagu agaggugggc 120
aggaggagcu gaggggcugg ggcuggggug uugaaguugg cuuugcaugc ccagcgaugc 180
gccucccugu gggaugucau cacccuggga accgggagug gcccuuggcu cacuguguuc 240
ugcaugguuu ggaucugaau uaauuguccu uucuucuaaa ucccaaccga acuucuucca 300
accuccaaac uggcuguaac cccaaaucca agccauuaac uacaccugac aguagcaauu 360
gucugauuaa ucacuggccc cuugaagaca gcagaauguc ccuuugcaau gaggaggaga 420
ucugggcugg gcgggccagc uggggaagca uuugacuauc uggaacuugu gugugccucc 480
ucagguaugg cagugacuca ccugguuuua auaaaacaac cugcaacauc ucauggucuu 540
ugaauaaagc cugaguagga agucuaga 568

<210> SEQ ID NO 62
<211> LENGTH: 289
<212> TYPE: RNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: 3' UTR-003 (alpha-actin UTR)

<400> SEQUENCE: 62
acacacucca ccuccagcac gcgacuucuc aggacgacga aucuucucaa uggggggggcg 60 gcugagcucc agccaccccg cagucacuuu cuuuguaaca acuuccguug cugccaucgu 120
aaacugacac aguguuuaua acguguacau acauuaacuu auuaccucau uuuguuauuu 180
uucgaaacaa agcccugugg aagaaaaugg aaaacuugaa gaagcauuaa agucauucug 240
uuaagcugcg uaaauggucu uugaauaaag ccugaguagg aagucuaga 289

<210> SEQ ID NO 63
<211> LENGTH: 379
<212> TYPE: RNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: 3' UTR-004 (Albumin UTR)

<400> SEQUENCE: 63
caucacauuu aaaagcaucu cagccuacca ugagaauaag agaaagaaaa ugaagaucaa 60
aagcuuauuc aucuguuuuu cuuuuucguu gguguaaagc caacacccug ucuaaaaaac 120
auaaauuucu uuaaucauuu ugccucuuuu cucugugcuu caauuaauaa aaaauggaaa 180
gaaucuaaua gagugguaca gcacuguuau uuuucaaaga uguguugcua uccugaaaau 240
ucuguagguu cuguggaagu uccaguguuc ucucuuauuc cacuucggua gaggauuucu 300
aguuucuugu gggcuaauua aauaaaucau uaauacucuu cuaauggucu uugaauaaag 360
ccugaguagg aagucuaga 379

<210> SEQ ID NO 64
<211> LENGTH: 118
<212> TYPE: RNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: 3' UTR-005 (?-globin UTR

<400> SEQUENCE: 64
gcugccuucu gcggggcuug ccuucuggcc augcccuucu ucucucccuu gcaccuguac 60
cucuuggucu uugaauaaag ccugaguagg aaggcggccg cucgagcaug caucuaga 118

<210> SEQ ID NO 65
<211> LENGTH: 908
<212> TYPE: RNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: 3' UTR-006 (G-CSF UTR)

<400> SEQUENCE: 65
gccaagcccu ccccauccca uguauuuauc ucuauuuaau auuuaugucu auuuaagccu 60
cauauuuaaa gacagggaag agcagaacgg agccccaggc cucugugucc uucccugcau 120
uucugaguuu cauucuccug ccuguagcag ugagaaaaag cuccuguccu cccaucccu 180 ggacugggag guagauaggu aaauaccaag uauuuauuac uaugacugcu ccccagcccu 240
ggcucugcaa ugggcacugg gaugagccgc ugugagcccc ugguccugag gguccccacc 300
ugggacccuu gagaguauca ggucucccac gugggagaca agaaaucccu guuuaauauu 360
uaaacagcag uguuccccau cugggucuu gcaccccuca cucuggccuc agccgacugc 420
acagcggccc cugcaucccc uuggcuguga ggccccugga caagcagagg uggccagagc 480
ugggaggcau ggcccugggg ucccacgaau uugcugggga aucucguuuu ucuucuuaag 540
acuuuuggga caugguuuga cuccccgaaca ucaccgacgc gucuccuguu uuucugggug 600
gccucgggac accugcccug cccccacgag ggucaggacu gugacucuuu uuagggccag 660
gcaggugccu ggacauuugc cuugcuggac ggggacuggg gaugugggag ggagcagaca 720
ggaggaauca ugucaggccu gugugugaaa ggaagcucca cugucacccu ccaccucuuc 780
accccccacu caccaguguc cccuccacug ucacauugua acugaacuuc aggauaaauaa 840 aguguuugcc uccauggucu uugaauaaag ccugaguagg aaggcggccg cucgagcaug 900
caucuaga 908

<210> SEQ ID NO 66
<211> LENGTH: 835
<212> TYPE: RNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: 3' UTR-007 (Col1a2; collagen, type I, alpha 2 UTR)

<400> SEQUENCE: 66
acucaaucua aauuaaaaaa gaaagaaauu ugaaaaaacu uucucuuugc cauuucuucu 60
ucuucuuuuu uaacugaaag cugaauccuu ccauuucuuc ugcacaucua cuugcuuaaa 120
uugugggcaa aagagaaaaa gaaggauuga ucagagcauu gugcaauaca guuucauuaa 180
cuccuucccc cgcuccccca aaaauuugaa uuuuuuuuuc aacacucuua caccuguuau 240
ggaaaauguc aaccuuugua agaaaaccaa aauaaaaauu gaaaaauaaa aaccauaaac 300
auuugcacca cuuguggcuu uugaauaucu uccacagagg gaaguuuaaa acccaaacuu 360
ccaaagguuu aaacuaccuc aaaacacuuu cccaugagug ugauccacau uguuaggugc 420
ugaccuagac agagaugaac ugagguccuu guuuuguuuu guucauaaua caaaggugcu 480
aauuaauagu auuucagaua cuugaagaau guugauggug cuagaagaau uugagaagaa 540
auacuccugu auugaguugu aucgugugguguauuuuuua aaaaauuuga uuuagcauuc 600
auauuuucca ucuuauuccc aauuaaaagu augcagauua uuugcccaaa ucuucuucag 660
auucagcauu uguucuuugc cagucucauu uucaucuucu uccaugguuc cacagaagcu 720
uuguuucuug ggcaagcaga aaaauuaaau uguaccuauu uuguauaugu gagauguuua 780
aauaaauugu gaaaaaaaug aaauaaagca uguuugguuu uccaaaagaa cauau 835

<210> SEQ ID NO 67
<211> LENGTH: 297
<212> TYPE: RNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: 3' UTR-008 (Col6a2; collagen, type VI, alpha 2 UTR)

<400> SEQUENCE: 67
cgccgccgcc cgggccccgc agucgagggu cgugagccca ccccguccau ggugcuaagc 60
gggcccgggu cccacacggc cagcaccgcu gcucacucgg acgacgcccu gggccugcac 120
cucuccagcu ccucccacgg gguccccgua gccccggccc ccgcccagcc ccaggucucc 180
ccaggcccuc cgcaggcugc ccggccuccc ucccccugca gccaucccaa ggcuccugac 240
cuaccuggcc ccugagcucu ggagcaagcc cugacccaau aaaggcuuug aacccau 297

<210> SEQ ID NO 68
<211> LENGTH: 602
<212> TYPE: RNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: 3' UTR-009 (RPN1; ribophorin I UTR)

<400> SEQUENCE: 68
ggggcuagag cccucuccgc acagcgugga gacggggcaa ggagggggu uauuaggauu 60 ggugguuuug uuuugcuuug uuuaaagccg ugggaaaaug gcacaacuuu accucugugg 120
gagaugcaac acugagagcc aaggggguggg aguugggaua auuuuuauau aaaagaaguu 180
uuuccacuuu gaauugcuaa aaguggcauu uuuccuaugu gcagucacuc cucucauuuc 240
uaaaauaggg acguggccag gcacggugge ucaugccugu aaucccagca cuuugggagg 300
ccgaggcagg cggcucacga ggucaggaga ucgagacuau ccuggcuaac acgguaaaac 360
ccugucucua cuaaaaguac aaaaaauuag cugggcgugg uggugggcac cuguaguccc 420
agcuacucgg gaggcugagg caggagaaag gcaugaaucc aagaggcaga gcuugcagug 480
agcugagauc acgccauugc acuccagccu gggcaacagu guuaagacuc ugucucaaau 540
auaaauaaau aaauaaauaa auaaauaaau aaauaaaaau aaagcgagau guugcccuca 600
aa 602

<210> SEQ ID NO 69
<211> LENGTH: 785
<212> TYPE: RNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: 3' UTR-010 (LRP1; low density lipoprotein receptor-related protein 1 UTR)

<400> SEQUENCE: 69
ggcccugccc cgucggacug cccccagaaa gccuccugcc cccugccagu gaaguccuuc 60
agugagcccc uccccagcca gcccuucccu ggccccgccg gauguauaaa uguaaaaaug 120
aaggaauuac auuuuauaug ugagcgagca agccggcaag cgagcacagu auuauuucuc 180 caucccucc cugccugcuc cuuggcaccc ccaugcugcc uucagggaga caggcaggga 240
gggcuugggg cugcaccucc uacccuccca ccagaacgca ccccacuggg agagcuggug 300
gugcagccuu ccccucccug uauaagacac uuugccaagg cucuccccuc ucgccccauc 360
ccugcuugcc cgcucccaca gcuuccugag ggcuaauucu gggaagggag aguucuuugc 420
ugccccuguc uggaagacgu ggcucugggu gagguaggcg ggaaaggaug gaguguuuua 480
guucuugggg gaggccaccc caaaccccag ccccaacucc aggggcaccu augagauggc 540
caugcucaac ccccucccca gacaggcccu cccugucucc agggccccca ccgagguucc 600
cagggcugga gacuuccucu gguaaacauu ccuccagccu ccccuccccu ggggacgcca 660
aggagguggg ccacacccag gaagggaaag cgggcagccc cguuuugggg acgugaacgu 720
uuuaauaauu uuugcugaau uccuuuacaa cuaaauaaca cagauauugu uauaaauaaa 780
auugu 785

<210> SEQ ID NO 70
<211> LENGTH: 3001
<212> TYPE: RNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: 3' UTR-011 (Nnt1; cardiotrophin-like cytokine
factor 1 UTR)

<400> SEQUENCE: 70
auauuaagga ucaagcuguu agcuaauaau gccaccucug caguuuuggg aacaggcaaa 60
uaaaguauca guauacaugg ugauguacau cuguagcaaa gcucuuggag aaaaugaaga 120
cugaagaaag caaagcaaaa acuguauaga gagauuuuuc aaaagcagua aucccucaau 180
uuuaaaaaag gauugaaaau ucuaaauguc uuucugugca uauuuuuugu guuaggaauc 240
aaaaguauuu uauaaaagga gaaagaacag ccucauuuua gauguagucc uguuggauuu 300
uuuaugccuc cucaguaacc agaaauguuu uaaaaaacua aguguuuagg auuucaagac 360
aacauuauac auggcucuga aauaucugac acaauguaaa cauugcaggc accugcauuu 420
uauguuuuuu uuuucaacaa augugacuaa uuugaaacuu uuaugaacuu cugagcuguc 480
cccuugcaau ucaaccgcag uuugaauuaa ucauaucaaa ucaguuuuaa uuuuuuaaau 540
uguacuucag agucuauauu ucaagggcac auuuucucac uacuauuuua auacauuaaa 600
ggacuaaaua aucuuucaga gaugcuggaa acaaaucauu ugcuuuauau guuucauuag 660
aauaccaaug aaacauacaa cuugaaaauu aguaauagua uuuuugaaga ucccauuucu 720
aauuggagau cucuuuaauu ucgaucaacu uauaaugugu aguacuauau uaagugcacu 780
ugaguggaau ucaacauuug acuaauaaaa ugaguucauc auguuggcaa gugauguggc 840
aauuaucucu ggugacaaaa gaguaaaauc aaauauuucu gccuguuaca aauaucaagg 900
aagaccugcu acuaugaaau agaugacauu aaucugucuu cacuguuuau aauacggaug 960
gauuuuuuuu caaaucagug uguguuuuga ggucuuaugu aauugaugac auuugagaga 1020
aaugguggcu uuuuuuagcu accucuuugu ucauuuaagc accaguaaag aucaugucuu 1080
uuuauagaag uguagauuuu cuuugugacu uugcuaucgu gccuaaagcu cuaaauauag 1140
gugaaugugu gaugaauacu cagauuauuu gucucucuau auaauuaguu ugguacuaag 1200
uuucucaaaa aauuauuaac acaugaaaga caaucucuaa accagaaaaa gaaguaguac 1260
aaauuuuguu acuguaaugc ucgcguuuag ugaguuuaaa acacacagua ucuuuugguu 1320
uuauaaucag uuucuauuuu gcugugccug agauuaagau cuguguaugu gugugugugu 1380
gugugugcgu uuguguguua aagcagaaaa gacuuuuuua aaaguuuuaa gugauaaaug 1440
caauuuguua auugaucuua gaucacuagu aaacucaggg cugaauuaua ccauguauau 1500
ucuauuagaa gaaaguaaac accaucuuua uuccugcccu uuuucuucuc ucaaaguagu 1560
uguaguuaua ucuagaaaga agcaauuuug auuucuugaa aagguaguuc cugcacucag 1620
uuuaaacuaa aaauaaucau acuuggauuu uauuuauuuu ugucauagua aaaauuuuaa 1680
uuuauauaua uuuuuauuua guauuaucuu auucuuugcu auuugccaau ccuuugucau 1740
caauuguguu aaaugaauug aaaauucaug cccuguucau uuuauuuuac uuuauugguu 1800
aggauauuua aaggauuuuu guauauauaa uuucuuaaau uaauauucca aaagguuagu 1860
ggacuuagau uauaaauuau ggcaaaaauc uaaaaacaac aaaaaugauu uuuauacauu 1920
cuauuucauu auuccucuuu uuccaauaag ucauacaauu gguagauaug acuuauuuua 1980

-continued uuuuuguauu auucacuaua ucuuuaugau auuuaaguau aaauaauuaa aaaaauuuau 2040
uguaccuuau agucugucac caaaaaaaaa aaauuaucug uagguaguga aaugcuaaug 2100
uugauuuguc uuuaagggcu uguuaacuau ccuuuauuuu cucauuuguc uuaaauuagg 2160
aguuuguguu uaaauuacuc aucuaagcaa aaaauguaua uaaaucccau uacuggguau 2220
auacccaaag gauuauaaau caugcugcua uaaagacaca ugcacacgua uguuuauugc 2280
agcacuauuc acaauagcaa agacuuggaa ccaacccaaa uguccaucaa ugauagacuu 2340
gauuaagaaa augugcacau auacaccaug gaauacuaug cagccauaaa aaaggaugag 2400
uucauguccu uuguagggac auggauaaag cuggaaacca ucauucugag caaacuauug 2460
caaggacaga aaaccaaaca cugcauguuc ucacucauag gugggaauug aacaaugaga 2520
acacuuggac acaaggugggg gaacaccaca caccagggcc ugucaugggg ugggggggagu 2580 ggggagggau agcauuagga gauauaccua auguaaauga ugaguuaaug ggugcagcac 2640
accaacaugg cacauguaua cauauguagc aaaccugcac guugugcaca uguacccuag 2700
aacuuaaagu auaauuaaaa aaaaaaagaa aacagaagcu auuuauaaag aaguuauuug 2760
cugaaauaaa ugugaucuuu cccauuaaaa aaauaaagaa auuuuggggu aaaaaaacac 2820
aauauauugu auucuugaaa aauucuaaga gaguggaugu gaaguguucu caccacaaaa 2880
gugauaacua auugagguaa ugcacauauu aauuagaaag auuuugucau uccacaaugu 2940
auauauacuu aaaaauaugu uauacacaau aaauacauac auuaaaaaau aaguaaaugu 3000
a 3001

<210> SEQ ID NO 71
<211> LENGTH: 1037
<212> TYPE: RNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: 3' UTR-012 (Col6a1; collagen, type VI, alpha 1
UTR)

<400> SEQUENCE: 71
cccacccugc acgccggcac caaacccugu ccucccaccc cuccccacuc aucacuaaac 60
agaguaaaau gugaugcgaa uuuucccgac caaccugauu cgcuagauuu uuuuuaagga 120
aaagcuugga aagccaggac acaacgcugc ugccugcuuu gugcaggguc cuccggggcu 180
cagcccugag uuggcaucac cugcgcaggg cccucugggg cucagcccug agcuagugu 240 accugcacag ggcccucuga ggcucagccc ugagcuggcg ucaccugugc agggcccucu 300
ggggcucagc ccugagcugg ccucaccugg guuccccacc ccgggcucuc cugcccugcc 360
cuccugcccg cccucccucc ugccugcgca gcuccuuccc uaggcaccuc ugugcugcau 420
cccaccagcc ugagcaagac gcccucucgg ggccugugcc gcacuagccu cccucuccuc 480
uguccccaua gcugguuuuu cccaccaauc cucaccuaac aguuacuuua caauuaaacu 540
caaagcaagc ucuucuccuc agcuuggggc agccauuggc cucugucucg uuuugggaaa 600
ccaaggucag gaggccguug cagacauaaa ucucggcgac ucggccccgu cuccugaggg 660
uccugcuggu gaccggccug gaccuuggcc cuacagcccu ggaggccgcu gcugaccagc 720
acugaccccg accucagaga guacucgcag ggcgcuggc ugcacucaag acccucgaga 780
uuaacggugc uaaccccguc ugcuccuccc ucccgcagag acuggggccu ggacuggaca 840
ugagagcccc uuggugccac agagggcugu gucuuacuag aaacaacgca aaccucuccu 900
uccucagaau agugaugugu ucgacguuuu aucaaaggcc cccuuucuau guucauguua 960
guuuugcucc uucuguguuu uuuucugaac cauauccaug uugcugacuu uuccaaauaa 1020
agguuuucac uccucuc 1037

<210> SEQ ID NO 72
<211> LENGTH: 577
<212> TYPE: RNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: 3' UTR-013 (Calr; calreticulin UTR)

<400> SEQUENCE: 72
agaggccugc cuccagggcu ggacugaggc cugagcgcuc cugccgcaga gcuggccgcg 60
ccaaauaaug ucucugugag acucgagaac uuucauuuuu uuccaggcug guucggauuu 120
gggguggauu uugguuuugu ucccccuccuc cacucucccc cacccccucc ccgcccuuuu 180
uuuuuuuuuu uuuuaaacug guauuuuauc uuugauucuc cuucagcccu caccccuggu 240
ucucaucuuu cuugaucaac aucuuuucuu gccucugucc ccuucucuca ucucuuagcu 300
ccccuccaac cugggggca guggugugga gaagccacag gccugagauu ucaucugcuc 360
uccuuccugg agcccagagg agggcagcag aagggggugg ugucuccaac ccccccagcac 420 ugaggaagaa cggggcucuu cucauuucac cccucccuuu cuccccugcc cccaggacug 480
ggccacuucu gggugggggca gugggucccca gauuggcuca cacugagaau guaagaacua 540
caaacaaaau uucuauuaaa uuaaauuuug ugucucc 577

<210> SEQ ID NO 73
<211> LENGTH: 2212
<212> TYPE: RNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: 3' UTR-014 (Col1a1; collagen, type I, alpha 1 UTR)

<400> SEQUENCE: 73
cucccuccau cccaaccugg cucccuccca cccaaccaac uuuccccccca acccggaaac 60 agacaagcaa cccaaacuga acccccucaa aagccaaaaa augggagaca auuucacaug 120
gacuuuggaa aauauuuuuu uccuuugcau ucaucucuca aacuuaguuu uuaucuuuga 180
ccaaccgaac augaccaaaa accaaaagug cauucaaccu uaccaaaaaa aaaaaaaaaa 240
aaagaauaaa uaaauaacuu uuuaaaaaag gaagcuuggu ccacuugcuu gaagacccau 300 gcgggggguaa gucccuuucu gcccguuggg cuuaugaaac cccaaugcug cccuuucugc 360
uccuuucucc acaccccccu uggggccucc ccuccacucc uucccaaauc ugucucccca 420
gaagacacag gaaacaaugu auugucugcc cagcaaucaa aggcaaugcu caaacaccca 480
aguggccccc acccucagcc cgcuccugcc cgcccagcac ccccaggccc ugggggaccu 540
gggguucuca gacugccaaa gaagccuugc caucuggcgc ucccauggcu cuugcaacau 600
cuccccuucg uuuuugaggg ggucaugccg ggggagccac cagccccuca cuggguucgg 660
aggagaguca ggaagggcca cgacaaagca gaaacaucgg auuuggggaa cgcgugucaa 720

```
ucccuugugc cgcagggcug ggcgggagag acuguucugu uccuugugua acuguguugc    780
ugaaagacua ccucguucuu gucuugaugu gucaccgggg caacugccug ggggcgggga    840
ugggggcagg guggaagcgg cuccccauuu uauaccaaag gugcuacauc uaugugaugg    900
gugggguggg gagggaauca cuggugcuau agaaauugag augccccccc aggccagcaa    960
auguuccuuu uuguucaaag ucuauuuuua uuccuugaua uuuuucuuuu uuuuuuuuuu   1020
uuuuugugga uggggacuug ugaauuuuuc uaaaggugcu auuuaacaug ggaggagagc   1080
gugugcggcu ccagcccagc ccgcugcuca cuuuccaccc ucucuccacc ugccucuggc   1140
uucucaggcc ucugcucucc gaccucucuc cucugaaacc cuccuccaca gcugcagccc   1200
auccucccgg cucccuccua gucuguccug cguccucugu ccccggguuu cagagacaac   1260
uucccaaagc acaaagcagu uuuuccccuu aggggugggga ggaagcaaaa gacucuguac   1320
cuauuuugua uguguauaau aauuugagau guuuuuaauu auuuugauug cuggaauaaa   1380
gcauguggaa augacccaaa cauaauccgc aguggccucc uaauuuccuu cuuuggaguu   1440
gggggagggg uagacauggg gaaggggcuu uggggugaug ggcuugccuu ccauuccugc   1500
ccuuucccuc cccacuauuc ucuucuagau cccuccauaa ccccacuccc cuuucucuca   1560
cccuucuuau accgcaaacc uuucuacuuc cucuuucauu uucuauucuu gcaauuuccu   1620
ugcaccuuuu ccaaauccuc uucuccccug caauaccaua caggcaaucc acgugcacaa   1680
cacacacaca cacucuucac aucuggggguu guccaaaccu cauacccacu ccccuucaag   1740
cccauccacu cuccaccccc uggaugcccu gcacuuggug gcggugggau gcucauggau   1800
acugggaggg ugaggggagu ggaacccgug aggaggaccu gggggccucu ccuugaacug   1860
acaugaaggg ucaucuggcc ucugcucccu ucucacccac gcugaccucc ugccgaagga   1920
gcaacgcaac aggagagggg ucugcugagc cuggcgaggg ucugggaggg accaggagga   1980
aggcgugcuc ccugcucgcu guccuggccc ugggggagug agggagacag acaccuggga   2040
gagcuguggg gaaggcacuc gcaccgugcu cuugggaagg aaggagaccu ggcccugcuc   2100
accacggacu gggugccucg accuccugaa uccccagaac acaacccccc ugggcugggg   2160
uggucugggg aaccaucgug cccccgccuc ccgccuacuc cuuuuuaagc uu           2212
```

<210> SEQ ID NO 74
<211> LENGTH: 729
<212> TYPE: RNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: 3' UTR-015 (Plod1; procollagen-lysine, 2-oxoglutarate 5-dioxygenase 1 UTR)

<400> SEQUENCE: 74

```
uuggccaggc cugacccucu uggaccuuuc uucuuugccg acaaccacug cccagcagcc     60
ucugggaccu cggggguccca gggaacccag uccagccucc uggcuguuga cuucccauug    120
cucuuggagc caccaaucaa agagauucaa agagauuccu gcaggccaga ggcggaacac    180
accuuuaugg cuggggcucu ccguggugu cuggacccag ccccuggaga caccauucac    240
uuuuacugcu uuguagugac ucgugcucuc caaccugucu uccugaaaaa ccaaggcccc    300
cuuccccccac cucuuccaug gggugagacu ugagcagaac aggggcuucc ccaaguugcc    360
cagaaagacu gucugggguga gaagccaugg ccagagcuuc ucccaggcac agguguugca    420
ccagggacuu cugcuucaag uuuuggggua aagacaccug gaucagacuc caagggcugc    480
```

ccugagucug ggacuucugc cuccauggcu ggucaugaga gcaaaccgua guccccugga 540
gacagcgacu ccagagaacc ucuugggaga cagaagaggc aucugugcac agcucgaucu 600
ucuacuugcc uguggggagg ggagugacag guccacacac cacacugggu cacccugucc 660
uggaugccuc ugaagagagg gacagaccgu cagaaacugg agaguuucua uuaaagguca 720
uuuaaacca 729

<210> SEQ ID NO 75
<211> LENGTH: 847
<212> TYPE: RNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: 3' UTR-016 (Nucb1; nucleobindin 1 UTR)

<400> SEQUENCE: 75
uccuccggga ccccagcccu caggauuccu gaugcuccaa ggcgacugau gggcgcugga 60
ugaaguggca cagucagcuu cccugggggc ugguguucaug uugggcuccu ggggcggggg 120
cacggccugg cauuucacgc auugcugcca ccccaggucc accugucucc acuuucacag 180
ccuccaaguc uguggcucuu cccuucuguc cuccgagggg cuugccuucu cucgugucca 240
gugaggugcu cagugaucgg cuuaacuuag agaagcccgc ccccuccccu ucuccgucug 300
ucccaagagg gucugcucug agccugcguu ccuagguggc ucggccucag cugccugggu 360
uguggccgcc cuagcauccu guaugcccac agcuacugga auccccgcug cugcuccggg 420
ccaagcuucu gguugauuaa ugagggcaug ggguggucccc ucaagaccuu ccccuaccuu 480
uuguggaacc agugaugccu caaagacagu guccccucca cagcugggug ccaggggcag 540
gggauccuca guauagccgg ugaacccuga uaccaggagc cugggccucc cugaaccccu 600
ggcuuccagc caucucaucg ccagccuccu ccuggaccuc uuggccccca gccccuuccc 660
cacacagccc cagaaggguc ccagagcuga ccccacucca ggaccuaggc ccagccccuc 720
agccucaucu ggagccccug aagaccaguc ccacccaccu uucuggccuc aucugacacu 780
gcuccgcauc cugcugugug uccuguucca uguuccgguu ccauccaaau acacuuucug 840
gaacaaa 847

<210> SEQ ID NO 76
<211> LENGTH: 110
<212> TYPE: RNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: 3' UTR-017 (?-globin)

<400> SEQUENCE: 76
gcuggagccu cgguggccau gcuucuugcc ccuugggccu ccccccagcc ccuccucccc 60
uuccugcacc cguacccccg uggucuuuga auaaagucug agugggcggc 110

<210> SEQ ID NO 77
<211> LENGTH: 119
<212> TYPE: RNA
<213> ORGANISM: Artificial Sequence
<220> FEATURE:
<223> OTHER INFORMATION: Description of Artificial Sequence: Synthetic
polynucleotide

<220> FEATURE:
<223> OTHER INFORMATION: 3' UTR-018

<400> SEQUENCE: 77
ugauaauagg cuggagccuc gguggccaug cuucuugccc cuugggccuc cccccagccc 60
cuccuccccu uccugcaccc guacccccgu ggucuuugaa uaaagucuga gugggcggc 119

<210> SEQ ID NO 78
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Syn'5 Promoter

<400> SEQUENCE: 78
attgggcacc cgtaaggg 18

<210> SEQ ID NO 79
<211> LENGTH: 133
<212> TYPE: RNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: (3' UTR with miR 142-3p binding site)

<400> SEQUENCE: 79
gcuggagccu cgguggccau gcuucuugcc ccuugggccu ccccccagcc ccuccucccc 60
uuccugcacc cguacccccu ccauaaagua ggaaacacua caguggucuu ugaauaaagu 120
cugagugggc ggc 133

<210> SEQ ID NO 80
<211> LENGTH: 22
<212> TYPE: RNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: (miR 146-3p sequence)

<400> SEQUENCE: 80
ccucugaaau ucaguucuuc ag 22

<210> SEQ ID NO 81
<211> LENGTH: 22
<212> TYPE: RNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: (miR 146-5p sequence)

<400> SEQUENCE: 81
ugagaacuga auuccauggg uu 22

<210> SEQ ID NO 82
<211> LENGTH: 22
<212> TYPE: RNA
<213> ORGANISM: Artificial Sequence
<220> FEATURE:

<223> OTHER INFORMATION: Description of Artificial Sequence: Synthetic
      oligonucleotide
<220> FEATURE:
<223> OTHER INFORMATION: (miR 155-3p sequence)

<400> SEQUENCE: 82
cuccuacaua uuagcauuaa ca 22

<210> SEQ ID NO 83
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: (miR 155-5p sequence)

<400> SEQUENCE: 83
uuaaugcuaa ucgugauagg ggu 23

<210> SEQ ID NO 84
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: (miR 126-3p sequence)

<400> SEQUENCE: 84
ucguaccgug aguaauaaug cg 22

<210> SEQ ID NO 85
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: miR-126-5p

<400> SEQUENCE: 85
cauuauuacu uuugguacgc g 21

<210> SEQ ID NO 86
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: miR 16-3p sequence

<400> SEQUENCE: 86
ccaguauuaa cugugcugcu ga 22

<210> SEQ ID NO 87
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: (miR 16-5p sequence)

<400> SEQUENCE: 87
uagcagcacg uaaauauugg cg 22

<210> SEQ ID NO 88
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: miR 21-3p sequence

<400> SEQUENCE: 88
caacaccagu cgaugggcug u 21

<210> SEQ ID NO 89
<211> LENGTH: 22
<212> TYPE: RNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: (miR 21-5p sequence)

<400> SEQUENCE: 89
uagcuuauca gacugauguu ga 22

<210> SEQ ID NO 90
<211> LENGTH: 22
<212> TYPE: RNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: (miR 223-3p sequence)

<400> SEQUENCE: 90
ugucaguuug ucaaauaccc ca 22

<210> SEQ ID NO 91
<211> LENGTH: 22
<212> TYPE: RNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: (miR 223-5p sequence)

<400> SEQUENCE: 91
cguguauuug acaagcugag uu 22

<210> SEQ ID NO 92
<211> LENGTH: 22
<212> TYPE: RNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: (miR 24-3p sequence)

<400> SEQUENCE: 92
uggcucaguu cagcaggaac ag 22

<210> SEQ ID NO 93
<211> LENGTH: 22
<212> TYPE: RNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: (miR 24-5p sequence)

<400> SEQUENCE: 93
ugccuacuga gcugauauca gu 22

<210> SEQ ID NO 94
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: (miR 27-3p sequence)

<400> SEQUENCE: 94
uucacagugg cuaaguuccg c 21

<210> SEQ ID NO 95
<211> LENGTH: 22
<212> TYPE: RNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: (miR 27-5p sequence)

<400> SEQUENCE: 95
agggcuuagc ugcuugugag ca 22

<210> SEQ ID NO 96
<211> LENGTH: 22
<212> TYPE: RNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: (miR 126-3p binding site)

<400> SEQUENCE: 96
cgcauuauua cucacgguac ga 22

<210> SEQ ID NO 97
<211> LENGTH: 141
<212> TYPE: RNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: (3' UTR with miR 126-3p binding site)

<400> SEQUENCE: 97
ugauaauagg cuggagccuc gguggccaug cuucuugccc cuugggccuc cccccagccc 60
cuccuccccu uccugcaccc guaccccccg cauuauuacu cacgguacga guggucuuug 120
aauaaagucu gagugggcgg c 141

<210> SEQ ID NO 98
<211> LENGTH: 164
<212> TYPE: RNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: 3' UTR (miR142+miR126 binding sites variant 1)

<400> SEQUENCE: 98
ugauaauagu ccauaaagua ggaaacacua cagcuggagc cucgguggcc augcuucuug 60
ccccuugggc cuccccccag ccccuccucc ccuuccugca cccguacccc ccgcauuauu 120
acucacggua cgaguggucu uugaauaaag ucugaguggg cggc 164

<210> SEQ ID NO 99
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: miR 155-5p sequence)

<400> SEQUENCE: 99
uuaaugcuaa uugugauagg ggu 23

<210> SEQ ID NO 100
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: (miR 155-5p binding site)

<400> SEQUENCE: 100
accccuauca caauuagcau uaa 23

<210> SEQ ID NO 101
<211> LENGTH: 188
<212> TYPE: RNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: (3 UTR with 3 miR 142-3p binding sites)

<400> SEQUENCE: 101
ugauaauagu ccauaaagua ggaaacacua cagcuggagc cucgguggcc augcuucuug 60
ccccuugggc cuccauaaag uaggaaacac uacauccccc cagccccucc uccccuuccu 120
gcacccguac ccccuccaua aaguaggaaa cacuacagug gucuuugaau aaagucugag 180
ugggcggc 188

<210> SEQ ID NO 102
<211> LENGTH: 140
<212> TYPE: RNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: 3' UTR with miR 142-5p binding site)

<400> SEQUENCE: 102
ugauaauagg cuggagccuc gguggccaug cuucuugccc cuugggccuc cccccagccc 60
cuccuccccu uccugcaccc guacccccag uagugcuuuc uacuuuaugg uggucuuuga 120
auaaagucug agugggcggc 140

<210> SEQ ID NO 103
<211> LENGTH: 182
<212> TYPE: RNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: (3' UTR with 3 miR 142-5p binding sites)

<400> SEQUENCE: 103
ugauaauaga guagugcuuu cuacuuuaug gcuggagccu cgguggccau gcuucuugcc 60
ccuugggcca guagugcuuu cuacuuuaug ucccccccagc cccuccuccc cuuccugcac 120
ccguaccccc aguagugcuu ucuacuuuau gguggucuuu gaauaaaguc ugagugggcg 180
gc 182

<210> SEQ ID NO 104
<211> LENGTH: 184
<212> TYPE: RNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: (3' UTR with 2 miR 142-5p binding sites and 1
miR 142-3p binding site)

<400> SEQUENCE: 104
ugauaauaga guagugcuuu cuacuuuaug gcuggagccu cgguggccau gcuucuugcc 60
ccuugggccu ccauaaagua ggaaacacua caucccccca gccccuccuc cccuuccugc 120
acccguaccc ccaguagugc uuucuacuuu augguggucu uugaauaaag ucugagugggg 180 cggc 184

<210> SEQ ID NO 105
<211> LENGTH: 142
<212> TYPE: RNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: (3' UTR with miR 155-5p binding site)

<400> SEQUENCE: 105
ugauaauagg cuggagccuc gguggccaug cuucuugccc cuugggccuc cccccagccc 60
cuccuccccu uccugcaccc guacccccac cccuaucaca auuagcauua aguggucuuu 120
gaauaaaguc ugagugggcg gc 142

<210> SEQ ID NO 106
<211> LENGTH: 188
<212> TYPE: RNA
<213> ORGANISM: Artificial Sequence
<220> FEATURE:

<223> OTHER INFORMATION: Description of Artificial Sequence: Synthetic
      polynucleotide
<220> FEATURE:
<223> OTHER INFORMATION: (3' UTR with 3 miR 155-5p binding sites)

<400> SEQUENCE: 106
ugauaauaga ccccuaucac aauuagcauu aagcuggagc cucgguggcc augcuucuug 60
ccccuugggc caccccuauc acaauuagca uuaaucccc cagccccucc uccccuuccu 120
gcacccguac ccccaccccu aucacaauua gcauuaagug gucuuugaau aaagucugag 180
ugggcggc 188

<210> SEQ ID NO 107
<211> LENGTH: 188
<212> TYPE: RNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: (3' UTR with 2 miR 155-5p binding sites and 1
      miR 142-3p binding site)

<400> SEQUENCE: 107
ugauaauaga ccccuaucac aauuagcauu aagcuggagc cucgguggcc augcuucuug 60
ccccuugggc cuccauaaag uaggaaacac uacaucccc cagccccucc uccccuuccu 120
gcacccguac ccccaccccu aucacaauua gcauuaagug gucuuugaau aaagucugag 180
ugggcggc 188

<210> SEQ ID NO 108
<211> LENGTH: 142
<212> TYPE: RNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: (3' UTR with miR 142-3p binding site, P3
      insertion)

<400> SEQUENCE: 108
ugauaauagg cuggagccuc gguggccaug cuucuugccc cuugggccuc cauaaaguag 60
gaaacacuac aucccccag ccccuccucc ccuuccugca cccguacccc cgugggucuuu 120 gaauaaaguc ugagugggcg gc 142

<210> SEQ ID NO 109
<211> LENGTH: 70
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: (5' UTR with miR142-3p binding site at position
      p1)

<400> SEQUENCE: 109
gggaaauaag aguccauaaa guaggaaaca cuacaagaaa agaagaguaa gaagaaauau 60
aagagccacc 70

<210> SEQ ID NO 110
<211> LENGTH: 70
<212> TYPE: RNA

<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: (5' UTR with miR142-3p binding site at position
p2)

<400> SEQUENCE: 110
gggaaauaag agagaaaaga agaguaaucc auaaaaguagg aaacacuaca gaagaaauau 60
aagagccacc 70

<210> SEQ ID NO 111
<211> LENGTH: 70
<212> TYPE: RNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: (5' UTR with miR142-3p binding site at position
p3)

<400> SEQUENCE: 111
gggaaauaag agagaaaaga agaguaagaa gaaauauaau ccauaaagua ggaaacacua 60
cagagccacc 70

<210> SEQ ID NO 112
<211> LENGTH: 181
<212> TYPE: RNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: (3' UTR with 3 miR 142-5p binding sites)

<400> SEQUENCE: 112
ugauaauaga guagugcuuu cuacuuuaug gcuggagccu cgguggccau gcuucuugcc 60
ccuugggcca guagugcuuu cuacuuuaug ucccccccagc cccucucccc uuccugcacc 120
cguaccccca guagugcuuu cuacuuuaug guggucuuug aauaaagucu gagugggcgg 180
c 181

<210> SEQ ID NO 113
<211> LENGTH: 1137
<212> TYPE: RNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: GALT-CO26

<400> SEQUENCE: 113
augucuagga gcgggaccga cccccagcag cggcagcagg ccagcgaggc cgacgccgcc 60
gcggccaccu ucagggccaa cgaccaucaa cacaucaggu auaacccccu ccaggacgag 120
uggguguugg uguccgccca ucggaugaag aggcccuggc agggccaggu ggagccccag 180
cuccugaaga ccgugccccg gcacgacccc cucaaccccc ugugccccgg cgcgauccgc 240
gccaacggcg aggugaaccc ccaguaugac agcacguucc uguucgacaa cgacuucccc 300
gcccugcagc ccgacgcccc cagccccggc ccaagcgacc auccccuguu ccaggccaag 360
uccgccaggg gcguguguaa ggugaugugc uuccacccau gguccgacgu gacccugccc 420

-continued

```
cugaugagcg ugcccgagau ccgcgccgug guggacgccu gggccagcgu gaccgaggag     480

cugggggccc aguacccuug ggugcaaauc uucgagaaua agggcgccau gaugggcugc     540

uccaaccccc acccccacug ucaggugugg gccagcaguu uccugcccga caucgcccag     600

cgcgaggagc ggucacagca ggccuacaag agccaacacg gcgaaccucu gcucauggag     660

uacagcaggc aggaacugcu gcggaaggag aggcuggucc ugaccagcga gcacuggcug     720

gugcuggugc ccuucugggc caccuggccc uaccagacac ugcugcugcc uaggcgacac     780

gugcgucggc ugcccgagcu gaccccugcc gaaagggacg accuggccag caucaugaag     840

aagcugcuca ccaaguacga caaccuguuu gaaaccagcu uccccuacag caugggcugg     900

cacggcgcac cuaccggcag cgaggccggc gccaacugga accacuggca gcugcaugcc     960

cacuacuauc cgccccuccu caggagcgcc accgugcgca aguucauggu gggcuaugag    1020

augcuggcgc aggcccagcg ugaccugacc cccgagcagg ccgccgagag gcugcgugcc    1080

cugccugagg ugcacuacca ccuggggcag aaggacagag aaacugcgac caucgcc       1137
```

<210> SEQ ID NO 114
<211> LENGTH: 1137
<212> TYPE: RNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: GALT-CO27

<400> SEQUENCE: 114

```
augagcaggu ccggcaccga cccccagcag aggcagcaag ccuccgaggc cgacgccgcc      60

gcggccaccu uccgggccaa cgaccaucag cauaucaggu auaacccccu ucaggacgag     120

ugggugcucg ugagcgccca ccggaugaag cgccccuggc aggggcaggu cgagccccag     180

cugcugaaga ccgugcccag gcacgauccg cugaacccgc ugugccccgg ggccauccgg     240

gccaacgggg aggugaaccc ccaguacgac agcaccuucc uguucgacaa cgacuucccc     300

gcccugcagc ccgaugcccc cagccccggg cccuccgacc acccccuguu ccaggccaag     360

agcgccagag gcgugugcaa ggucaugugc uuucaucccu ggagcgacgu gacccugccc     420

cugauguccg ugcccgagau cagagcuguc guggacgccu gggccuccgu gaccgaggag     480

cucggcgccc aguaccccug ggugcagauc uucgagaaca aaggcgccau gaugggcugc     540

agcaaccccc acccacacug ccaggugugg gccagcagcu uccugcccga caucgcccag     600

agagaggaga ggagccagca ggccuauaag agccagcaug gcgagccccu gcugauggag     660

uacagcagac aggagcugcu gaggaaagag aggcuggugc ugacaagcga gcacuggcug     720

gugcuggugc ccuuuugggc cacuuggcca uaccagaccc ugcugcugcc ccggcggcau     780

gucaggagac ugccugagcu gacucccgcc gagcgggaug accuggccag caucaugaag     840

aagcugcuca ccaaauacga caaccucuuc gaaaccagcu uccccuacag cauggggugg     900

cacggggccc ccaccggcag cgaagccgga gccaauugga aucauuggca gcuccaugcc     960

cauuacuauc cgccccugcu cagaagcgcc accgugcgga aguucauggu gggcuacgag    1020

augcucgccc aggcccagcg ggaccugacc cccgagcagg cugccgagcg gcugagggcc    1080

cugcccgagg ugcacuauca ccugggccag aaagauaggg aaacagccac uaucgcc       1137
```

<210> SEQ ID NO 115
<211> LENGTH: 1137

<212> TYPE: RNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: GALT-CO28

<400> SEQUENCE: 115
augagcagga gcggcaccga cccccagcag aggcagcagg ccagcgaagc cgacgccgcc 60
gccgccaccu uccgggccaa cgaucaccag cacauccgcu acaacccucu ccaggacgag 120
ugggugcucg ugagcgccca caggaugaag cggcccuggc agggccaggu ggagccccag 180
cuccugaaga ccgugcccag acacgacccc cugaacccgc ucugccccgg cgccaucaga 240
gccaacggcg aggugaaccc ccaguacgac agcaccuucc uguucgacaa cgacuucccc 300
gcccuccagc ccgaugcccc cagccccggu cccuccgacc auccccuguu ccaggccaag 360
uccgccagag gcgugugcaa ggugaugugc uuccaccccu ggagcgacgu gacccucccc 420
cugaugucgg ugcccgaaau cagggccgug guggacgccu gggccagcgu gaccgaggag 480
cugggggccc aguaucccug gguccagauc uucgagaaca agggggccau gaugggcugu 540
agcaaccccc acccacacug ccaggugugg gccuccuccu uccugcccga caucgcccaa 600
agggaggagc ggucccagca agccuacaag ucccagcacg gugagccccu gcugauggaa 660
uauagcagac aggagcugcu gaggaaggag cgccuggucc ugaccagcga gcacuggcug 720
gugcuggucc ccuuuugggc caccuggccc uaccagacgc ugcugcugcc ucgcagacau 780
gugaggaggc ugccggagcu gacccccgcc gagcgggacg accuggcaag caucaugaag 840
aagcugcuga ccaaguacga caaccuguuc gagacuuccu ucccguacag caugggcugg 900
cacggcgccc cgaccggaag cgaggccggc gcgaacugga accacuggca gcugcaugcg 960
cauuacuacc cgccccugcu gcggucagcc accguccgca aguucauggu gggcuacgaa 1020
augcuggccc aggcgcagag ggaccucacc cccgagcagg ccgccgaaag acugcgugcg 1080
cugccggagg ugcacuacca ccugggccag aaggaccgcg aaaccgcgac caucgca 1137

<210> SEQ ID NO 116
<211> LENGTH: 1137
<212> TYPE: RNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: GALT-CO29

<400> SEQUENCE: 116
augucacgga gcggcaccga cccgcagcag aggcagcagg ccagcgaggc agacgccgcc 60
gccgccaccu ucagggccaa cgaccaucag cacaucagau acaacccccu acaggacgag 120
ugggugcucg ucagcgccca cagaaugaag cggcccuggc aggggcaggu ggagccccag 180
cuccugaaga ccgugcccag gcacgacccc cucaaucccc ugugcccugg cgccauuagg 240
gccaacggcg aggugaaccc ccaguacgac ucaaccuucc uguuugacaa cgacuucccc 300
gcccugcagc ccgaugcccc gagccccggg cccagcgacc acccccuguu ccaggccaag 360
ucggccaggg gcgugugcaa ggugaugugc uuccaccccu ggagcgaugu cacccugccc 420
cugaugucgg ugcccgagau ccgcgccgug guggacgccu gggccagcgu gaccgaggag 480
cugggcgccc aauaccccug ggugcagauc uuugagaaca aaggcgccau gaugggcugu 540

-continued

```
agcaaccccc acccccacug ucaggugugg gccagcagcu uucugcccga caucgcccag    600

agggaggagc gcucccagca ggcuuacaag agccagcacg gagagccccu gcucauggag    660

uacucgcgac aggagcugcu ccggaaggaa cggcuggucc ugaccuccga gcacuggcuc    720

gugcuggugc cguucugggc cacauggccc uaccagaccc ugcugcuacc ccgcagacac    780

guucgccgac ugcccgagcu gaccccugcc gagagagacg accuggcgag caucaugaag    840

aagcugcuca ccaaguauga caacuuauuc gaaaccuccu ucccuuacag caugggcugg    900

cacggcgccc ccaccggcag cgaggcgggc gccaacugga accacuggca gcugcaugcc    960

cacuacuacc caccccugcu gcggagcgcc accgugagaa aguucauggu gggcuacgag   1020

augcuggccc aggcccaacg ggaucugacc cccgagcagg ccgccgagcg gcugagggcc   1080

cuccccgagg uacacuacca ucucggccag aaggaccggg aaaccgccac caucgcc      1137
```

```
<210> SEQ ID NO 117
<211> LENGTH: 1137
<212> TYPE: RNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: GALT-CO30

<400> SEQUENCE: 117

augagcagaa gcggcaccga cccccagcag cggcagcagg ccagcgaggc cgacgccgcc     60

gccgcaaccu uccgcgccaa cgaccaccag cacaucagau acaacccccu ccaggacgag    120

uggguccucg uguccgccca uagaaugaag aggccauggc agggccaggu agaaccucaa    180

cugcugaaga ccguccccog gcaugacccc cucaaucccc ucugcccggg ggccauccga    240

gcgaaugggg aggucaaccc ccaguacgac agcaccuucc uguucgacaa cgacuucccc    300

gcccugcagc ccgacgcccc gagccccgga cccagcgacc acccccuguu ccaggccaaa    360

uccgcccggg gcgucugcaa ggugaugugc uuucaccccu gguccgacgu gacccugccc    420

cucauguccg ugcccgagau cagggccgug guggacgcuu gggccagcgu cacggaggag    480

cucggcgccc aguaccccug gguccagauc uucgagaaca agggcgccau gaugggggugc   540

uccaacccuc acccccacug ccaggugugg gccagcagcu uucugcccga cauugcccag    600

cgggaggaga ggucccagca ggccuacaag agucagcacg gggagccccu gcugauggag    660

uacucccggc aggagcuccu gaggaaagag cgcuuggugc ugacaagcga gcacuggcug    720

gugcucgugc ccuucugggc cacuuggccc uaccagaccc ugcugcugcc cagacggcac    780

gugcggcggc ugcccgagcu gacacccgcc gagagggacg aucucgccag cauuaugaag    840

aagcugcuga ccaaguauga caaccuguuu gagacuagcu uucccuacag caugggcugg    900

cacggggccc ccacgggcuc cgaggccggc gccaacugga accacuggca gcugcacgcc    960

cacuauuauc cgccccugcu ccggagcgcc accgugagaa aguuuauggu gggcuaugag   1020

augcuggccc aagcgcaacg ggaucugacc cccgagcagg ccgccgagcg ucugagagcc   1080

cugccugagg ugcacuauca ccuggggcag aaggaccggg agacggcaac caucgcc      1137
```

```
<210> SEQ ID NO 118
<211> LENGTH: 1137
<212> TYPE: RNA
<213> ORGANISM: Artificial Sequence
<220> FEATURE:
<223> OTHER INFORMATION: Description of Artificial Sequence: Synthetic
      polynucleotide
```

<220> FEATURE:
<223> OTHER INFORMATION: GALT-CO31

<400> SEQUENCE: 118
augagccgca gcggcaccga cccgcaacaa agacagcagg ccuccgaggc cgacgccgcc 60
gccgcuaccu uuagggccaa cgaccaccag cauauccgcu acaaucccu ccaggacgag 120 ugggugcucg ugagcgccca ccguaugaag aggcccuggc agggacaggu ggaaccccag 180
cugcugaaga ccguaccccg gcacgacccc cugaaccccc ugugccccgg ggccaucaga 240
gccaauggag aggugaaccc ccaguacgac uccaccuucc uguucgauaa ugauuuuccg 300
gcccugcagc ccgacgcccc cagccccggc ccaagcgacc acccucuguu ccaggccaag 360
agcgccaggg gcguuugcaa ggucaugugc uuccaccccu ggagcgacgu gacccugccc 420
cugaugucgg ugcccgagau cagggccgug guggacgccu gggccagcgu gacggaggaa 480
cucggcgccc aguaccccug gguacagauc uucgagaaca agggugccau gaugggcugc 540
agcaacccac auccccacug ucaggugugg gccagcucau uccugccuga caucgcccag 600
cgugaggaga ggagucagca ggccuauaag agccagcaug gggagccccu ccugauggag 660
uacagcagac aagagcugcu caggaaggag agacuggugc ugaccagcga gcauuggcug 720
gugcuggugc ccuuuugggc cacauggccc uaccagaccc uccugcugcc gagacgccac 780
gugcgccggc ugcccgagcu gacucccgcc gagagggacg accucgcuag caucaugaag 840
aaacugcuga ccaaguacga caaccuguuu gagacaagcu uucccuacuc caugggaugg 900
cacggcgccc ccaccggcuc cgaggccggc gccaacugga accacuggca gcugcacgcc 960
cacuacuauc ccccgcugcu gcggagcgcc accgugagga aauucauggu gggcuacgag 1020
augcucgcuc aggcccaacg ggaccugacc cccgagcagg cggccgagag gcuccgagcu 1080
cugcccgagg ugcauuacca ucugggccag aaggauaggg aaaccgccac caucgcc 1137

<210> SEQ ID NO 119
<211> LENGTH: 1137
<212> TYPE: RNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: GALT-CO32

<400> SEQUENCE: 119
augagcagga gcggaaccga cccgcagcag aggcagcagg ccagcgaagc cgacgccgcc 60
gccgccaccu uccgggccaa cgaccaccaa cacaucaggu acaacccgcu ccaggacgag 120
ugggugcucg uuagcgccca ucgcaugaag cggccguggc aaggccaggu ggagccgcag 180
cugcugaaga ccgugccgcg ccacgacccg cugaacccgc ugugcccugg cgccauccgg 240
gccaacggcg aggugaaccc ucaguacgac agcaccuucc uguucgacaa ugauuucccg 300
gccuugcagc cggacgcccc uuccccggga ccguccgacc acccgcuguu ccaagccaag 360
uccgcccggg gcgugugcaa ggugaugugc uuccacccgu gguccgacgu gacccugccg 420
cugaugagcg ugccugagau cagagccgug guggacgccu gggccuccgu gacugaggag 480
cucggcgccc aguacccaug gguccagauc uucgagaaca agggugccau gaugggcugc 540
agcaacccgc acccgcacug ccaagugugg gccagcuccu uccugccgga uauugcccag 600
cgggaggagc ggagccagca agcauacaag agccagcaug gcgagccgcu cuugauggag 660
uacuccaggc aggagcugcu gagaaaggag cggcuggugc ugaccucuga gcacuggcug 720

```
gugcucgugc cguucugggc caccuggccu uaccagaccc ugcugcugcc gaggcggcac    780

gugcgccggc ugccagagcu gacgccagcc gagcgagacg aucuggccuc caucaugaag    840

aagcuacuga ccaaguauga caaccuguuc gaaacgagcu ucccguacag caugggcugg    900

cacggcgccc cgaccggcag cgaggccggc gccaacugga aucacuggca gcugcaugcc    960

cauuacuacc cgccgcuccu ccgcagcgcc accgugagga aguucauggu gggcuacgag   1020

augcuggccc aggcccagcg ggaccugacc ccggagcagg cggccgagag acugagggcc   1080

cucccggagg uccauuacca ccugggccag aaggaccggg agacggccac caucgcc      1137
```

<210> SEQ ID NO 120
<211> LENGTH: 1137
<212> TYPE: RNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: GALT-CO33

<400> SEQUENCE: 120

```
augucccgca gcggcacgga cccgcagcag cggcagcagg ccagcgaggc cgacgccgcg     60

gccgccaccu uccgggccaa cgaccaccag cacaucaggu acaacccacu ccaagacgag    120

ugggugcucg ugagcgccca ccggaugaag aggccguggc agggacaggu ugagccgcaa    180

cugcugaaga ccgugccaag acacgauccg cugaacccgc ucugcccggg cgccauccgu    240

gccaacggcg aggucaaccc acaguaugac agcaccuucc uguucgacaa cgacuucccg    300

gcccugcagc cggacgcgcc uagcccugga ccguccgacc acccgcuguu ccaggccaag    360

uccgcuaggg gcgugugcaa ggugaugugc uuccauccgu gguccgaugu cacccugccg    420

cucauguccg ugccggagau ccgggccgug guggaugccu gggccagcgu caccgaggag    480

cugggcgcgc aguacccuug gguccagauc uucgagaaca agggcgccau gaugggguugc    540

agcaacccgc acccacacug ccaggugugg gccagcagcu uccugccgga caucgcacag    600

agggaggagc ggagccaaca ggccuacaag ucccagcacg gcgagccacu gcugauggag    660

uacagcaggc aggagcugcu gcggaaggag cggcuggugc ucaccuccga acauuggcug    720

guucuggugc cguucugggc caccuggccu uaccagaccc ugcugcuccc gaggcggcac    780

gugcgcaggc ugccggagcu gacaccggcc gagcgcgacg accuggccag caucaugaag    840

aagcugcuca ccaaguacga uaaccuguuc gagacauccu ucccguacag caugggcugg    900

cacggcgccc cuaccggcuc cgaggccggc gccaacugga accacuggca gcugcacgcc    960

cacuacuacc caccgcugcu gagaagcgcc accgucagaa aguucauggu gggauaugag   1020

augcuggccc aggcucagag agaucugacc ccggagcagg ccgccgagag gcuccgcgcc   1080

cucccagaag ugcacuacca ucugggccag aaggacaggg agacggccac caucgcc      1137
```

<210> SEQ ID NO 121
<211> LENGTH: 1137
<212> TYPE: RNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: GALT-CO34

<400> SEQUENCE: 121

```
augagccgga gcggcaccga cccgcagcag cgucagcaag ccagcgaggc cgacgccgcc     60

gccgccacgu uccgggccaa cgaccaccag cacauuaggu acaacccgcu ccaggacgag    120

uggguccucg ugagcgccca caggaugaag aggccauggc agggacaagu ugagccacag    180

cugcugaaga ccgugccacg gcacgacccg cucaacccuc ugugcccggg cgccauccgc    240

gccaacggcg aggugaaccc acaguacgac agcaccuucc uguucgacaa cgacuucccu    300

gcccuccagc cggacgcccc gagcccugga ccguccgacc auccgcuguu ccaggccaag    360

uccgcgcggg gcgugugcaa ggugaugugc uuccauccgu ggagcgacgu gacccugccg    420

cugauguccg ugccugagau acgggccgug guggacgccu gggccagcgu gacagaggag    480

cucggcgccc aguacccuug ggugcagauc uucgagaaca agggugccau gauggguugc    540

agcaacccgc acccgcauug ccaggugugg gccagcagcu uccugccuga caucgcccag    600

cgggaggagc gcagccagca ggcuuacaag agccagcacg gcgagccgcu gcugauggag    660

uacucuaggc aggagcugcu gagaaaggag aggcuggugc ugaccagcga acacuggcuc    720

gugcuggugc cguucugggc aaccuggccg uaccagaccc ugcugcugcc gaggcggcau    780

gugagaaggc ucccggagcu gaccccagcc gagcgcgacg accucgccag caucaugaag    840

aagcuccuga ccaaguacga caaccuguuc gagacgagcu ucccguauuc caugggcugg    900

cacggagccc cgacaggcag cgaggccggc gccaacugga aucacuggca gcugcaugcc    960

cacuacuacc cgccgcuccu gcggagcgcc accguccgca aguucauggu gggcuacgag   1020

augcuggccc aggcccagag ggaccucacc ccggagcagg ccgccgagag gcugcgggcc   1080

cugccggagg uccacuacca ccucggccag aaggauagag aaaccgccac gaucgcg      1137


<210> SEQ ID NO 122
<211> LENGTH: 1137
<212> TYPE: RNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: GALT-CO35

<400> SEQUENCE: 122

augagcagga gcggcaccga cccucagcag aggcaacagg ccuccgaggc cgacgcggcg     60

gccgccaccu ucagggccaa cgaccaccag cacauccgau acaacccgcu ccaagacgag    120

ugggugcucg ucuccgccca ccgcaugaag cggccguggc aaggucaagu ugaaccacag    180

cugcugaaga ccgugccgag gcacgauccg cugaaccccgc ugugcccggg agccauccgg    240

gccaacggcg aggugaaccc ucaguacgac agcacauucc uguucgacaa cgacuucccg    300

gcccugcagc cggacgcccc aagcccgggc ccaagcgacc auccgcuguu ccaagccaag    360

uccgcccgcg gcgugugcaa ggugaugugc uuccacccgu gguccgacgu gacccugccg    420

cugaugagcg ugccggagau ccgggccgug guggaugccu gggccagcgu gaccgaggaa    480

uuaggcgccc aguacccaug ggugcagauc uucgagaaca agggagccau gaugggcugc    540

agcaacccgc acccgcacug ccaagugugg gccagcuccu uccugccgga caucgcccag    600

cgcgaggagc ggagccagca ggccuacaag agucagcacg gcgagccgcu gcugauggag    660

uacucuaggc aggagcugcu caggaaggag aggcuggugc ugaccagcga gcacugguug    720

gugcuggugc cuuucugggc caccuggcca uaccagaccc ugcugcugcc gagaaggcac    780

gucagaagac ugccggaacu gaccccggcc gagagggacg accuggccuc cauuaugaag    840
```

```
aagcuccuga ccaaguacga caaucuguuc gagacguccu ucccuuacag caugguuugg    900

cacggcgccc cgaccggcag cgaggcagga gccaacugga accacuggca gcugcacgcc    960

cacuacuacc cgccgcugcu cagguccgcc accguucgga aguucauggu gggcuacgaa   1020

augcuggccc aggcccagcg cgaccucacc ccagagcagg ccgccgagcg gcugcgggcc   1080

cugccggagg ugcacuacca ccugggccag aaggaccgcg agacagccac caucgcu      1137


<210> SEQ ID NO 123
<211> LENGTH: 1137
<212> TYPE: RNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: GALT-CO36

<400> SEQUENCE: 123

augagcaggu caggaaccga cccgcagcag cgccaacagg ccuccgaggc cgacgccgcc     60

gccgcgaccu uccgagccaa cgaccaucaa cacaucaggu auaacccguu gcaggacgag    120

ugggugcucg uguccgccca ucggaugaag cggccguggc agggacaggu ggagccgcag    180

cugcucaaga ccguuccgcg ccacgacccg cucaacccgc uguguccggg cgccauccgg    240

gccaacggcg aggugaaccc gcaguacgac agcaccuucc uguucgacaa cgauuucccu    300

gcccugcagc cagaugcccc gagcccgggc ccuagcgauc acccgcuguu ccaggccaag    360

agcgcccggg gcgucuguaa ggugaugugc uuccacccau ggagcgacgu cacccugccg    420

cugauguccg ugccagagau ccgcgccgug guggacgccu gggcgagcgu gaccgaggag    480

cugggagccc aauacccuug ggugcagauc uucgagaaua agggcgcuau gaugggcugc    540

uccaacccgc acccgcacug ccaggugugg gccagcuccu uccucccgga uaucgcccag    600

cgggaggaga gaagccagca ggccuacaag ucccagcacg gcgagccgcu gcucauggag    660

uauuccaggc aggagcuccu caggaaggaa aggcuugugc ugacgagcga gcacuggcug    720

gugcuggugc cguucugggc caccuggccg uaccagaccc uccugcugcc gcgccgacac    780

gucaggaggc ugccggagcu gaccccggcc gagagggaug accuggccuc cauaaugaag    840

aaguuacuga cuaaguauga caacuuguuc gaaaccagcu ucccuuacag caugggcugg    900

cauggcgccc cgaccggcuc cgaagccggc gccaacugga accauuggca acuccacgcc    960

cacuacuacc cgccgcucuu aaggagcgcc accgugagga aguucauggu gggauacgag   1020

augcuggccc aggcccaaag ggaccucacc ccggagcagg ccgcggagag gcugcgugcc   1080

cugccugagg uccacuacca ccugggccag aaggacaggg aaaccgcgac caucgcc      1137


<210> SEQ ID NO 124
<211> LENGTH: 1137
<212> TYPE: RNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: GALT-CO37

<400> SEQUENCE: 124

augagccgga gcggcaccga cccccagcag cggcagcagg ccagcgaggc cgacgcugcc     60

gccgccaccu uccgggccaa cgaccaccag cacauccggu acaacccccu gcaggacgag    120

ugggugcugg ugagcgccca ccggaugaag cggcccuggc agggccaggu ggagccccag    180
```

cugcugaaga ccgugccccg gcacgacccc cugaacccuc ugugcccagg agccauccgc 240
gccaacggcg aggugaaucc ucaguacgac agcaccuucc uguucgacaa cgacuucccc 300
gcccugcagc ccgacgcccc cagccccggc cccagcgacc auccauuauu ccaggccaag 360
agcgcccggg gcgugugcaa ggugaugugc uuccaccccu ggagcgacgu gacccugccc 420
cugaugagcg ugcccgagau cagagccgug guggacgccu gggccagcgu gaccgaggag 480
cugggcgccc aguaccccug ggugcagauc uucgagaaca agggcgccau gaugggcugc 540
agcaaccccc acccccacug ccaggugugg gccucaagcu uccugcccga caucgcccag 600
cgggaggagc ggagccaaca ggccuacaag ucacagcacg gcgagccccu gcugauggag 660
uacagccggc aggagcugcu gcggaaggag cggcuggugc ugaccagcga gcacuggcuc 720
gugcucgugc ccuucugggc caccuggccc uaccagaccc ugcugcugcc uagacggcac 780
gugcggcggc ugcccgagcu gacccccgcc gagcgggacg accuggccag caucaugaag 840
aagcuccuga ccaaguacga uaacuuauuc gaaacaagcu uccccuacag caugggcugg 900
cacggcgccc ccaccggcuc agaggccggc gcuaacugga accacuggca gcugcacgcc 960
cacuacuacc cgccucugcu gagaagcgcc accgugcgga aguucauggu gggcuacgag 1020
augcuggccc aggcccagag agacuuaacc ccugagcagg ccgccgagag gcuccgggcc 1080
uugccagagg ugcacuacca ccugggacag aaggaccggg agacggccac caucgcc 1137

<210> SEQ ID NO 125
<211> LENGTH: 1137
<212> TYPE: RNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: GALT-CO38

<400> SEQUENCE: 125
augagccgga gcggcaccga cccccagcag cggcagcagg ccagcgaggc cgacgcagcc 60
gccgcuaccu uccgggccaa cgaccaccag cacauccggu acaacccccu gcaggacgag 120
ugggugcugg ugagcgccca ccggaugaag cggcccuggc agggccaggu ggagccccag 180
cugcugaaga ccgugccccg gcacgacccc cugaauccuc ugugcccagg agccaucaga 240
gccaacggcg aggugaaccc ucaguacgac agcaccuucc uguucgacaa cgacuucccc 300
gcccugcagc ccgacgcccc cagccccggc cccagcgacc auccgcuguu ccaggccaag 360
agcgcccggg gcgugugcaa ggugaugugc uuccaccccu ggagcgacgu gacccugccc 420
cugaugagcg ugcccgagau ccgagccgug guggacgccu gggccagcgu gaccgaggag 480
cugggcgccc aguaccccug ggugcagauc uucgagaaca agggcgccau gaugggcugc 540
agcaaccccc acccccacug ccaggugugg gccucgagcu uccugcccga caucgcccag 600
cgggaggagc ggagccagca agcauacaag ucacagcacg gcgagccccu gcugauggag 660
uacagccggc aggagcugcu gcggaaggag cggcuggugc ugaccagcga gcacuggcug 720
guccuggugc ccuucugggc caccuggccc uaccagaccc ugcuguugcc uagacggcac 780
gugcggcggc ugcccgagcu gacccccgcc gagcgggacg accuggccag caucaugaag 840
aaguugcuga caaaguauga caaucuguuc gaaaccagcu uccccuacag caugggcugg 900
cacggcgccc ccaccggcag cgaagccggc gccaacugga accacuggca gcugcacgcc 960
cacuacuacc cuccucugcu ccgcagcgcc accgugcgga aguucauggu gggcuacgag 1020
augcuggccc aggcacagcg ggaccugacc ccugagcagg ccgcugagag acugcgggcc 1080 cuccccggagg ugcacuacca ccucggccag aaggaccggg aaacggccac caucgcc 1137

<210> SEQ ID NO 126
<211> LENGTH: 1137
<212> TYPE: RNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: GALT-CO39

<400> SEQUENCE: 126
augagccgga gcggcaccga cccccagcag cggcagcagg ccagcgaggc cgacgcagcc 60
gccgcgaccu uccgggccaa cgaccaccag cacauccggu acaacccccu gcaggacgag 120
ugggugcugg ugagcgccca ccggaugaag cggcccuggc agggccaggu ggagccccag 180
cugcugaaga ccgugccccg gcacgacccc cugaacccuc ugugcccagg agccauuaga 240
gccaauggcg aggugaaccc acaguacgac agcaccuucc uguucgacaa cgacuucccc 300
gcccugcagc ccgacgcccc cagccccggc cccagcgacc acccgcuuuu ccaggccaag 360
agcgcccggg gcgugugcaa ggugaugugc uuccaccccu ggagcgacgu gacccugccc 420
cugaugagcg ugcccgagau cagagccgug guggacgccu gggccagcgu gaccgaggag 480
cugggcgccc aguaccccug ggugcagauc uucgagaaca agggcgccau gaugggcugc 540
agcaaccccc acccccacug ccaggugugg gccucuagcu uccugcccga caucgcccag 600
cgggaggagc ggagccagca agccuacaag ucucagcacg gcgagccccu gcugauggag 660
uacagccggc aggagcugcu gcggaaggag cggcuggugc ugaccagcga gcacuggcug 720
guccucgugc ccuucugggc caccuggccc uaccagaccc ugcugcuccc uagacggcac 780
gugcggcggc ugcccgagcu gacccccgcc gagcgggacg accuggccag caucaugaag 840
aagcugcuca ccaaguauga uaaucuguuc gagacaagcu uccccuacag caugggcugg 900
cacggcgccc ccaccgguuc agaggccggc gccaacugga accacuggca gcugcacgcc 960
cacuacuacc caccuuuguu gcguagcgcc accgugcgga aguucauggu gggcuacgag 1020
augcuggccc aggcccagcg cgaucugacc ccagagcagg ccgccgagag gcugcgggcc 1080
uuaccugagg ugcacuacca ccucggccag aaggaccggg aaaccgccac caucgcc 1137

<210> SEQ ID NO 127
<211> LENGTH: 1137
<212> TYPE: RNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: GALT-CO40

<400> SEQUENCE: 127
augagccgga gcggcaccga cccccagcag cggcagcagg ccagcgaggc cgacgccgca 60
gccgcuaccu uccgggccaa cgaccaccag cacauccggu acaacccccu gcaggacgag 120
ugggugcugg ugagcgccca ccggaugaag cggcccuggc agggccaggu ggagccccag 180
cugcugaaga ccgugccccg gcacgacccc cugaauccuc ucugcccugg agccauuaga 240
gccaacggcg aggugaaccc acaguacgac agcaccuucc uguucgacaa cgacuucccc 300

-continued

```
gcccugcagc ccgacgcccc cagccccggc cccagcgacc acccucuguu ccaggccaag    360

agcgcccggg gcgugugcaa ggugaugugc uuccacccau ggagcgacgu gacccugccc    420

cugaugagcg ugcccgagau cagagcugug guggacgccu gggccagcgu gaccgaggag    480

cugggcgccc aguaccccug ggugcagauc uucgagaaca agggcgccau gaugggcugc    540

agcaacccc acccccacug ccaggugugg gcuucuagcu uccugcccga caucgcccag    600

cgggaggagc ggagccagca ggcguacaag ucccagcacg gcgagccccu gcugauggag    660

uacagccggc aggagcugcu gcggaaggag cggcuggugc ugaccagcga gcacuggcuc    720

guguuagugc ccuucugggc caccuggccc uaccagaccc ugcugcugcc ucgucggcac    780

gugcggcggc ugcccgagcu gacccccgcc gagcgggacg accuggccag caucaugaag    840

aagcuccuga caaaguauga caaccuauuc gaaaccagcu uccccuacag caugggcugg    900

cacggcgccc ccaccggcag cgaagccggc gccaacugga accacuggca gcugcacgcc    960

cacuacuauc caccucugcu gcgcagcgcc accgugcgga aguucauggu gggcuacgag   1020

augcuggccc aggcccagcg cgaccugacc ccugagcagg cugccgaacg acugcgggcc   1080

cugccagaag ugcacuacca ccucggccag aaggaccggg agacugccac caucgcc      1137
```

```
<210> SEQ ID NO 128
<211> LENGTH: 1137
<212> TYPE: RNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: GALT-CO41

<400> SEQUENCE: 128
```

```
augagccgga gcggcaccga cccccagcag cggcagcagg ccagcgaggc cgacgcugca     60

gccgccaccu uccgggccaa cgaccaccag cacauccggu acaacccccu gcaggacgag    120

ugggugcugg ugagcgccca ccggaugaag cggcccuggc agggccaggu ggagccccag    180

cugcugaaga ccgugccccg gcacgacccc cugaaccccuc ugugcccugg ugccauccga    240

gccaacggcg aggugaaccc acaguacgac agcaccuucc uguucgacaa cgacuucccc    300

gcccugcagc ccgacgcccc cagccccggc cccagcgacc auccucuguu ccaggccaag    360

agcgcccggg gcgugugcaa ggugaugugc uuccaccccu ggagcgacgu gacccugccc    420

cugaugagcg ugcccgagau cagagcagug guggacgccu gggccagcgu gaccgaggag    480

cugggcgccc aguaccccug ggugcagauc uucgagaaca agggcgccau gaugggcugc    540

agcaaccccc acccccacug ccaggugugg gcuagcagcu uccugcccga caucgcccag    600

cgggaggagc ggagccagca ggcuuacaag ucucagcacg gcgagccccu gcugauggag    660

uacagccggc aggagcugcu gcggaaggag cggcuggugc ugaccagcga gcacugguua    720

gucuuggugc ccuucugggc caccuggccc uaccagaccc ugcugcugcc aagacggcac    780

gugcggcggc ugcccgagcu gacccccgcc gagcgggacg accuggccag caucaugaag    840

aagcuccuga caaaguacga uaaccuuuuc gagacaagcu uccccuacag caugggcugg    900

cacggcgccc caaccggcuc cgaggccggc gcuaacugga accacuggca gcugcacgcc    960

cacuacuacc cuccucuuuu gagaagcgcc accgugcgga aguucauggu gggcuacgag   1020

augcuggccc aggcccagag ggaccugacc ccugagcagg ccgccgagag auuacgggcu   1080

cucccagagg ugcacuacca ccugggacag aaggaccggg agacagccac caucgcc      1137
```

<210> SEQ ID NO 129
<211> LENGTH: 1137
<212> TYPE: RNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: GALT-CO42

<400> SEQUENCE: 129
augagccgga gcggcaccga cccccagcag cggcagcagg ccagcgaggc cgacgccgcc 60
gccgccaccu uccgggccaa cgaccaccag cacauccggu acaacccccu gcaggacgag 120
ugggugcugg ugagcgccca ccggaugaag cggcccuggc agggccaggu ggagccccag 180
cugcugaaga ccgugccccg gcacgacccc cugaaccccc ugugccccgg cgccauccgg 240
gccaacggcg aggugaaccc ccaguacgac agcaccuucc uguucgacaa cgacuucccc 300
gcccugcagc ccgacgcccc cagccccggc cccagcgacc acccccuguu ccaggccaag 360
agcgcccggg gcgugugcaa ggugaugugc uuccaccccu ggagcgacgu gacccugccc 420
cugaugagcg ugcccgagau ccgggccgug guggacgccu gggccagcgu gaccgaggag 480
cugggcgccc aguaccccug ggugcagauc uucgagaaca agggcgccau gaugggcugc 540
agcaaccccc acccccacug ccaggugugg gccagcagcu uccugcccga caucgcccag 600
cgggaggagc ggagccagca ggccuacaag agccagcacg gcgagccccu gcugauggag 660
uacagccggc aggagcugcu gcggaaggag cggcuggugc ugaccagcga gcacuggcug 720
gugcuggugc ccuucugggc caccuggccc uaccagaccc ugcugcugcc ccggcggcac 780
gugcggcggc ugcccgagcu gacccccgcc gagcgggacg accuggccag caucaugaag 840
aagcugcuga ccaaguacga caaccuguuc gagaccagcu uccccuacag caugggcugg 900
cacggcgccc ccaccggcag cgaggccggc gccaacugga accacuggca gcugcacgcc 960
cacuacuacc cgccccugcu gcggagcgcc accgugcgga aguucauggu gggcuacgag 1020
augcuggccc aggcccagcg ggaccugacc cccgagcagg ccgccgagcg gcugcgggcc 1080
cugcccgagg ugcacuacca ccugggccag aaggaccggg agaccgccac caucgcc 1137

<210> SEQ ID NO 130
<211> LENGTH: 1137
<212> TYPE: RNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: GALT-CO43

<400> SEQUENCE: 130
augagccgga gcggcaccga cccccagcag cggcagcagg ccagcgaggc cgacgccgcc 60
gccgccaccu uccgggccaa cgaccaccag cacaucaggu acaacccgcu gcaggacgag 120
ugggugcugg ugagcgcgca caggaugaag aggccguggc aggggcaggu ggagccgcag 180
cugcugaaga cggugccgag gcacgacccg cugaacccgc ugugcccggg ggcgaucagg 240
gcgaacgggg aggugaaccc gcaguacgac agcacguucc uguucgacaa cgacuucccg 300
gcgcugcagc cggacgcgcc gagcccgggg ccgagcgacc acccgcuguu ccaggcgaag 360
agcgcgaggg gggugugcaa ggugaugugc uuccacccgu ggagcgacgu gacgcugccg 420
cugaugagcg ugccggagau cagggcggug guggacgcgu gggcgagcgu gacggaggag 480
cugggggcgc aguacccgug ggugcagauc uucgagaaca agggggcgau gaugggggugc 540 agcaacccgc acccgcacug ccaggugugg gcgagcagcu uccugccgga caucgcgcag 600
agggaggaga ggagccagca ggcguacaag agccagcacg gggagccgcu gcugauggag 660
uacagcaggc aggagcugcu gaggaaggag aggcuggugc ugacgagcga gcacuggcug 720
gugcuggugc cguucugggc gacguggccg uaccagacgc ugcugcugcc gaggaggcac 780
gugaggaggc ugccggagcu gacgccggcg gagagggacg accuggcgag caucaugaag 840
aagcugcuga cgaaguacga caaccuguuc gagacgagcu ucccguacag caugggggugg 900 cacggggcgc cgacggggag cgaggcgggg gcgaacugga accacuggca gcugcacgcg 960
cacuacuacc cgccgcugcu gaggagcgcg acggugagga aguucauggu gggguacgag 1020
augcuggcgc aggcgcagag ggaccugacg ccggagcagg cggcggagag gcugagggcg 1080
cugccggagg ugcacuacca ccuggggcag aaggacaggg agacggcgac gaucgcg 1137

<210> SEQ ID NO 131
<211> LENGTH: 1137
<212> TYPE: RNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: GALT-CO44

<400> SEQUENCE: 131
augagccgga gcggcaccga cccccagcag cggcagcagg ccagcgaggc cgacgccgcc 60
gccgccaccu uccgggccaa cgaccaccag cacauccgcu acaacccccu ccaggacgag 120
uggguccucg ucuccgccca ccgcaugaag cgccccuggc agggccaggu cgagccccag 180
cuccucaaga ccgucccccg ccacgacccc cucaaccccc ucugccccgg cgccauccgc 240
gccaacggcg aggucaaccc ccaguacgac uccaccuucc ucuucgacaa cgacuucccc 300
gcccuccagc ccgacgcccc cucccccggc cccuccgacc acccccucuu ccaggccaag 360
uccgcccgcg gcgucugcaa ggucaugugc uuccaccccu gguccgacgu cacccucccc 420
cucauguccg ucccccgagau ccgcgccguc gucgacgccu gggccuccgu caccgaggag 480
cucggcgccc aguaccccug gguccagauc uucgagaaca agggcgccau gaugggcugc 540
uccaaccccc acccccacug ccaggucugg gccuccuccu uccuccccga caucgcccag 600
cgcgaggagc gcucccagca ggccuacaag ucccagcacg gcgagccccu ccucauggag 660
uacucccgcc aggagcuccu ccgcaaggag cgccucgucc ucaccuccga gcacuggcuc 720
guccucgucc ccuucugggc caccuggccc uaccagaccc uccuccuccc ccgccgccac 780
guccgccgcc ucccccgagcu cacccccgcc gagcgcgacg accucgccuc caucaugaag 840
aagcuccuca ccaaguacga caaccucuuc gagaccuccu uccccuacuc caugggcugg 900
cacggcgccc ccaccggcuc cgaggccggc gccaacugga accacuggca gcuccacgcc 960
cacuacuacc cgccccuccu ccgcuccgcc accguccgca aguucauggu cggcuacgag 1020
augcucgccc aggcccagcg cgaccucacc cccgagcagg ccgccgagcg ccuccgcgcc 1080 cucccccgagg uccacuacca ccucggccag aaggaccgcg agaccgccac caucgcc 1137

<210> SEQ ID NO 132
<211> LENGTH: 1348
<212> TYPE: RNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: #1

<400> SEQUENCE: 132

```
gggaaauaag agagaaaaga agaguaagaa gaaauauaag agccaccaug ucuaggagcg     60
ggaccgaccc ccagcagcgg cagcaggcca gcgaggccga cgccgccgcg gccaccuuca    120
gggccaacga ccaucaacac aucagguaua accccucca ggacgagugg guguuggugu    180
ccgcccaucg gaugaagagg cccuggcagg gccaggugga gccccagcuc cugaagaccg    240
ugccccggca cgaccccuc aacccccugu gccccggcgc gauccgcgcc aacggcgagg    300
ugaaccccca guaugacagc acguuccugu ucgacaacga cuuccccgcc cugcagcccg    360
acgcccccag ccccggccca agcgaccauc cccuguucca ggccaagucc gccaggggcg    420
uguguaaggu gaugugcuuc cacccauggu ccgacgugac ccugccccug augagcgugc    480
ccgagauccg cgccguggug gacgccuggg ccagcgugac cgaggagcug ggggcccagu    540
acccuugggu gcaaaucuuc gagaauaagg gcgccaugau gggcugcucc aacccccacc    600
cccacuguca ggugugggcc agcaguuucc ugcccgacau cgcccagcgc gaggagcggu    660
cacagcaggc cuacaagagc caacacggcg aaccucugcu cauggaguac agcaggcagg    720
aacugcugcg gaaggagagg cugguccuga ccagcgagca cuggcuggug cuggugcccu    780
ucugggccac cuggcccuac cagacacugc ugcugccuag gcgacacgug cgucggcugc    840
ccgagcugac cccugccgaa agggacgacc uggccagcau caugaagaag cugcucacca    900
aguacgacaa ccuguuugaa accagcuucc ccuacagcau gggcuggcac ggcgcaccua    960
ccggcagcga ggccggcgcc aacuggaacc acuggcagcu gcaugcccac uacuauccgc   1020
cccuccucag gagcgccacc gugcgcaagu ucauggugggg cuaugagaug cuggcgcagg   1080
cccagcguga ccugaccccc gagcaggccg ccgagaggcu gcgugcccug ccugaggugc   1140
acuaccaccu ggggcagaag gacagagaaa cugcgaccau cgccugauaa uaguccauaa   1200
aguaggaaac acuacagcug gagccucggu ggccaugcuu cuugccccuu gggccucccc   1260
ccagccccuc cuccccuucc ugcacccgua cccccgcau uauuacucac gguacgagug   1320
gucuuugaau aaagucugag ugggcggc                                      1348
```

<210> SEQ ID NO 133
<211> LENGTH: 1348
<212> TYPE: RNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: #2

<400> SEQUENCE: 133

```
gggaaauaag agagaaaaga agaguaagaa gaaauauaag agccaccaug agcagguccg     60
gcaccgaccc ccagcagagg cagcaagccu ccgaggccga cgccgccgcg gccaccuucc    120
gggccaacga ccaucagcau aucagguaua acccccuuca ggacgagugg gugcucguga    180
gcgcccaccg gaugaagcgc cccuggcagg ggcaggucga gccccagcug cugaagaccg    240
ugcccaggca cgauccgcug aacccgcugu gccccggggc cauccgggcc aacggggagg    300
ugaaccccca guacgacagc accuuccugu ucgacaacga cuuccccgcc cugcagcccg    360
```

```
augcccccag ccccgggccc uccgaccacc cccuguucca ggccaagagc gccagaggcg    420

ugugcaaggu caugugcuuu caucccugga gcgacgugac ccugccccug auguccgugc    480

ccgagaucag agcugucgug gacgccuggg ccuccgugac cgaggagcuc ggcgcccagu    540

accccugggu gcagaucuuc gagaacaaag gcgccaugau gggcugcagc aacccccacc    600

cacacugcca ggugugggcc agcagcuucc ugcccgacau cgcccagaga gaggagagga    660

gccagcaggc cuauaagagc cagcauggcg agccccugcu gauggaguac agcagacagg    720

agcugcugag gaaagagagg cuggugcuga caagcgagca cuggcuggug cuggugcccu    780

uuugggccac uuggccauac cagacccugc ugcugccccg gcggcauguc aggagacugc    840

cugagcugac ucccgccgag cgggaugacc uggccagcau caugaagaag cugcucacca    900

aauacgacaa ccucuucgaa accagcuucc ccuacagcau ggggguggcac ggggccccca    960

ccggcagcga agccggagcc aauuggaauc auuggcagcu ccaugcccau uacuauccgc   1020

cccugcucag aagcgccacc gugcggaagu ucaugguggg cuacgagaug cucgcccagg   1080

cccagcggga ccugaccccc gagcaggcug ccgagcggcu gagggcccug cccgaggugc   1140

acuaucaccu gggccagaaa gauagggaaa cagccacuau cgccugauaa uaguccauaa   1200

aguaggaaac acuacagcug gagccucggu ggccaugcuu cuugccccuu gggccucccc   1260

ccagccccuc cuccccuucc ugcacccgua cccccccgcau uauuacucac gguacgagug   1320

gucuuugaau aaagucugag ugggcggc                                       1348


<210> SEQ ID NO 134
<211> LENGTH: 1348
<212> TYPE: RNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: #3

<400> SEQUENCE: 134

gggaaauaag agagaaaaga agaguaagaa gaaauauaag agccaccaug agcaggagcg     60

gcaccgaccc ccagcagagg cagcaggcca gcgaagccga cgccgccgcc gccaccuucc    120

gggccaacga ucaccagcac auccgcuaca acccucucca ggacgagugg gugcucguga    180

gcgcccacag gaugaagcgg cccuggcagg gccaggugga gccccagcuc cugaagaccg    240

ugcccagaca cgaccccccug aacccgcucu gccccggcgc caucagagcc aacggcgagg    300

ugaaccccca guacgacagc accuuccugu ucgacaacga cuucccccgcc cuccagcccg    360

augcccccag ccccgguccc uccgaccauc cccuguucca ggccaagucc gccagaggcg    420

ugugcaaggu gaugugcuuc caccccugga gcgacgugac ccuccccccug augucggugc    480

ccgaaaucag ggccguggug gacgccuggg ccagcgugac cgaggagcug gggggcccagu    540

aucccugggu ccagaucuuc gagaacaagg gggccaugau gggcuguagc aacccccacc    600

cacacugcca ggugugggcc uccuccuucc ugcccgacau cgcccaaagg gaggagcggu    660

cccagcaagc cuacaagucc cagcacggug agccccugcu gauggaauau agcagacagg    720

agcugcugag gaaggagcgc cugguccuga ccagcgagca cuggcuggug cugguccccu    780

uuugggccac cuggcccuac cagacgcugc ugcugccucg cagacaugug aggaggcugc    840

cggagcugac cccccgccgag cgggacgacc uggcaagcau caugaagaag cugcugacca    900

aguacgacaa ccuguucgag acuuccuucc cguacagcau gggcuggcac ggcgccccga    960
```

ccggaagcga ggccggcgcg aacuggaacc acuggcagcu gcaugcgcau uacuacccgc 1020
cccugcugcg gucagccacc guccgcaagu ucauggugg cuacgaaaug cuggcccagg 1080
cgcagaggga ccucaccccc gagcaggccg ccgaaagacu gcgugcgcug ccggaggugc 1140
acuaccaccu gggccagaag gaccgcgaaa ccgcgaccau cgcaugauaa uaguccauaa 1200
aguaggaaac acuacagcug gagccucggu ggccaugcuu cuugccccuu gggccucccc 1260
ccagccccuc cucccuucc ugcacccgua cccccgcau uauuacucac gguacgagug 1320
gucuuugaau aaagucugag ugggcggc 1348

<210> SEQ ID NO 135
<211> LENGTH: 1348
<212> TYPE: RNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: #4

<400> SEQUENCE: 135
gggaaauaag agagaaaaga agaguaagaa gaaauauaag agccaccaug ucacggagcg 60
gcaccgaccc gcagcagagg cagcaggcca gcgaggcaga cgccgccgcc gccaccuuca 120
gggccaacga ccaucagcac aucagauaca accccuaca ggacgagugg gugcucguca 180
gcgcccacag aaugaagcgg cccuggcagg ggcaggugga gccccagcuc cugaagaccg 240
ugcccaggca cgacccccuc aaucccugu gcccuggcgc cauuagggcc aacggcgagg 300
ugaaccccca guacgacuca accuuccugu uugacaacga cuuccccgcc cugcagcccg 360
augccccgag ccccgggccc agcgaccacc cccuguucca ggccaagucg gccaggggcg 420
ugugcaaggu gaugugcuuc caccccugga gcgaugucac ccugccccug augucggugc 480
ccgagauccg cgccguggug gacgccuggg ccagcgugac cgaggagcug ggcgcccaau 540
accccugggu gcagaucuuu gagaacaaag gcgccaugau gggcuguagc aaccccacc 600 cccacuguca ggugugggcc agcagcuuuc ugcccgacau cgcccagagg gaggagcgcu 660
cccagcaggc uuacaagagc cagcacggag agccccugcu cauggaguac ucgcgacagg 720
agcugcuccg gaaggaacgg cugguccuga ccuccgagca cuggcucgug cuggugccgu 780
ucugggccac auggcccuac cagacccugc ugcuaccccg cagacacguu cgccgacugc 840
ccgagcugac cccugccgag agagacgacc uggcgagcau caugaagaag cugcucacca 900
aguaugacaa cuuauucgaa accuccuucc cuuacagcau gggcuggcac ggcgccccca 960
ccggcagcga ggcgggcgcc aacuggaacc acuggcagcu gcaugcccac uacuacccac 1020
cccugcugcg gagcgccacc gugagaaagu ucauggugg cuacgagaug cuggcccagg 1080
cccaacggga ucugaccccc gagcaggccg ccgagcggcu gagggcccuc cccgagguac 1140
acuaccaucu cggccagaag gaccgggaaa ccgccaccau cgccugauaa uaguccauaa 1200
aguaggaaac acuacagcug gagccucggu ggccaugcuu cuugccccuu gggccucccc 1260
ccagccccuc cucccuucc ugcacccgua cccccgcau uauuacucac gguacgagug 1320
gucuuugaau aaagucugag ugggcggc 1348

<210> SEQ ID NO 136
<211> LENGTH: 1348
<212> TYPE: RNA
<213> ORGANISM: Artificial Sequence
<220> FEATURE:

<223> OTHER INFORMATION: Description of Artificial Sequence: Synthetic
      polynucleotide
<220> FEATURE:
<223> OTHER INFORMATION: #5

<400> SEQUENCE: 136
gggaaauaag agagaaaaga agaguaagaa gaaauauaag agccaccaug agcagaagcg     60
gcaccgaccc ccagcagcgg cagcaggcca gcgaggccga cgccgccgcc gcaaccuucc    120
gcgccaacga ccaccagcac aucagauaca acccccucca ggacgagugg guccucgugu    180
ccgcccauag aaugaagagg ccauggcagg gccagguaga accucaacug cugaagaccg    240
ucccccggca ugaccccuc aaucccccucu gcccgggggc cauccgagcg aauggggagg    300
ucaaccccca guacgacagc accuuccugu ucgacaacga cuuccccgcc cugcagcccg    360
acgccccgag ccccggaccc agcgaccacc cccuguucca ggccaaaucc gcccggggcg    420
ucugcaaggu gaugugcuuu caccccuggu ccgacgugac ccugccccuc auguccgugc    480
ccgagaucag ggccguggug gacgcuuggg ccagcgucac ggaggagcuc ggcgcccagu    540
accccugggu ccagaucuuc gagaacaagg gcgccaugau ggggugcucc aacccucacc    600
cccacugcca ggugugggcc agcagcuuuc ugcccgacau ugcccagcgg gaggagaggu    660
cccagcaggc cuacaagagu cagcacgggg agccccugcu gauggaguac ucccggcagg    720
agcuccugag gaaagagcgc uuggugcuga caagcgagca cuggcuggug cucgugcccu    780
ucugggccac uuggcccuac cagacccugc ugcugcccag acggcacgug cggcggcugc    840
ccgagcugac acccgccgag agggacgauc ucgccagcau uaugaagaag cugcugacca    900
aguaugacaa ccuguuugag acuagcuuuc ccuacagcau gggcuggcac ggggccccca    960
cgggcuccga ggccggcgcc aacuggaacc acuggcagcu gcacgcccac uauuauccgc   1020
cccugcuccg gagcgccacc gugagaaagu uuauggugg cuaugagaug cuggcccaag   1080
cgcaacggga ucugaccccc gagcaggccg ccgagcgucu gagagcccug ccugaggugc   1140
acuaucaccu ggggcagaag gaccgggaga cggcaaccau cgccugauaa uaguccauaa   1200
aguaggaaac acuacagcug gagccucggu ggccaugcuu cuugccccuu gggccucccc   1260
ccagccccuc cuccccuucc ugcacccgua cccccccgcau uauuacucac gguacgagug   1320
gucuuugaau aaagucugag ugggcggc                                      1348

<210> SEQ ID NO 137
<211> LENGTH: 1348
<212> TYPE: RNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: #6

<400> SEQUENCE: 137
gggaaauaag agagaaaaga agaguaagaa gaaauauaag agccaccaug agccgcagcg     60
gcaccgaccc gcaacaaaga cagcaggccu ccgaggccga cgccgccgcc gcuaccuuua    120
gggccaacga ccaccagcau auccgcuaca auccccucca ggacgagugg gugcucguga    180
gcgcccaccg uaugaagagg cccuggcagg gacaggugga accccagcug cugaagaccg    240
uaccccggca cgaccccccug aacccccugu gccccggggc caucagagcc aauggagagg    300
ugaaccccca guacgacucc accuuccugu ucgauaauga uuuuccggcc cugcagcccg    360
acgcccccag ccccggccca agcgaccacc cucuguucca ggccaagagc gccaggggcg    420

-continued uuugcaaggu caugugcuuc caccccugga gcgacgugac ccugccccug augucggugc 480
ccgagaucag ggccguggug gacgccuggg ccagcgugac ggaggaacuc ggcgcccagu 540
accccugggu acagaucuuc gagaacaagg gugccaugau gggcugcagc aacccacauc 600
cccacuguca ggugugggcc agcucauucc ugccugacau cgcccagcgu gaggagagga 660
gucagcaggc cuauaagagc cagcaugggg agccccuccu gauggaguac agcagacaag 720
agcugcucag gaaggagaga cuggugcuga ccagcgagca uuggcuggug cuggugcccu 780
uuugggccac auggcccuac cagacccucc ugcugccgag acgccacgug cgccggcugc 840
ccgagcugac ucccgccgag agggacgacc ucgcuagcau caugaagaaa cugcugacca 900
aguacgacaa ccuguuugag acaagcuuuc ccuacuccau gggauggcac ggcgccccca 960
ccggcuccga ggccggcgcc aacuggaacc acuggcagcu gcacgcccac uacuaucccc 1020
cgcugcugcg gagcgccacc gugaggaaau ucaugguggg cuacgagaug cucgcucagg 1080
cccaacggga ccugaccccc gagcaggcgg ccgagaggcu ccgagcucug cccgaggugc 1140
auuaccaucu gggccagaag gauagggaaa ccgccaccau cgccugauaa uaguccauaa 1200
aguaggaaac acuacagcug gagccucggu ggccaugcuu cuugccccuu gggccucccc 1260
ccagccccuc cuccccuucc ugcacccgua cccccgcau uauuacucac gguacgagug 1320
gucuuugaau aaagucugag ugggcggc 1348

<210> SEQ ID NO 138
<211> LENGTH: 1348
<212> TYPE: RNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: #7

<400> SEQUENCE: 138
gggaaauaag agagaaaaga agaguaagaa gaaauauaag agccaccaug agcaggagcg 60
gaaccgaccc gcagcagagg cagcaggcca gcgaagccga cgccgccgcc gccaccuucc 120
gggccaacga ccaccaacac aucagguaca acccgcucca ggacgagugg gugcucguua 180
gcgcccaucg caugaagcgg ccguggcaag gccaggugga gccgcagcug cugaagaccg 240
ugccgcgcca cgacccgcug aacccgcugu gcccuggcgc cauccgggcc aacggcgagg 300
ugaacccuca guacgacagc accuuccugu ucgacaauga uuucccggcc uugcagccgg 360
acgccccuuc cccgggaccg uccgaccacc cgcuguucca agccaagucc gcccggggcg 420
ugugcaaggu gaugugcuuc cacccguggu ccgacgugac ccugccgcug augagcgugc 480
cugagaucag agccguggug gacgccuggg ccuccgugac ugaggagcuc ggcgcccagu 540
acccaugggu ccagaucuuc gagaacaagg gugccaugau gggcugcagc aacccgcacc 600
cgcacugcca agugugggcc agcuccuucc ugccggauau ugcccagcgg gaggagcgga 660
gccagcaagc auacaagagc cagcauggcg agccgcucuu gauggaguac uccaggcagg 720
agcugcugag aaaggagcgg cuggugcuga ccucugagca cuggcuggug cucgugccgu 780
ucugggccac cuggccuuac cagacccugc ugcugccgag gcggcacgug cgccggcugc 840
cagagcugac gccagccgag cgagacgauc uggccuccau caugaagaag cuacugacca 900
aguaugacaa ccuguucgaa acgagcuucc cguacagcau gggcuggcac ggcgccccga 960
ccggcagcga ggccggcgcc aacuggaauc acuggcagcu gcaugcccau uacuacccgc 1020
cgcuccuccg cagcgccacc gugaggaagu ucaugguggg cuacgagaug cuggcccagg 1080
cccagcggga ccugaccccg gagcaggcgg ccgagagacu gagggcccuc ccggaggucc 1140
auuaccaccu gggccagaag gaccgggaga cggccaccau cgccugauaa uaguccauaa 1200
aguaggaaac acuacagcug gagccucggu ggccaugcuu cuugccccuu gggccucccc 1260
ccagccccuc cuccccuucc ugcacccgua cccccccgcau uauuacucac gguacgagug 1320
gucuuugaau aaagucugag ugggcggc 1348

<210> SEQ ID NO 139
<211> LENGTH: 1348
<212> TYPE: RNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: #8

<400> SEQUENCE: 139
gggaaauaag agagaaaaga agaguaagaa gaaauauaag agccaccaug ucccgcagcg 60
gcacggaccc gcagcagcgg cagcaggcca gcgaggccga cgccgcggcc gccaccuucc 120
gggccaacga ccaccagcac aucagguaca acccacucca agacgagugg gugcucguga 180
gcgcccaccg gaugaagagg ccguggcagg gacagguuga gccgcaacug cugaagaccg 240
ugccaagaca cgauccgcug aacccgcucu gcccgggcgc cauccgugcc aacggcgagg 300
ucaacccaca guaugacagc accuuccugu ucgacaacga cuucccggcc cugcagccgg 360
acgcgccuag cccuggaccg uccgaccacc cgcuguucca ggccaagucc gcuaggggcg 420
ugugcaaggu gaugugcuuc cauccguggu ccgaugucac ccugccgcuc auguccgugc 480
cggagauccg ggccguggug gaugccuggg ccagcgucac cgaggagcug ggcgcgcagu 540
acccuugggu ccagaucuuc gagaacaagg gcgccaugau ggguugcagc aacccgcacc 600
cacacugcca ggugugggcc agcagcuucc ugccggacau cgcacagagg gaggagcgga 660
gccaacaggc cuacaagucc cagcacggcg agccacugcu gauggaguac agcaggcagg 720
agcugcugcg gaaggagcgg cuggugcuca ccuccgaaca uuggcugguu cuggugccgu 780
ucugggccac cuggccuuac cagacccugc ugcucccgag gcggcacgug cgcaggcugc 840
cggagcugac accggccgag cgcgacgacc uggccagcau caugaagaag cugcucacca 900
aguacgauaa ccuguucgag acauccuucc cguacagcau gggcuggcac ggcgccccua 960
ccggcuccga ggccggcgcc aacuggaacc acuggcagcu gcacgcccac uacuacccac 1020
cgcugcugag aagcgccacc gucagaaagu ucaugguggg auaugagaug cuggcccagg 1080
cucagagaga ucugaccccg gagcaggccg ccgagaggcu ccgcgcccuc ccagaagugc 1140
acuaccaucu gggccagaag gacagggaga cggccaccau cgccugauaa uaguccauaa 1200
aguaggaaac acuacagcug gagccucggu ggccaugcuu cuugccccuu gggccucccc 1260
ccagccccuc cuccccuucc ugcacccgua cccccccgcau uauuacucac gguacgagug 1320
gucuuugaau aaagucugag ugggcggc 1348

<210> SEQ ID NO 140
<211> LENGTH: 1348
<212> TYPE: RNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: #9

<400> SEQUENCE: 140
gggaaauaag agagaaaaga agaguaagaa gaaauauaag agccaccaug agccggagcg 60
gcaccgaccc gcagcagcgu cagcaagcca gcgaggccga cgccgccgcc gccacguucc 120
gggccaacga ccaccagcac auuagguaca acccgcucca ggacgagugg guccucguga 180
gcgcccacag gaugaagagg ccauggcagg gacaaguuga gccacagcug cugaagaccg 240
ugccacggca cgacccgcuc aacccucugu gcccgggcgc cauccgcgcc aacggcgagg 300
ugaacccaca guacgacagc accuuccugu ucgacaacga cuucccugcc cuccagccgg 360
acgccccgag cccuggaccg uccgaccauc cgcuguucca ggccaagucc gcgcggggcg 420
ugugcaaggu gaugugcuuc cauccgugga gcgacgugac ccugccgcug auguccgugc 480
cugagauacg ggccguggug gacgccuggg ccagcgugac agaggagcuc ggcgcccagu 540
acccuugggu gcagaucuuc gagaacaagg gugccaugau ggguugcagc aacccgcacc 600
cgcauugcca ggugugggcc agcagcuucc ugccugacau cgcccagcgg gaggagcgca 660
gccagcaggc uuacaagagc cagcacggcg agccgcugcu gauggaguac ucuaggcagg 720
agcugcugag aaaggagagg cuggugcuga ccagcgaaca cuggcucgug cuggugccgu 780
ucugggcaac cuggccguac cagacccugc ugcugccgag gcggcaugug agaaggcucc 840
cggagcugac cccagccgag cgcgacgacc ucgccagcau caugaagaag cuccugacca 900
aguacgacaa ccuguucgag acgagcuucc cguauuccau gggcuggcac ggagccccga 960
caggcagcga ggccggcgcc aacuggaauc acuggcagcu gcaugcccac uacuacccgc 1020
cgcuccugcg gagcgccacc guccgcaagu ucauggugggg cuacgagaug cuggcccagg 1080
cccagaggga ccucaccccg gagcaggccg ccgagaggcu gcgggcccug ccggagaggucc 1140 acuaccaccu cggccagaag gauagagaaa ccgccacgau cgcgugauaa uaguccauaa 1200
aguaggaaac acuacagcug gagccucggu ggccaugcuu cuugccccuu gggccucccc 1260
ccagccccuc cuccccuucc ugcacccgua cccccgcau uauuacucac gguacgagug 1320
gucuuugaau aaagucugag ugggcggc 1348

<210> SEQ ID NO 141
<211> LENGTH: 1348
<212> TYPE: RNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: #10

<400> SEQUENCE: 141
gggaaauaag agagaaaaga agaguaagaa gaaauauaag agccaccaug agcaggagcg 60
gcaccgaccc ucagcagagg caacaggccu ccgaggccga cgcggcggcc gccaccuuca 120
gggccaacga ccaccagcac auccgauaca acccgcucca agacgagugg gugcucgucu 180
ccgcccaccg caugaagcgg ccguggcaag gucaaguuga accacagcug cugaagaccg 240
ugccgaggca cgauccgcug aacccgcugu gcccgggagc cauccgggcc aacggcgagg 300
ugaacccuca guacgacagc acauuccugu ucgacaacga cuucccggcc cugcagccgg 360
acgccccaag cccgggccca agcgaccauc cgcuguucca agccaagucc gcccgcggcg 420

```
ugugcaaggu gaugugcuuc cacccguggu ccgacgugac ccugccgcug augagcgugc    480

cggagauccg ggccguggug gaugccuggg ccagcgugac cgaggaauua ggcgcccagu    540

acccaugggu gcagaucuuc gagaacaagg gagccaugau gggcugcagc aacccgcacc    600

cgcacugcca agugugggcc agcuccuucc ugccggacau cgcccagcgc gaggagcgga    660

gccagcaggc cuacaagagu cagcacggcg agccgcugcu gauggaguac ucuaggcagg    720

agcugcucag gaaggagagg cuggugcuga ccagcgagca cugguuggug cuggugccuu    780

ucugggccac cuggccauac cagacccugc ugcugccgag aaggcacguc agaagacugc    840

cggaacugac cccggccgag agggacgacc uggccuccau uaugaagaag cuccugacca    900

aguacgacaa ucuguucgag acguccuucc cuuacagcau ggguuggcac ggcgccccga    960

ccggcagcga ggcaggagcc aacuggaacc acuggcagcu gcacgcccac uacuacccgc   1020

cgcugcucag guccgccacc guucggaagu ucaugguggg cuacgaaaug cuggcccagg   1080

cccagcgcga ccucacccca gagcaggccg ccgagcggcu gcgggcccug ccggaggugc   1140

acuaccaccu gggccagaag gaccgcgaga cagccaccau cgcuugauaa uaguccauaa   1200

aguaggaaac acuacagcug gagccucggu ggccaugcuu cuugccccuu gggccucccc   1260

ccagccccuc cuccccuucc ugcacccgua cccccgcau uauuacucac gguacgagug   1320

gucuuugaau aaagucugag ugggcggc                                      1348
```

<210> SEQ ID NO 142
<211> LENGTH: 1348
<212> TYPE: RNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: #11

<400> SEQUENCE: 142

```
gggaaauaag agagaaaaga agaguaagaa gaaauauaag agccaccaug agcaggucag     60

gaaccgaccc gcagcagcgc caacaggccu ccgaggccga cgccgccgcc gcgaccuucc    120

gagccaacga ccaucaacac aucagguaua acccguugca ggacgagugg gugcucgugu    180

ccgcccaucg gaugaagcgg ccguggcagg gacaggugga gccgcagcug cucaagaccg    240

uuccgcgcca cgacccgcuc aacccgcugu guccgggcgc cauccgggcc aacggcgagg    300

ugaacccgca guacgacagc accuuccugu ucgacaacga uuucccugcc cugcagccag    360

augccccgag cccgggcccu agcgaucacc cgcuguucca ggccaagagc gcccggggcg    420

ucuguaaggu gaugugcuuc cacccaugga gcgacgucac ccugccgcug auguccgugc    480

cagagauccg cgccguggug gacgccuggg cgagcgugac cgaggagcug ggagcccaau    540

acccuugggu gcagaucuuc gagaauaagg gcgcuaugau gggcugcucc aacccgcacc    600

cgcacugcca ggugugggcc agcuccuucc ucccggauau cgcccagcgg gaggagagaa    660

gccagcaggc cuacaagucc cagcacggcg agccgcugcu cauggaguau uccaggcagg    720

agcuccucag gaaggaaagg cuugugcuga cgagcgagca cuggcuggug cuggugccgu    780

ucugggccac cuggccguac cagacccucc ugcugccgcg ccgacacguc aggaggcugc    840

cggagcugac cccggccgag agggaugacc uggccuccau aaugaagaag uuacugacua    900

aguaugacaa cuuguucgaa accagcuucc cuuacagcau gggcuggcau ggcgccccga    960

ccggcuccga agccggcgcc aacuggaacc auuggcaacu ccacgcccac uacuacccgc   1020
```

cgcucuuaag gagcgccacc gugaggaagu ucauggugg auacgagaug cuggcccagg 1080
cccaaaggga ccucaccccg gagcaggccg cggagaggcu gcgugcccug ccugaggucc 1140
acuaccaccu gggccagaag gacagggaaa ccgcgaccau cgccugauaa uaguccauaa 1200
aguaggaaac acuacagcug gagccucggu ggccaugcuu cuugccccuu gggccucccc 1260
ccagccccuc cuccccuucc ugcacccgua cccccgcau uauuacucac gguacgagug 1320
gucuuugaau aaagucugag ugggcggc 1348

<210> SEQ ID NO 143
<211> LENGTH: 1348
<212> TYPE: RNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: #12

<400> SEQUENCE: 143
gggaaauaag agagaaaaga agaguaagaa gaaauauaag agccaccaug agccggagcg 60
gcaccgaccc ccagcagcgg cagcaggcca gcgaggccga cgcugccgcc gccaccuucc 120
gggccaacga ccaccagcac auccgguaca accccccugca ggacgagugg gugcuggug a 180 gcgcccaccg gaugaagcgg cccuggcagg gccaggugga gccccagcug cugaagaccg 240
ugccccggca cgaccccug aacccucugu gcccaggagc cauccgcgcc aacggcgagg 300
ugaauccuca guacgacagc accuuccugu ucgacaacga cuuccccgcc cugcagcccg 360
acgcccccag ccccggcccc agcgaccauc cauuauucca ggccaagagc gcccggggcg 420
ugugcaaggu gaugugcuuc caccccugga gcgacgugac ccugccccug augagcgugc 480
ccgagaucag agccguggug gacgccuggg ccagcgugac cgaggagcug ggcgcccagu 540
accccugggu gcagaucuuc gagaacaagg gcgccaugau gggcugcagc aacccccacc 600
cccacugcca ggugugggcc ucaagcuucc ugcccgacau cgcccagcgg gaggagcgga 660
gccaacaggc cuacaaguca cagcacggcg agccccugcu gauggaguac agccggcagg 720
agcugcugcg gaaggagcgg cuggugcuga ccagcgagca cuggcucgug cucgugcccu 780
ucugggccac cuggcccuac cagacccugc ugcugccuag acggcacgug cggcggcugc 840
ccgagcugac ccccgccgag cgggacgacc uggccagcau caugaagaag cuccugacca 900
aguacgauaa cuuauucgaa acaagcuucc ccuacagcau gggcuggcac ggcgccccca 960
ccggcucaga ggccggcgcu aacuggaacc acuggcagcu gcacgcccac uacuacccgc 1020
cucugcugag aagcgccacc gugcggaagu ucauggugg cuacgagaug cuggcccagg 1080
cccagagaga cuuaaccccu gagcaggccg ccgagaggcu ccgggccuug ccagaggugc 1140
acuaccaccu gggacagaag gaccgggaga cggccaccau cgccugauaa uaguccauaa 1200
aguaggaaac acuacagcug gagccucggu ggccaugcuu cuugccccuu gggccucccc 1260
ccagccccuc cuccccuucc ugcacccgua cccccgcau uauuacucac gguacgagug 1320
gucuuugaau aaagucugag ugggcggc 1348

<210> SEQ ID NO 144
<211> LENGTH: 1348
<212> TYPE: RNA
<213> ORGANISM: Artificial Sequence
<220> FEATURE:
<223> OTHER INFORMATION: Description of Artificial Sequence: Synthetic
polynucleotide

<220> FEATURE:
<223> OTHER INFORMATION: #13

<400> SEQUENCE: 144
gggaaauaag agagaaaaga agaguaagaa gaaauauaag agccaccaug agccggagcg 60
gcaccgaccc ccagcagcgg cagcaggcca gcgaggccga cgcagccgcc gcuaccuucc 120
gggccaacga ccaccagcac auccgguaca accccccugca ggacgagugg gugcugguga 180
gcgcccaccg gaugaagcgg cccuggcagg gccaggugga gccccagcug cugaagaccg 240
ugccccggca cgaccccug aauccucugu gcccaggagc caucagagcc aacggcgagg 300
ugaacccuca guacgacagc accuuccugu ucgacaacga cuuccccgcc cugcagcccg 360
acgcccccag ccccggcccc agcgaccauc cgcuguucca ggccaagagc gcccggggcg 420
ugugcaaggu gaugugcuuc caccccugga gcgacgugac ccugccccug augagcgugc 480
ccgagauccg agccguggug gacgccuggg ccagcgugac cgaggagcug ggcgcccagu 540
accccugggu gcagaucuuc gagaacaagg gcgccaugau gggcugcagc aaccccccacc 600 cccacugcca ggugugggcc ucgagcuucc ugcccgacau cgcccagcgg gaggagcgga 660
gccagcaagc auacaaguca cagcacggcg agccccugcu gauggaguac agccggcagg 720
agcugcugcg gaaggagcgg cuggugcuga ccagcgagca cuggcugguc cuggugcccu 780
ucugggccac cuggcccuac cagacccugc uguugccuag acggcacgug cggcggcugc 840
ccgagcugac ccccgccgag cgggacgacc uggccagcau caugaagaag uugcugacaa 900
aguaugacaa ucuguucgaa accagcuucc ccuacagcau gggcuggcac ggcgccccca 960
ccggcagcga agccggcgcc aacuggaacc acuggcagcu gcacgcccac uacuacccuc 1020
cucugcuccg cagcgccacc gugcggaagu ucaugguggg cuacgagaug cuggcccagg 1080
cacagcggga ccugaccccu gagcaggccg cugagagacu gcgggcccuc ccggaggugc 1140
acuaccaccu cggccagaag gaccgggaaa cggccaccau cgccugauaa uaguccauaa 1200
aguaggaaac acuacagcug gagccucggu ggccaugcuu cuugccccuu gggccucccc 1260
ccagccccuc cuccccuucc ugcacccgua cccccgcau uauuacucac gguacgagug 1320
gucuuugaau aaagucugag ugggcggc 1348

<210> SEQ ID NO 145
<211> LENGTH: 1348
<212> TYPE: RNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: #14

<400> SEQUENCE: 145
gggaaauaag agagaaaaga agaguaagaa gaaauauaag agccaccaug agccggagcg 60
gcaccgaccc ccagcagcgg cagcaggcca gcgaggccga cgcagccgcc gcgaccuucc 120
gggccaacga ccaccagcac auccgguaca acccccugca ggacgagugg gugcugguga 180
gcgcccaccg gaugaagcgg cccuggcagg gccaggugga gccccagcug cugaagaccg 240
ugccccggca cgaccccug aacccucugu gcccaggagc cauuagagcc aauggcgagg 300
ugaacccaca guacgacagc accuuccugu ucgacaacga cuuccccgcc cugcagcccg 360
acgcccccag ccccggcccc agcgaccacc cgcuuuucca ggccaagagc gcccggggcg 420
ugugcaaggu gaugugcuuc caccccugga gcgacgugac ccugccccug augagcgugc 480

```
ccgagaucag agccguggug gacgccuggg ccagcgugac cgaggagcug ggcgcccagu    540

accccugggu gcagaucuuc gagaacaagg gcgccaugau gggcugcagc aaccccccacc    600

cccacugcca ggugugggcc ucuagcuucc ugcccgacau cgcccagcgg gaggagcgga    660

gccagcaagc cuacaagucu cagcacggcg agccccugcu gauggaguac agccggcagg    720

agcugcugcg gaaggagcgg cuggugcuga ccagcgagca cuggcugguc cucgugcccu    780

ucugggccac cuggcccuac cagacccugc ugcucccuag acggcacgug cggcggcugc    840

ccgagcugac ccccgccgag cgggacgacc uggccagcau caugaagaag cugcucacca    900

aguaugauaa ucuguucgag acaagcuucc ccuacagcau gggcuggcac ggcgccccca    960

ccgguucaga ggccggcgcc aacuggaacc acuggcagcu gcacgcccac uacuacccac   1020

cuuuguugcg uagcgccacc gugcggaagu ucauggugg cuacgagaug cuggcccagg   1080

cccagcgcga ucugacccca gagcaggccg ccgagaggcu gcgggccuua ccugaggugc   1140

acuaccaccu cggccagaag gaccgggaaa ccgccaccau cgccugauaa uaguccauaa   1200

aguaggaaac acuacagcug gagccucggu ggccaugcuu cuugccccuu gggccucccc   1260

ccagccccuc cuccccuucc ugcacccgua cccccccgcau uauuacucac gguacgagug   1320

gucuuugaau aaagucugag ugggcggc                                     1348
```

```
<210> SEQ ID NO 146
<211> LENGTH: 1348
<212> TYPE: RNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: #15

<400> SEQUENCE: 146
```

```
gggaaauaag agagaaaaga agaguaagaa gaaauauaag agccaccaug agccggagcg     60

gcaccgaccc ccagcagcgg cagcaggcca gcgaggccga cgccgcagcc gcuaccuucc    120

gggccaacga ccaccagcac auccgguaca accccccugca ggacgagugg gugcuggugga   180

gcgcccaccg gaugaagcgg cccuggcagg gccaggugga gccccagcug cugaagaccg    240

ugccccggca cgacccccug aauccucucu gcccuggagc cauuagagcc aacggcgagg    300

ugaacccaca guacgacagc accuuccugu ucgacaacga cuuccccgcc cugcagcccg    360

acgcccccag ccccggcccc agcgaccacc cucuguucca ggccaagagc gcccggggcg    420

ugugcaaggu gaugugcuuc cacccaugga gcgacgugac ccugccccug augagcgugc    480

ccgagaucag agcugugug gacgccuggg ccagcgugac cgaggagcug ggcgcccagu    540

accccugggu gcagaucuuc gagaacaagg gcgccaugau gggcugcagc aaccccccacc    600

cccacugcca ggugugggcu ucuagcuucc ugcccgacau cgcccagcgg gaggagcgga    660

gccagcaggc guacaagucc cagcacggcg agccccugcu gauggaguac agccggcagg    720

agcugcugcg gaaggagcgg cuggugcuga ccagcgagca cuggcucgug uuagugcccu    780

ucugggccac cuggcccuac cagacccugc ugcugccucg ucggcacgug cggcggcugc    840

ccgagcugac ccccgccgag cgggacgacc uggccagcau caugaagaag cuccugacaa    900

aguaugacaa ccuauucgaa accagcuucc ccuacagcau gggcuggcac ggcgccccca    960

ccggcagcga agccggcgcc aacuggaacc acuggcagcu gcacgcccac uacuauccac   1020

cucugcugcg cagcgccacc gugcggaagu ucauggugg cuacgagaug cuggcccagg   1080
```

cccagcgcga ccugaccccu gagcaggcug ccgaacgacu gcgggcccug ccagaagugc 1140
acuaccaccu cggccagaag gaccgggaga cugccaccau cgccugauaa uaguccauaa 1200
aguaggaaac acuacagcug gagccucggu ggccaugcuu cuugccccuu gggccucccc 1260
ccagccccuc cuccccuucc ugcacccgua cccccgcau uauuacucac gguacgagug 1320
gucuuugaau aaagucugag ugggcggc 1348

<210> SEQ ID NO 147
<211> LENGTH: 1348
<212> TYPE: RNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: #16

<400> SEQUENCE: 147
gggaaauaag agagaaaaga agaguaagaa gaaauauaag agccaccaug agccggagcg 60
gcaccgaccc ccagcagcgg cagcaggcca gcgaggccga cgcugcagcc gccaccuucc 120
gggccaacga ccaccagcac auccgguaca acccccugca ggacgagugg gugcugguga 180
gcgcccaccg gaugaagcgg cccuggcagg gccaggugga gccccagcug cugaagaccg 240
ugccccggca cgacccccug aacccucugu gcccuggugc cauccgagcc aacggcgagg 300
ugaacccaca guacgacagc accuuccugu ucgacaacga cuuccccgcc cugcagcccg 360
acgcccccag ccccggcccc agcgaccauc cucuguucca ggccaagagc gcccggggcg 420
ugugcaaggu gaugugcuuc caccccugga gcgacgugac ccugccccug augagcgugc 480
ccgagaucag agcaguggug gacgccuggg ccagcgugac cgaggagcug ggcgcccagu 540
accccugggu gcagaucuuc gagaacaagg gcgccaugau gggcugcagc aacccccacc 600
cccacugcca ggugugggcu agcagcuucc ugcccgacau cgcccagcgg gaggagcgga 660
gccagcaggc uuacaagucu cagcacggcg agccccugcu gauggaguac agccggcagg 720
agcugcugcg gaaggagcgg cuggugcuga ccagcgagca cugguuaguc uuggugcccu 780
ucugggccac cuggcccuac cagacccugc ugcugccaag acggcacgug cggcggcugc 840
ccgagcugac ccccgccgag cgggacgacc uggccagcau caugaagaag cuccugacaa 900
aguacgauaa ccuuuucgag acaagcuucc ccuacagcau gggcuggcac ggcgccccaa 960
ccggcuccga ggccggcgcu aacuggaacc acuggcagcu gcacgcccac uacuacccuc 1020
cucuuuugag aagcgccacc gugcggaagu ucaugguggg cuacgagaug cuggcccagg 1080
cccagaggga ccugaccccu gagcaggccg ccgagagauu acgggcucuc ccagaggugc 1140
acuaccaccu gggacagaag gaccgggaga cagccaccau cgccugauaa uaguccauaa 1200
aguaggaaac acuacagcug gagccucggu ggccaugcuu cuugccccuu gggccucccc 1260
ccagccccuc cuccccuucc ugcacccgua cccccgcau uauuacucac gguacgagug 1320
gucuuugaau aaagucugag ugggcggc 1348

<210> SEQ ID NO 148
<211> LENGTH: 1348
<212> TYPE: RNA
<213> ORGANISM: Artificial Sequence
<220> FEATURE:
<223> OTHER INFORMATION: Description of Artificial Sequence: Synthetic polynucleotide
<220> FEATURE:

<223> OTHER INFORMATION: #17

<400> SEQUENCE: 148
gggaaauaag agagaaaaga agaguaagaa gaaauauaag agccaccaug agccggagcg 60
gcaccgaccc ccagcagcgg cagcaggcca gcgaggccga cgccgccgcc gccaccuucc 120
gggccaacga ccaccagcac auccgguaca acccccugca ggacgagugg gugcugguga 180
gcgcccaccg gaugaagcgg cccuggcagg gccaggugga gccccagcug cugaagaccg 240
ugccccggca cgacccccug aacccccugu gccccggcgc cauccgggcc aacggcgagg 300
ugaaccccca guacgacagc accuuccugu ucgacaacga cuuccccgcc cugcagcccg 360
acgcccccag ccccggcccc agcgaccacc cccuguucca ggccaagagc gcccggggcg 420
ugugcaaggu gaugugcuuc caccccugga gcgacgugac ccugccccug augagcgugc 480
ccgagauccg ggccguggug gacgccuggg ccagcgugac cgaggagcug ggcgcccagu 540
accccugggu gcagaucuuc gagaacaagg gcgccaugau gggcugcagc aacccccacc 600
cccacugcca ggugugggcc agcagcuucc ugcccgacau cgcccagcgg gaggagcgga 660
gccagcaggc cuacaagagc cagcacggcg agccccugcu gauggaguac agccggcagg 720
agcugcugcg gaaggagcgg cuggugcuga ccagcgagca cuggcuggug cuggugcccu 780
ucugggccac cuggcccuac cagacccugc ugcugccccg gcggcacgug cggcggcugc 840
ccgagcugac ccccgccgag cgggacgacc uggccagcau caugaagaag cugcugacca 900
aguacgacaa ccuguucgag accagcuucc ccuacagcau gggcuggcac ggcgccccca 960
ccggcagcga ggccggcgcc aacuggaacc acuggcagcu gcacgcccac uacuacccgc 1020
cccugcugcg gagcgccacc gugcggaagu ucauggugggg cuacgagaug cuggcccagg 1080
cccagcggga ccugaccccc gagcaggccg ccgagcggcu gcgggcccug cccgaggugc 1140
acuaccaccu gggccagaag gaccgggaga ccgccaccau cgccugauaa uaguccauaa 1200
aguaggaaac acuacagcug gagccucggu ggccaugcuu cuugccccuu gggccucccc 1260
ccagccccuc cuccccuucc ugcacccgua cccccgcau uauuacucac gguacgagug 1320
gucuuugaau aaagucugag ugggcggc 1348

<210> SEQ ID NO 149
<211> LENGTH: 1348
<212> TYPE: RNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: #18

<400> SEQUENCE: 149
gggaaauaag agagaaaaga agaguaagaa gaaauauaag agccaccaug agccggagcg 60
gcaccgaccc ccagcagcgg cagcaggcca gcgaggccga cgccgccgcc gccaccuucc 120
gggccaacga ccaccagcac aucagguaca acccgcugca ggacgagugg gugcugguga 180
gcgcgcacag gaugaagagg ccguggcagg ggcaggugga gccgcagcug cugaagacgg 240
ugccgaggca cgacccgcug aacccgcugu gcccgggggc gaucagggcg aacggggagg 300
ugaacccgca guacgacagc acguuccugu ucgacaacga cuucccggcg cugcagccgg 360
acgcgccgag cccggggccg agcgaccacc cgcuguucca ggcgaagagc gcgagggggg 420
ugugcaaggu gaugugcuuc cacccgugga gcgacgugac gcugccgcug augagcgugc 480

-continued

```
cggagaucag ggcgguggug gacgcguggg cgagcgugac ggaggagcug ggggcgcagu    540

acccgugggu gcagaucuuc gagaacaagg gggcgaugau ggggugcagc aacccgcacc    600

cgcacugcca ggugugggcg agcagcuucc ugccggacau cgcgcagagg gaggagagga    660

gccagcaggc guacaagagc cagcacgggg agccgcugcu gauggaguac agcaggcagg    720

agcugcugag gaaggagagg cuggugcuga cgagcgagca cuggcuggug cuggugccgu    780

ucugggcgac guggccguac cagacgcugc ugcugccgag gaggcacgug aggaggcugc    840

cggagcugac gccggcggag agggacgacc uggcgagcau caugaagaag cugcugacga    900

aguacgacaa ccuguucgag acgagcuucc cguacagcau ggggguggcac ggggcgccga    960

cggggagcga ggcgggggcg aacuggaacc acuggcagcu gcacgcgcac uacuacccgc   1020

cgcugcugag gagcgcgacg gugaggaagu ucaugguggg guacgagaug cuggcgcagg   1080

cgcagaggga ccugacgccg gagcaggcgg cggagaggcu gagggcgcug ccggaggugc   1140

acuaccaccu ggggcagaag gacagggaga cggcgacgau cgcgugauaa uaguccauaa   1200

aguaggaaac acuacagcug gagccucggu ggccaugcuu cuugccccuu gggccucccc   1260

ccagccccuc cuccccuucc ugcacccgua cccccgcau uauuacucac gguacgagug   1320

gucuuugaau aaagucugag ugggcggc                                      1348
```

<210> SEQ ID NO 150
<211> LENGTH: 1348
<212> TYPE: RNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: #19

<400> SEQUENCE: 150

```
gggaaauaag agagaaaaga agaguaagaa gaaauauaag agccaccaug agccggagcg     60

gcaccgaccc ccagcagcgg cagcaggcca gcgaggccga cgccgccgcc gccaccuucc    120

gggccaacga ccaccagcac auccgcuaca acccccucca ggacgagugg guccucgucu    180

ccgcccaccg caugaagcgc cccuggcagg gccaggucga gccccagcuc cucaagaccg    240

ucccccgcca cgacccccuc aacccccucu gccccggcgc cauccgcgcc aacggcgagg    300

ucaaccccca guacgacucc accuuccucu ucgacaacga cuuccccgcc cuccagcccg    360

acgcccccuc ccccggcccc uccgaccacc cccucuucca ggccaagucc gcccgcggcg    420

ucugcaaggu caugugcuuc caccccuggu ccgacgucac ccucccccuc auguccgucc    480

ccgagauccg cgccgucguc gacgccuggg ccuccgucac cgaggagcuc ggcgcccagu    540

accccugggu ccagaucuuc gagaacaagg gcgccaugau gggcugcucc aacccccacc    600

cccacugcca ggucugggcc uccuccuucc uccccgacau cgcccagcgc gaggagcgcu    660

cccagcaggc cuacaagucc cagcacggcg agccccuccu cauggaguac ucccgccagg    720

agcuccuccg caaggagcgc cucguccuca ccuccgagca cuggcucguc cucgucccu    780

ucugggccac cuggcccuac cagacccucc uccuccccg ccgccacguc cgccgccucc    840

ccgagcucac ccccgccgag cgcgacgacc ucgccuccau caugaagaag cuccucacca    900

aguacgacaa ccucuucgag accuccuucc ccuacuccau gggcuggcac ggcgcccca    960

ccggcuccga ggccggcgcc aacuggaacc acuggcagcu ccacgcccac uacuacccgc   1020

cccuccuccg cuccgccacc guccgcaagu ucauggucgg cuacgagaug cucgcccagg   1080
```

cccagcgcga ccucaccccc gagcaggccg ccgagcgccu ccgcgcccuc cccgagguccc 1140 acuaccaccu cggccagaag gaccgcgaga ccgccaccau cgccugauaa uaguccauaa 1200
aguaggaaac acuacagcug gagccucggu ggccaugcuu cuugccccuu gggccucccc 1260
ccagccccuc cuccccuucc ugcacccgua ccccccgcau uauuacucac gguacgagug 1320
gucuuugaau aaagucugag ugggcggc 1348

<210> SEQ ID NO 151
<211> LENGTH: 810
<212> TYPE: RNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Human GALT isoform 2

<400> SEQUENCE: 151
augacccucu caacccucug uguccugggg ccauccgagc caacggagag uaaggucaug 60
ugcuuccacc ccuggucgga uguaacgcug ccacucaugu cgguccccuga gauccgggcu 120 guuguugaug caugggccuc agucacagag gagcugggug cccaguaccc uugggugcag 180
aucuuugaaa acaaaggugc caugaugggc uguucuaacc cccaccccca cugccaggua 240
ugggccagca guuuccugcc agauauugcc cagcgugagg agcgaucuca gcaggccuau 300
aagagucagc auggagagcc ccugcuaaug gaguacagcc gccaggagcu acucaggaag 360
gaacgucugg uccuaaccag ugagcacugg uuaguacugg uccccuucug ggcaacaugg 420
cccuaccaga cacugcugcu gccccgucgg caugugcggc ggcuaccuga gcugaccccu 480
gcugagcgug augaucuagc cuccaucaug aagaagcucu ugaccaagua ugacaaccuc 540
uuugagacgu ccuuucccua cuccaugggc uggcaugggg cucccacagg aucagaggcu 600
ggggccaacu ggaaccauug gcagcugcac gcucauuacu acccuccgcu ccugcgcucu 660
gccacugucc ggaaauucau gguuggcuac gaaaugcuug cucaggcuca gagggaccuc 720
accccugagc aggcugcaga gagacuaagg gcacuuccug agguucauua ccaccugggg 780
cagaaggaca gggagacagc aaccaucgcc 810

<210> SEQ ID NO 152
<211> LENGTH: 609
<212> TYPE: RNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Mouse GALT isoform 2

<400> SEQUENCE: 152
augaugggcu guucuaaccc ccaucccccac ugccagguuu gggcuagcag cuuccugcca 60
gauaucgccc agcgugaaga gcgaucccag cagaccuauc acagccagca uggaaaaccu 120
uuguuauugg aauaugguca ccaagagcuc cucaggaagg aacgucuggu ccuaaccagu 180
gagcacugga uaguucuggu ccccuucugg gcaguguggc cuuuccagac acuucugcug 240
ccccggcggc acgugcggcg gcuaccugag cugaaccccg cugagcguga ugaucucgcc 300
uccaucauga agaagcucuu gaccaaguac gacaaucuau uugagacauc cuuucccuac 360
uccaugggcu ggcauggggc ucccacggga uuaaagacug gagccaccug ugaccacugg 420
cagcuccacg cccacuacua ccccccacuu cugcgauccg caacuguccg gaaguucaug 480
guuggcuaug aaaugcuugc ccaggcccag cgugaccuca cucccgaaca ggccgcagaa 540
agauuaaggg cgcuucccga gguacacuau ugccuggcgc agaaagacaa ggaaacggca 600
gccauugcu 609

<210> SEQ ID NO 153
<211> LENGTH: 1137
<212> TYPE: RNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Human GALT isoform 1

<400> SEQUENCE: 153
augucgcgca guggaaccga uccucagcaa cgccagcagg cgucagaggc ggacgccgca 60
gcagcaaccu uccgggcaaa cgaccaucag cauauccgcu acaacccgcu gcaggaugag 120
ugggugcugg ugucagcuca ccgcaugaag cggcccuggc agggucaagu ggagccccag 180
cuucugaaga cagugccccg ccaugacccu cucaacccuc uguguccugg ggccauccga 240
gccaacggag aggugaaucc ccaguacgau agcaccuucc uguuugacaa cgacuuccca 300
gcucugcagc cugaugcccc caguccagga cccagugauc auccccuuuu ccaagcaaag 360
ucugcucgag gagucuguaa ggucaugugc uuccaccccu ggucggaugu aacgcugcca 420
cucaugucgg ucccugagau ccgggcuguu guugaugcau gggccucagu cacagaggag 480
cugggugccc aguacccuug ggugcagauc uuugaaaaca aaggugccau gaugggcugu 540
ucuaaccccc acccccacug ccagguaugg gccagcaguu uccugccaga uauugcccag 600
cgugaggagc gaucucagca ggccuauaag agucagcaug gagagccccu gcuaauggag 660
uacagccgcc aggagcuacu caggaaggaa cgucuggucc uaaccaguga gcacugguua 720 guacugguce ccuucugggc aacauggccc uaccagacac ugcugcugcc ccgucggcau 780
gugcggcggc uaccugagcu gaccccugcu gagcgugaug aucuagccuc caucaugaag 840
aagcucuuga ccaaguauga caaccucuuu gagacguccu uucccuacuc caugggcugg 900 caugggggcuc ccacaggauc agaggcuggg gccaacugga accauuggca gcugcacgcu 960
cauuacuacc cuccgcuccu gcgcucugcc acuguccgga aauucauggu uggcuacgaa 1020
augcuugcuc aggcucagag ggaccucacc ccugagcagg cugcagagag acuaagggca 1080
cuuccugagg uucauuacca ccuggggcag aaggacaggg agacagcaac caucgcc 1137

<210> SEQ ID NO 154
<211> LENGTH: 1080
<212> TYPE: RNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Mouse GALT11-methyl-pseudouridine modified mRNA

<400> SEQUENCE: 154
auggcagcga ccuuccgggc gagcgaacac cagcauauuc gcuacaaccc gcuccaggac 60
gagugggugu uagugucggc ucaucgcaug aagcggcccu ggcaaggaca aguggagccc 120
cagcuucuga agacagugcc ccgccacgac ccacucaacc cucugugucc cggggccaca 180
cgagcuaaug gggaggugaa uccccacuau gaugguaccu uucuguuuga caaugacuuc 240
ccggcucugc agcccgaugc uccggaucca ggacccagug accacccucu cuuccgagca 300
gaggccgcca gaggaguuug uaaggucaug ugcuuccacc ccuggucgga ugugacgcug 360
ccacucaugu cugucccuga gauccgagcu gucaucgaug caugggccuc agucacagag 420
gagcugggug cccaguaccc uugggugcag aucuuugaaa auaaaggagc caugaugggc 480
uguucuaacc cccaucccca cugccagguu ugggcuagca gcuuccugcc agauaucgcc 540
cagcgugaag agcgauccca gcagaccuau cacagccagc auggaaaacc uuuguuauug 600
gaauaugguc accaagagcu ccucaggaag gaacgucugg uccuaaccag ugagcacugg 660
auaguucugg ucccuucug ggcagugugg ccuuuccaga cacuucugcu gccccggcgg 720
cacgugcggc ggcuaccuga gcugaacccc gcugagcgug augaucucgc cuccaucaug 780
aagaagcucu ugaccaagua cgacaaucua uuugagacau ccuuucccua cuccaugggc 840
uggcaugggg cucccacggg auuaaagacu ggagccaccu gugaccacug gcagcuccac 900
gcccacuacu acccccacu ucugcgaucc gcaacugucc ggaaguucau gguuggcuau 960
gaaaugcuug cccaggccca gcgugaccuc acucccgaac aggccgcaga aagauuaagg 1020
gcgcuucccg agguacacua uugccuggcg cagaaagaca aggaaacggc agccauugcu 1080

<210> SEQ ID NO 155
<211> LENGTH: 85
<212> TYPE: RNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: miR-126

<400> SEQUENCE: 155
cgcuggcgac gggacauuau uacuuuuggu acgcgcugug acacuucaaa cucguaccgu 60
gaguaauaau gcgccgucca cggca 85

<210> SEQ ID NO 156
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: miR-126-5p binding site

<400> SEQUENCE: 156
cgcguaccaa aaguaauaau g 21

<210> SEQ ID NO 157
<211> LENGTH: 69
<212> TYPE: RNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: NTFIX ORF

<400> SEQUENCE: 157
augcuucuug ccccuugggc cuccccccag ccccuccucc ccuuccugca cccguacccc 60 cgugguc uu 69

<210> SEQ ID NO 158

<211> LENGTH: 1303
<212> TYPE: RNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: #20

<400> SEQUENCE: 158
gggaaauaag agagaaaaga agaguaagaa gaaauauaag agccaccaug ucgcgcagug 60
gaaccgaucc ucagcaacgc cagcaggcgu cagaggcgga cgccgcagca gcaaccuucc 120
gggcaaacga ccaucagcau auccgcuaca acccgcugca ggaugagugg gugcuggugu 180
cagcucaccg caugaagcgg cccuggcagg gucaagugga gccccagcuu cugaagacag 240
ugccccgcca ugacccucuc aacccucugu guccuggggc cauccgagcc aacggagagg 300
ugaaucccca guacgauagc accuuccugu uugacaacga cuucccagcu cugcagccug 360
augcccccag uccaggaccc agugaucauc cccuuuucca agcaaagucu gcucgaggag 420
ucuguaaggu caugugcuuc caccccuggu cggauguaac gcugccacuc augucggucc 480
cugagauccg ggcuguuguu gaugcauggg ccucagucac agaggagcug ggugcccagu 540
acccuugggu gcagaucuuu gaaaacaaag gugccaugau gggcuguucu aacccccacc 600
cccacugcca gguaugggcc agcaguuucc ugccagauau ugcccagcgu gaggagcgau 660
cucagcaggc cuauaagagu cagcauggag agccccugcu aauggaguac agccgccagg 720
agcuacucag gaaggaacgu cugguccuaa ccagugagca cugguuagua cugguccccu 780
ucugggcaac auggcccuac cagacacugc ugcugccccg ucggcaugug cggcggcuac 840
cugagcugac cccugcugag cgugaugauc uagccuccau caugaagaag cucuugacca 900
aguaugacaa ccucuuugag acguccuuuc ccuacuccau gggcuggcau ggggcuccca 960
caggaucaga ggcuggggcc aacuggaacc auuggcagcu gcacgcucau uacuacccuc 1020
cgcuccugcg cucugccacu guccggaaau ucaugguugg cuacgaaaug cuugcucagg 1080
cucagaggga ccucaccccu gagcaggcug cagagagacu aagggcacuu ccugagguuc 1140
auuaccaccu ggggcagaag gacagggaga cagcaaccau cgccugauaa uaggcuggag 1200 ccucggugc caugcuucuu gccccuuggg ccucccccca gccccuccuc cccuuccugc 1260
acccguaccc ccguggucuu ugaauaaagu cugagugggc ggc 1303

<210> SEQ ID NO 159
<211> LENGTH: 1246
<212> TYPE: RNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: #21

<400> SEQUENCE: 159
gggaaauaag agagaaaaga agaguaagaa gaaauauaag agccaccaug gcagcgaccu 60
uccgggcgag cgaacaccag cauauucgcu acaacccgcu ccaggacgag ugggguguuag 120 ugucggcuca ucgcaugaag cggcccuggc aaggacaagu ggagccccag cuucugaaga 180
cagugccccg ccacgaccca cucaacccuc uguguccegg ggccacacga gcuaaugggg 240
aggugaaucc ccacuaugau gguaccuuuc uguuugacaa ugacuucccg gcucugcagc 300
ccgaugcucc ggauccagga cccagugacc acccucucuu ccgagcagag gccgccagag 360

```
gaguuuguaa ggucaugugc uuccaccccu ggucggaugu gacgcugcca cucaugucug    420

ucccugagau ccgagcuguc aucgaugcau gggccucagu cacagaggag cugggugccc    480

aguacccuug ggugcagauc uuugaaaaua aaggagccau gaugggcugu ucuaaccccc    540

auccccacug ccagguuugg gcuagcagcu uccugccaga uaucgcccag cgugaagagc    600

gaucccagca gaccuaucac agccagcaug gaaaaccuuu guuauuggaa uauggucacc    660

aagagcuccu caggaaggaa cgucuggucc uaaccaguga gcacuggaua guucuggucc    720

ccuucugggc aguguggccu uuccagacac uucugcugcc ccggcggcac gugcggcggc    780

uaccugagcu gaaccccgcu gagcgugaug aucucgccuc caucaugaag aagcucuuga    840

ccaaguacga caaucuauuu gagacauccu uucccuacuc caugggcugg cauggggcuc    900

ccacgggauu aaagacugga gccaccugug accacuggca gcuccacgcc cacuacuacc    960

ccccacuucu gcgauccgca acuguccgga aguucauggu uggcuaugaa augcuugccc   1020

aggcccagcg ugaccucacu cccgaacagg ccgcagaaag auuaagggcg cuucccgagg   1080

uacacuauug ccuggcgcag aaagacaagg aaacggcagc cauugcuuga uaauaggcug   1140

gagccucggu ggccaugcuu cuugccccuu gggccucccc ccagccccuc cuccccuucc   1200

ugcacccgua cccccguggu cuuugaauaa agucugagug ggcggc                  1246
```

```
<210> SEQ ID NO 160
<211> LENGTH: 1363
<212> TYPE: RNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: #22

<400> SEQUENCE: 160

gggaaauaag agagaaaaga agaguaagaa gaaauauaag acagcgcguc aacauugccg     60

aaucgccggg acucaucaca aucugccucu uggguuaucu cuugucggca gauaccuucu    120

uggaucacga aaacgcgaac aaaauucuua aucgcccgaa gcgguauaac uccgggaaac    180

uugaggaguu ucagggcaau cuugaacgag acgaggagaa cuccuuugag gaggcgaggg    240

aauuugaaaa cacagagcga acaacggagu uuuggaagca auacguaggg gaccagucga    300

auccccucag gggaucuaaa gacaucaaua gcuacugccc guuuggguuu gaagggaaga    360

acuagcugac caacaucaaa aacggacgcu agcaguuuug uaagaacucg gcugacaaua    420

agguagucuc cacagaggga uaccggcugg cggagaacca aaaauccgag cccgcagucc    480

cguucccuug gaggagcuca cagacuagca aguugacgag agcggagacu guauuccccg    540

acgacuacgu caacagcacc gaagccgaaa caauccucga uaacaucacg cagagcacuc    600

aguccuucaa cuuuacgagg gucguagagg acgcgaaacc cggucaguuc cccuggcagg    660

uauugaacgg aaaagucgcc uuuugagguu ccauugucaa cgagaagauu gucacagcgg    720

cacacugcgu agaaacagga aaaaucacgg uagcgggaga gcauaacauu gaagagacag    780

agcacacgga acaaaagcga aucaucagaa ucauuccaca ccauaacuau aacgcggcaa    840

ucaauaagua caaucacgac aucgcacuuu uggagcuuga cgaaccuuug cuuaauucgu    900

acgucacccc uauuuguauu gccgacaaag aguauacaaa caucuucuug aaauucggcu    960

ccggguacgu aucgggcugg ggcagauucc auaaggguag auccgcacug uugcaauacc   1020

ucaggccccu cgaucgagcc acuugucugc gguccaccaa auucacaauc uacaacaauu   1080
```

ucucgggauu ccaagggaga gauagcugcc agggagacuc agggggaccc cacacggaag 1140
ucgaggggac gucauuucug acgggaauua ucucgggaga ggcgaagggg aacaucuaca 1200
cuaaaucacg guucaauugg aucaaggaaa agacgaaacu cacgugauaa uaggcuggag 1260
ccucgguggc caugcuucuu gccccuuggg ccucccccca gccccuccuc cccuuccugc 1320
acccguaccc ccguggucuu ugaauaaagu cugagugggc ggc 1363

<210> SEQ ID NO 161
<211> LENGTH: 976
<212> TYPE: RNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: #23

<400> SEQUENCE: 161
gggaaauaag agagaaaaga agaguaagaa gaaauauaag agccaccaug acccucucaa 60
cccucugugu ccuggggcca uccgagccaa cggagaguaa ggucaugugc uuccaccccu 120
ggucggaugu aacgcugcca cucaugucgg ucccugagau ccgggcuguu guugaugcau 180
gggccucagu cacagaggag cugggugccc aguacccuug ggugcagauc uuugaaaaca 240
aaggugccau gaugggcugu ucuaaccccc acccccacug ccagguaugg gccagcaguu 300
uccugccaga uauugcccag cgugaggagc gaucucagca ggccuauaag agucagcaug 360
gagagccccu gcuaauggag uacagccgcc aggagcuacu caggaaggaa cgucuggucc 420
uaaccaguga gcacugguua guacuggucc ccuucugggc aacauggccc uaccagacac 480
ugcugcugcc ccgucggcau gugcggcggc uaccugagcu gaccccugcu gagcgugaug 540
aucuagccuc caucaugaag aagcucuuga ccaaguauga caaccucuuu gagacguccu 600
uucccuacuc caugggcugg caugggggcuc ccacaggauc agaggcuggg gccaacugga 660
accauuggca gcugcacgcu cauuacuacc cuccgcuccu gcgcucugcc acuguccgga 720
aauucauggu uggcuacgaa augcuugcuc aggcucagag ggaccucacc ccugagcagg 780
cugcagagag acuaagggca cuuccugagg uucauuacca ccuggggcag aaggacaggg 840
agacagcaac caucgccuga uaauaggcug gagccucggu ggccaugcuu cuugccccuu 900
gggccucccc ccagccccuc cuccccuucc ugcacccgua cccccguggu cuuugaauaa 960
agucugagug ggcggc 976

<210> SEQ ID NO 162
<211> LENGTH: 775
<212> TYPE: RNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: #24

<400> SEQUENCE: 162
gggaaauaag agagaaaaga agaguaagaa gaaauauaag agccaccaug augggcuguu 60
cuaaccccca uccccacugc cagguuuggg cuagcagcuu ccugccagau aucgcccagc 120
gugaagagcg aucccagcag accuaucaca gccagcaugg aaaaccuuug uuauuggaau 180
auggucacca agagcuccuc aggaaggaac gucugguccu aaccagugag cacuggauag 240

-continued uucugguccc cuucugggca guguggccuu uccagacacu ucugcugccc cggcggcacg 300
ugcggcggcu accugagcug aaccccgcug agcgugauga ucucgccucc aucaugaaga 360
agcucuugac caaguacgac aaucuauuug agacauccuu ucccuacucc augggcuggc 420 augggggcucc cacgggauua aagacuggag ccaccuguga ccacuggcag cuccacgccc 480
acuacuaccc cccacuucug cgauccgcaa cuguccggaa guucaugguu ggcuaugaaa 540
ugcuugccca ggcccagcgu gaccucacuc ccgaacaggc cgcagaaaga uuaagggcgc 600
uucccgaggu acacuauugc cuggcgcaga aagacaagga aacggcagcc auugcuugau 660
aauaggcugg agccucggug gccaugcuuc uugccccuug ggccuccccc cagccccucc 720
uccccuuccu gcacccguac cccgugguc uuugaauaaa gucugagugg gcggc 775

<210> SEQ ID NO 163
<211> LENGTH: 164
<212> TYPE: RNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: 3' UTR (miR142+miR126 binding sites variant 2)

<400> SEQUENCE: 163
ugauaauagu ccauaaagua ggaaacacua cagcuggagc cucgguggcc uagcuucuug 60
ccccuugggc cuccccccag ccccuccucc ccuuccugca cccguacccc ccgcauuauu 120
acucacggua cgaguggucu uugaauaaag ucugaguggg cggc 164

<210> SEQ ID NO 164
<211> LENGTH: 142
<212> TYPE: RNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: (3' UTR with miR 142-3p binding site variant 2)

<400> SEQUENCE: 164
ugauaauagg cuggagccuc gguggccuag cuucuugccc cuugggccuc cccccagccc 60
cuccuccccu uccugcaccc guacccccuc cauaaaguag gaaacacuac aguggucuuu 120
gaauaaaguc ugagugggcg gc 142

<210> SEQ ID NO 165
<211> LENGTH: 119
<212> TYPE: RNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: (3' UTR, no miR binding sites variant 2)

<400> SEQUENCE: 165
ugauaauagg cuggagccuc gguggccuag cuucuugccc cuugggccuc cccccagccc 60
cuccuccccu uccugcaccc guacccccgu ggucuuugaa uaaagucuga gugggcggc 119

<210> SEQ ID NO 166
<211> LENGTH: 141
<212> TYPE: RNA
<213> ORGANISM: Artificial Sequence
<220> FEATURE:

<223> OTHER INFORMATION: Description of Artificial Sequence: Synthetic
polynucleotide
<220> FEATURE:
<223> OTHER INFORMATION: (3' UTR with miR 126-3p binding site variant 3)

<400> SEQUENCE: 166
ugauaauagg cuggagccuc gguggccuag cuucuugccc cuugggccuc cccccagccc 60
cuccuccccu uccugcaccc guacccccg cauuauuacu cacgguacga guggucuuug 120
aauaaagucu gagugggcgg c 141

<210> SEQ ID NO 167
<211> LENGTH: 188
<212> TYPE: RNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: (3' UTR with 3 miR 142-3p binding sites variant
2)

<400> SEQUENCE: 167
ugauaauagu ccauaaagua ggaaacacua cagcuggagc cucgguggcc uagcuucuug 60
ccccuugggc cuccauaaag uaggaaacac uacaucccc cagcccucc uccccuuccu 120 gcacccguac ccccuccaua aaguaggaaa cacuacagug gucuuugaau aaagucugag 180
ugggcggc 188

<210> SEQ ID NO 168
<211> LENGTH: 142
<212> TYPE: RNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: (3'UTR with miR 142-3p binding site, P1
insertion variant 2)

<400> SEQUENCE: 168
ugauaauagu ccauaaagua ggaaacacua cagcuggagc cucgguggcc uagcuucuug 60
ccccuugggc cuccccccag ccccuccucc ccuuccugca cccguacccc cgguggucuuu 120 gaauaaaguc ugagugggcg gc 142

<210> SEQ ID NO 169
<211> LENGTH: 142
<212> TYPE: RNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: (3'UTR with miR 142-3p binding site, P2
insertion variant 2)

<400> SEQUENCE: 169
ugauaauagg cuggagccuc gguggcucca uaaaguagga aacacuacac uagcuucuug 60
ccccuugggc cuccccccag ccccuccucc ccuuccugca cccguacccc cguggucuuu 120
gaauaaaguc ugagugggcg gc 142

<210> SEQ ID NO 170
<211> LENGTH: 142
<212> TYPE: RNA

<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: (3'UTR with miR 142-3p binding site, P3
insertion variant 2)

<400> SEQUENCE: 170
ugauaauagg cuggagccuc gguggccuag cuucuugccc cuugggccuc cauaaaguag 60
gaaacacuac auccccccag ccccuccucc ccuuccugca cccguacccc cguggucuuu 120
gaauaaaguc ugagugggcg gc 142

<210> SEQ ID NO 171
<211> LENGTH: 142
<212> TYPE: RNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: (3'UTR with miR 155-5p binding site variant 2)

<400> SEQUENCE: 171
ugauaauagg cuggagccuc gguggccuag cuucuugccc cuugggccuc cccccagccc 60
cuccuccccu uccugcaccc guacccccac ccuaucaca auuagcauua agugucuuu 120 gaauaaaguc ugagugggcg gc 142

<210> SEQ ID NO 172
<211> LENGTH: 188
<212> TYPE: RNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: (3' UTR with 3 miR 155-5p binding sites variant
2)

<400> SEQUENCE: 172
ugauaauaga ccccuaucac aauuagcauu aagcuggagc cucgguggcc uagcuucuug 60
ccccuugggc caccccuauc acaauuagca uuaaucccc cagccccucc uccccuuccu 120
gcacccguac ccccaccccu aucacaauua gcauuaagug gucuuugaau aaagucugag 180
ugggcggc 188

<210> SEQ ID NO 173
<211> LENGTH: 188
<212> TYPE: RNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: (3'UTR with 2 miR 155-5p binding sites and 1
miR 142-3p binding site variant 2)

<400> SEQUENCE: 173
ugauaauaga ccccuaucac aauuagcauu aagcuggagc cucgguggcc uagcuucuug 60
ccccuugggc cuccauaaag uaggaaacac uacaucccc cagccccucc uccccuuccu 120
gcacccguac ccccaccccu aucacaauua gcauuaagug gucuuugaau aaagucugag 180
ugggcggc 188

<210> SEQ ID NO 174
<211> LENGTH: 5
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 174

Gly Gly Gly Gly Ser
1 5

<210> SEQ ID NO 175
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (2)..(5)
<223> OTHER INFORMATION: a, c, t, g, unknown or other
<220> FEATURE:
<221> NAME/KEY: modified_base
<222> LOCATION: (7)..(7)
<223> OTHER INFORMATION: a, c, t, g, unknown or other
<220> FEATURE:
<221> NAME/KEY: modified_base
<222> LOCATION: (10)..(10)
<223> OTHER INFORMATION: a, c, t, g, unknown or other
<220> FEATURE:
<221> NAME/KEY: modified_base
<222> LOCATION: (14)..(14)
<223> OTHER INFORMATION: a, c, t, g, unknown or other
<220> FEATURE:
<221> NAME/KEY: modified_base
<222> LOCATION: (16)..(17)
<223> OTHER INFORMATION: a, c, t, g, unknown or other
<220> FEATURE:
<221> NAME/KEY: modified_base
<222> LOCATION: (19)..(19)
<223> OTHER INFORMATION: a, c, t, g, unknown or other

<400> SEQUENCE: 175
gnnnnwncrn ctcncnnwnd 20

<210> SEQ ID NO 176
<211> LENGTH: 120
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 176
aaaaaaaaaa aaaaaaaaaa aaaaaaaaaa aaaaaaaaaa aaaaaaaaaa aaaaaaaaaa 60
aaaaaaaaaa aaaaaaaaaa aaaaaaaaaa aaaaaaaaaa aaaaaaaaaa aaaaaaaaaa 120

<210> SEQ ID NO 177
<211> LENGTH: 120
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 177
tttttttttt tttttttttt tttttttttt tttttttttt tttttttttt tttttttttt 60
tttttttttt tttttttttt tttttttttt tttttttttt tttttttttt tttttttttt    120

<210> SEQ ID NO 178
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 178

Met Ser Arg Ser Gly Thr Asp Pro Gln Gln Arg Gln Gln Ala Ser Glu
1               5                   10                  15

Ala

<210> SEQ ID NO 179
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 179

Met Thr Leu Ser Thr Leu Cys Val Leu Gly Pro Ser Glu Pro Thr Glu
1               5                   10                  15

Ser